(12) United States Patent
Kim et al.

(10) Patent No.: US 11,690,289 B2
(45) Date of Patent: Jun. 27, 2023

(54) ORGANIC COMPOUND CONTAINING HETEROCYCLIC RING AND HAVING LOW LUMO PROPERTIES, AND ORGANIC ELECTROLUMINESCENT DEVICE USING THE SAME

(71) Applicants: Samsung Display Co., Ltd., Yongin-si (KR); Doosan Solus Co., Ltd., Iksan-si (KR)

(72) Inventors: Seulong Kim, Yongin-si (KR); Hojun Son, Yongin-si (KR); Hyobum Song, Yongin-si (KR); Jaehoon Hwang, Yongin-si (KR); Hoemoon Kim, Yongin-si (KR); Hocheol Park, Yongin-si (KR); Minsik Eum, Yongin-si (KR); Songie Han, Yongin-si (KR)

(73) Assignees: Samsung Display Co., Ltd., Yongin-si (KR); Solus Advanced Materials Co., Ltd., Iksan-si (KR)

( * ) Notice: Subject to any disclaimer, the term of this patent is extended or adjusted under 35 U.S.C. 154(b) by 253 days.

(21) Appl. No.: 17/071,757

(22) Filed: Oct. 15, 2020

(65) Prior Publication Data
US 2021/0167296 A1    Jun. 3, 2021

(30) Foreign Application Priority Data

Dec. 3, 2019 (KR) .................. 10-2019-0159363

(51) Int. Cl.
*H01L 51/50* (2006.01)
*H01L 51/00* (2006.01)
*C07D 471/04* (2006.01)

(52) U.S. Cl.
CPC ...... *H01L 51/0072* (2013.01); *H01L 51/0052* (2013.01); *H01L 51/0067* (2013.01); *C07D 471/04* (2013.01); *H01L 51/5072* (2013.01)

(58) Field of Classification Search
None
See application file for complete search history.

(56) References Cited

U.S. PATENT DOCUMENTS 9,246,175 B2    1/2016   Pak et al.
2018/0166647 A1*  6/2018  Shin .................. H01L 51/5092
2019/0181354 A1   6/2019  Shin et al.

FOREIGN PATENT DOCUMENTS

JP    2008-106015 A    5/2008
KR   10-2017-0116500 A   10/2017
(Continued)

OTHER PUBLICATIONS

Li, Chen et al., "A phenanthroline derivative as exciton blocking material for organic solar cells", Dyes and Pigments, 97 (2013) 258-261, Elsevier Applied Science Publishers Barking, GB, vol. 97, No. 1, Dec. 19, 2012 (Dec. 19, 2012), pp. 258-261, XP028969402, ISSN: 0143-7208, DOI: 10.1016/J.DYEPIG.2012.12.003 (4 pages).
EPO Search Report dated Apr. 6, 2021 for corresponding European Patent Application No. 20211663.8 (7 pages).

*Primary Examiner* — Gregory D Clark
(74) *Attorney, Agent, or Firm* — Lewis Roca Rothgerber Christie LLP

(57) ABSTRACT

An organic light-emitting device includes: a first electrode; a second electrode facing the first electrode; an organic layer between the first electrode and the second electrode and including an emission layer; and at least one heterocyclic compound represented by Formula 1:

(Continued)

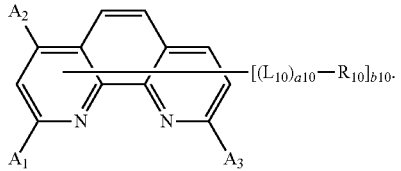

Formula 1

The organic light-emitting device including at least one heterocyclic compound as represented above may have a low driving voltage, high emission efficiency, and improved lifetime characteristics.

20 Claims, 4 Drawing Sheets

(56) References Cited

FOREIGN PATENT DOCUMENTS

| KR | 10-2018-0067321 | A | 6/2018 |
| KR | 10-1926769 | B1 | 12/2018 |
| KR | 10-1911432 | B1 | 1/2019 |
| KR | 10-1984677 | B1 | 5/2019 |
| KR | 1020190053606 | A | 5/2019 |
| KR | 10-2019-0070795 | A | 6/2019 |
| KR | 1020200132290 | A | 11/2020 |

\* cited by examiner

| 190 |
|-----|
| 150 |
| 110 |

| 190 |
|---|
| 150 |
| 110 |
| 210 |

| 220 |
|---|
| 190 |
| 150 |
| 110 |

| 220 |
|-----|
| 190 |
| 150 |
| 110 |
| 210 |

ORGANIC COMPOUND CONTAINING HETEROCYCLIC RING AND HAVING LOW LUMO PROPERTIES, AND ORGANIC ELECTROLUMINESCENT DEVICE USING THE SAME

CROSS-REFERENCE TO RELATED APPLICATION

This application claims priority to and the benefit of Korean Patent Application No. 10-2019-0159363, filed on Dec. 3, 2019, in the Korean Intellectual Property Office, the entire content of which is incorporated herein by reference.

BACKGROUND

1. Field

One or more aspects of embodiments of the present disclosure relate to a heterocyclic compound and an organic light-emitting device including the same.

2. Description of the Related Art

Organic light-emitting devices (OLEDs) are self-emitting devices that have advantages such as wide viewing angles, excellent contrast, quick response times, excellent luminance, and/or excellent driving voltage characteristics, and can produce full-color images.

An organic light-emitting device may have a structure in which a first electrode, a hole transport region, an emission layer, an electron transport region, and a second electrode are sequentially positioned in this order on a substrate. Holes injected from the first electrode move to the emission layer via the hole transport region, while electrons injected from the second electrode move to the emission layer via the electron transport region. Carriers, such as the holes and electrons, may then recombine in the emission layer to generate excitons. When the excitons transition from an excited state to a ground state, light is emitted.

SUMMARY

One or more aspects of embodiments of the present disclosure are directed toward a novel heterocyclic compound and an organic light-emitting device including the same.

Additional aspects will be set forth in part in the description which follows and, in part, will be apparent from the description, or may be learned by practice of the presented embodiments.

According to one or more embodiments, provided is a heterocyclic compound represented by Formula 1:

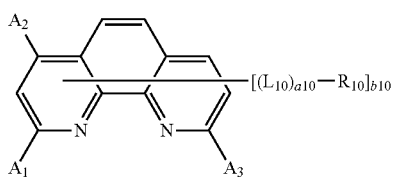

Formula 1

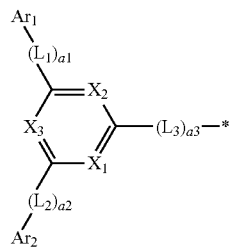

Formula 2

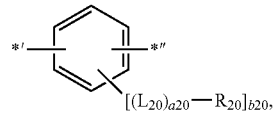

Formula 3 wherein, in Formulae 1 to 3, $A_1$ to $A_3$ may each independently be selected from a group represented by Formula 2, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$($Q_1$), and —P(=O)($Q_1$)($Q_2$), at least one of $A_1$ to $A_3$ is a group represented by Formula 2, $X_1$ may be N or C($R_{31}$), $X_2$ may be N or C($R_{32}$), $X_3$ may be N or C($R_{33}$), at least one of $X_1$ to $X_3$ is N, $L_1$, $L_2$, $L_{10}$, and $L_{20}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1, a2, a10, and a20 may each independently be an integer selected from 0 to 5, $L_3$ may be a group represented by Formula 3, a3 may be an integer selected from 0 to 5, $Ar_1$ and $Ar_2$ may each independently be selected from deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), $R_{10}$, $R_{20}$, and $R_{31}$ to $R_{33}$ may each independently be selected from hydrogen, deuterium, —F, —Cl, —Br, —I, a hydroxyl group, a cyano group, a nitro group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$($Q_1$), and —P(=O)($Q_1$)($Q_2$), optionally at least two neighboring groups selected from $R_{10}$, $R_{20}$, and $R_{31}$ to $R_{33}$ are linked to one another to form a substituted or unsubstituted $C_5$-$C_{60}$ carbocyclic group or a substituted or unsubstituted $C_1$-$C_{60}$ heterocyclic group, b10 is an integer selected from 1 to 5, b20 is an integer selected from 1 to 4, \*, \*', and \*" are each a binding site to a neighboring atom, at least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, a substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group, and substituted ring may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —P($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —P($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group.

According to one or more embodiments, provided is an organic light-emitting device including: a first electrode; a second electrode facing to the first electrode; an organic layer between the first electrode and the second electrode and including an emission layer; and the above-described at least one heterocyclic compound.

BRIEF DESCRIPTION OF THE DRAWINGS

These and/or other aspects will become apparent and more readily appreciated from the following description of the embodiments, taken in conjunction with the accompanying drawings in which:

FIGS. 1-4 are schematic views respectively illustrating structures of organic light-emitting devices according to embodiments of the present disclosure.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure."

Reference will now be made in more detail to embodiments, examples of which are illustrated in the accompanying drawings. Effects, features, and a method of achieving the present disclosure should become obvious by referring to example embodiments of the present disclosure with reference to the attached drawings. The present disclosure may, however, be embodied in many different forms and should not be construed as being limited to the embodiments set forth herein.

Hereinafter, example embodiments of the present disclosure will be described in more detail with reference to the attached drawings. In the following description and drawings, constituent elements which are substantially the same, or correspond constituent elements are assigned the same or like reference numerals, and overlapping descriptions thereof will not be provided.

As used herein, the singular forms "a", "an" and "the" are intended to include the plural forms as well, unless the context clearly indicates otherwise.

As used herein, the terms "comprises," "comprising," "includes," "including," "have," and "having" are intended to indicate the presence of features, elements, and/or components stated in the specification, but not to preclude the presence or addition of one or more other features, elements, and/or components.

In the following embodiments, when an element such as a layer, a film, a region or a component is referred to as being "on" another layer or region, it can be "directly on" the other layer or region (without any intervening films, regions, or components therebetween), or intervening films, regions, or components may also be present.

In the drawings, for convenience of explanation, the size of components or elements may be exaggerated or reduced. In other words, because the size and thickness of components in the drawings are arbitrarily illustrated for convenience of explanation, the present concept is not limited to the following embodiments.

According to an embodiment of the present disclosure, provided is a heterocyclic compound represented by Formula 1.

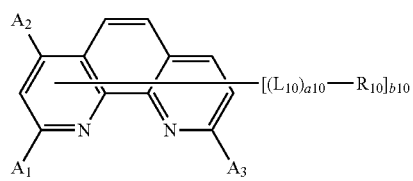

Formula 1

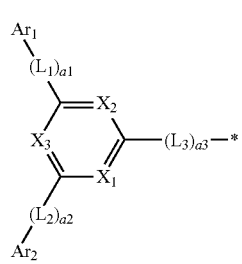

Formula 2

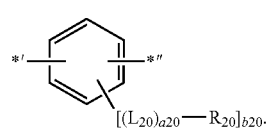

Formula 3

In Formula 1, $A_1$ to $A_3$ may each independently be selected from a group represented by Formula 2, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$($Q_1$), and —P(=O)($Q_1$)($Q_2$), and at least one of $A_1$ to $A_3$ may be a group represented by Formula 2, In one or more embodiments, one of $A_1$ to $A_3$ may be a group represented by Formula 2, and the others may each independently be selected from a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one or more embodiments, one of $A_1$ to $A_3$ may be a group represented by Formula 2, and the others may each independently be selected from:

a methyl group, an ethyl group, a propyl group, an isobutyl group, a sec-butyl group, a ter-butyl group, a pentyl group, an iso-amyl group, and a hexyl group; and a methyl group, an ethyl group, a propyl group, an isobutyl group, a sec-butyl group, a ter-butyl group, a pentyl group, an iso-amyl group, and a hexyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group;

a phenyl group, a naphthyl group, a pyridyl group, a pyrimidyl group, a triazinyl group, a quinolinyl group, an isoquinolinyl group, a biphenyl group, and a terphenyl group; and a phenyl group, a naphthyl group, a pyridyl group, a pyrimidyl group, a triazinyl group, a quinolinyl group, an isoquinolinyl group, a biphenyl group, and a terphenyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group.

In Formula 2, $X_1$ may be N or $C(R_{31})$, $X_2$ may be N or $C(R_{32})$, $X_3$ may be N or $C(R_{33})$, and at least one of $X_1$ to $X_3$ may be N.

In one or more embodiments, one of $X_1$ to $X_3$ may be N.

In one or more embodiments, two of $X_1$ to $X_3$ may be N.

In one or more embodiments, $X_1$ to $X_3$ may each be N.

In Formulae 1 to 3, $L_1$, $L_2$, $L_{10}$ and $L_{20}$ may each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, In one or more embodiments, $L_1$, $L_2$, $L_{10}$ and $L_{20}$ may each independently be selected from a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a spiro-fluorene-benzofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a spiro-fluorene-benzofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a phenyl group substituted with a $C_1$-$C_{10}$ alkyl group, a biphenyl group, a terphenyl group, a naphthyl group, a pyridinyl group, a pyrimidyl group, a quinolinyl group, and an isoquinolinyl group.

In one or more embodiments, $L_1$, $L_2$, $L_{10}$ and $L_{20}$ may each independently be a group represented by one of Formulae 3-1 to 3-99.

3-1
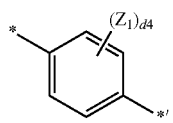

3-2
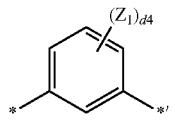

3-3
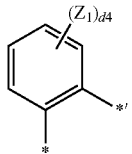

3-4
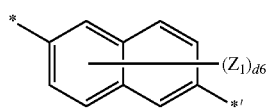

3-5
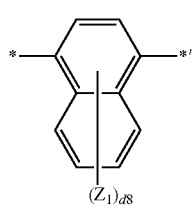

3-6
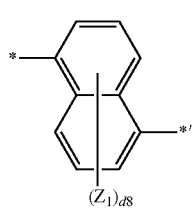

3-7
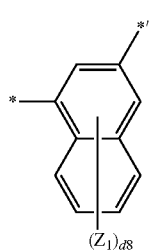

3-8
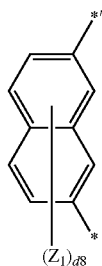

3-9
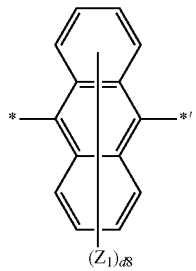

3-10
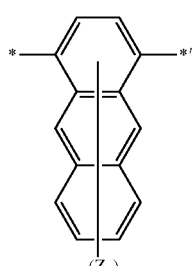

3-11
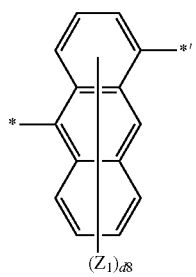

3-12
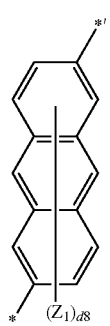

3-13
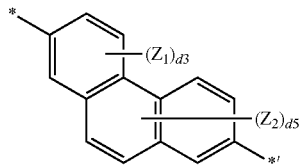

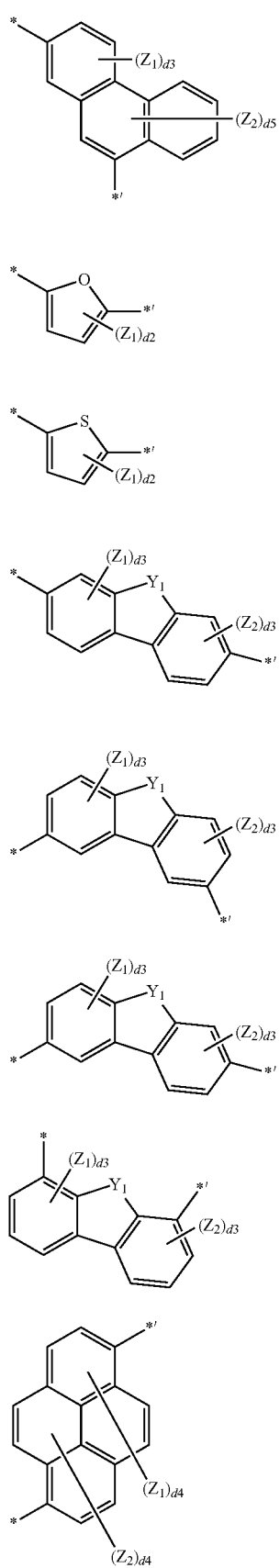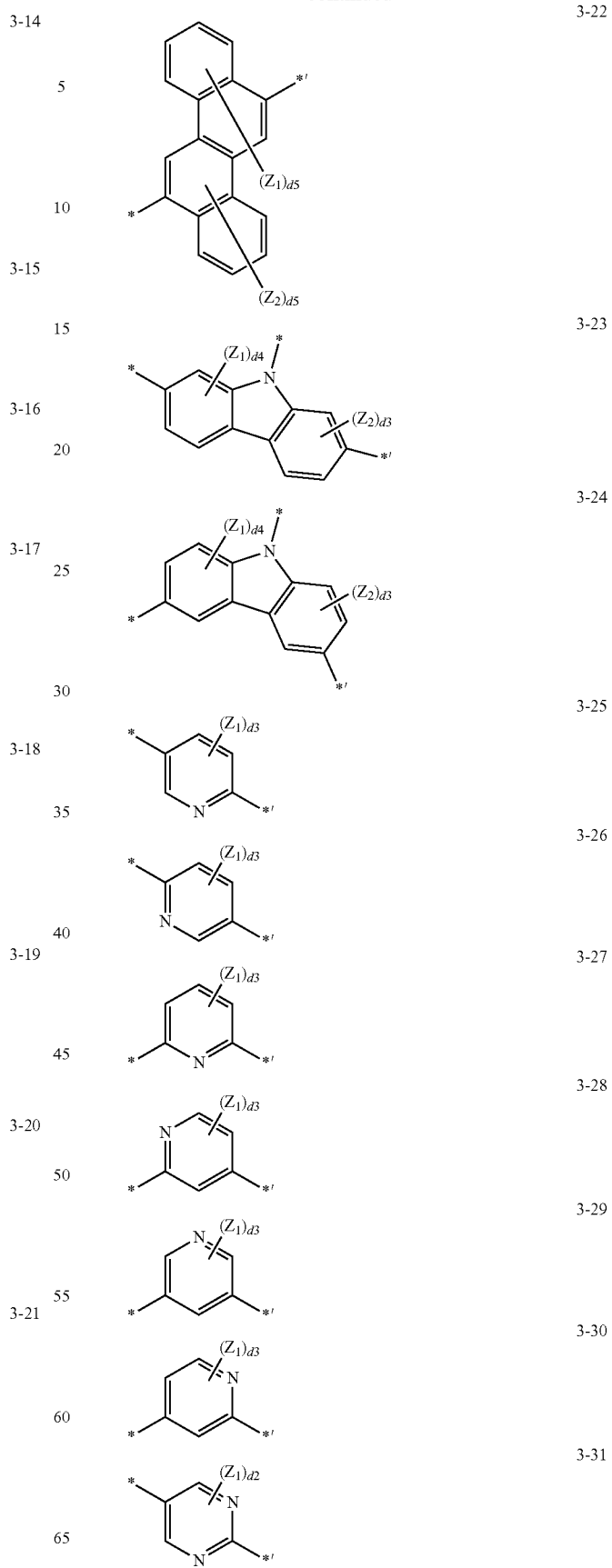

3-32 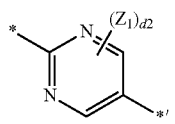
3-33 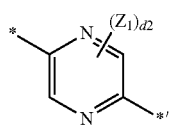
3-34 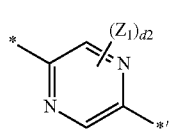
3-35 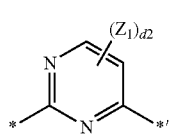
3-36 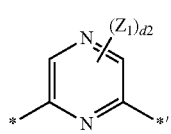
3-37 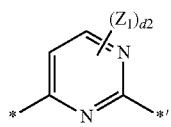
3-38 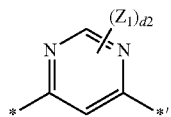
3-39 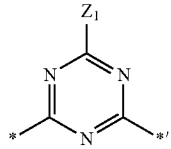
3-40 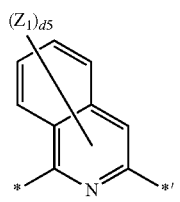
3-41 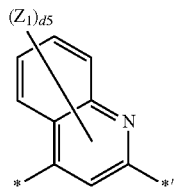
3-42 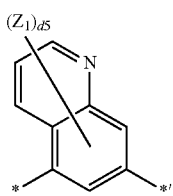
3-43 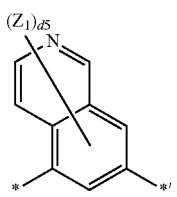
3-44 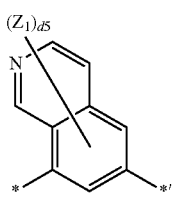
3-45 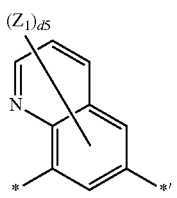
3-46 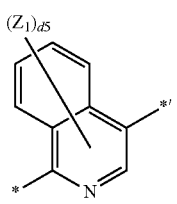
3-47 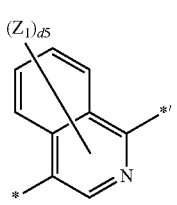
3-48 
3-49 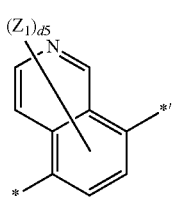

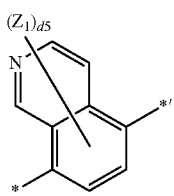
3-50
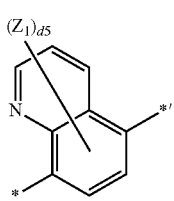
3-51
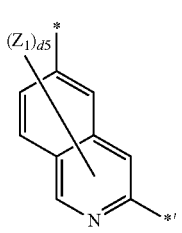
3-52
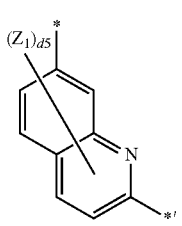
3-53
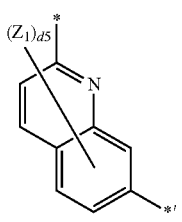
3-54
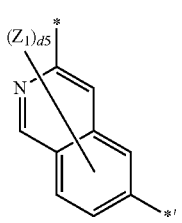
3-55
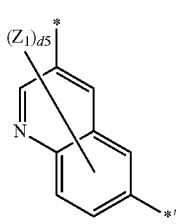
3-56
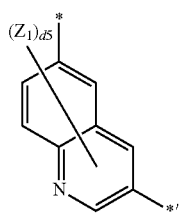
3-57
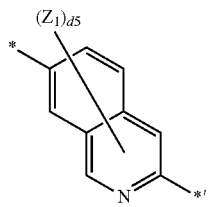
3-58
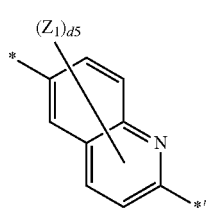
3-59
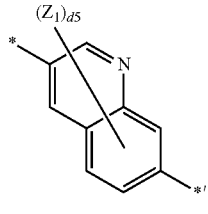
3-60
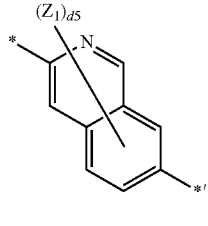
3-61
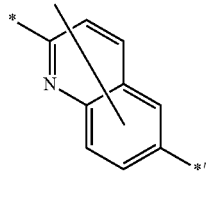
3-62
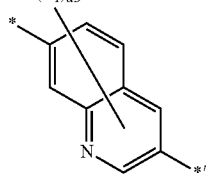
3-63

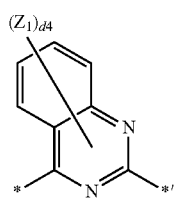
3-64
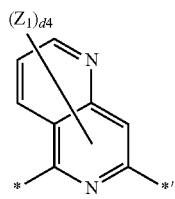
3-65
3-66
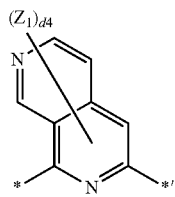
3-67
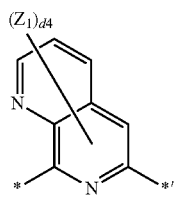
3-68
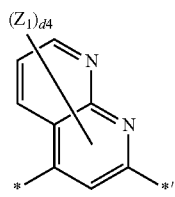
3-69
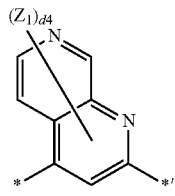
3-70
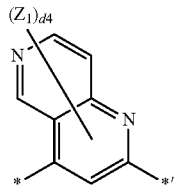
3-71
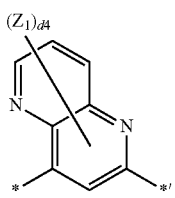
3-72
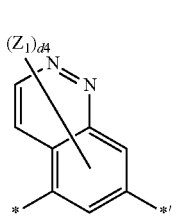
3-73
3-74
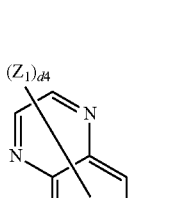
3-75
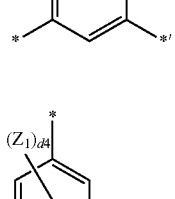
3-76
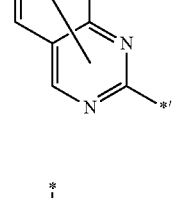
3-77
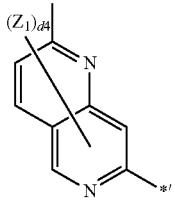
3-78
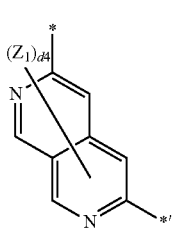

3-79 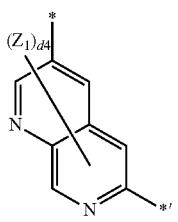
3-80 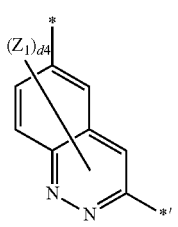
3-81 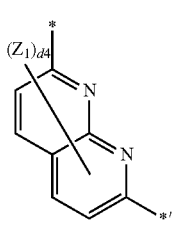
3-82 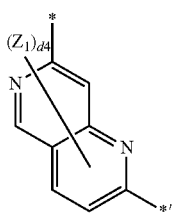
3-83 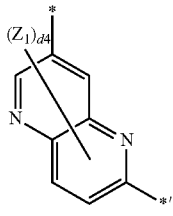
3-84 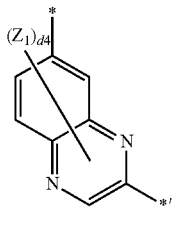
3-85 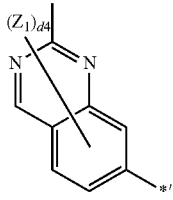
3-86 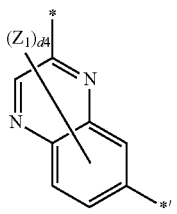
3-87 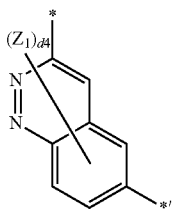
3-88 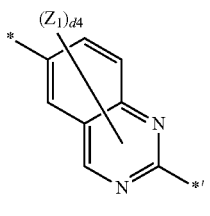
3-89 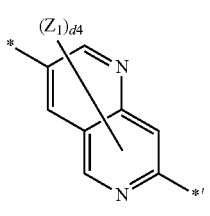
3-90 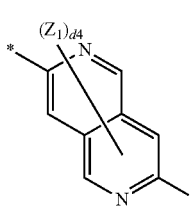
3-91 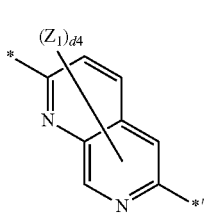
3-92 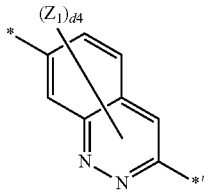

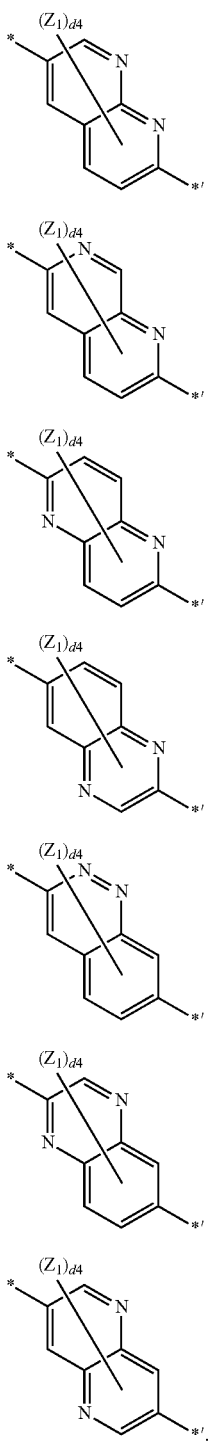

In Formulae 3-1 to 3-99, $Y_1$ may be O, S, $C(Z_3)(Z_4)$, $N(Z_5)$, or $Si(Z_6)(Z_7)$, $Z_1$ to $Z_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, $Q_{31}$ to $Q_{33}$ may each independently be selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, d2 may be an integer selected from 0 to 2, d3 may be an integer selected from 0 to 3, d4 may be an integer selected from 0 to 4, d5 may be an integer selected from 0 to 5, d6 may be an integer selected from 0 to 6, d8 may be an integer selected from 0 to 8, and

* and *' may each be a binding site to a neighboring atom.

In Formulae 1 to 3, a1, a2, a10, and a20 may each independently be an integer selected from 0 to 5.

In Formula 2, $L_3$ may be a group represented by Formula 3.

In one or more embodiments, $L_3$ may be a group represented by one of

Formulae 4-1 to 4-3.

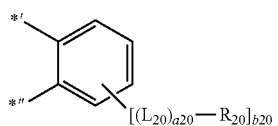

4-1

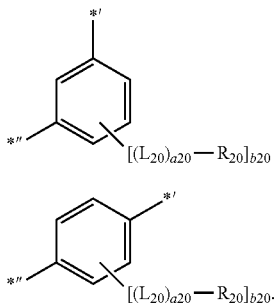

4-2

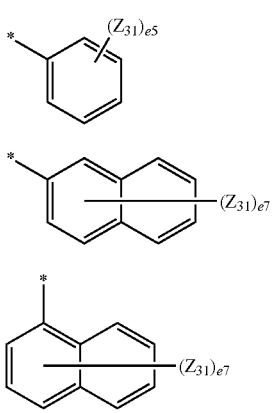

4-3

In Formulae 4-1 to 4-3,
$L_{20}$, a20, $R_{20}$, and b20 may be as defined herein in the specification, and
*' and *''' may each be a binding site to a neighboring atom.

In Formula 2, a3 may be an integer selected from 0 to 5.

In Formula 2, $Ar_1$ and $Ar_2$ may each independently be selected from deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$).

In one or more embodiments, $Ar_1$ and $Ar_2$ may each independently be selected from deuterium, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_1$-$C_{60}$ heteroaryl group.

In one or more embodiments, $Ar_1$ and $Ar_2$ may each independently be selected from deuterium, and a group represented by one selected from Formulae 5-1 to 5-26 and Formulae 6-1 to 6-55:

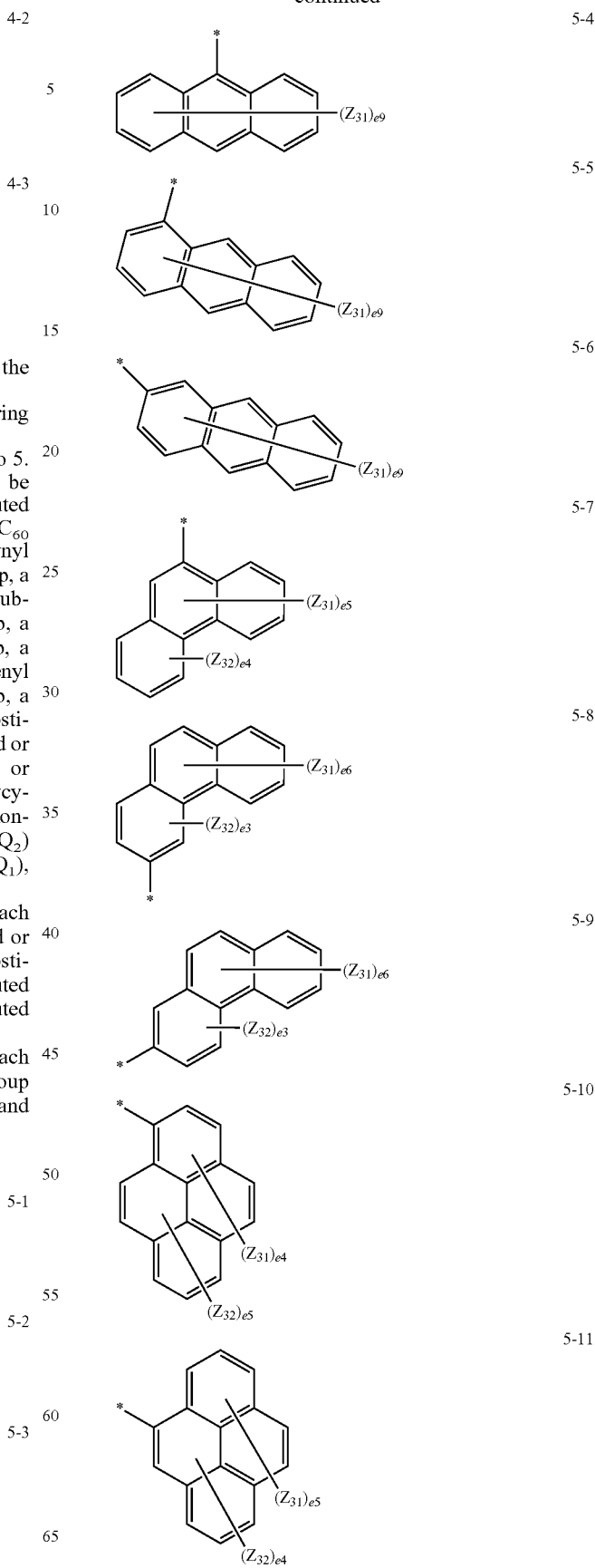

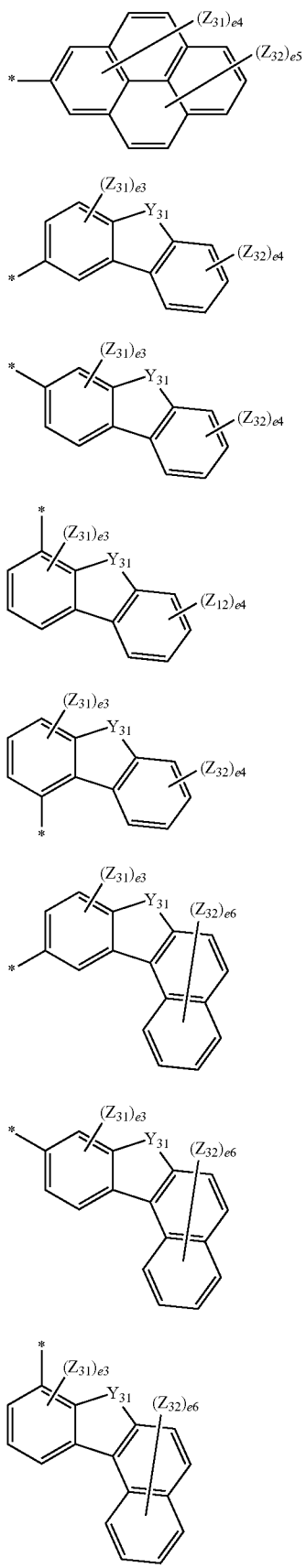
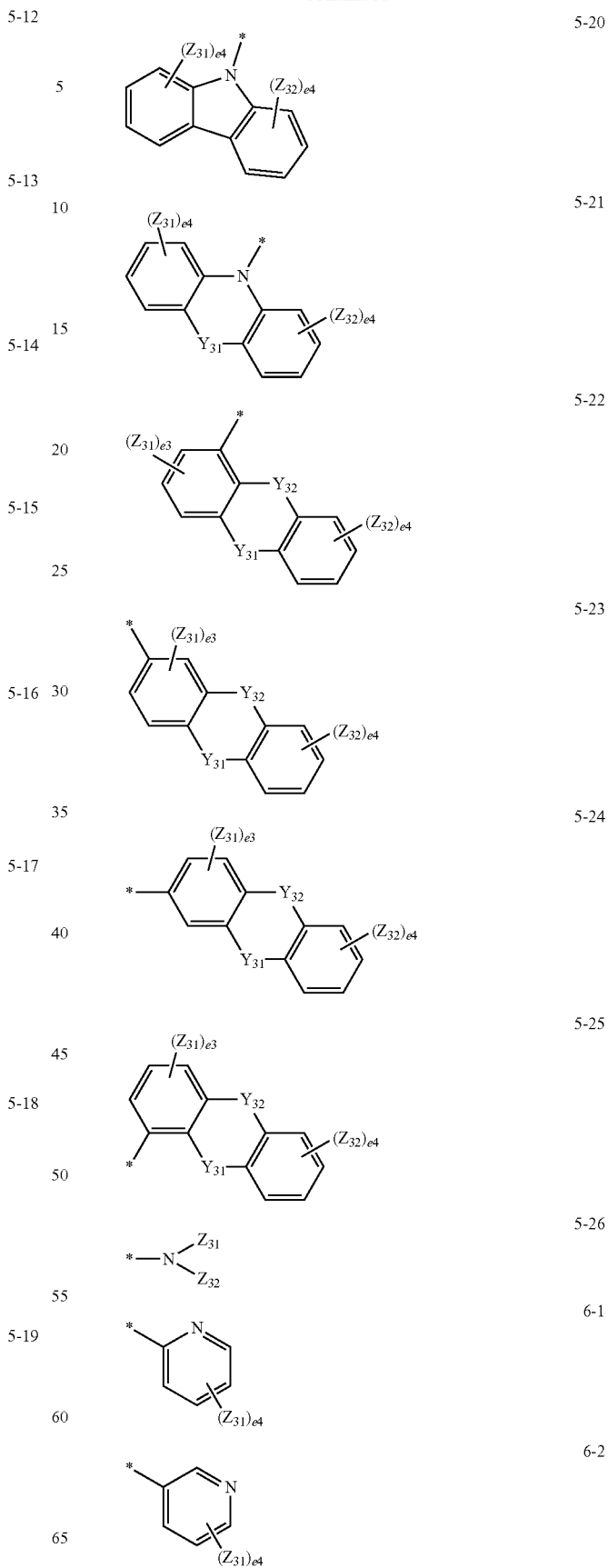

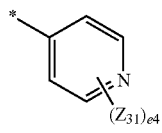 6-3
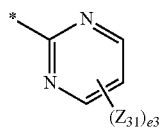 6-4
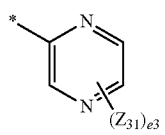 6-5
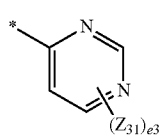 6-6
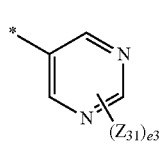 6-7
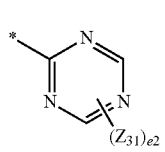 6-8
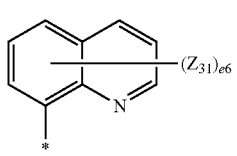 6-9
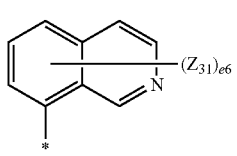 6-10
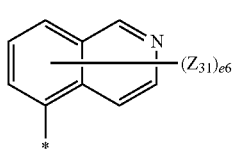 6-11
 6-12
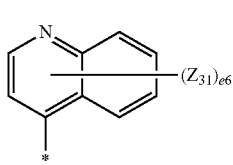 6-13
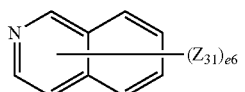 6-14
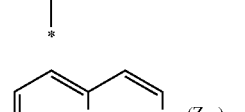 6-15
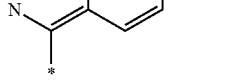 6-16
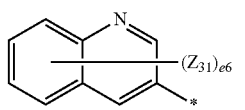 6-17
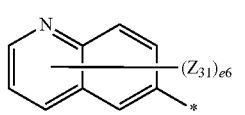 6-18
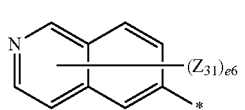 6-19
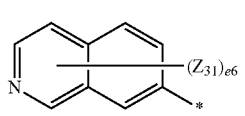 6-20
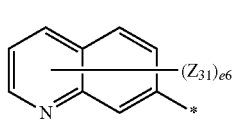 6-21
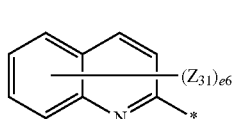 6-22
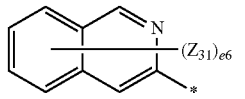 6-23
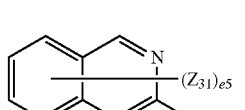 6-24
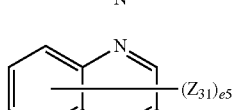 6-25
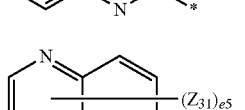 6-26
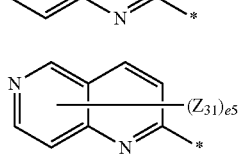

6-27
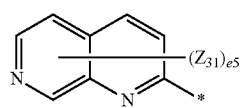
6-28
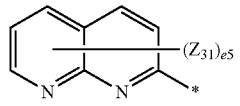
6-29
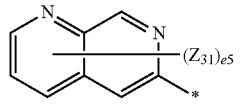
6-30
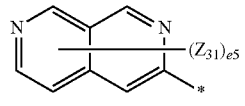
6-31
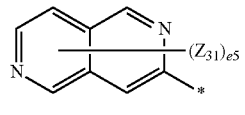
6-32
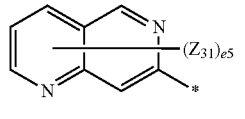
6-33
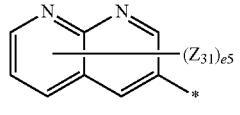
6-34
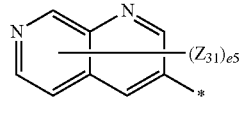
6-35
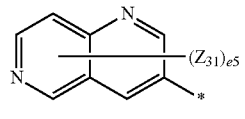
6-36
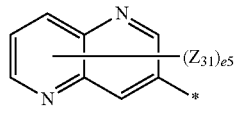
6-37
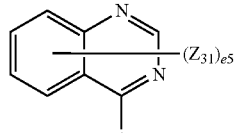
6-38
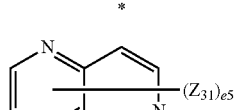
6-39

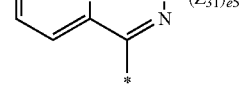
6-40
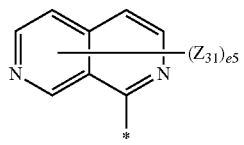
6-41

6-42
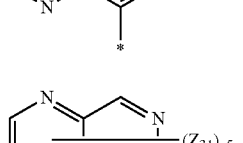
6-43
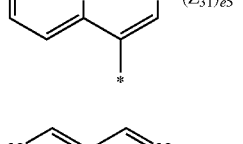
6-44
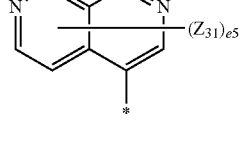
6-45
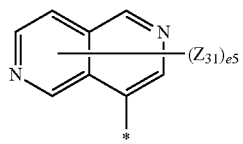
6-46
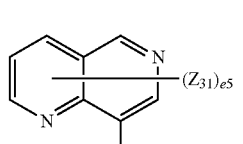
6-47
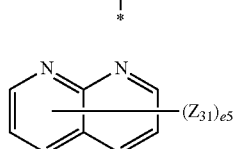
6-48
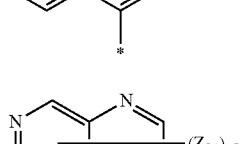
6-49
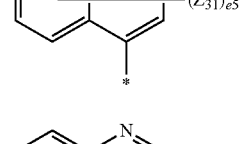
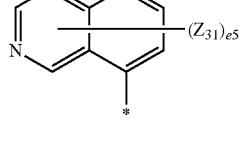
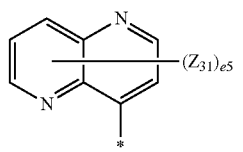

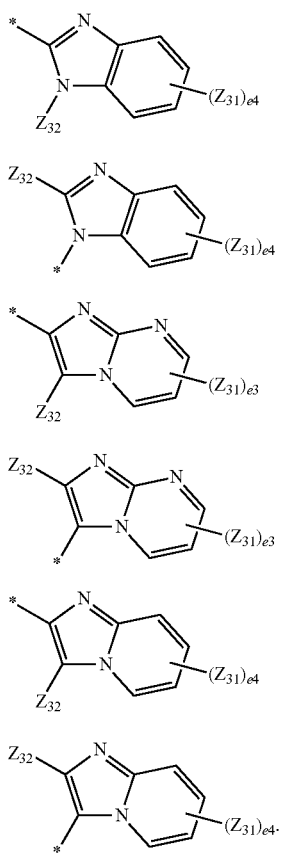

In Formulae 5-1 to 5-26 and Formulae 6-1 to 6-55, $Y_{31}$ and $Y_{32}$ may each independently be O, S, $C(Z_{33})(Z_{34})$, $N(Z_{33})$, or $Si(Z_{33})(Z_{34})$, $Z_{31}$ to $Z_{34}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkenyl group, a $C_1$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a phenanthrenyl group, an anthracenyl group, a triperylenyl group, a pyridinyl group, a pyrimidinyl group, a carbazolyl group, and a triazinyl group, e2 may be 1 or 2,
e3 may be an integer selected from 1 to 3,
e4 may be an integer selected from 1 to 4,
e5 may be an integer selected from 1 to 5,
e6 may be an integer selected from 1 to 6,
e7 may be an integer selected from 1 to 7,
e9 may be an integer selected from 1 to 9, and
* may be a binding site to a neighboring atom.

In one or more embodiments, $Ar_1$ and $Ar_2$ may each independently be selected from:

a phenyl group, a naphthyl group, a pyridyl group, a pyrimidyl group, a triazinyl group, a quinolinyl group, an isoquinolinyl group, a biphenyl group, and a terphenyl group; and a phenyl group, a naphthyl group, a pyridyl group, a pyrimidyl group, a triazinyl group, a quinolinyl group, an isoquinolinyl group, a biphenyl group, and a terphenyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group.

In Formulae 1 to 3, $R_{10}$, $R_{20}$, and $R_{31}$ to $R_{33}$ may each independently be selected from hydrogen, deuterium, —F, —Cl, —Br, —I, a hydroxyl group, a cyano group, a nitro group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$P(Q_1)(Q_2)$, —$C(=O)(Q_1)$, —$S(=O)_2(Q_1)$, and —$P(=O)(Q_1)(Q_2)$, where $Q_1$ to $Q_3$ are as defined herein.

In one or more embodiments, $R_{10}$, $R_{20}$, and $R_{31}$ to $R_{33}$ may each independently be selected from:

hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$); and —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and $Q_1$ to $Q_3$, and $Q_{31}$ to $Q_{33}$ are each independently selected from:

a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group.

In one or more embodiments, $R_{10}$ and $R_{20}$ may each independently be selected from:

a methyl group, an ethyl group, a propyl group, an isobutyl group, a sec-butyl group, a tert-butyl group, a pentyl group, an iso-amyl group, and a hexyl group; and a methyl group, an ethyl group, a propyl group, an isobutyl group, a sec-butyl group, a tert-butyl group, a pentyl group, an iso-amyl group, and a hexyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group;

a phenyl group, a naphthyl group, a pyridyl group, a pyrimidyl group, a triazinyl group, a quinolinyl group, an isoquinolinyl group, a biphenyl group, and a terphenyl group; and a phenyl group, a naphthyl group, a pyridyl group, a pyrimidyl group, a triazinyl group, a quinolinyl group, an isoquinolinyl group, a biphenyl group, and a terphenyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group.

In Formulae 1 to 3, optionally at least two neighboring groups selected from $R_{10}$, $R_{20}$, and $R_{31}$ to $R_{33}$ may be linked to one another to form a substituted or unsubstituted $C_5$-$C_{60}$ carbocyclic group, or a substituted or unsubstituted $C_1$-$C_{60}$ heterocyclic group, In one or more embodiments, optionally at least two neighboring groups among $R_{10}$, $R_{20}$, and $R_{31}$ to $R_{33}$ may be linked to one another to form a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzimidazole, a benzofuran, a benzothiophene, an isobenzothiophene, a benzoxazole, an isobenzoxazole, a triazole, an oxadiazole, a triazine, a dibenzofuran or a dibenzothiophene; or a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzimidazole, a benzofuran, a benzothiophene, an isobenzothiophene, a benzoxazole, an isobenzoxazole, a triazole, an oxadiazole, a triazine, a dibenzofuran, or a dibenzothiophene, each substituted with at least one selected from deuterium, —F, —Cl, —Br, —I, a cyano group, and a $C_1$-$C_{60}$ alkyl group.

In Formulae 1 to 3, b10 may be an integer selected from 1 to 5.

In Formulae 1 to 3, b20 may bean integer selected from 1 to 4.

In one or more embodiments, a10 may be 0, and $R_{10}$ may be hydrogen. For example, -[($L_{10}$)$_{a10}$-$R_{10}$]$_{b10}$ may represent hydrogen.

In one or more embodiments, a20 may be 0, and $R_{20}$ may be hydrogen. For example, -[($L_{20}$)$_{a20}$-$R_{20}$]$_{b20}$ may represent hydrogen.

In one or more embodiments, a10 and a20 may each be 0, and $R_{10}$ and $R_{20}$ may each be hydrogen. For example, -[($L_{10}$)$_{a10}$-$R_{10}$]$_{b10}$ and -[($L_{20}$)$_{a20}$-$R_{20}$]$_{b20}$ may each represent hydrogen.

In Formulae 1 to 3, *, *' and *" may each be a binding site to a neighboring atom.

At least one of the substituents of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group; and substituted ring is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —P($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —P($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In one or more embodiments, the heterocyclic compound may be a compound represented by one of Formulae 11-1 to 11-3.

Formula 11-1
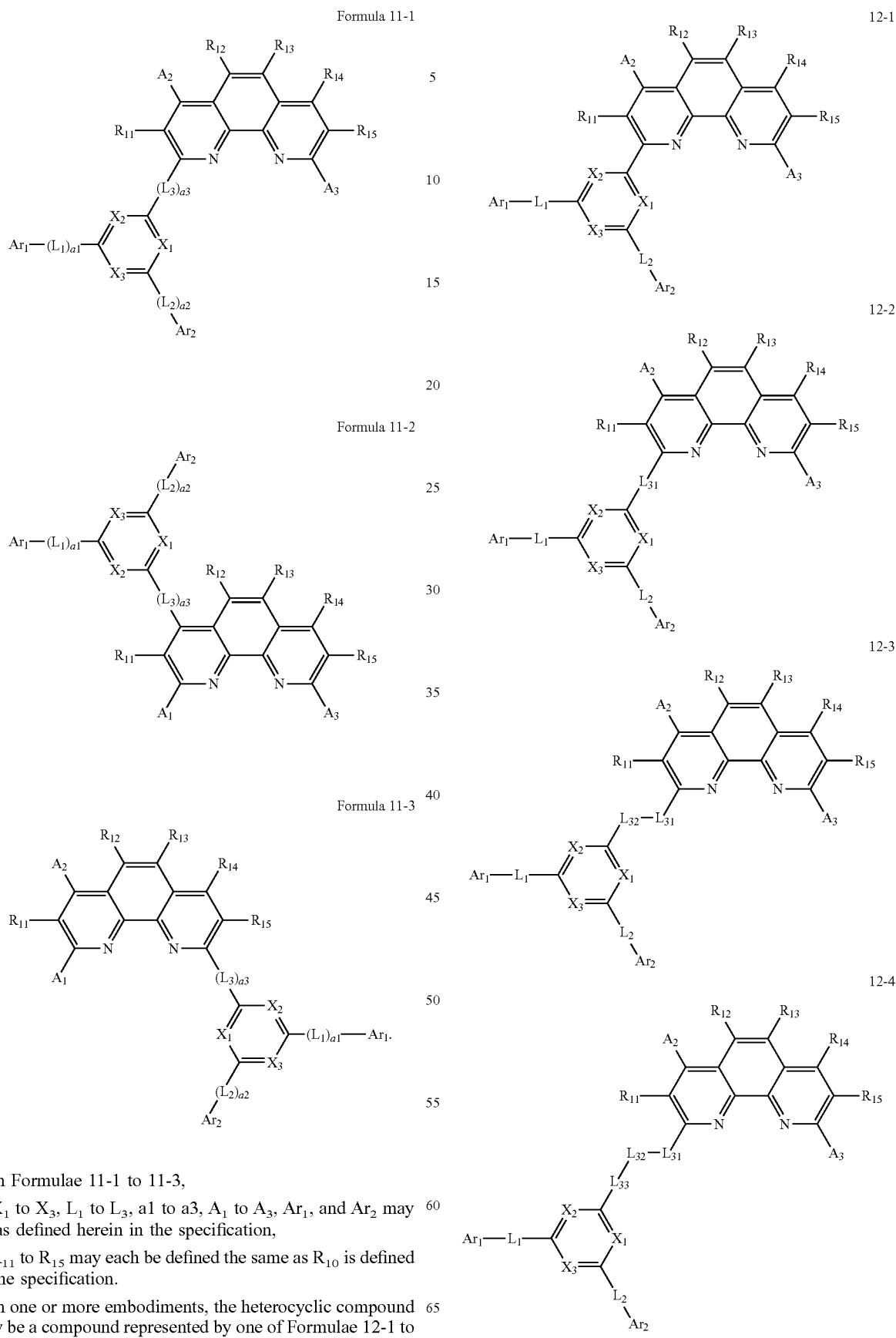
Formula 11-2
Formula 11-3
In Formulae 11-1 to 11-3,
$X_1$ to $X_3$, $L_1$ to $L_3$, a1 to a3, $A_1$ to $A_3$, $Ar_1$, and $Ar_2$ may be as defined herein in the specification,
$R_{11}$ to $R_{15}$ may each be defined the same as $R_{10}$ is defined in the specification.
In one or more embodiments, the heterocyclic compound may be a compound represented by one of Formulae 12-1 to 12-12.

12-5
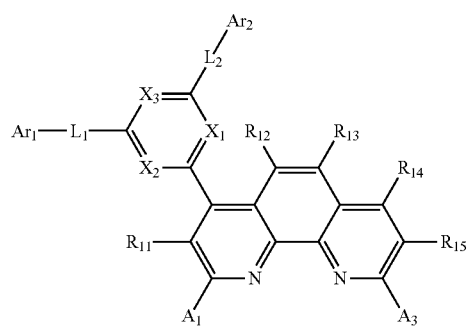
12-6
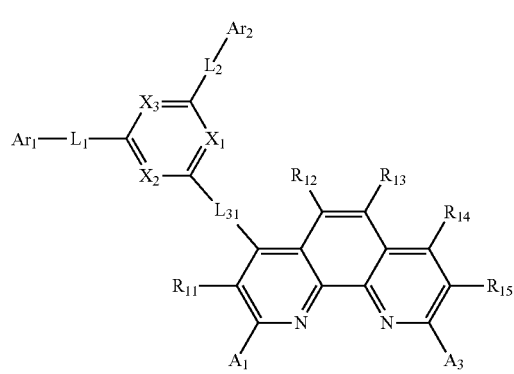
12-7
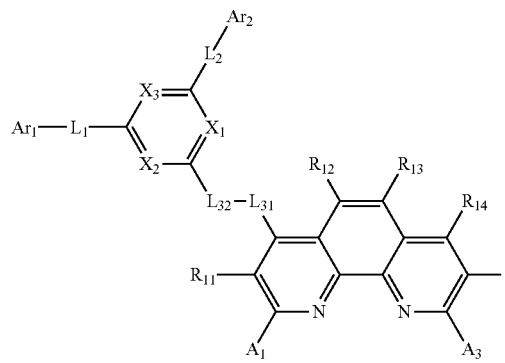
12-8
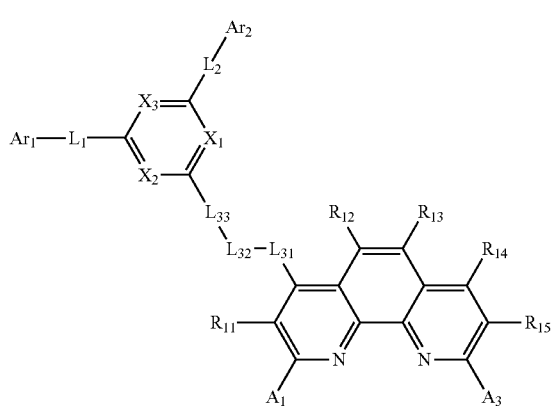
12-9
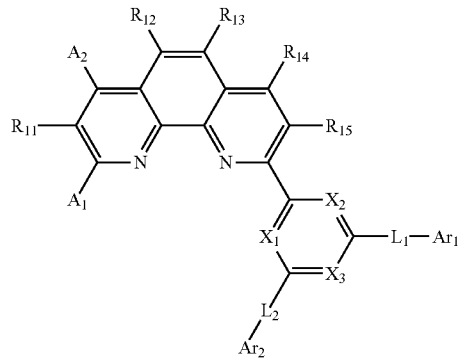
12-10
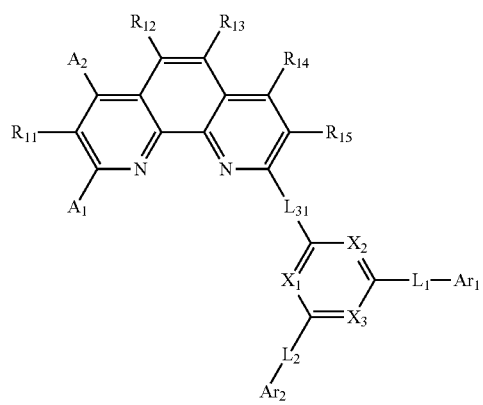
12-11
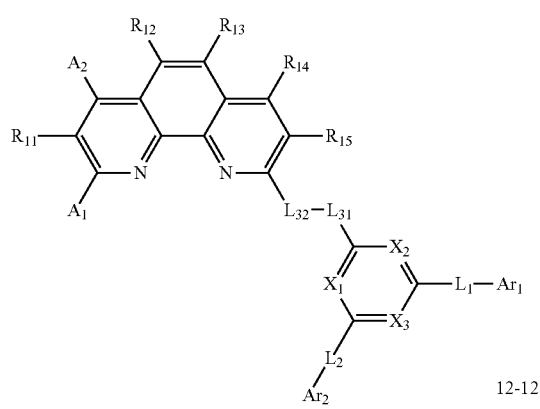
12-12
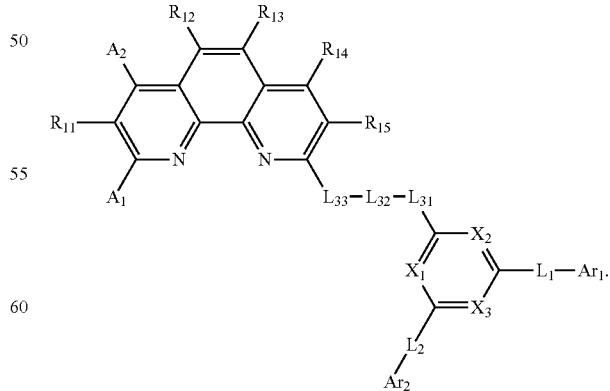
In Formulae 12-1 to 12-12,
$X_1$ to $X_3$, $L_1$, $L_2$, $A_1$ to $A_3$, $Ar_1$, and $Ar_2$ may be as defined herein in the specification $L_{31}$ to $L_{33}$ may each be defined the same as $L_3$ herein in the specification,
$R_{11}$ to $R_{15}$ may each be defined the same as $R_{10}$ herein in the specification.
In one or more embodiments, the heterocyclic compound may be selected from Compounds 1 to 1272 as follows.
1
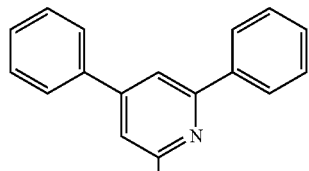
2
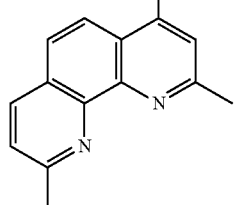
3
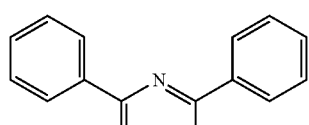
4
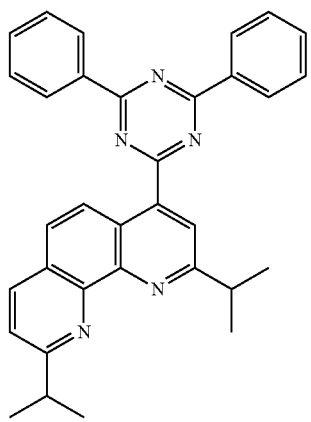
5
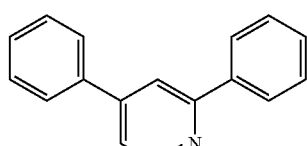
6
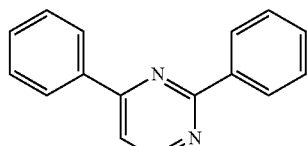

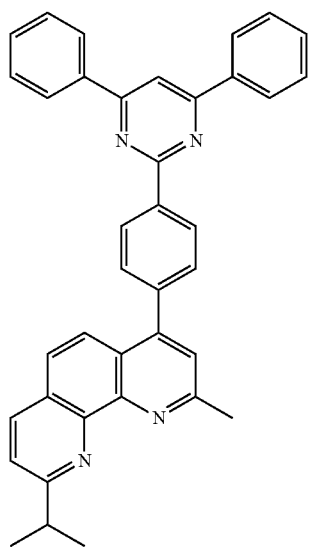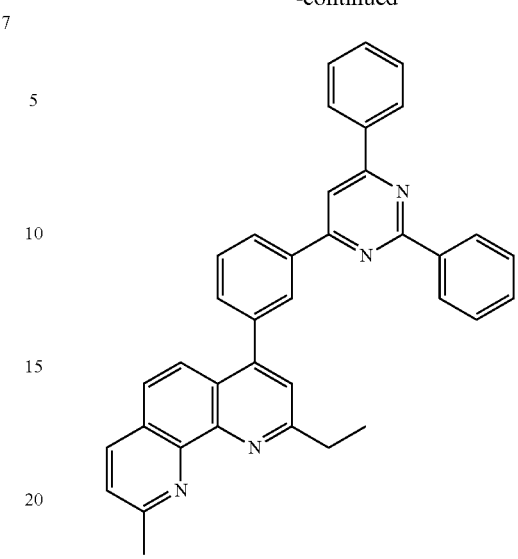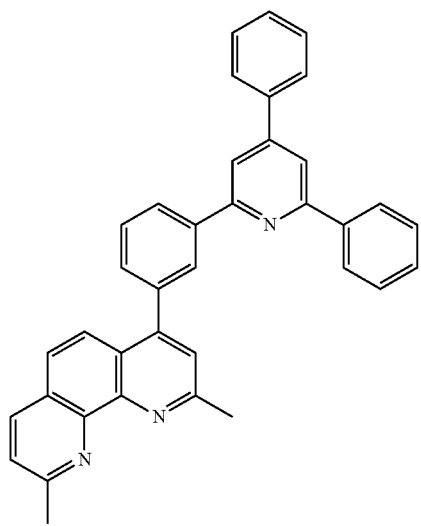

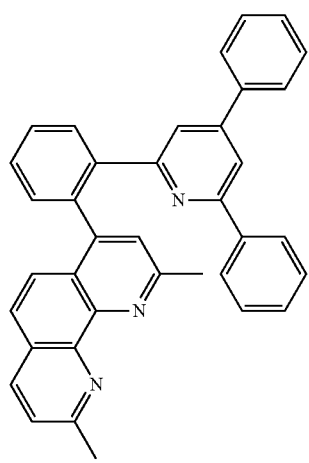
13
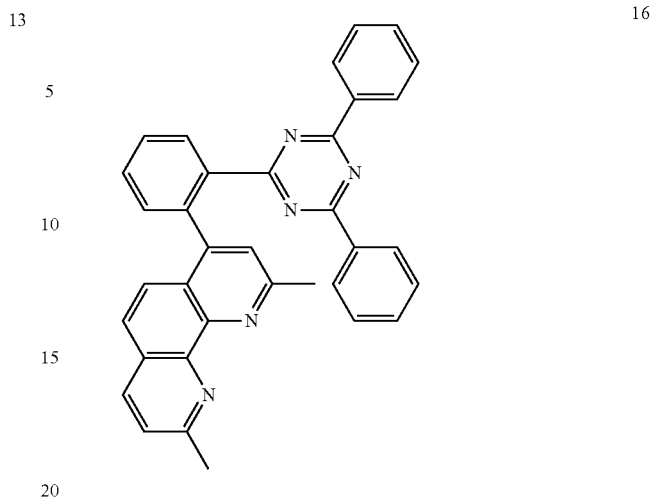
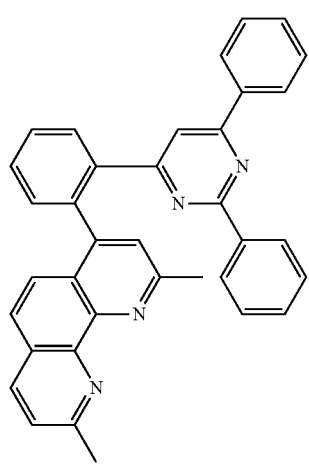
14
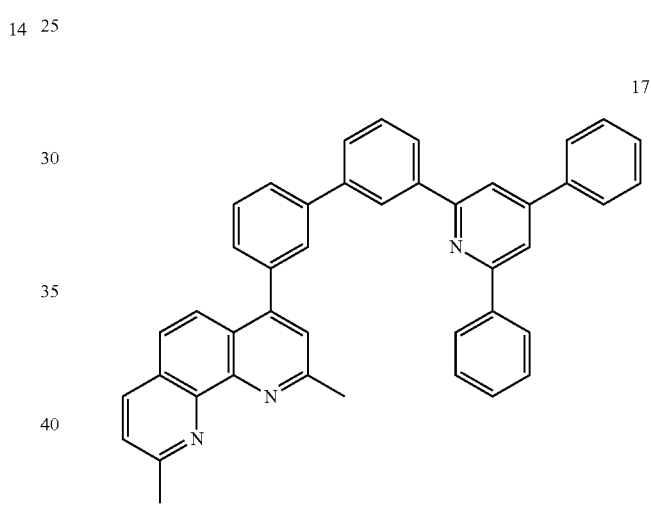
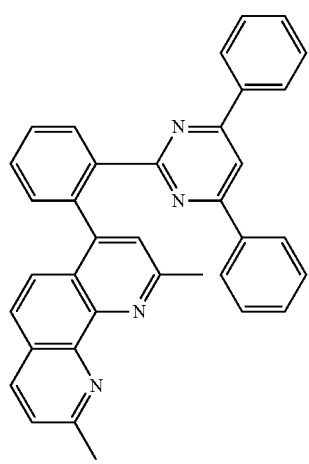
15
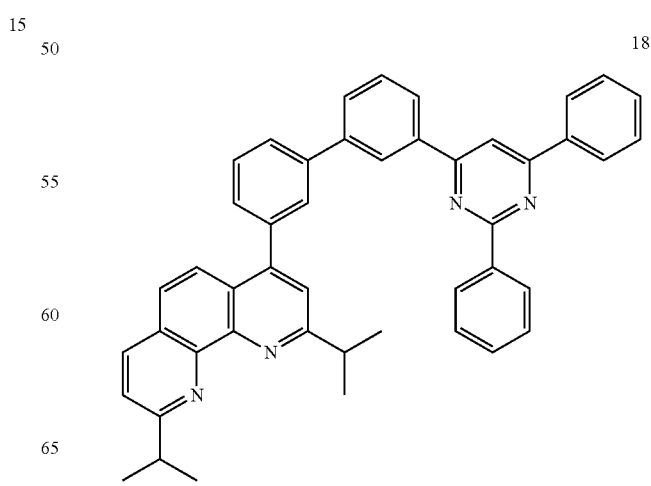

-continued
19
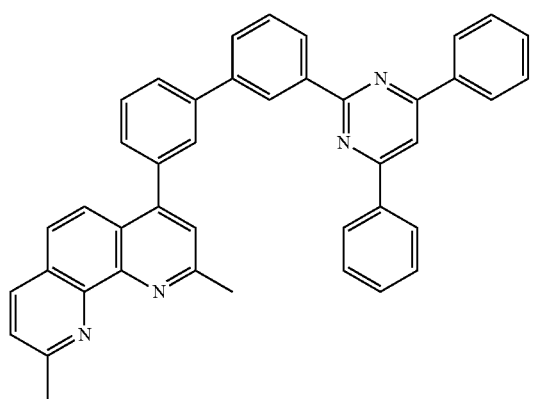
20
22
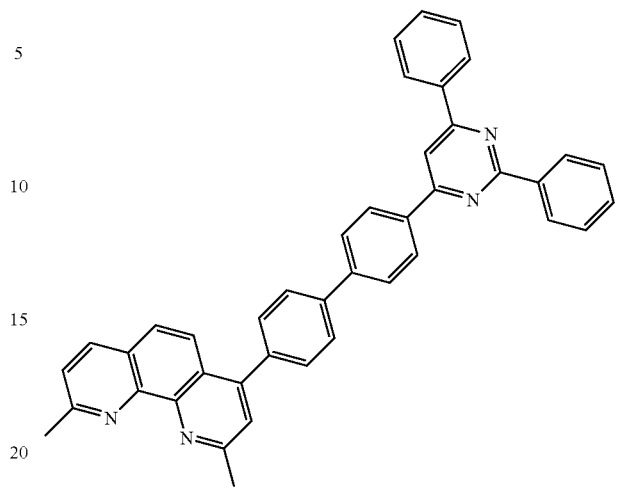
23
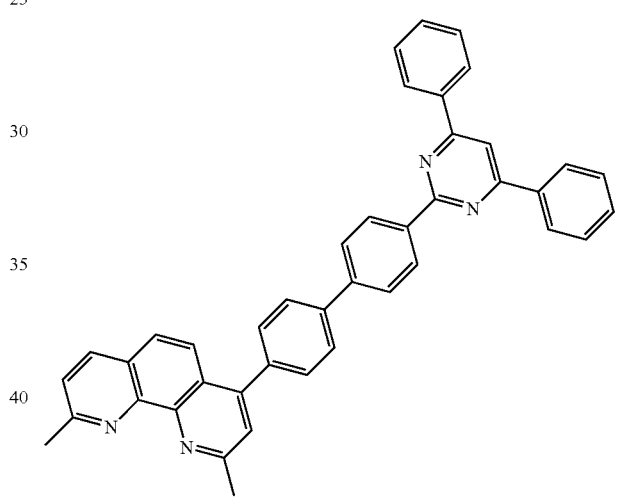
21
24
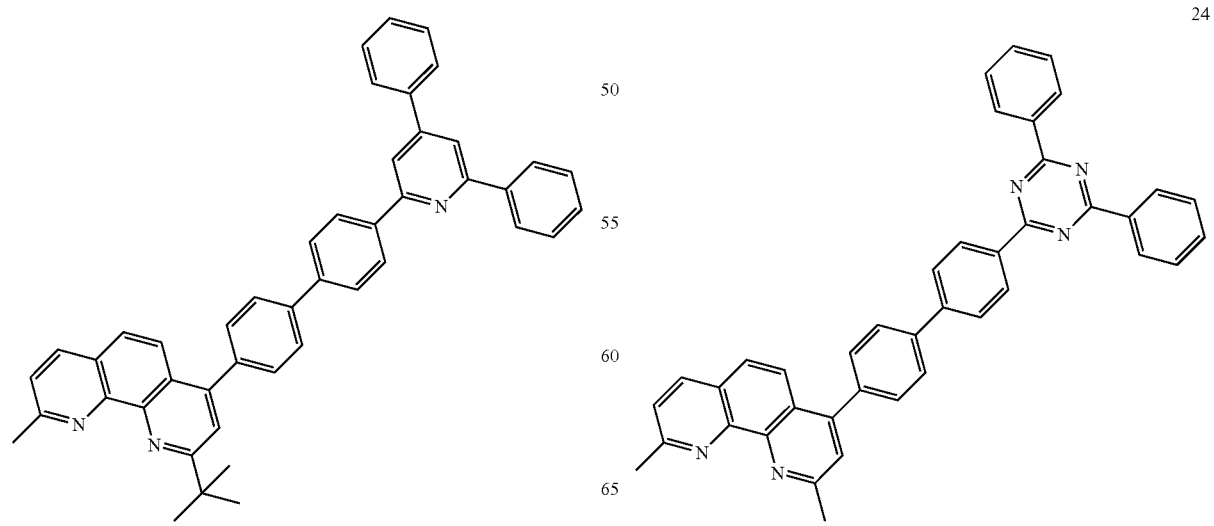

25
-continued
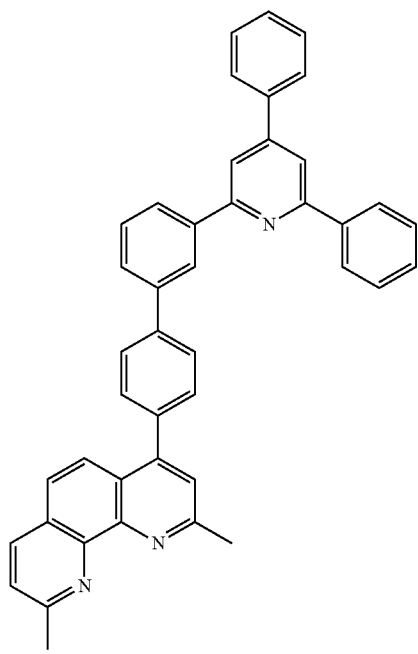
27
-continued
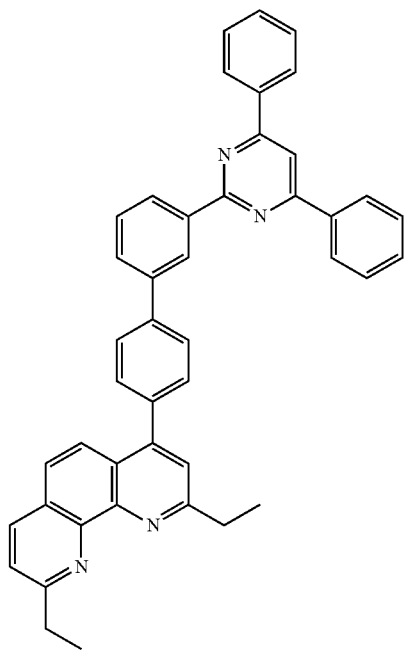
26
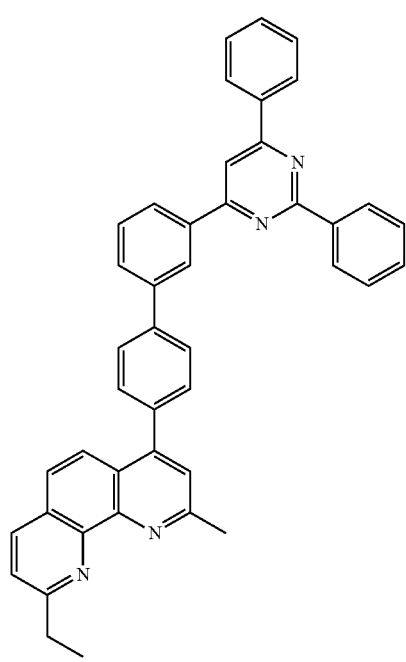
28
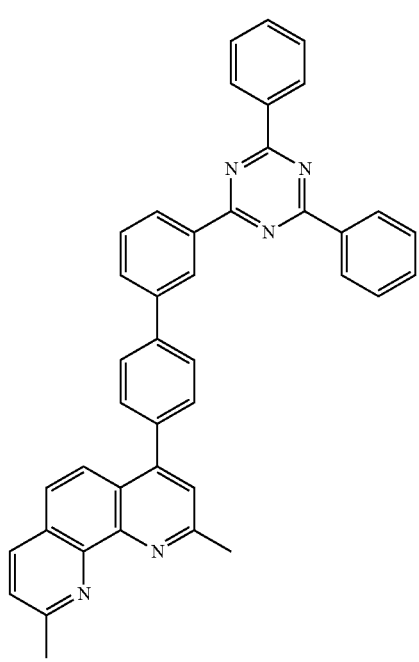

29
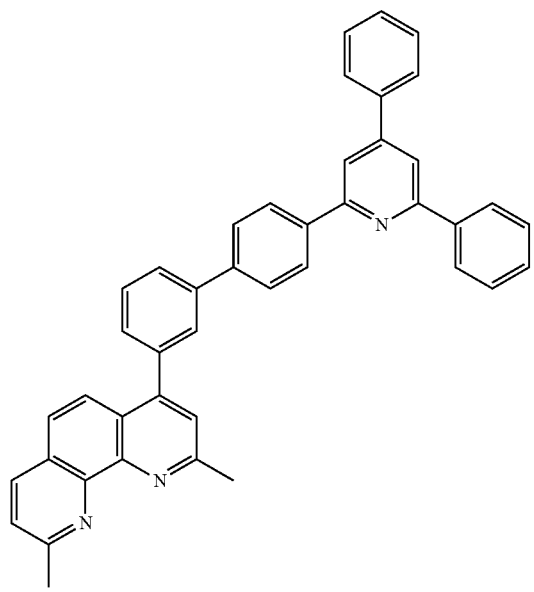
30
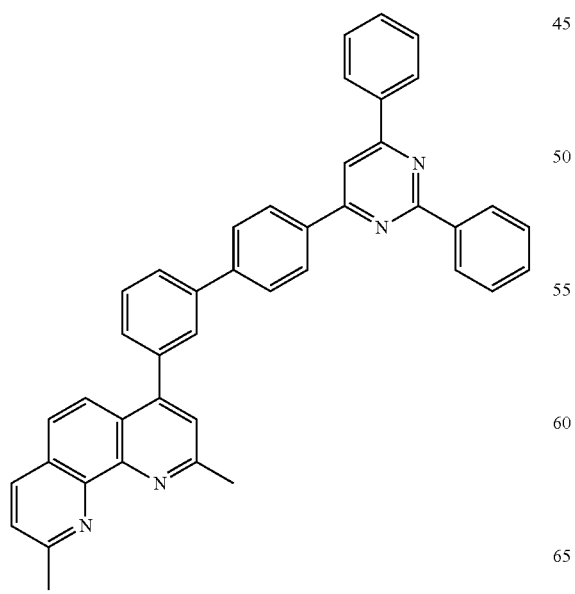
31
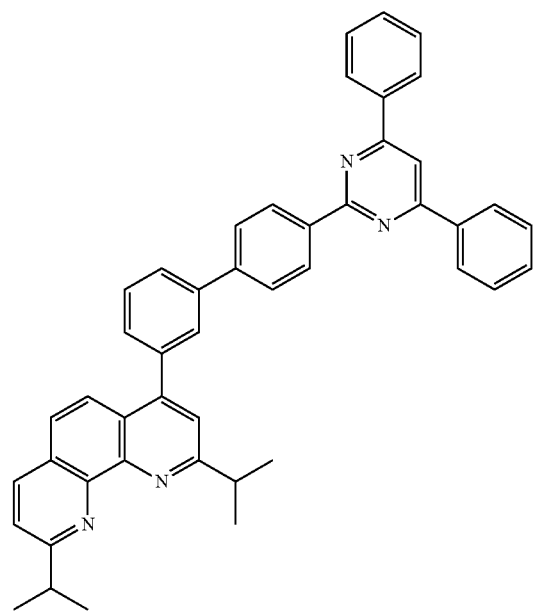
32
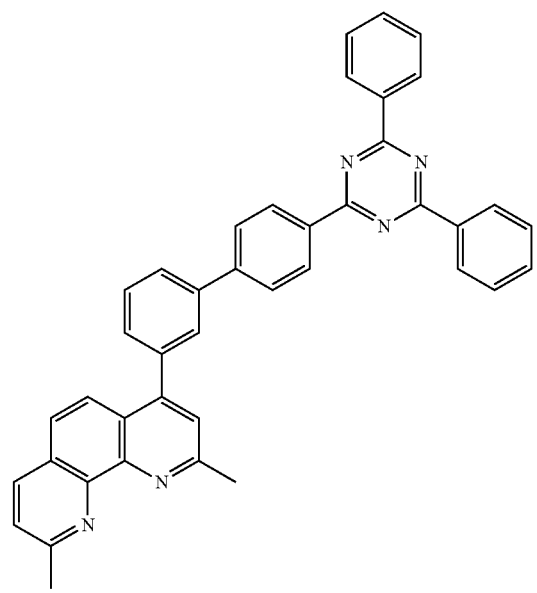

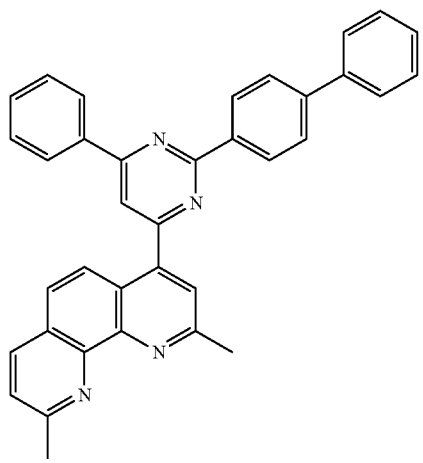
33
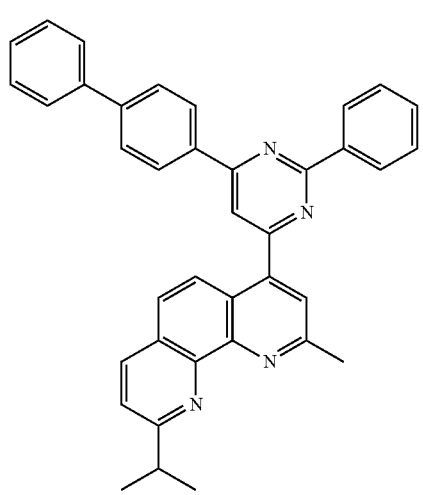
34
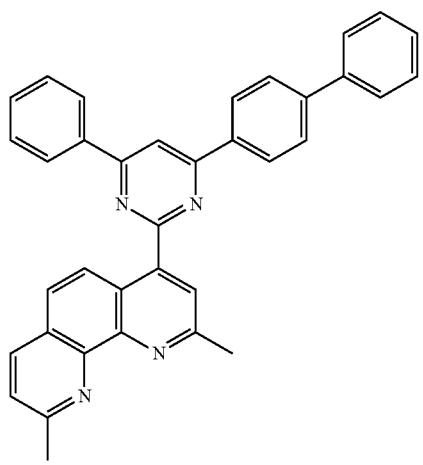
35
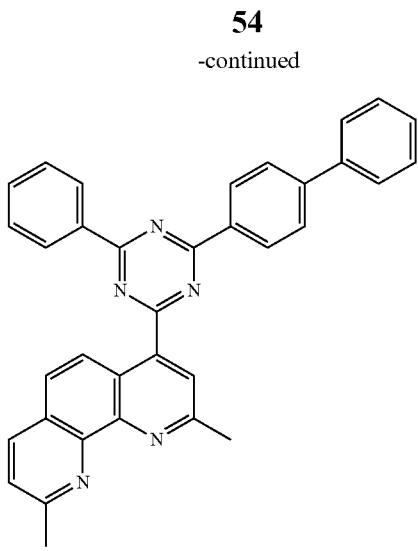
36
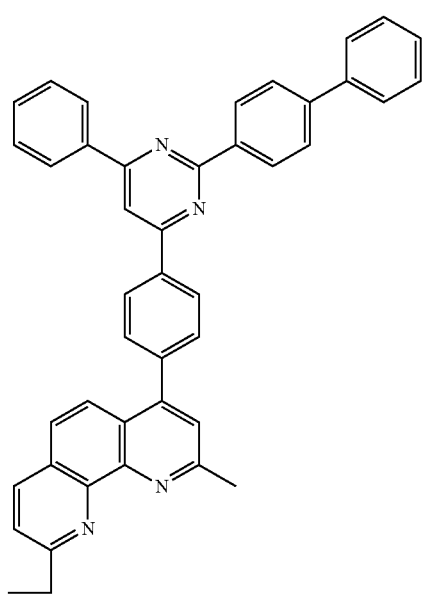
37
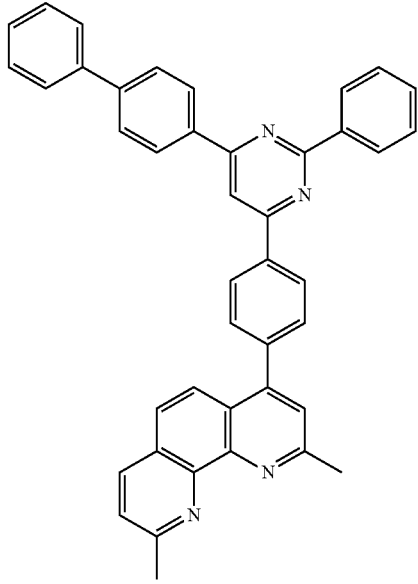
38

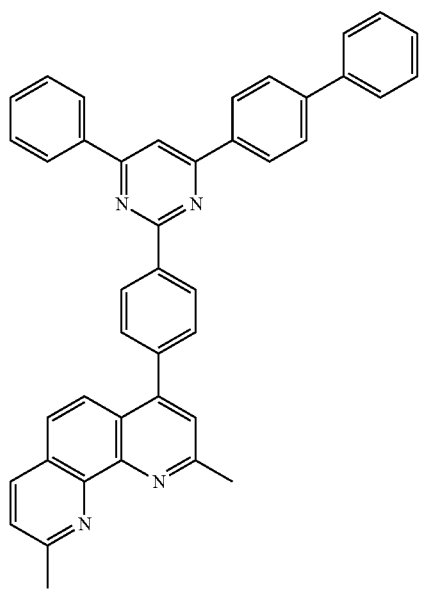
39
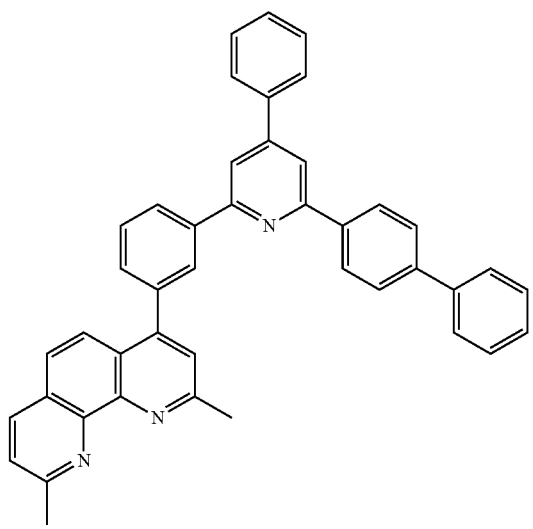
41
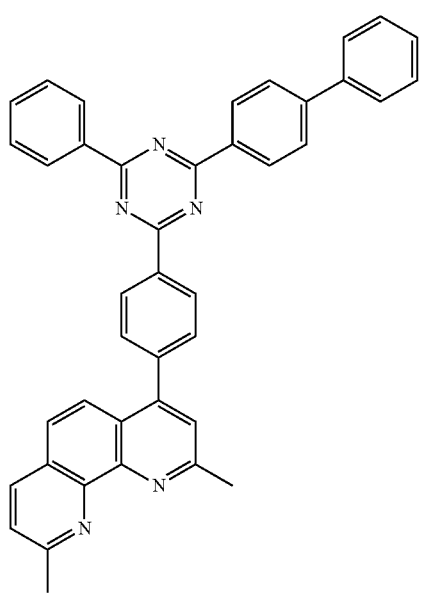
40
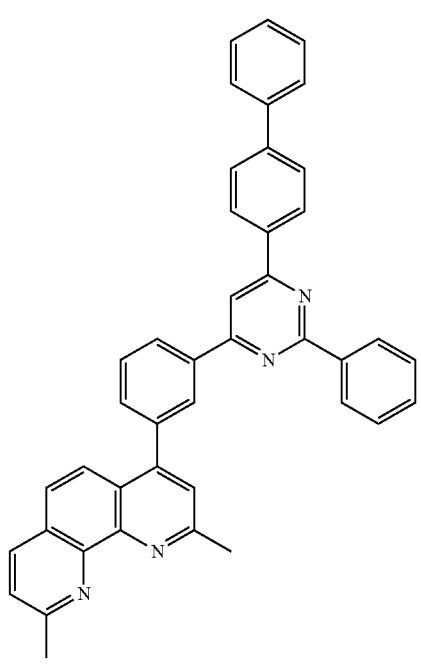
42

43
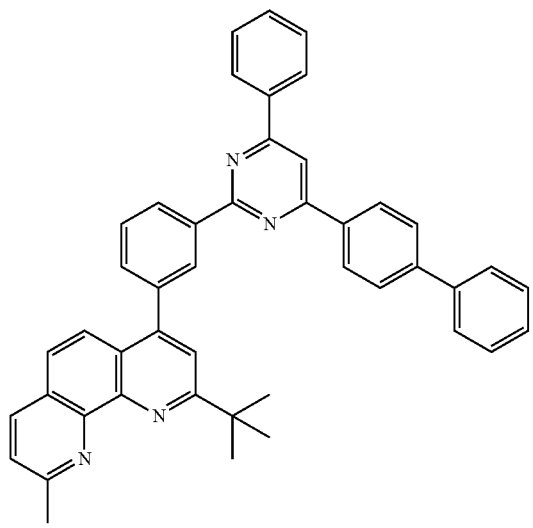
44
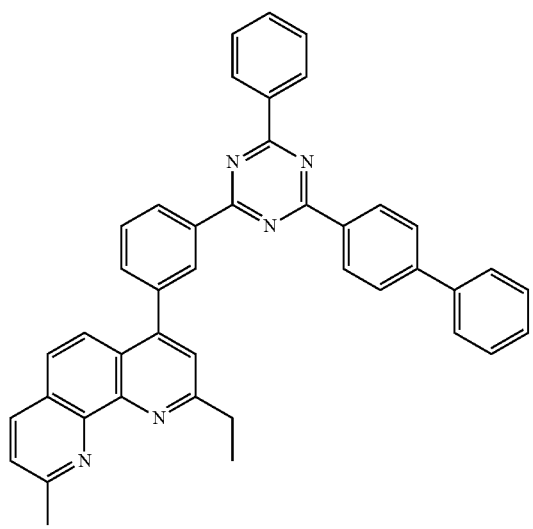
45
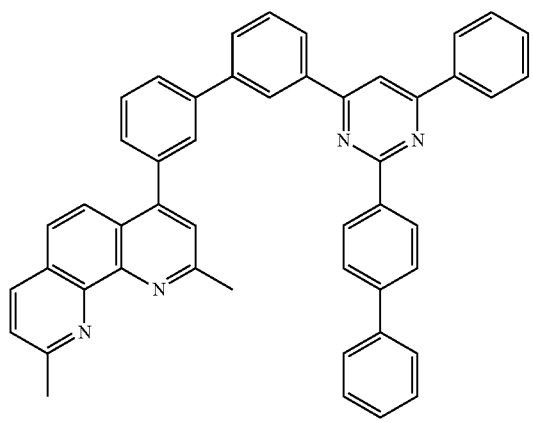
46
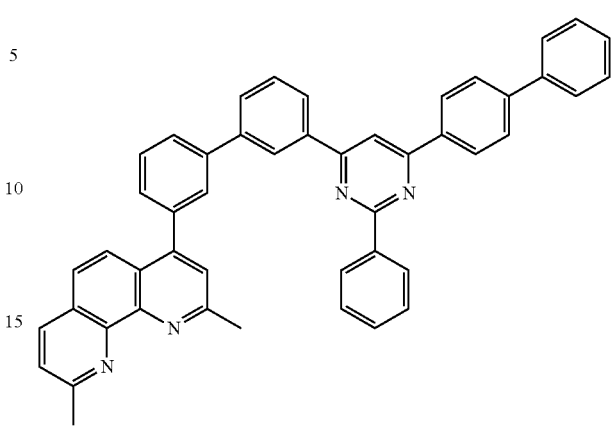
47
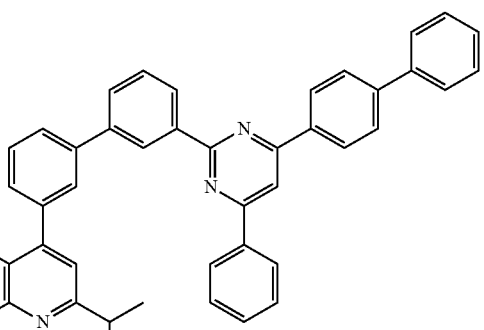
48
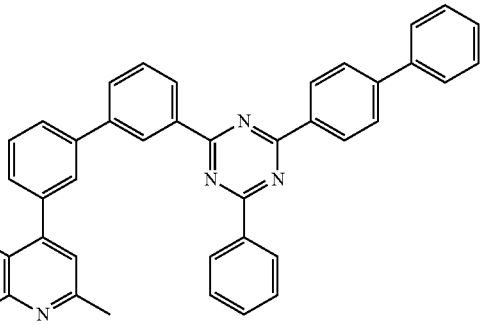

49
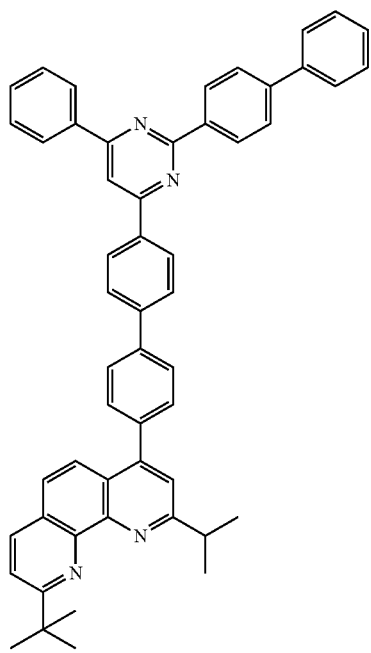
51
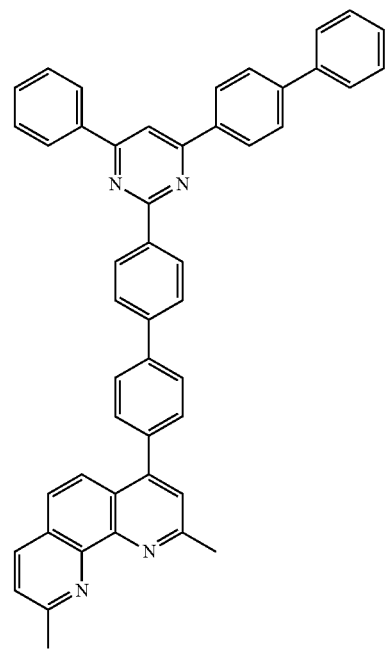
50
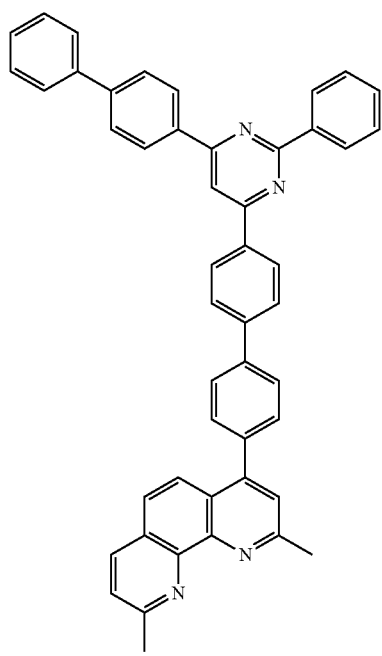
52
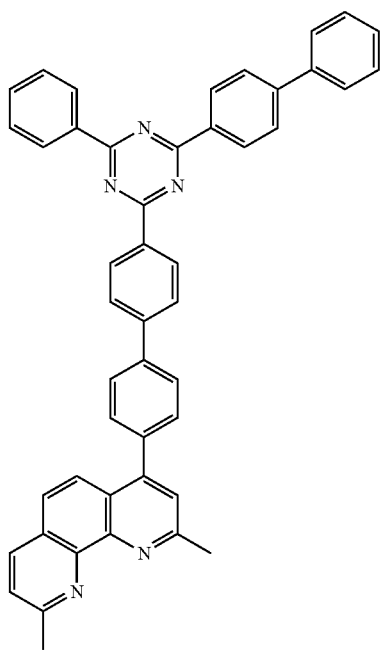

53
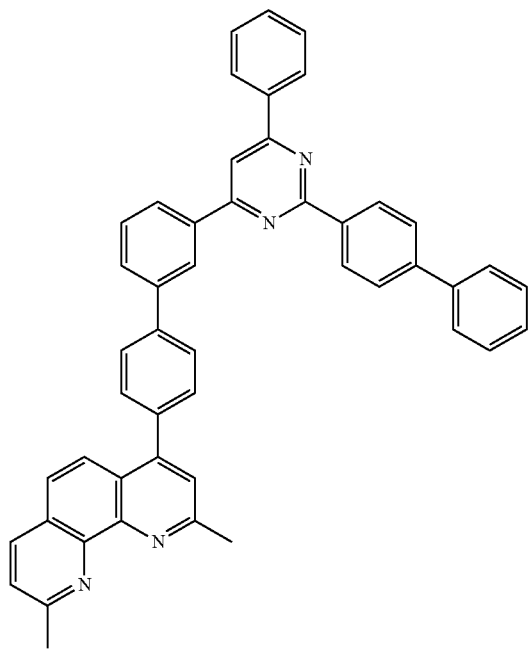
54
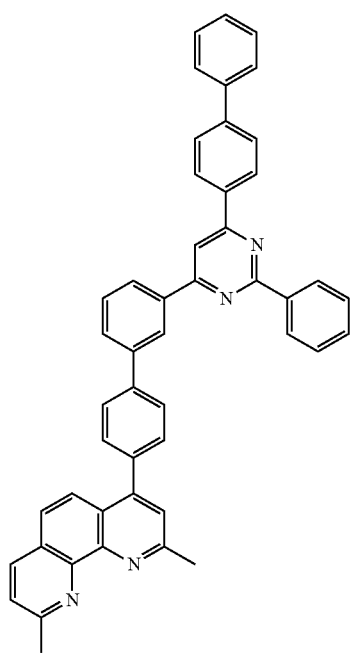
55
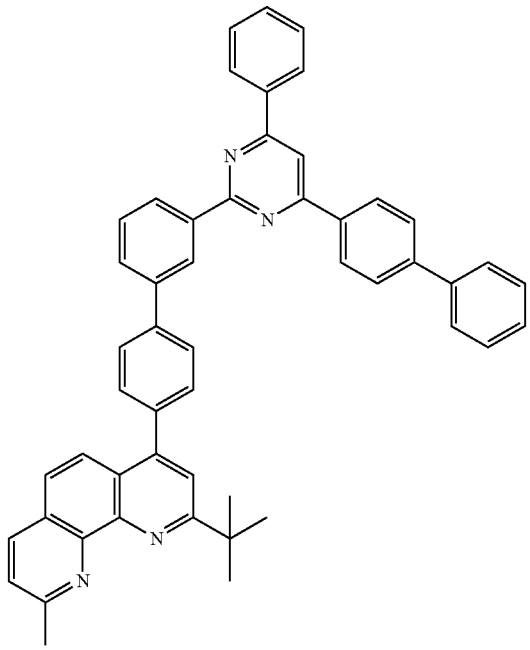
56
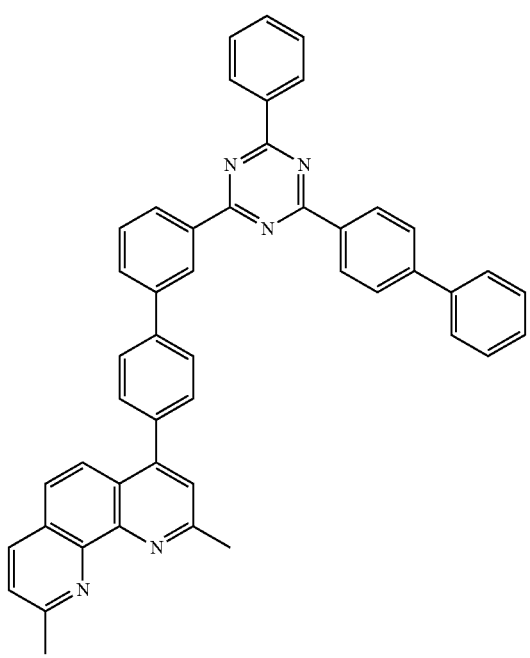

57
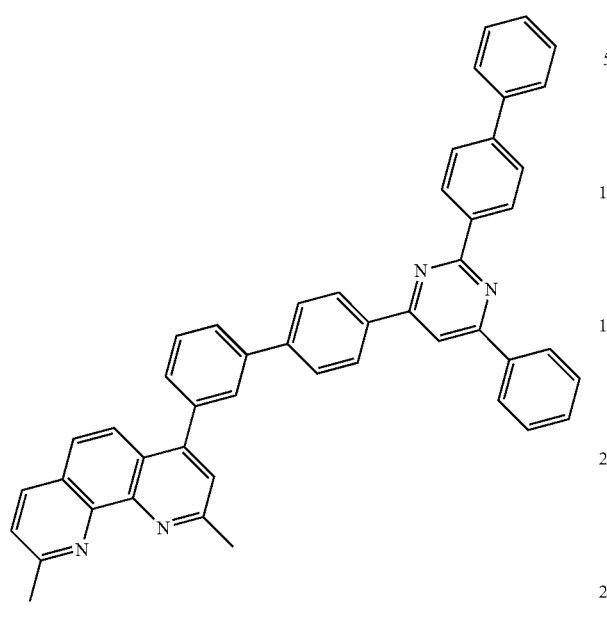
58
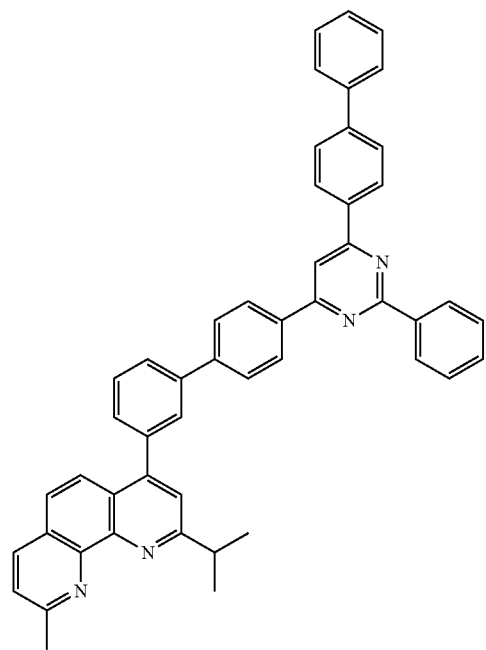
59
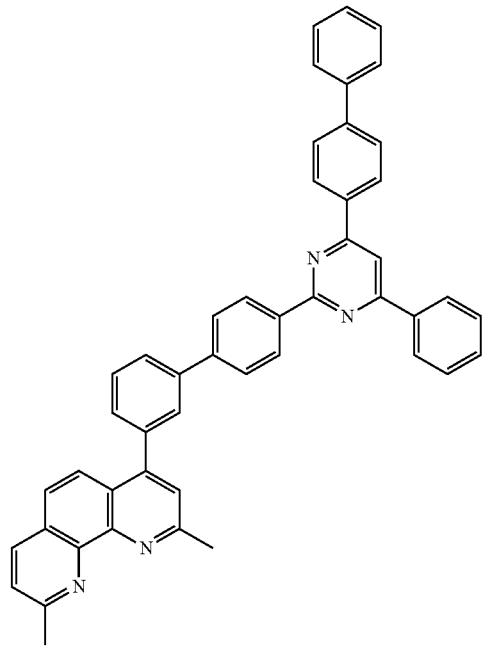
60
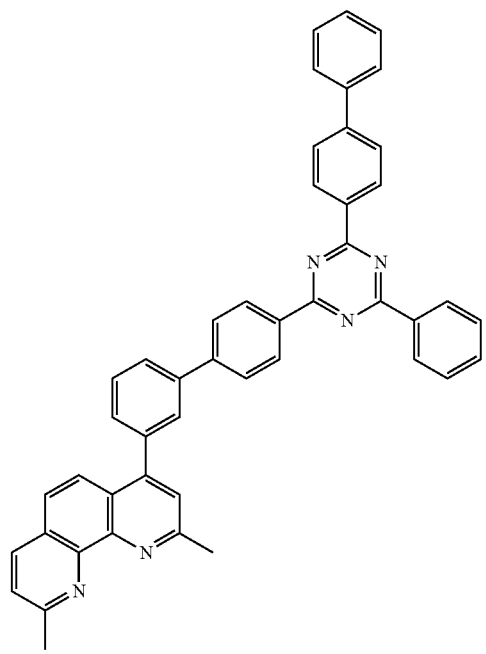

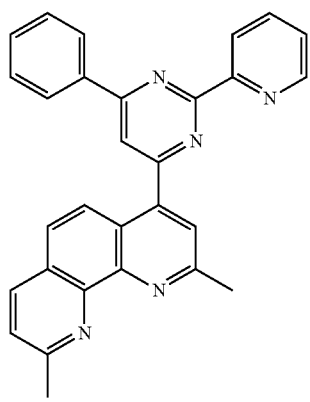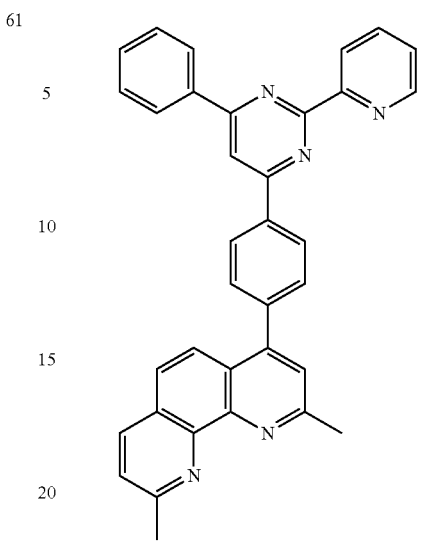

67
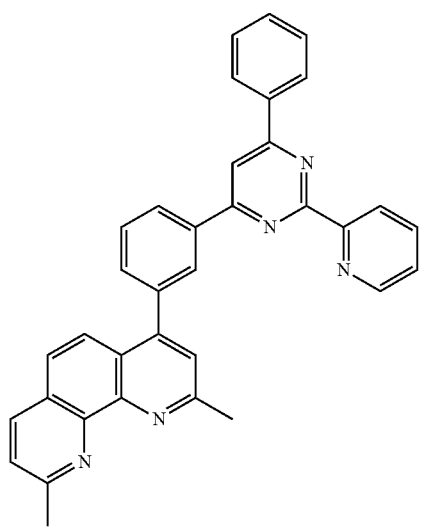
68
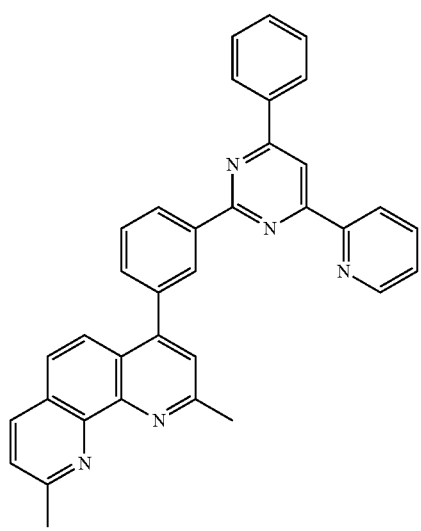
69
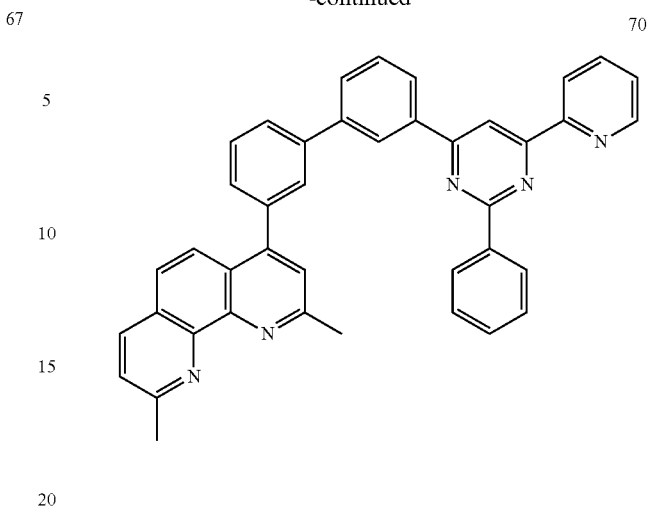
70
71
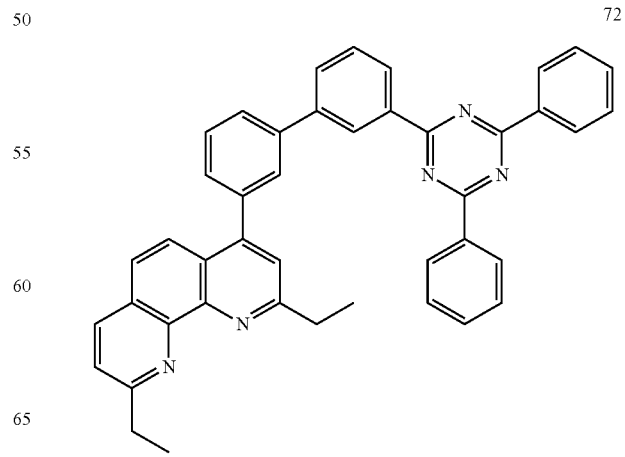
72

69
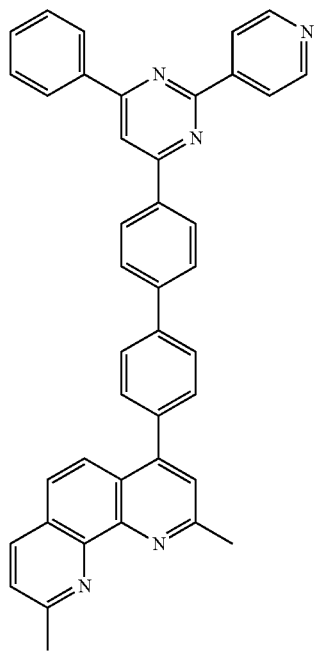
70
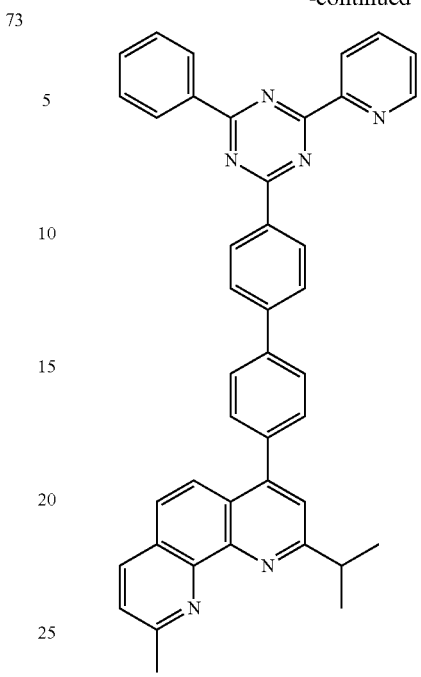
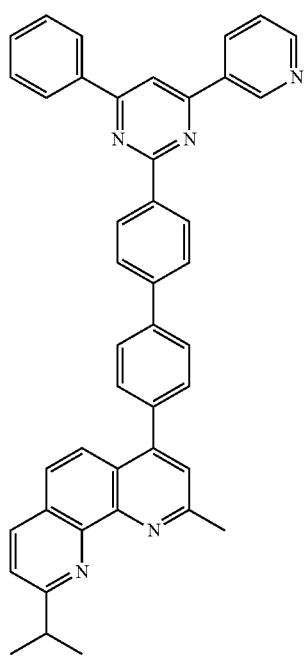
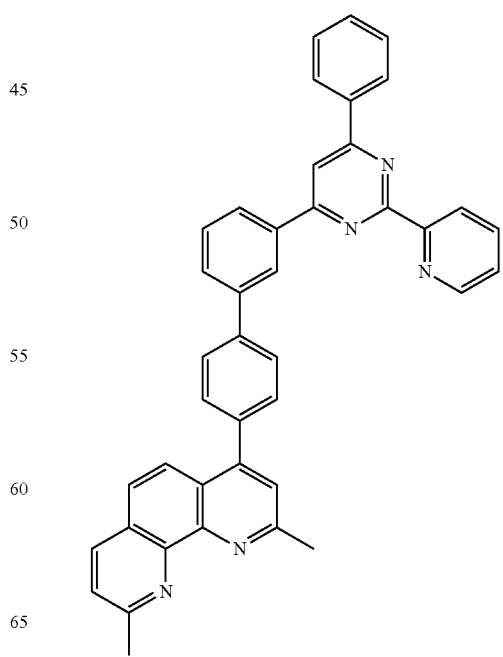

77
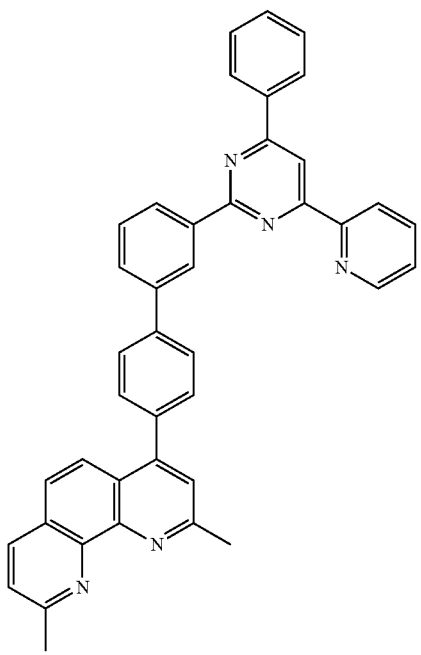
79
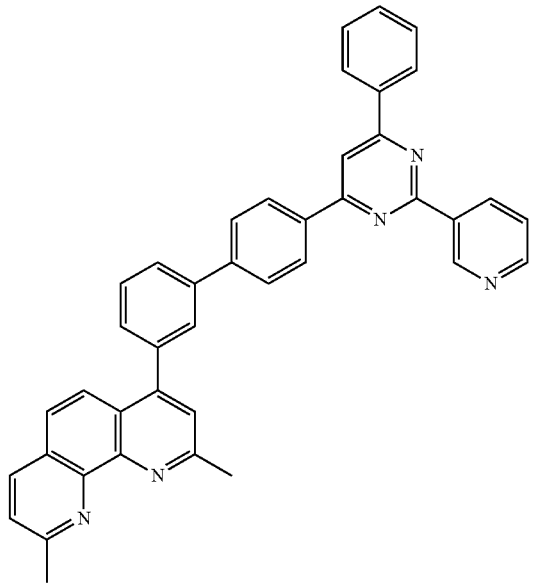
78
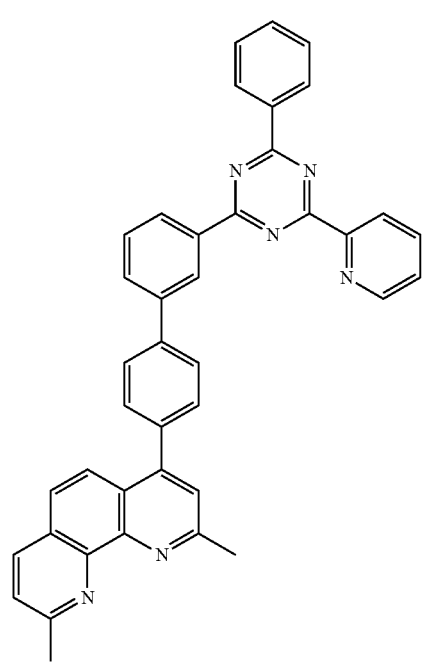
80
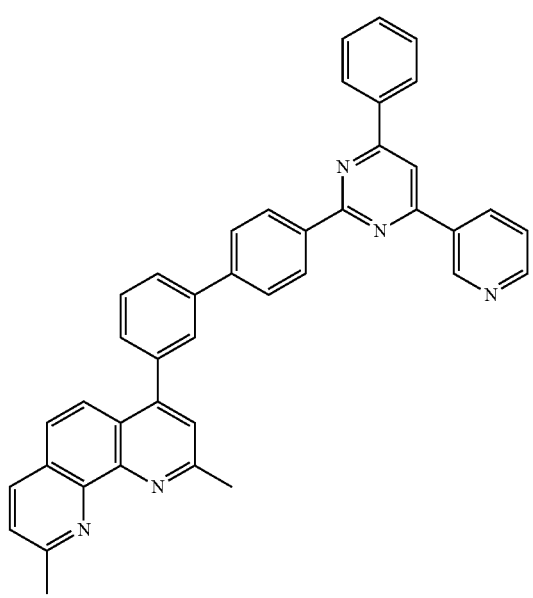

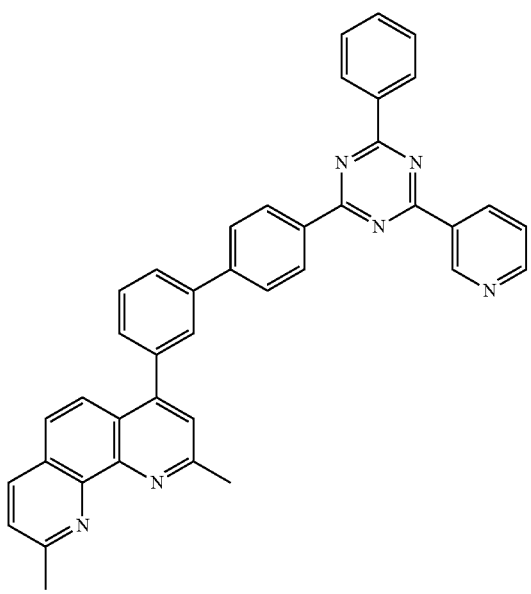
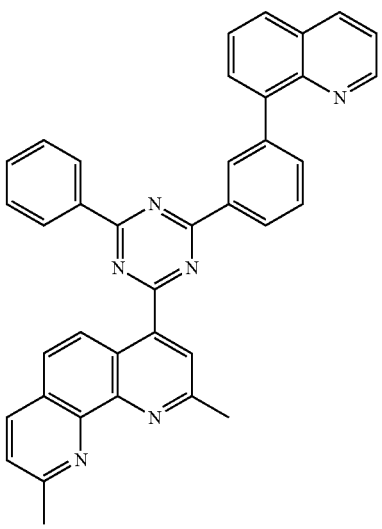

86
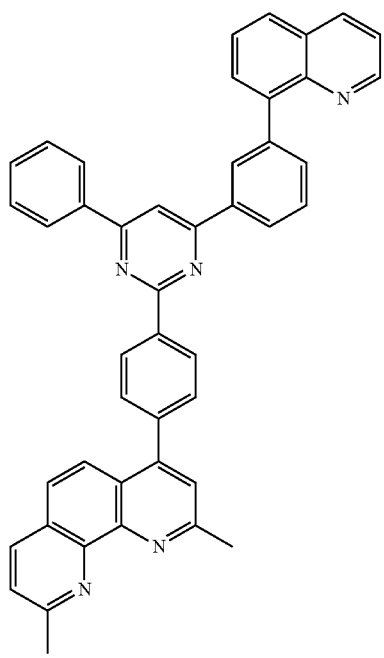
87
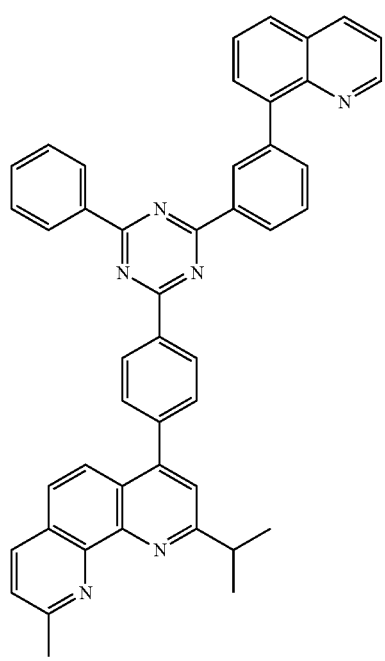
88
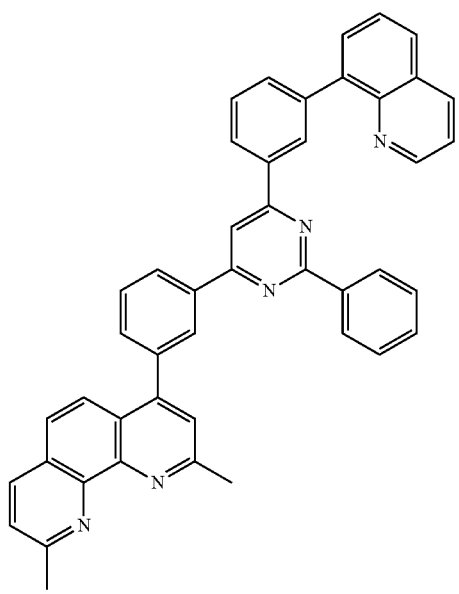
89
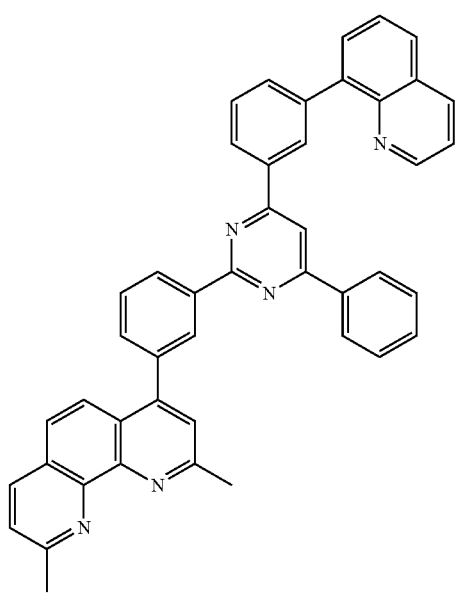

90
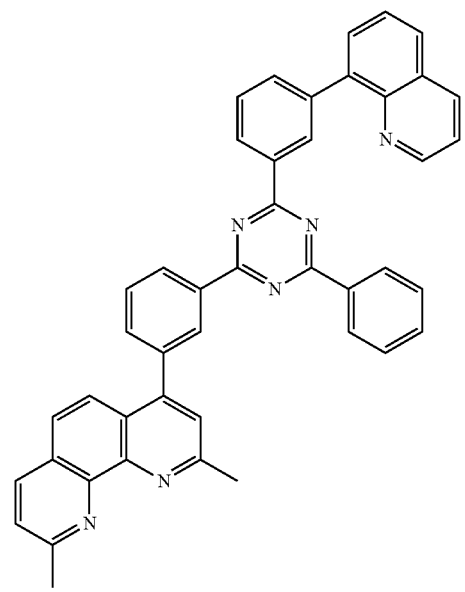
91
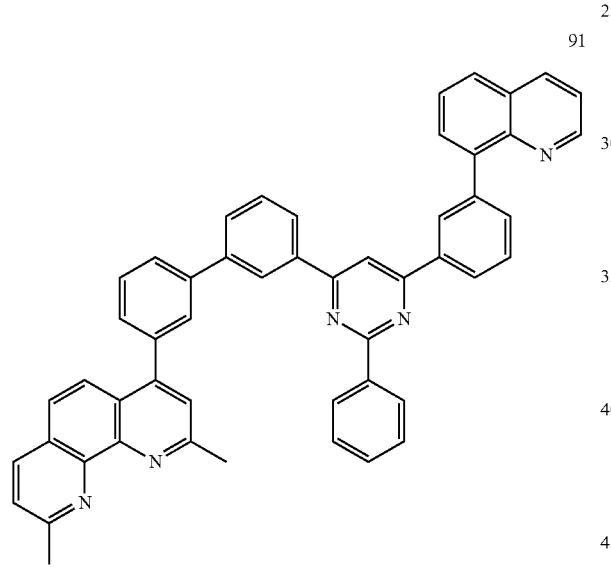
92
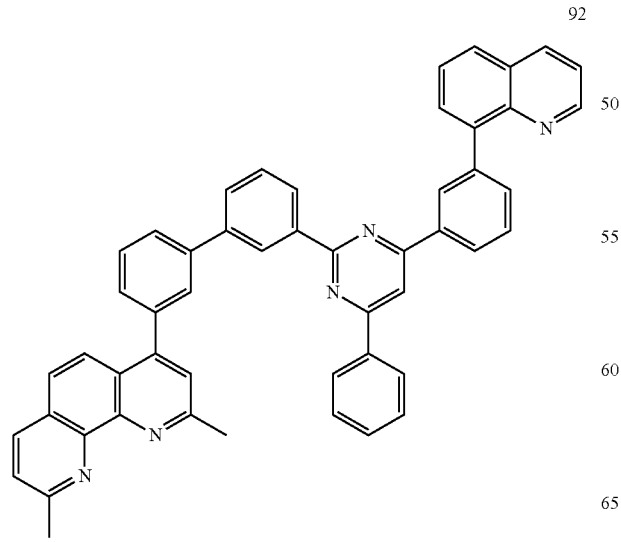
93
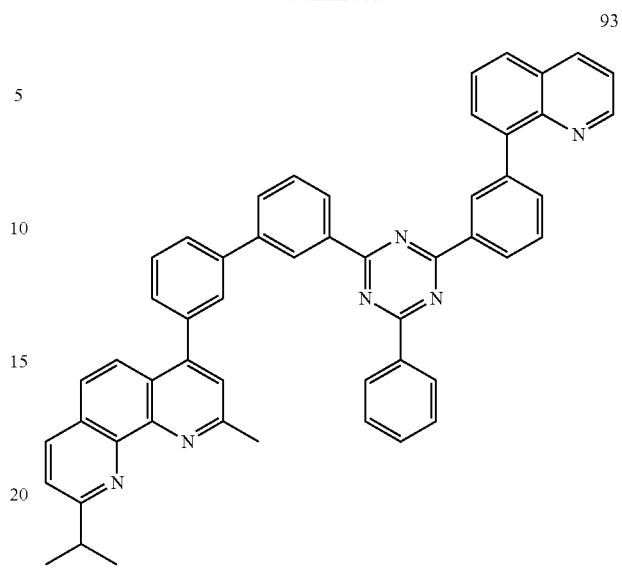
94
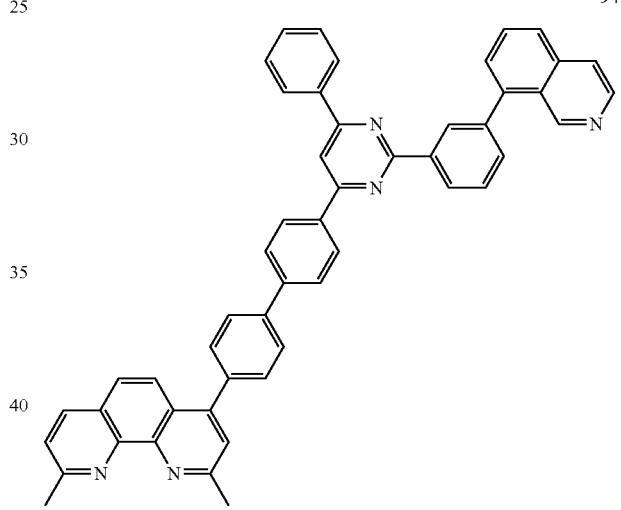
95
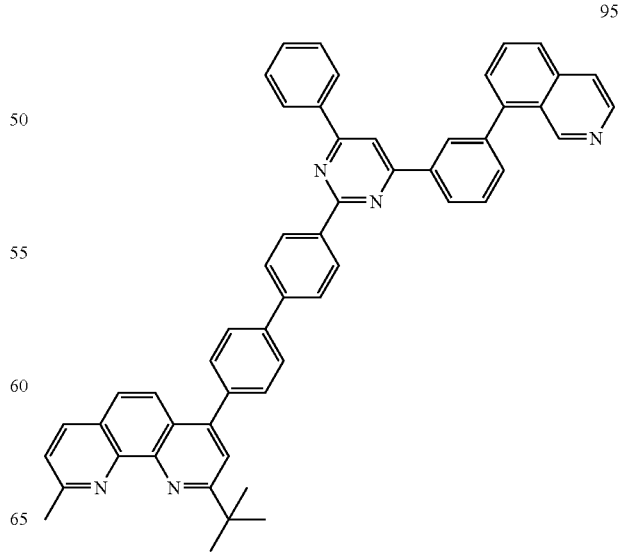

96
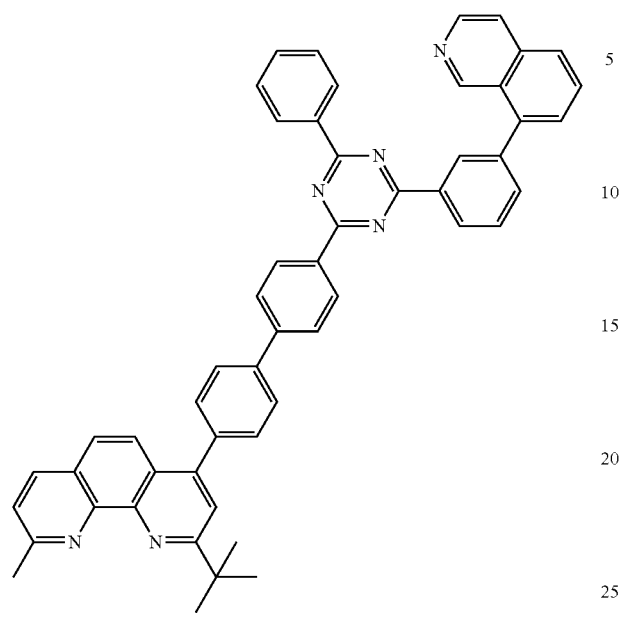
98
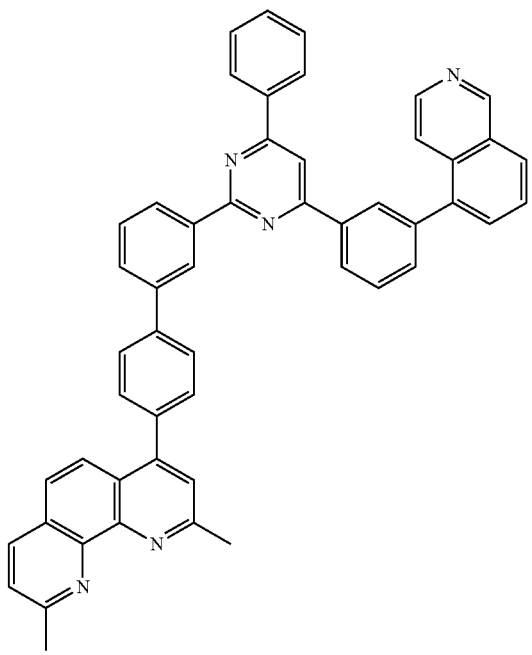
97
99
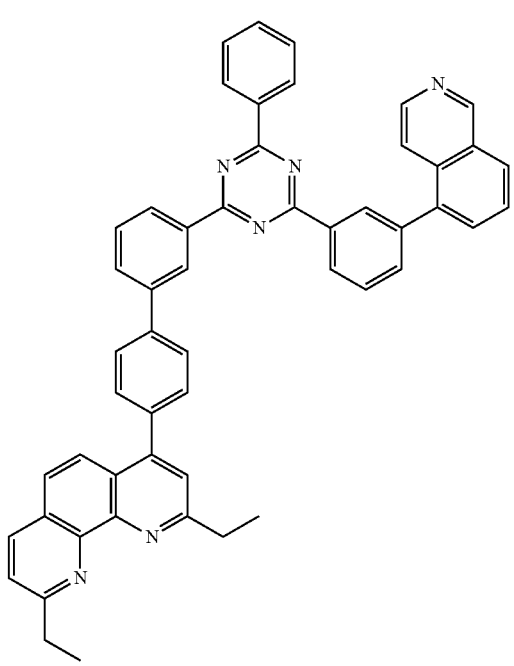

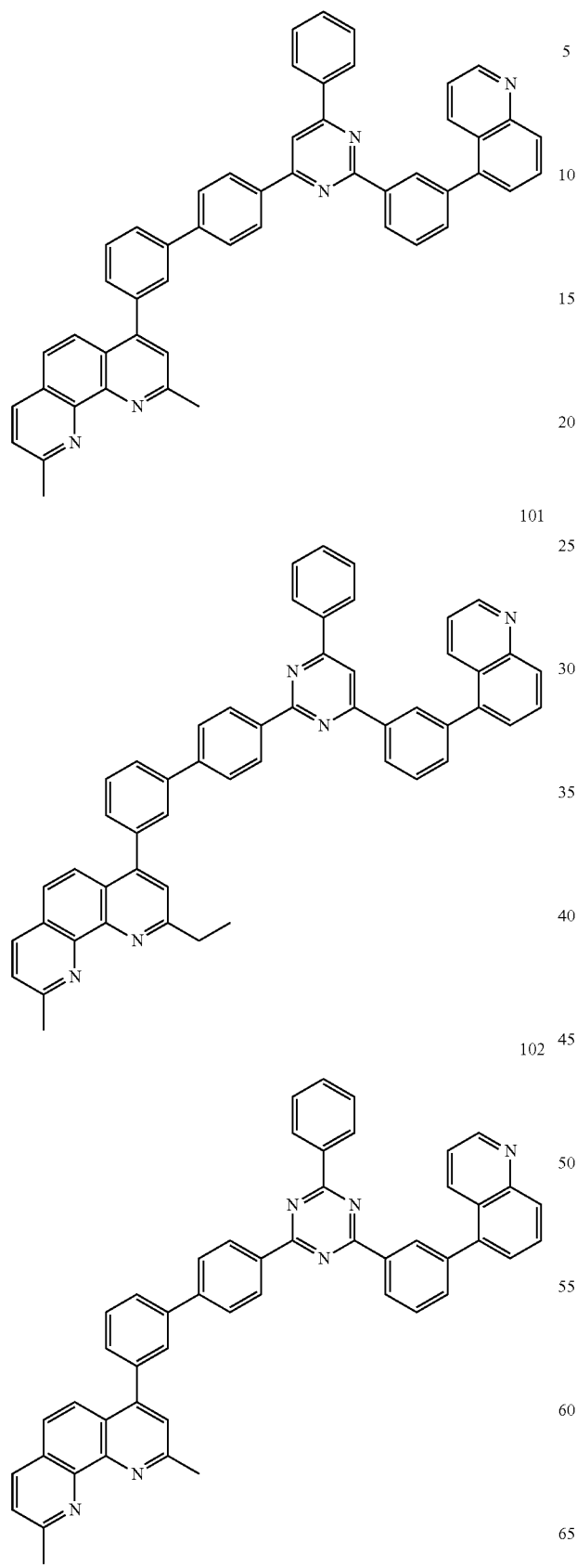
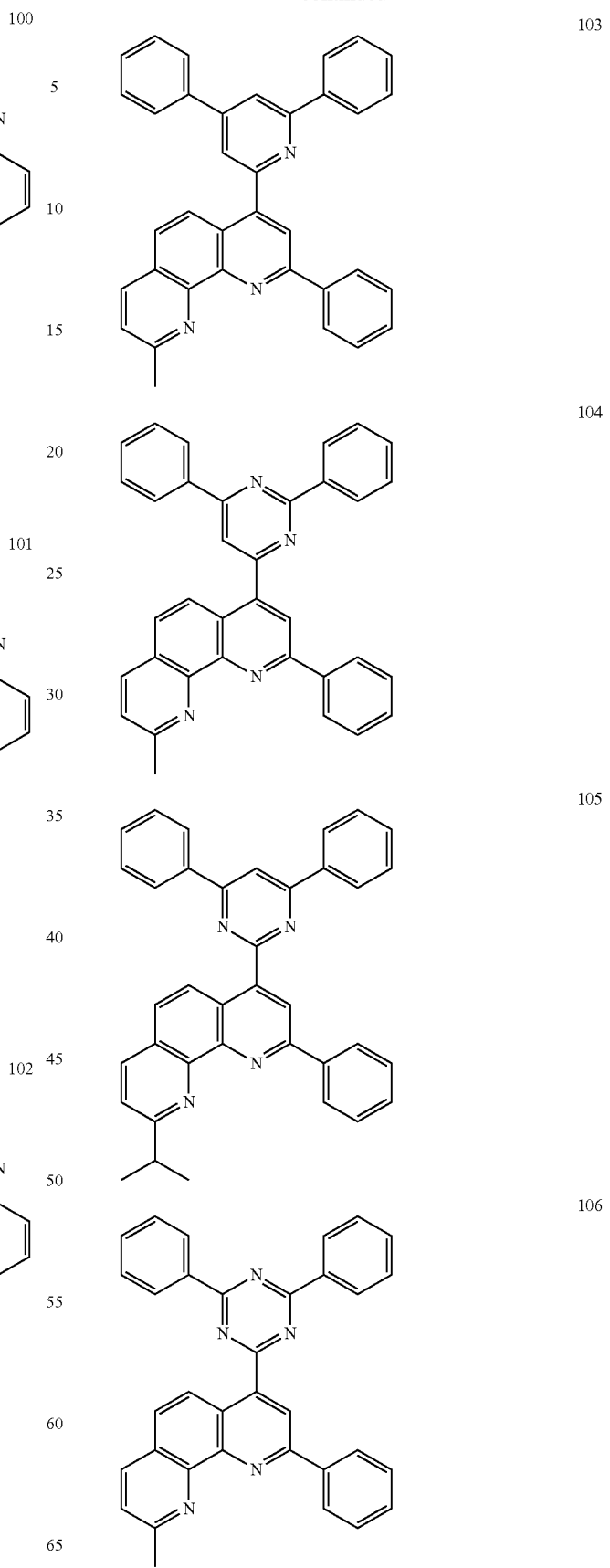

107
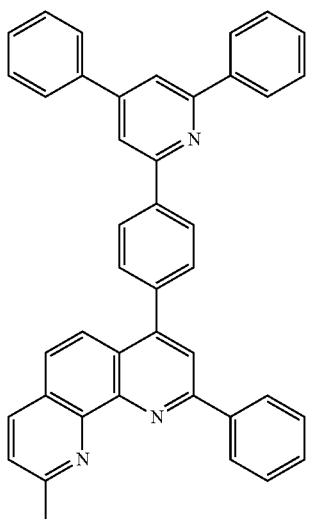
108
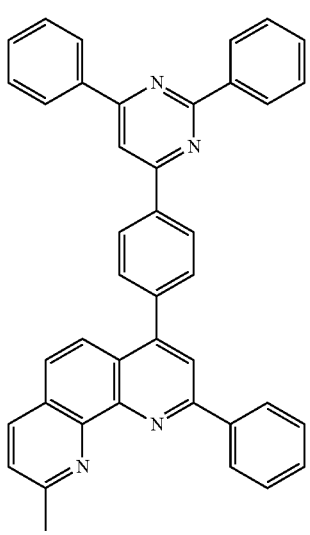
109
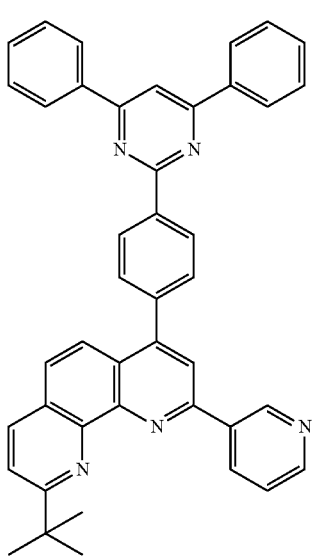
110
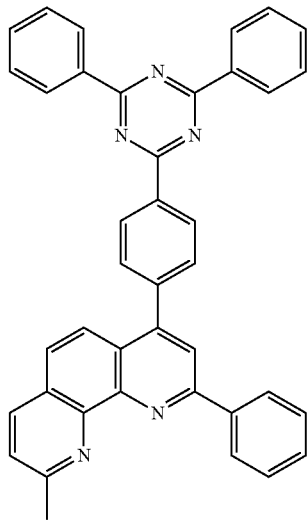
111
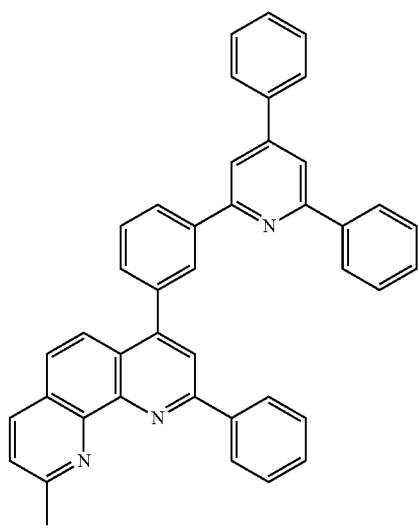
112
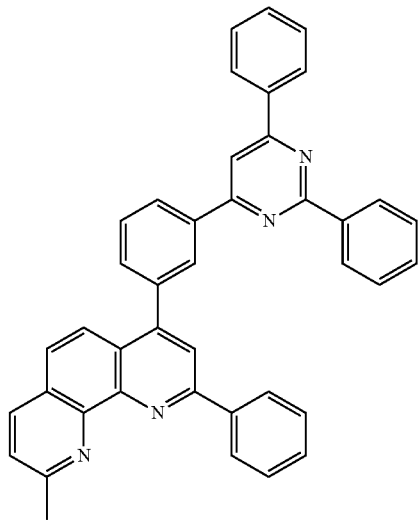

113
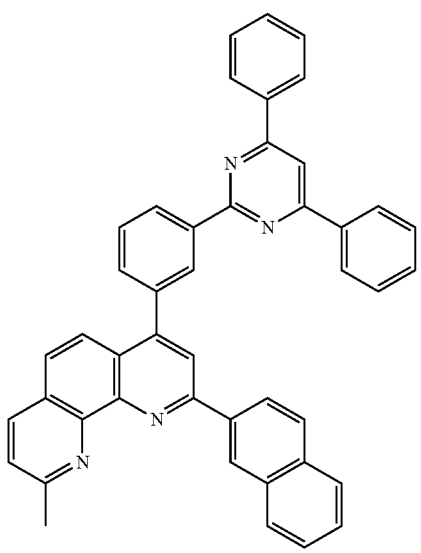
114
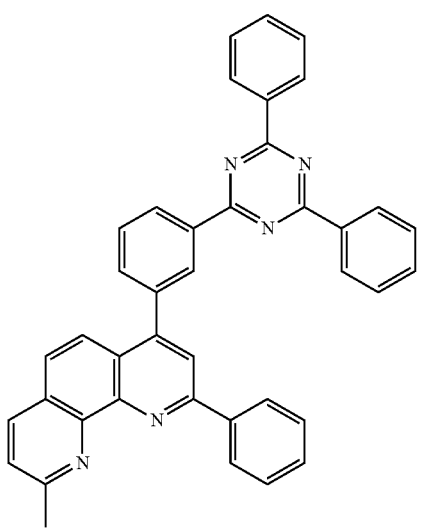
115
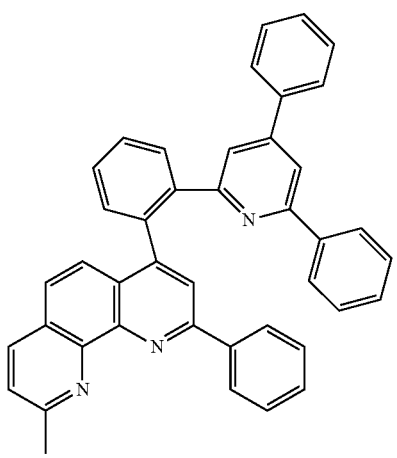
116
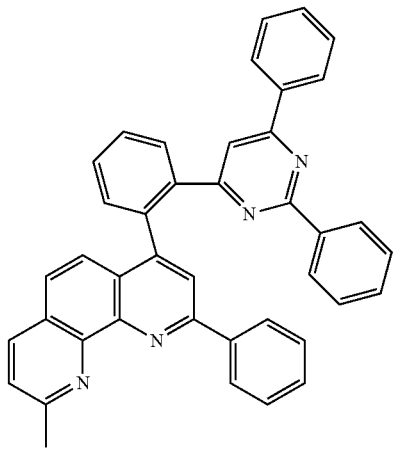
117
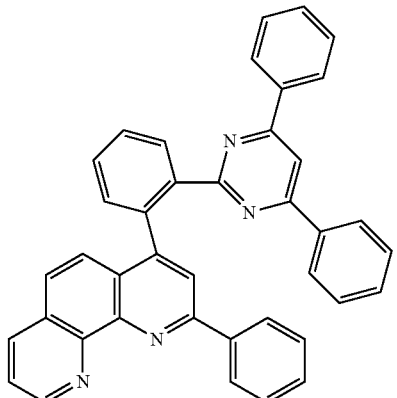
118
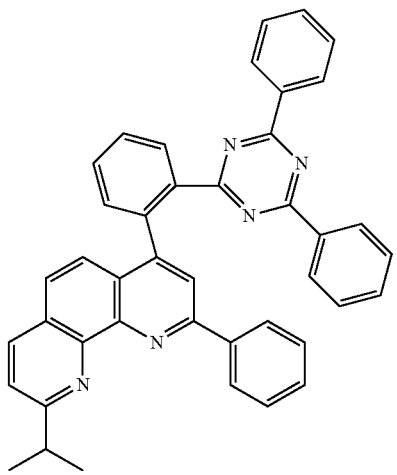

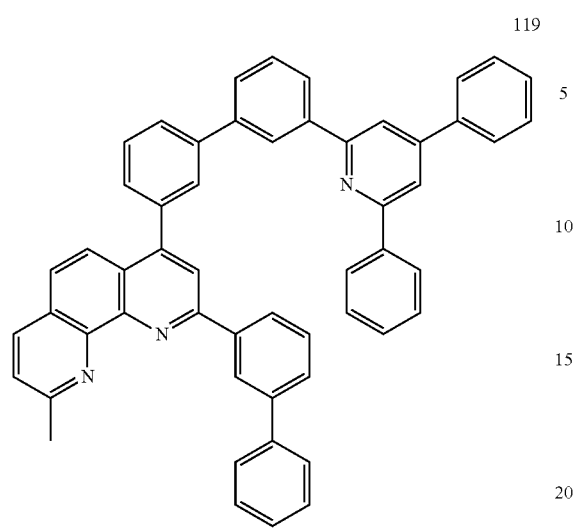
119
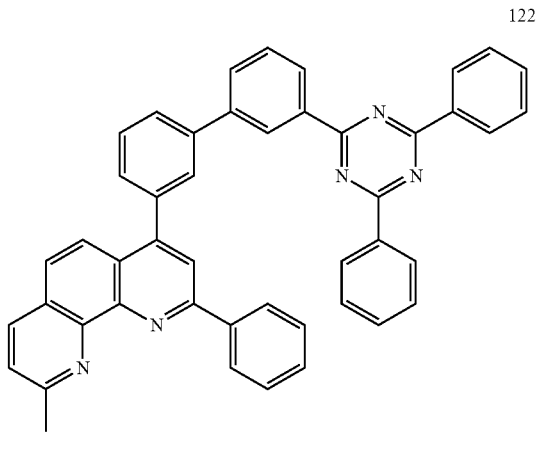
122
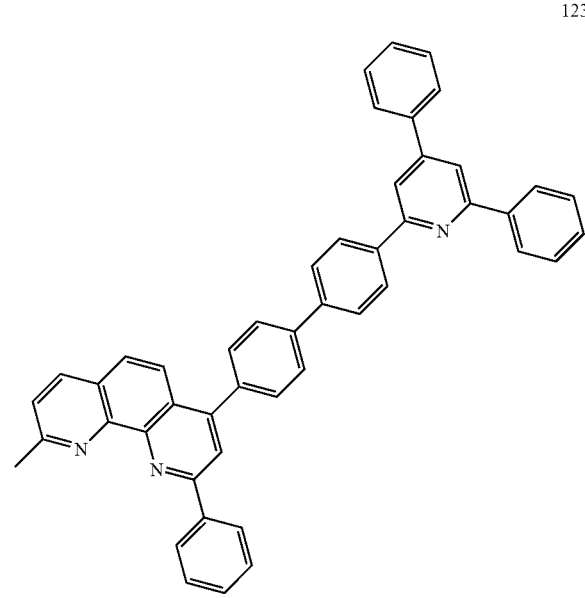
123
120
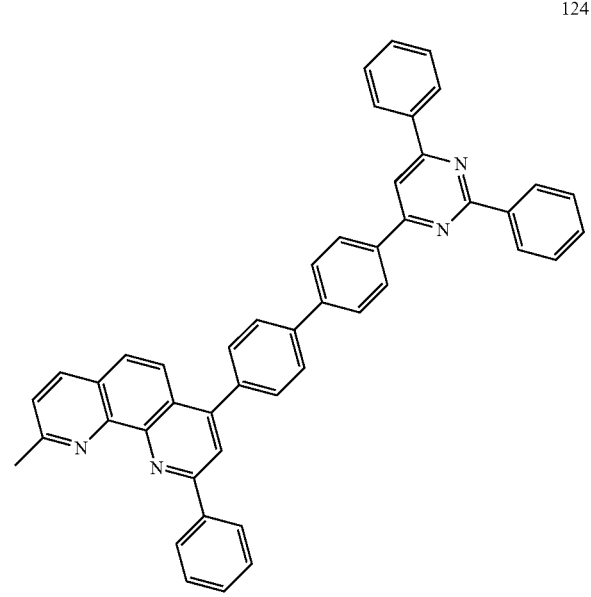
124
121

125
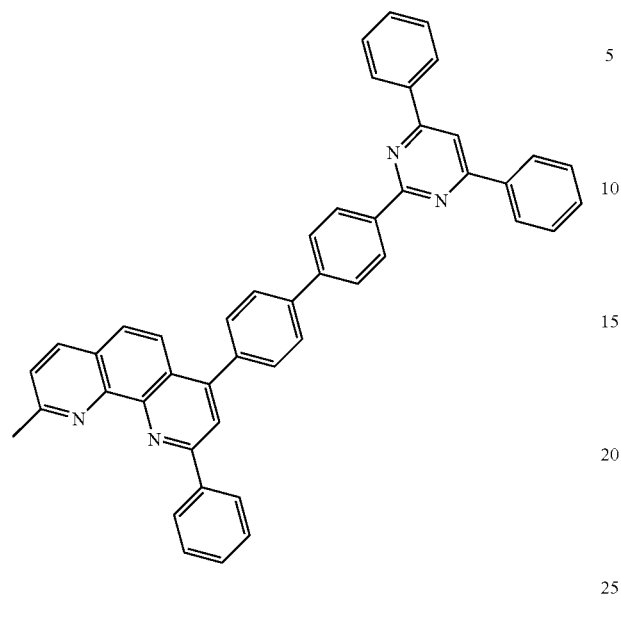
127
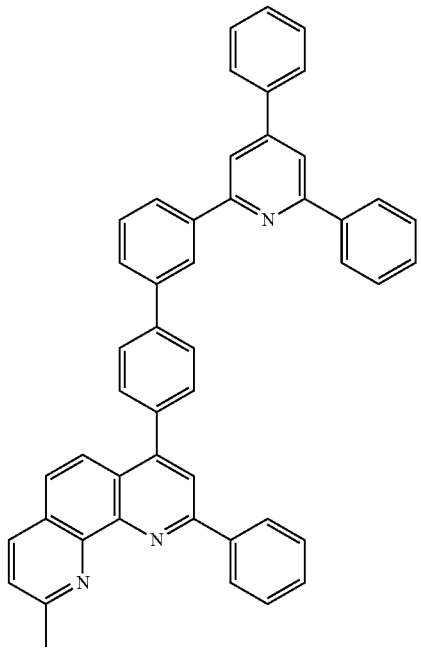
126
128
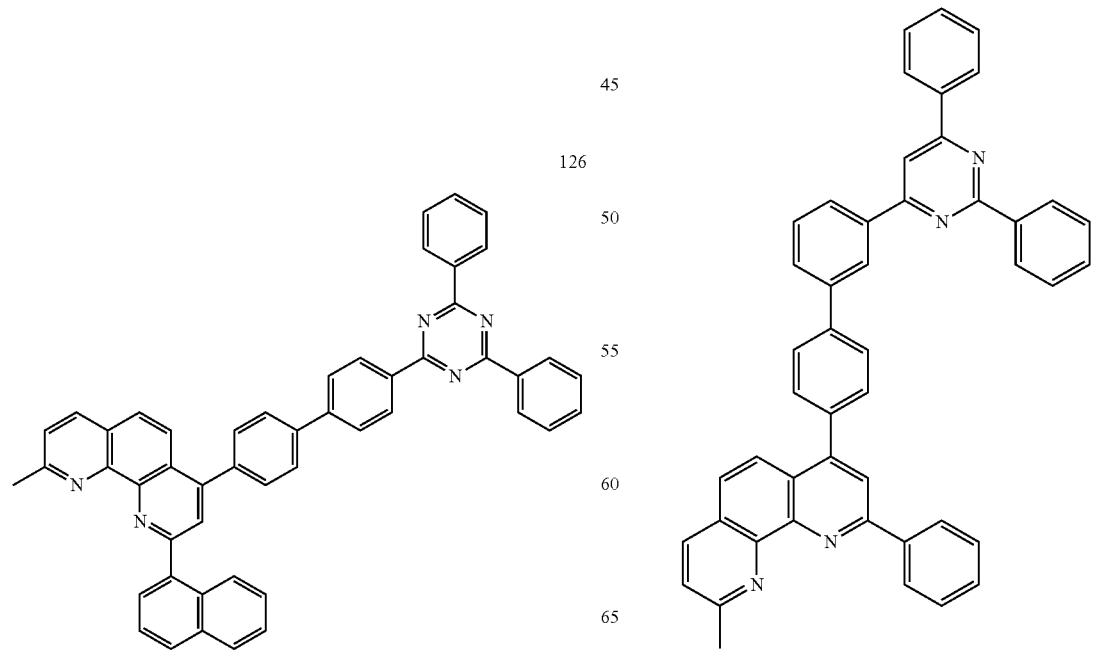

129
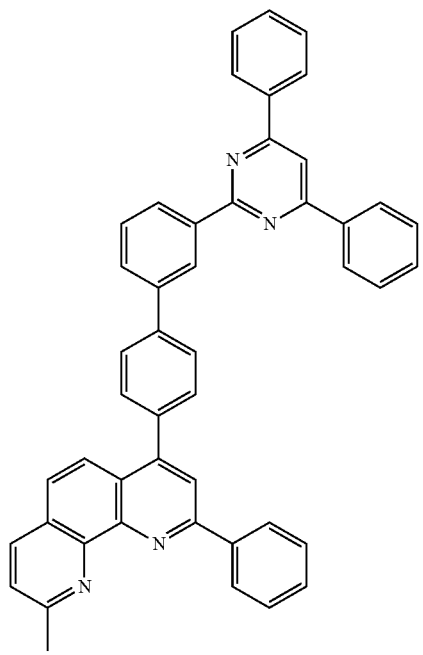
130
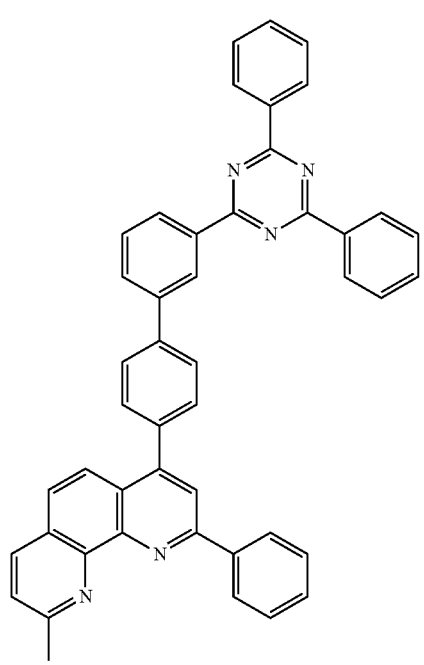
131
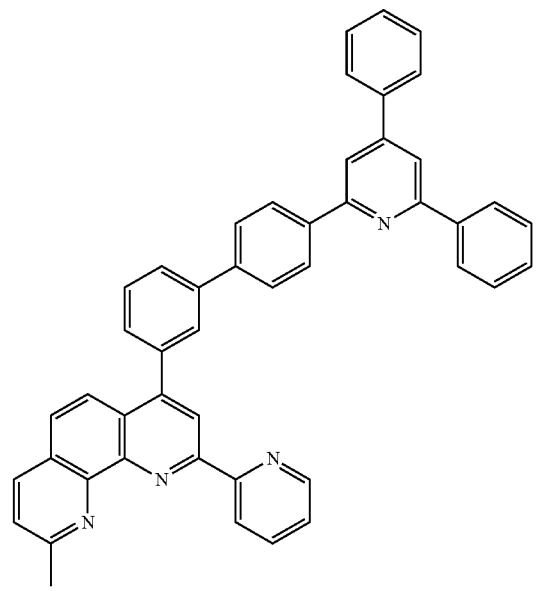
132
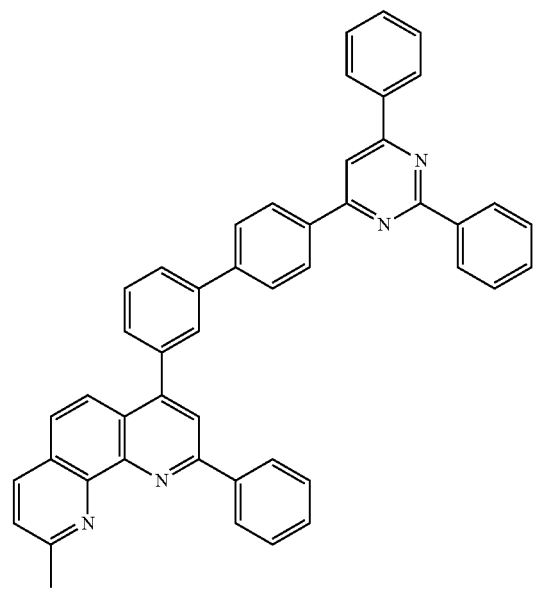

133
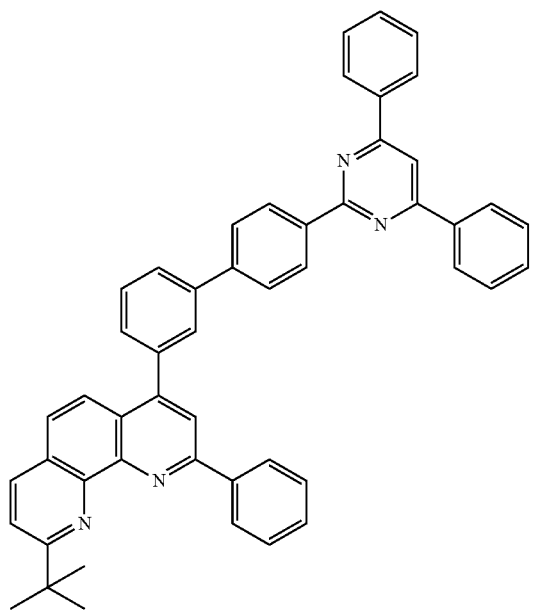
134
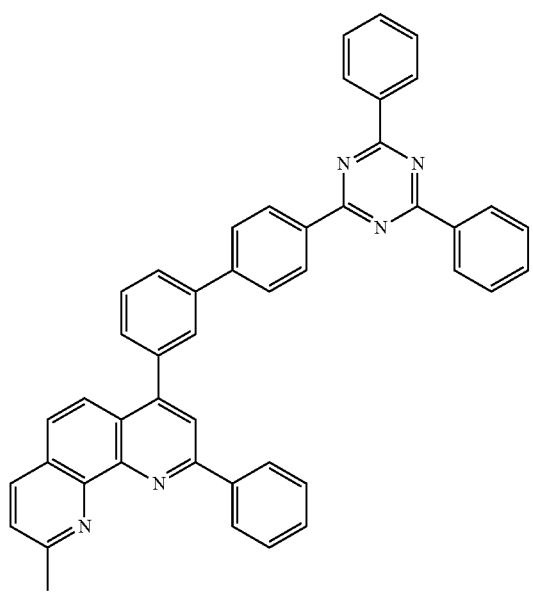
135
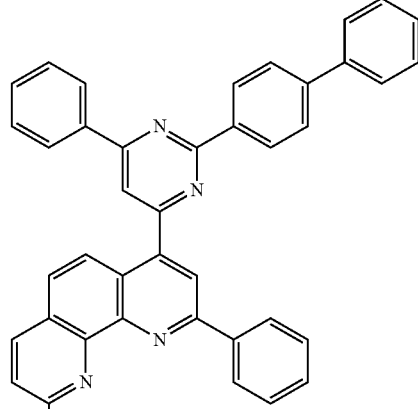
136
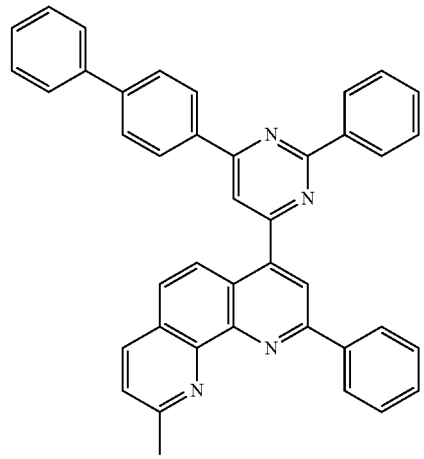
137
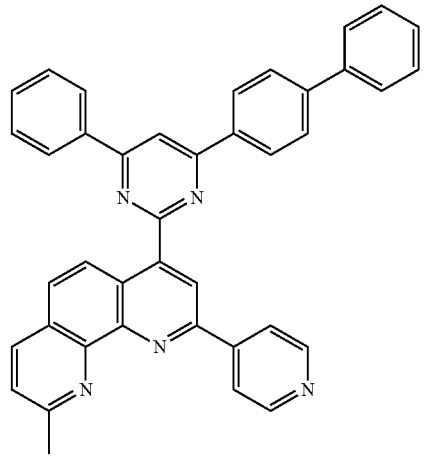

138
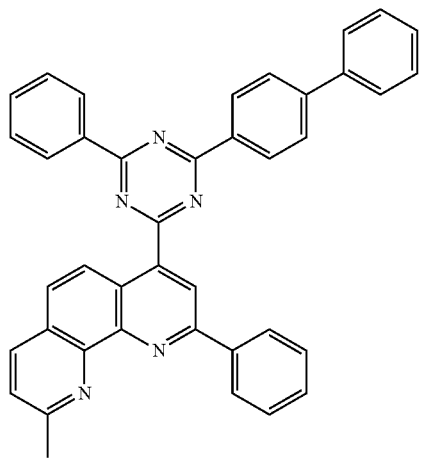
139
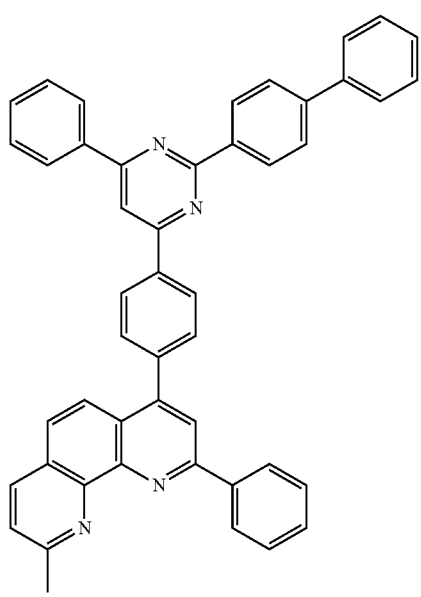
140
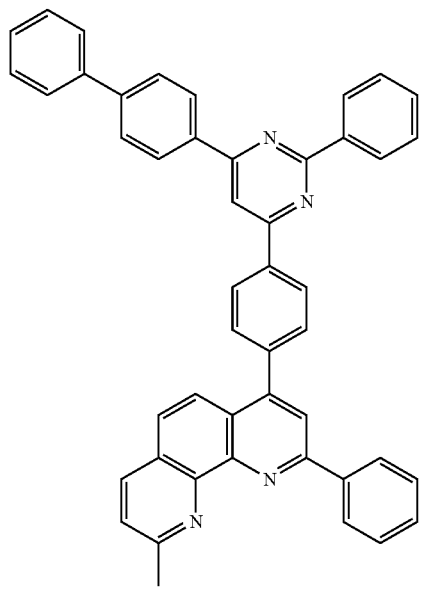
141
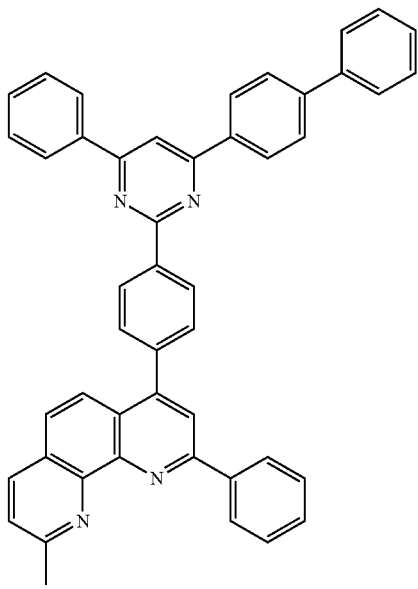
142
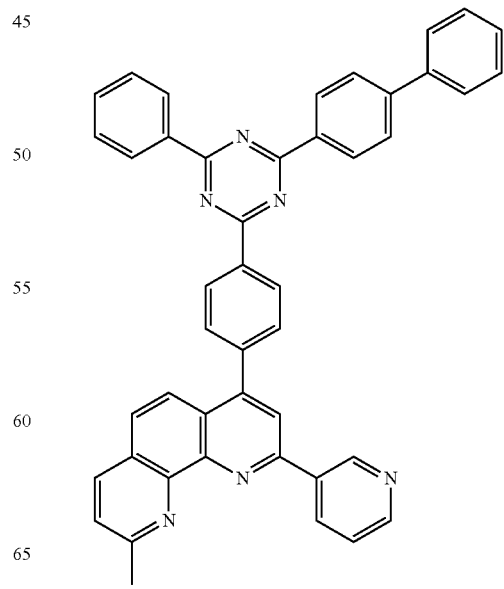

143
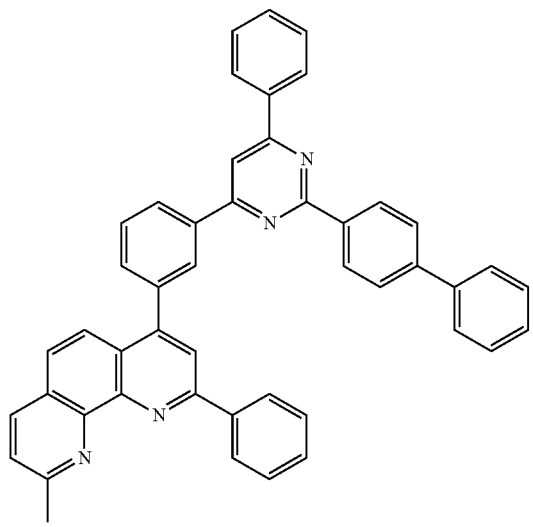
144
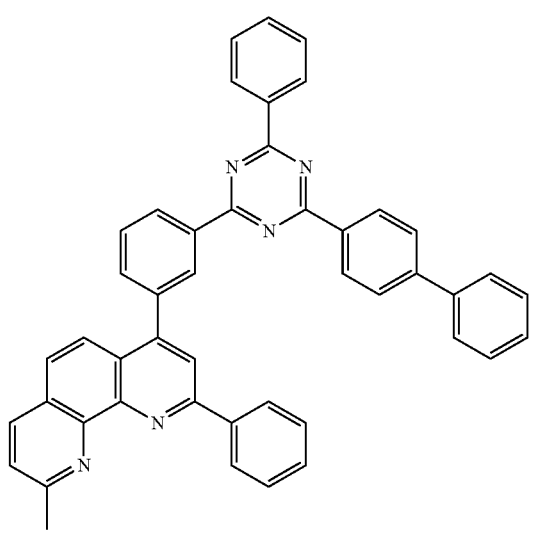
145
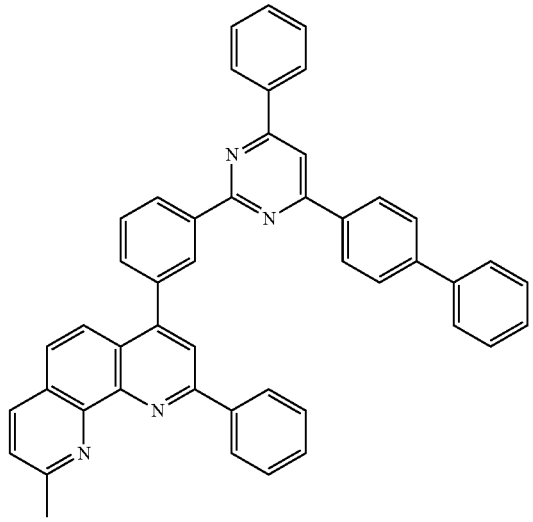
146
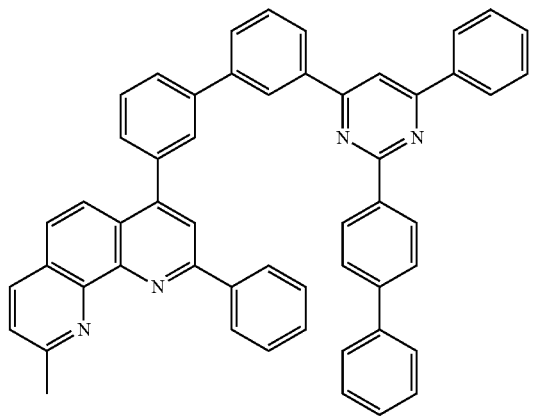
147

148
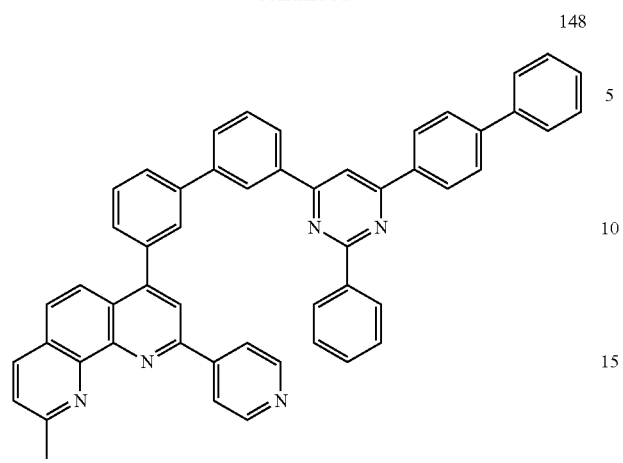
149
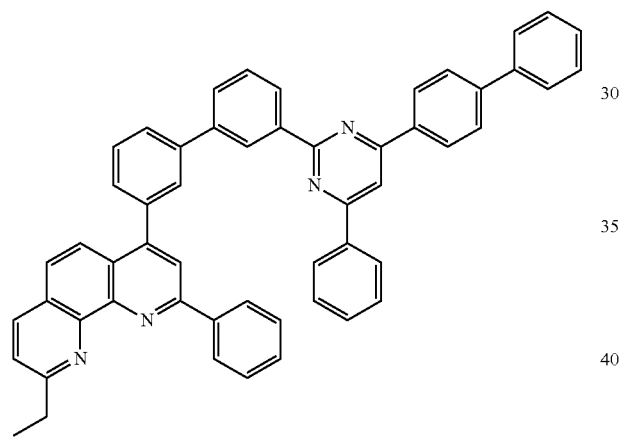
150
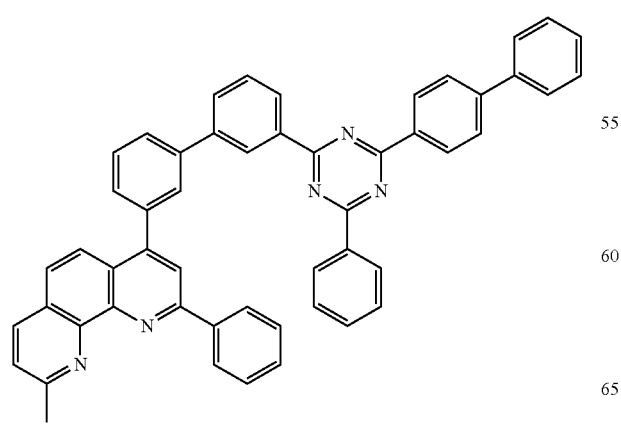
151
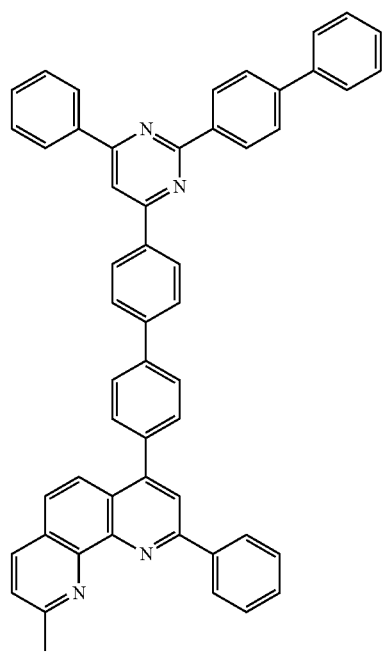
152
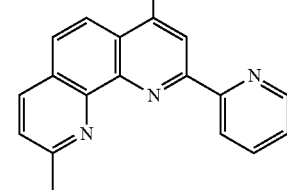

153
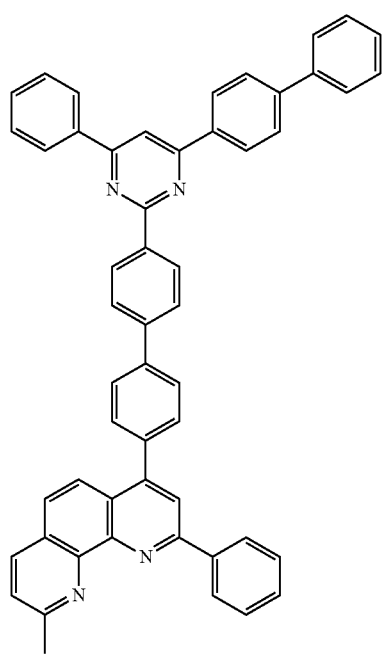
154
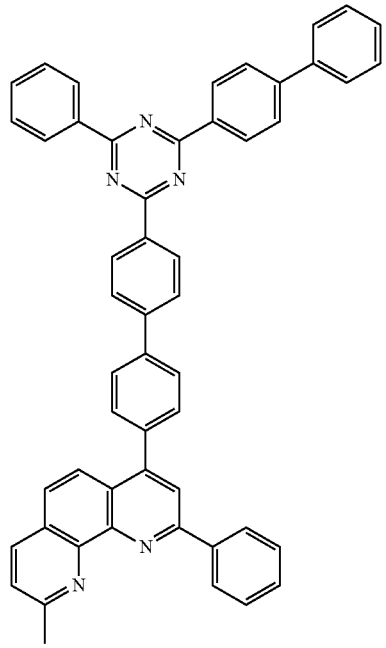
155
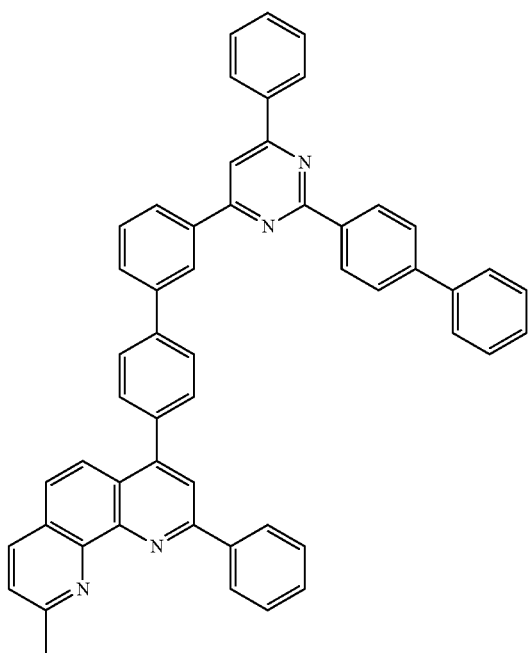
156
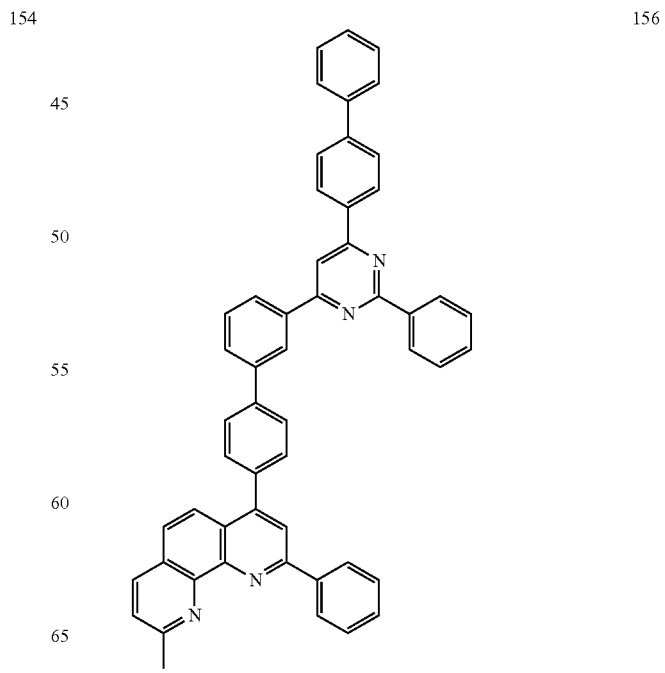

157 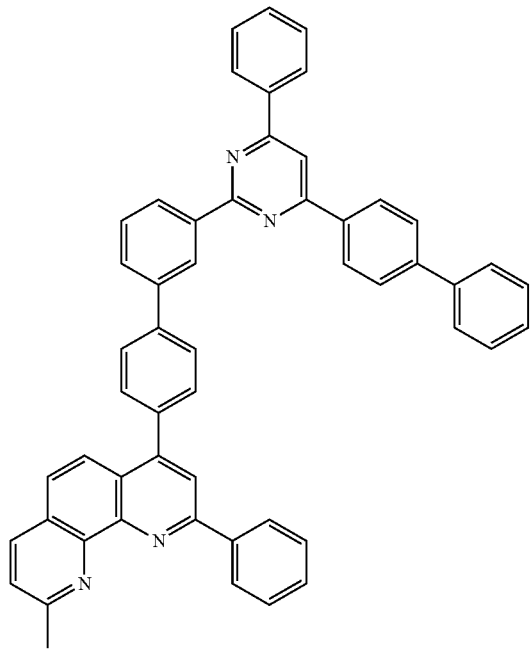
158 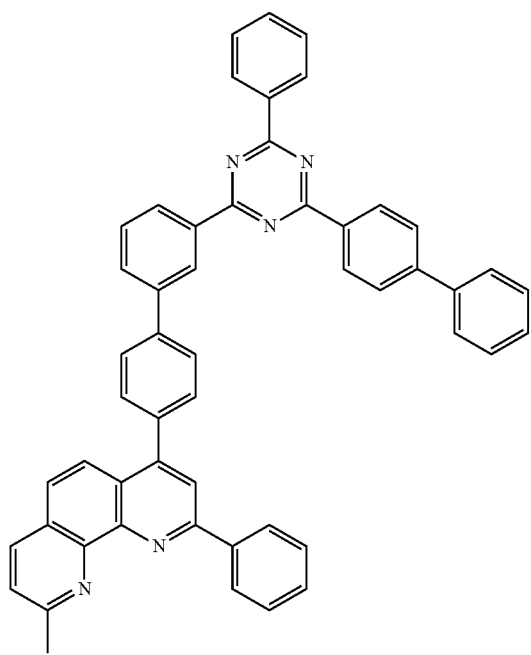
159 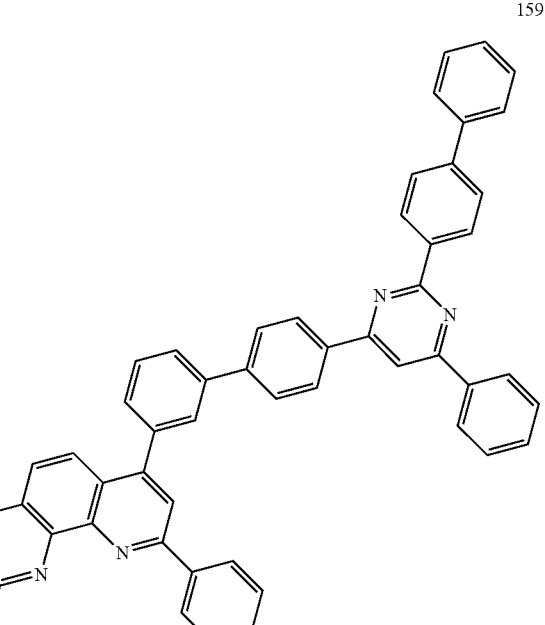
160 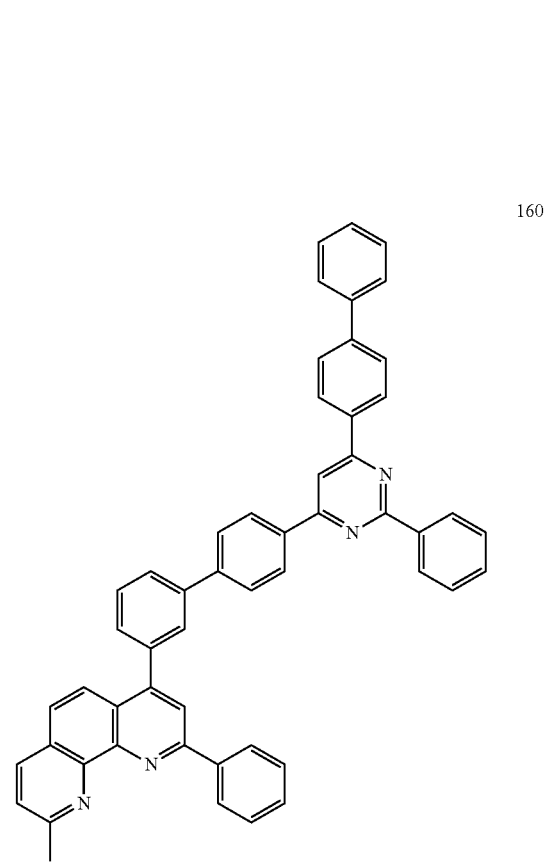

161
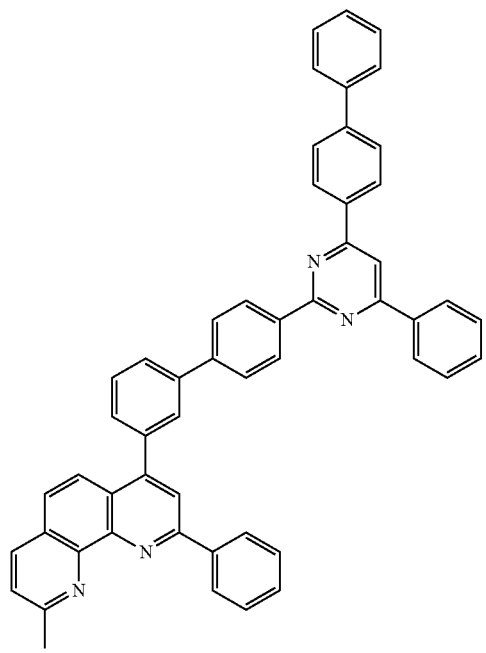
162
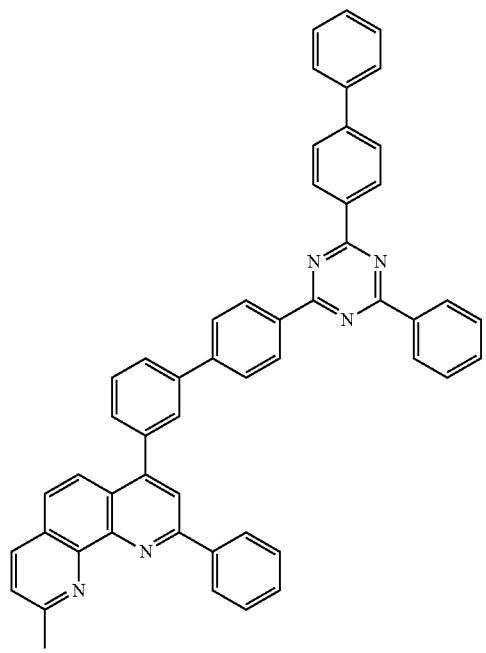
163
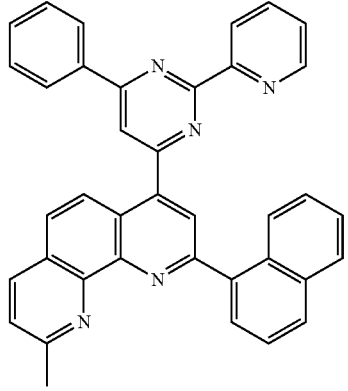
164
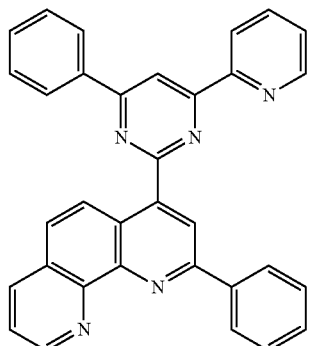
165

107
-continued
166
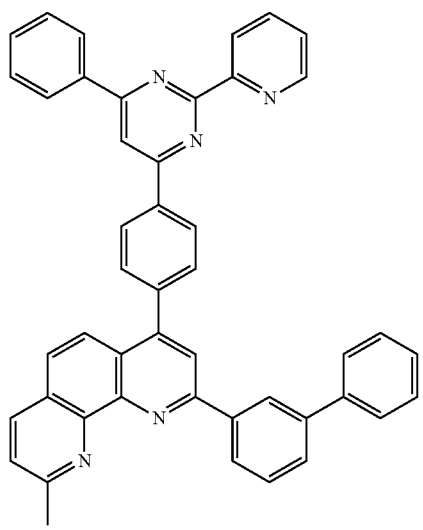
167
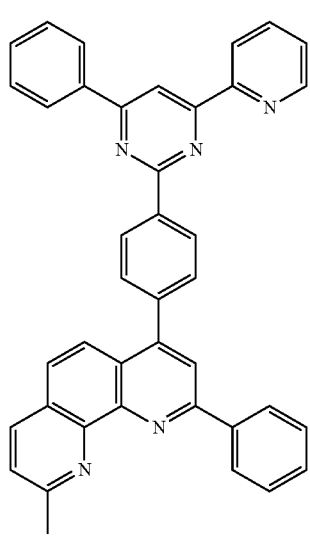
168
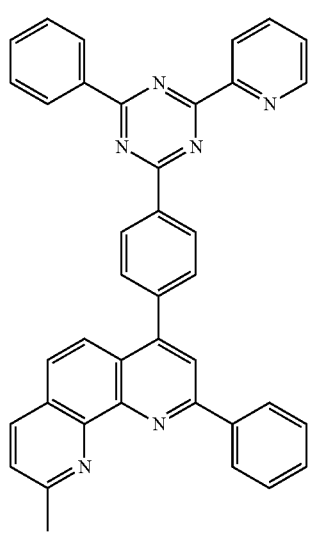
108
-continued
169
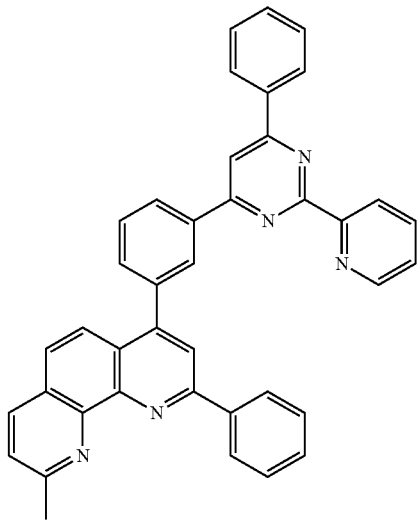
170
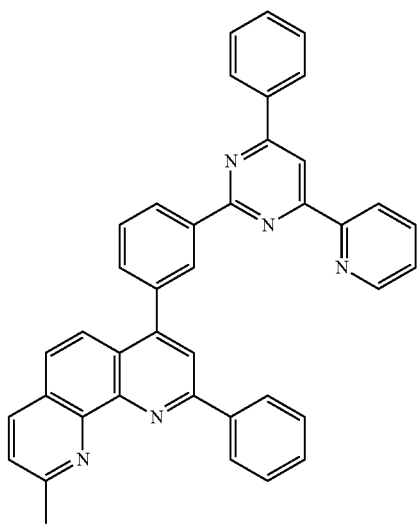
171
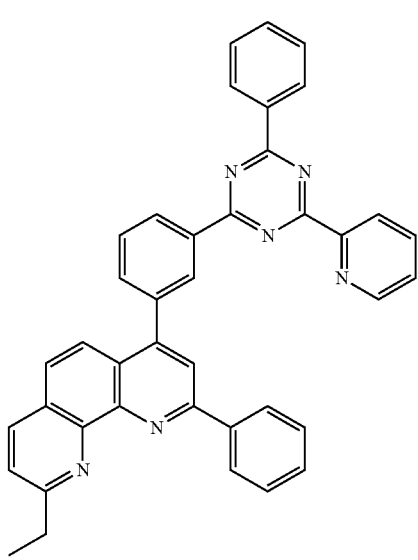

172
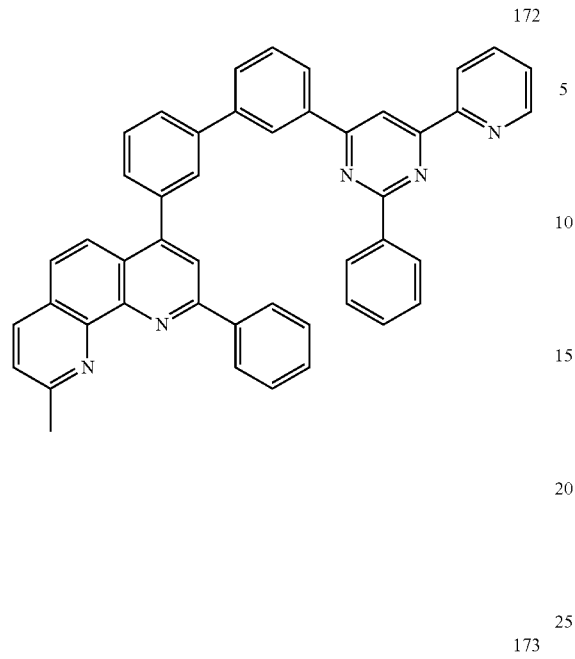
173
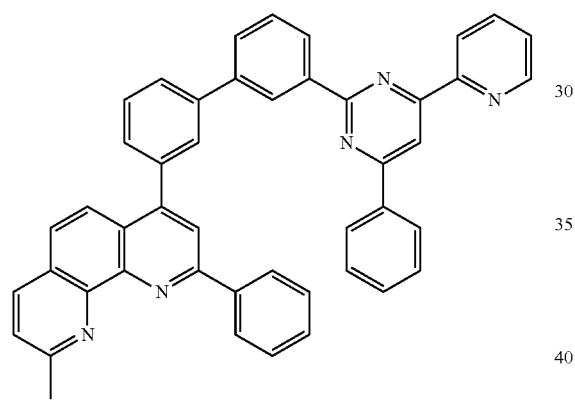
174
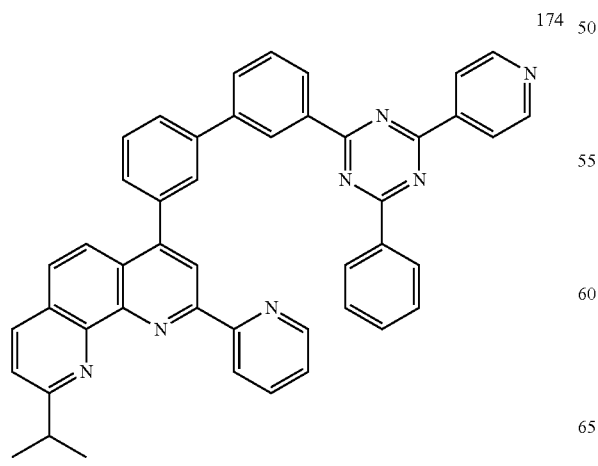
175
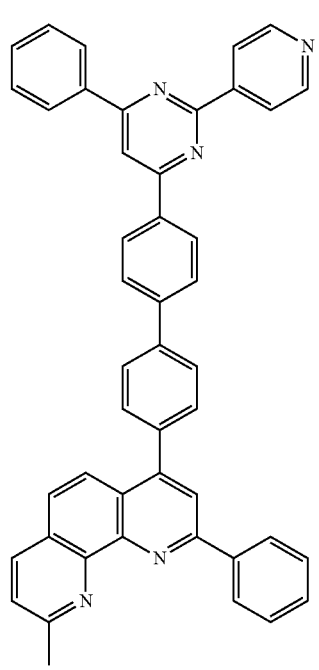
176
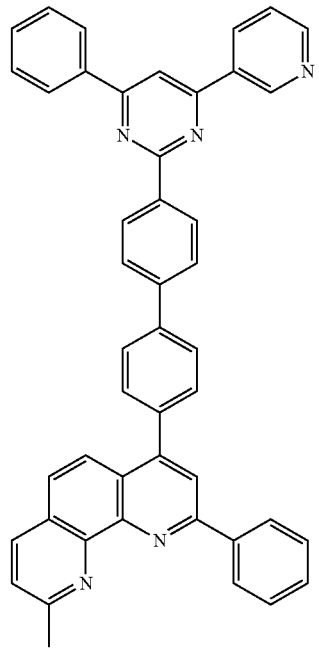

111
-continued
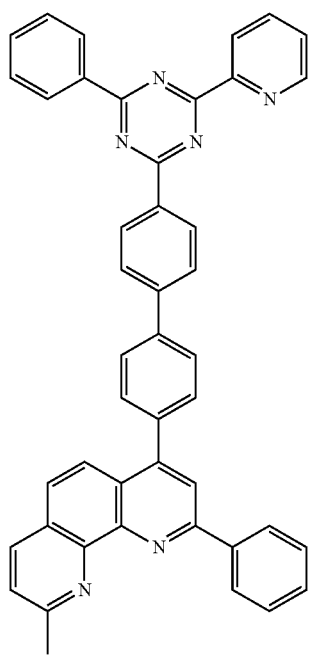
112
-continued
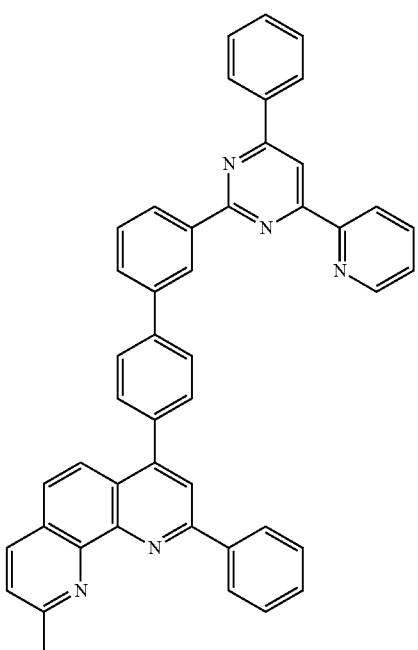
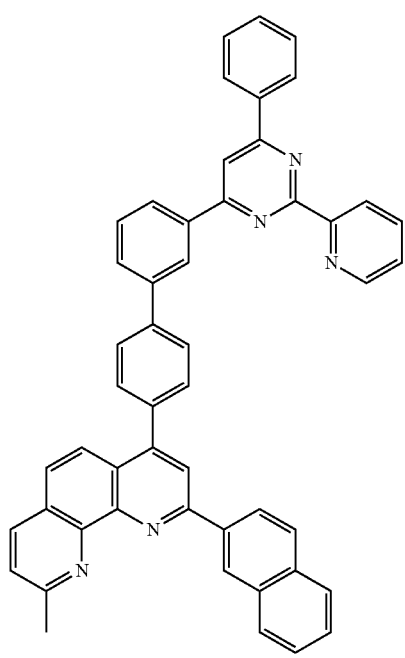
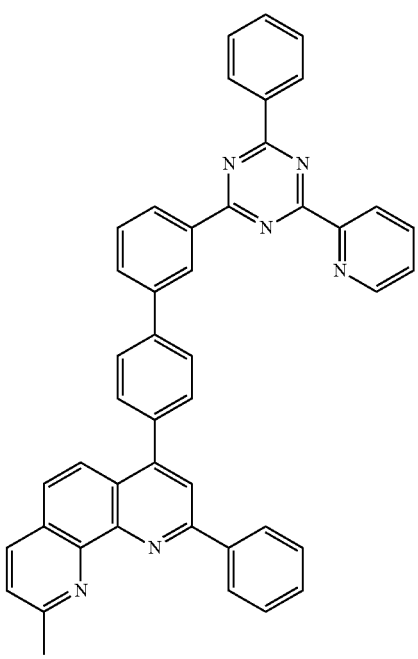

113
-continued
181
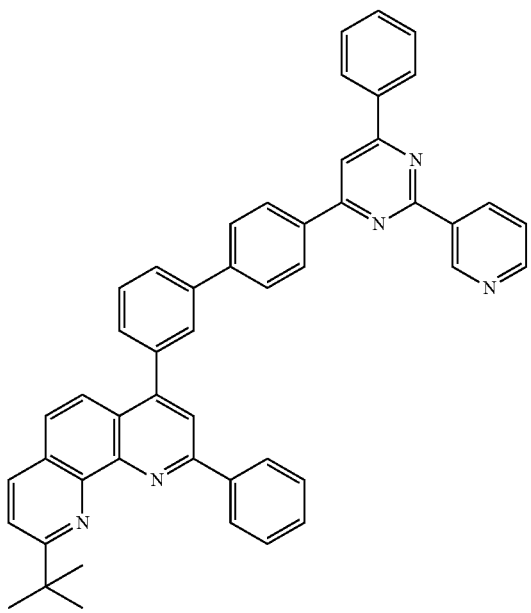
182
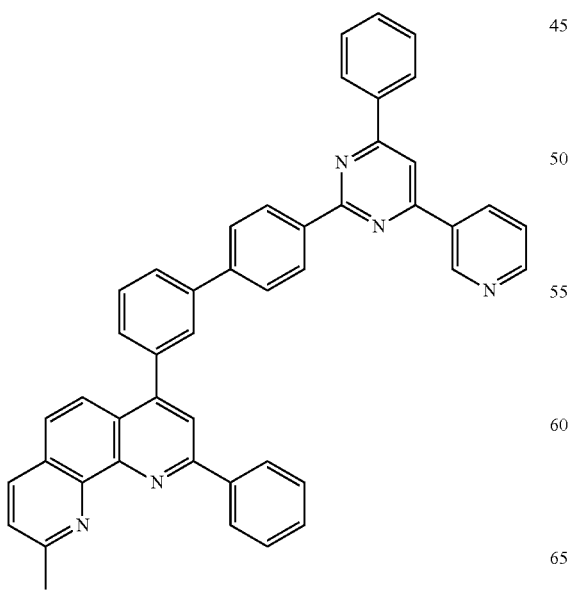
114
-continued
183
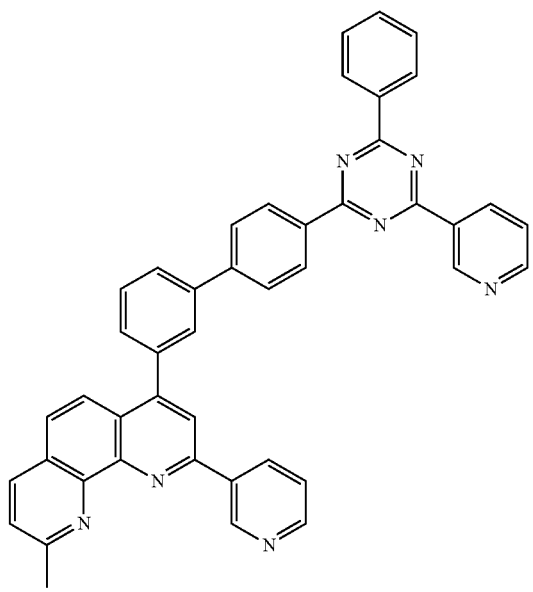
184
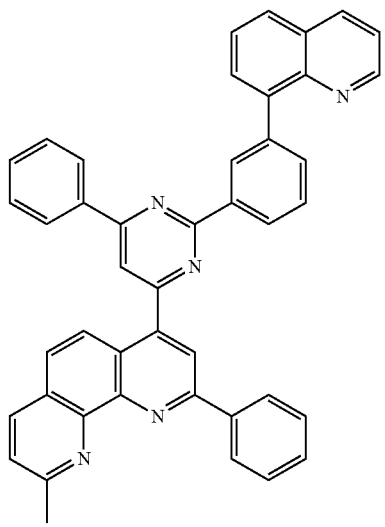

185
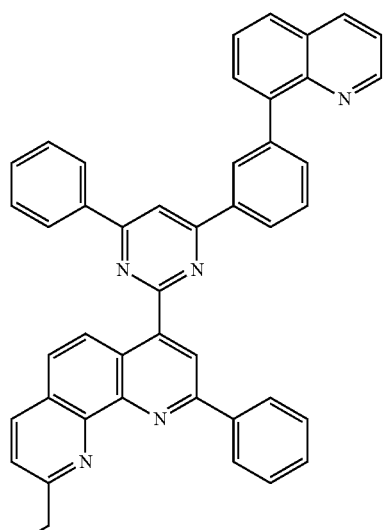
186
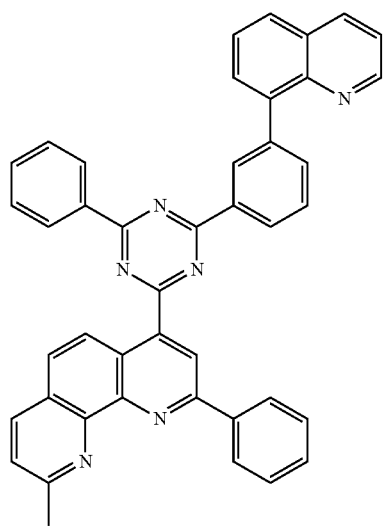
187
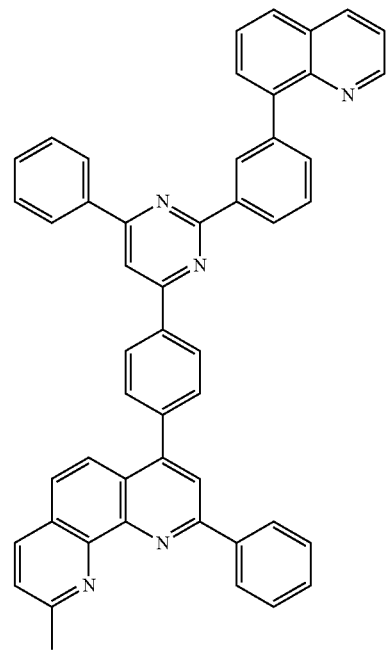
188
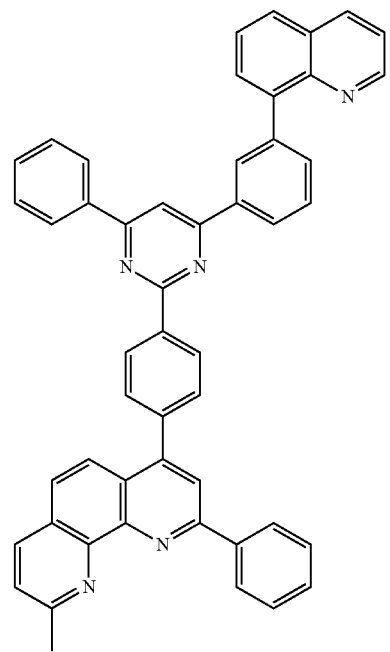

189
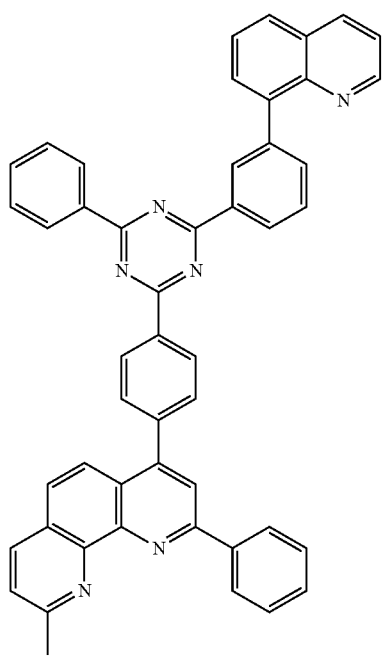
190
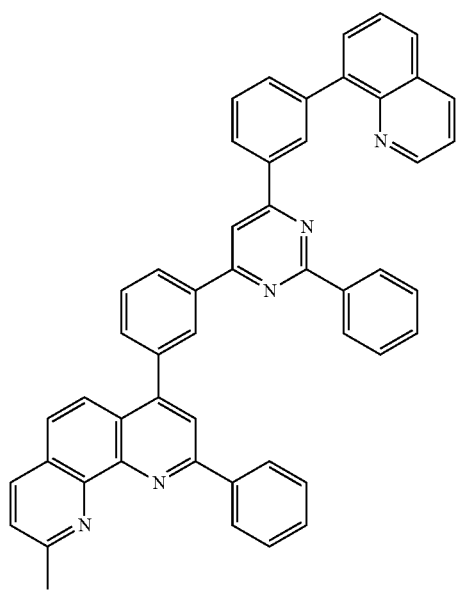
191
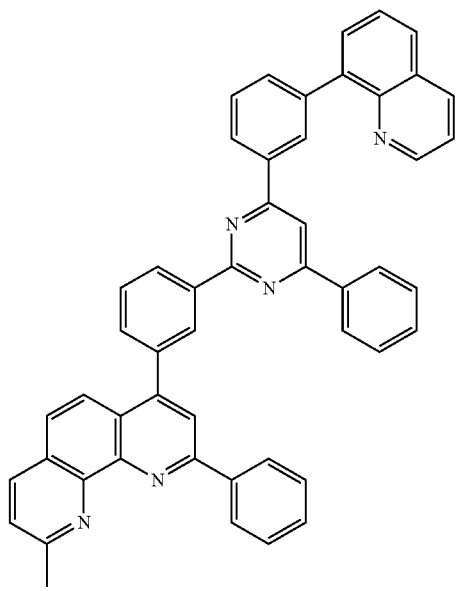
192
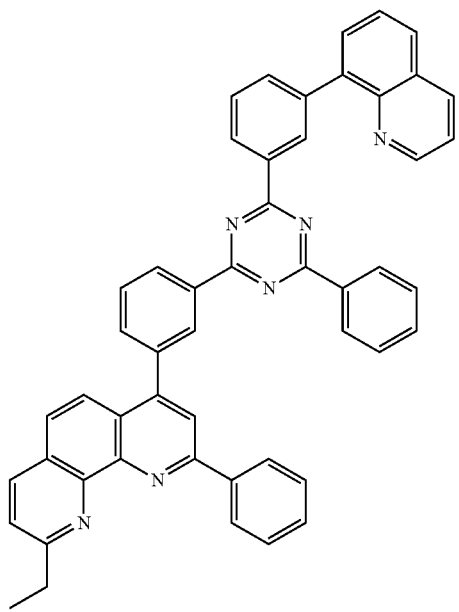

193
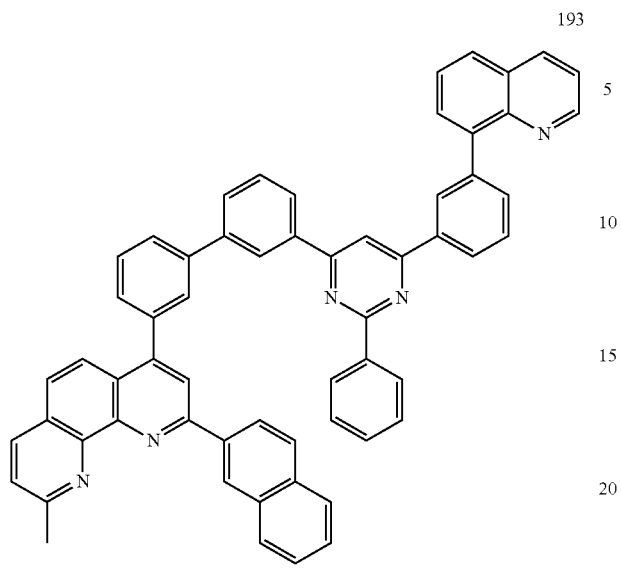
194
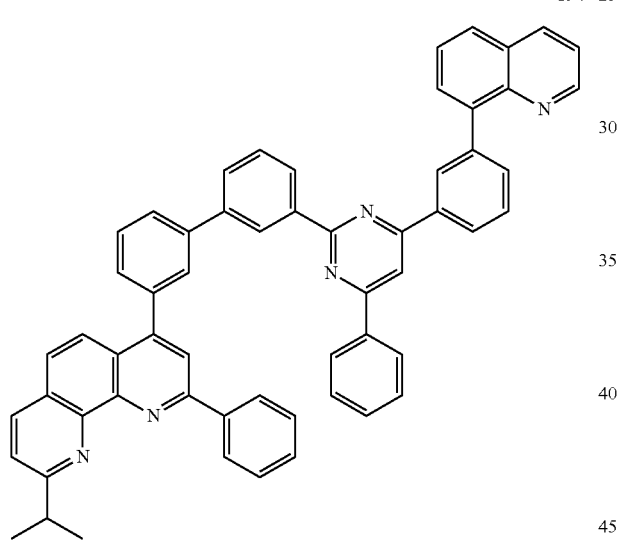
195
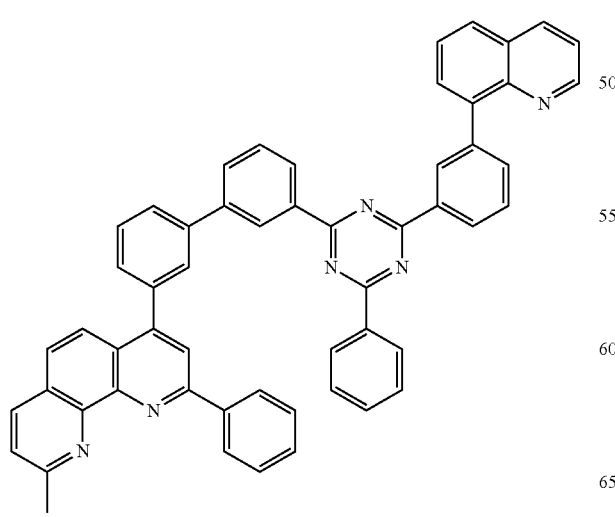
196
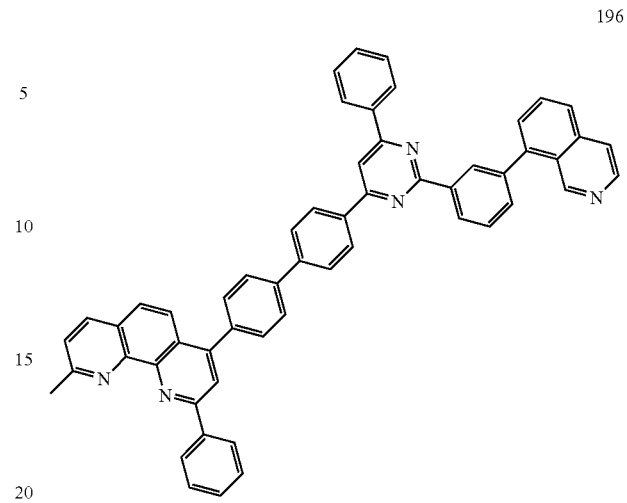
197
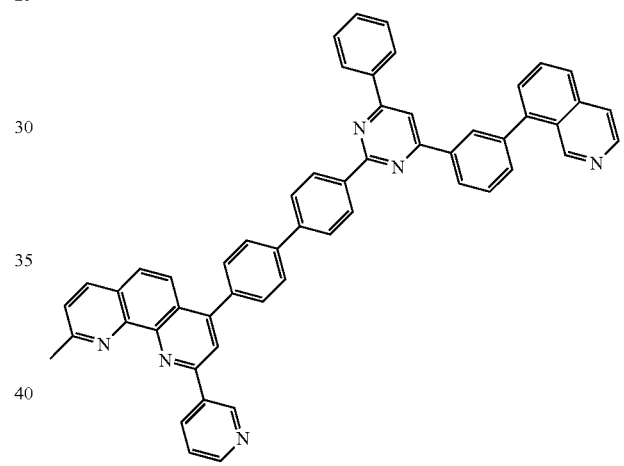
198
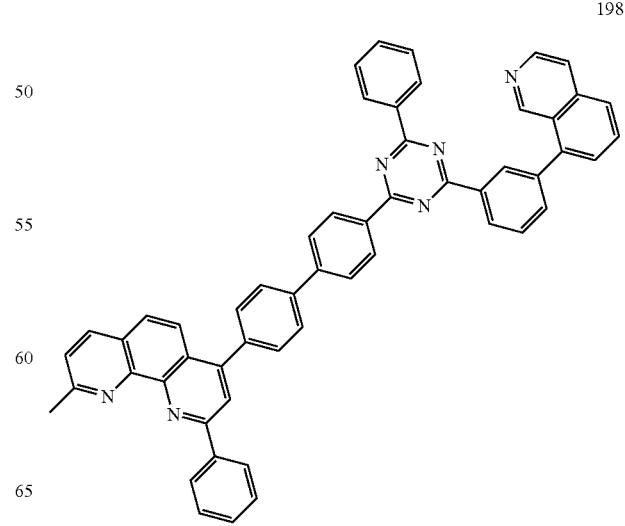

199
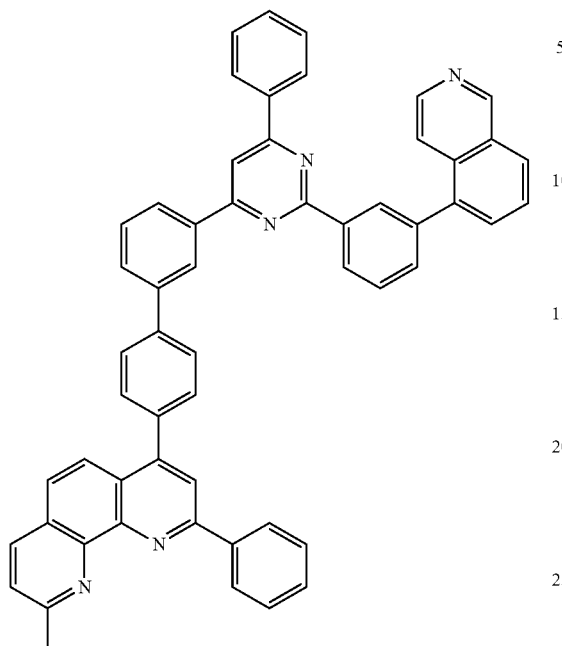
201
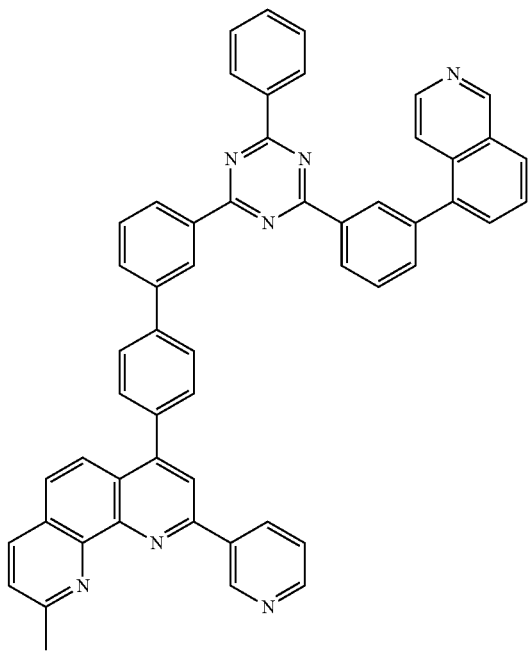
200
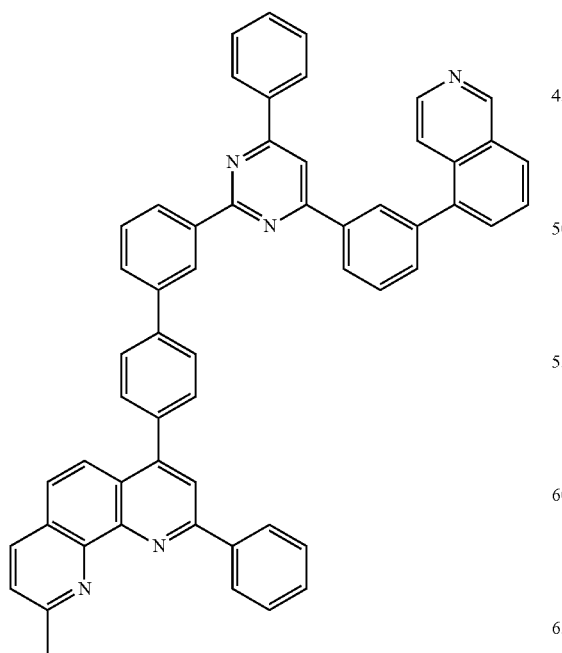
202
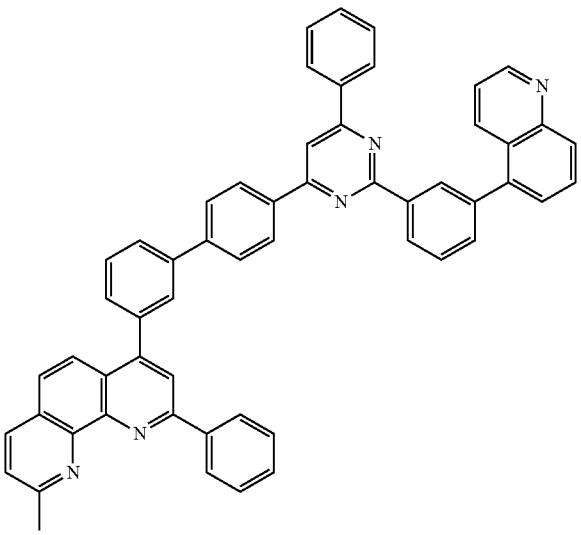

203
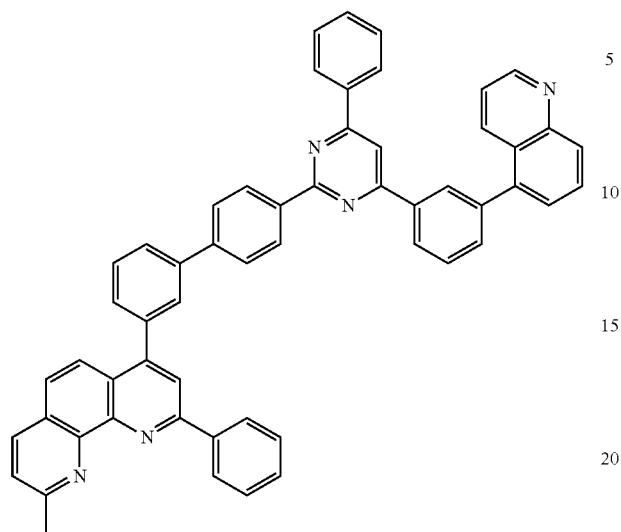
204
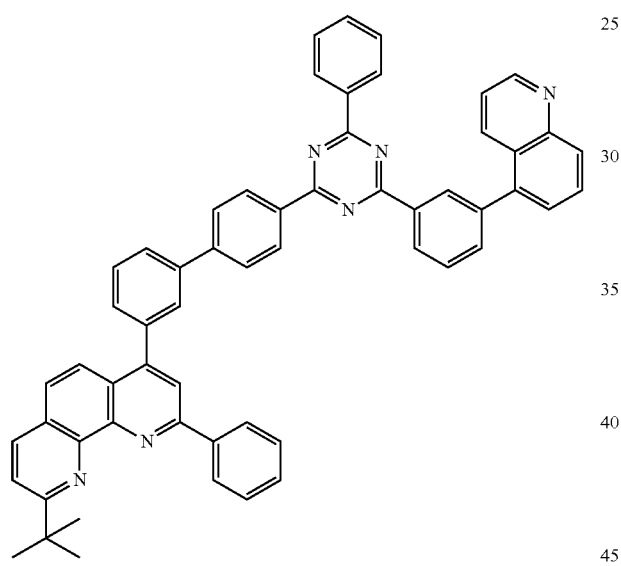
205
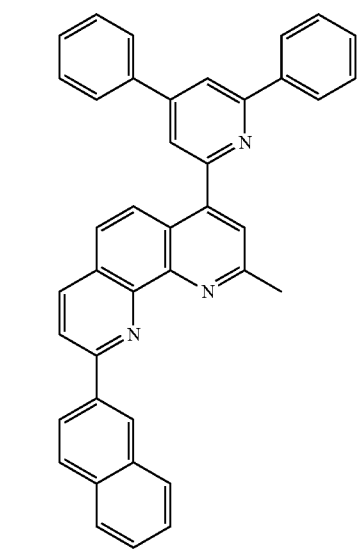
206
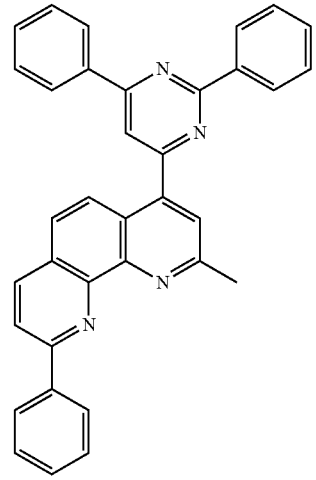
207
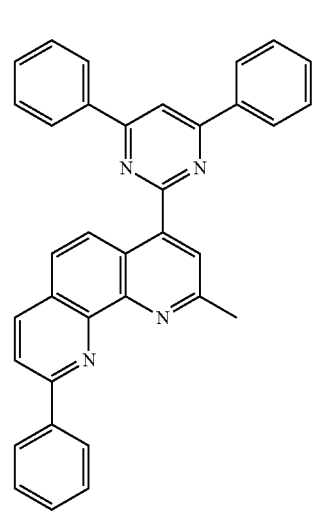
208

125
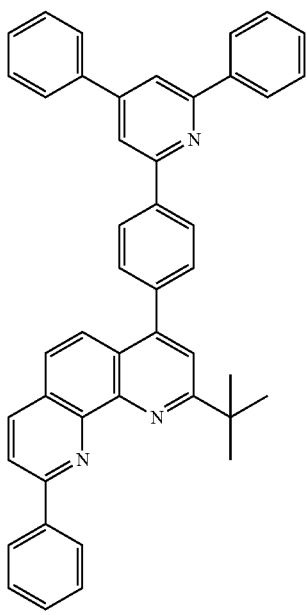
209
126
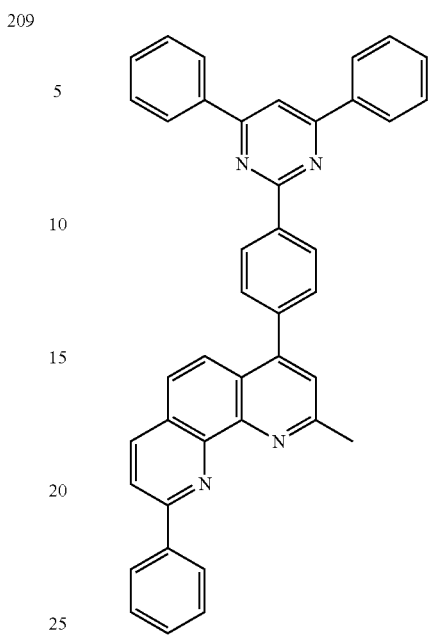
211
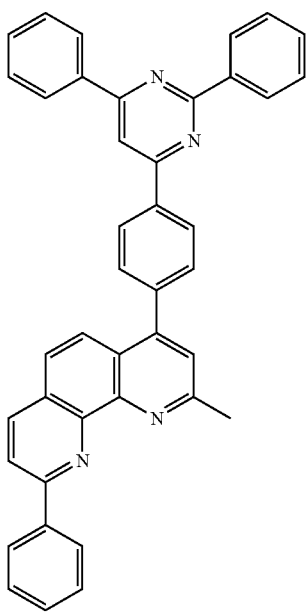
210
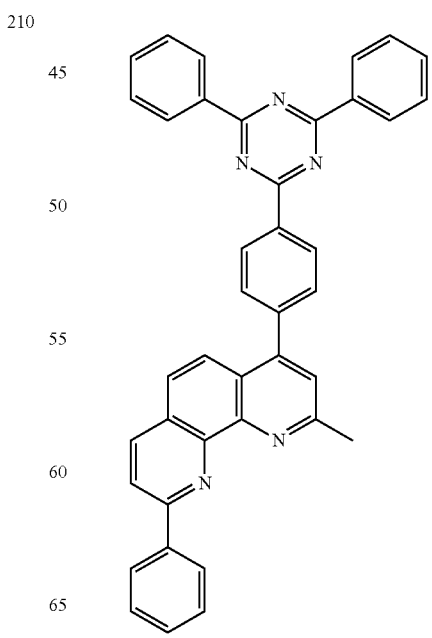
212

213
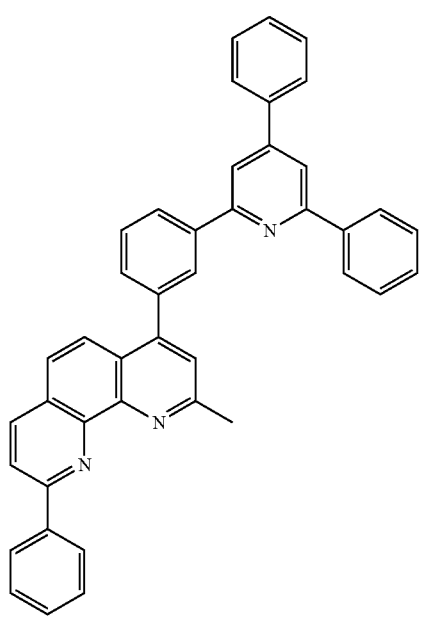
214
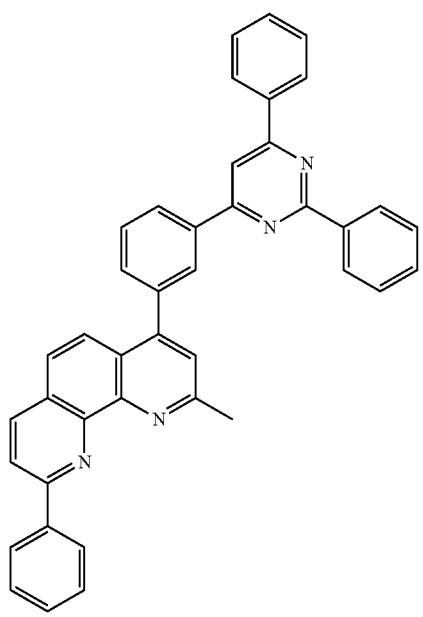
215
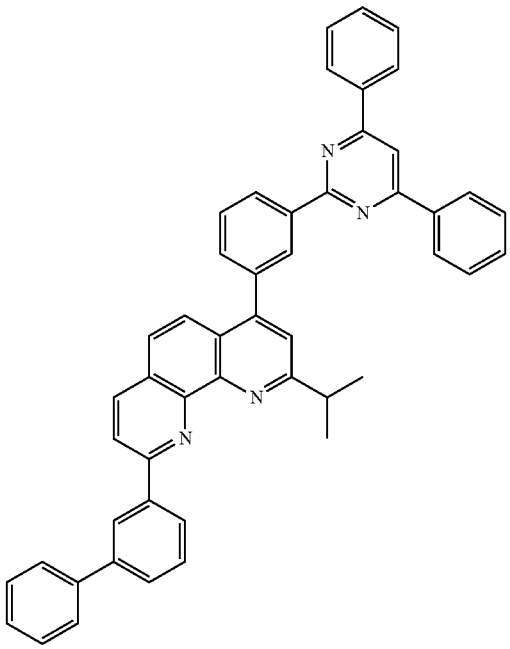
216
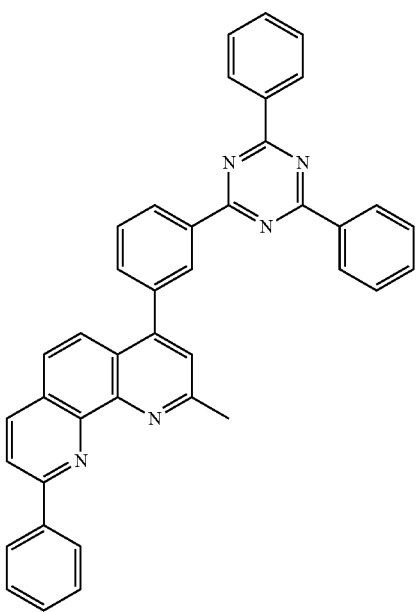

217
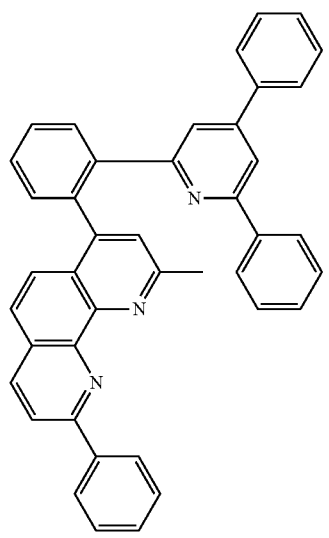
218
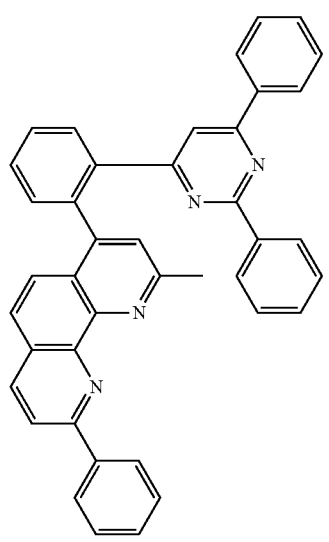
219
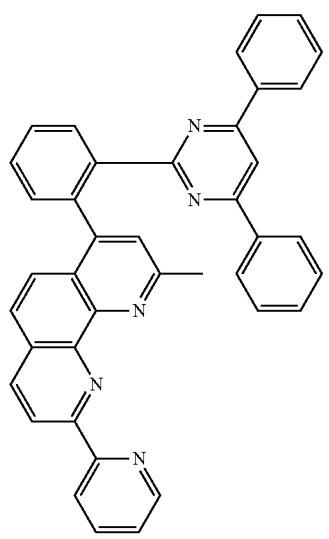
220
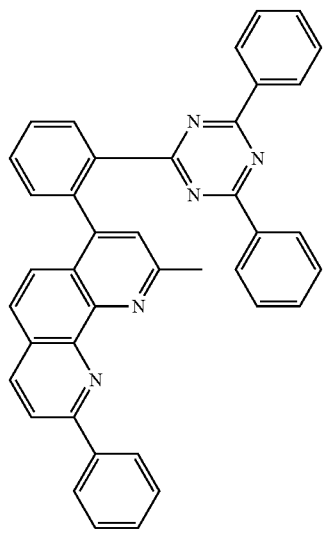
221
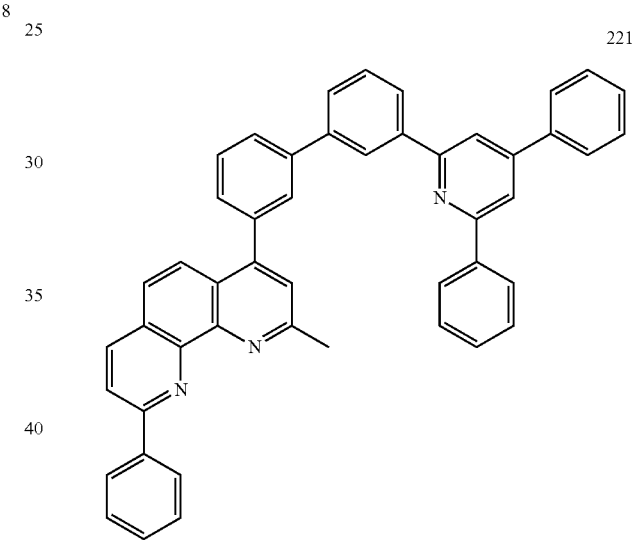
222
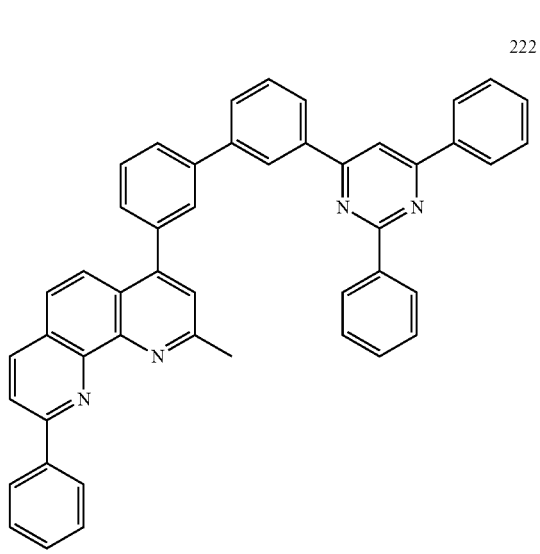

131
-continued
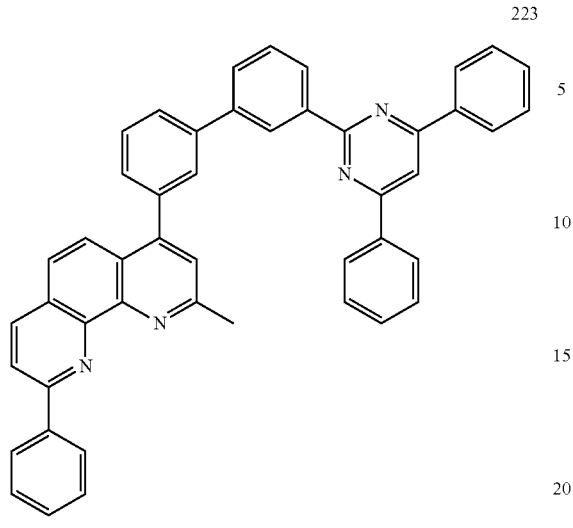
223
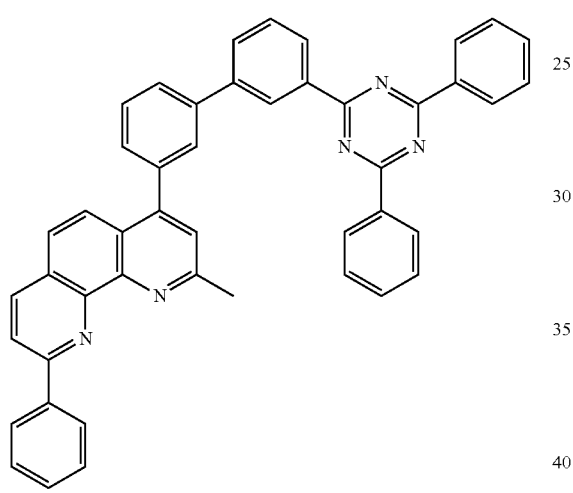
224

225
132
-continued
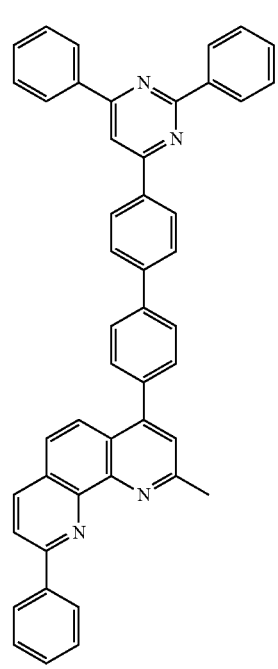
226
227

133
-continued
228
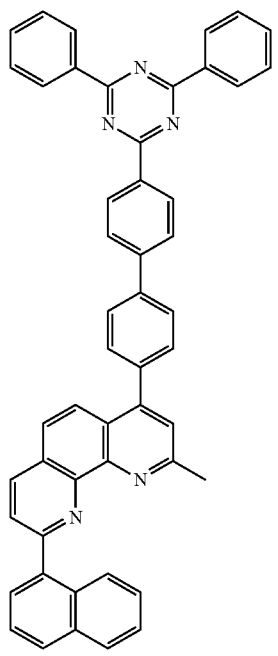
134
-continued
230
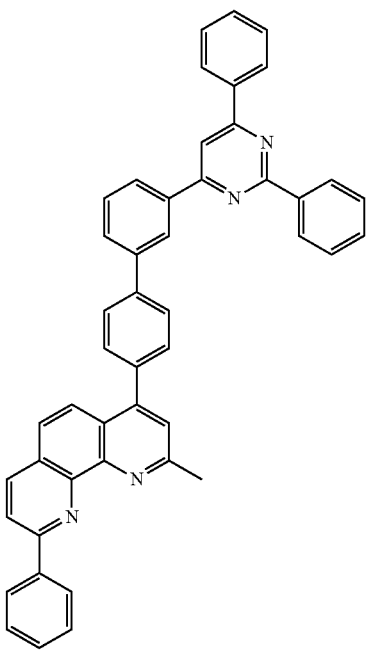
229
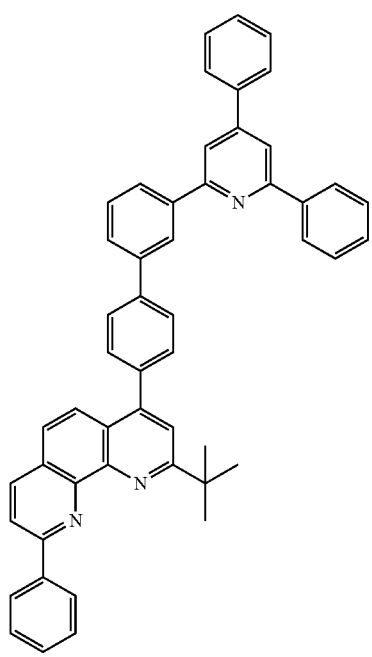
231
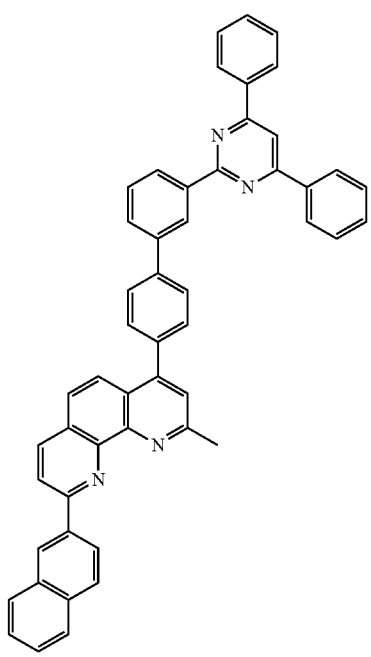

232
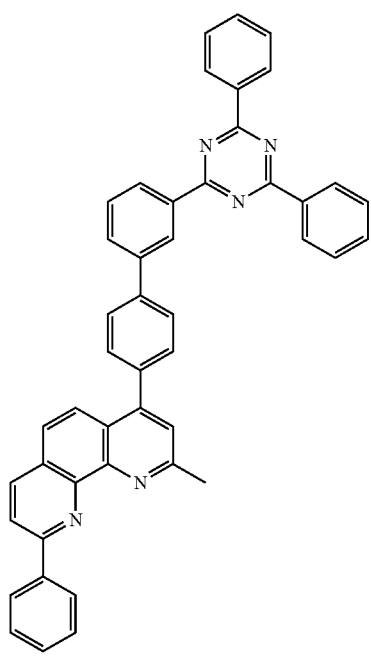
233
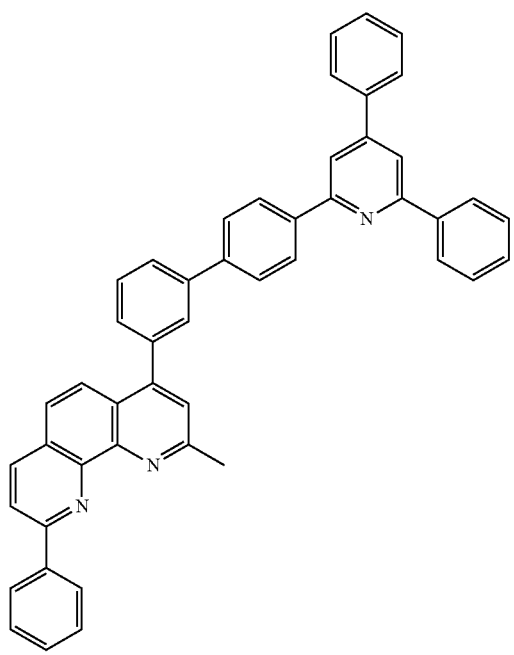
234
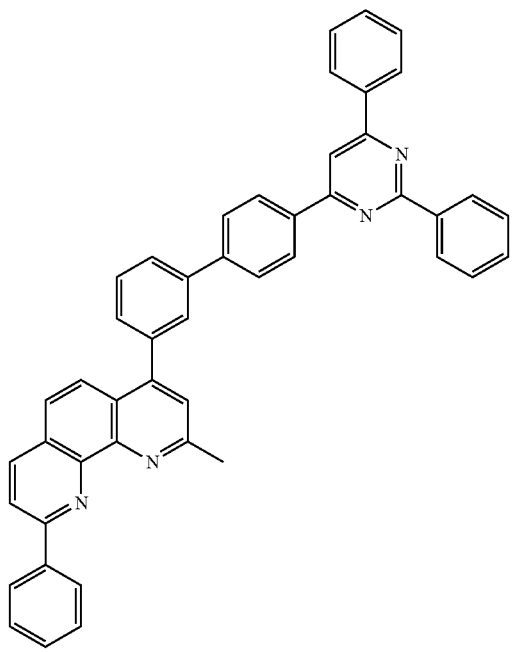
235
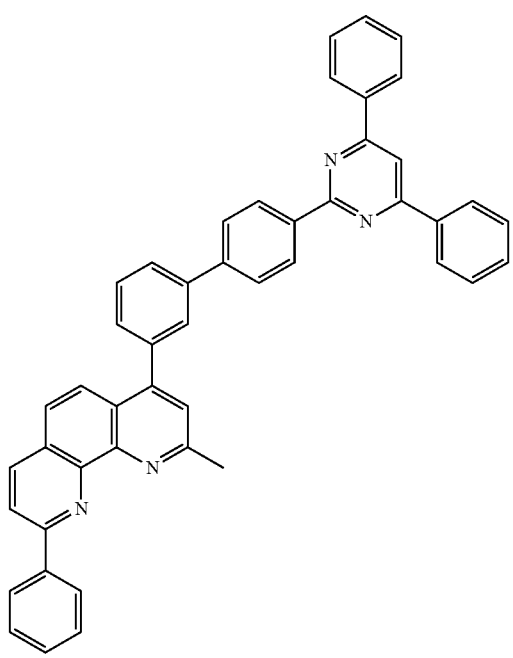

236
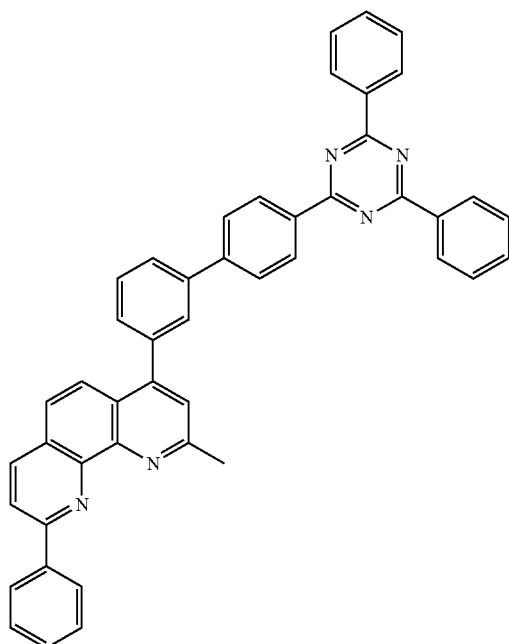
237
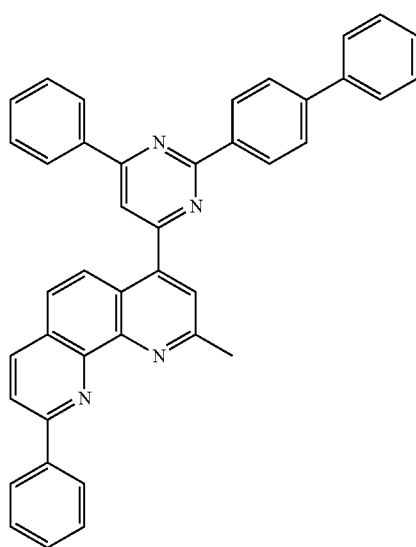
238
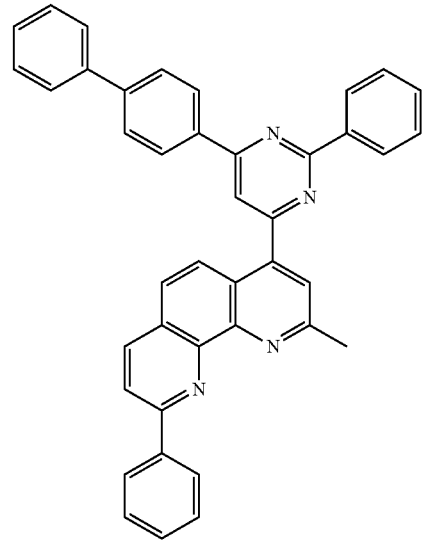
239
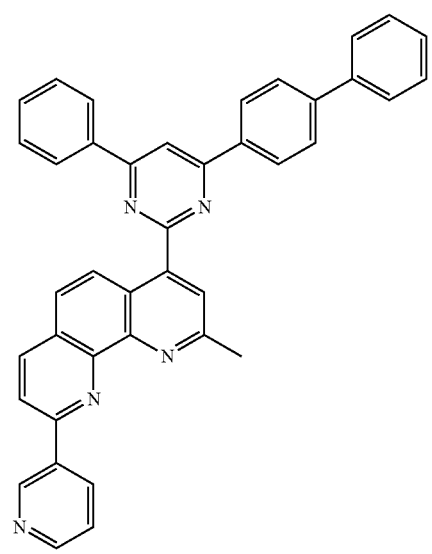
240
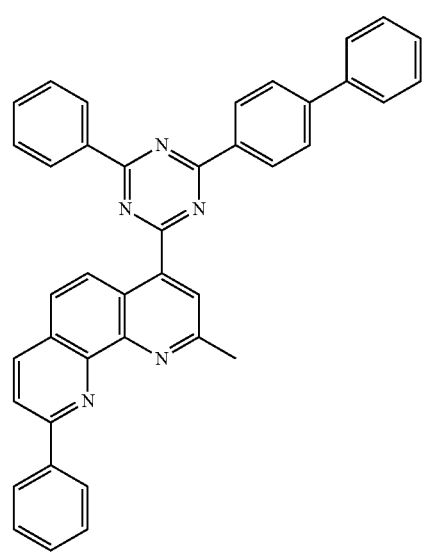

241
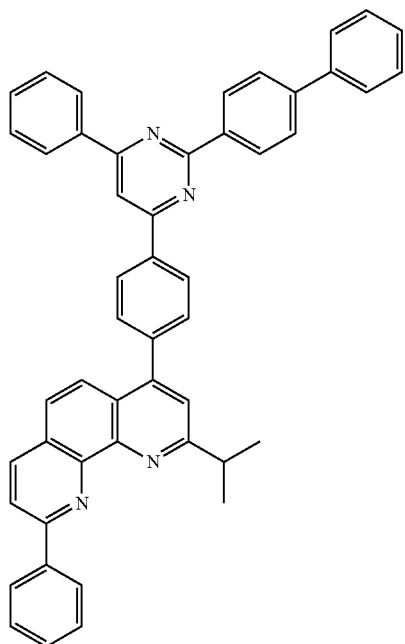
139
242
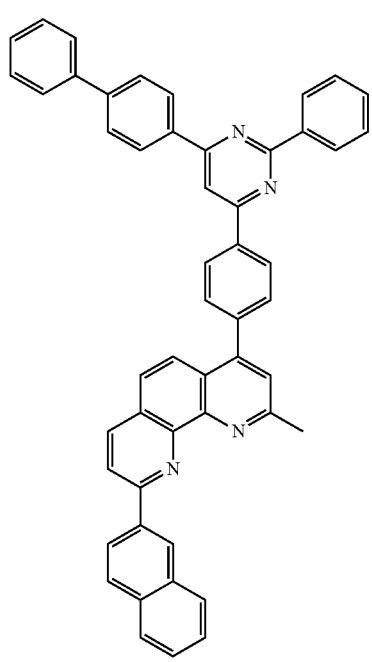
243
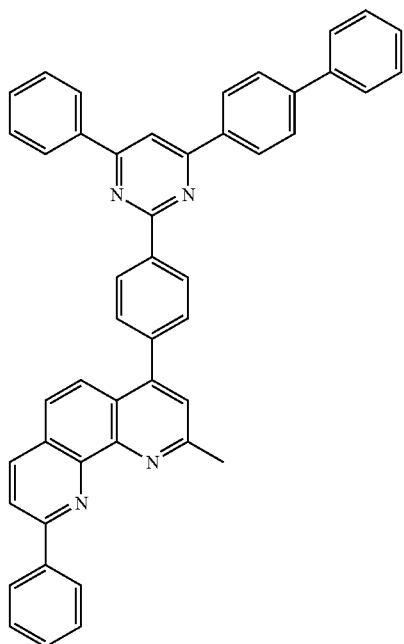
140
244
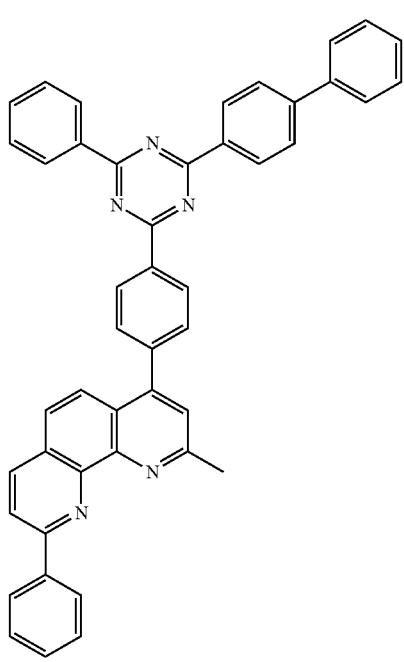

245
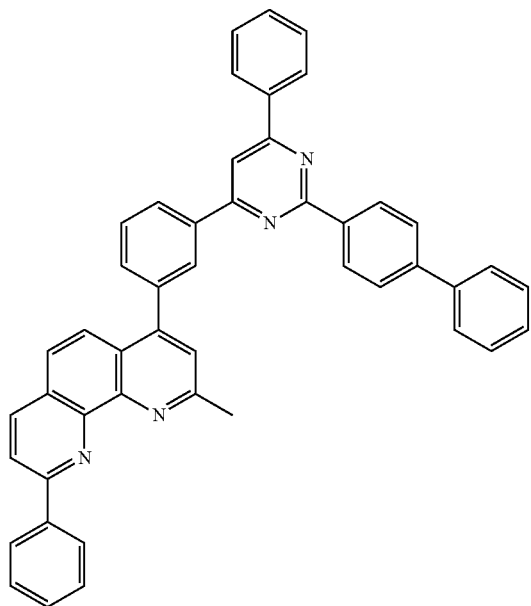
246
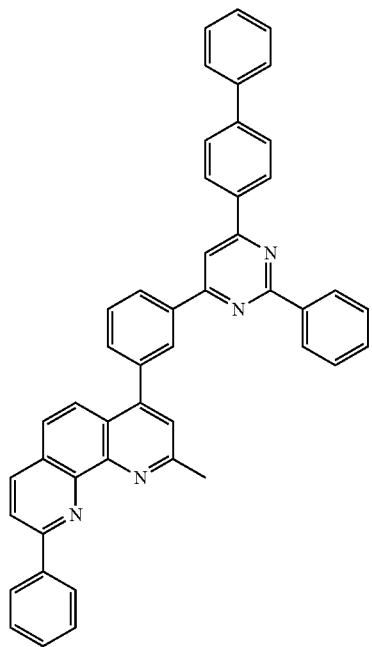
247
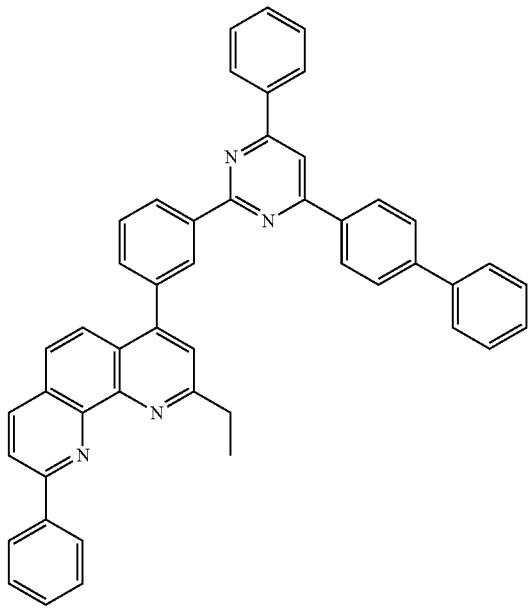
248
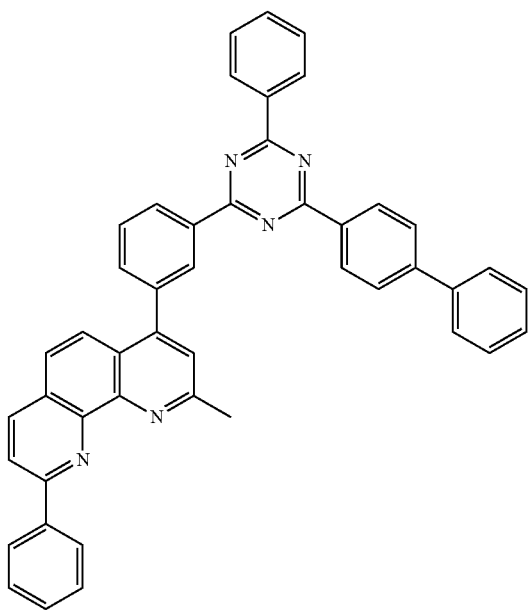

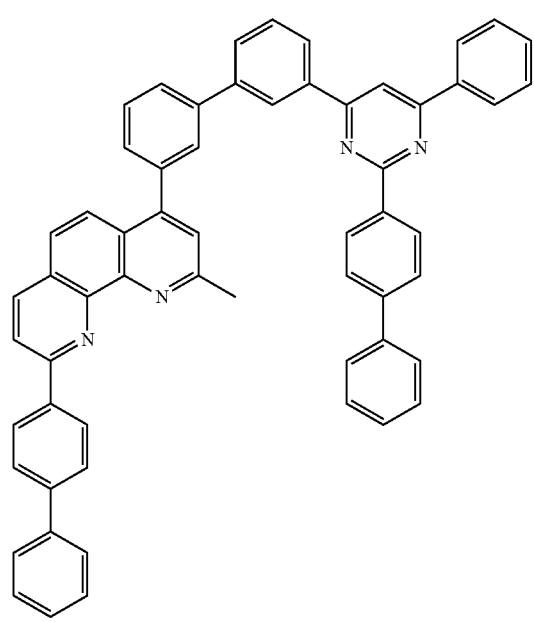
249
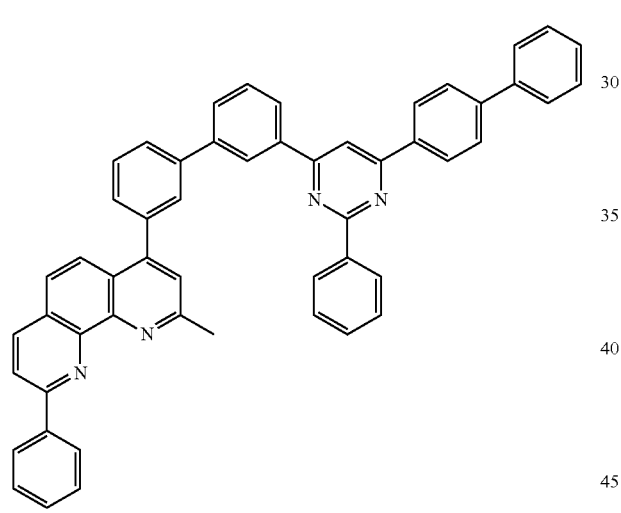
250
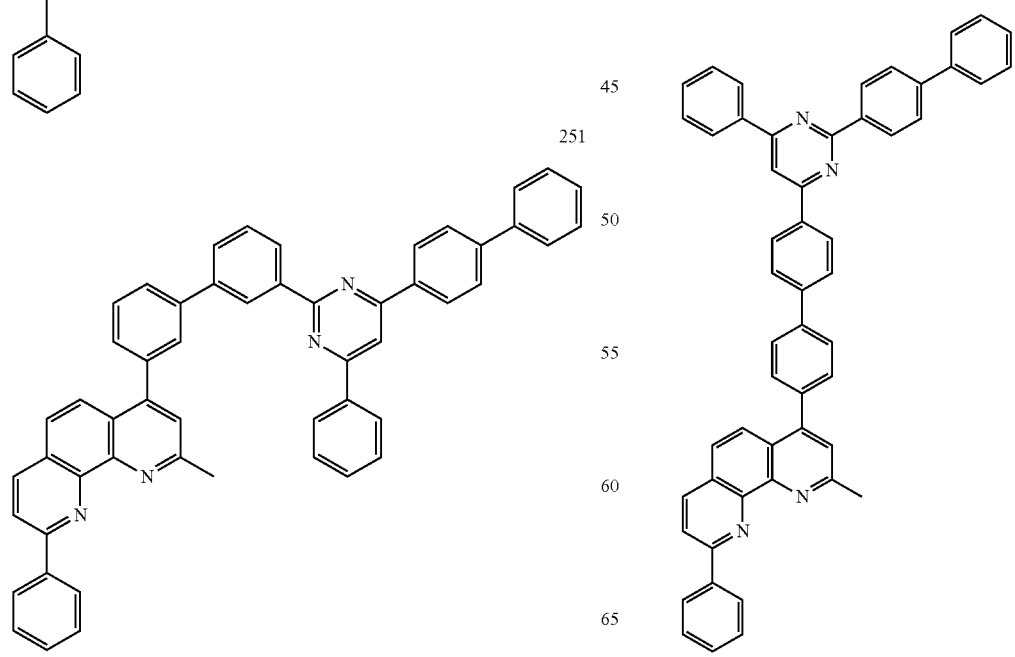
251
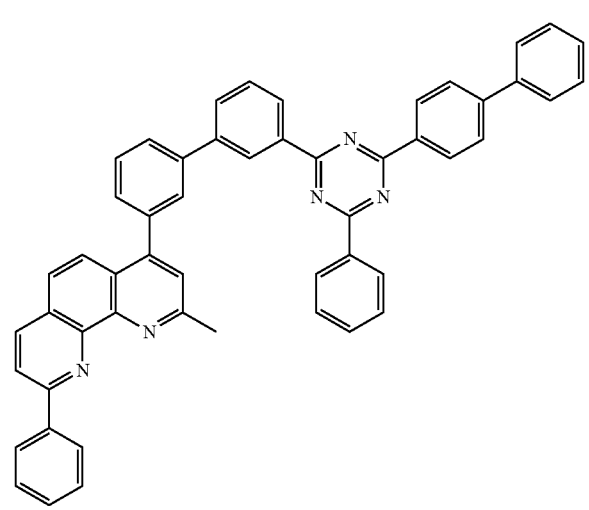
252
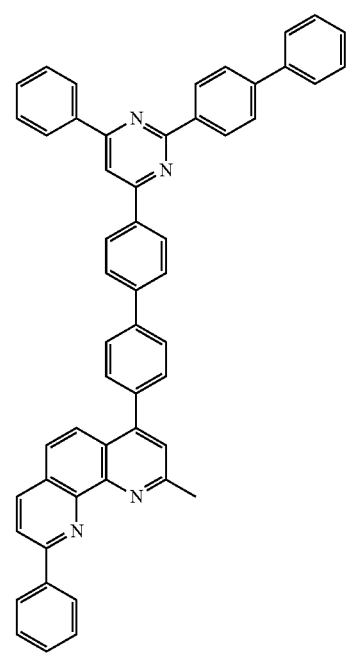
253

254
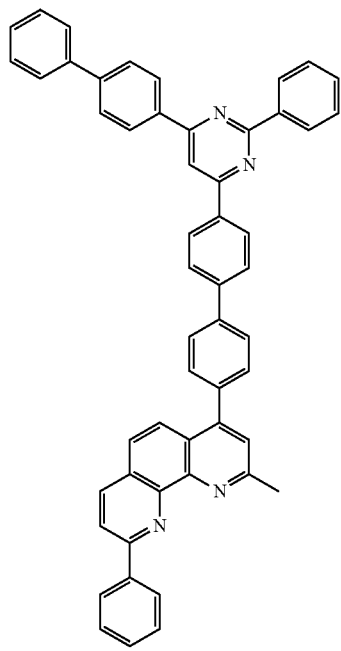
255
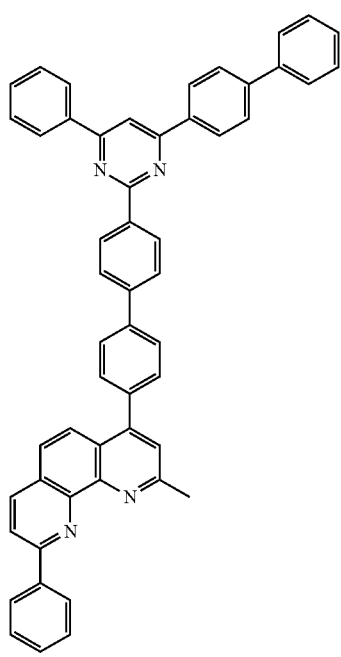
256
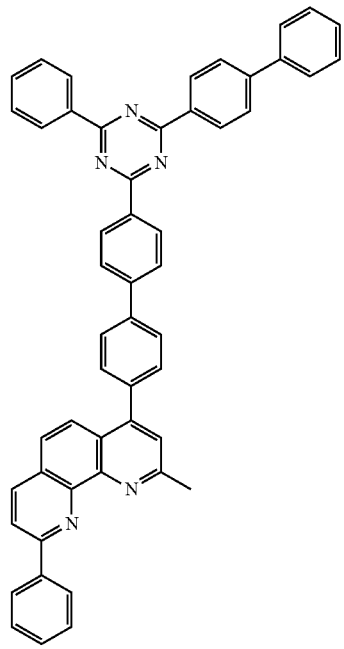
257
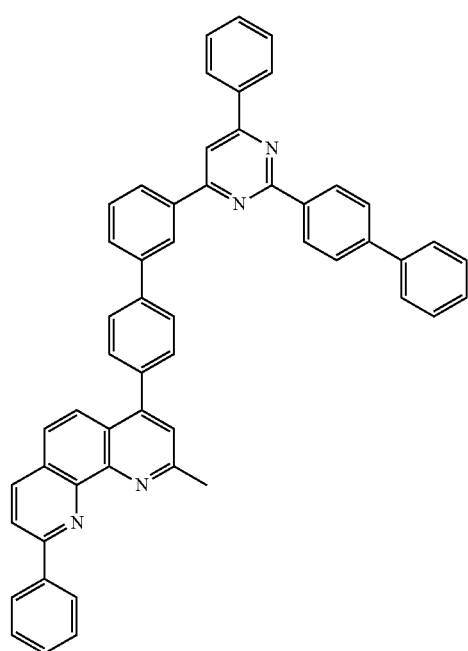

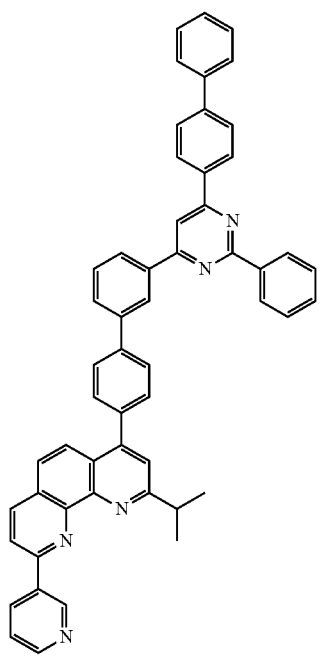
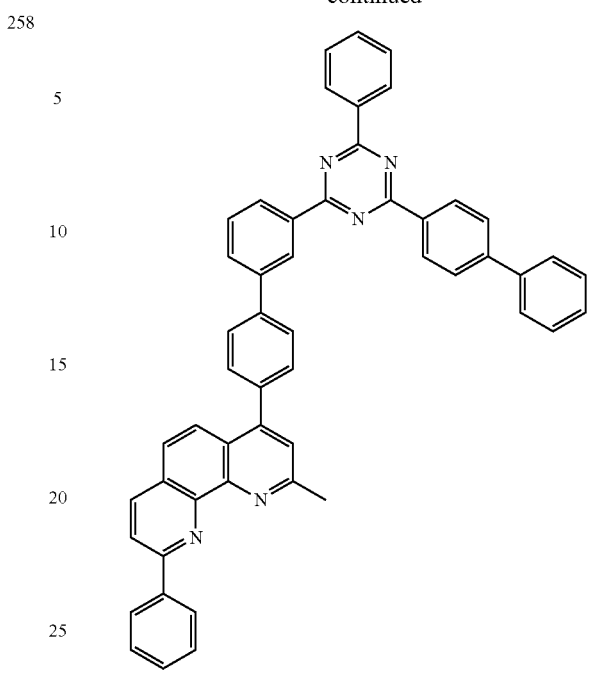
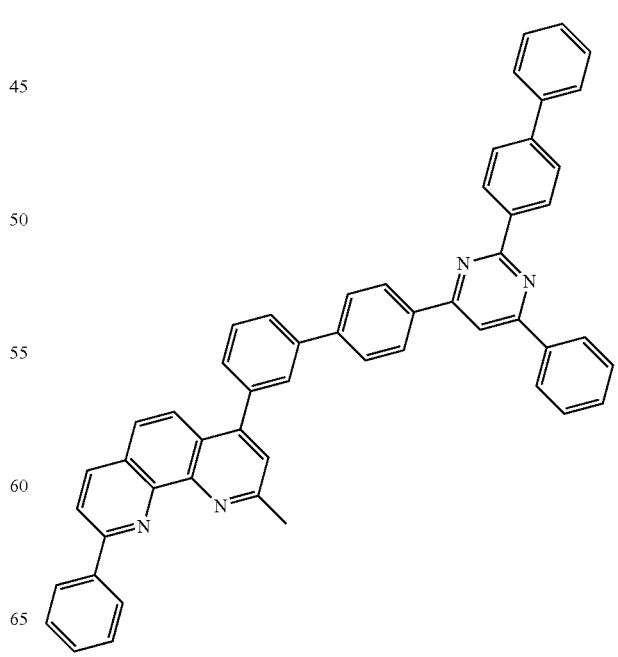

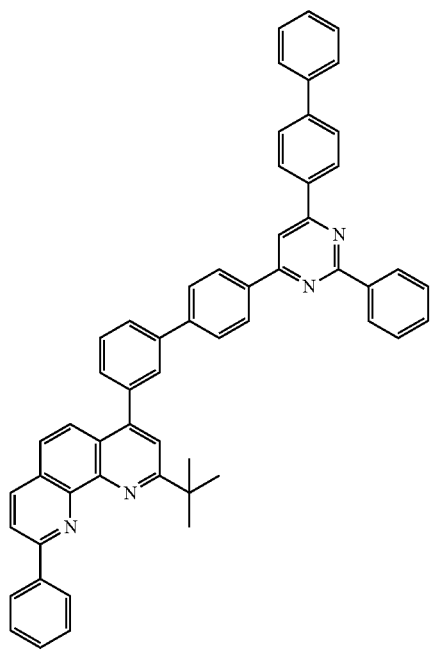
262
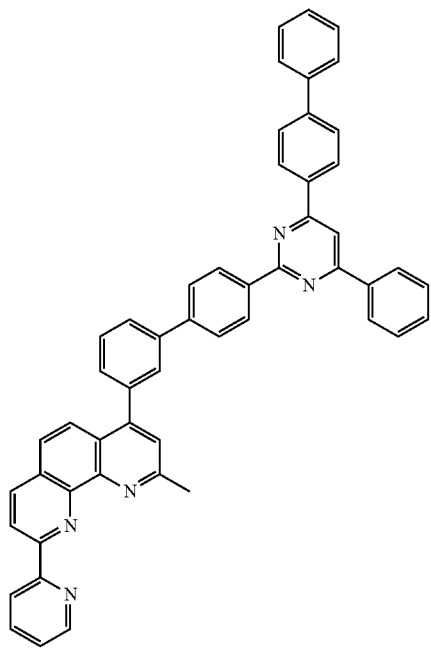
263
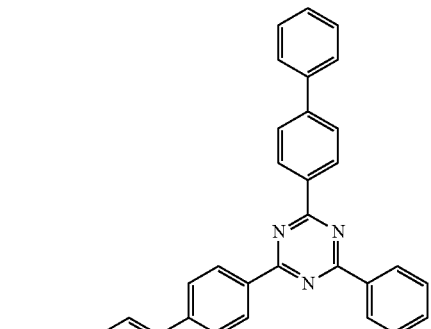
264
265
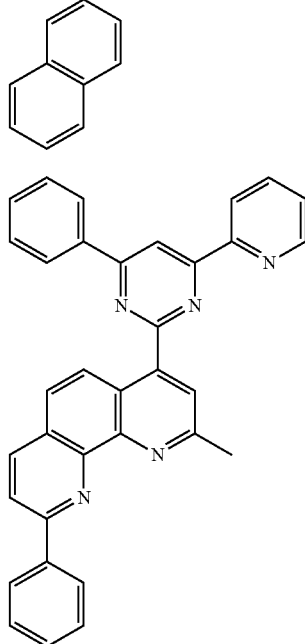
266

151
-continued
267
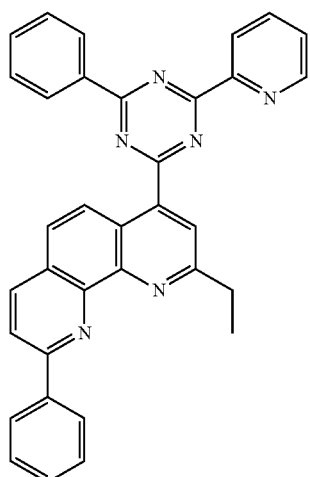
152
-continued
269
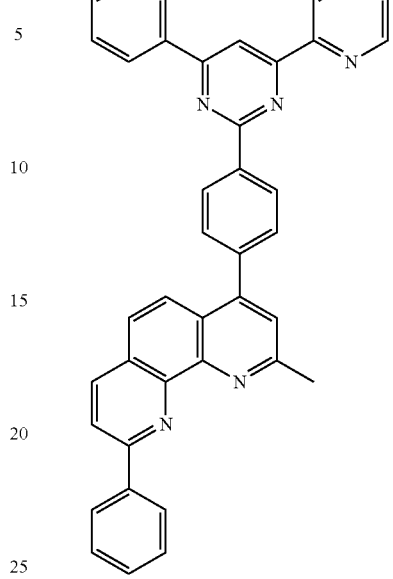
268
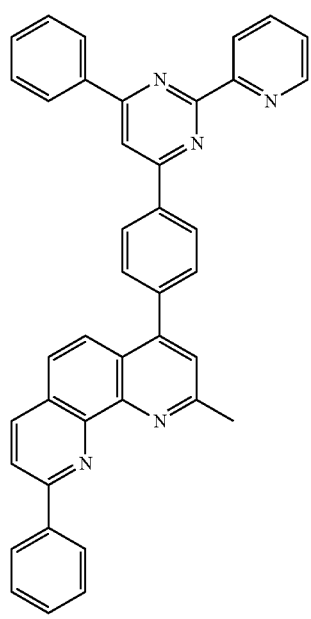
270
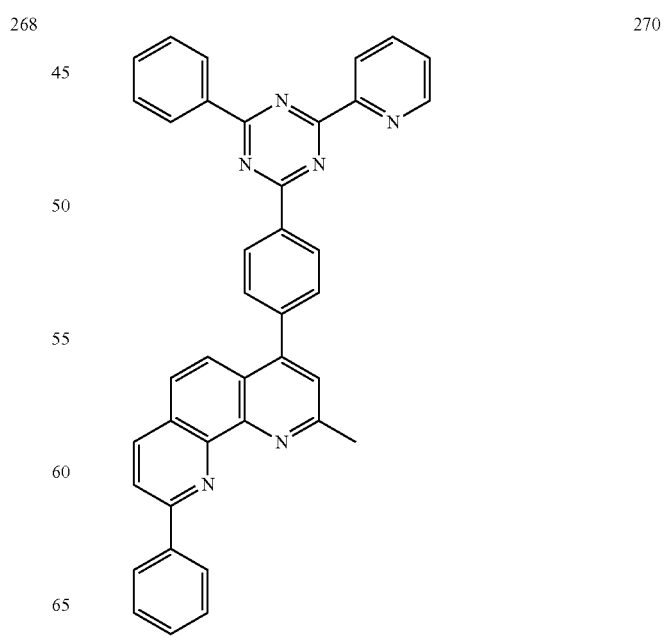

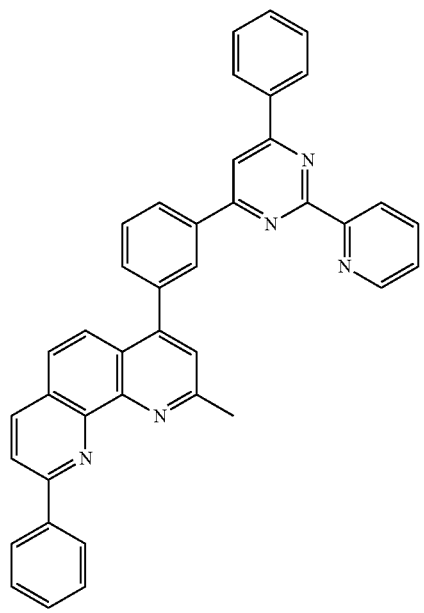
271
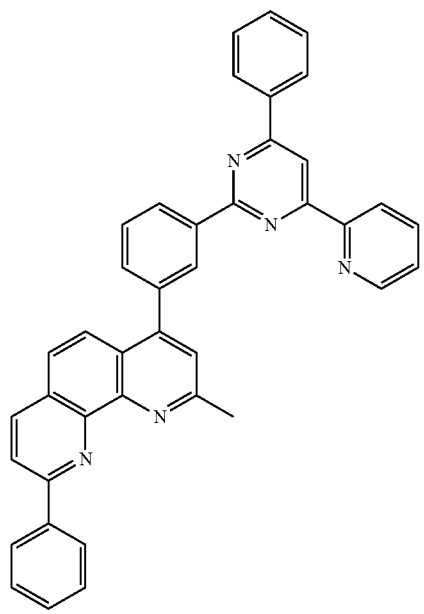
272
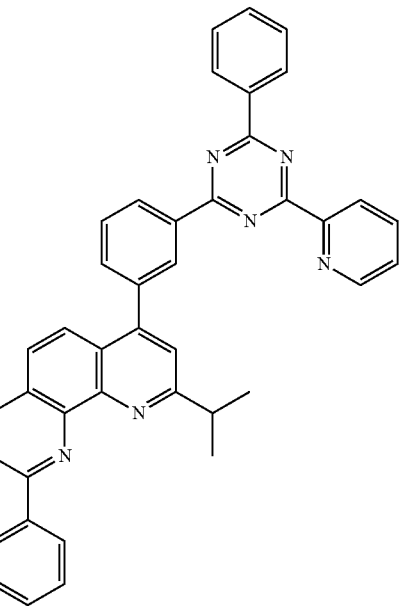
273
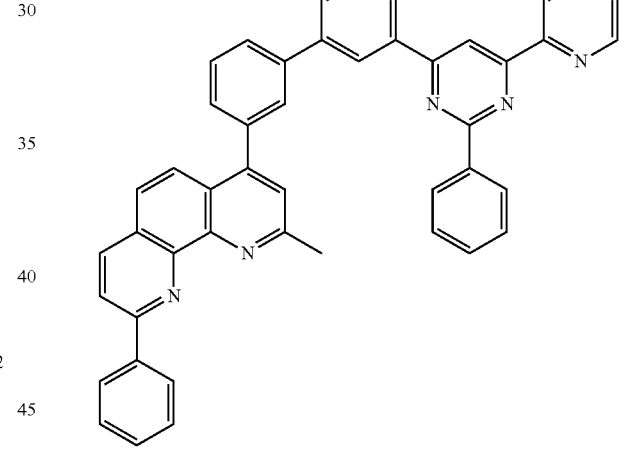
274
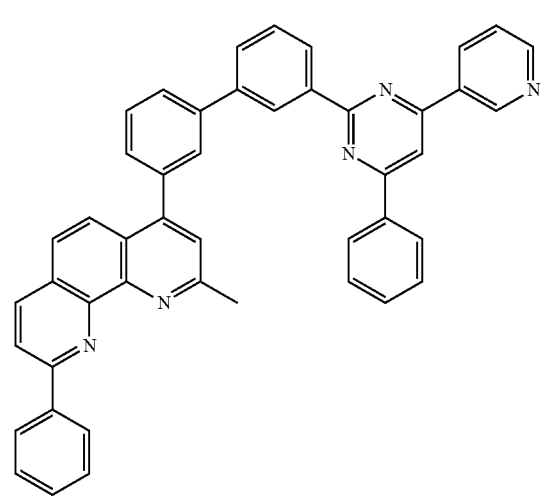
275

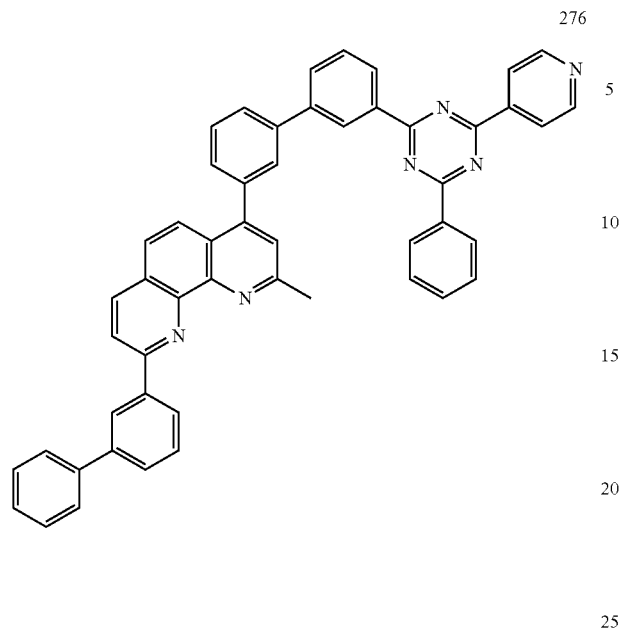
276
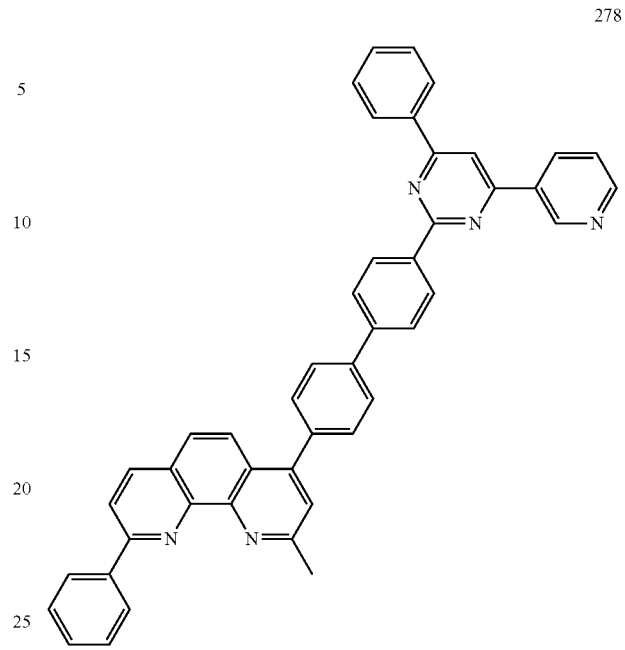
278
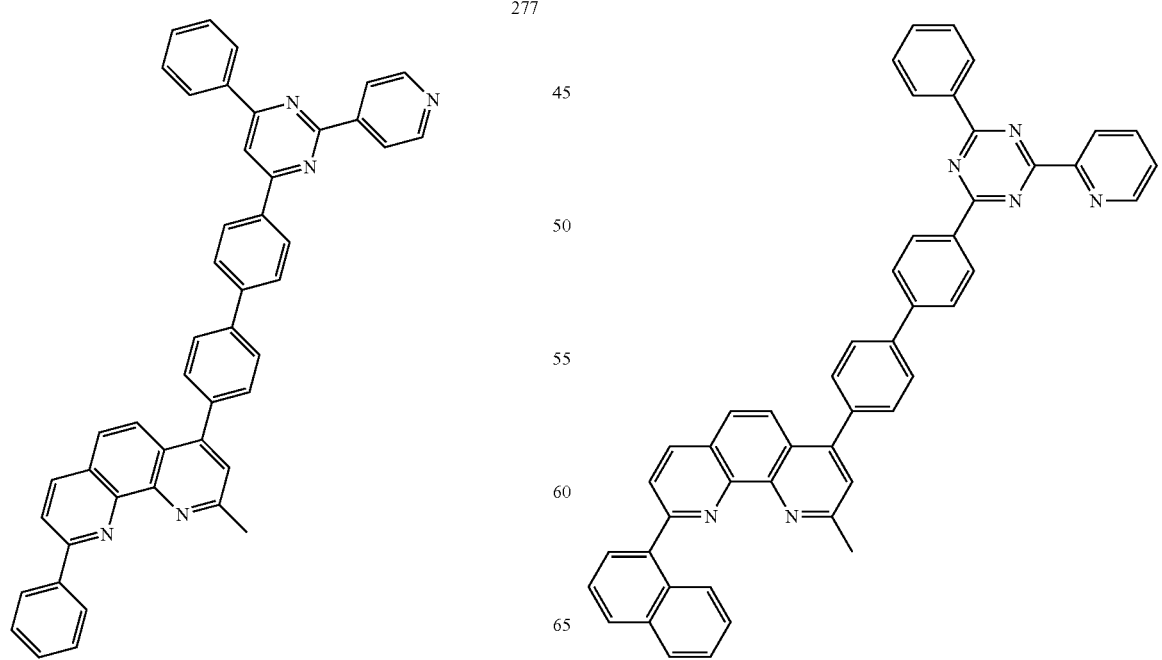
277
279

280
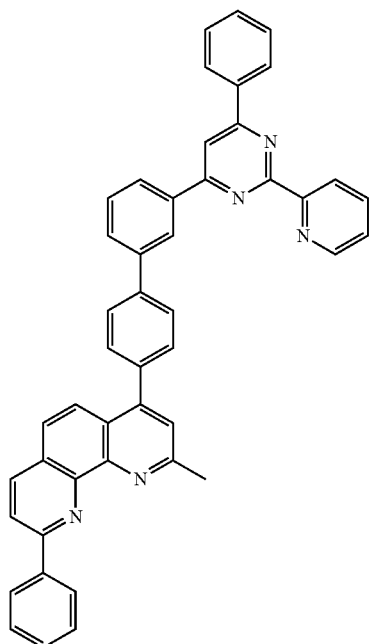
281
282
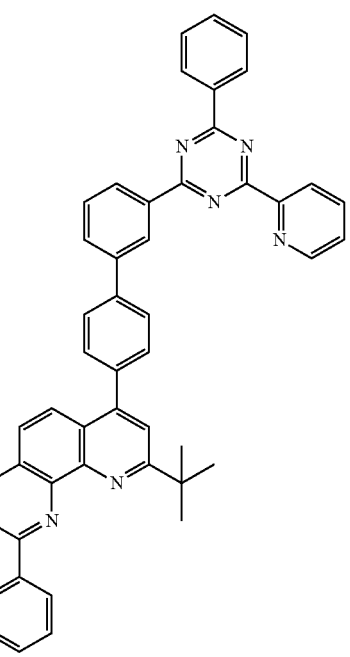
283

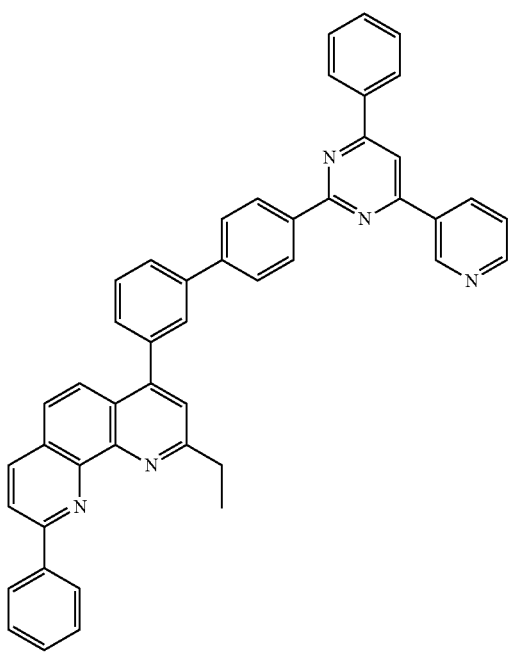
284
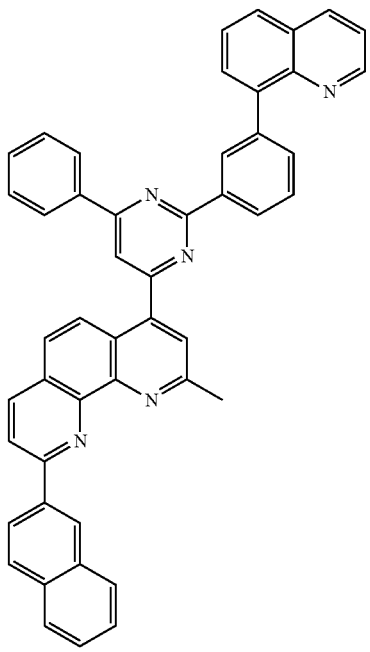
286
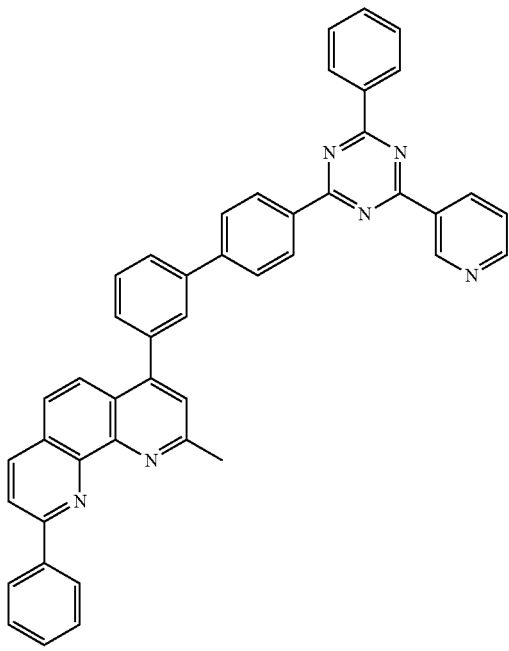
285
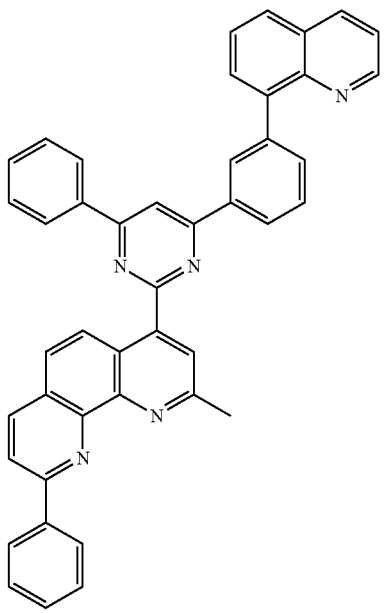
287

161
-continued
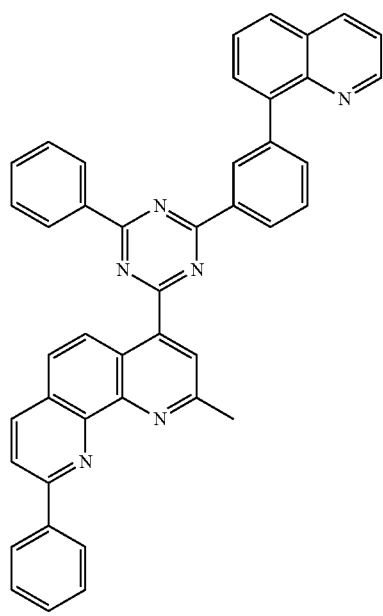
288
162
-continued
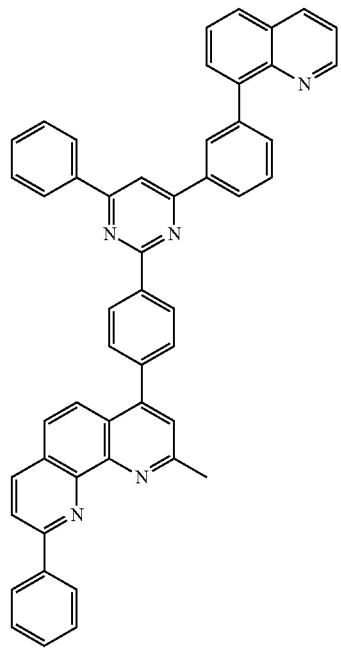
290
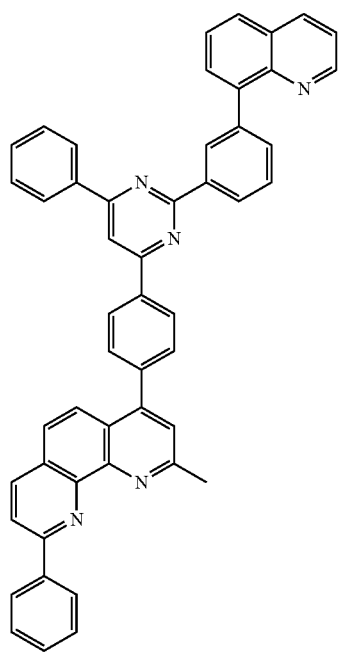
289
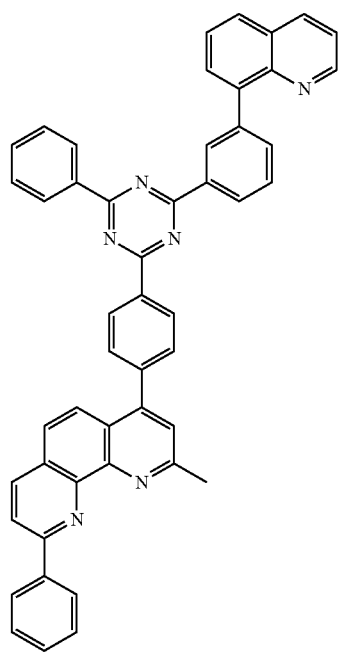
291

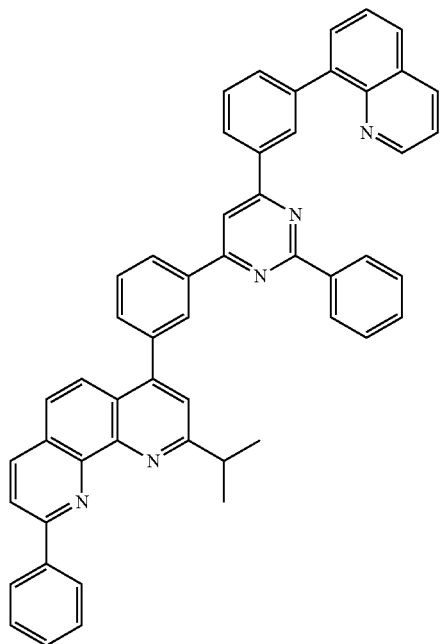
292
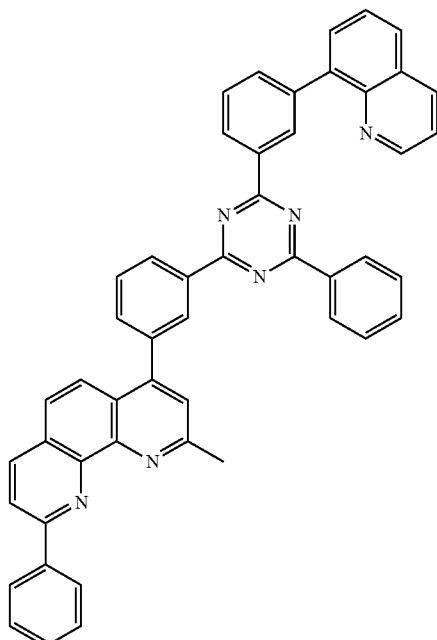
294
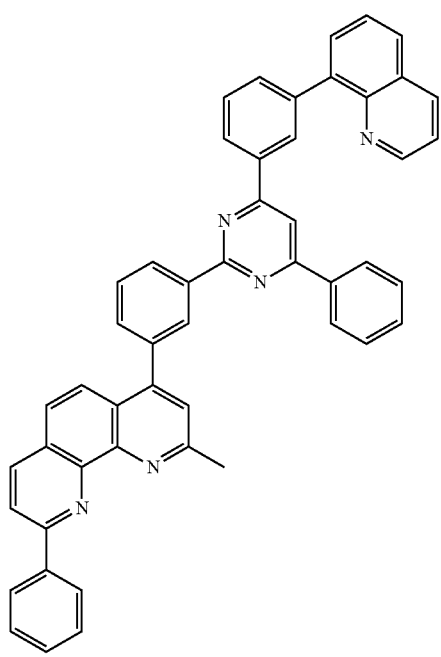
293
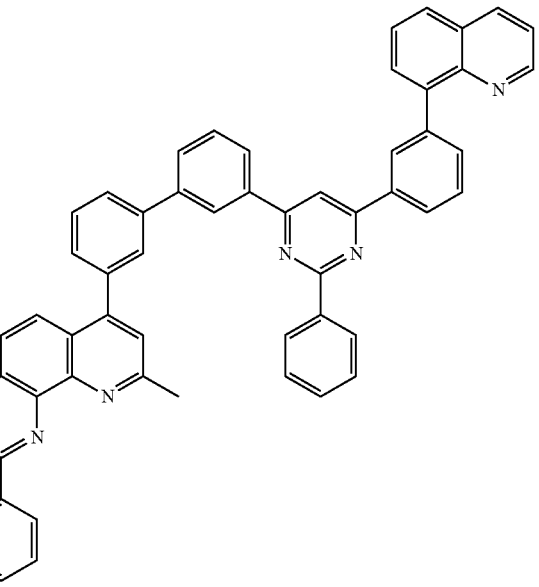
295

296
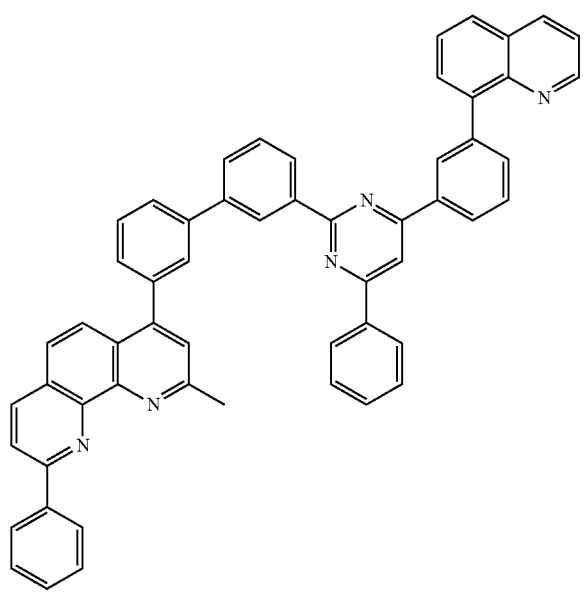
297
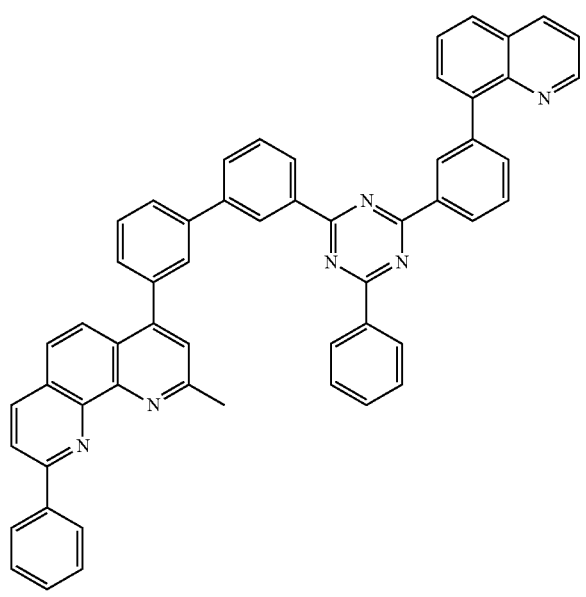
298
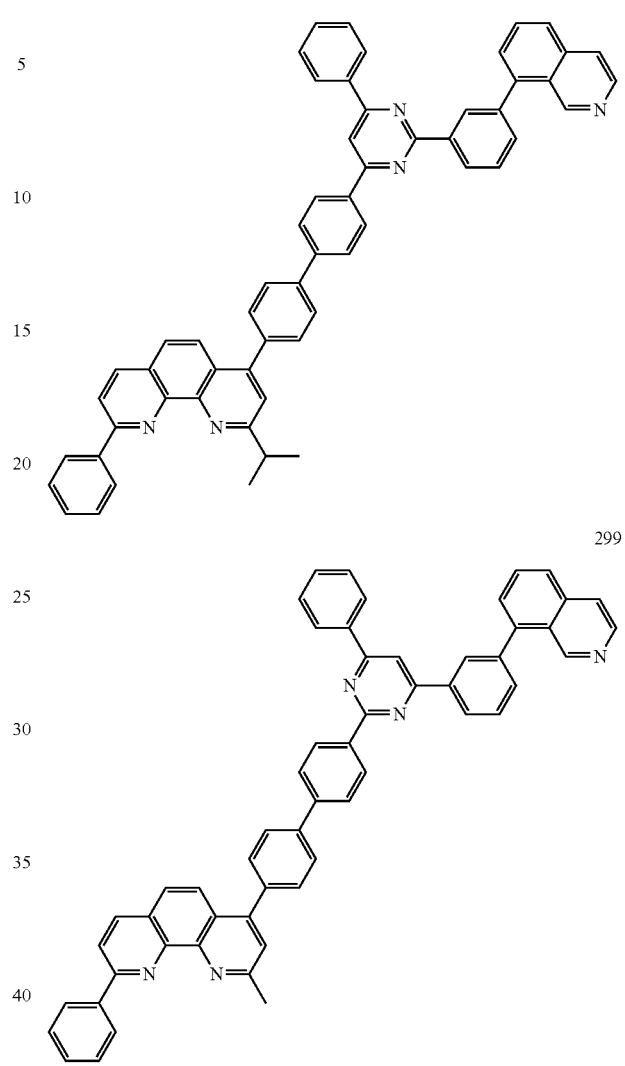
299
300
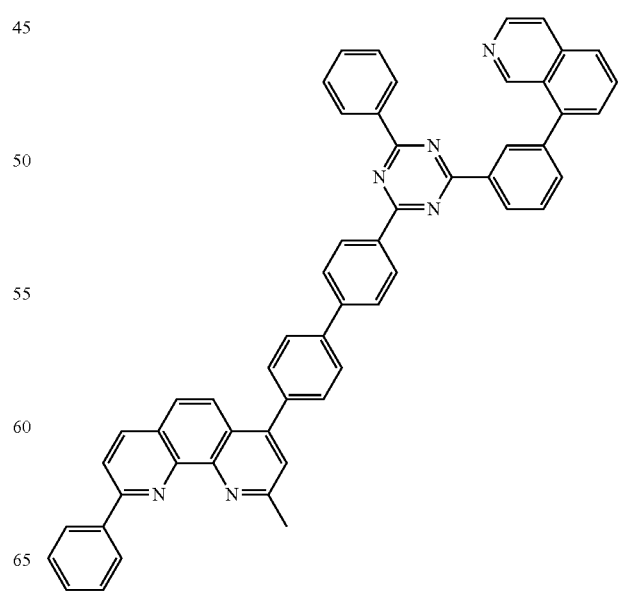

167
-continued
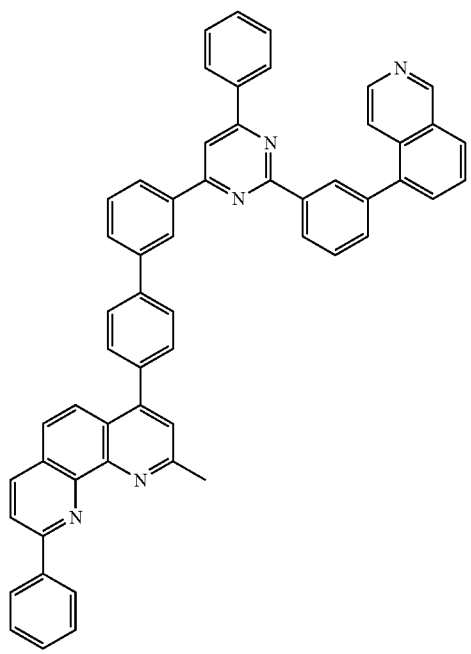
301
168
-continued
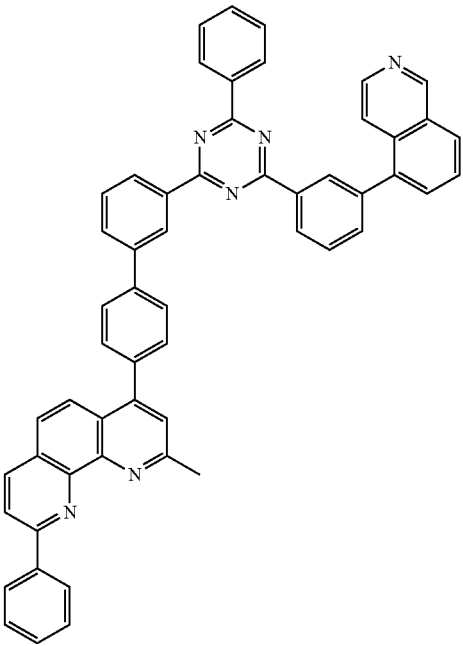
303
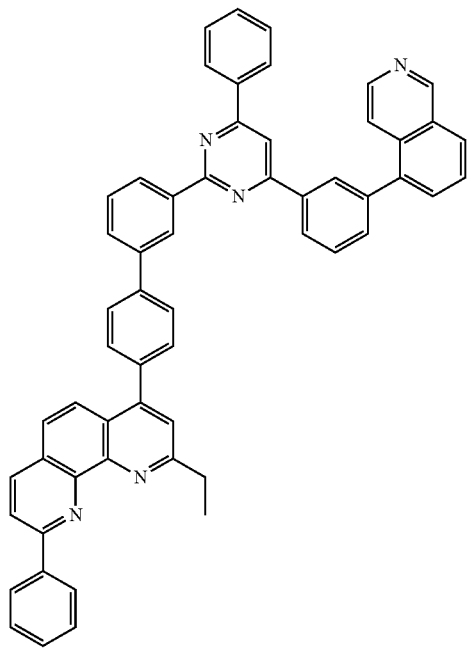
302
304

305
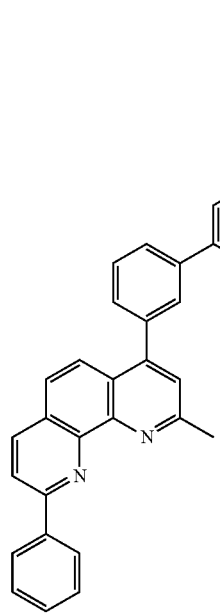
307
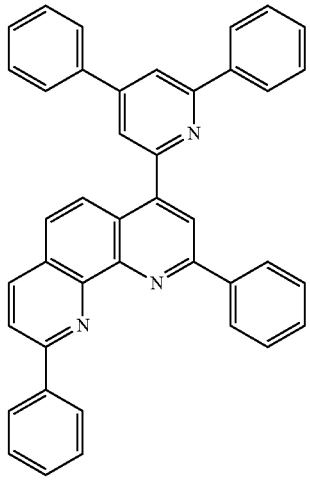
308
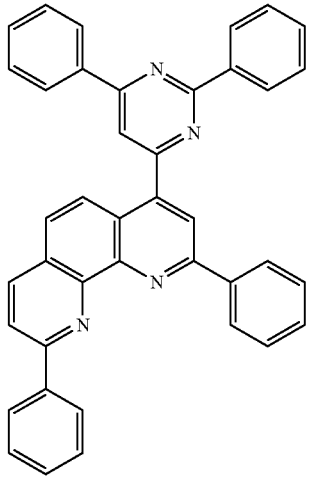
306
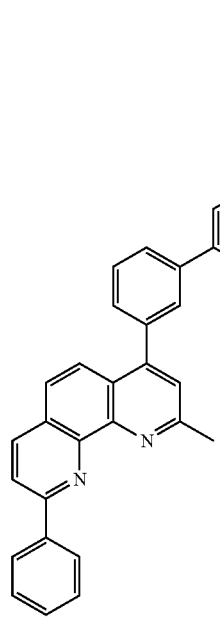
309
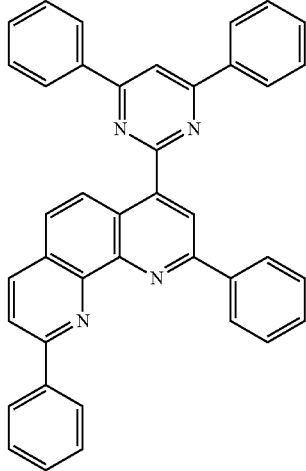

171
-continued
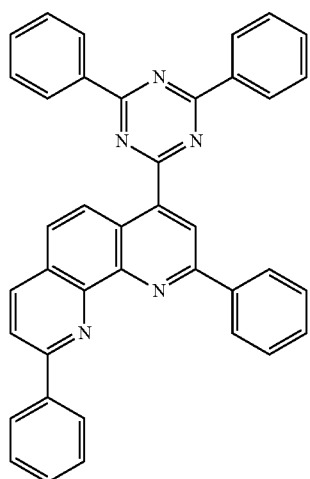
310
172
-continued
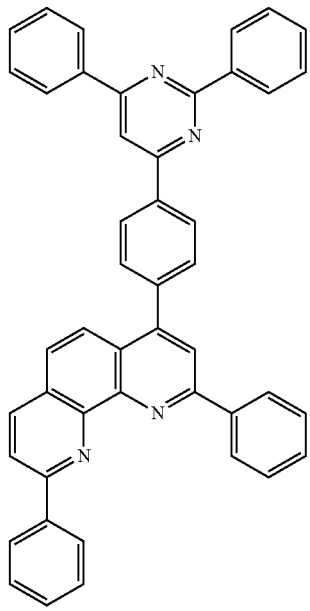
312
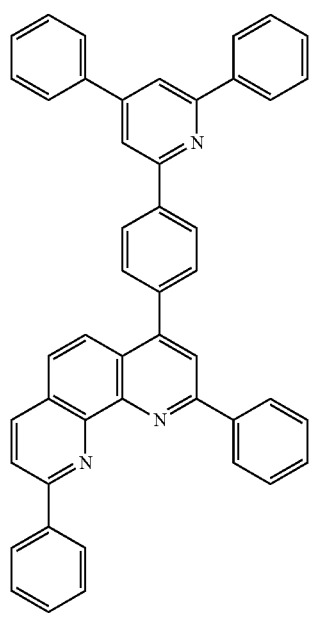
311
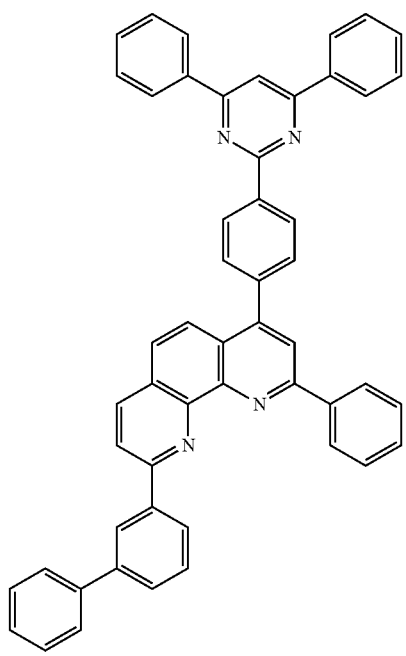
313

173
-continued
314
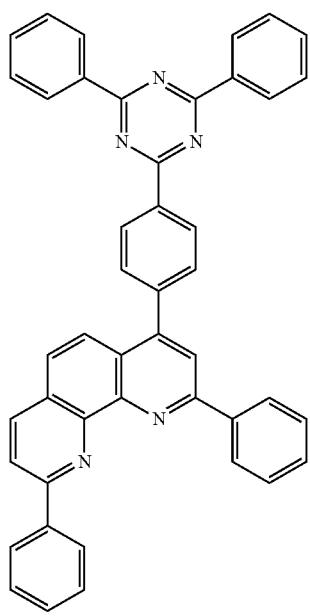
174
-continued
316
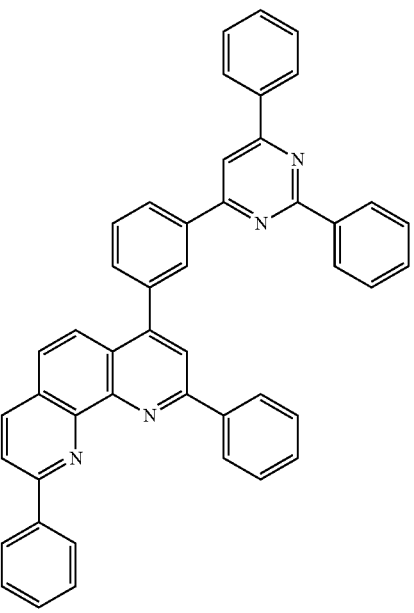
315
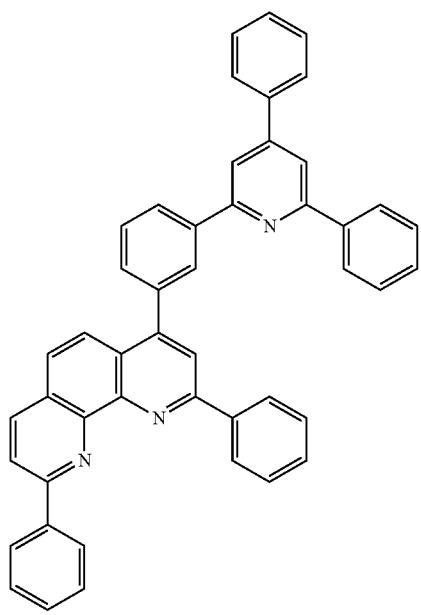
317
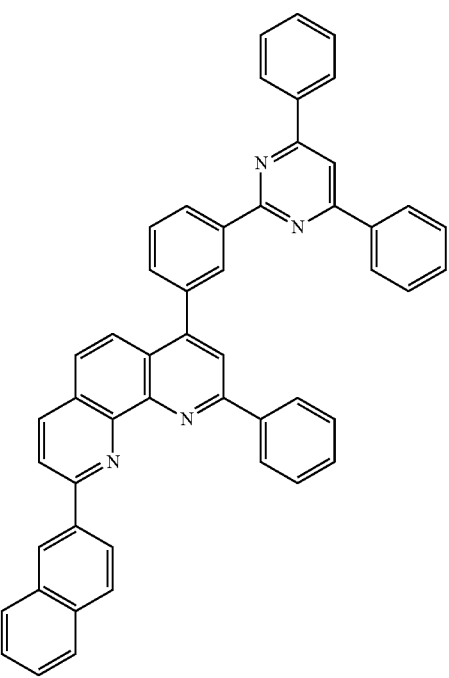

318
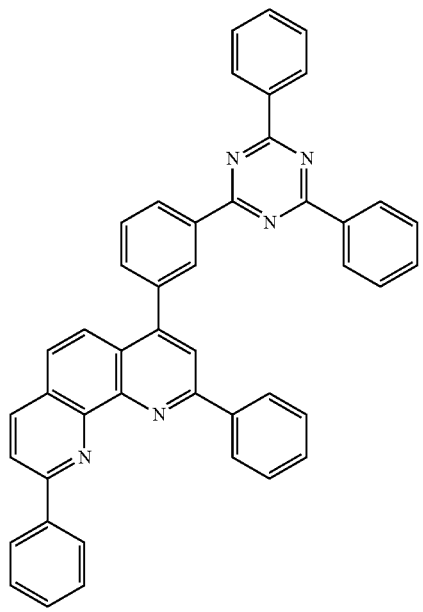
319
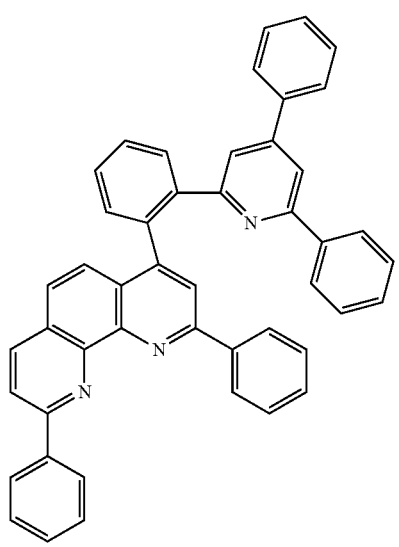
320
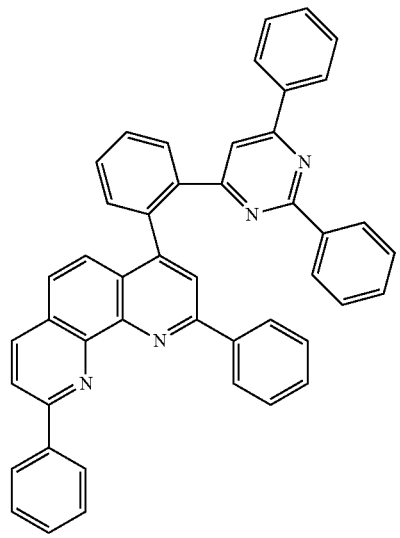
321
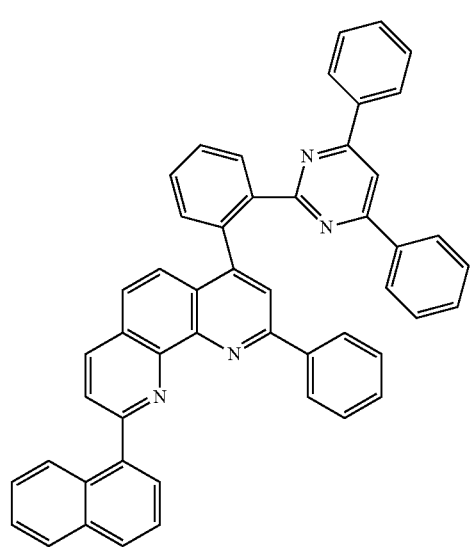
322
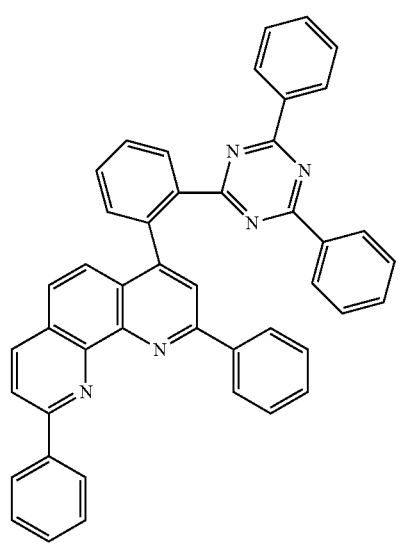

323
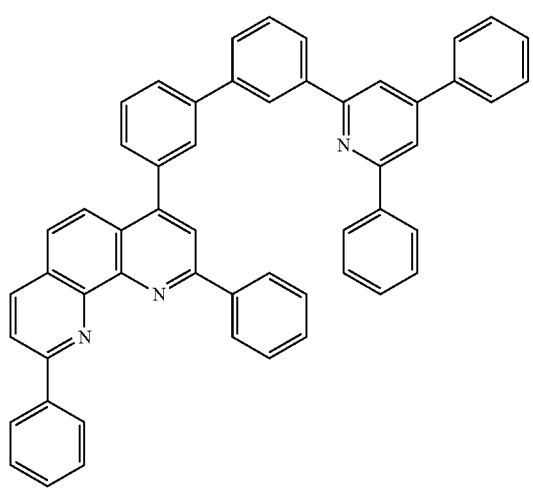
324
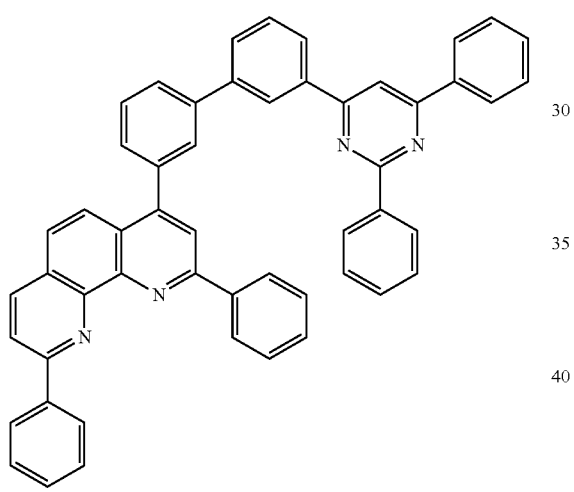
325
326
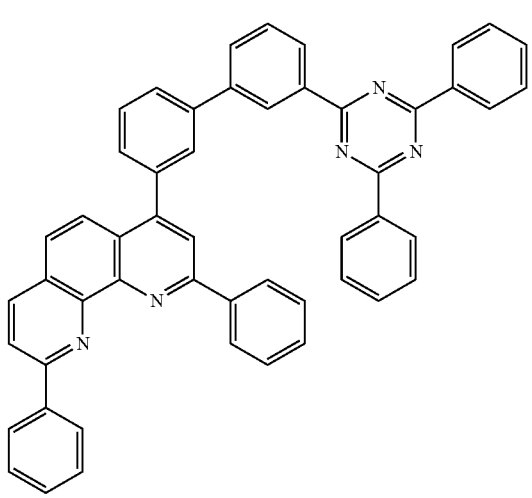
327
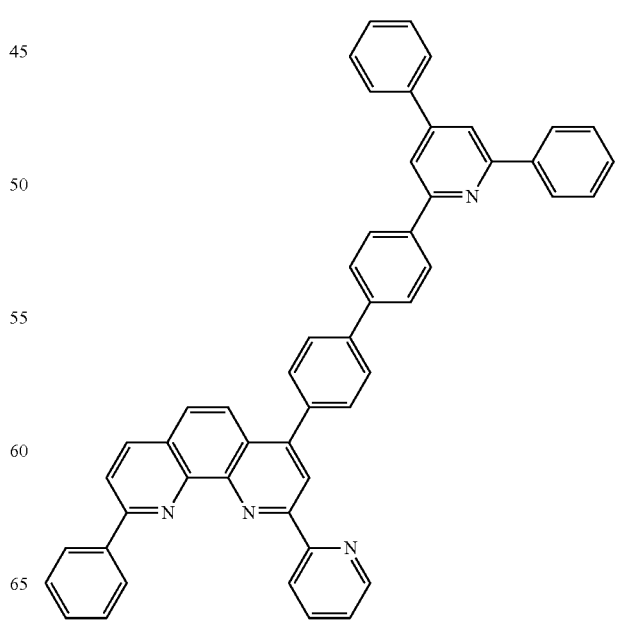

-continued
328
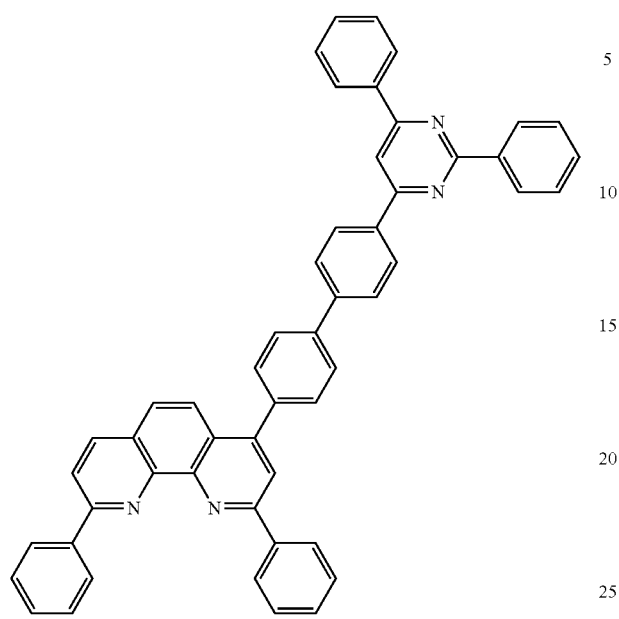
329
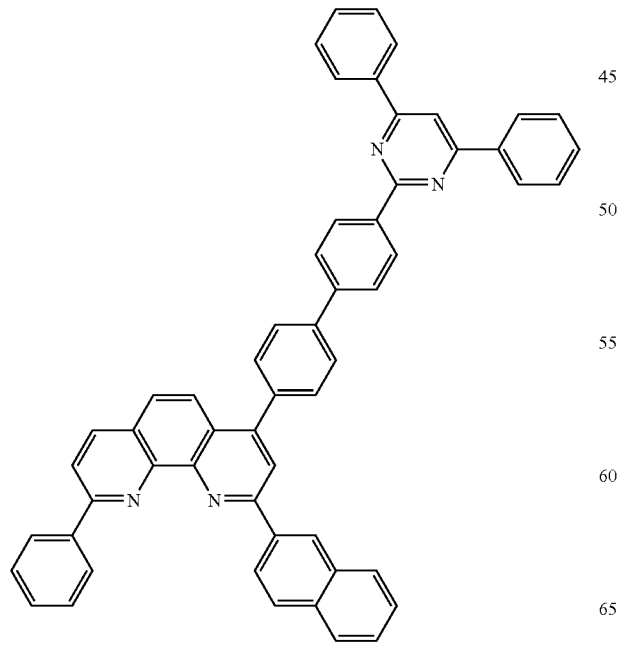
-continued
330
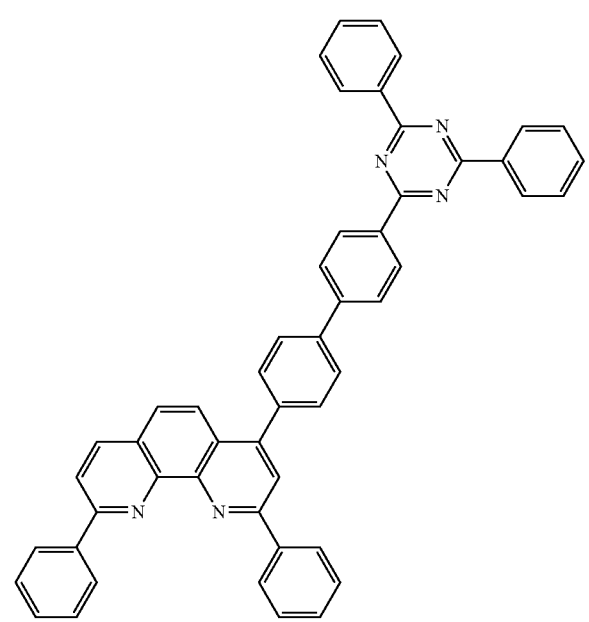
331
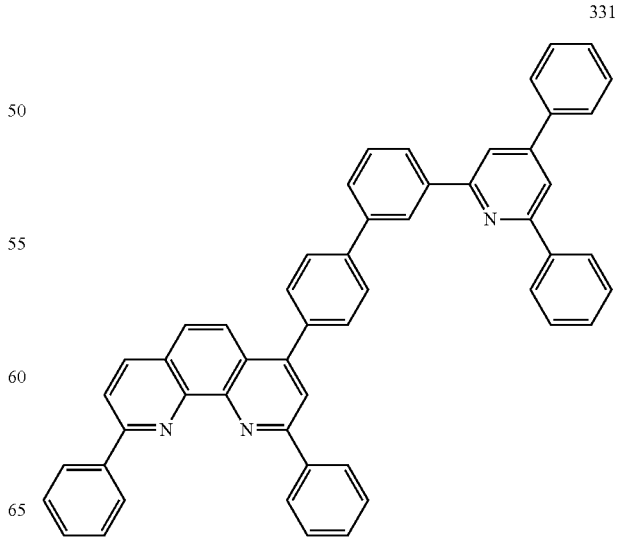

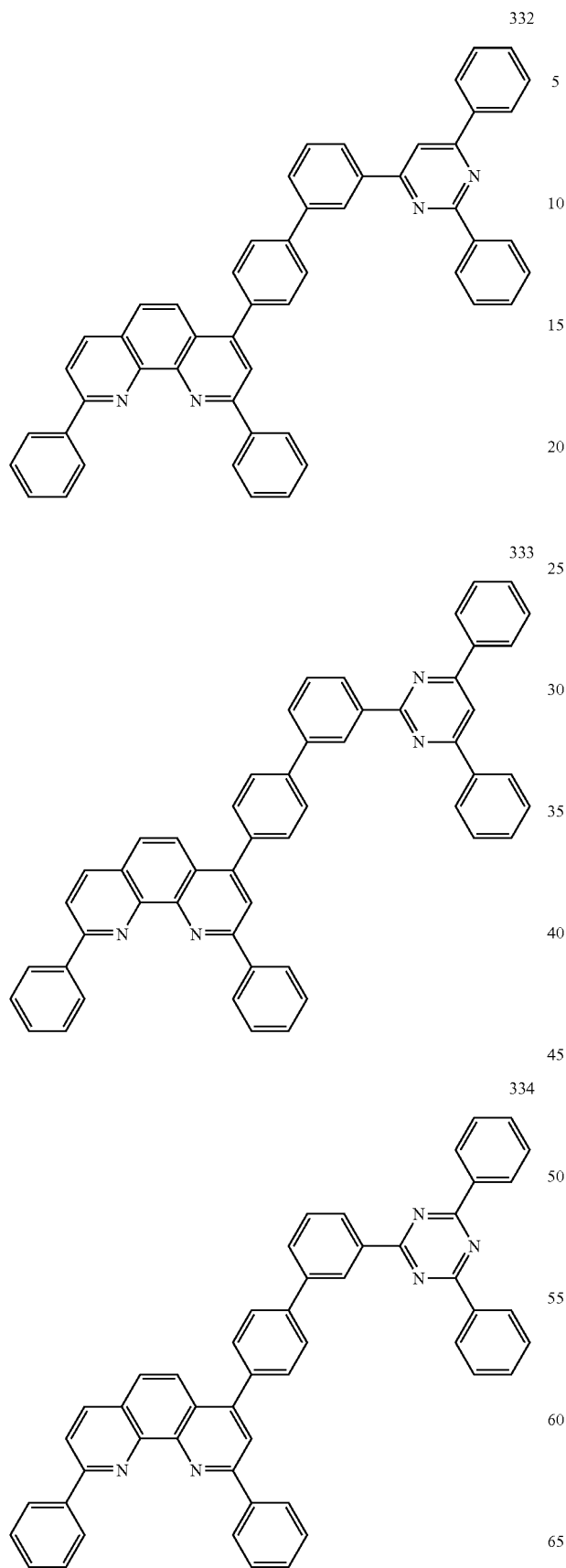
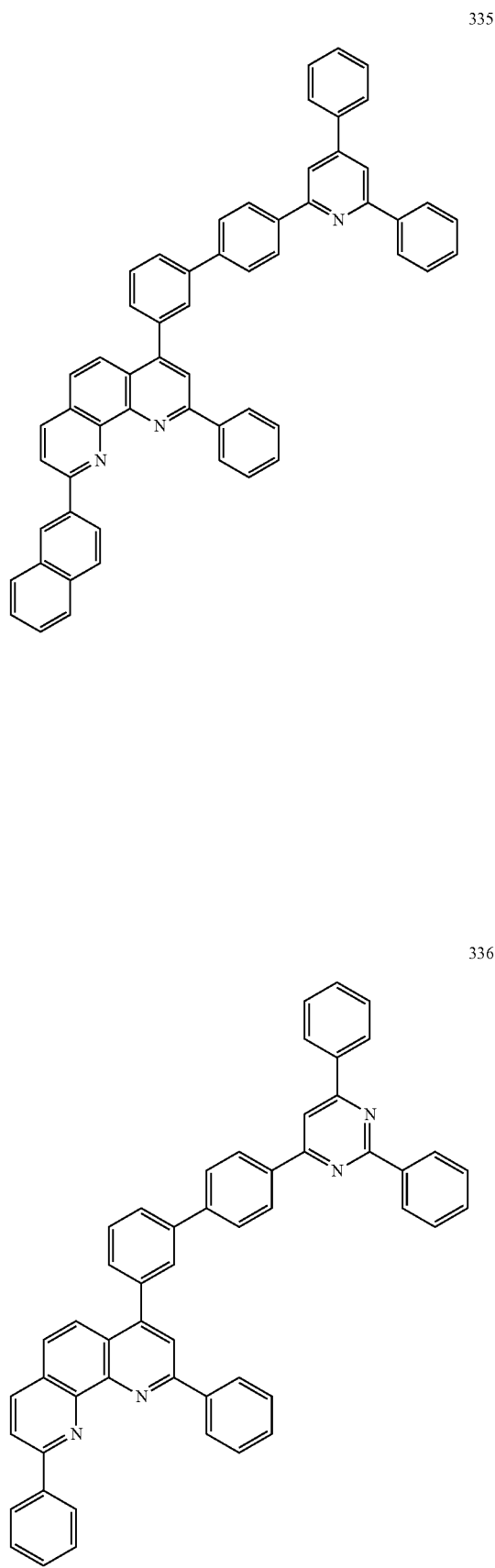

337
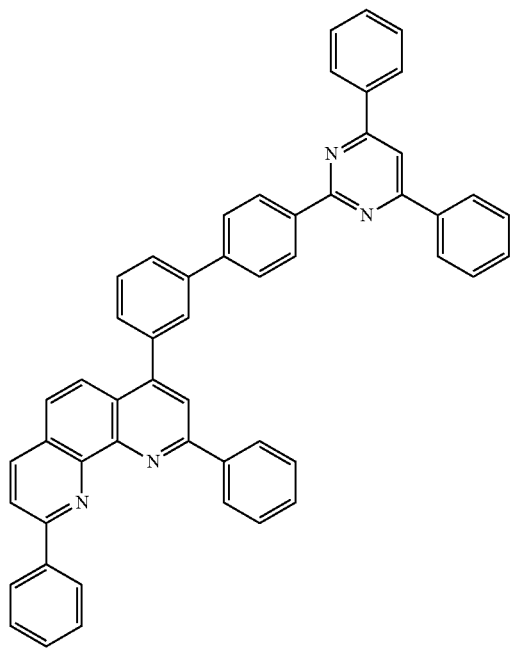
338
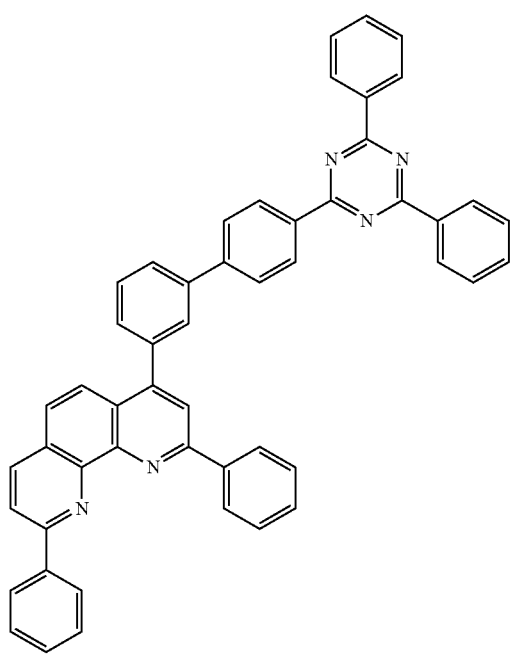
339
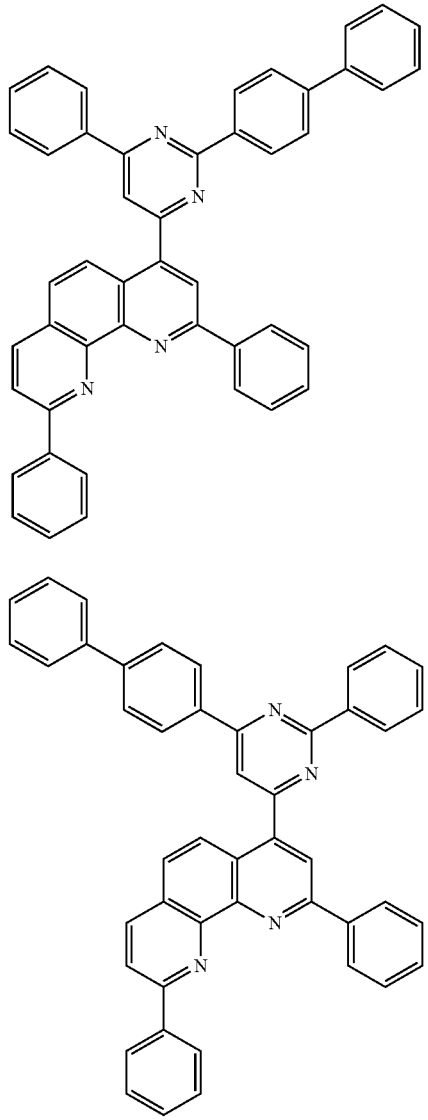
340
341
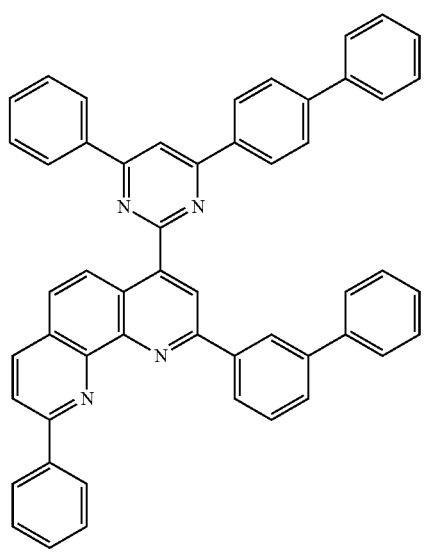

342
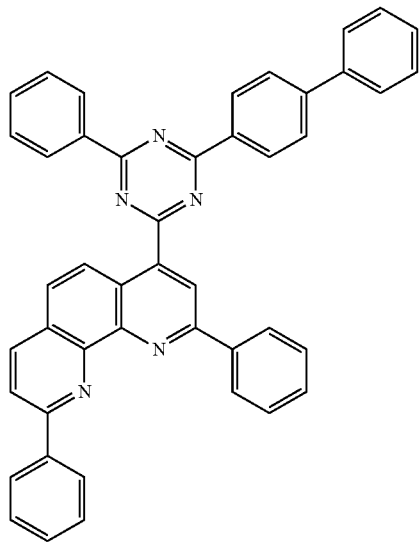
344
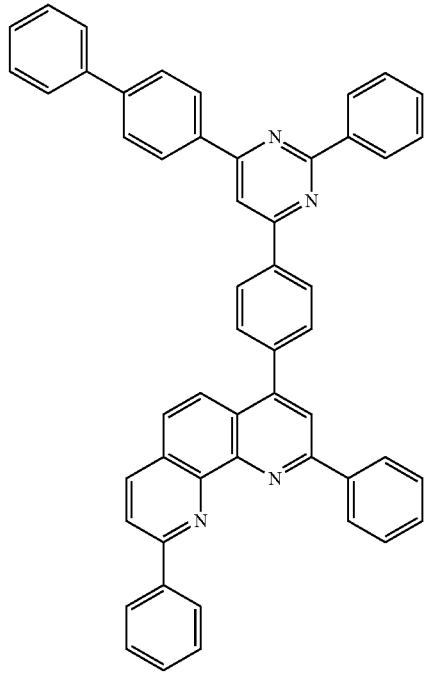
343
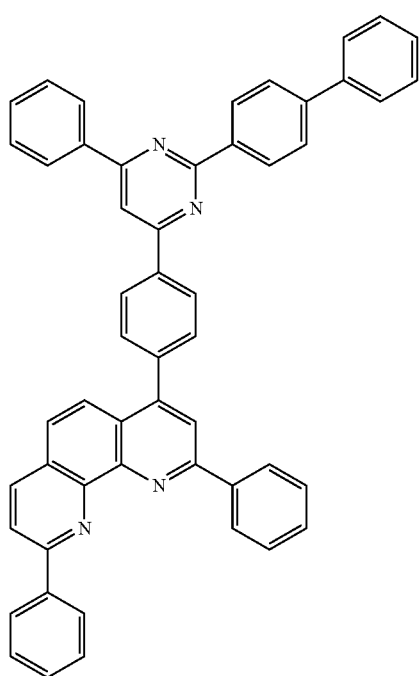
345
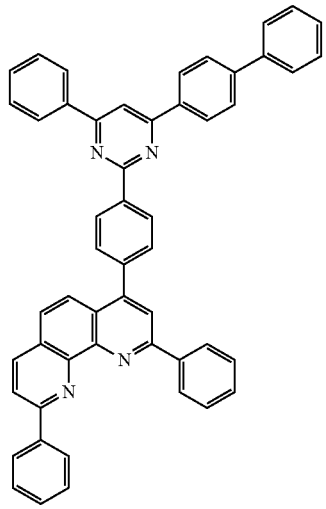

187
-continued
346
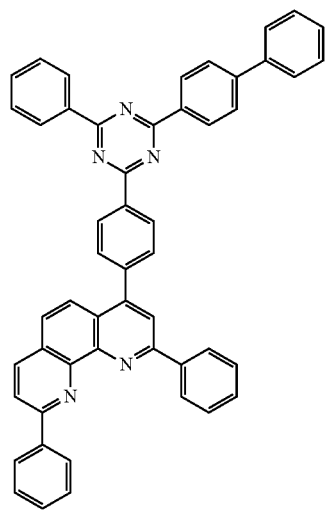
188
-continued
348
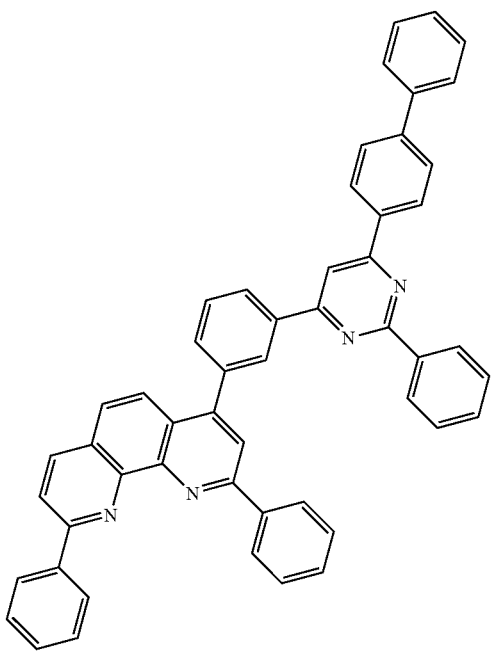
347
349
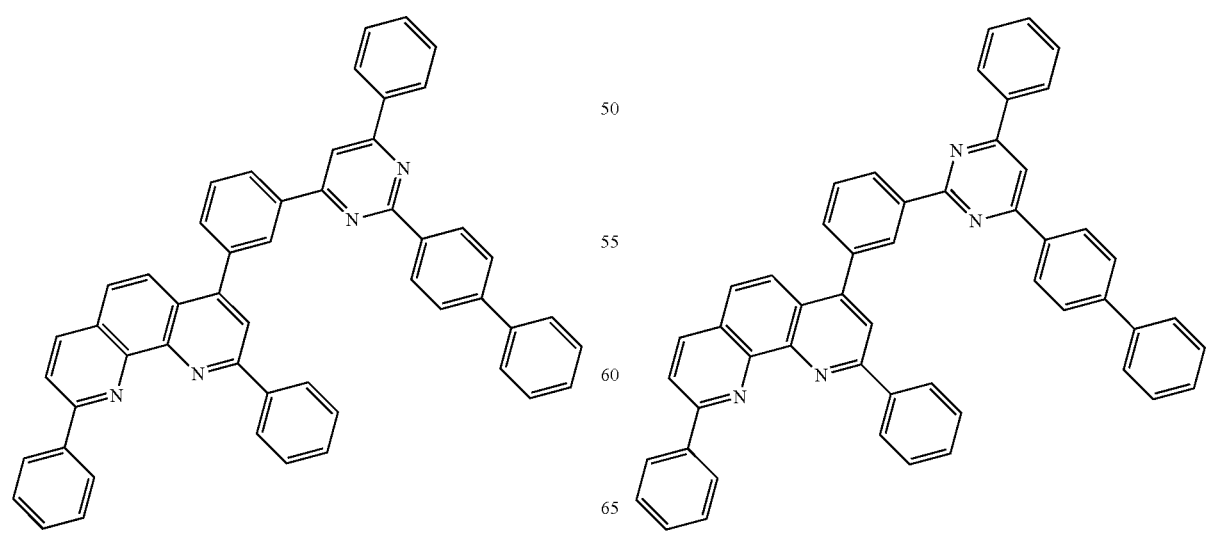

350
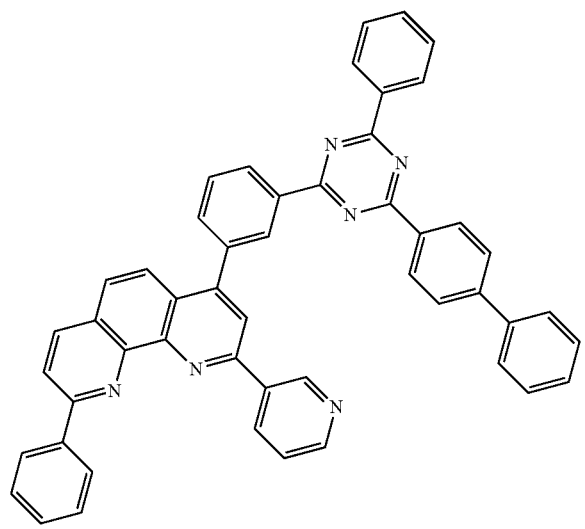
351
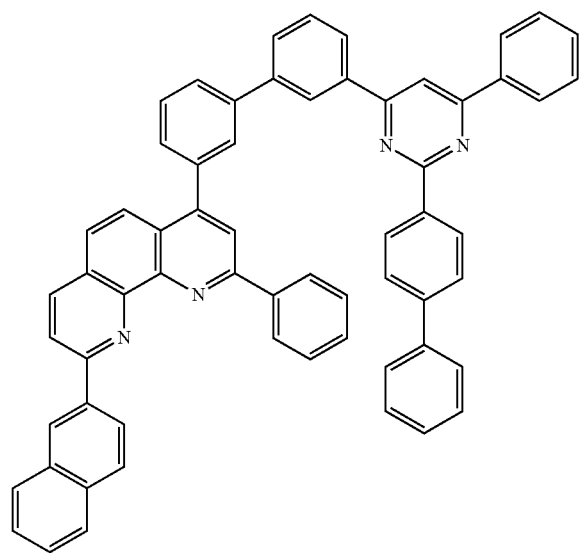
352
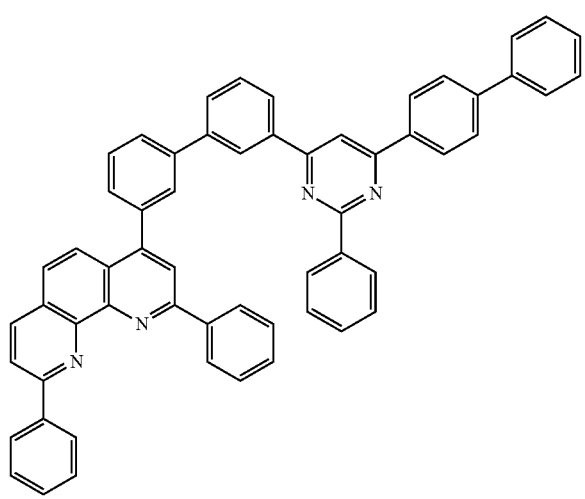
353
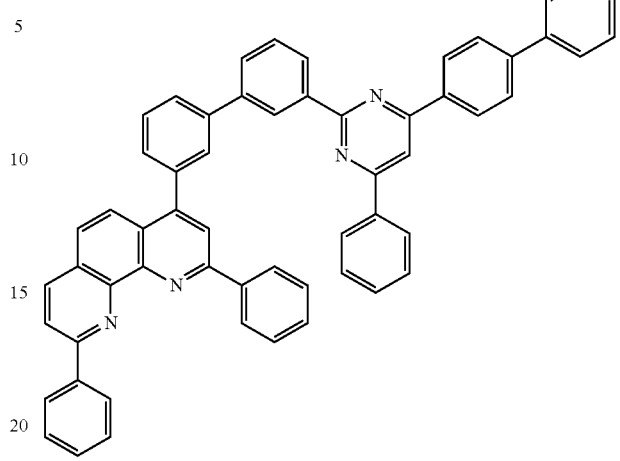
354
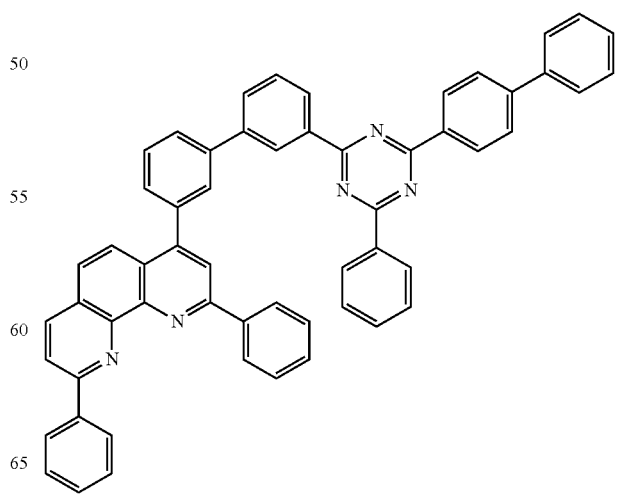

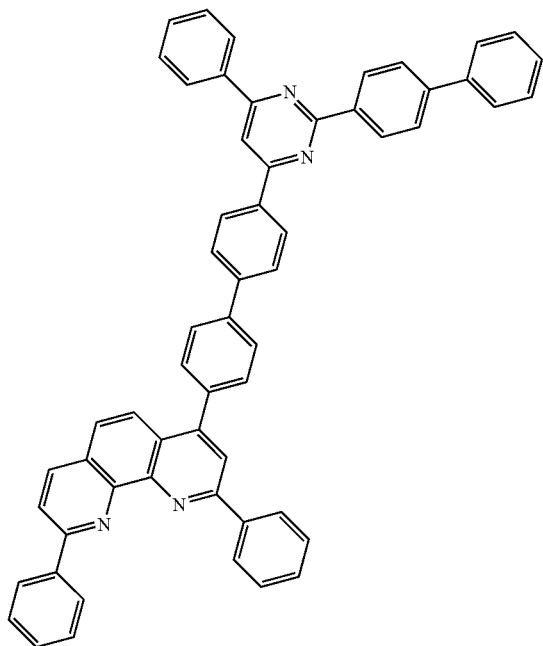
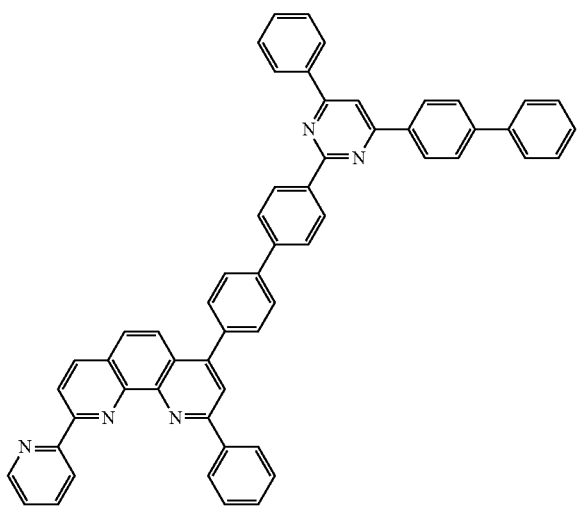
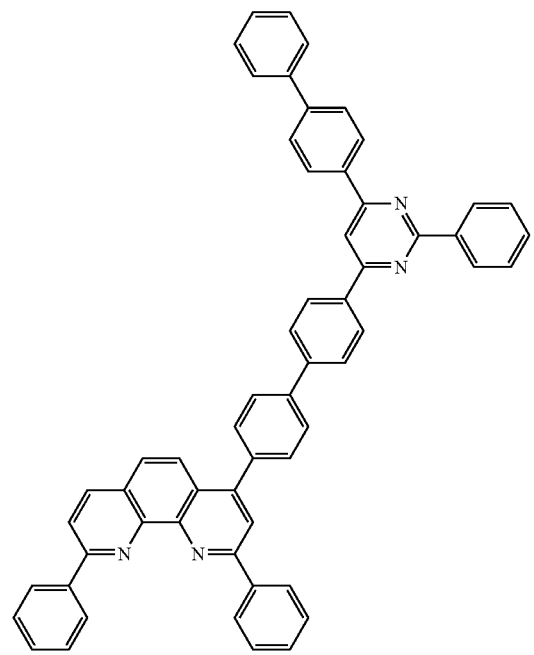

193
-continued
194
-continued
360
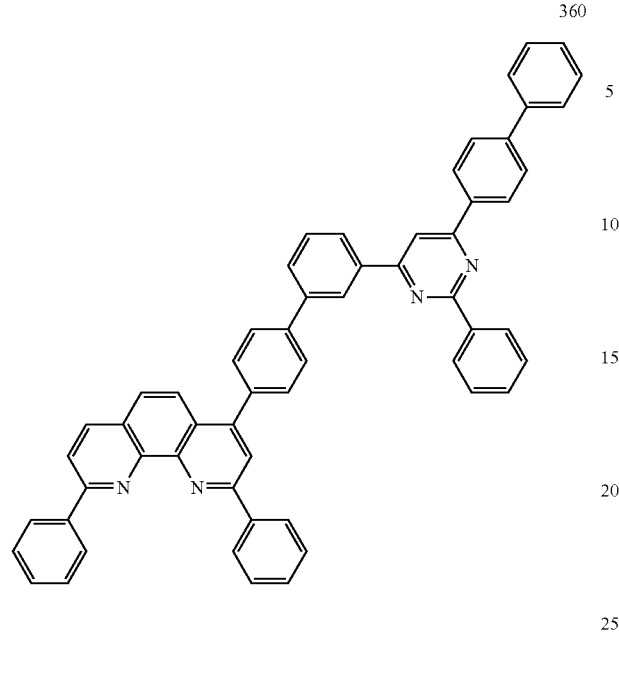
363
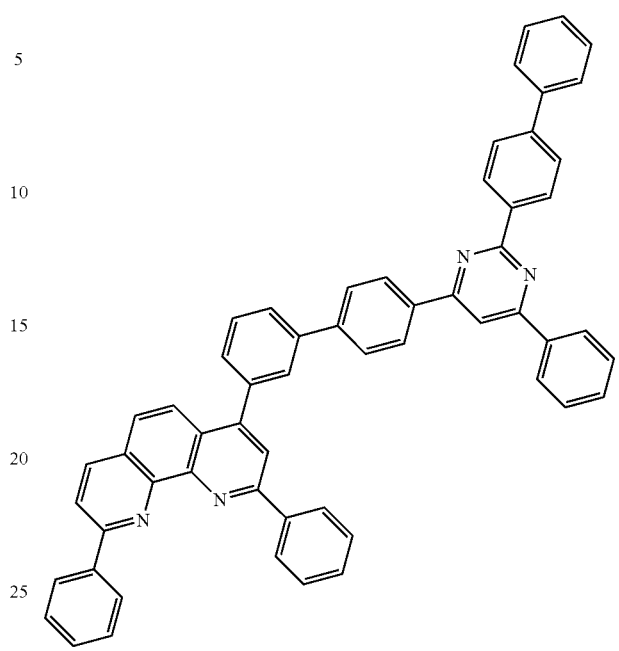
361
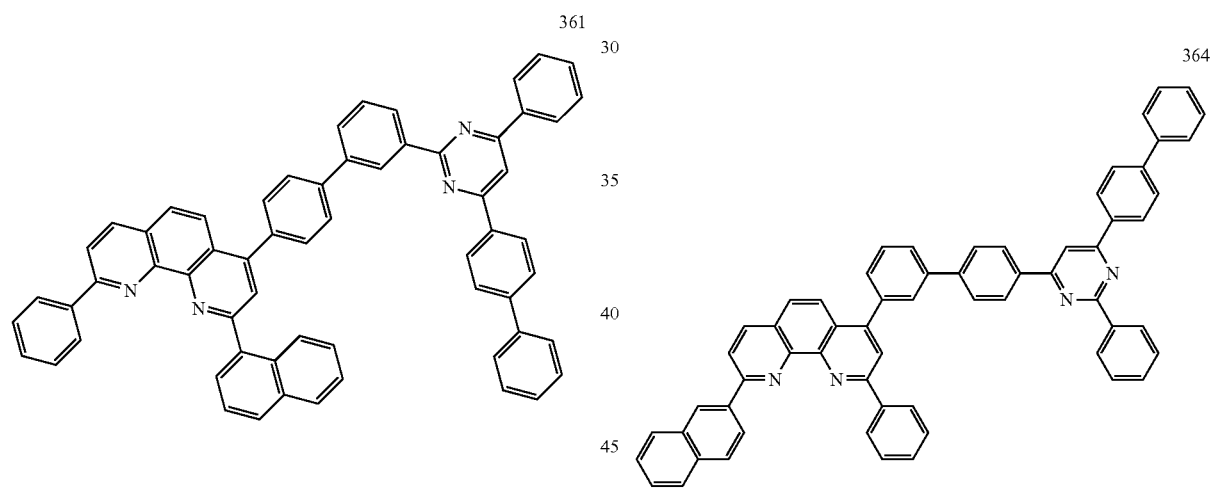
364
362
365
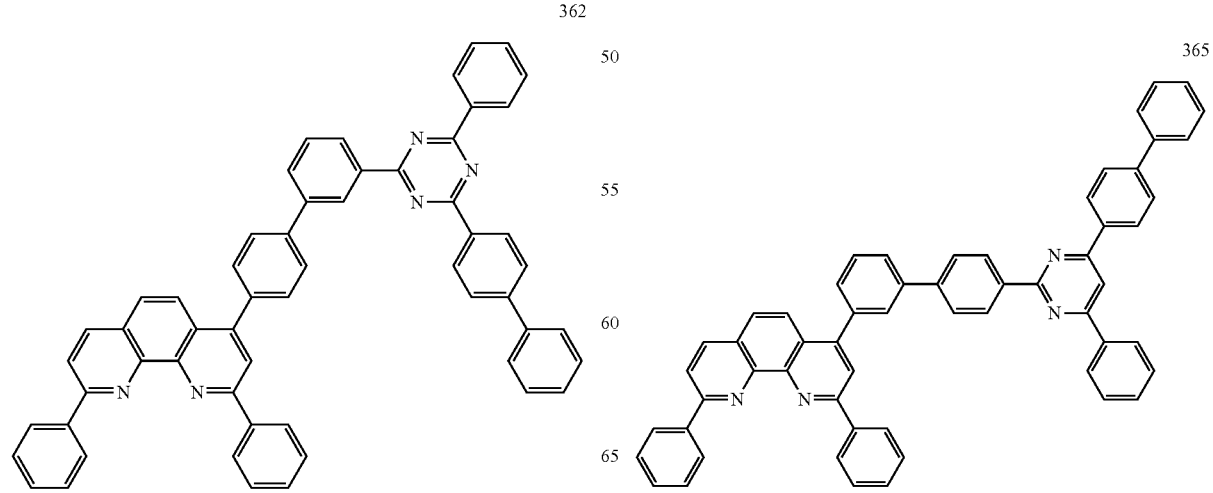

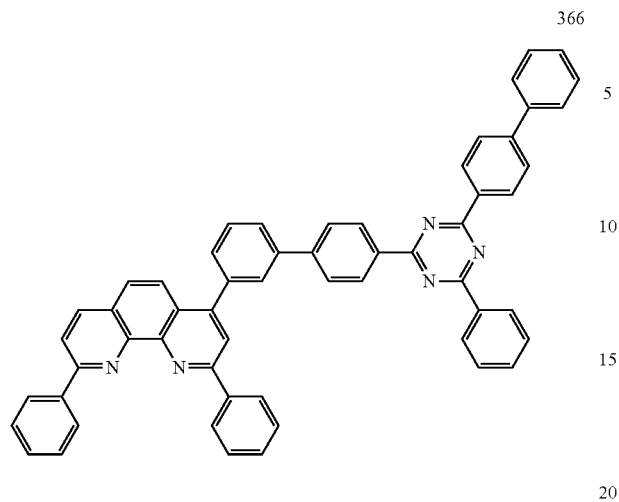
366
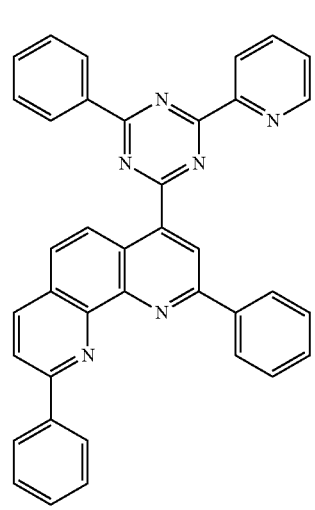
369
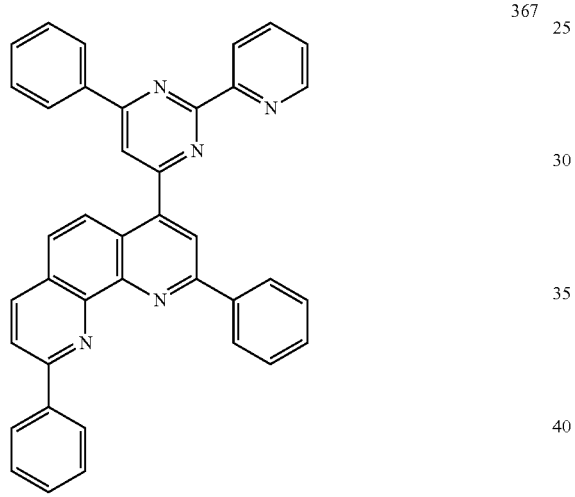
367
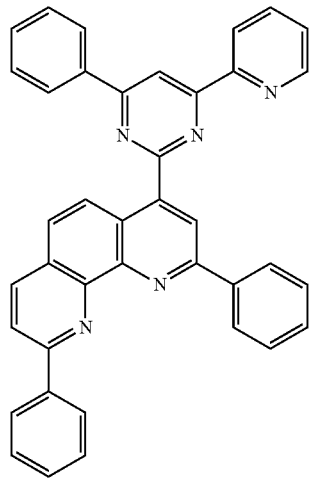
368
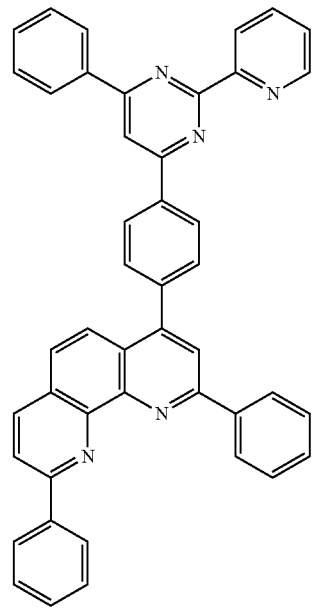
370

197
-continued
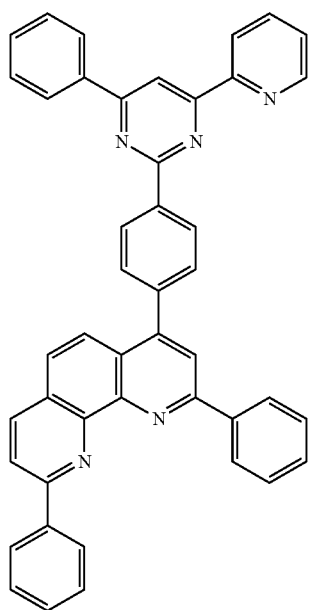
371
198
-continued
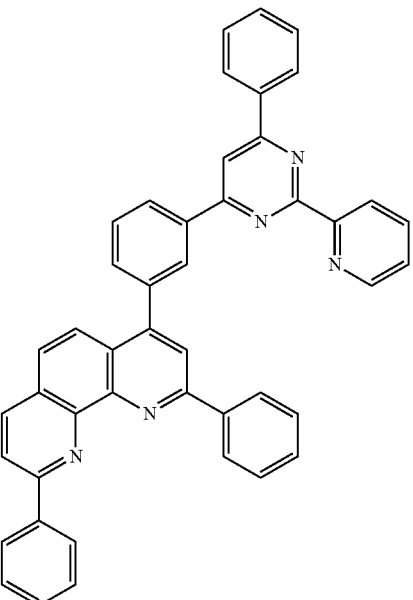
373
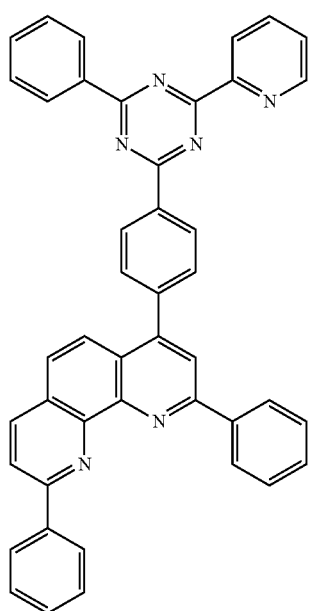
372
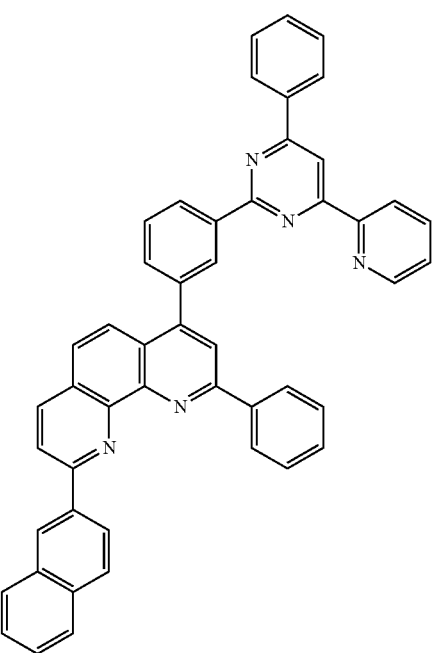
374

199
-continued
375
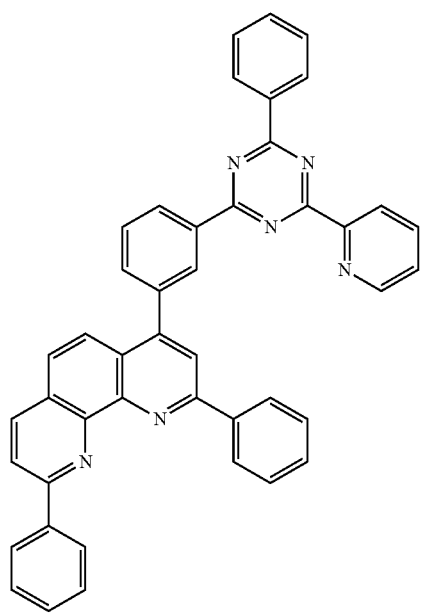
376
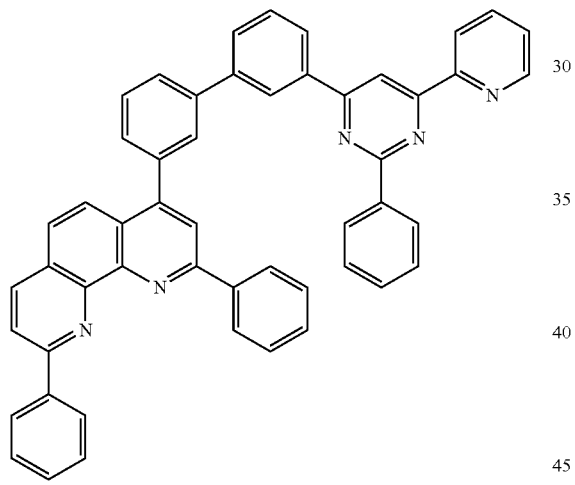
377
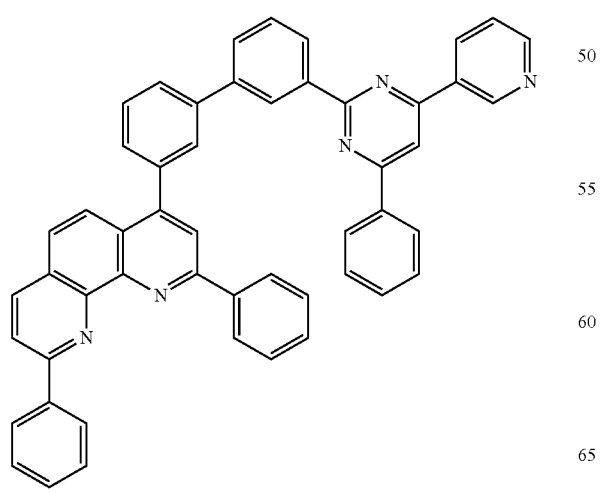
200
-continued
378
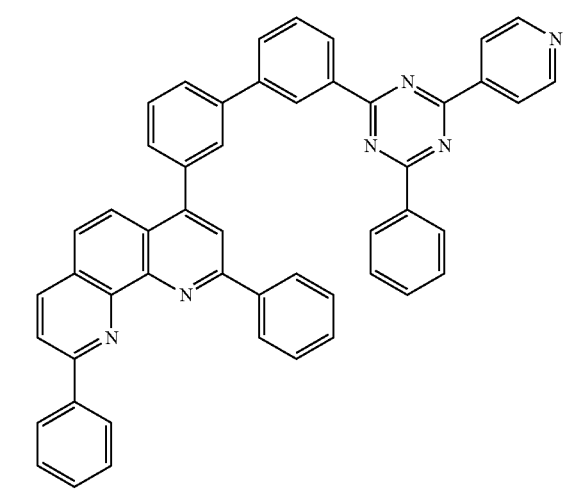
379
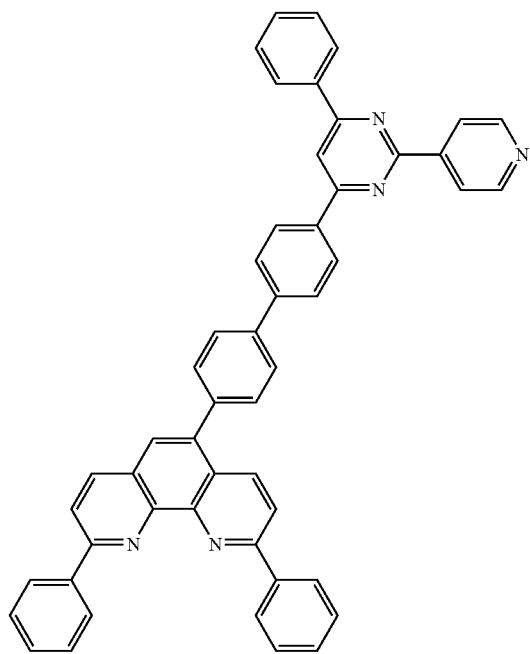

201
-continued
380
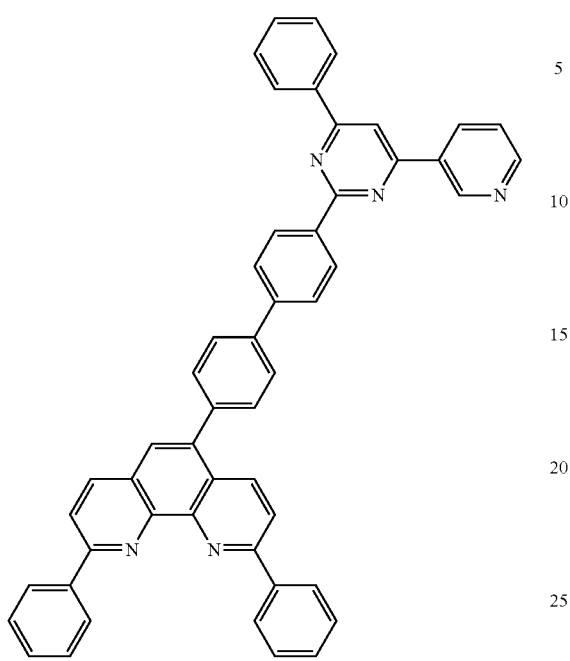
381
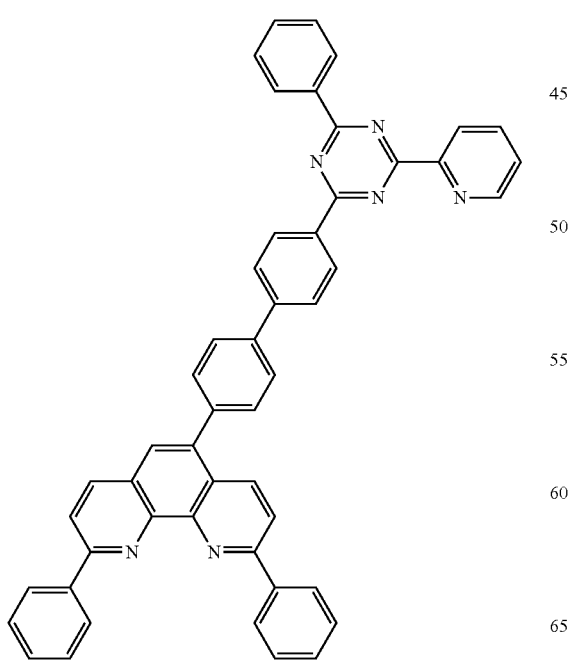
202
-continued
382
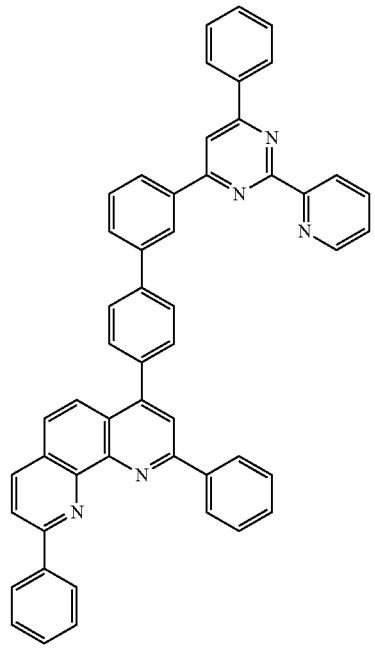
383
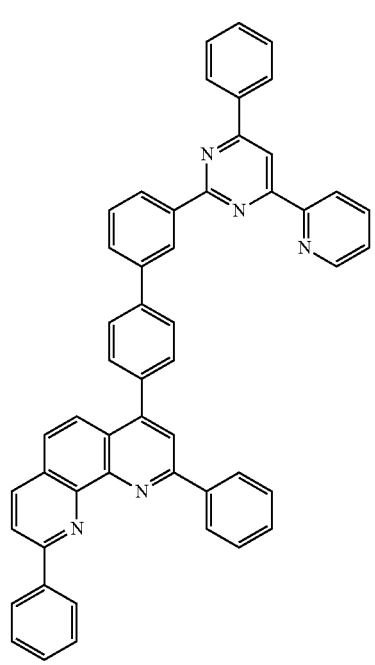

384
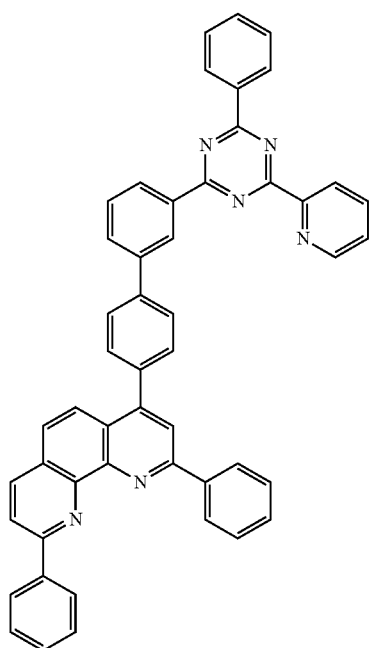
385
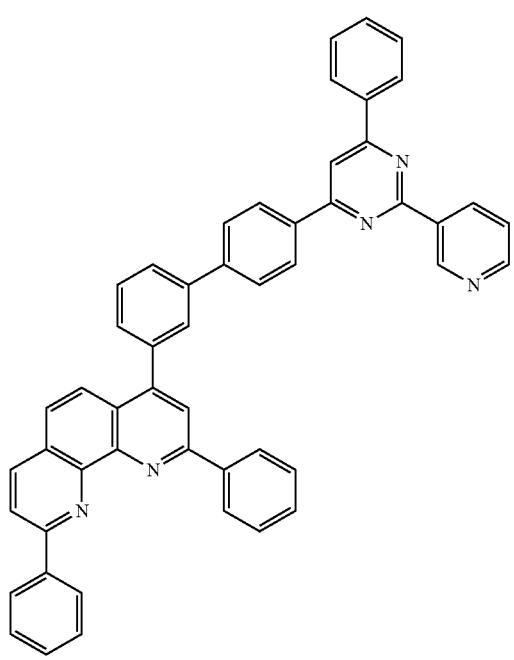
386
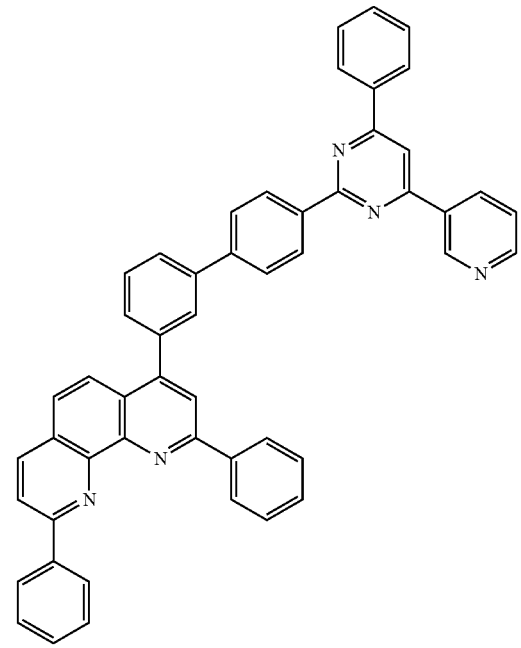
387
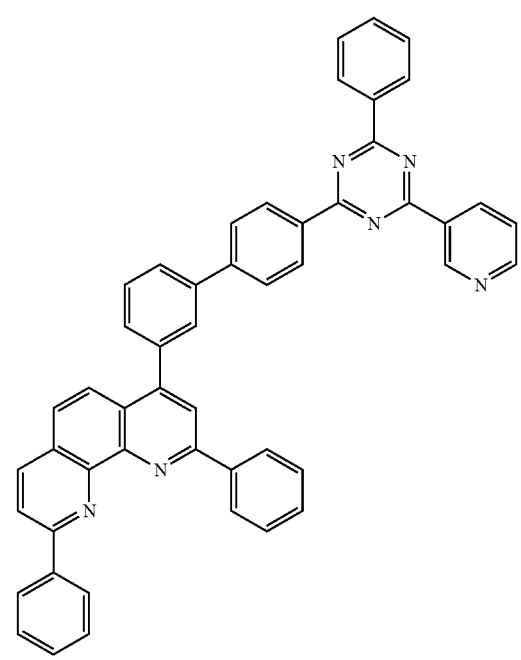

205
-continued
388
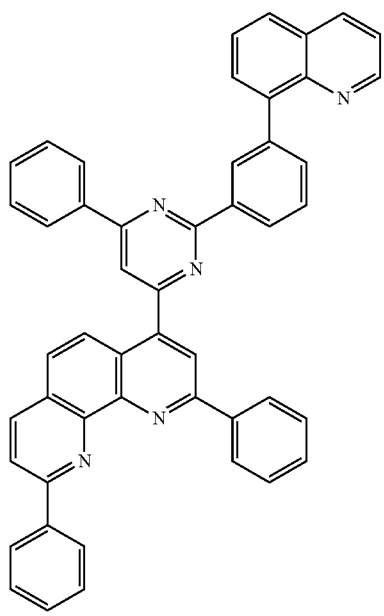
389
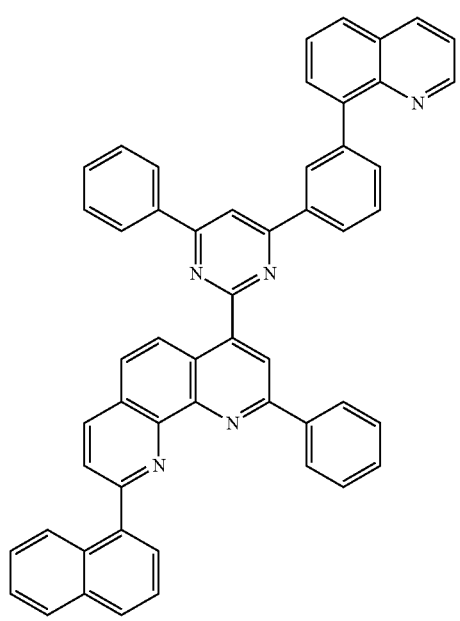
206
-continued
390
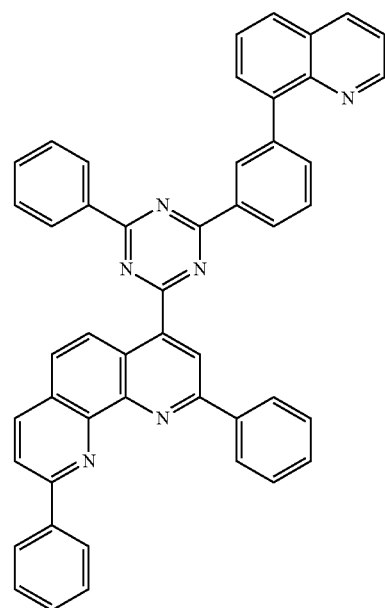
391
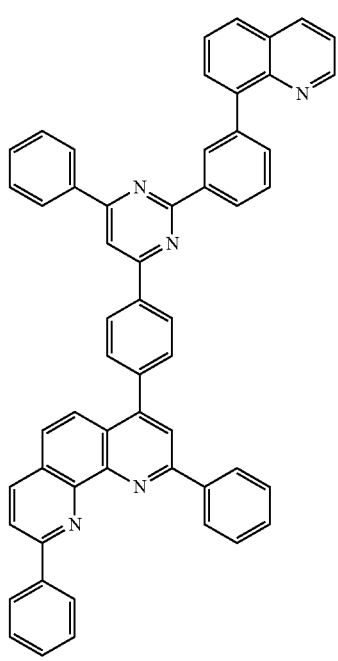

392
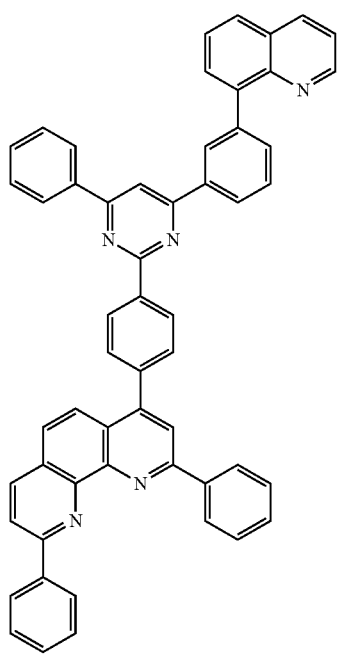
393
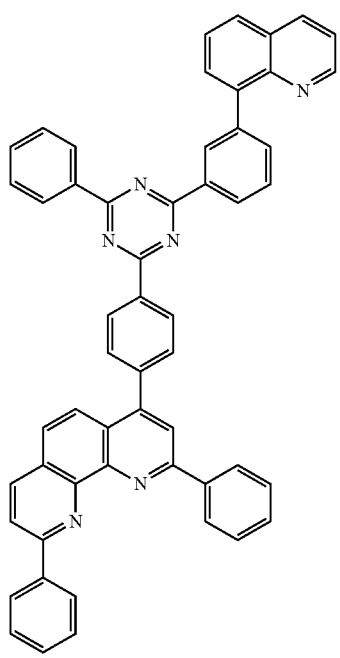
394
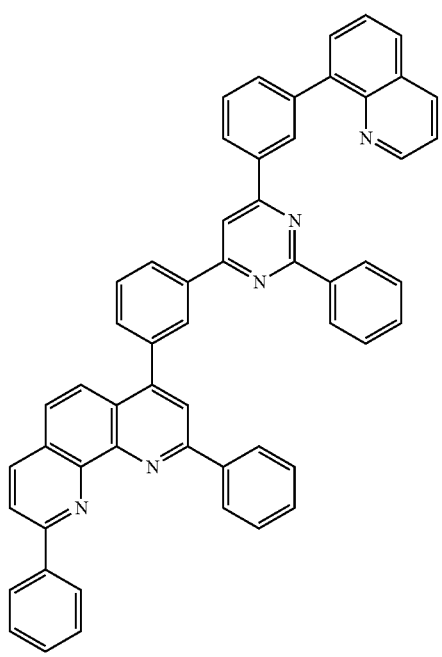
395
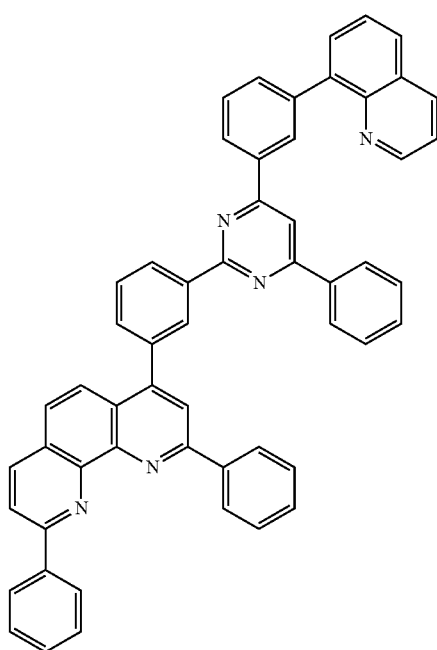

396
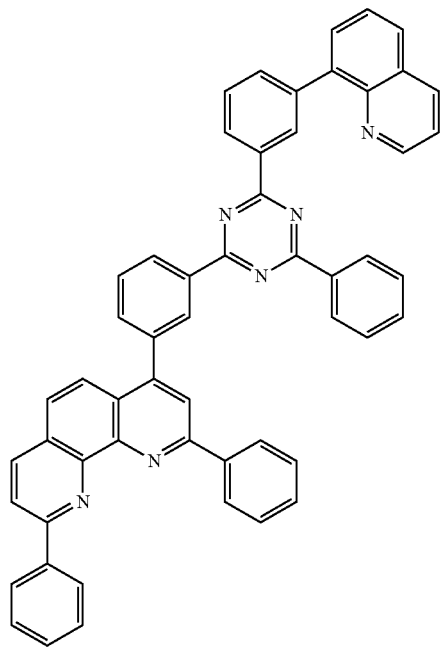
397
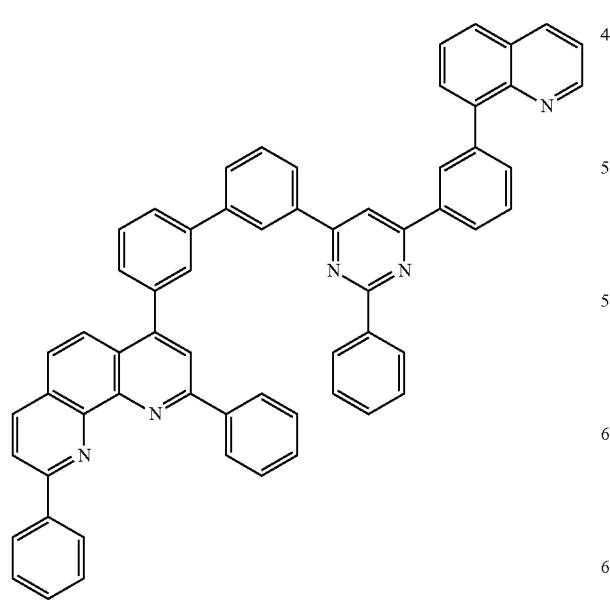
398
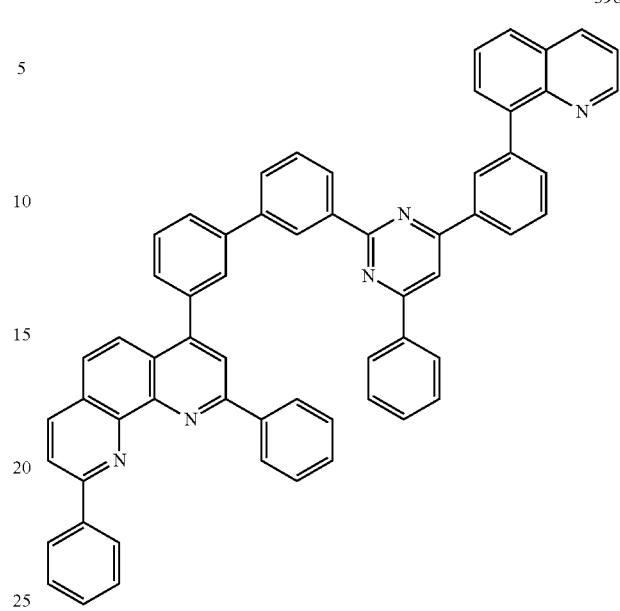
399
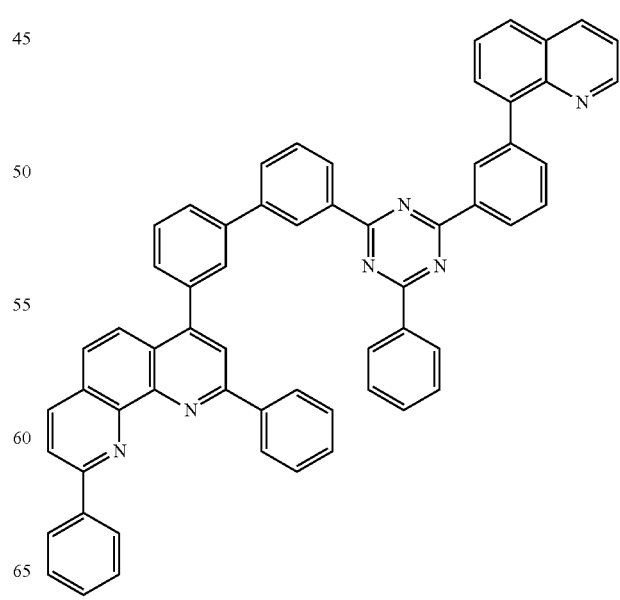

211
-continued
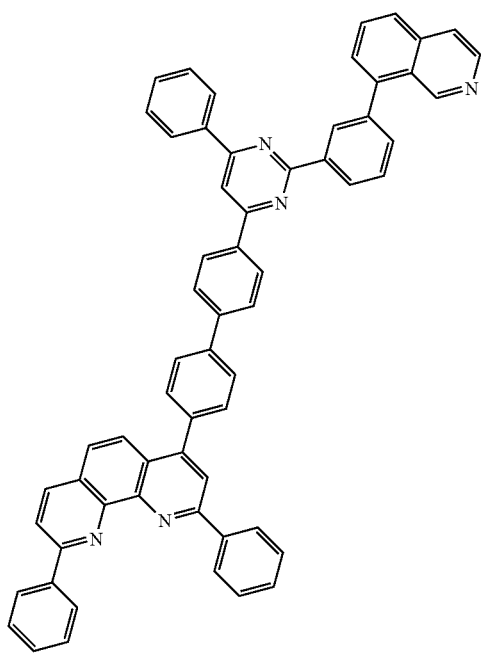
212
-continued
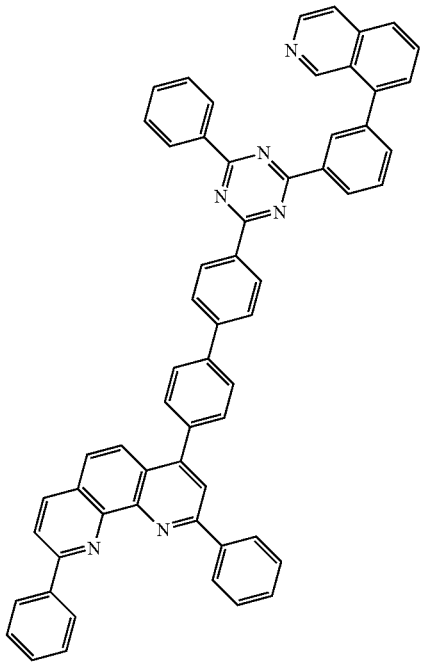
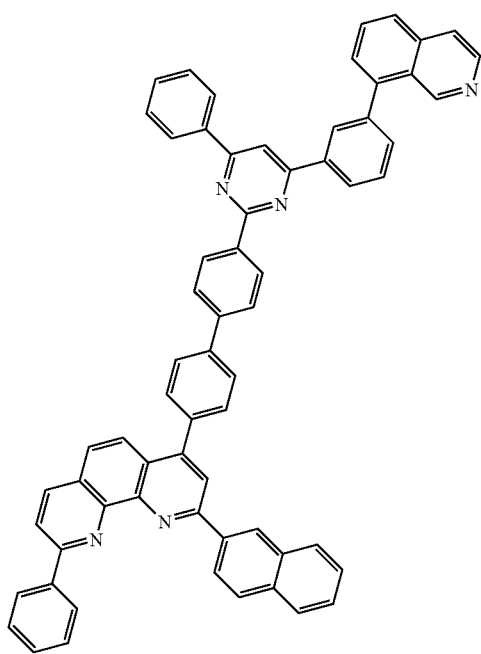
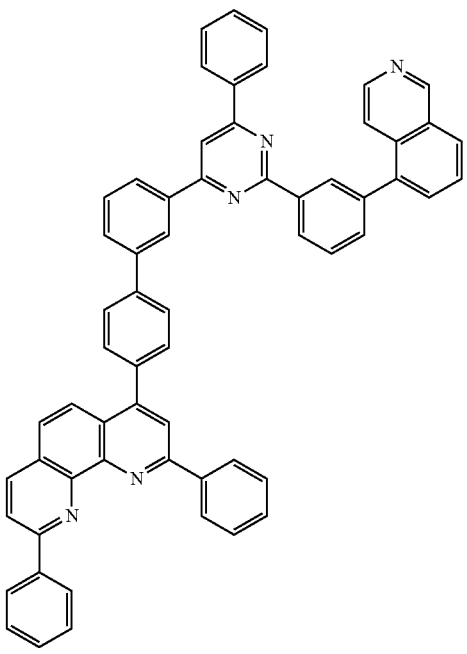

213
-continued
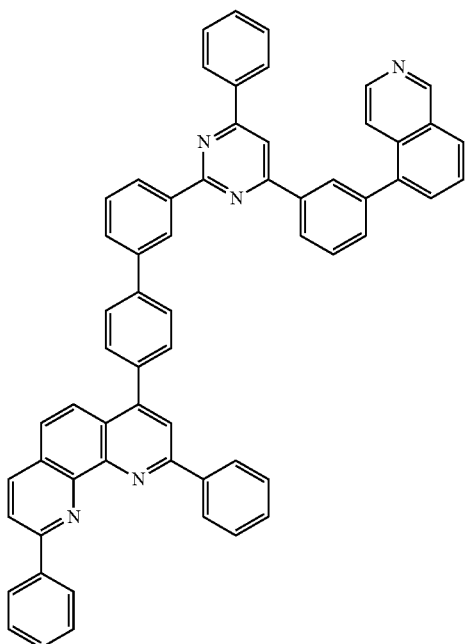
404
214
-continued
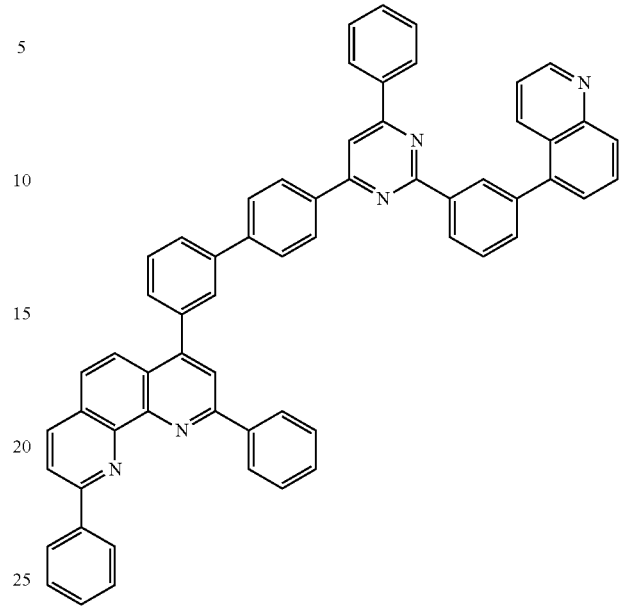
406
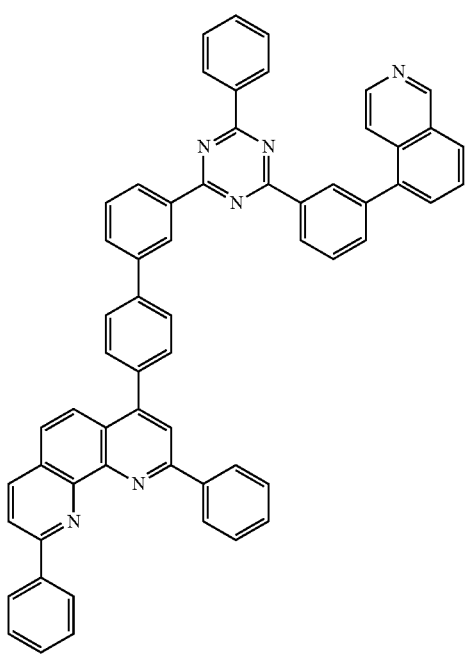
405
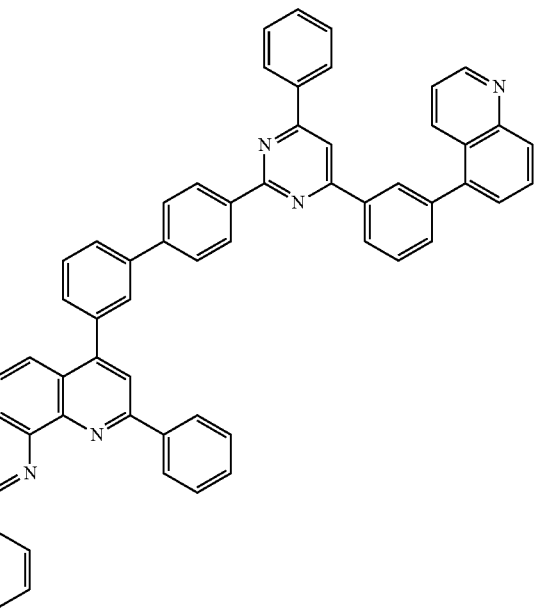
407

408
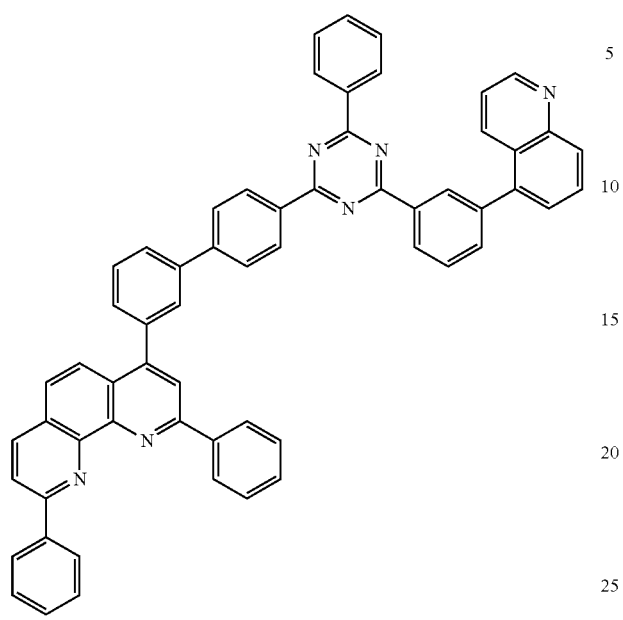
409
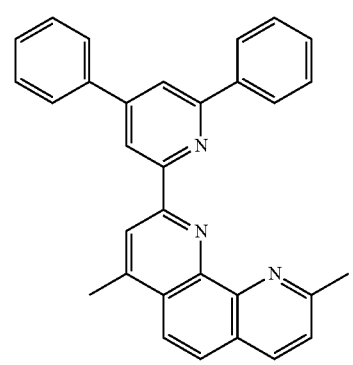
410
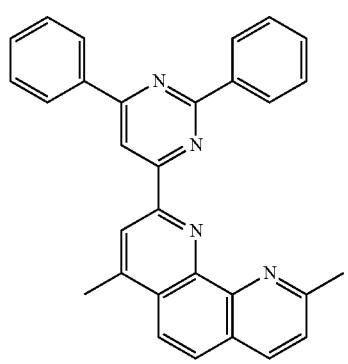
411
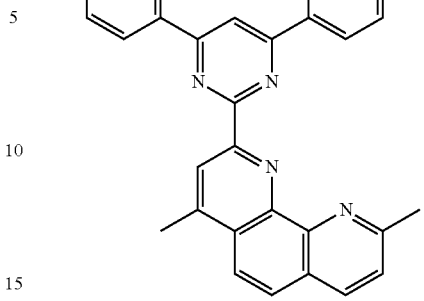
412
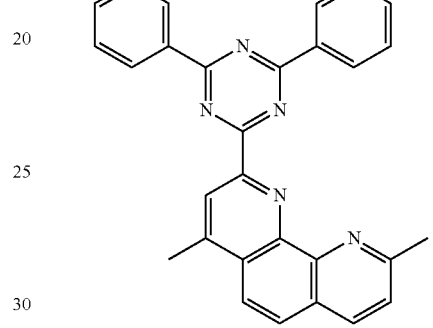
413
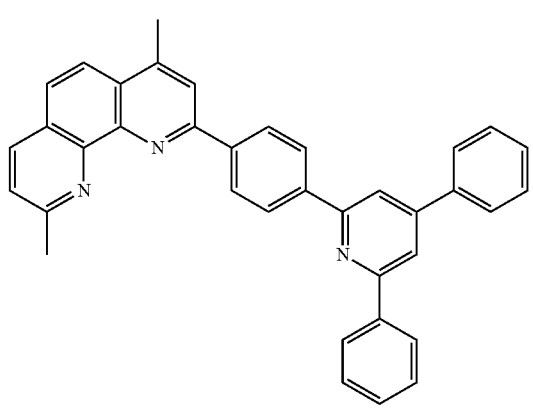
414
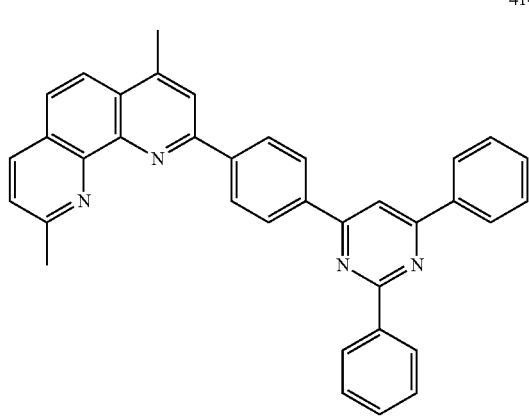

415
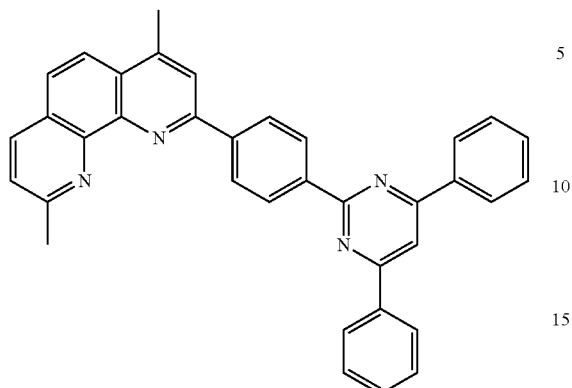
416
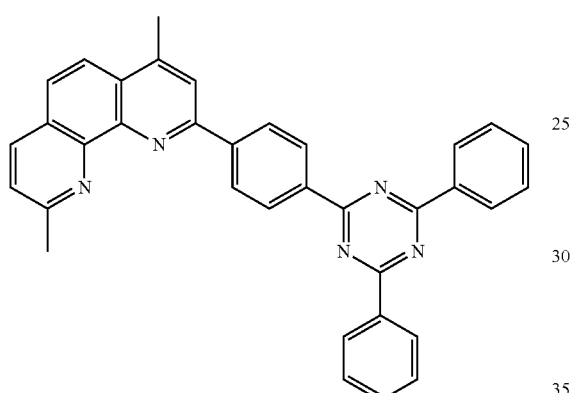
417
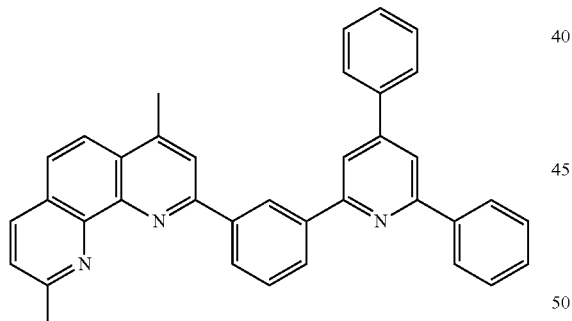
418
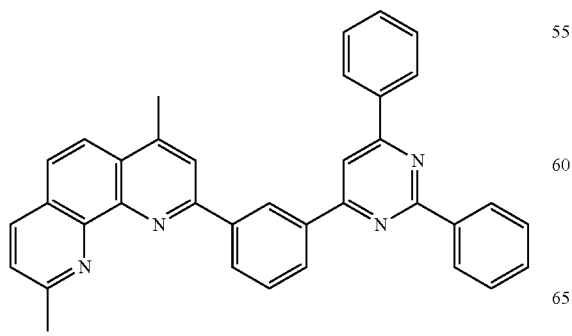
419
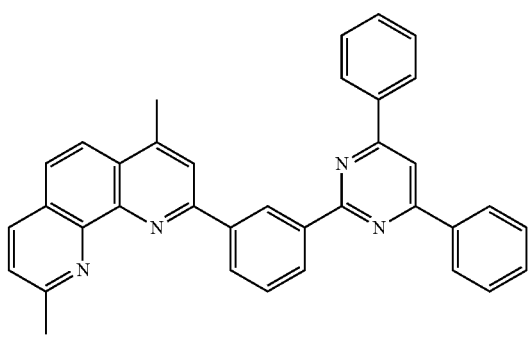
420
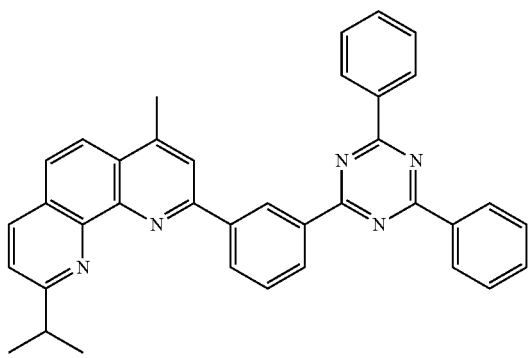
421
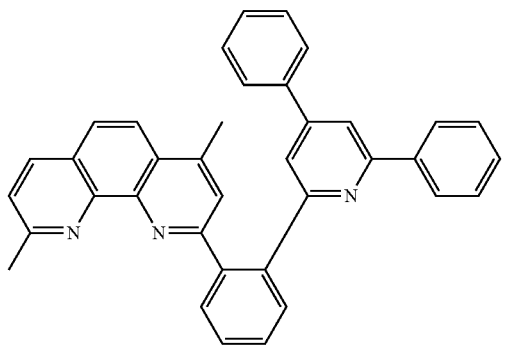
422
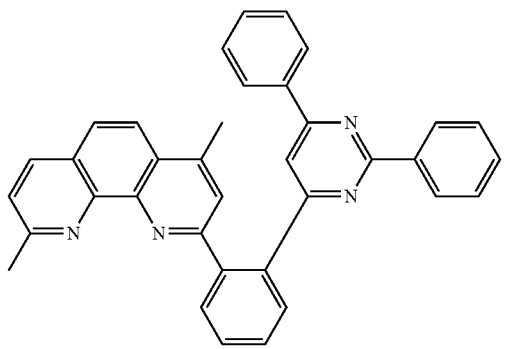

-continued
423
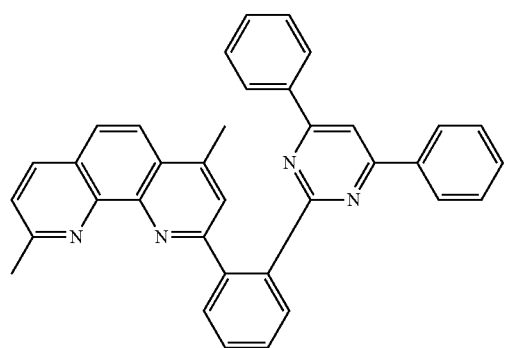
424
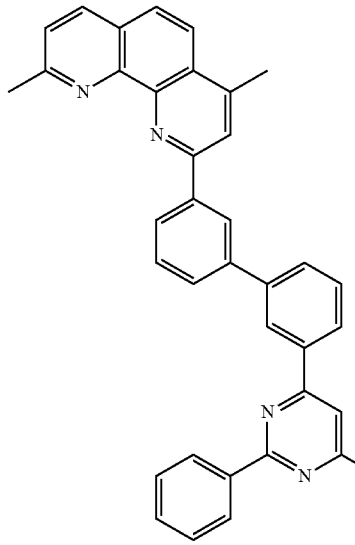
425
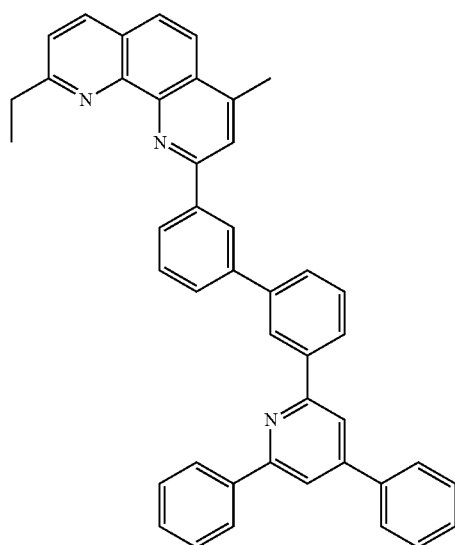
-continued
426
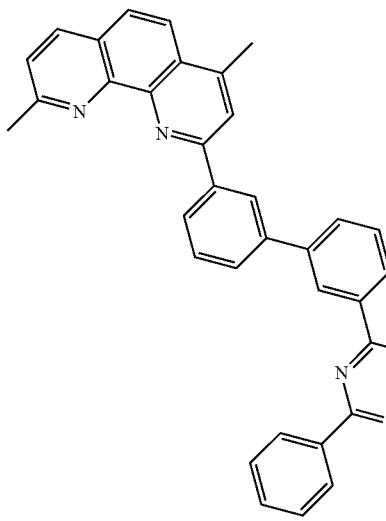
427
428
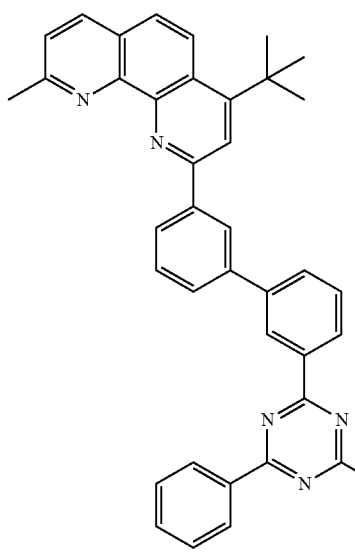

221
-continued
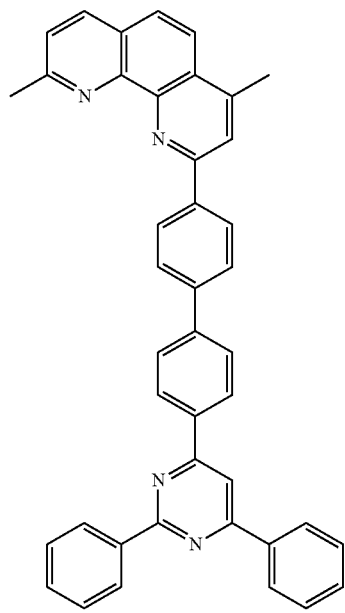
429
222
-continued
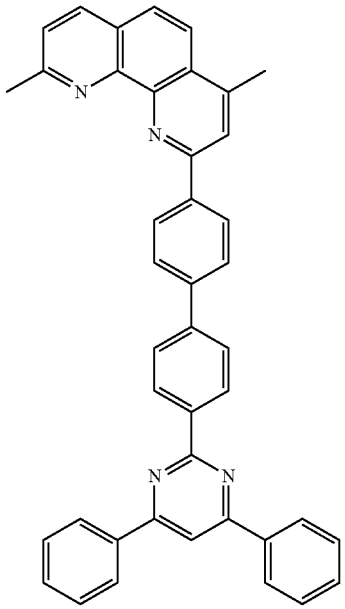
431
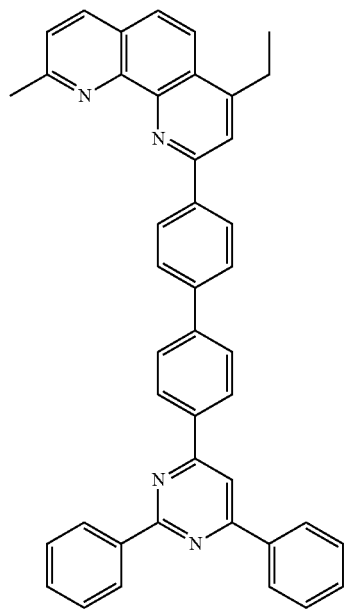
430
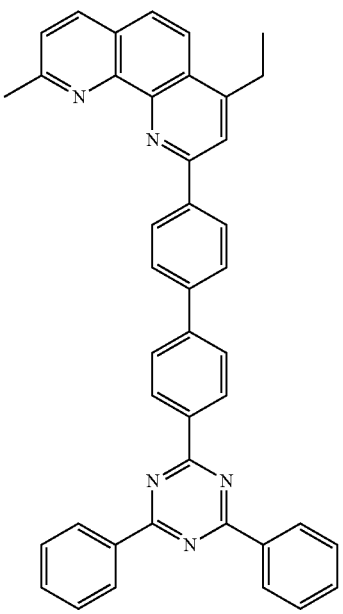
432

223
-continued
433
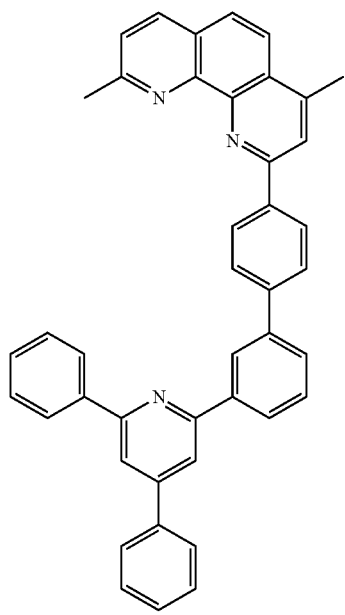
224
-continued
435
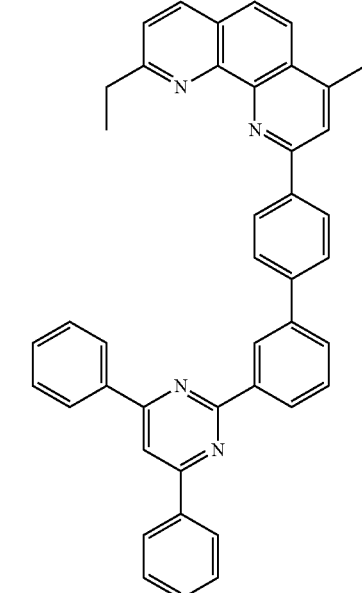
434
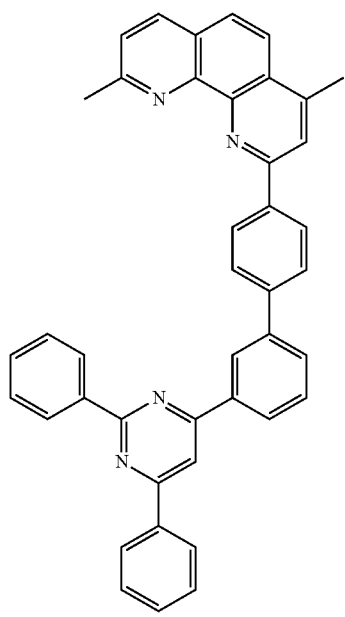
436
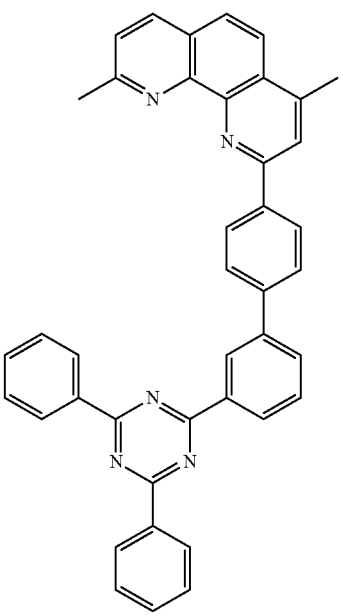

-continued
437
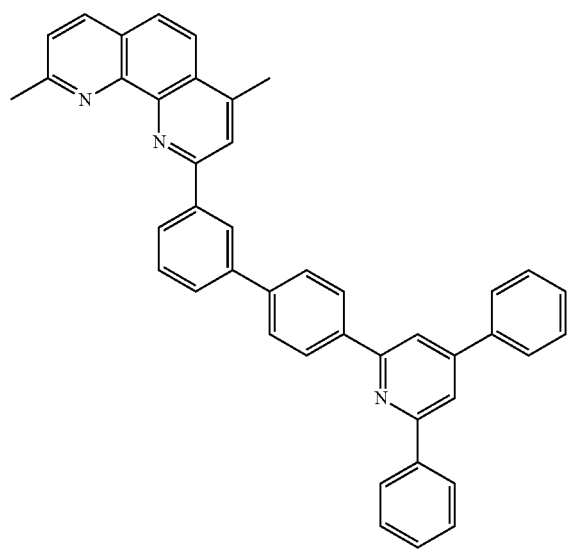
438
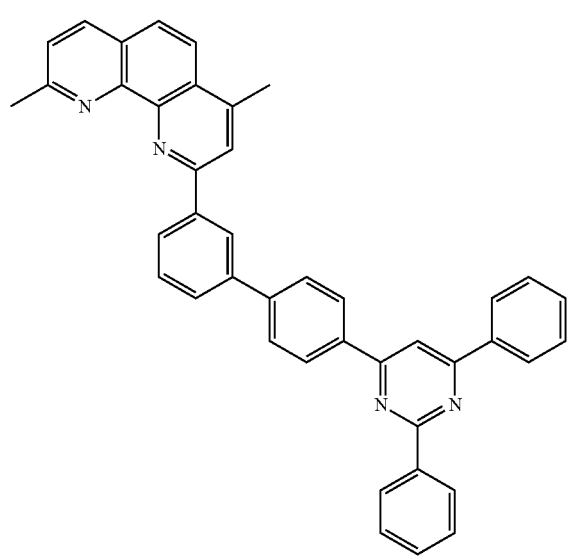
-continued
439
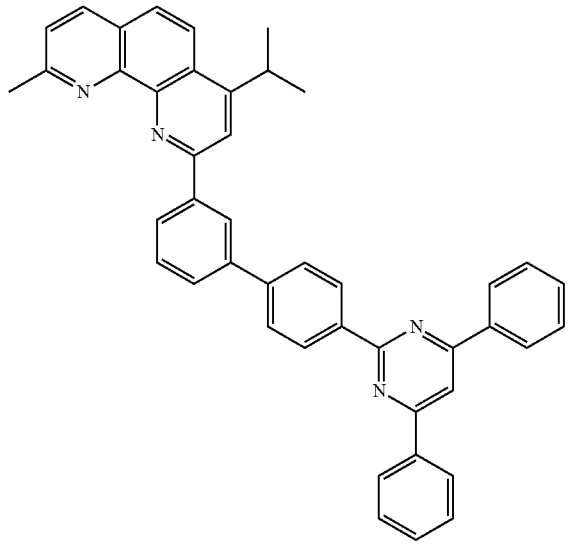
440
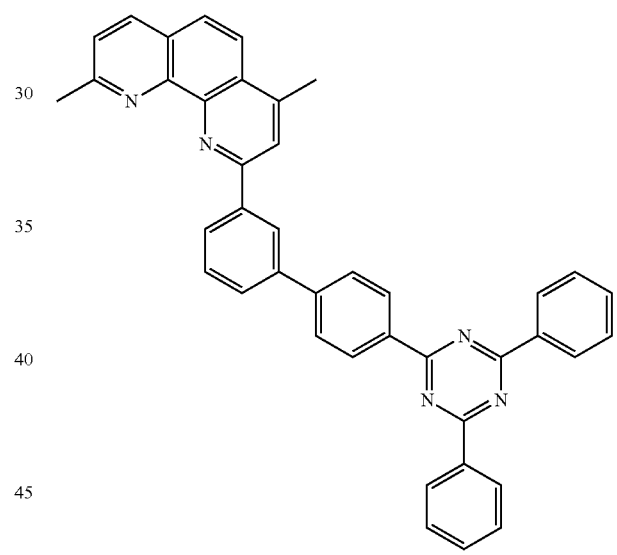
441
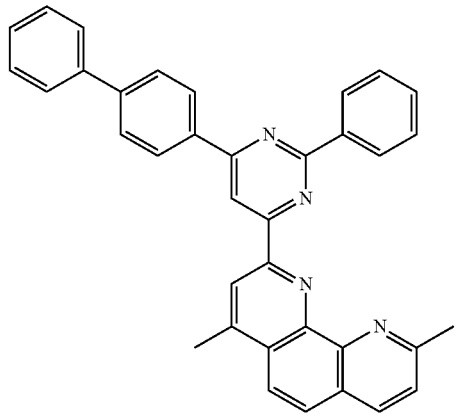

442
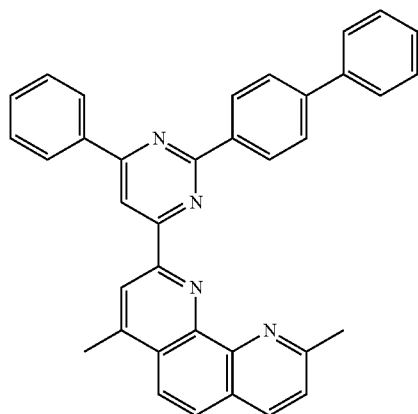
443
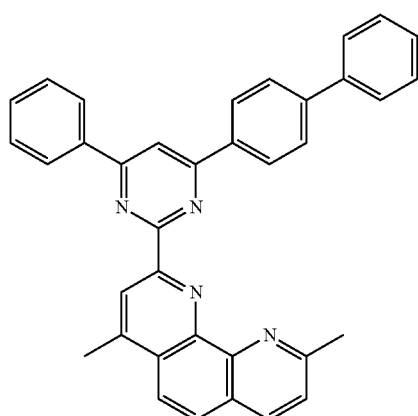
444
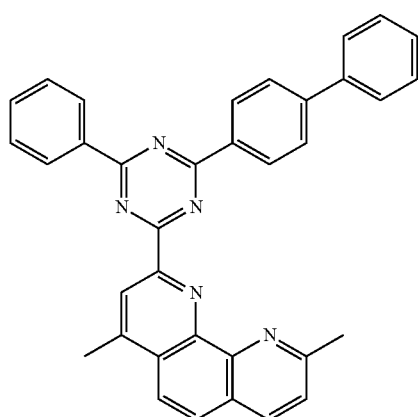
445
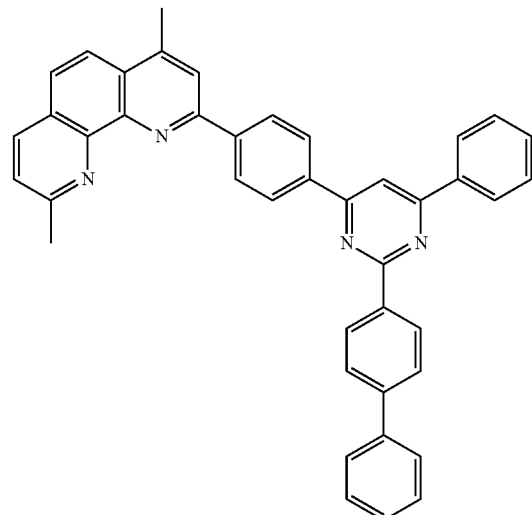
446
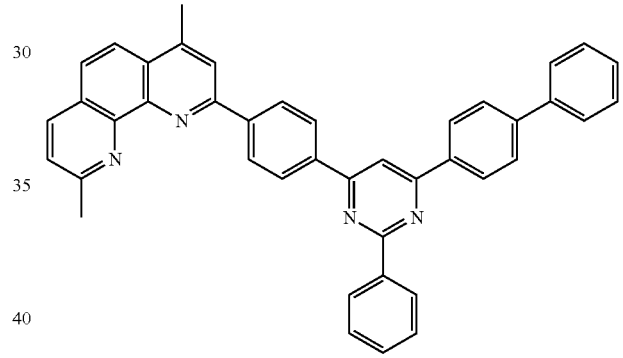
447
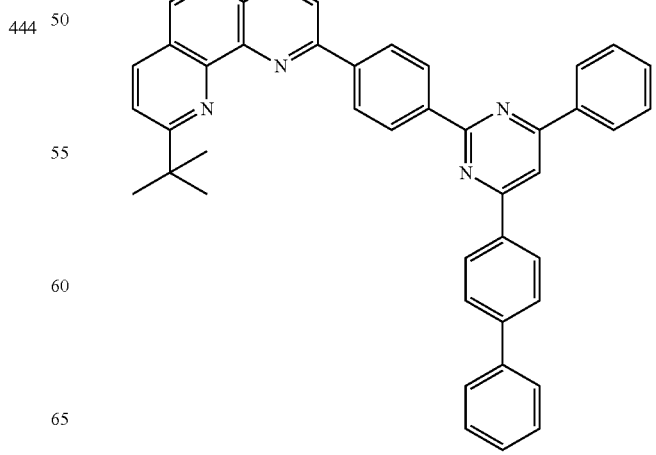

229
-continued
448
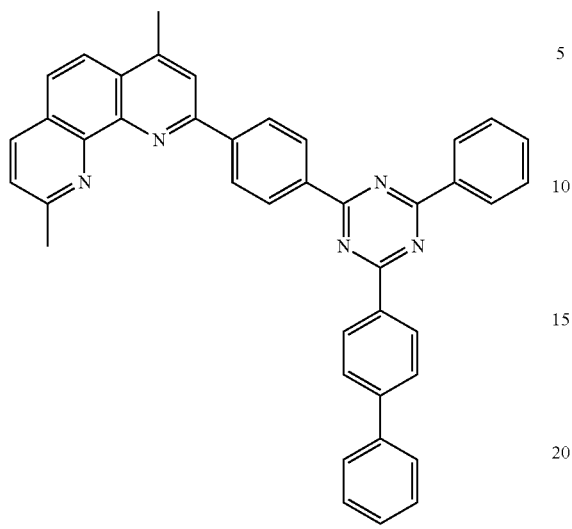
449
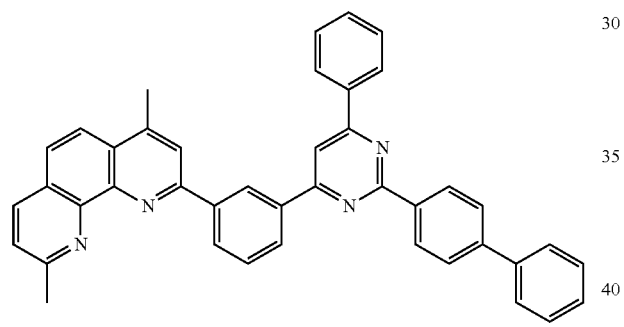
450
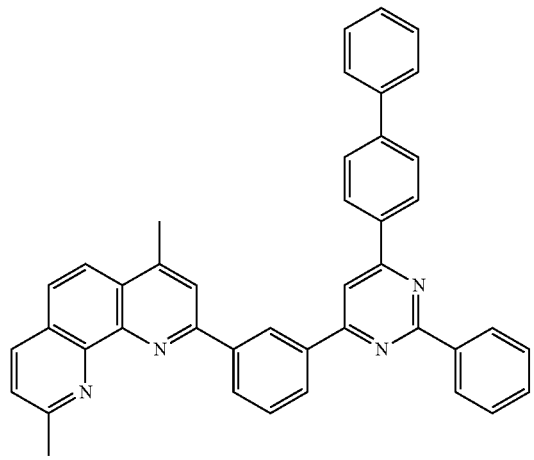
230
-continued
451
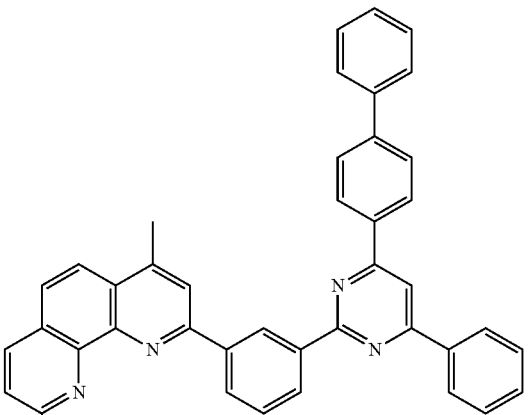
452
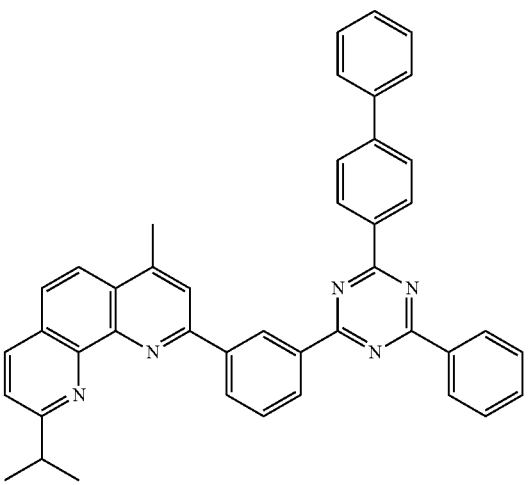
453
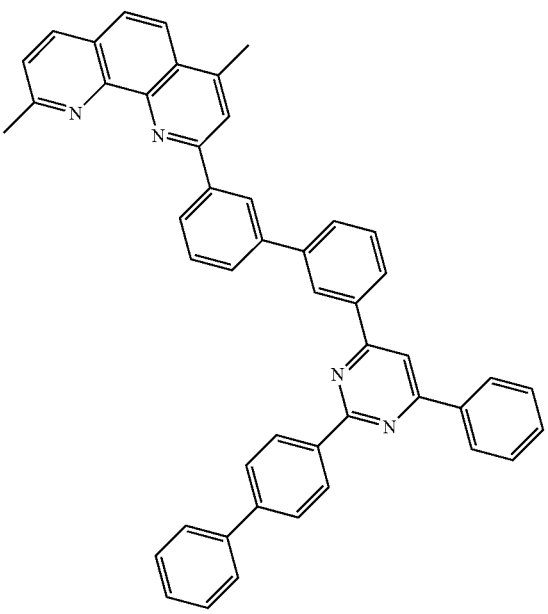

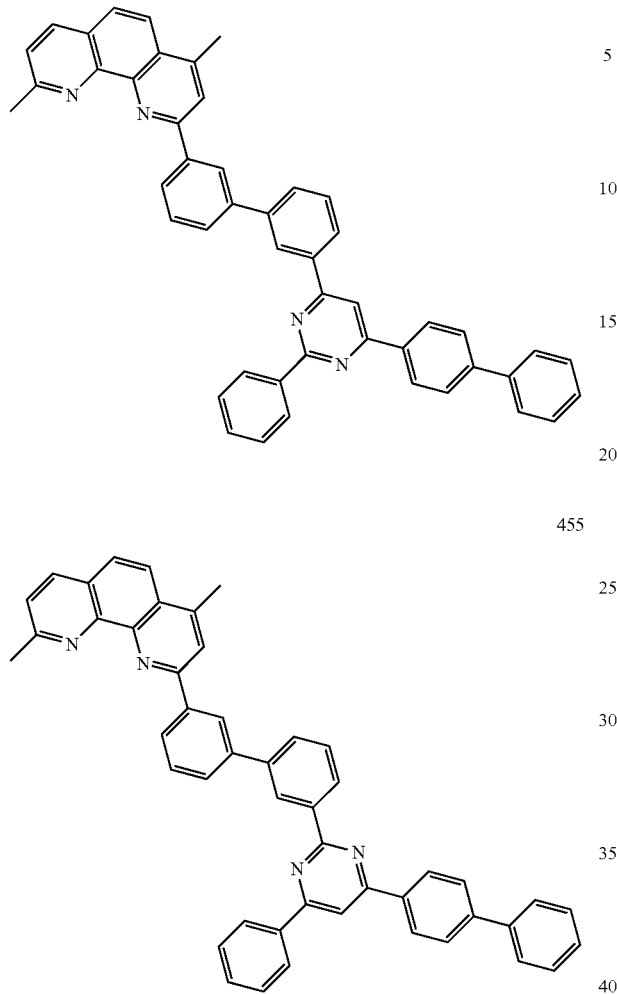
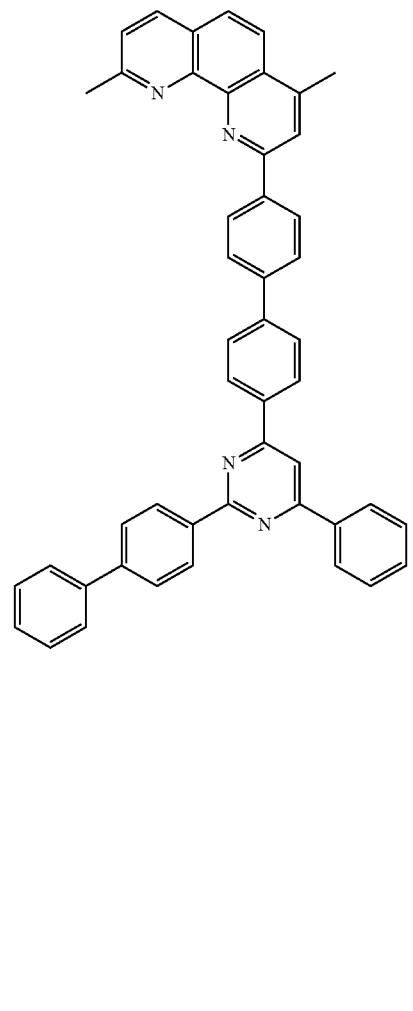
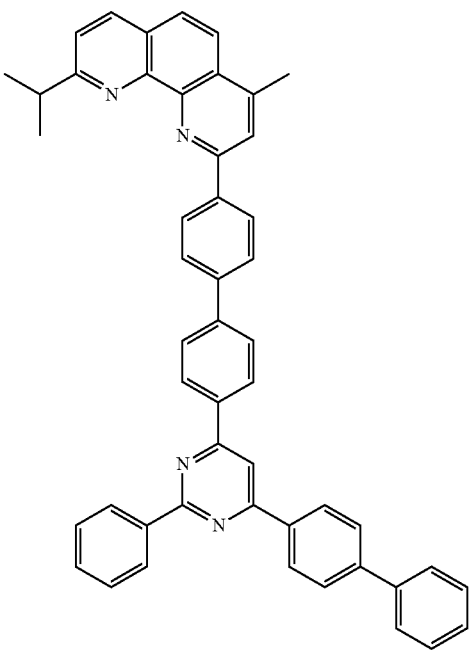

233
-continued
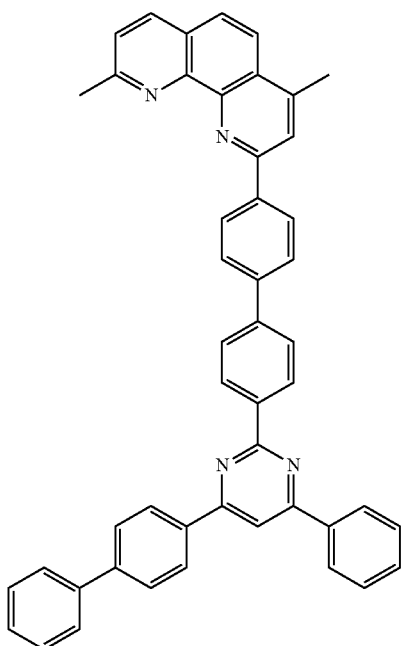
459
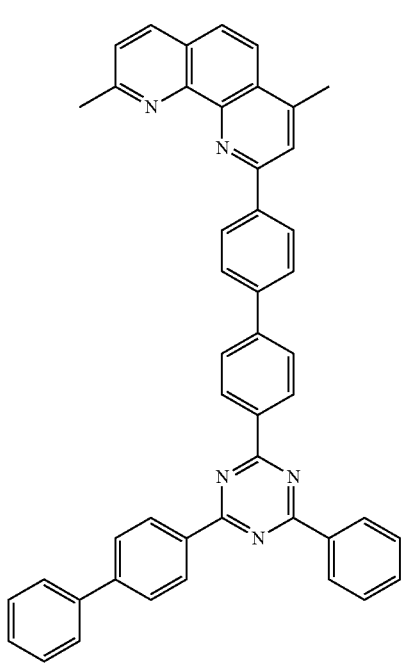
460
234
-continued
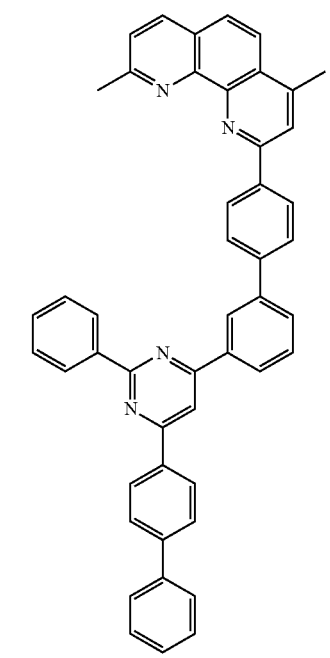
461
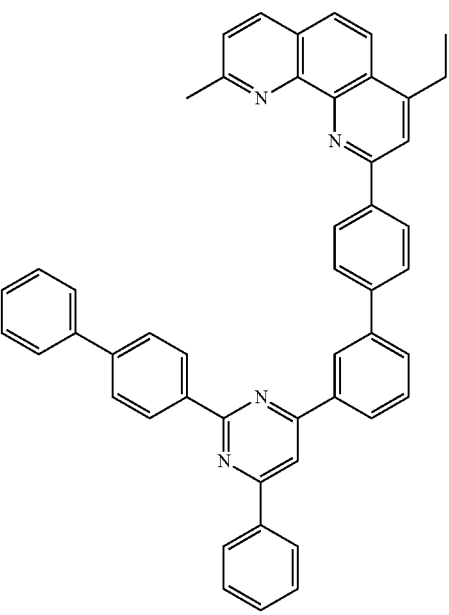
462

235
236
463
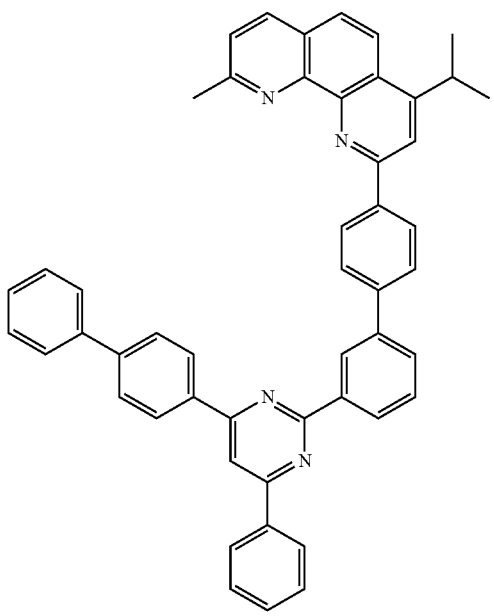
464
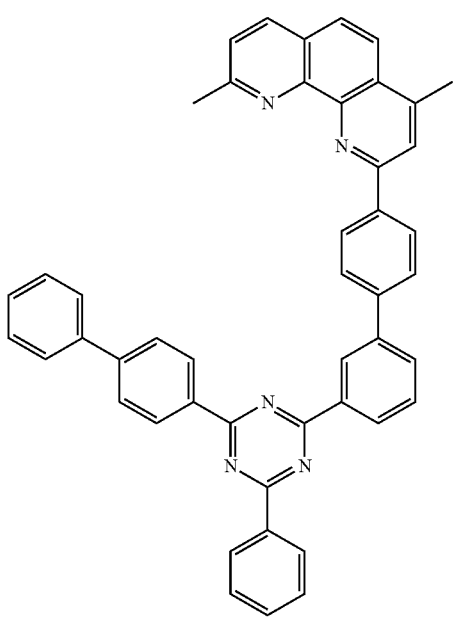
465
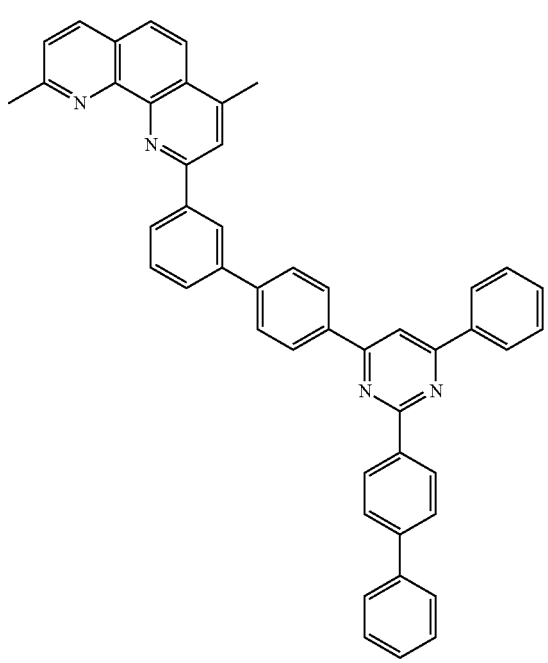
466
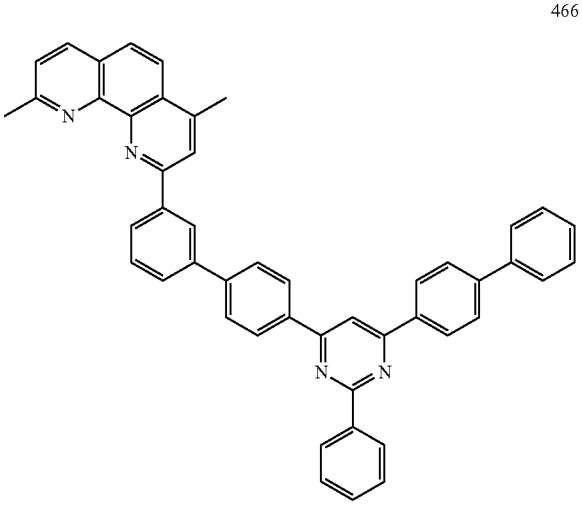

-continued
467
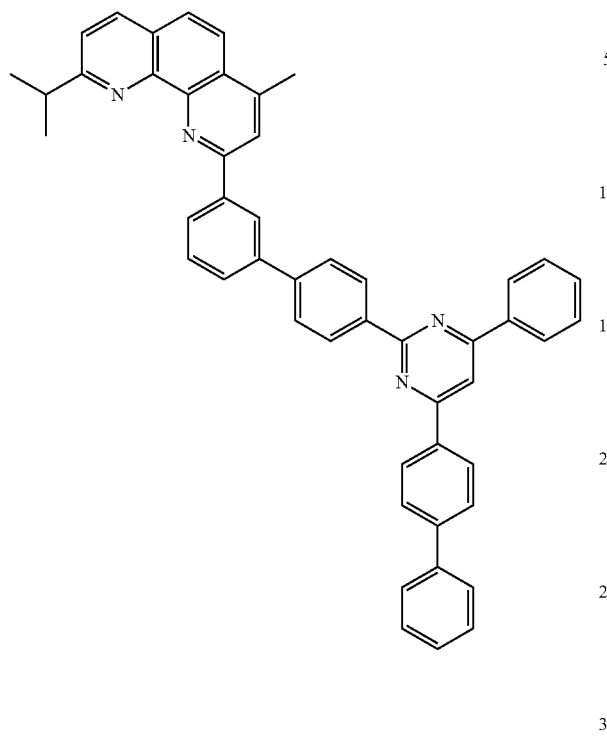
468
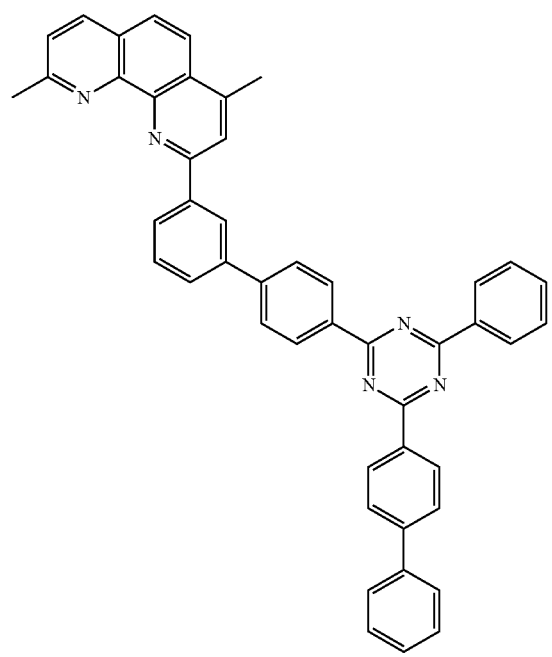
-continued
469
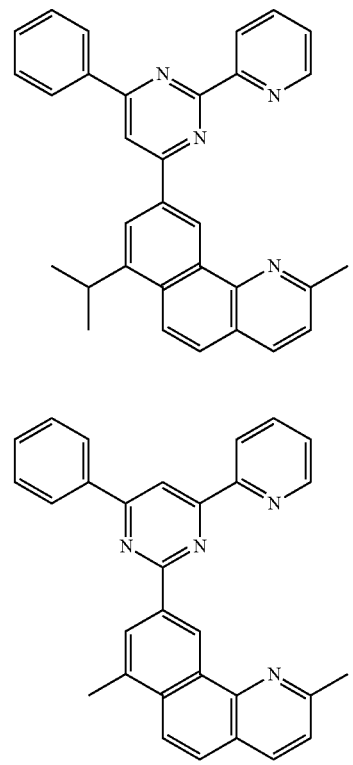
470
471
472
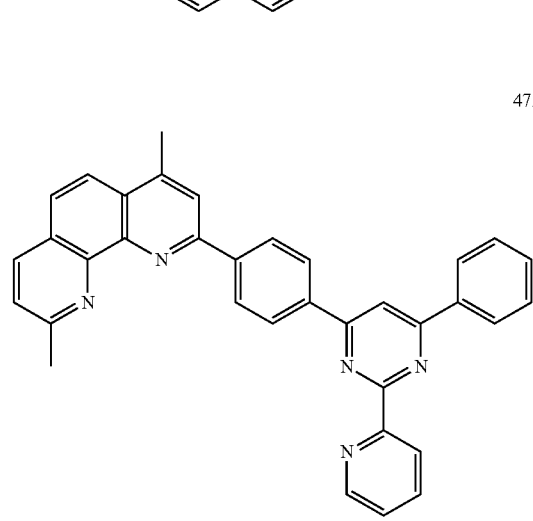

-continued
473
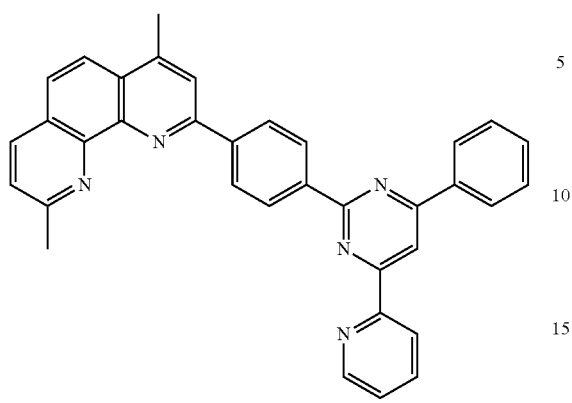
474
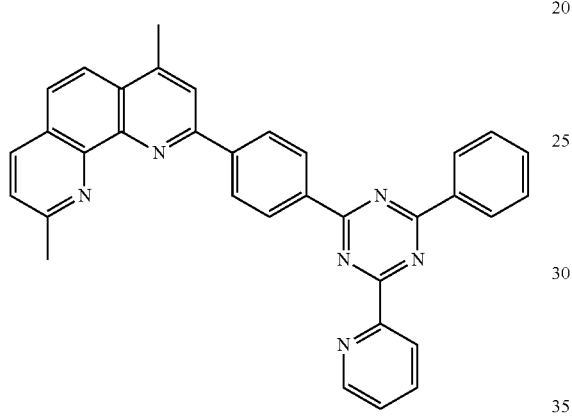
475
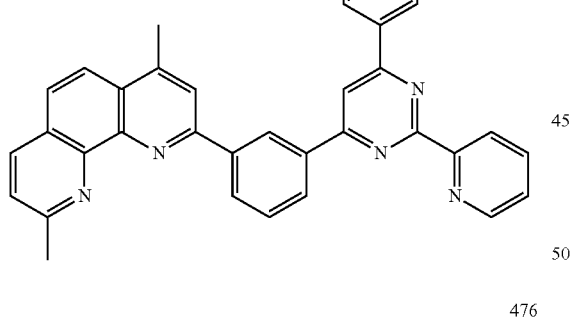
476
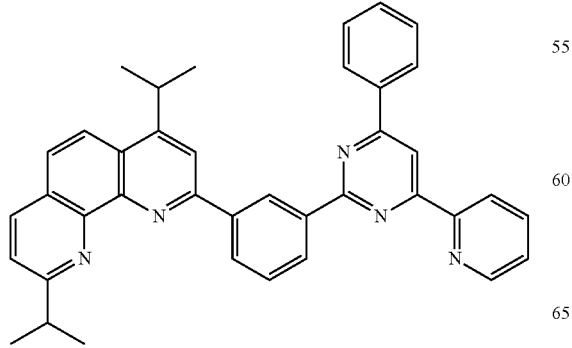
-continued
477
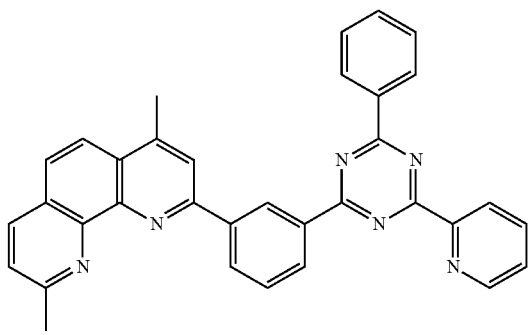
478
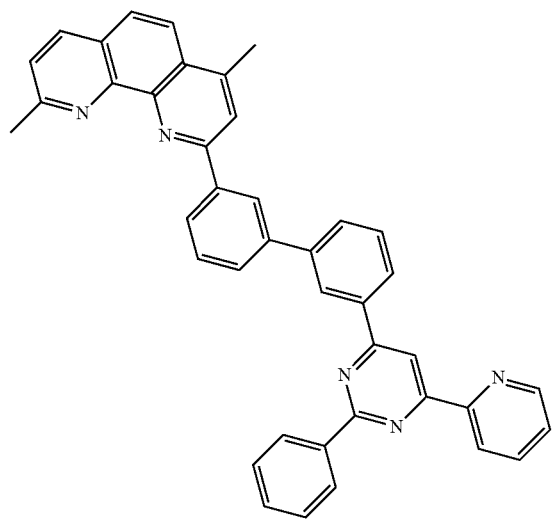
479
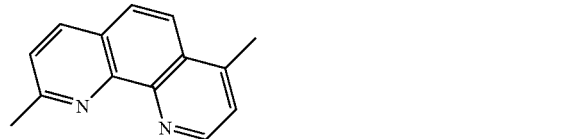
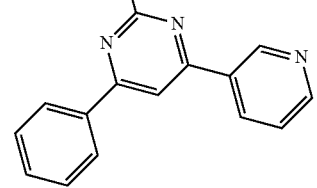

241
-continued
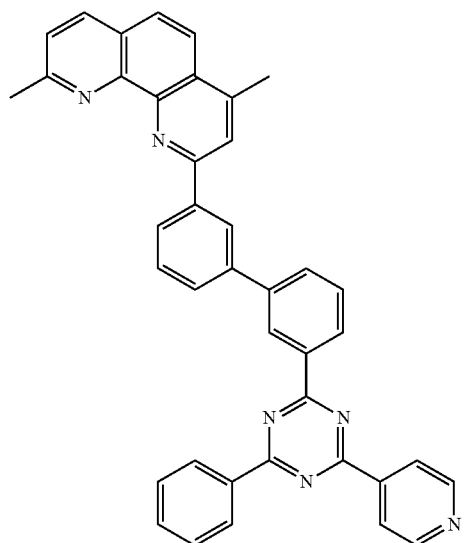
480
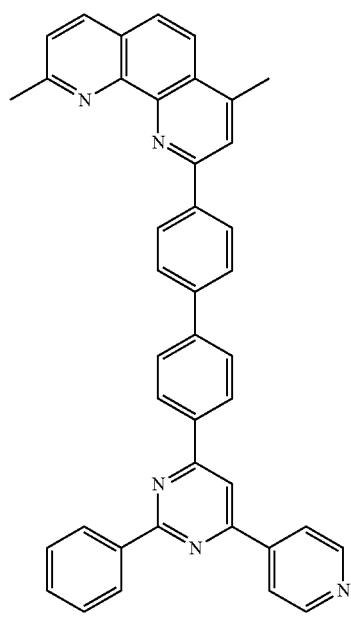
481
242
-continued
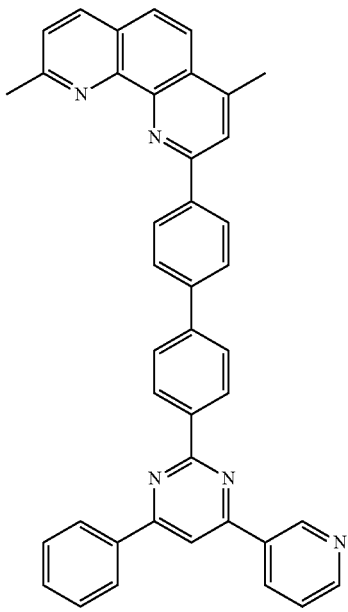
482
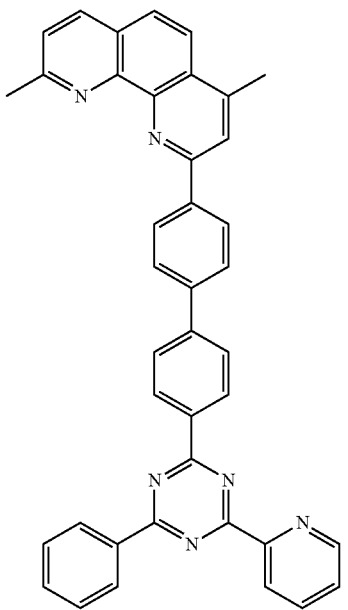
483

484
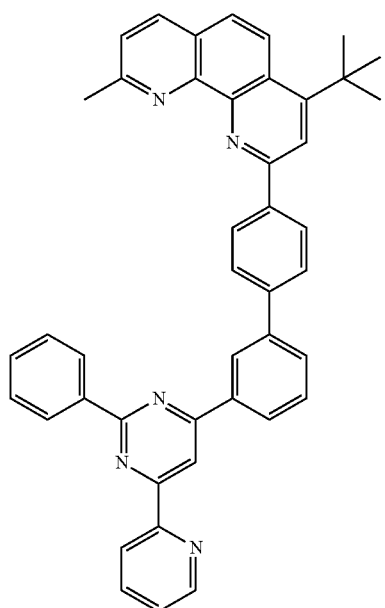
485
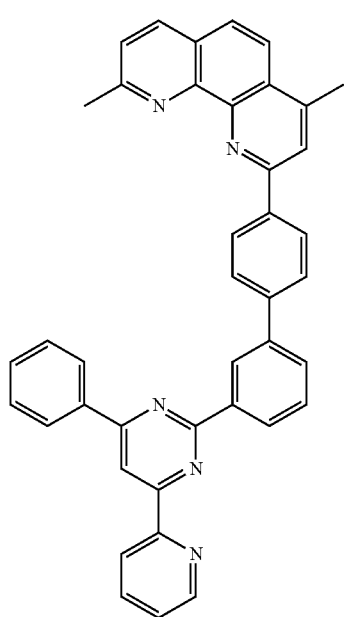
486
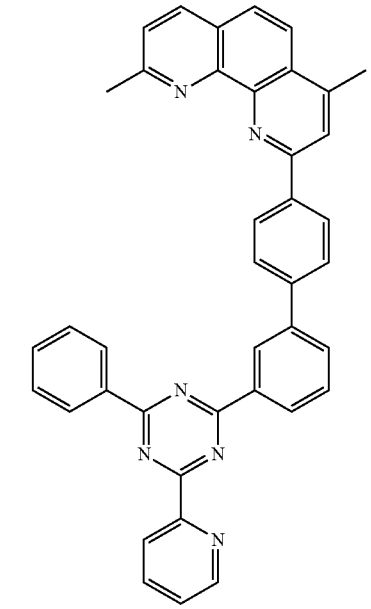
487
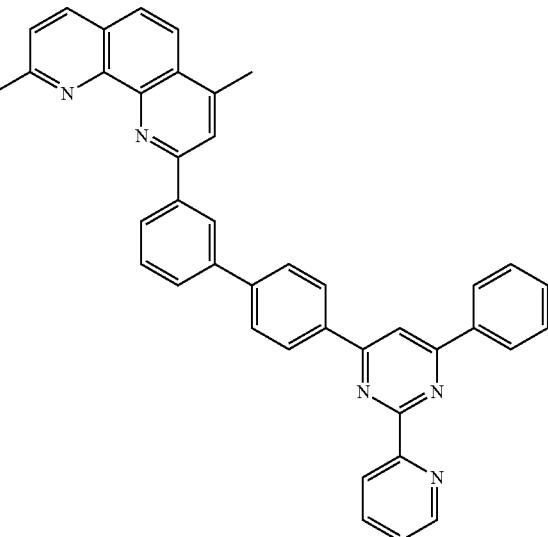

245
-continued
488
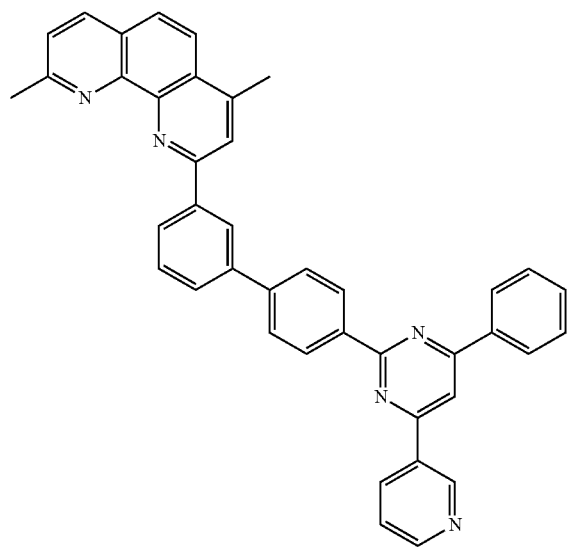
489
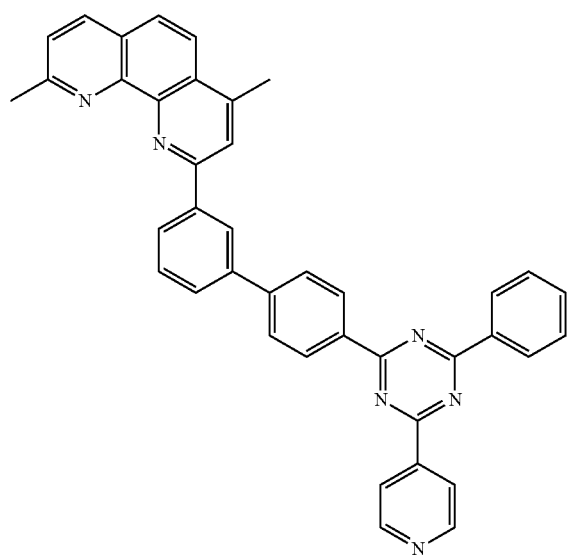
490
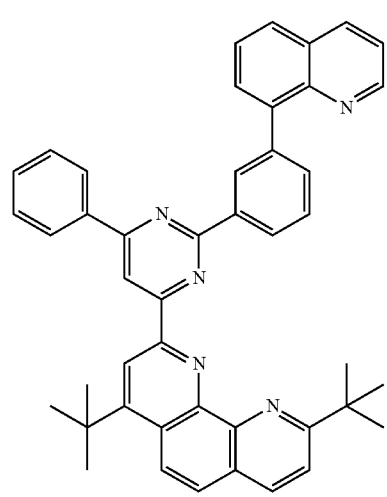
246
-continued
491
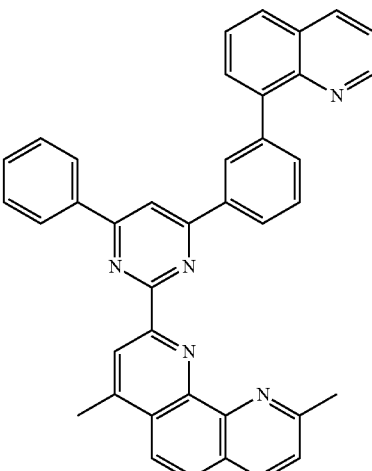
492
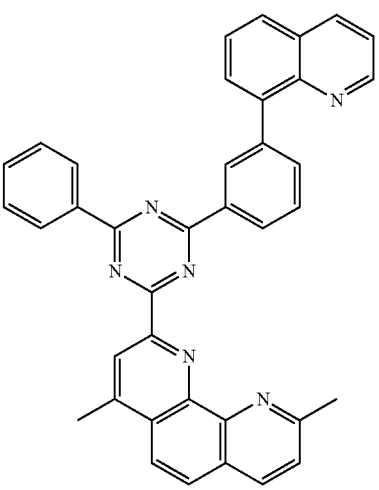
493
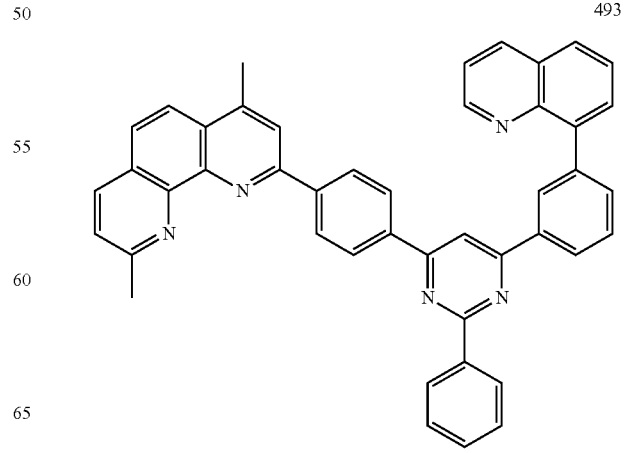

494
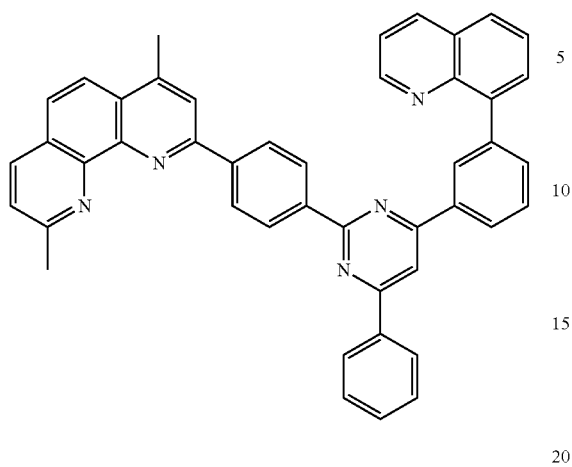
497
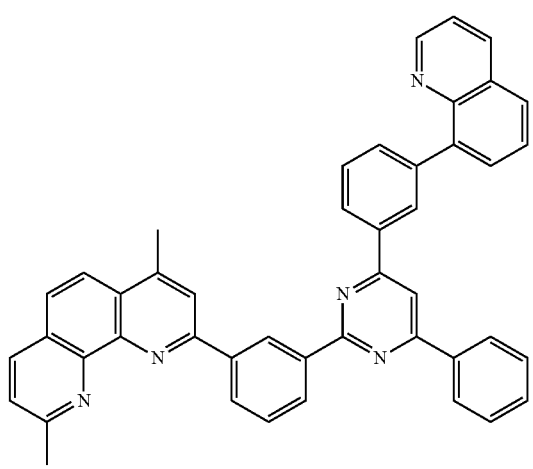
495
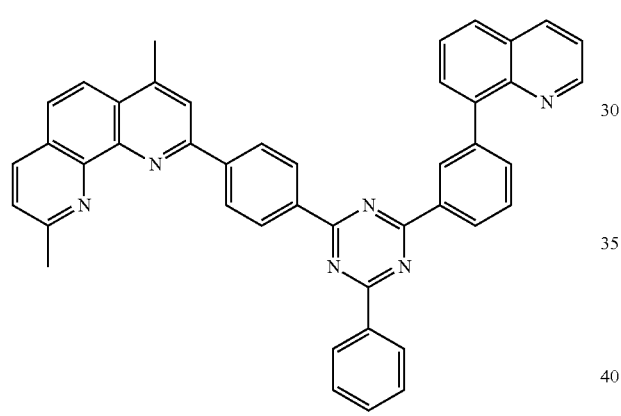
498
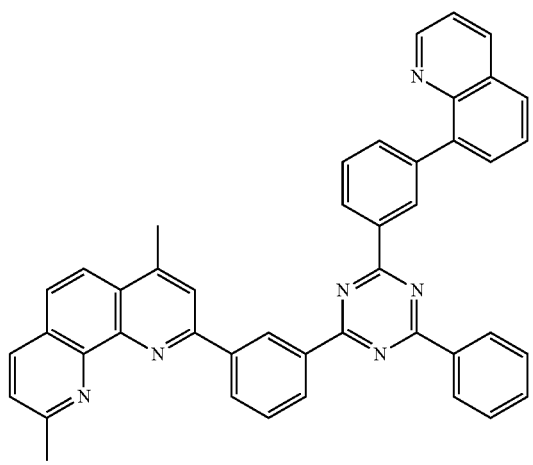
496
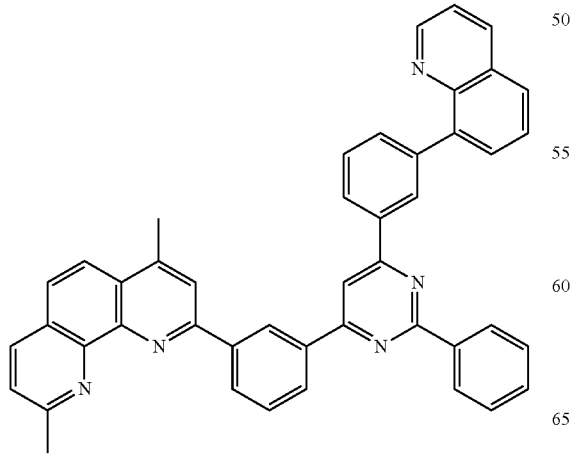
499
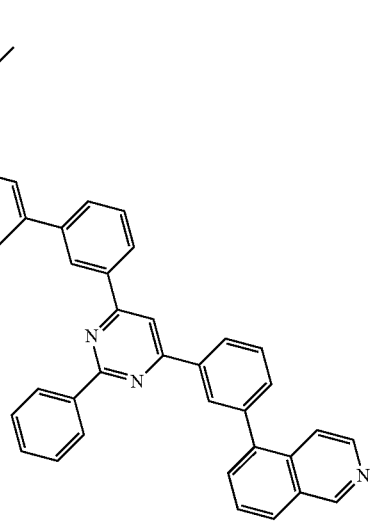

-continued
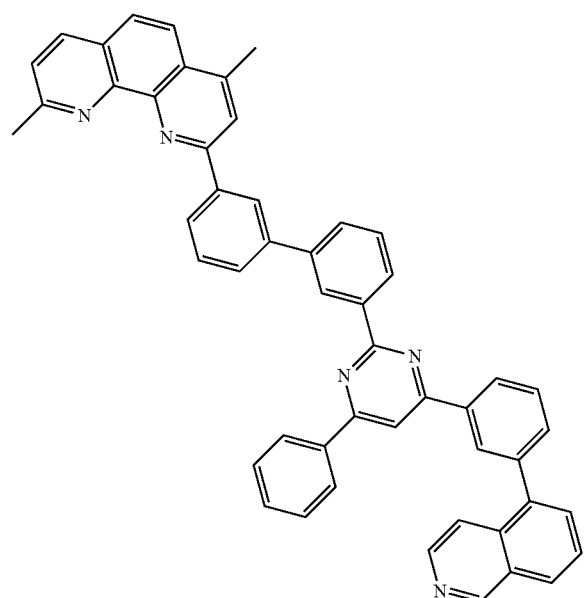
500
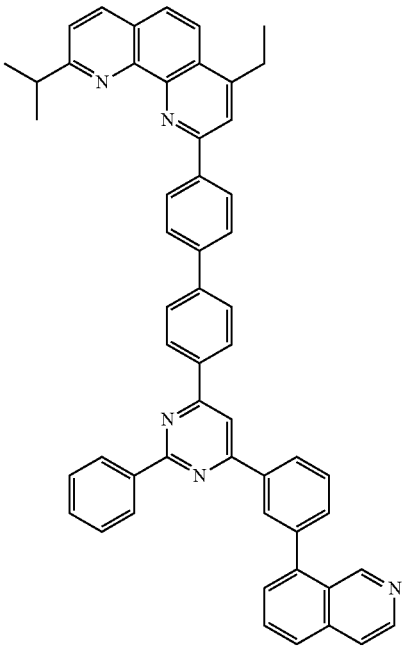
502
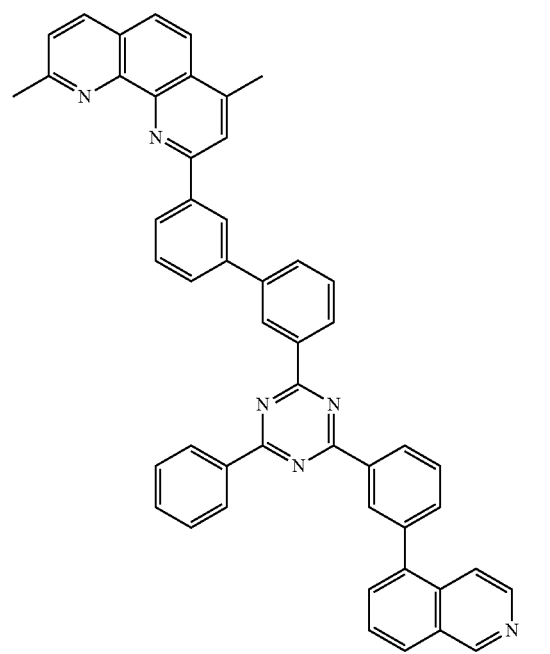
501
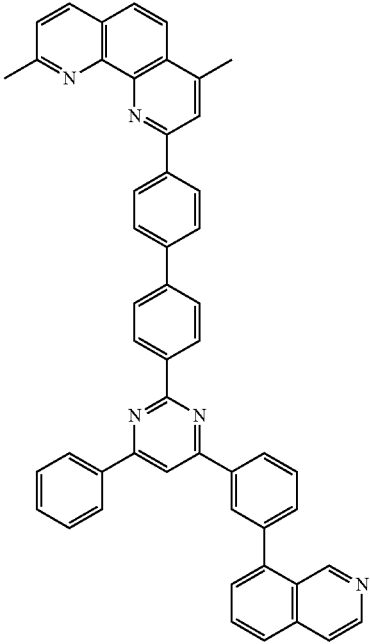
503

251
-continued
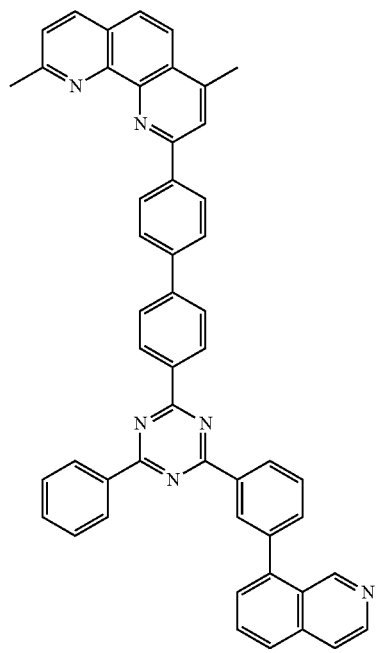
252
-continued
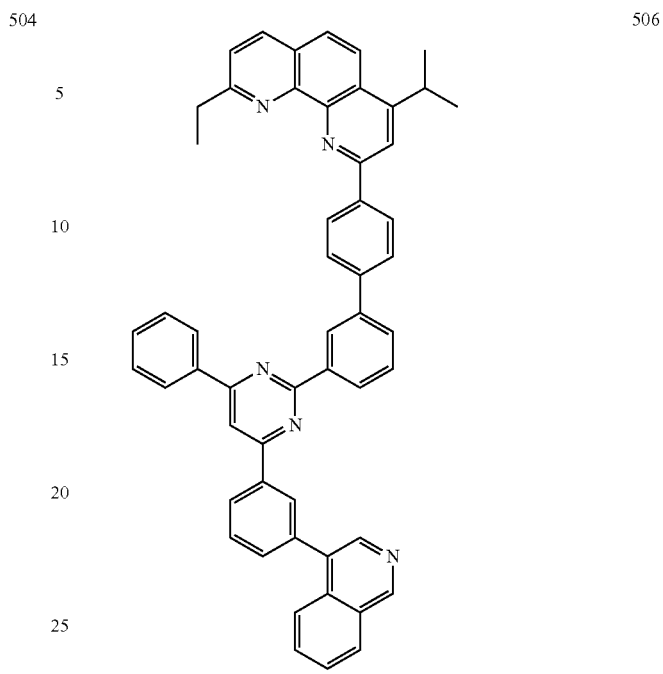
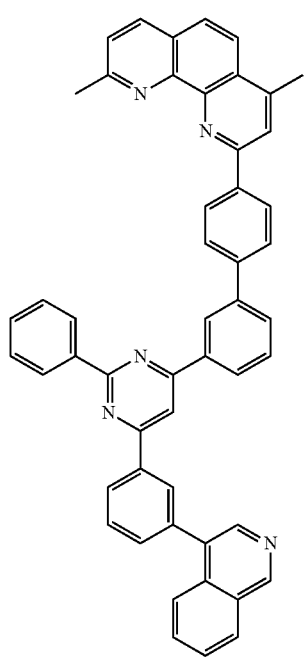
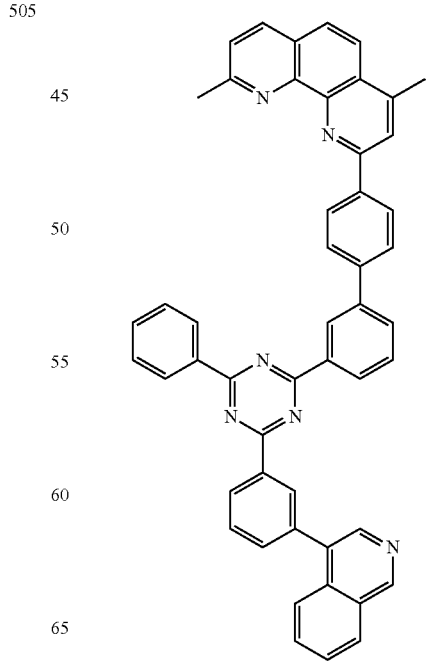

253
-continued
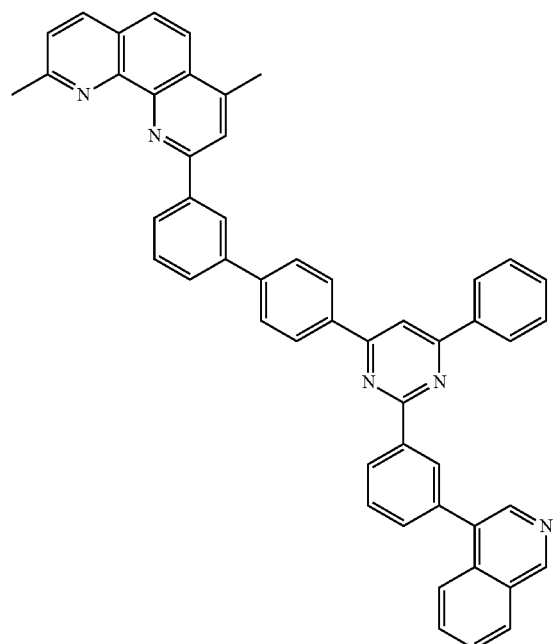
508
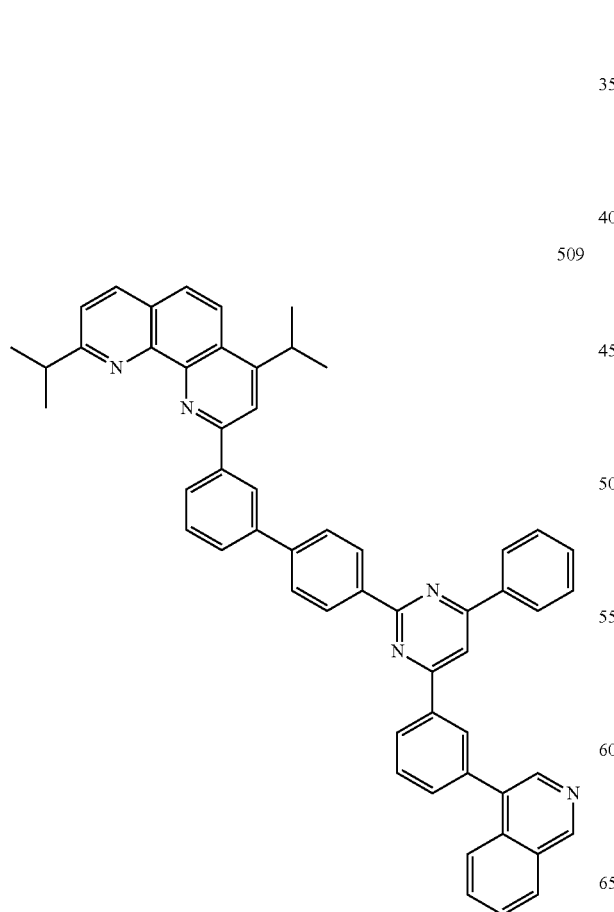
509
254
-continued
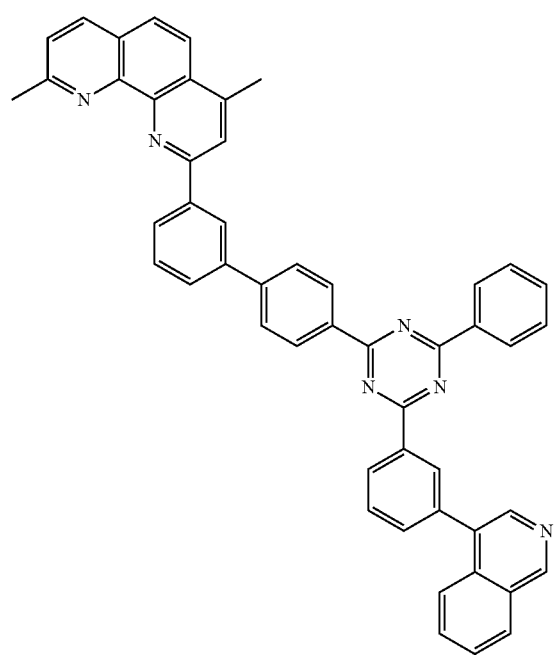
510
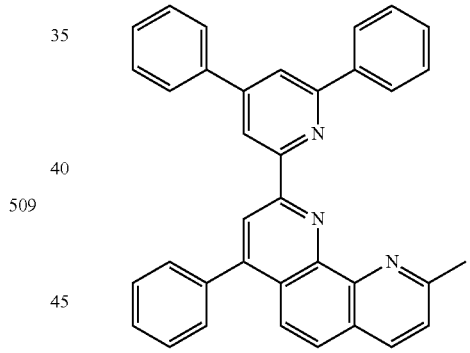
511
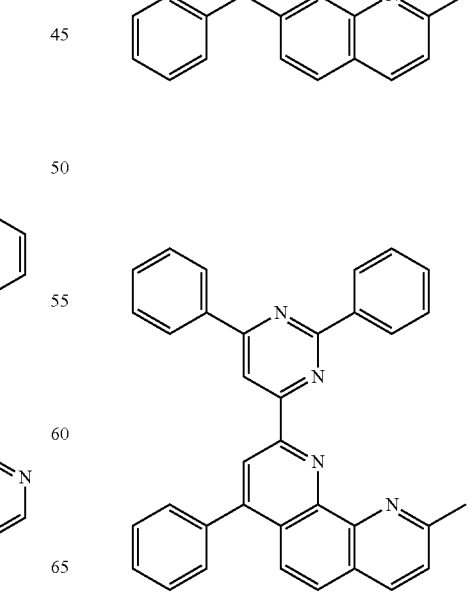
512

255
-continued
513
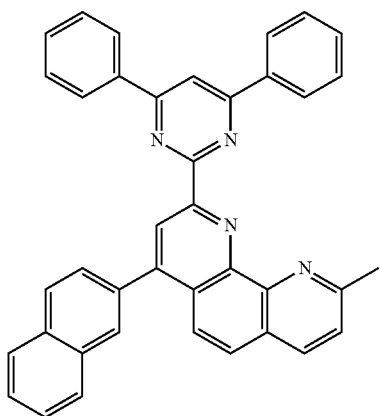
514
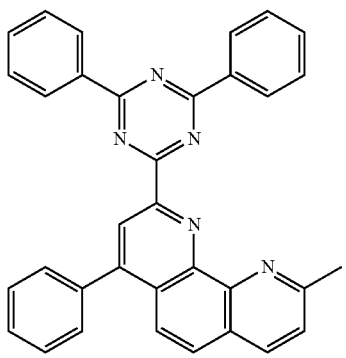
515
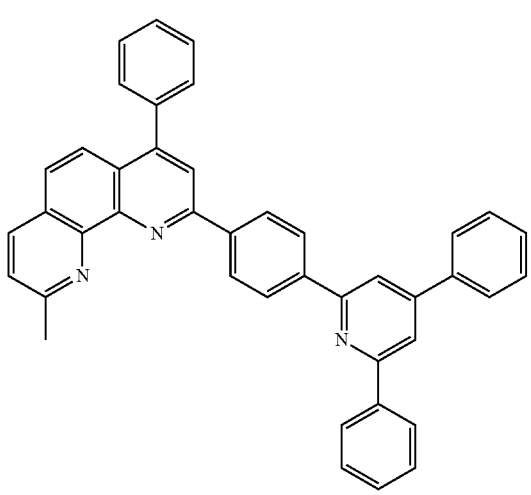
256
-continued
516
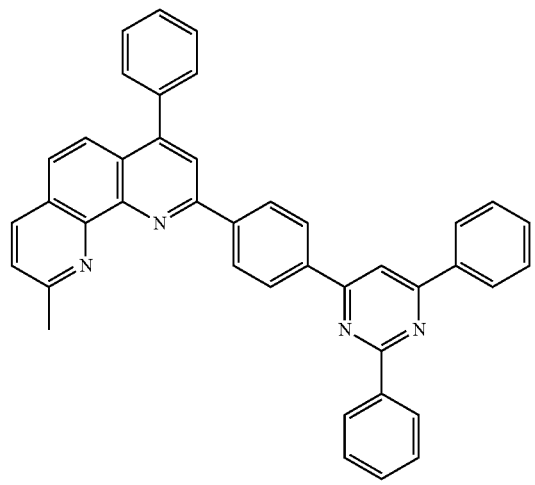
517
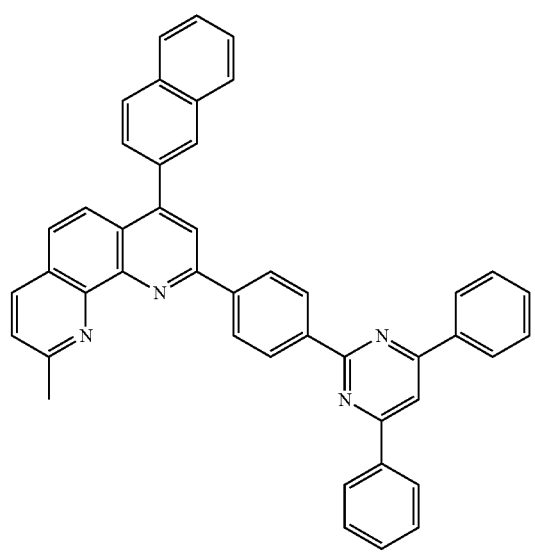
518
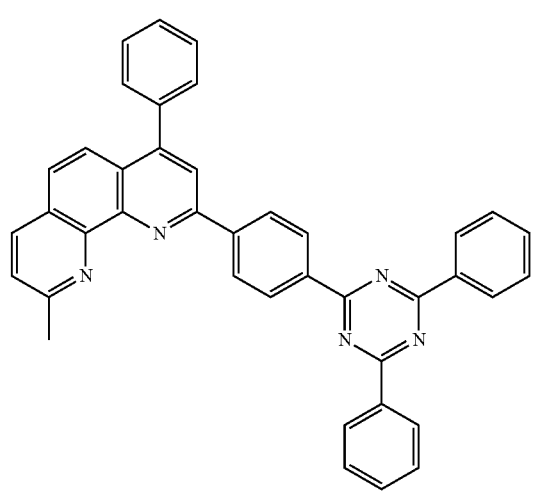

-continued
519
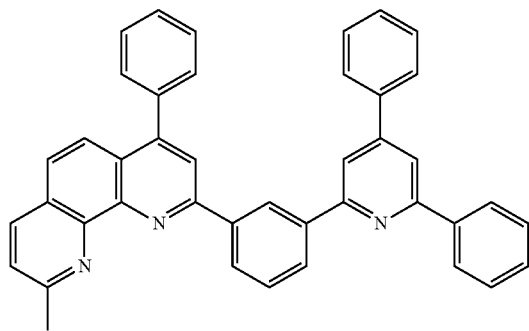
520
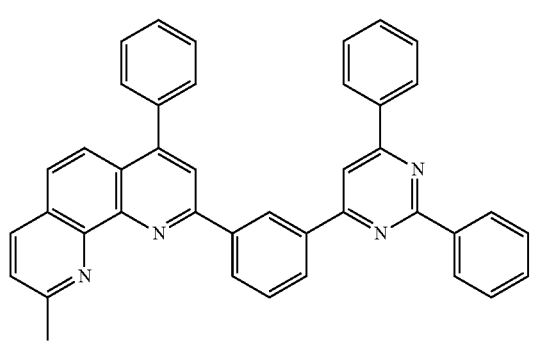
521
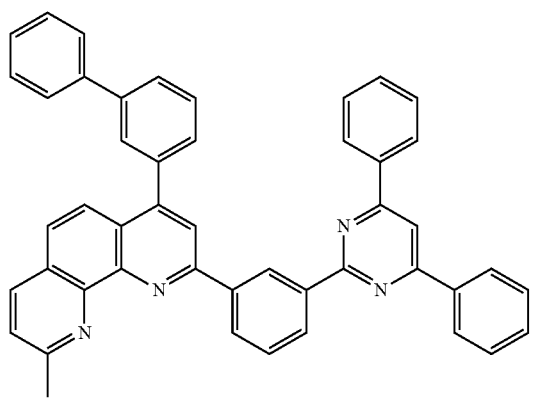
522
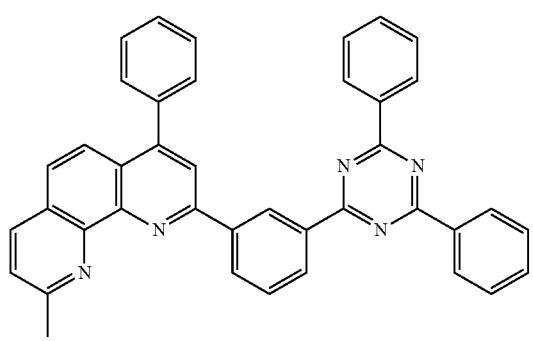
-continued
523
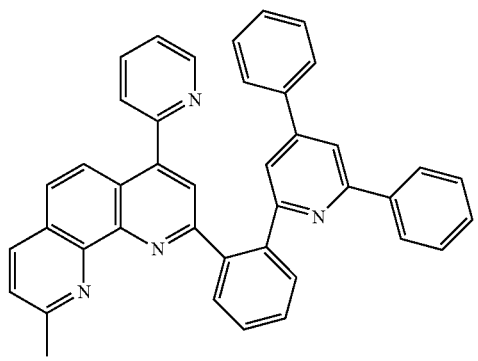
524
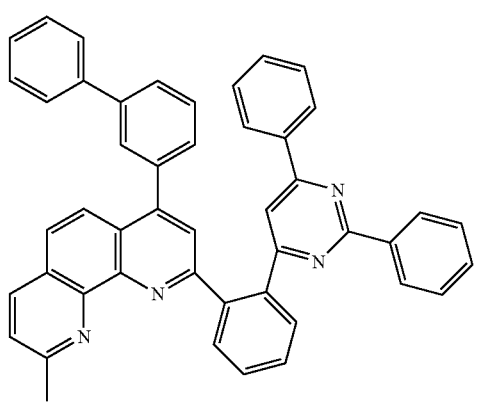
525
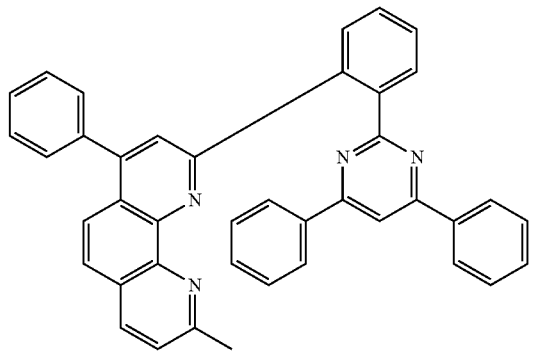
526
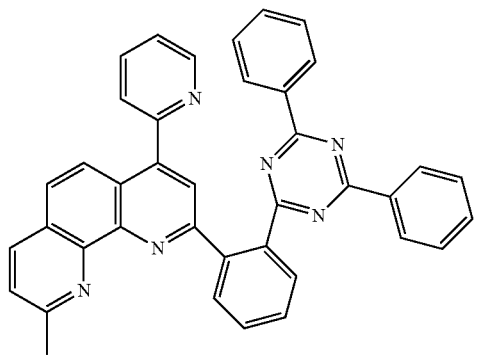

259
-continued
527
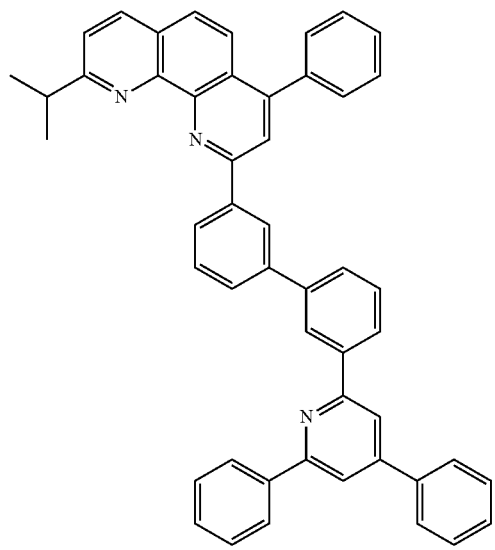
528
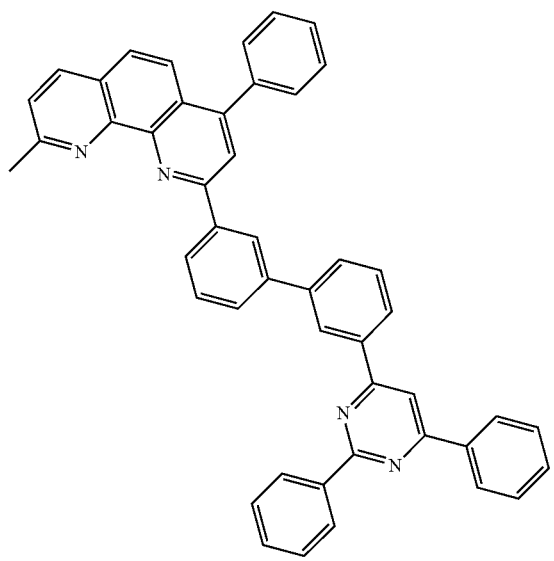
260
-continued
529
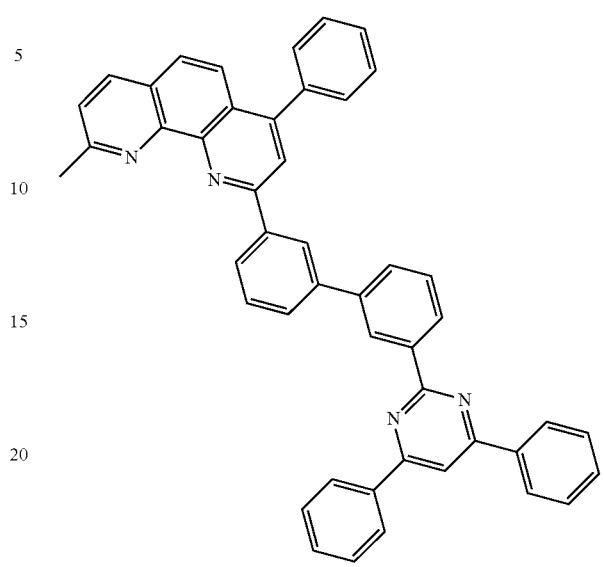
530
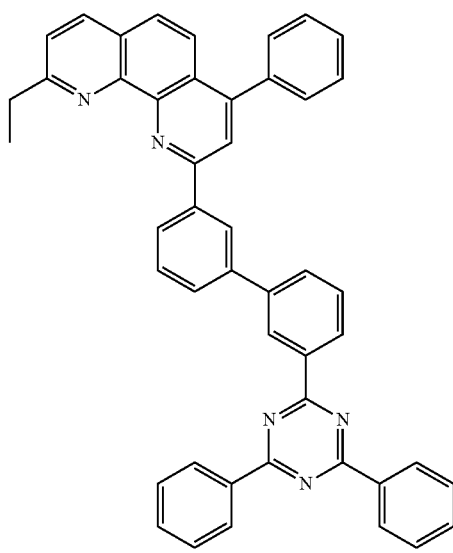

261
-continued
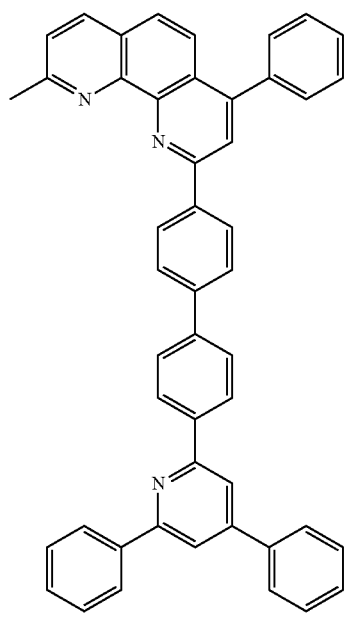
531
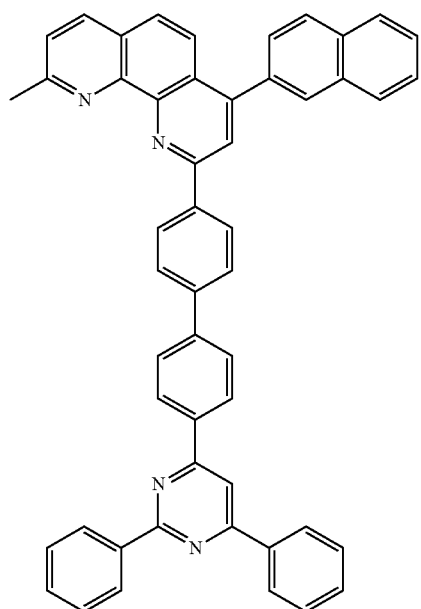
532
262
-continued
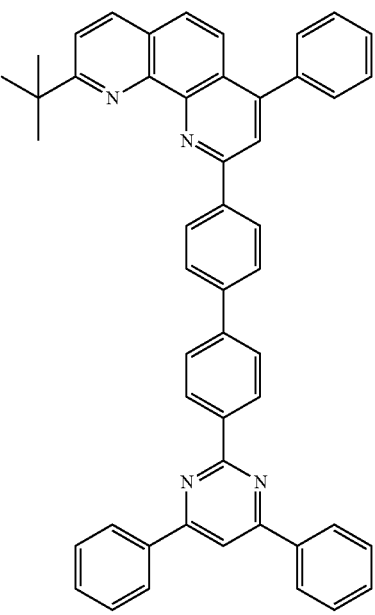
533
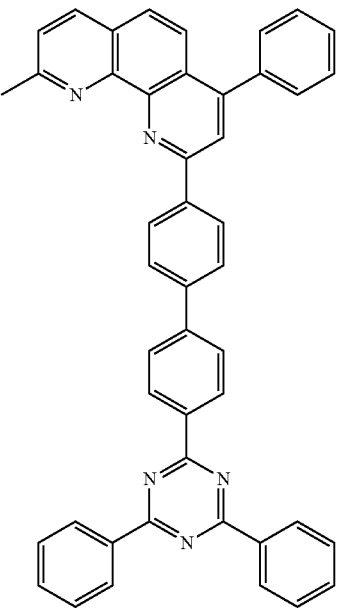
534

535
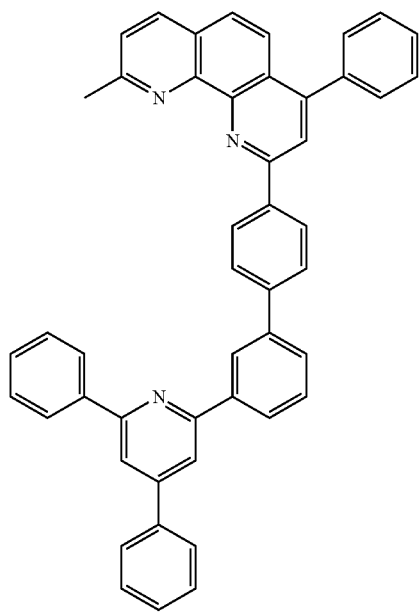
536
537
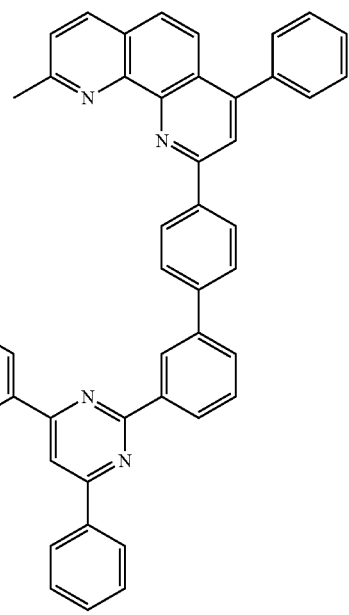
538

265
-continued
539
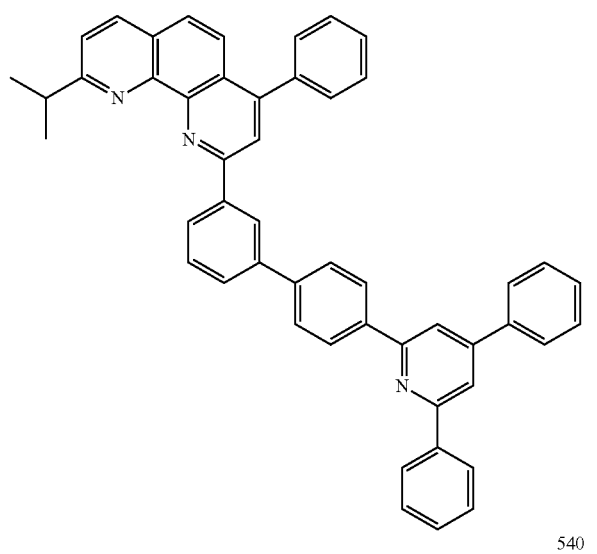
540
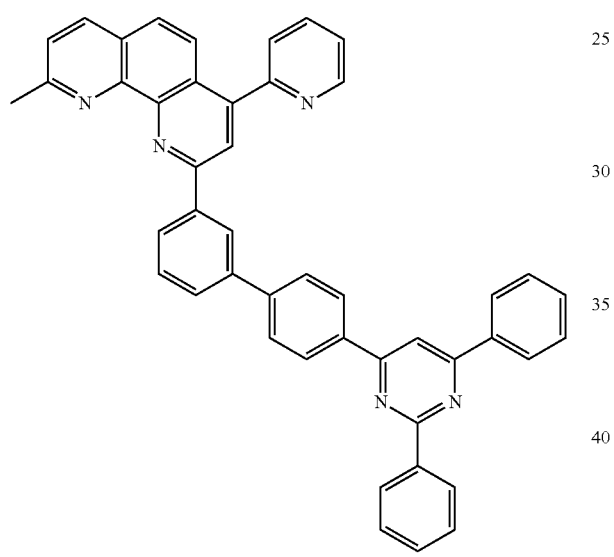
541
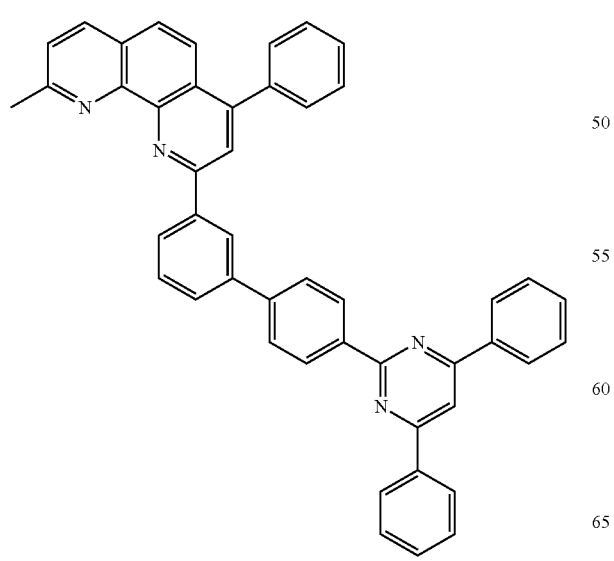
266
-continued
542
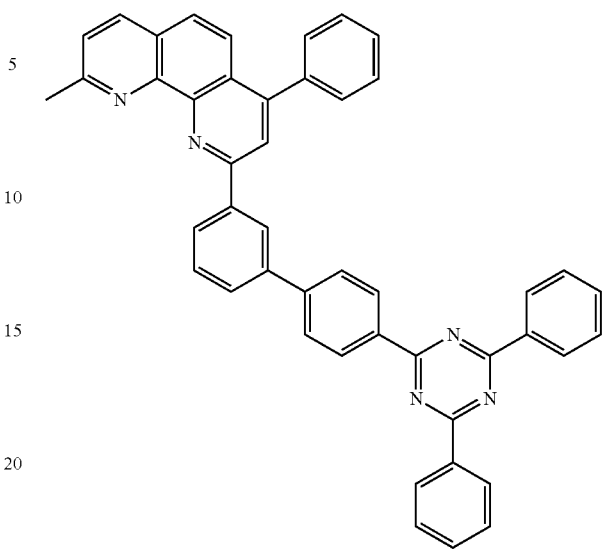
543
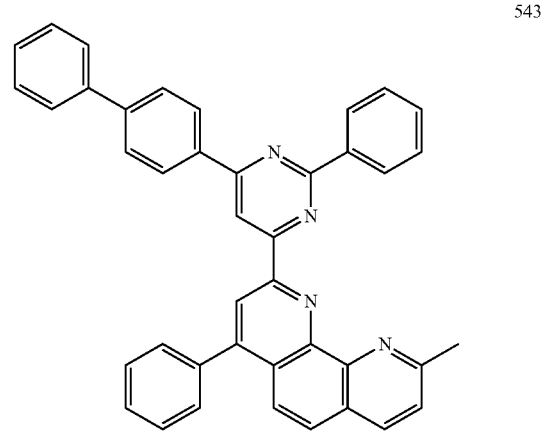
544
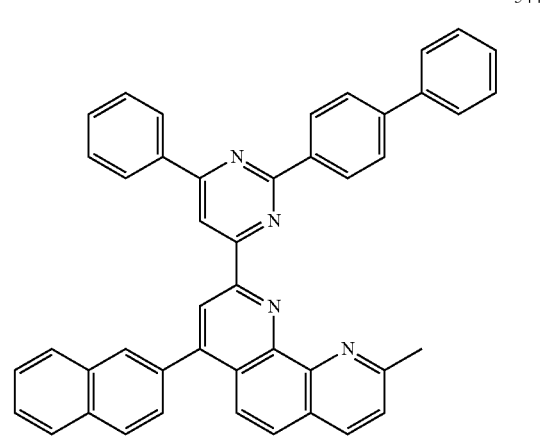

545
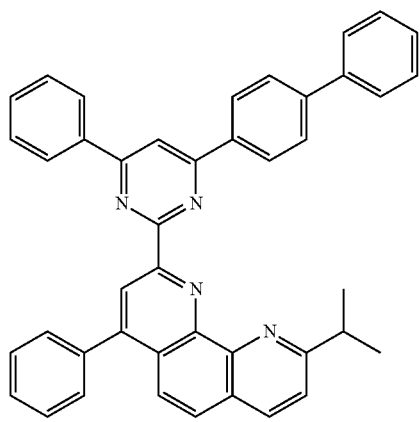
546
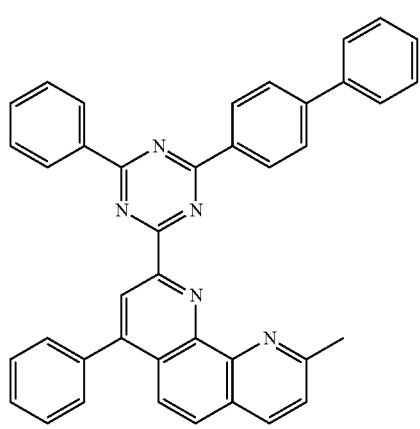
547
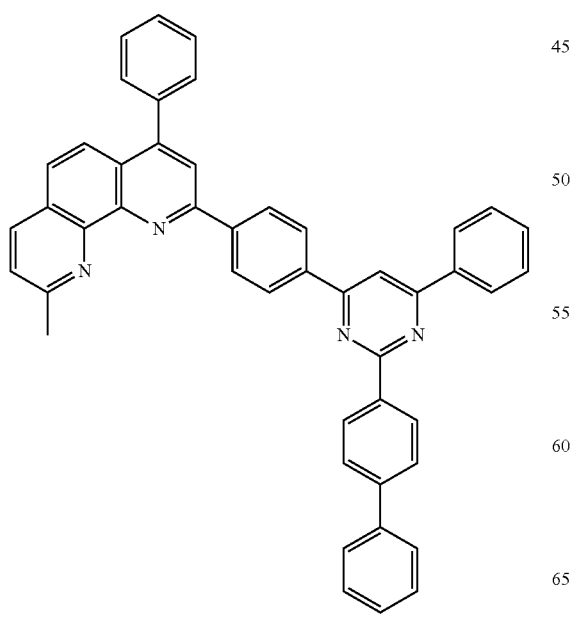
548
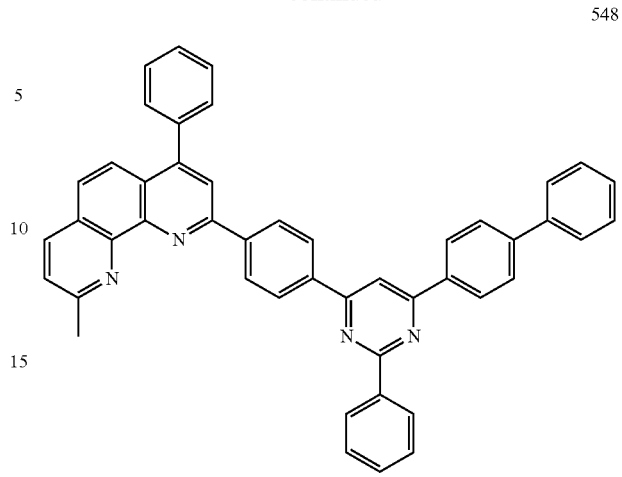
549
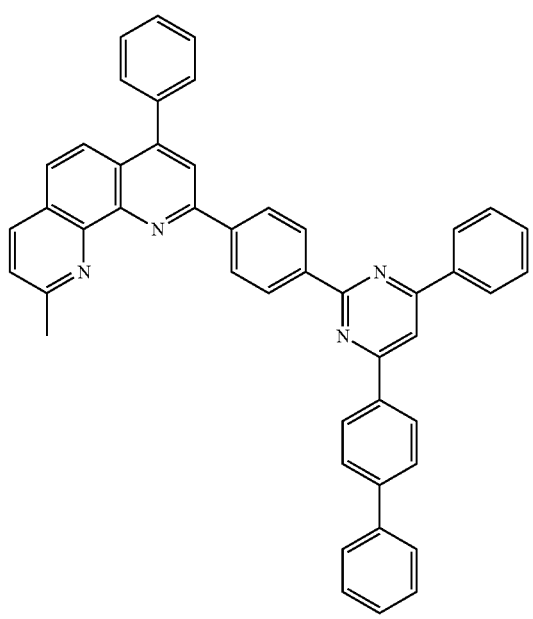

550
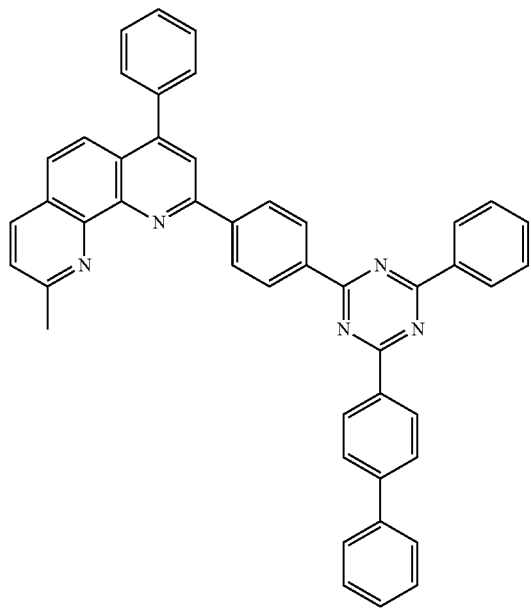
551
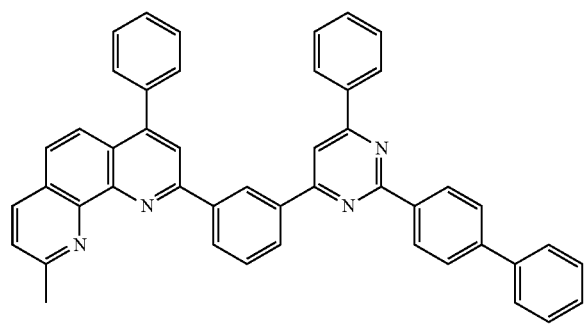
552
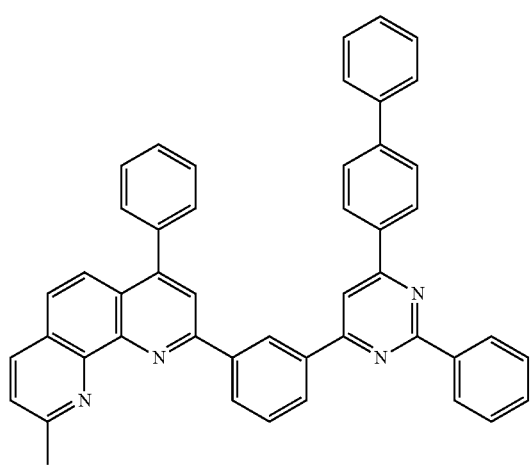
553
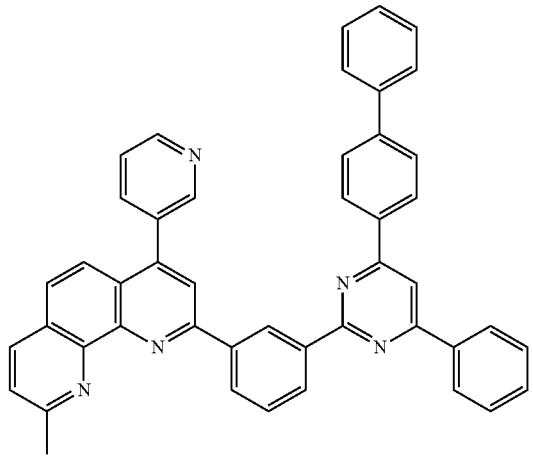
554
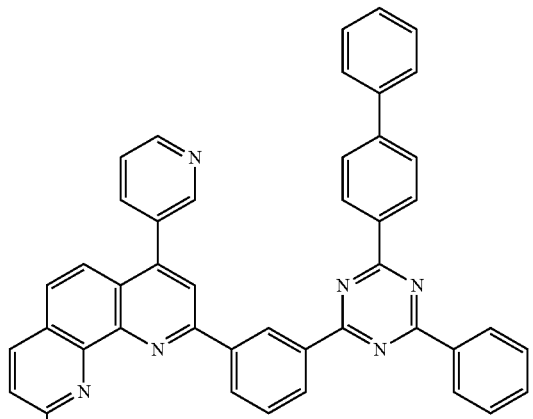
555
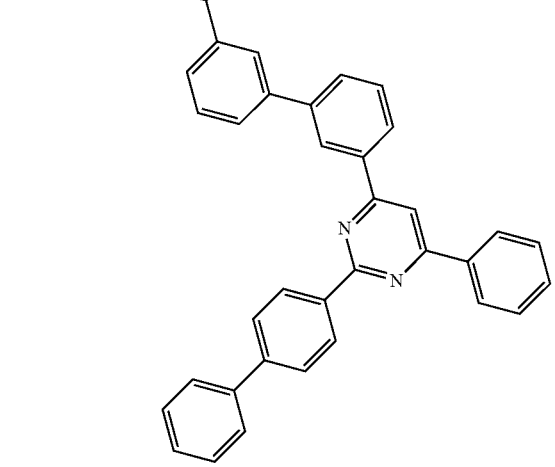

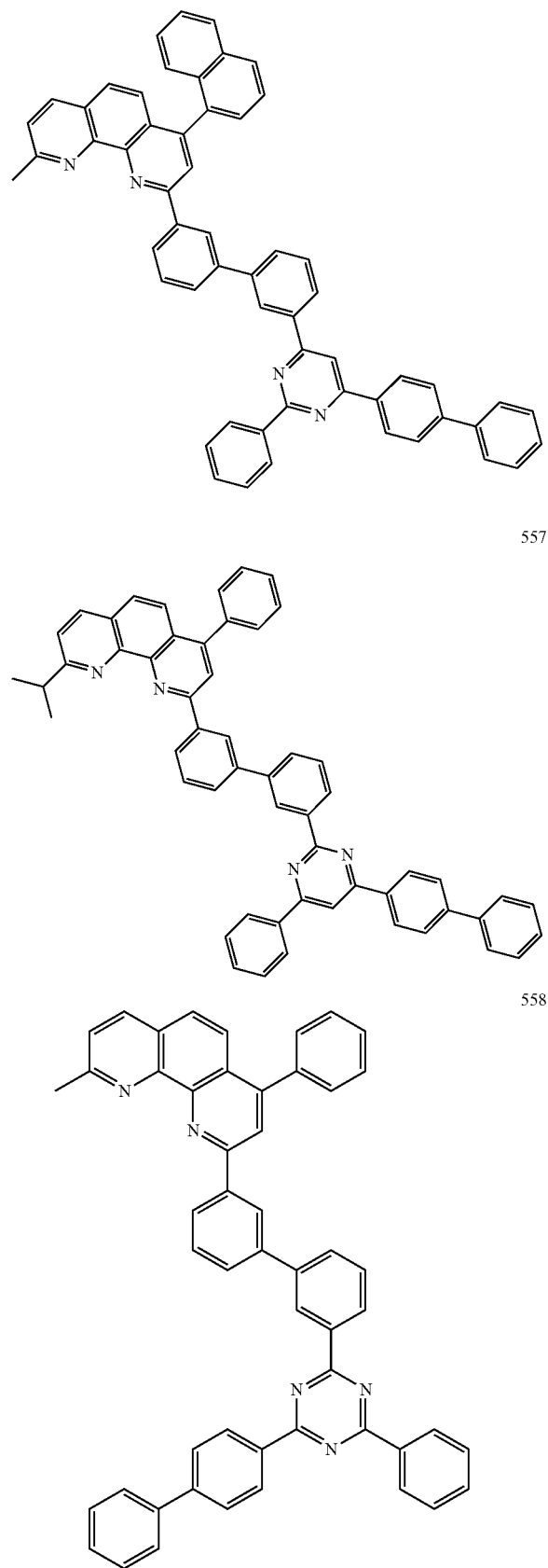

561 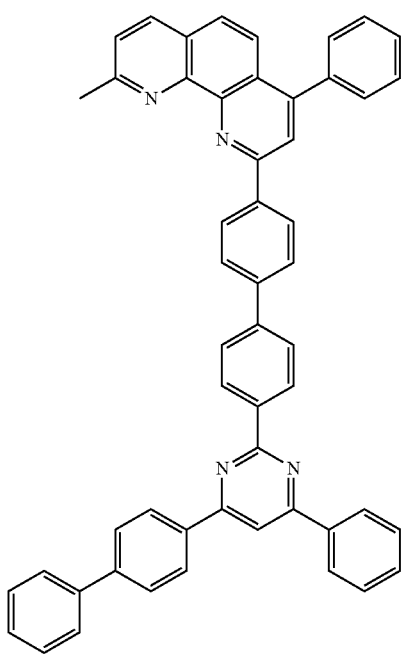
562 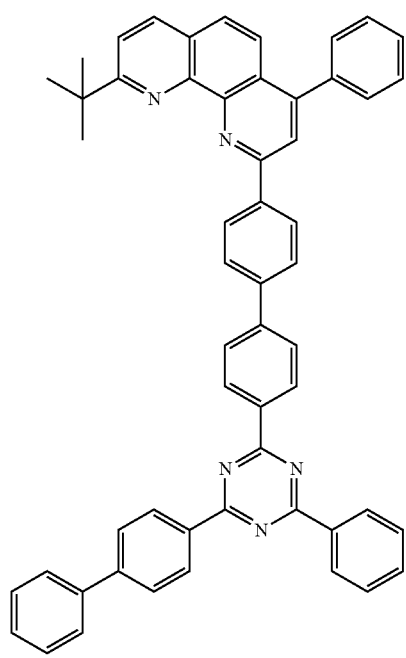
563 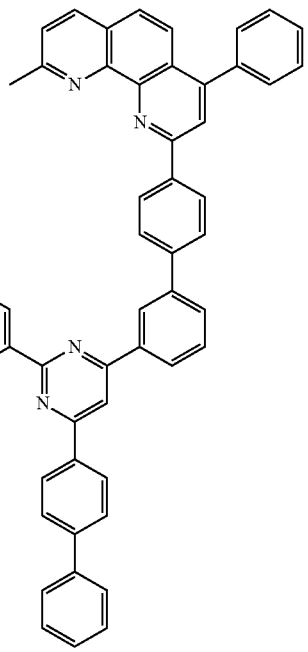
564 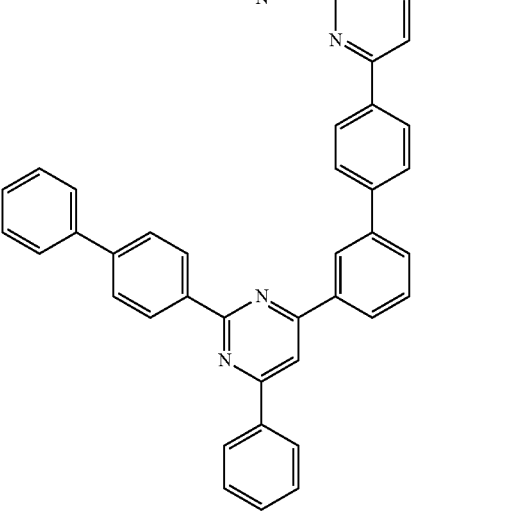

565
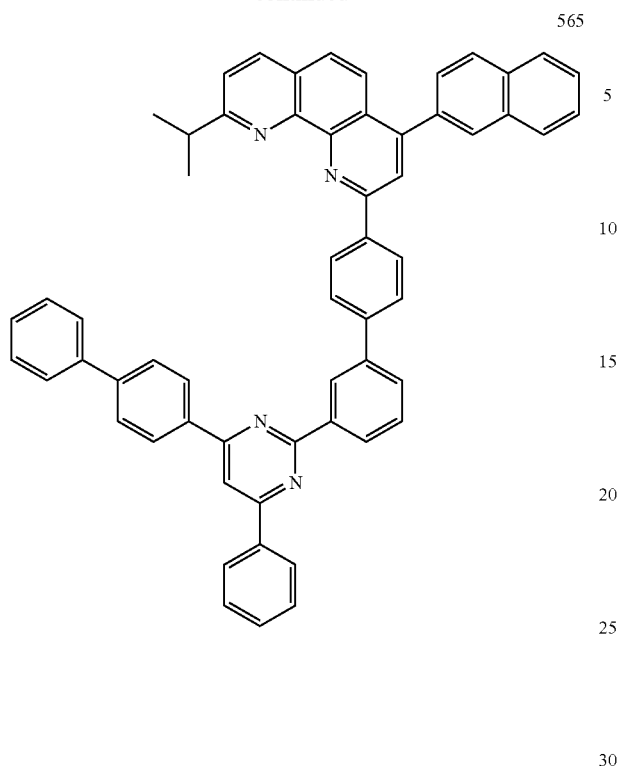
566
567
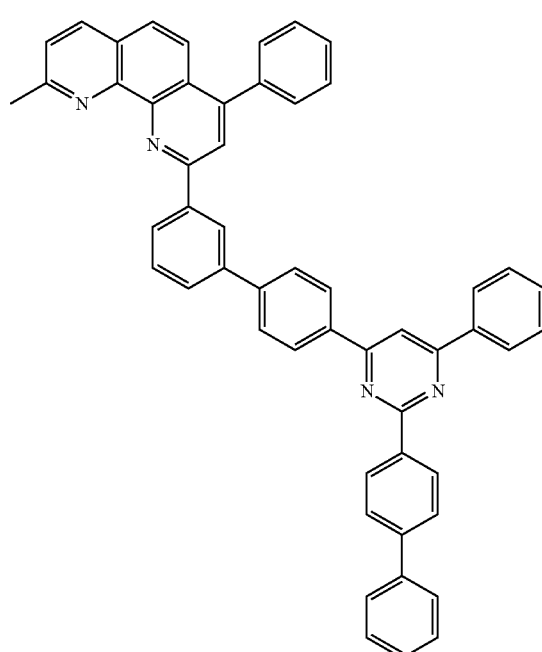
568
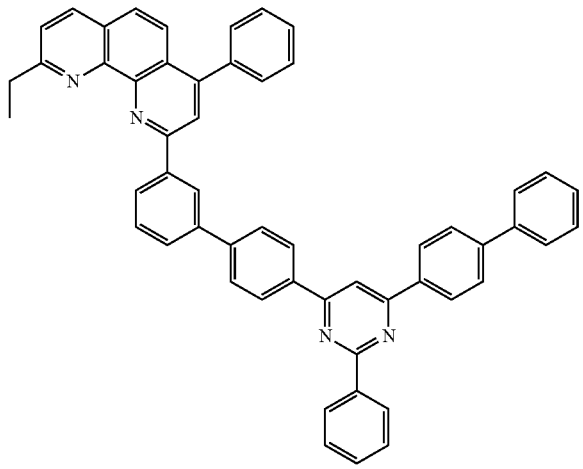

277
-continued
569
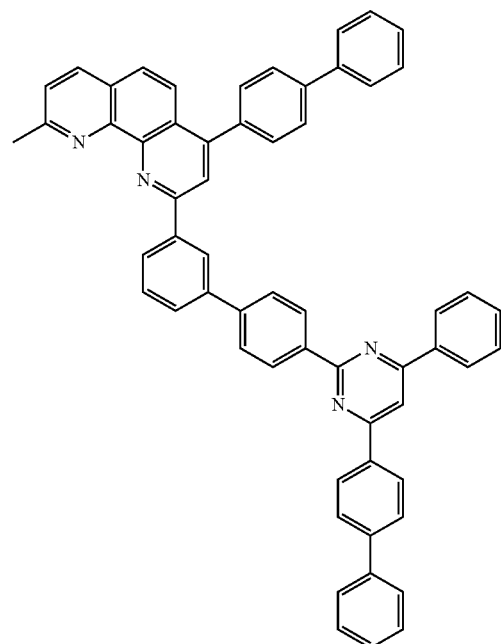
570
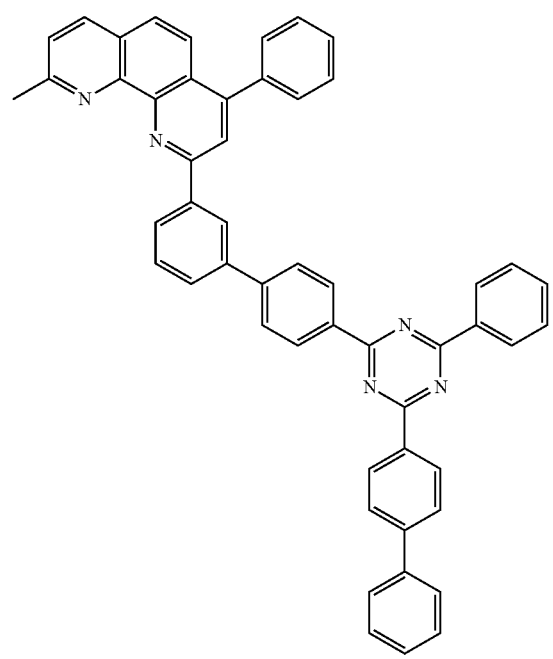
278
-continued
571
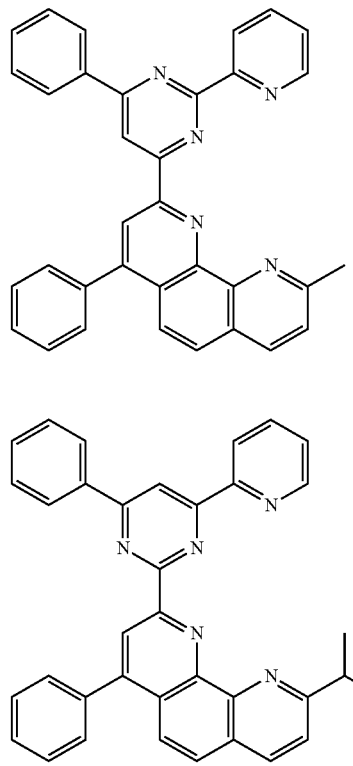
572
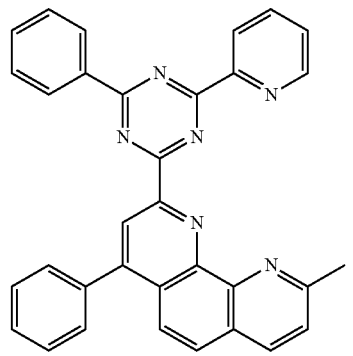
573
574
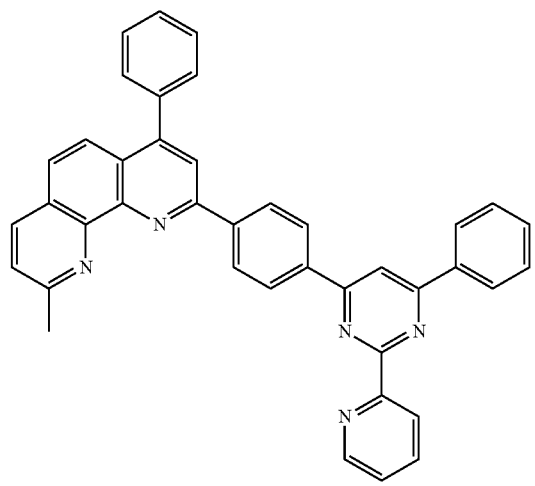

575
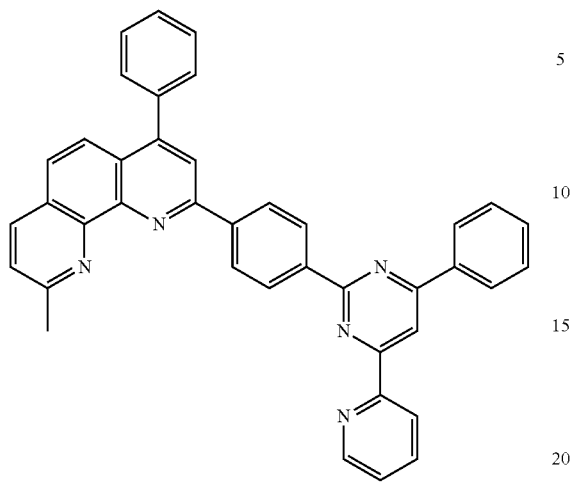
576
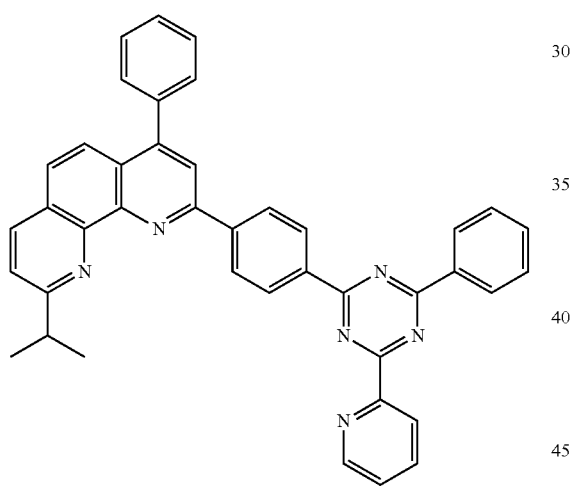
577
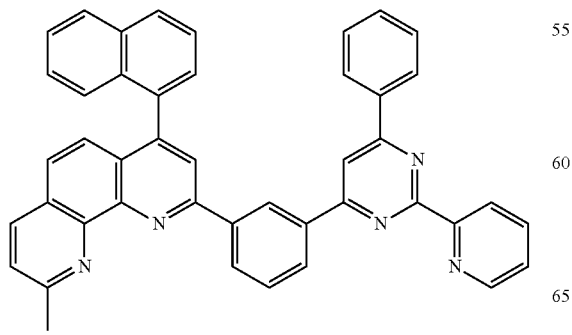
578
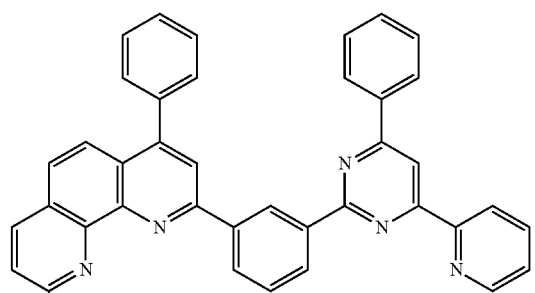
579
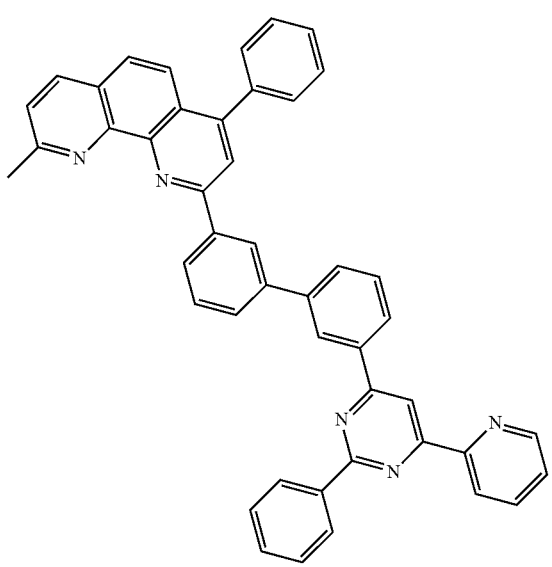
580

281
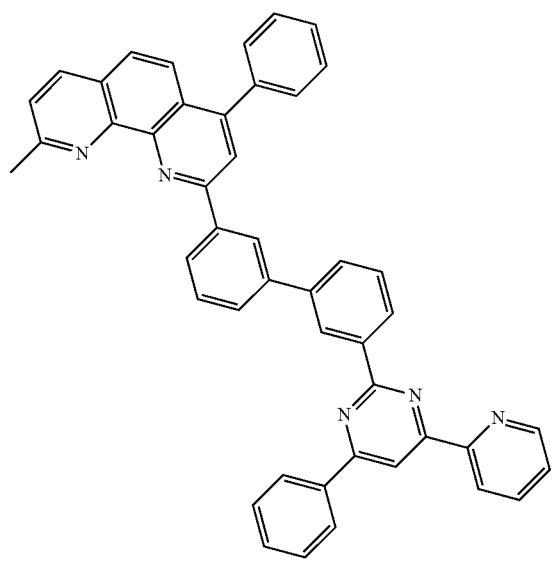
582
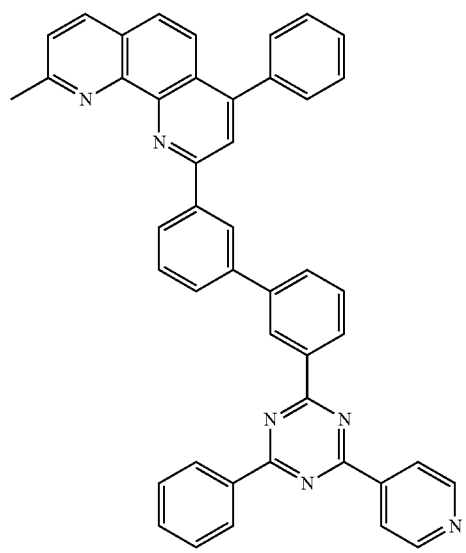
282
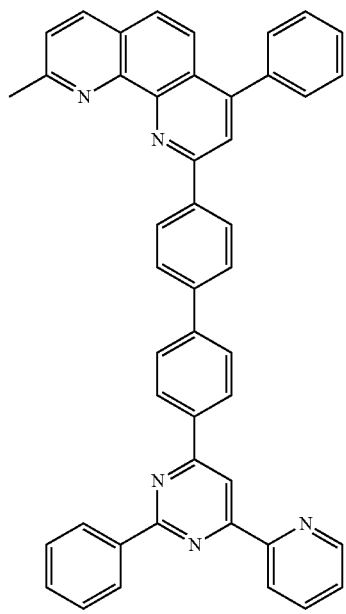
584
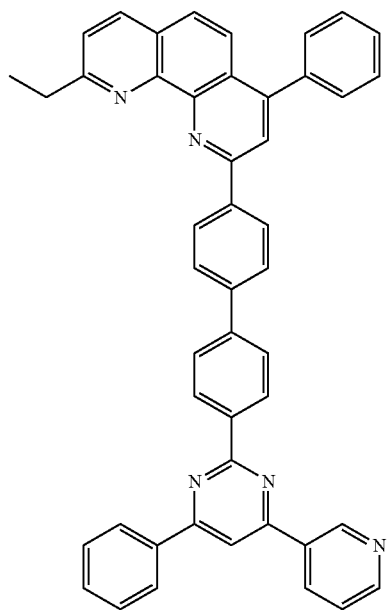

283
-continued
585
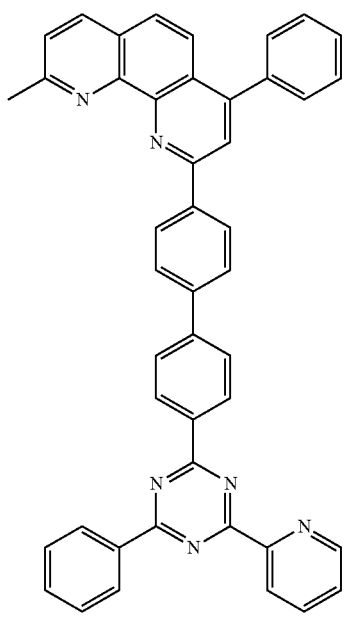
586
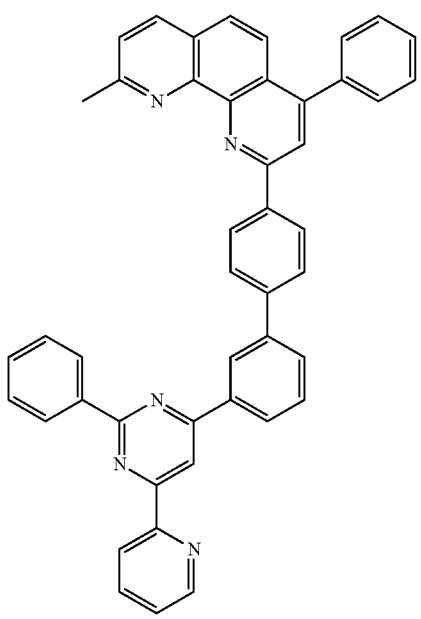
284
-continued
587
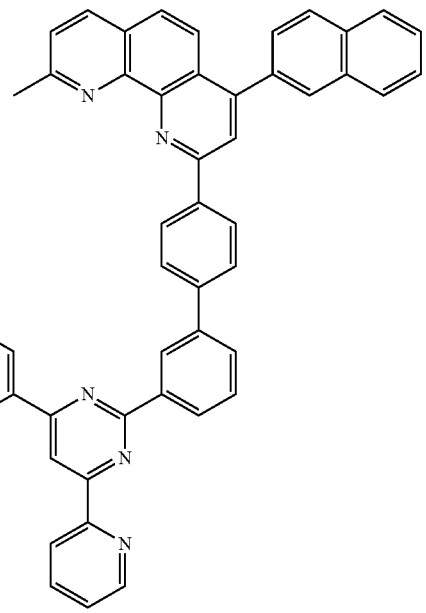
588
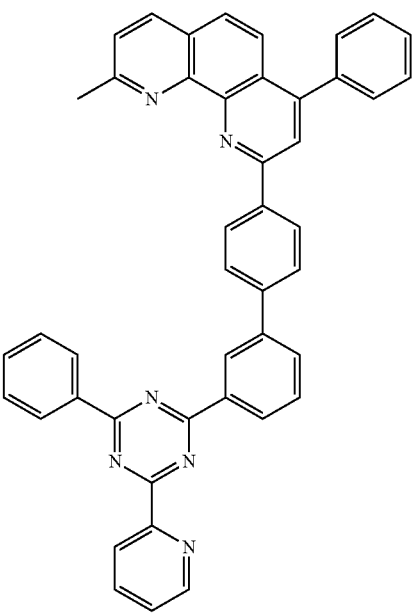

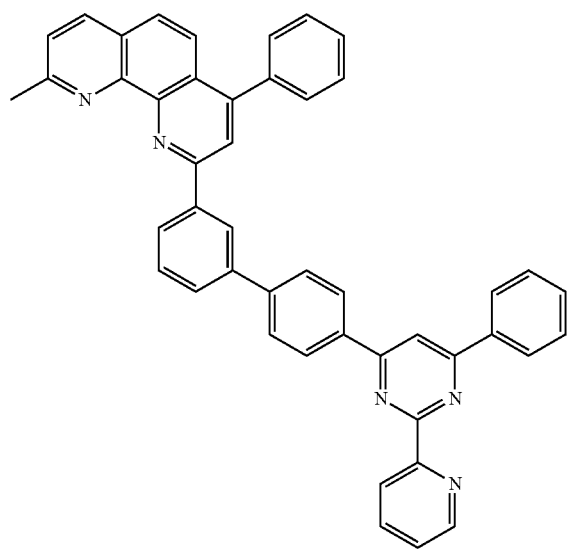
589
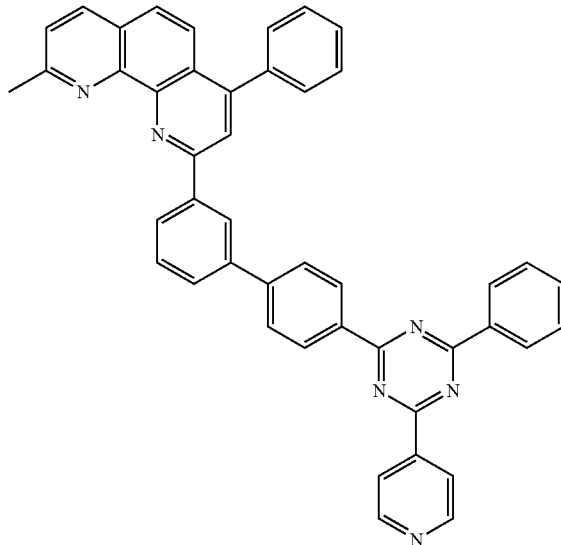
591
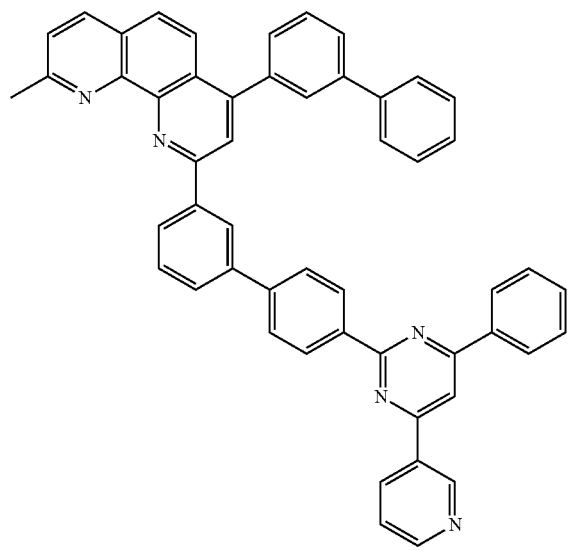
590
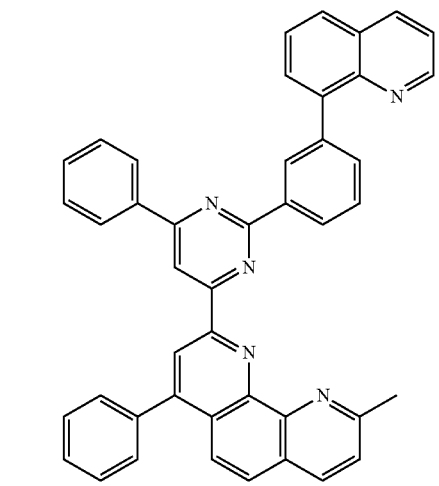
592
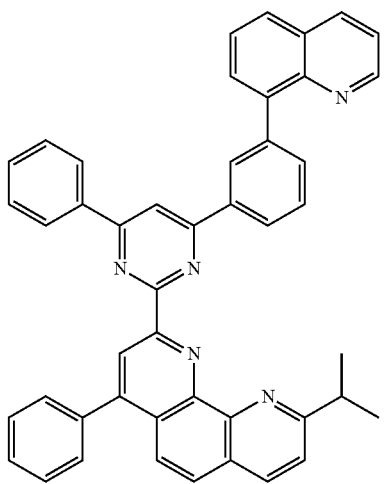
593

594
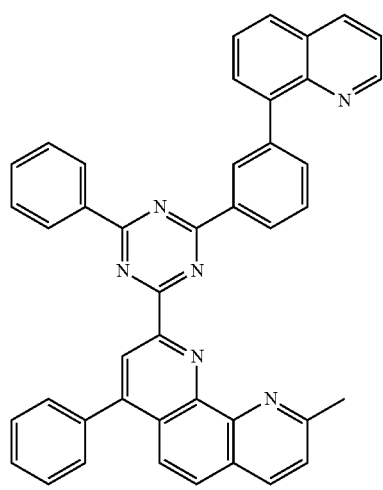
595
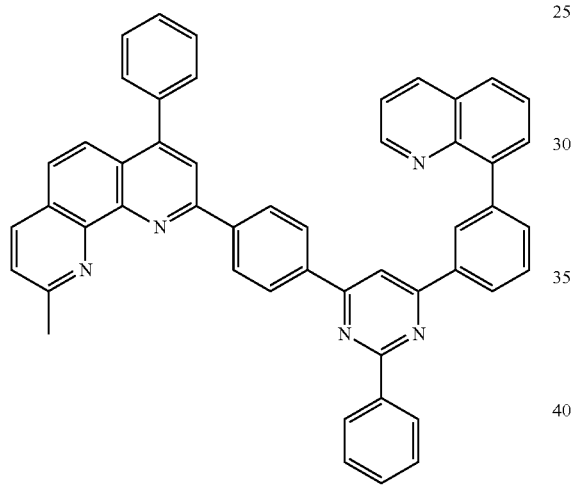
596
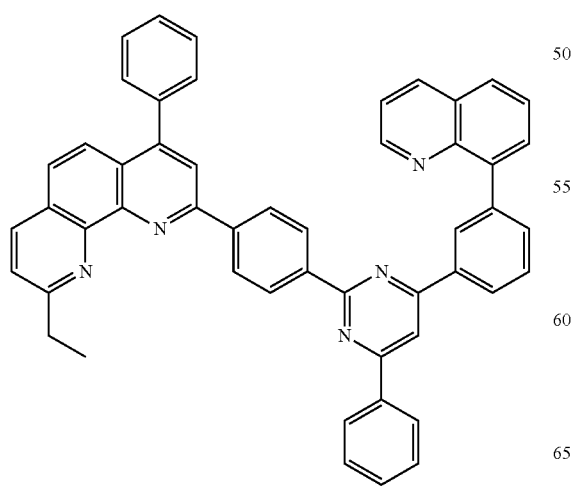
597
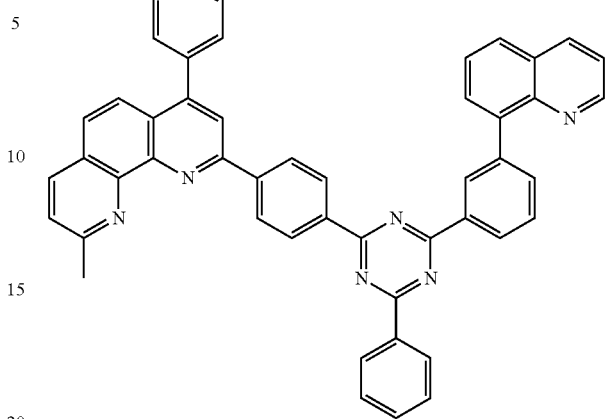
598
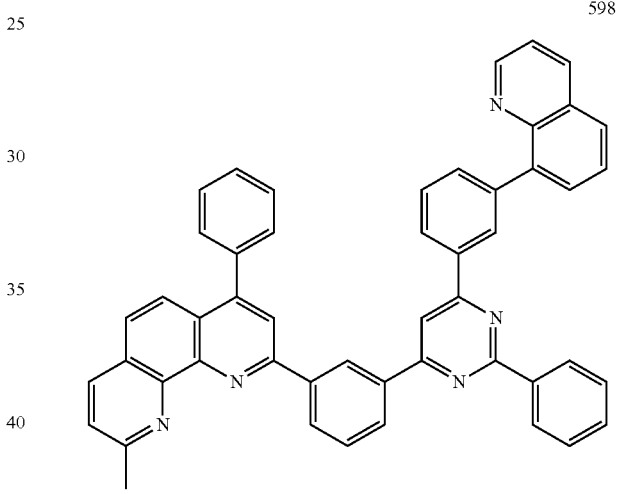
599
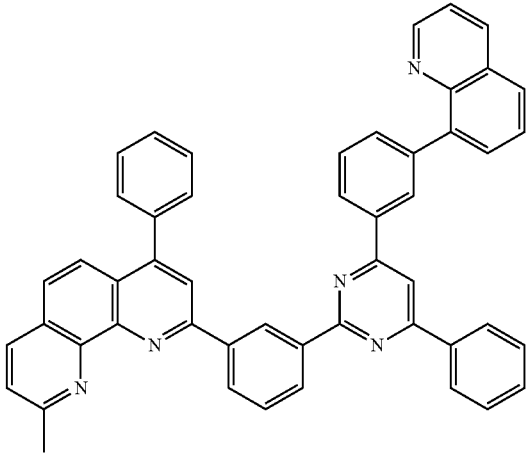

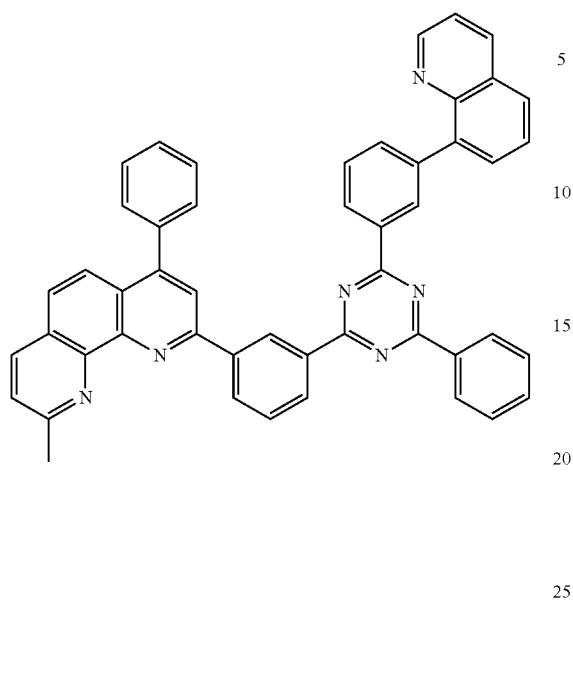
600
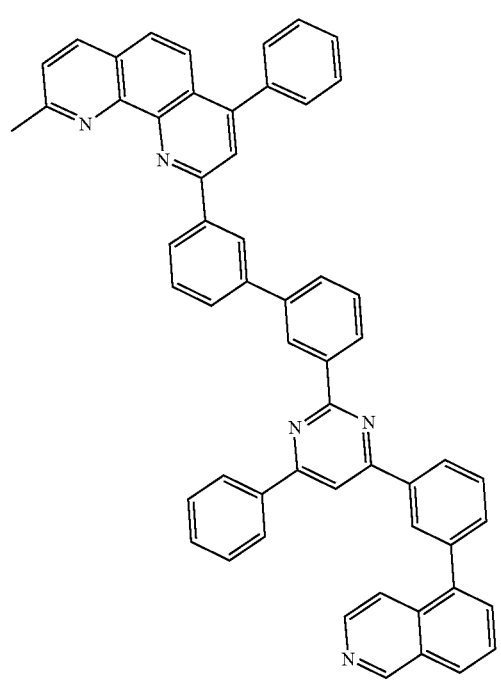
602
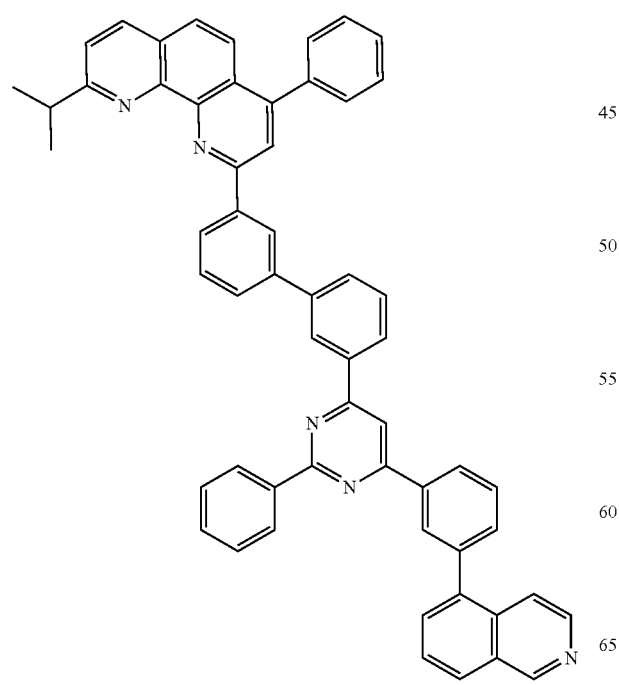
601
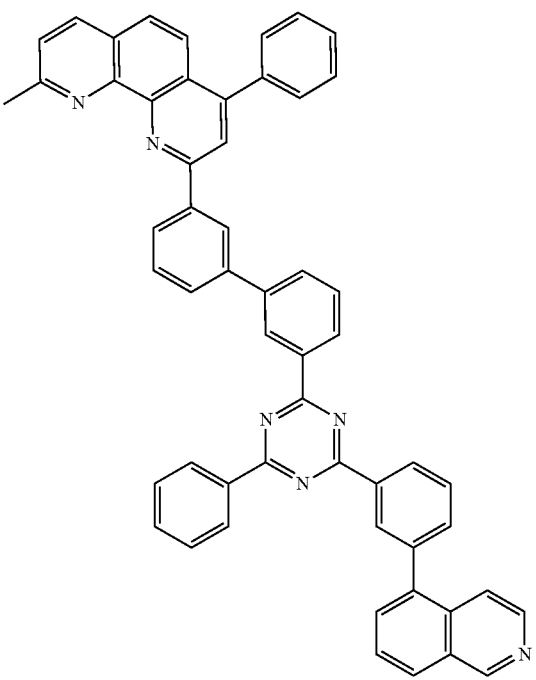
603

291
-continued
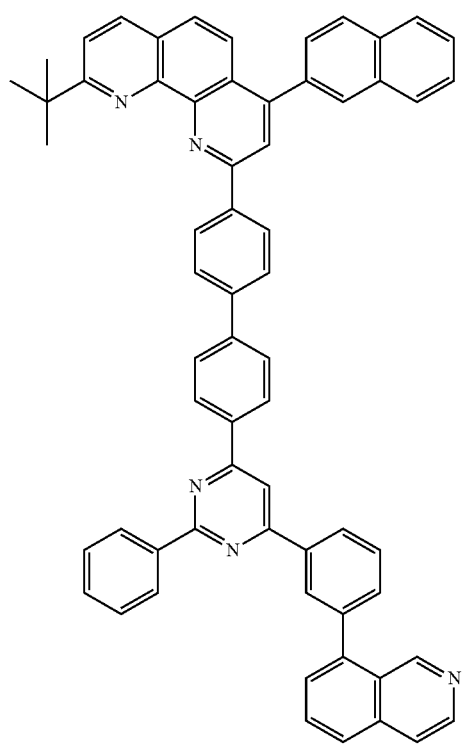
604
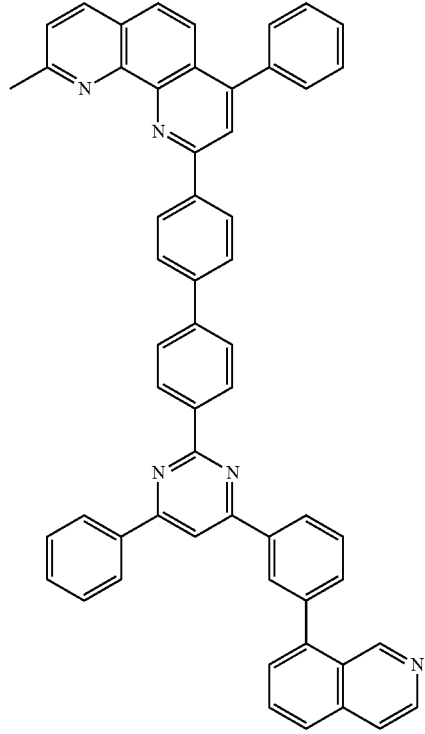
605
292
-continued
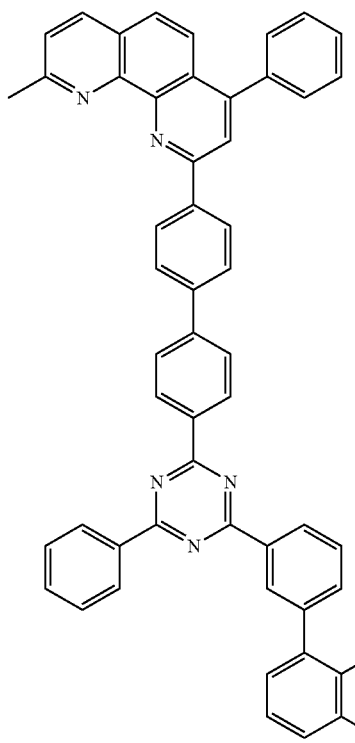
606
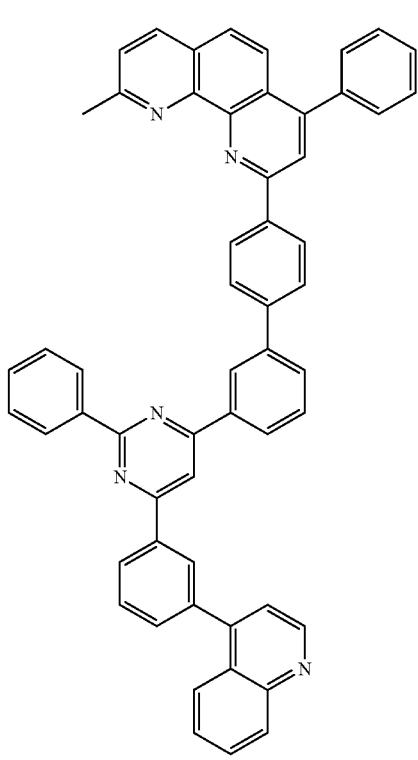
607

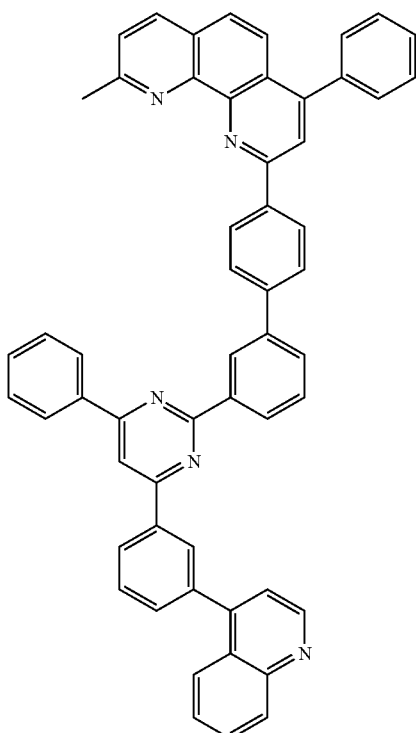
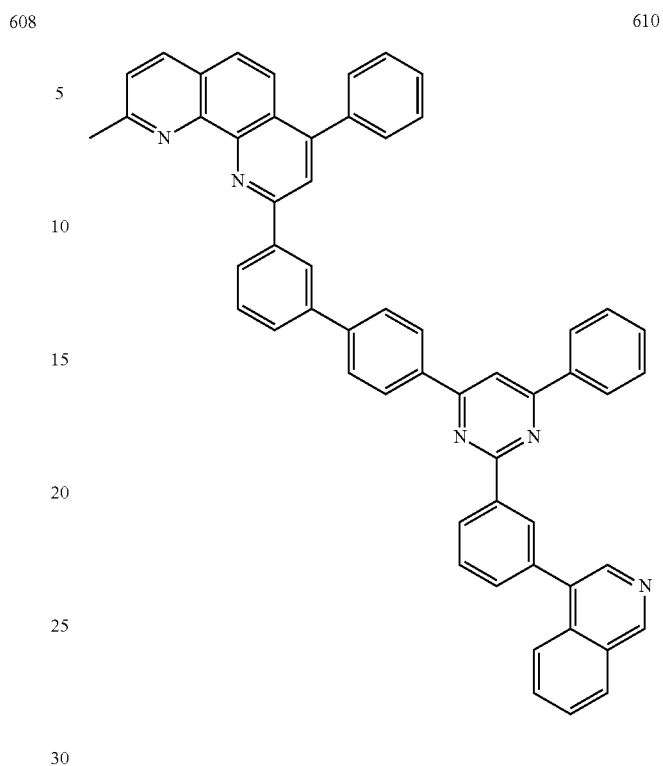
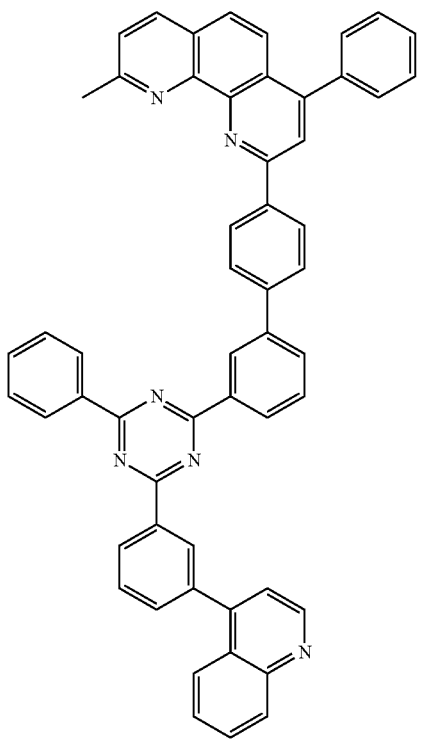

612
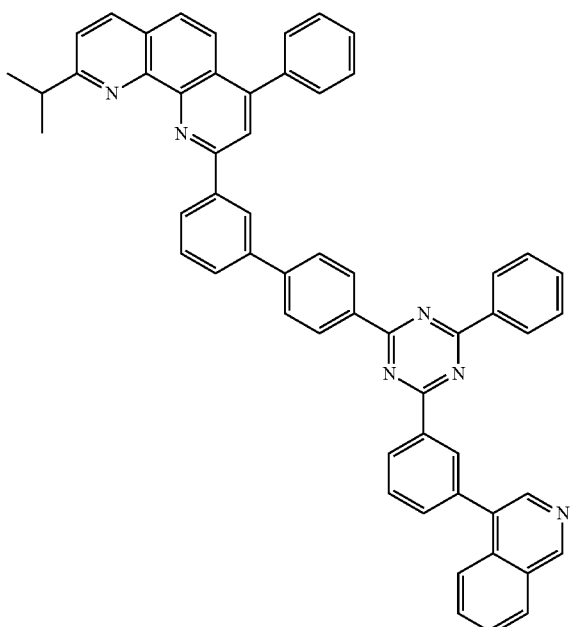
613
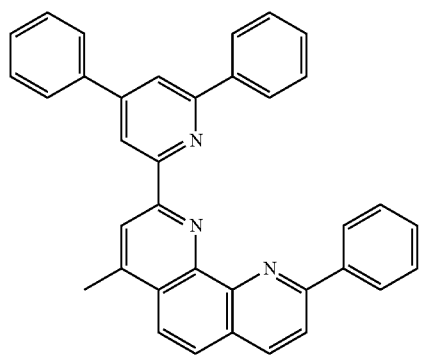
614
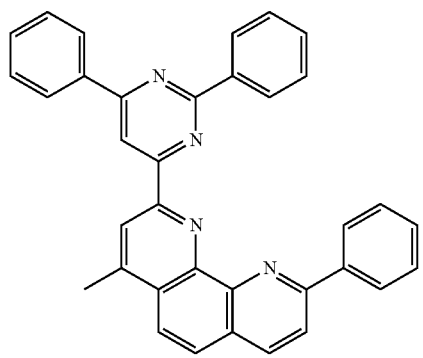
615
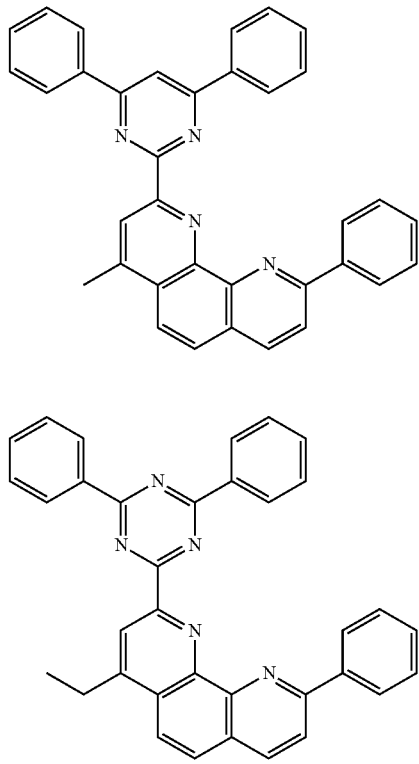
616
617
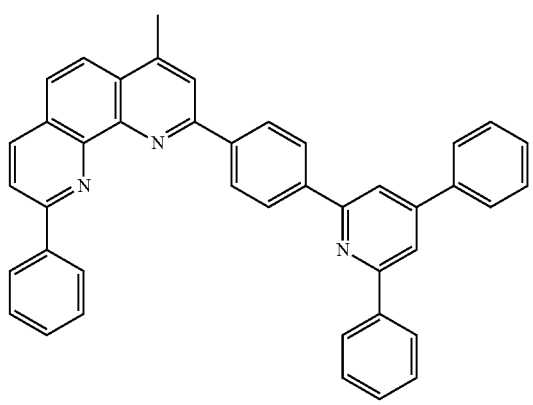
618
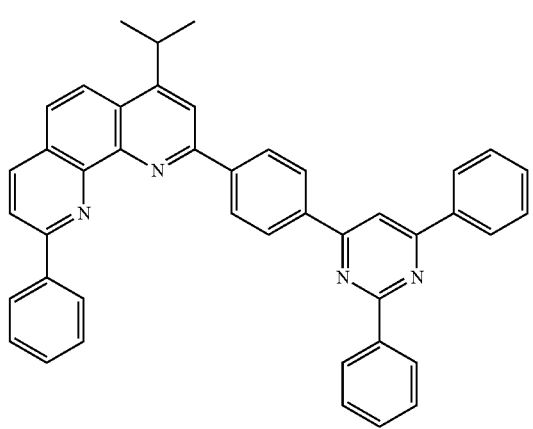

619
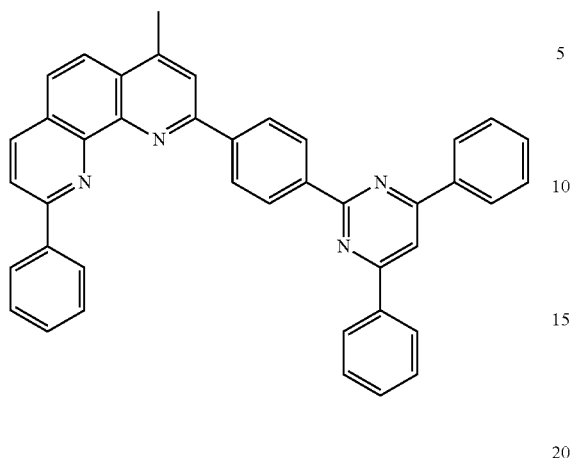
620
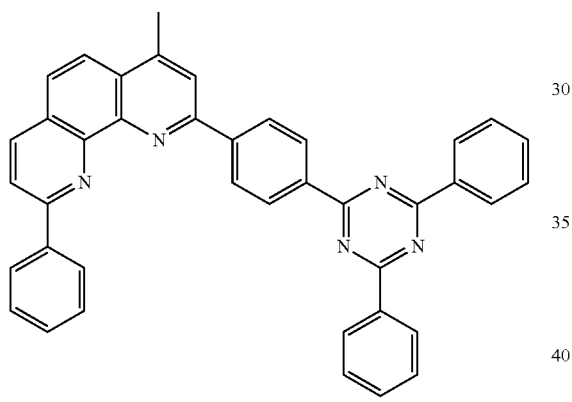
621
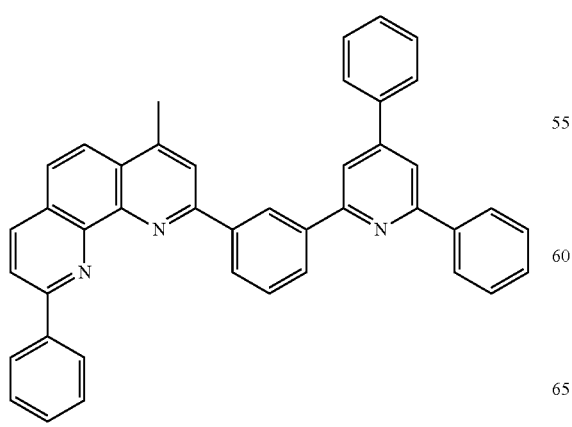
622
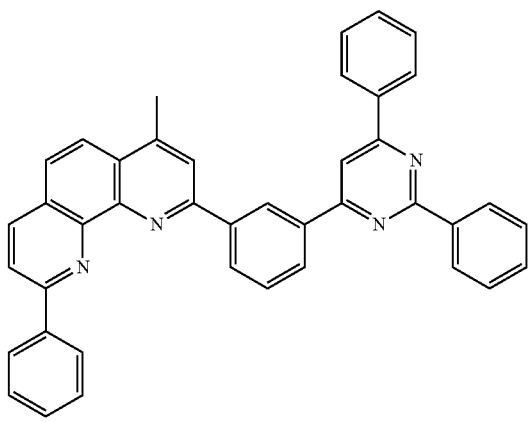
623
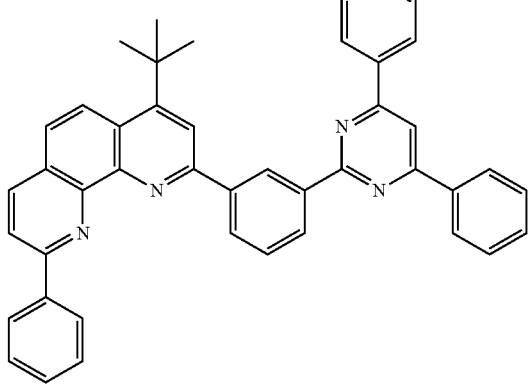
624
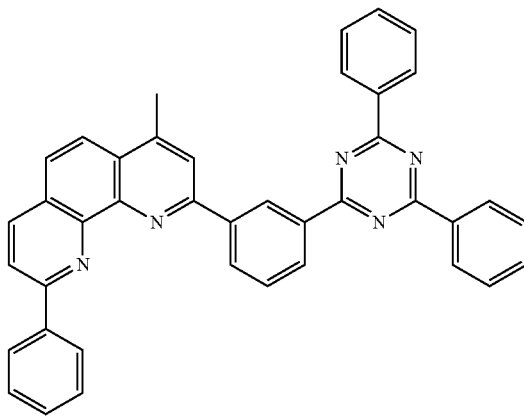

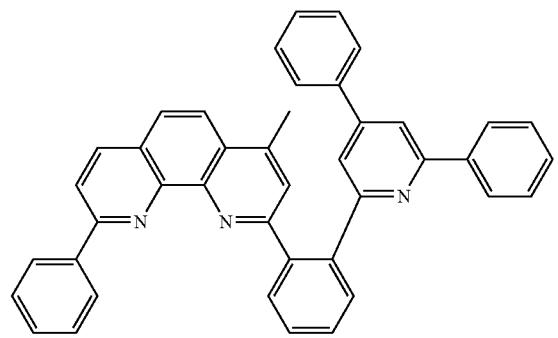
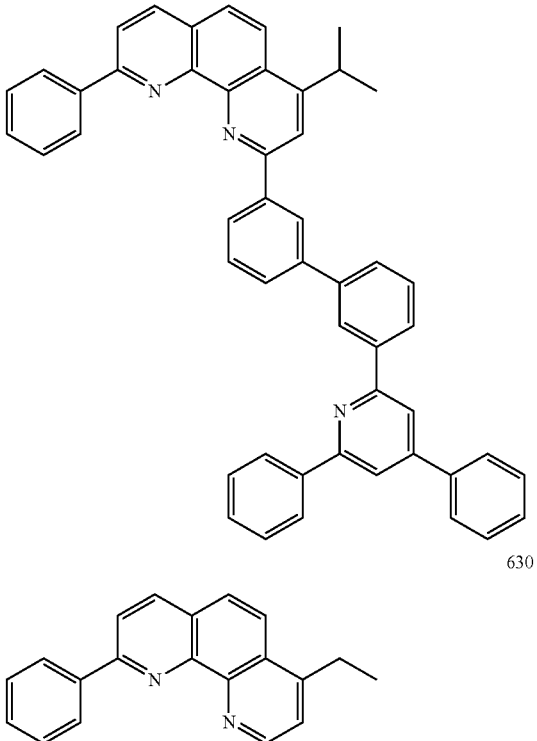
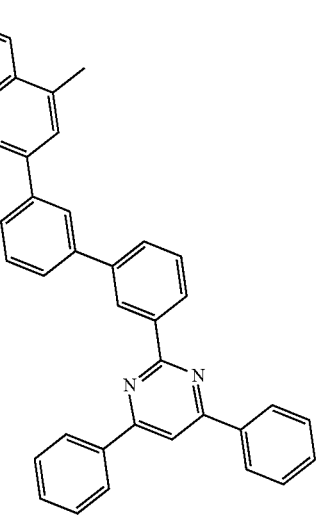

301
-continued
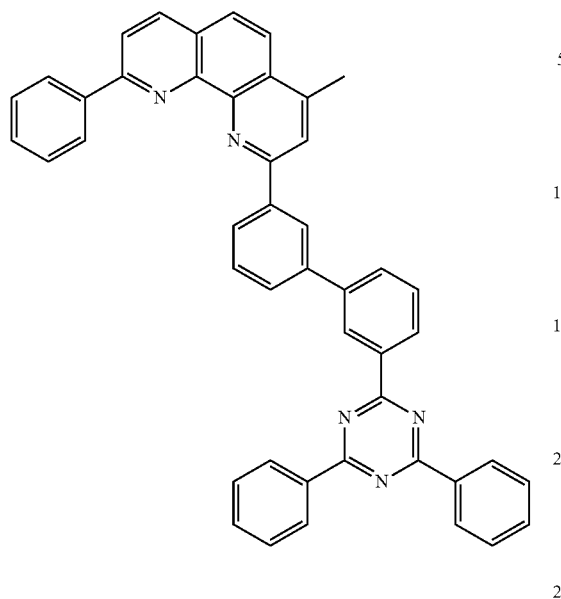
632
302
-continued
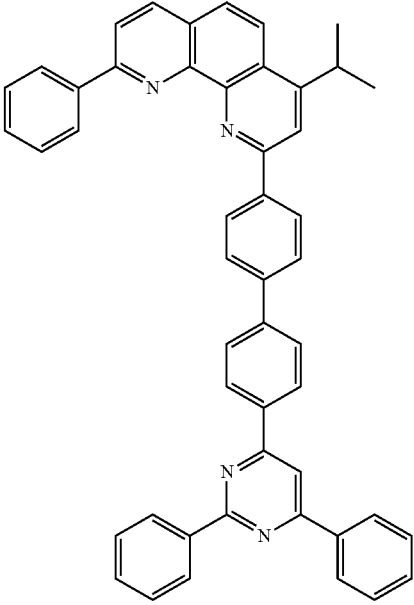
634
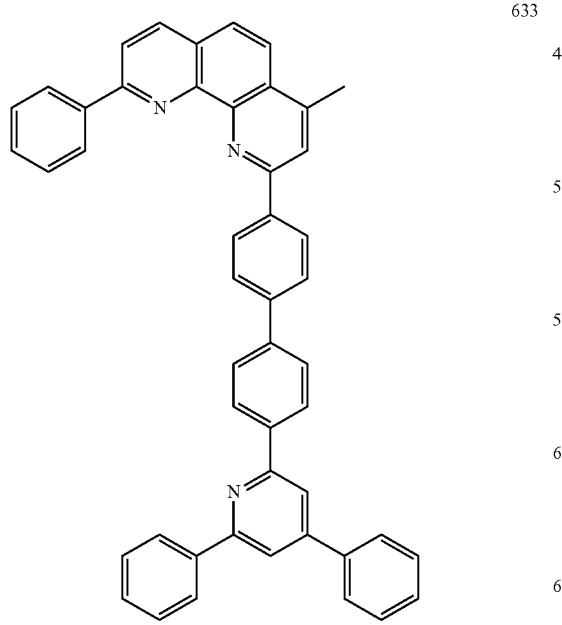
633
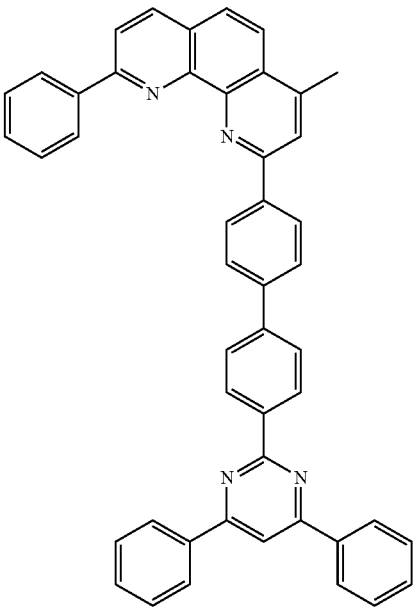
635

303
-continued
304
-continued
636
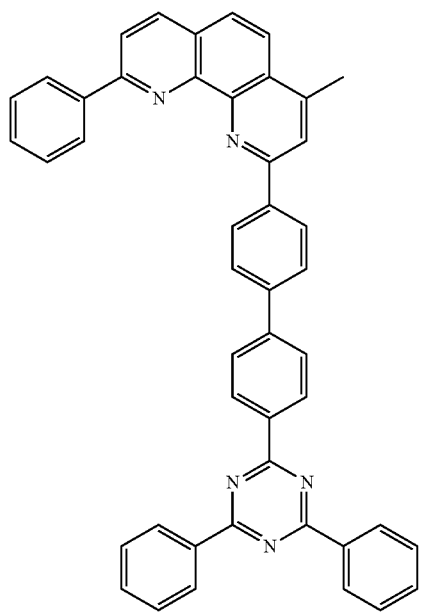
638
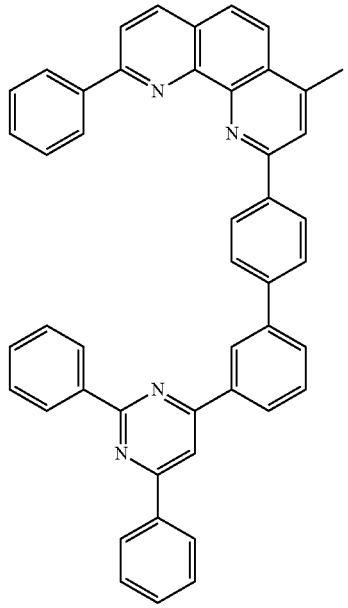
637
639

305
-continued
640
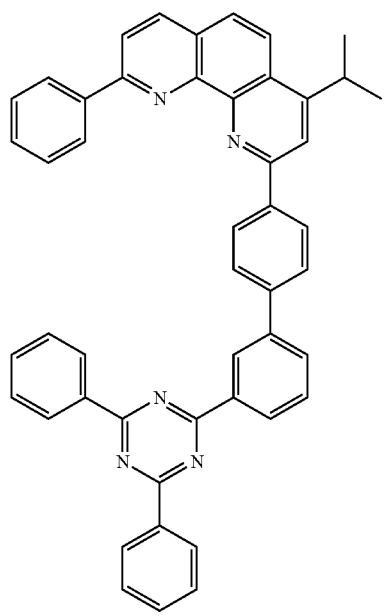
641
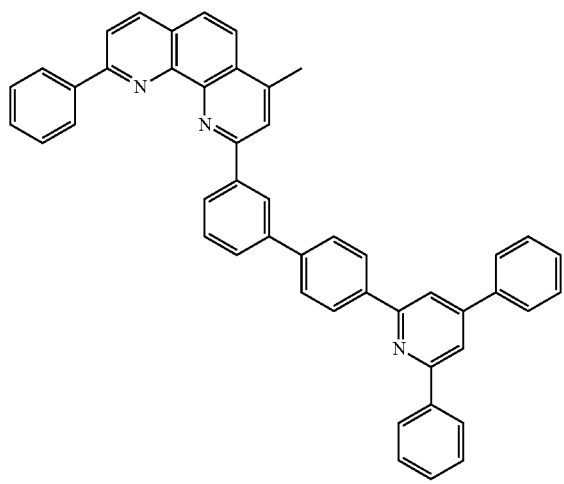
642
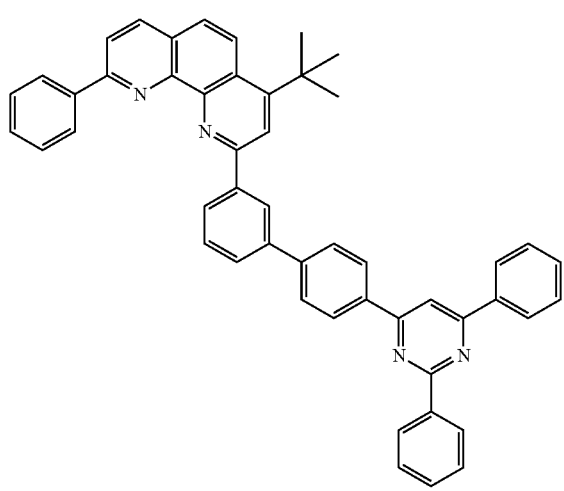
306
-continued
643
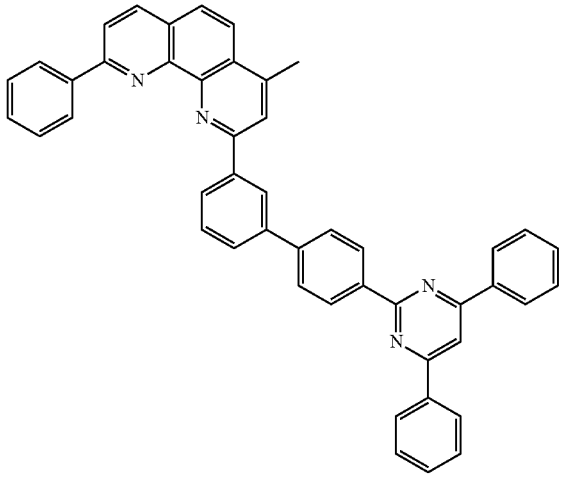
644
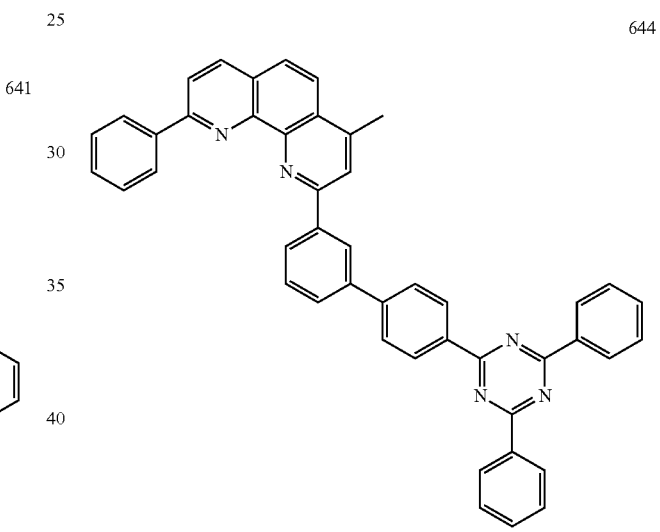
645
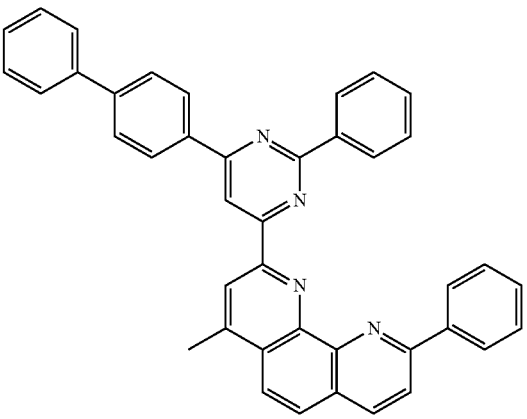

646
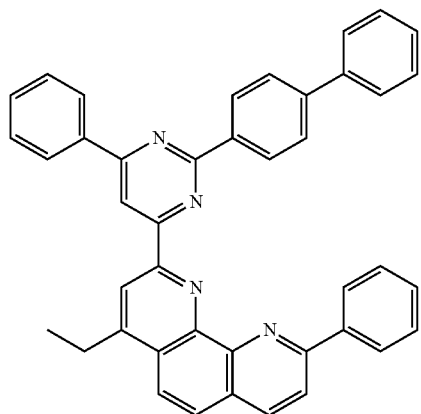
647
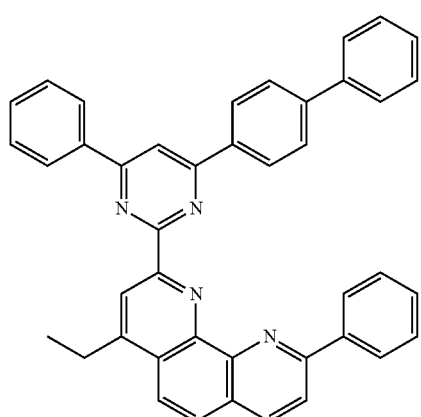
648
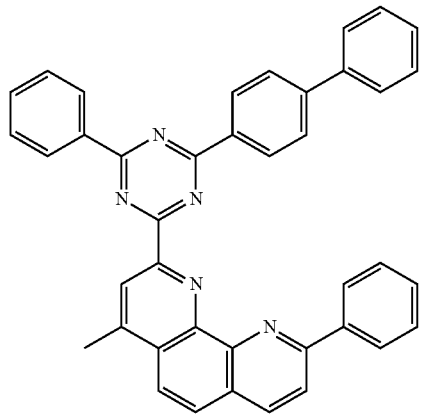
649
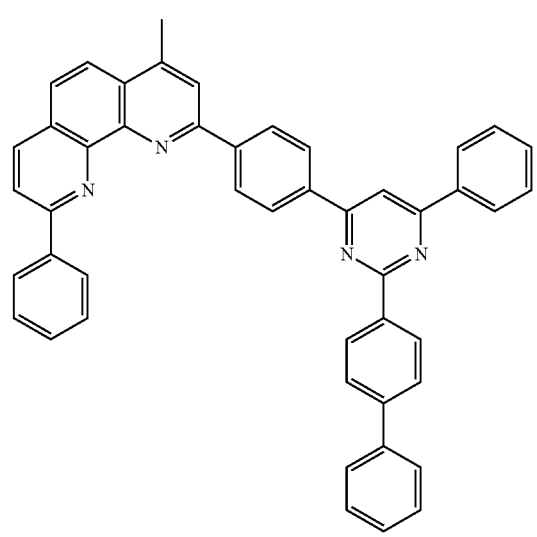
650
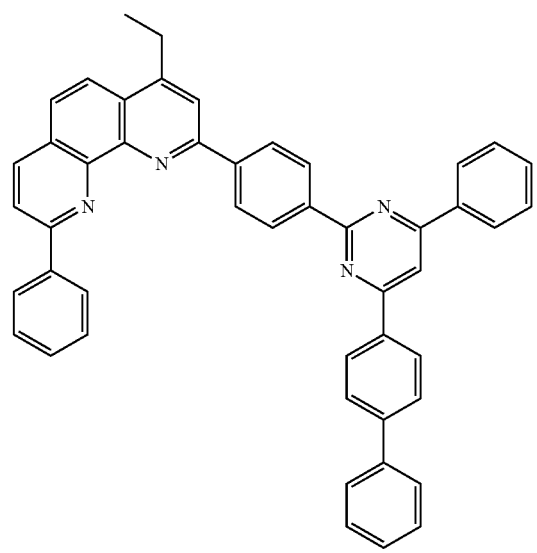
651

652
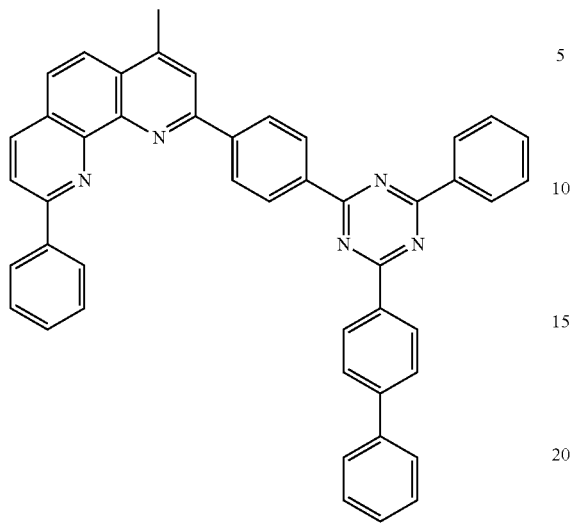
653
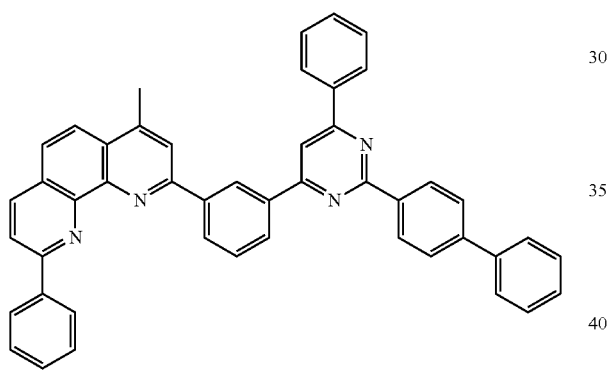
654
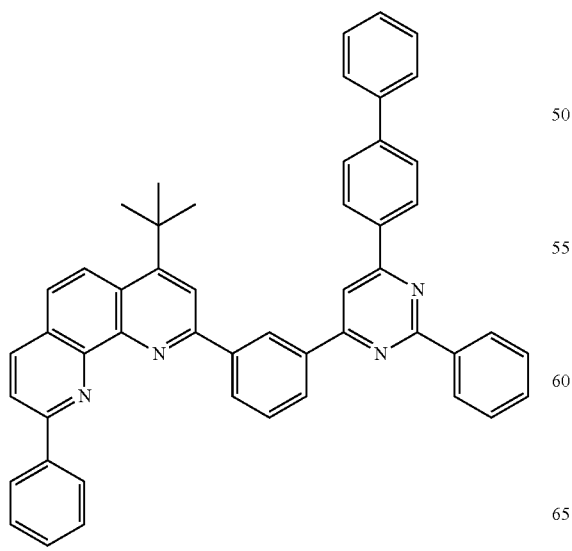
655
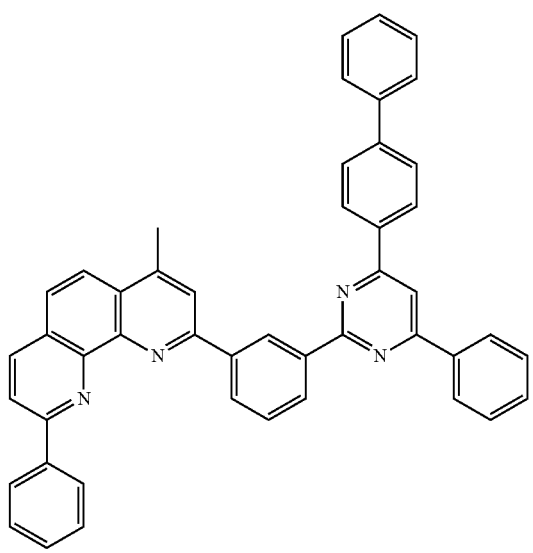
656
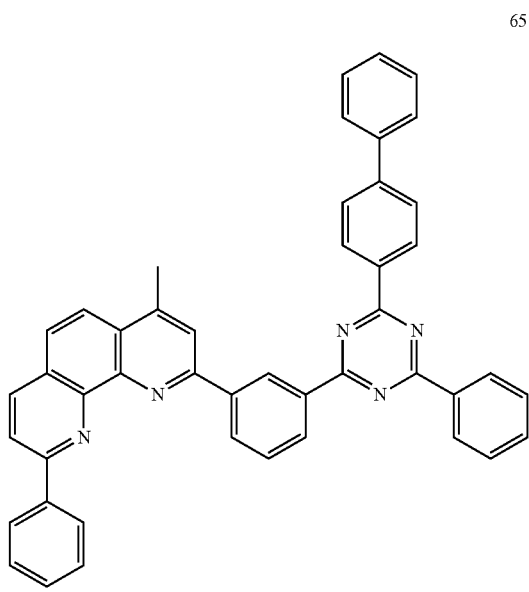

311
-continued
657
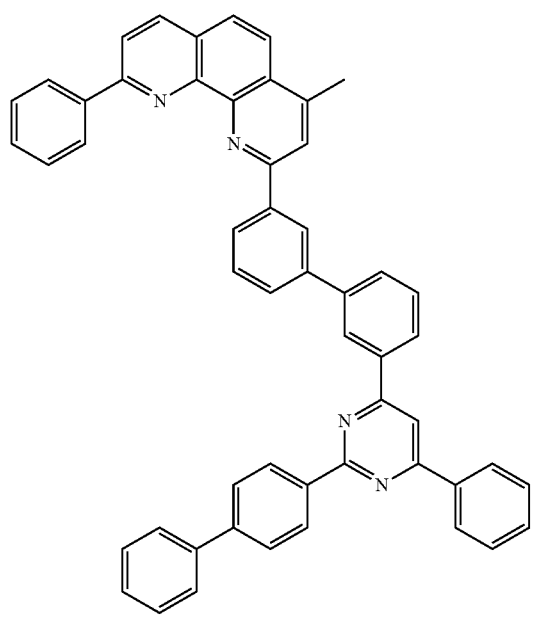
658
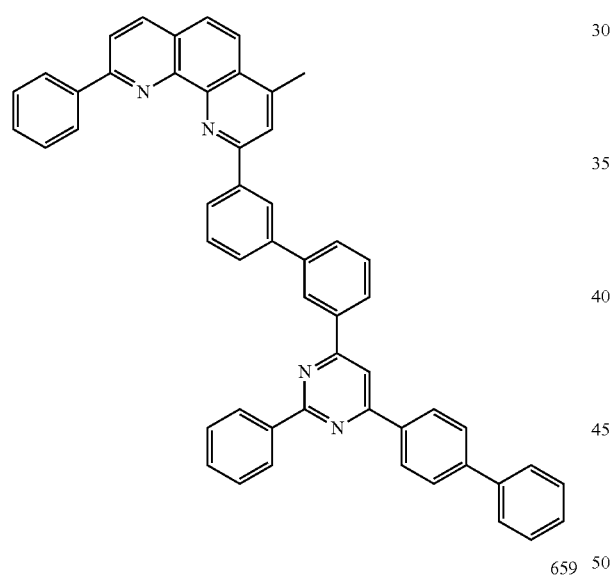
659
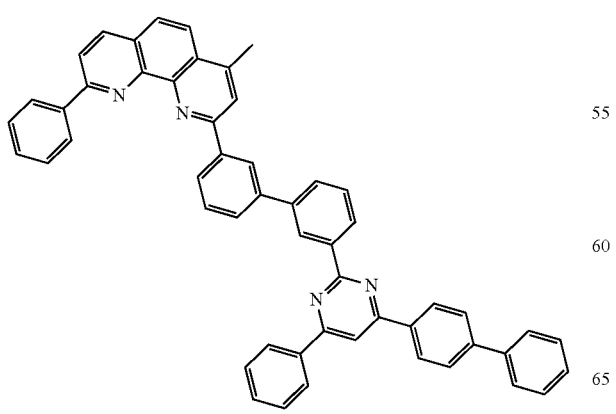
312
-continued
660
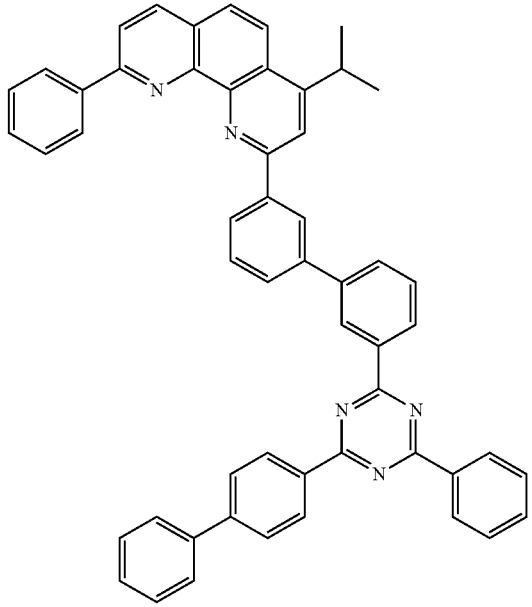
661
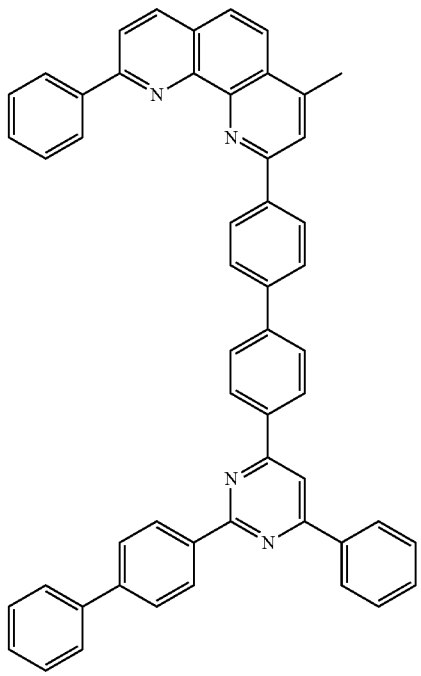

313
-continued
662
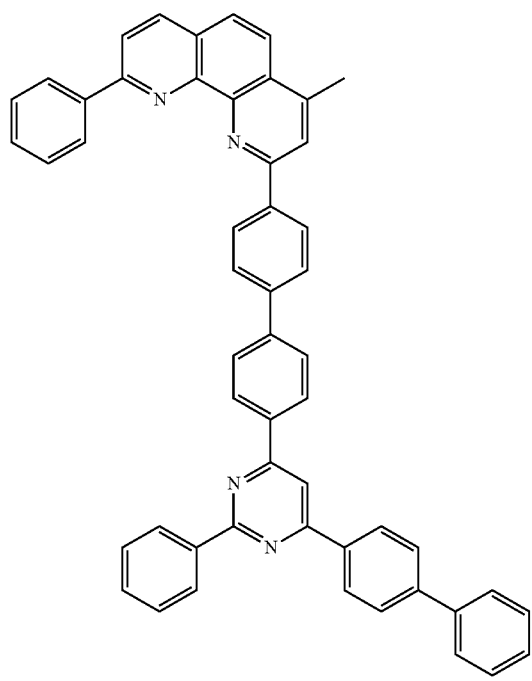
663
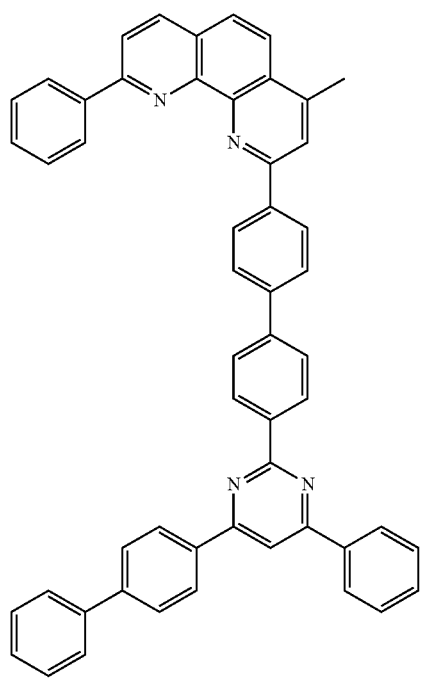
314
-continued
664
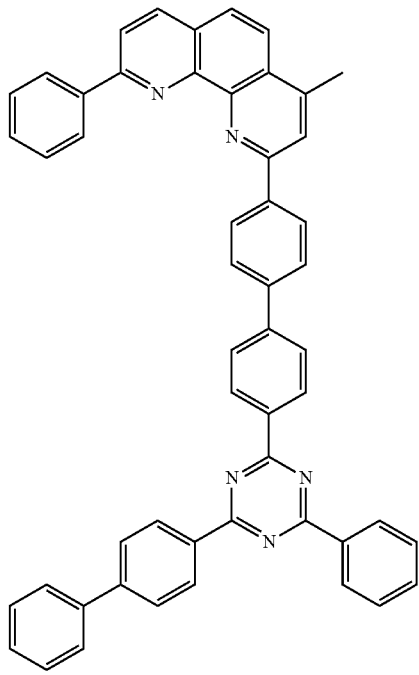
665

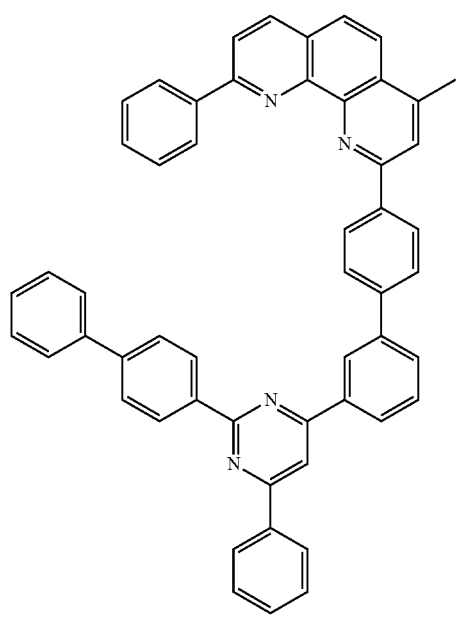
666
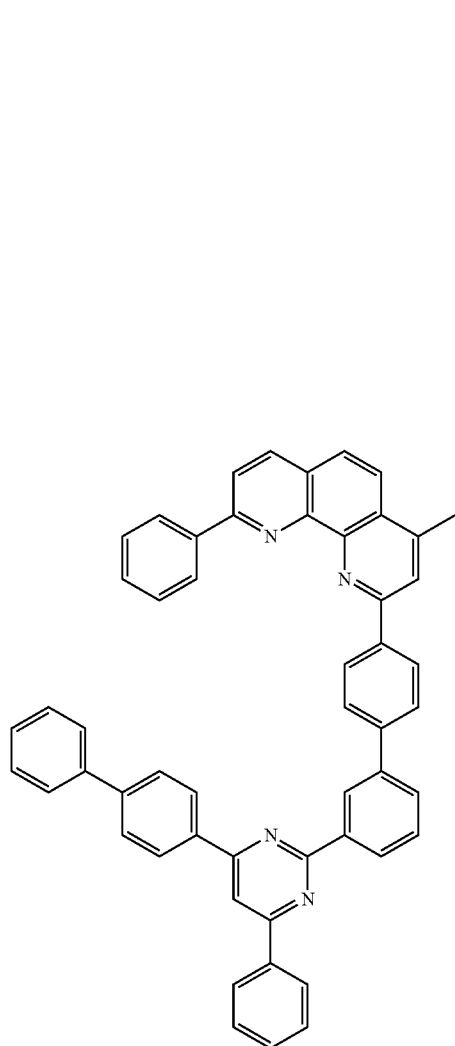
667
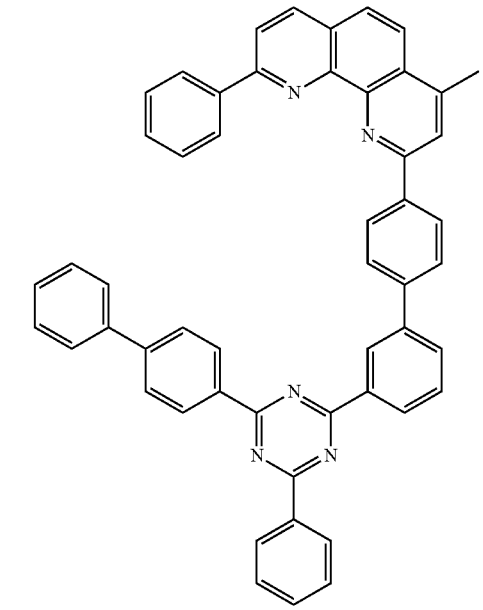
668
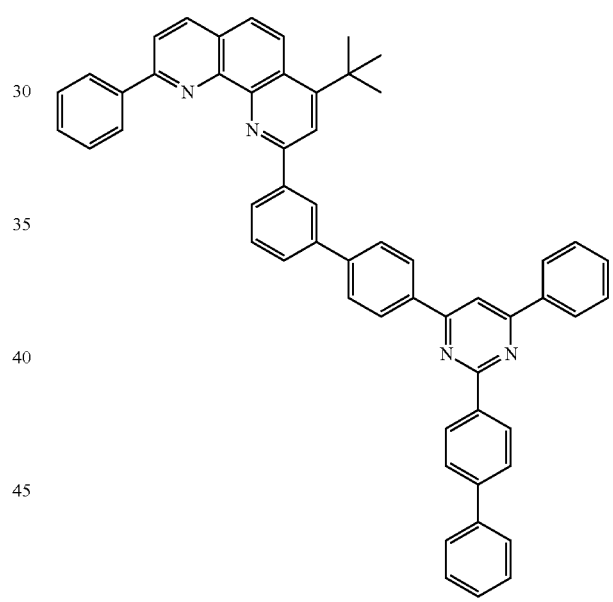
669
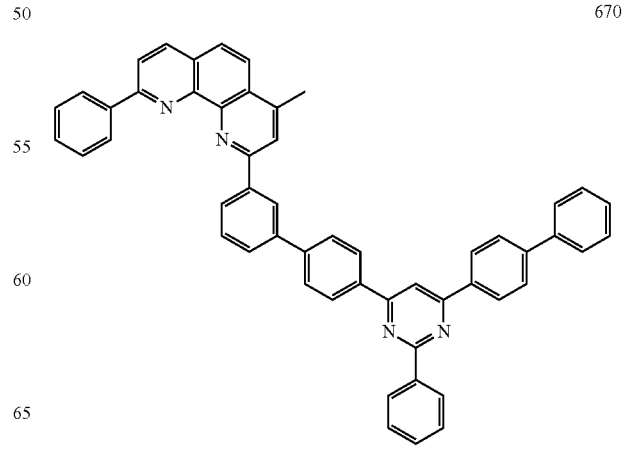
670

317
-continued
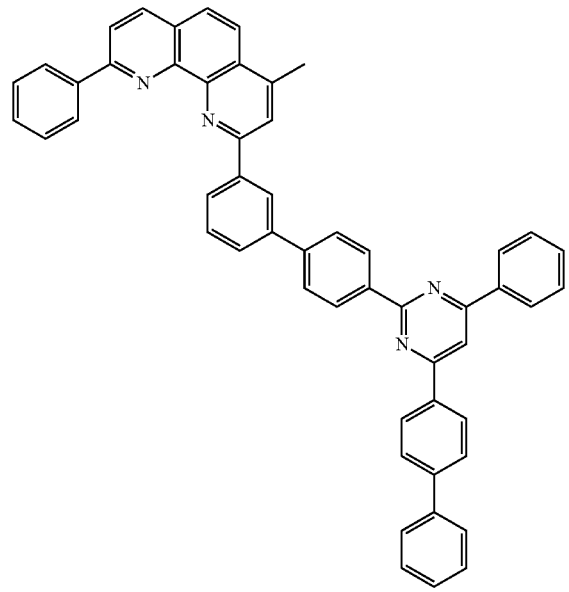
671
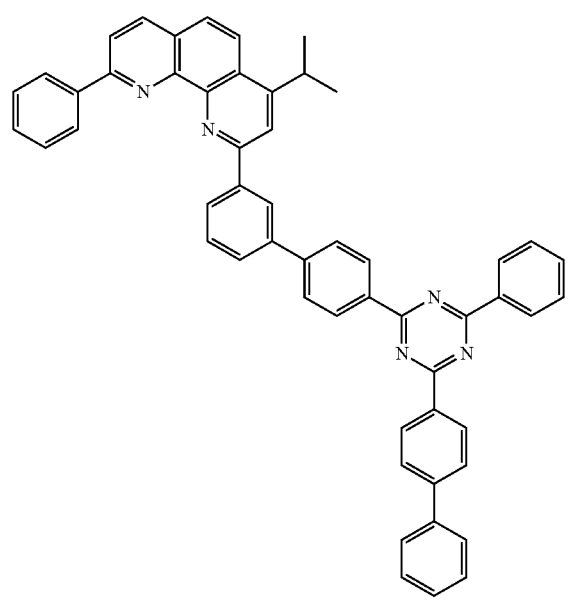
672
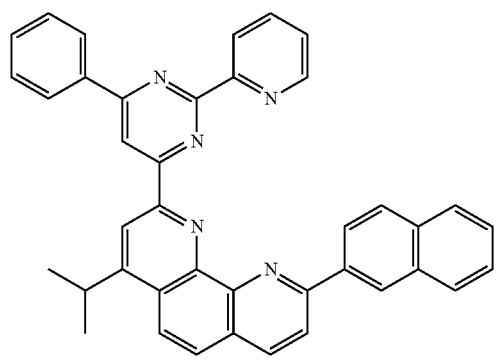
673
318
-continued
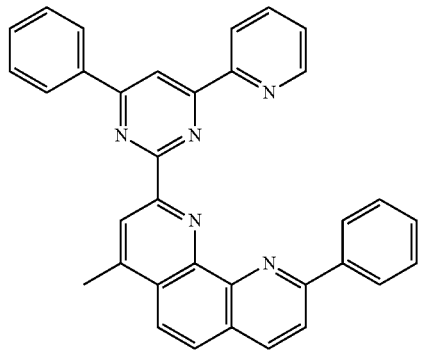
674
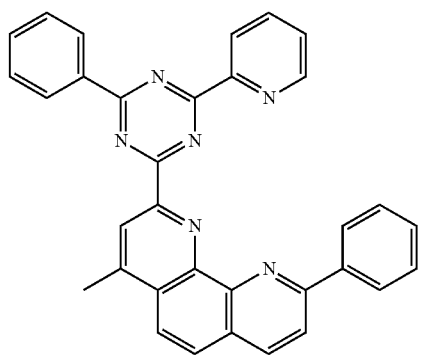
675
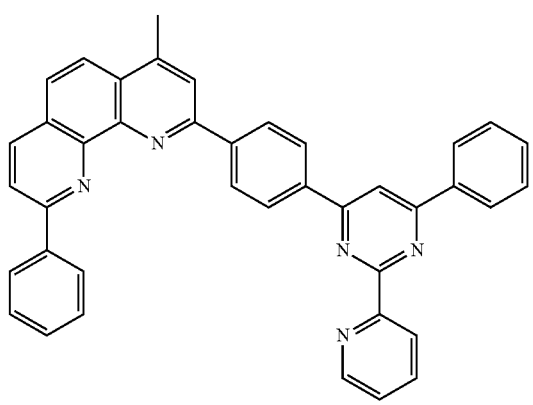
676
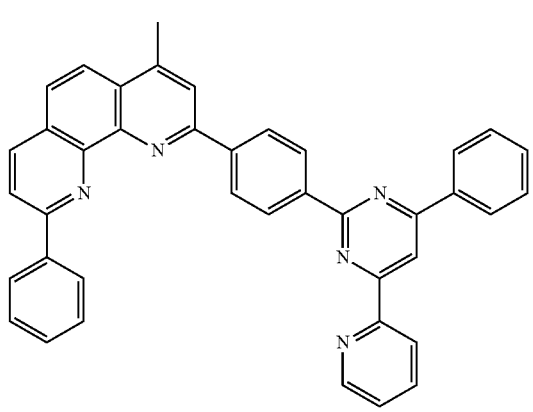
677

678

679

680
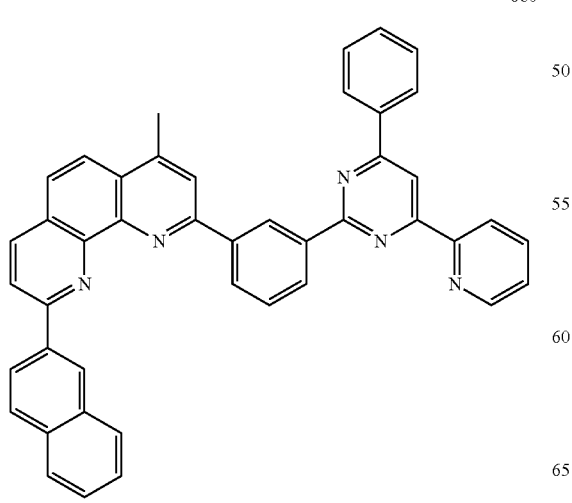
681
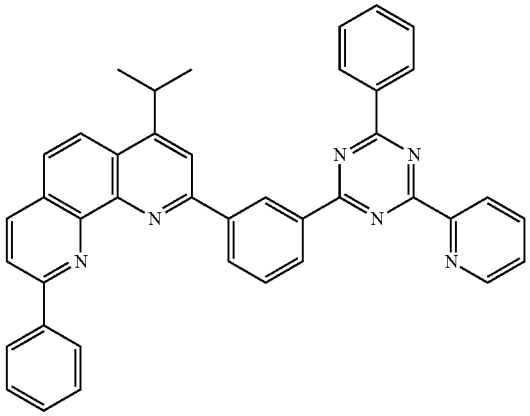
682
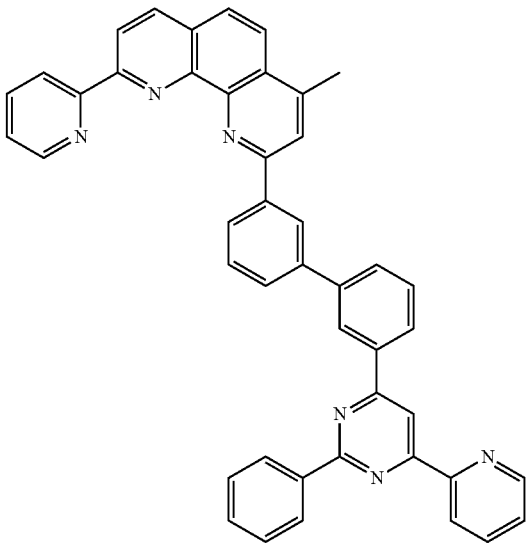
683
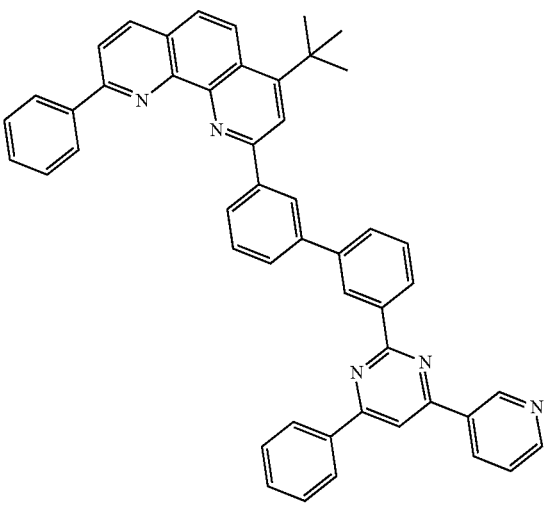

321
-continued
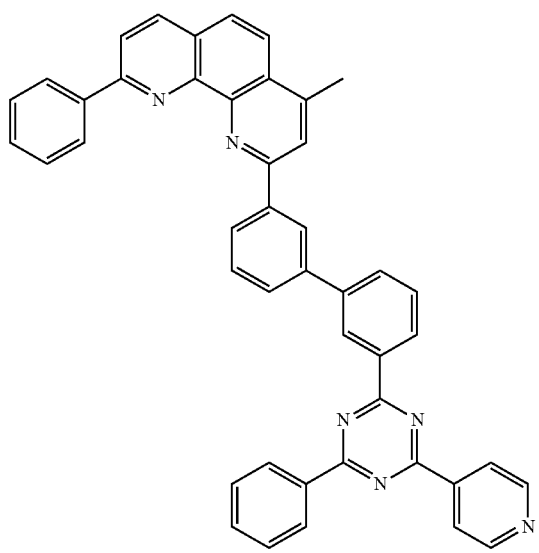
322
-continued
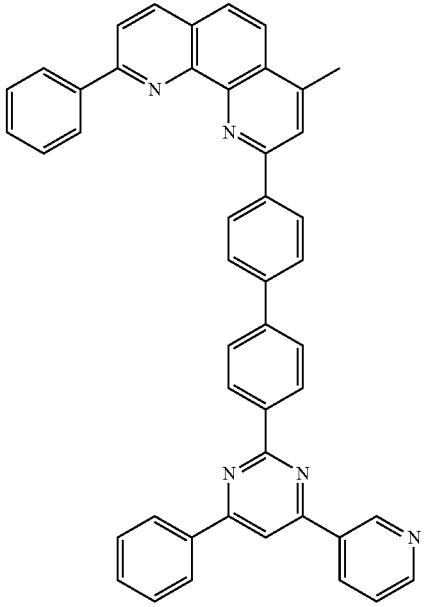
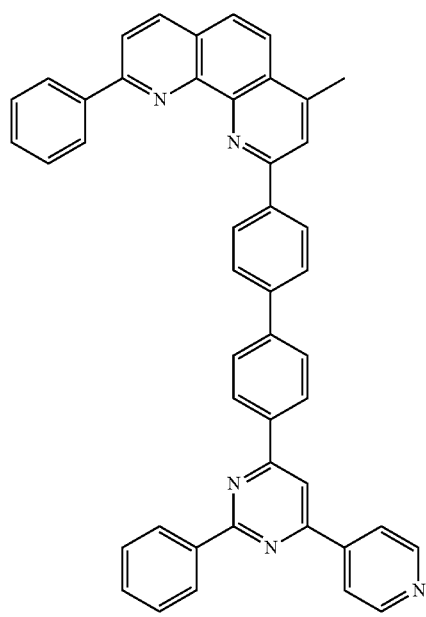
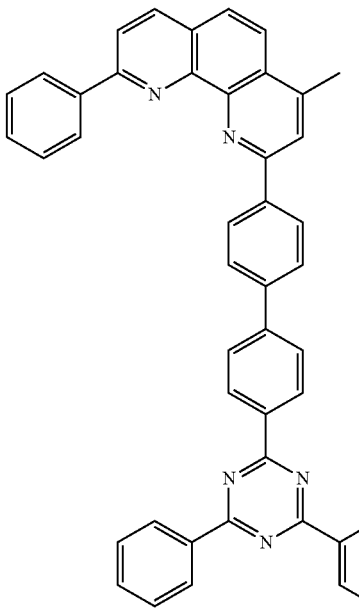

323
-continued
688
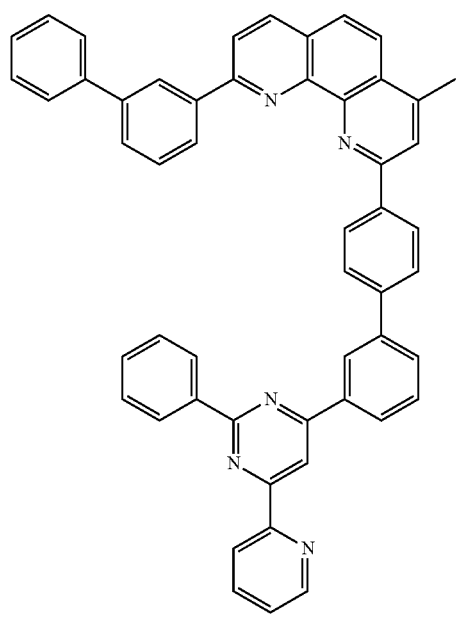
689
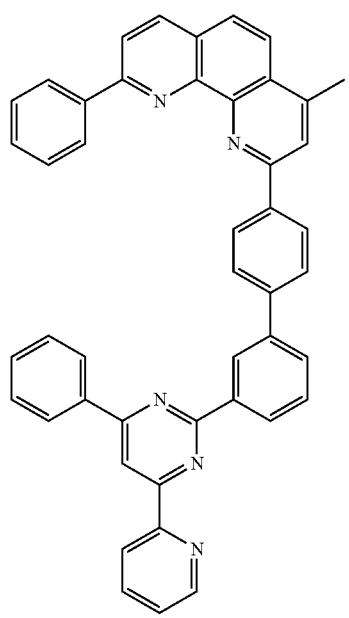
324
-continued
690
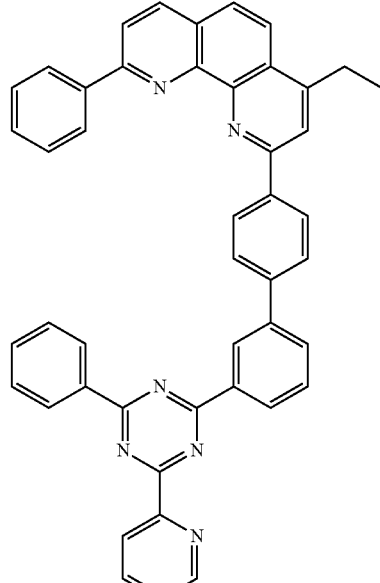
691
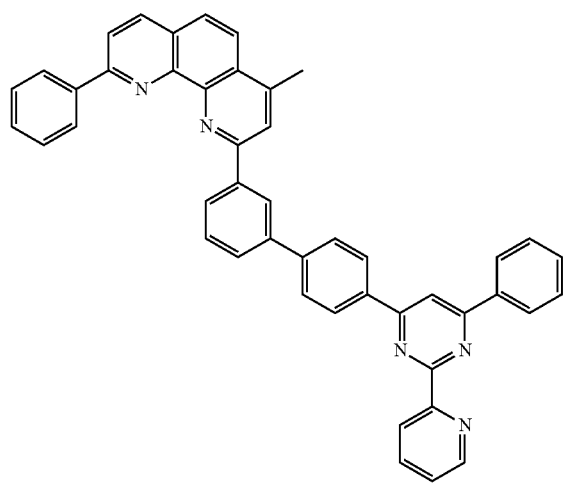
692

-continued
693
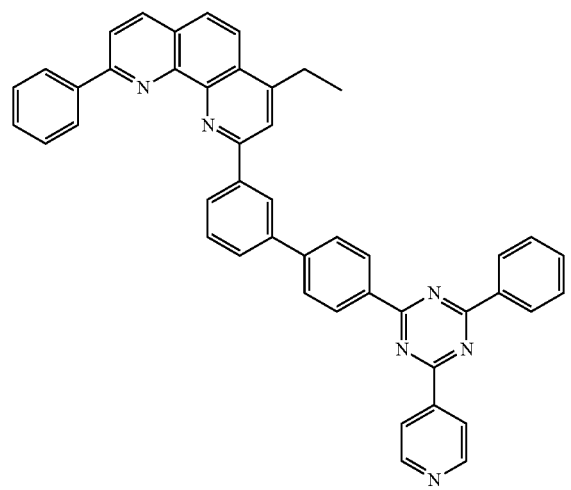
694
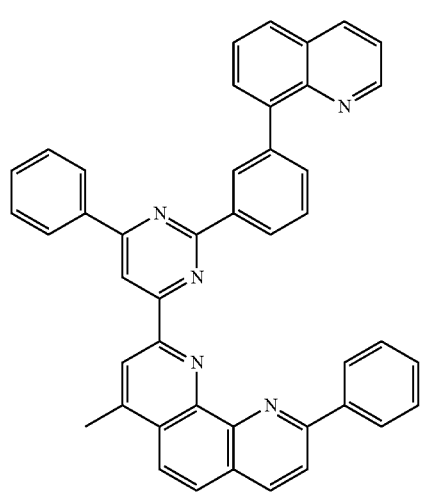
695
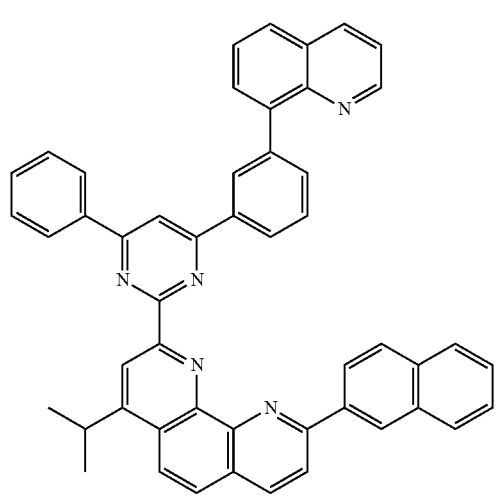
-continued
696
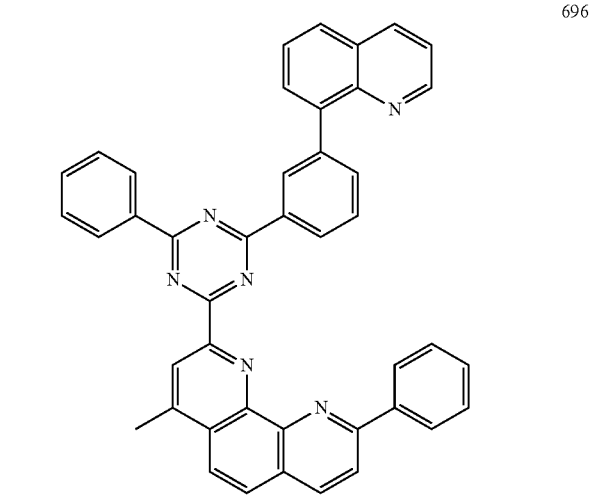
697
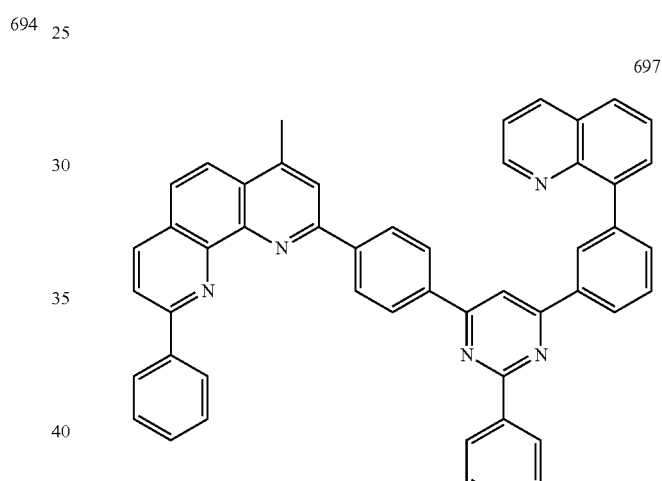
698
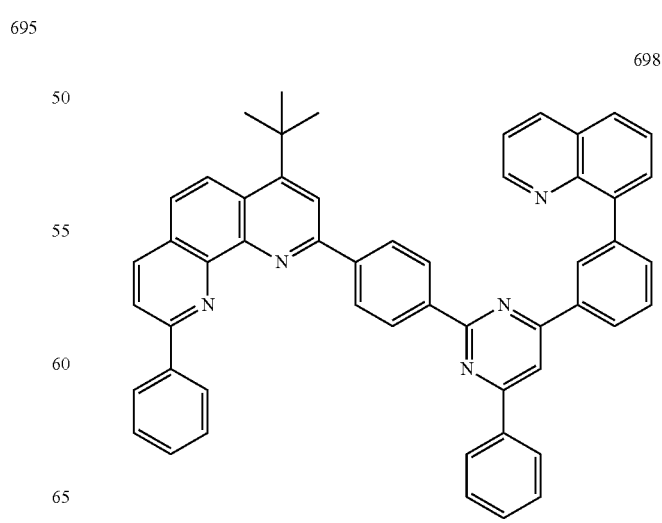

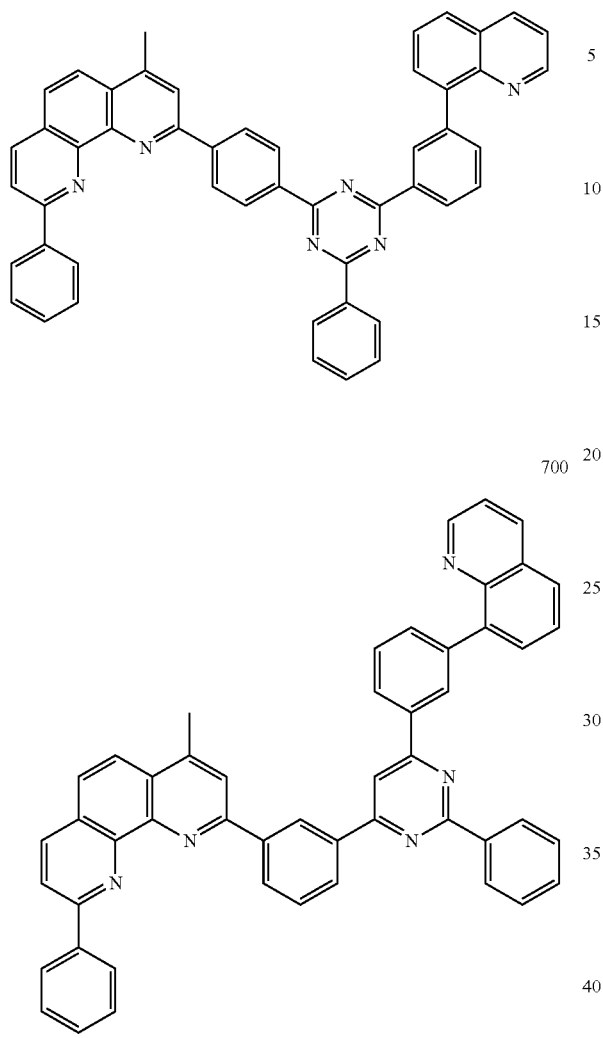
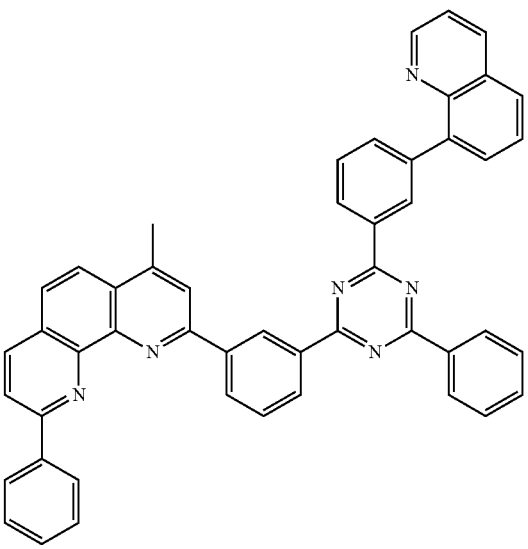
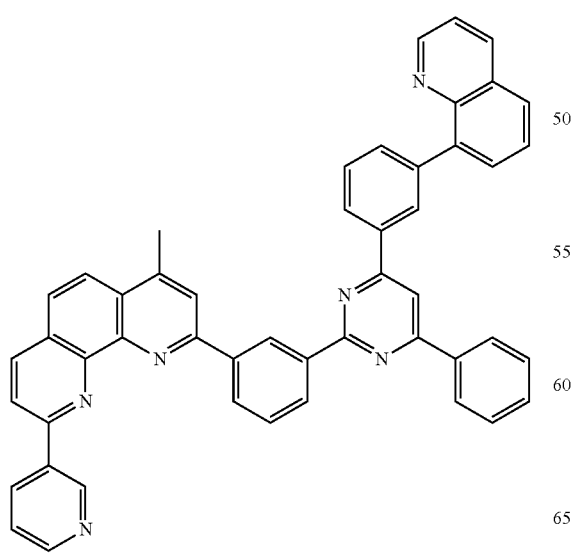
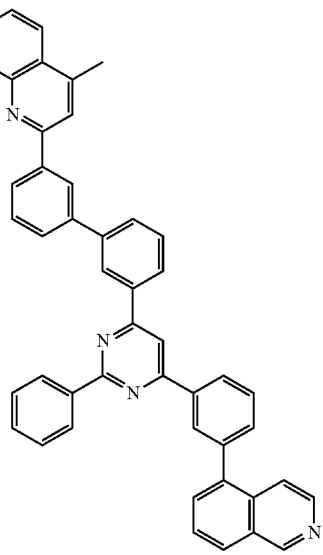

329
-continued
704
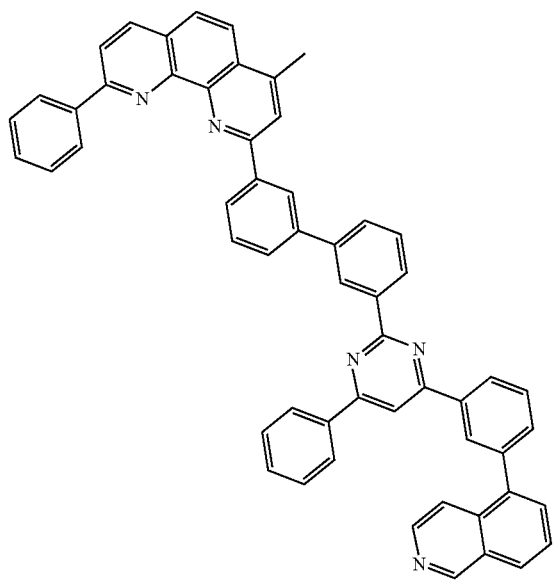
705
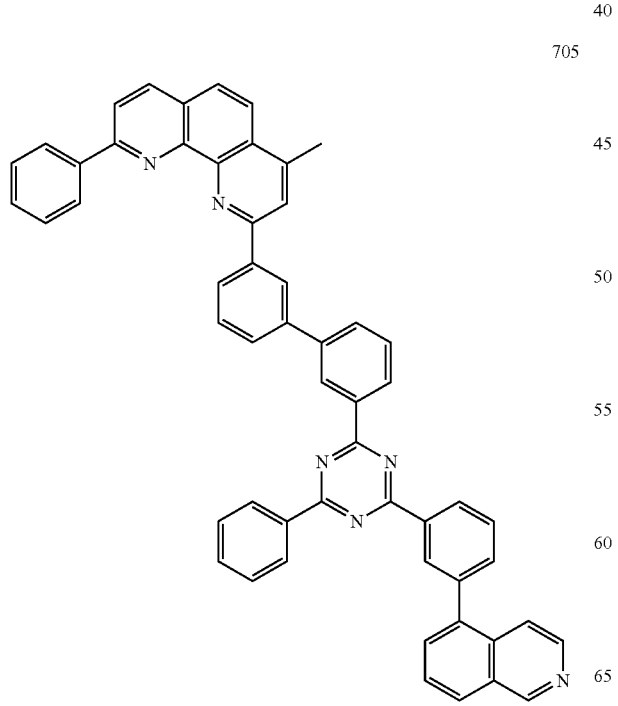
330
-continued
706
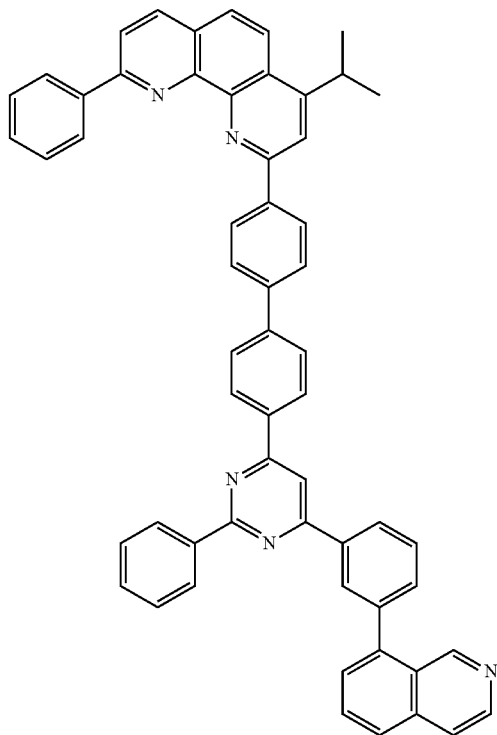
707
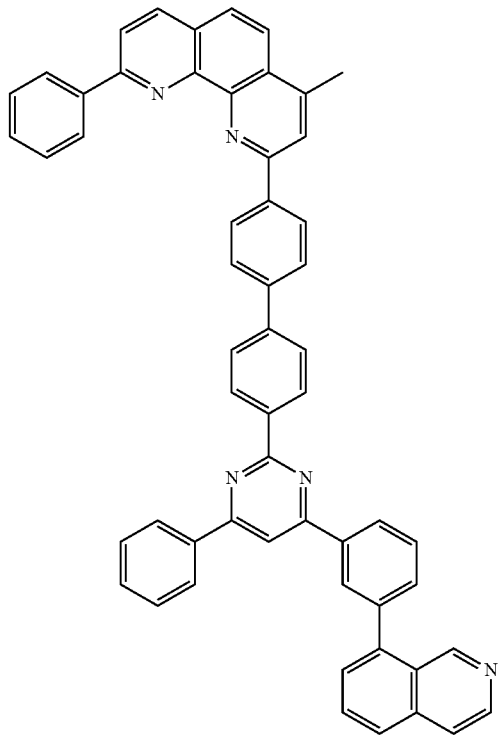

331
-continued
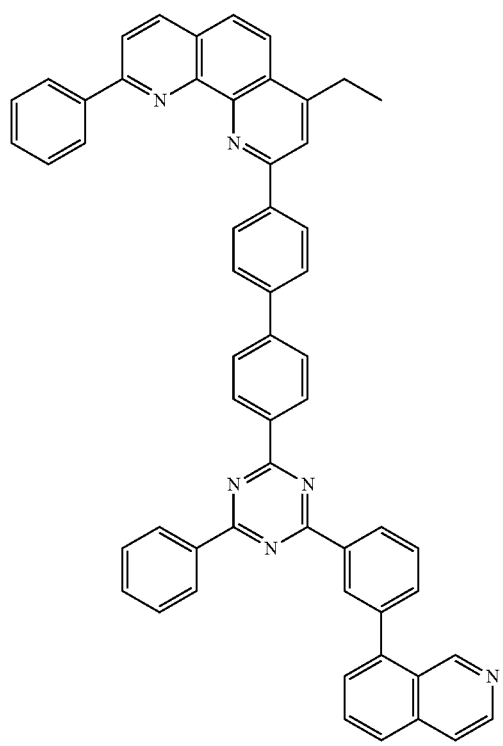
708
709
332
-continued
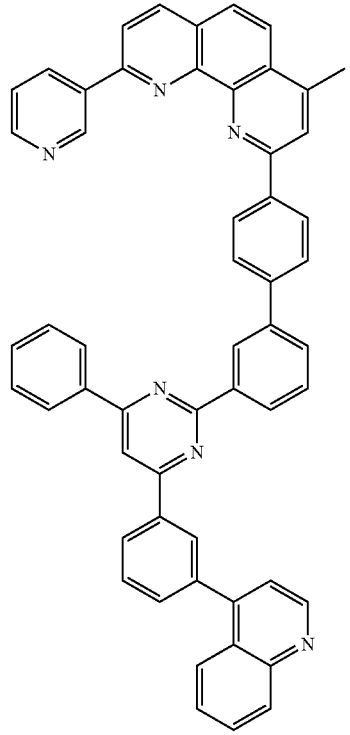
710
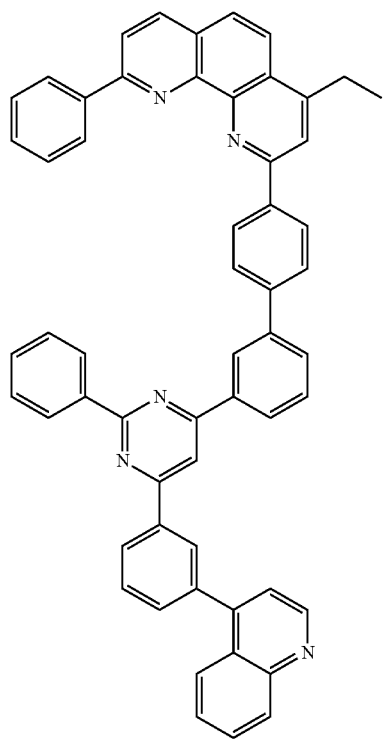
711

333
-continued
712
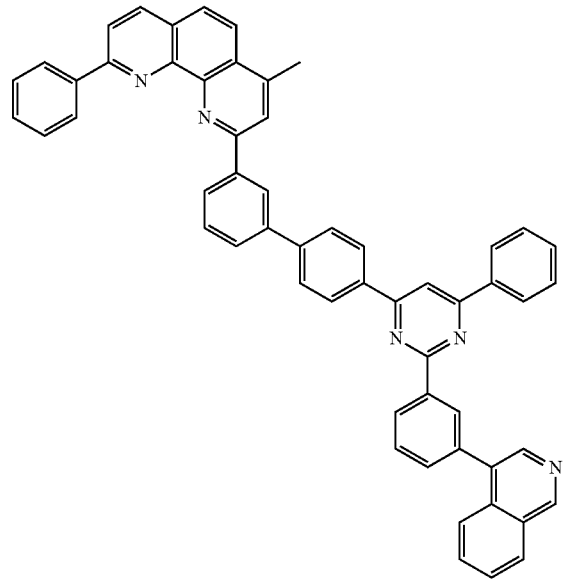
713
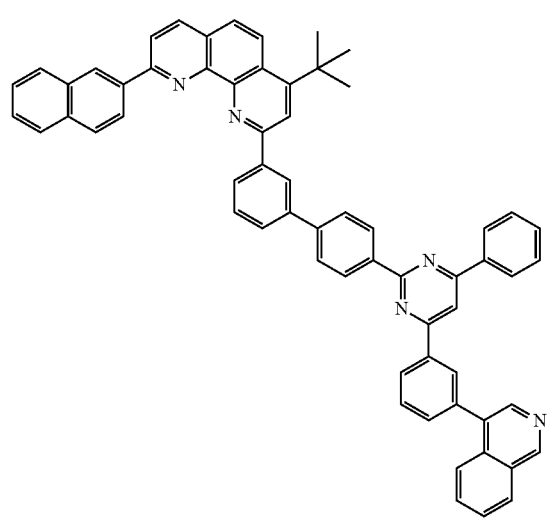
334
-continued
714
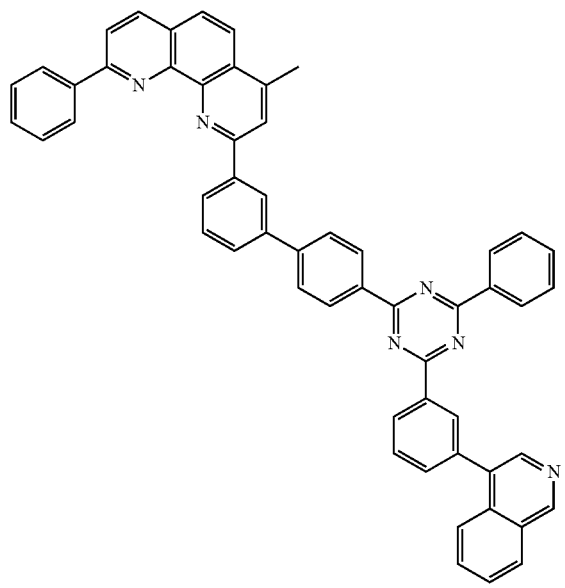
715
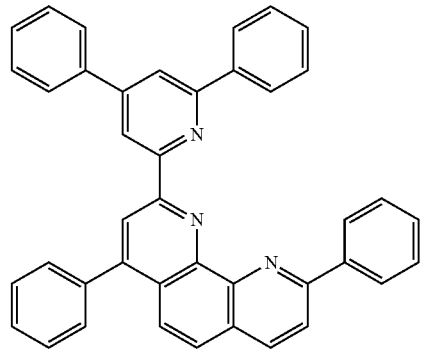
716
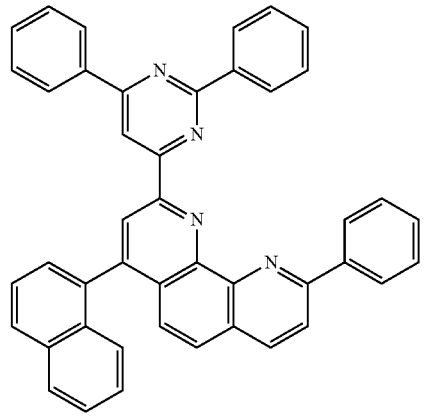

717
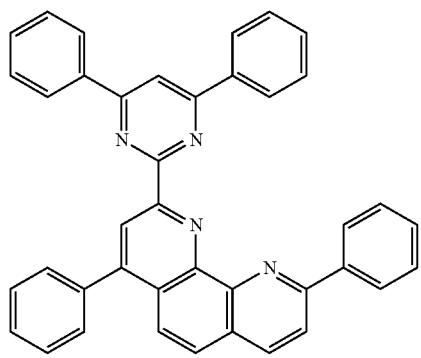
718
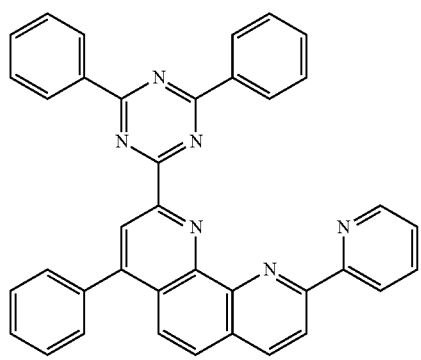
719
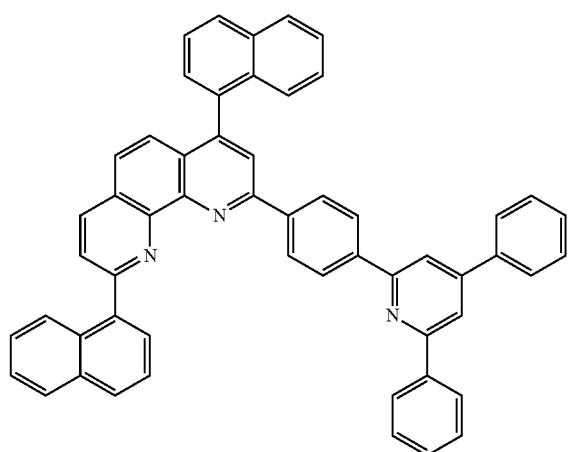
720
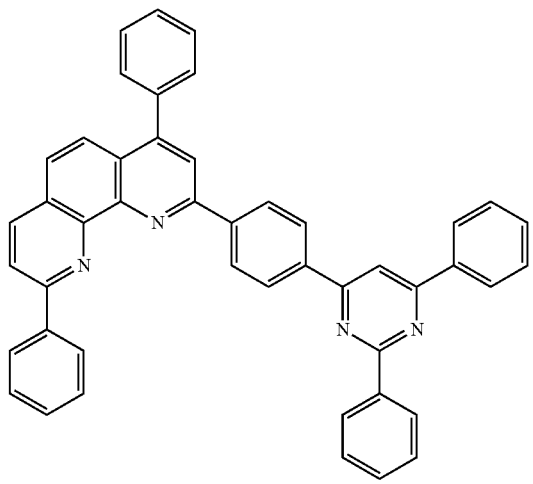
721
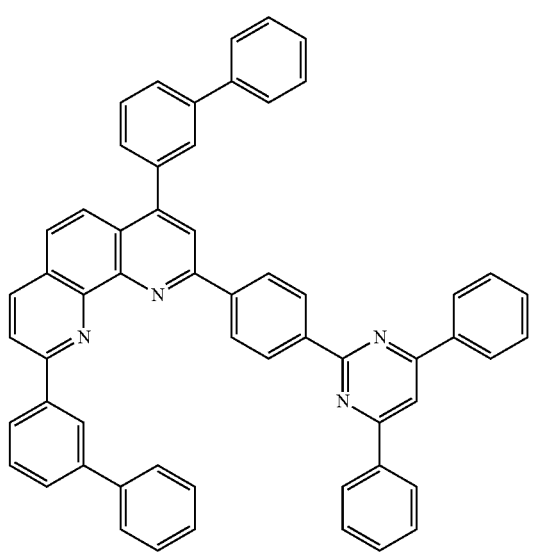
722
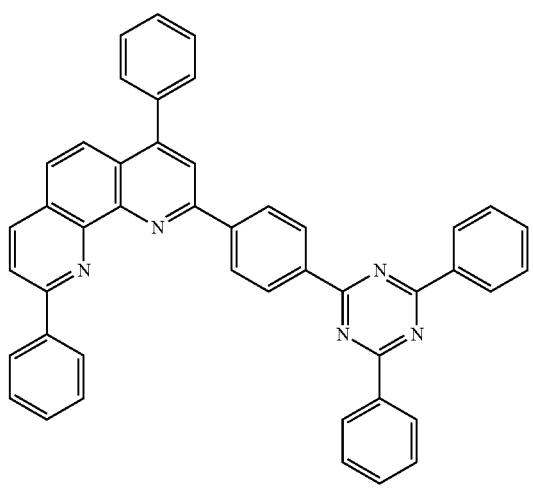

337                           338
-continued                    -continued
723
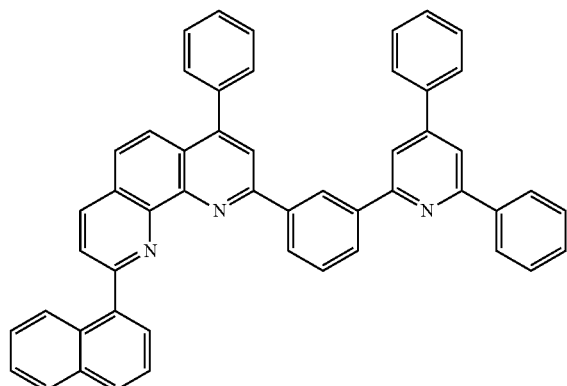
726
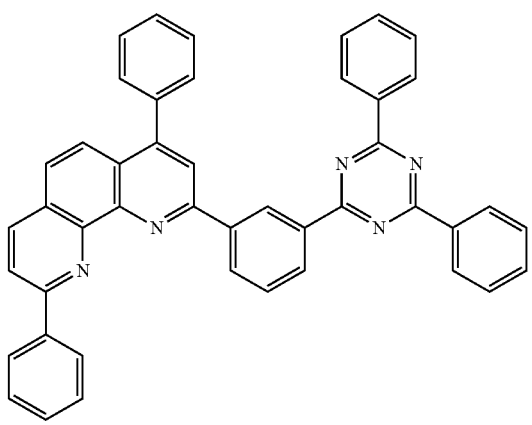
724
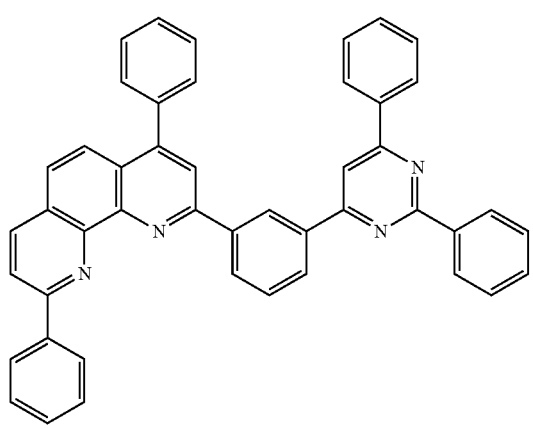
727
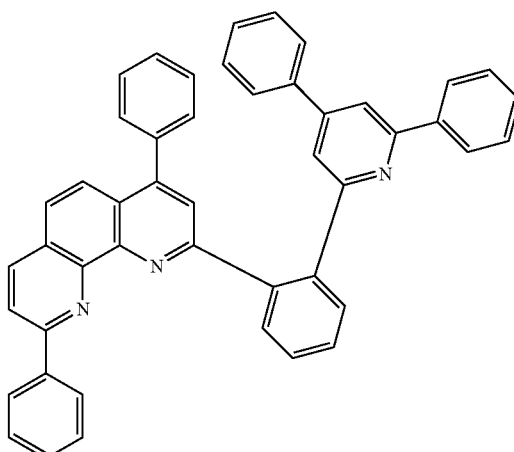
725
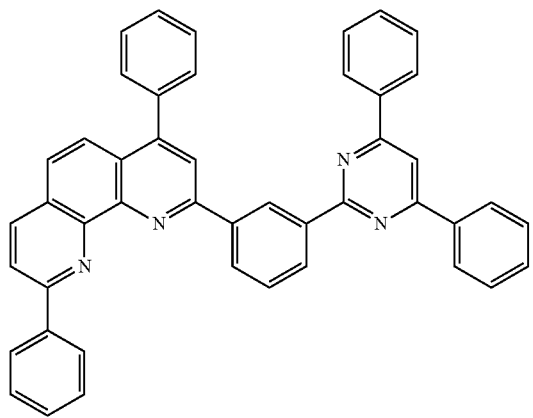
728
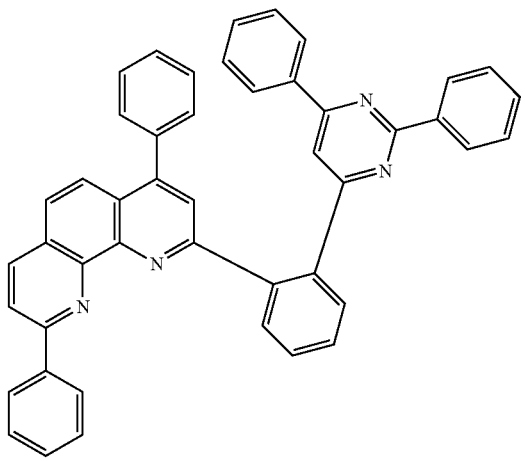

339
-continued
729
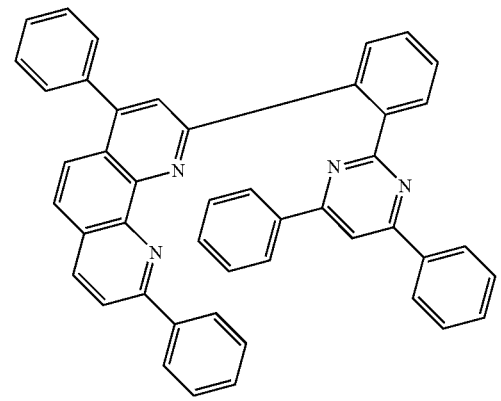
730
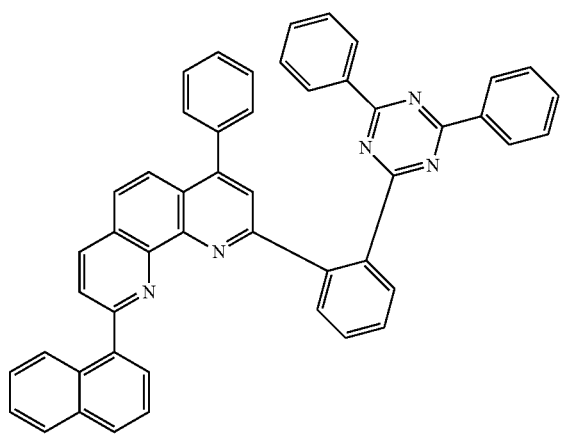
731
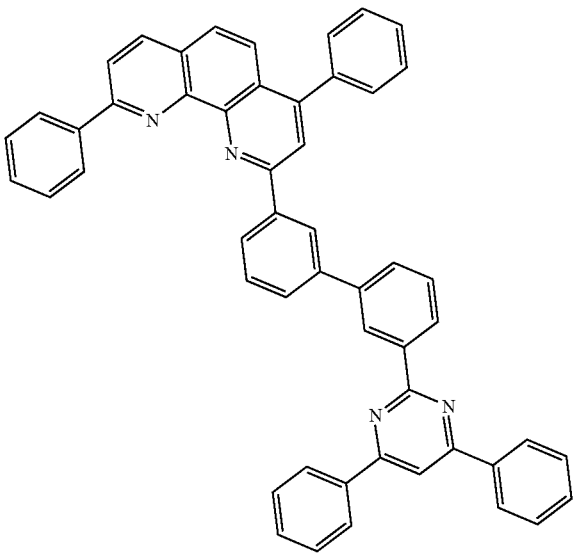
340
-continued
732
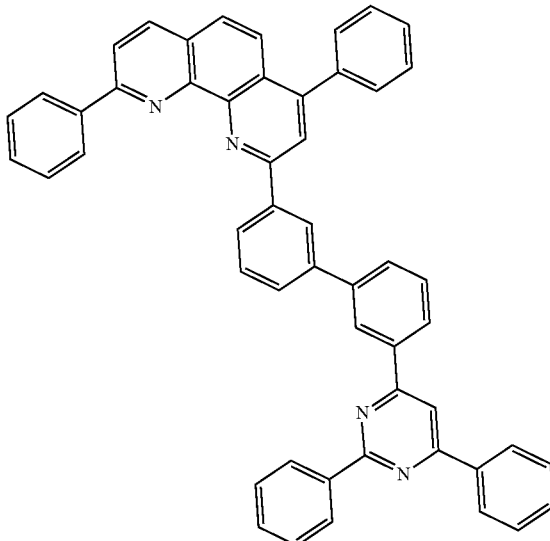
733

341
-continued
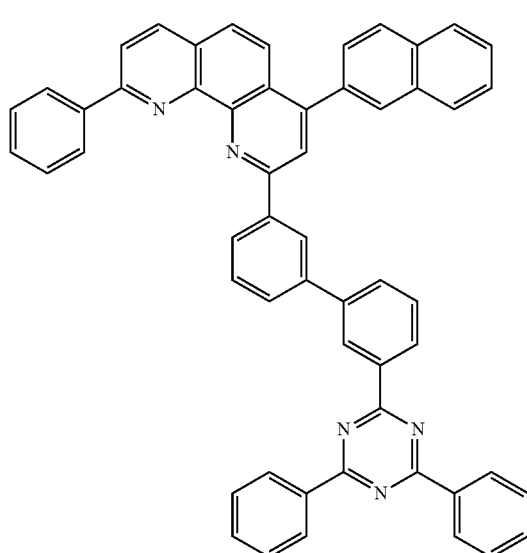
734
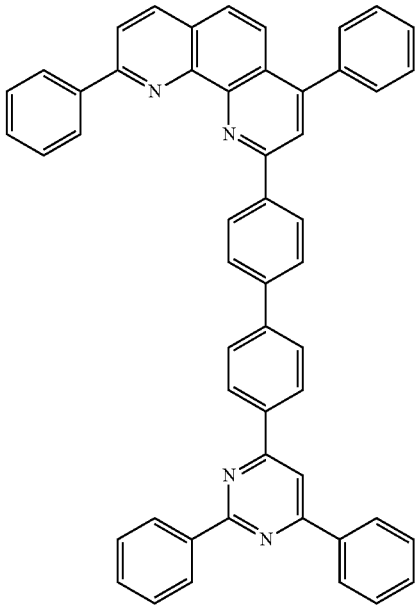
736
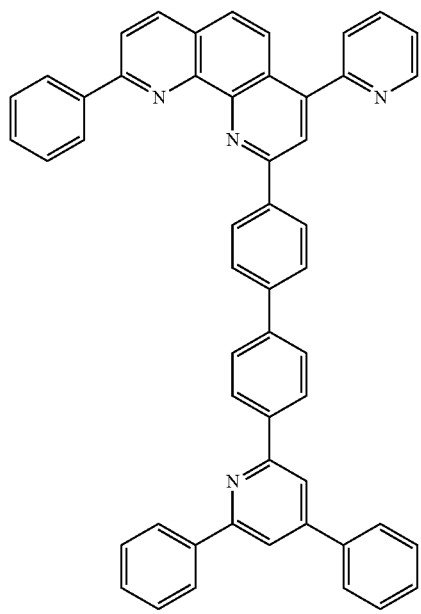
735
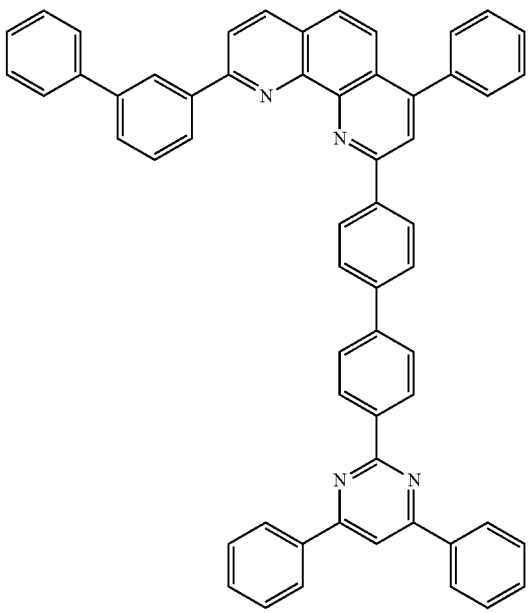
737

343
-continued
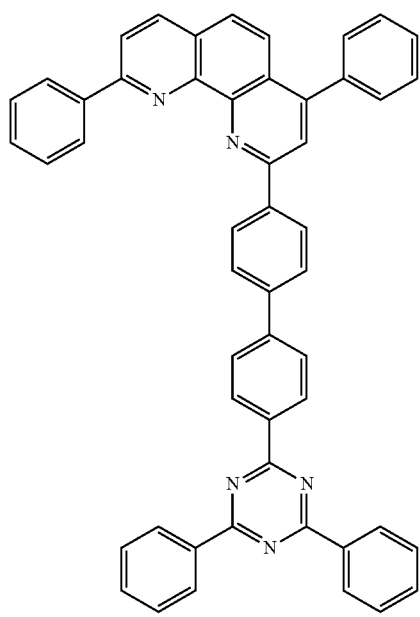
738
739
344
-continued
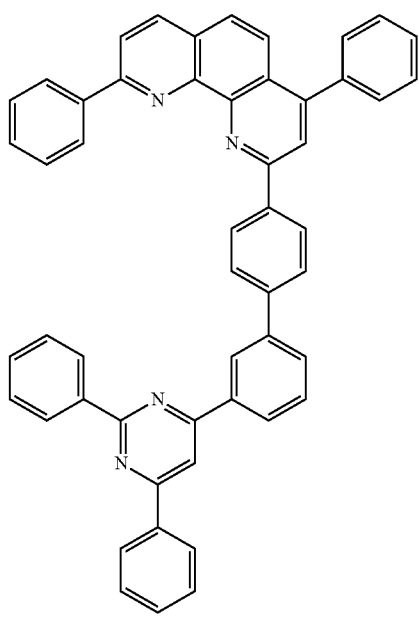
740
741

-continued
742
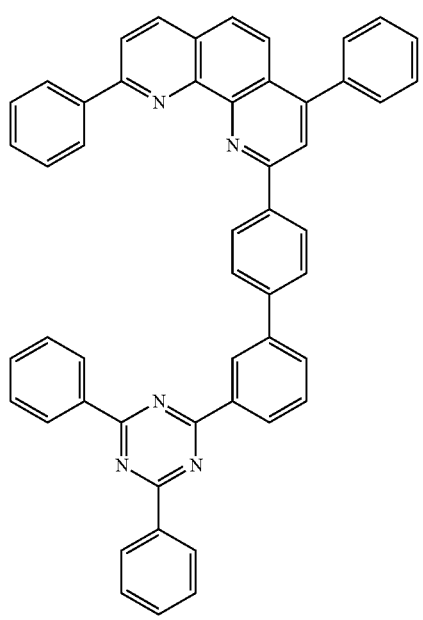
743
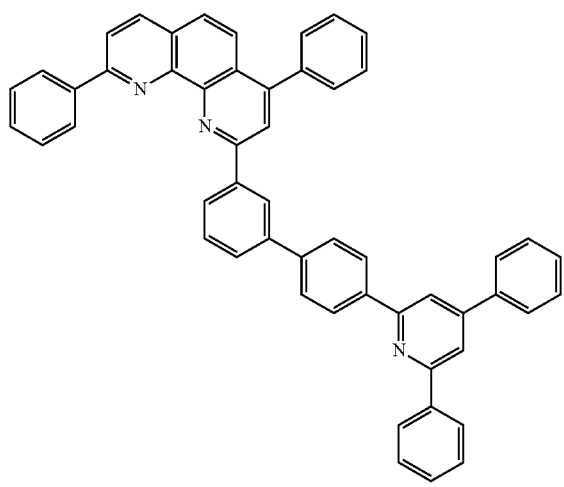
744
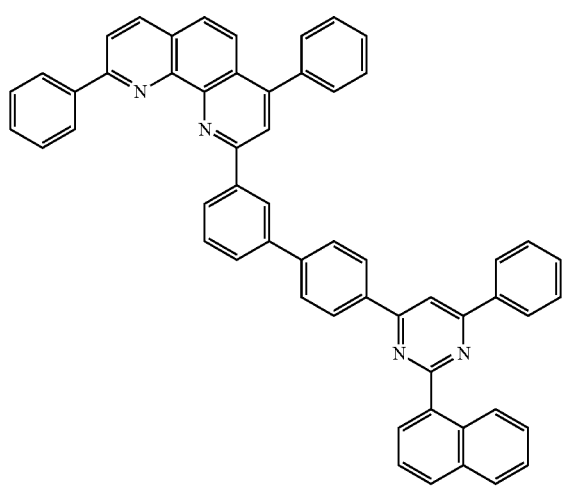
-continued
745
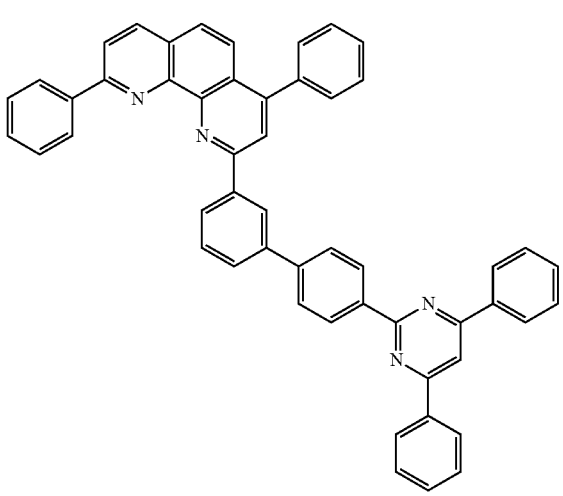
746
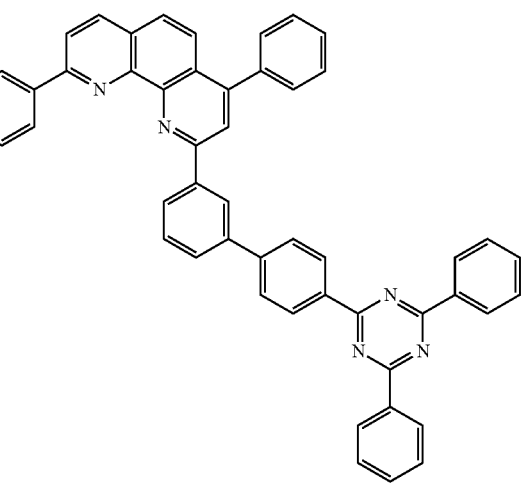
747
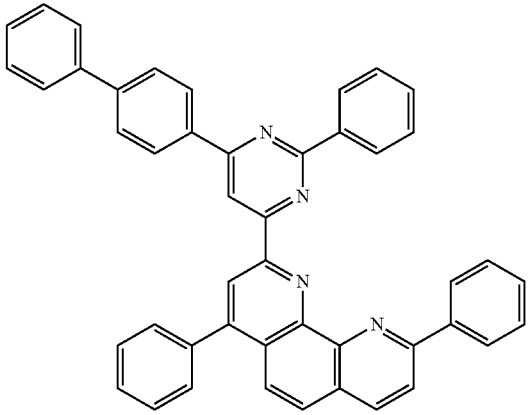

748
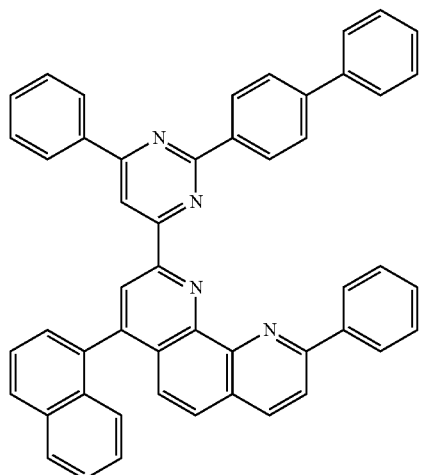
749
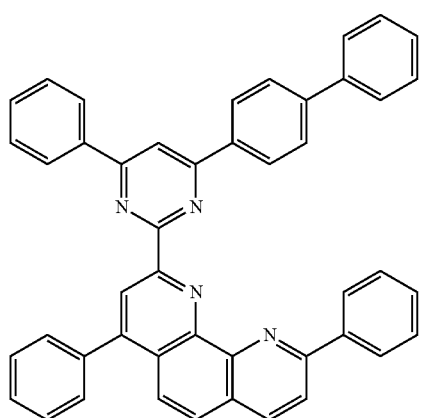
750
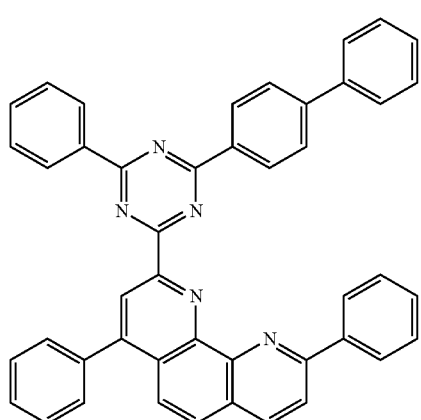
751
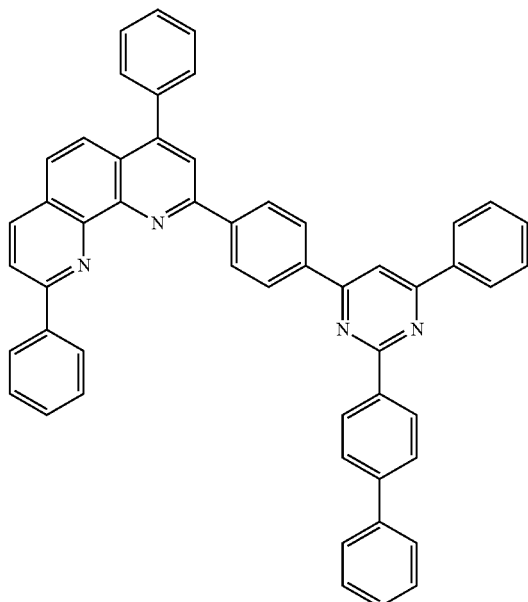
752
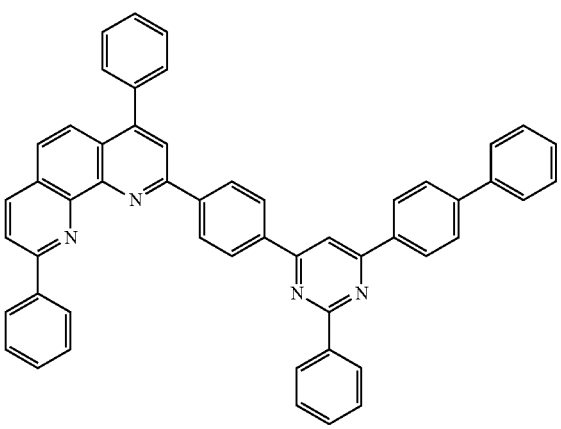

349
-continued
753
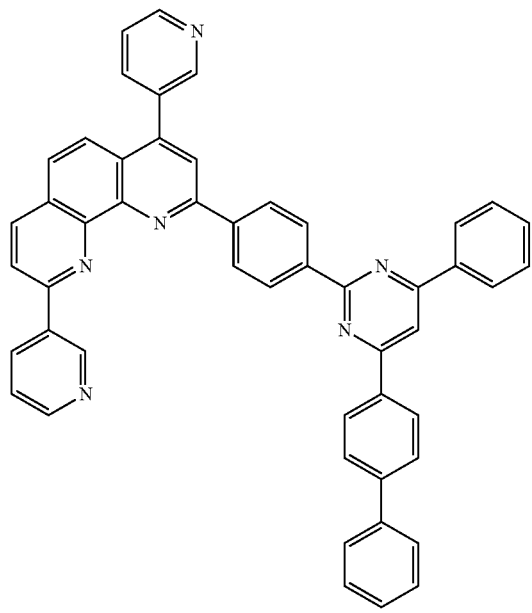
754
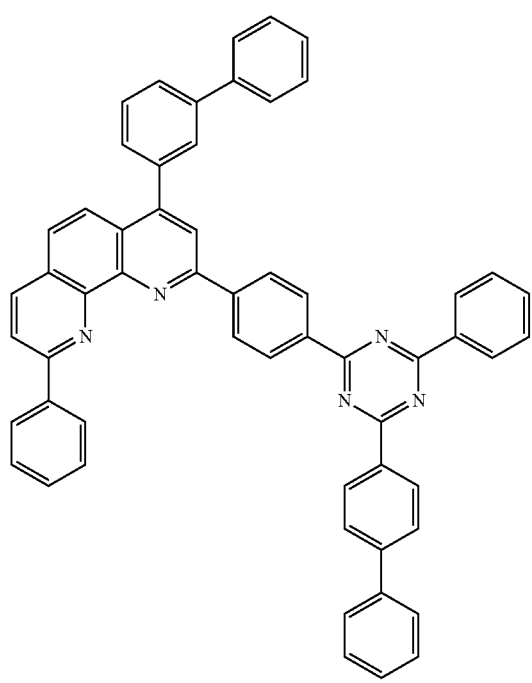
350
-continued
755
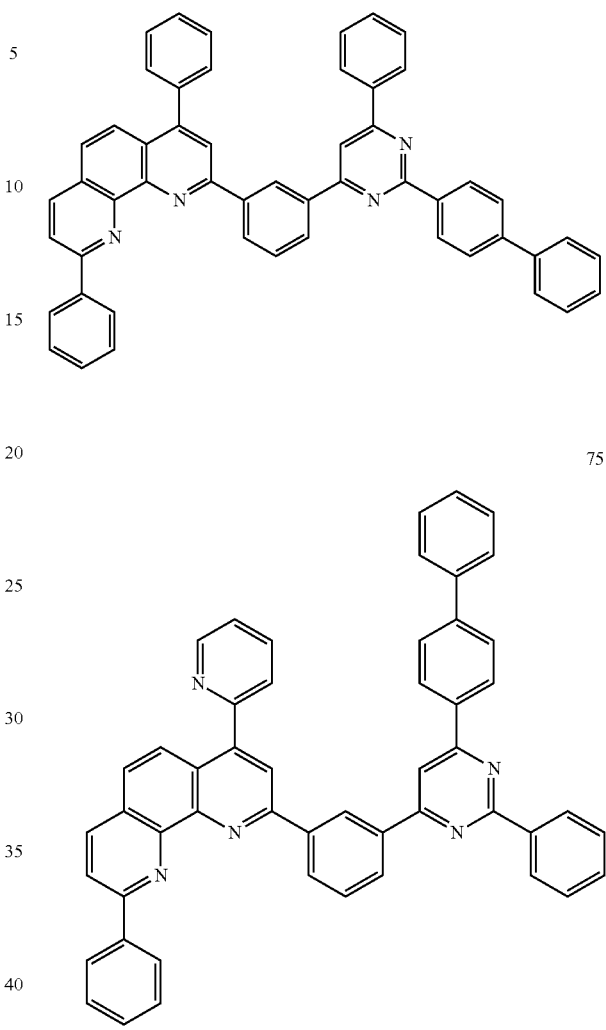
756
757
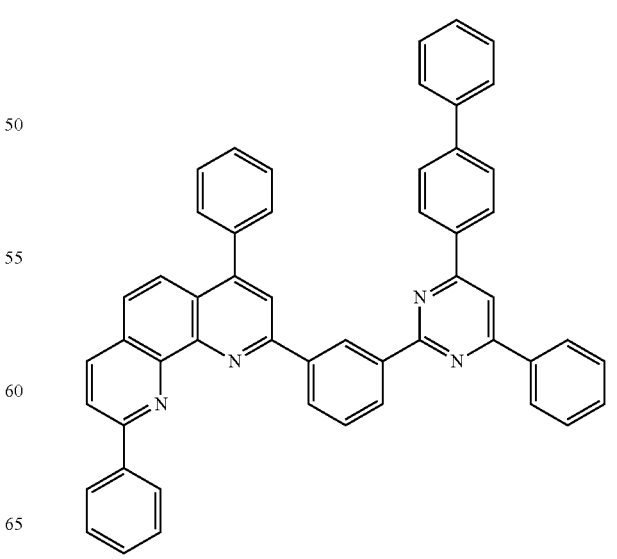

351
-continued
758
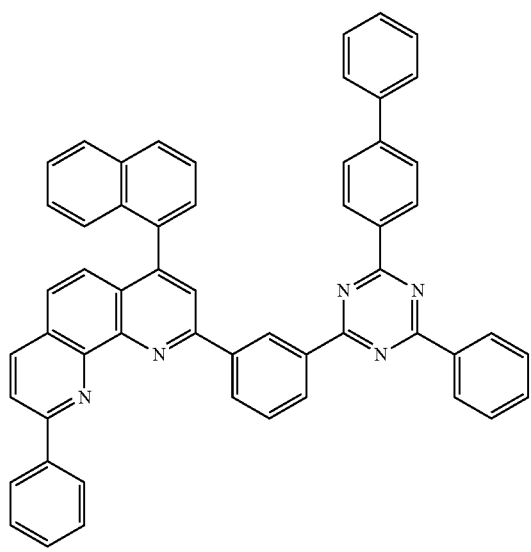
759
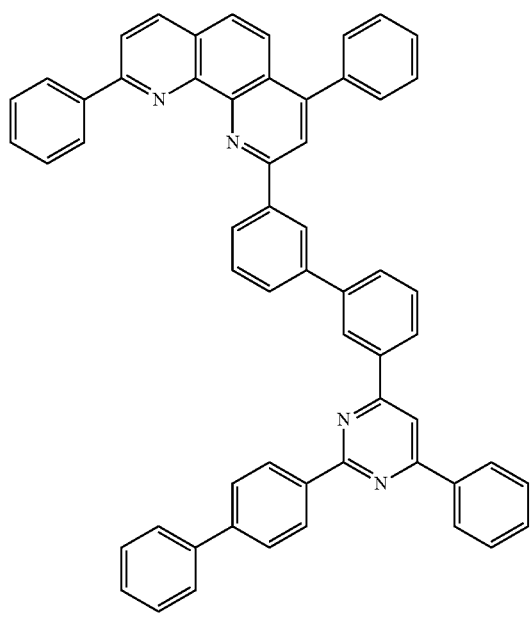
352
-continued
760
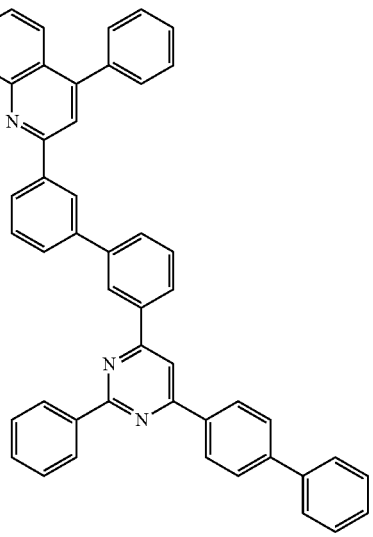
761
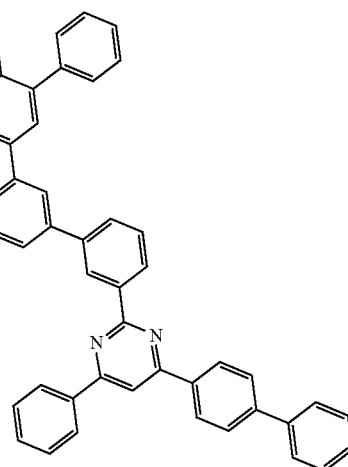

353
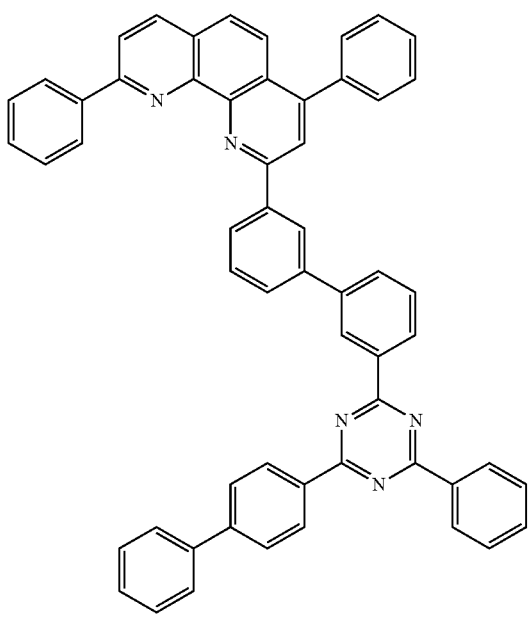
354
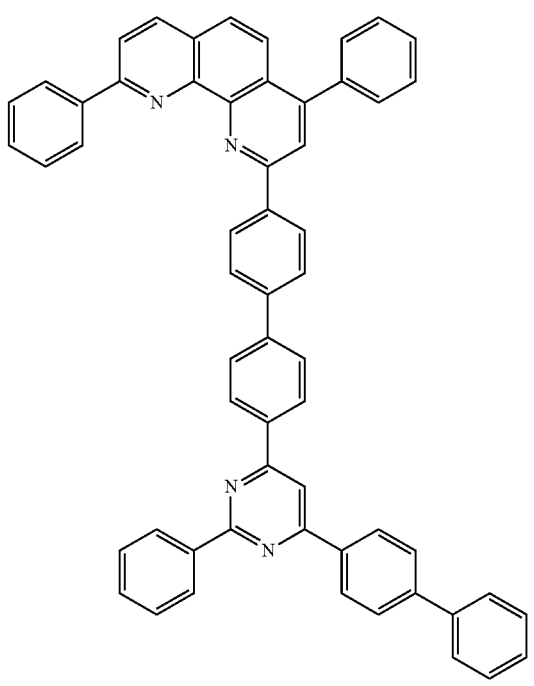
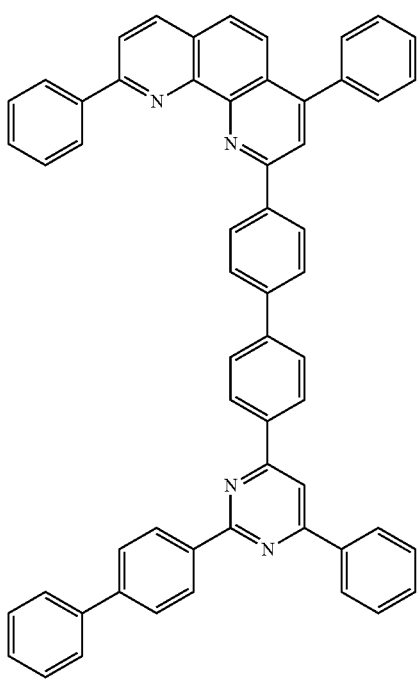
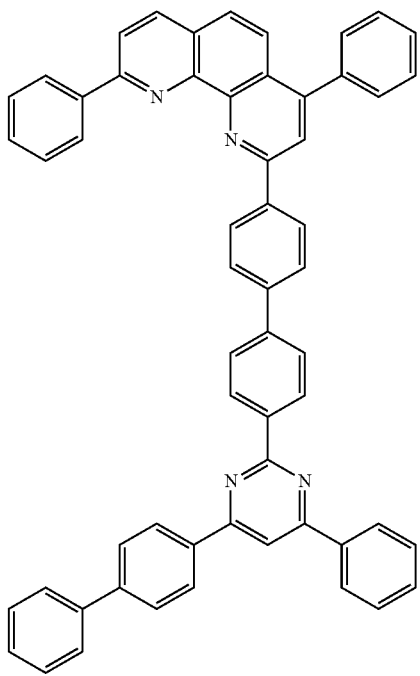

355
-continued
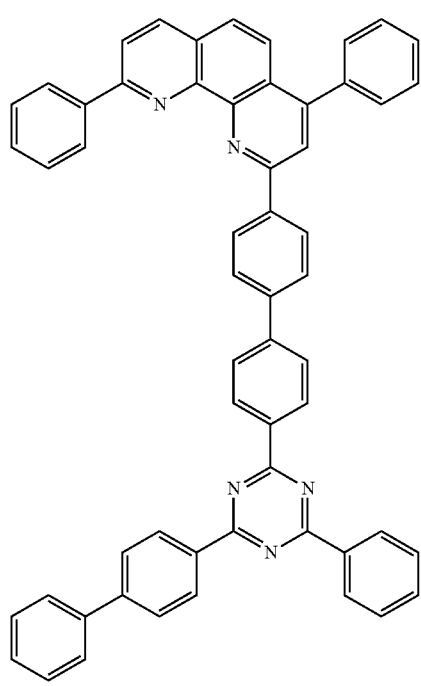
766
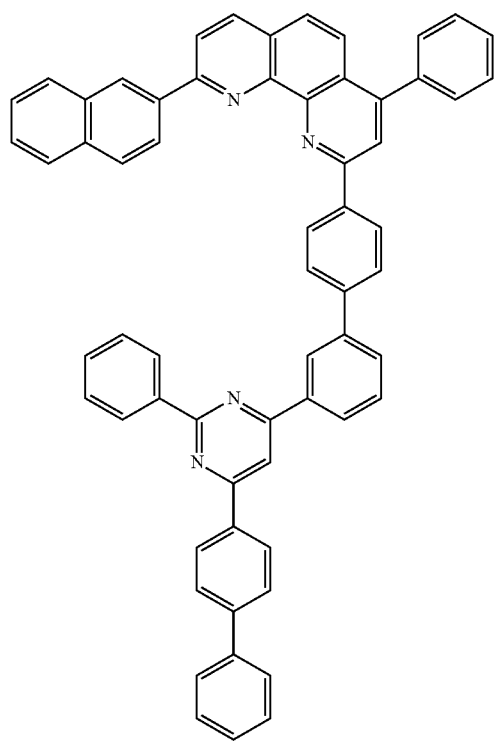
767
356
-continued
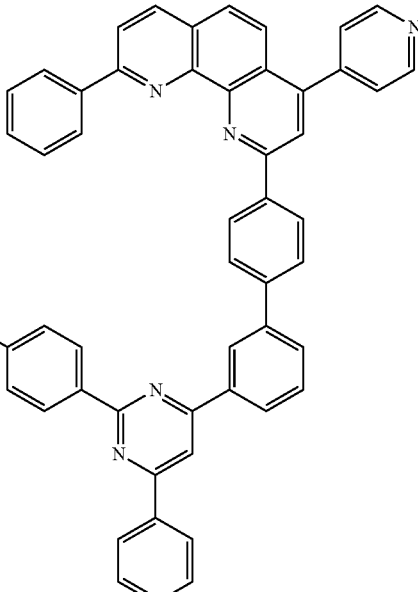
768
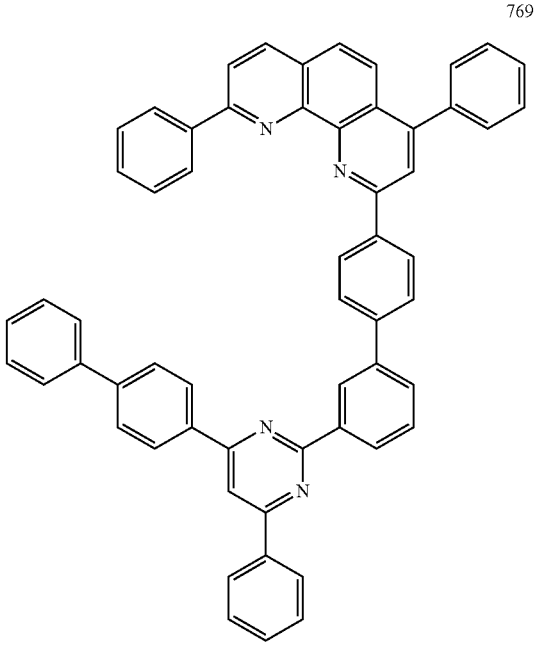
769

-continued
770
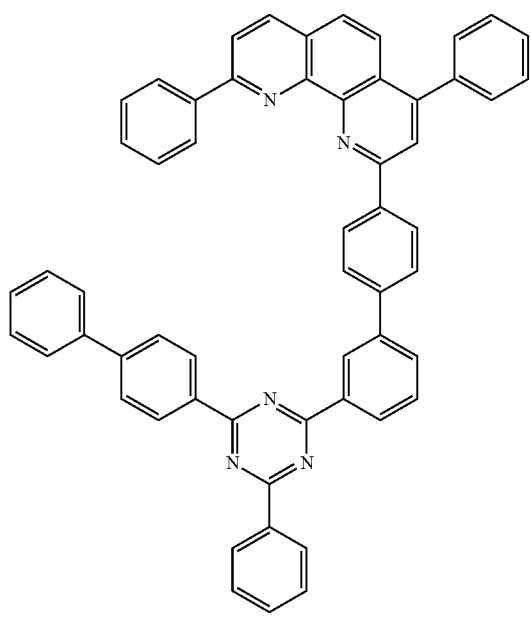
771
772
-continued
773
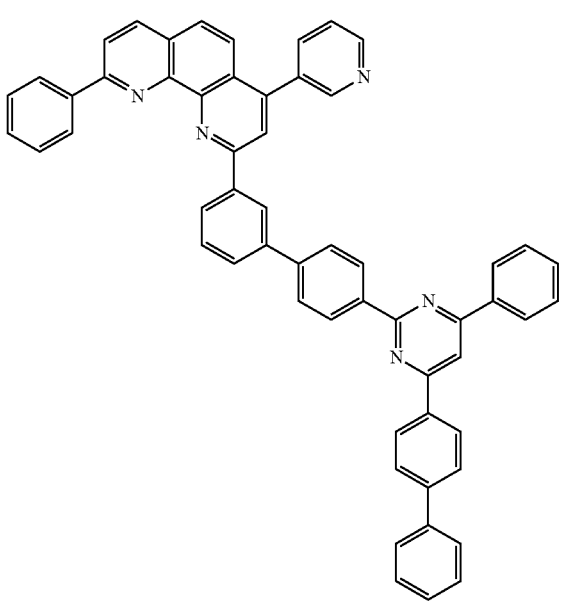
774
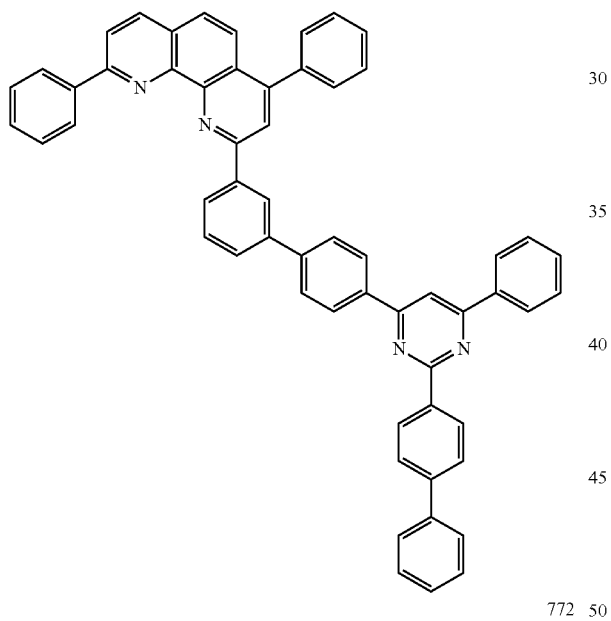
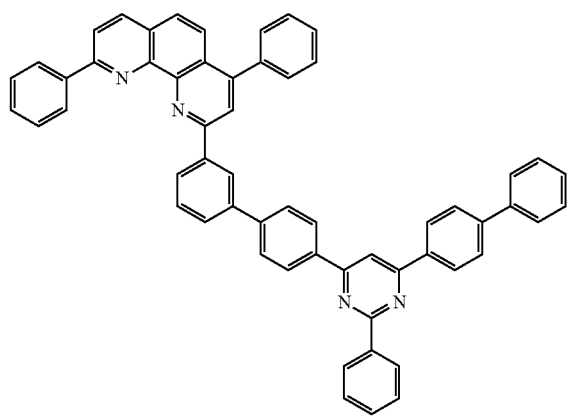
775
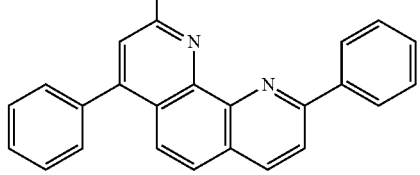

776
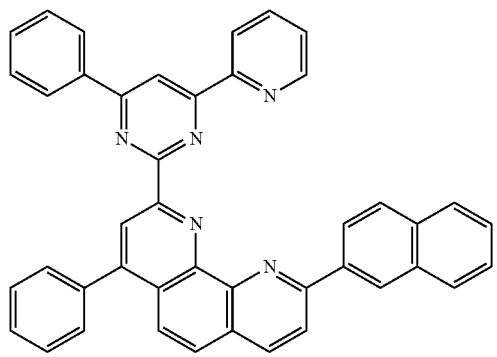
777
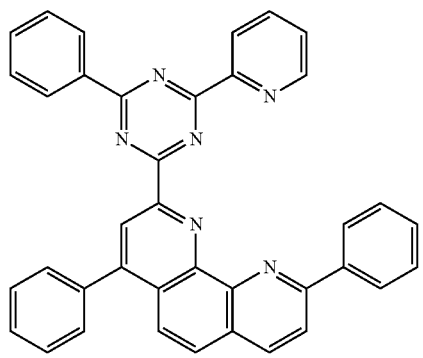
778
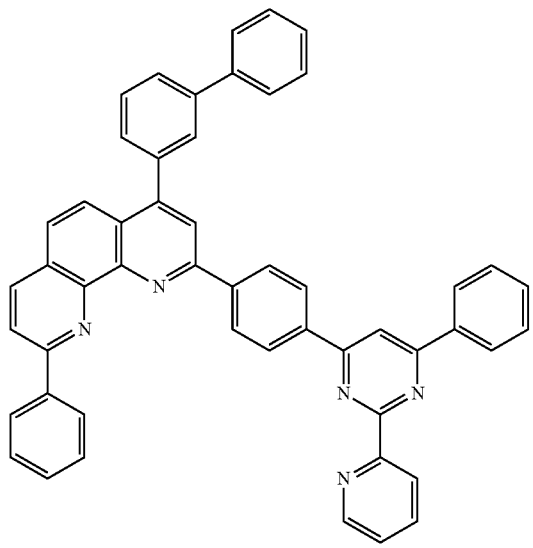
779
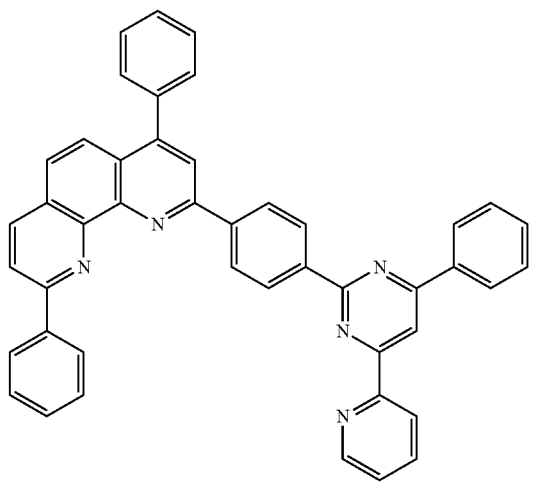
780
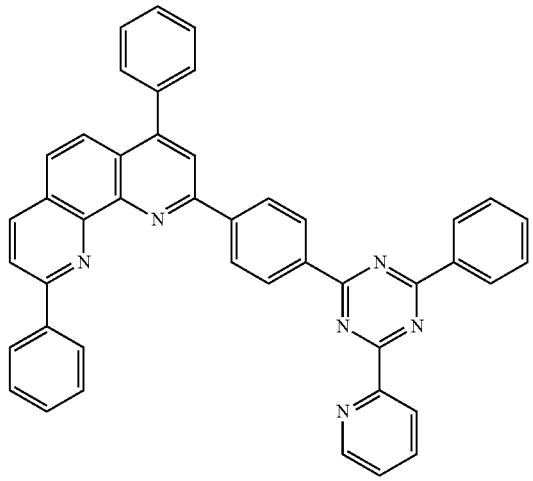
781
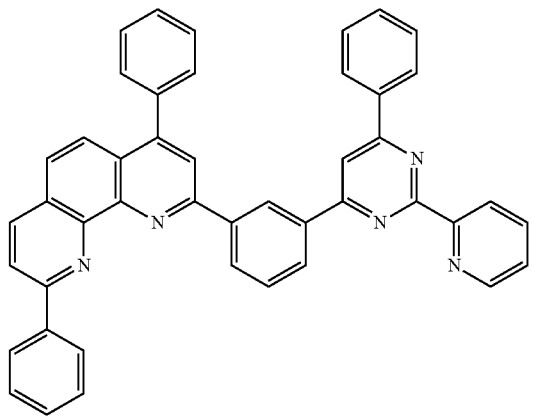

782
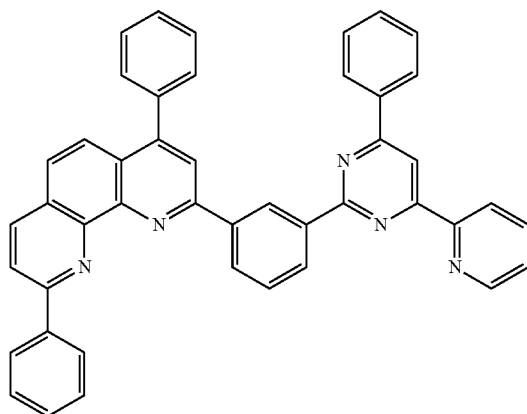
783
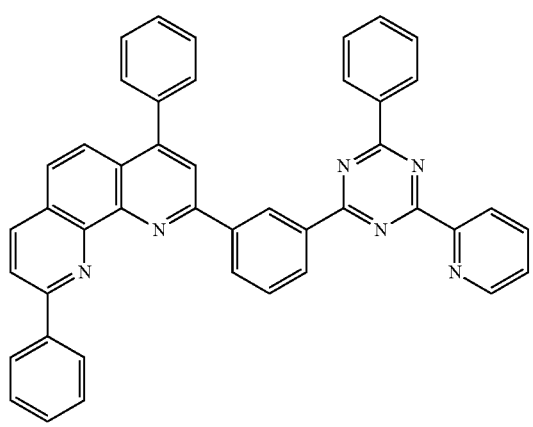
784
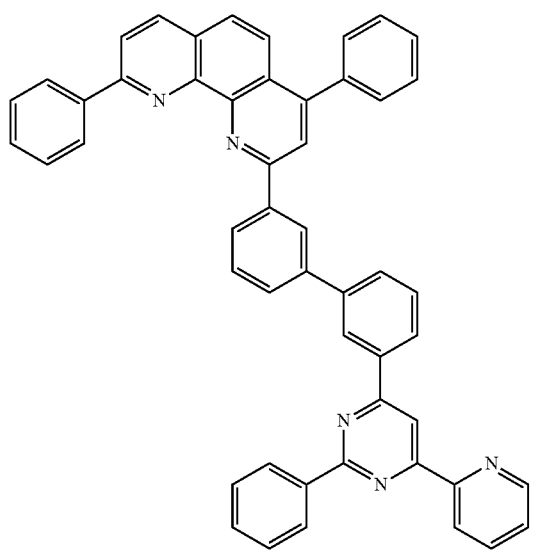
785
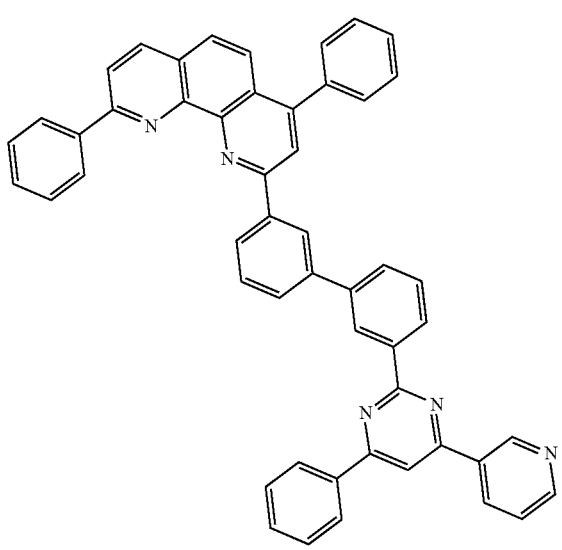
786
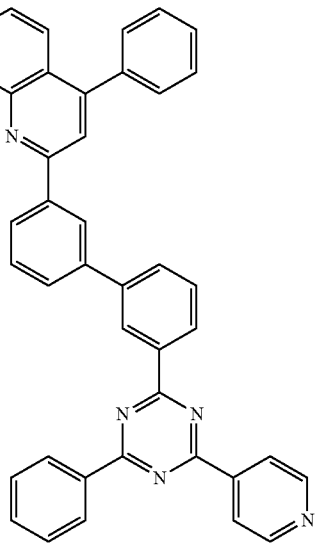

363
-continued
364
-continued
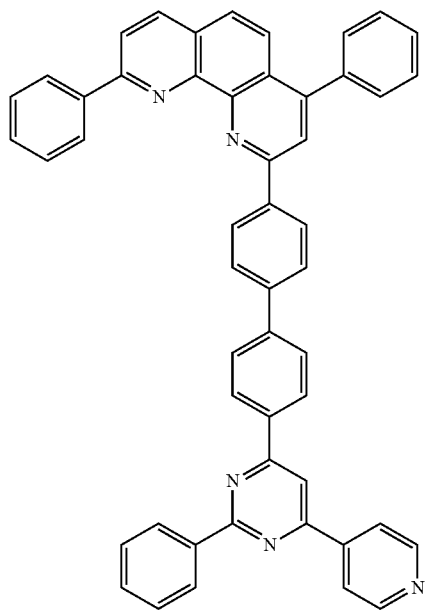
787
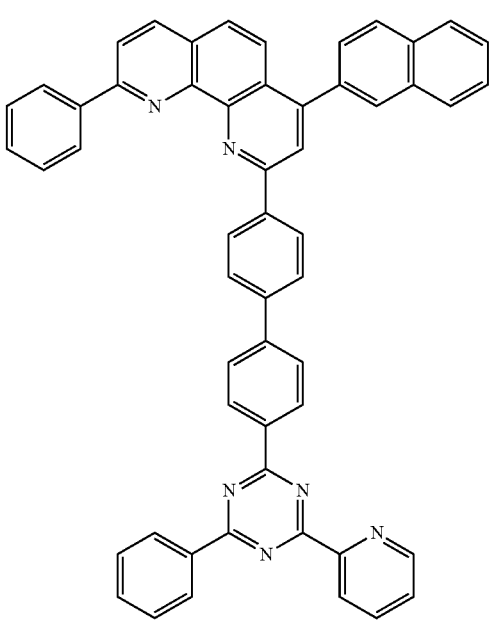
789
788
790

365
-continued
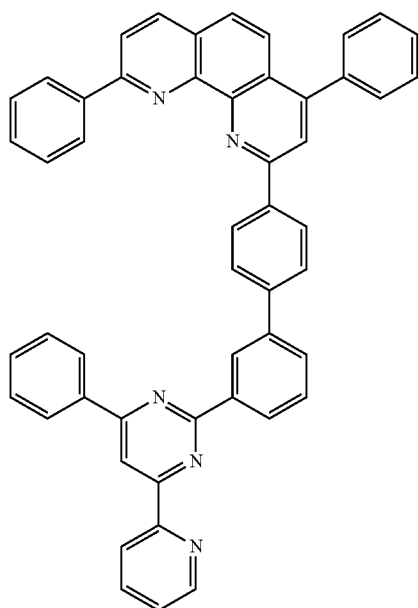
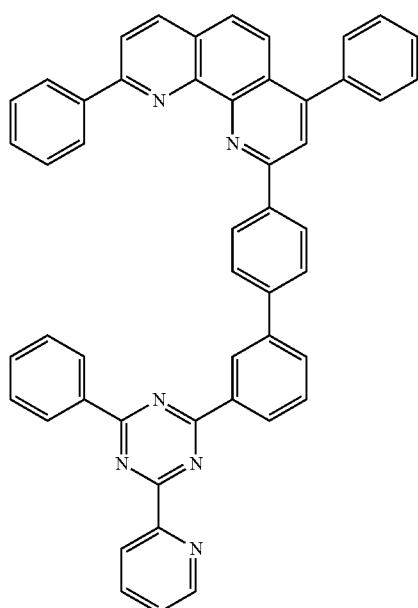
366
-continued
791
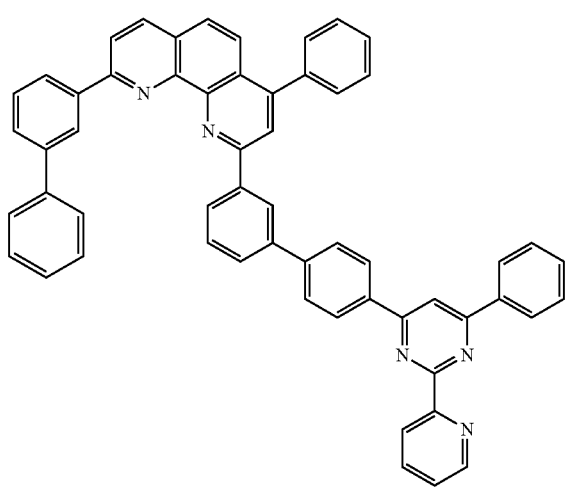
792
794
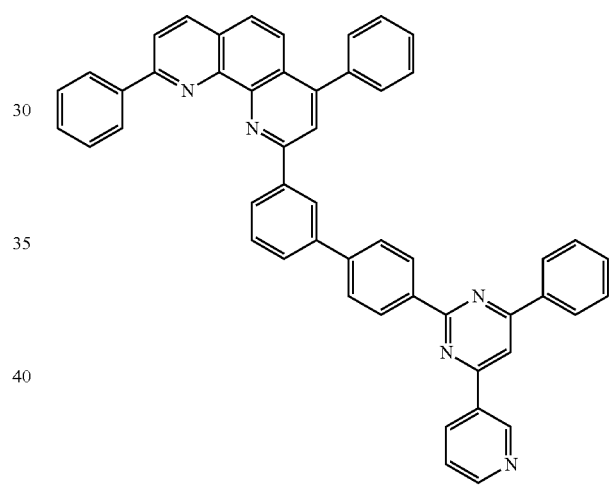
793
795

796
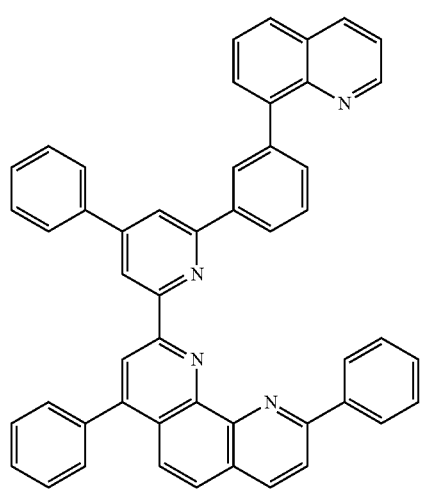
797
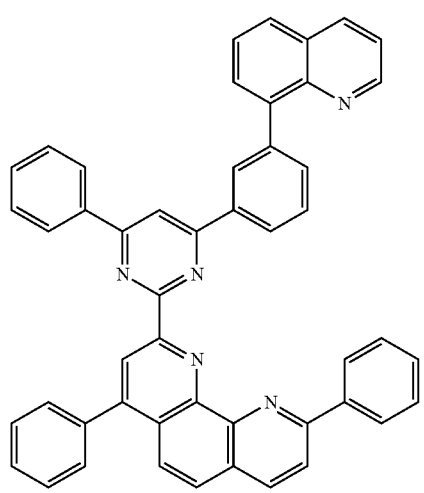
798
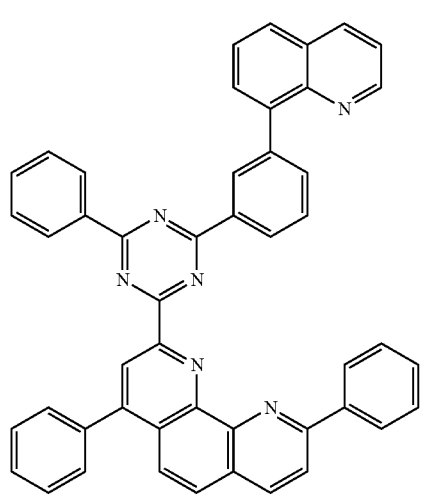
799
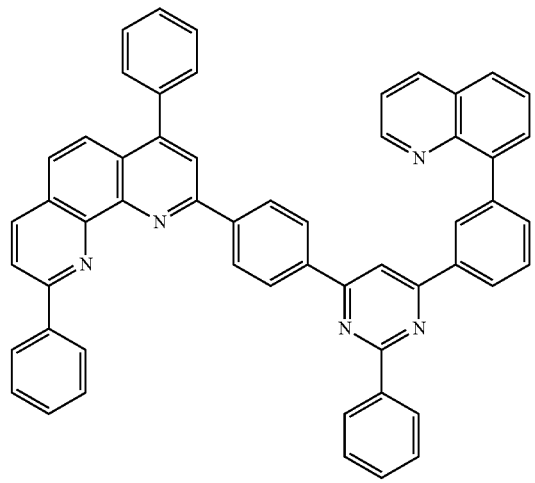
800
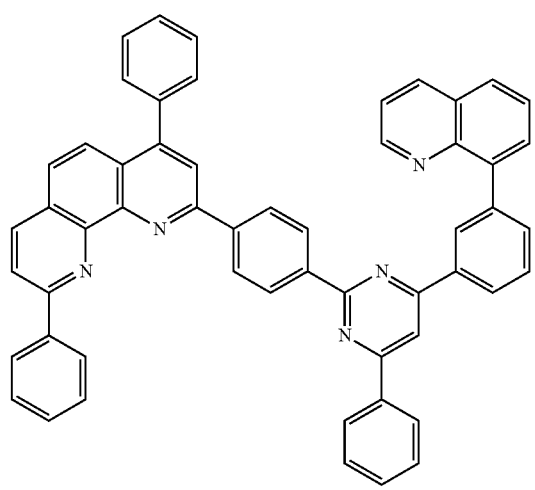
801
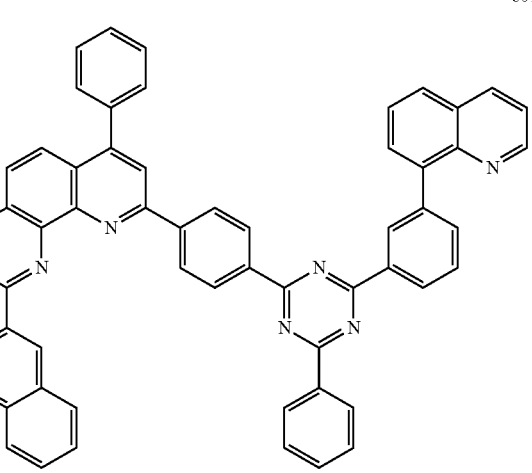

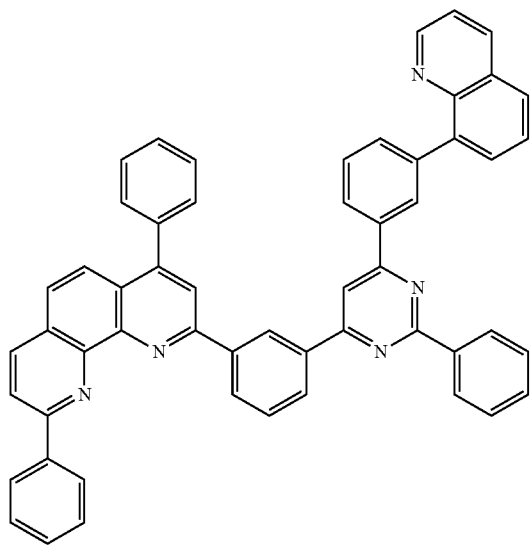
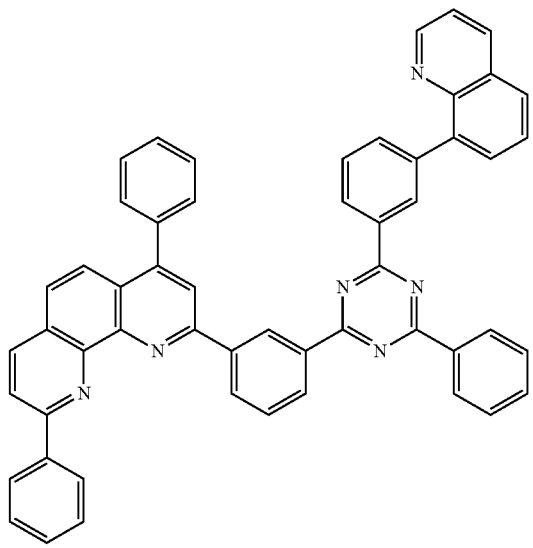
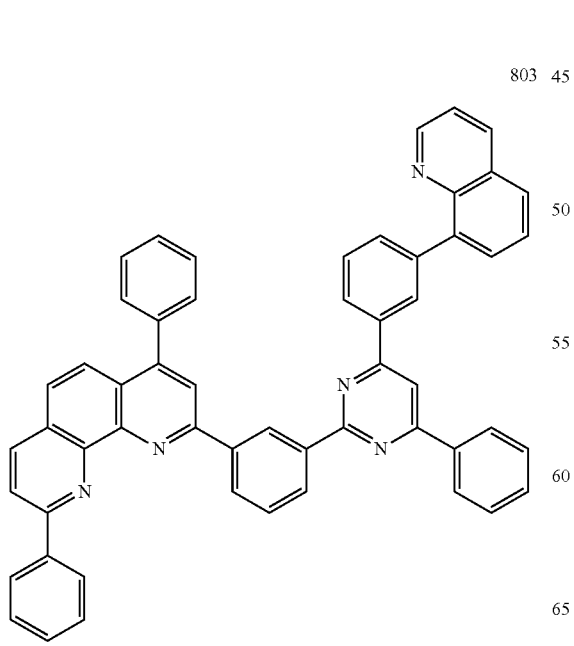

-continued
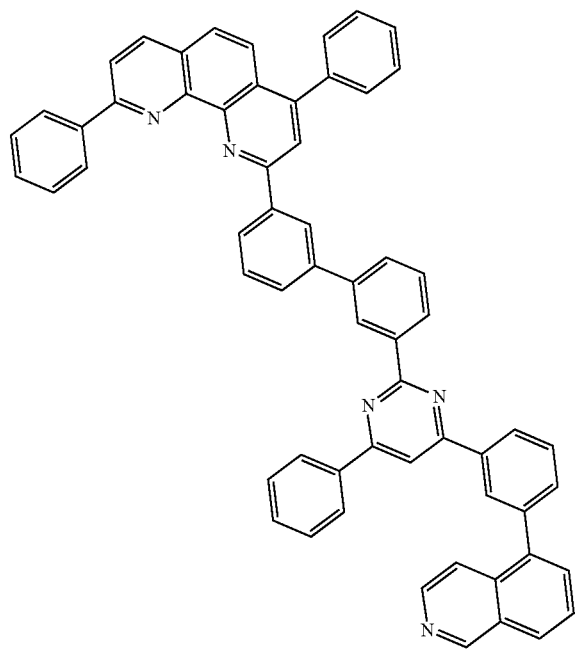
806
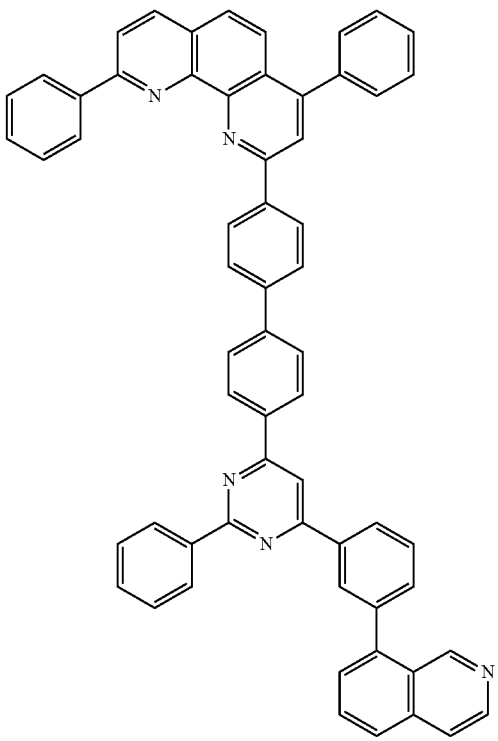
808
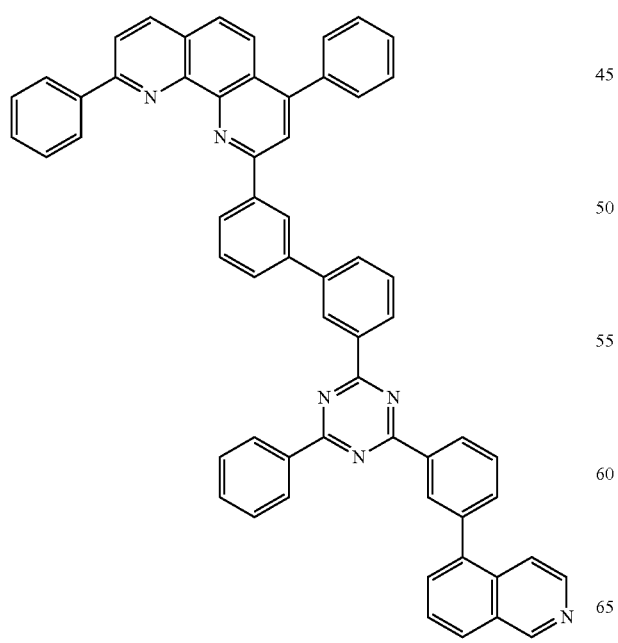
807
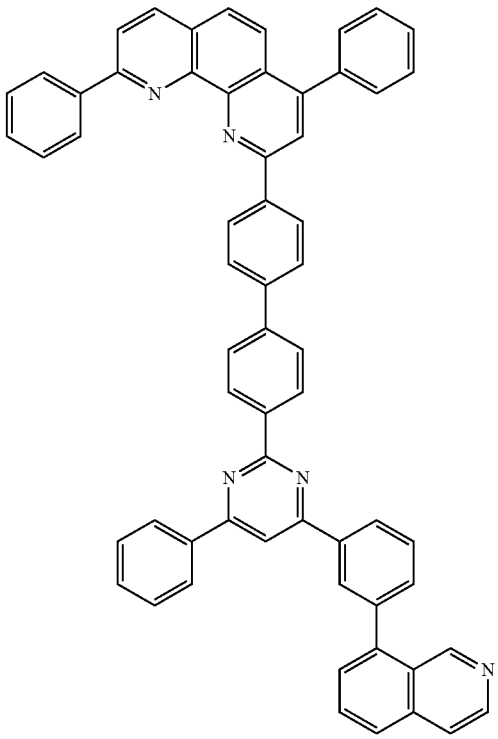
809

373
-continued
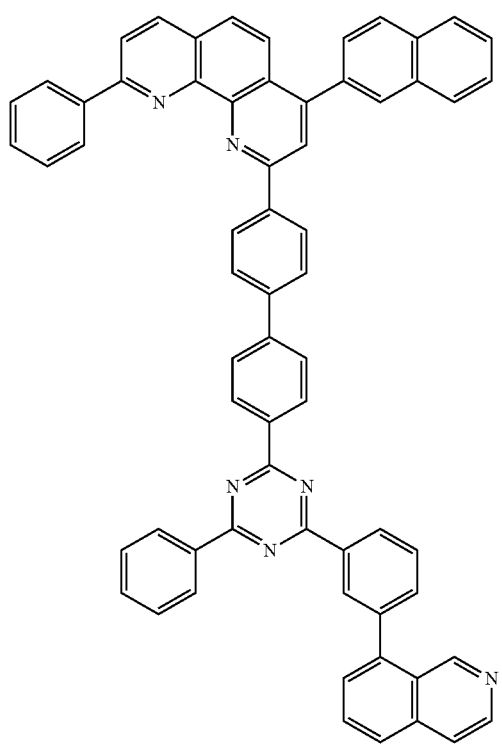
810
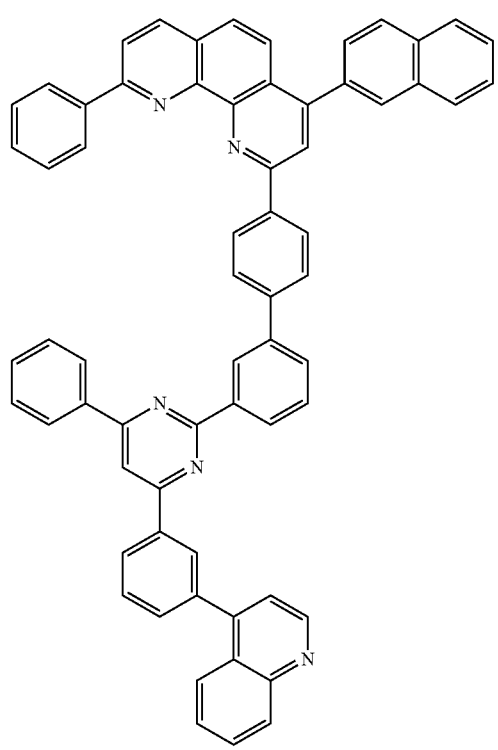
812
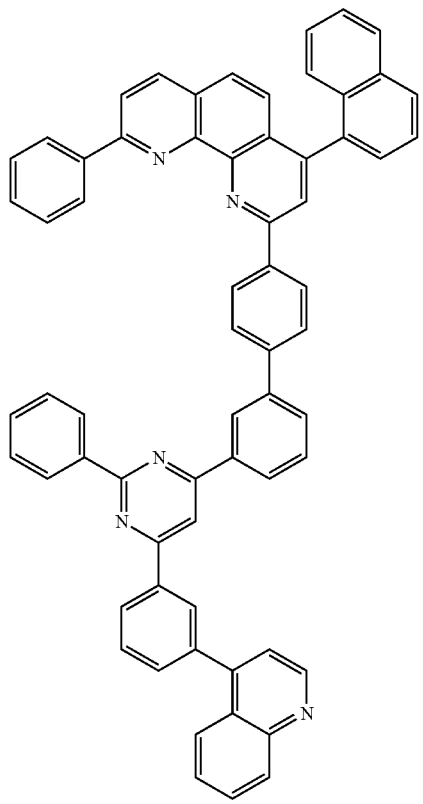
811
374
-continued
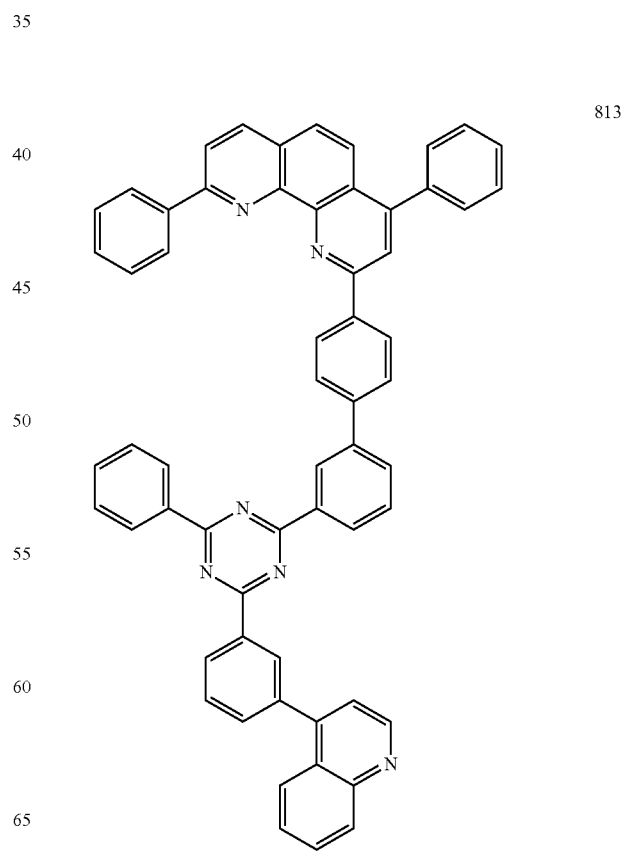
813

375
-continued
814
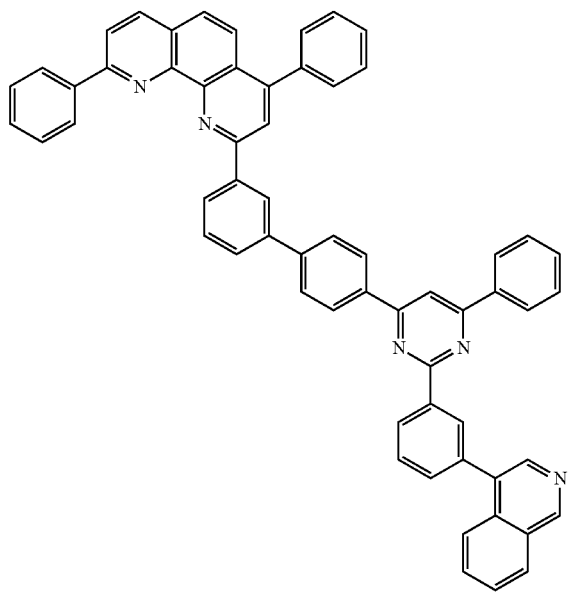
815
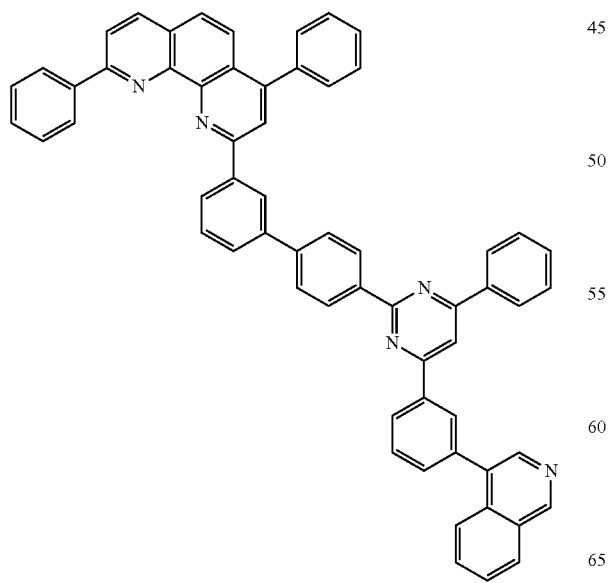
376
-continued
816
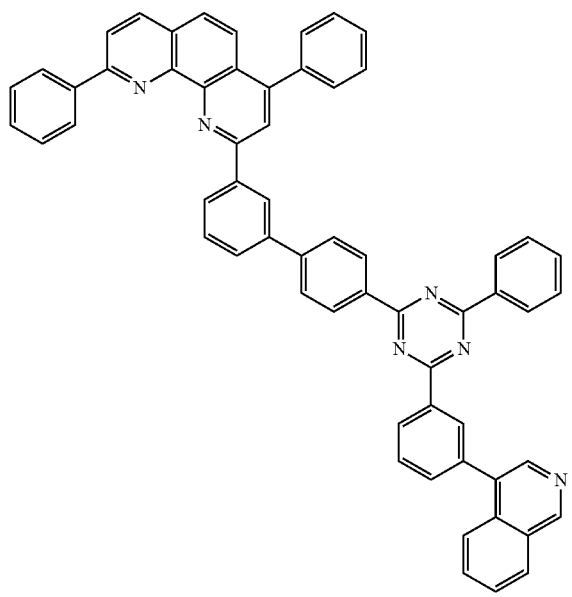
817
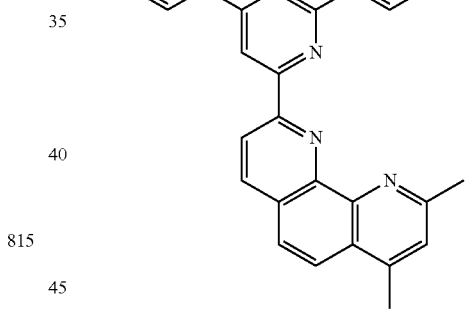
818
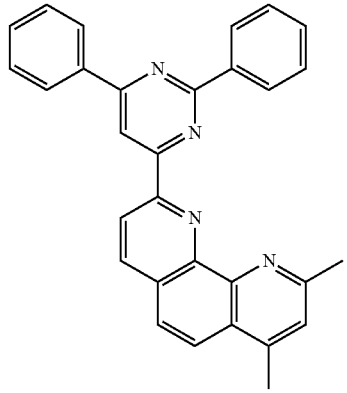

819 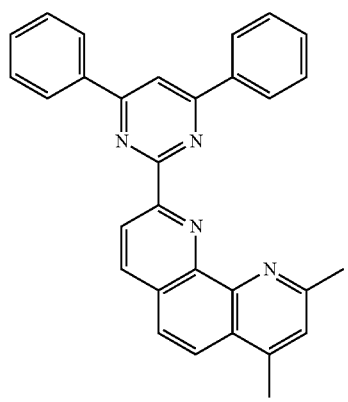
820 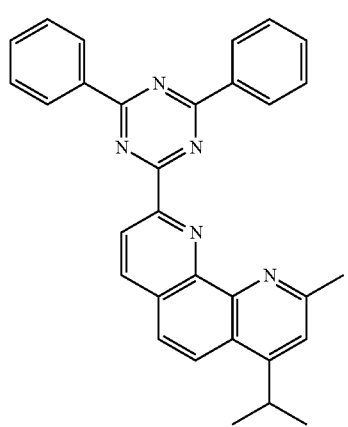
821 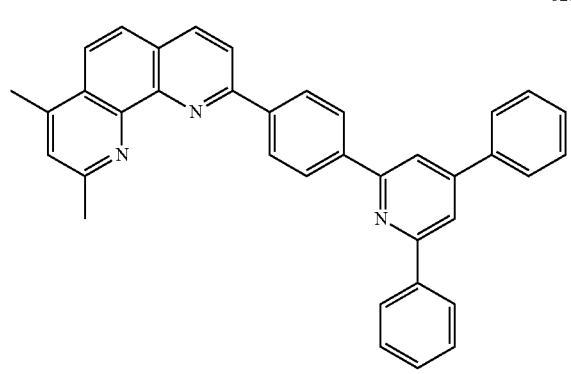
822 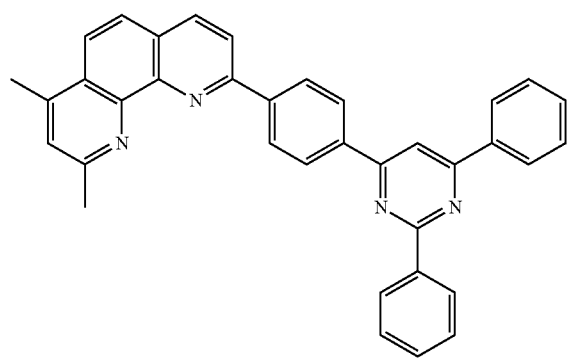
823 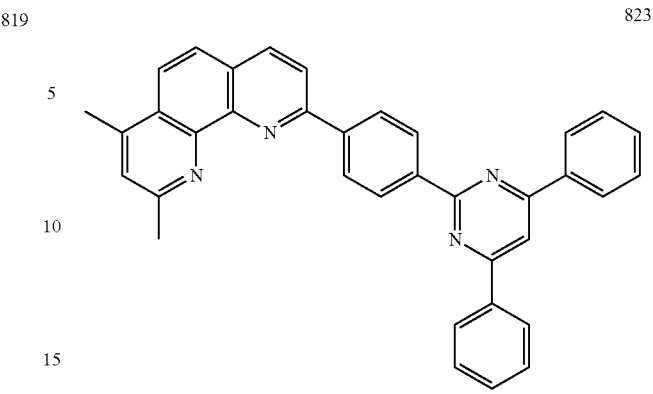
824 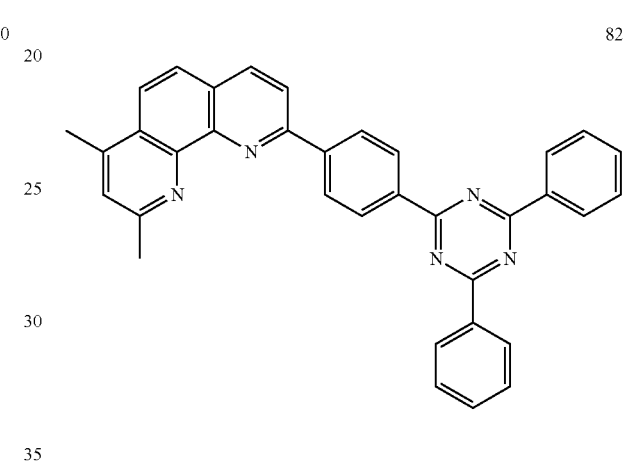
825 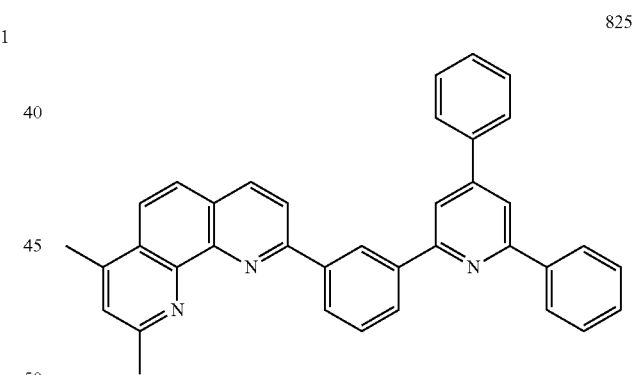
826 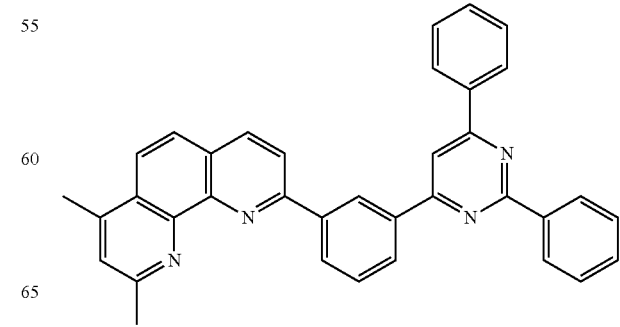

-continued
827
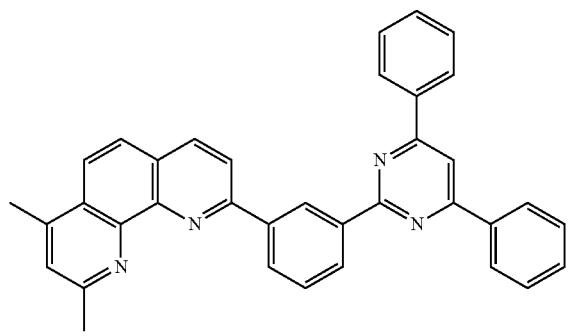
828
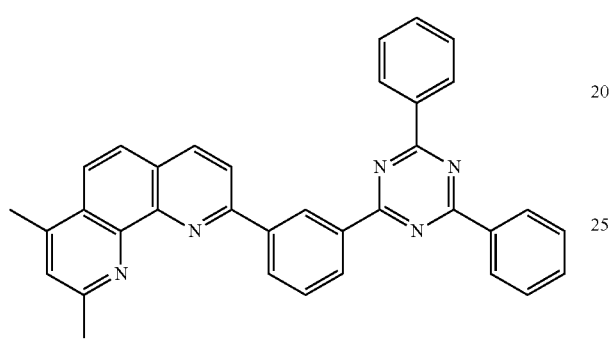
829
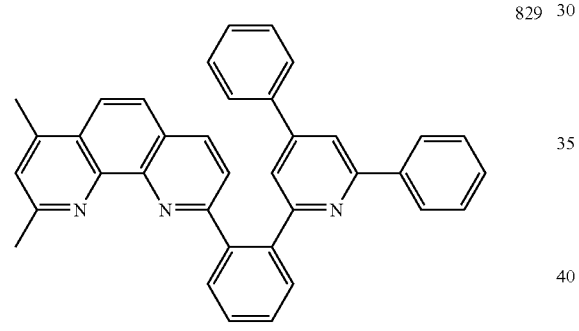
830
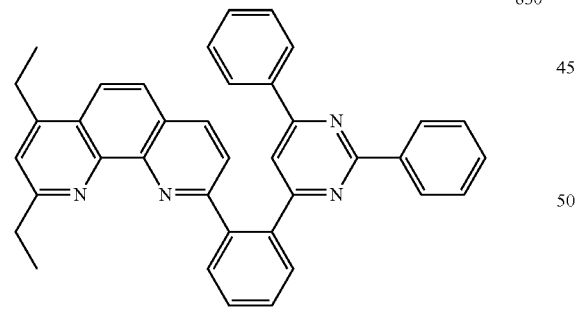
831
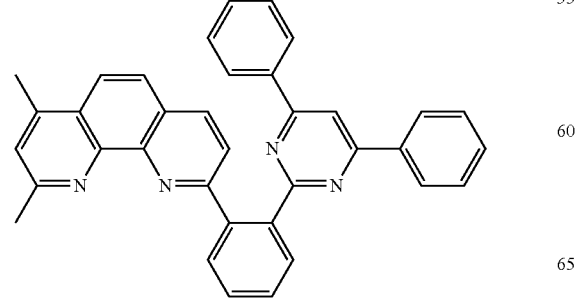
-continued
832
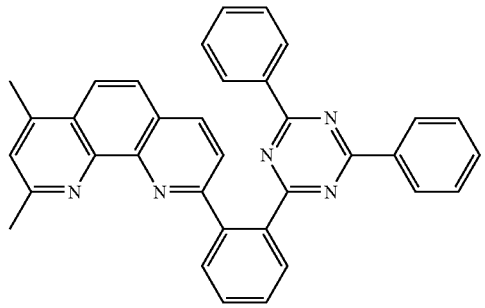
833
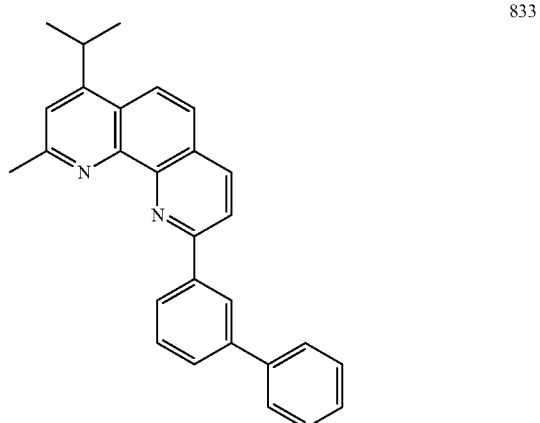
834
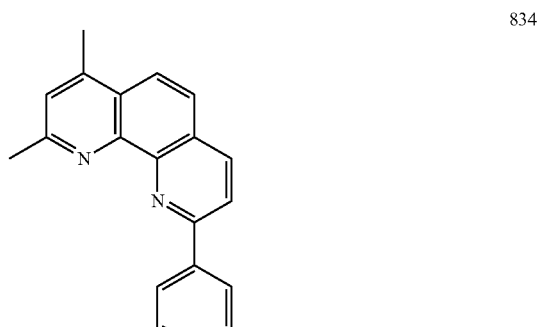
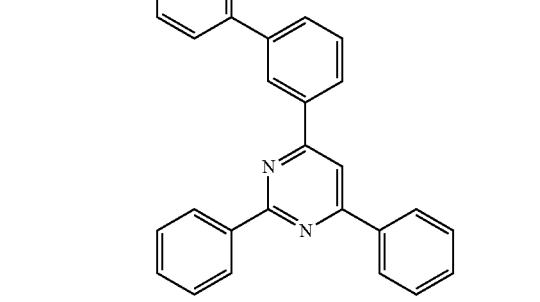

835
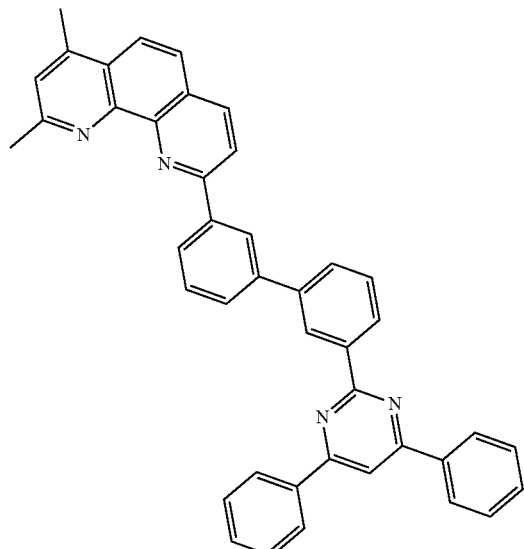
836
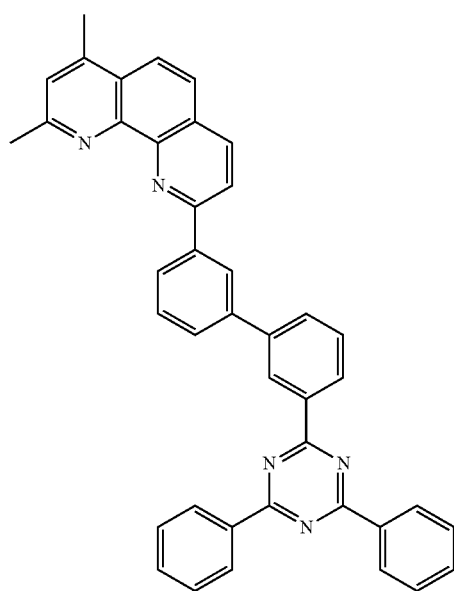
837
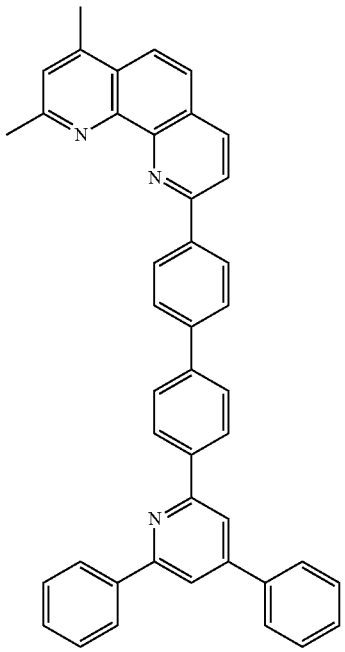
838
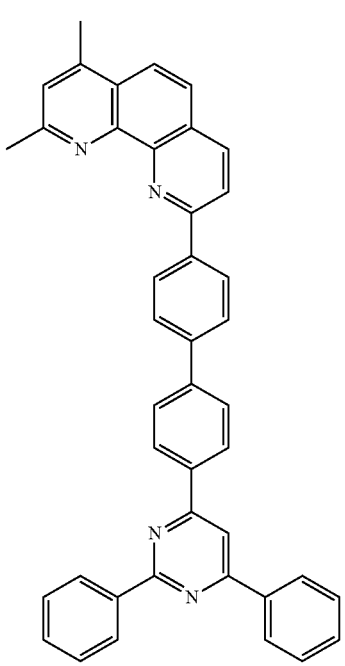

383
-continued
839
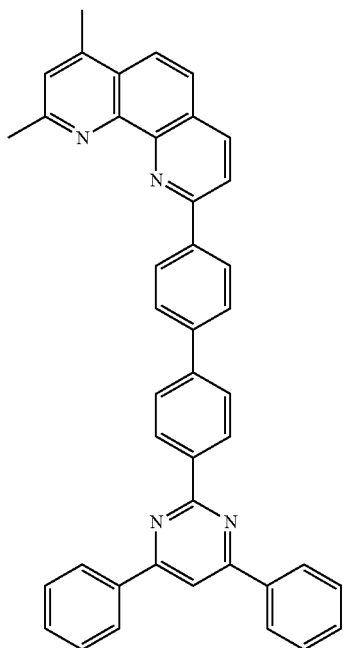
840
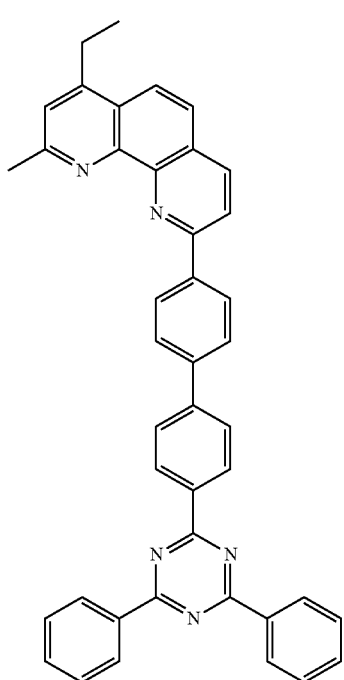
384
-continued
841
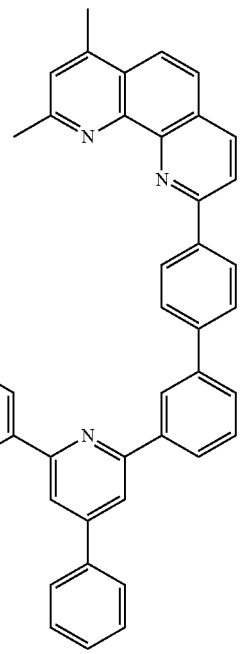
842
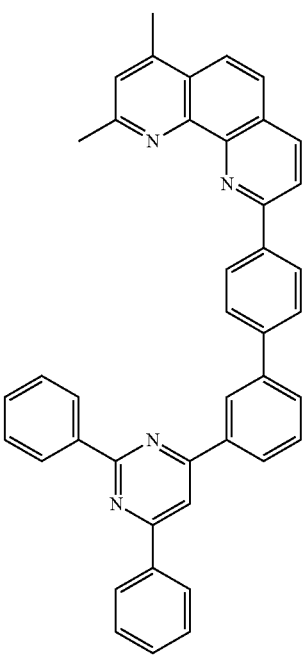

843
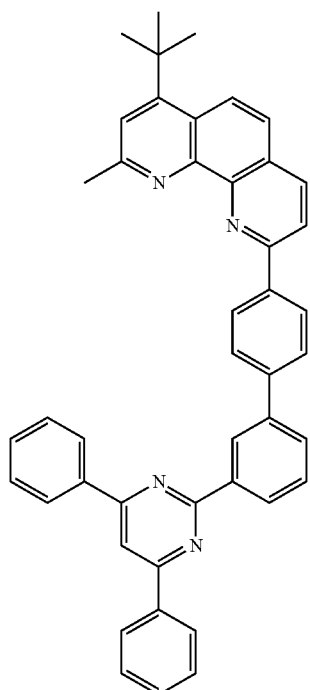
845
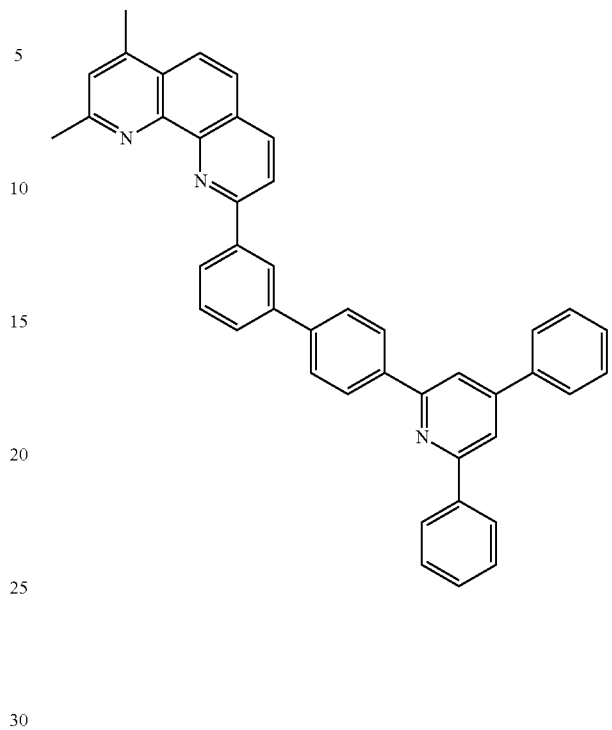
844
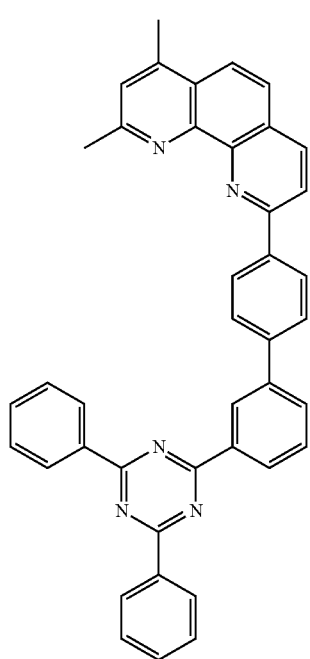
846
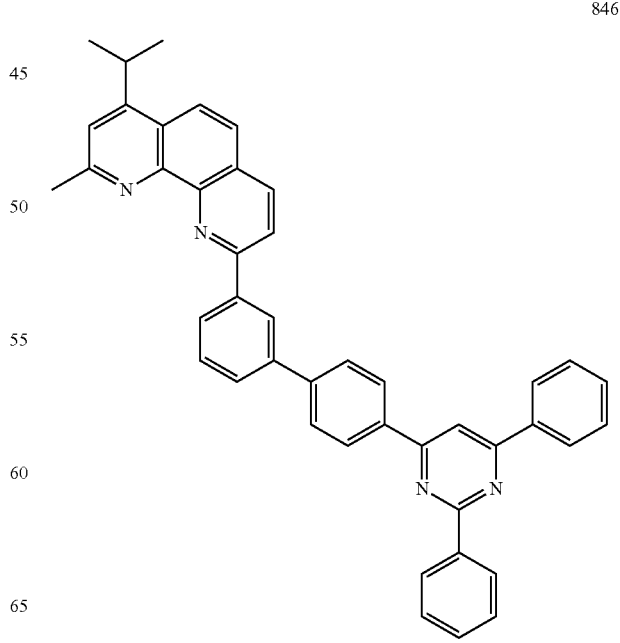

847
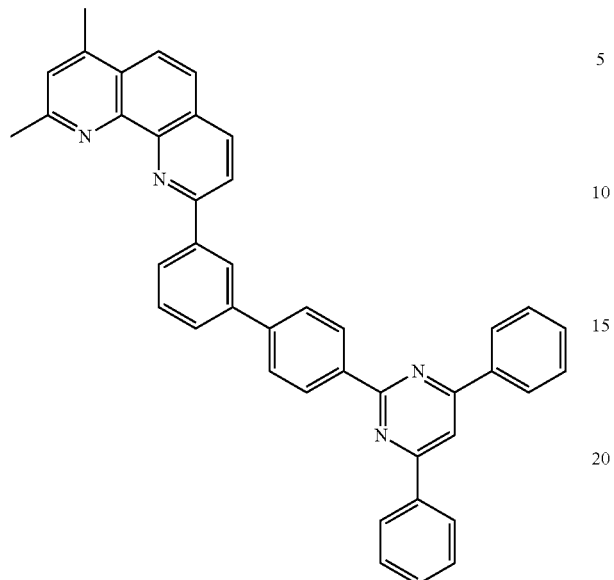
848
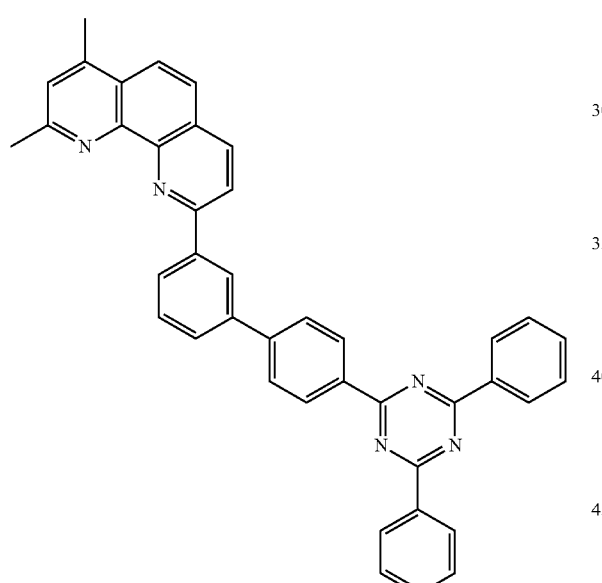
849
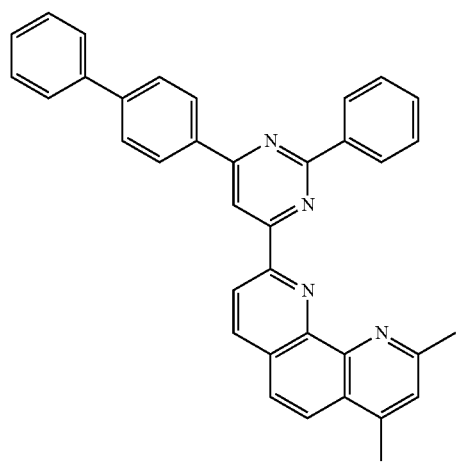
850
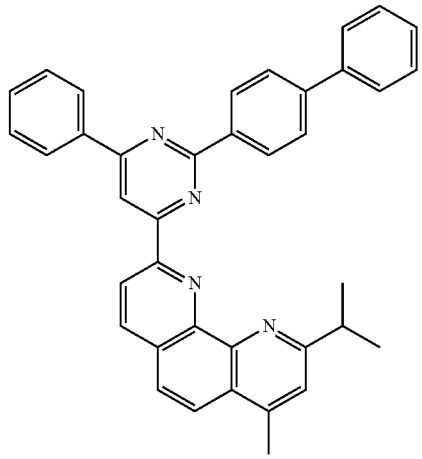
851
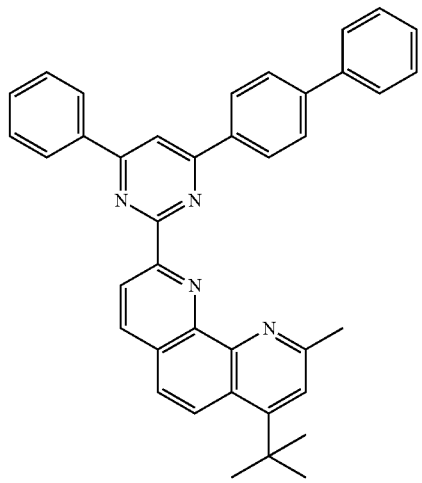
852
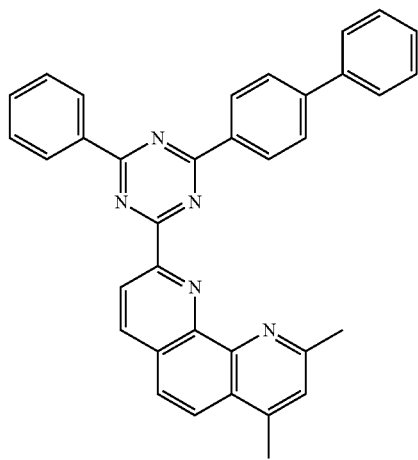

389
-continued
853
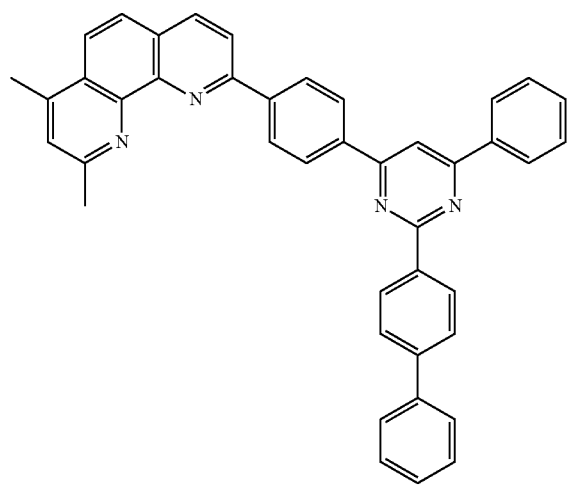
854
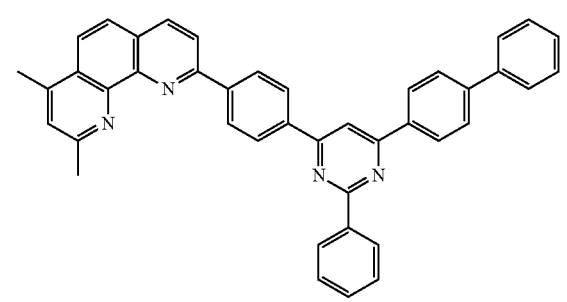
855
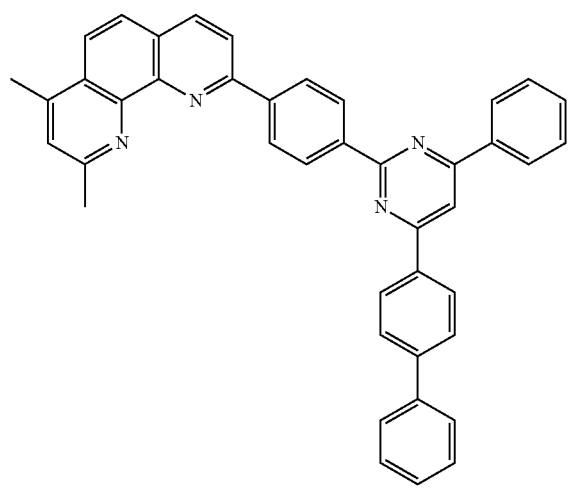
390
-continued
856
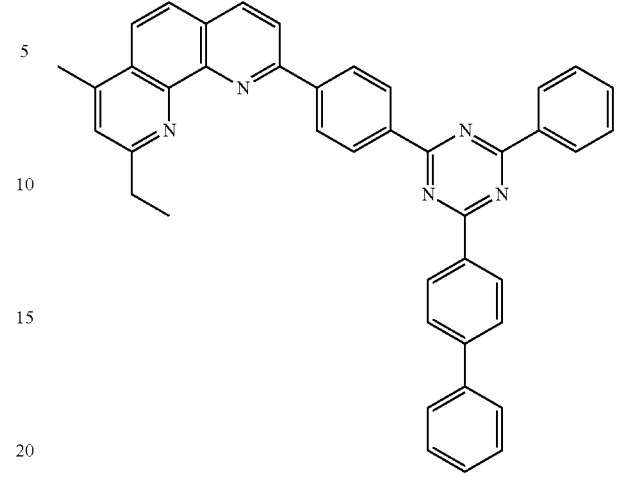
857
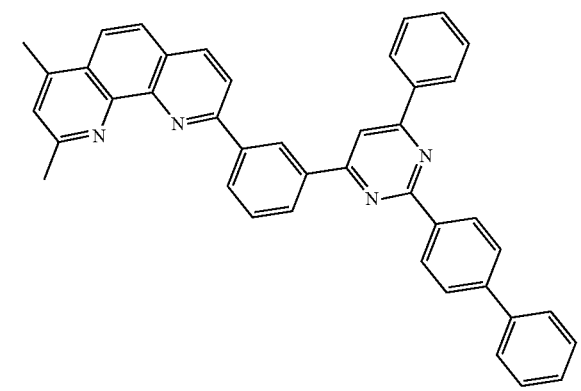
858
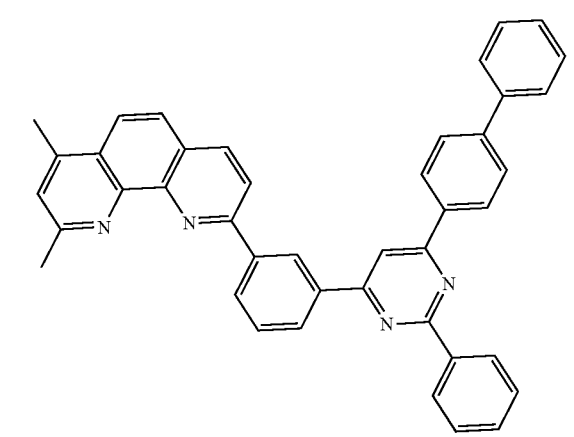

391
-continued
859
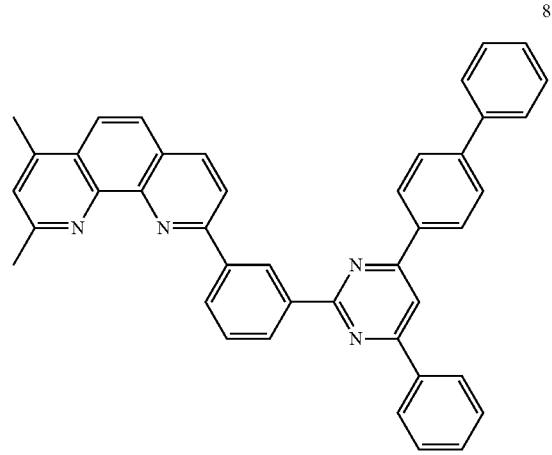
860
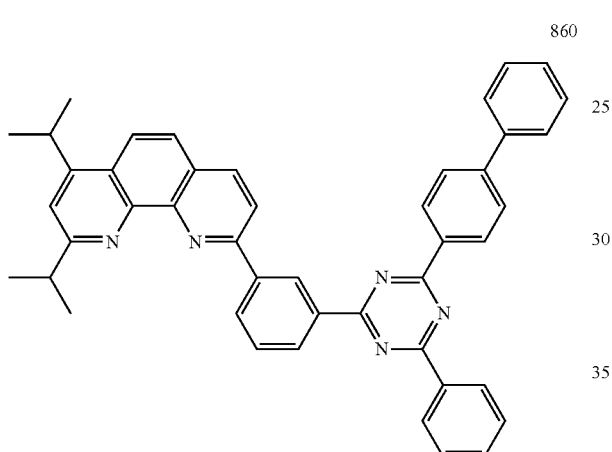
861
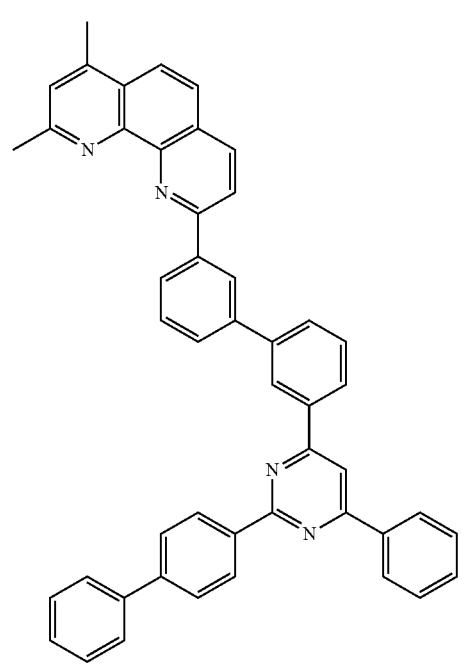
392
-continued
862
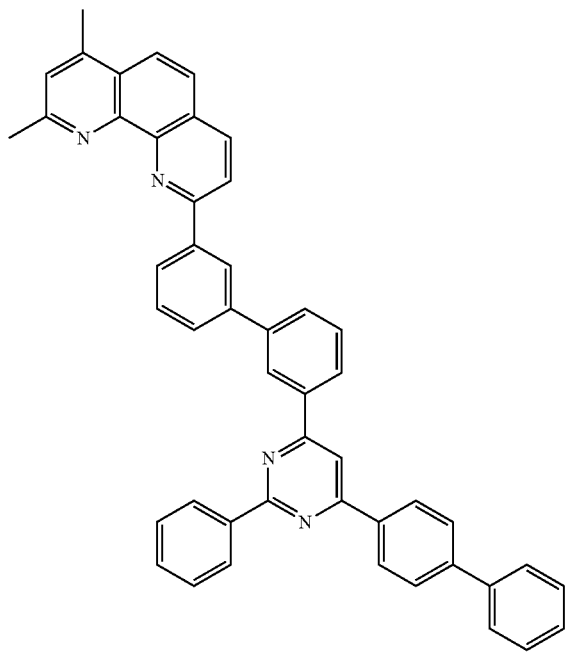
863
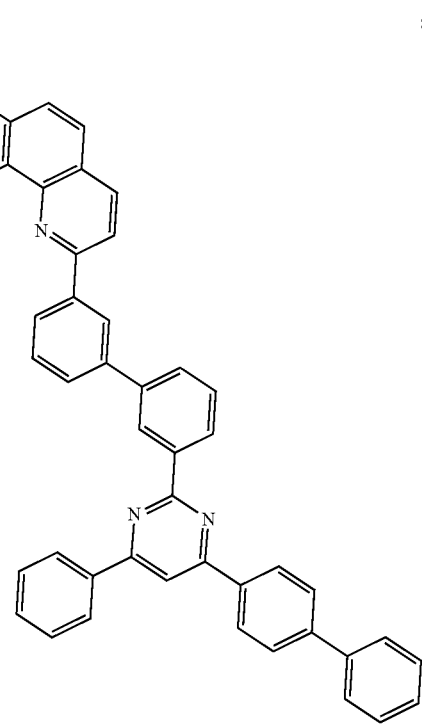

393
-continued
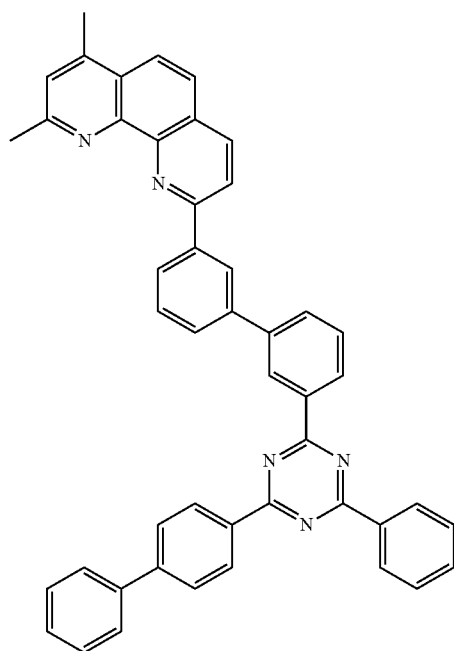
864
394
-continued
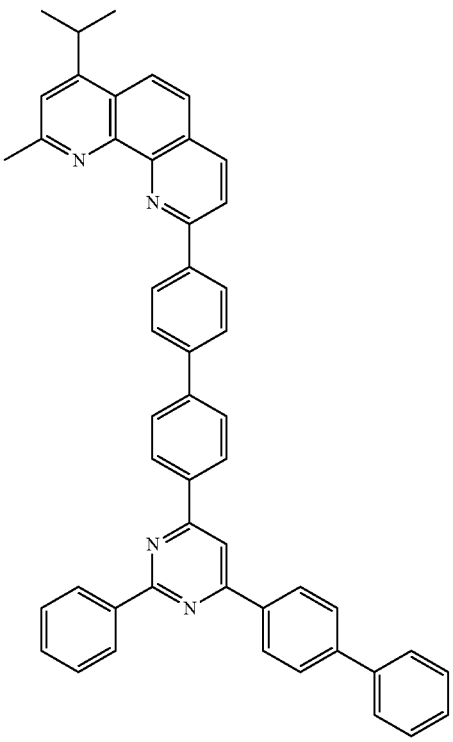
866
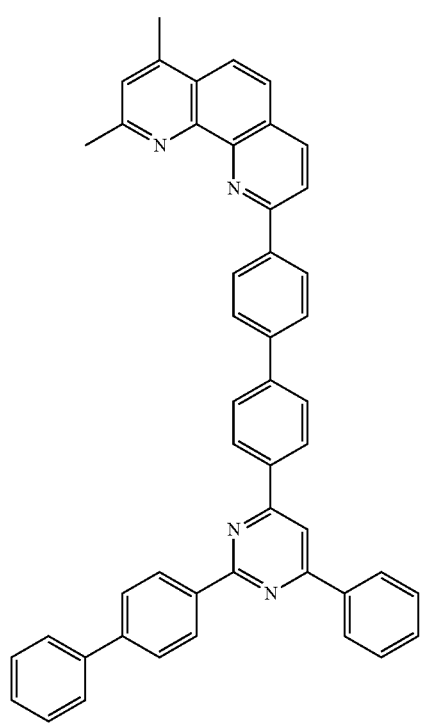
865
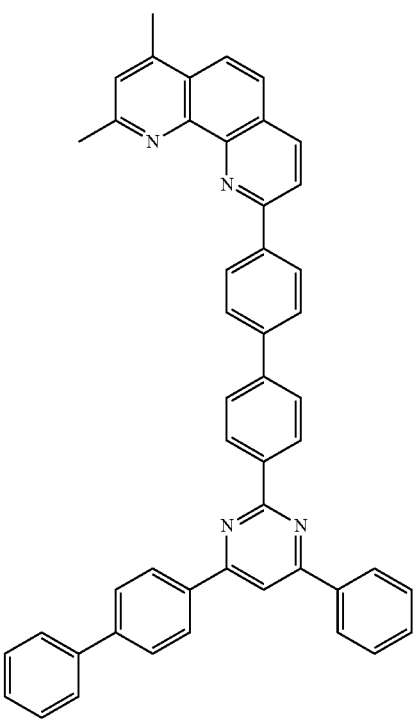
867

395
-continued

868

869

396
-continued

870

871

-continued
872
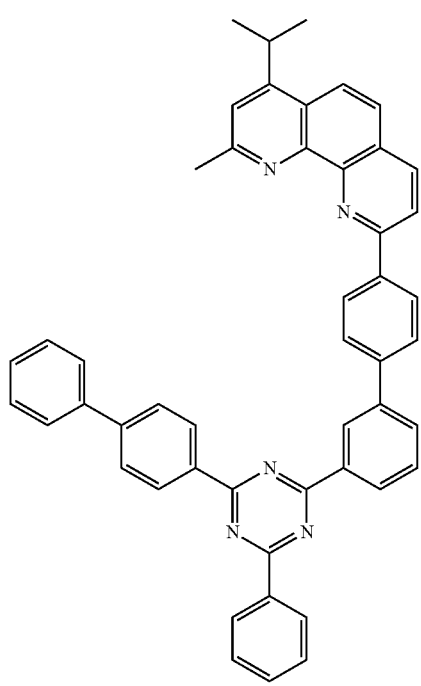
873
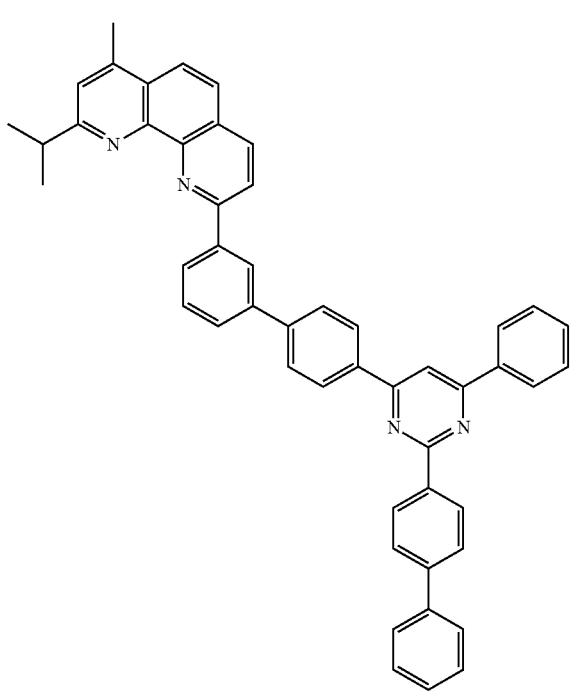
-continued
874
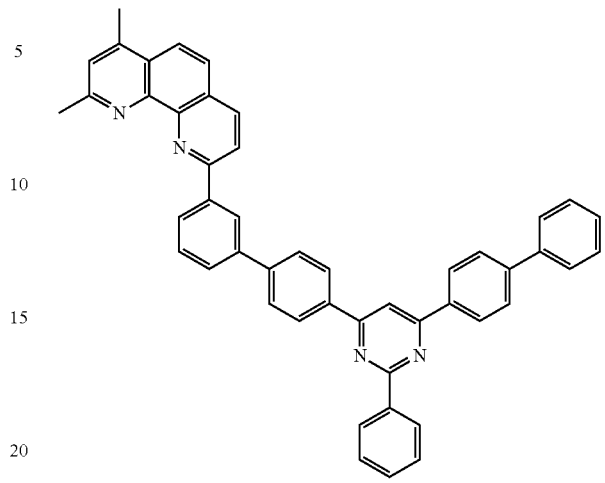
875
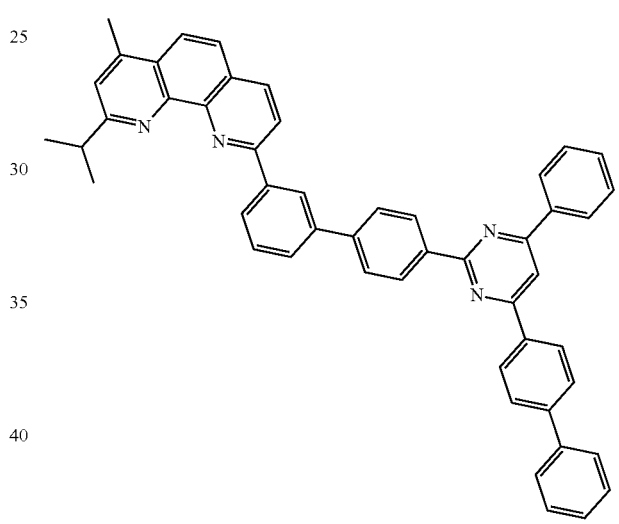
876
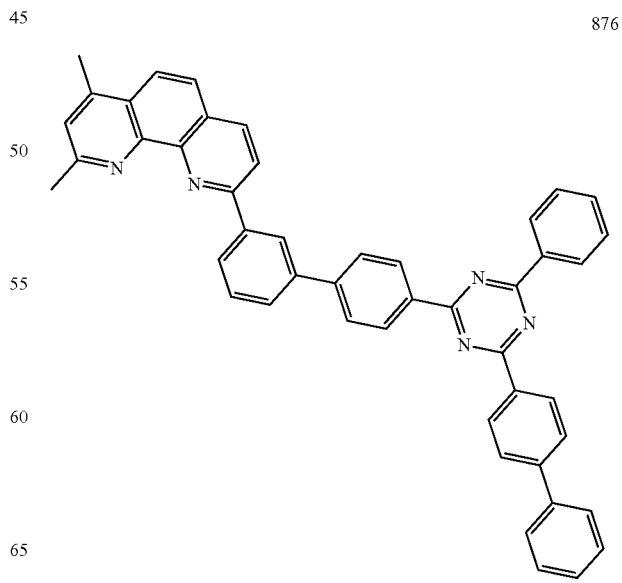

399
-continued
877 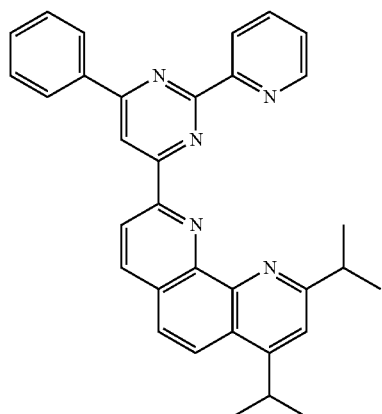
878 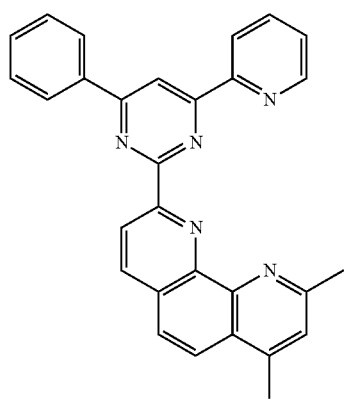
879 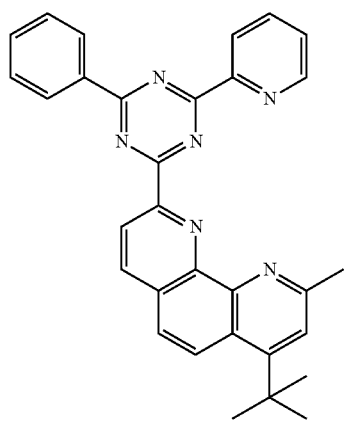
880 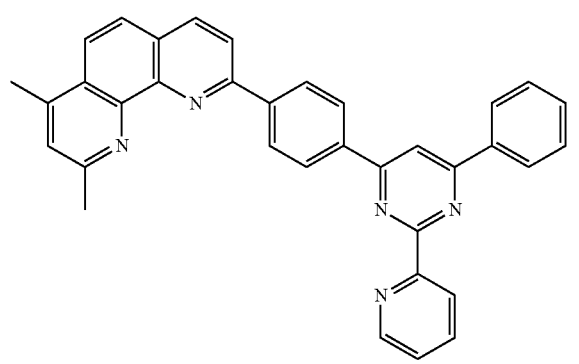
400
-continued
881 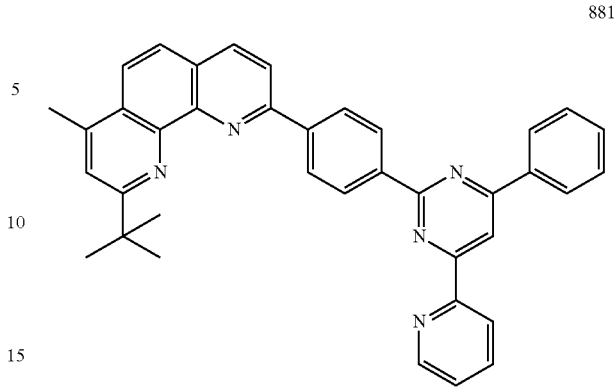
882 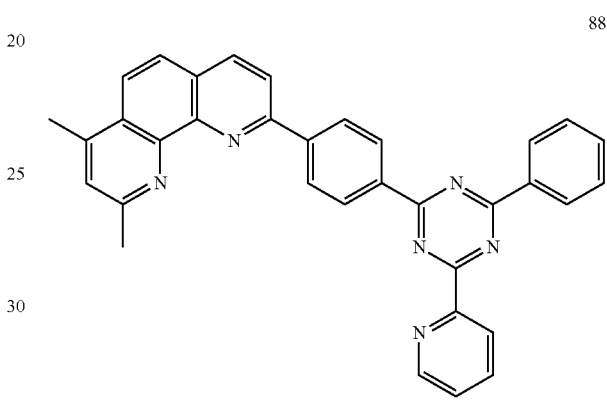
883 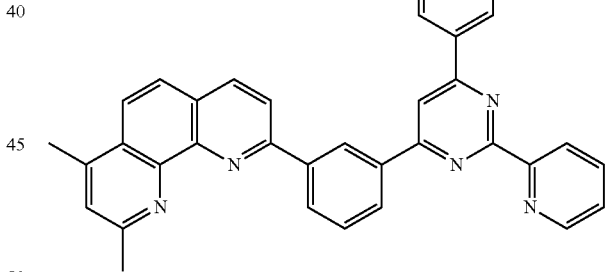
884 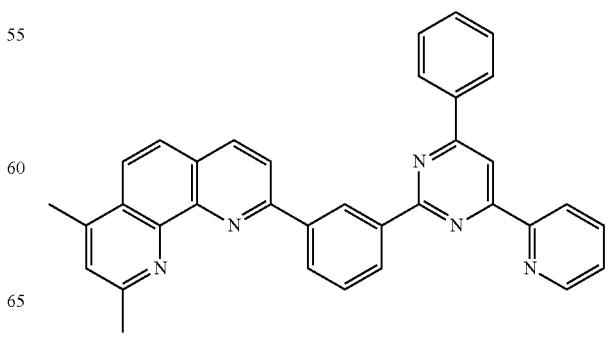

401
-continued
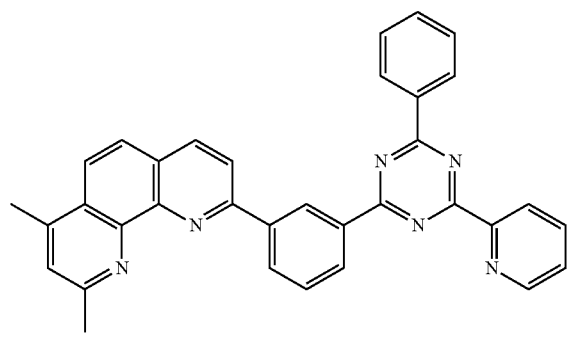
885
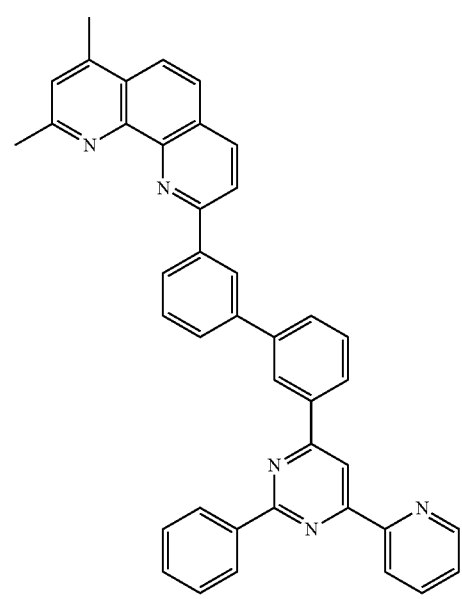
886
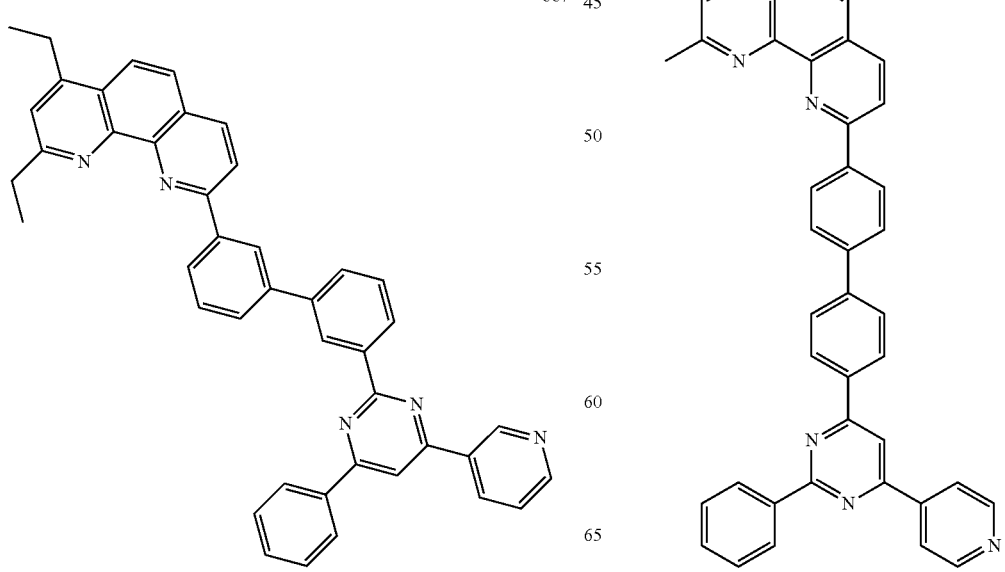
887
402
-continued
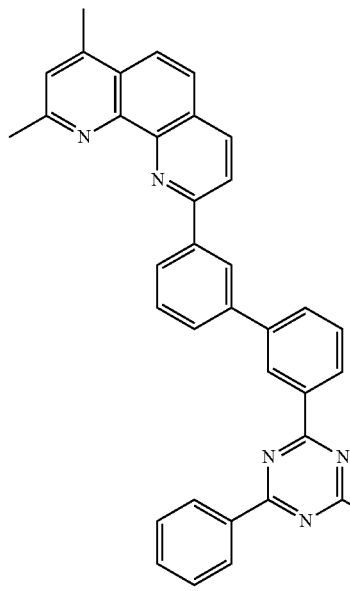
888
889

403
-continued
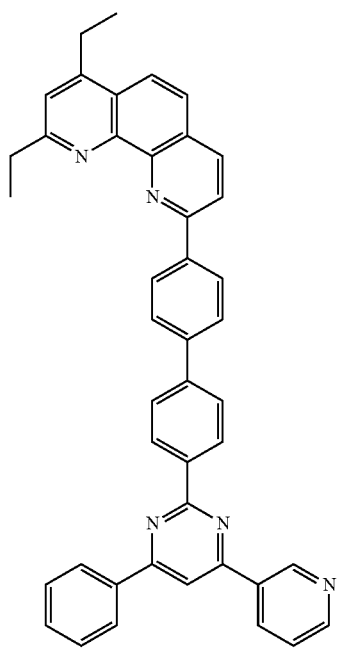
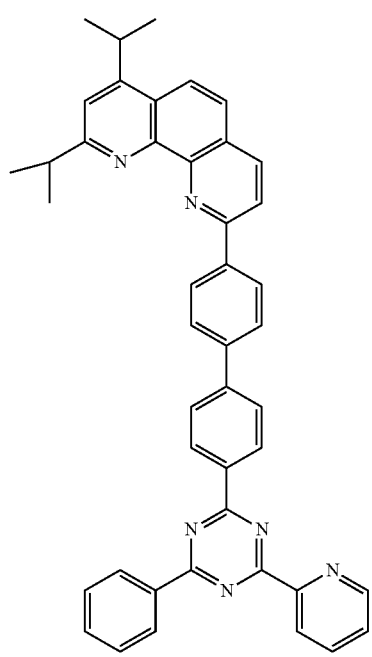
404
-continued
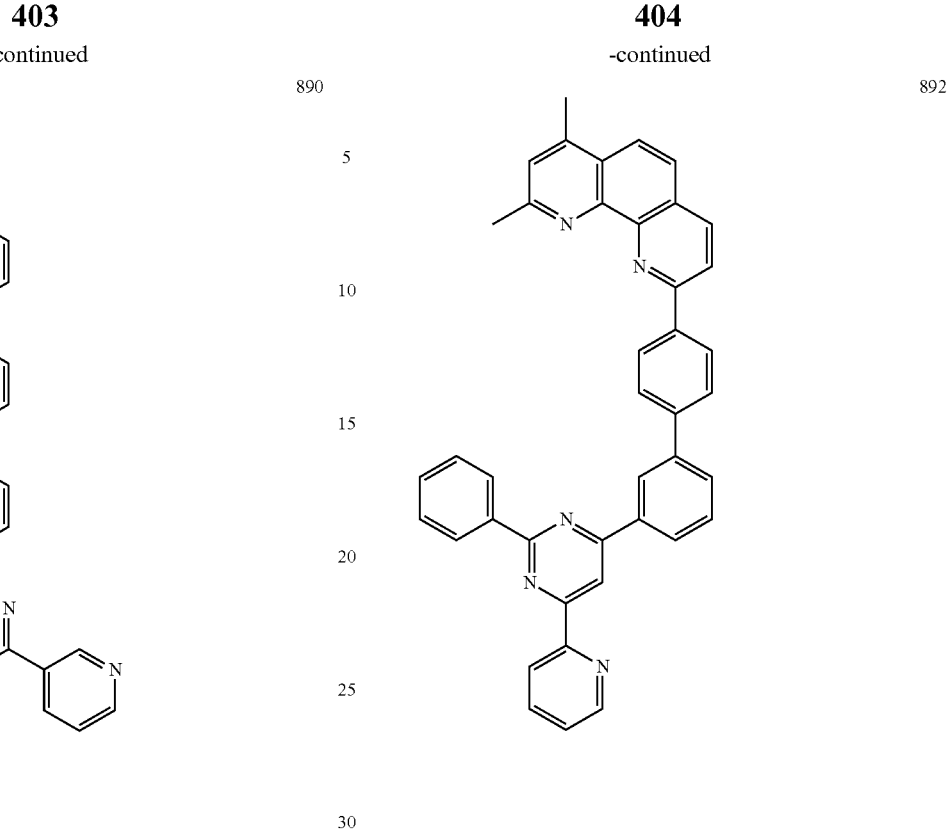
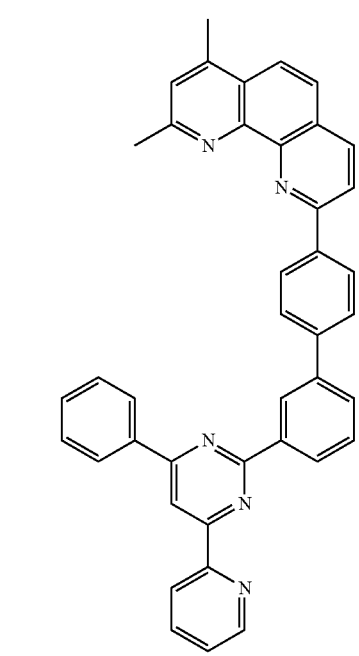

405
-continued
894
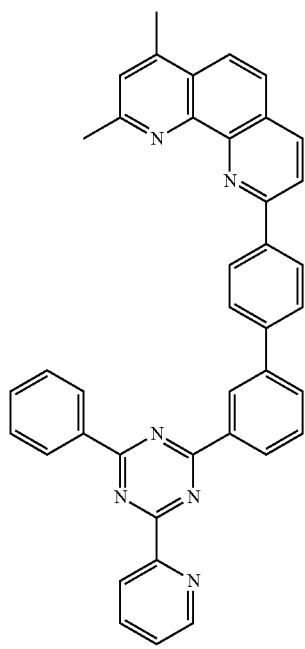
406
-continued
896
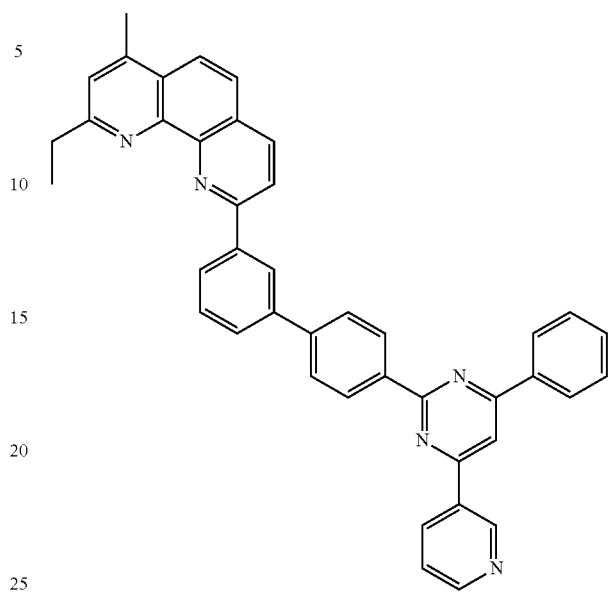
895
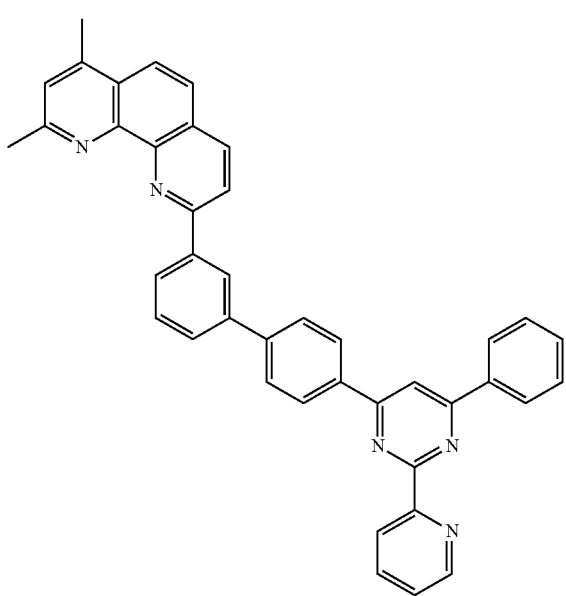
897
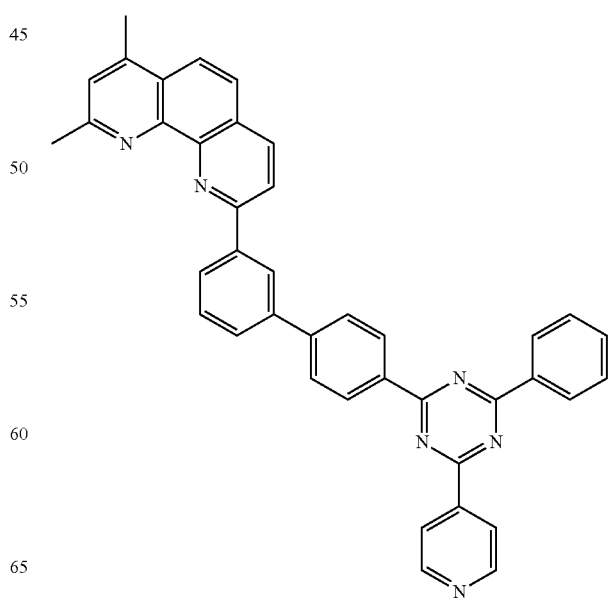

898
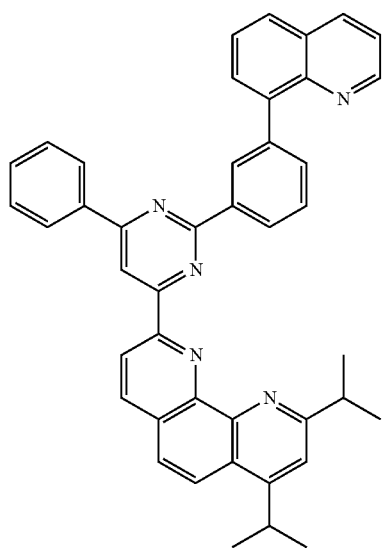
899
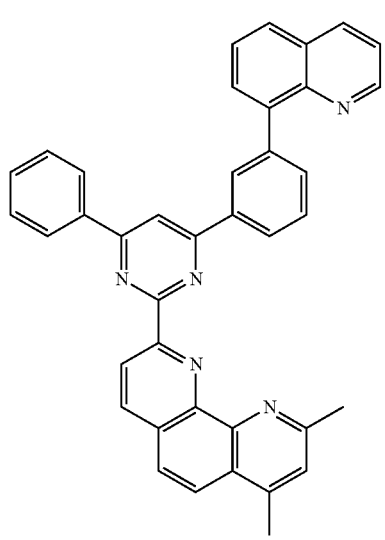
900
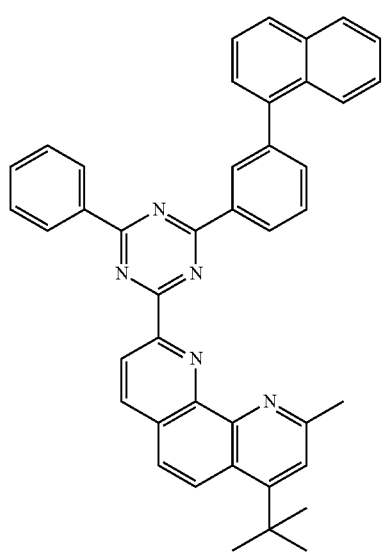
901
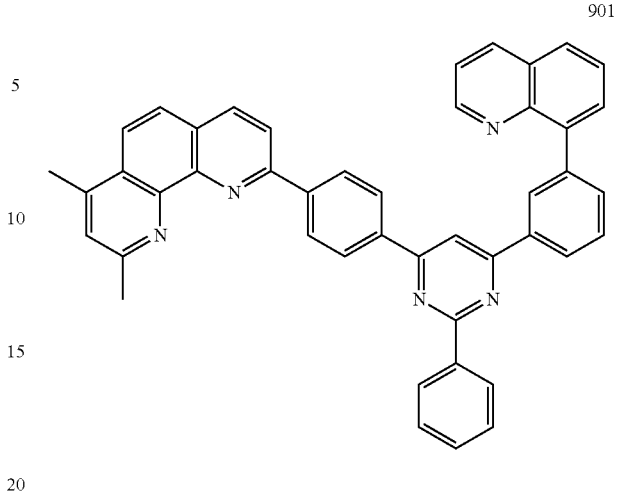
902
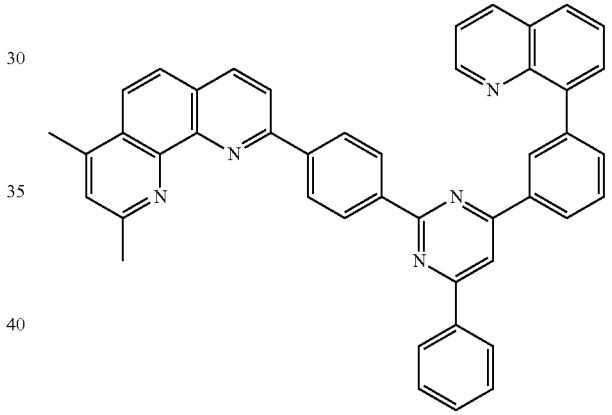
903

-continued
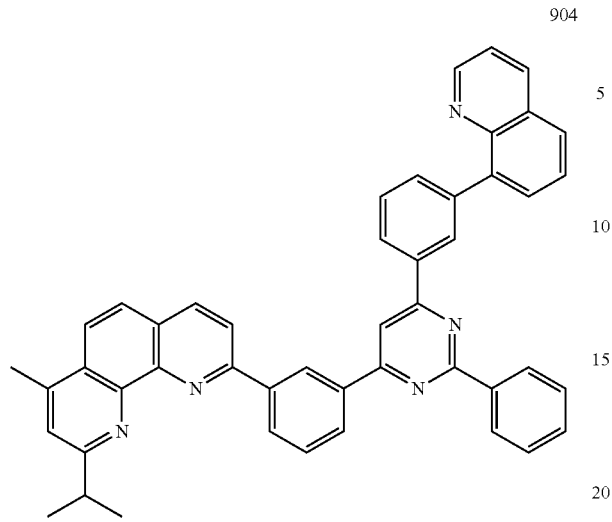
904
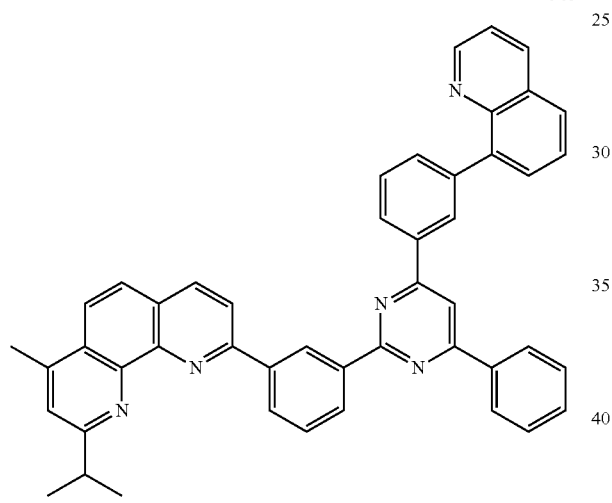
905
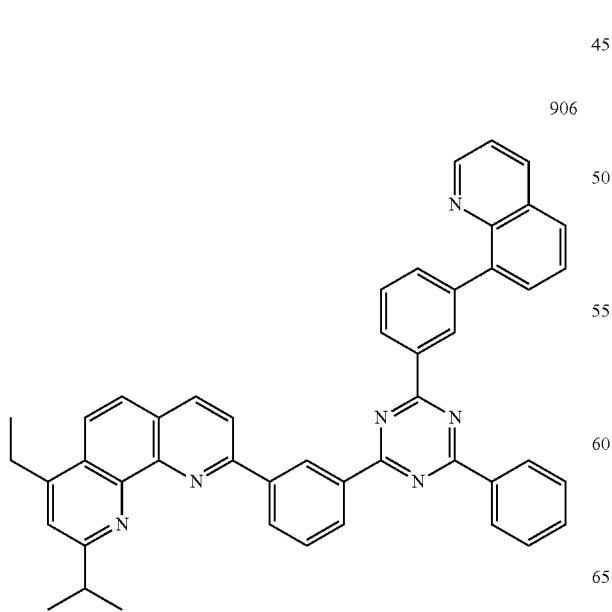
906
-continued
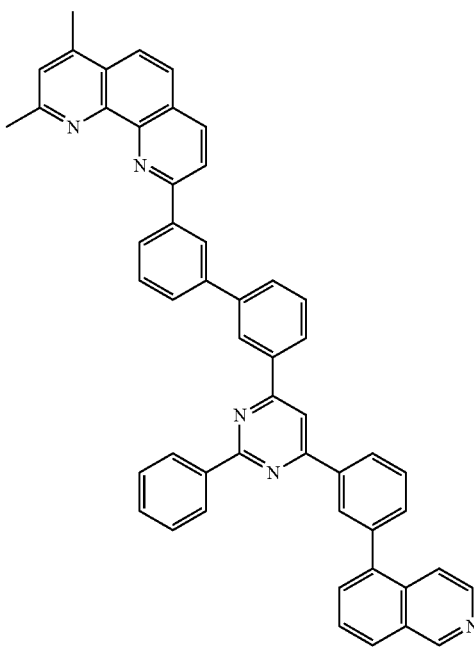
907
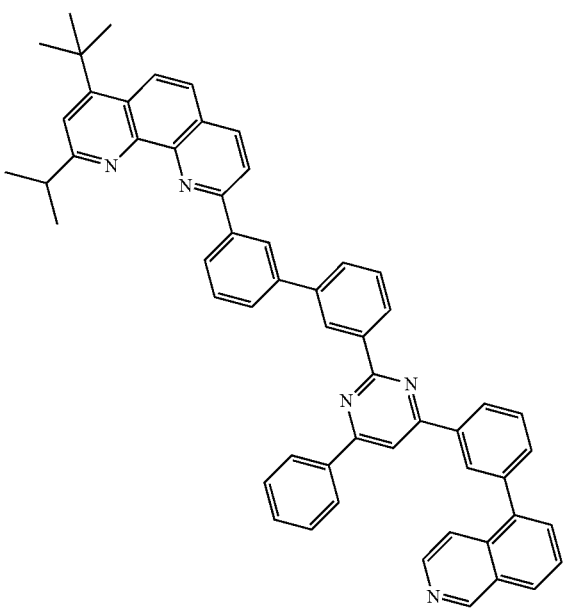
908

411
-continued
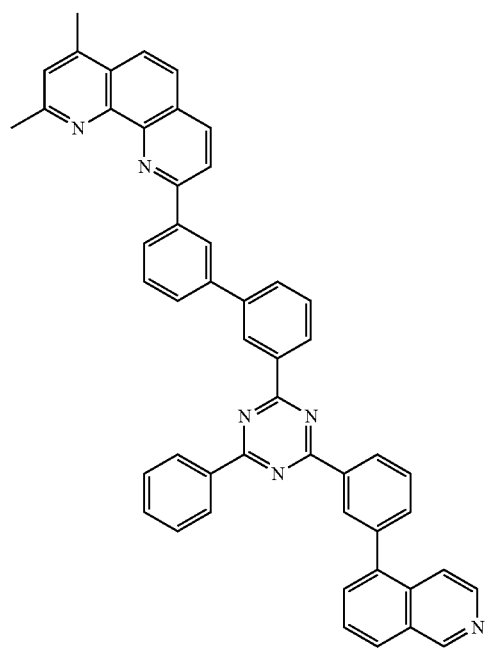
909
412
-continued
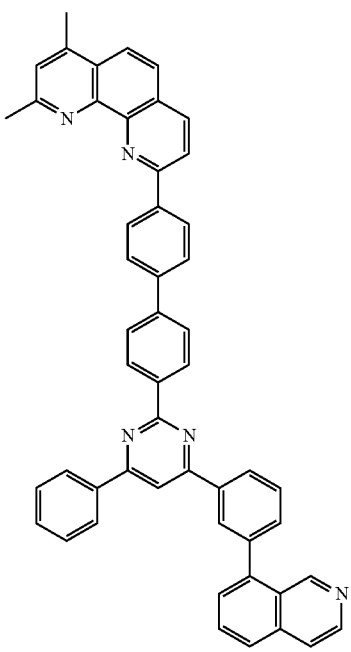
911
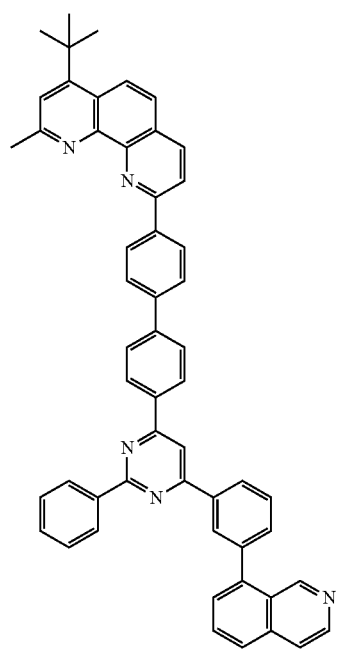
910
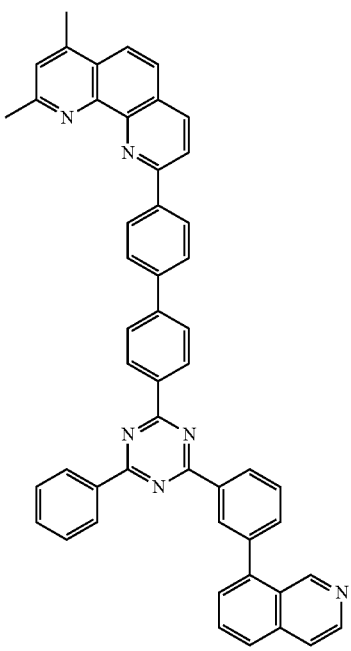
912

413
-continued
914
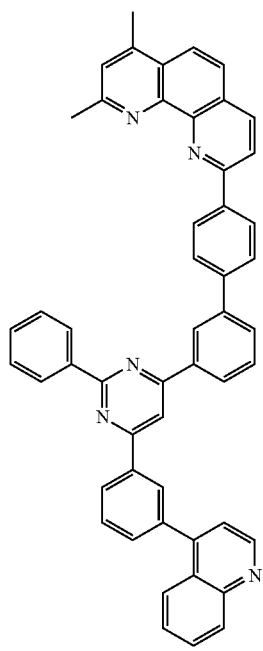
913
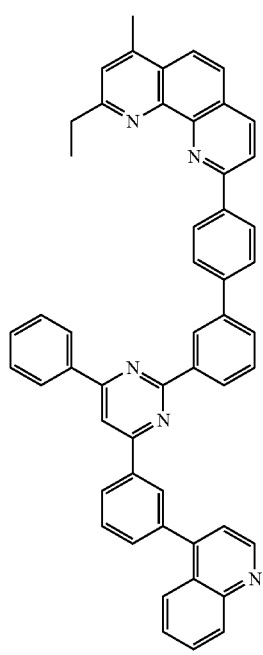
414
-continued
915
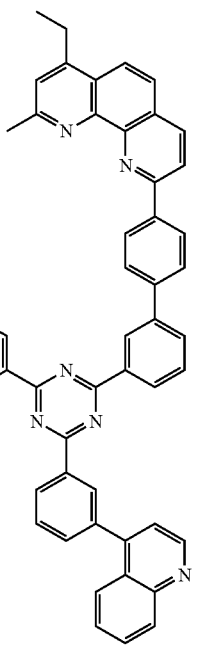
916
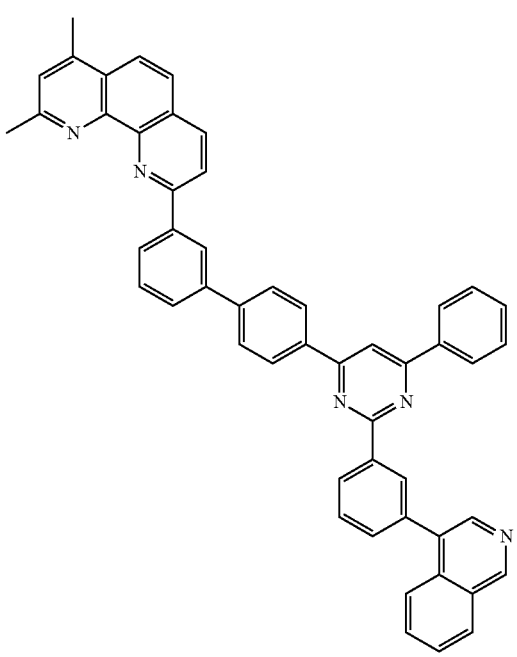

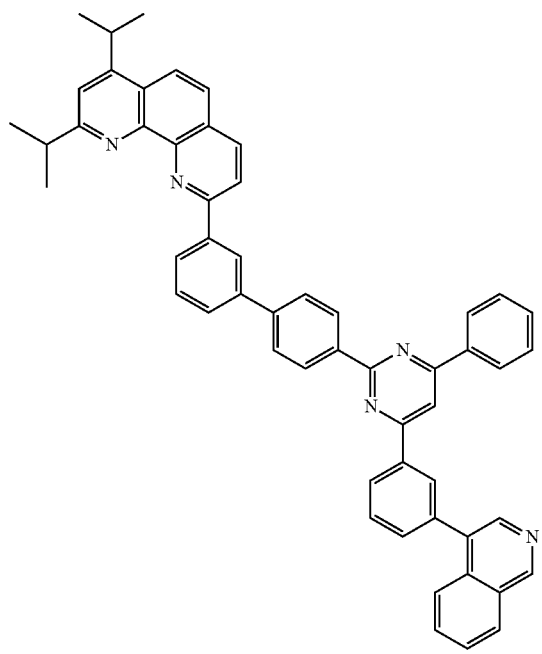
917
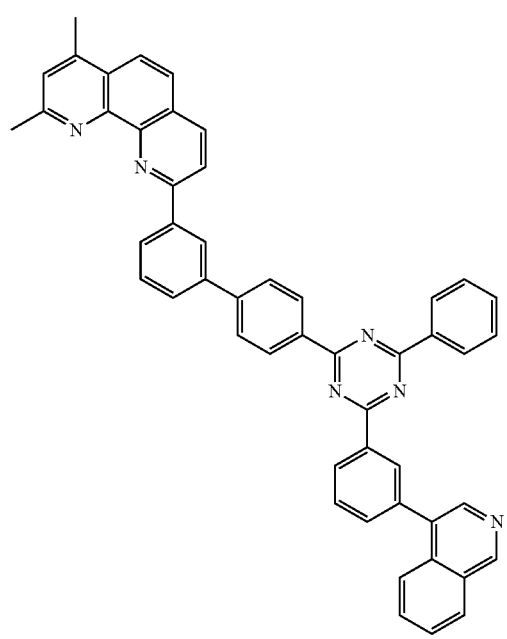
918
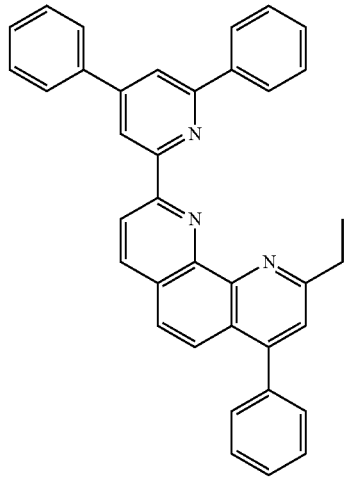
919
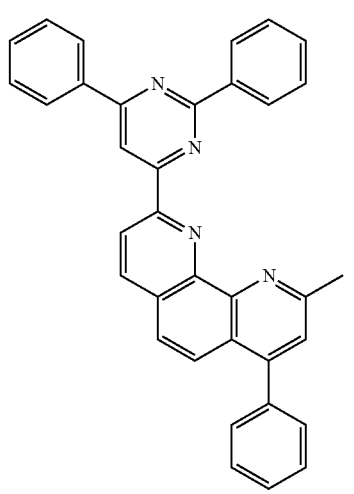
920
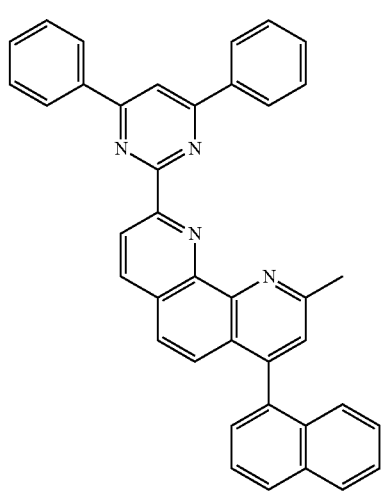
921

922
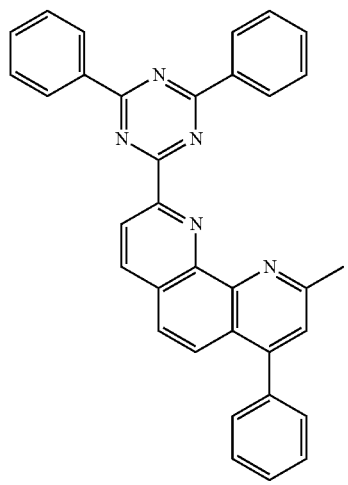
923
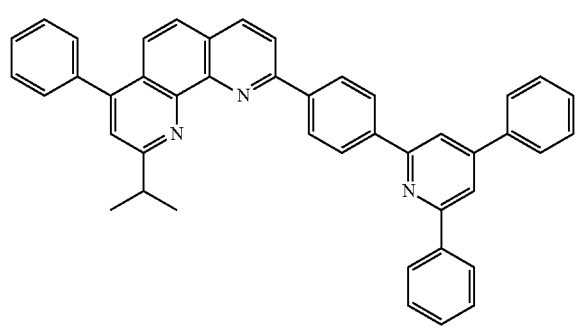
924
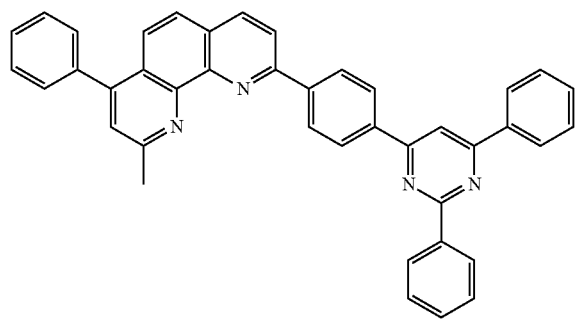
925
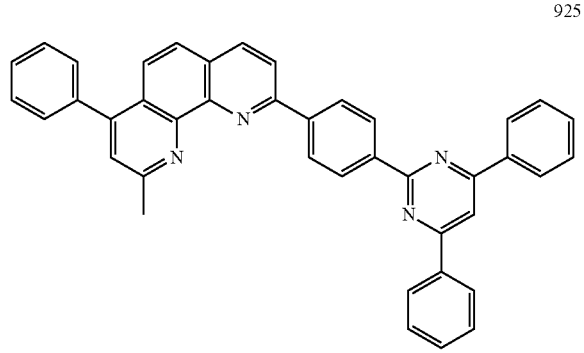
926
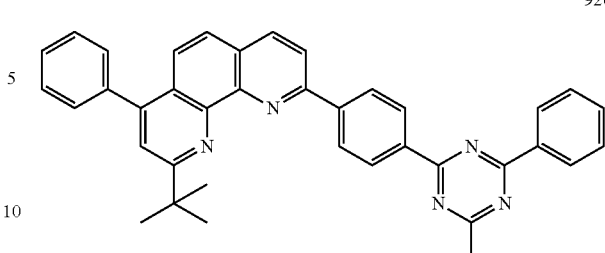
927
928
929
930
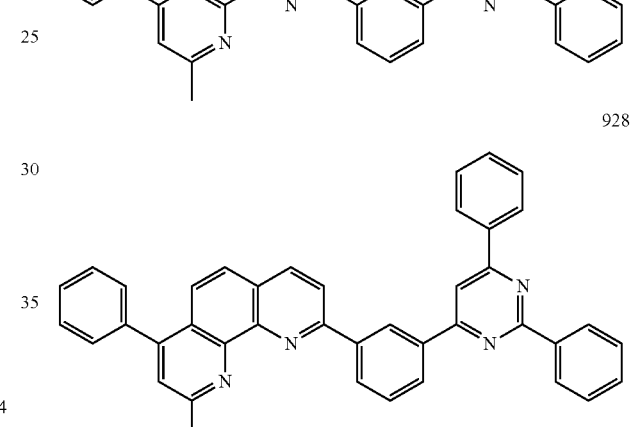
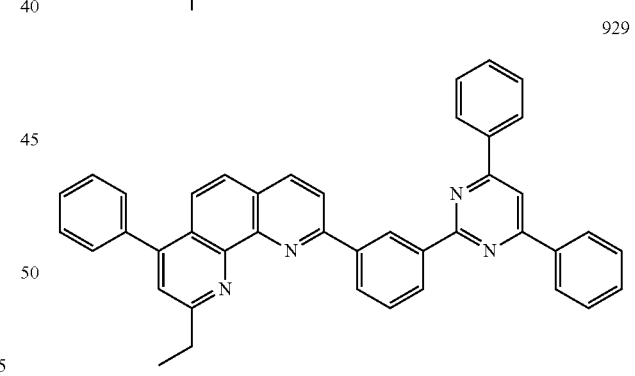
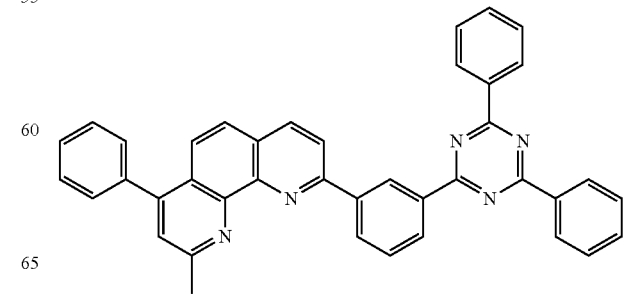

931
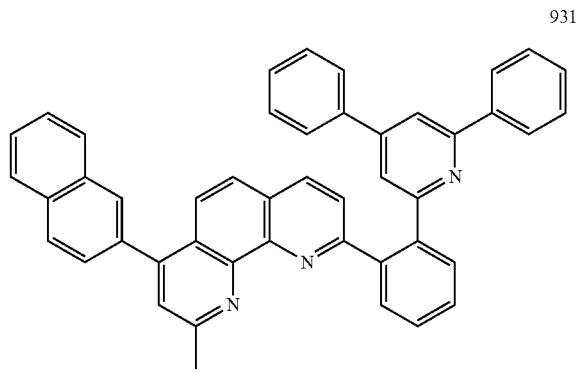
932
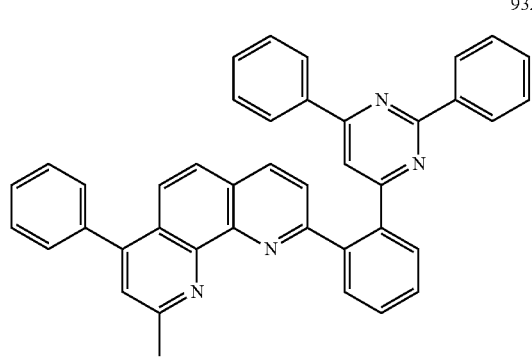
933
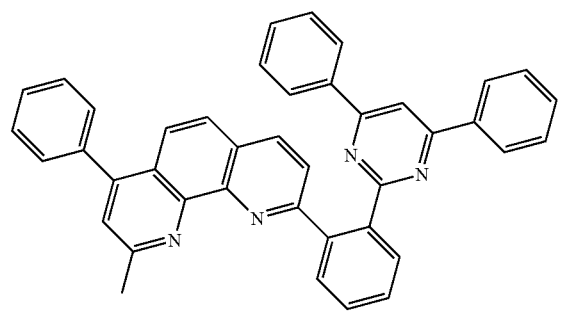
934
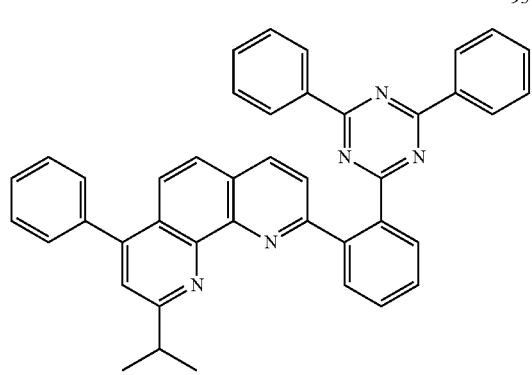
935
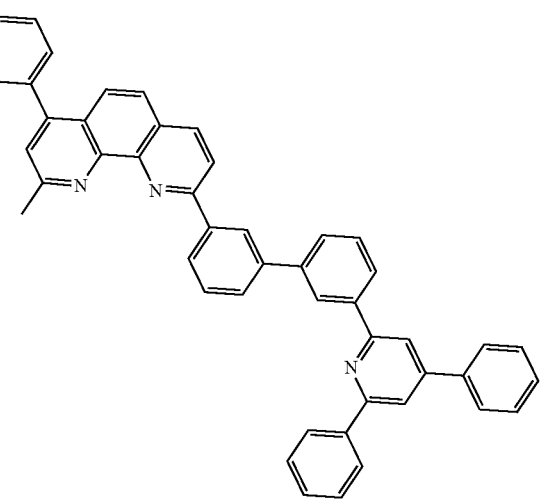
936
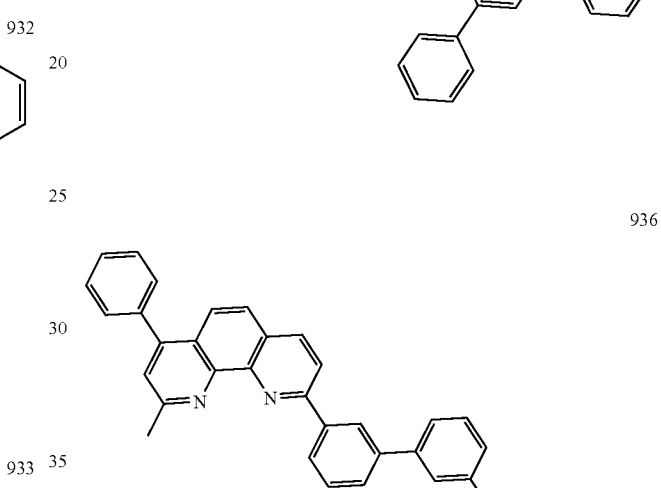
937
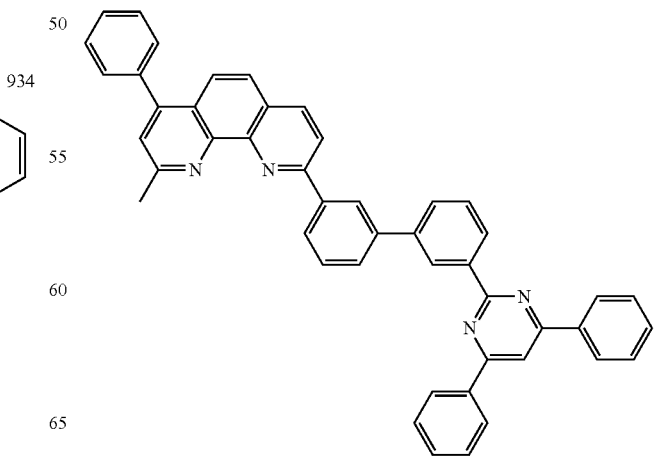

421
-continued
938
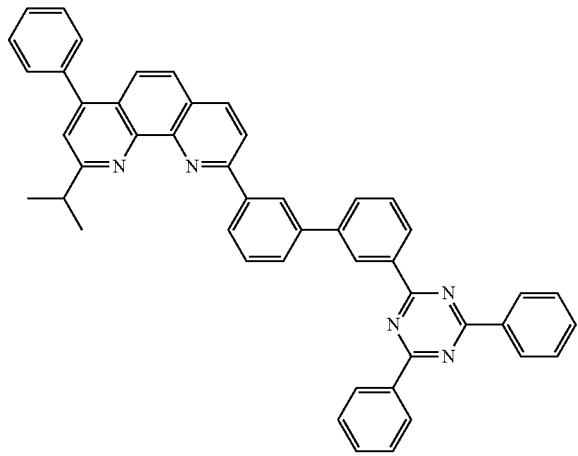
939
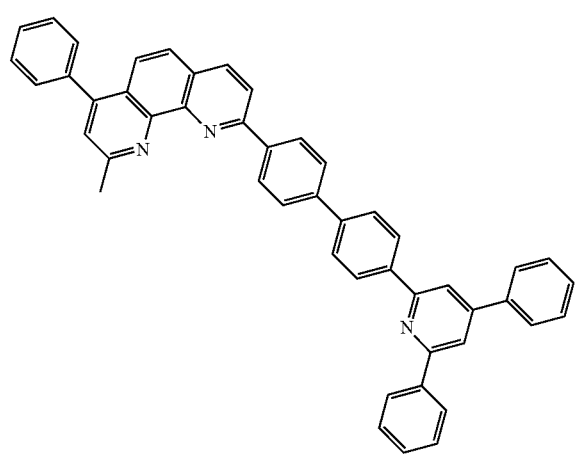
940
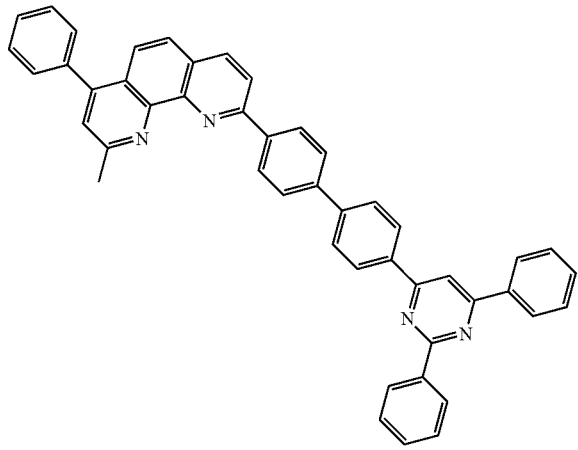
422
-continued
941
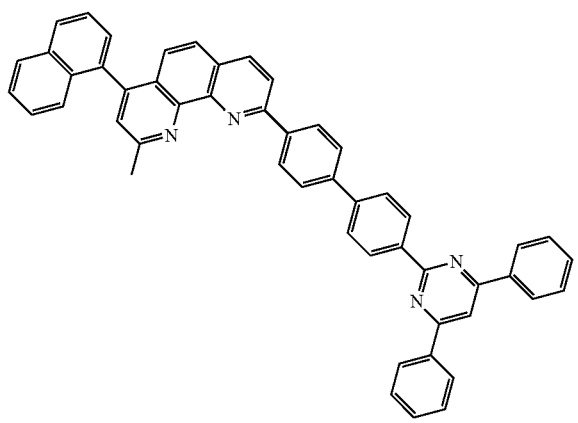
942
943

423
-continued
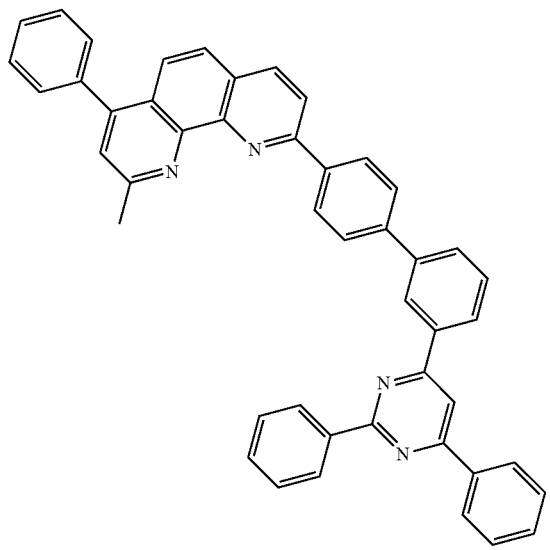
944
424
-continued
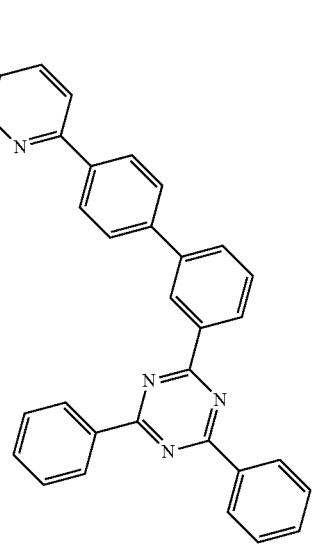
946
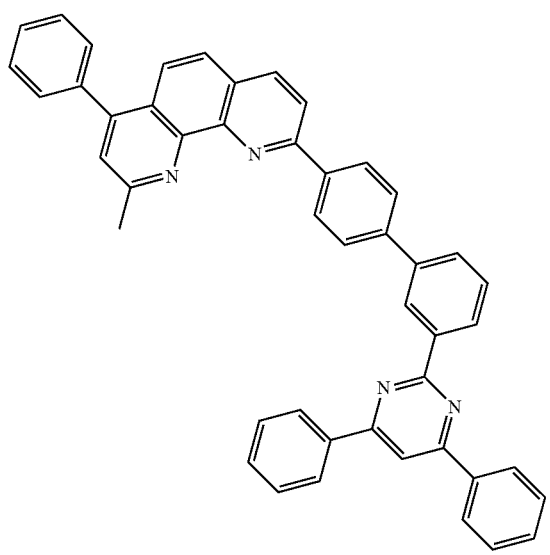
945
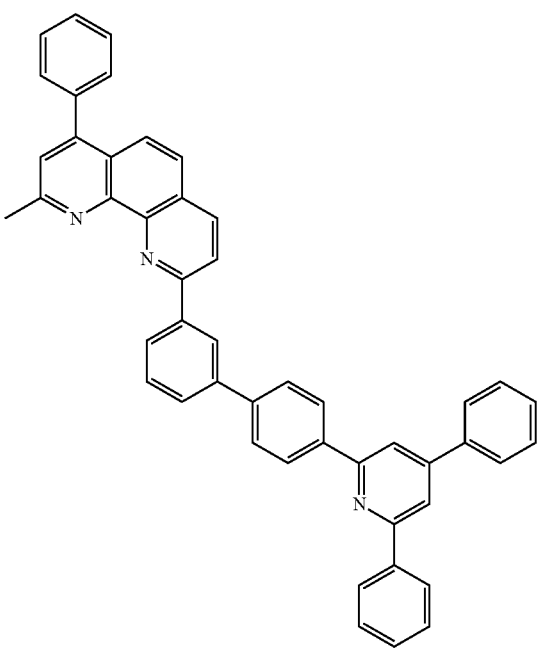
947

948
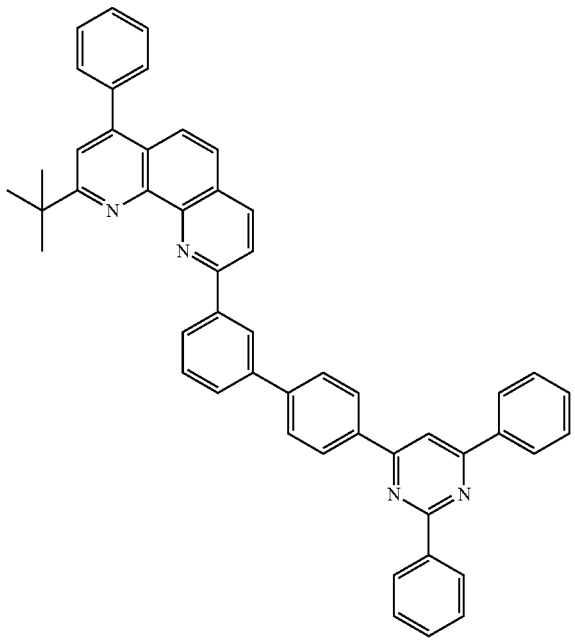
949
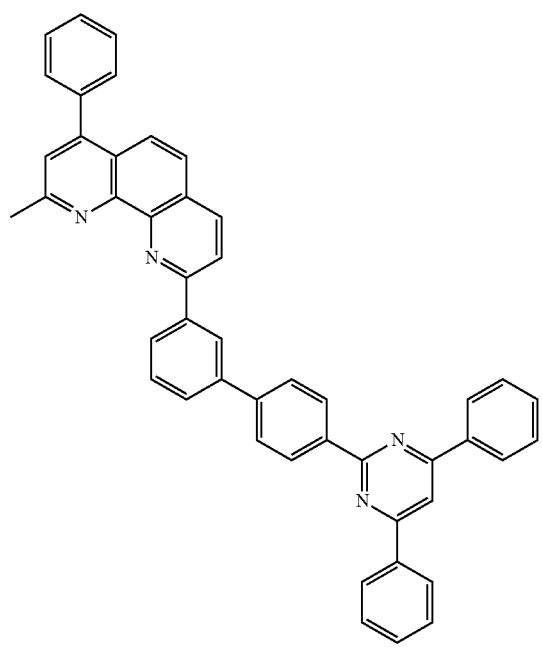
950
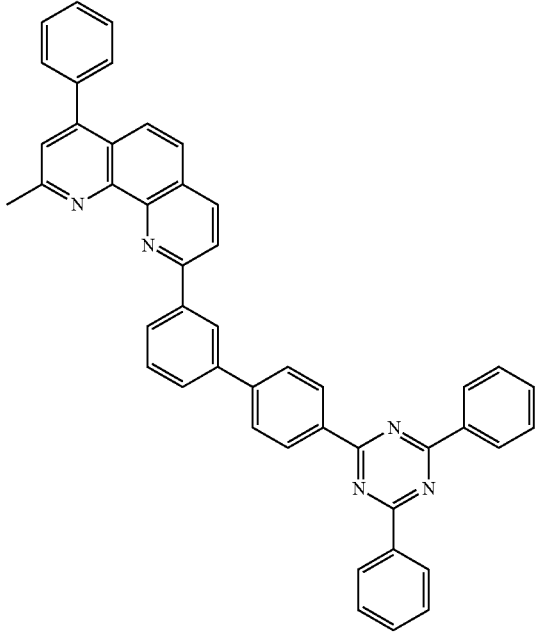
951
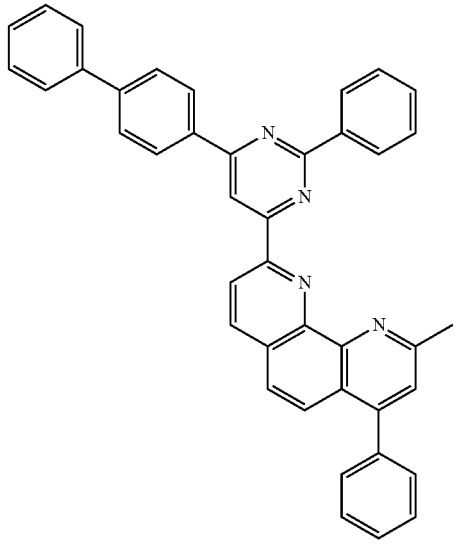

427
-continued
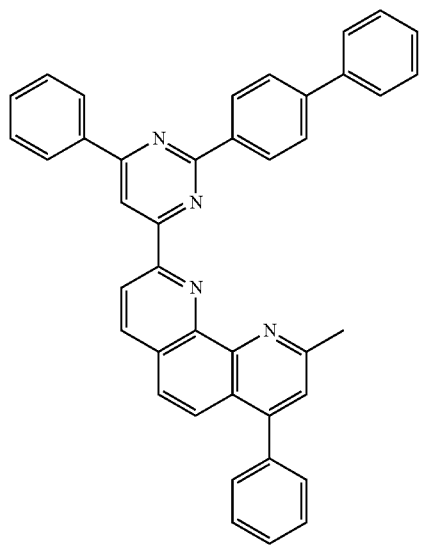
952
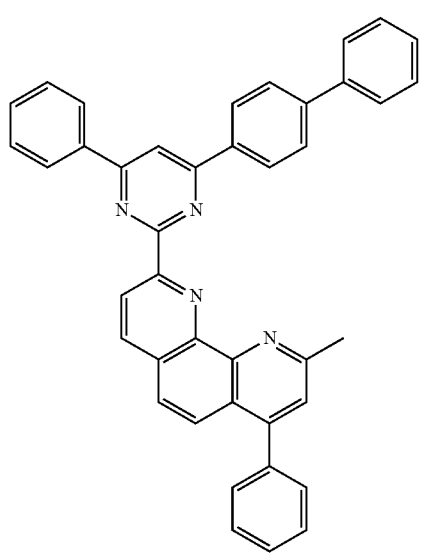
953
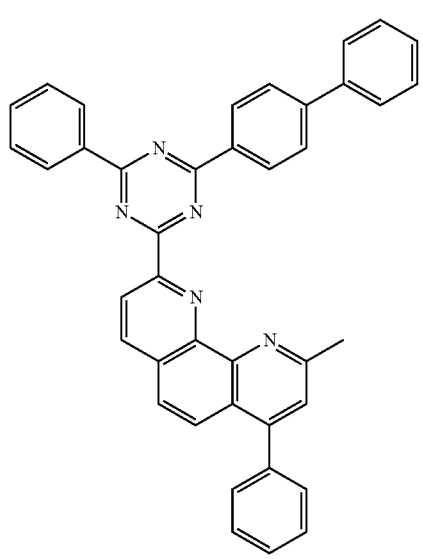
954
428
-continued
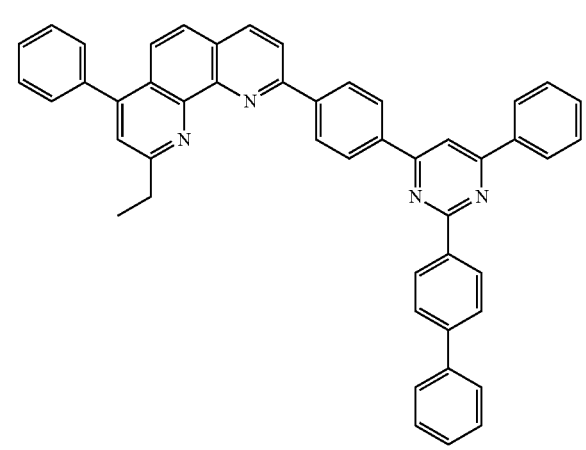
955
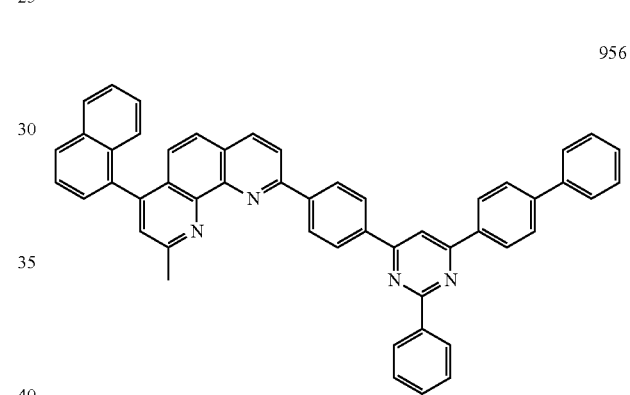
956
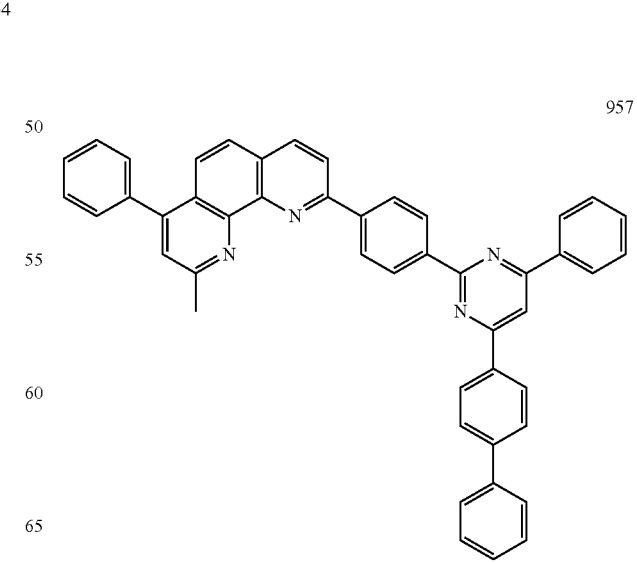
957

429
-continued
958
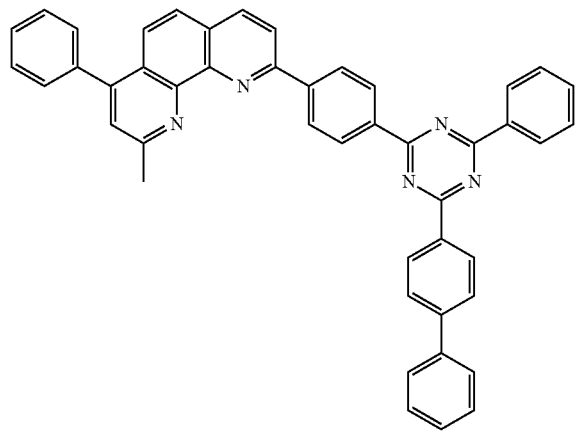
959
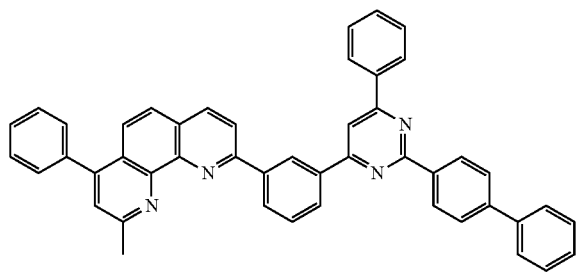
960
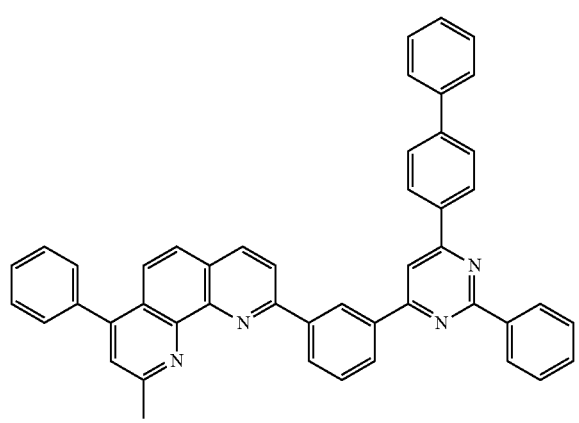
961
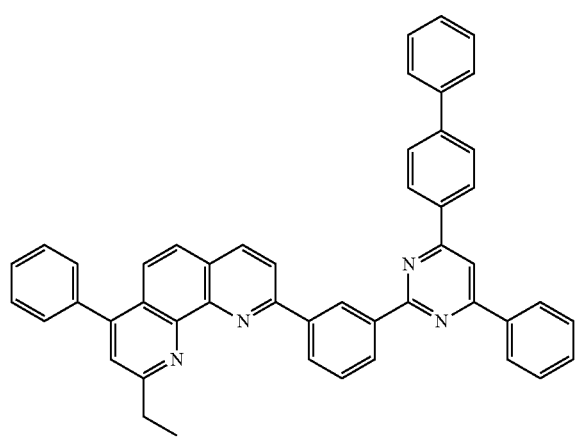
430
-continued
962
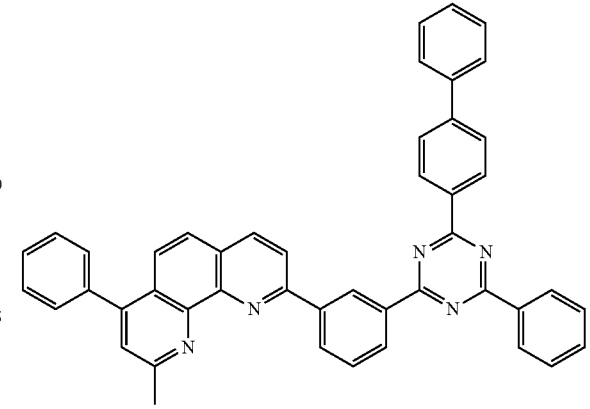
963
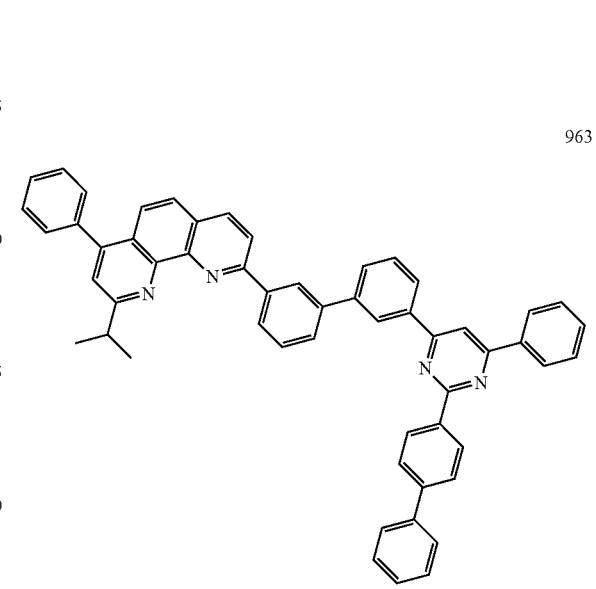
964
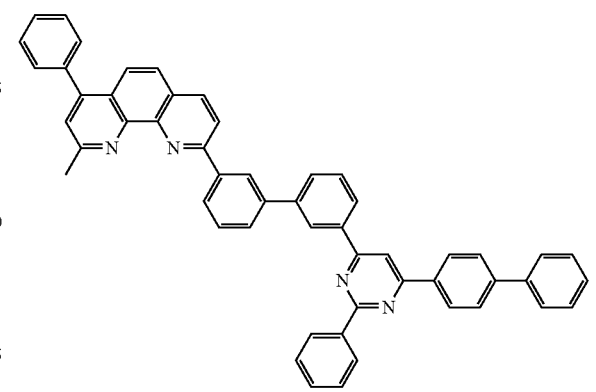

965
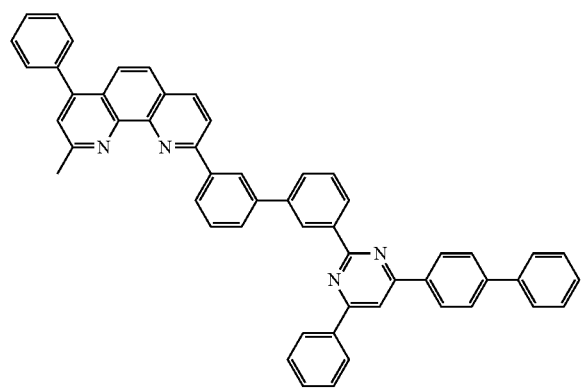
966
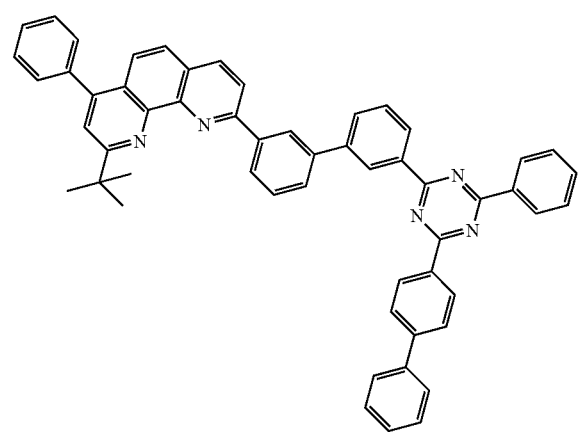
967
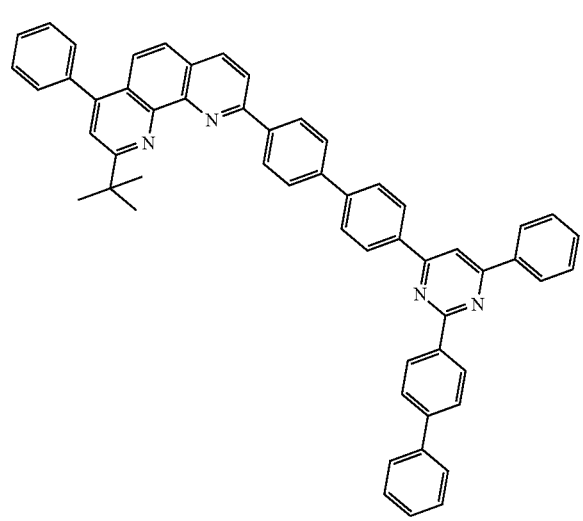
968
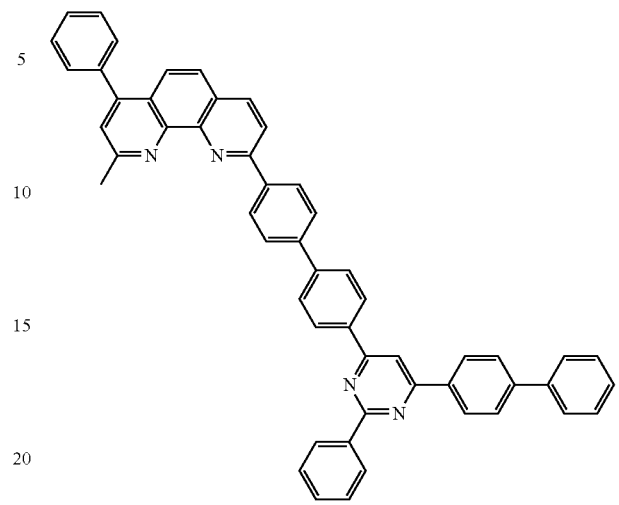
969
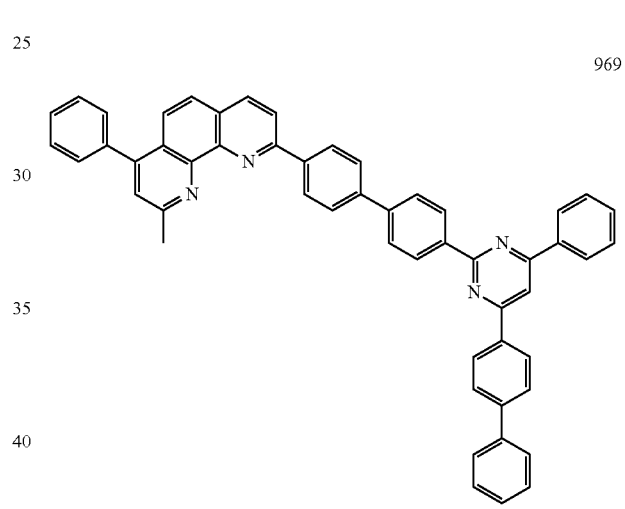
970
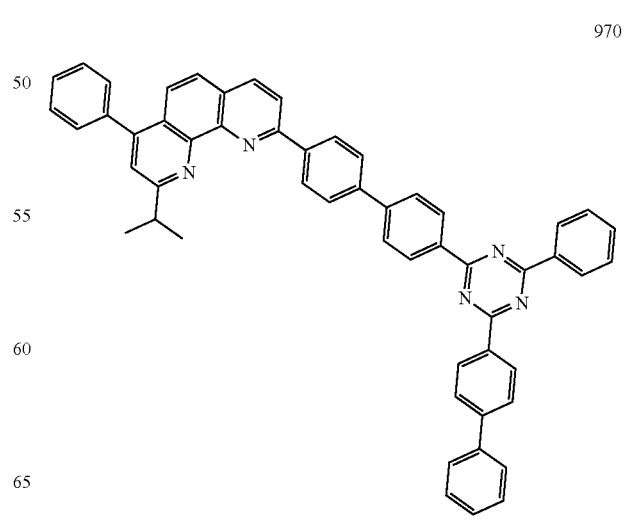

433
-continued
971
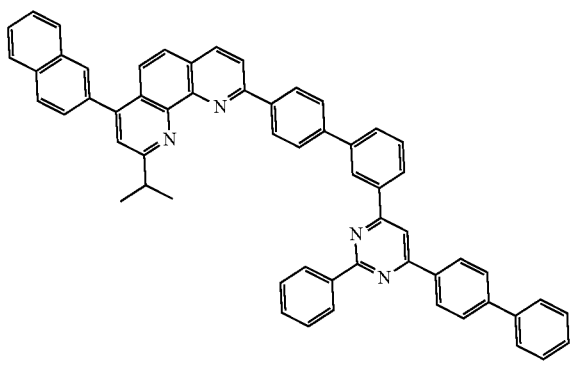
972
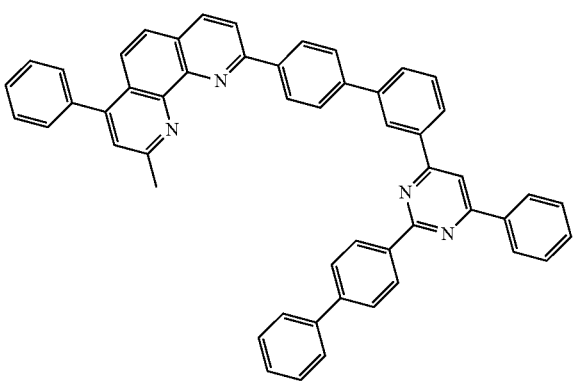
973
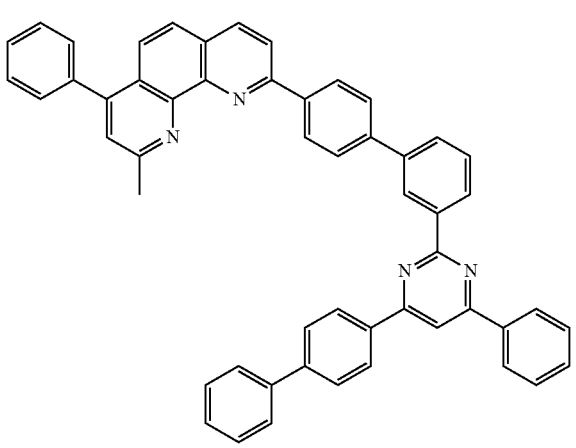
434
-continued
974
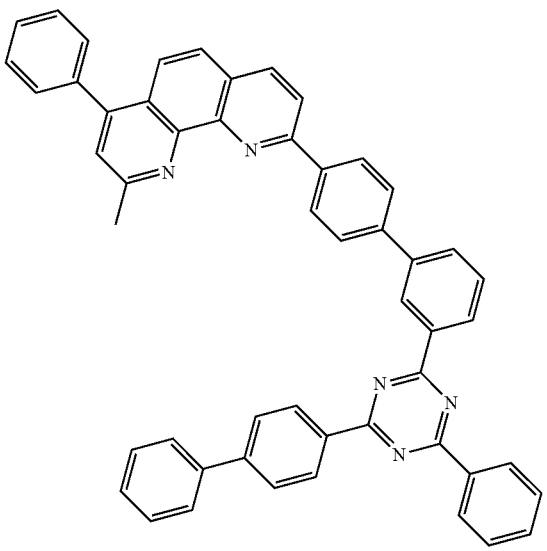
975
976
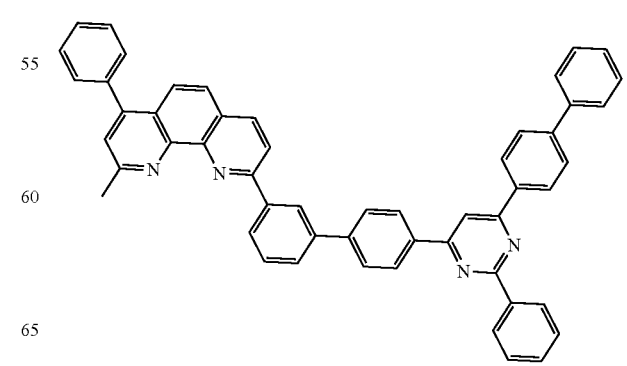

977
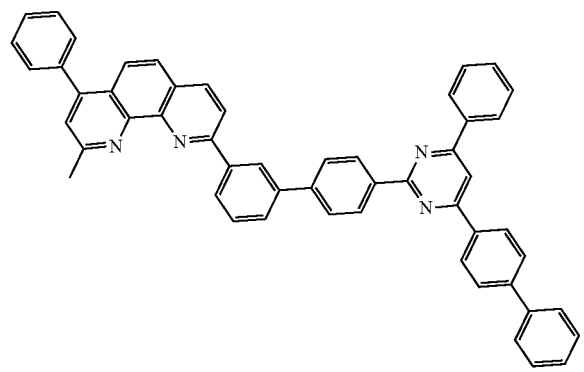
978
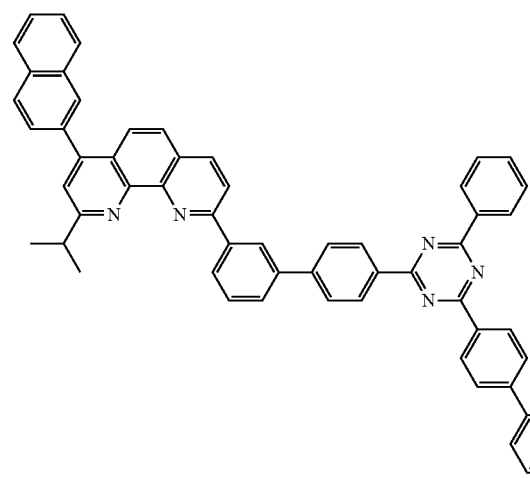
979
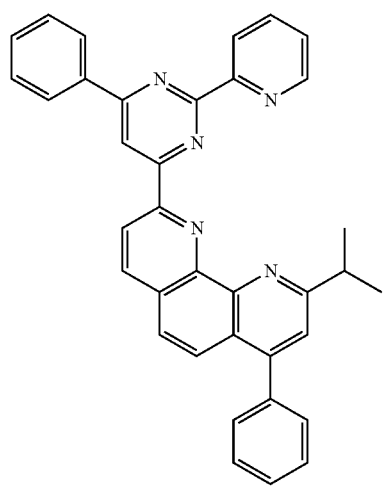
980
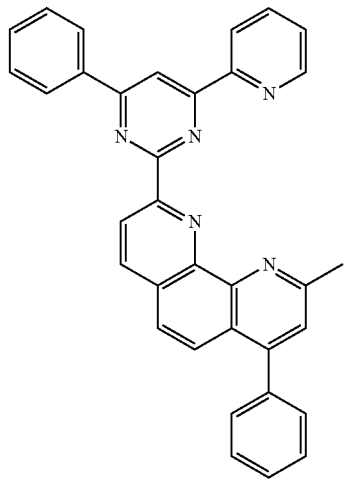
981
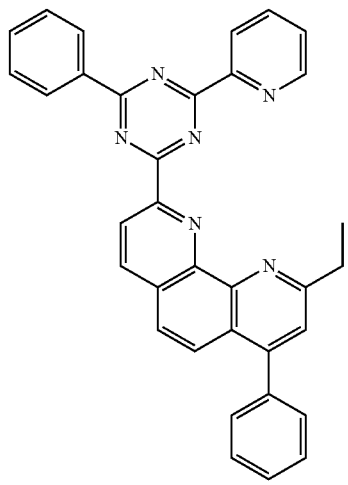
982
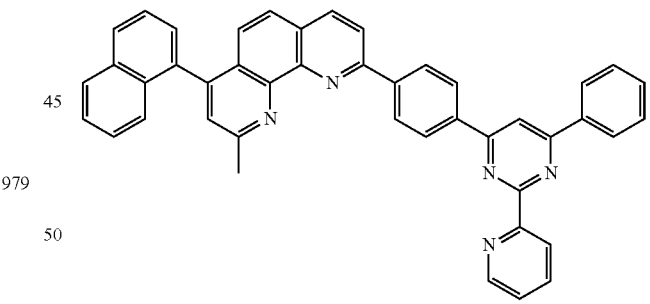
983
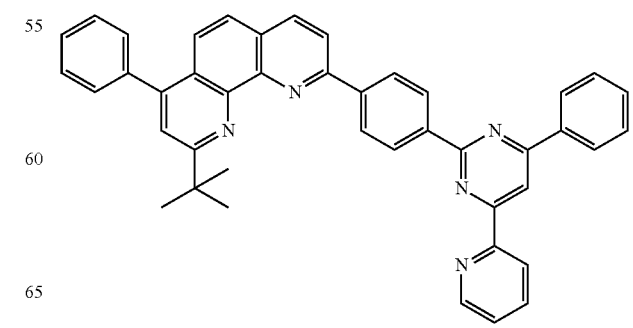

984
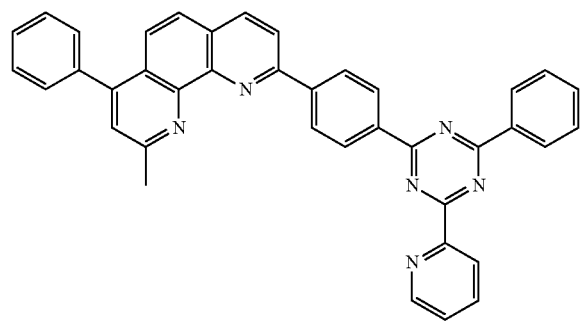
985
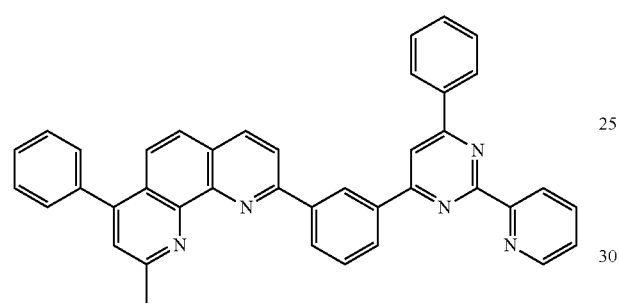
986

987
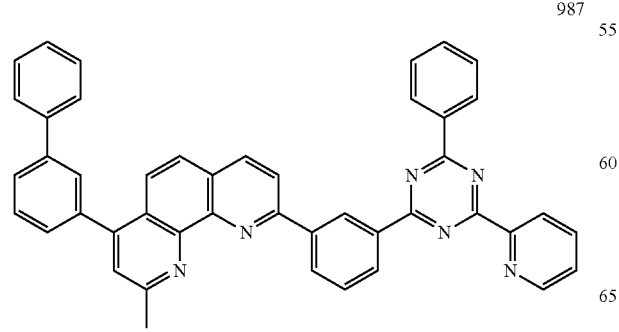
988
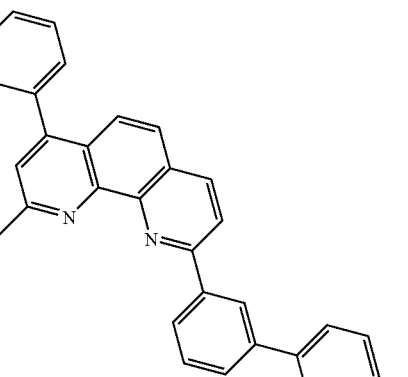
989
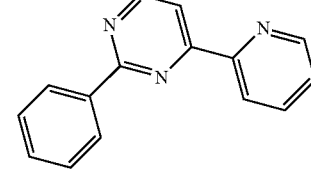

990
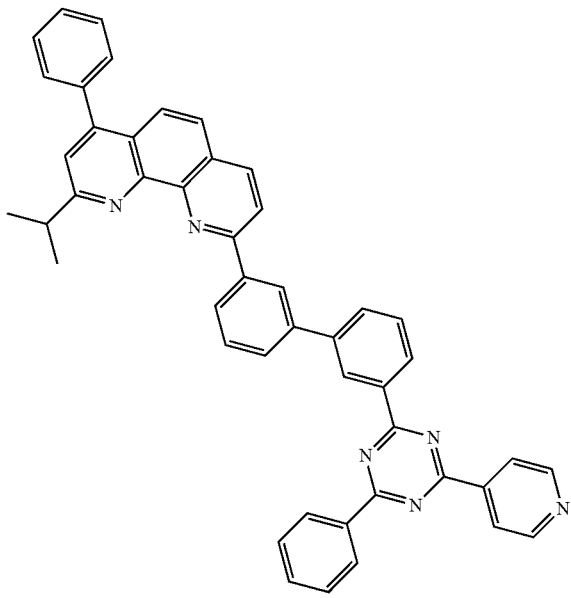
991
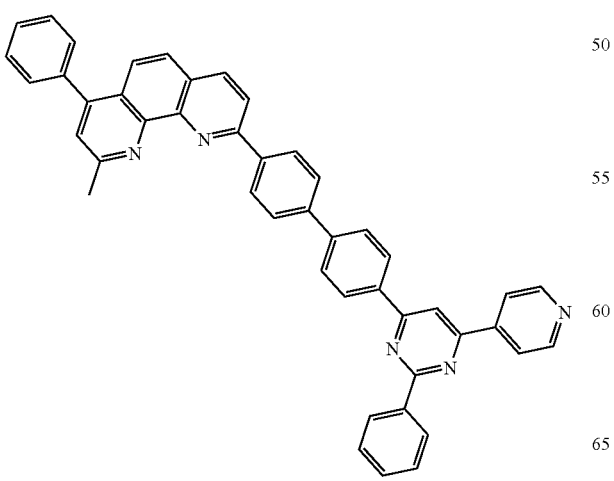
992
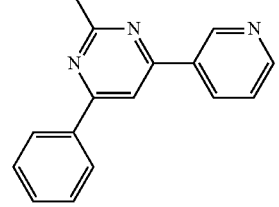
993
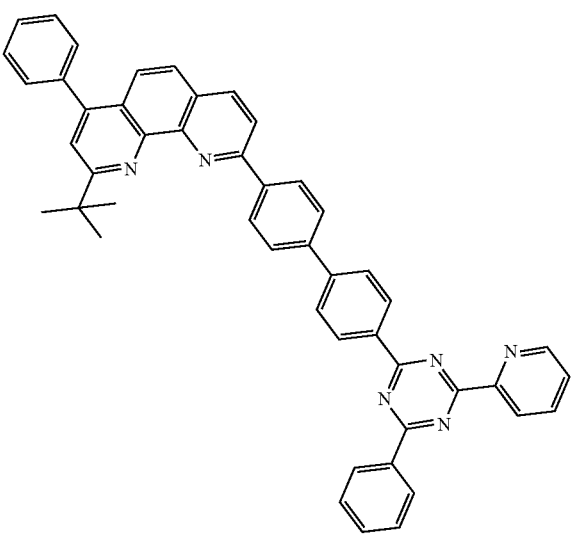

441
-continued
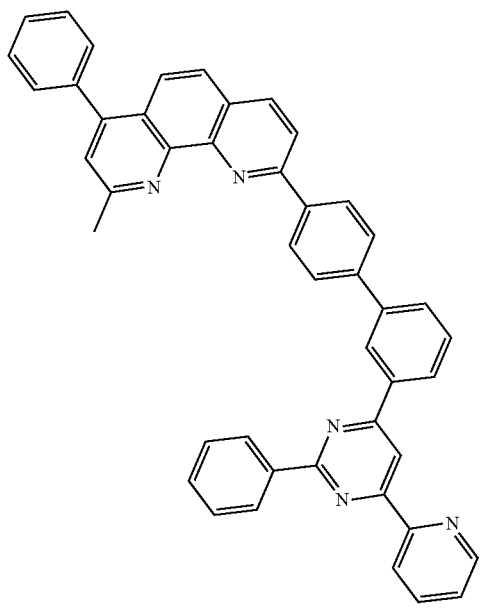
442
-continued
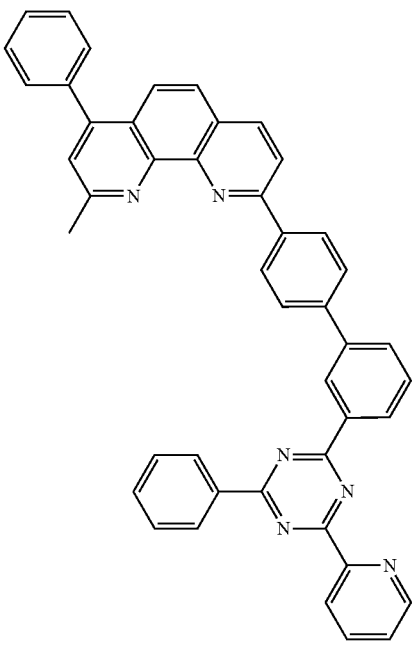
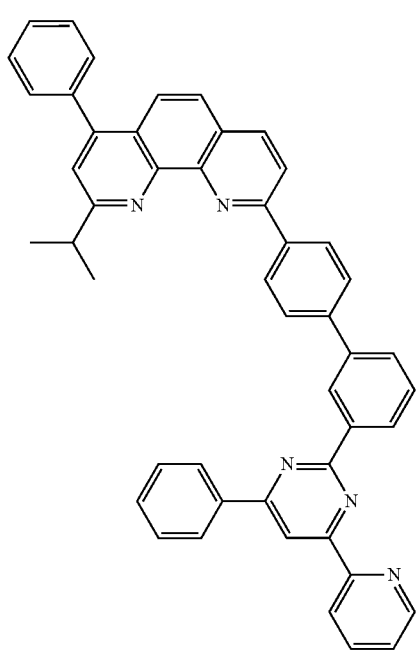
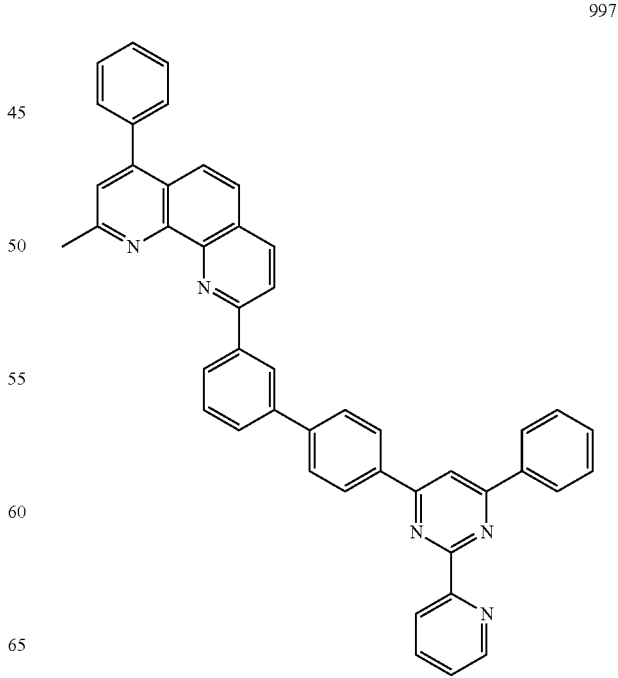

998
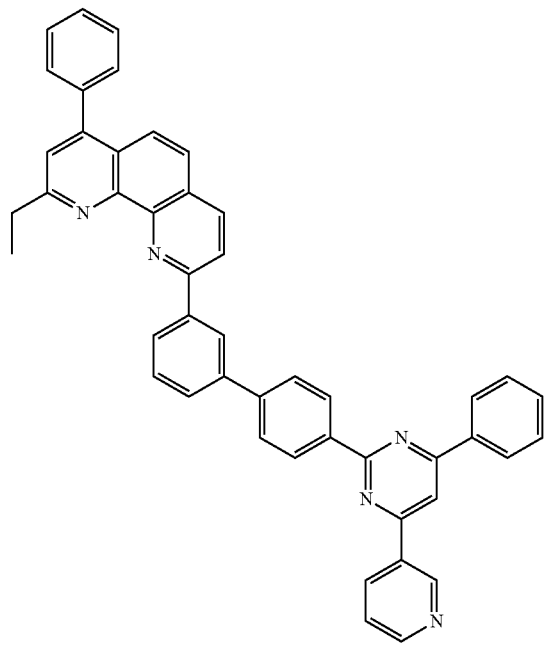
999
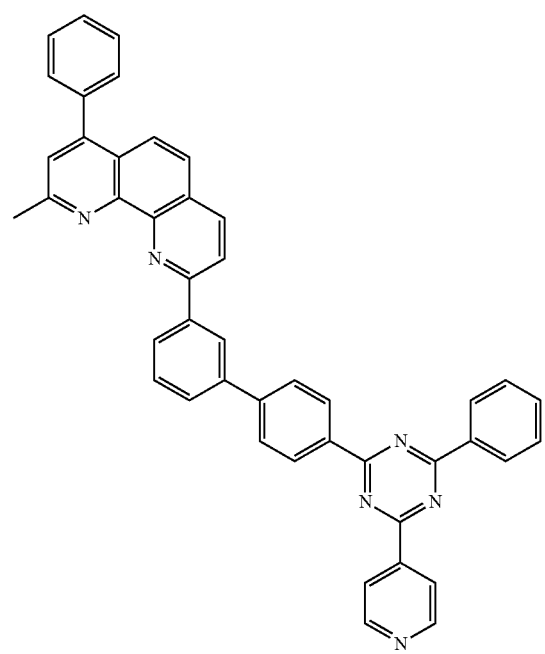
1000
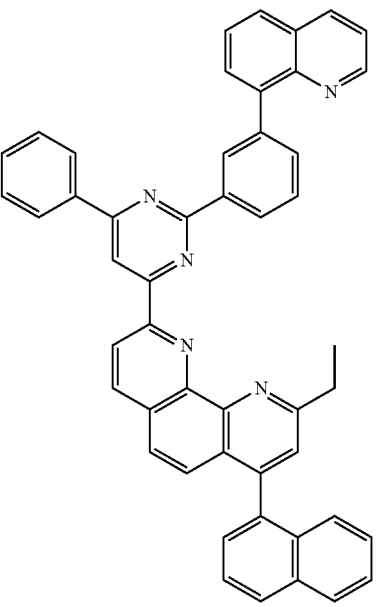
1001
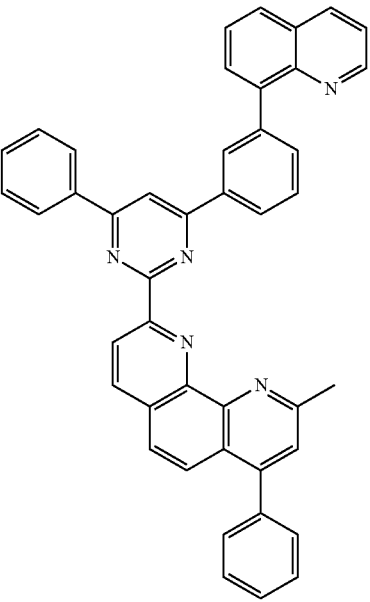

-continued
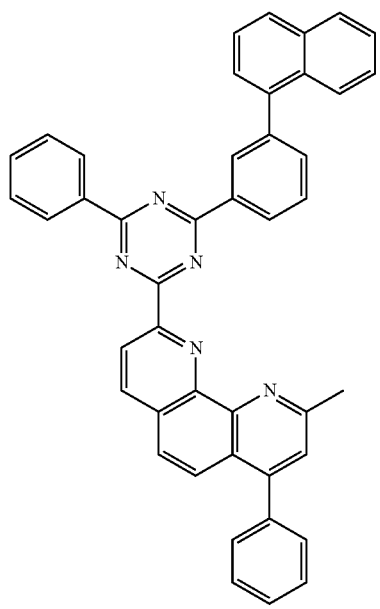
1002
1003
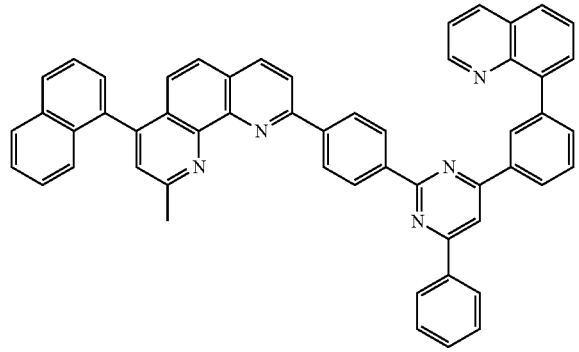
1004
-continued
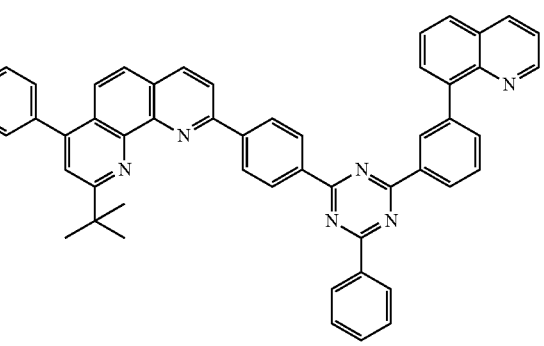
1005
1006
1007

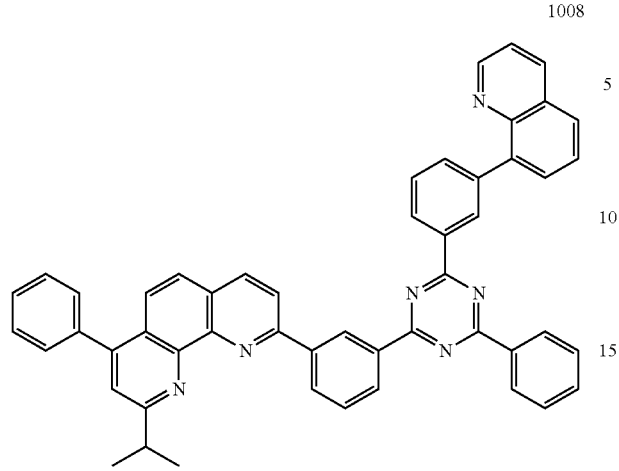
1008
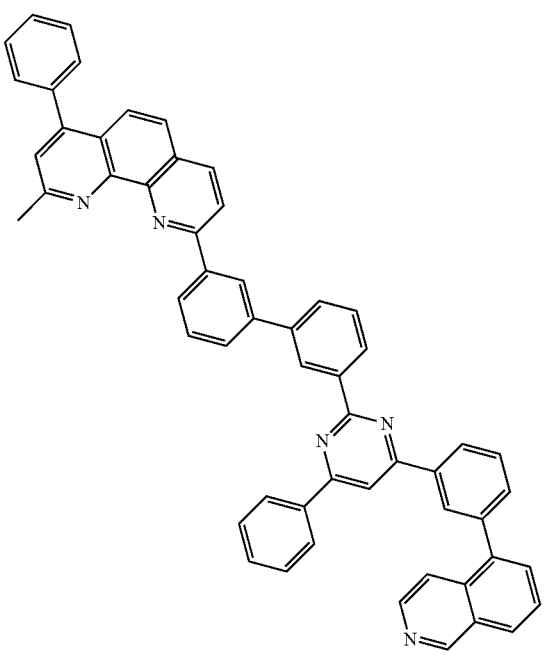
1010
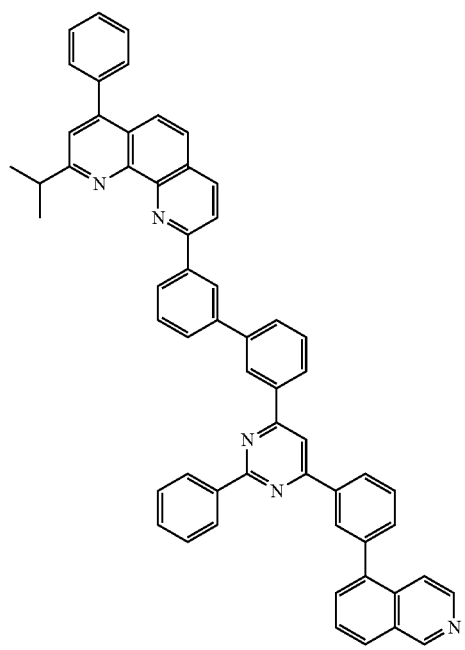
1009
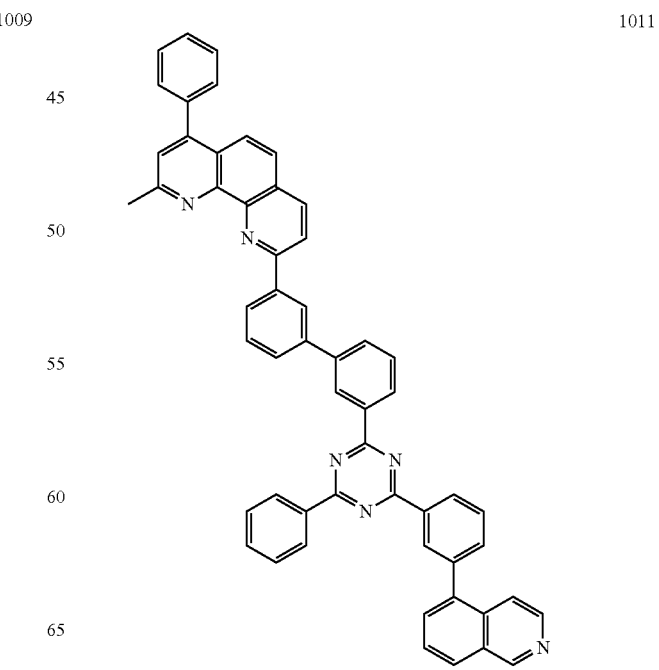
1011

449
-continued
1012
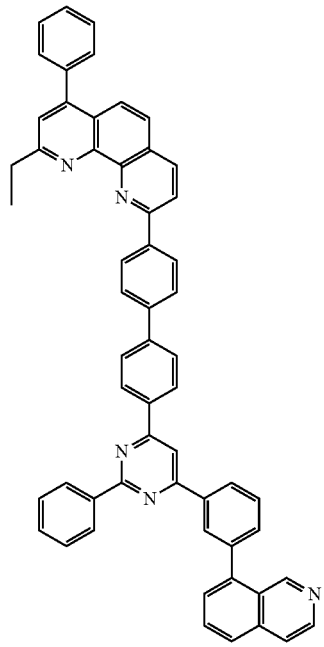
1013
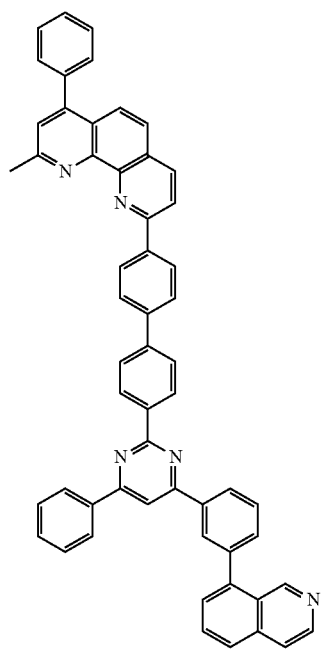
450
-continued
1014
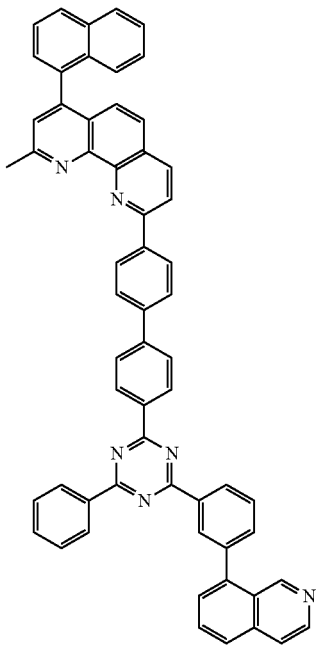
1015
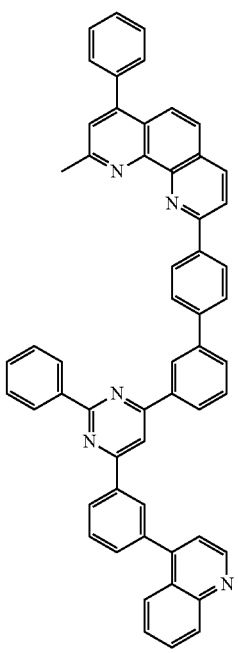

451
-continued
1016
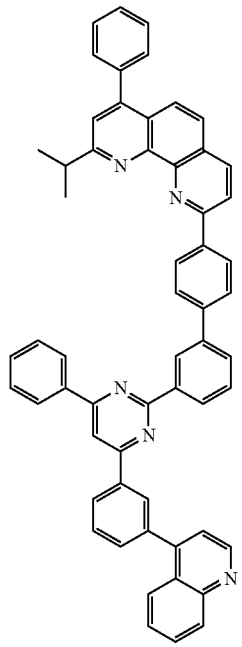
1018
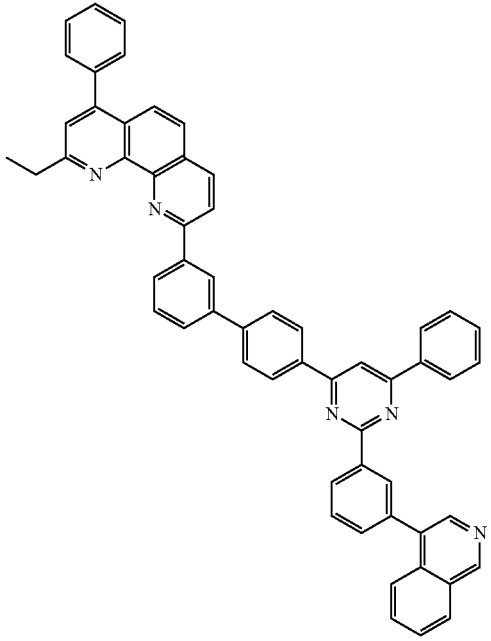
1017
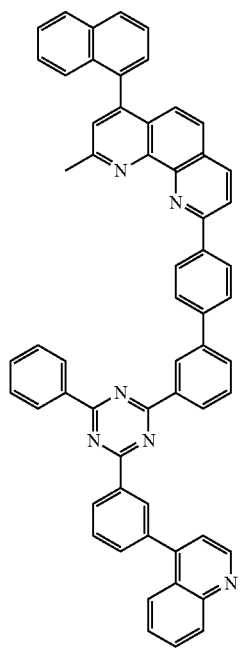
452
-continued
1019
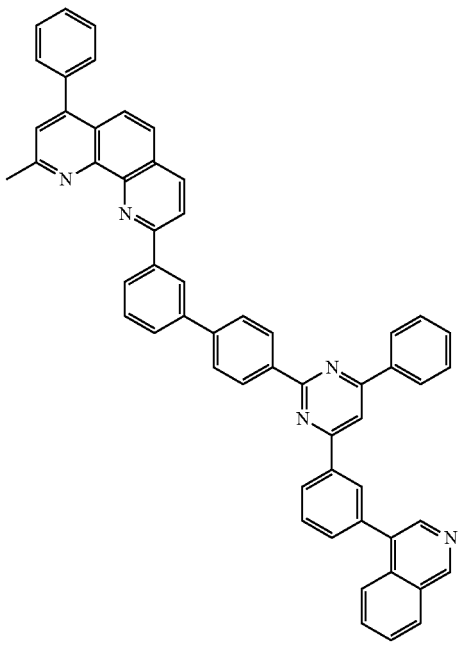

| 1020 | 1023 |
|---|---|
| 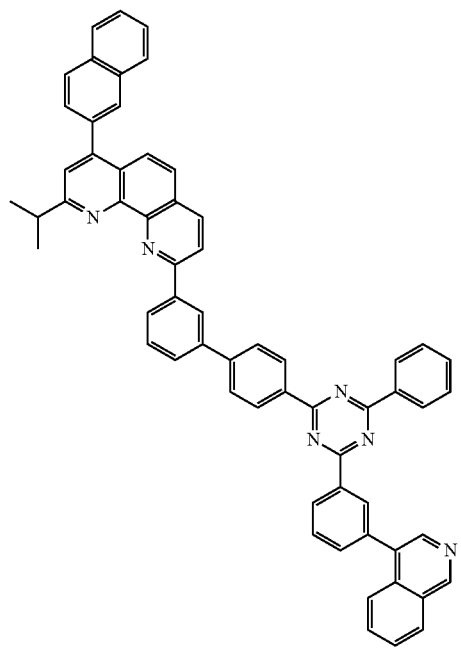 | 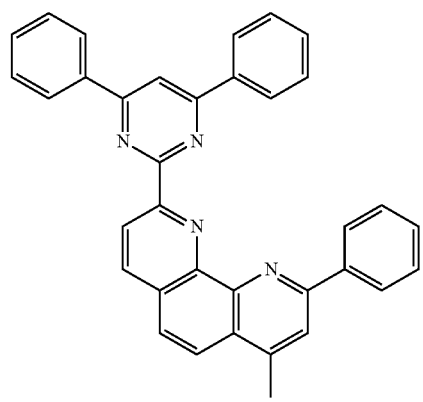 |
| 1021 | 1024 |
| 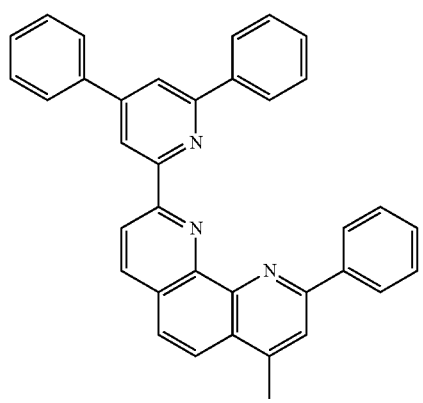 | 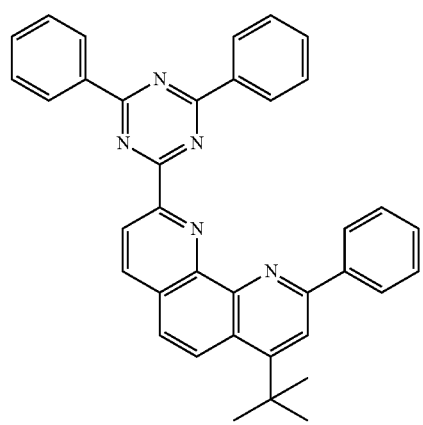 |
| 1022 | 1025 |
| 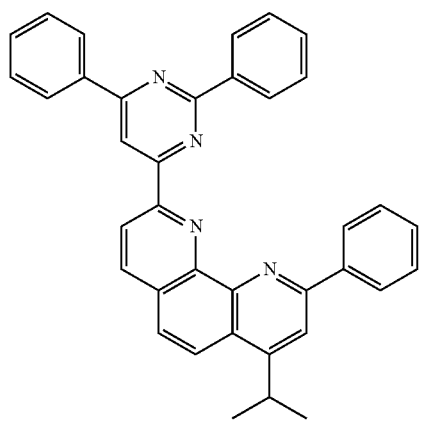 | 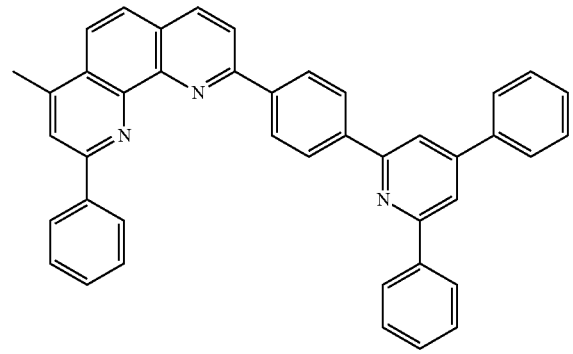 |
|  | 1026 |
|  | 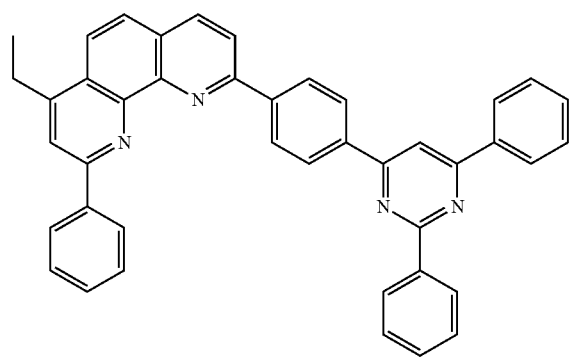 |

-continued
1027
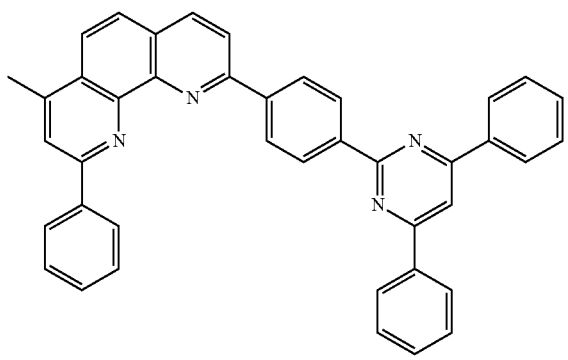
1028
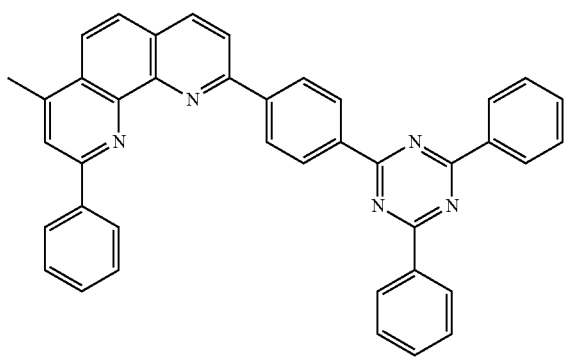
1029
1030
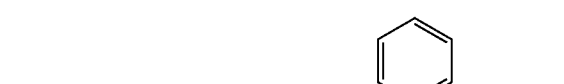
-continued
1031
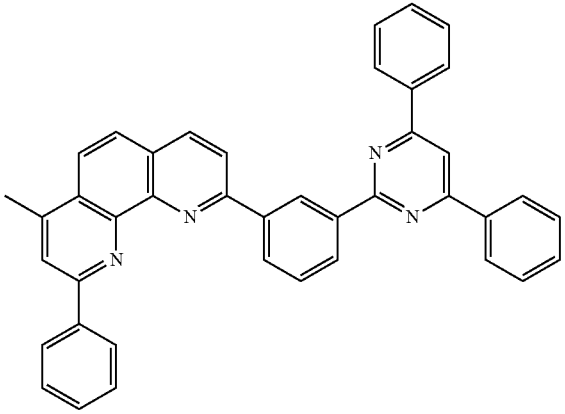
1032
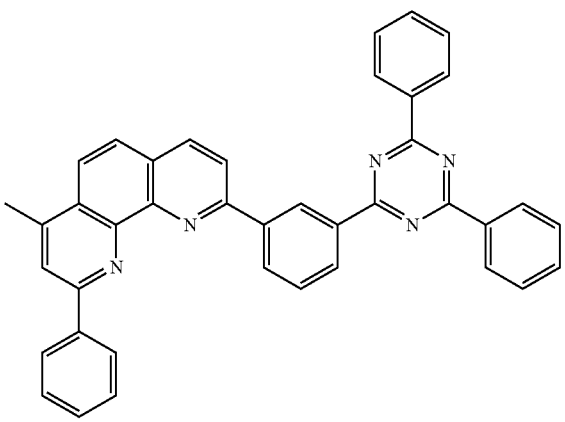
1033
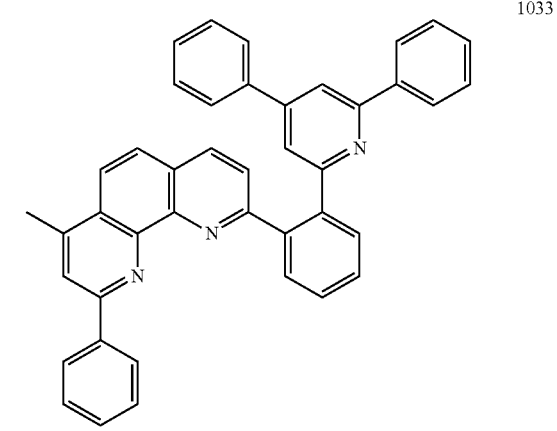 [SMILES: Cc1cc(-c2ccccc2)nc2c1ccc1ccc(-c3ccccc3-c3nc(-c4ccccc4)nc(-c4ccccc4)n3)nc12]

457
-continued
1034
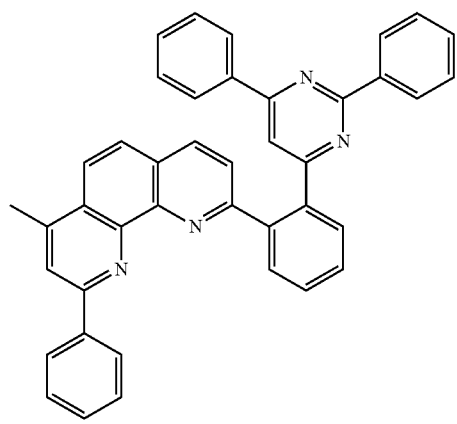
1035
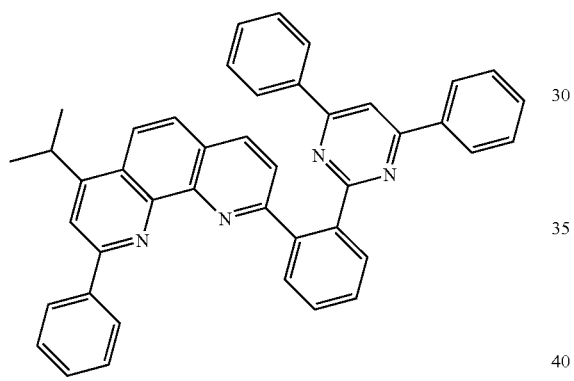
1036
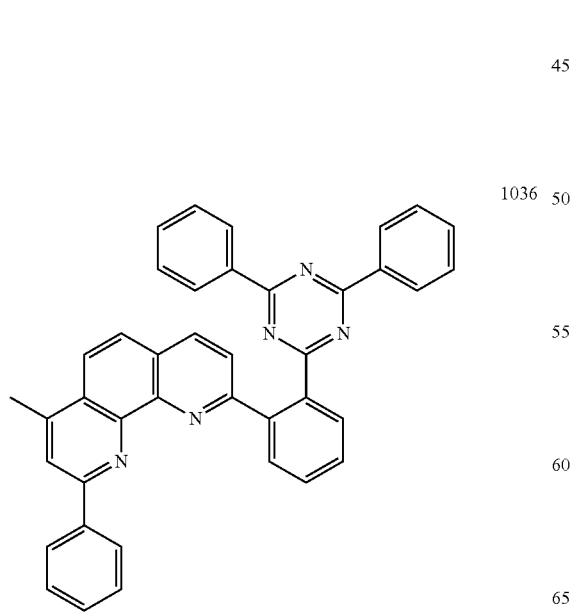
458
1037
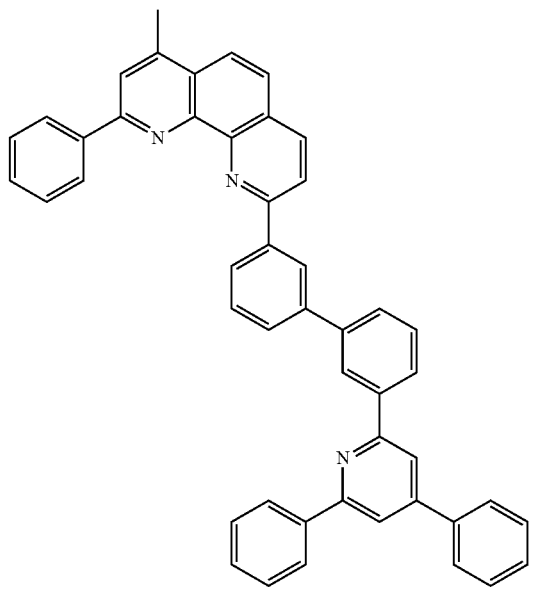
1038
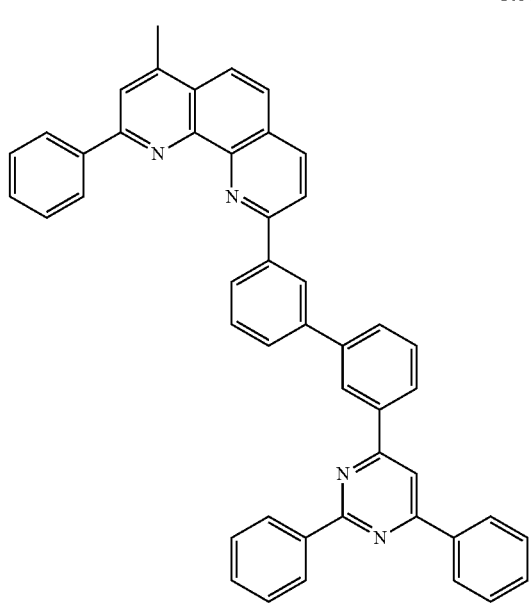

1039
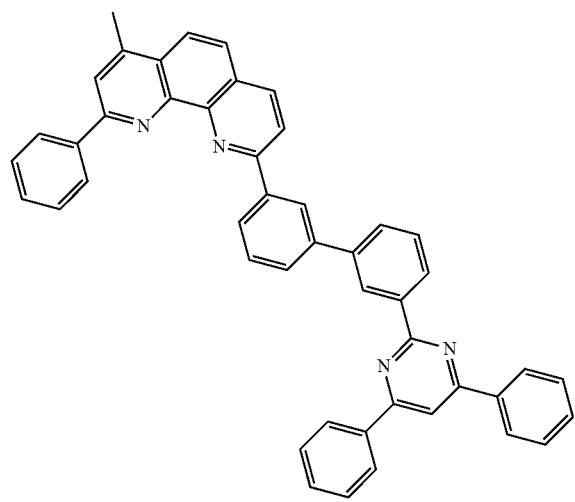
1040
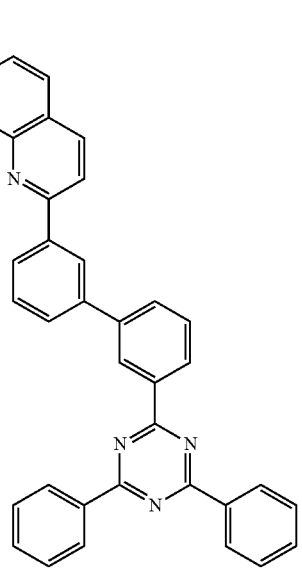
1041
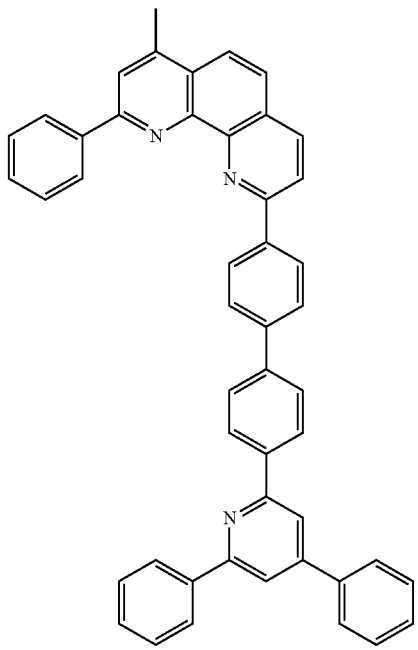
1042
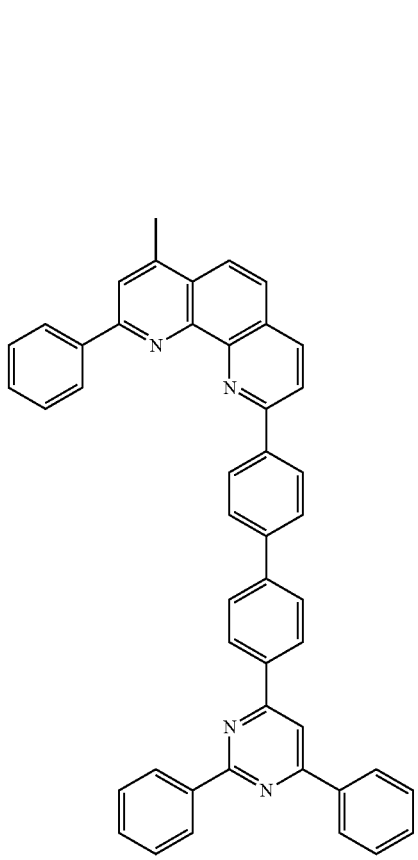

1043
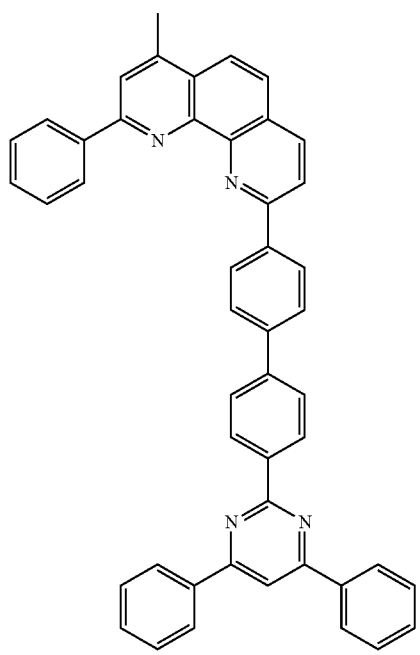
1044
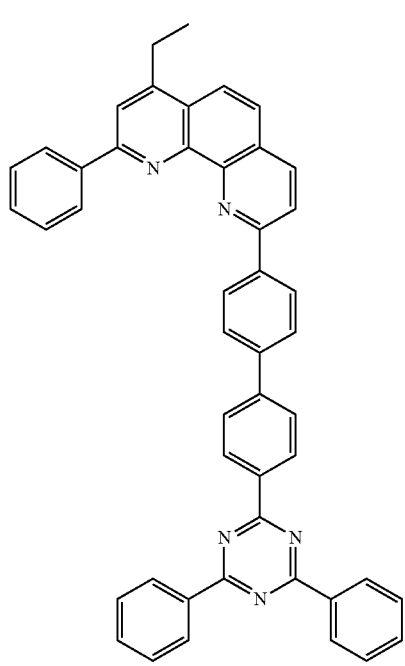
1045
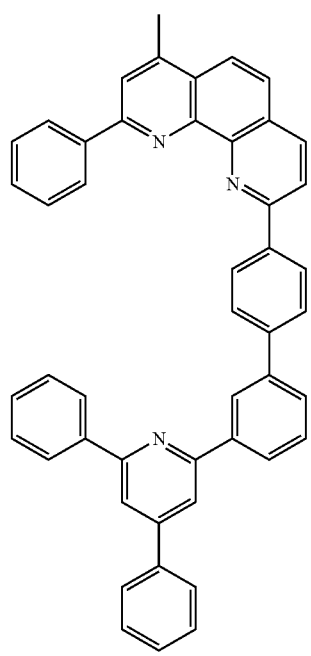
1046
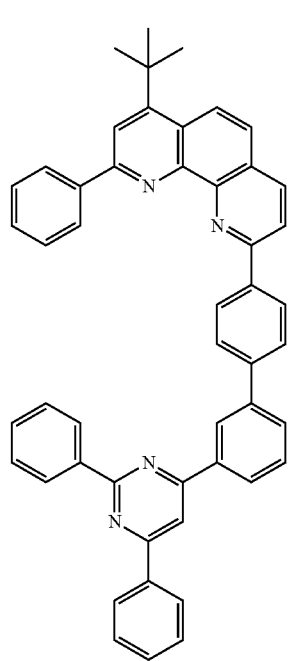

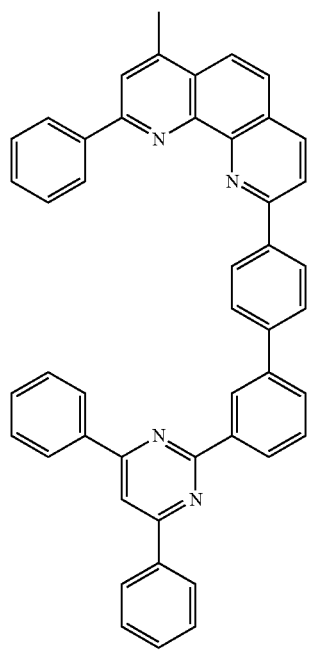
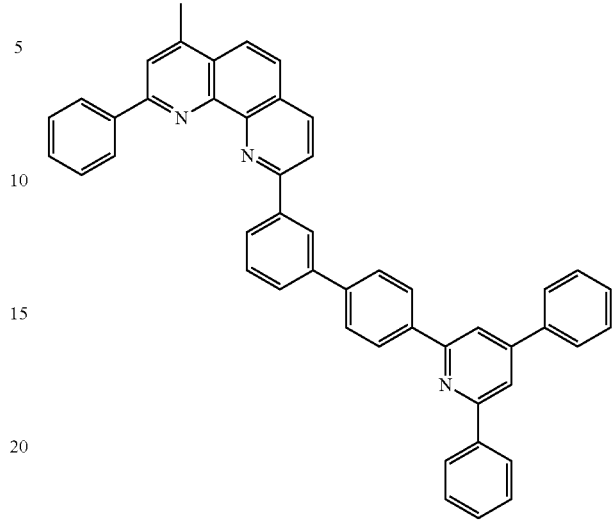
1047
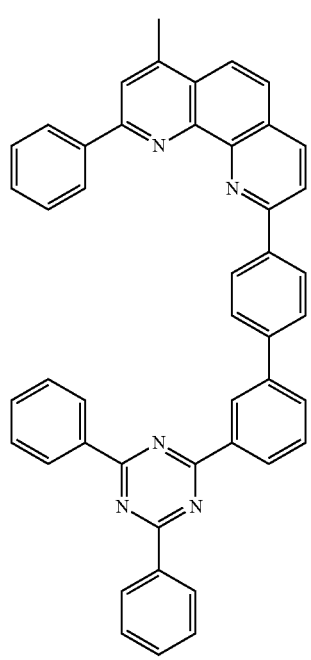
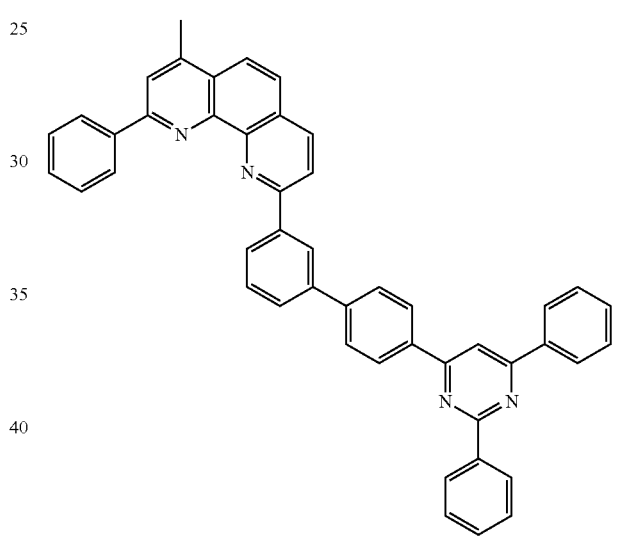
1048
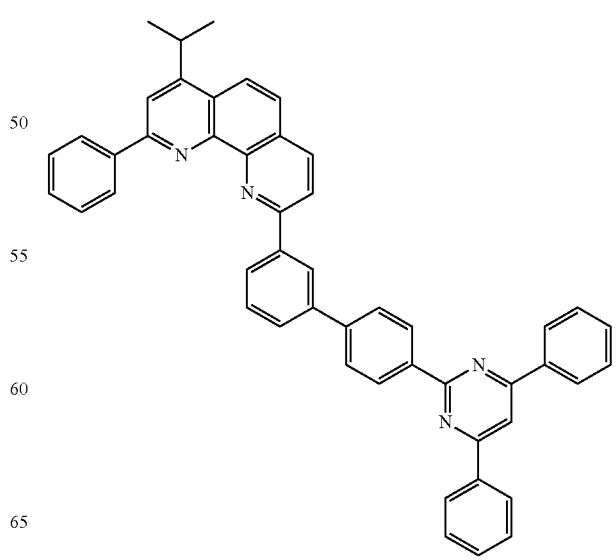
1049
1050
1051

465
-continued
1052
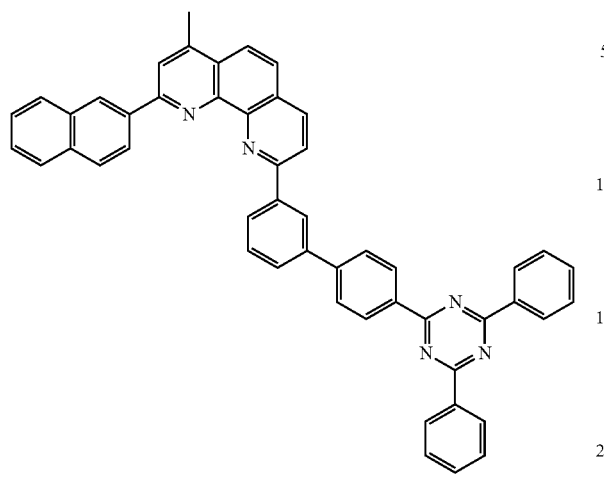
1053
1054
466
-continued
1055
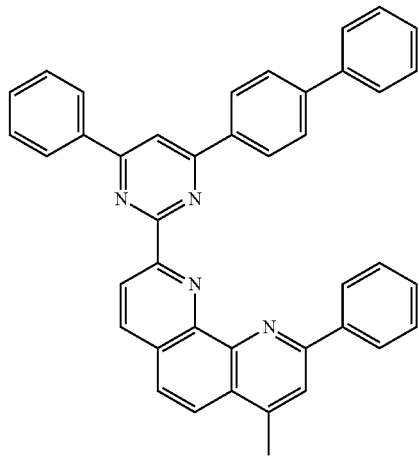
1056
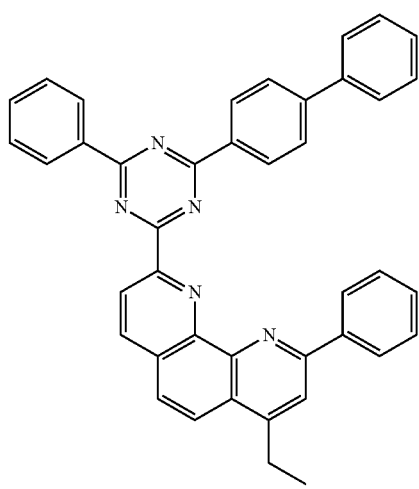
1057
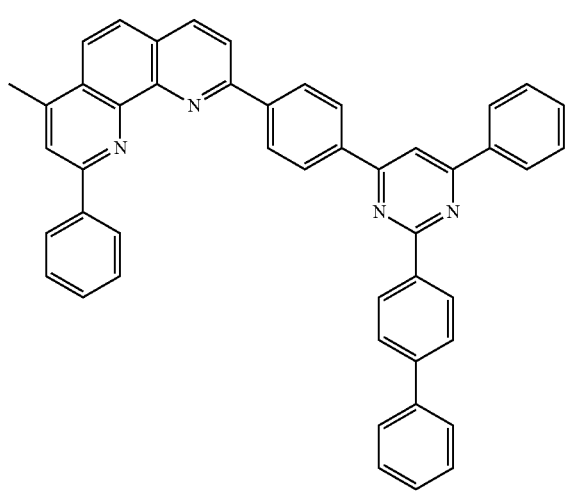

1058
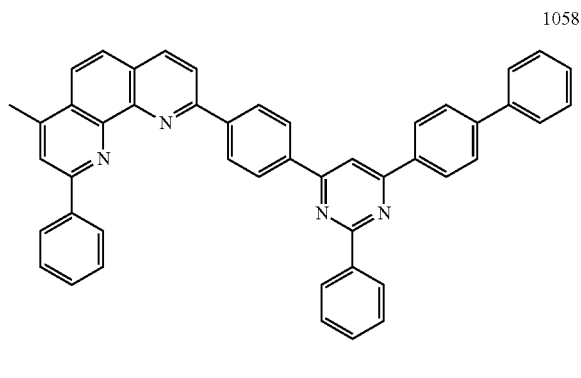
1059
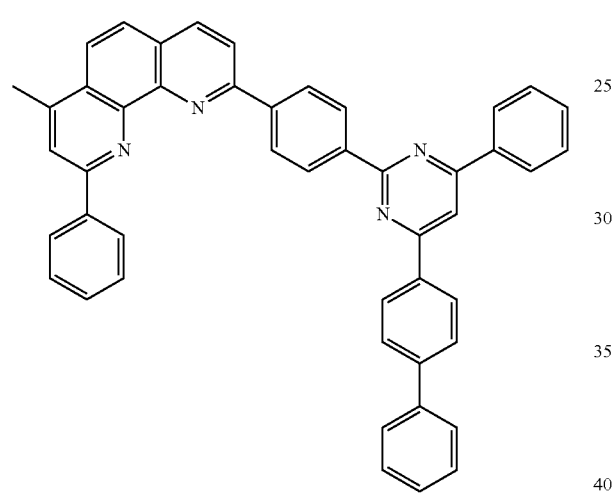
1060
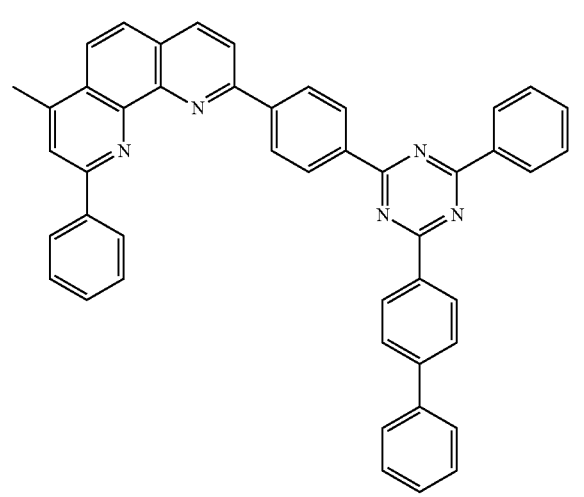
1061
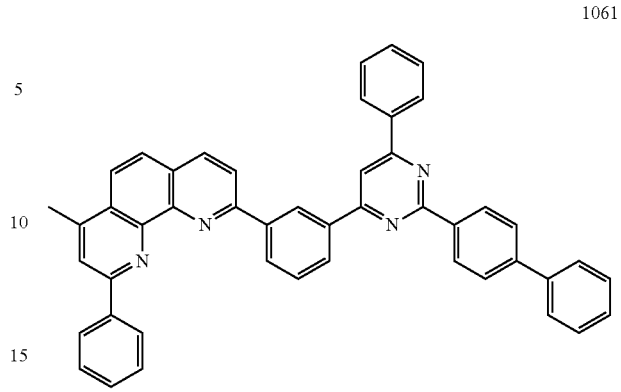
1062
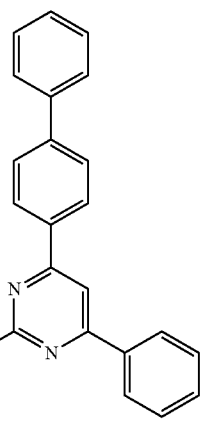
1063

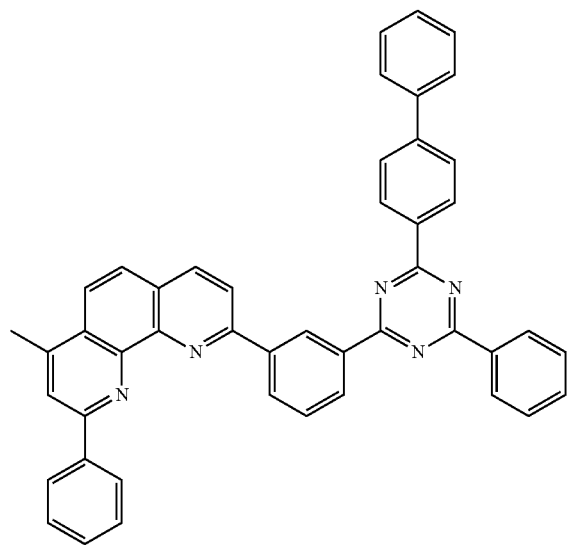
1064
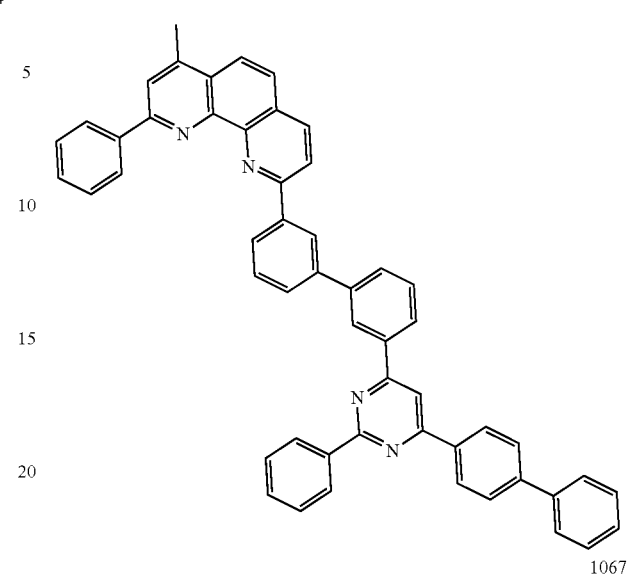
1066
1065
1067
1068
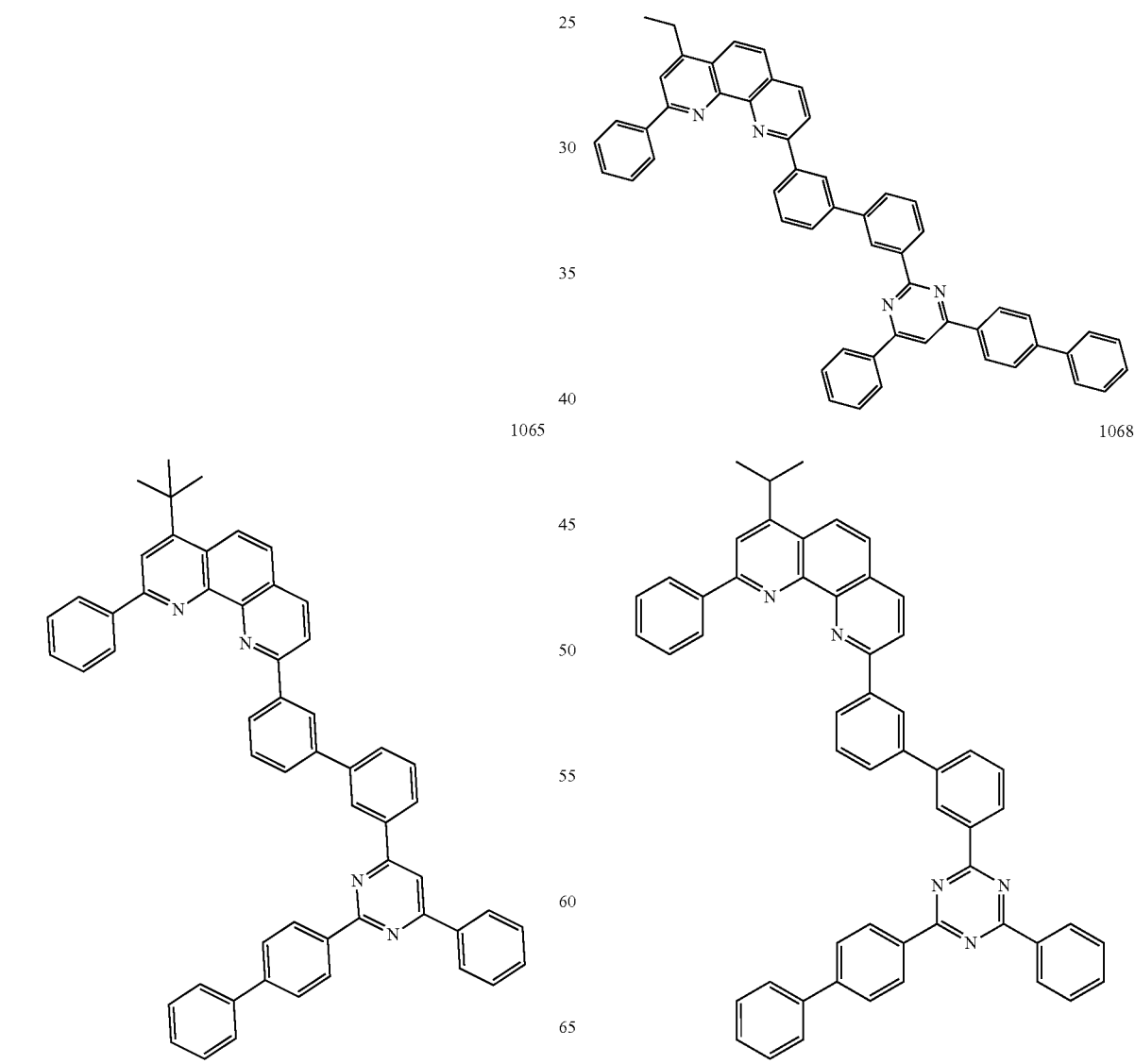

471
-continued
1069
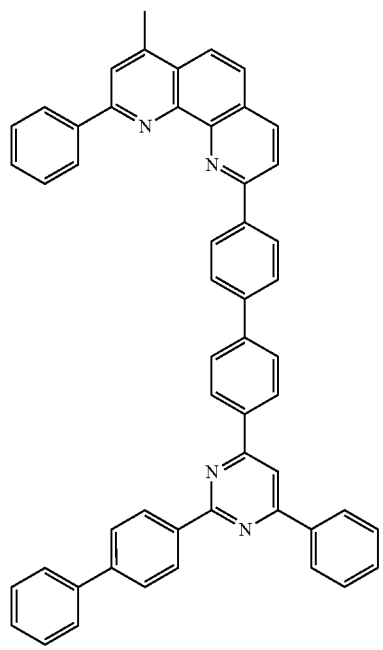
472
-continued
1071
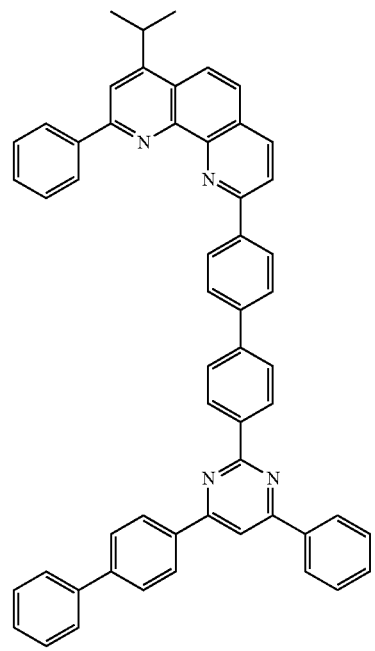
1070
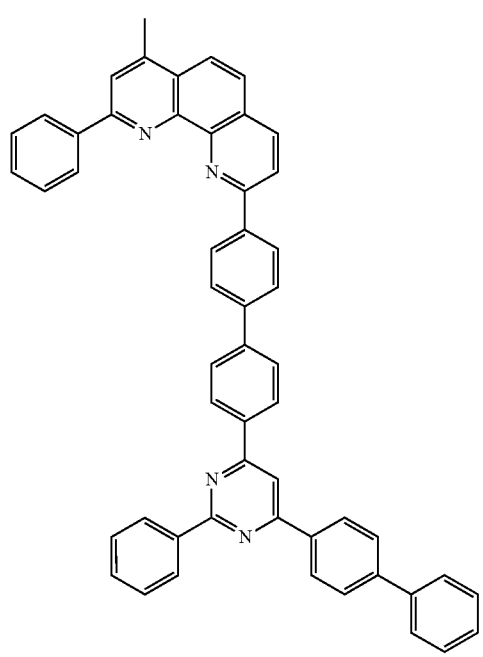
1072
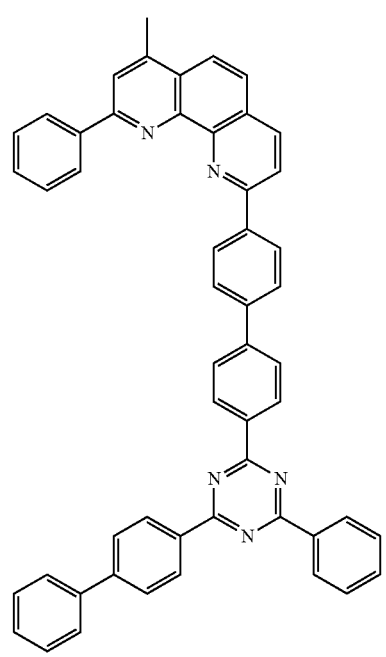

1073
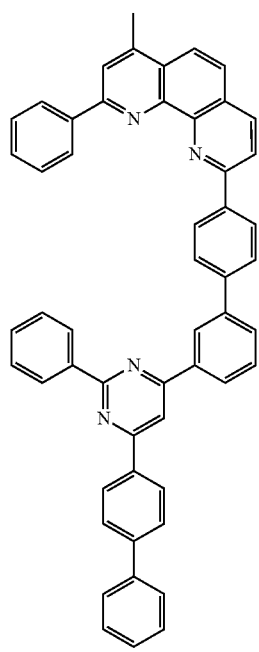
1074
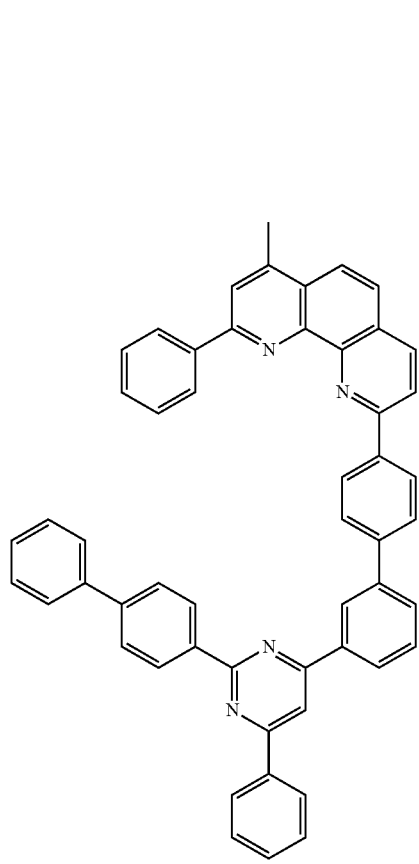
1075
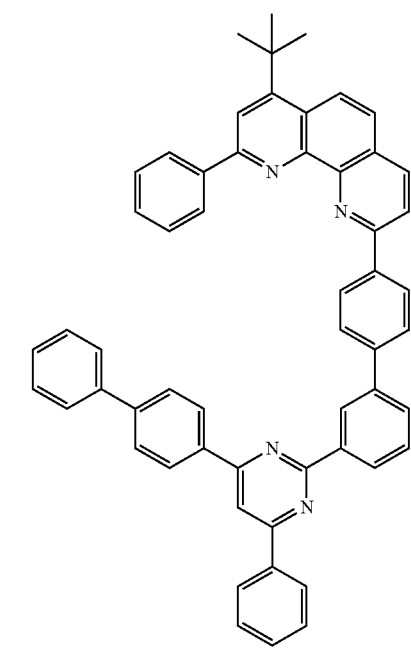
1076
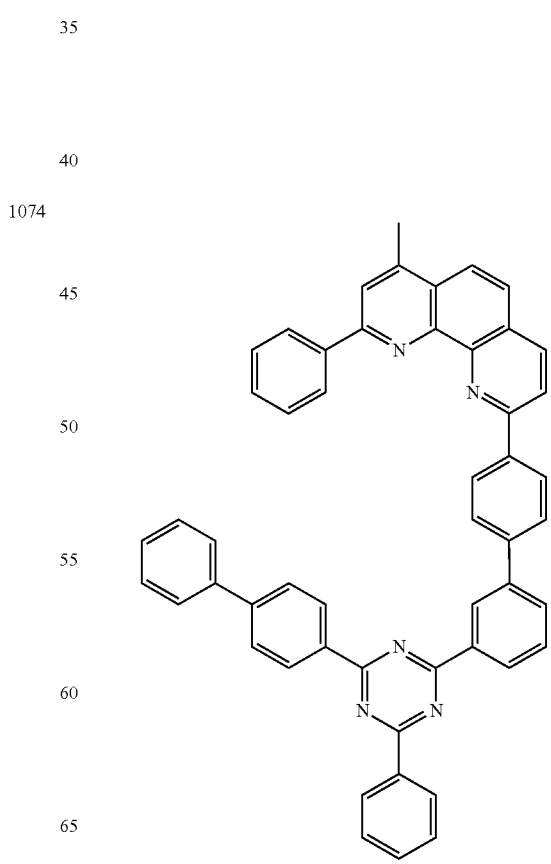

475
-continued
1077
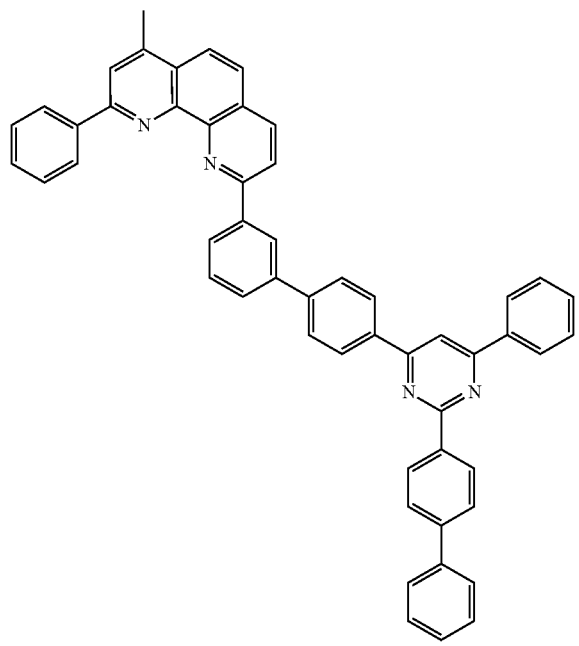
1078
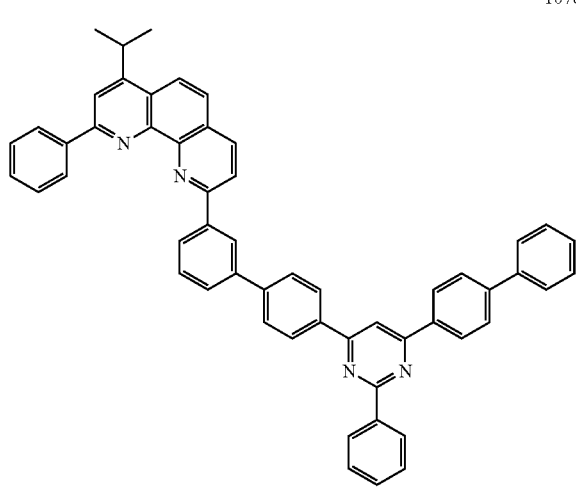
476
-continued
1079
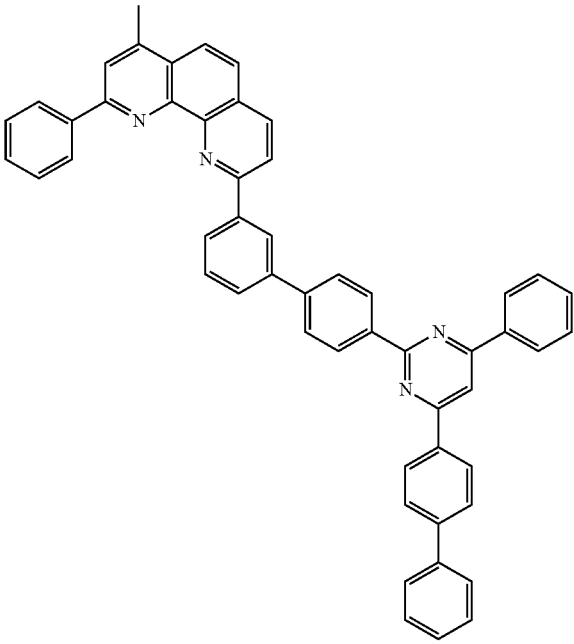
1080
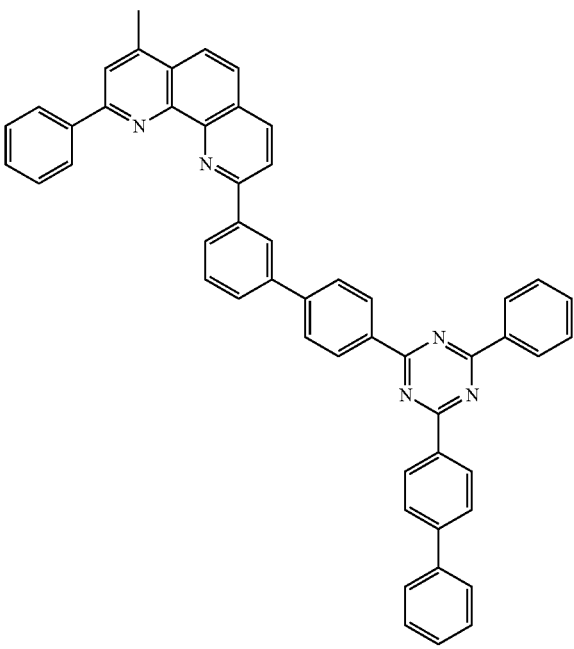

1081
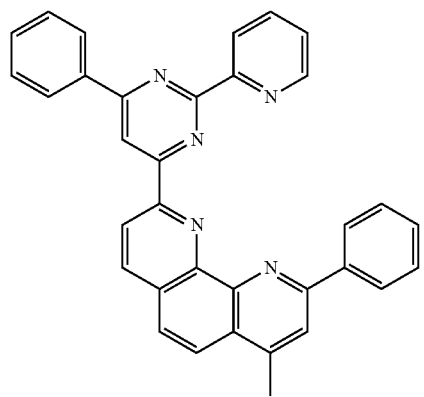
1082
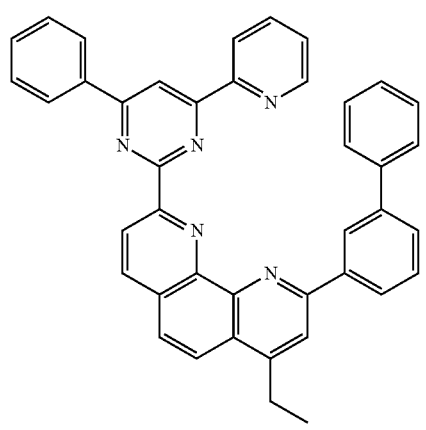
1083
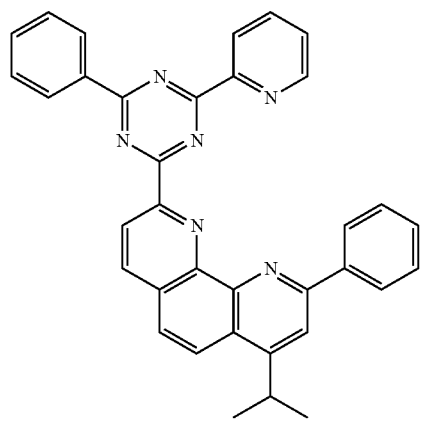
1084
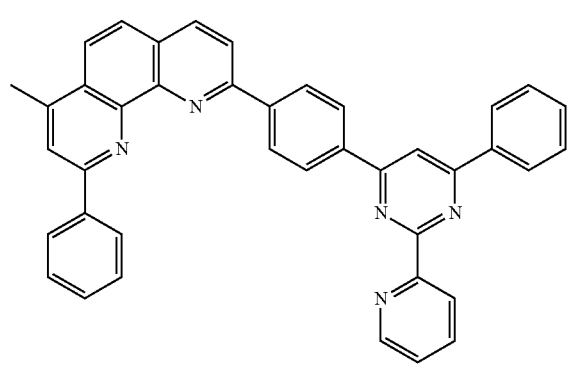
1085
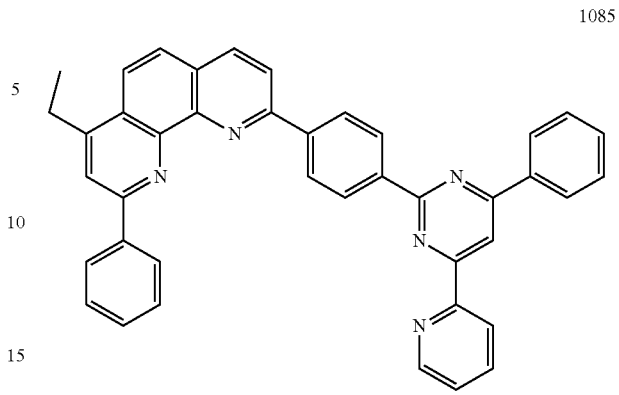
1086
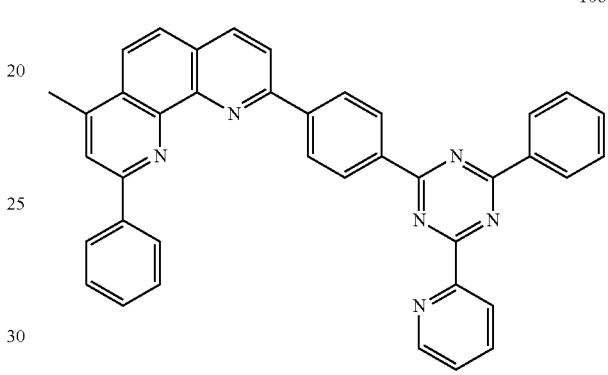
1087
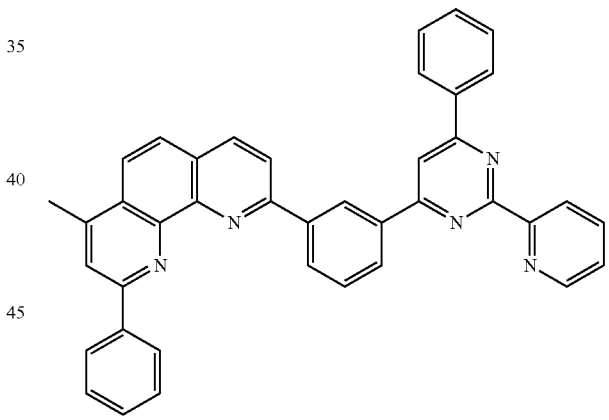
1088
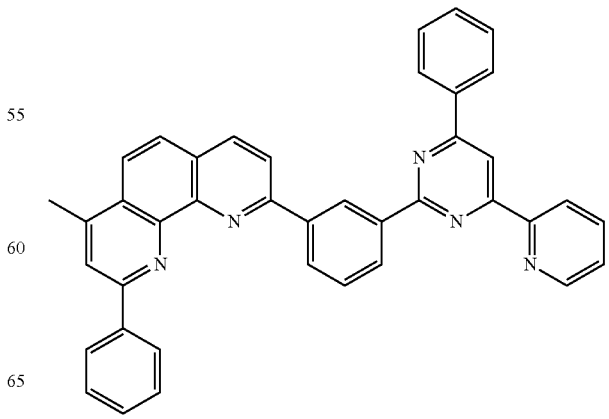

1089
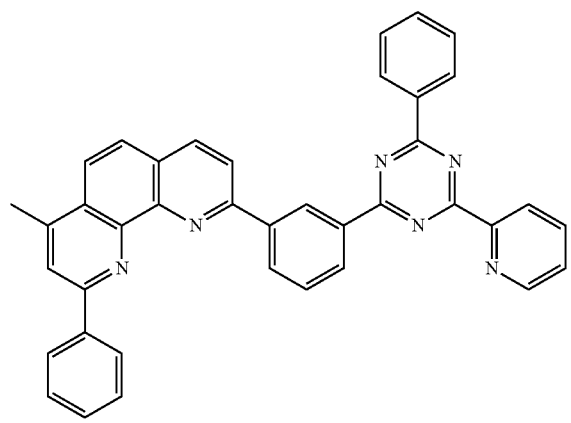
1090
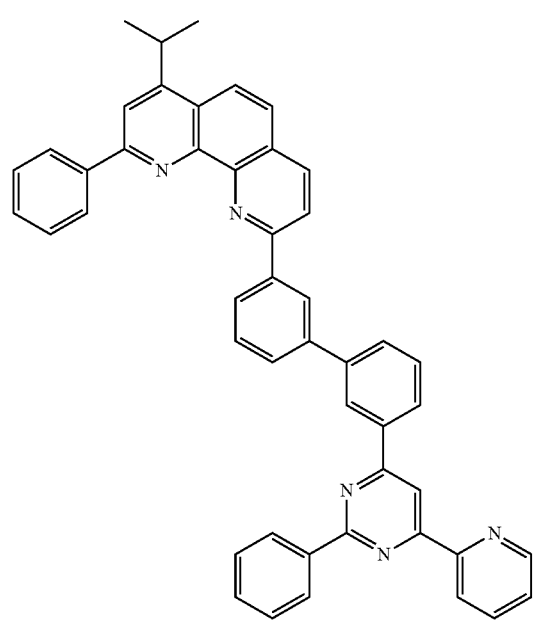
1091
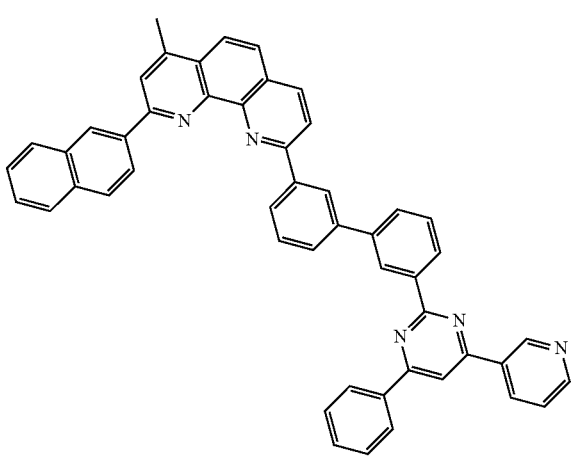
1092
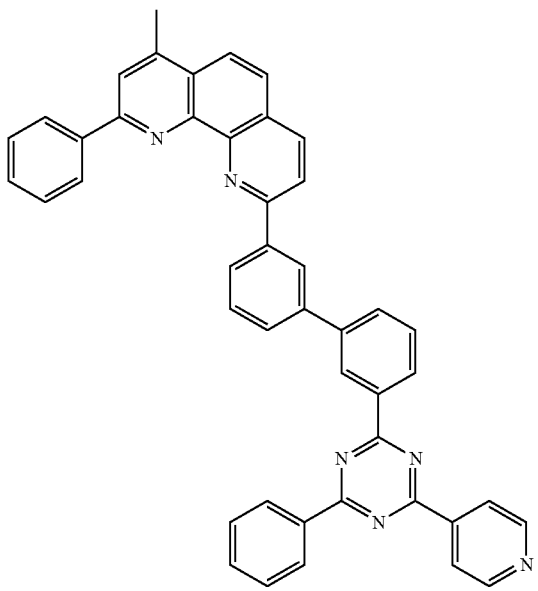
1093
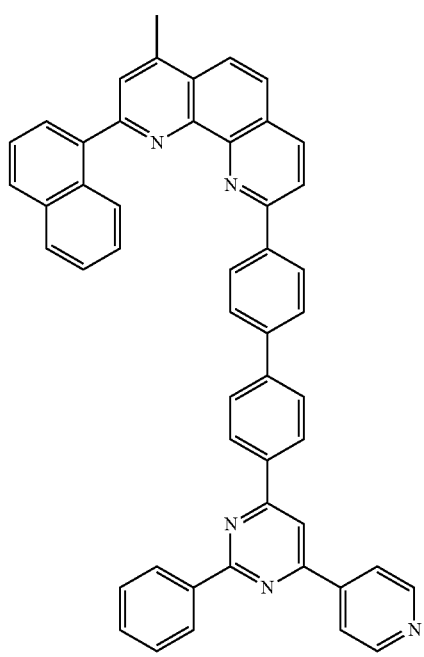

-continued
1094
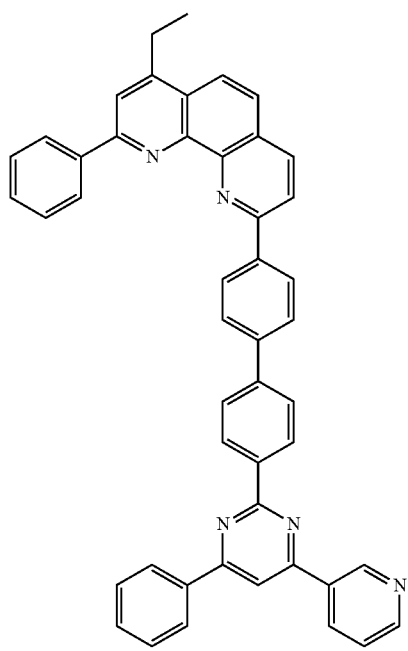
1095
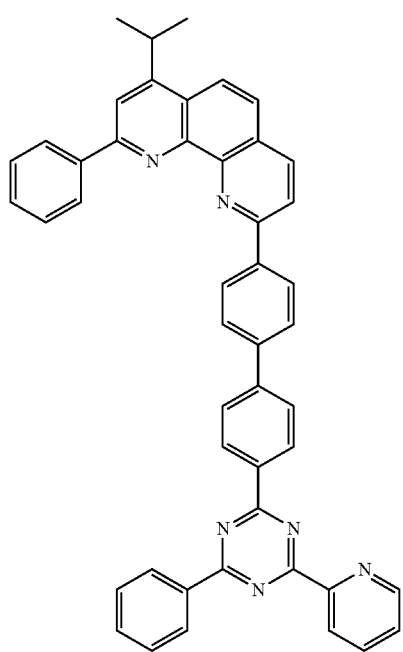
-continued
1096
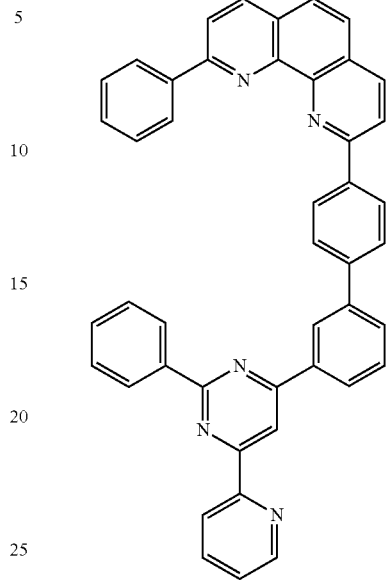
1097
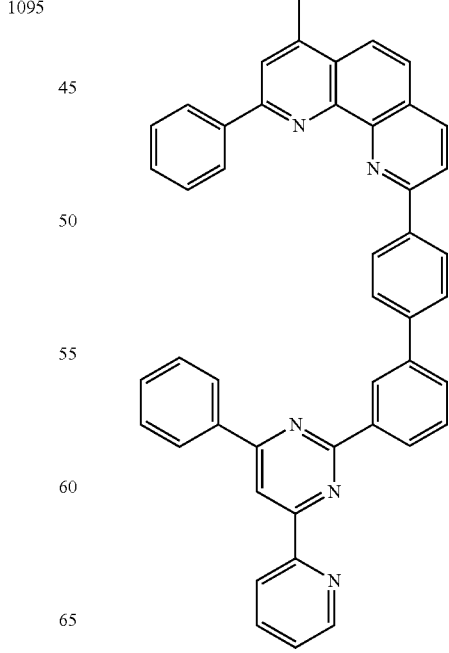

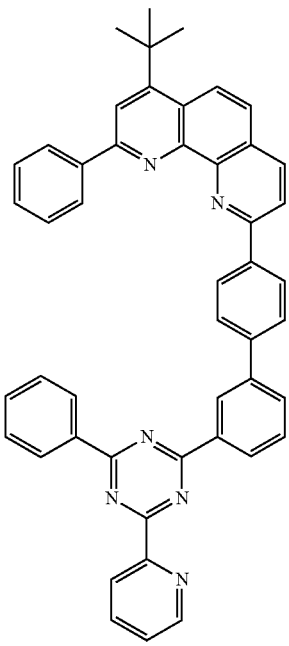
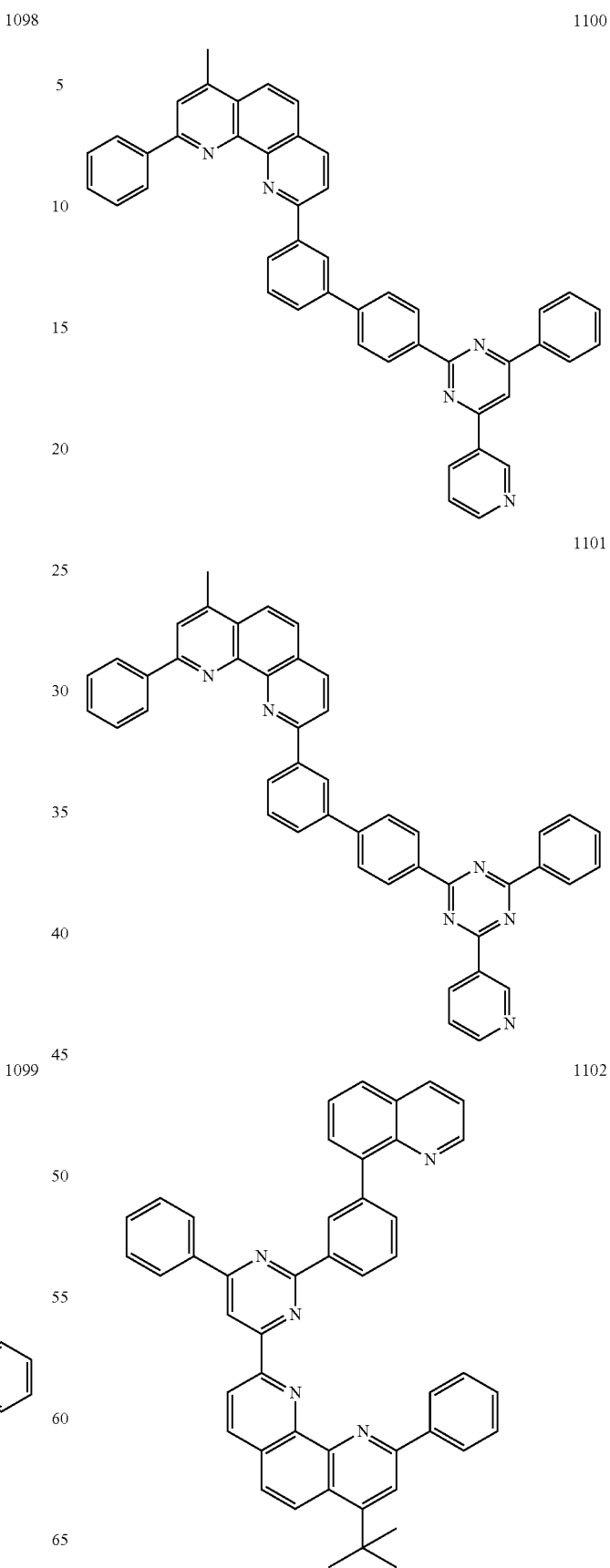

1103
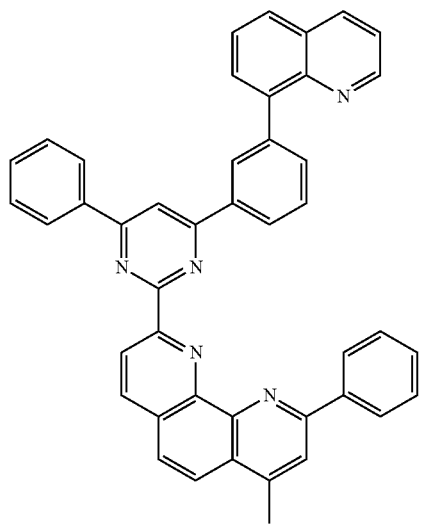
1104
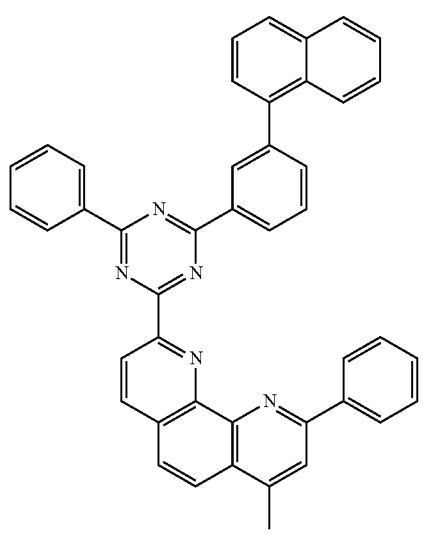
1105
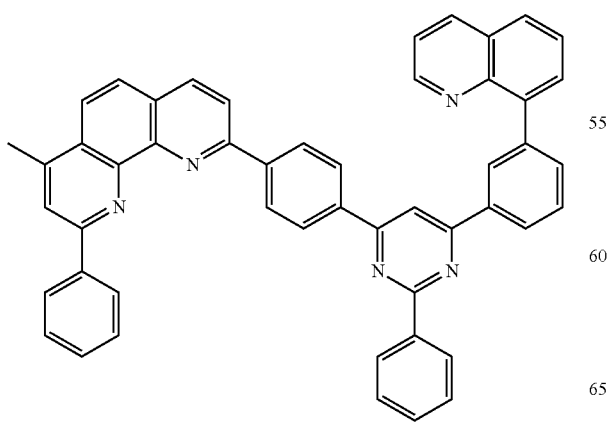
1106
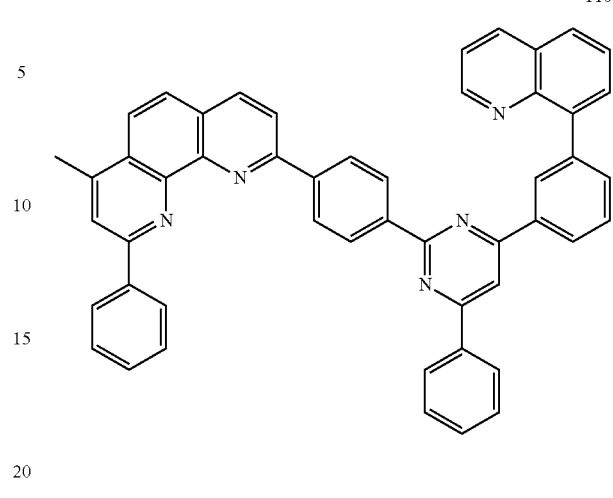
1107
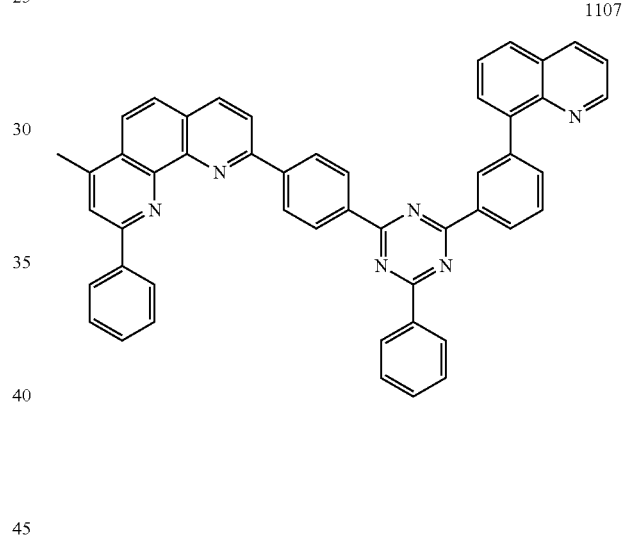
1108
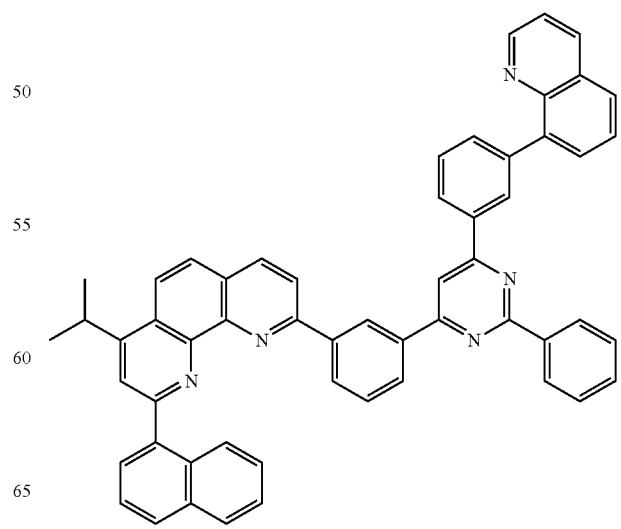

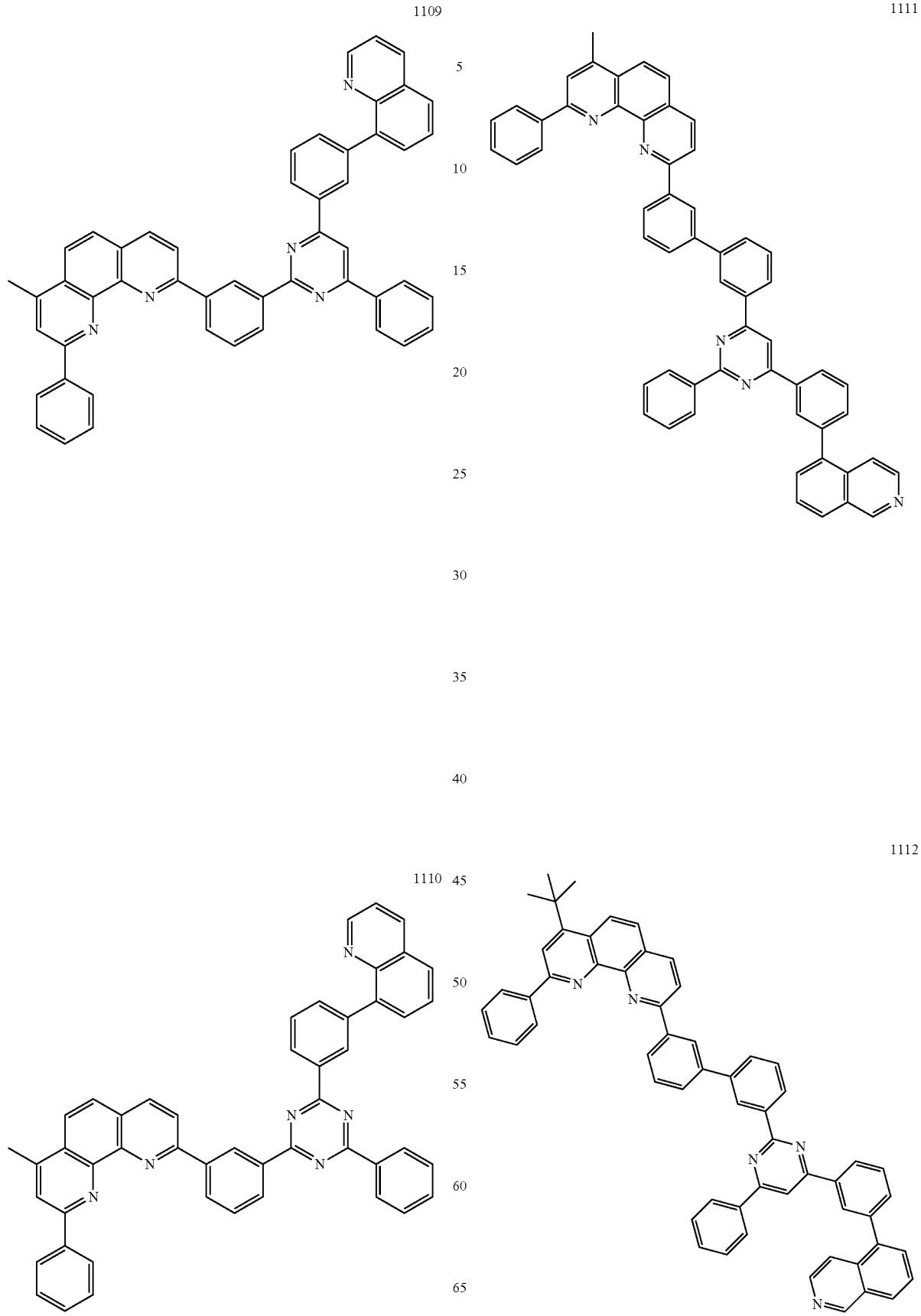

489
-continued
1113
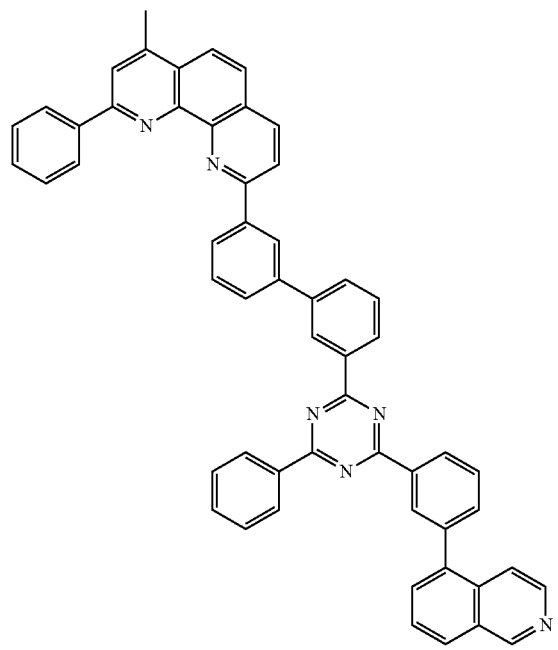
1114
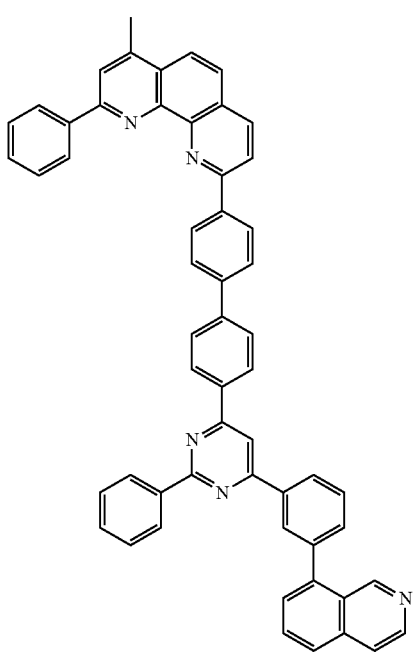
490
-continued
1115
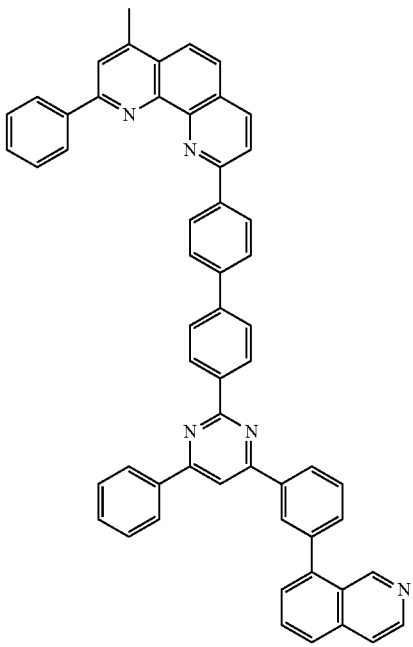
1116
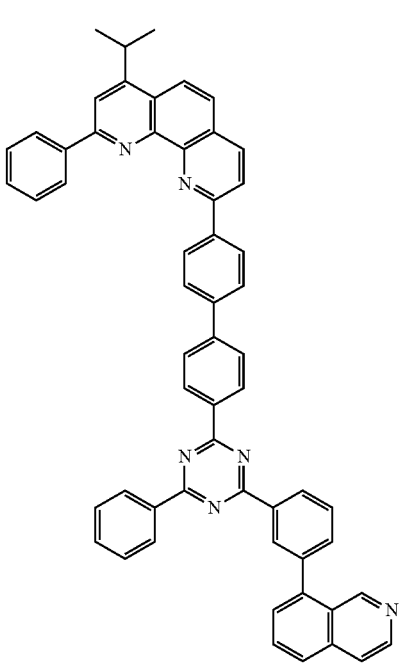

491
-continued
1117
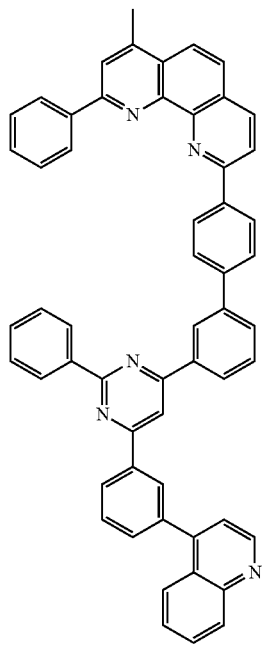
1118
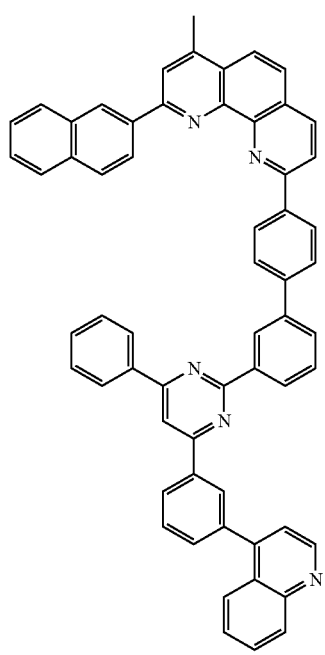
492
-continued
1119
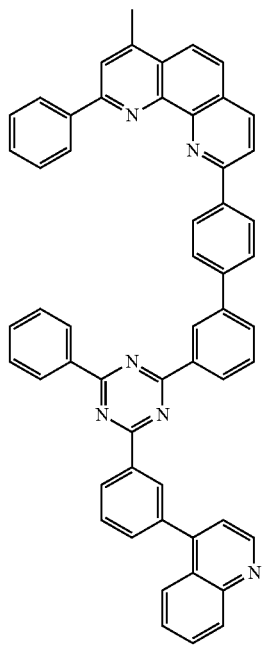
1120
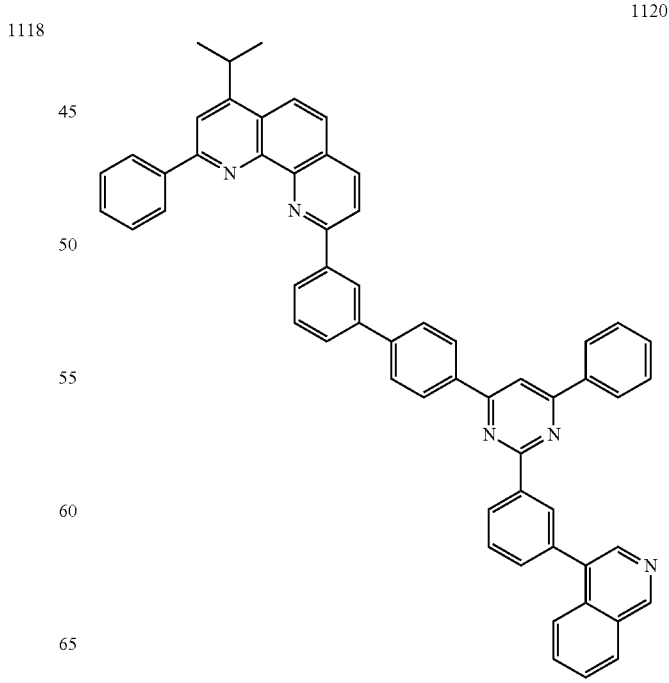

493
-continued
1121
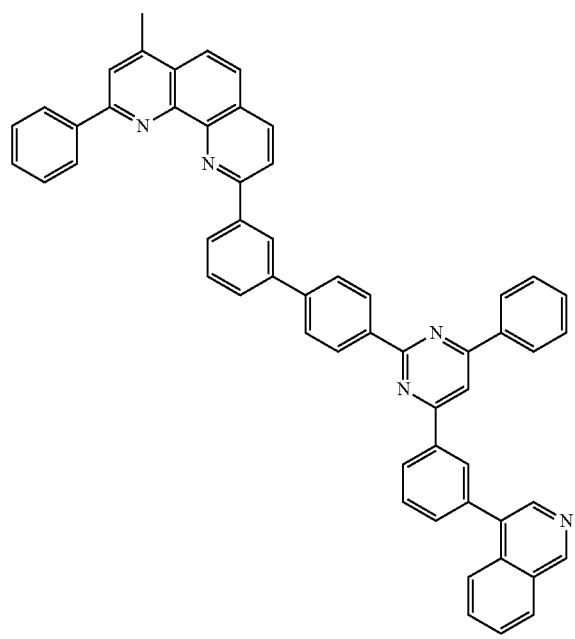
1122
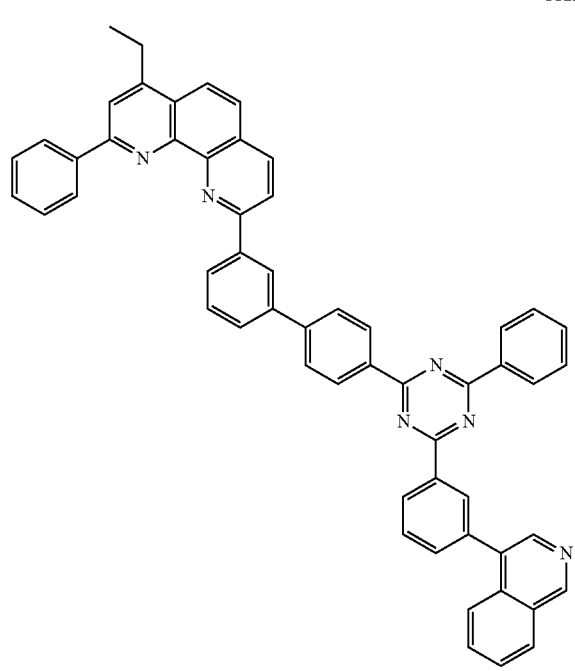
494
-continued
1123
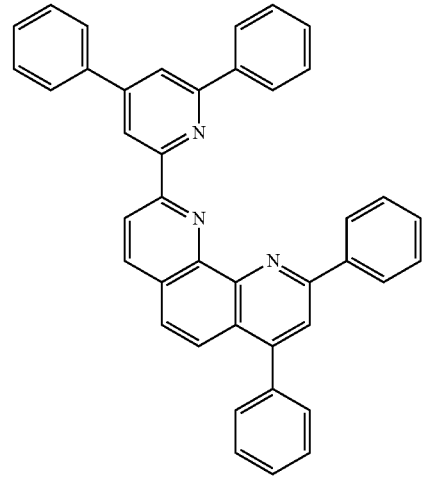
1124
1125
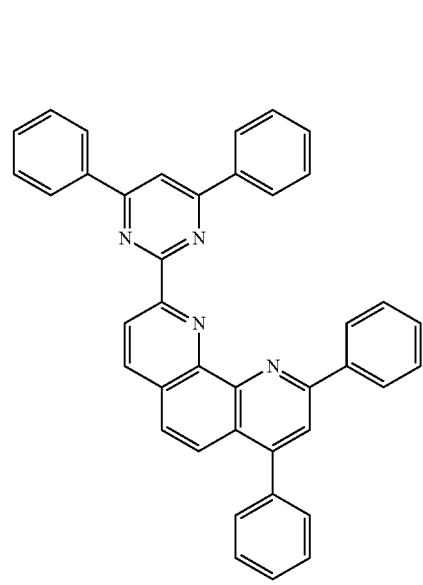

1126
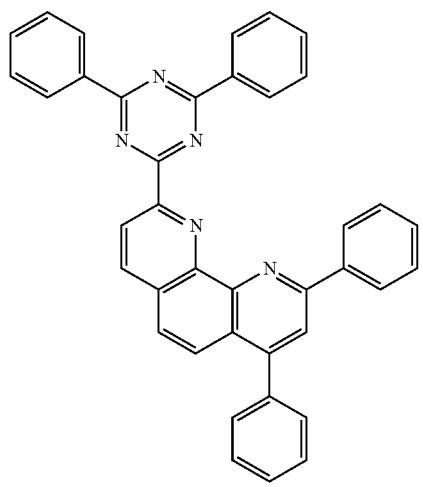
1127
1130
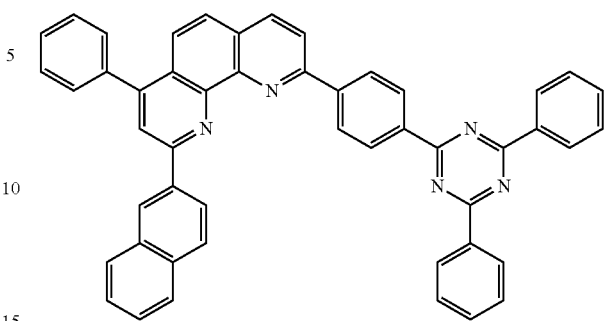
1131
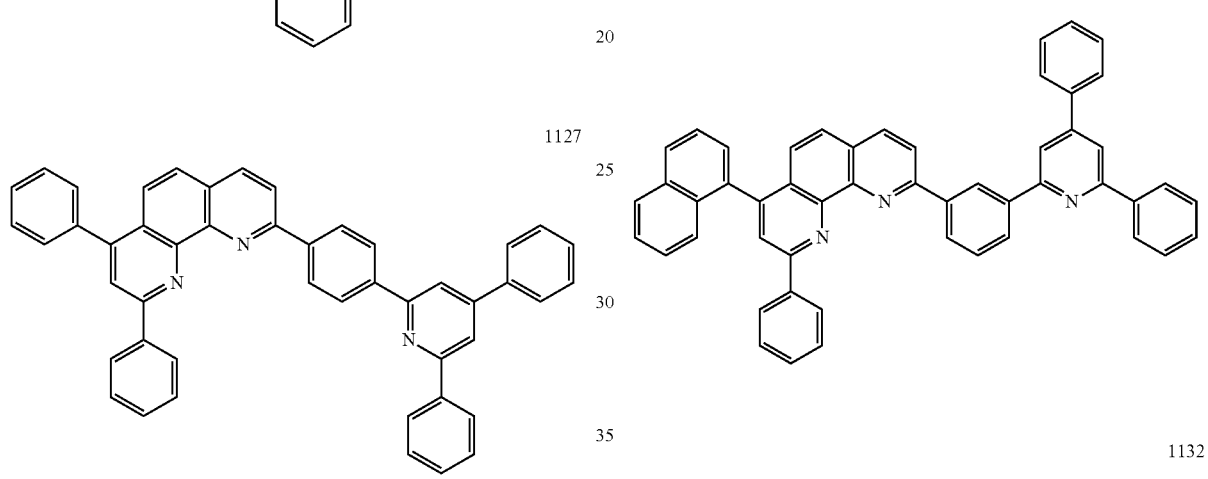
1128
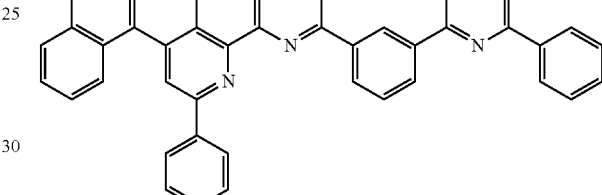
1132
1129
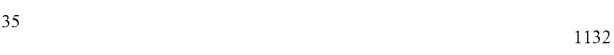
1133
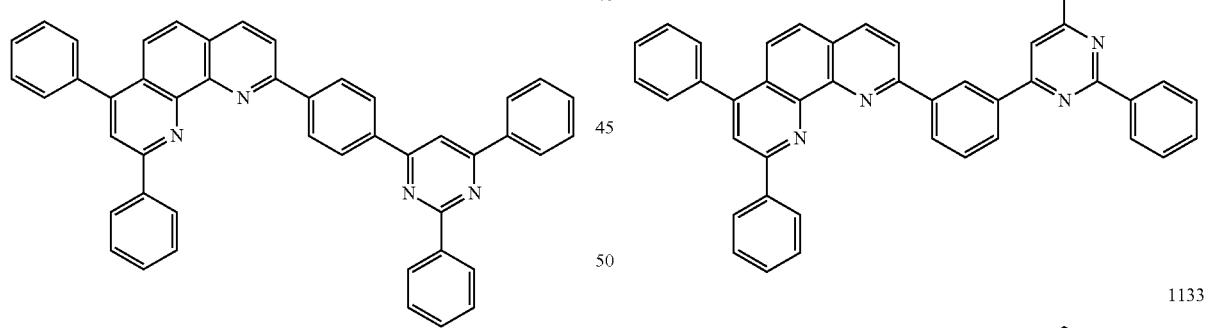
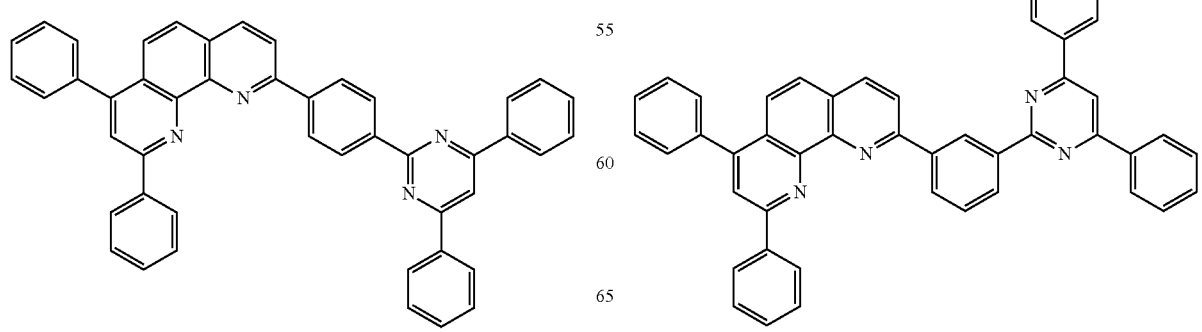

1134
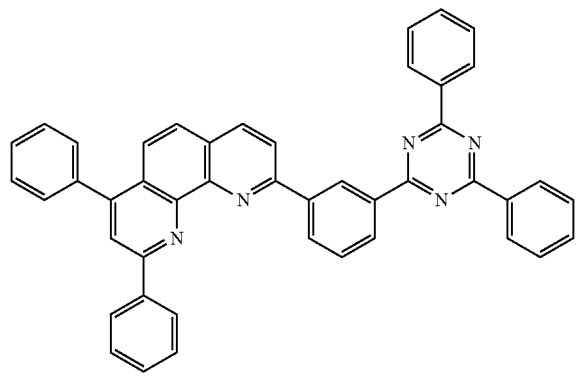
1135
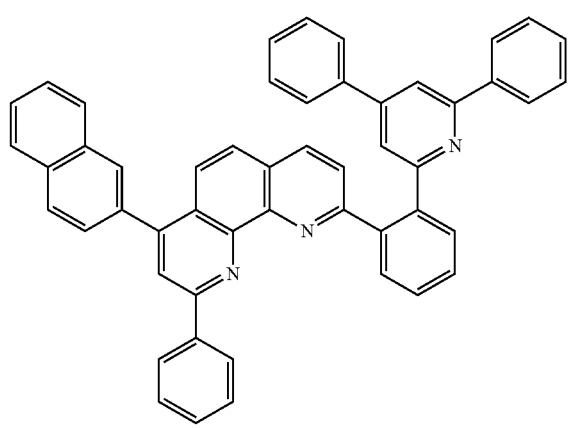
1136
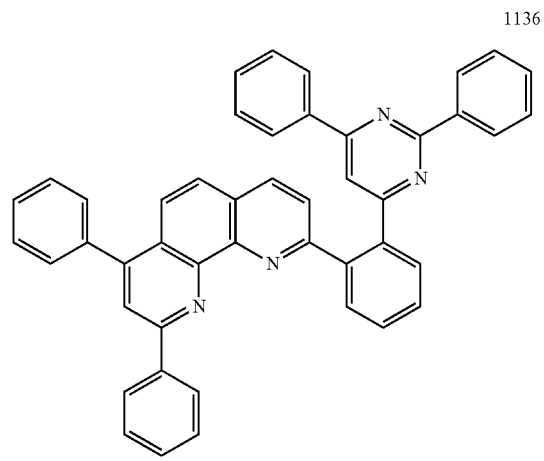
1137
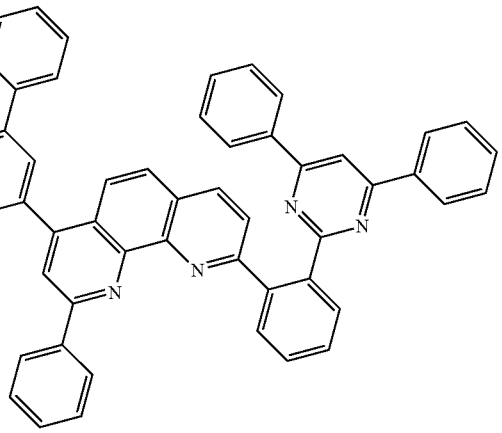
1138
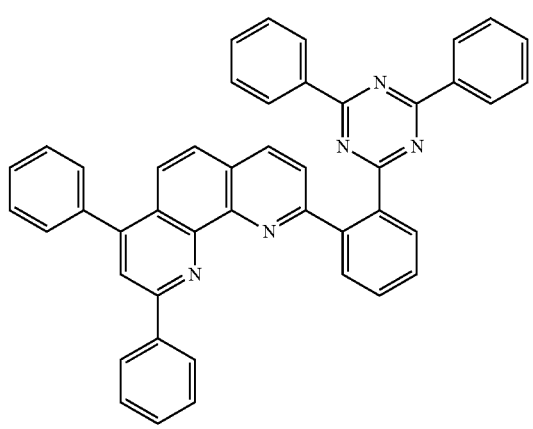
1139
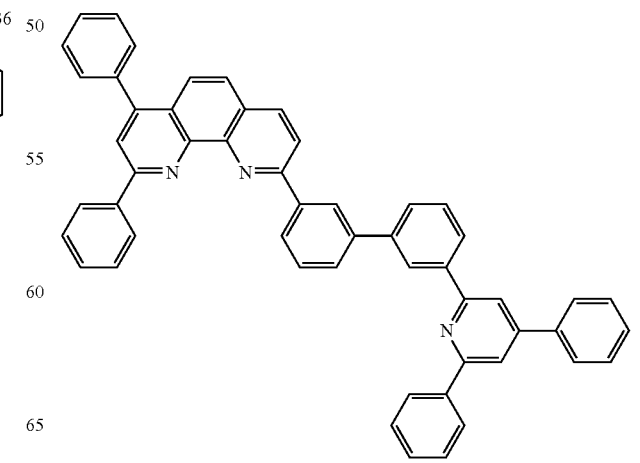

499
-continued
1140
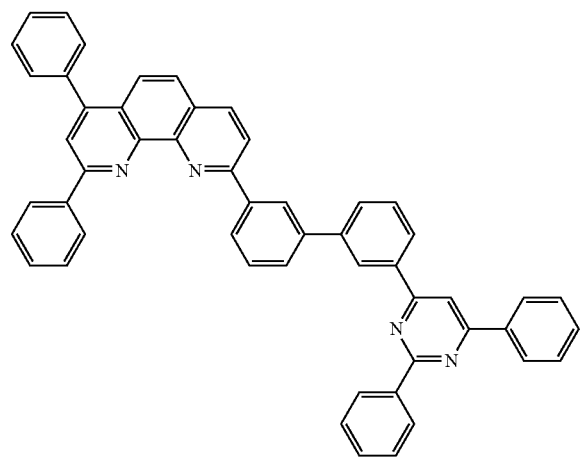
1141
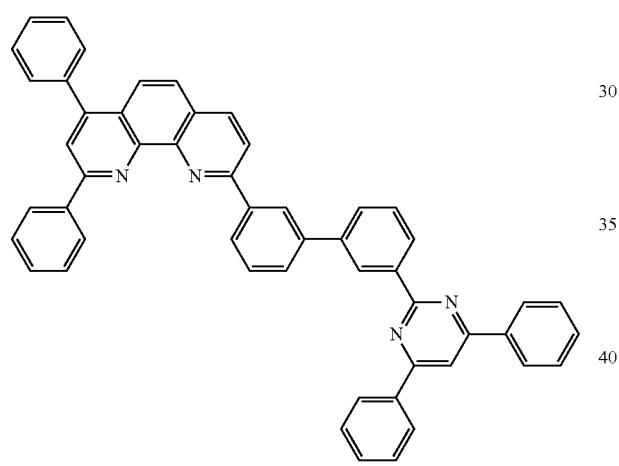
1142

500
-continued
1143
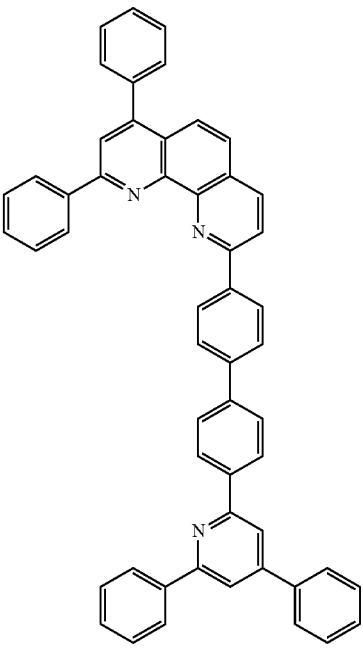
1144
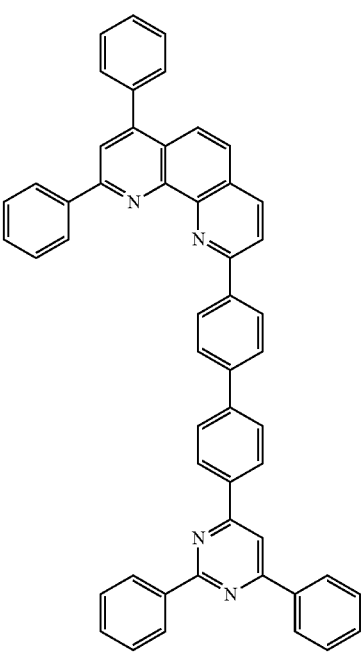

1145
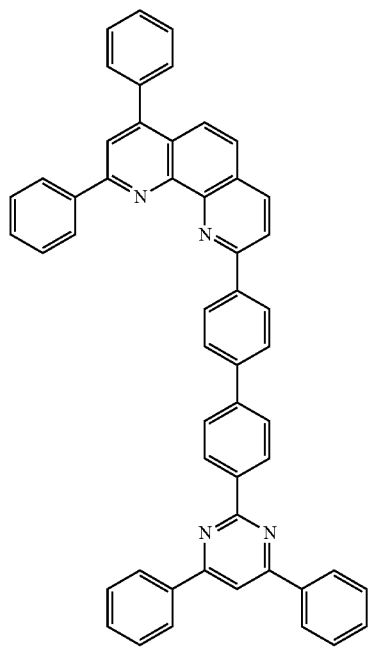
1147
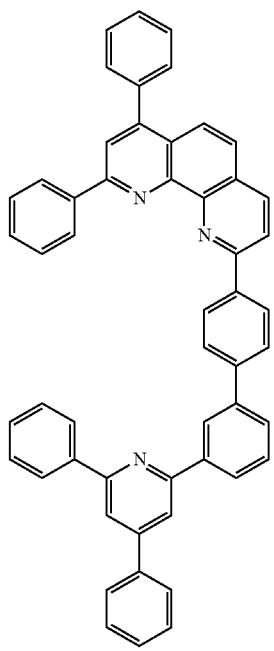
1146
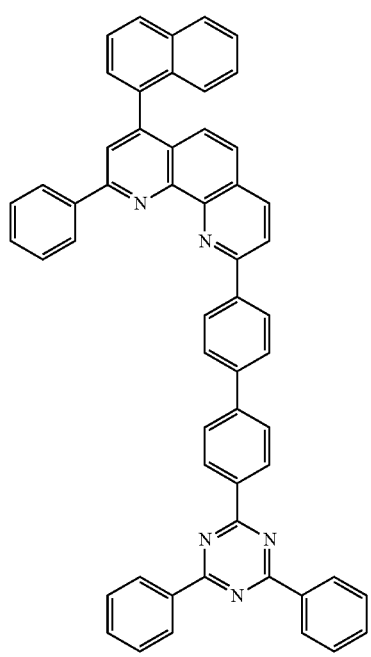
1148
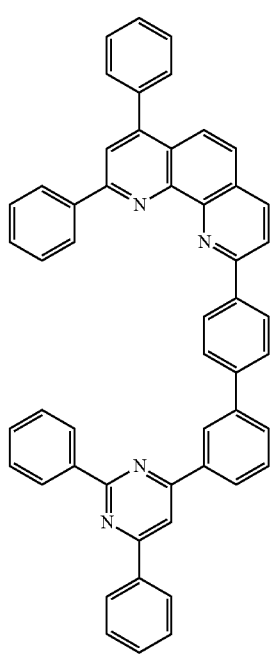

503
-continued
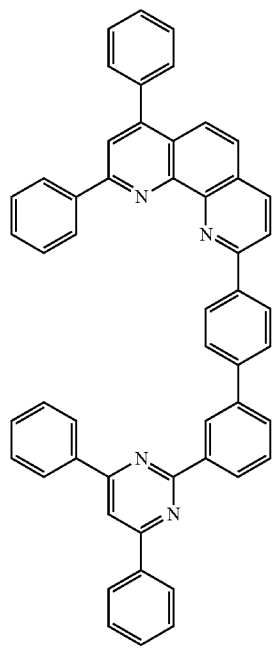
504
-continued
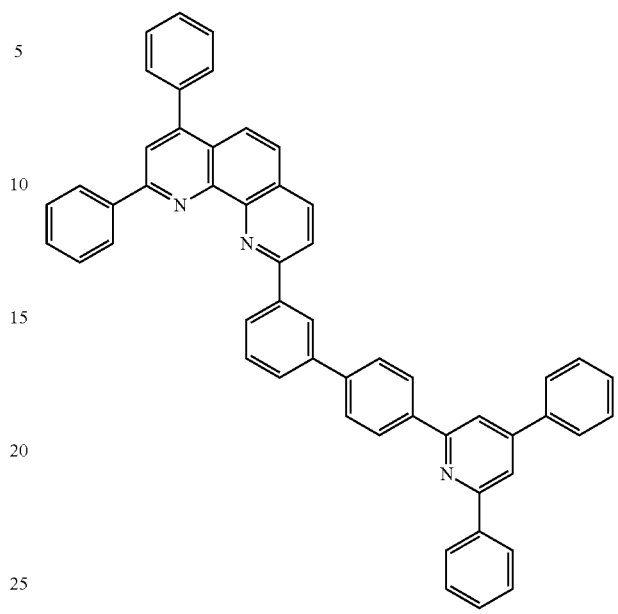
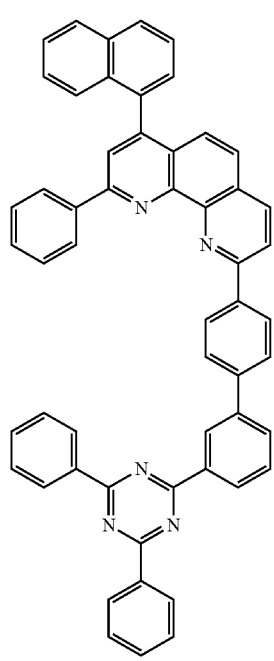
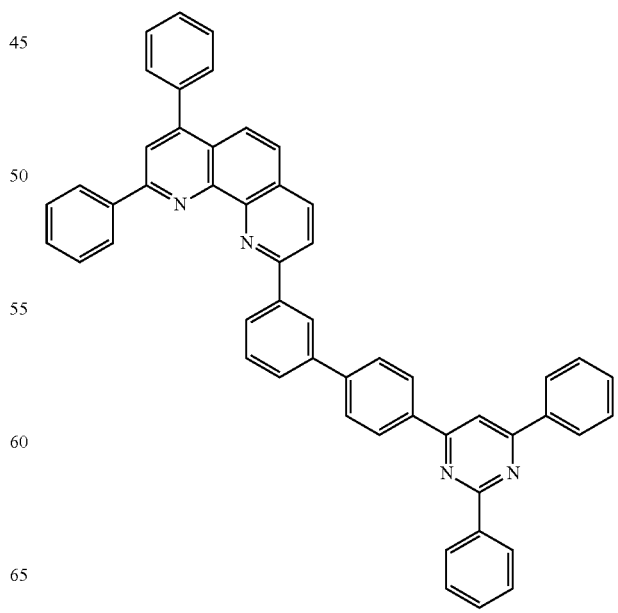

1153
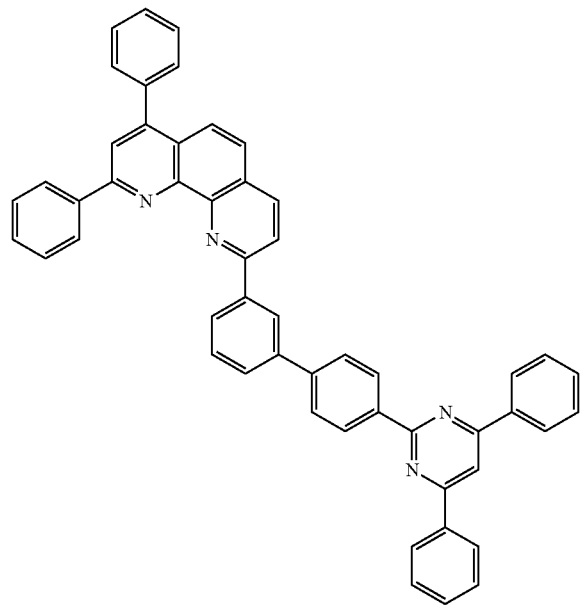
1154
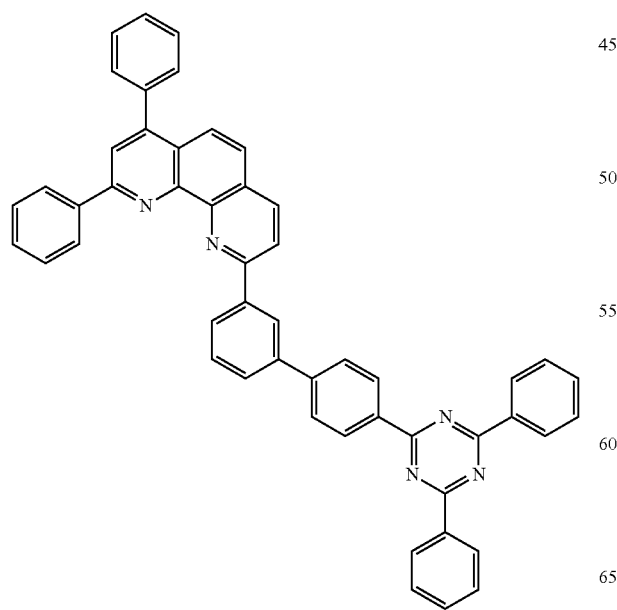
1155
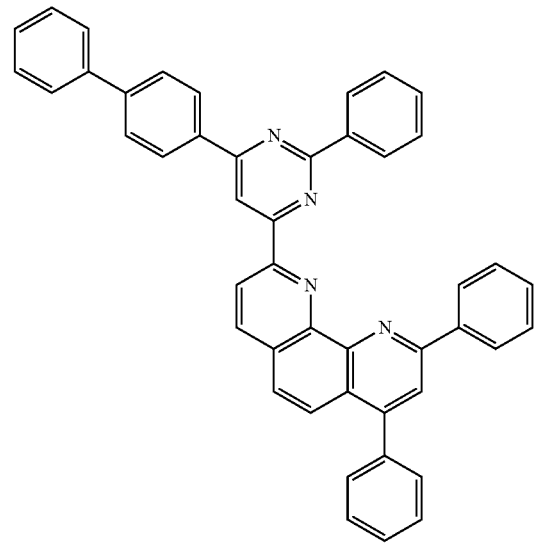
1156
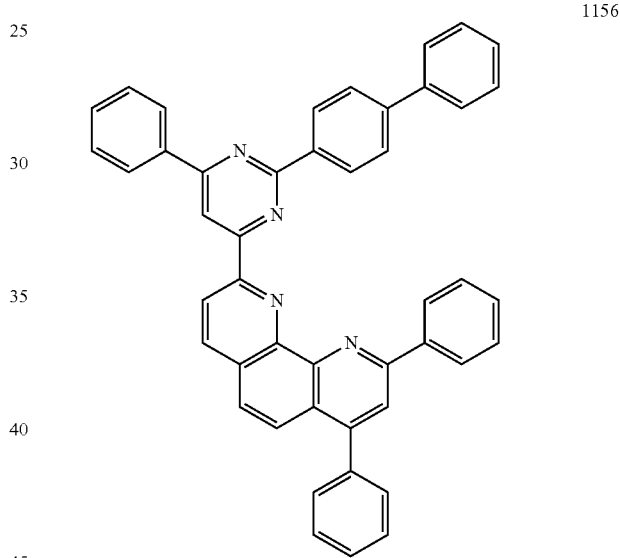
1157
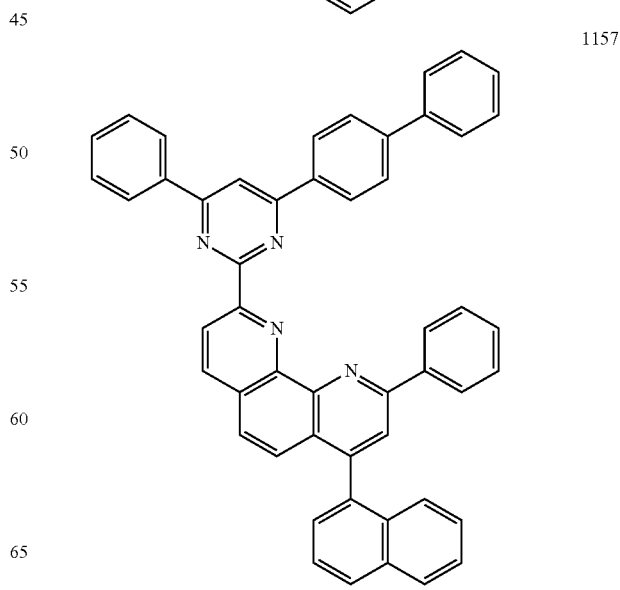

1158
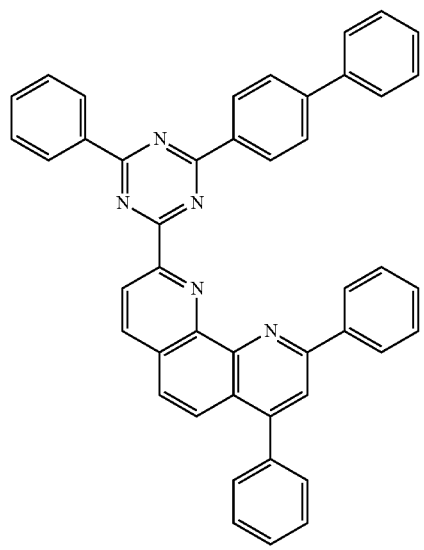
1159
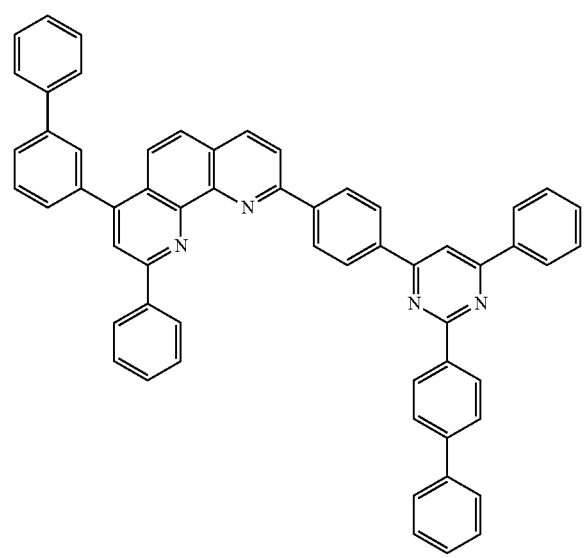
1160
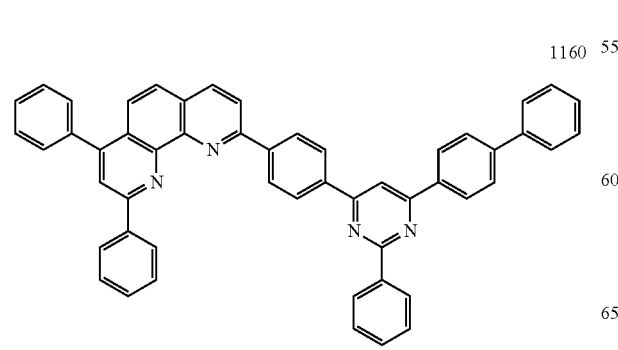
1161
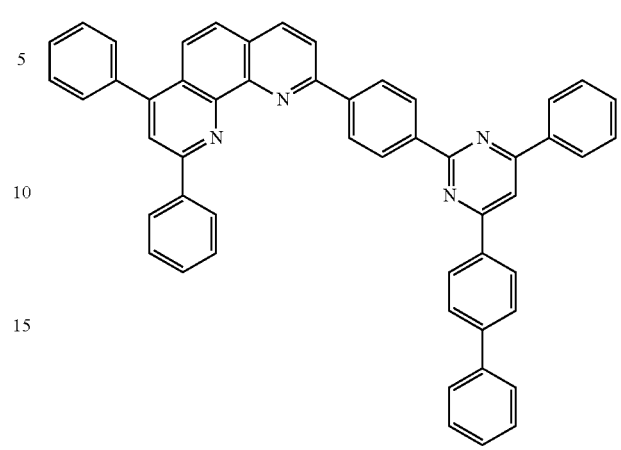
1162
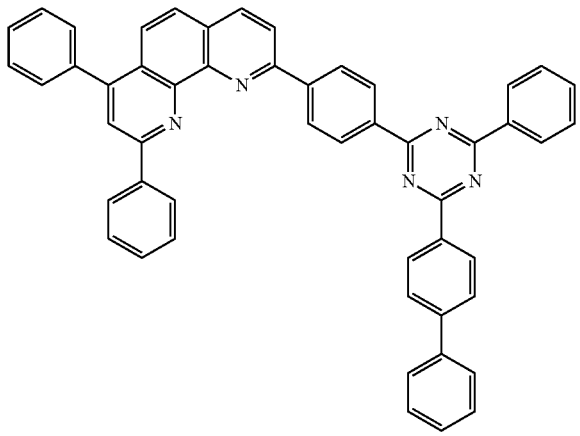
1163
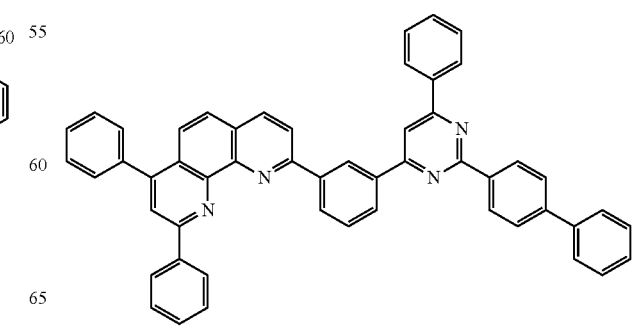

509
-continued
1164
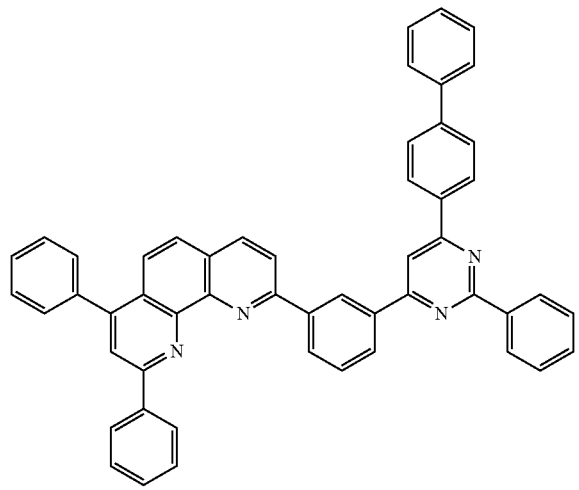
1165
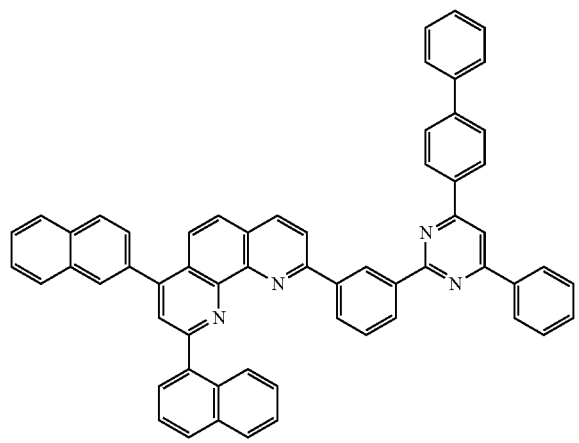
1166
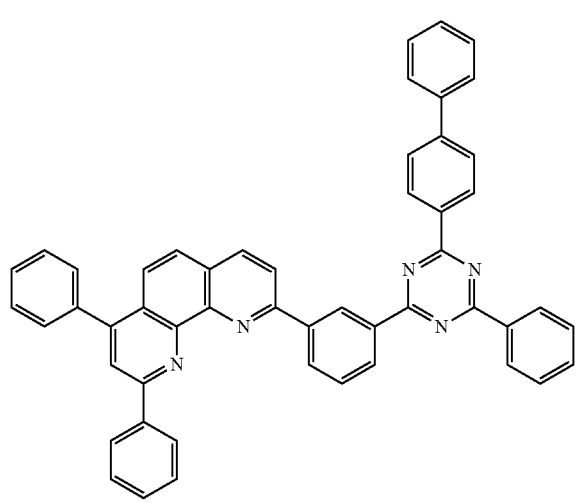
510
-continued
1167
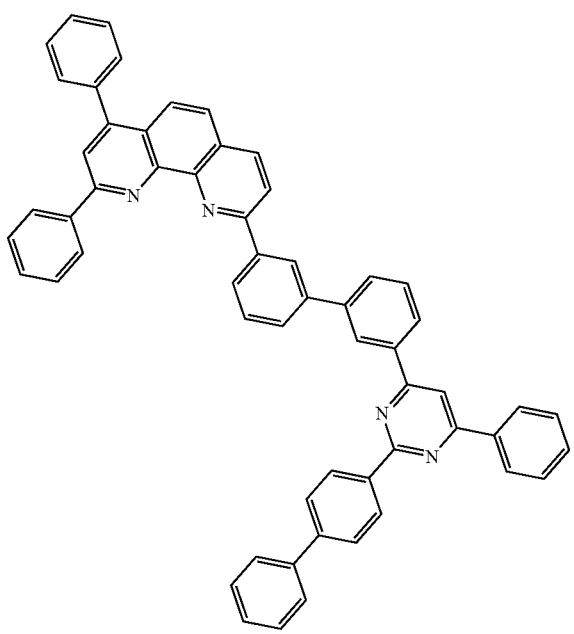
1168
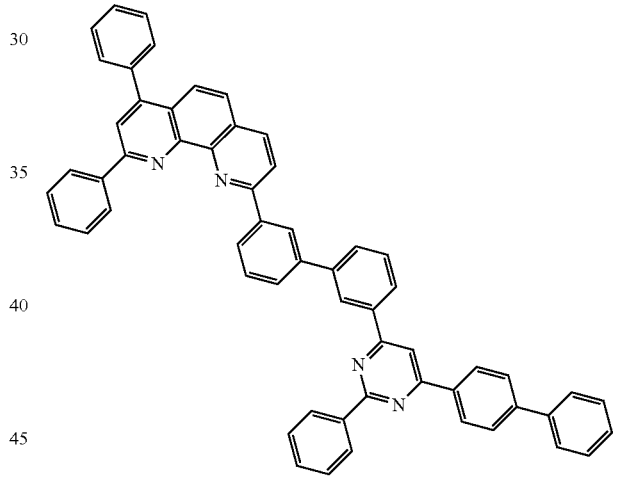
1169
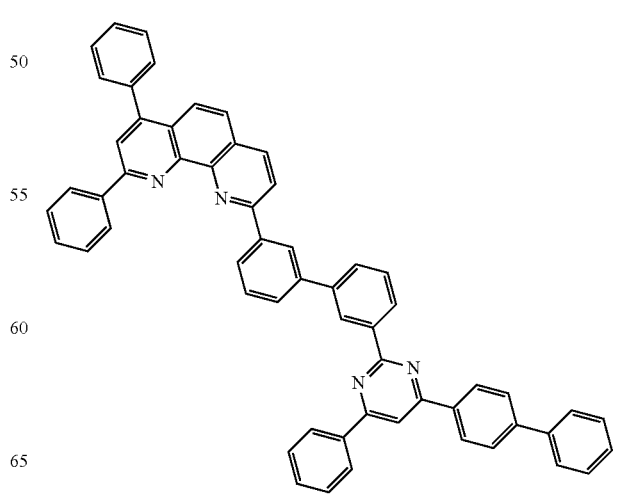

511
-continued
1170
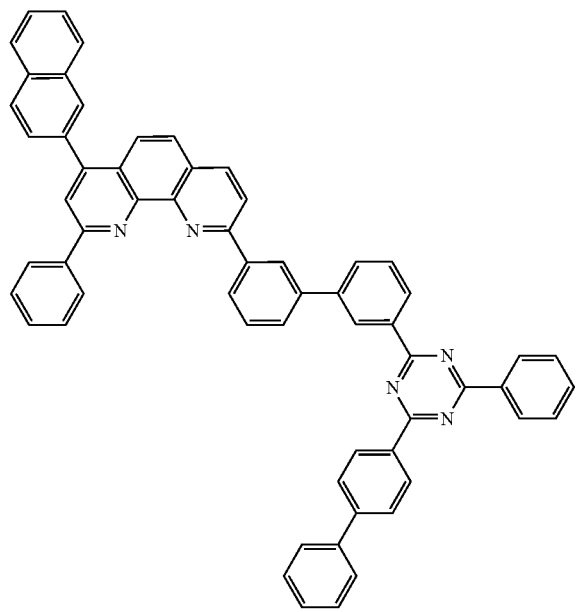
1171
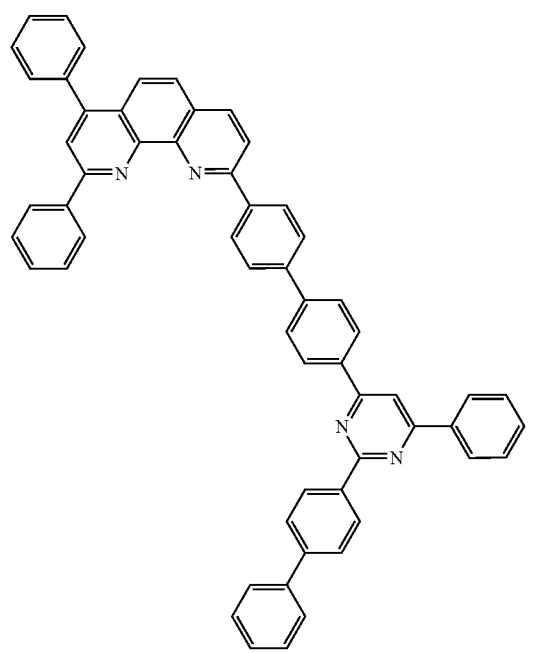
512
-continued
1172
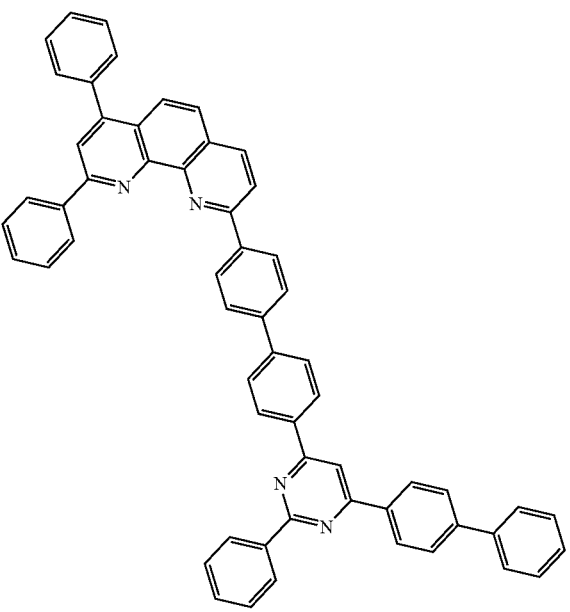
1173
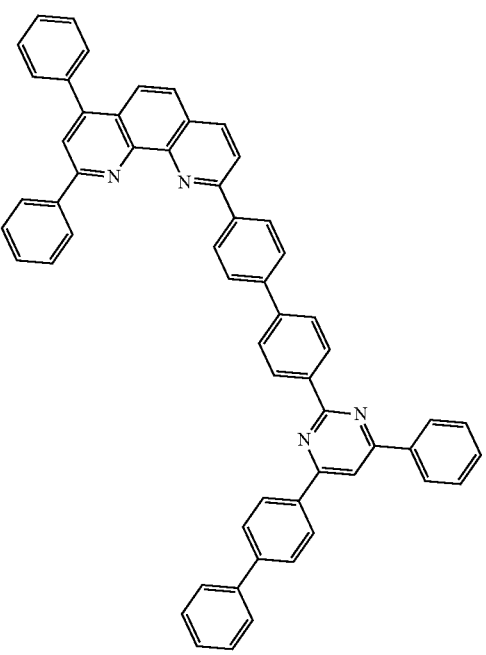

513
-continued
514
-continued
1174
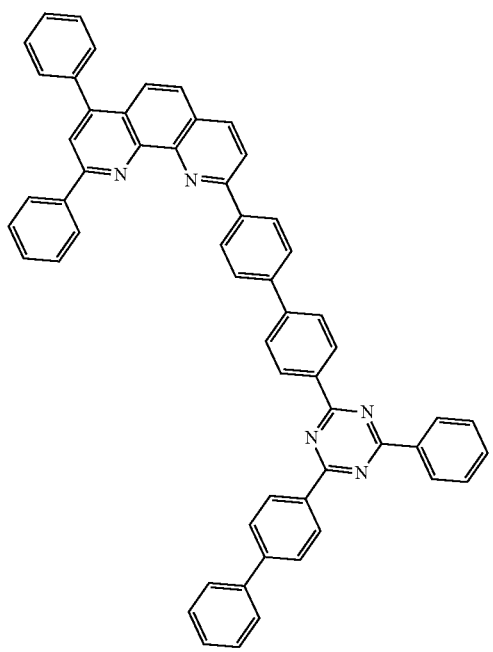
1176
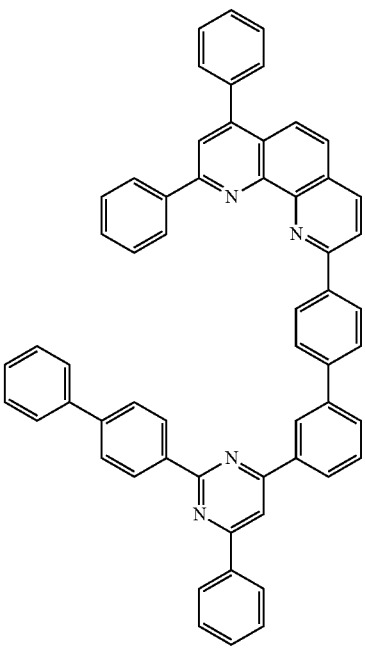
1175
1177

515
-continued
1178
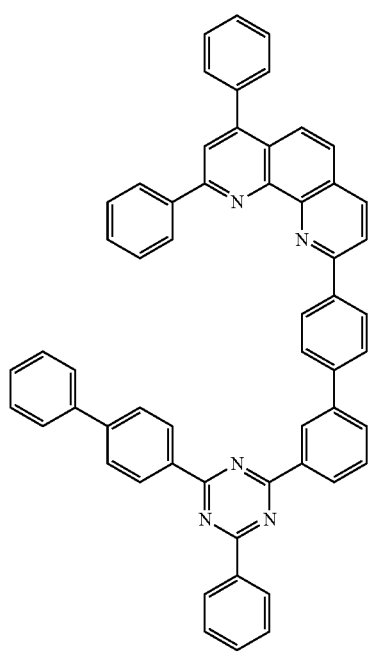
1179
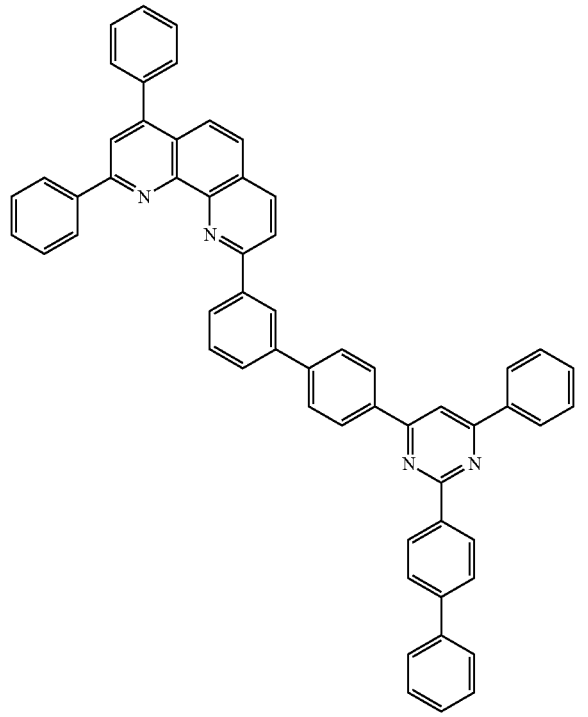
516
-continued
1180
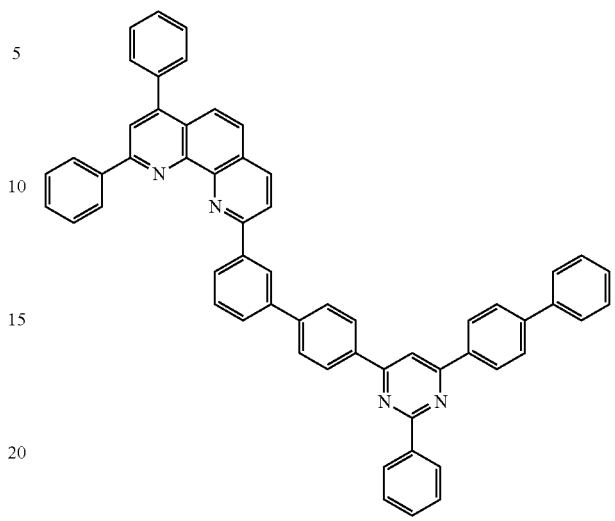
1181
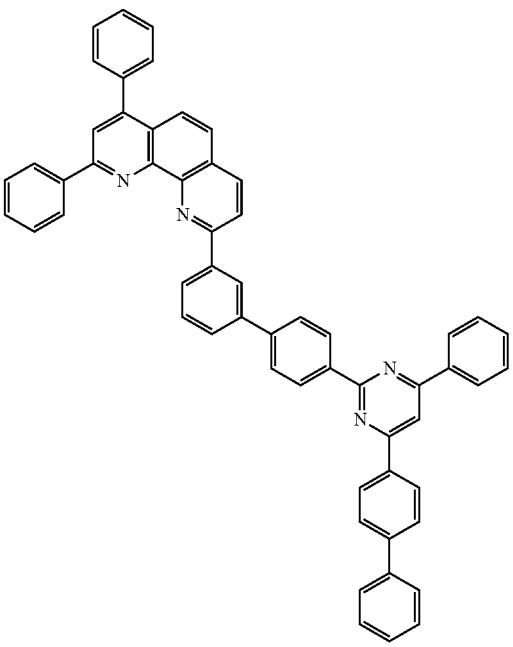

1182
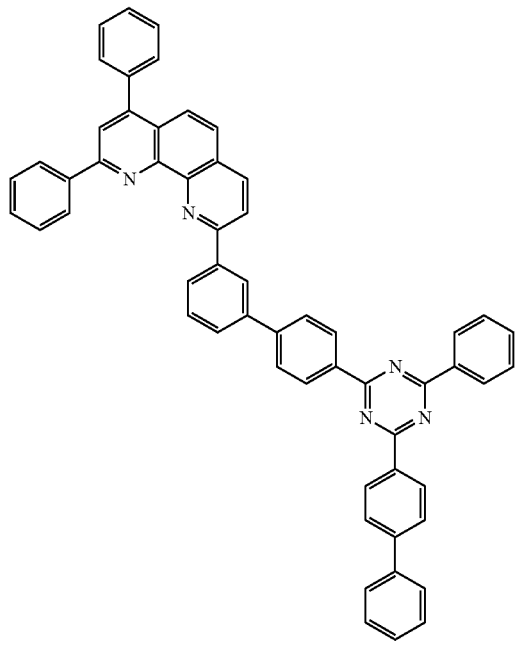
1183
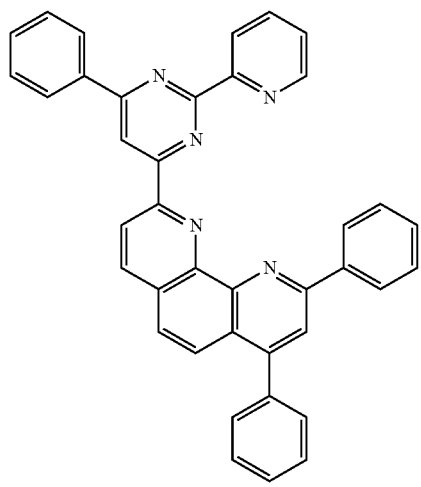
1184
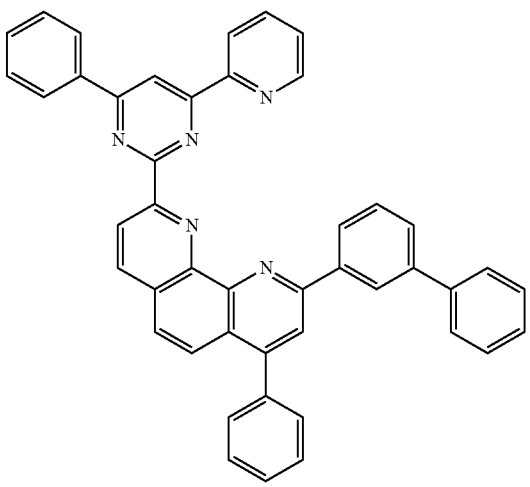
1185
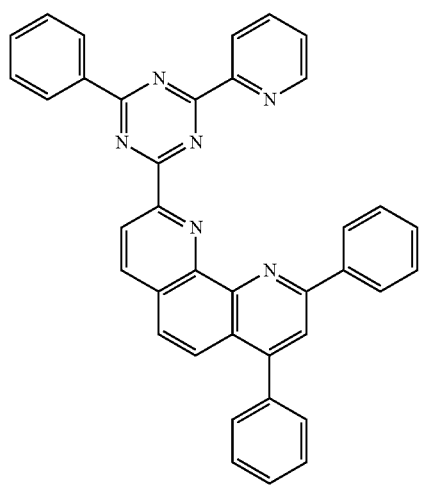
1186
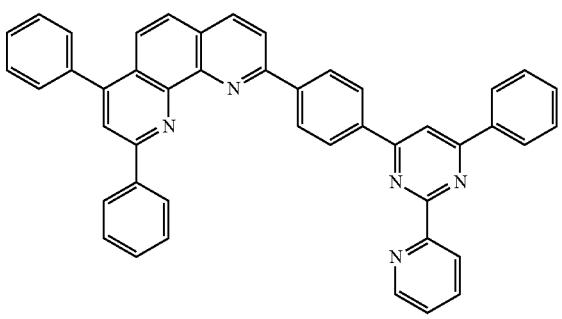

-continued
1187
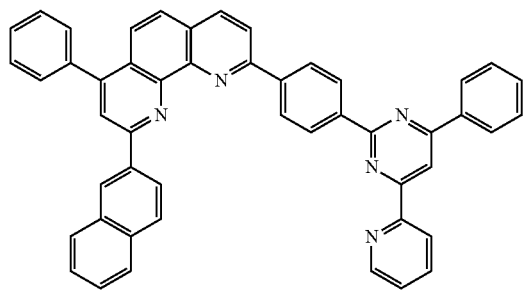
1188
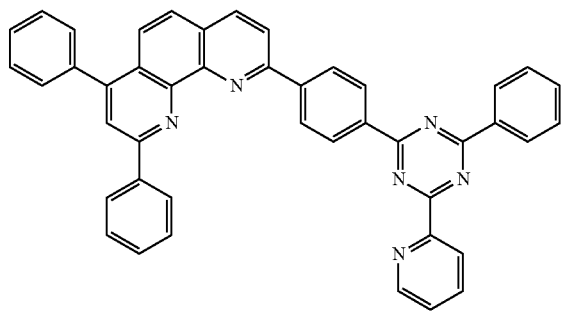
1189
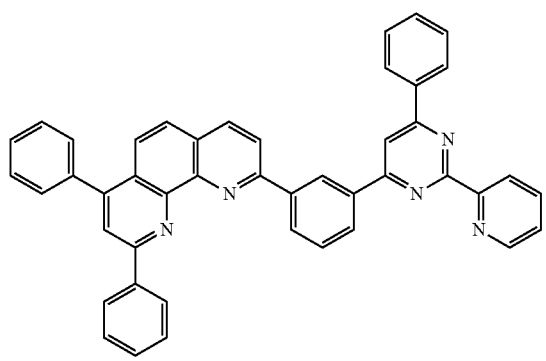
1190
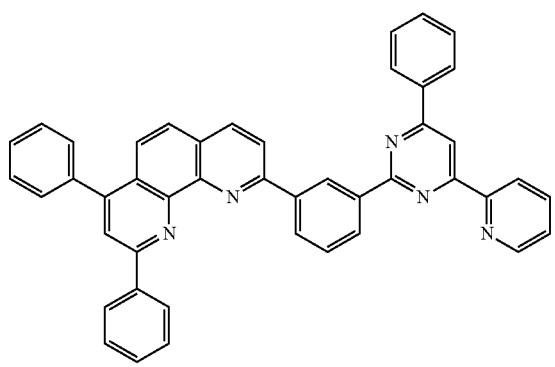
1191
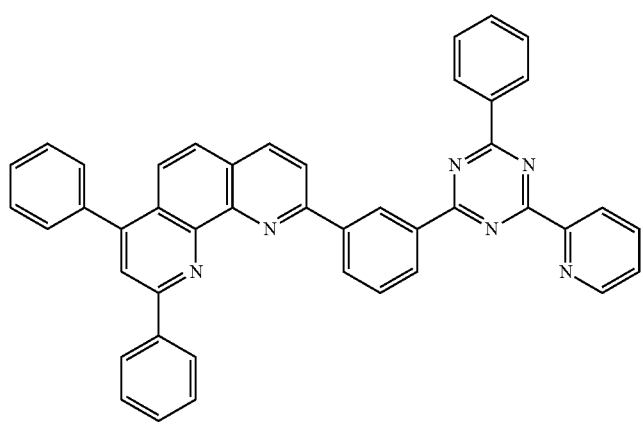
1192
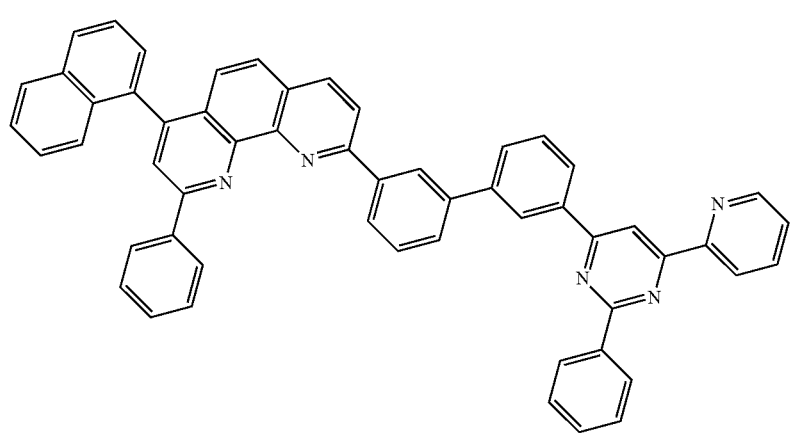

-continued
1193
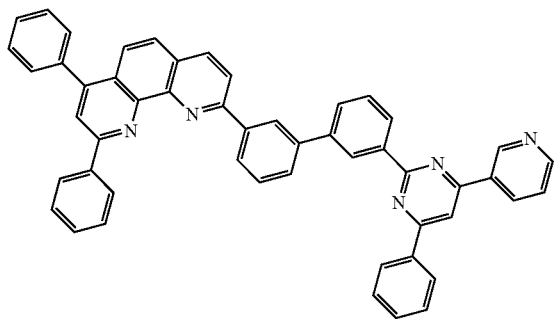
1194
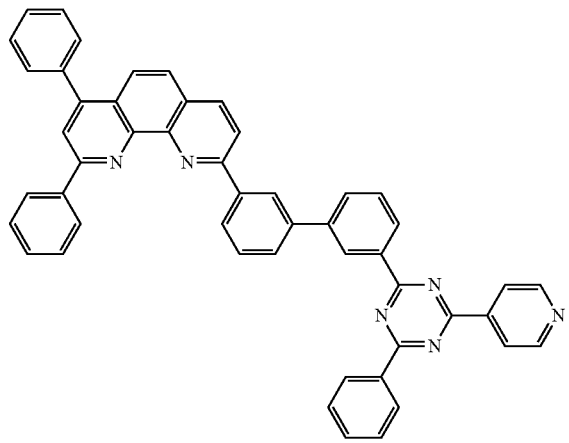
1195
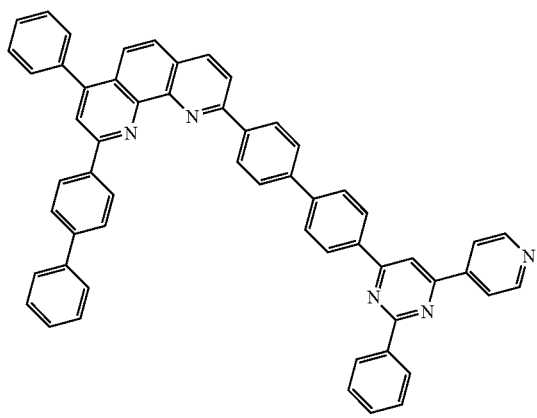
1196
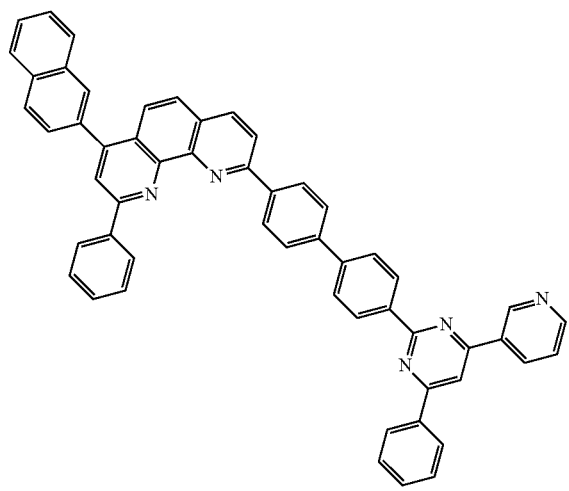
1197
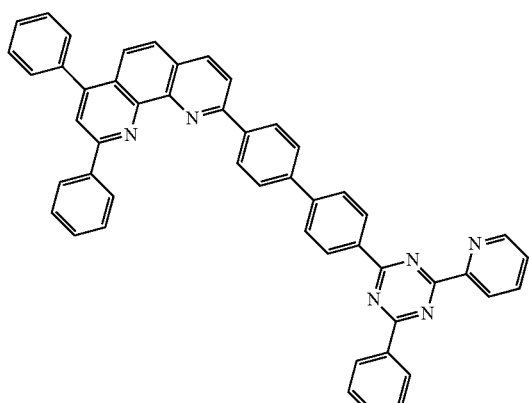
1198
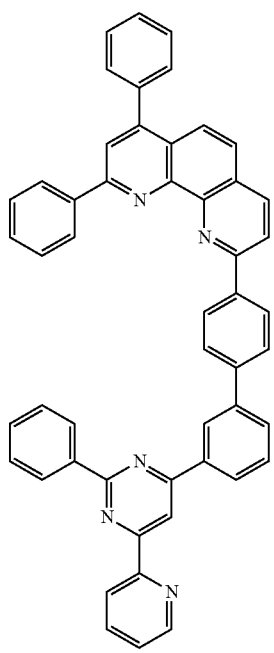

-continued
1199
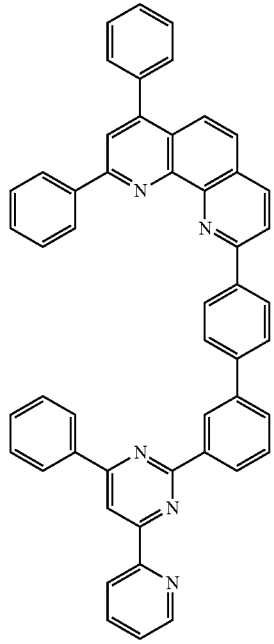
1200
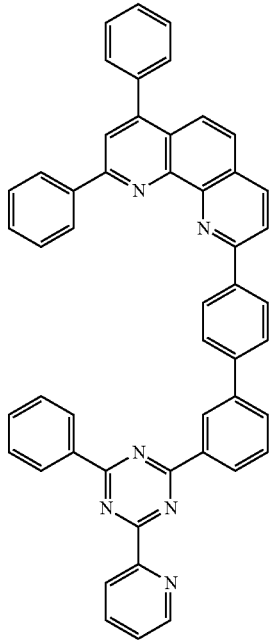
1201
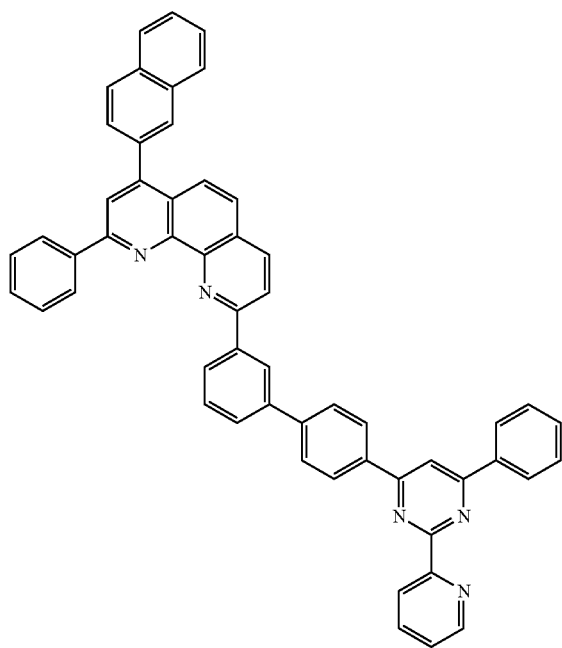
1202
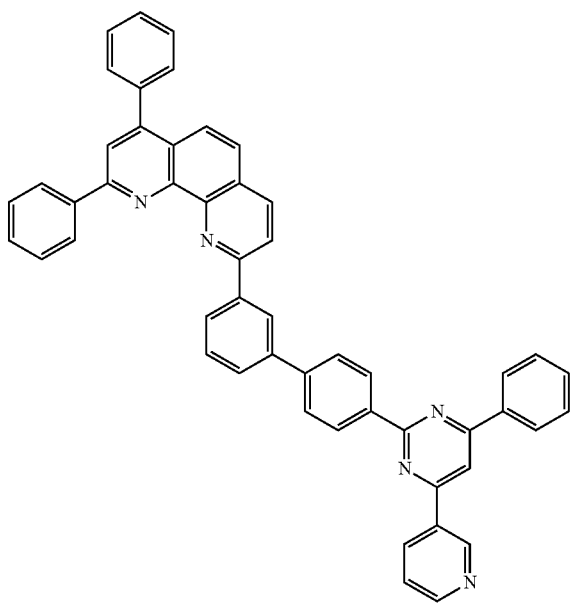

-continued
1203
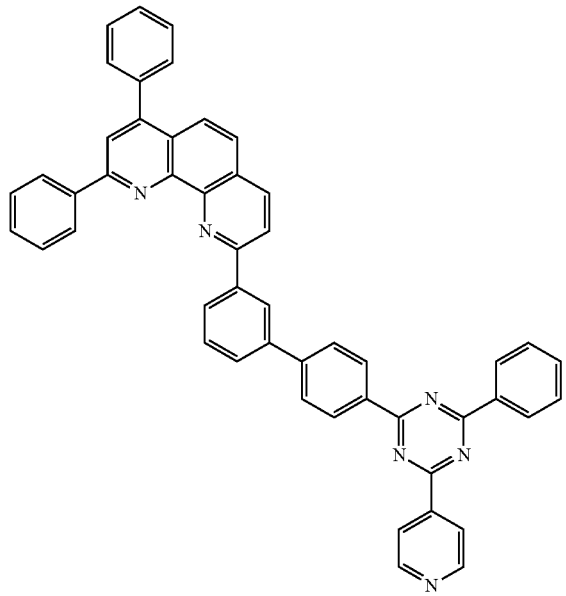
1204
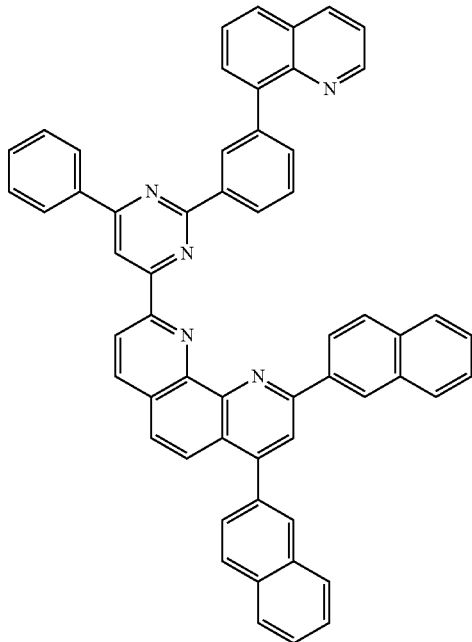
1205
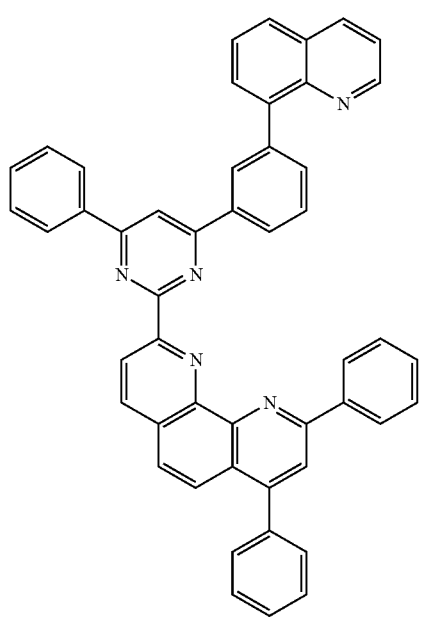
1206
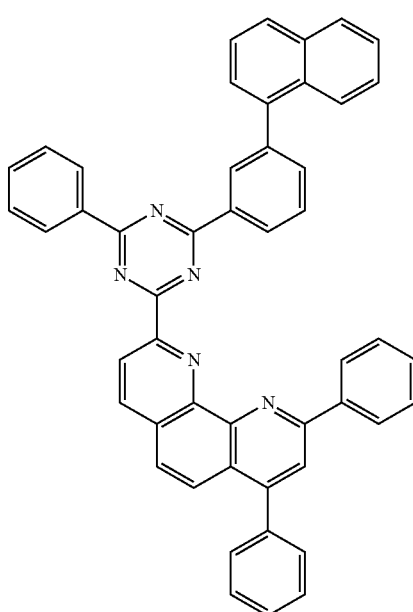
1207
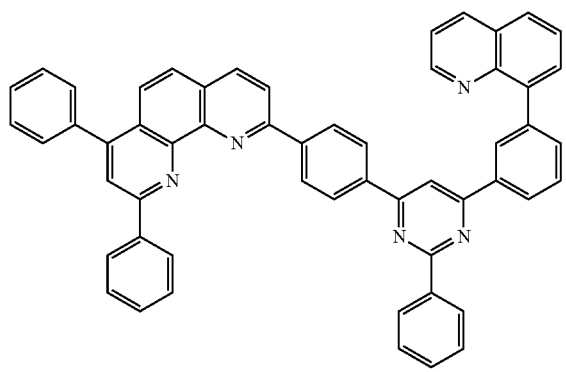
1208
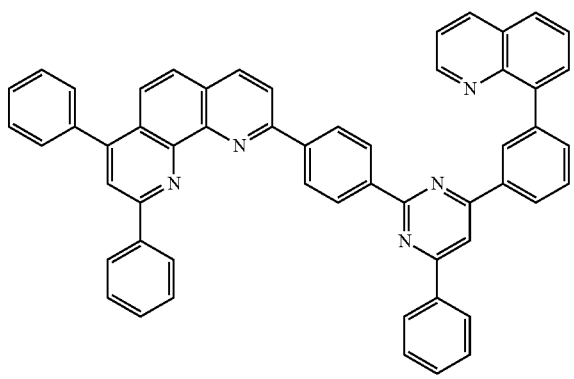

-continued
1209
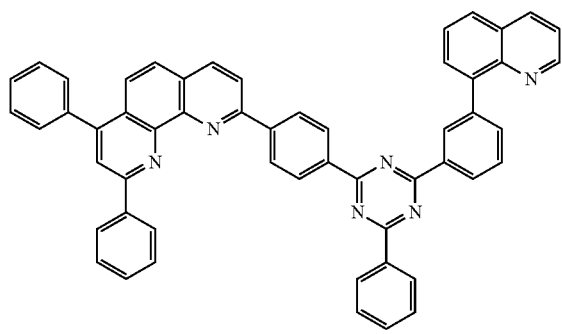
1210
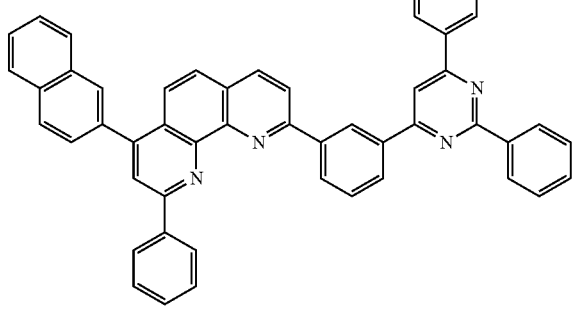
1211
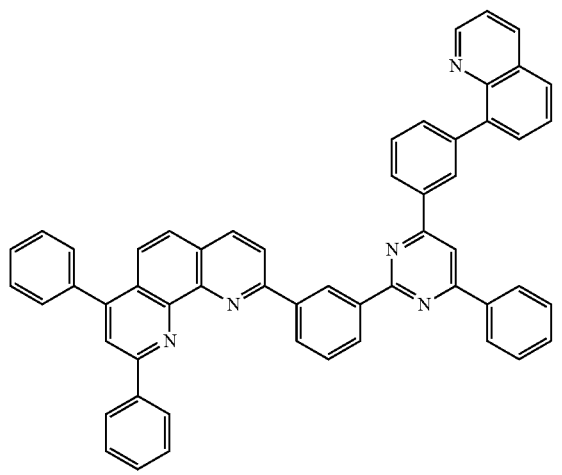
1212
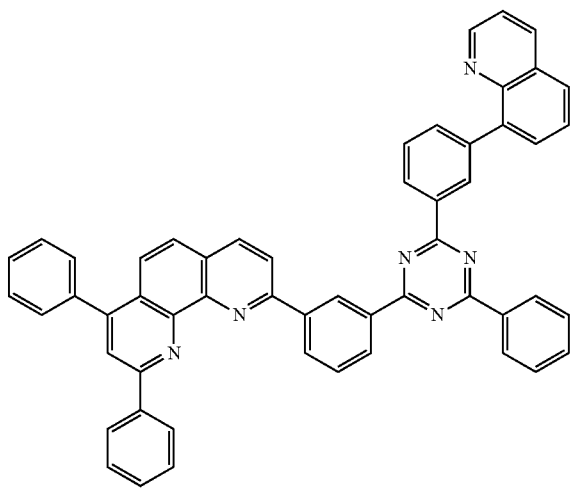
1213
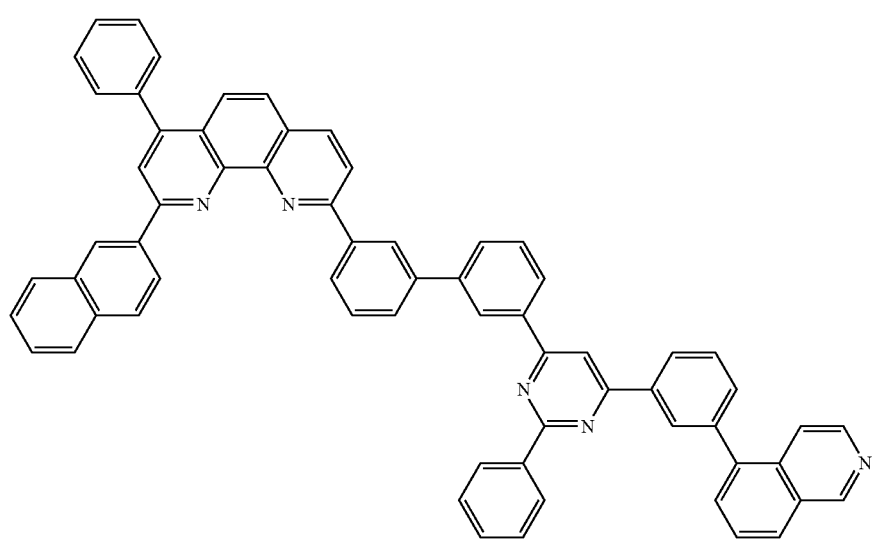

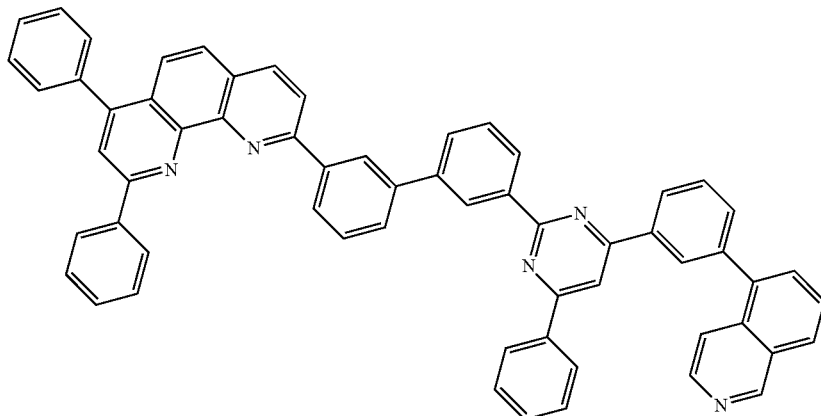
1214
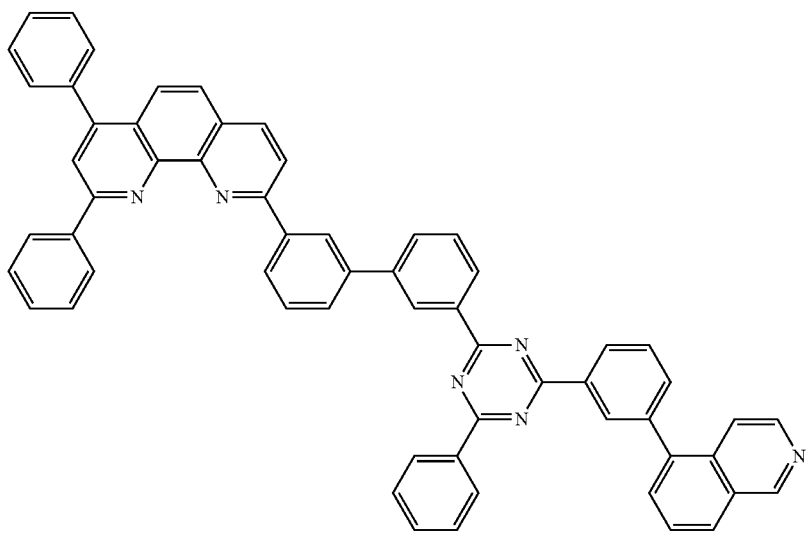
1215
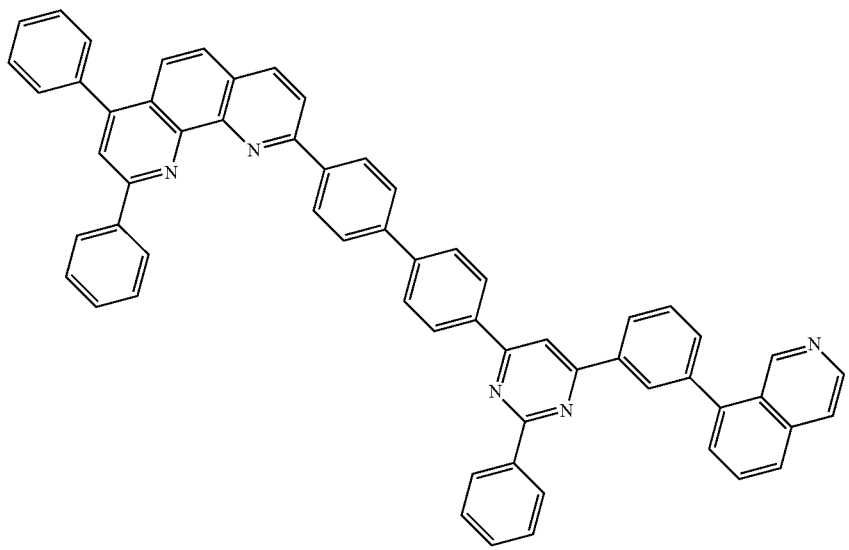
1216

-continued
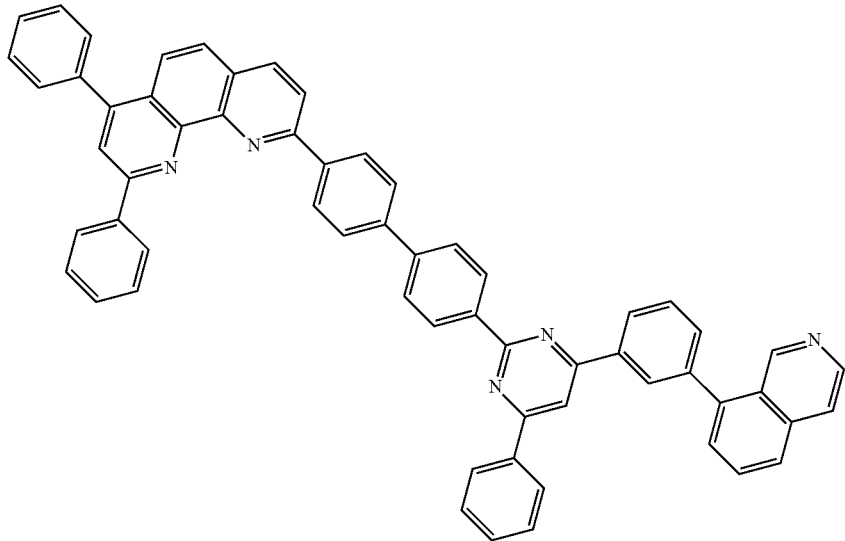
1217
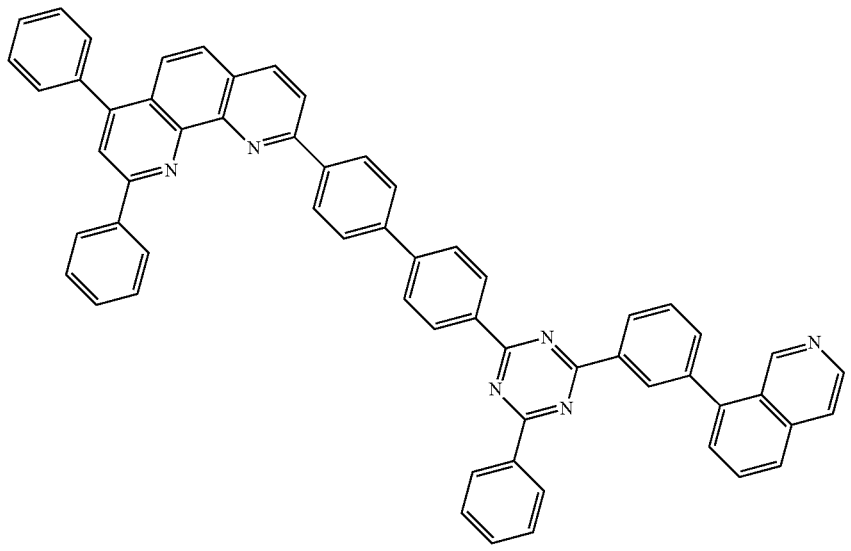
1218
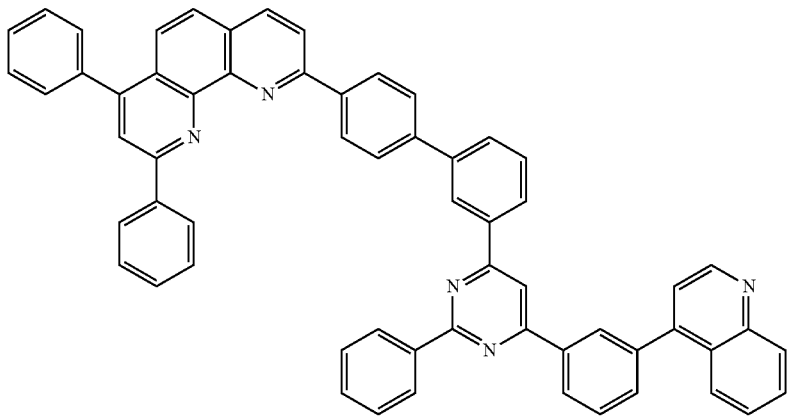
1219

1220
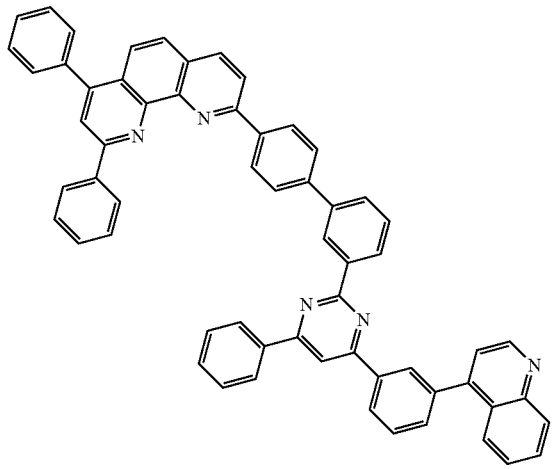
1221
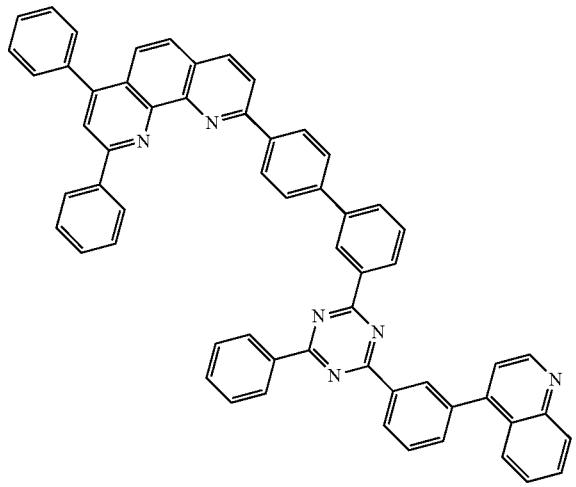
1222
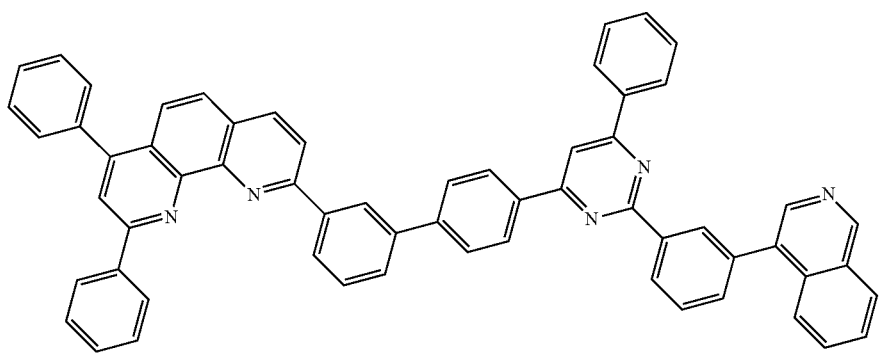
1223
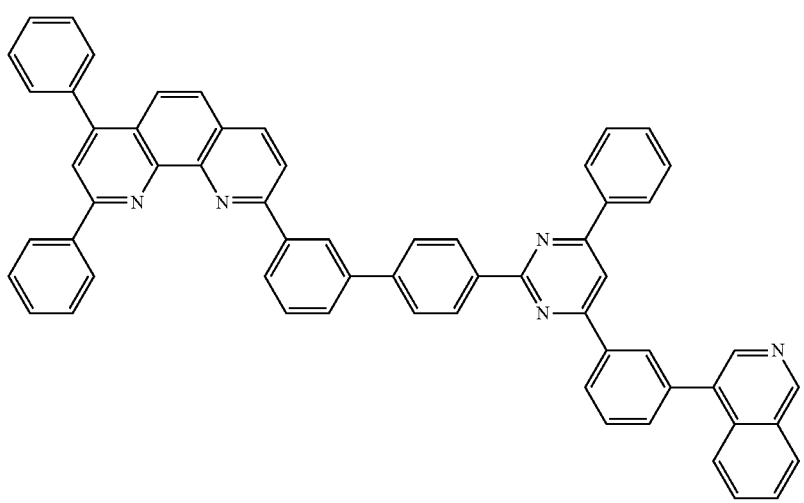

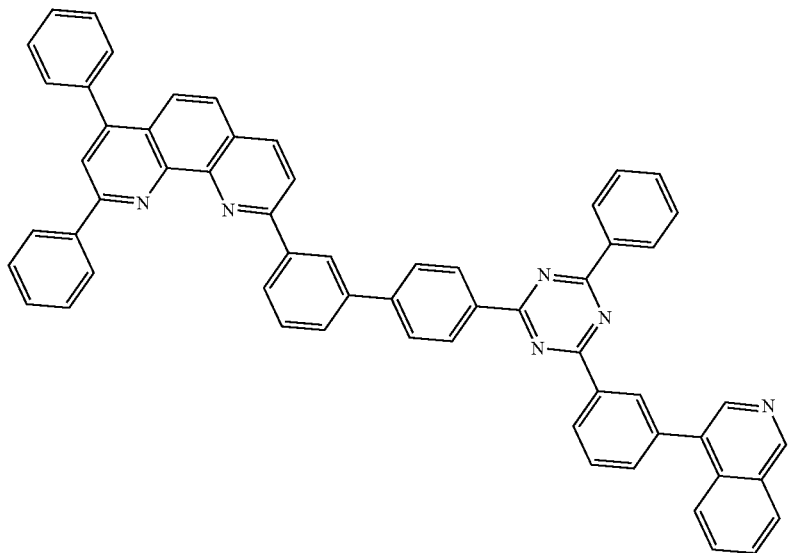
1224
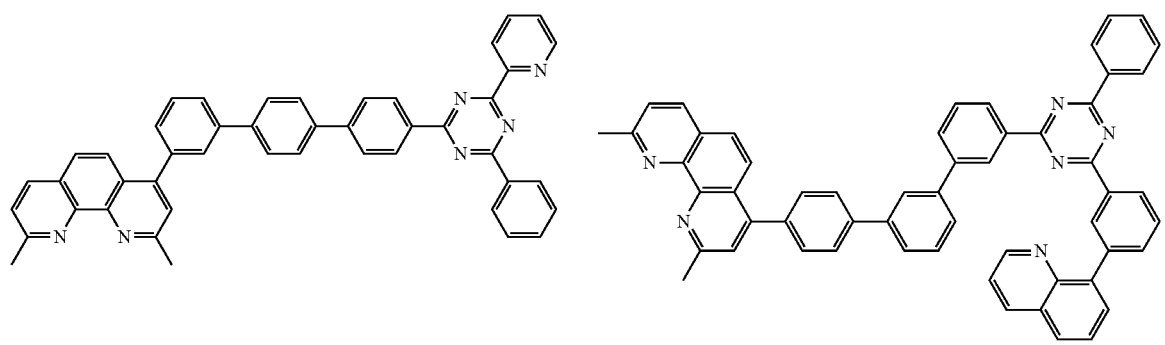
1225 1226
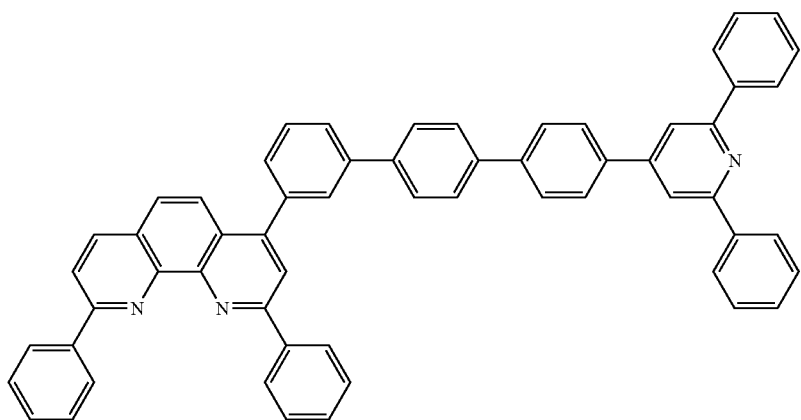
1227

-continued
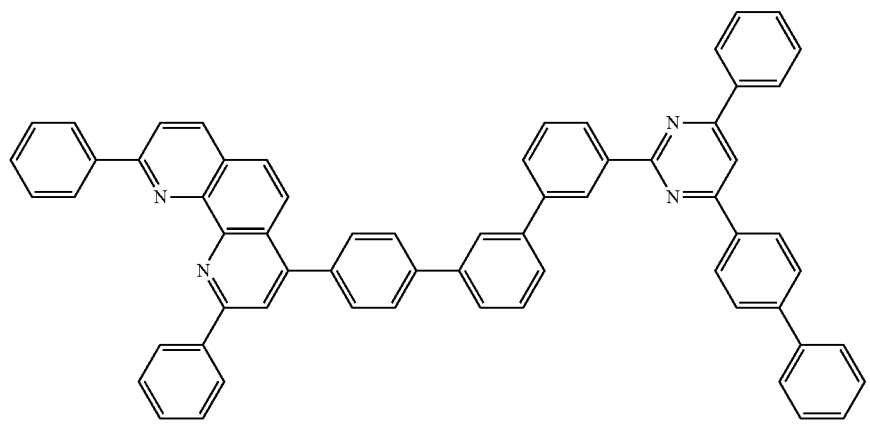
1228
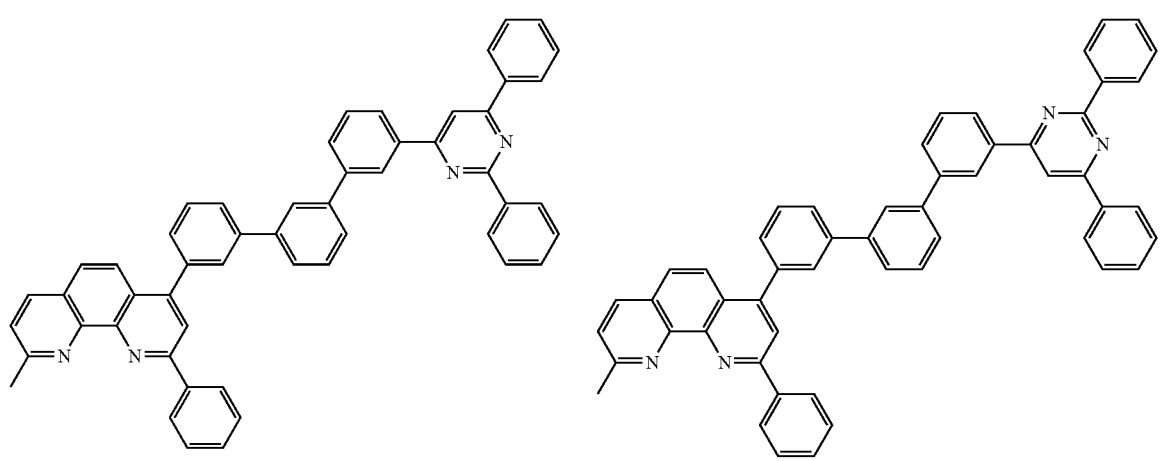
1229
1230
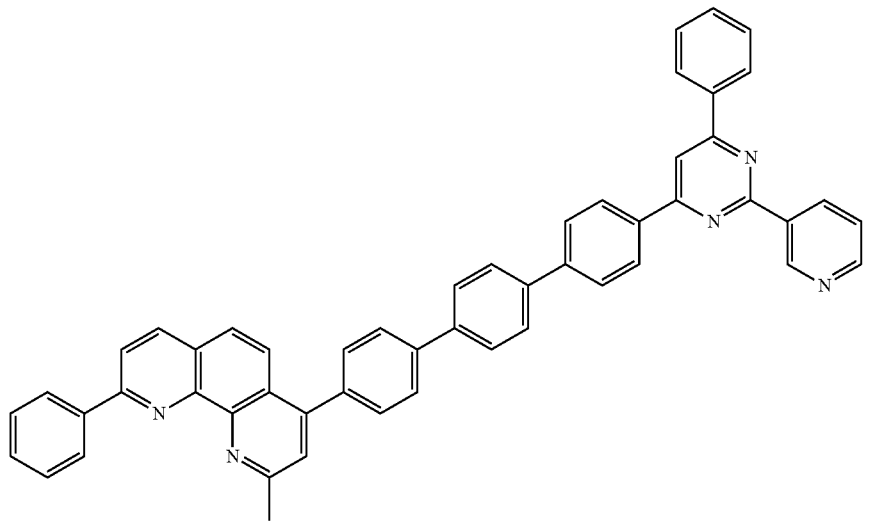
1231

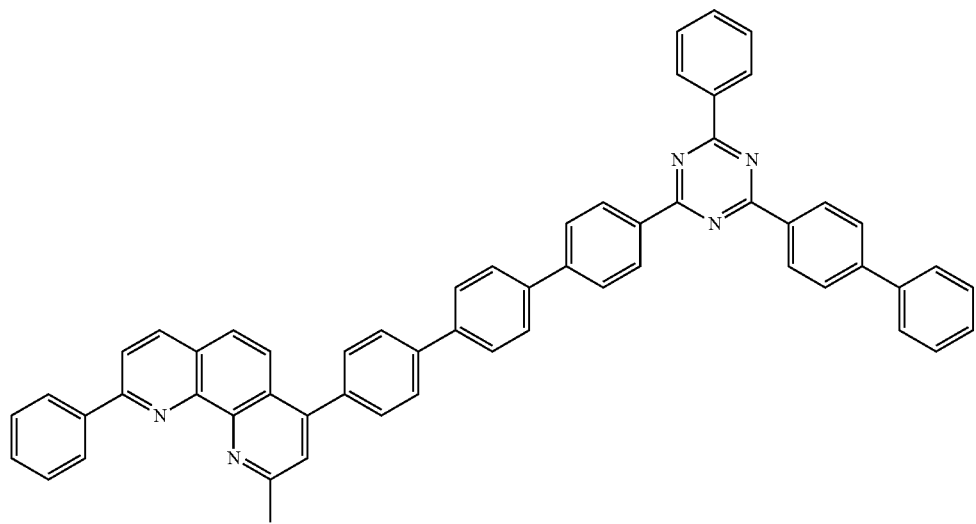
1232
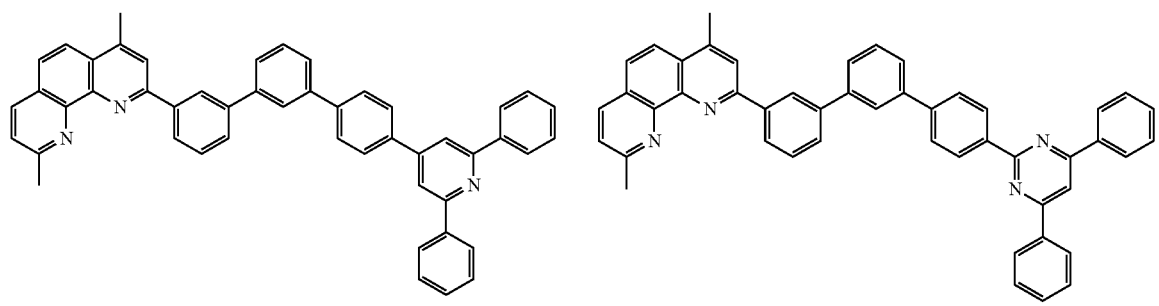
1233
1234
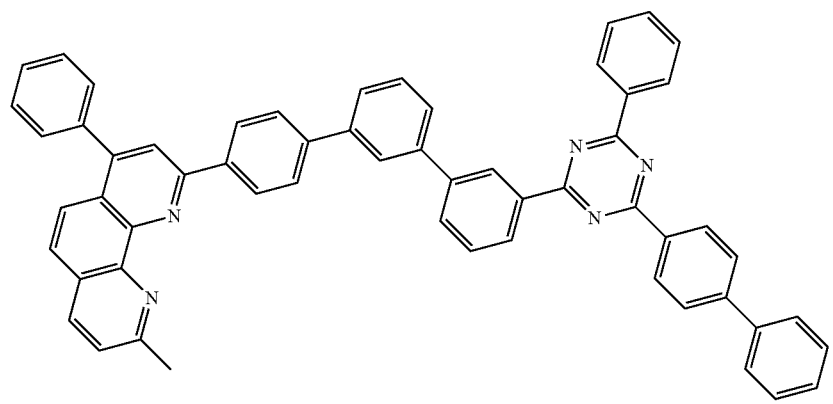
1235

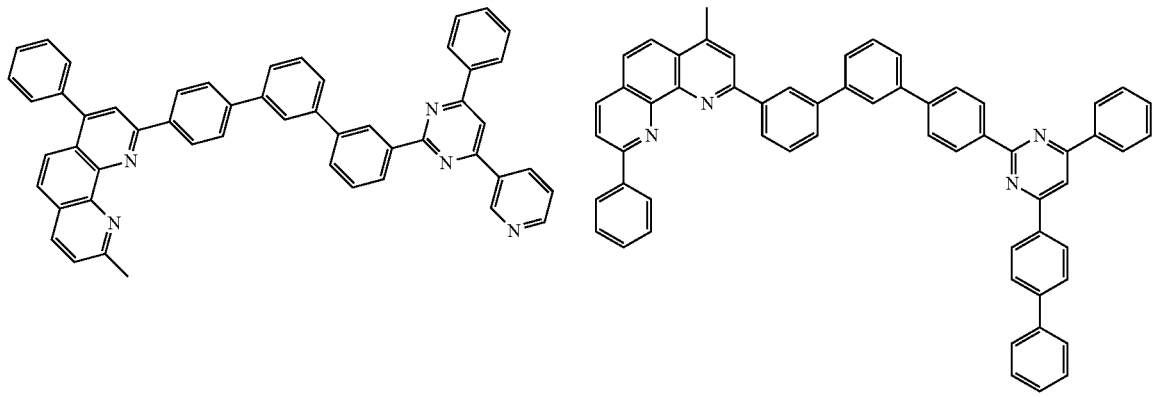
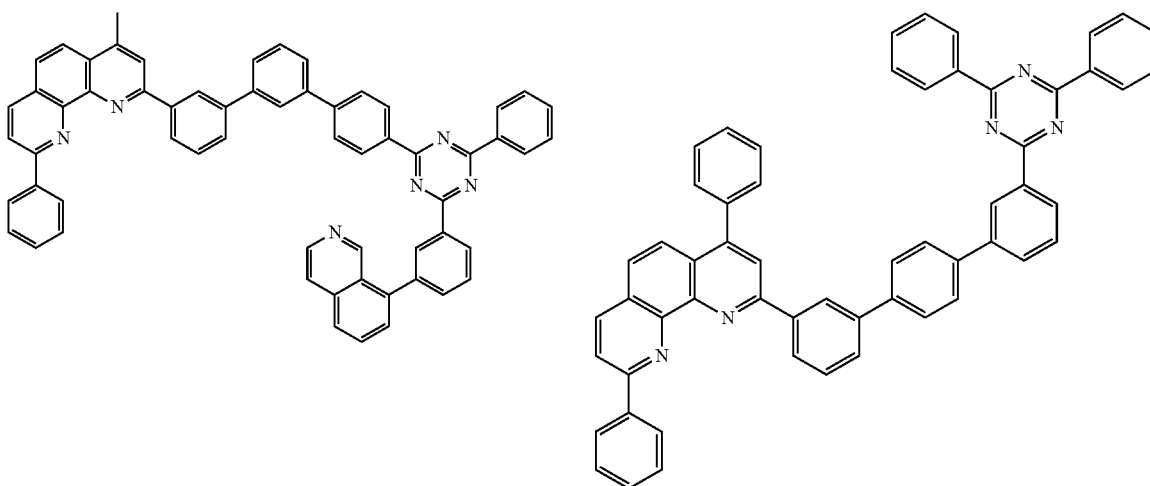
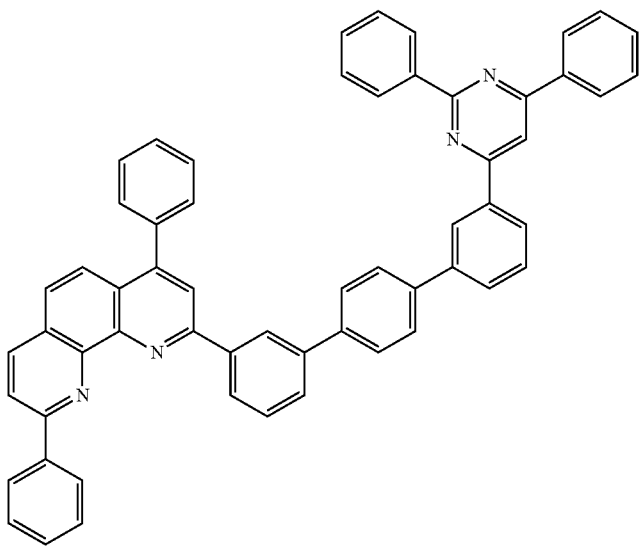

-continued
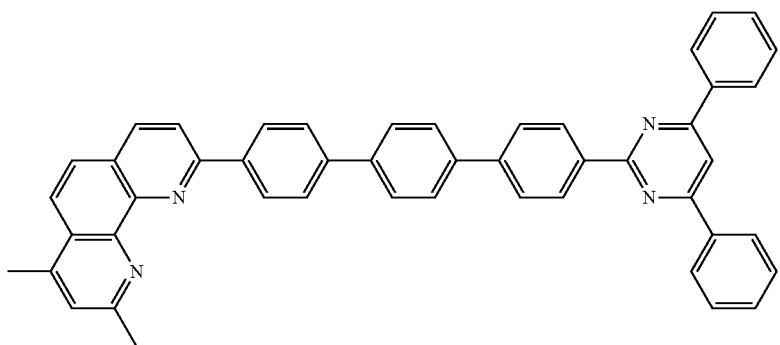
1241
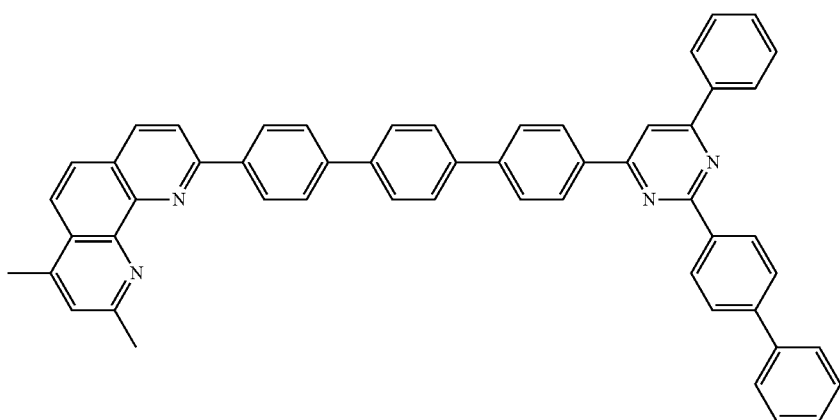
1242
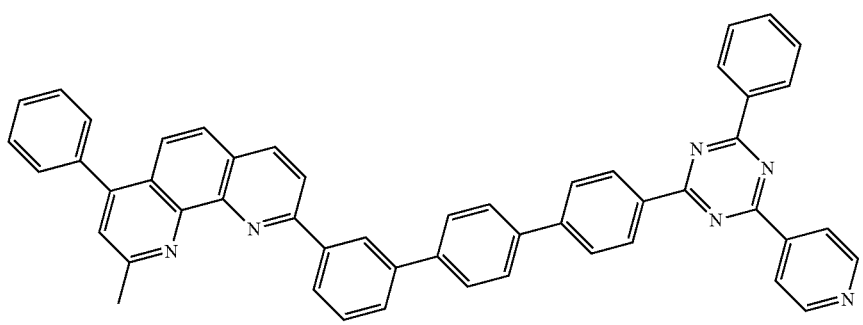
1243
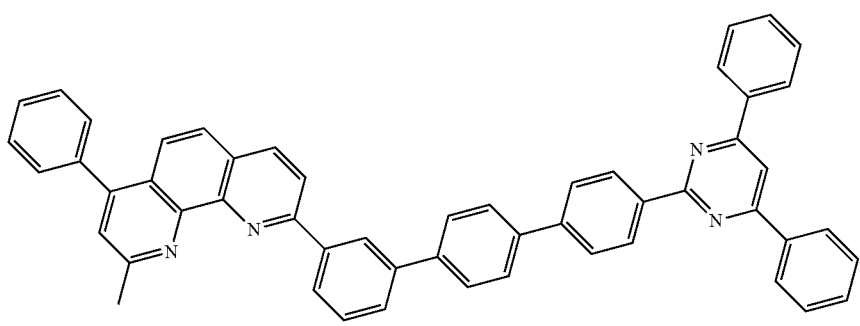
1244

-continued
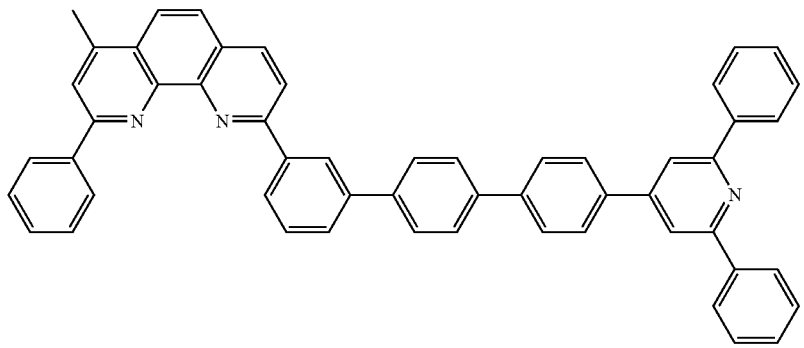
1245
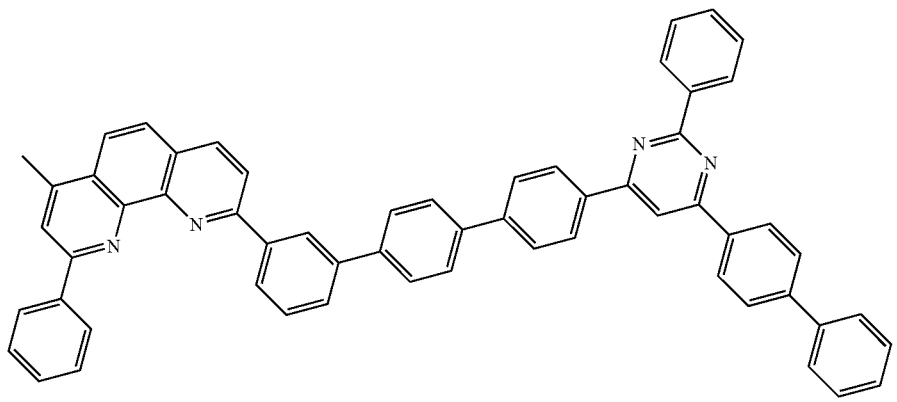
1246
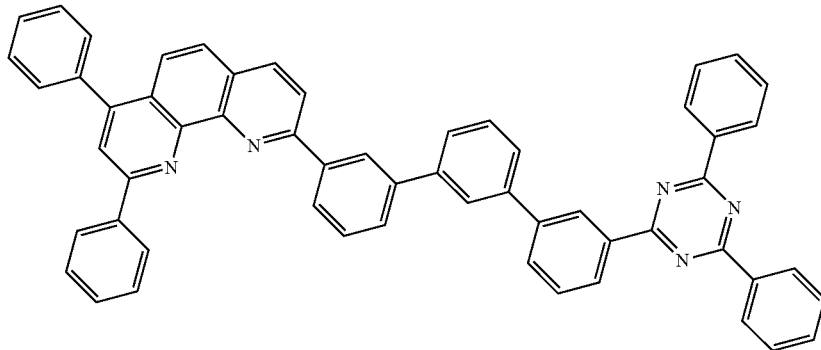
1247
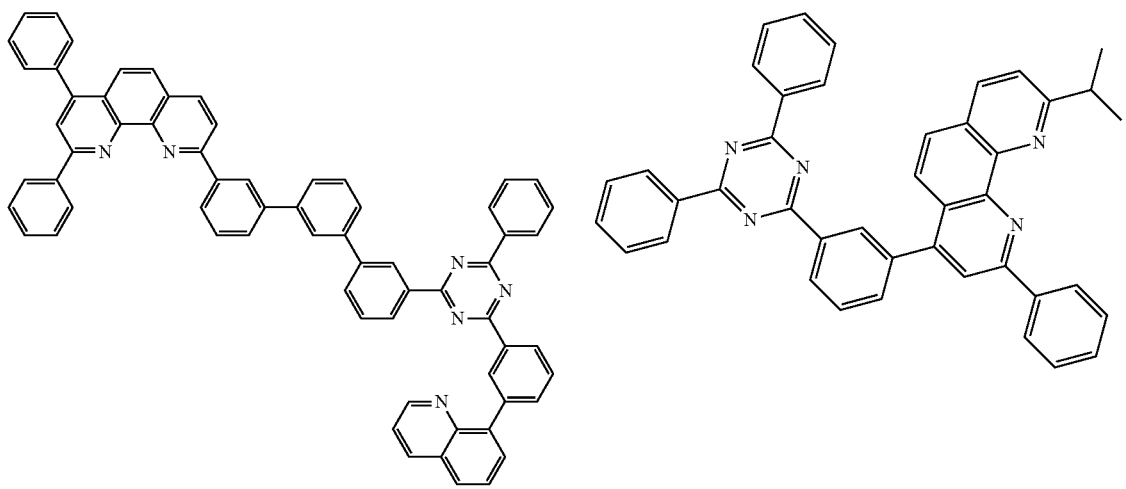
1248  1249

-continued
1250
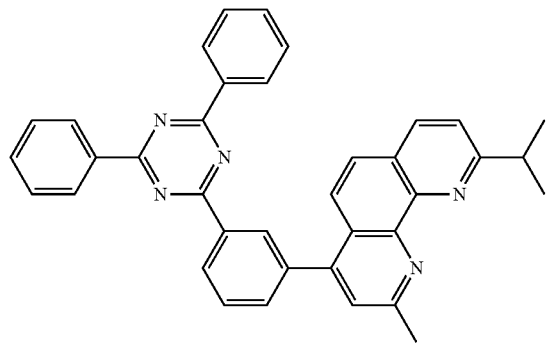
1251
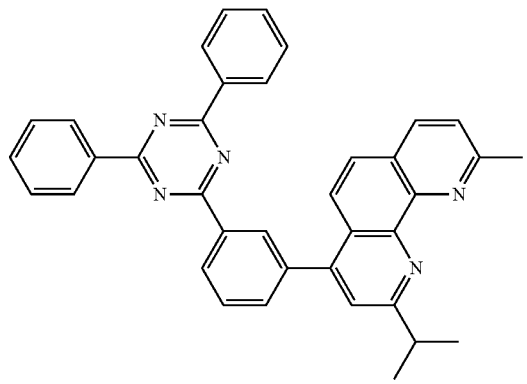
1252
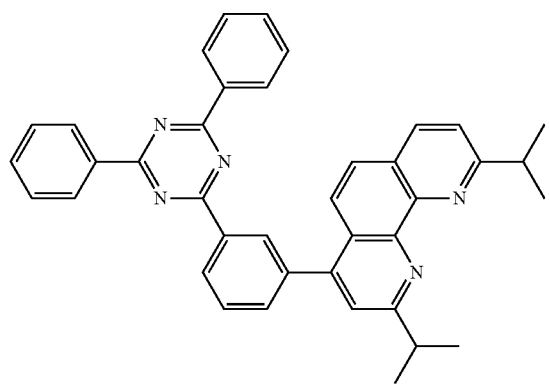
1253
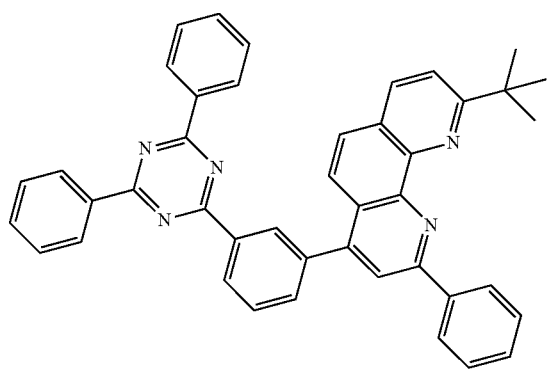
1254
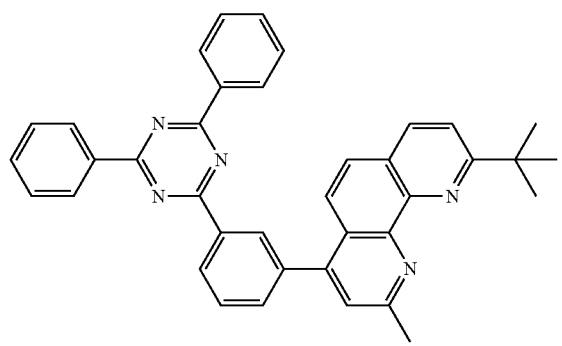
1255
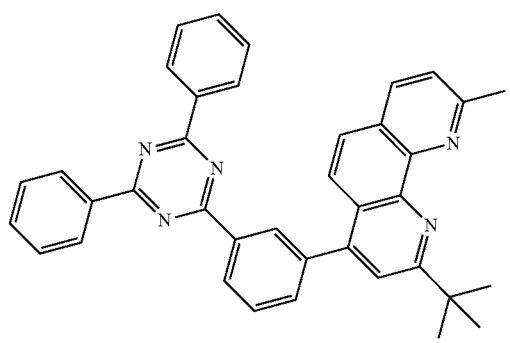
1256
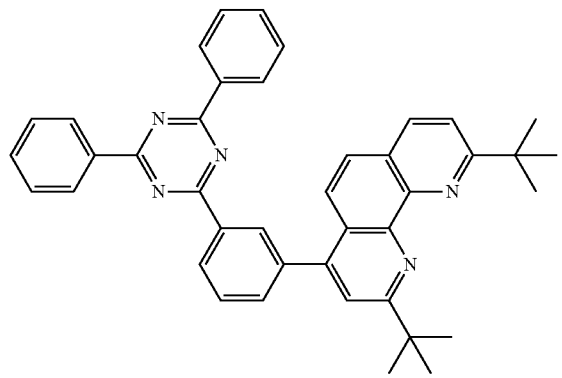
1257
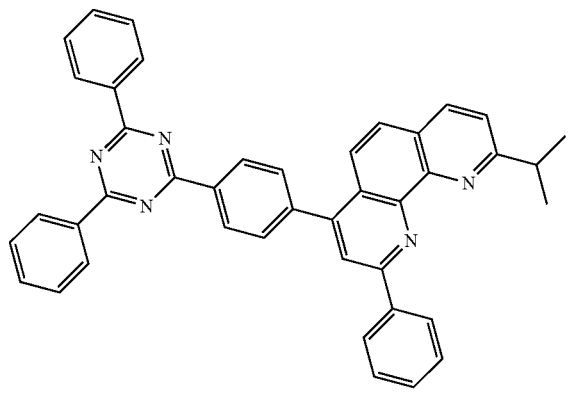

-continued
1258
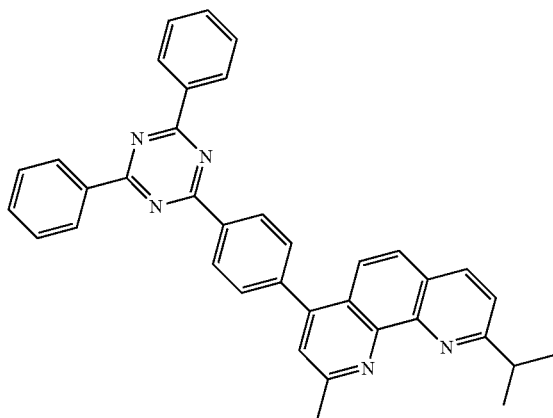
1259
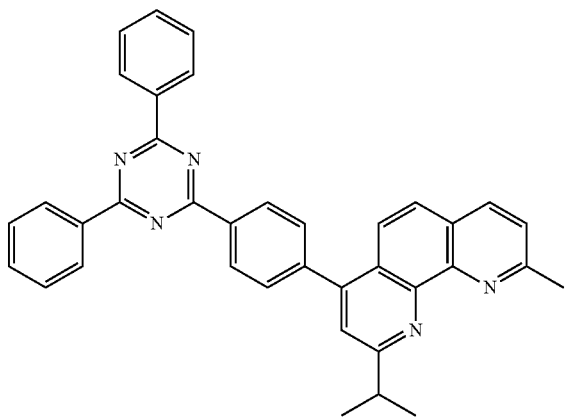
1260
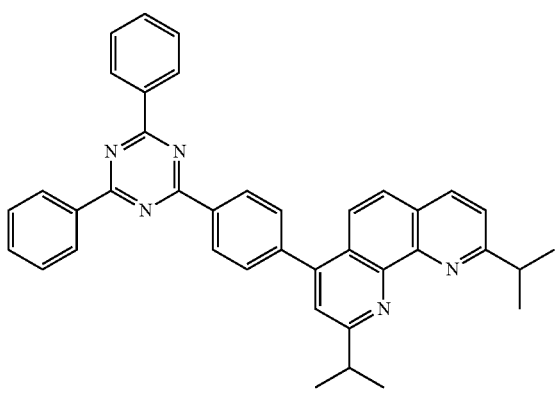
1261
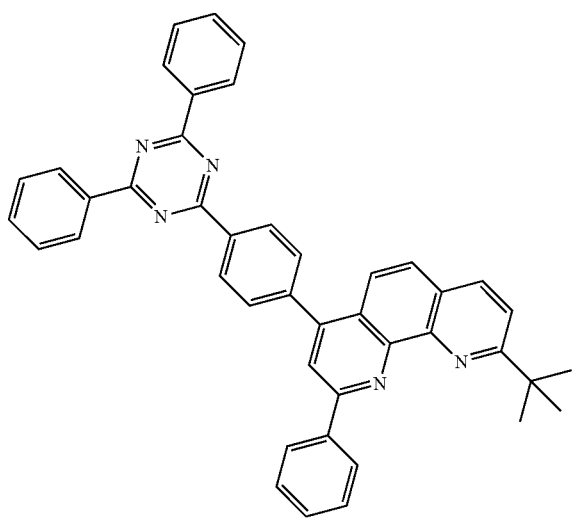
1262
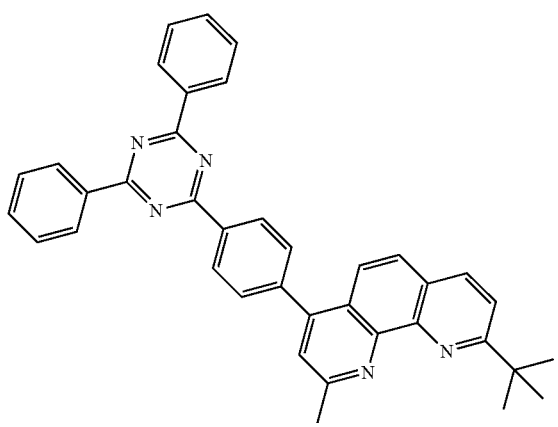
1263
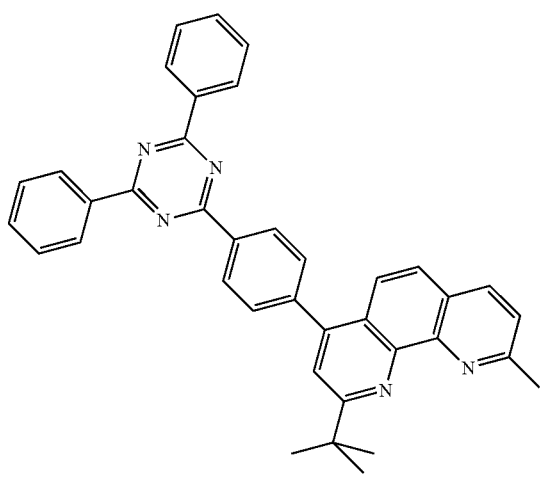

551
552
-continued
1264
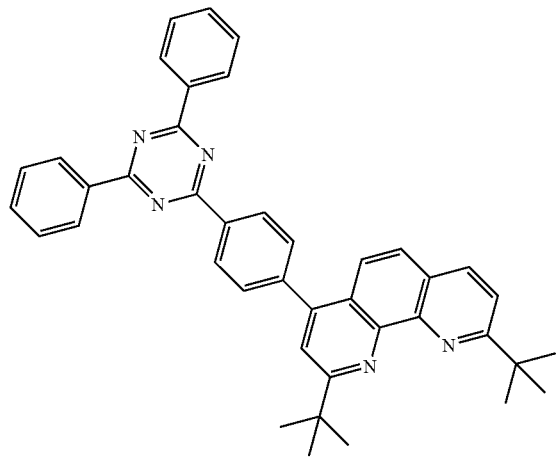
1265
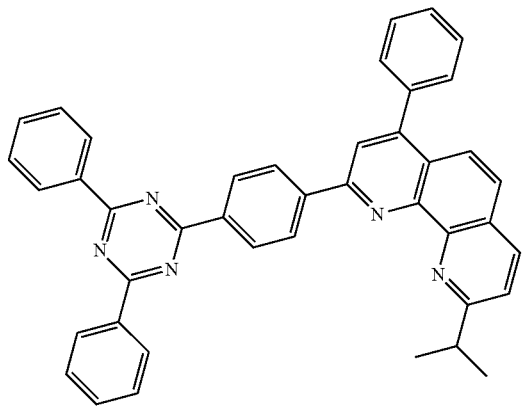
1266
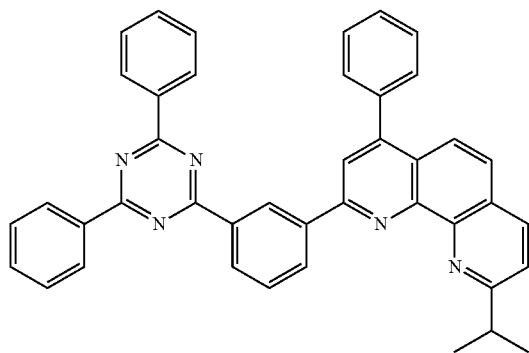
1267
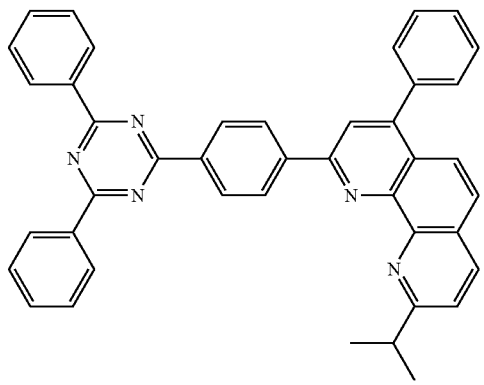
1268
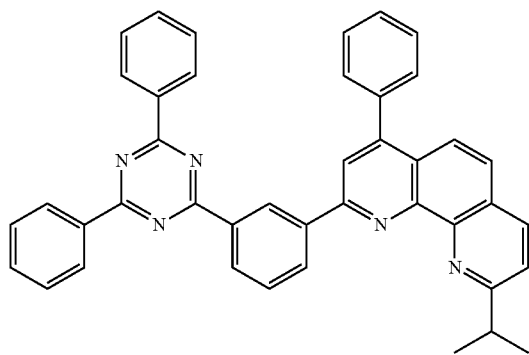
1269
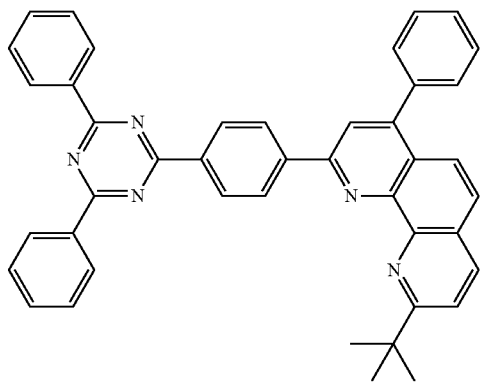

-continued

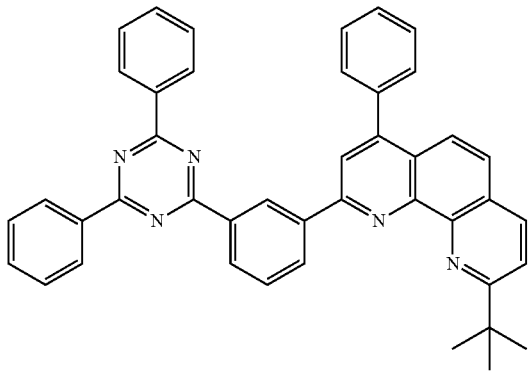

1270

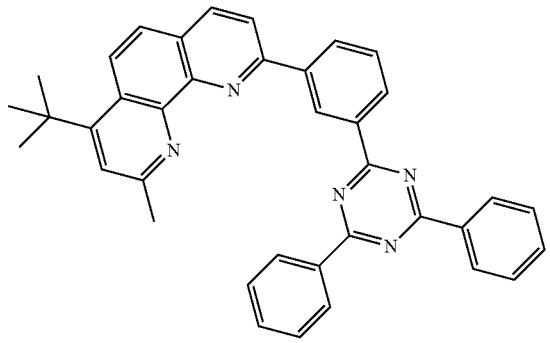

1271

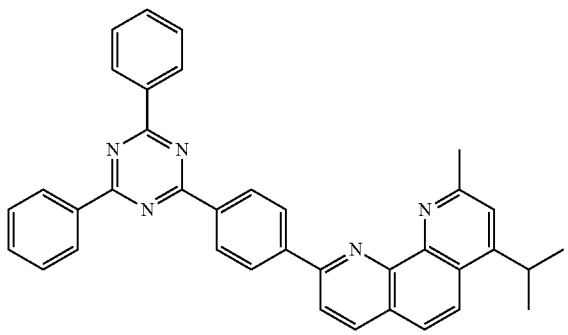

1272

The heterocyclic compound represented by Formula 1 may have a structure in which $A_1$, $A_2$, and $A_3$ positions of a phenanthroline core are substituted. The $A_1$, $A_2$, and $A_3$ positions correspond to 2-, 4-, and 9-positions of phenanthroline.

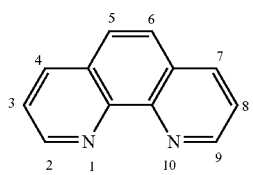

The $A_1$, $A_2$, and $A_3$ positions are electrophilic sites among nine substitutable positions of phenanthroline. Accordingly, when the $A_1$, $A_2$, and $A_3$ positions of the heterocyclic compound according to one or more embodiments are substituted with an alkyl group, an aryl group, a heteroaryl group, and/or the like, electrical stability and thermal stability may be increased. Accordingly, when manufacturing a device, the stability of materials may be increased, and a reduction in lifetime characteristics caused due to the deterioration of materials, such as thermal denaturation, may be prevented or reduced. Accordingly, it is expected that the heterocyclic compound represented by Formula 1 has a long lifespan.

In addition, in the heterocyclic compound represented by Formula 1, at least one of $A_1$, $A_2$, and $A_3$, which is a group represented by Formula 2, may include a π electron-depleted nitrogen-containing group. The group represented by Formula 2 may be electrochemically stable and have excellent (or suitable) electron transport characteristics, due to the linkage of phenanthroline (having excellent characteristics as an electron withdrawing group (EWG)) and a nitrogen-containing hetero-ring by a linking group. The phenanthroline has a low lowest unoccupied molecular orbital (LUMO) energy level, and may lower an electron barrier in an organic light-emitting device to facilitate the flow of electrons. Due to the additional bonding of a nitrogen-containing hetero-ring (for example, a triazine) to the phenanthroline, electron mobility may be increased, thus improving electron transport characteristics. Accordingly, due to such structure, the heterocyclic compound represented by Formula 1 may have excellent (or suitable) electron transport capability, and may increase the mobility of electrons, thus preventing or reducing a reduction in efficiency under low current conditions and controlling the charge balance to be suitable under high-current conditions, so that lifetime and efficiency may be increased.

Therefore, an electronic device, for example, an organic light-emitting device, using the heterocyclic compound represented by Formula 1, may have a low driving voltage and excellent emission efficiency and lifetime characteristics.

A synthesis method of the heterocyclic compound represented by Formula 1 may be understood by a person of ordinary skill in the art with reference to the examples to be described below.

At least one heterocyclic compound represented by Formula 1 may be used between a pair of electrodes in an organic light-emitting device. For example, the heterocyclic compound may be included in an electron transport region. In other embodiments, the heterocyclic compound represented by Formula 1 may be used as a material of a capping layer on the outside of a pair of electrodes of an organic light-emitting device.

According to one or more embodiments, there is provided an organic light-emitting device including: a first electrode;

a second electrode facing to the first electrode; an organic layer between the first electrode and the second electrode and including an emission layer; and at least one heterocyclic compound represented by Formula 1 as described above.

In one or more embodiments, the at least one heterocyclic compound may be included in the organic layer.

As used herein, the expression that the "(organic layer) may include at least one heterocyclic compound" may be construed as meaning that the "(organic layer) may include one heterocyclic compound corresponding to Formula 1, or at least two different heterocyclic compounds corresponding to Formula 1."

For example, the organic layer may include only Compound 1 as the heterocyclic compound. In this embodiment, Compound 1 may be in the emission layer of the organic light-emitting device. In some embodiments, the organic layer may include Compound 1 and Compound 2 as heterocyclic compounds. In this embodiment, Compound 1 and Compound 2 may be in the same layer (for example, Compound 1 and Compound 2 may both be in the emission layer) or in different layers (for example, Compound 1 may be in the emission layer, and Compound 2 may be in the electron transport layer).

In one or more embodiments, the first electrode of the organic light-emitting device may be an anode, the second electrode of the organic light-emitting device may be a cathode, the organic layer of the organic light-emitting device may further include a hole transport region between the first electrode and the emission layer, and an electron transport region between the emission layer and the second electrode, the hole transport region may include at least one selected from a hole injection layer, a hole transport layer, a buffer layer, an emission auxiliary layer, and an electron blocking layer, the electron transport region may include at least one selected from a hole blocking layer, an electron transport layer, and an electron injection layer.

In one or more embodiments, the electron transport region may include the heterocyclic compound.

For example, the electron transport region may include the electron transport layer and the electron injection layer, and at least one selected from the electron transport layer and the electron injection layer may include the heterocyclic compound.

In one or more embodiments, at least one layer selected from the electron transport layer and the electron injection layer may further include an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combination thereof.

In one or more embodiments, the emission layer may include a host and a dopant.

In one or more embodiments, the hole transport region may include a p-dopant, and a LUMO level of the p-dopant may be −3.5 eV or less.

Electronic Apparatus

According to one or more embodiments, there is provided an electronic apparatus including: a substrate; and an organic light-emitting device on the substrate. The organic light-emitting device is as described above herein.

In one or more embodiments, the electric apparatus may include a color conversion layer located in at least one traveling direction of light emitted from the organic light-emitting device including quantum dots.

Quantum Dots

The emission layer included in the organic light-emitting device according to one or more embodiment may include a quantum dot material.

In some embodiments, the color conversion layer included in the electronic apparatus according to one or more embodiments may include a quantum dot material.

The quantum dots, which are particles having a crystalline structure of several to tens of nanometers in size, may include (e.g., may consist of) several hundreds or several thousands of atoms.

Due to having a very small size, the quantum dots may have a quantum confinement effect, which refers to the phenomenon that a band gap of an object is increased when the object has a small size of nanometers. Accordingly, when the quantum dots are irradiated with light of a wavelength having an energy level greater than the bandgap of the quantum dots, the quantum dots may absorb the light to transit to an excited state. The quantum dots may fall to a ground state while emitting light of a specific wavelength. At this time, the wavelength of the emitted light may have a value corresponding to the bandgap.

The core of the quantum dots may include a Group II-VI compound, a Group III-VI compound, a Group III-V compound, a Group IV-VI compound, a Group IV element or compound, a Group compound, or a combination thereof.

The Group II-VI compound may be selected from the group consisting of: binary compounds selected from the group consisting of CdS, CdSe, CdTe, ZnS, ZnSe, ZnTe, ZnO, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and quaternary compounds selected from the group consisting of CdZnSeS, CdZnSeTe, CdZnSTe, CdHgSeS, CdHgSeTe, CdHgSTe, HgZnSeS, HgZnSeTe, HgZnSTe, and mixtures thereof.

The Group III-VI compound may include: a binary compound such as $In_2S_3$ and/or $In_2Se_3$; a ternary compound such as $InGaS_3$ and/or $InGaSe_3$; or any combination thereof.

The Group III-V compound may include: a binary compound selected from the group consisting of GaN, GaP, GaAs, GaSb, AlN, AlP, AlAs, AlSb, InN, InP, InAs, InSb, and mixtures thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, GaAlNP, and mixtures thereof; and a quaternary compound selected from the group consisting of GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. The Group III-V compound may further include a Group II element (for example, InZnP).

The Group IV-VI compound may be selected from the group consisting of: binary compounds selected from the group consisting of SnS, SnSe, SnTe, PbS, PbSe, PbTe, and mixtures thereof; ternary compounds selected from the group consisting of SnSeS, SnSeTe, SnSTe, PbSeS, PbSeTe, PbSTe, SnPbS, SnPbSe, SnPbTe, and mixtures thereof; and quaternary compounds selected from the group consisting of SnPbSSe, SnPbSeTe, SnPbSTe, and mixtures thereof. The Group IV element may be selected from the group consisting of Si, Ge, and a mixture thereof. The Group IV compound may be a binary compound selected from the group consisting of SiC, SiGe, and a mixture thereof.

The Group compound may include: a ternary compound such as AgInS, $AgInS_2$, CuInS, $CuInS_2$, $CuGaO_2$, $AgGaO_2$, and/or $AgAlO_2$; or any combination thereof.

The binary compound, ternary compound, and/or quaternary compound may be present in a particle at a uniform concentration, or may be present in the same particle in different states with partially different concentration distributions. The quantum dots may have a core/shell structure in which one quantum dot surrounds another quantum dot. The interface between the core and shell may have a concentration gradient in which the concentration of atoms present in the shell gradually decreases toward the core.

In some embodiments, the quantum dots may have a core-shell structure having a core including nanocrystals as described above, and a shell surrounding the core. The shell of the quantum dots may serve as a protective layer for preventing or reducing chemical denaturation of the core to maintain semiconductor characteristics, and/or a charging layer for imparting electrophoretic properties to the quantum dots. The shell may be a single layer or a multilayer. The interface between the core and shell may have a concentration gradient in which the concentration of atoms present in the shell gradually decreases toward the core. The shell of the quantum dots may include, for example, an oxide of a metal, an oxide of a non-metal, a semiconductor compound, or a combination thereof.

For example, the oxide of a metal or the oxide of a non-metal may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; or a ternary compound such as $MgAl_2O_4$, $CoFe_2O_4$, $NiFe_2O_4$, and/or $CoMn_2O_4$. However, embodiments are not limited thereto.

The semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, or AlSb. However, embodiments are not limited thereto.

The quantum dot may have a full width of half maximum (FWHM) of emission wavelength spectrum of about 45 nm or less, for example, about 40 nm or less, for example, about 30 nm or less. When the FWHM is within these ranges, color purity and color reproducibility may be improved. In addition, light emitted through such quantum dots may move in a forward direction, thus increasing a light viewing angle.

The shape of the quantum dots is not specifically limited and may be any suitable shape used in the art. For example, the quantum dots as spherical, pyramidal multi-arm, and/or cubic nanoparticles, and/or as nanotubes, nanowires, nanofibers, and/or nanoplate particles may be used.

According to the particle size of the quantum dots, color of emitted light may be controlled. Accordingly, the quantum dots may emit light of a variety of colors, for example, blue, red, and green.

The term "organic layer" used herein may refer to a single layer and/or a plurality of layers between the first electrode and the second electrode of the organic light-emitting device. The material included in the "organic layer" is not limited to an organic material.

Description of FIG. 1

Figure 1:
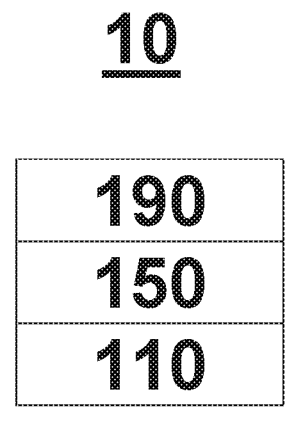

FIG. 1 is a schematic cross-sectional view of an organic light-emitting device 10 according to an example embodiment. The organic light-emitting device 10 may include a first electrode 110, an organic layer 150, and a second electrode 190.

Hereinafter, a structure of the organic light-emitting device 10 according to an embodiment and a method of manufacturing the organic light-emitting device according to an embodiment will be described with reference to FIG. 1

First Electrode 110

In FIG. 1, a substrate may be additionally located under the first electrode 110 or above the second electrode 190. The substrate may be a glass substrate and/or a plastic substrate, each having excellent (or suitable) mechanical strength, thermal stability, transparency, surface smoothness, ease of handling, and/or water resistance.

The first electrode 110 may be formed by providing, onto the substrate, a material for forming the first electrode 110, for example, by deposition or sputtering. When the first electrode 110 is an anode, the material for forming the first electrode 110 may be selected from materials having a high-work function to facilitate hole injection.

The first electrode 110 may be a reflective electrode, a semi-transmissive electrode, or a transmissive electrode. When the first electrode 110 is a transmissive electrode, a material for forming the first electrode 110 may be selected from indium tin oxide (ITO), indium zinc oxide (IZO), tin oxide ($SnO_2$), zinc oxide (ZnO), and any combinations thereof, but embodiments are not limited thereto. In some embodiments, when the first electrode 110 is a semi-transmissive electrode or a reflective electrode, a material for forming the first electrode 110 may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments are not limited thereto.

The first electrode 110 may have a single-layered structure, or a multi-layered structure including two or more layers. In some embodiments, the first electrode 110 may have a triple-layered structure of ITO/Ag/ITO. However, embodiments are not limited thereto.

Organic Layer 150

The organic layer 150 may be located on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region of Organic Layer 150

The hole transport region may have i) a single-layered structure consisting of a single layer consisting of a single material, ii) a single-layered structure consisting of a single layer including a plurality of different materials, or iii) a multi-layered structure having a plurality of layers including a plurality of different materials.

The hole transport region may include at least one selected from a hole injection layer, a hole transport layer, an emission auxiliary layer, and an electron blocking layer.

For example, the hole transport region may have a single-layered structure consisting of a single layer including a plurality of different materials, or a multi-layered structure of, for example, a hole injection layer/hole transport layer, a hole injection layer/hole transport layer/emission auxiliary layer, a hole injection layer/emission auxiliary layer, a hole transport layer/emission auxiliary layer, or a hole injection layer/hole transport layer/electron blocking layer, wherein the layers of each structure are sequentially stacked on the first electrode 110 in the stated order, but embodiments are not limited thereto.

The hole transport region may include at least one selected from m-MTDATA, TDATA, 2-TNATA, NPB (NPD), β-NPB, TPD, a spiro-TPD, a spiro-NPB, methylated NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202.

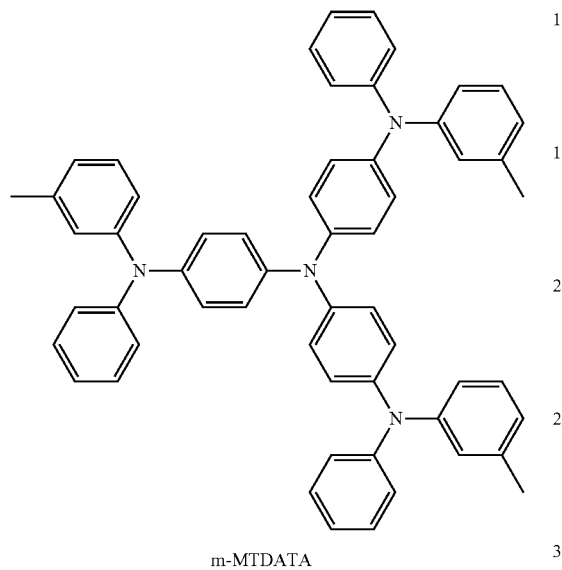

m-MTDATA

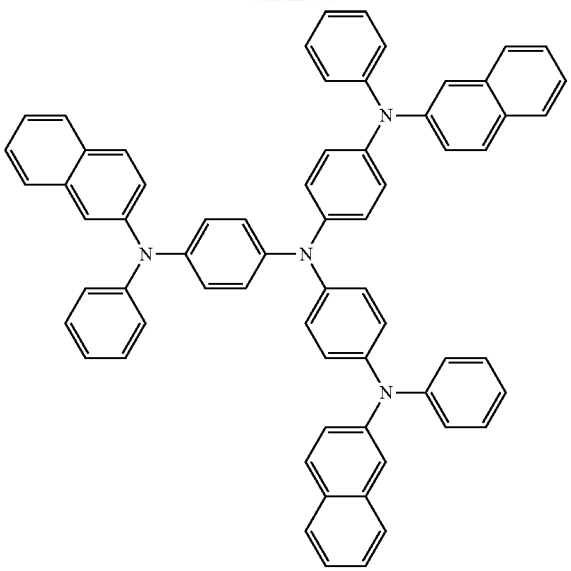

2-TNATA

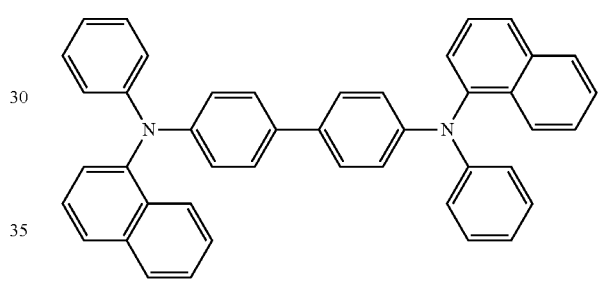

NPB

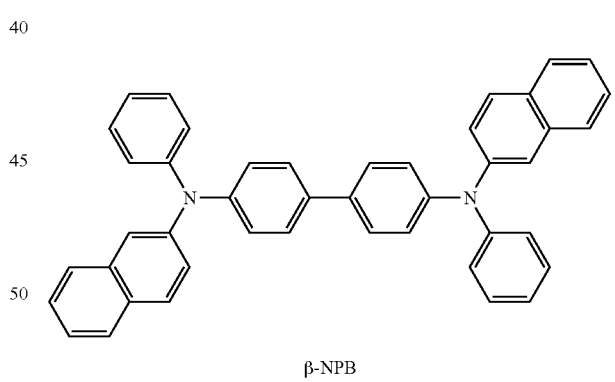

β-NPB

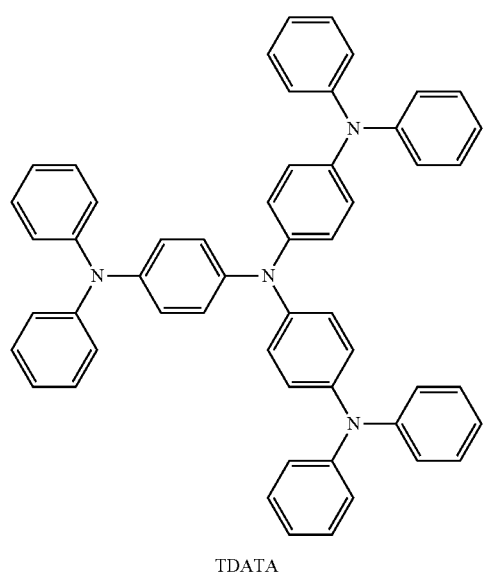

TDATA

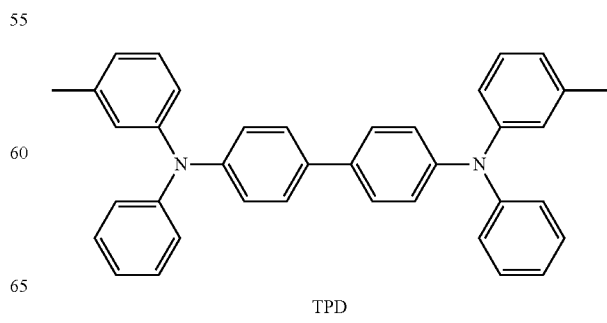

TPD

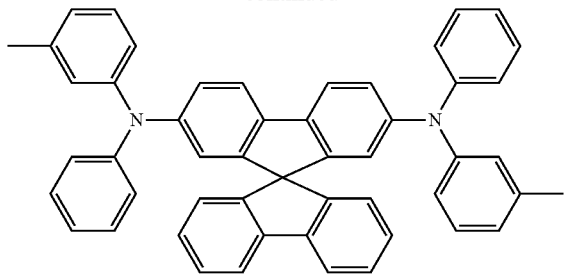

Spiro-TPD

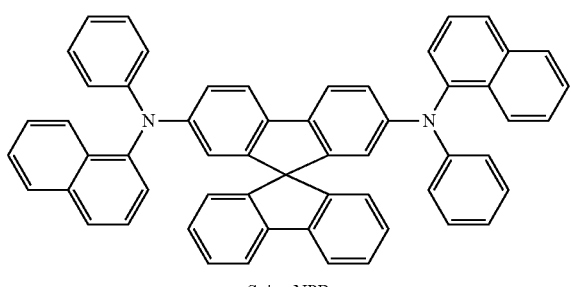

Spiro-NPB

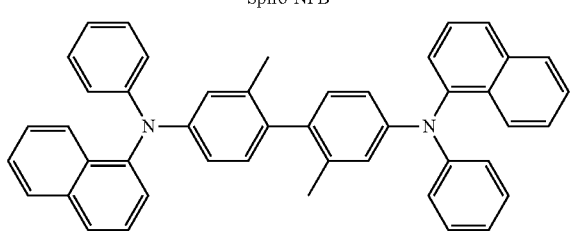

methylated NPB

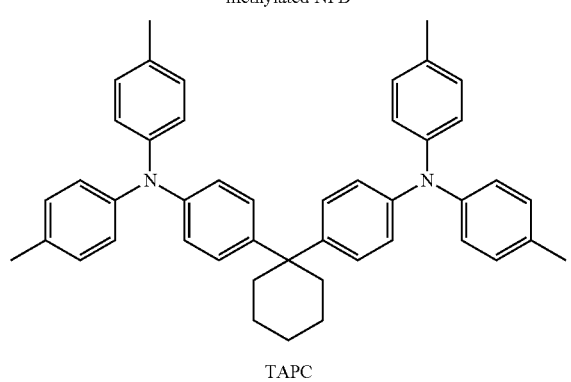

TAPC

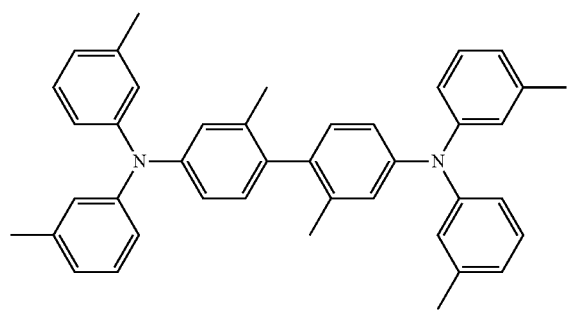

HMTPD

Formula 201

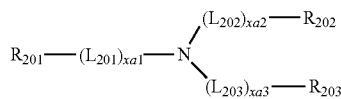

-continued

Formula 202

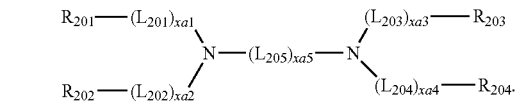

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer selected from 0 to 3, xa5 may be an integer selected from 1 to 10, $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 202, $R_{201}$ and $R_{202}$ may optionally be linked via a single bond, a dimethyl-methylene group, and/or a diphenyl-methylene group, and $R_{203}$ and $R_{204}$ may optionally be linked via a single bond, a dimethyl-methylene group, and/or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ are each independently selected from a $C_1$-$C_{10}$ alkyl group, a $C_{10}$ alkoxy group, a phenyl group, a biphenyl group, a terphenyl group, and a naphthyl group.

In some embodiments, xa1 to xa4 may each independently be 0, 1, or 2.

In some embodiments, xa5 may be 1, 2, 3, or 4.

In some embodiments, $R_{201}$ to $R_{204}$, and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substitute with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may be as defined herein in the specification.

In some embodiments, in Formula 201, at least one of $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group. However, embodiments are not limited thereto.

In some embodiments, in Formula 202, i) $R_{201}$ and $R_{202}$ may be linked via a single bond, and/or ii) $R_{203}$ and $R_{204}$ may be linked via a single bond.

In some embodiments, in Formula 202, at least one of $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group. However, embodiments are not limited thereto.

The compound represented by Formula 201 may be represented by Formula 201A.

Formula 201A

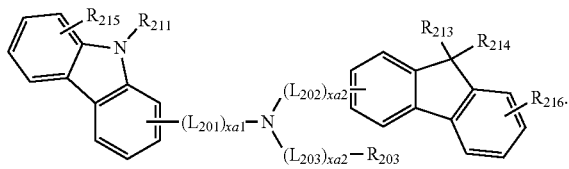

For example, the compound represented by Formula 201 may be represented by Formula 201A(1), but embodiments are not limited thereto.

Formula 201A(1)

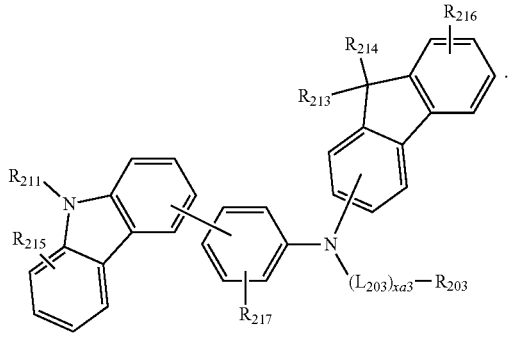

In some embodiments, the compound represented by Formula 201 may be represented by Formula 201A-1, but embodiments are not limited thereto.

Formula 201A-1

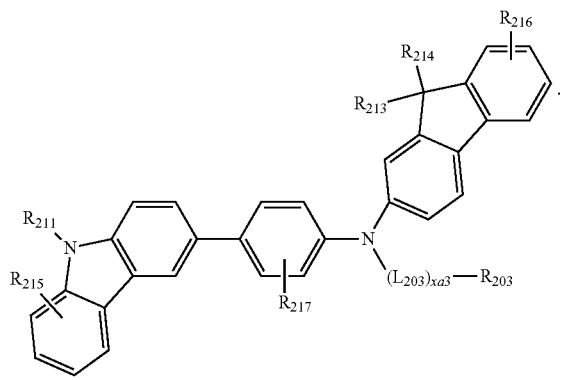

In some embodiments, the compound represented by Formula 202 may be represented by Formula 202A.

Formula 202A

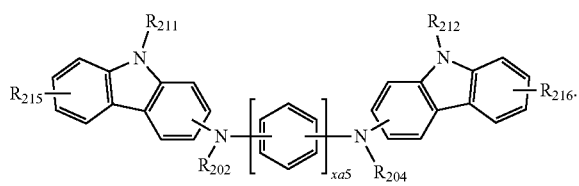

In some embodiments, the compound represented by Formula 202 may be represented by Formula 202A-1.

Formula 202A-1

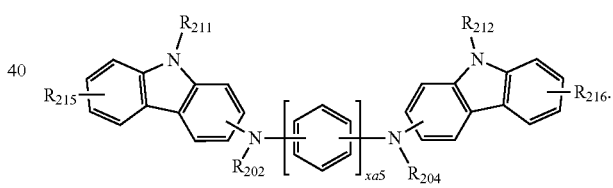

In Formulae 201A, 201A(1), 201A-1, 202A, and 202A-1, $L_{201}$ to $L_{203}$, xa1 to xa3, xa5 and $R_{202}$ to $R_{204}$ may be as defined herein in the specification, $R_{211}$ and $R_{212}$ may be defined the same as $R_{203}$ herein in the specification, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments are not limited thereto.

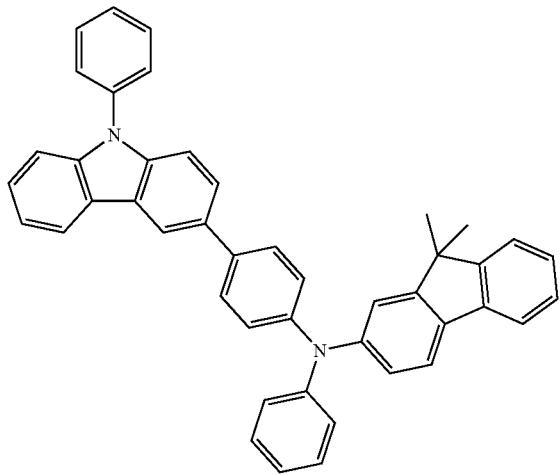

HT1

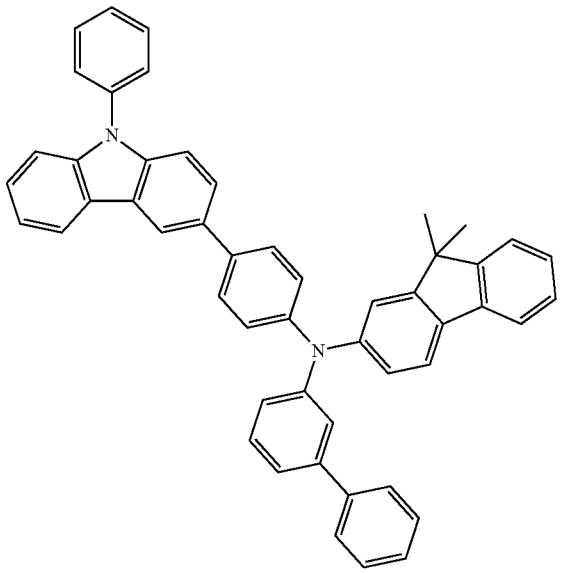

HT2

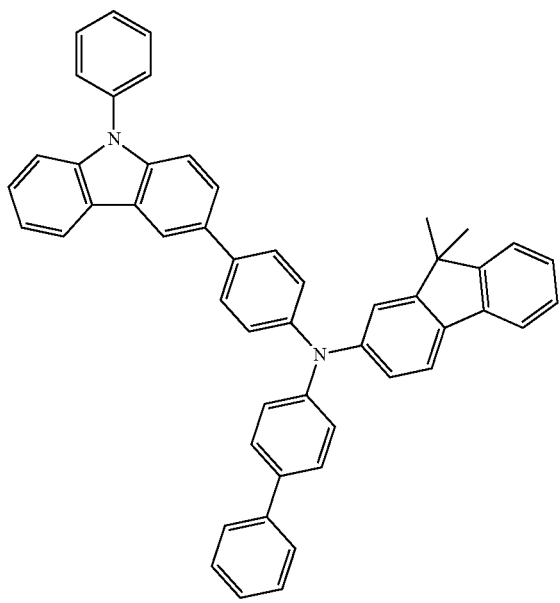

HT3

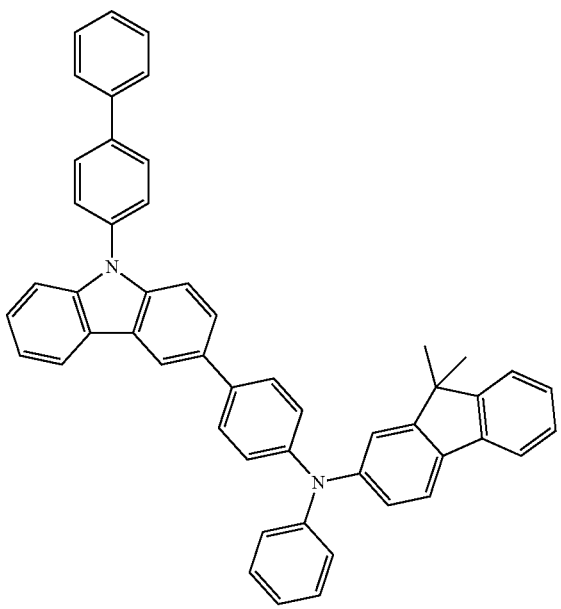

HT4

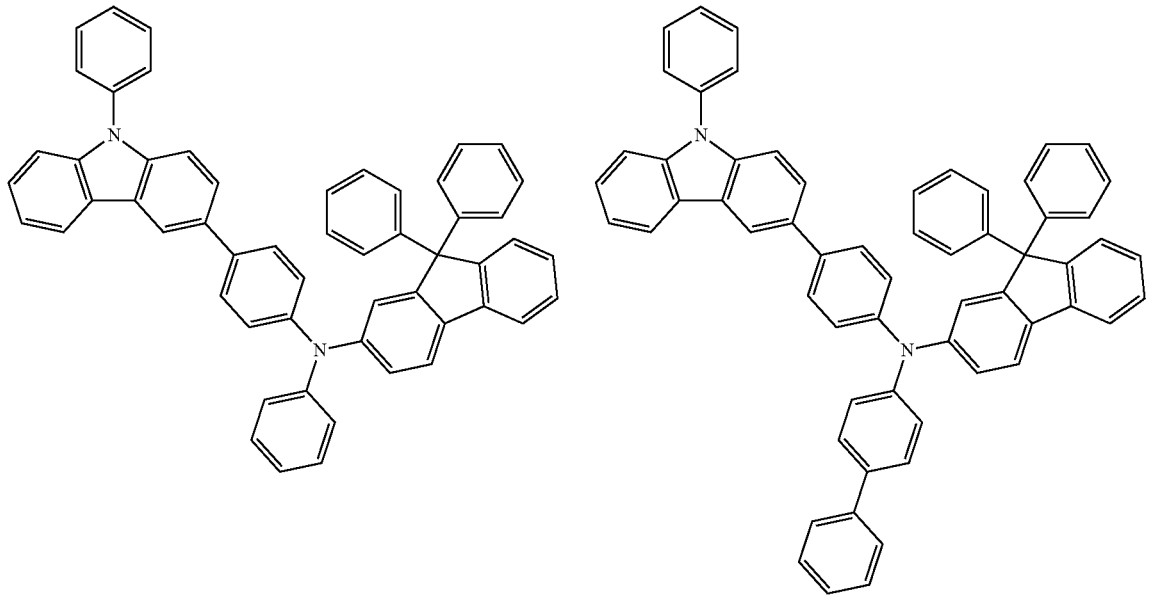
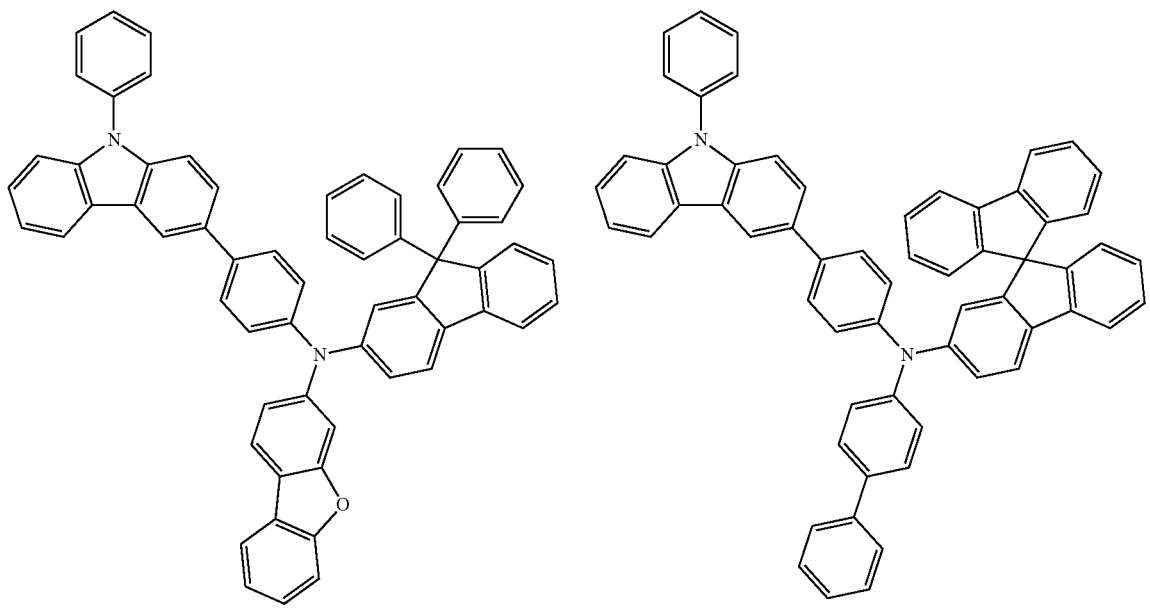

-continued
571 HT9
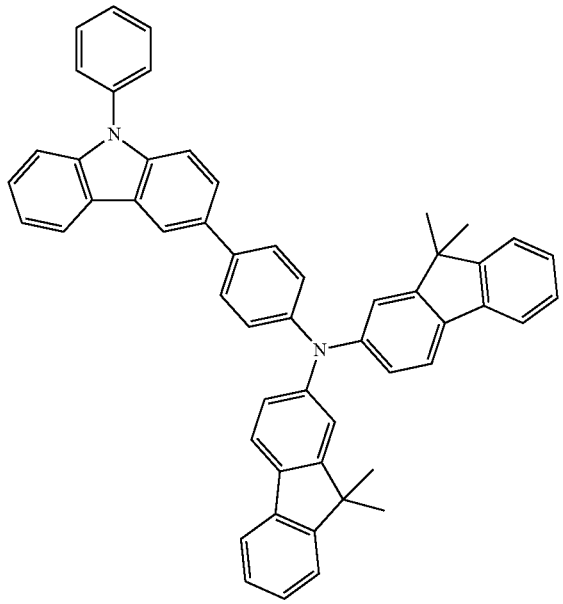
572 HT10
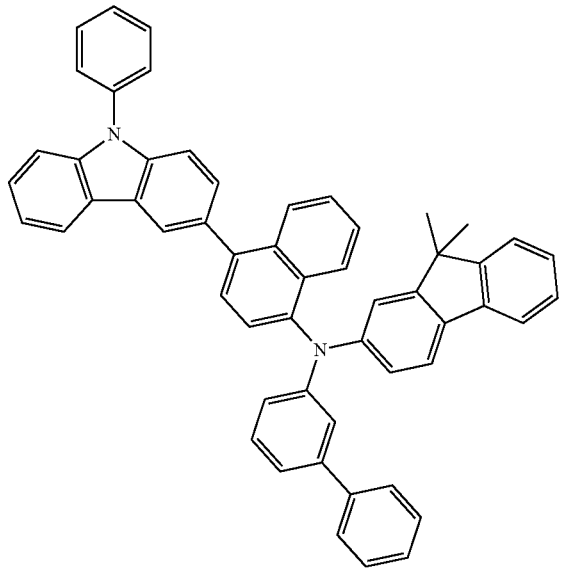
HT11
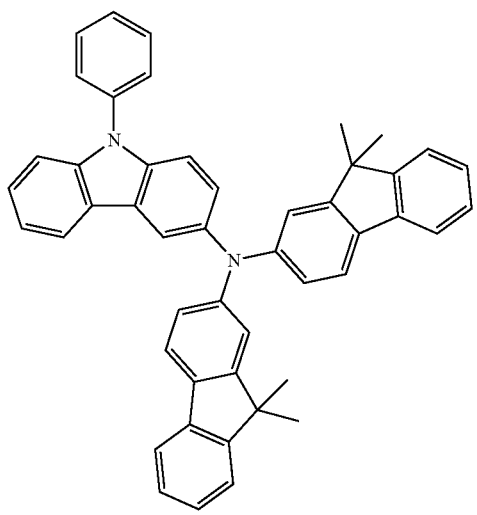
HT12
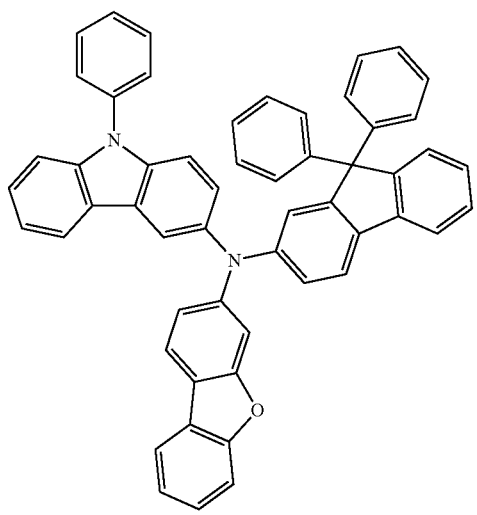

-continued
HT13
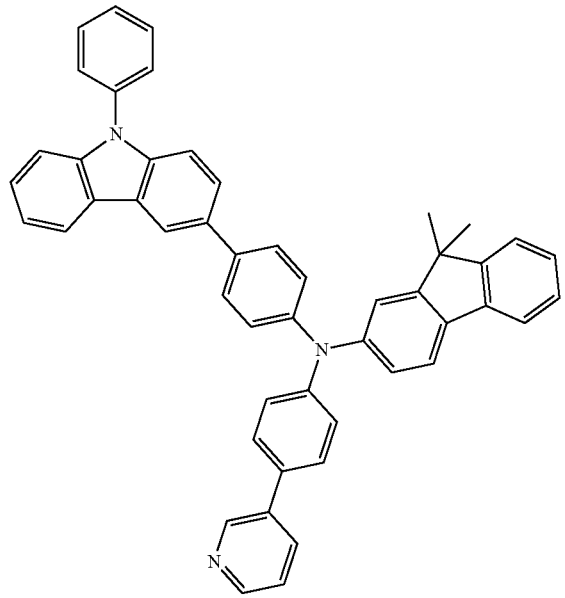
HT14
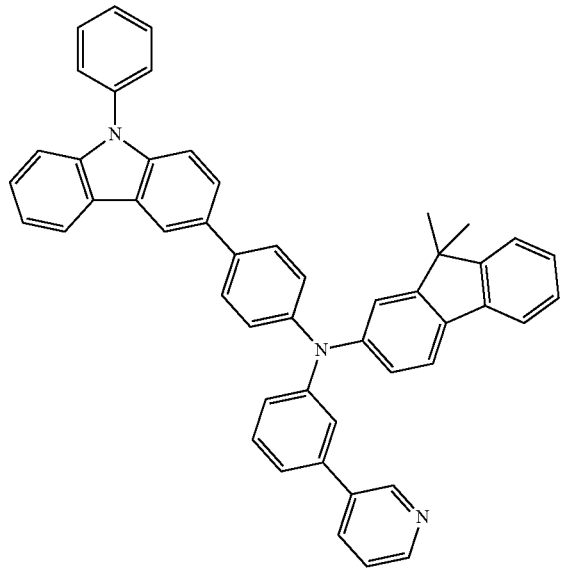
HT15
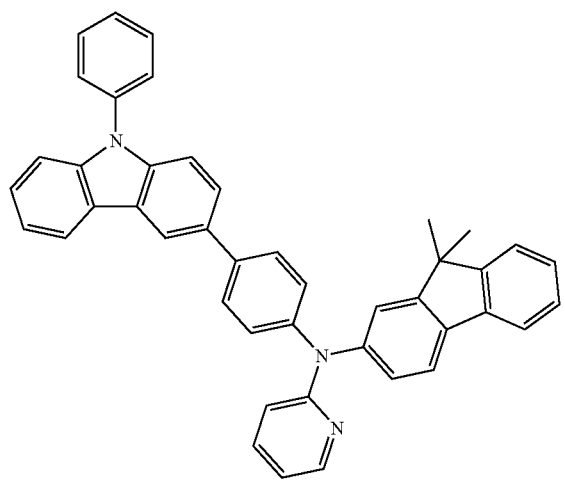
HT16
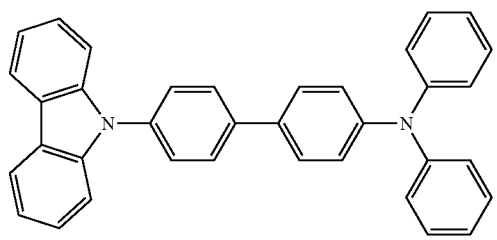
HT17
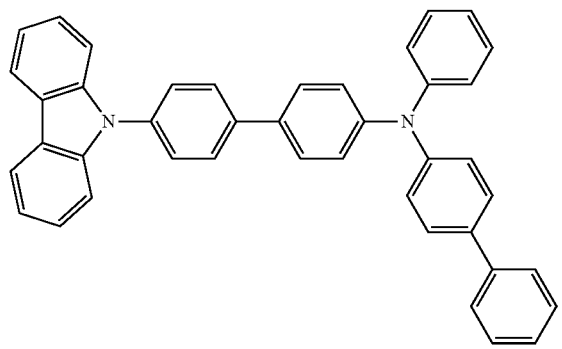
HT18
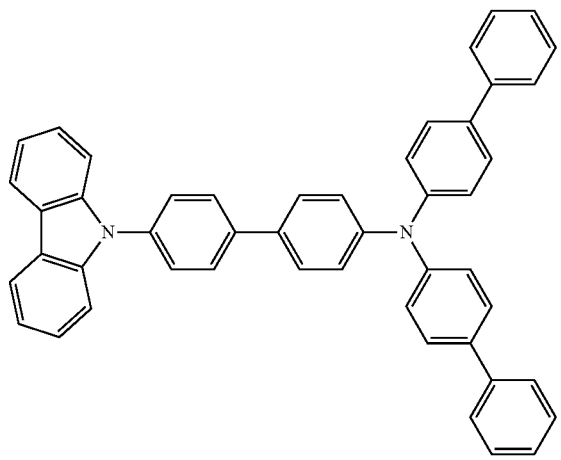

-continued
HT19
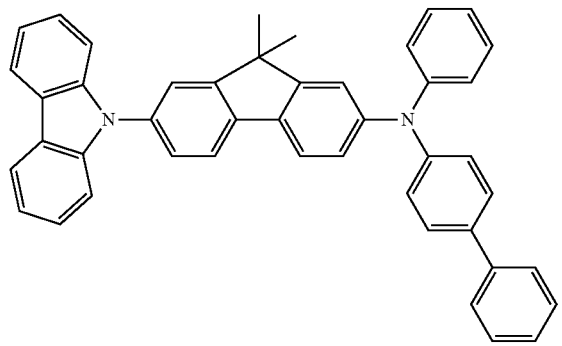
HT20
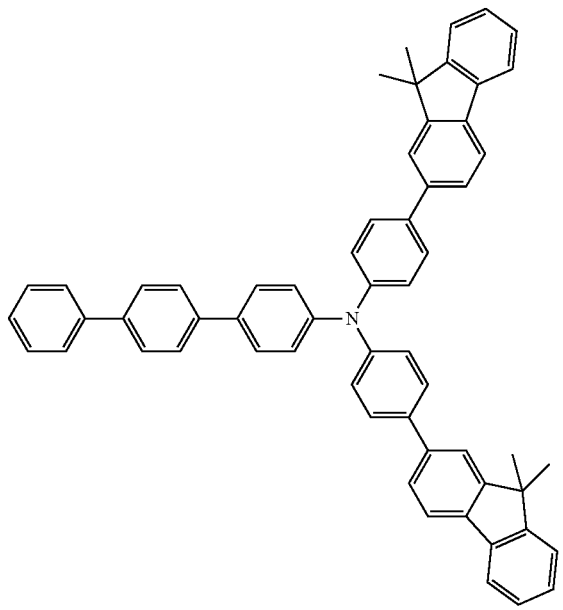
HT21
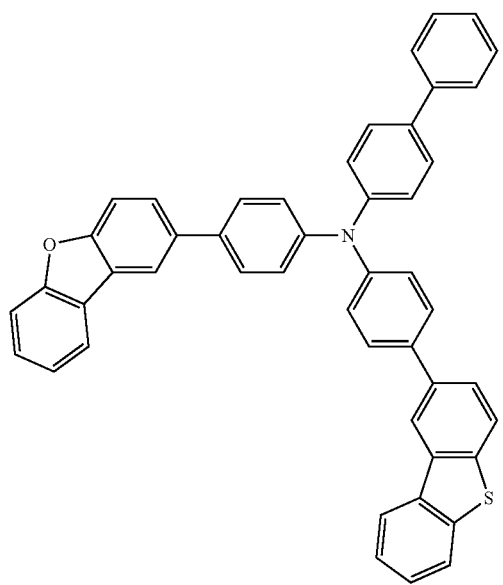
HT22
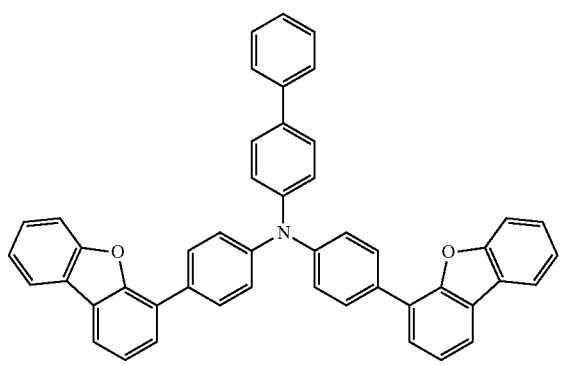

HT23
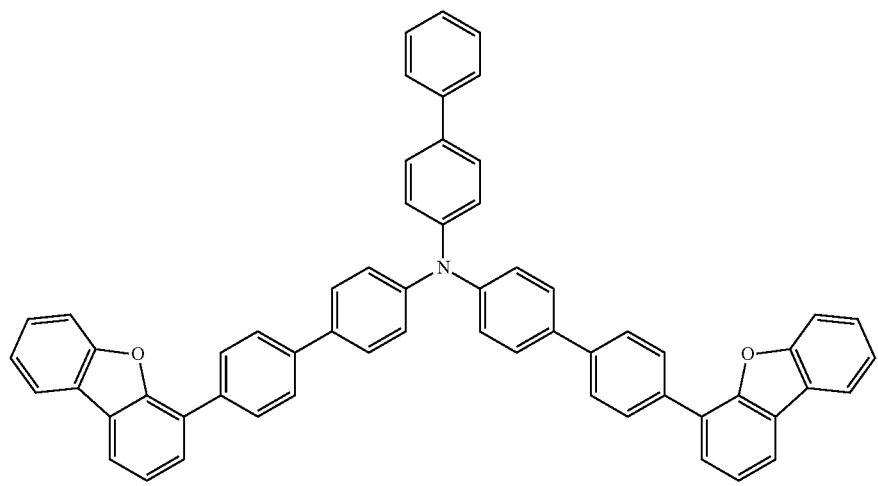
HT24
HT25
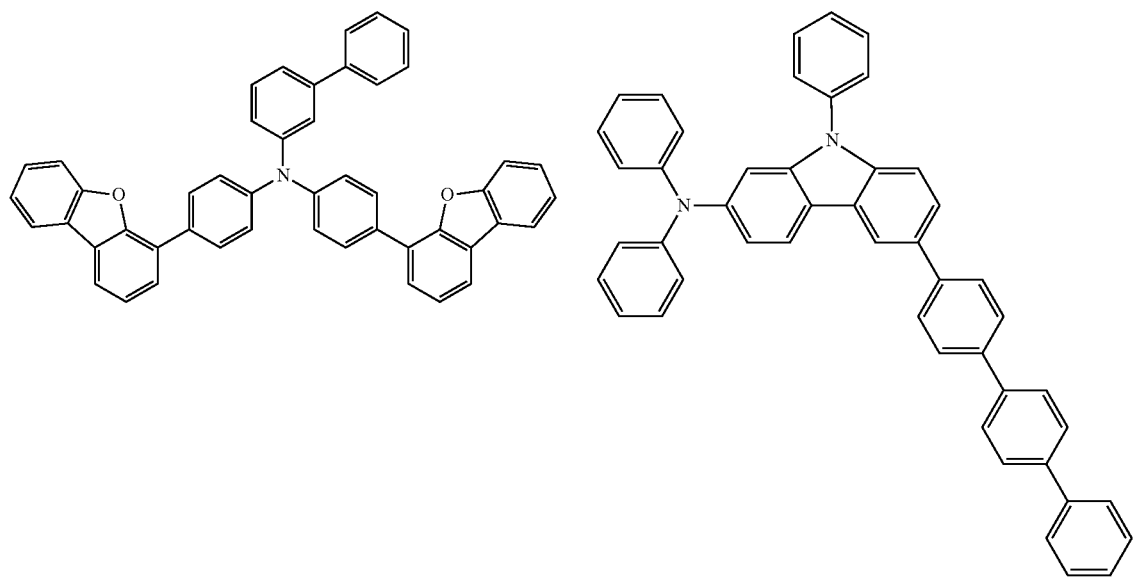
HT26
HT27
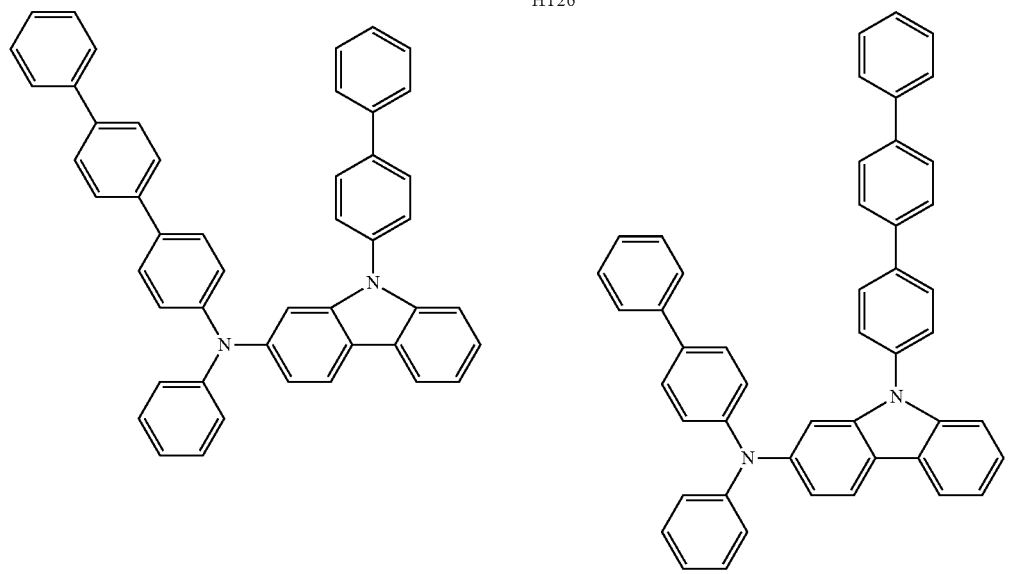

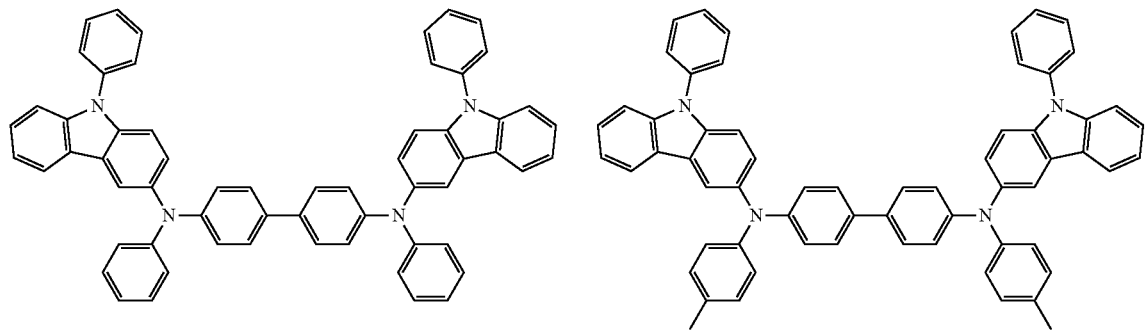
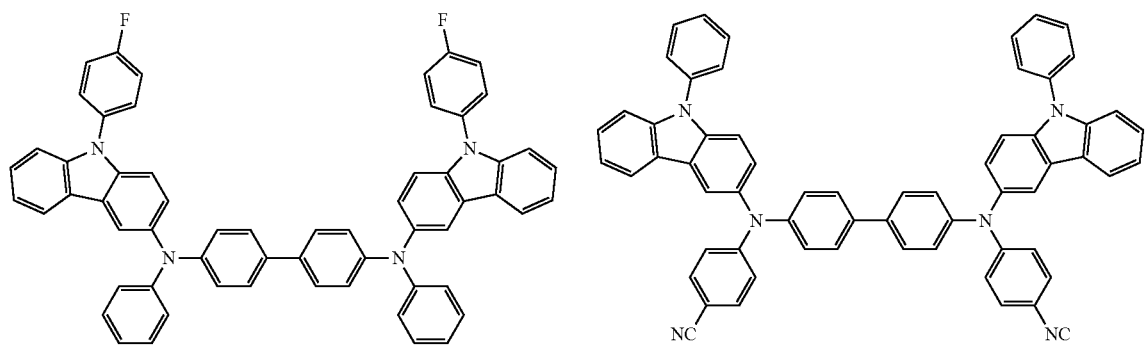
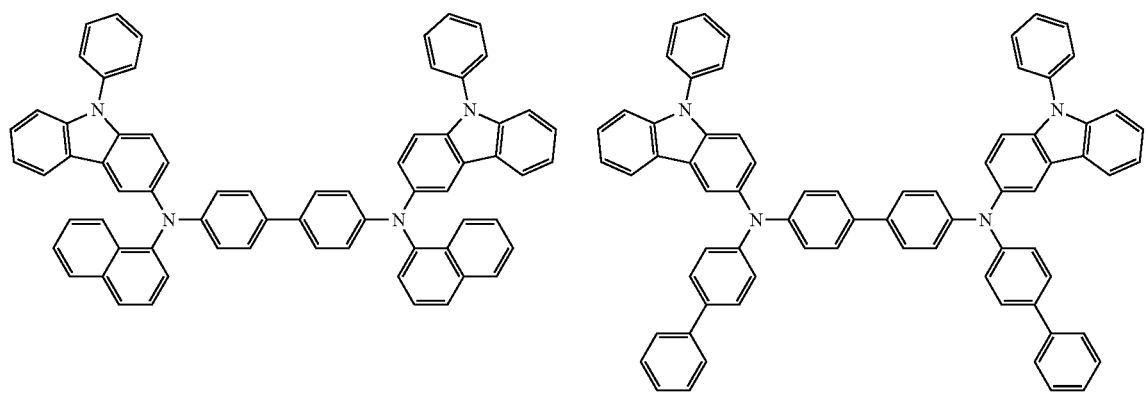

-continued
HT34
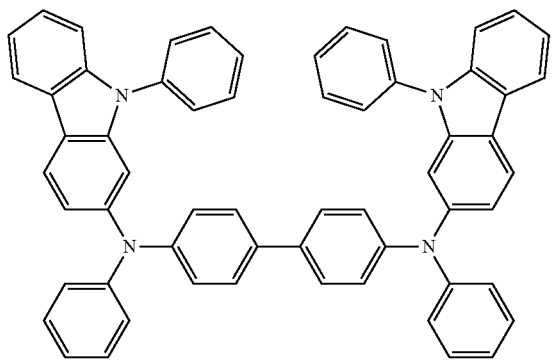
HT35
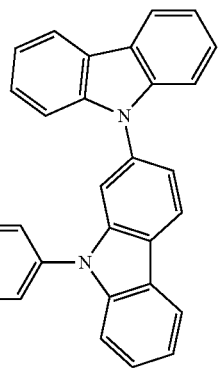
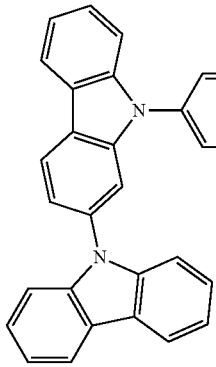
HT36
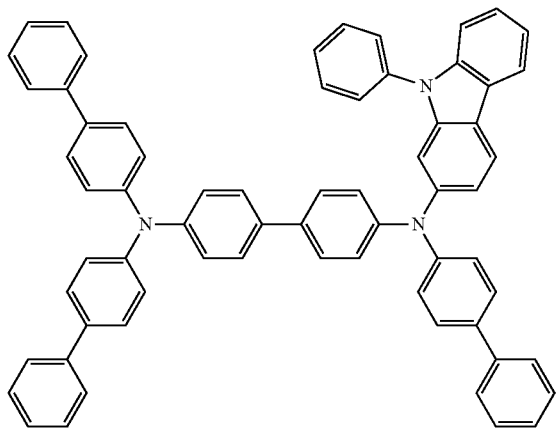
HT37
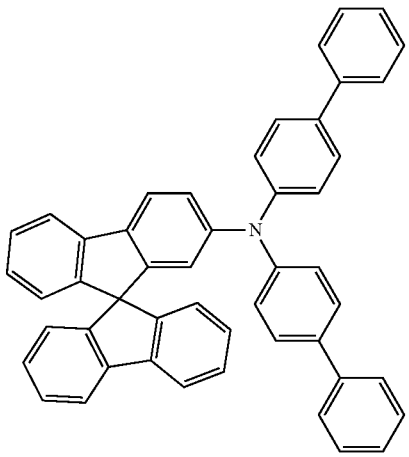
HT38
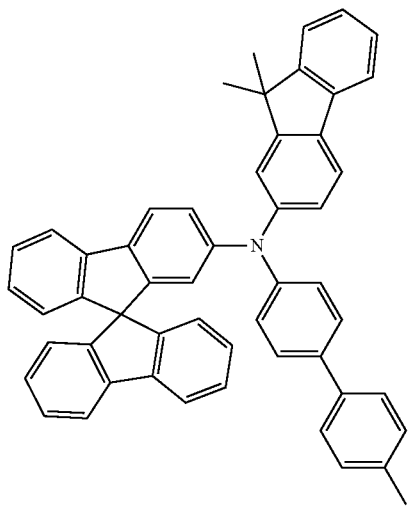
HT39
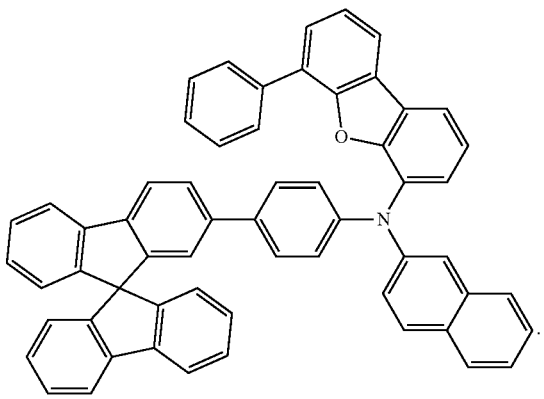
The thickness of the hole transport region may be in a range of about 100 (Angstroms) Å to about 10,000 Å, and in some embodiments, about 100 Å to about 1,000 Å. When the hole transport region includes at least one of a hole injection layer or a hole transport layer, the thickness of the hole injection layer may be in a range of about 100 Å to about 9,000 Å, and in some embodiments, about 100 Å to about 1,000 Å, and the thickness of the hole transport layer may be in a range of about 50 Å to about 2,000 Å, and in some embodiments, about 100 Å to about 1,500 Å. When the thicknesses of the hole transport region, the hole injection layer, and the hole transport layer are within any of these ranges, excellent (or suitable) hole transport characteristics may be obtained without a substantial increase in driving voltage.

The emission auxiliary layer may increase light emission efficiency by compensating for an optical resonance distance according to the wavelength of light emitted from the emission layer. The electron blocking layer may reduce or eliminate the flow of electrons from the electron transport region. The emission auxiliary layer and the electron blocking layer may each independently include any of the suitable materials mentioned above.

p-Dopant

The hole transport region may include a charge generating material as well as the aforementioned materials, to improve conductive properties of the hole transport region. The charge generating material may be substantially homogeneously or non-homogeneously dispersed in the hole transport region.

The charge-generating material may be, for example, a p-dopant.

In one or more embodiments, a lowest unoccupied molecular orbital (LUMO) of the p-dopant may be −3.5 eV or less.

The p-dopant may include at least one selected from a quinone derivative, a metal oxide, and a cyano group-containing compound, but embodiments are not limited thereto.

For example, the p-dopant may be selected from a quinone derivative, such as tetracyanoquinodimethane (TCNQ) and/or 2,3,5,6-tetrafluoro-7,7,8,8-tetracyanoquinodimethane (F4-TCNQ);

a metal oxide, such as tungsten oxide and/or molybdenum oxide;

1,4,5,8,9,12-hexaazatriphenylene-hexacarbonitrile (HAT-CN); and a compound represented by Formula 221, but embodiments are not limited thereto.

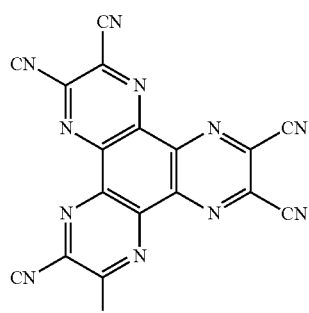

HAT-CN

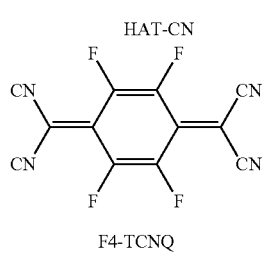

F4-TCNQ

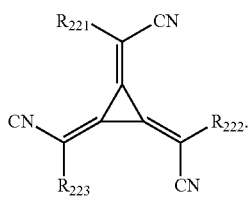

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one of $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in the Organic Layer 150

When the organic light-emitting device 10 is a full color organic light-emitting device, the emission layer may be patterned into a red emission layer, a green emission layer, or a blue emission layer, according to a sub-pixel. In one or more embodiments, the emission layer may have a stacked structure in which two or more layers selected from a red emission layer, a green emission layer, and a blue emission layer are stacked on one another in direct contact with or separated from each other. In one or more embodiments, the emission layer may have a structure in which two or more materials selected from a red light-emitting material, a green light-emitting material, and a blue light-emitting material may be mixed in a single layer, and thus emit white light.

The emission layer may include a host and a dopant. The dopant may include at least one of a phosphorescent dopant or a fluorescent dopant.

The amount of the dopant in the emission layer may be, for example, in a range of about 0.01 parts to about 15 parts by weight with respect to 100 parts by weight of the host, but embodiments are not limited thereto.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Host in Emission Layer

The host may include a compound represented by Formula 301.

$$[Ar_{301}]_{xb11}\text{-}[(L_{301})_{xb1}\text{-}R_{301}]_{xb21} \quad \text{Formula 301}$$

In Formula 301, $Ar_{301}$ may be selected from a substituted or unsubstituted $C_5$-$C_{60}$ carbocyclic group and a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer selected from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer selected from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In some embodiments, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

When xb11 in Formula 301 is 2 or greater, at least two $Ar_{301}$(s) may be linked to one another via a single bond.

In one or more embodiments, the compound represented by Formula 301 may be represented by Formula 301-1 or Formula 301-2:

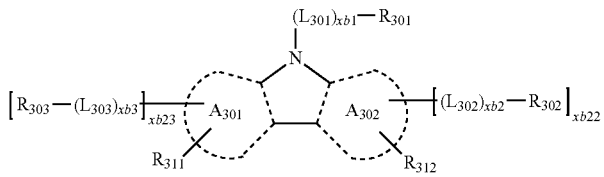

Formula 301-1

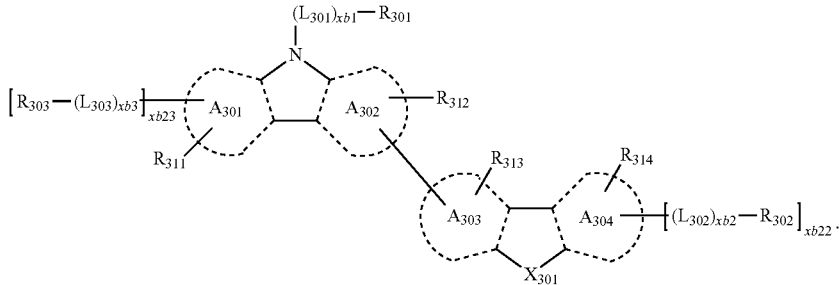

Formula 301-2

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and dinaphthothiophene group, $X_{301}$ may be O, S or N—[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1 or 2, $L_{301}$, xb1, $R_{301}$, and $Q_{31}$ to $Q_{33}$ may be as defined herein, $L_{302}$ to $L_{304}$ may be defined the same as $L_{301}$ is defined herein, xb2 to xb4 may each be defined the same as xb1 is defined herein, and $R_{302}$ to $R_{304}$ may each independently defined the same as $R_{301}$ is defined herein.

For example, in Formulae 301, 301-1 and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may be as defined herein.

In some embodiments, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may be as defined herein.

In some embodiments, the host may include an alkaline earth metal complex. For example, the host may be selected from a beryllium (Be) complex (for example, Compound H55), a magnesium (Mg) complex, and a zinc (Zn) complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55. However, embodiments are not limited thereto.

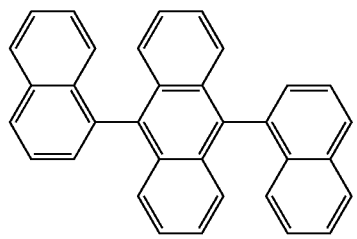

H1

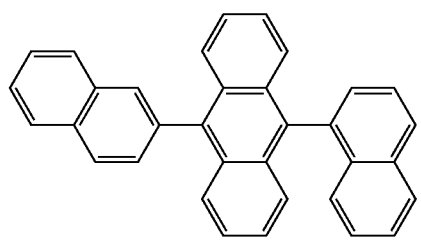

H2

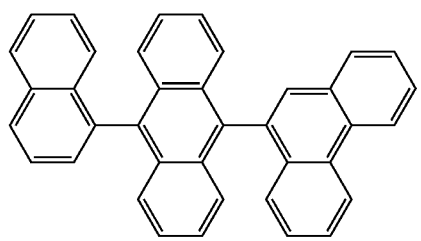

H3

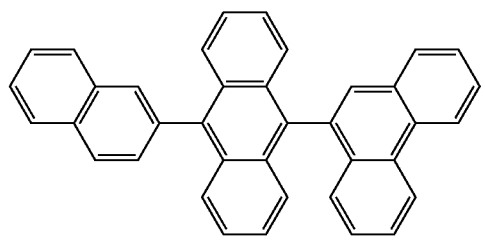

H4

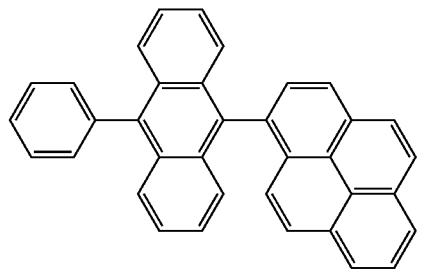

H5

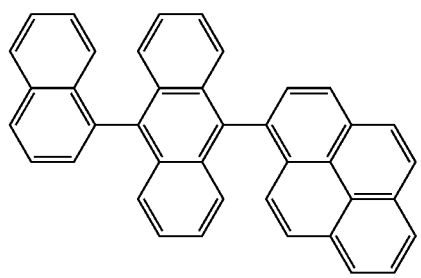

H6

H7
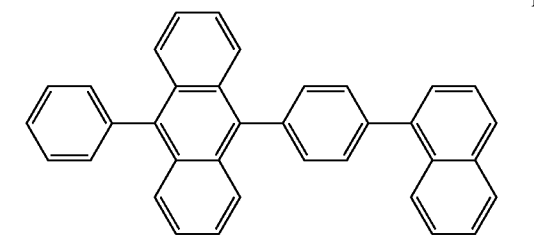
H8
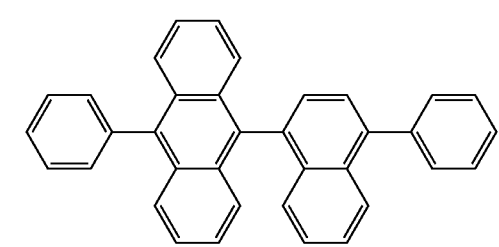
H9
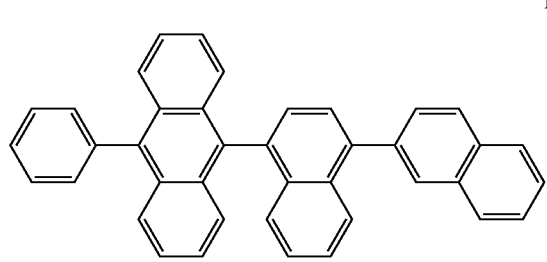
H10
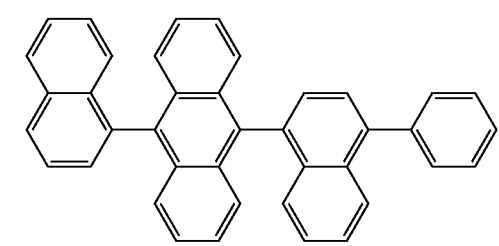
H11
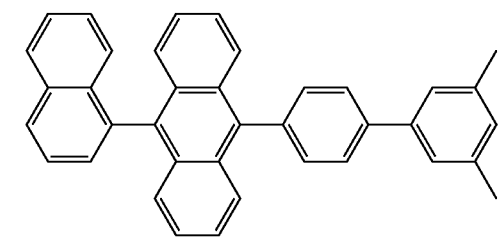
H12
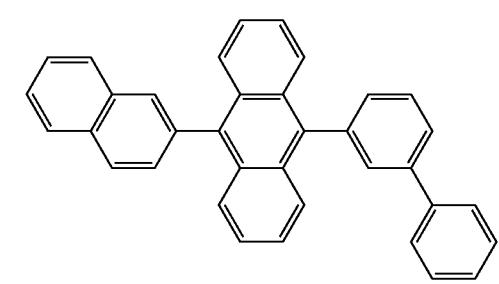
H13
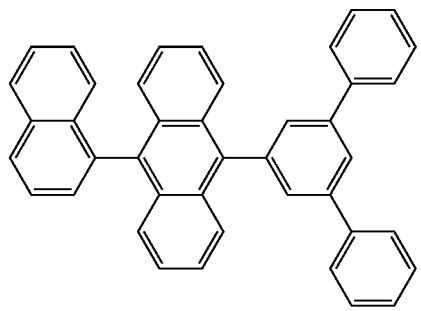
H14
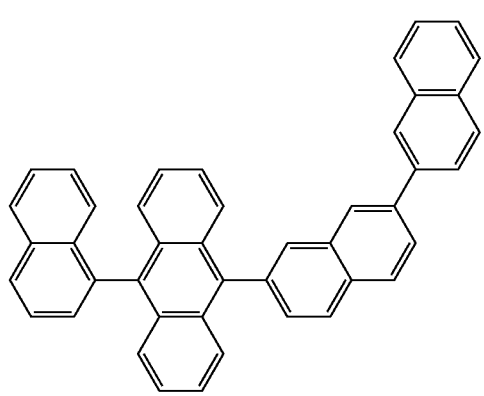
H15
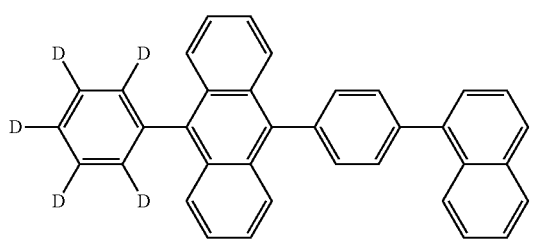
H16
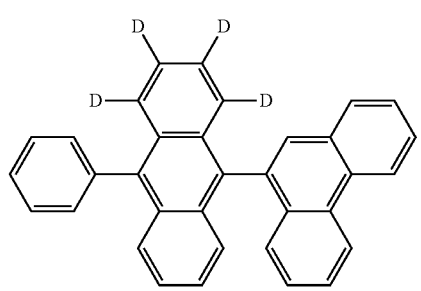
H17
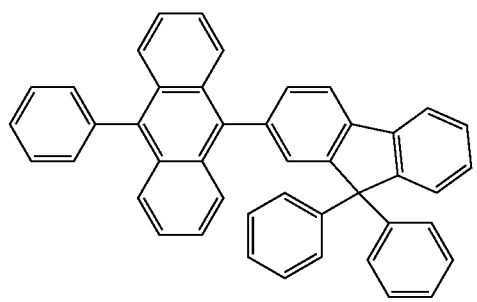

-continued
H18
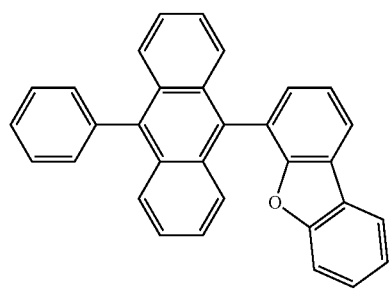
H19
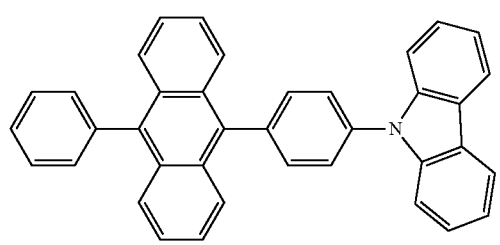
H20
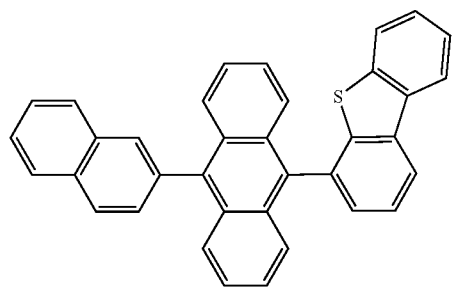
H21
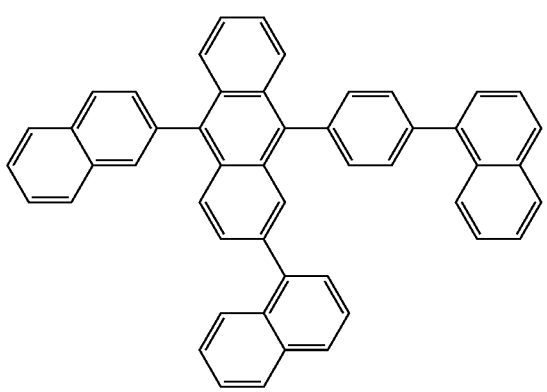
H22
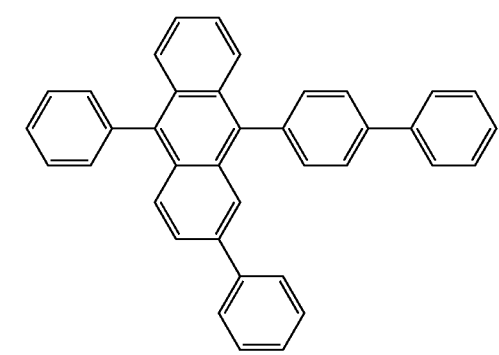
-continued
H23
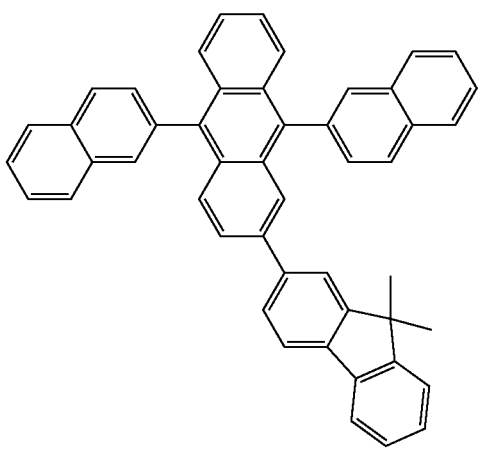
H24
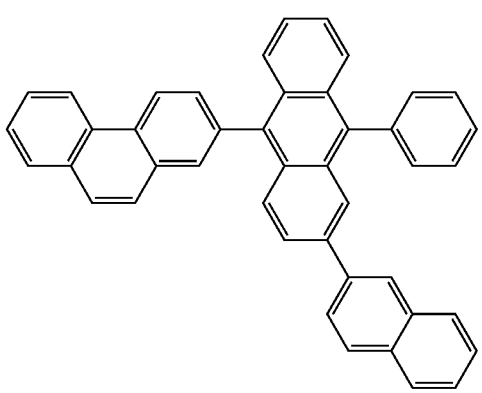
H25
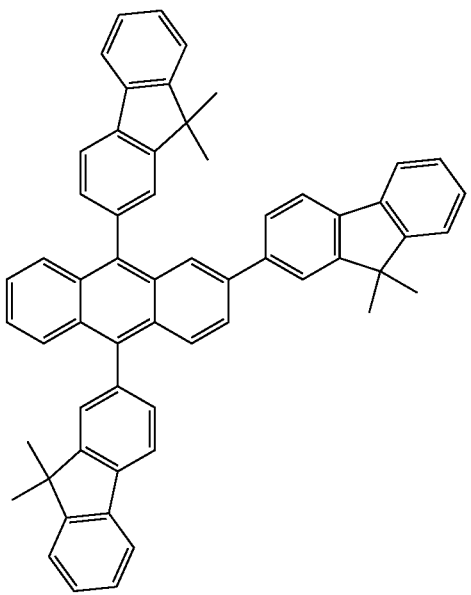

595
-continued
596
-continued
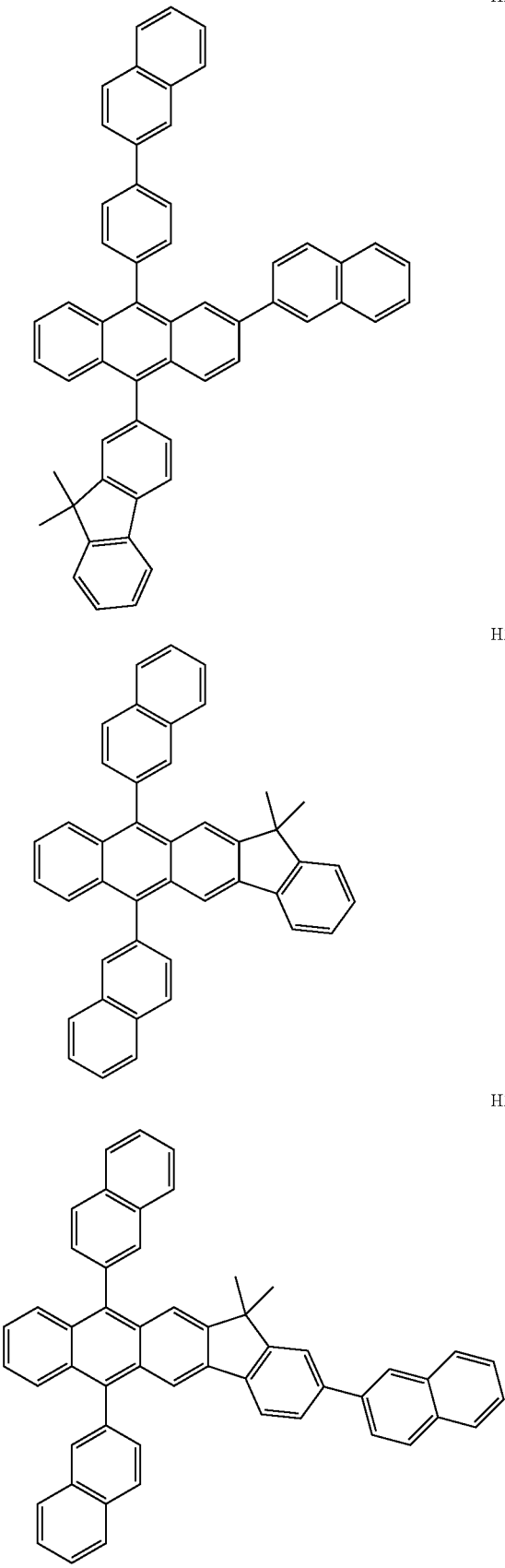
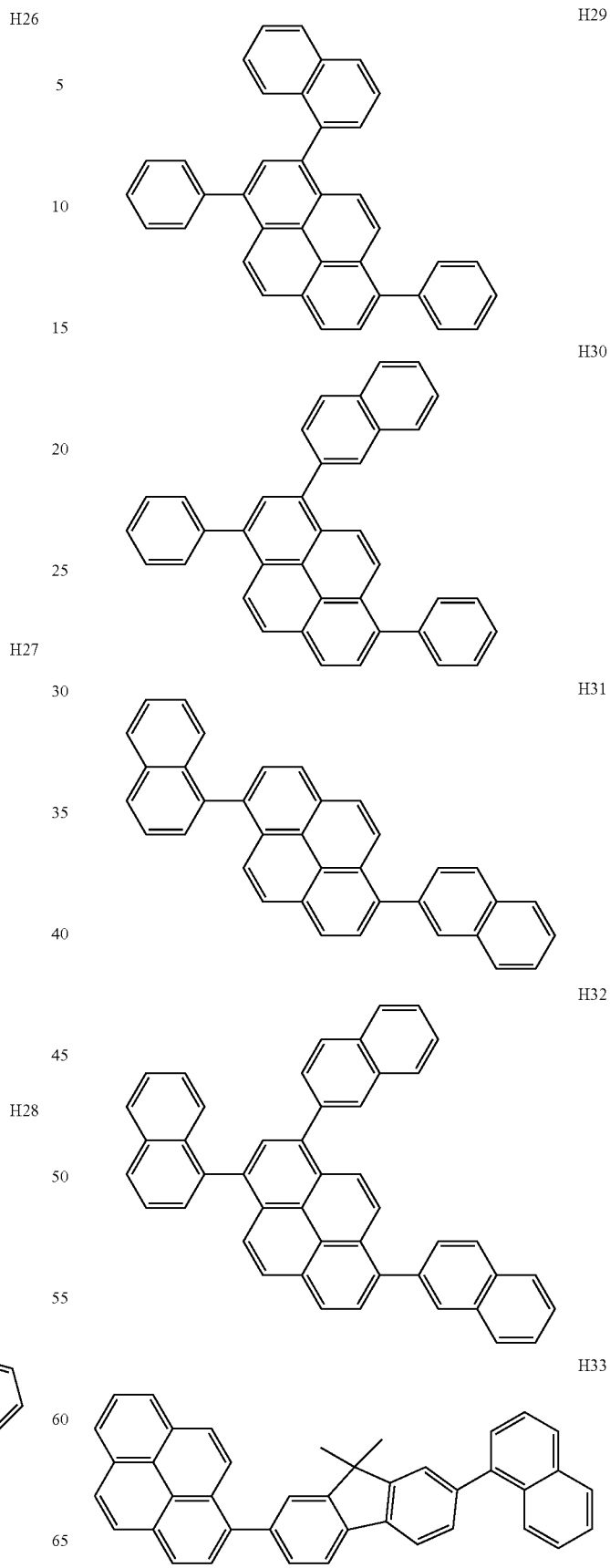

597
-continued
H34
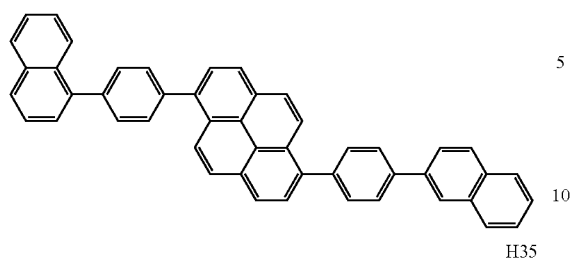
H35
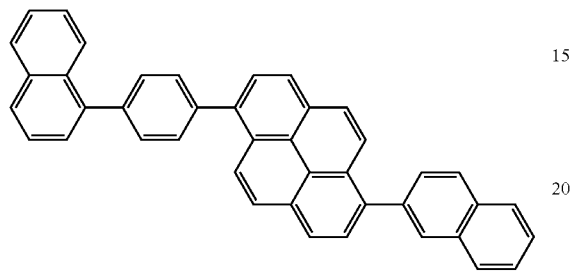
H36
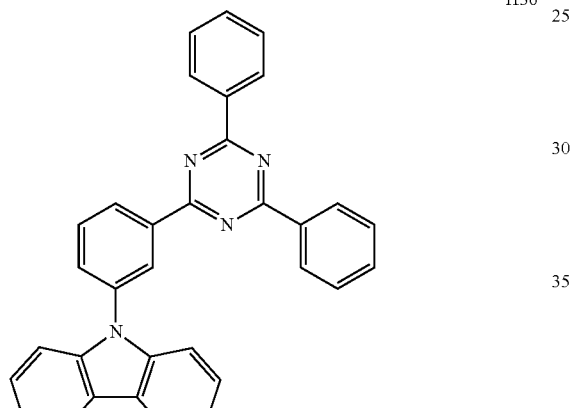
H37
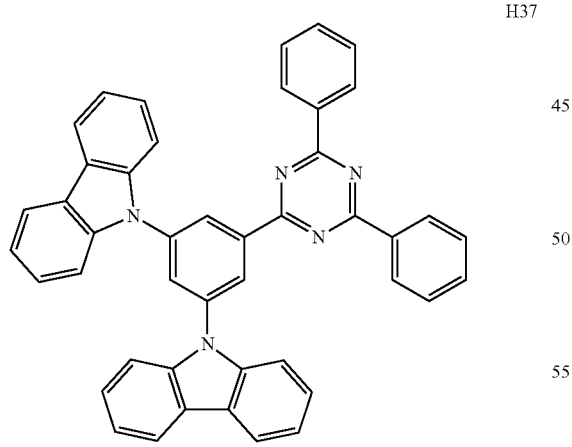
H38
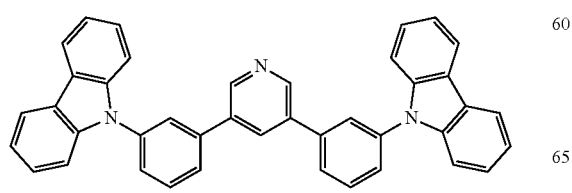
598
-continued
H39
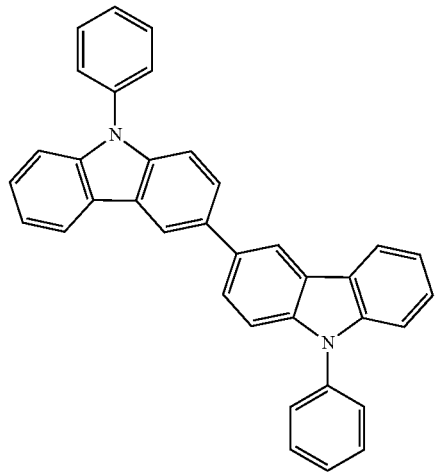
H40
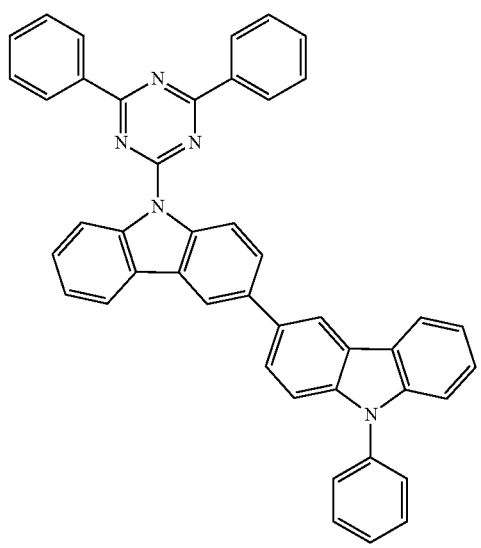
H41
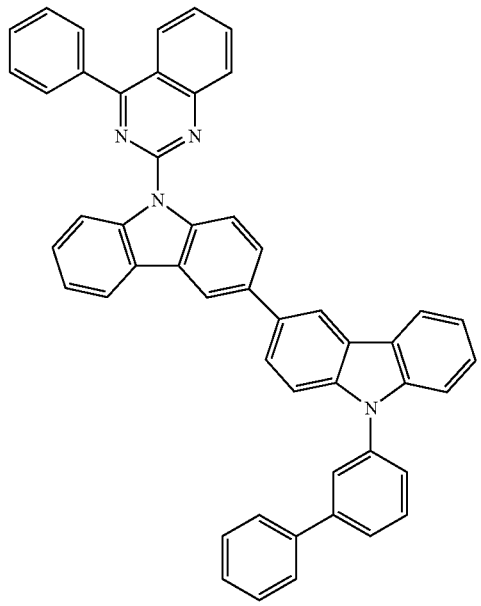

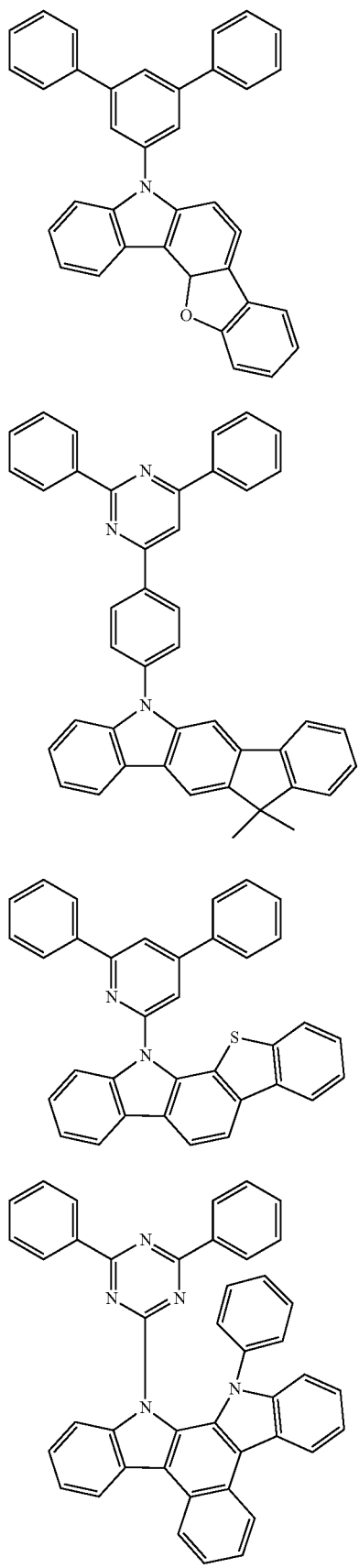
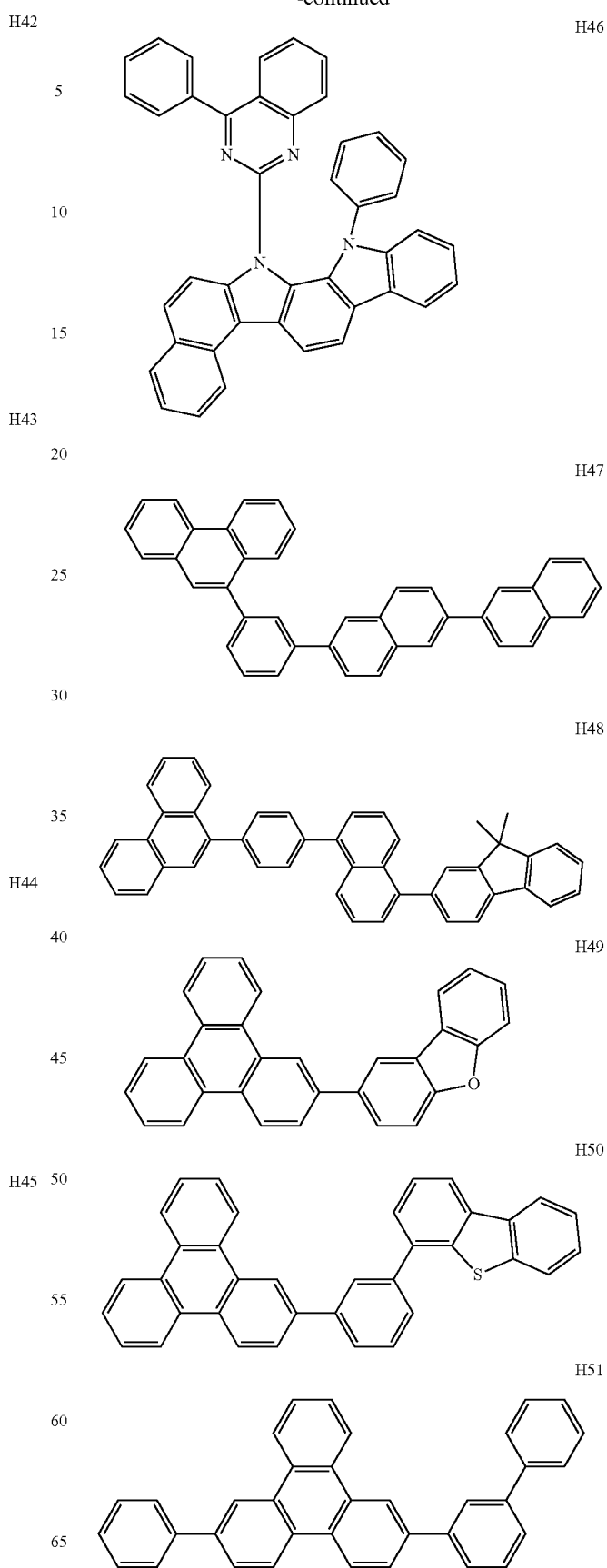

-continued

H52
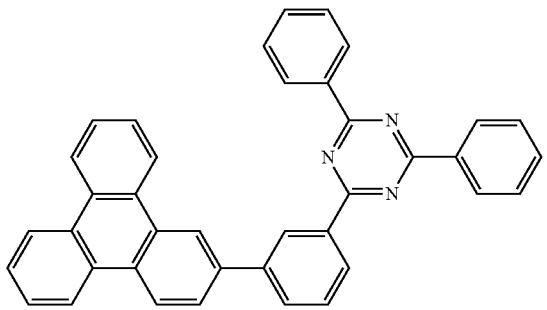

H53
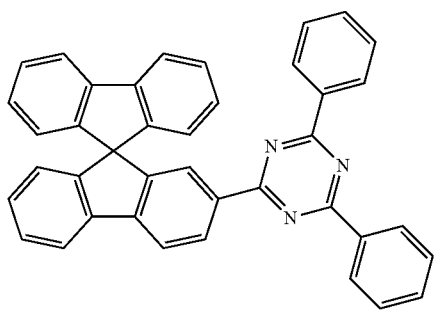

H54
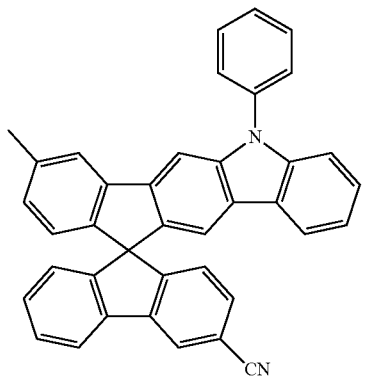

H55
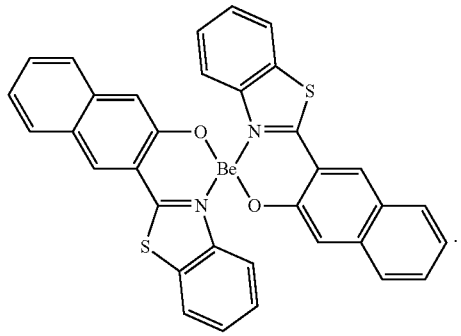

Phosphorescent Dopant Included in Emission Layer of the Organic Layer 150

The phosphorescent dopant may include an organometallic complex represented by Formula 401.

$$M(L_{401})_{xc1}(L_{402})_{xc2}$$ Formula 401

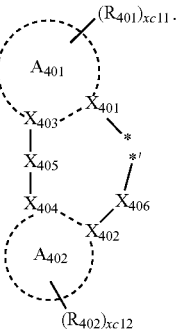

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from the ligands represented by Formula 402, xc1 may be 1, 2, or 3, and when xc1 is 2 or greater, two or more $L_{401}(s)$ may be the same or different, $L_{402}$ may be an organic ligand, xc2 may be an integer selected from 0 to 4, and when xc2 is 2 or greater, two or more $L_{402}(s)$ may be the same or different, $X_{401}$ to $X_{404}$ may each independently be nitrogen or carbon, $X_{401}$ and $X_{403}$ may be linked to each other via a single bond or a double bond, and $X_{402}$ and $X_{404}$ may be linked to each other via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*', wherein $Q_{411}$ and $Q_{412}$ may each independently be hydrogen, deuterium, $C_1$-$C_{20}$ alkyl group, a $C_1$-$C_{20}$ alkoxy group, a phenyl group, a biphenyl group, a terphenyl group, or a naphthyl group, $X_{406}$ may be a single bond, 0, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer selected from 0 to 10, In Formula 402, * and *' are each a binding site to M in Formula 401.

In one or more embodiments, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In some embodiments, in Formula 402, i) $X_{401}$ may be nitrogen, and $X_{402}$ may be carbon, or ii) $X_{401}$ and $X_{402}$ may both be nitrogen.

In some embodiments, in Formula 402, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group.

However, embodiments are not limited thereto.

In some embodiments, in Formula 401, when xc1 is 2 or greater, two $A_{401}$(s) of two or more $L_{401}$(s) may optionally be linked via $X_{407}$, which is a linking group, or two $A_{402}$(s) may optionally be linked via $X_{408}$, which is a linking group (see e.g., Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-' or *—C($Q_{413}$)=C($Q_{414}$)-*' (wherein $Q_{413}$ and $Q_{414}$ may each independently be hydrogen, deuterium, $C_1$-$C_{20}$ alkyl group, a $C_1$-$C_{20}$ alkoxy group, a phenyl group, a biphenyl group, a terphenyl group, or a naphthyl group). However, embodiments are not limited thereto.

In Formula 401, $L_{402}$ may be any suitable monovalent, divalent, or trivalent organic ligand. For example, $L_{402}$ may be selected from a halogen, a diketone (for example, acetylacetonate), carboxylic acid (for example, picolinate), —C(=O), isonitrile, —CN, and phosphorus (for example, phosphine and/or phosphate). However, embodiments are not limited thereto.

In other embodiments, the phosphorescent dopant may be selected from Compounds PD1 to PD25. However, embodiments are not limited thereto.

PD1

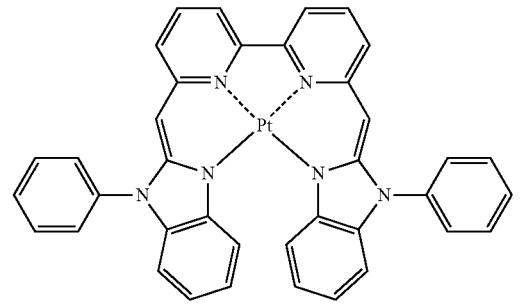

PD2

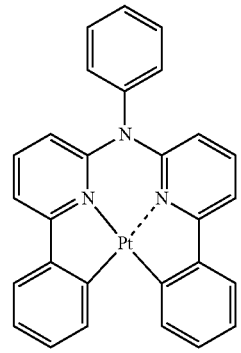

PD3

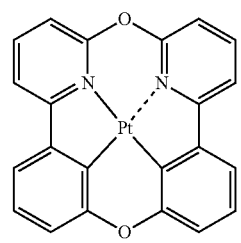

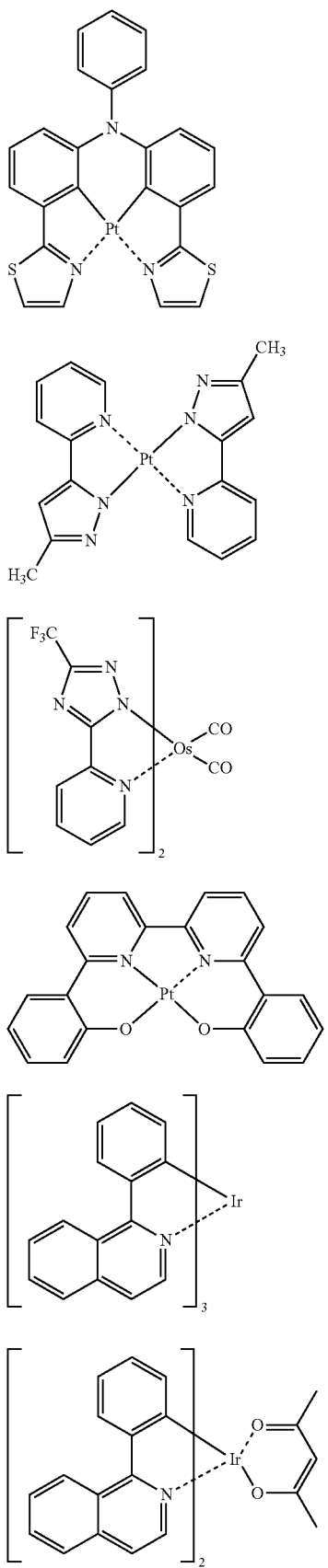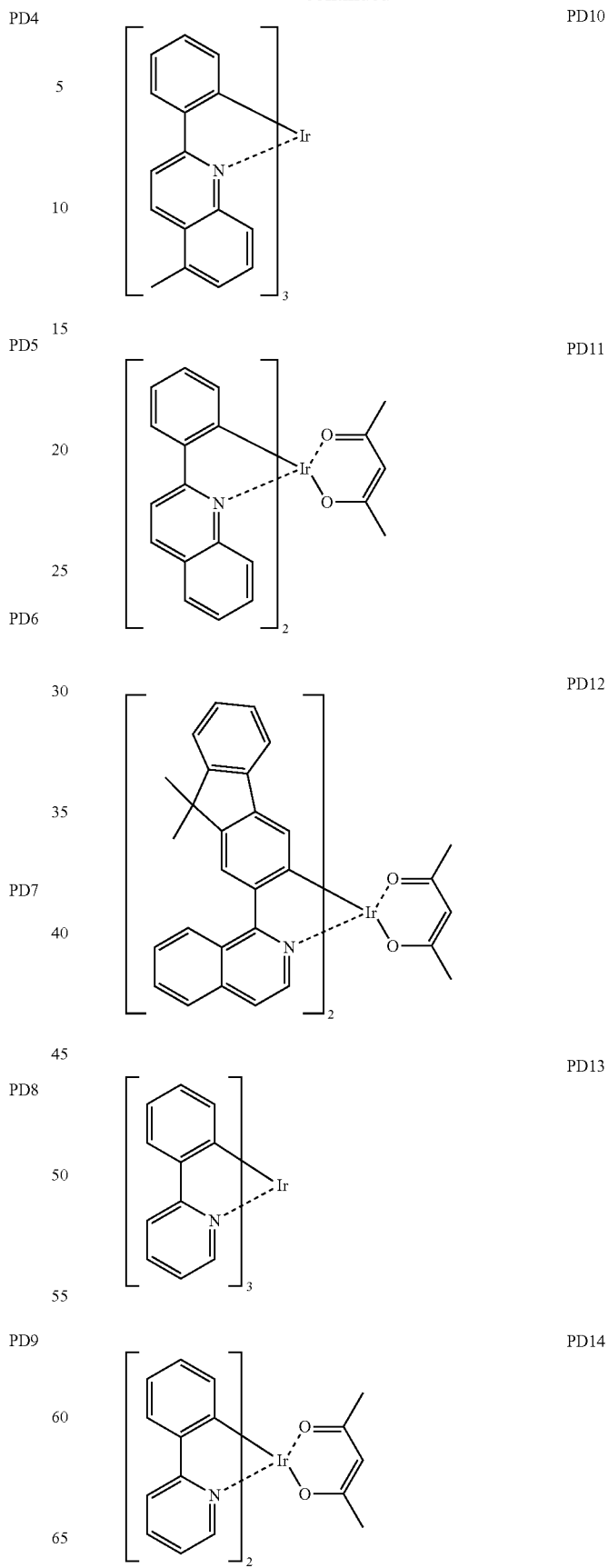

PD15 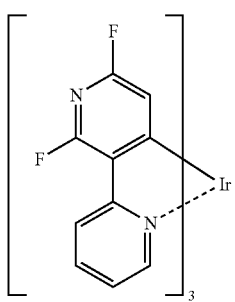
PD16 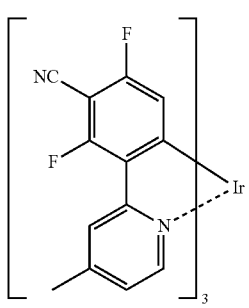
PD17 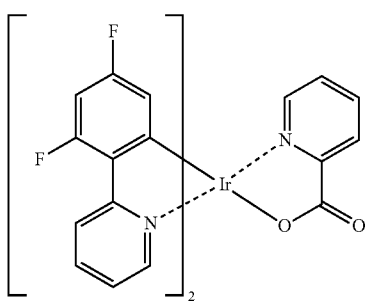
PD18 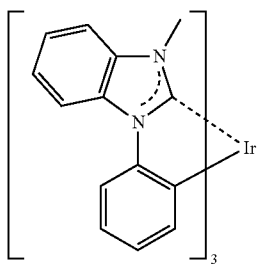
PD19 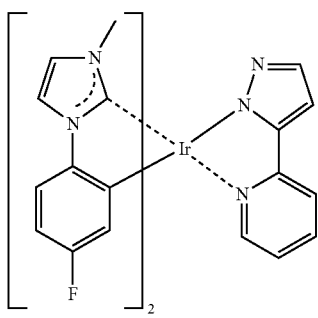
PD20 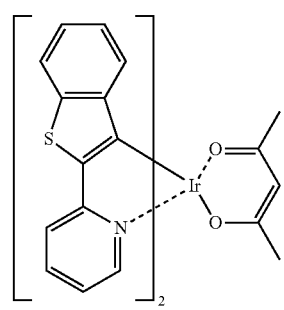
PD21 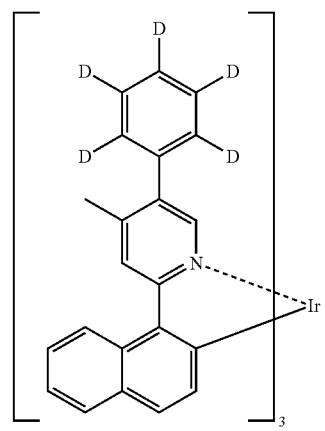
PD22 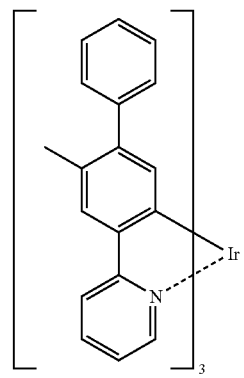
PD23 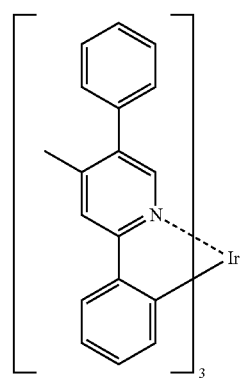

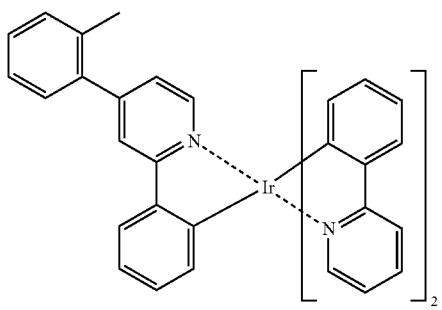

PD24

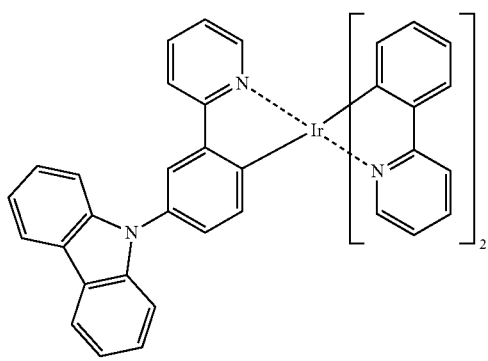

PD25

Fluorescent Dopant in Emission Layer

The fluorescent dopant may include an arylamine compound or a styrylamine compound.

The fluorescent dopant may include a compound represented by Formula 501.

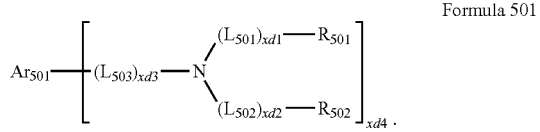

Formula 501

In Formula 501, $Ar_{501}$ may be a substituted or unsubstituted $C_5$-$C_{60}$ carbocyclic group, or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer selected from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer selected from 1 to 6.

In one or more embodiments, in Formula 501, $Ar_{501}$ may be selected from:

a naphthalene group, a heptalene group, a fluorene group, spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, and an indenophenanthrene group; and a naphthalene group, a heptalene group, a fluorene group, spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In some embodiments, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In some embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group and —Si($Q_{31}$)($Q_{32}$)($Q_{33}$), and $Q_{31}$ to $Q_{33}$ may each independently be selected from a $C_1$-$C_{10}$ alkyl group, a alkoxy group, a phenyl group, a biphenyl group, a terphenyl group, and a naphthyl.

In some embodiments, in Formula 501, xd4 may be 2. However, embodiments are not limited thereto.

For example, the fluorescent dopant may be selected from Compounds FD1 to FD22.

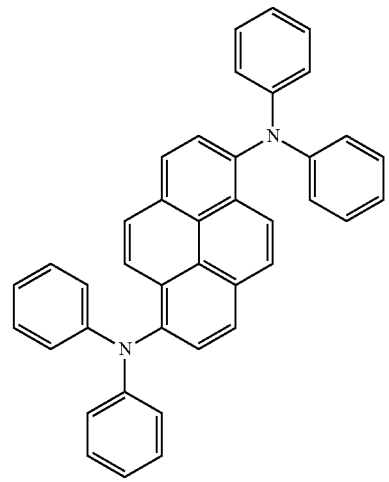

FD1

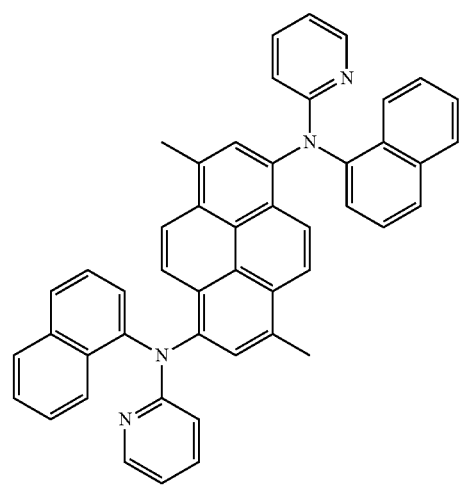

FD2

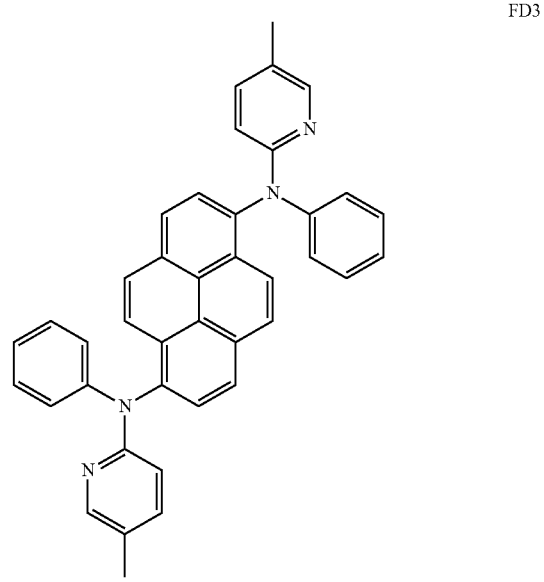

FD3

FD4
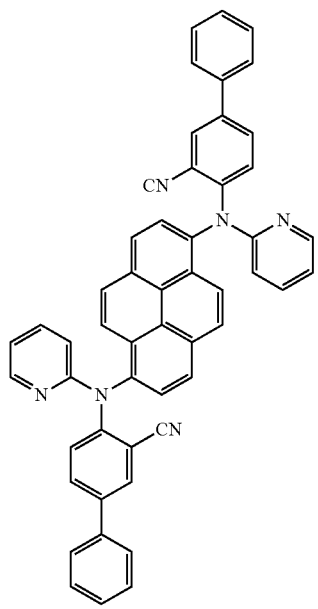
FD5

FD6

FD7
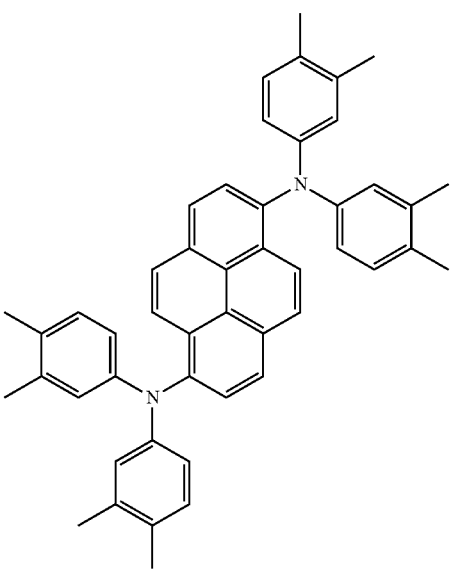
FD8
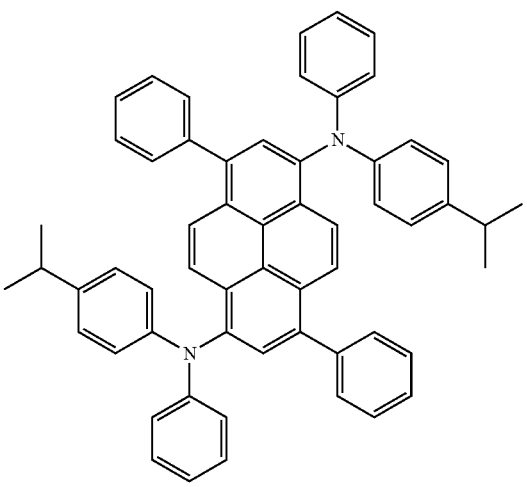
FD9
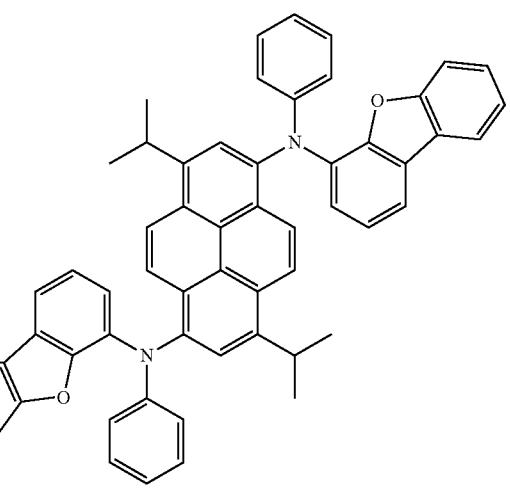

FD10
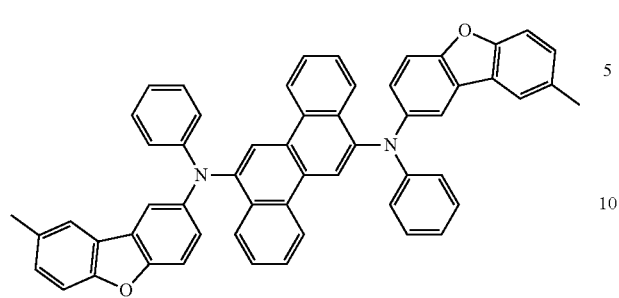
FD11
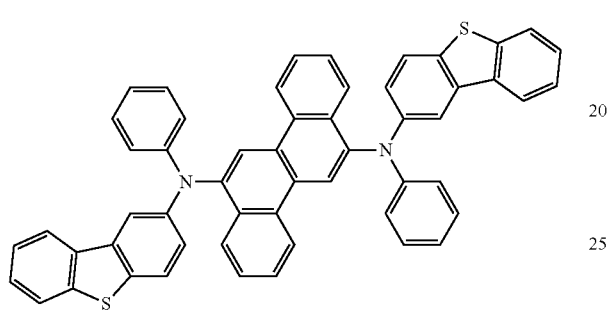
FD12
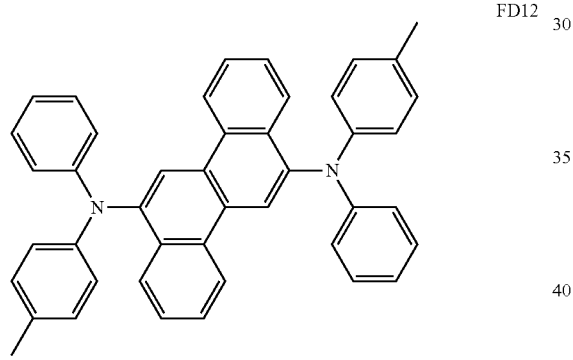
FD13
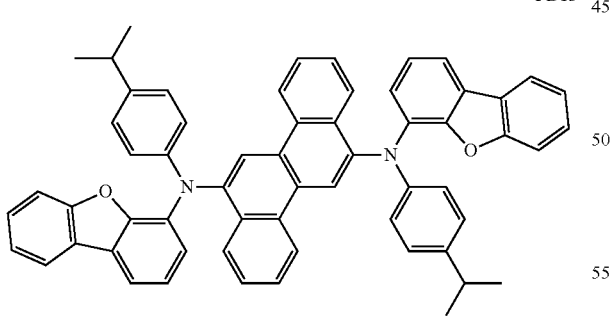
FD14
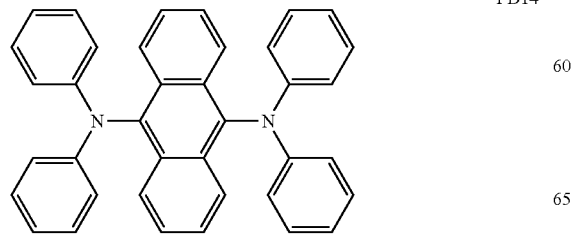
FD15
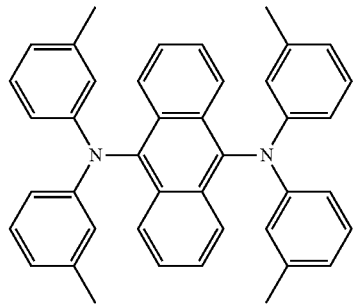
FD16
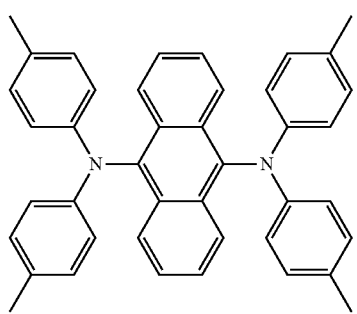
FD17
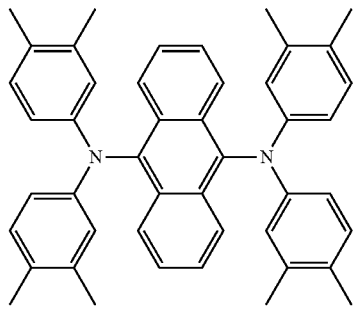
FD18
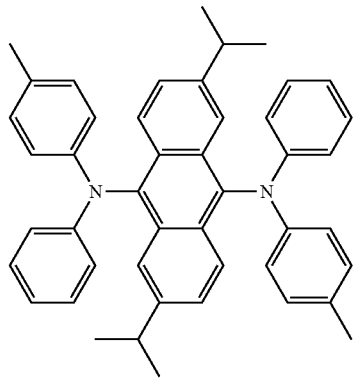

FD19
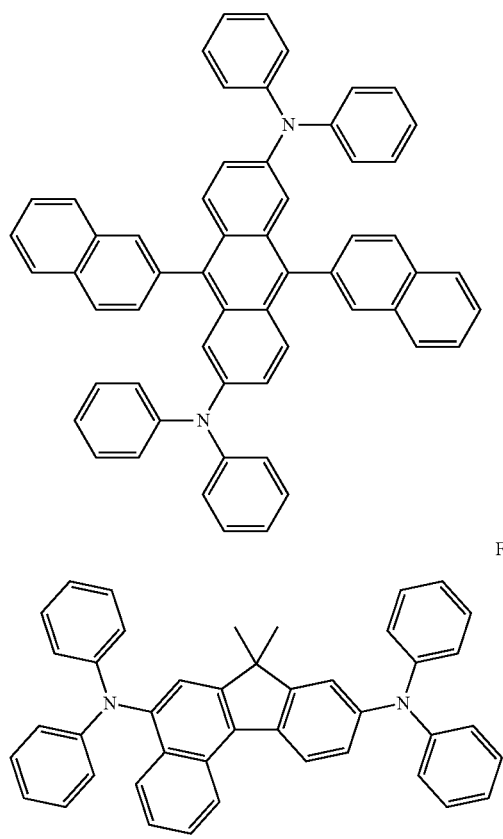
FD20
FD21
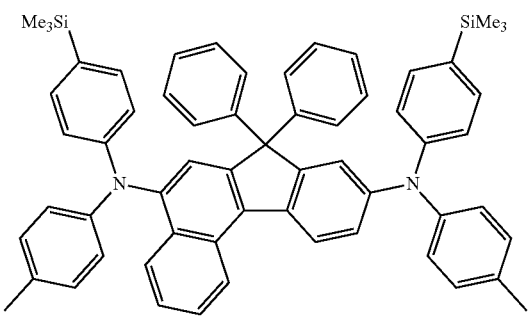
FD22
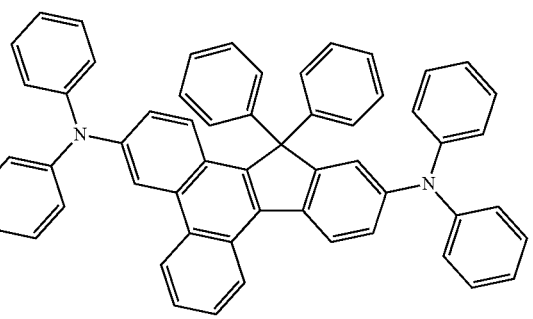
In some embodiments, the fluorescent dopant may be selected from the following compounds (shown below). However, embodiments are not limited thereto.
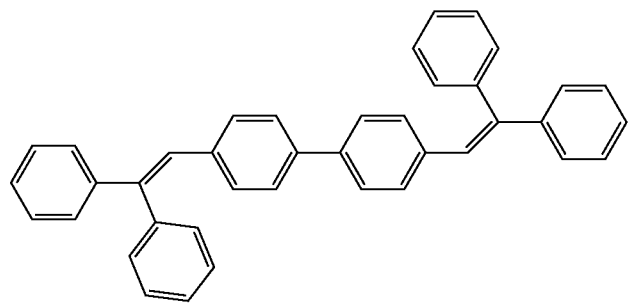
DPVBi
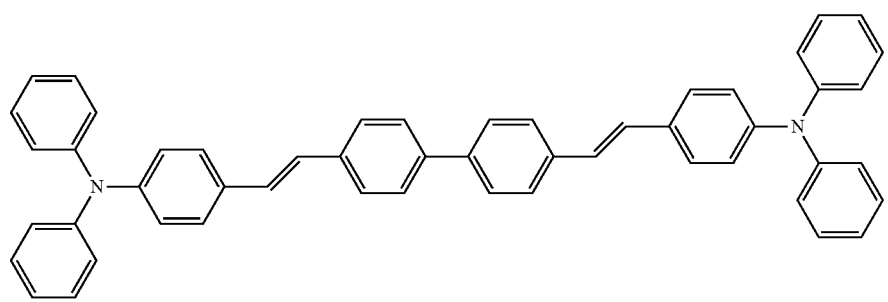
DPAVBi

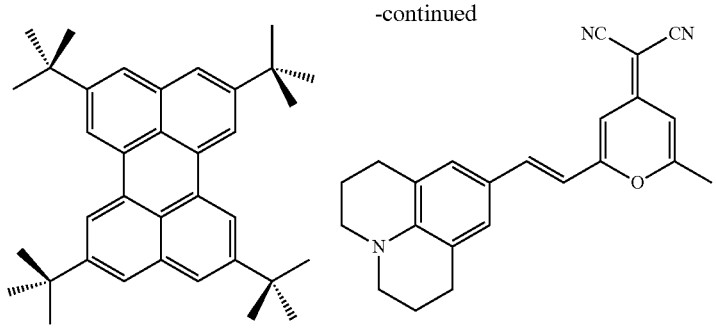

TBPe

DCM

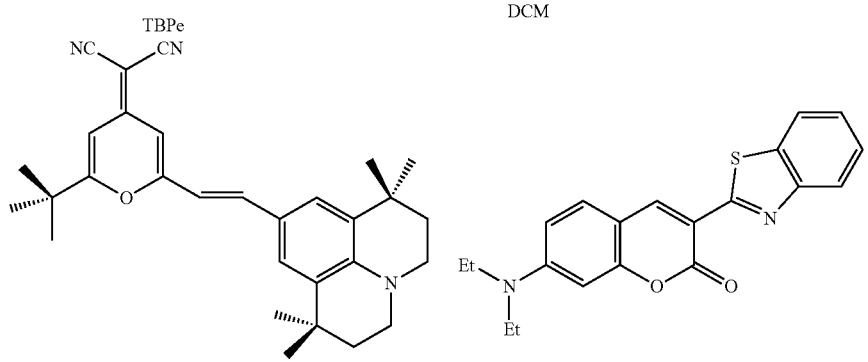

DCJTB

Coumarin 6

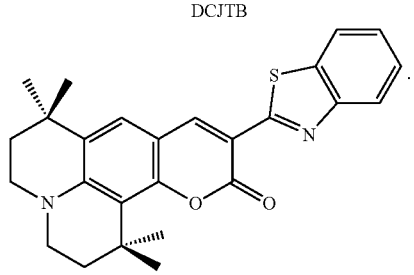

C545T

Electron Transport Region of the Organic Layer (150)

The electron transport region may have i) a single-layered structure consisting of a single layer consisting of a single material, ii) a single-layered structure consisting of a single layer including a plurality of different materials, or iii) a multi-layered structure each having a plurality of layers, each having a plurality of different materials.

The electron transport region may include at least one selected from a buffer layer, a hole blocking layer, an electron control layer, an electron transport layer, and an electron injection layer, but embodiments are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in the stated order, but embodiments are not limited thereto.

The electron transport region (for example, the buffer layer, the hole blocking layer, the electron control layer, and/or the electron transport layer in the electron transport region) may include a metal-free compound including at least one π electron-depleted nitrogen-containing ring.

The term "π electron-depleted nitrogen-containing ring" as used herein refers to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which at least two 5-membered to 7-membered heteromonocyclic groups, each having at least one *—N=*' moiety, are condensed, or iii) a heteropolycyclic group in which at least one of a 5-membered to 7-membered heteromonocyclic group, each having at least one *—N=*' moiety, is condensed with at least one $C_5$-$C_{60}$ carbocyclic group.

Examples of the π electron-depleted nitrogen-containing ring may include imidazole, pyrazole, thiazole, isothiazole, oxazole, isoxazole, pyridine, pyrazine, pyrimidine, pyridazine, indazole, purine, quinoline, isoquinoline, benzoquinoline, phthalazine, naphthyridine, quinoxaline, quinazoline, cinnoline, phenanthridine, acridine, phenanthroline, phenazine, benzimidazole, isobenzothiazole, benzoxazole, isobenzoxazole, triazole, tetrazole, oxadiazole, triazine, thiadiazole, imidazopyridine, imidazopyrimidine, and azacarbazole, but embodiments are not limited thereto.

In some embodiments, the electron transport region may include a compound represented by Formula 601.

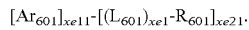

Formula 601

In Formula 601, $Ar_{601}$ may be selected from a substituted or unsubstituted $C_5$-$C_{60}$ carbocyclic group and a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_{601})(Q_{602})(Q_{603})$, $-C(=O)(Q_{601})$, $-S(=O)_2(Q_{601})$, and $-P(=O)(Q_{601})(Q_{602})$, wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In an embodiment, at least one selected from $Ar_{601}$(s) in the number of xe11 and $R_{601}$(s) in the number of xe21 may include the π electron-depleted nitrogen-containing ring.

In some embodiments, in Formula 601, $Ar_{601}$ may be selected from a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $-Si(Q_{31})(Q_{32})(Q_{33})$, $-S(=O)_2(Q_{31})$, and $-P(=O)(Q_{31})(Q_{32})$, and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or greater, at least two $Ar_{601}$(s) may be bound via a single bond.

In one or more embodiments, $Ar_{601}$ in Formula 601 may be an anthracene group.

In one or more embodiments, a compound represented by Formula 601 may be represented by Formula 601-1.

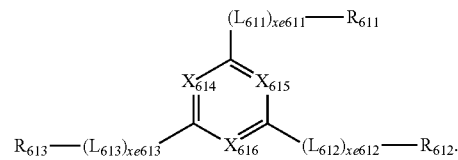

Formula 601-1

In Formula 601-1, $X_{614}$ may be N or $C(R_{614})$, $X_{615}$ may be N or $C(R_{615})$, $X_{616}$ may be N or $C(R_{616})$, at least one selected from $X_{614}$ to $X_{616}$ may be N, $L_{611}$ to $L_{613}$ may each independently be understood by referring to the descriptions for $L_{601}$ provided herein, xe611 to xe613 may each independently be understood by referring to the descriptions for xe1 provided herein, $R_{611}$ to $R_{613}$ may each independently be understood by referring to the descriptions for $R_{601}$ provided herein, and $R_{614}$ to $R_{616}$ may each independently be selected from hydrogen, deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an embodiment, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments are not limited thereto.

In one or more embodiments, xe1 and xe611 to xe613 in Formulae 601 and 601-1 may each independently be 0, 1, or 2.

In one or more embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), wherein Q$_{601}$ and Q$_{602}$ may be understood by referring to the descriptions thereof provided herein.

The electron transport region may include at least one compound selected from Compounds ET1 to ET36, but embodiments are not limited thereto.

ET2

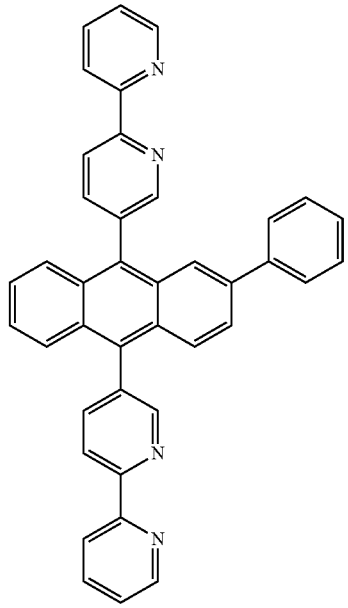

ET3

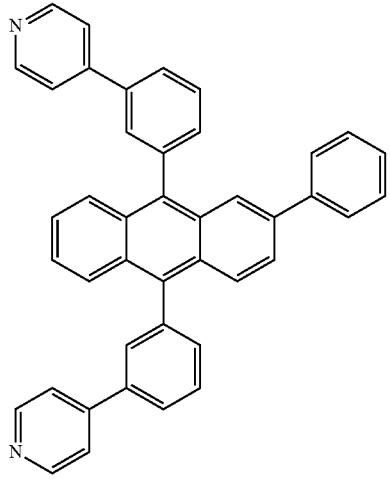

ET1

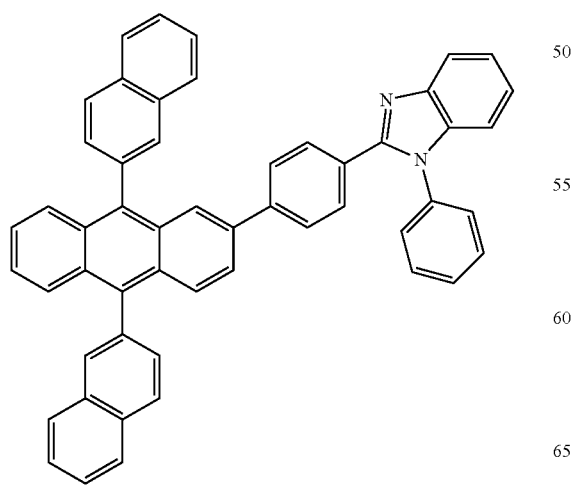

ET4

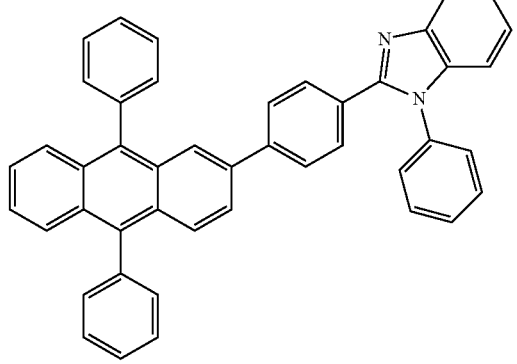

627
-continued
ET5
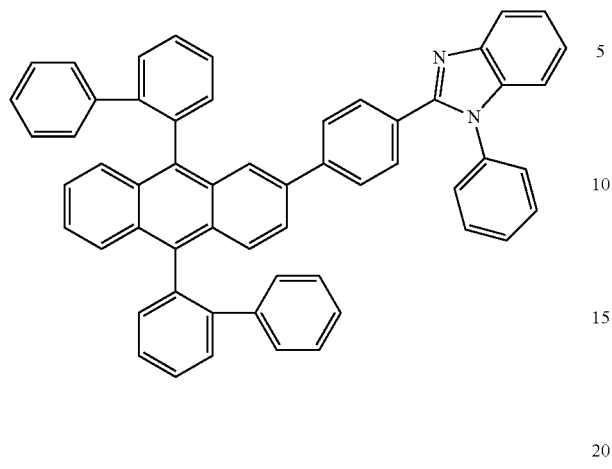
ET6
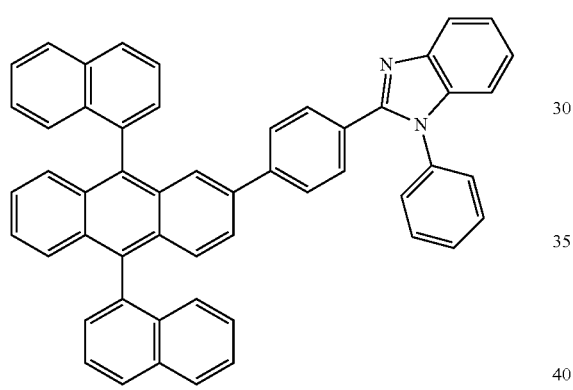
ET7
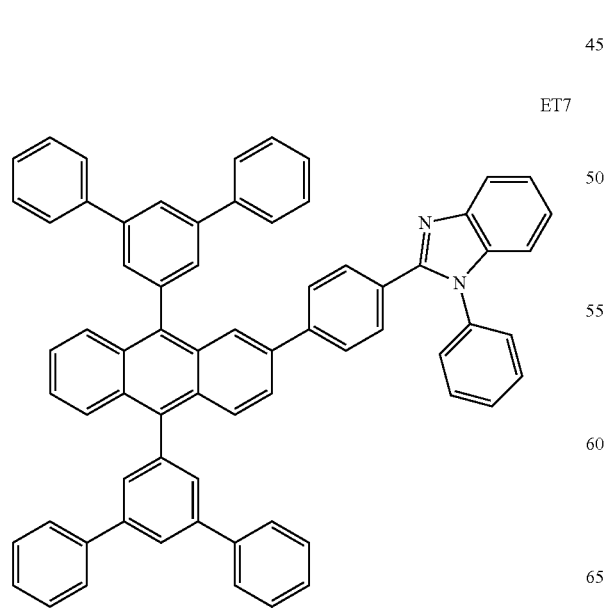
628
-continued
ET8
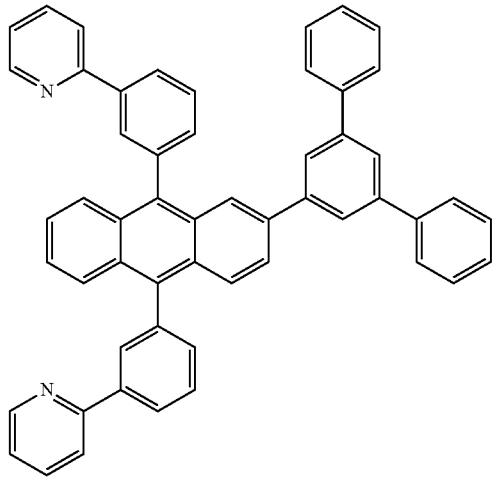
ET9
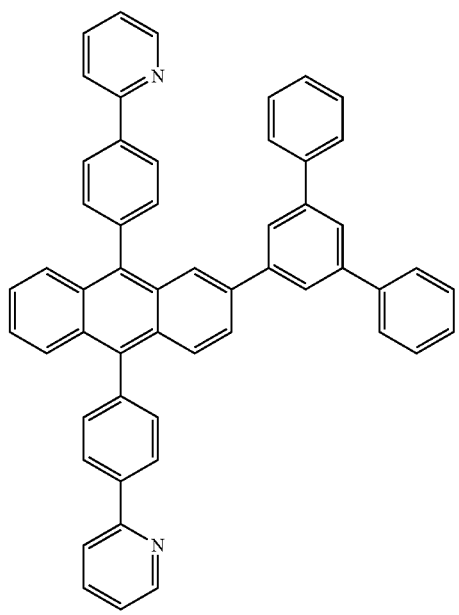

ET10
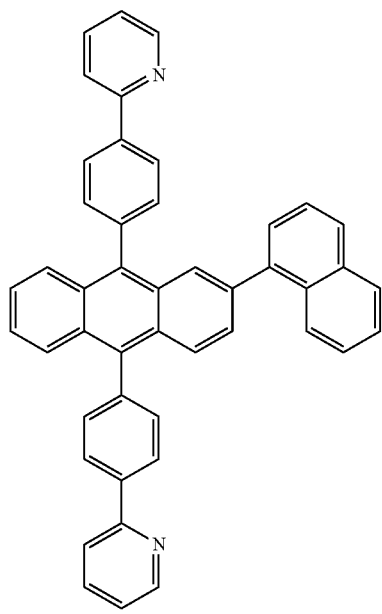
ET11
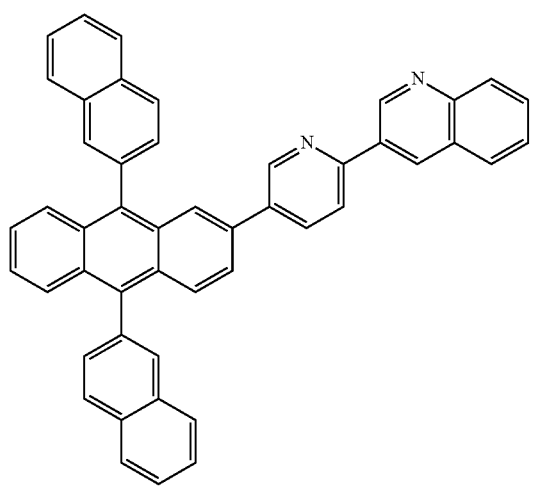
ET12
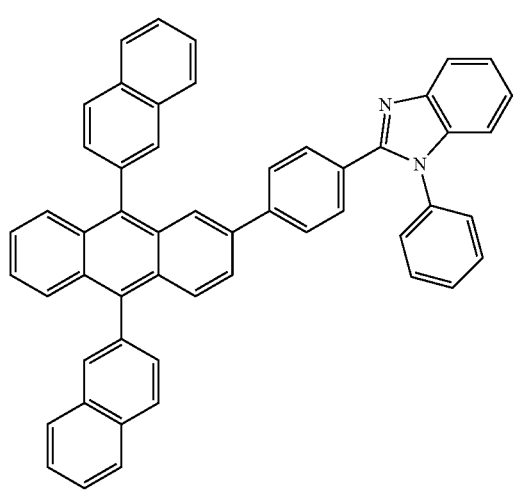
ET13
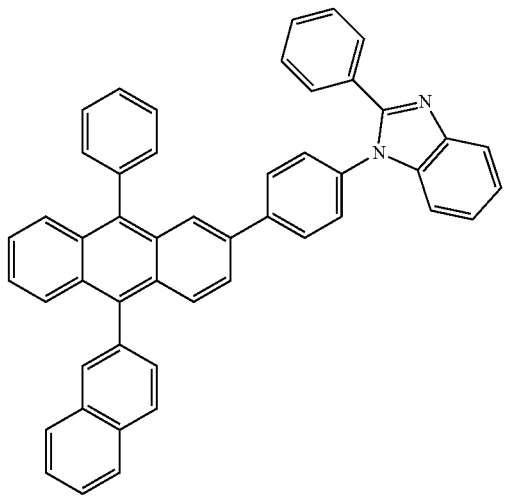
ET14
ET15
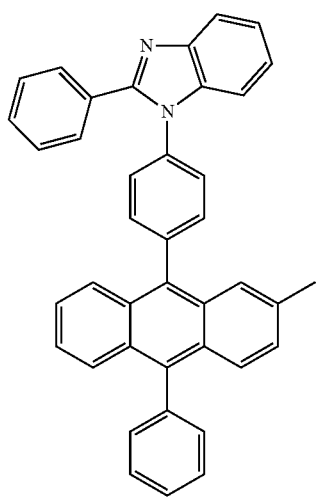

ET16
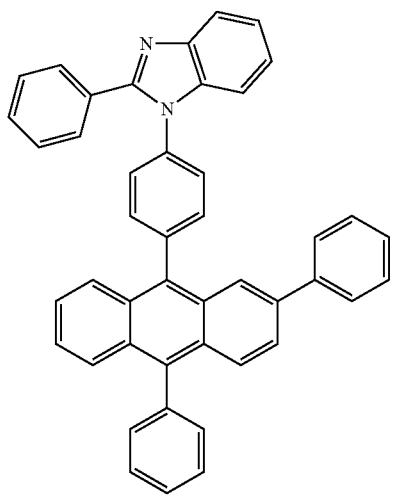
ET17
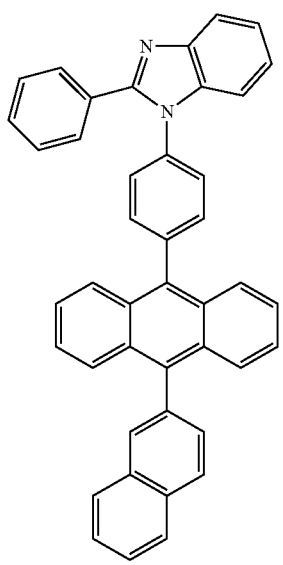
ET18
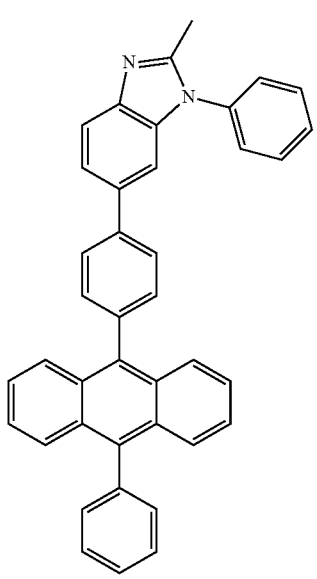
ET19
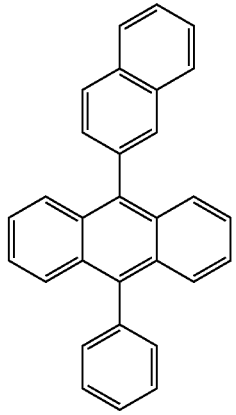
ET20
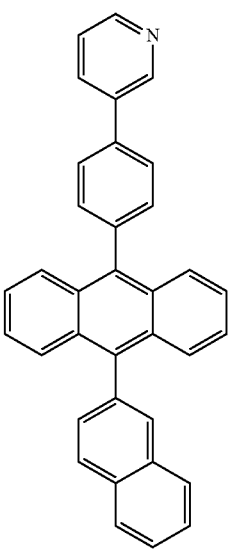
ET21
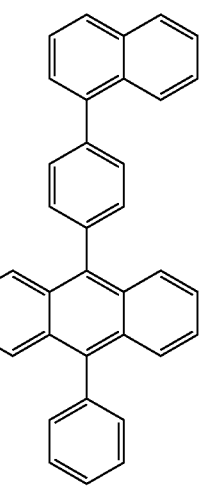

-continued
ET22
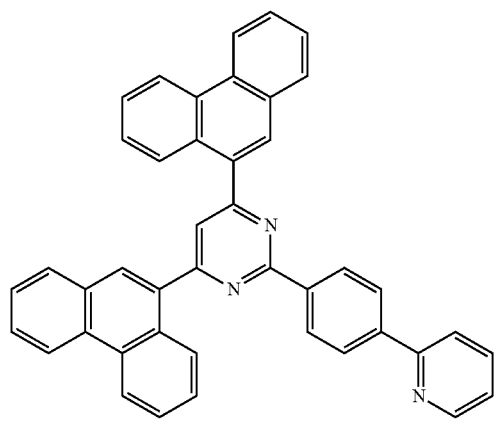
ET23
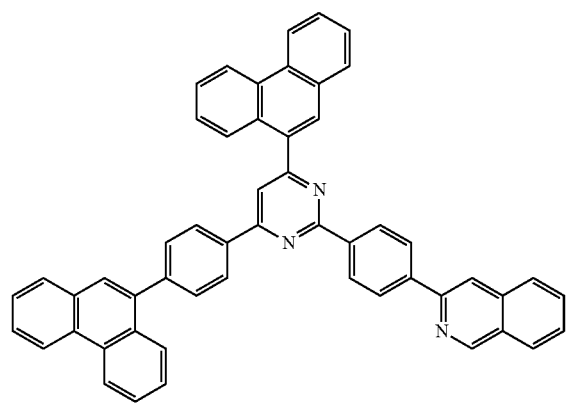
ET24
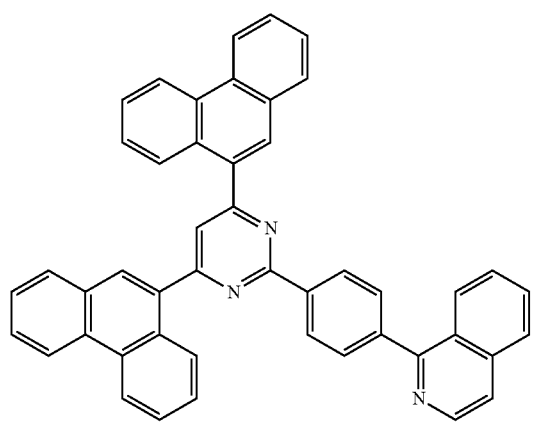
-continued
ET25
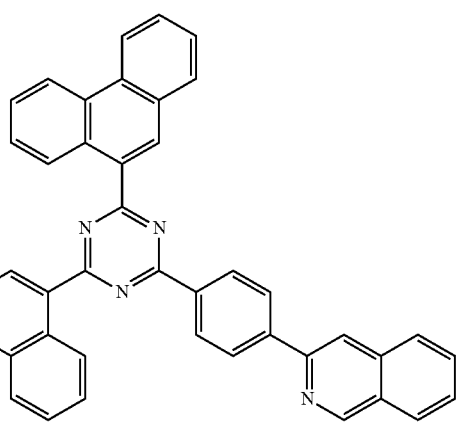
ET26
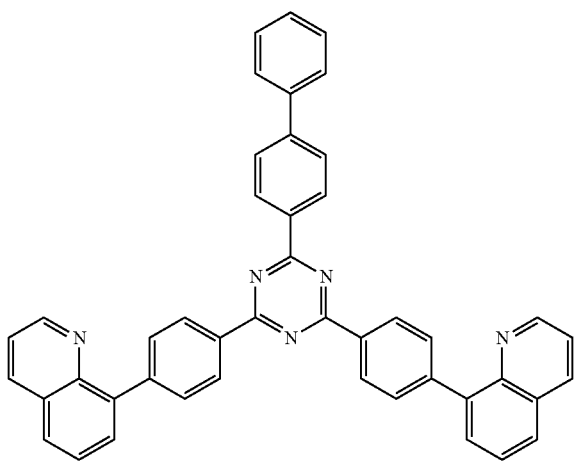
ET27
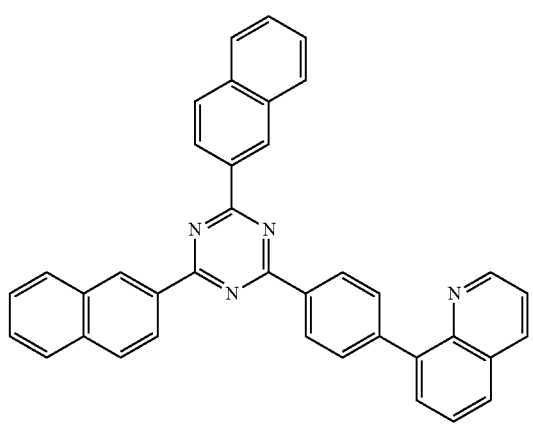

ET28
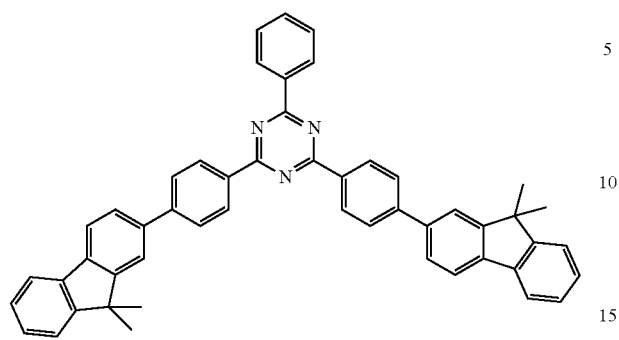
ET29
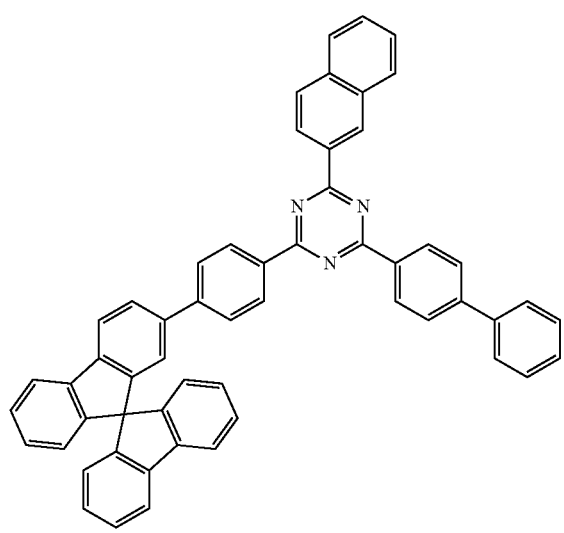
ET30
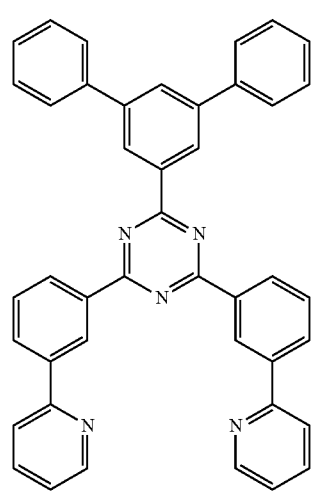
ET31
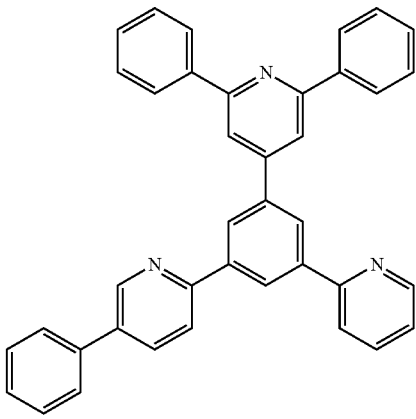
ET32
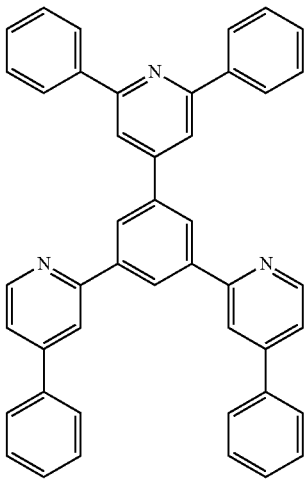
ET33
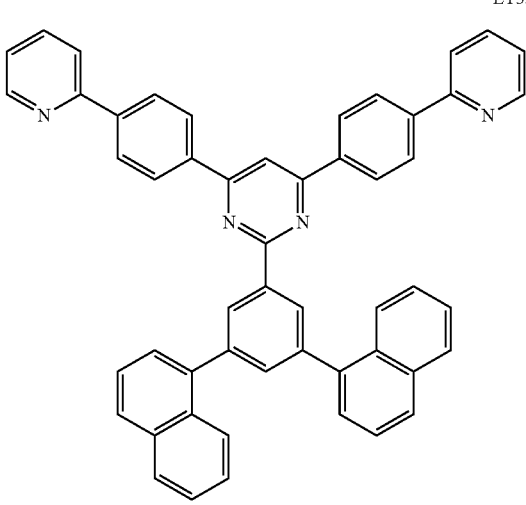

ET34

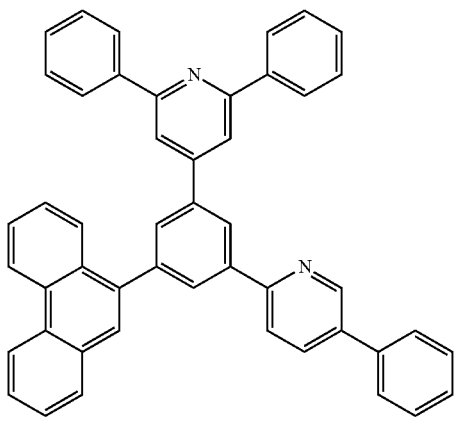

ET35

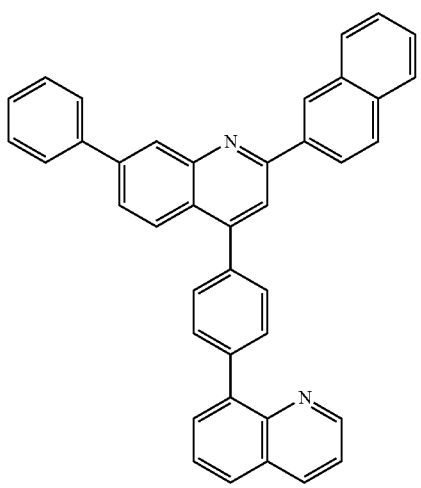

ET36

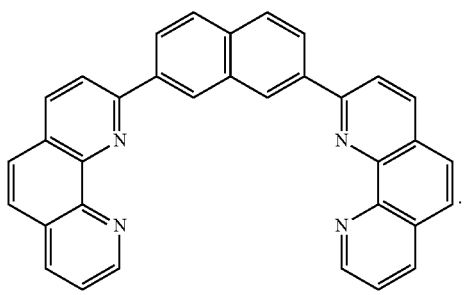

In some embodiments, the electron transport region may include at least one compound selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

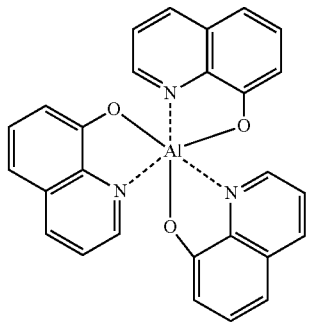

Alq₃



BAlq

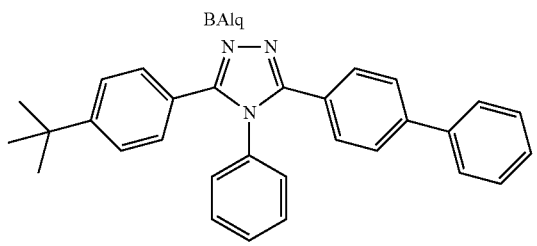

TAZ

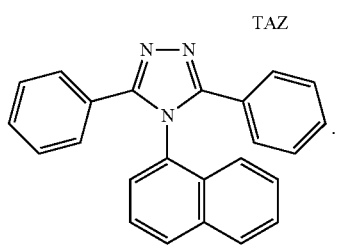

NTAZ

The thicknesses of the buffer layer, the hole blocking layer, and the electron control layer may each independently be in a range of about 20 Å to about 1,000 Å, and in some embodiments, about 30 Å to about 300 Å. When the thicknesses of the buffer layer, the hole blocking layer, and/or the electron control layer are within any of these ranges, excellent (or improved) hole blocking characteristics and/or excellent (or improved) electron controlling characteristics may be obtained without a substantial increase in driving voltage.

The thickness of the electron transport layer may be in a range of about 100 Å to about 1,000 Å, and in some embodiments, about 150 Å to about 500 Å. When the thickness of the electron transport layer is within any of these ranges, excellent (or improved) electron transport characteristics may be obtained without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth metal complex. The alkali metal complex may include a metal ion selected from a lithium (Li) ion, a sodium (Na) ion, a potassium (K) ion, a rubidium (Rb) ion, and a cesium (Cs) ion. The alkaline earth metal complex may include a metal ion selected from a beryllium (Be) ion, a magnesium (Mg) ion, a calcium (Ca) ion, a strontium (Sr) ion, and a barium (Ba) ion. Each ligand coordinated with the metal ion of the alkali metal complex and the alkaline earth metal complex may independently be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy phenyloxadiazole, a hydroxy phenylthiadiazole, a hydroxy phenylpyridine, a hydroxy phenylbenzimidazole, a hydroxy phenylbenzothiazole, a bipyridine, a phenanthroline, and a cyclopentadiene, but embodiments are not limited thereto.

For example, the metal-containing material may include a Li complex. The Li complex may include, e.g., Compound ET-D1 (LiQ) and/or Compound ET-D2.

ET-D1

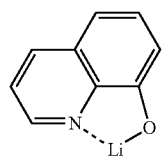

ET-D2

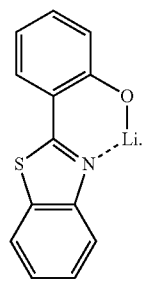

The electron transport region may include an electron injection layer that facilitates injection of electrons from the second electrode 190. The electron injection layer may be in direct contact with the second electrode 190.

The electron injection layer may have i) a single-layered structure consisting of a single layer consisting of a single material, ii) a single-layered structure consisting of a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be selected from Li, Na, K, Rb, and Cs. In an embodiment, the alkali metal may be Li, Na, or Cs.

In one or more embodiments, the alkali metal may be Li or Cs, but is not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth metal compound, and the rare earth metal compound may each independently be selected from oxides and halides (e.g., fluorides, chlorides, bromides, and/or iodines) of an alkali metal, an alkaline earth metal, and a rare earth metal, respectively.

The alkali metal compound may be selected from alkali metal oxides (such as $Li_2O$, $Cs_2O$, and/or $K_2O$), and alkali metal halides (such as LiF, NaF, CsF, KF, LiI, NaI, CsI, KI, and/or RbI). In an embodiment, the alkali metal compound may be selected from LiF, $Li_2O$, NaF, LiI, NaI, CsI, KI, and RbI, but embodiments are not limited thereto.

The alkaline earth-metal compound may be selected from alkaline earth-metal compounds, such as BaO, SrO, CaO, $Ba_xSr_{1-x}O$ (wherein 0<x<1), and/or $Ba_xCa_{1-x}O$ (wherein 0<x<1). In an embodiment, the alkaline earth metal compound may be selected from BaO, SrO, and CaO, but embodiments are not limited thereto.

The rare earth metal compound may be selected from $YbF_3$, $ScF_3$, $Sc_2O_3$, $Y_2O_3$, $Ce_2O_3$, $GdF_3$, and $TbF_3$. In an embodiment, the rare earth metal compound may be selected from YbF3, ScF3, TbF3, $YbI_3$, $ScI_3$, and $TbI_3$, but embodiments are not limited thereto.

The alkali metal complex, the alkaline earth metal complex, and the rare earth metal complex may respectively include ions of the above-described alkali metal, alkaline earth metal, and rare earth metal. The ligands coordinated with the metal ion of the alkali metal complex, the alkaline earth metal complex, and the rare earth metal complex may each independently be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy phenyloxadiazole, a hydroxy phenylthiadiazole, a hydroxy phenylpyridine, a hydroxy phenylbenzimidazole, a hydroxy phenylbenzothiazole, a bipyridine, a phenanthroline, and a cyclopentadiene, but embodiments are not limited thereto.

In one or more embodiments, the electron injection layer may include a combination of an alkali metal compound and a rare earth metal compound. For example, the electron injection layer may be formed by co-deposition of RbI and Yb. For example, the electron injection layer may be formed by co-deposition of KI and Yb.

The electron injection layer may include (e.g., may consist of) an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof as described above. In some embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or the combination thereof may be homogeneously or non-homogeneously dispersed in a matrix with (e.g., including) the organic material.

The thickness of the electron injection layer may be in a range of about 1 Å to about 100 Å, and in some embodiments, about 3 Å to about 90 Å. When the thickness of the electron injection layer is within any of these ranges, excellent (or improved) electron injection characteristics may be obtained without a substantial increase in driving voltage.

Second Electrode 190

The second electrode 190 may be on the organic layer 150. In an embodiment, the second electrode 190 may be a cathode, that is an electron injection electrode. In this embodiment, a material for forming the second electrode 190 may be a material having a low work function, for example, a metal, an alloy, an electrically conductive compound, or a combination thereof.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), silver-magnesium (Ag—Mg), ytterbium (Yb), silver-ytterbium (Ag—Yb), ITO, and IZO, but embodiments are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
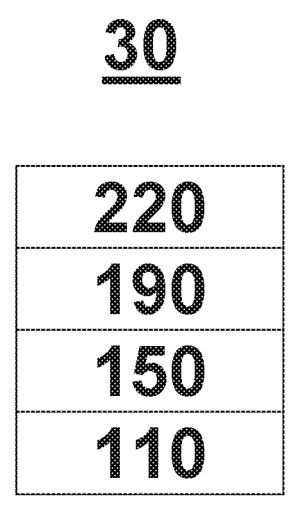
Figure 4:
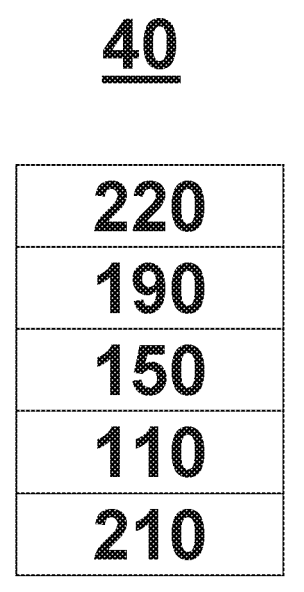

Description of FIGS. 2 to 4

Figure 2:
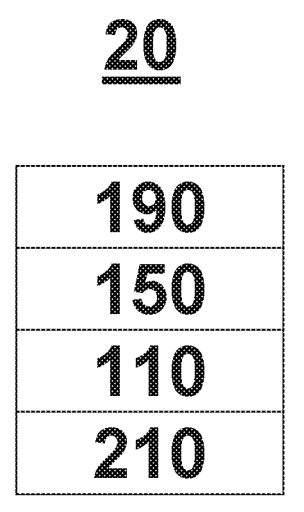

Referring to FIG. 2, an organic light-emitting device 20 has a first capping layer 210, the first electrode 110, the organic layer 150, and the second electrode 190 structure, wherein the layers are sequentially stacked in this stated order. Referring to FIG. 3, an organic light-emitting device 30 has the first electrode 110, the organic layer 150, the second electrode 190, and a second capping layer 220 structure, wherein the layers are sequentially stacked in this stated order. Referring to FIG. 4, an organic light-emitting device 40 has the first capping layer 210, the first electrode 110, the organic layer 150, the second electrode 190, and the second capping layer 220 structure, wherein the layers are stacked in this stated order.

The first electrode 110, the organic layer 150, and the second electrode 190 illustrated in FIGS. 2 to 4 may be substantially the same as those illustrated in FIG. 1.

In the organic light-emitting devices 20 and 40, light emitted from the emission layer in the organic layer 150 may pass through the first electrode 110 (which may be a semi-transmissive electrode or a transmissive electrode) and through the first capping layer 210 to the outside. In the organic light-emitting devices 30 and 40, light emitted from the emission layer in the organic layer 150 may pass through the second electrode 190 (which may be a semi-transmissive electrode or a transmissive electrode) and through the second capping layer 220 to the outside.

The first capping layer 210 and the second capping layer 220 may improve the external luminescence efficiency based on the principle of constructive interference.

The first capping layer 210 and the second capping layer 220 may each independently be a capping layer including an organic material, an inorganic capping layer including an inorganic material, or a composite capping layer including an organic material and an inorganic material.

At least one of the first capping layer 210 or the second capping layer 220 may each independently include at least one material selected from carbocyclic compounds, heterocyclic compounds, amine-based compounds, porphine derivatives, phthalocyanine derivatives, naphthalocyanine derivatives, alkali metal complexes, and alkaline earth metal complexes. The carbocyclic compound, the heterocyclic compound, and the amine-based compound may each independently be optionally be substituted with a substituent containing at least one element selected from O, N, S, Se, Si, F, Cl, Br, and I. In an embodiment, at least one of the first capping layer 210 and the second capping layer 220 may each independently include an amine-based compound.

In one or more embodiments, at least one of the first capping layer 210 or the second capping layer 220 may each independently include a compound represented by Formula 201 or a compound represented by Formula 202.

In one or more embodiments, at least one of the first capping layer 210 or the second capping layer 220 may each independently include a compound selected from Compounds HT28 to HT33 and Compounds CP1 to CP5, but embodiments are not limited thereto.

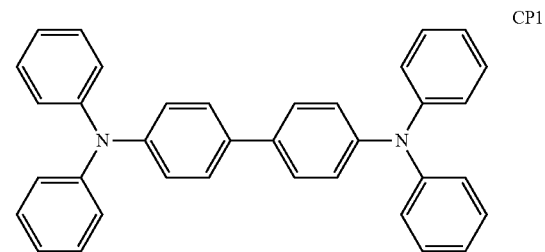

CP1

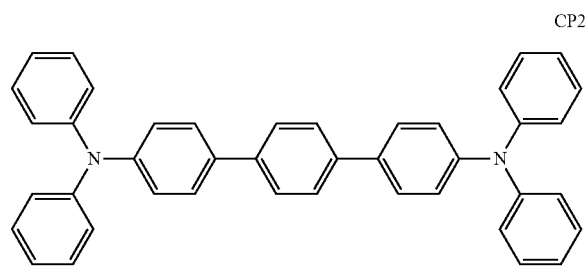

CP2

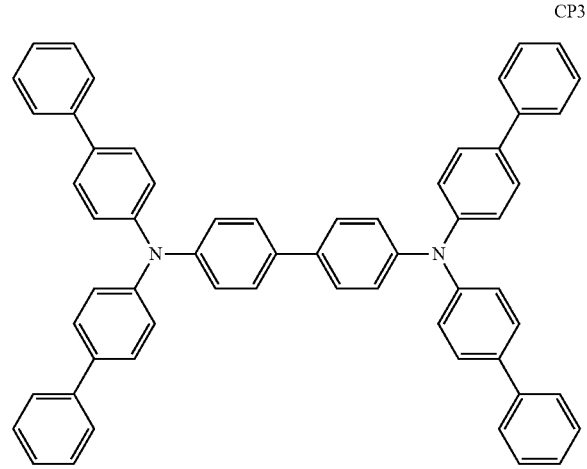

CP3

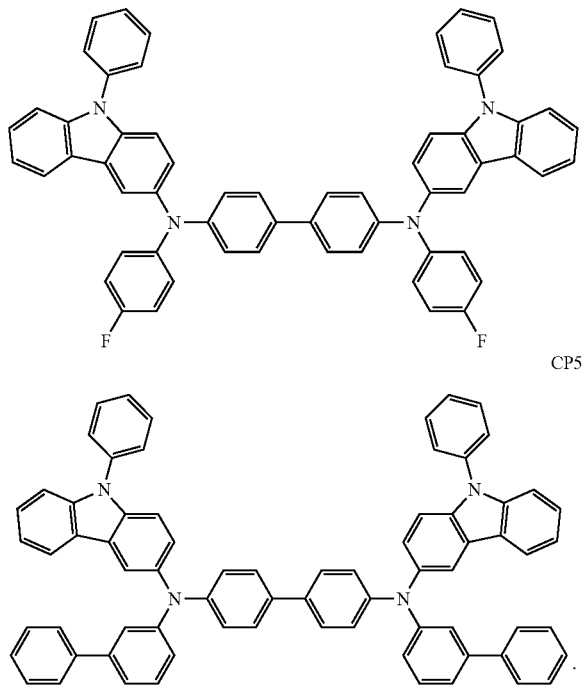

CP4

CP5

Hereinbefore, the organic light-emitting device has been described with reference to FIGS. 1 to 4, but embodiments are not limited thereto.

The layers constituting the hole transport region, the emission layer, and the layers constituting the electron transport region may be formed in a specific region by using one or more suitable methods such as vacuum deposition, spin coating, casting, Langmuir-Blodgett (LB) deposition, ink-jet printing, laser printing, and/or laser-induced thermal imaging.

When the layers constituting the hole transport region, the emission layer, and the layers constituting the electron transport region are formed by vacuum deposition, the vacuum deposition may be performed at a deposition temperature in a range of about 100° C. to about 500° C., at a vacuum degree in a range of about $10^{-8}$ torr to about $10^{-3}$ torr, and at a deposition rate in a range of about 0.01 Angstroms per second (Å/sec) to about 100 Å/sec, depending on the material to be included in each layer and the structure of each layer to be formed.

When the layers constituting the hole transport region, the emission layer, and the layers constituting the electron transport region are formed by spin coating, the spin coating may be performed at a coating rate of about 2,000 revolutions per minute (rpm) to about 5,000 rpm, and at a heat treatment temperature of about 80° C. to about 200° C., depending on the material to be included in each layer and the structure of each layer to be formed.

General Definitions of Substituents

The term "$C_1$-$C_{60}$ alkyl group" as used herein refers to a linear or branched aliphatic hydrocarbon monovalent group having 1 to 60 carbon atoms. Non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle and/or at either terminus of the $C_2$-$C_{60}$ alkyl group. Non-limiting examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle and/or at either terminus of the $C_2$-$C_{60}$ alkyl group. Non-limiting examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein Ani is a $C_1$-$C_1$ alkyl group). Non-limiting examples thereof include a methoxy group, an ethoxy group, and an isopropyloxy group.

The term "$C_3$-$C_{10}$ cycloalkyl group" as used herein refers to a monovalent saturated hydrocarbon monocyclic group including 3 to 10 carbon atoms. Non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group including at least one heteroatom selected from N, O, Si, P, and S as a ring-forming atom, and 1 to 10 carbon atoms. Non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in its ring, and is not aromatic. Non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group including at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group" as used herein refers to a divalent group having the same structure as the $C_1$-$C_{10}$ heterocycloalkyl group.

The term "$C_6$-$C_{60}$ aryl group" as used herein refers to a monovalent group having a carbocyclic aromatic system having 6 to 6 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. The term "$C_6$-$C_{60}$ arylene group" as used herein refers to a divalent group having the same structure as the $C_6$-$C_{60}$ aryl group. When the $C_6$-$C_{60}$ aryl group and the $C_6$-$C_{60}$ arylene group each independently include two or more rings, the respective rings may be fused.

The term "$C_1$-$C_{60}$ heteroaryl group" as used herein refers to a monovalent group having a heterocyclic aromatic system having at least one heteroatom selected from N, O, Si, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. The term "$C_1$-$C_{60}$ heteroarylene group" as used herein refers to a divalent group having a heterocyclic aromatic system having the same structure as the $C_1$-$C_{60}$ heteroaryl group. When the $C_1$-$C_{60}$ heteroaryl group and the $C_1$-$C_{60}$ heteroarylene group each independently include two or more rings, the respective rings may be fused.

The term "$C_6$-$C_{60}$ aryloxy group" as used herein refers to a group represented by —$OA_{102}$ (wherein $A_{102}$ is the $C_6$-$C_{60}$ aryl group). The term "$C_6$-$C_{60}$ arylthio group" as used herein refers to a group represented by —$SA_{103}$ (wherein $A_{103}$ is the $C_6$-$C_{60}$ aryl group).

The term "monovalent non-aromatic condensed polycyclic group" as used herein refers to a monovalent group that has two or more rings condensed to each other and only carbon atoms as ring forming atoms (e.g., 8 to 60 carbon atoms), wherein the entire molecular structure is non-aromatic. Non-limiting examples of the monovalent non-aromatic condensed polycyclic group may include a 1,2,3,4-tetrahydronaphthalenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more condensed rings and at least one heteroatom selected from N, O, Si, P, and S, in addition to carbon atoms (e.g., 1 to 60 carbon atoms), as a ring-forming atom, wherein the entire molecular structure is non-aromatic. Non-limiting examples of the monovalent non-aromatic condensed heteropolycyclic group may include a 1,2,3,4-tetrahydroquinolinyl group. The term "divalent non-aromatic condensed heteropolycyclic group" as used herein refers to a divalent group having substantially the same structure as the monovalent non-aromatic condensed heteropolycyclic group.

The term "$C_5$-$C_{60}$ carbocyclic group" as used herein refers to a monocyclic or polycyclic group having 5 to 60 carbon atoms only as ring-forming atoms. The $C_5$-$C_{60}$ carbocyclic group may be an aromatic carbocyclic group or a non-aromatic carbocyclic group. The term "$C_5$-$C_{60}$ carbocyclic group" as used herein may refer to a benzene ring, a monovalent group (e.g., a phenyl group), or a divalent group (e.g., a phenylene group). In addition, the $C_5$-$C_{60}$ carbocyclic group may be varied, for example, as a trivalent group or a tetravalent group, according to the number of substituents connected to the $C_5$-$C_{60}$ carbocyclic group. For example, the "benzene group" may represent a benzene ring, a phenyl group, a phenylene group, or a trivalent or tetravalent group corresponding to these groups.

The term "$C_1$-$C_{60}$ heterocyclic group" as used herein refers to a group having substantially the same structure as the $C_5$-$C_{60}$ carbocyclic group, except that at least one heteroatom selected from N, O, Si, P, and S is used as a ring-forming atom, in addition to carbon atoms (e.g., 1 to 60 carbon atoms).

As used herein, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

"Ph" used herein represents a phenyl group, "Me" used herein represents a methyl group, "Et" used herein represents an ethyl group, "ter-Bu" or "But" used herein represents a tert-butyl group, "OMe" used herein represents a methoxy group, and "D" may refer to deuterium.

The term "biphenyl group" as used herein may refer to a phenyl group substituted with at least one phenyl group. The "biphenyl group" may be described as "a substituted phenyl group" having a "$C_6$-$C_{60}$ aryl group" as a substituent.

The term "terphenyl group" as used herein may refer to a phenyl group substituted with at least two phenyl groups. The "terphenyl group" may be described as "a substituted phenyl group" having a "$C_6$-$C_{60}$ aryl group substituted with a $C_6$-$C_{60}$ aryl group" as a substituent.

The symbols * and *' as used herein, unless defined otherwise, refer to a binding site to a neighboring atom in a corresponding formula.

Hereinafter, compounds and organic light-emitting devices according to one or more embodiments will be described in more detail with reference to Synthesis Examples and Examples. However, these examples are only for illustrative purposes and are not intended to limit the scope of the one or more embodiments of the present disclosure. The wording "B was used instead of A" used in describing Synthesis Examples may refer to an amount of B used that was identical to an amount of A used in terms of molar equivalents.

Synthesis Example 1. Synthesis of Compound 12

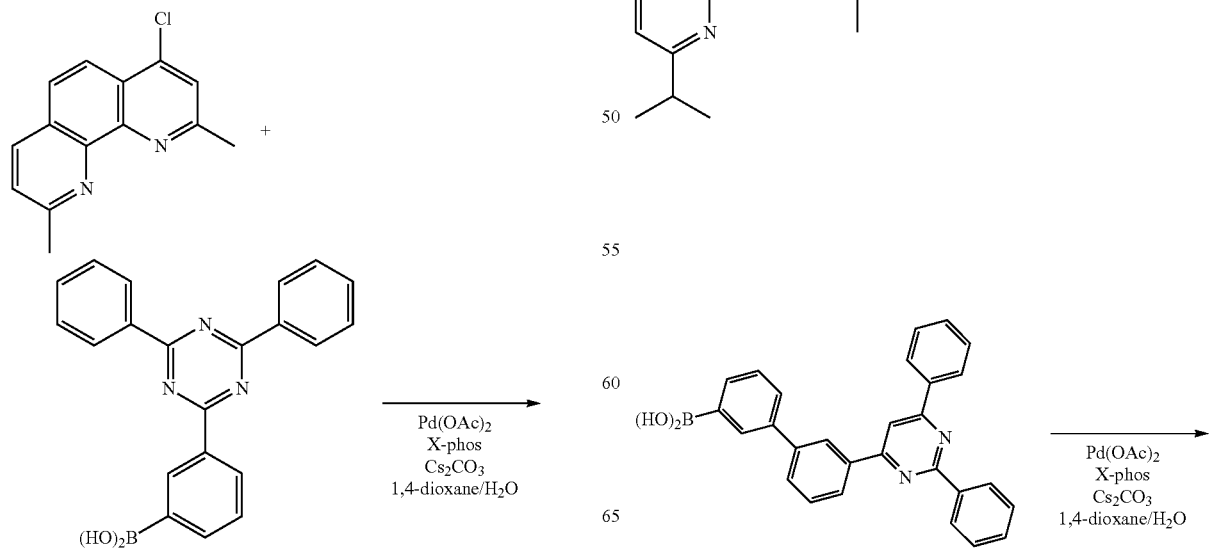

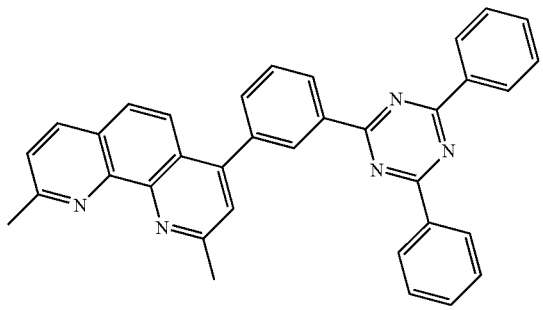

12

4-chloro-2,9-dimethyl-1,10-phenanthroline (12.1 g, 50 mmol), (3-(4,6-diphenyl-1,3,5-triazin-2-yl)phenyl)boronic acid (21.2 g, 60 mmol), $Cs_2CO_3$ (32.6 g, 100 mmol), X-phos (4.8 g, 10 mmol), $Pd(OAc)_2$ (0.6 g, 5 mol %), and 1,4-dioxane/$H_2O$ (400 ml/100 ml) were mixed under nitrogen atmosphere and stirred at 120° C. for 12 hours.

After termination of the reaction, extraction was carried out with methylene chloride, and magnesium sulfate ($MgSO_4$) was added thereto and then filtered to obtain an organic layer. After removing the solvent from the obtained organic layer, the resulting product was purified by column chromatography to obtain Compound 12 (17.5 g, Yield: 68%).

Mass: $[(M+H)^+]$: 516

Synthesis Example 2. Synthesis of Compound 18

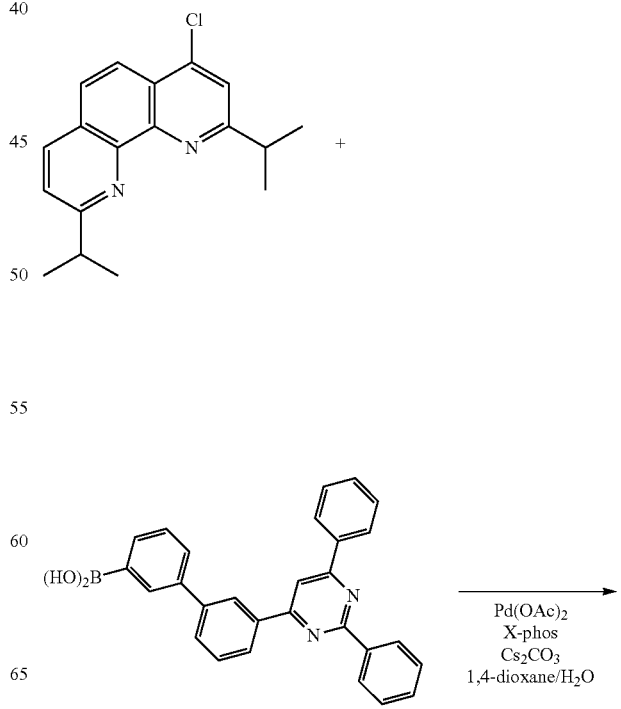

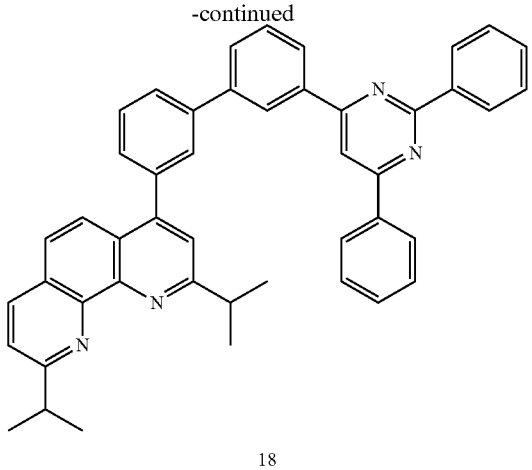

18

Compound 18 (23.3 g, Yield: 72%) was obtained through substantially the same process as in Synthesis Example 1, except that 4-chloro-2,9-diisopropyl-1,10-phenanthroline (14.9 g, 50 mmol) and (3'-(2,6-diphenylpyrimidin-4-yl)-[1,1'-biphenyl]-3-yl)boronic acid (25.7 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 647

Synthesis Example 3. Synthesis of Compound 90

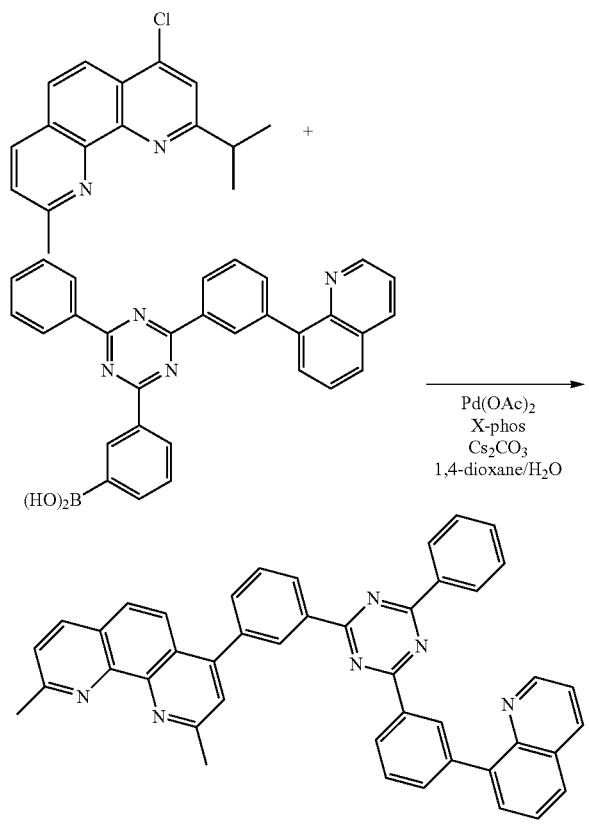

90

Compound 90 (21.2 g, Yield: 66%) was obtained through substantially the same process as in Synthesis Example 1, except that (3-(4-phenyl-6-(3-(quinolin-8-yl)phenyl)-1,3,5-triazin-2-yl)phenyl)boronic acid (28.8 g, 60 mmol) was used instead of (3-(4,6-diphenyl-1,3,5-triazin-2-yl)phenyl)boronic acid.

Mass: [(M+H)$^+$]: 643

Synthesis Example 4. Synthesis of Compound 126

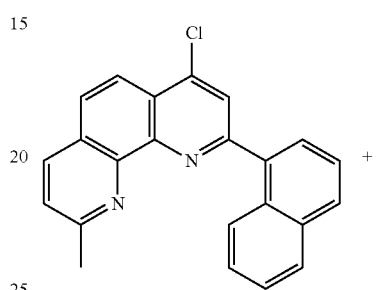

+

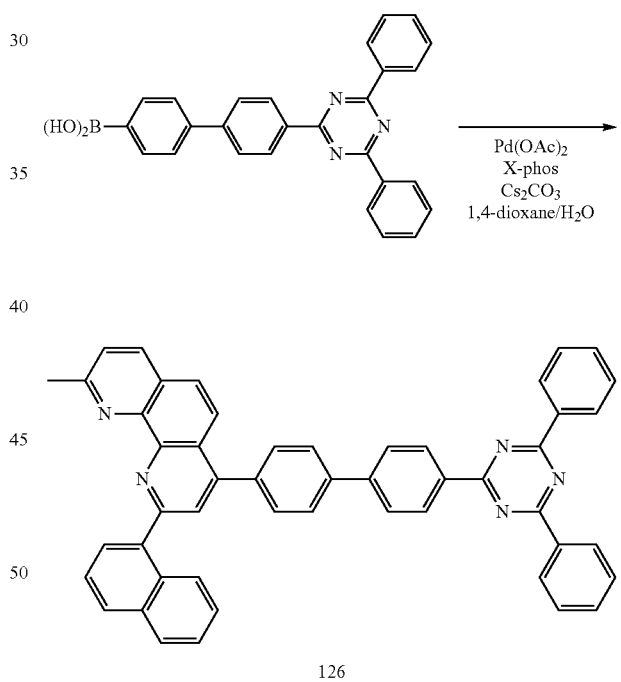

126

Compound 126 (26.4 g, Yield: 75%) was obtained through substantially the same process as in Synthesis Example 1, except that 4-chloro-9-methyl-2-(naphthalen-1-yl)-1,10-phenanthroline (17.7 g, 50 mmol) and (4'-(4,6-diphenyl-1,3,5-triazin-2-yl)-[1,1'-biphenyl]-4-yl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 704

Synthesis Example 5. Synthesis of Compound 160

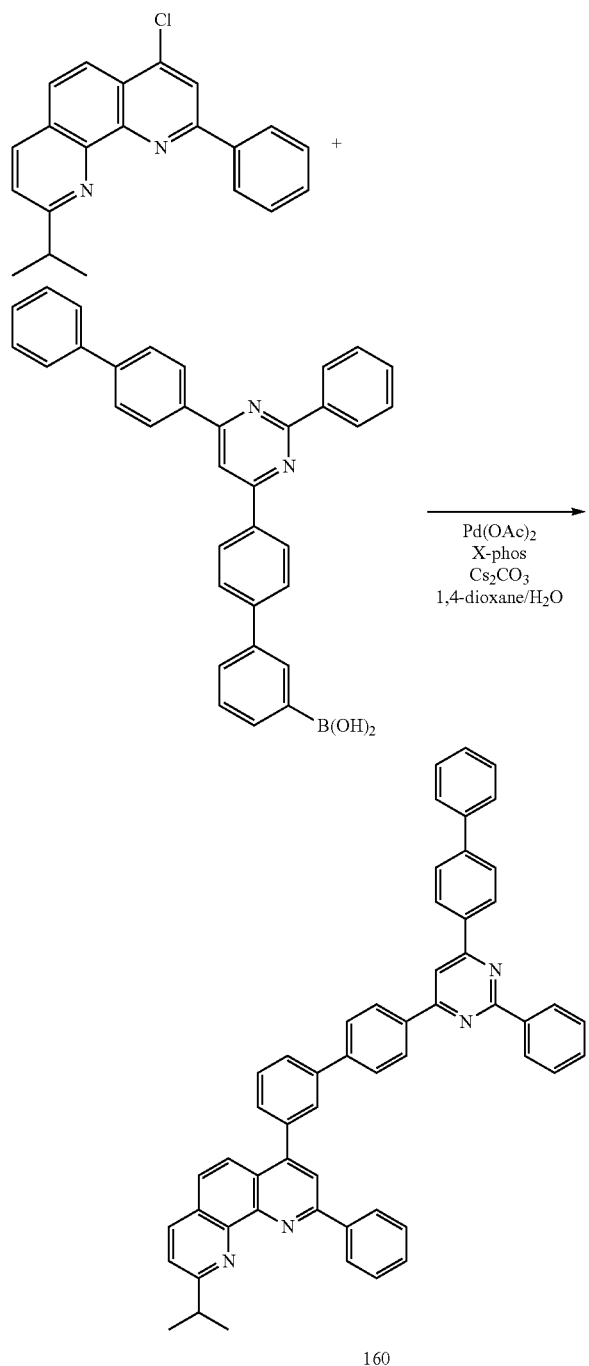

Compound 160 (26.8 g, Yield: 70%) was obtained through substantially the same process as in Synthesis Example 1, except that 4-chloro-9-isopropyl-2-phenyl-1,10-phenanthroline (16.6 g, 50 mmol) and (4'-(6-([1,1'-biphenyl]-4-yl)-2-phenylpyrimidin-4-yl)-[1,1'-biphenyl]-3-yl)boronic acid (30.3 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 757

Synthesis Example 6. Synthesis of Compound 190

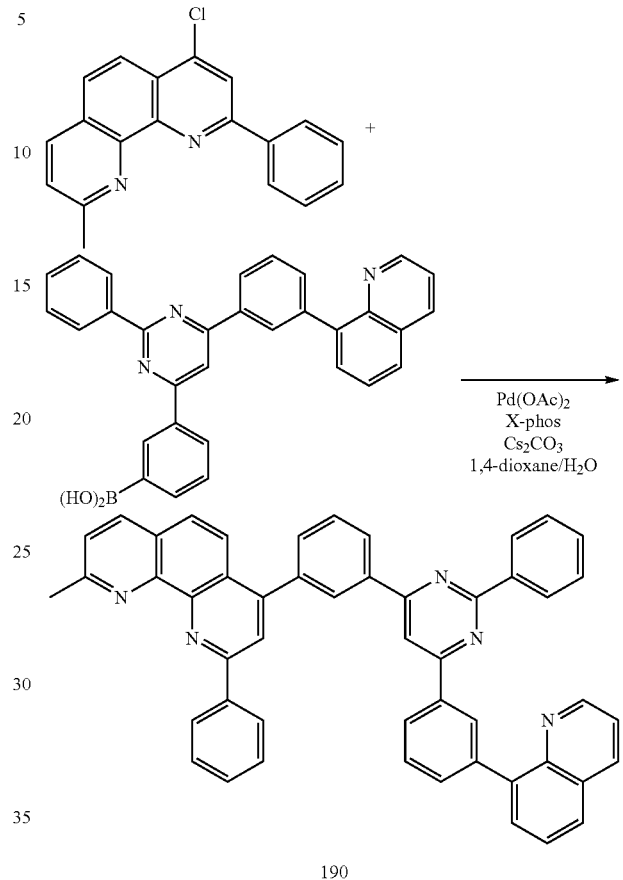

Compound 190 (22.9 g, Yield: 65%) was obtained through substantially the same process as in Synthesis Example 1, except that 4-chloro-9-methyl-2-phenyl-1,10-phenanthroline (15.2 g, 50 mmol) and (3-(2-phenyl-6-(3-(quinolin-8-yl)phenyl)pyrimidin-4-yl)phenyl)boronic acid (28.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 704

Synthesis Example 7. Synthesis of Compound 209

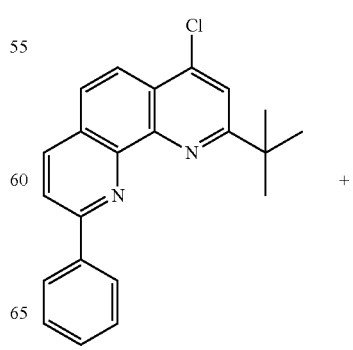

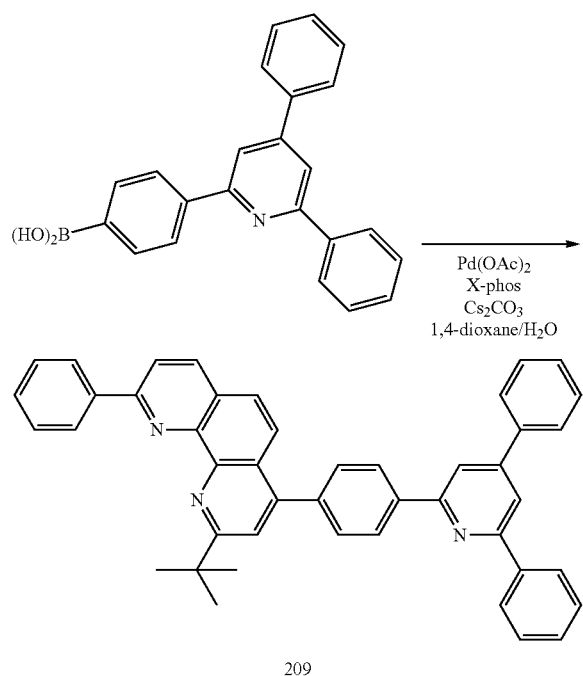

209

Compound 209 (20.4 g, Yield: 66%) was obtained through substantially the same process as in Synthesis Example 1, except that 2-(4-chloro-9-phenyl-1,10-phenanthrolin-2-yl)-2-methylpropan-1-ylium (17.3 g, 50 mmol) and (4-(4,6-diphenylpyridin-2-yl)phenyl)boronic acid (21.1 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 618

Synthesis Example 8. Synthesis of Compound 236

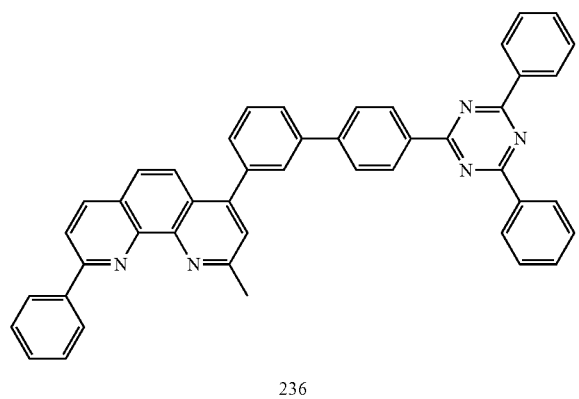

236

Compound 236 (22.2 g, Yield: 68%) was obtained through substantially the same process as in Synthesis Example 1, except that 4-chloro-2-methyl-9-phenyl-1,10-phenanthroline (15.2 g, 50 mmol) and (4'-(4,6-diphenyl-1,3,5-triazin-2-yl)-[1,1'-biphenyl]-3-yl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 654

Synthesis Example 9. Synthesis of Compound 275

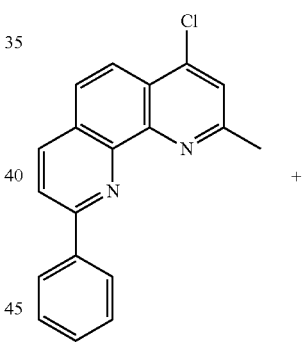

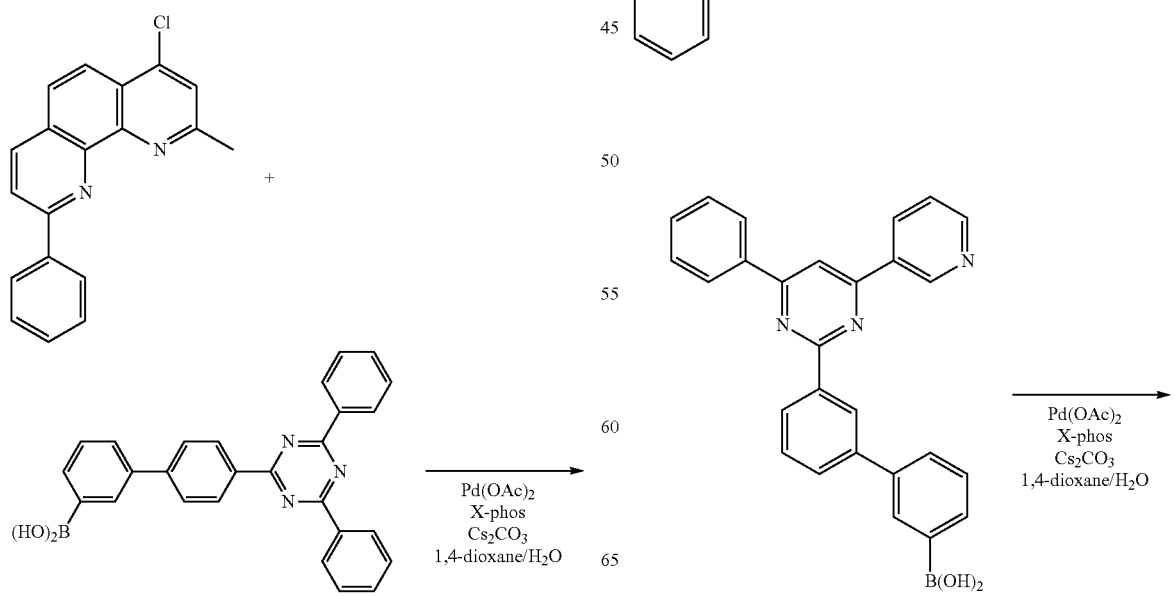

-continued

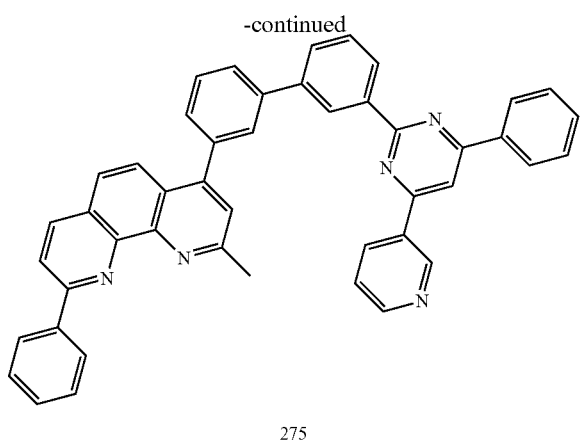

275

Compound 275 (20.3 g, Yield: 62%) was obtained through substantially the same process as in Synthesis Example 1, except that 4-chloro-2-methyl-9-phenyl-1,10-phenanthroline (15.2 g, 50 mmol) and (3'-(4-phenyl-6-(pyridin-3-yl)pyrimidin-2-yl)-[1,1'-biphenyl]-3-yl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)⁺]: 654

Synthesis Example 10. Synthesis of Compound 313

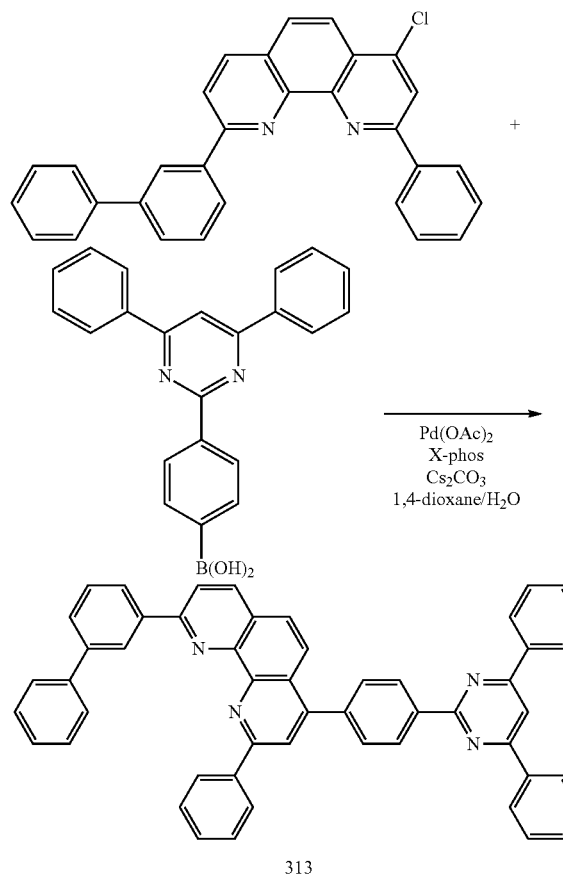

313

Compound 313 (27.5 g, Yield: 77%) was obtained through substantially the same process as in Synthesis Example 1, except that 9-([1,1'-biphenyl]-3-yl)-4-chloro-2-phenyl-1,10-phenanthroline (22.2 g, 50 mmol) and (4-(4,6-diphenylpyrimidin-2-yl)phenyl)boronic acid (21.2 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)⁺]: 715

Synthesis Example 11. Synthesis of Compound 318

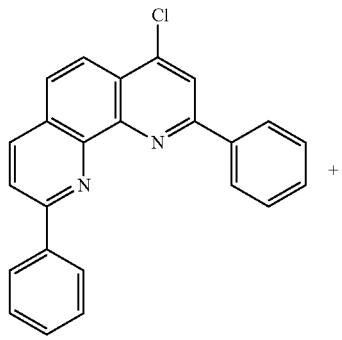

+

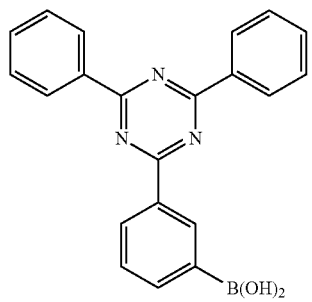

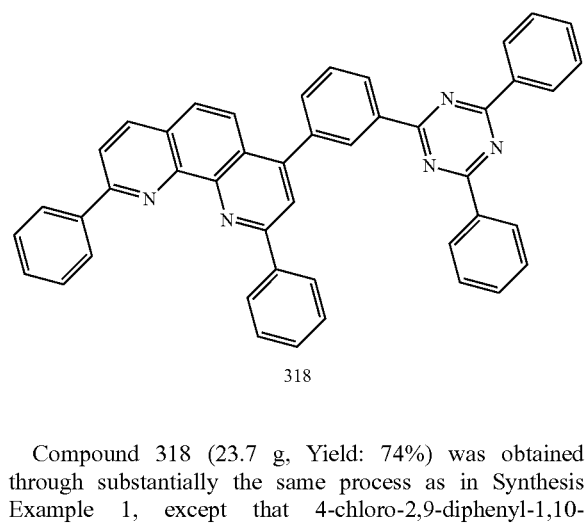

318

Compound 318 (23.7 g, Yield: 74%) was obtained through substantially the same process as in Synthesis Example 1, except that 4-chloro-2,9-diphenyl-1,10-phenanthroline (18.3 g, 50 mmol) was used instead of 4-chloro-2,9-dimethyl-1,10-phenanthroline.

Mass: [(M+H)⁺]: 640

Synthesis Example 12. Synthesis of Compound 387

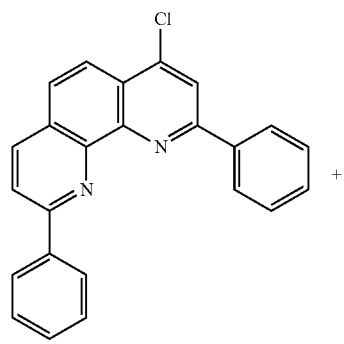

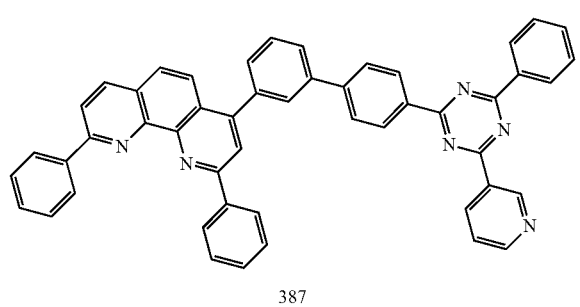

Compound 387 (25.8 g, Yield: 72%) was obtained through substantially the same process as in Synthesis Example 1, except that 4-chloro-2,9-diphenyl-1,10-phenanthroline (18.3 g, 50 mmol) and (4'-(4-phenyl-6-(pyridin-3-yl)-1,3,5-triazin-2-yl)-[1,1'-biphenyl]-3-yl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)⁺]: 717

Synthesis Example 13. Synthesis of Compound 420

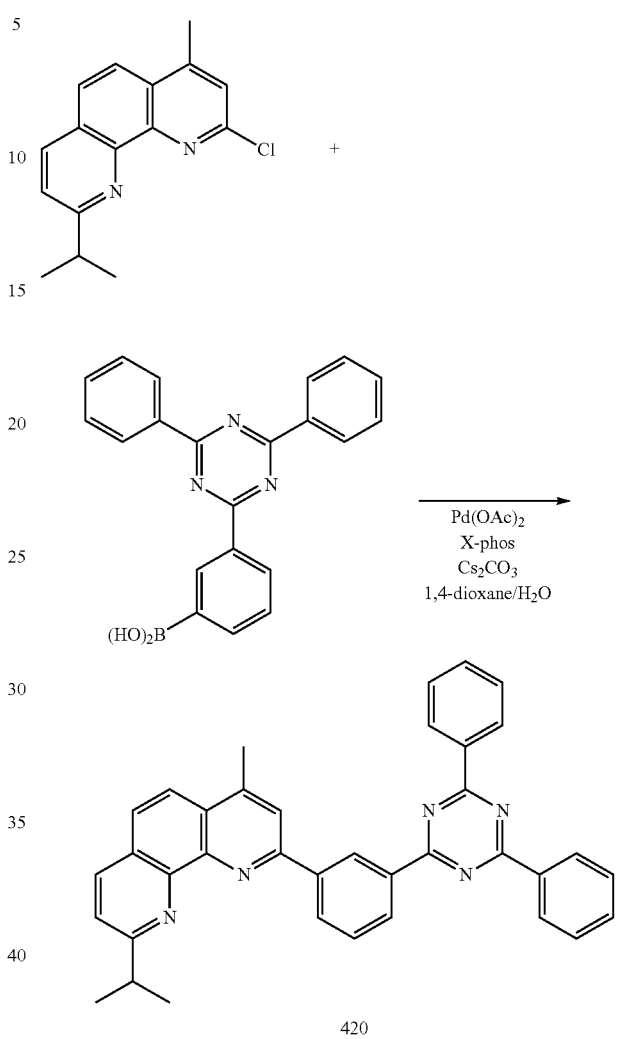

Compound 420 (18.5 g, Yield: 68%) was obtained through substantially the same process as in Synthesis Example 1, except that 2-chloro-9-isopropyl-4-methyl-1,10-phenanthroline (13.5 g, 50 mmol) was used instead of 4-chloro-2,9-dimethyl-1,10-phenanthroline.

Mass: [(M+H)⁺]: 544

Synthesis Example 14. Synthesis of Compound 449

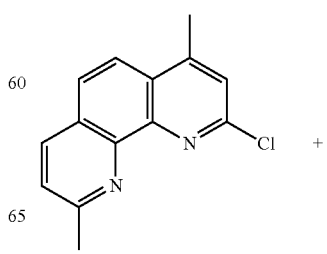

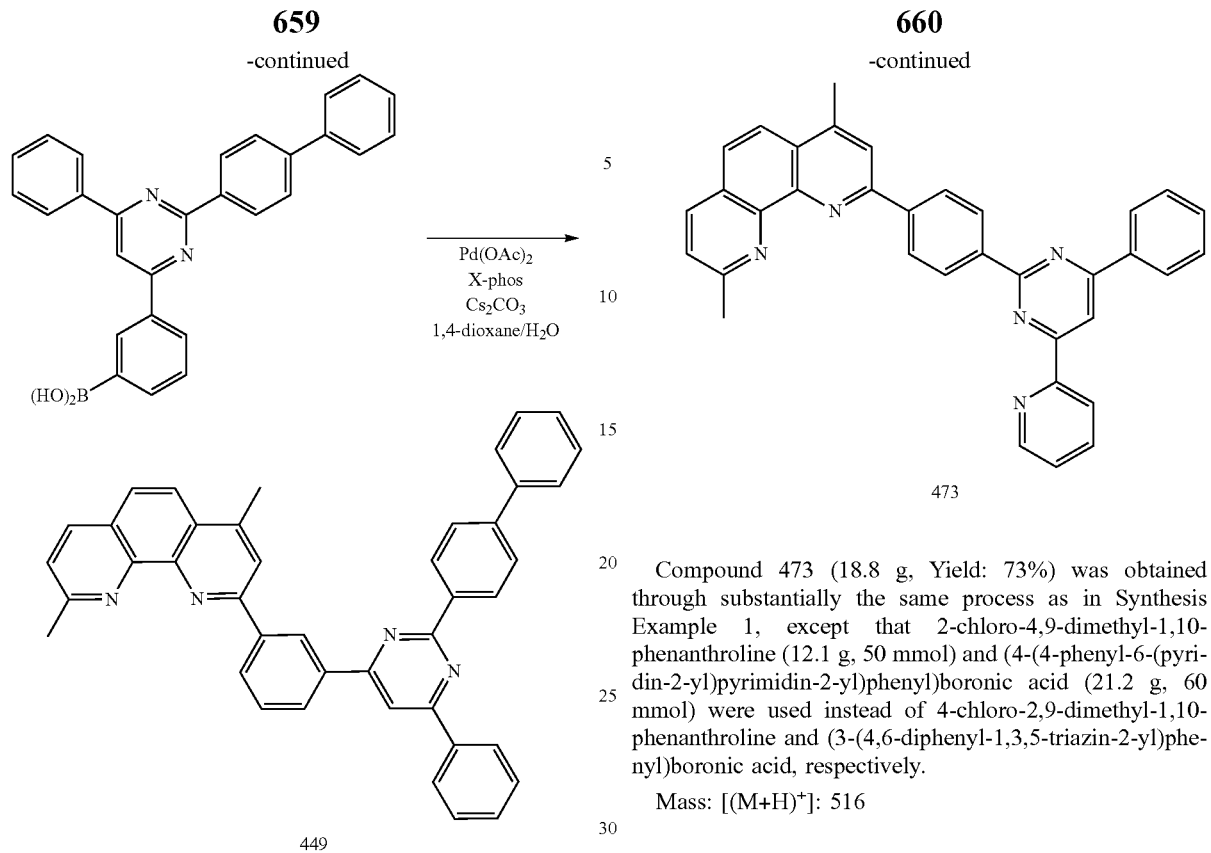

Compound 449 (21.3 g, Yield: 72%) was obtained through substantially the same process as in Synthesis Example 1, except that 2-chloro-4,9-dimethyl-1,10-phenanthroline (12.1 g, 50 mmol) and (3-(2-([1,1'-biphenyl]-4-yl)-6-phenylpyrimidin-4-yl)phenyl)boronic acid (25.7 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 591

Synthesis Example 15. Synthesis of Compound 473

Compound 473 (18.8 g, Yield: 73%) was obtained through substantially the same process as in Synthesis Example 1, except that 2-chloro-4,9-dimethyl-1,10-phenanthroline (12.1 g, 50 mmol) and (4-(4-phenyl-6-(pyridin-2-yl)pyrimidin-2-yl)phenyl)boronic acid (21.2 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 516

Synthesis Example 16. Synthesis of Compound 516

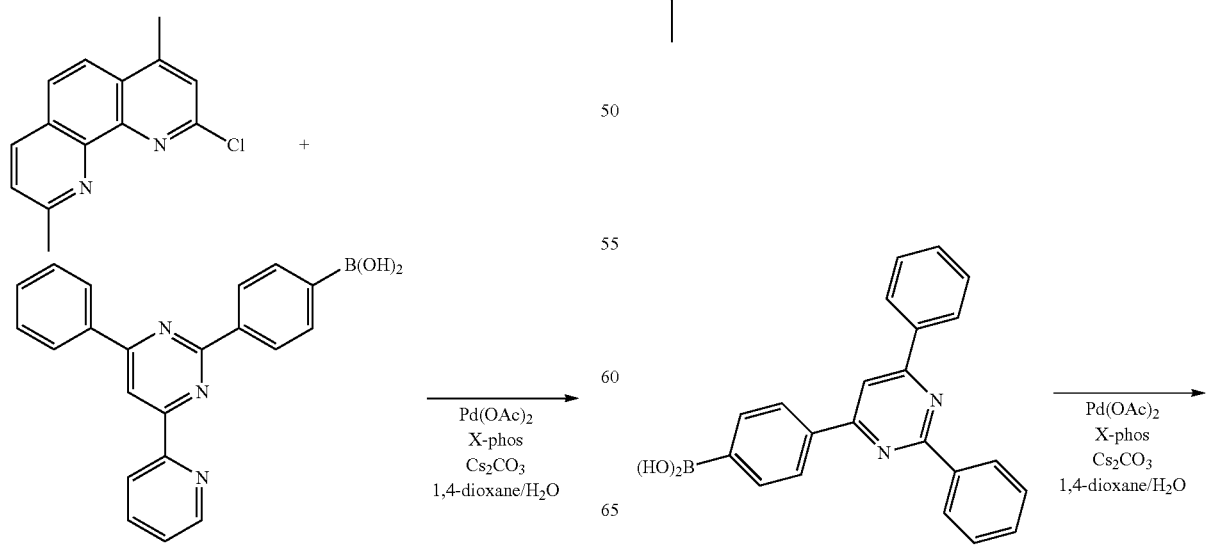

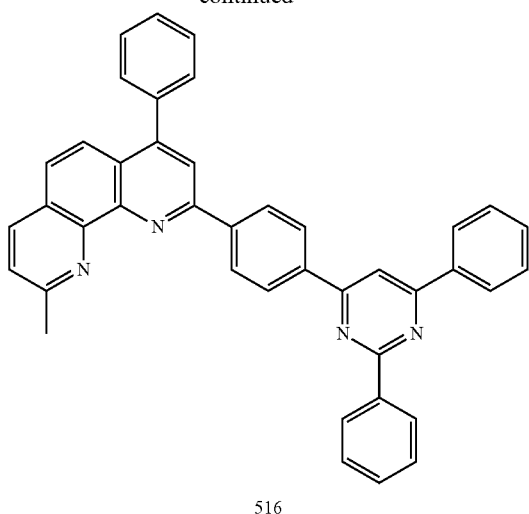

516

Compound 516 (19.6 g, Yield: 68%) was obtained through substantially the same process as in Synthesis Example 1, except that 2-chloro-9-methyl-4-phenyl-1,10-phenanthroline (15.2 g, 50 mmol) and (4-(2,6-diphenylpyrimidin-4-yl)phenyl)boronic acid (21.1 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 577

Synthesis Example 17. Synthesis of Compound 536

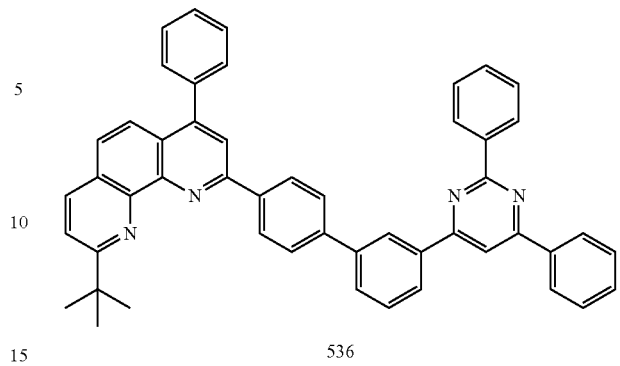

536

Compound 536 (22.9 g, Yield: 66%) was obtained through substantially the same process as in Synthesis Example 1, except that 9-(tert-butyl)-2-chloro-4-phenyl-1,10-phenanthroline (17.3 g, 50 mmol) and (3'-(2,6-diphenylpyrimidin-4-yl)-[1,1'-biphenyl]-4-yl)boronic acid (25.7 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 695

Synthesis Example 18. Synthesis of Compound 597

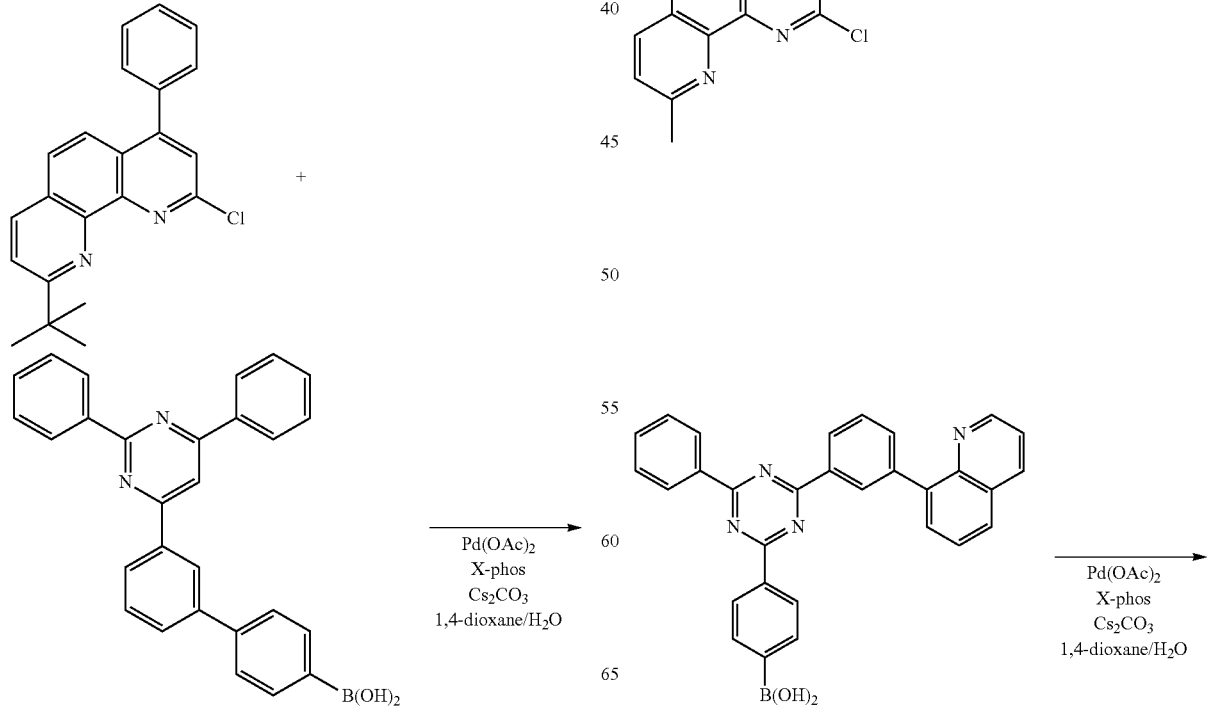

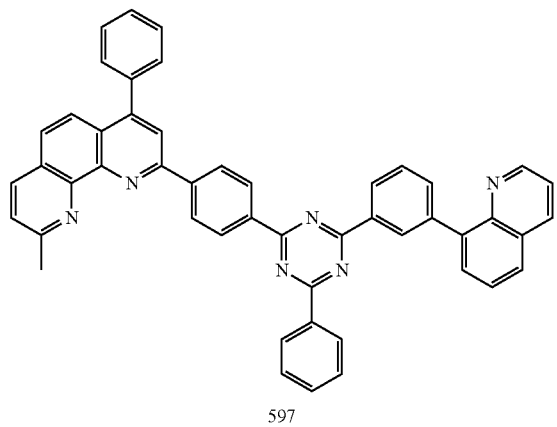

597

Compound 597 (24.7 g, Yield: 70%) was obtained through substantially the same process as in Synthesis Example 1, except that 2-chloro-9-methyl-4-phenyl-1,10-phenanthroline (15.2 g, 50 mmol) and (4-(4-phenyl-6-(3-(quinolin-8-yl)phenyl)-1,3,5-triazin-2-yl)phenyl)boronic acid (28.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 705

Synthesis Example 19. Synthesis of Compound 637

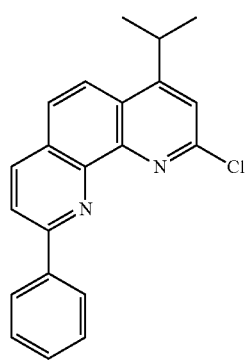

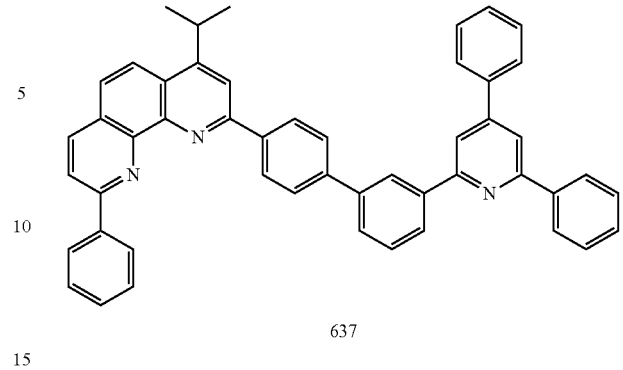

637

Compound 637 (24.5 g, Yield: 72%) was obtained through substantially the same process as in Synthesis Example 1, except that 2-chloro-4-isopropyl-9-phenyl-1,10-phenanthroline (16.6 g, 50 mmol) and (3'-(4,6-diphenylpyridin-2-yl)-[1,1'-biphenyl]-4-yl)boronic acid (25.6 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 680

Synthesis Example 20. Synthesis of Compound 658

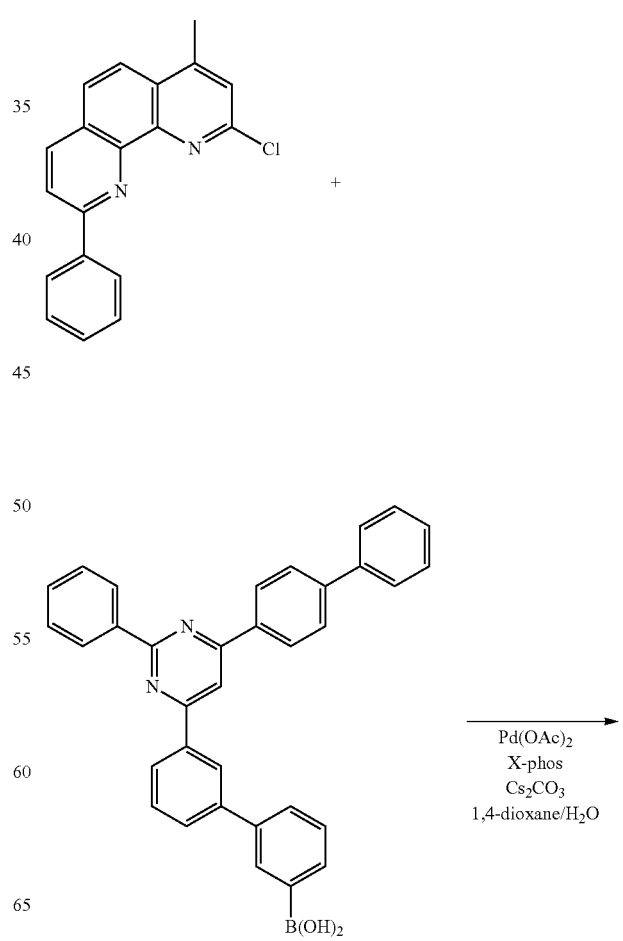

665
-continued

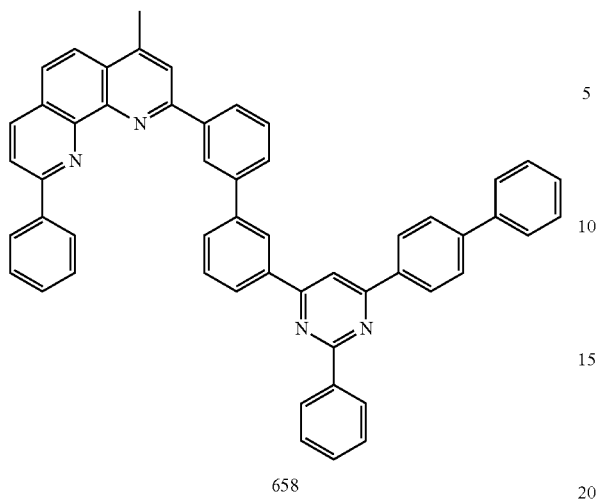

658

Compound 658 (22.6 g, Yield: 62%) was obtained through substantially the same process as in Synthesis Example 1, except that 2-chloro-4-methyl-9-phenyl-1,10-phenanthroline (15.2 g, 50 mmol) and (3'-(6-([1,1'-biphenyl]-4-yl)-2-phenylpyrimidin-4-yl)-[1,1'-biphenyl]-3-yl)boronic acid (30.3 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 729

Synthesis Example 21. Synthesis of Compound 693

666
-continued

693

Compound 693 (21.4 g, Yield: 64%) was obtained through substantially the same process as in Synthesis Example 1, except that 2-chloro-4-ethyl-9-phenyl-1,10-phenanthroline (15.9 g, 50 mmol) and (4'-(4-phenyl-6-(pyridin-4-yl)-1,3,5-triazin-2-yl)-[1,1'-biphenyl]-3-yl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 669

Synthesis Example 22. Synthesis of Compound 724

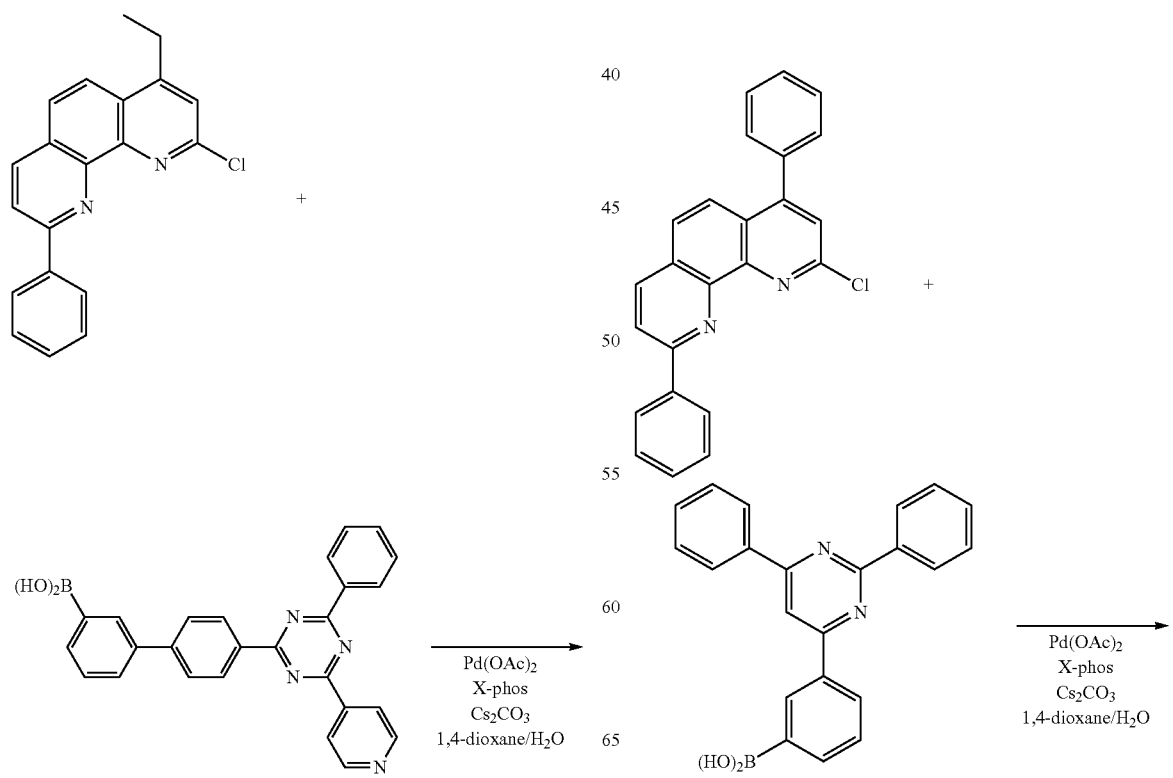

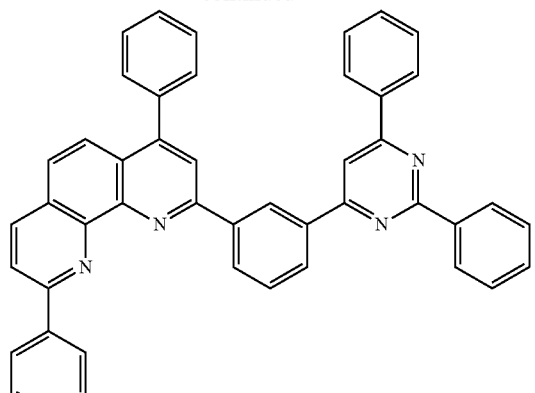

724

Compound 724 (21.1 g, Yield: 66%) was obtained through substantially the same process as in Synthesis Example 1, except that 2-chloro-4,9-diphenyl-1,10-phenanthroline (18.3 g, 50 mmol) and (3-(2,6-diphenylpyrimidin-4-yl)phenyl)boronic acid (21.1 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 639

Synthesis Example 23. Synthesis of Compound 758

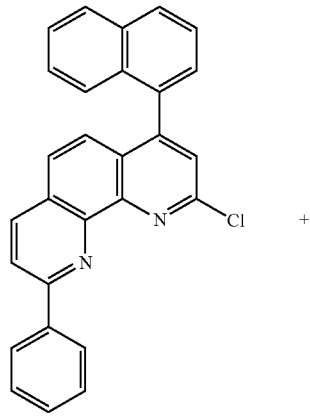

+

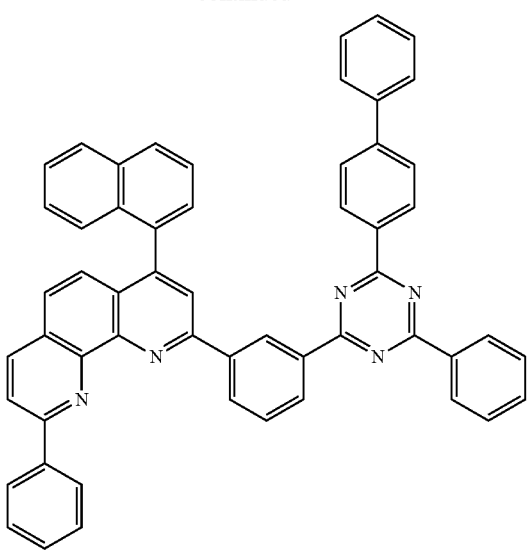

758

Compound 758 (26.0 g, Yield: 68%) was obtained through substantially the same process as in Synthesis Example 1, except that 2-chloro-4-(naphthalen-1-yl)-9-phenyl-1,10-phenanthroline (20.9 g, 50 mmol) and (3-(4-([1,1'-biphenyl]-4-yl)-6-phenyl-1,3,5-triazin-2-yl)phenyl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 766

Synthesis Example 24. Synthesis of Compound 802

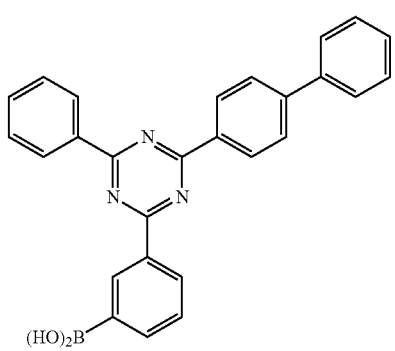

+

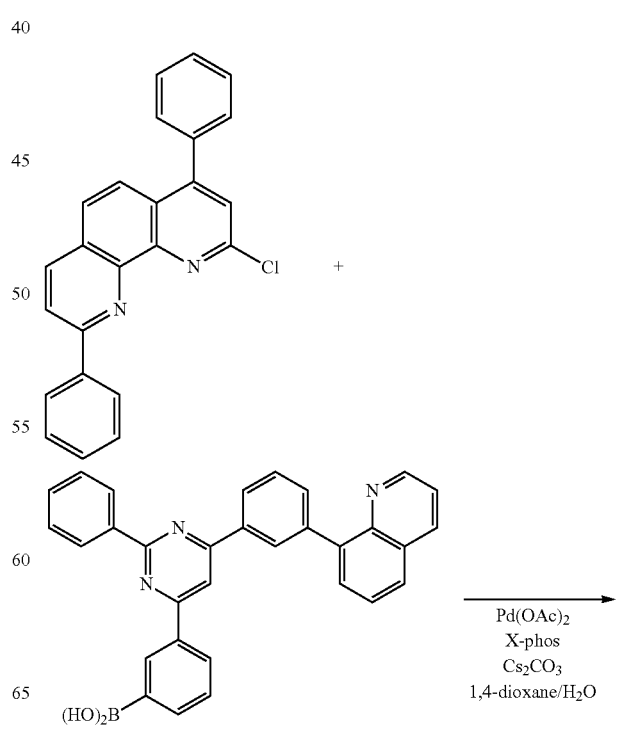

→ Pd(OAc)$_2$
X-phos
Cs$_2$CO$_3$
1,4-dioxane/H$_2$O

-continued

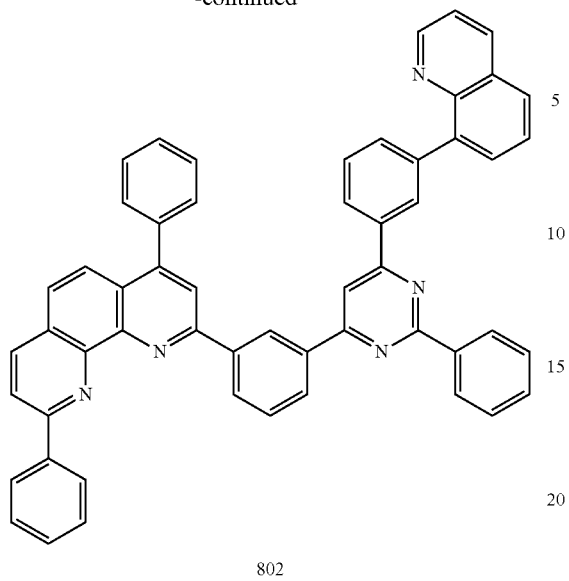

802

Compound 802 (26.8 g, Yield: 70%) was obtained through substantially the same process as in Synthesis Example 1, except that 2-chloro-4,9-diphenyl-1,10-phenanthroline (18.3 g, 50 mmol) and (3-(2-phenyl-6-(3-(quinolin-8-yl)phenyl)pyrimidin-4-yl)phenyl)boronic acid (28.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 766

Synthesis Example 25. Synthesis of Compound 833

-continued

833

Compound 833 (20.4 g, Yield: 66%) was obtained through substantially the same process as in Synthesis Example 1, except that 9-chloro-4-isopropyl-2-methyl-1,10-phenanthroline (13.5 g, 50 mmol) and (3'-(4,6-diphenylpyridin-2-yl)-[1,1'-biphenyl]-3-yl)boronic acid (25.6 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 618

Synthesis Example 26. Synthesis of Compound 846

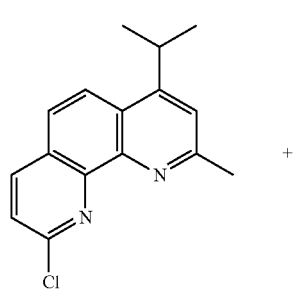

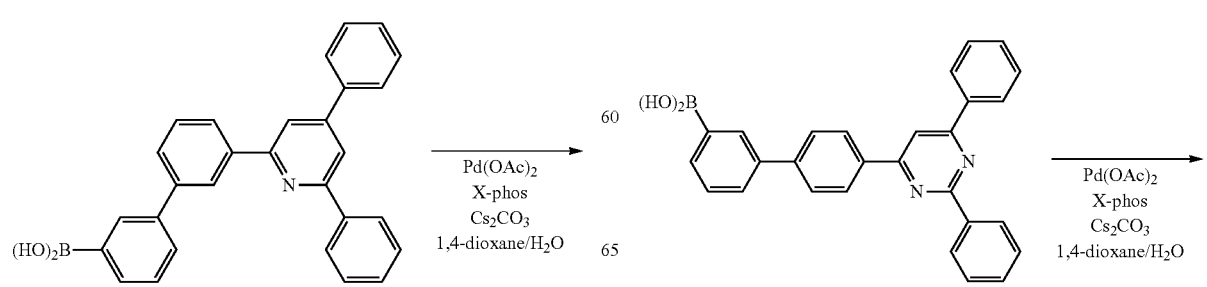

-continued

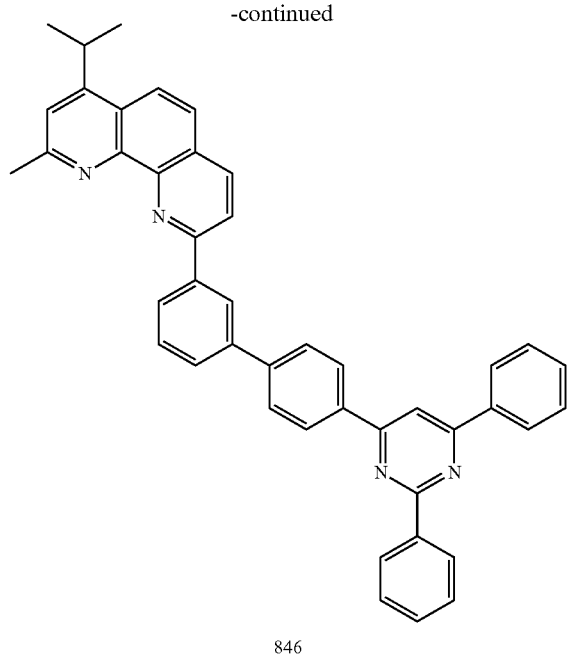

846

Compound 846 (18.9 g, Yield: 64%) was obtained through substantially the same process as in Synthesis Example 1, except that 9-chloro-4-isopropyl-2-methyl-1,10-phenanthroline (12.1 g, 50 mmol) and (4'-(2,6-diphenylpyrimidin-4-yl)-[1,1'-biphenyl]-3-yl)boronic acid (25.7 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 619

Synthesis Example 27. Synthesis of Compound 872

-continued

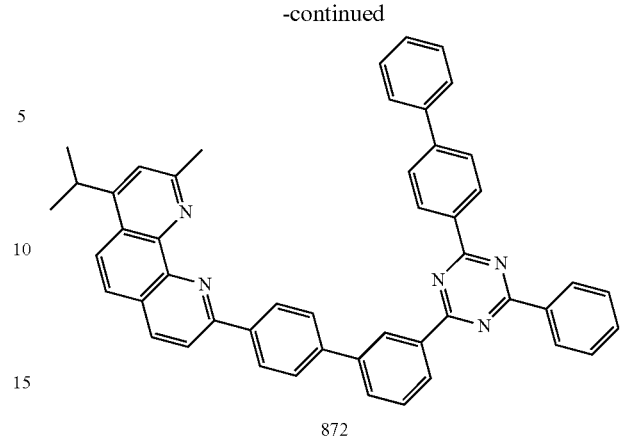

872

Compound 872 (22.6 g, Yield: 65%) was obtained through substantially the same process as in Synthesis Example 1, except that 9-chloro-4-isopropyl-2-methyl-1,10-phenanthroline (13.5 g, 50 mmol) and (3'-(4-([1,1'-biphenyl]-4-yl)-6-phenyl-1,3,5-triazin-2-yl)-[1,1'-biphenyl]-4-yl) boronic acid (30.3 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 696

Synthesis Example 28. Synthesis of Compound 932

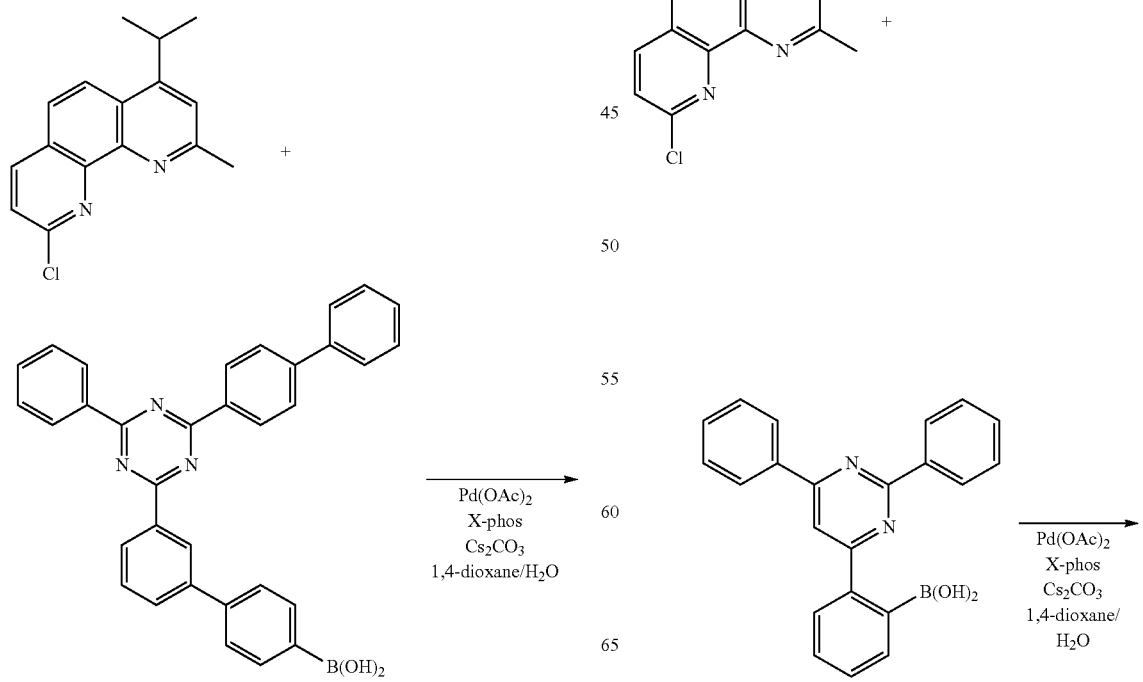

-continued

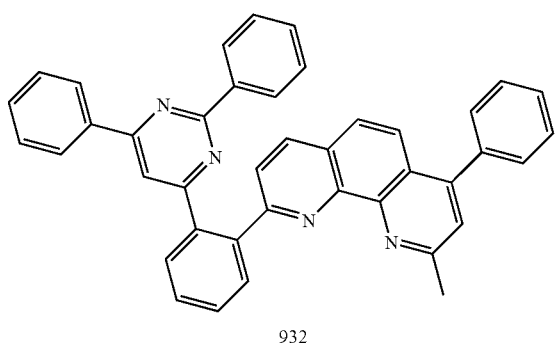

932

Compound 932 (21.6 g, Yield: 75%) was obtained through substantially the same process as in Synthesis Example 1, except that 9-chloro-2-methyl-4-phenyl-1,10-phenanthroline (15.2 g, 50 mmol) and (2-(2,6-diphenylpyrimidin-4-yl)phenyl)boronic acid (21.1 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 577

Synthesis Example 29. Synthesis of Compound 948

-continued

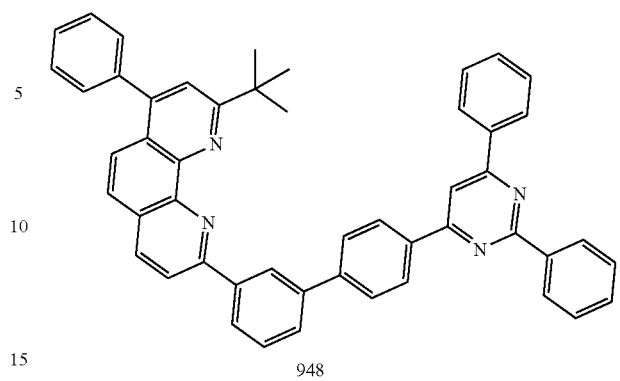

948

Compound 948 (25.0 g, Yield: 72%) was obtained through substantially the same process as in Synthesis Example 1, except that 2-(9-chloro-4-phenyl-1,10-phenanthrolin-2-yl)-2-methylpropan-1-ylium (17.3 g, 50 mmol) and (4'-(2,6-diphenylpyrimidin-4-yl)-[1,1'-biphenyl]-3-yl)boronic acid (25.7 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 695

Synthesis Example 30. Synthesis of Compound 987

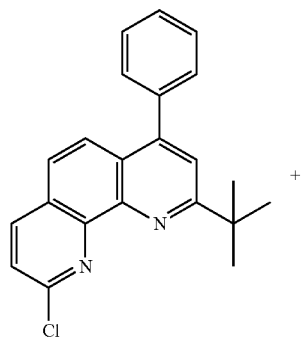

+

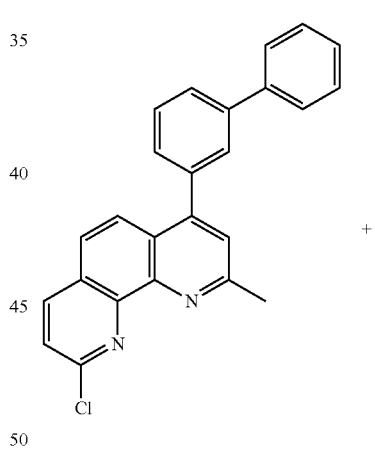

+

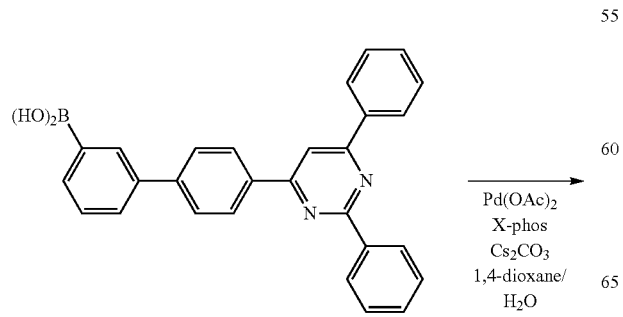

$\xrightarrow{\text{Pd(OAc)}_2 \\ \text{X-phos} \\ \text{Cs}_2\text{CO}_3 \\ \text{1,4-dioxane/} \\ \text{H}_2\text{O}}$

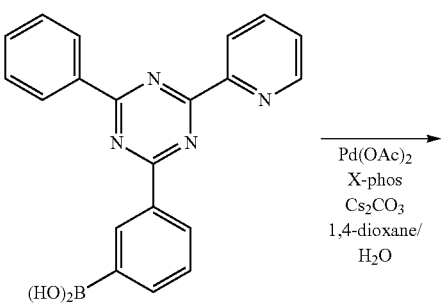

$\xrightarrow{\text{Pd(OAc)}_2 \\ \text{X-phos} \\ \text{Cs}_2\text{CO}_3 \\ \text{1,4-dioxane/} \\ \text{H}_2\text{O}}$ -continued

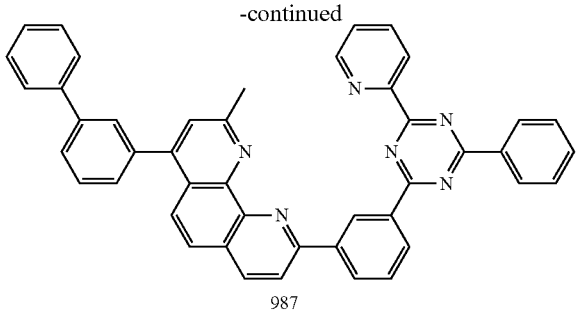

987

Compound 987 (23.9 g, Yield: 73%) was obtained through substantially the same process as in Synthesis Example 1, except that 4-([1,1'-biphenyl]-3-yl)-9-chloro-2-methyl-1,10-phenanthroline (19.0 g, 50 mmol) and (3-(4-phenyl-6-(pyridin-2-yl)-1,3,5-triazin-2-yl)phenyl)boronic acid (21.3 g, 60 mmol) were used instead of 4-chloro-2,9-dimethyl-1,10-phenanthroline and (3-(4,6-diphenyl-1,3,5-triazin-2-yl)phenyl)boronic acid, respectively.
Mass: [(M+H)$^+$]: 655

Synthesis Example 31. Synthesis of Compound 1026

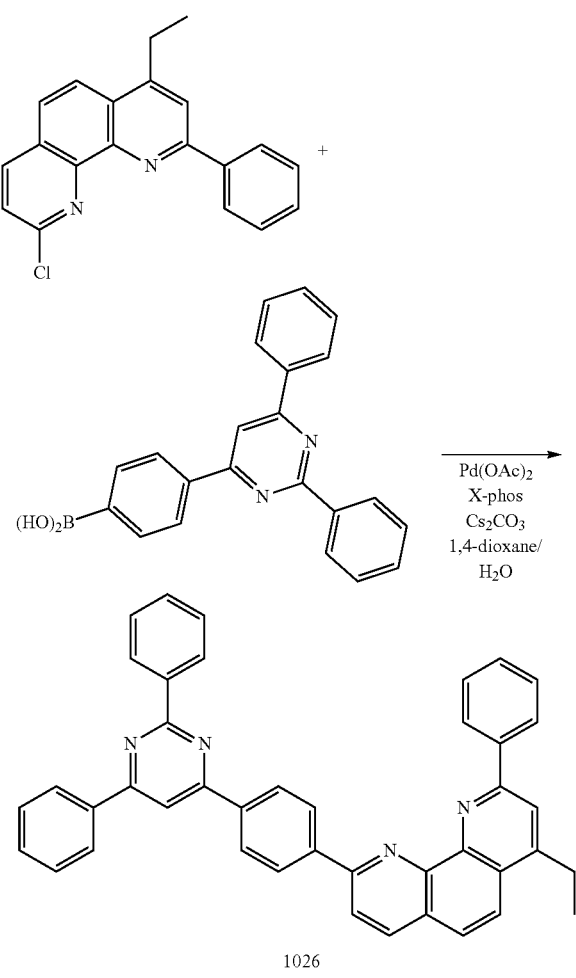

1026

Compound 1026 (20.7 g, Yield: 70%) was obtained through substantially the same process as in Synthesis Example 1, except that 9-chloro-4-ethyl-2-phenyl-1,10-phenanthroline (15.9 g, 50 mmol) and (4-(2,6-diphenylpyrimidin-4-yl)phenyl)boronic acid (21.1 g, 60 mmol) were used instead of 4-chloro-2,9-dimethyl-1,10-phenanthroline and (3-(4,6-diphenyl-1,3,5-triazin-2-yl)phenyl)boronic acid, respectively.
Mass: [(M+H)$^+$]: 591

Synthesis Example 32. Synthesis of Compound 1072

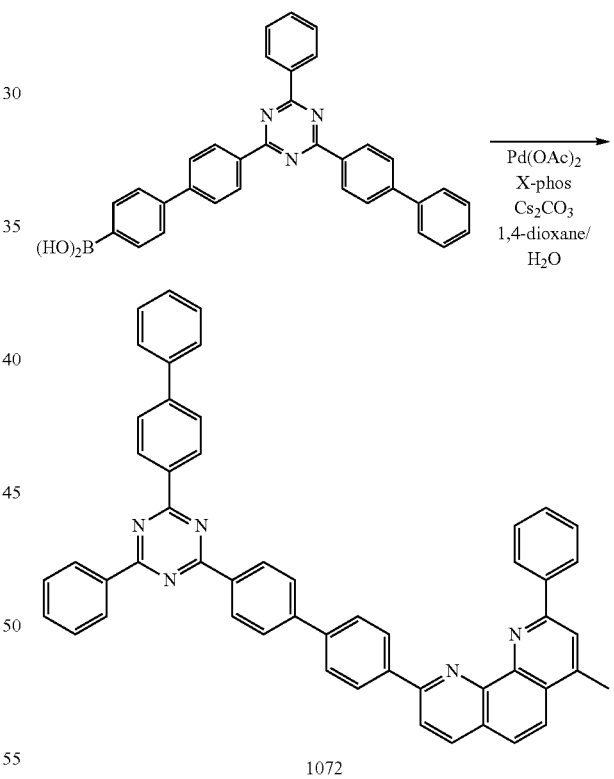

1072

Compound 1072 (24.8 g, Yield: 68%) was obtained through substantially the same process as in Synthesis Example 1, except that 9-chloro-4-methyl-2-phenyl-1,10-phenanthroline (15.2 g, 50 mmol) and (4'-(4-([1,1'-biphenyl]-4-yl)-6-phenyl-1,3,5-triazin-2-yl)-[1,1'-biphenyl]-4-yl)boronic acid (30.32 g, 60 mmol) were used instead of 4-chloro-2,9-dimethyl-1,10-phenanthroline and (3-(4,6-diphenyl-1,3,5-triazin-2-yl)phenyl)boronic acid, respectively.
Mass: [(M+H)$^+$]: 730

Synthesis Example 33. Synthesis of Compound 1097

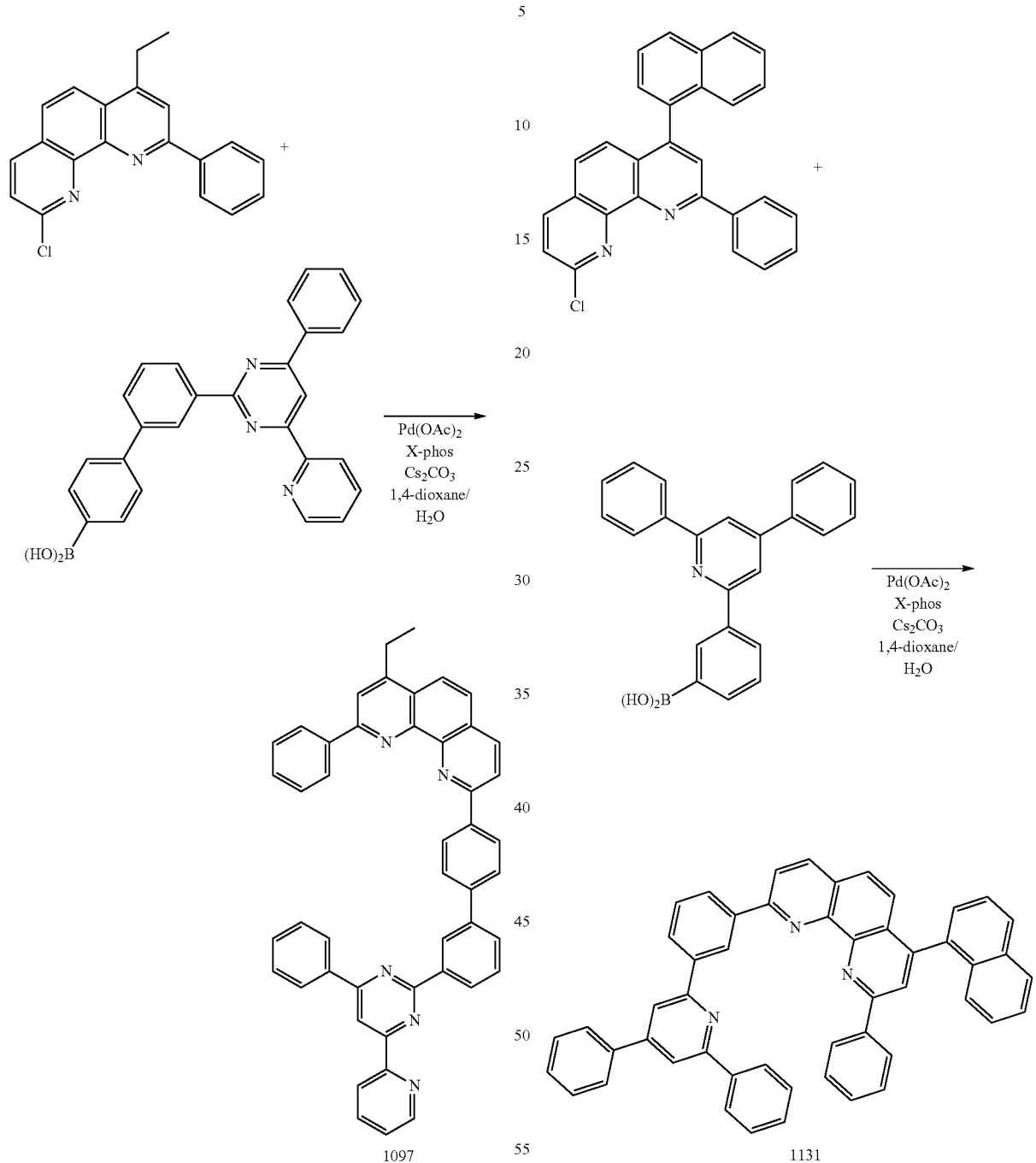

Compound 1097 (23.7 g, Yield: 71%) was obtained through substantially the same process as in Synthesis Example 1, except that 9-chloro-4-ethyl-2-phenyl-1,10-phenanthroline (15.9 g, 50 mmol) and (3'-(4-phenyl-6-(pyridin-2-yl)pyrimidin-2-yl)-[1,1'-biphenyl]-4-yl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 669

Synthesis Example 34. Synthesis of Compound 1131

Compound 1131 (22.4 g, Yield: 65%) was obtained through substantially the same process as in Synthesis Example 1, except that 9-chloro-4-(naphthalen-1-yl)-2-phenyl-1,10-phenanthroline (20.9 g, 50 mmol) and (3-(4,6-diphenylpyridin-2-yl)phenyl)boronic acid (21.1 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 688

679
Synthesis Example 35. Synthesis of Compound 1133

680
Synthesis Example 36. Synthesis of Compound 1146

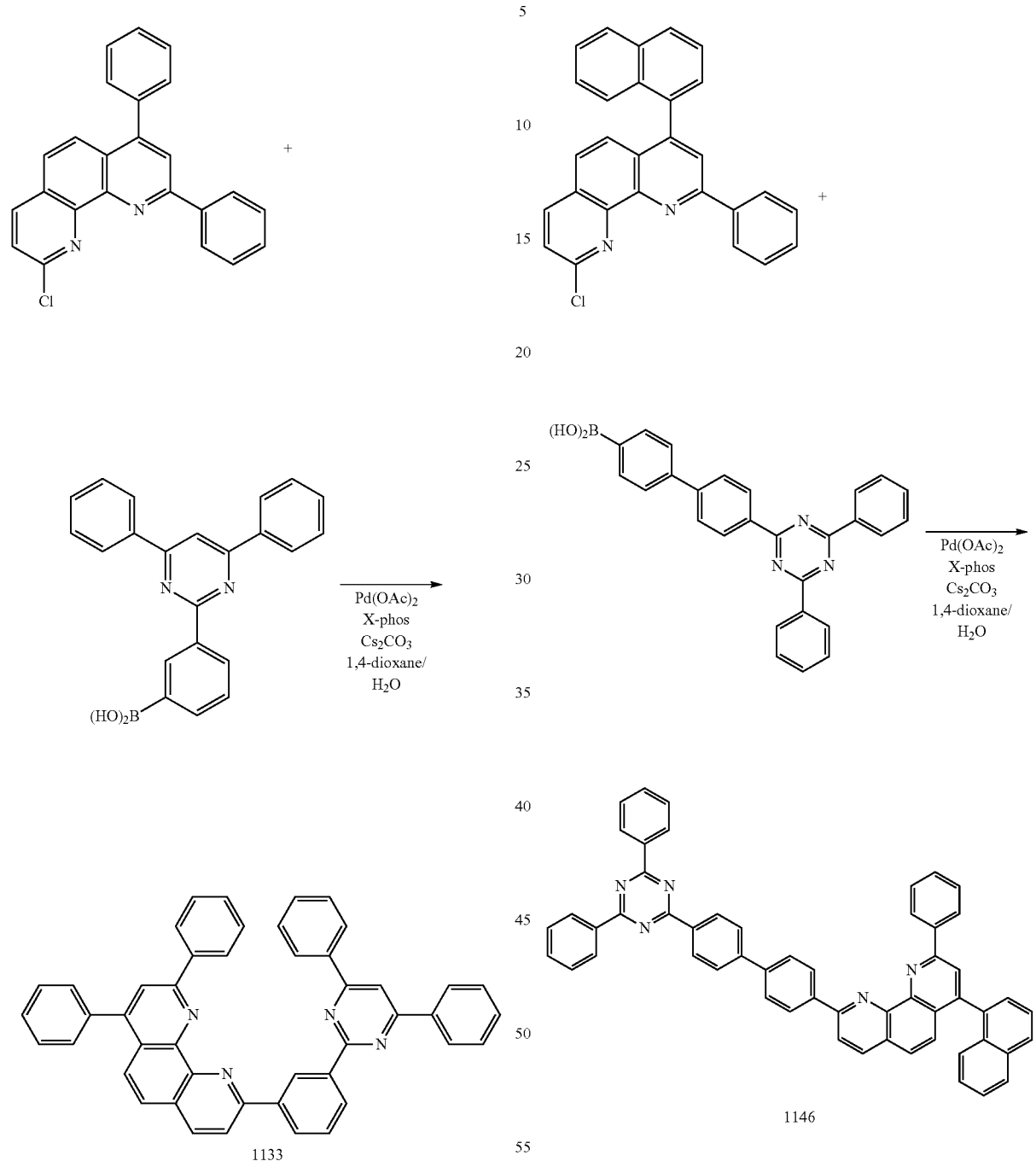

Compound 1133 (20.4 g, Yield: 64%) was obtained through substantially the same process as in Synthesis Example 1, except that 9-chloro-2,4-diphenyl-1,10-phenanthroline (18.3 g, 50 mmol) and (3-(4,6-diphenylpyrimidin-2-yl)phenyl)boronic acid (21.1 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: $[(M+H)^+]$: 639

Compound 1146 (25.3 g, Yield: 66%) was obtained through substantially the same process as in Synthesis Example 1, except that 9-chloro-4-(naphthalen-1-yl)-2-phenyl-1,10-phenanthroline (20.9 g, 50 mmol) and (4'-(4,6-diphenyl-1,3,5-triazin-2-yl)-[1,1'-biphenyl]-4-yl)boronic acid (25.8 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: $[(M+H)^+]$: 766

Synthesis Example 37. Synthesis of Compound 1239

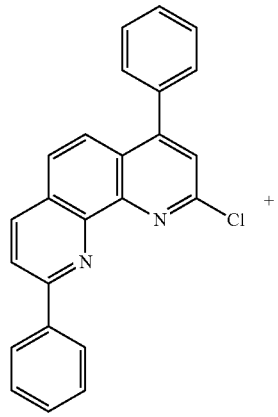

+

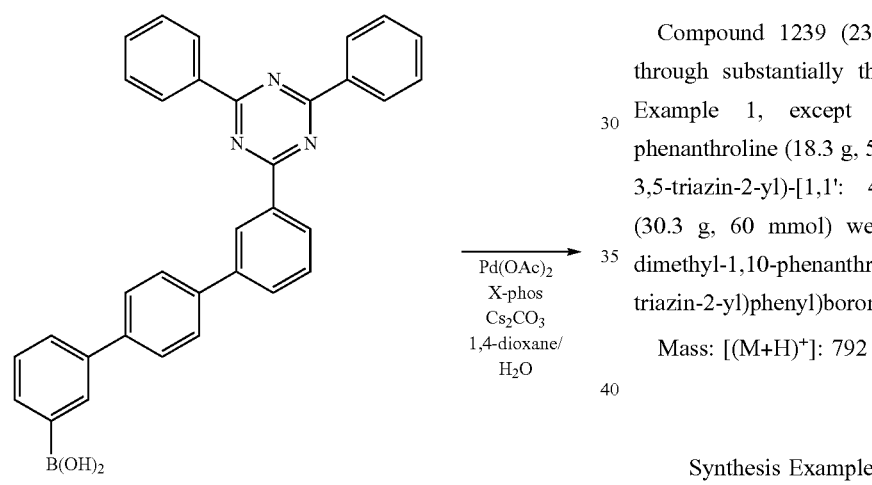

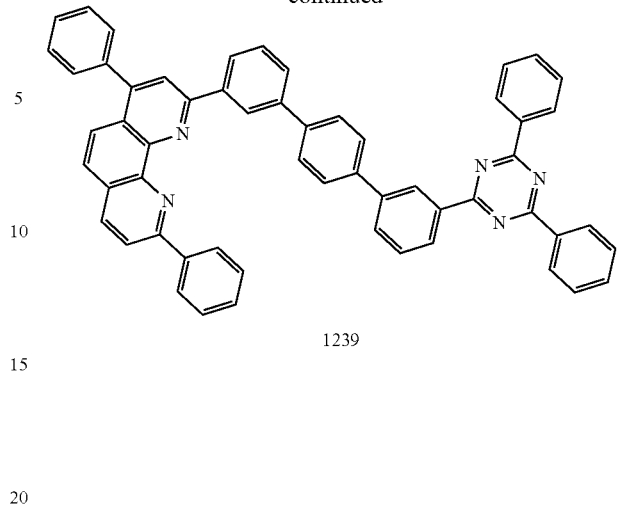

Compound 1239 (23.8 g, Yield: 60%) was obtained through substantially the same process as in Synthesis Example 1, except that 2-chloro-4,9-diphenyl-1,10-phenanthroline (18.3 g, 50 mmol) and ((3"-(4,6-diphenyl-1,3,5-triazin-2-yl)-[1,1': 4',1"-terphenyl]-3-yl)boronic acid (30.3 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)$^+$]: 792

Synthesis Example 38. Synthesis of Compound 1248

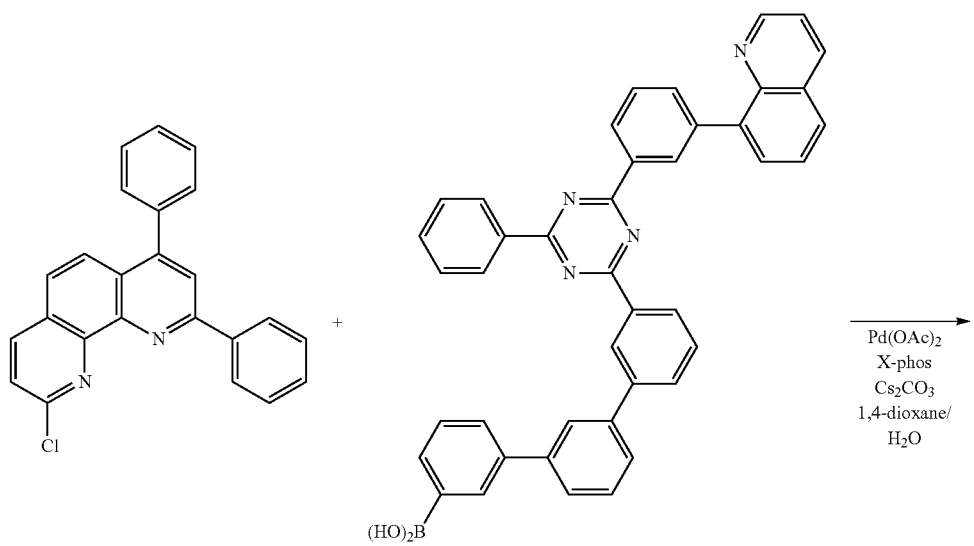

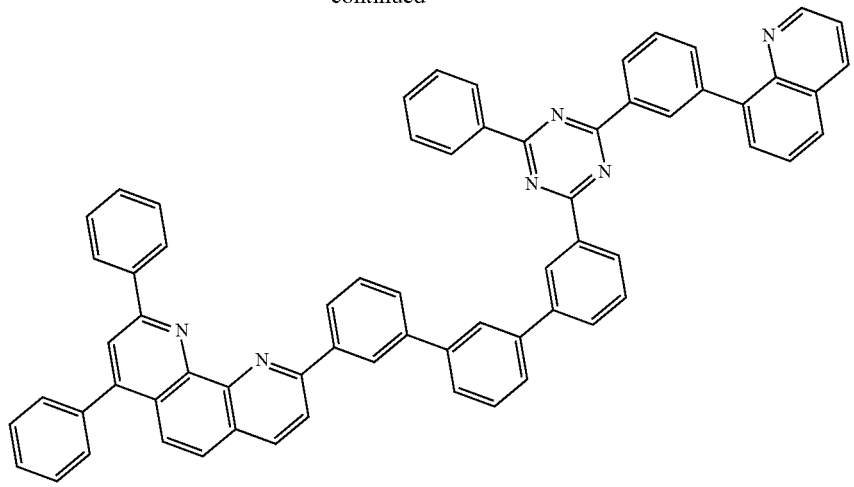

1248

Compound 1248 (28.9 g, Yield: 63%) was obtained through substantially the same process as in Synthesis Example 1, except that 9-chloro-2,4-diphenyl-1,10-phenanthroline (18.3 g, 50 mmol) and (3"-(4-phenyl-6-(3-(quinolin-8-yl)phenyl)-1,3,5-triazin-2-yl)-[1,1': 3',1"-terphenyl]-3-yl)boronic acid (37.9 g, 60 mmol) were used instead of 4-chloro-2,9-dimethyl-1,10-phenanthroline and (3-(4,6-diphenyl-1,3,5-triazin-2-yl)phenyl)boronic acid, respectively.

Mass: [(M+H)⁺]: 920

Synthesis Example 39. Synthesis of Compound 1250

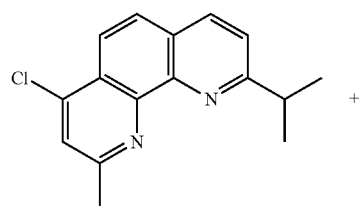 +

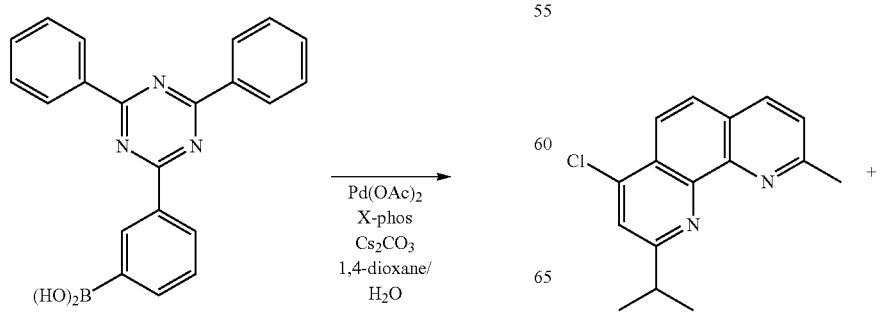

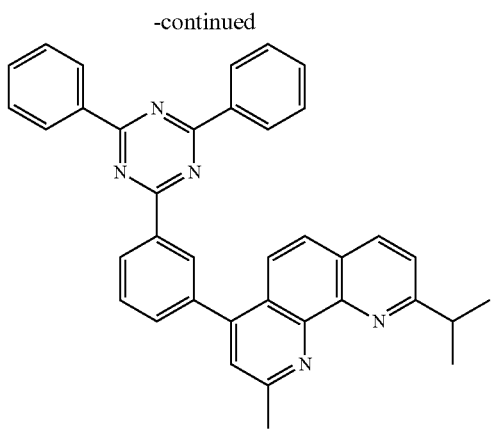

1250

Compound 1250 (17.4 g, Yield: 64%) was obtained through substantially the same process as in Synthesis Example 1, except that 4-chloro-9-isopropyl-2-methyl-1,10-phenanthroline (13.5 g, 50 mmol) was used instead of 4-chloro-2,9-dimethyl-1,10-phenanthroline.

Mass: [(M+H)⁺]: 544

Synthesis Example 40. Synthesis of Compound 1251

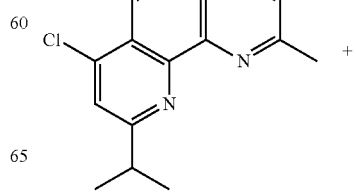 +

-continued

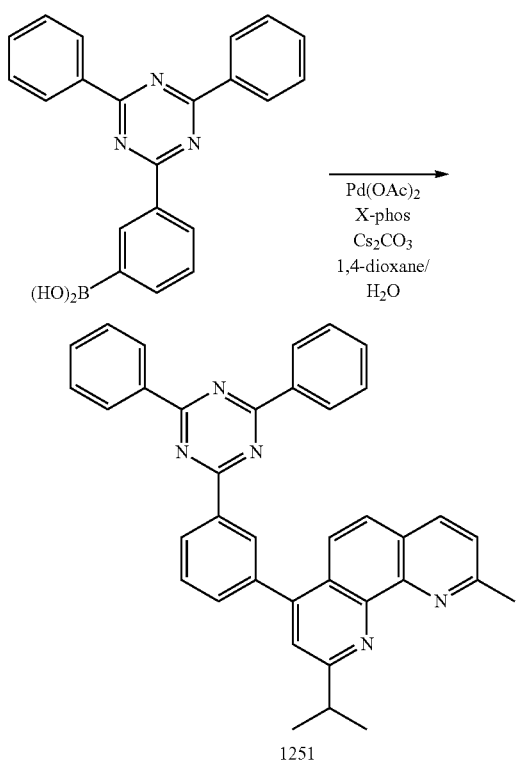

1251

Compound 1251 (17.7 g, Yield: 65%) was obtained through substantially the same process as in Synthesis Example 1, except that 4-chloro-2-isopropyl-9-methyl-1,10-phenanthroline (13.5 g, 50 mmol) was used instead of 4-chloro-2,9-dimethyl-1,10-phenanthroline.

Mass: [(M+H)$^+$]: 544

Synthesis Example 41. Synthesis of Compound 1252

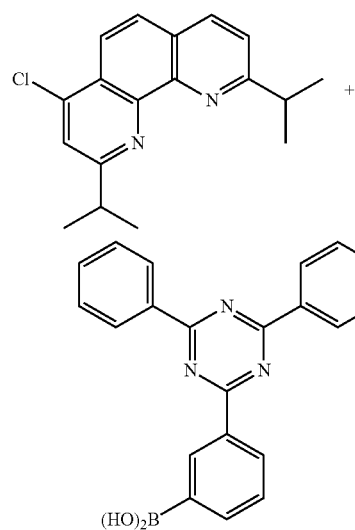

-continued

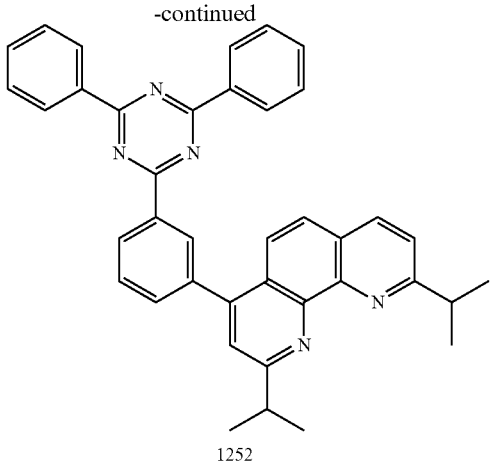

1252

Compound 1252 (16.8 g, Yield: 59%) was obtained through substantially the same process as in Synthesis Example 1, except that 4-chloro-2,9-diisopropyl-1,10-phenanthroline (14.9 g, 50 mmol) was used instead of 4-chloro-2,9-dimethyl-1,10-phenanthroline.

Mass: [(M+H)$^+$]: 572

Synthesis Example 42 Synthesis of Compound 1268

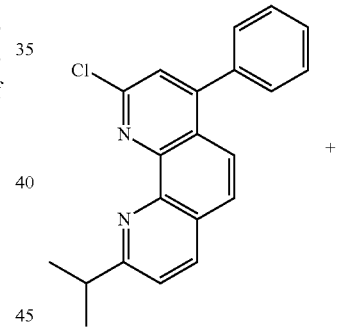

+

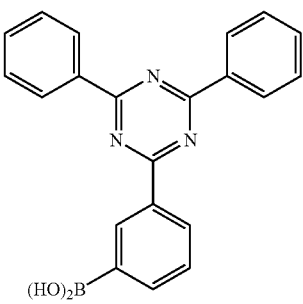

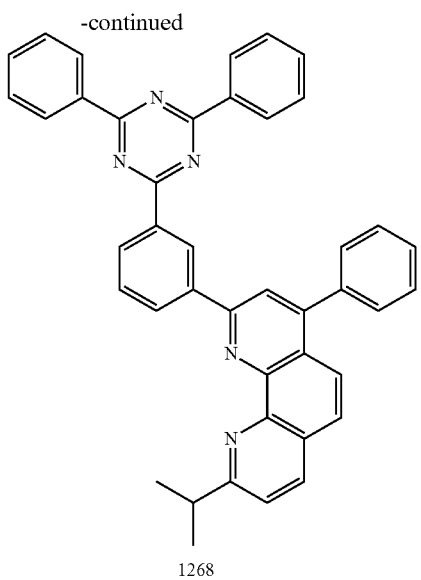

1268

Compound 1268 (18.2 g, Yield: 60%) was obtained through substantially the same process as in Synthesis Example 1, except that 2-chloro-9-isopropyl-4-phenyl-1,10-phenanthroline (16.6 g, 50 mmol) was used instead of 4-chloro-2,9-dimethyl-1,10-phenanthroline.
Mass: [(M+H)$^+$]: 606

Examples 1 to 26. Manufacture of Blue-Light-Emitting Organic Electroluminescent Devices After high-purity sublimation purification of the compounds synthesized in the above synthesis examples, using any suitable high-purity sublimation purification method, blue-light-emitting organic electroluminescent devices were manufactured as follows.

First, a glass substrate coated with a 1500 Å-thick indium tin oxide (ITO) film was ultrasonically washed with distilled water. After the washing with distilled water, the glass substrate was ultrasonically washed with a solvent such as isopropyl alcohol, acetone, methanol, and/or the like, dried, and then transferred to a UV OZONE cleaner (Powersonic 405, HWASHIN TECHNOLOGY CO.). Then, the substrate was washed with UV for 5 minutes and then transferred to a vacuum deposition apparatus.

On the ITO electrode prepared as above, DS-205 (DOOSAN ELECTRONICS, CO., LTD, 80 nm)/NPB (15 nm)/ADN+5% DS-405 (DOOSAN ELECTRONICS, CO., LTD, 30 nm)/compound of the present embodiments (30 nm) as shown in Table 1/LiF (1 nm)/Al (200 nm) were sequentially stacked one another to manufacture an organic electroluminescent device.

Comparative Examples 1 to 8. Manufacture of Blue-Light-Emitting Organic Electroluminescent Devices Blue-light-emitting organic electroluminescent devices were manufactured through substantially the same process as in Example 1, except that Alq$_3$ and Compound A to Compound G were used, respectively, instead of Compound 12, as the material of the electron transport layer.

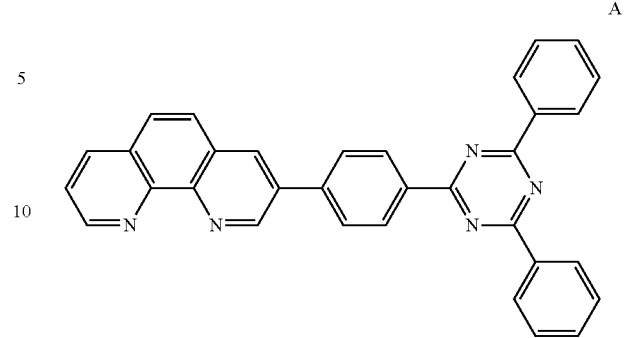

A

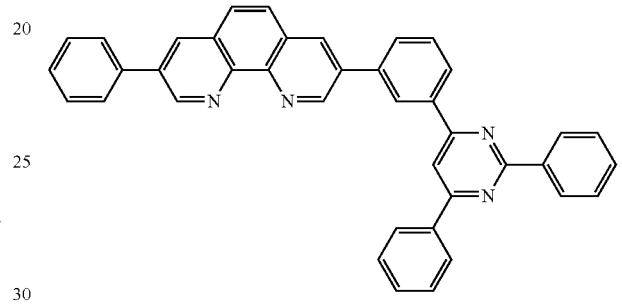

B

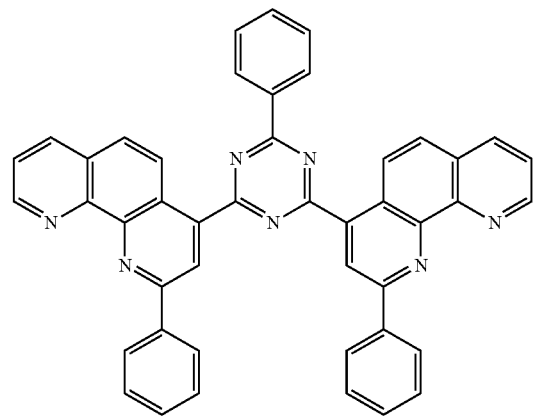

C

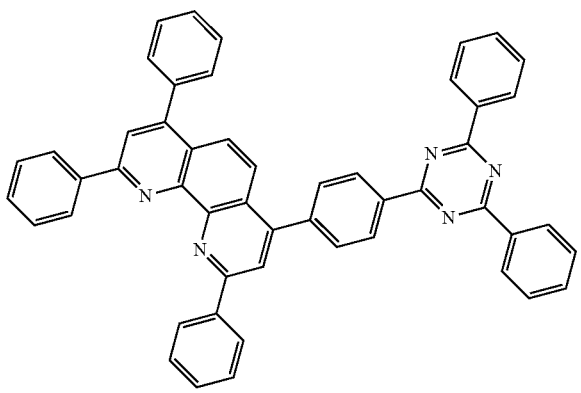

D

-continued

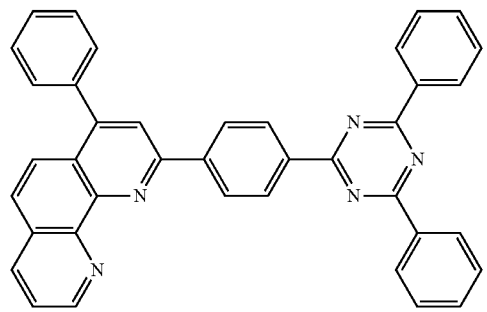

E

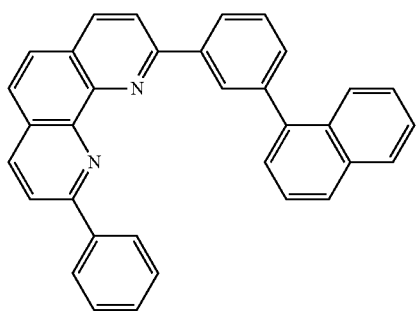

F

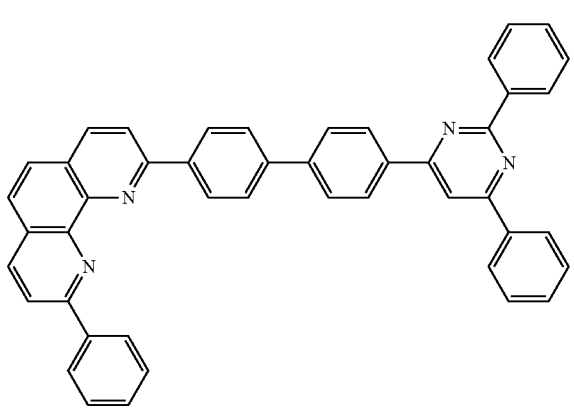

G

Evaluation Example 1

The driving voltage, current efficiency, and emission wavelength of the blue-light-emitting organic electroluminescent devices manufactured in Examples 1 to 26 and Comparative Examples 1 to 8 were measured at a current density of 10 mA/cd. The results are shown in Table 1.

TABLE 1

| Sample | Electron transport layer | Driving voltage (V) | Emission peak (nm) | Current efficiency (cd/A) |
|---|---|---|---|---|
| Example 1 | Compound 12 | 4.0 | 457 | 8.0 |
| Example 2 | Compound 90 | 4.1 | 456 | 7.9 |
| Example 3 | Compound 126 | 4.0 | 457 | 7.3 |
| Example 4 | Compound 160 | 4.0 | 456 | 7.9 |
| Example 5 | Compound 209 | 4.2 | 456 | 7.3 |
| Example 6 | Compound 236 | 4.0 | 458 | 7.5 |
| Example 7 | Compound 318 | 4.1 | 458 | 7.8 |
| Example 8 | Compound 313 | 4.1 | 454 | 7.5 |
| Example 9 | Compound 387 | 4.0 | 457 | 7.5 |
| Example 10 | Compound 473 | 4.1 | 458 | 7.6 |
| Example 11 | Compound 516 | 4.0 | 454 | 7.4 |

TABLE 1-continued

| Sample | Electron transport layer | Driving voltage (V) | Emission peak (nm) | Current efficiency (cd/A) |
|---|---|---|---|---|
| Example 12 | Compound 536 | 4.0 | 454 | 7.4 |
| Example 13 | Compound 597 | 4.1 | 455 | 7.8 |
| Example 14 | Compound 637 | 4.1 | 455 | 7.8 |
| Example 15 | Compound 658 | 4.1 | 457 | 7.5 |
| Example 16 | Compound 693 | 4.2 | 457 | 7.5 |
| Example 17 | Compound 833 | 4.2 | 457 | 7.2 |
| Example 18 | Compound 846 | 4.0 | 454 | 7.7 |
| Example 19 | Compound 872 | 4.0 | 454 | 7.7 |
| Example 20 | Compound 1146 | 4.0 | 455 | 7.6 |
| Example 21 | Compound 1026 | 4.1 | 455 | 7.5 |
| Example 22 | Compound 1072 | 4.2 | 455 | 7.4 |
| Example 23 | Compound 1239 | 4.2 | 456 | 7.6 |
| Example 24 | Compound 1250 | 4.0 | 455 | 7.9 |
| Example 25 | Compound 1251 | 4.0 | 456 | 8.0 |
| Example 26 | Compound 1252 | 4.0 | 456 | 7.9 |
| Comparative Example 1 | Alq$_3$ | 4.7 | 458 | 5.6 |
| Comparative Example 2 | Compound A | 4.3 | 460 | 6.2 |
| Comparative Example 3 | Compound B | 4.5 | 459 | 6.4 |
| Comparative Example 4 | Compound C | 4.6 | 457 | 6.0 |
| Comparative Example 5 | Compound D | 4.4 | 458 | 6.7 |
| Comparative Example 6 | Compound E | 4.4 | 456 | 6.8 |
| Comparative Example 7 | Compound F | 4.8 | 459 | 6.4 |
| Comparative Example 8 | Compound G | 4.6 | 458 | 6.9 |

As shown in Table 1, the blue-light-emitting organic electroluminescent devices (Examples 1 to 26) using the compounds according to embodiments of the present disclosure in the electron transport layer were found to exhibit excellent performance in terms of driving voltage, emission peak, and current efficiency, as compared to the blue-light-emitting organic electroluminescent device (Comparative Example 1) using conventional Alq$_3$ in the electron transport layer, and the blue-light-emitting organic electroluminescent devices (Comparative Examples 2 to 8) in which the compounds have different binding sites.

As described above, according to the one or more embodiments, an organic light-emitting device including at least one heterocyclic compound as represented above may have a low driving voltage, high emission efficiency, and improved lifetime characteristics.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims and their equivalents.

What is claimed is:
1. An organic light-emitting device comprising:
a first electrode;
a second electrode facing the first electrode;
an organic layer between the first electrode and the second electrode and including an emission layer; and
at least one heterocyclic compound represented by Formula 1:

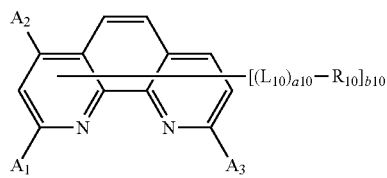

Formula 1

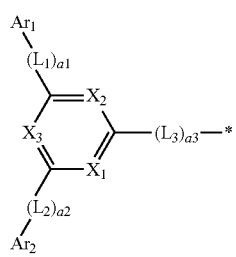

Formula 2

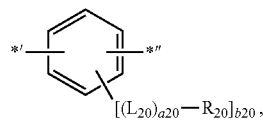

Formula 3 wherein, in Formulae 1 to 3,
$A_1$ to $A_3$ are each independently selected from a group represented by Formula 2, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$($Q_1$), and —P(=O)($Q_1$)($Q_2$), at least one of $A_1$ to $A_3$ is a group represented by Formula 2,
$X_1$ is N or C($R_{31}$), $X_2$ is N or C($R_{32}$), $X_3$ is N or C($R_{33}$),
at least one of $X_1$ to $X_3$ is N,
$L_1$, $L_2$, $L_{10}$, and $L_{20}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
a1, a2, a10, and a20 are each independently an integer from 0 to 5,
$L_3$ is a group represented by Formula 3,
a3 is an integer from 0 to 5,
$Ar_1$ and $Ar_2$ are each independently selected from deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$),
$R_{10}$, $R_{20}$, and $R_{31}$ to $R_{33}$ are each independently selected from hydrogen, deuterium, —F, —Cl, —Br, —I, a hydroxyl group, a cyano group, a nitro group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$($Q_1$), and —P(=O)($Q_1$)($Q_2$), neighboring groups among any selected from $R_{10}$, $R_{20}$, and $R_{31}$ to $R_{33}$ are optionally linked to one another to form a substituted or unsubstituted $C_5$-$C_{60}$ carbocyclic group or a substituted or unsubstituted $C_1$-$C_{60}$ heterocyclic group, b10 is an integer from 1 to 5, b20 is an integer from 1 to 4,

*, *', and *'' are each a binding site to a respective neighboring atom, at least one substituent of the substituted $C_5$-$C_{60}$ carbocyclic group, the substituted $C_1$-$C_{60}$ heterocyclic group, substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group, is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —P($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —P($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group.

2. The organic light-emitting device of claim 1, wherein the first electrode is an anode, the second electrode is a cathode, the organic layer further comprises a hole transport region between the first electrode and the emission layer, and an electron transport region between the emission layer and the second electrode, the hole transport region comprises at least one selected from a hole injection layer, a hole transport layer, a buffer layer, an emission auxiliary layer, and an electron blocking layer, and the electron transport region comprises at least one selected from a hole blocking layer, an electron transport layer, and an electron injection layer.

3. The organic light-emitting device of claim 2, wherein the electron transport region comprises the at least one heterocyclic compound.

4. The organic light-emitting device of claim 3, wherein the electron transport region comprises the electron transport layer and the electron injection layer, and at least one selected from the electron transport layer and the electron injection layer comprises the at least one heterocyclic compound.

5. The organic light-emitting device of claim 4, wherein at least one layer selected from the electron transport layer and the electron injection layer further comprises an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combination thereof.

6. The organic light-emitting device of claim 1, wherein the emission layer comprises a host and a dopant.

7. The organic light-emitting device of claim 2, wherein the hole transport region comprises a p-dopant, and a lowest unoccupied molecular orbital (LUMO) level of the p-dopant is −3.5 eV or less.

8. An electronic apparatus comprising:
a substrate;
the organic light-emitting device of claim 1 on the substrate; and
a color conversion layer in at least one traveling direction of light emitted from the organic light-emitting device, the color conversion layer comprising one or more quantum dots.

9. A heterocyclic compound represented by Formula 1:

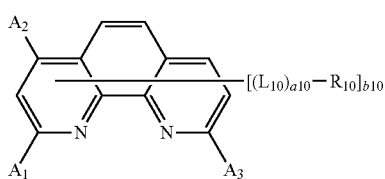

Formula 1

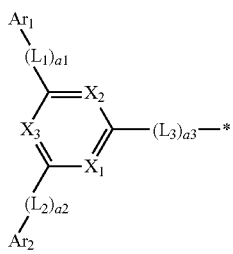

Formula 2

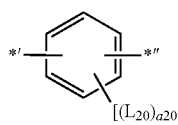

Formula 3 wherein, in Formulae 1 to 3, $A_1$ to $A_3$ are each independently selected from a group represented by Formula 2, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O)($Q_1$), —S(=O)$_2$ ($Q_1$), and —P(=O)($Q_1$)($Q_2$), at least one of $A_1$ to $A_3$ is a group represented by Formula 2, $X_1$ is N or C($R_{31}$), $X_2$ is N or C($R_{32}$), $X_3$ is N or C($R_{33}$), at least one of $X_1$ to $X_3$ is N, $L_1$, $L_2$, $L_{10}$, and $L_{20}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1, a2, a10, and a20 are each independently an integer selected from 0 to 5, $L_3$ is a group represented by Formula 3, a3 is an integer from 0 to 5, $Ar_1$ and $Ar_2$ are each independently selected from deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$ ($Q_1$), and —P(=O)($Q_1$)($Q_2$), $R_{10}$, $R_{20}$, and $R_{31}$ to $R_{33}$ are each independently selected from hydrogen, deuterium, —F, —Cl, —Br, —I, a hydroxyl group, a cyano group, a nitro group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —P($Q_1$)($Q_2$), —C(=O) ($Q_1$), —S(=O)$_2$($Q_1$), and —P(=O)($Q_1$)($Q_2$), two neighboring groups among any selected from $R_{10}$, $R_{20}$, and $R_{31}$ to $R_{33}$ are optionally linked to one another to form a substituted or unsubstituted $C_5$-$C_{60}$ carbocyclic group or a substituted or unsubstituted $C_1$-$C_{60}$ heterocyclic group, b10 is an integer from 1 to 5, b20 is an integer from 1 to 4,

*, *', and *'' are each a binding site to a neighboring atom, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted the divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —P($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —P($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —P($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_1$-$C_{60}$ heteroaryl group, a monovalent non-aromatic condensed polycyclic group, a monovalent non-aromatic condensed heteropolycyclic group, a biphenyl group, and a terphenyl group.

10. The heterocyclic compound of claim 9, wherein one of $A_1$ to $A_3$ is a group represented by Formula 2, and remaining ones of $A_1$ to $A_3$ are each independently selected from a substituted or unsubstituted $C_1$-$C_{60}$ alkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

11. The heterocyclic compound of claim 9, wherein one of $A_1$ to $A_3$ is a group represented by Formula 2, and remaining ones of $A_1$ to $A_3$ are each independently selected from:

a methyl group, an ethyl group, a propyl group, an isobutyl group, a sec-butyl group, a ter-butyl group, a pentyl group, an iso-amyl group, and a hexyl group; and a methyl group, an ethyl group, a propyl group, an isobutyl group, a sec-butyl group, a ter-butyl group, a pentyl group, an iso-amyl group, and a hexyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group;

a phenyl group, a naphthyl group, a pyridyl group, a pyrimidyl group, a triazinyl group, a quinoline group, an isoquinoline group, a biphenyl group, and a terphenyl group; and a phenyl group, a naphthyl group, a pyridyl group, a pyrimidyl group, a triazinyl group, a quinoline group, an isoquinoline group, a biphenyl group, and a terphenyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group.

12. The heterocyclic compound of claim 9, wherein $L_1$, $L_2$, $L_{10}$, and $L_{20}$ are each independently a group represented by one of Formulae 3-1 to 3-99:

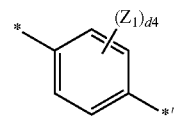

3-1

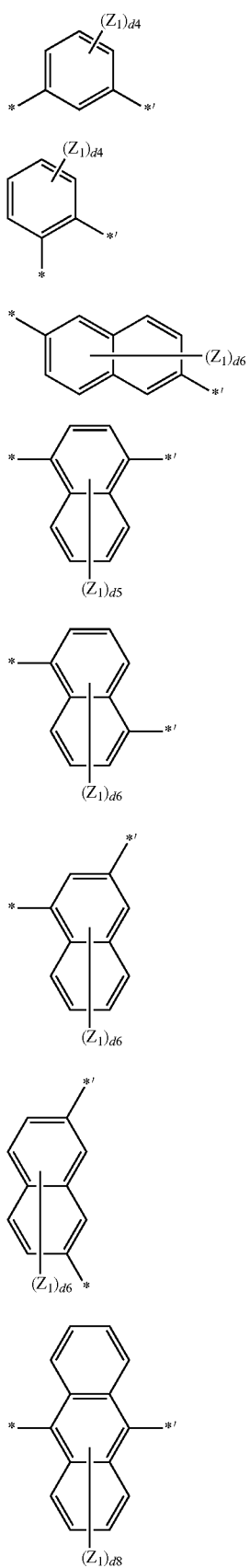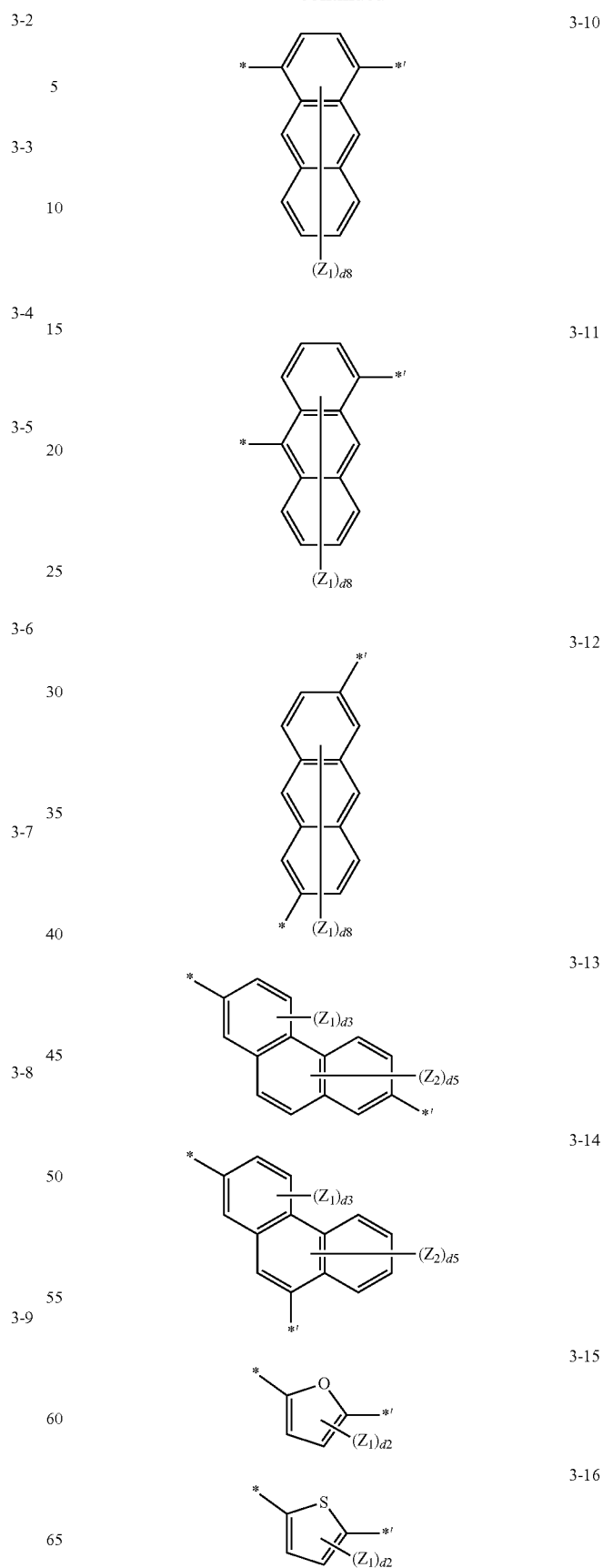

-continued
| | |
|---|---|
| 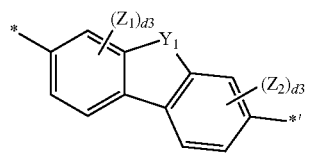 | 3-17 |
| 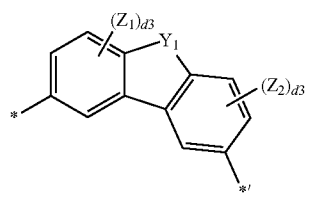 | 3-18 |
| 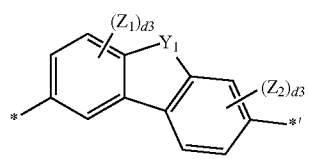 | 3-19 |
| 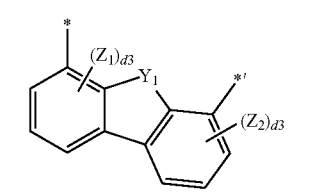 | 3-20 |
| 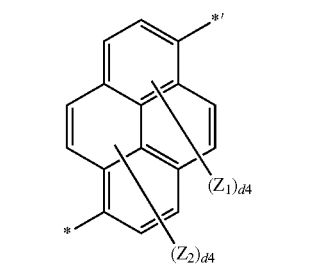 | 3-21 |
| 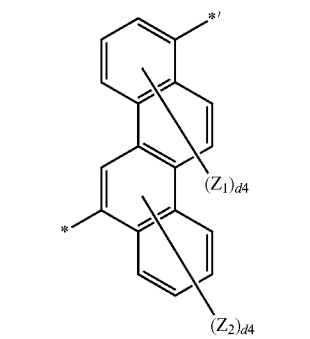 | 3-22 |
| 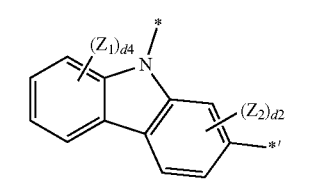 | 3-23 |
-continued
| | |
|---|---|
| 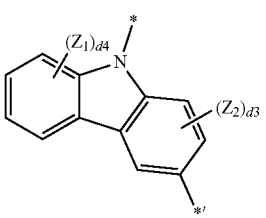 | 3-24 |
| 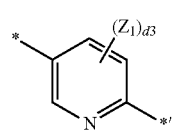 | 3-25 |
| 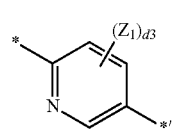 | 3-26 |
| 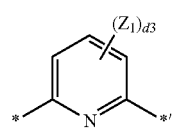 | 3-27 |
| 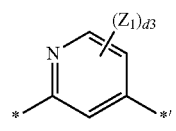 | 3-28 |
| 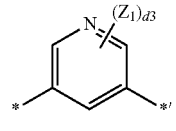 | 3-29 |
| 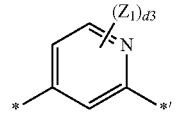 | 3-30 |
| 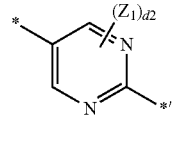 | 3-31 |
| 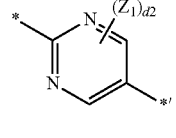 | 3-32 |
| 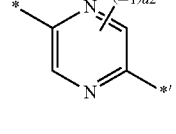 | 3-33 |
| 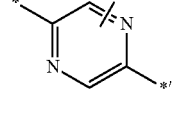 | 3-34 |

-continued
3-35 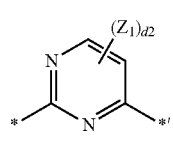
3-36 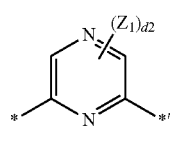
3-37 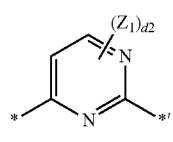
3-38 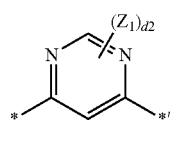
3-39 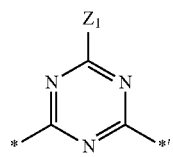
3-40 
3-41 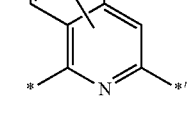
3-42 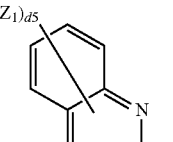
3-43 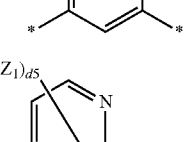
3-44 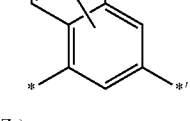
-continued
3-45 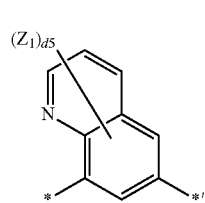
3-46 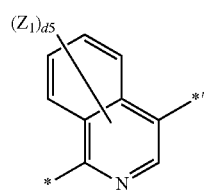
3-47 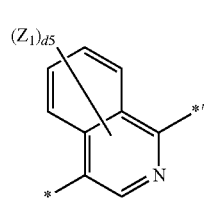
3-48 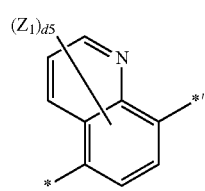
3-49 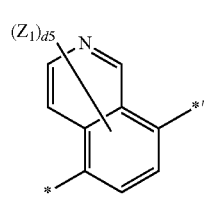
3-50 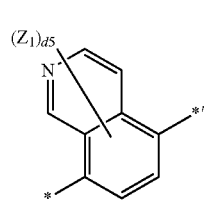
3-51 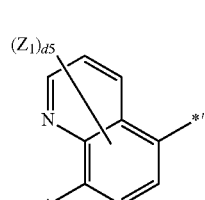
3-52 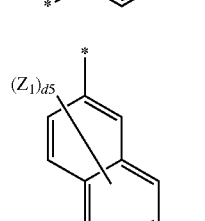

3-53 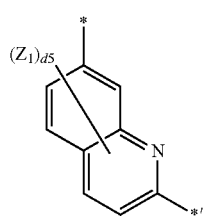
3-54 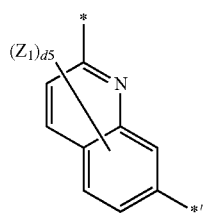
3-55 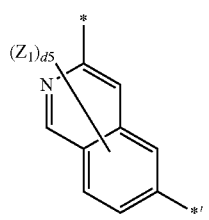
3-56 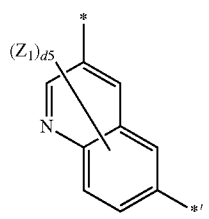
3-57 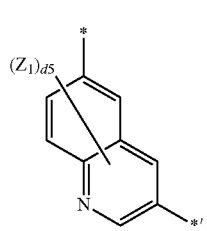
3-58 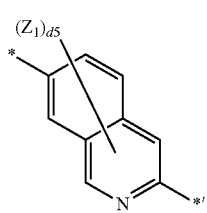
3-59 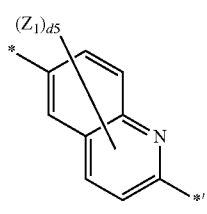
3-60 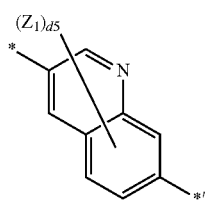
3-61 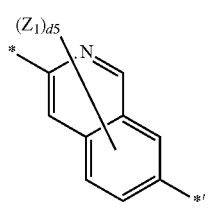
3-62 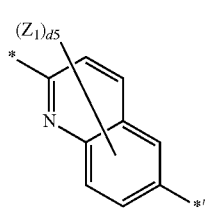
3-63 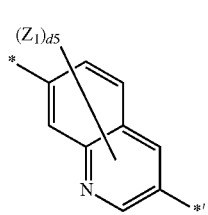
3-64 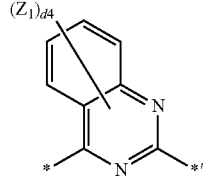
3-65 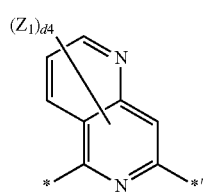
3-66 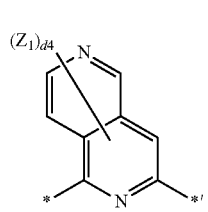
3-67 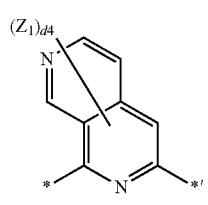

707
-continued
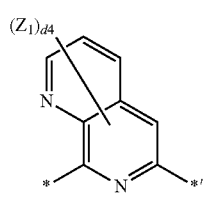
3-68
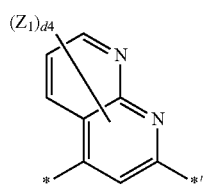
3-69
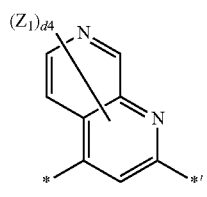
3-70
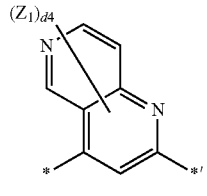
3-71
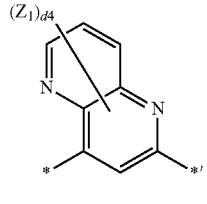
3-72
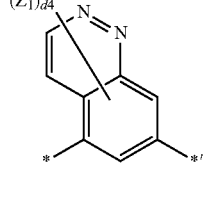
3-73
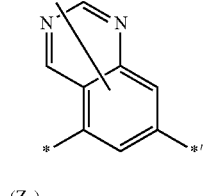
3-74
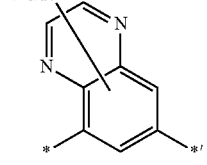
3-75
708
-continued
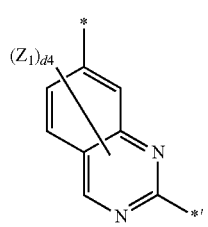
3-76
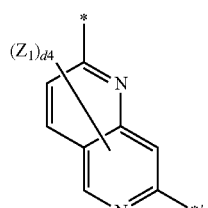
3-77
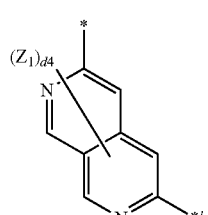
3-78
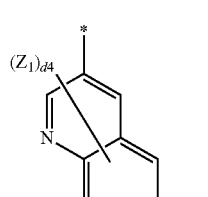
3-79
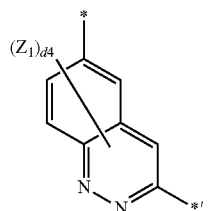
3-80
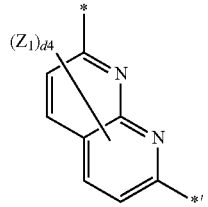
3-81
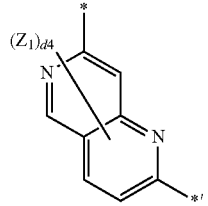
3-82

| | |
|---|---|
| 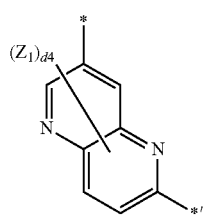 3-83 | 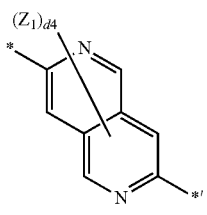 3-90 |
| 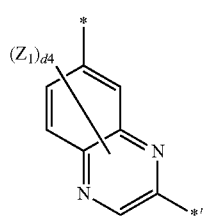 3-84 | 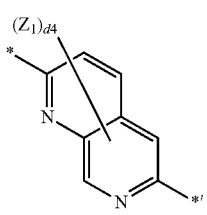 3-91 |
| 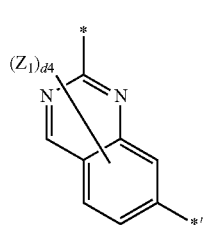 3-85 | 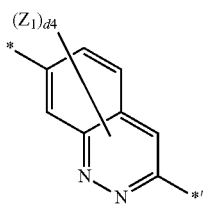 3-92 |
| 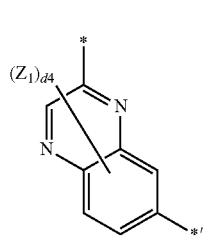 3-86 | 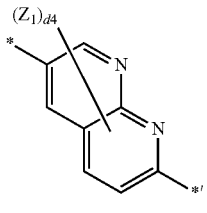 3-93 |
| 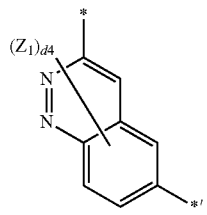 3-87 | 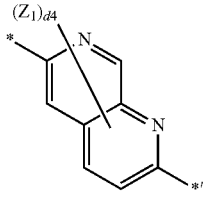 3-94 |
| 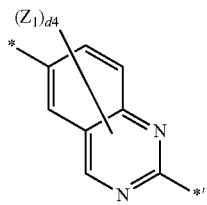 3-88 | 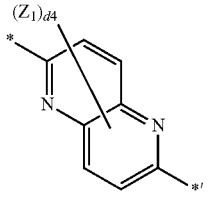 3-95 |
| 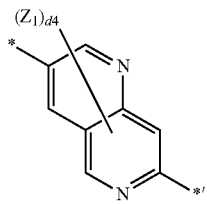 3-89 | 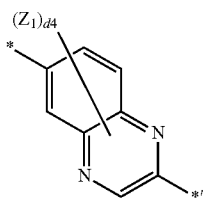 3-96 |

-continued

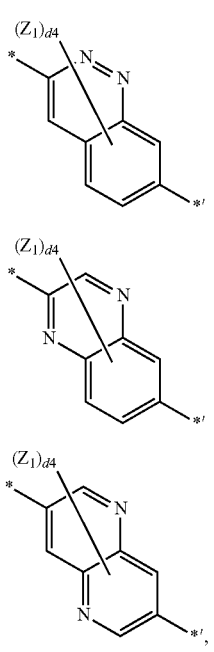

3-97


3-98


3-99 wherein, in Formulae 3-1 to 3-99, $Y_1$ is O, S, $C(Z_3)(Z_4)$, $N(Z_5)$, or $Si(Z_6)(Z_7)$, $Z_1$ to $Z_7$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, —$Si(Q_{31})(Q_{32})(Q_{33})$, —$N(Q_{31})(Q_{32})$, —$B(Q_{31})(Q_{32})$, —$C(\!\!=\!\!O)(Q_{31})$, —$S(\!\!=\!\!O)_2(Q_{31})$, and —$P(\!\!=\!\!O)(Q_{31})(Q_{32})$, $Q_{31}$ to $Q_{33}$ are each independently selected from:
a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group; and
a phenyl group, a biphenyl group, a terphenyl group, a naphthyl group, a pyridinyl group, a pyrimidinyl group, a pyrazinyl group, a quinolinyl group, an isoquinolinyl group, a quinoxalinyl group, and a quinazolinyl group, each substituted with at least one selected from a $C_1$-$C_{10}$ alkyl group, a $C_1$-$C_{10}$ alkoxy group, and a phenyl group, d2 is an integer selected from 0 to 2,
d3 is an integer selected from 0 to 3,
d4 is an integer selected from 0 to 4,
d5 is an integer selected from 0 to 5,
d6 is an integer selected from 0 to 6,
d8 is an integer selected from 0 to 8, and
*' and *'' are each a binding site to a neighboring atom.

13. The heterocyclic compound of claim 9, wherein $L_3$ is a group represented by one of Formulae 4-1 to 4-3:

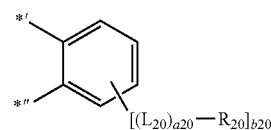

4-1

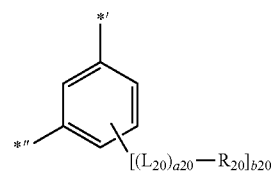

4-2

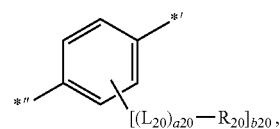

4-3 wherein, in Formulae 4-1 to 4-3,
$L_{20}$, a20, $R_{20}$, and b20 are as defined in Formula 3,
*' and *'' are each a binding site to a neighboring atom.

14. The heterocyclic compound of claim 9, wherein $Ar_1$ and $Ar_2$ are each independently selected from deuterium and a group represented by one selected from Formulae 5-1 to 5-26 and Formulae 6-1 to 6-55:

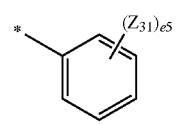

5-1

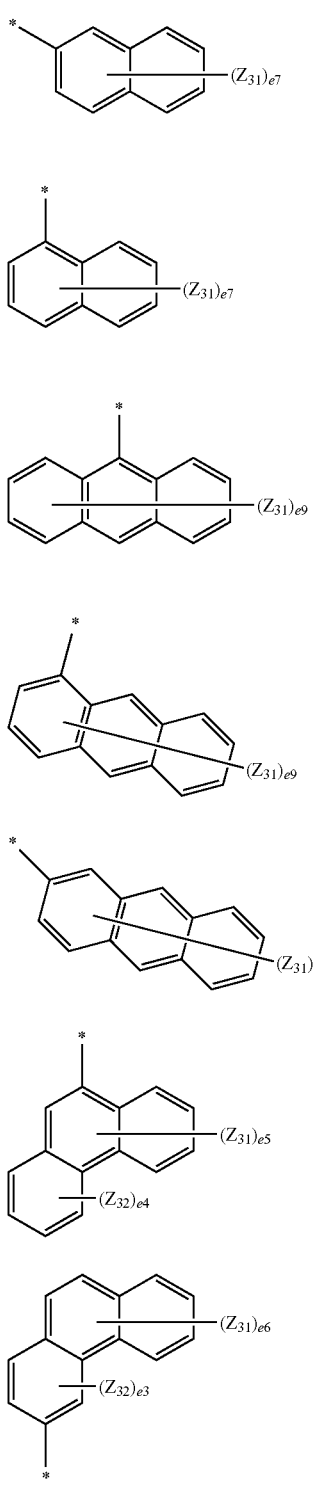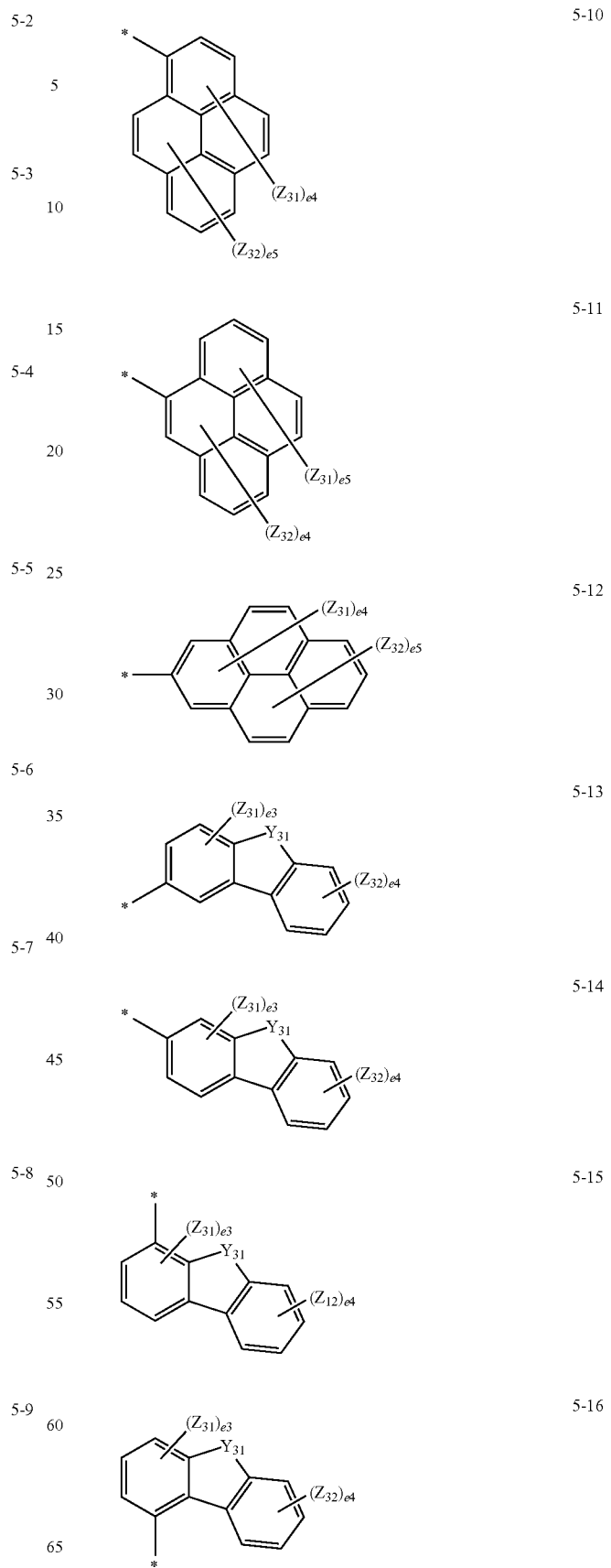

| 715 -continued | | 716 -continued | |
|---|---|---|---|
| 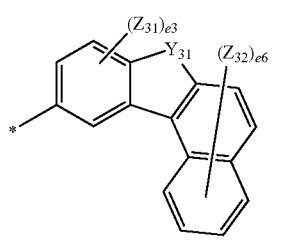 |  | 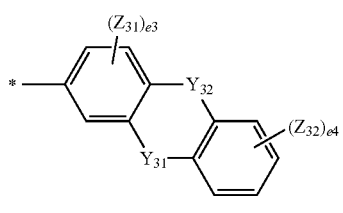 | 5-24 |
|  | 5-17 |  |  |
| 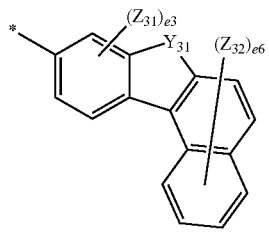 | 5-18 | 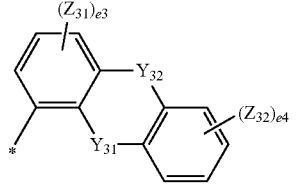 | 5-25 |
| 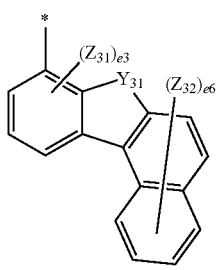 | 5-19 | 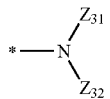 | 5-26 |
| 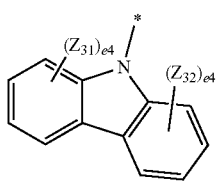 |  | 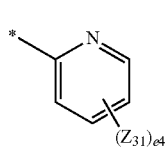 | 6-1 |
| 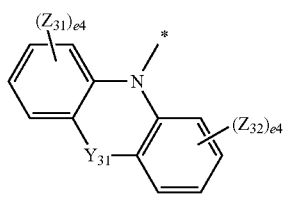 | 5-20 | 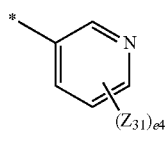 | 6-2 |
|  | 5-21 |  | 6-3 |
| 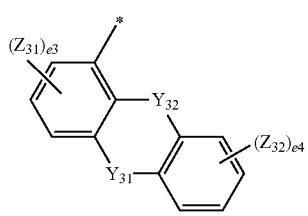 | 5-22 | 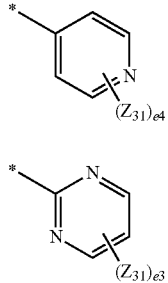 | 6-4 |
|  |  |  | 6-5 |
| 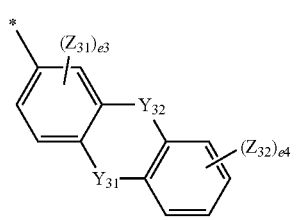 | 5-23 | 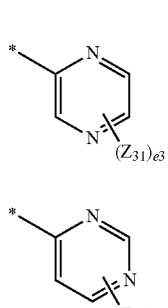 | 6-6 |
|  |  | 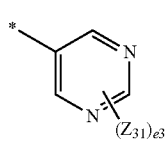 | 6-7 |

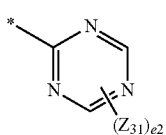
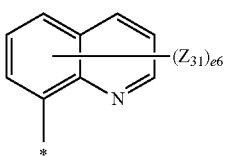
6-8
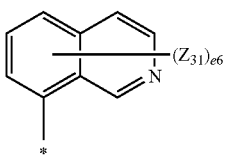
6-9

6-10
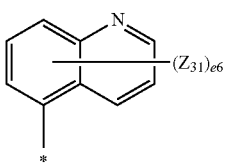
6-11
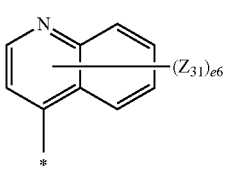
6-12
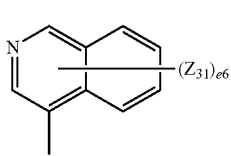
6-13

6-14
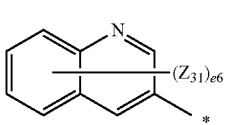
6-15
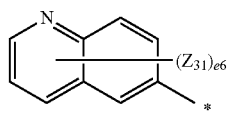
6-16
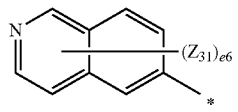
6-17
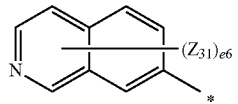
6-18
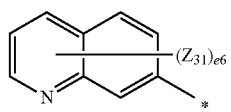
6-19
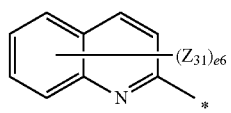
6-20
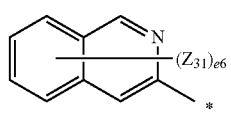
6-21
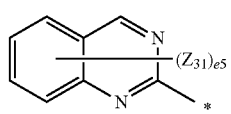
6-22
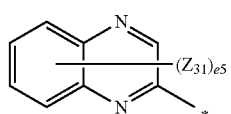
6-23
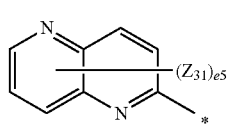
6-24
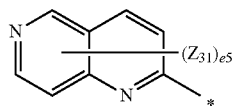
6-25
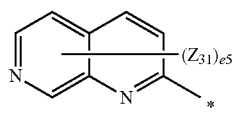
6-26
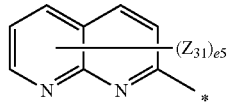
6-27
6-28

| | | | |
|---|---|---|---|
| 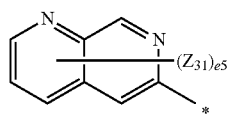 | 6-29 | 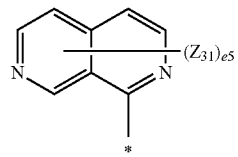 | 6-40 |
| 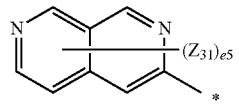 | 6-30 | 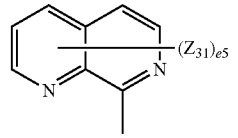 | 6-41 |
| 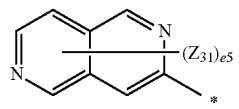 | 6-31 | 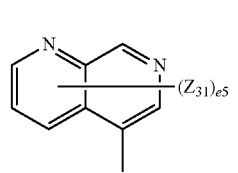 | 6-42 |
| 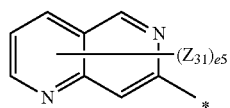 | 6-32 | 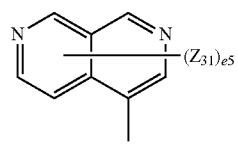 | 6-43 |
| 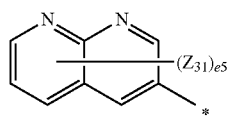 | 6-33 | 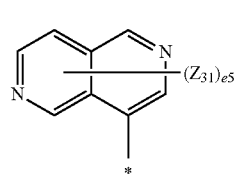 | 6-44 |
| 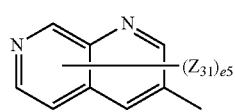 | 6-34 | 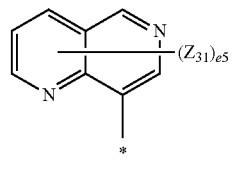 | 6-45 |
| 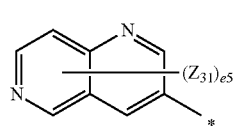 | 6-35 | 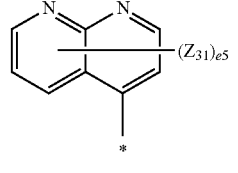 | 6-46 |
| 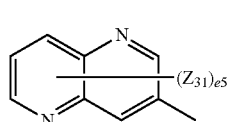 | 6-36 | 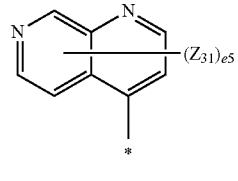 | 6-47 |
| 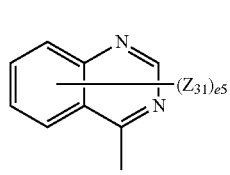 | 6-37 | 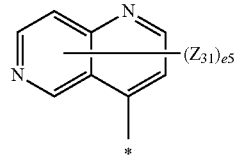 | 6-48 |
| 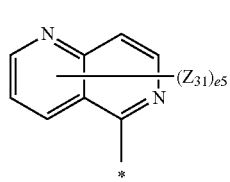 | 6-38 | | |
| 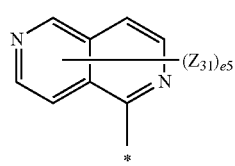 | 6-39 | | |

-continued

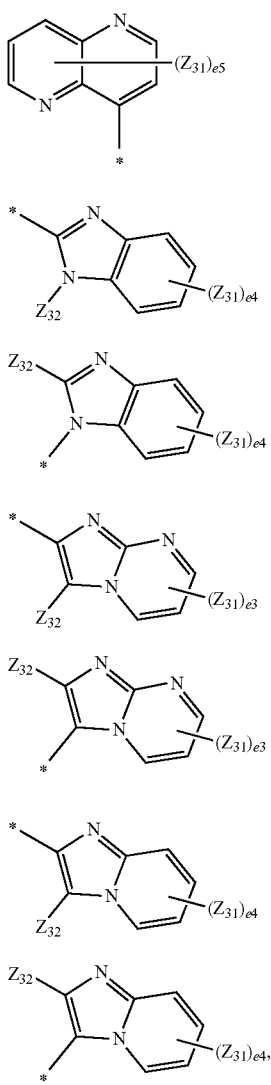

wherein, in Formulae 5-1 to 5-26 and Formulae 6-1 to 6-55, $Y_{31}$ and $Y_{32}$ are each independently O, S, $C(Z_{33})(Z_{34})$, $N(Z_{33})$, or $Si(Z_{33})(Z_{34})$, $Z_{31}$ to $Z_{34}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkenyl group, a $C_1$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a phenanthrenyl group, an anthracenyl group, a triperylenyl group, a pyridinyl group, a pyrimidinyl group, a carbazolyl group, and a triazinyl group, e2 is 1 or 2,
e3 is an integer selected from 1 to 3,
e4 is an integer selected from 1 to 4,
e5 is an integer selected from 1 to 5,
e6 is an integer selected from 1 to 6,
e7 is an integer selected from 1 to 7,
e9 is an integer selected from 1 to 9, and
* is a binding site to a neighboring atom.

15. The heterocyclic compound of claim 9, wherein $Ar_1$ and $Ar_2$ are each independently selected from:
a phenyl group, a naphthyl group, a pyridyl group, a pyrimidyl group, a triazinyl group, a quinolinyl group, an isoquinolinyl group, a biphenyl group, and a terphenyl group; and
a phenyl group, a naphthyl group, a pyridyl group, a pyrimidyl group, a triazinyl group, a quinolinyl group, an isoquinolinyl group, a biphenyl group, and a terphenyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group.

16. The heterocyclic compound of claim 9, wherein $R_{10}$ and $R_{20}$ are each independently selected from:
a methyl group, an ethyl group, a propyl group, an isobutyl group, a sec-butyl group, a tert-butyl group, a pentyl group, an iso-amyl group, and a hexyl group; and
a methyl group, an ethyl group, a propyl group, an isobutyl group, a sec-butyl group, a tert-butyl group, a pentyl group, an iso-amyl group, and a hexyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group;
a phenyl group, a naphthyl group, a pyridyl group, a pyrimidyl group, a triazinyl group, a quinolinyl group, an isoquinolinyl group, a biphenyl group, and a terphenyl group; and
a phenyl group, a naphthyl group, a pyridyl group, a pyrimidyl group, a triazinyl group, a quinolinyl group, an isoquinolinyl group, a biphenyl group, and a terphenyl group, each substituted with at least one selected from deuterium, —F, —Cl, —Br, —I, a hydroxyl group, a cyano group, a nitro group, an amino group, a $C_1$-$C_{60}$ alkyl group, a $C_6$-$C_{60}$ aryl group, and a $C_2$-$C_{60}$ heteroaryl group.

17. The heterocyclic compound of claim 9, wherein a10 and a20 are each 0, and
$R_{10}$ and $R_{20}$ are each hydrogen.

18. The heterocyclic compound of claim 9, wherein the heterocyclic compound is a compound represented by one of Formulae 11-1 to 11-3:

Formula 11-1

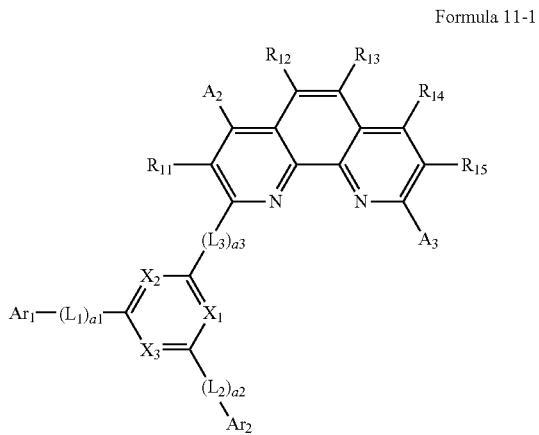

Formula 11-2
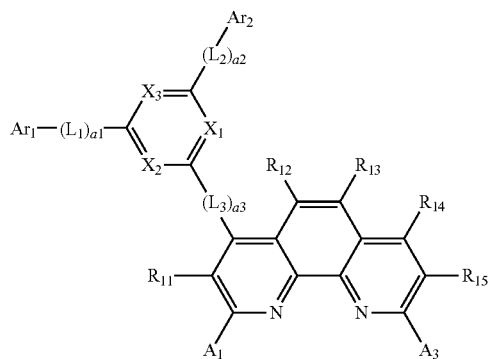
Formula 11-3
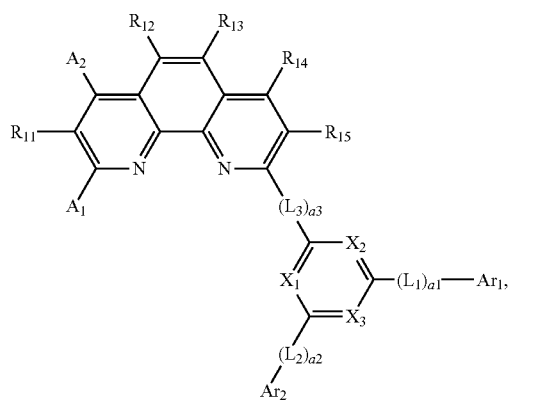
wherein, in Formulae 11-1 to 11-3,
X₁ to X₃, L₁ to L₃, a1 to a3, A₁ to A₃, Ar₁, and Ar₂ are as defined in Formulae 1 and 2, and
R₁₁ to R₁₅ are each defined the same as R₁₀ in Formula 1.
19. The heterocyclic compound of claim 9, wherein the heterocyclic compound is a compound represented by one of Formulae 12-1 to 12-12:
12-1
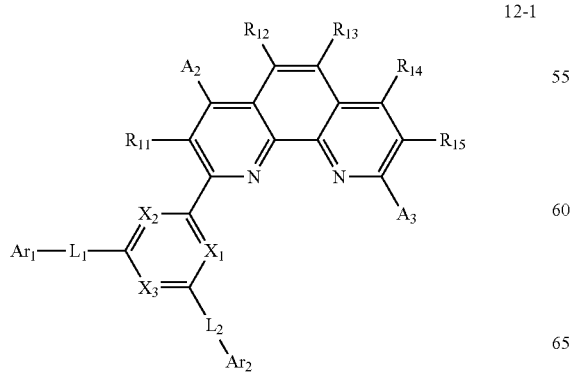
12-2
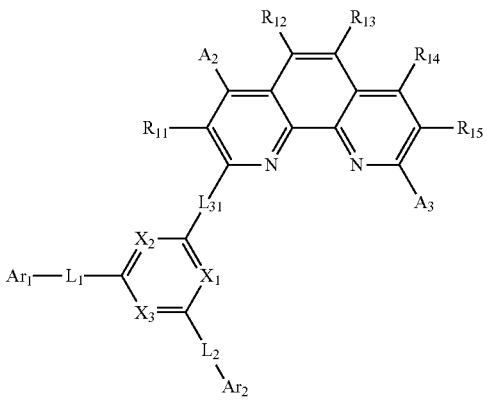
12-3
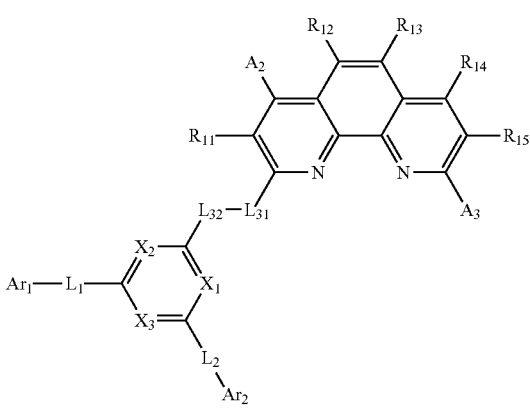
12-4
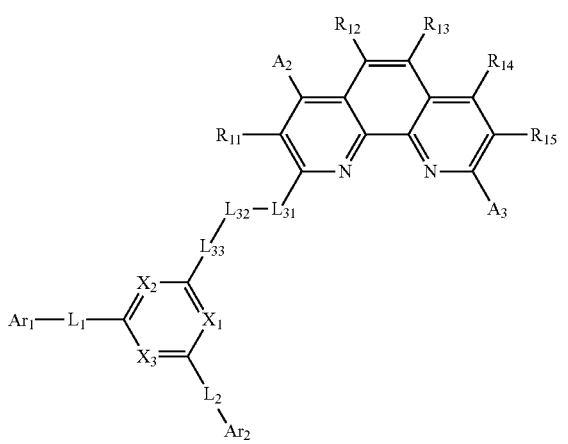
12-5
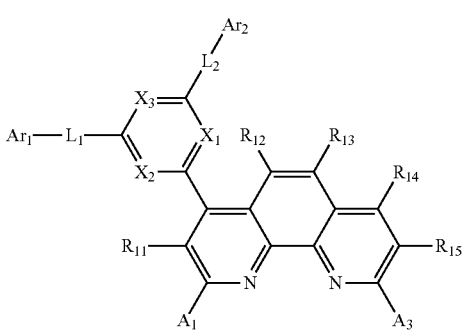

12-6
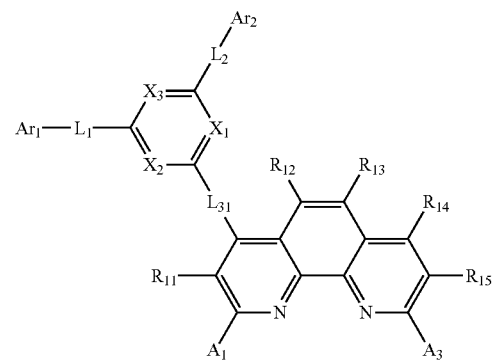
12-7
12-8
12-9
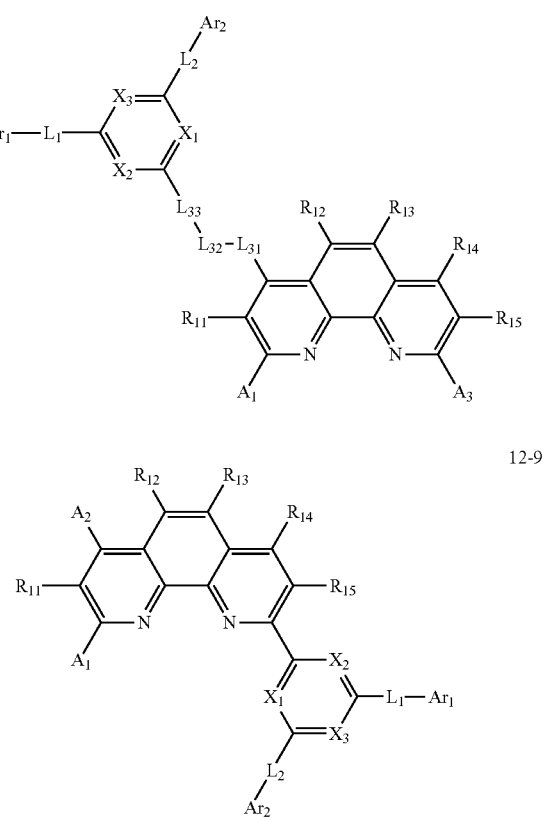
12-10
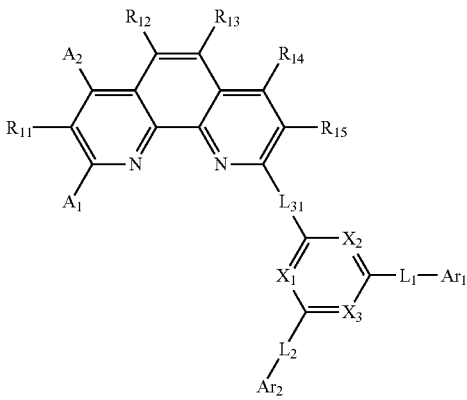
12-11
12-12
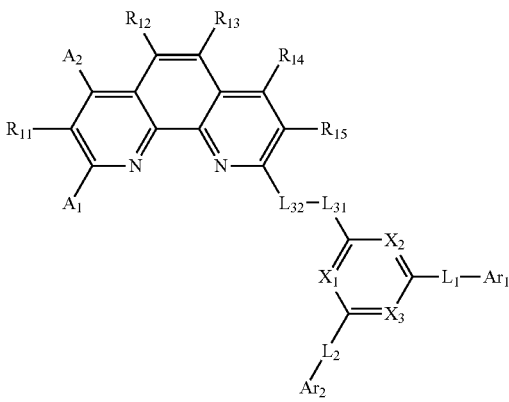
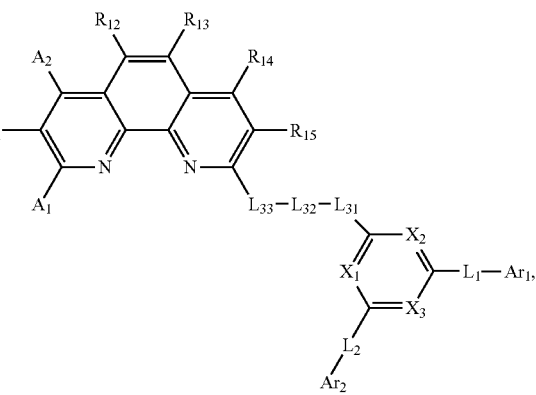
wherein, in Formulae 12-1 to 12-12,
$X_1$ to $X_3$, $L_1$, $L_2$, $A_1$ to $A_3$, $Ar_1$, and $Ar_2$ are as defined in Formulae 1 and 2,
$L_{31}$ to $L_{33}$ are each defined the same as $L_3$ in Formula 2, and
$R_{11}$ to $R_{15}$ are each defined the same as $R_{10}$ in Formula 1.
20. The heterocyclic compound of claim 9, wherein the heterocyclic compound is selected from Compounds 1 to 1272 below:

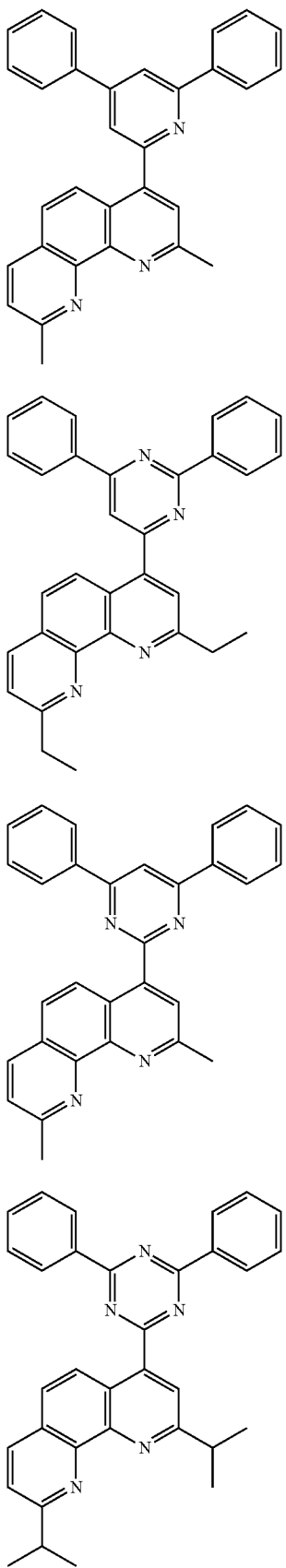
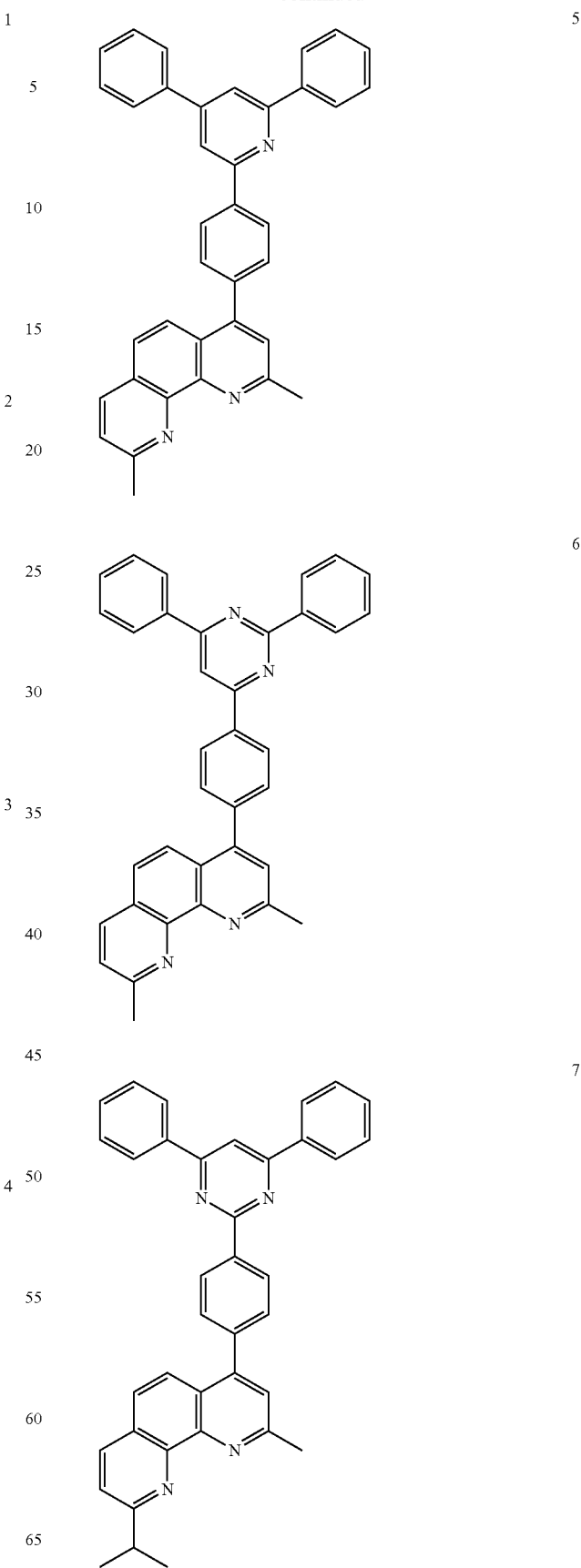

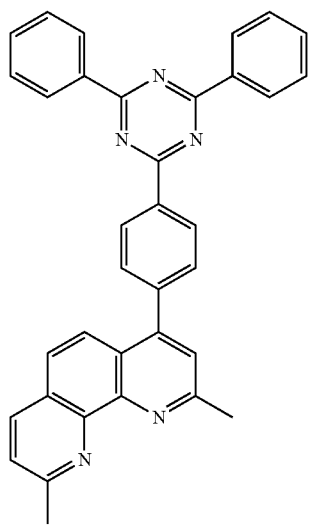
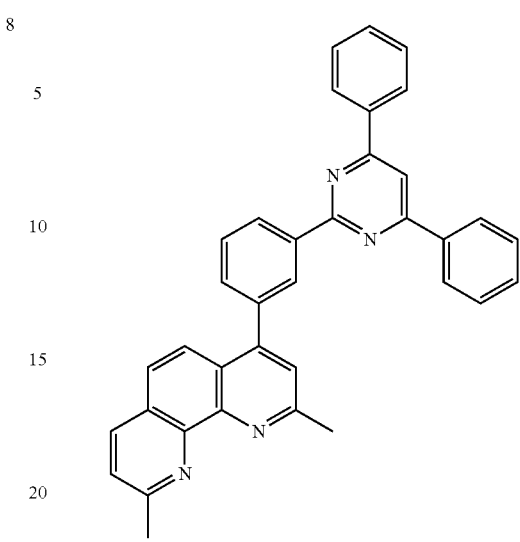
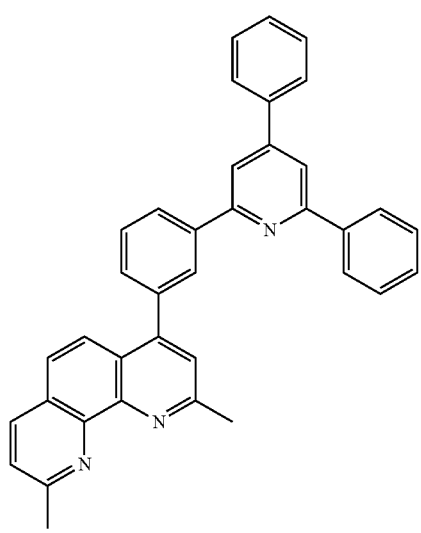
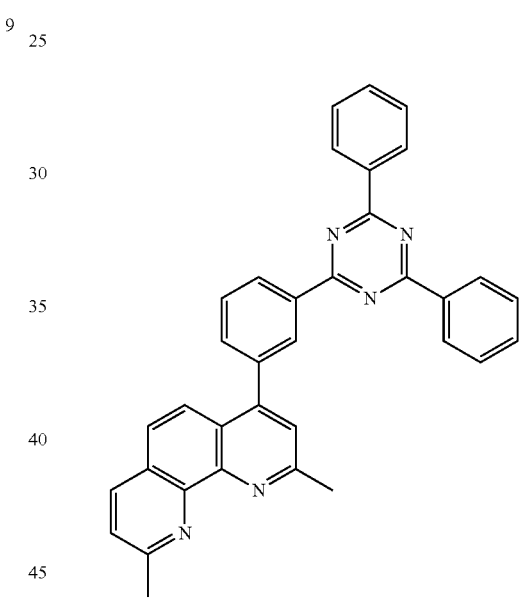
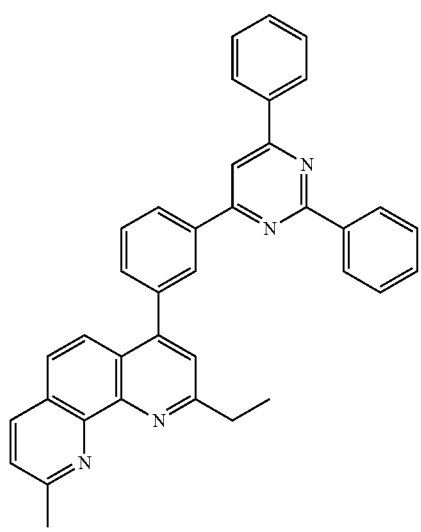
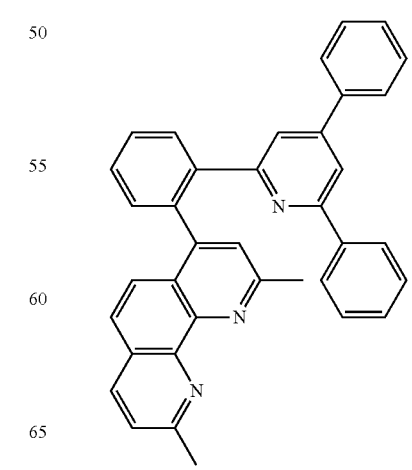

731
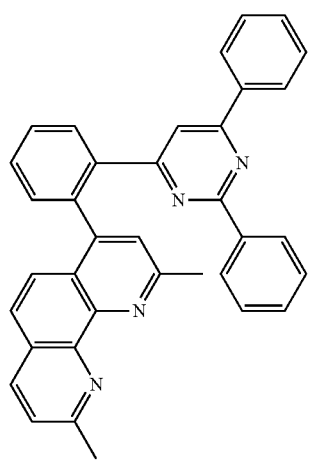
14
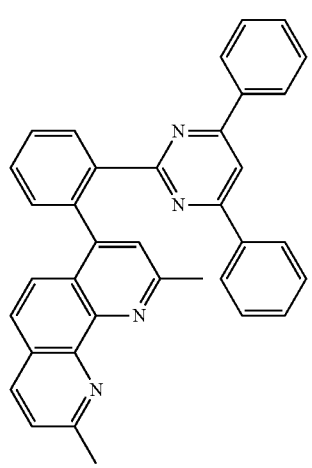
15
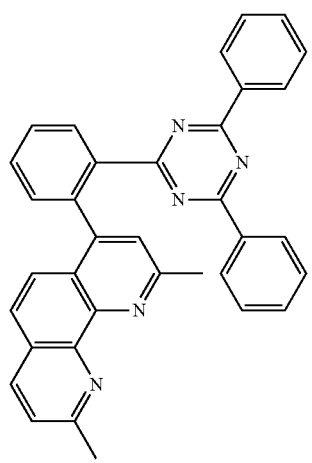
16
732
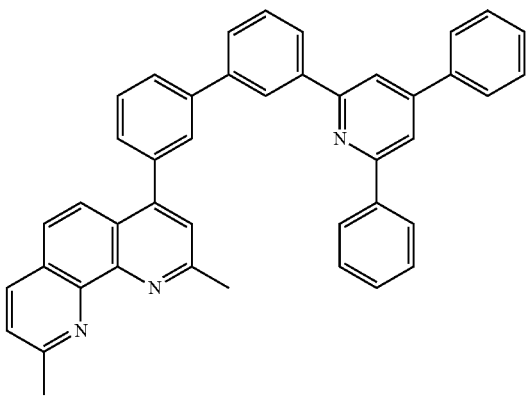
17
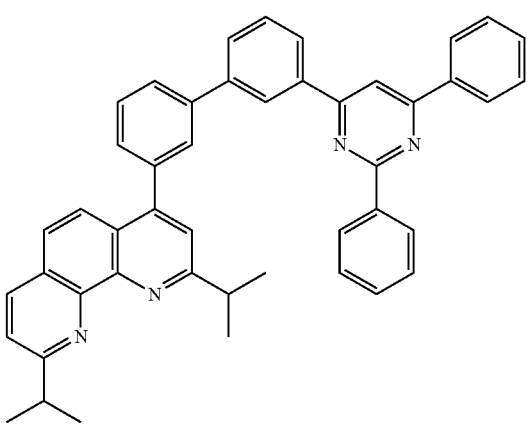
18
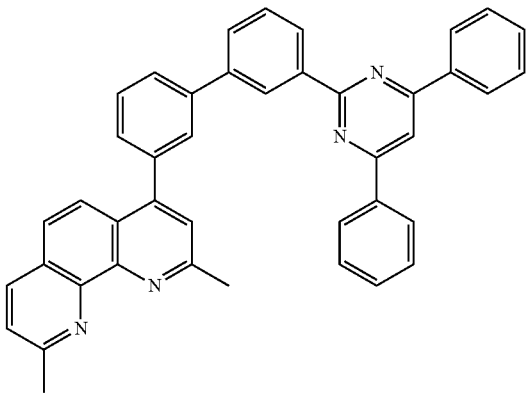
19

20
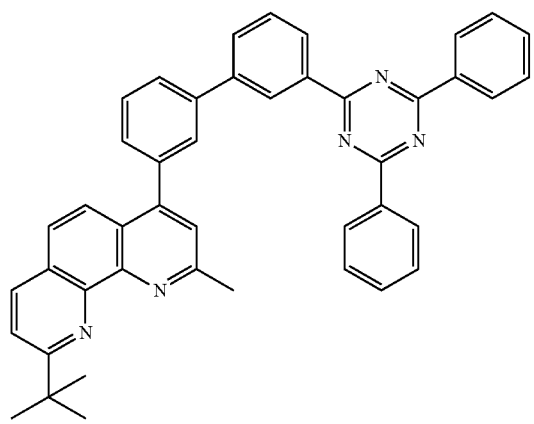
21
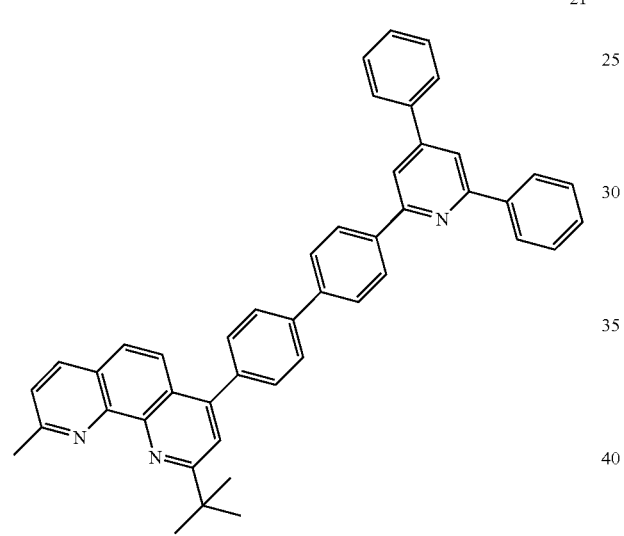
22
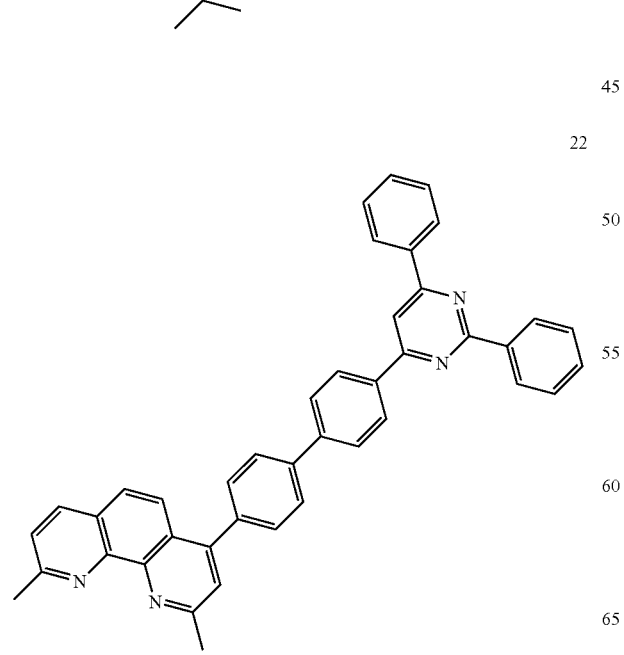
23
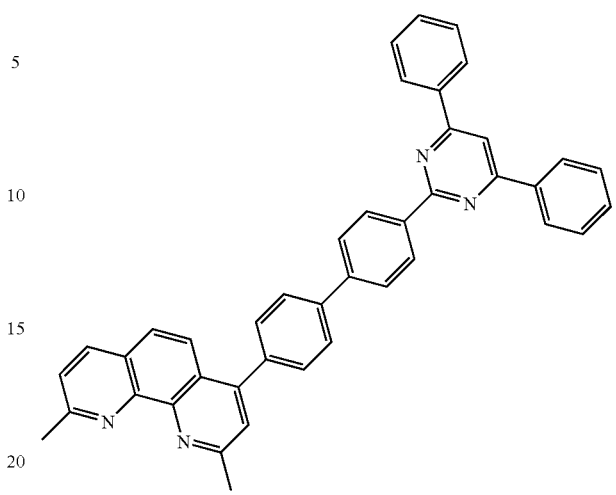
24
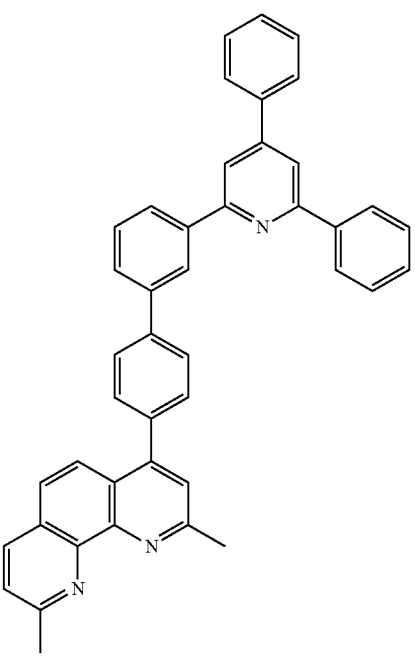
25

735
-continued
26
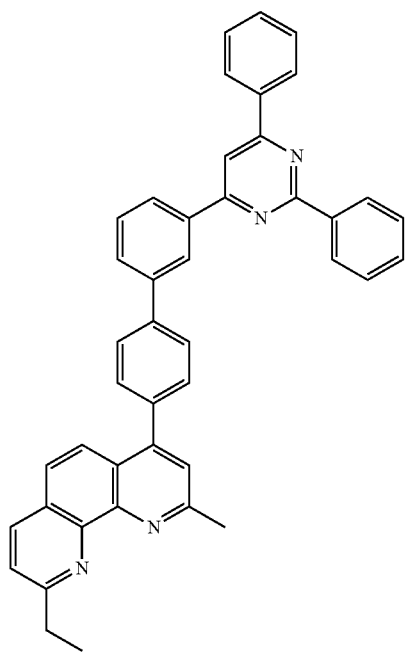
27
736
-continued
28
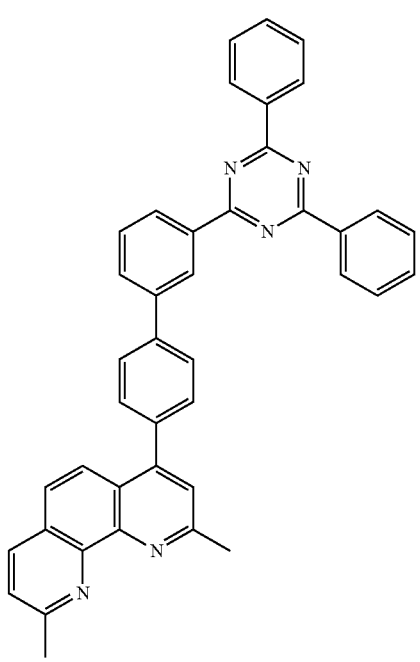
29
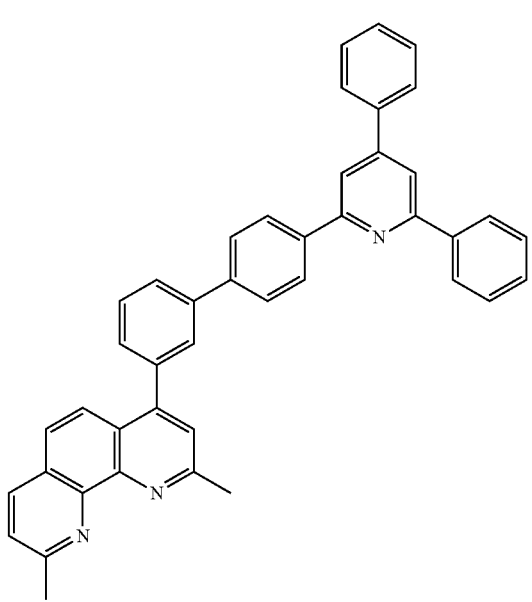

737
-continued
30
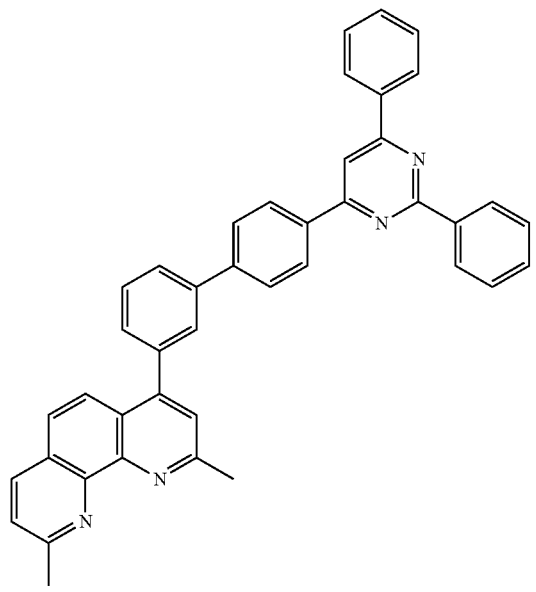
31
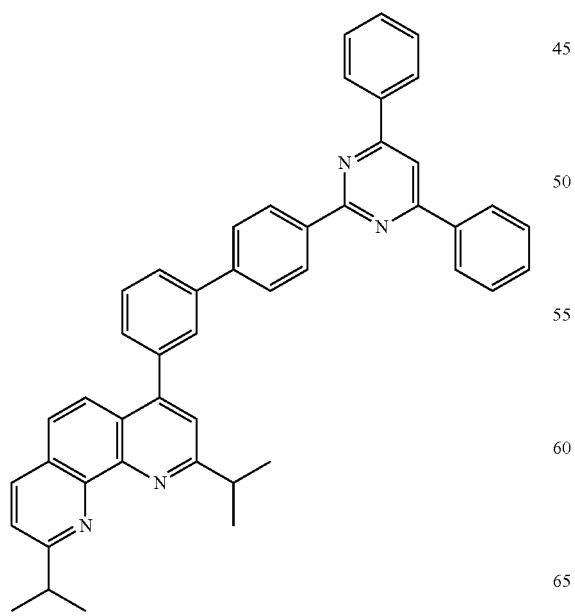
738
-continued
32
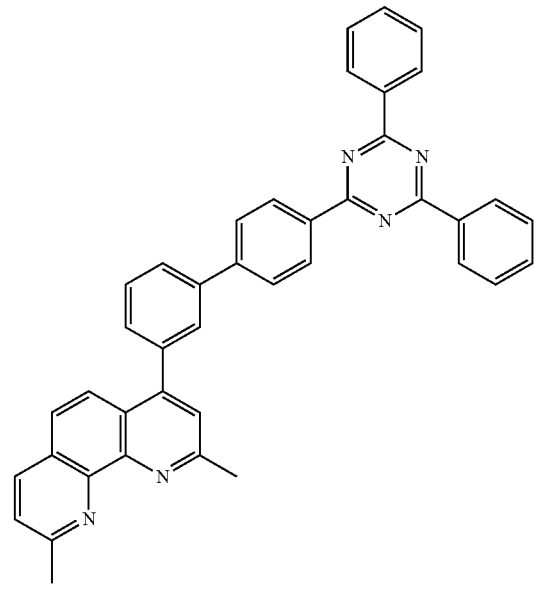
33
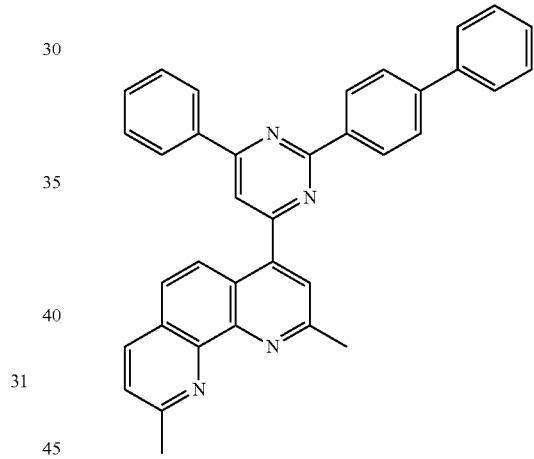
34
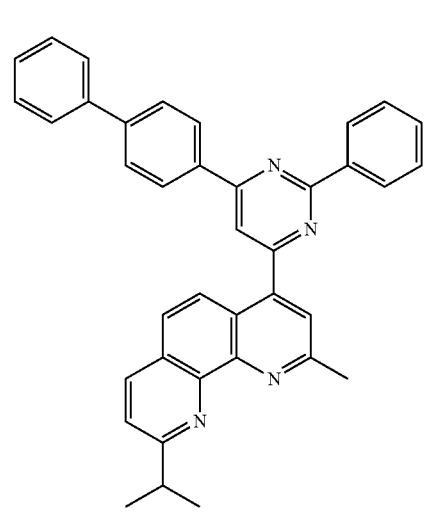

35
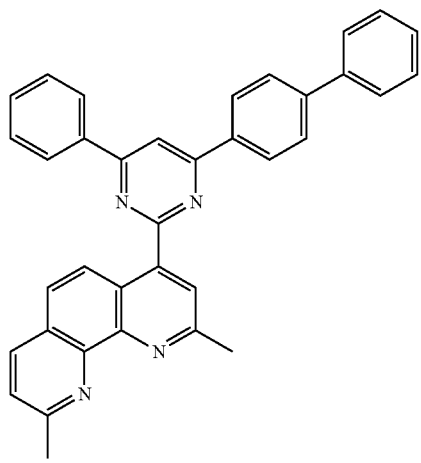
36
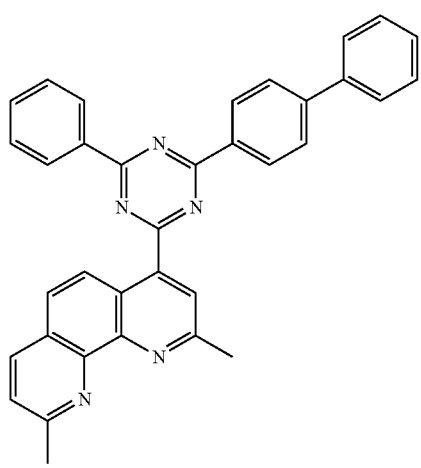
37
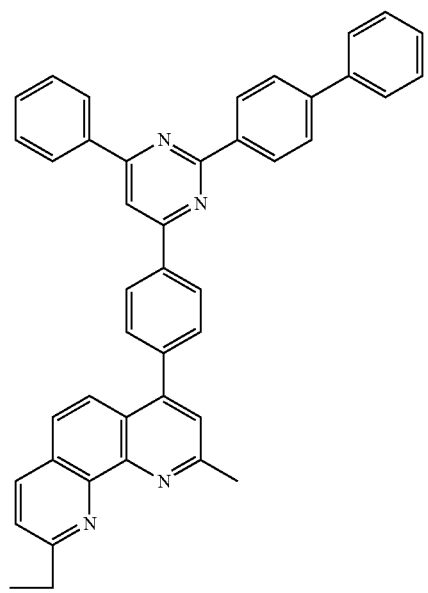
38
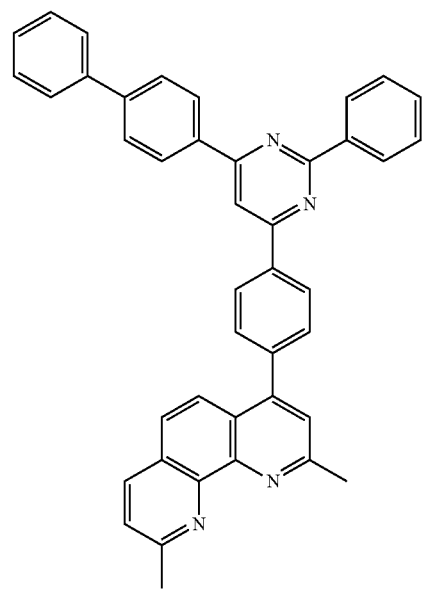
39
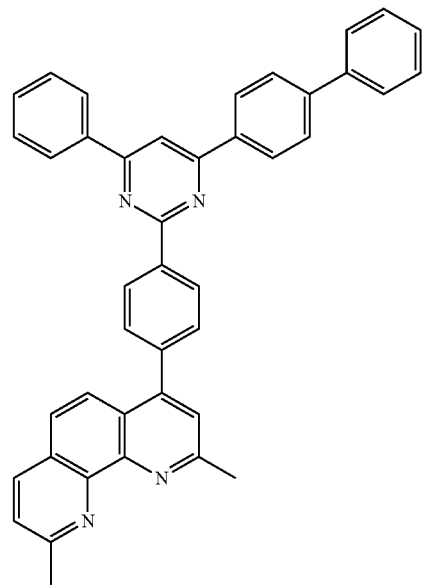

741
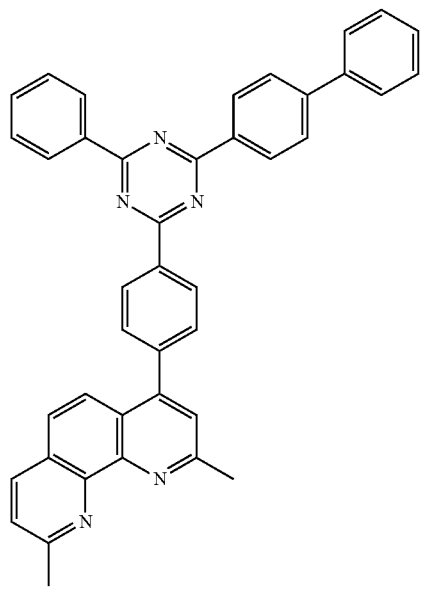
40
742
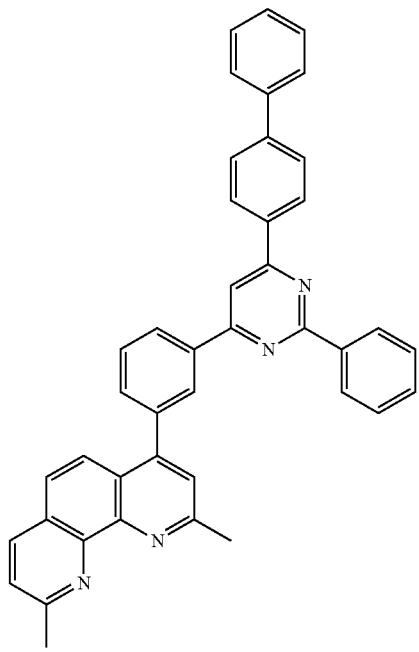
42
41
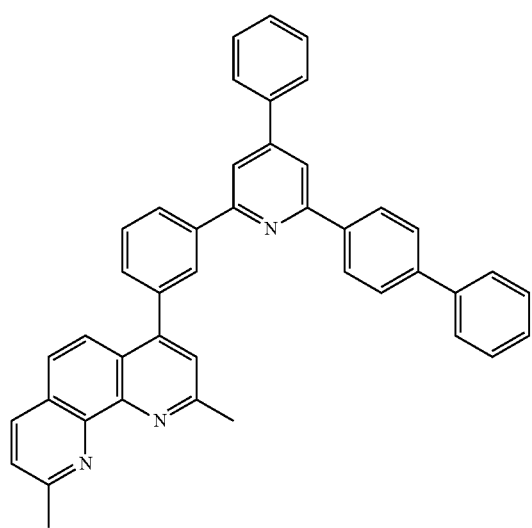
43
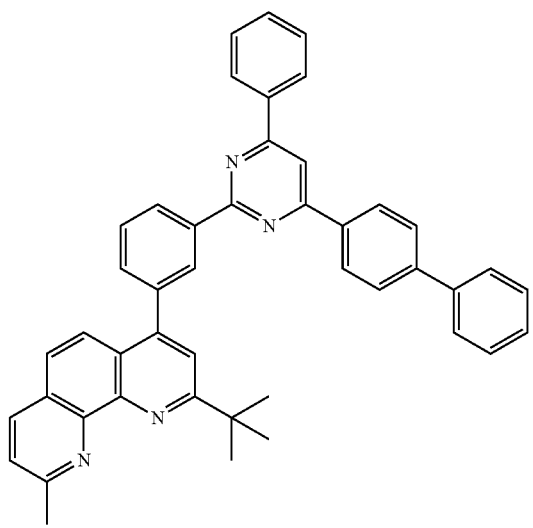

743
44
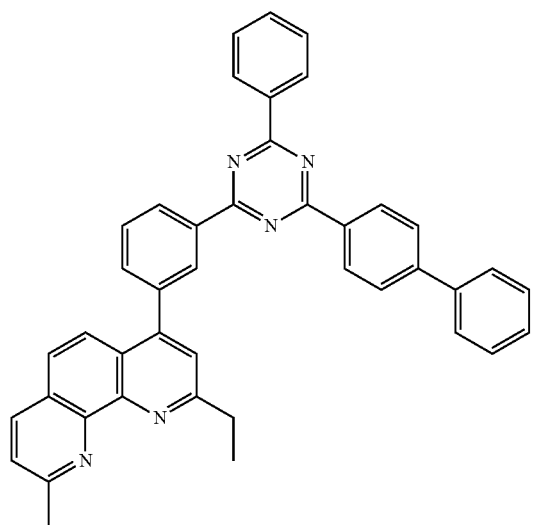
45
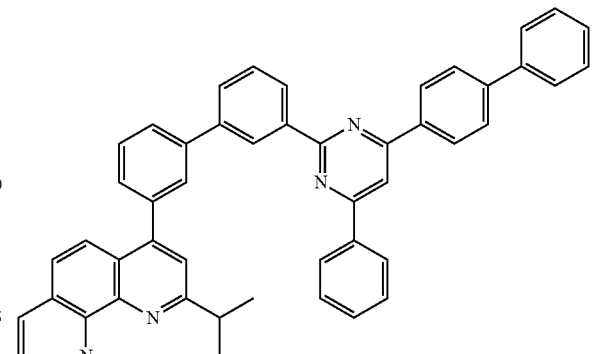
46
744
47
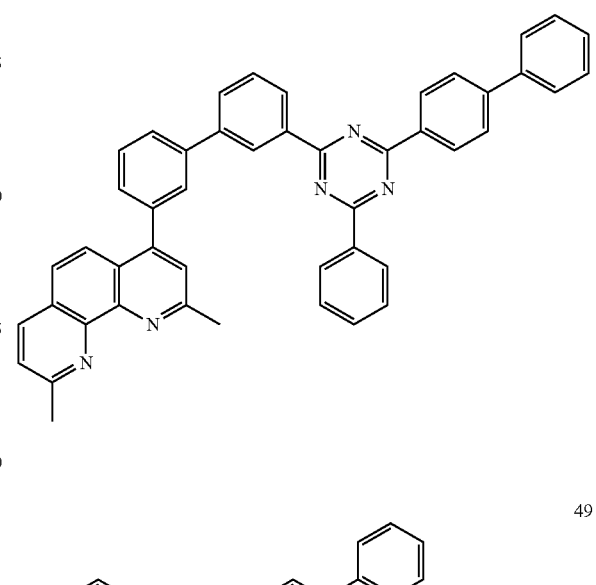
48
49
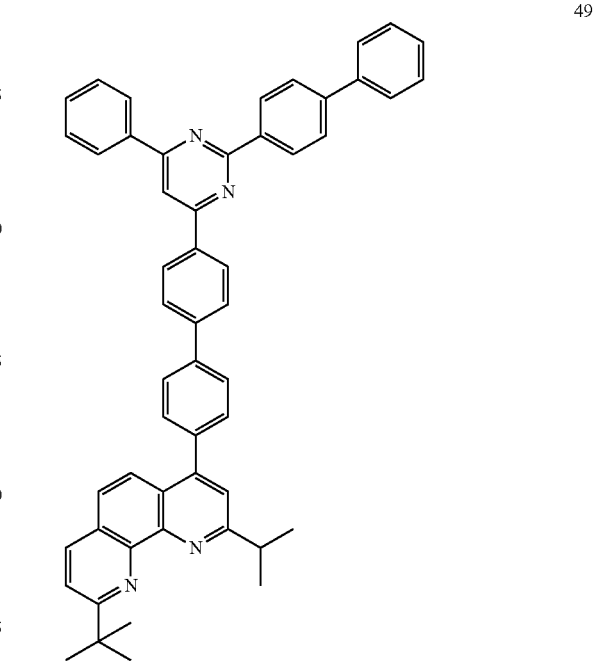

745
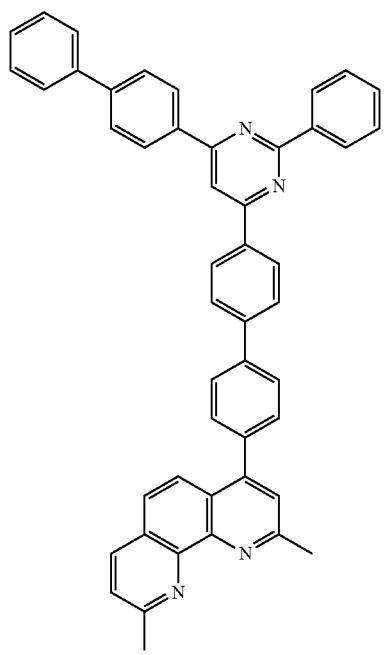
746
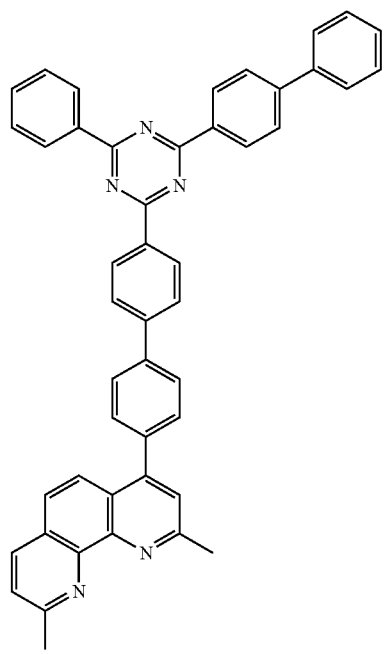
51
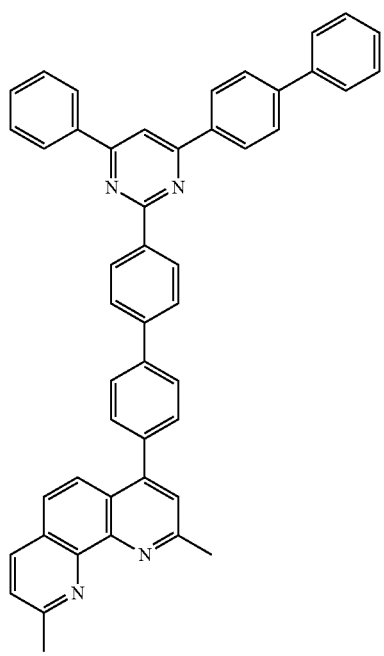
53
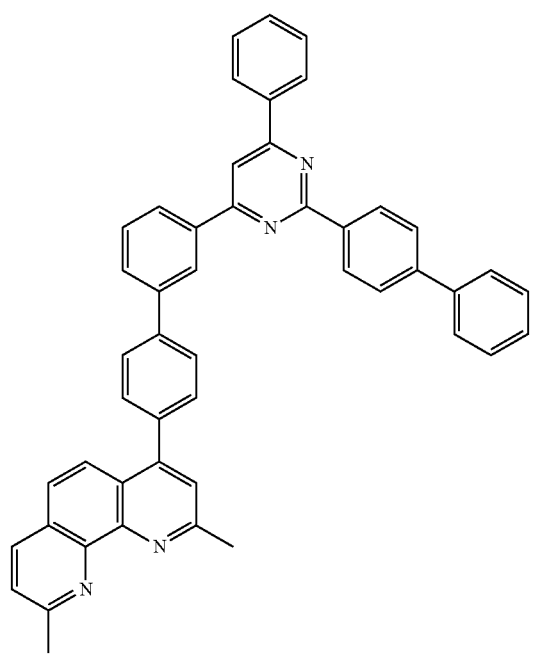

747
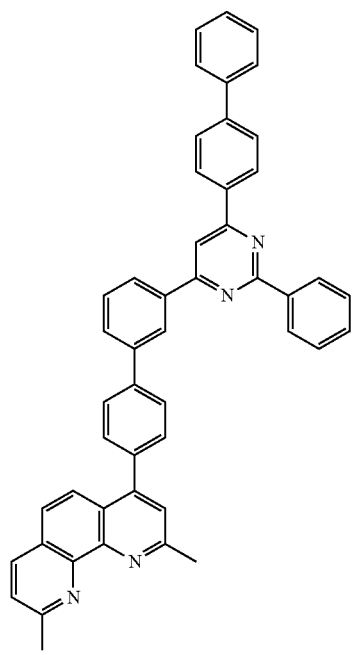
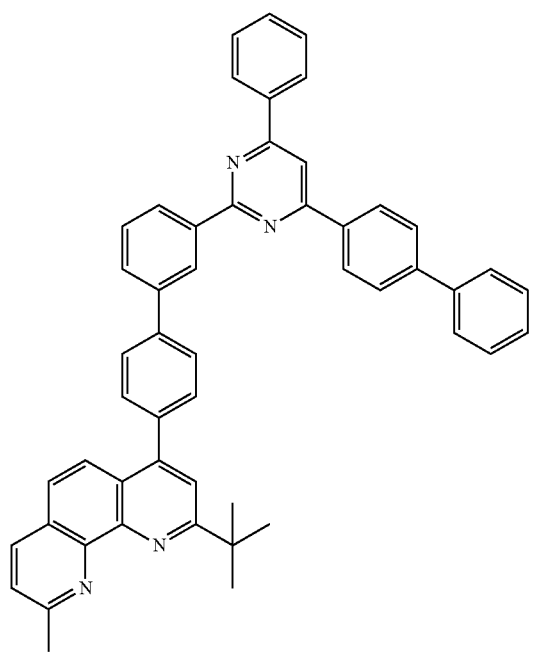
748
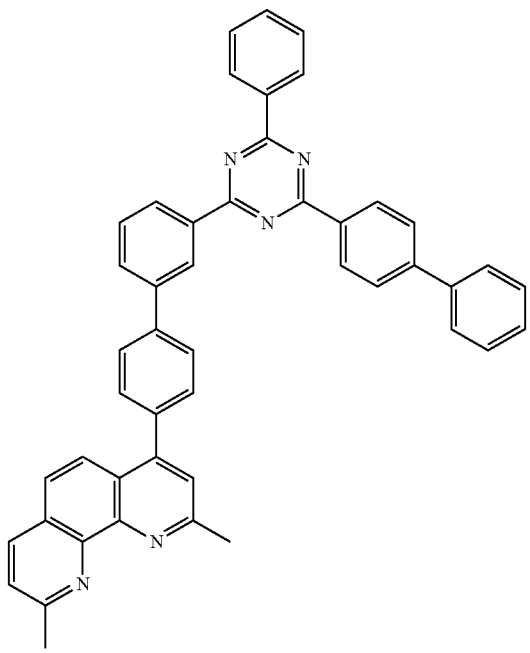
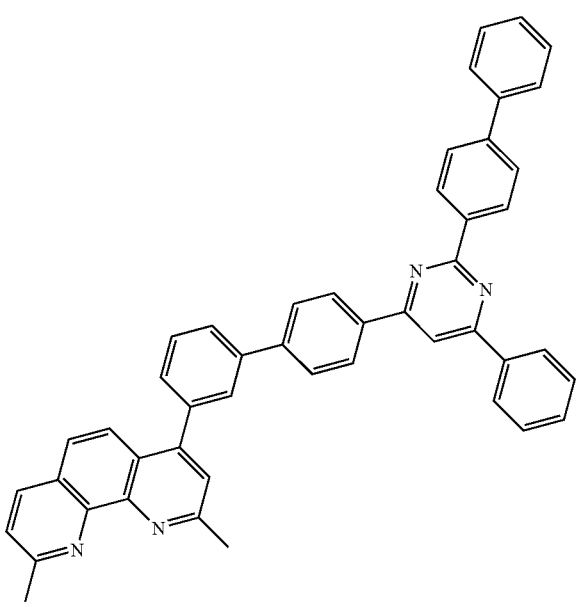

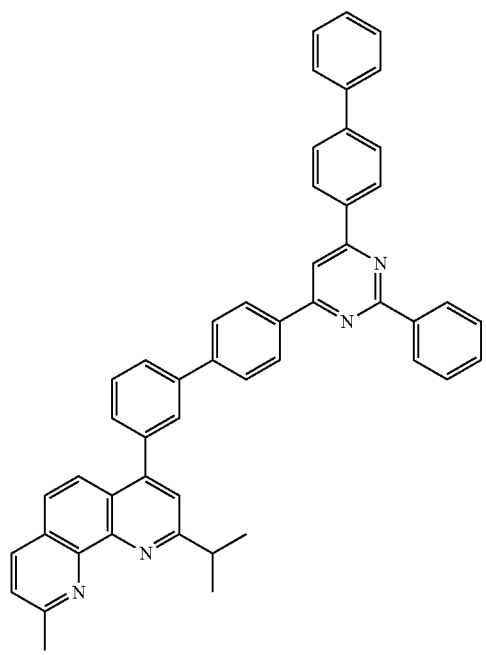
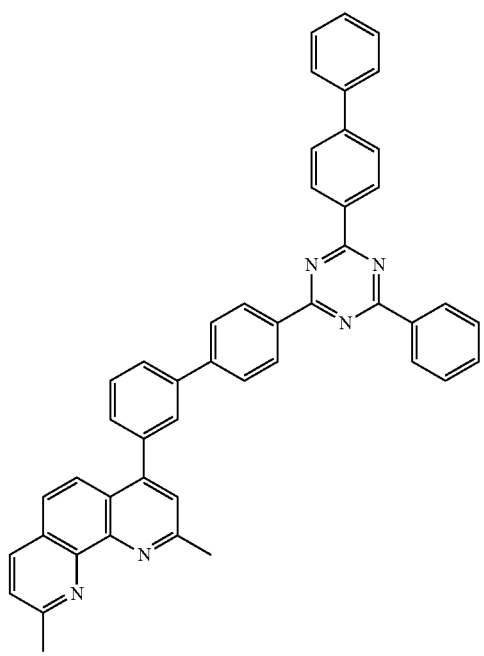

751
63
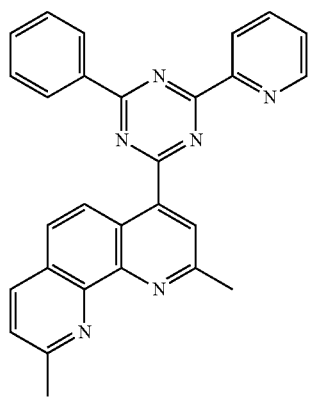
64
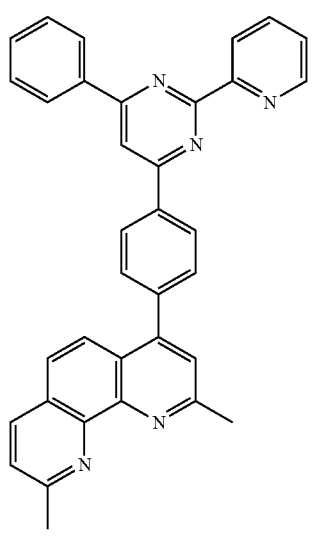
65
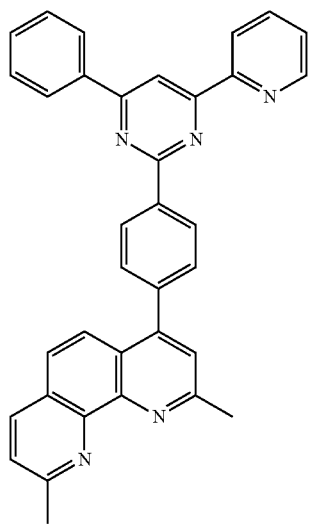
752
66
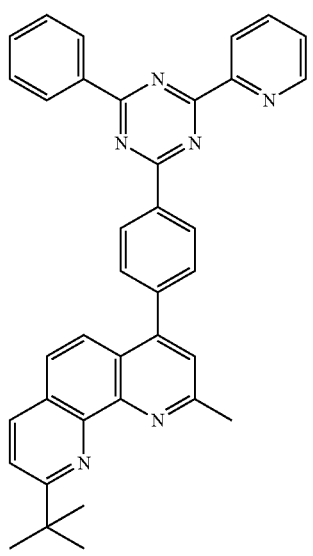
67
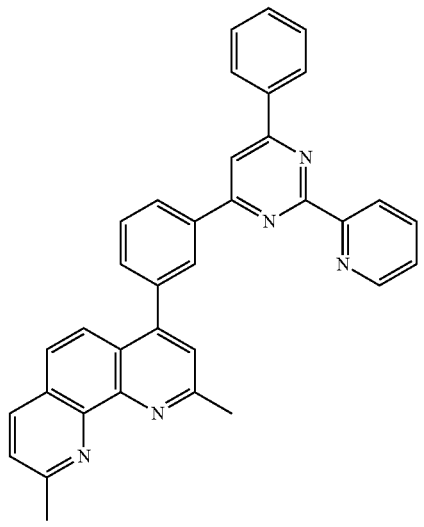
68
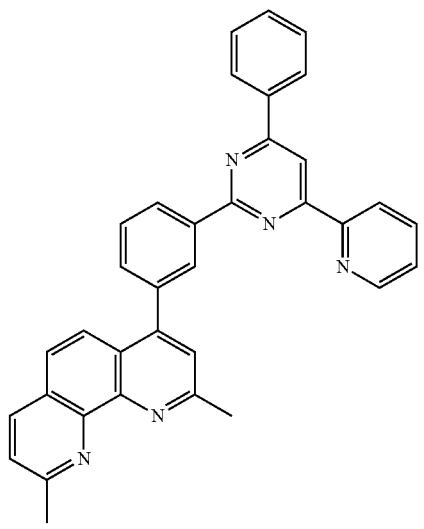

753
-continued
69
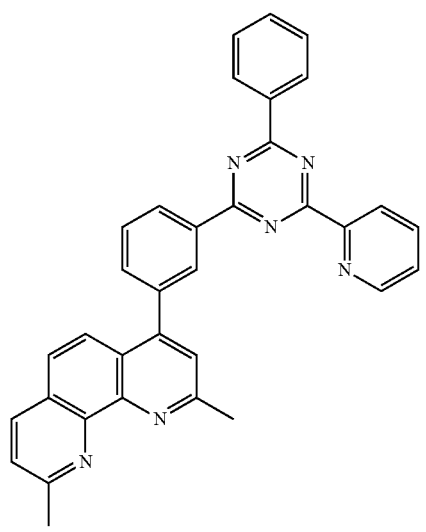
70

71
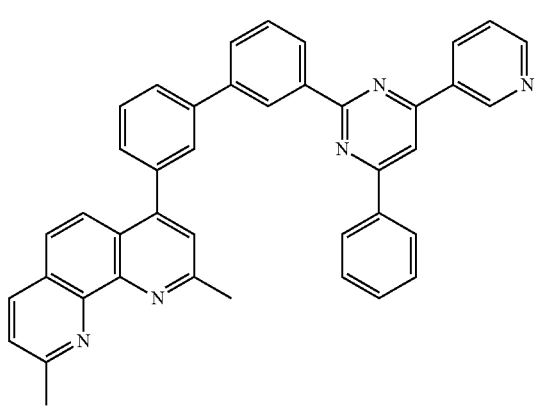
754
-continued
72
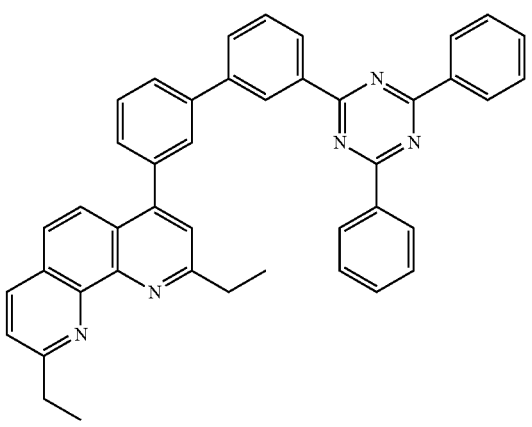
73
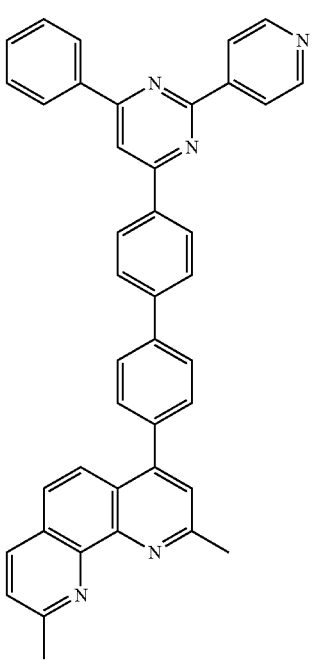

755
-continued
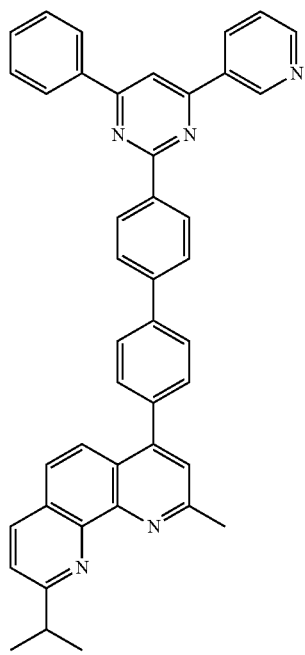
756
-continued
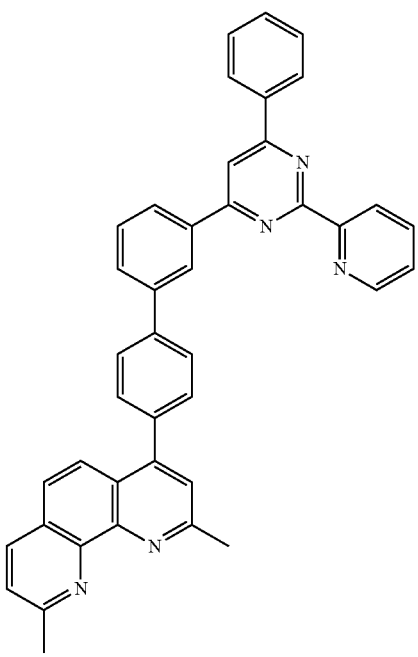

757
-continued
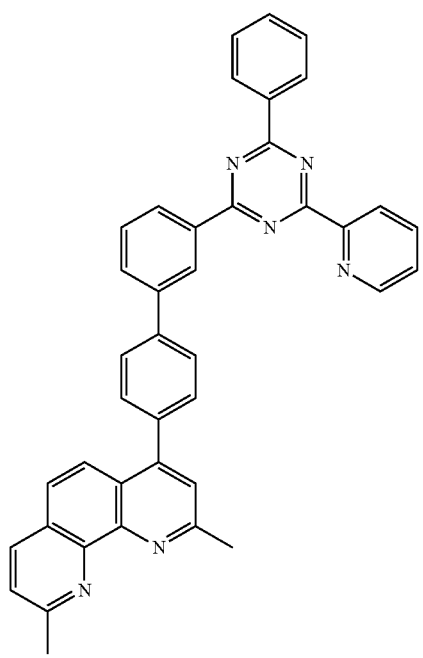
78
759
758
-continued
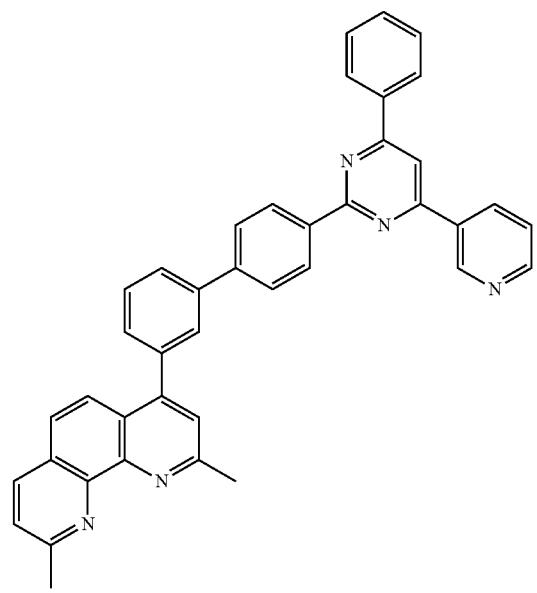
80
81
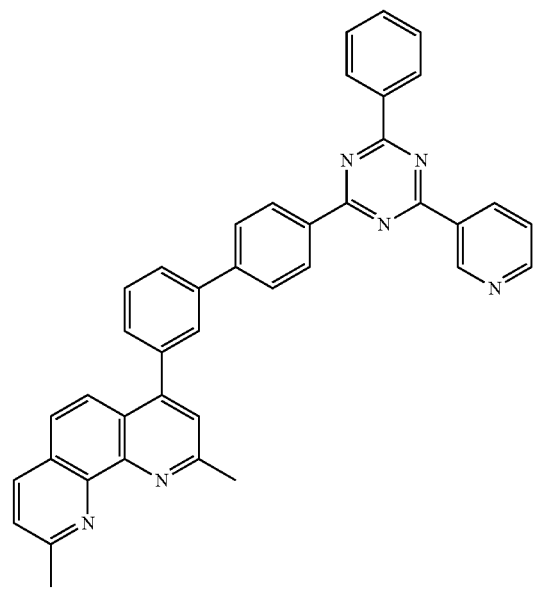

82
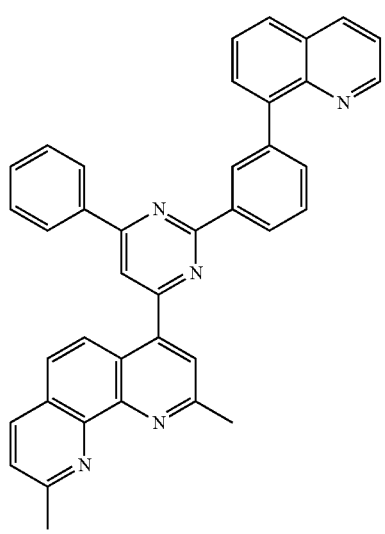
83
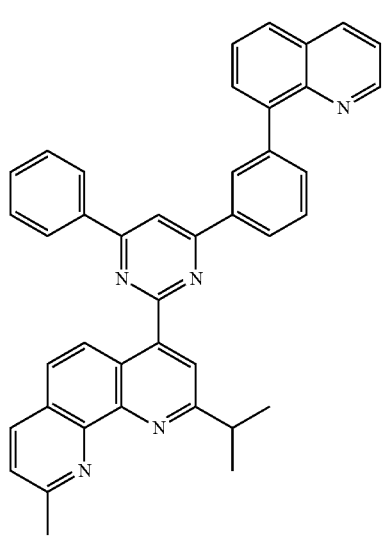
84
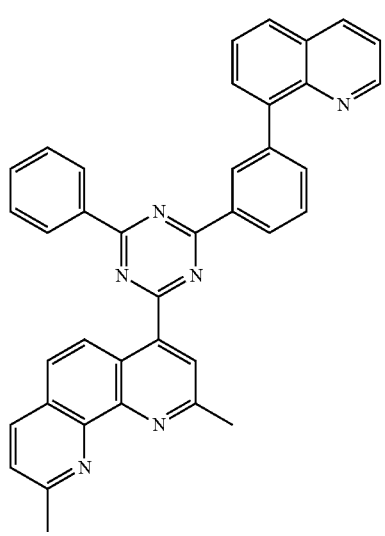
85
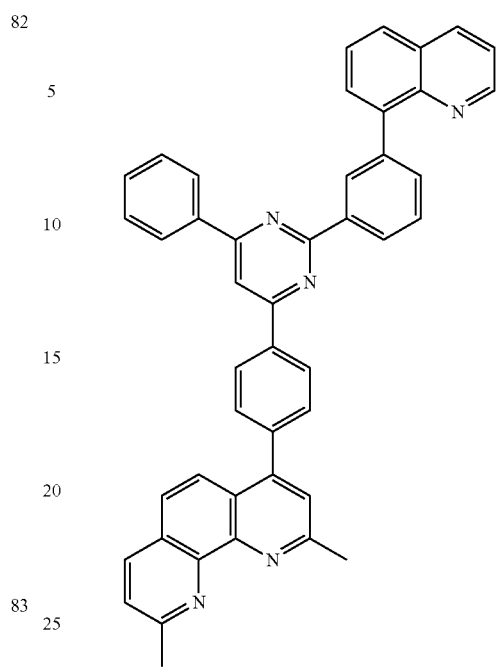
86
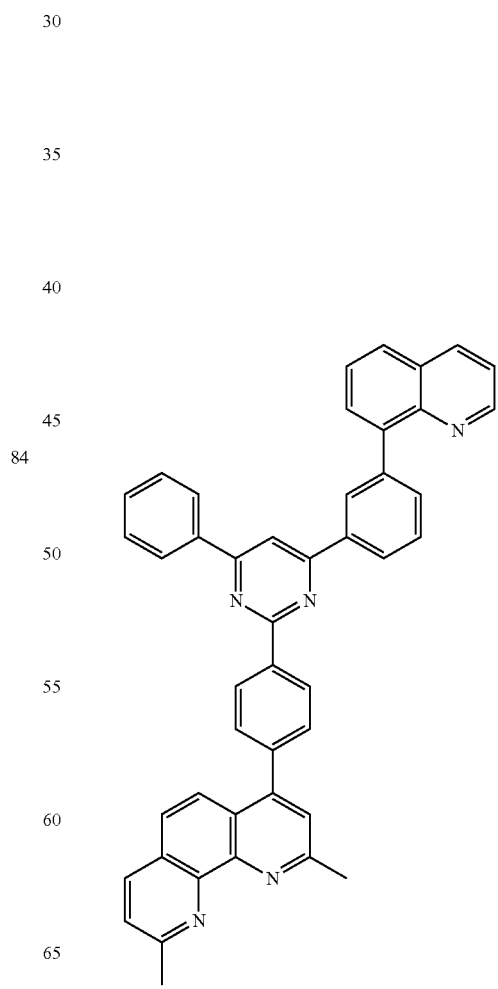

761
-continued
87
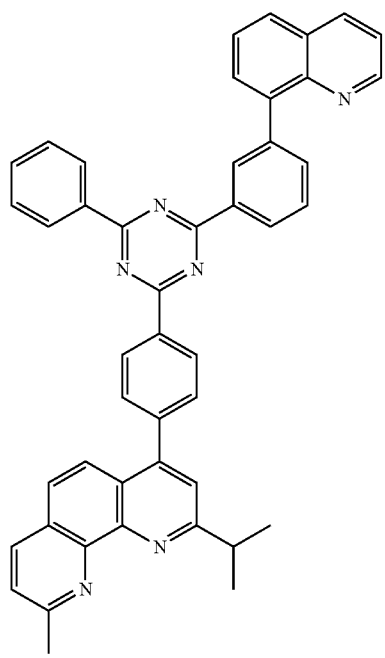
88
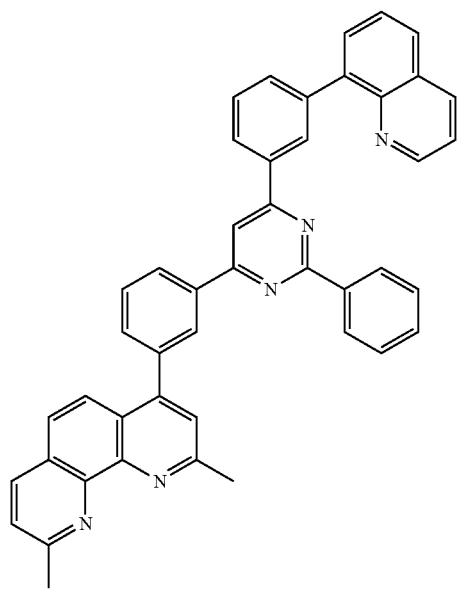
762
-continued
89
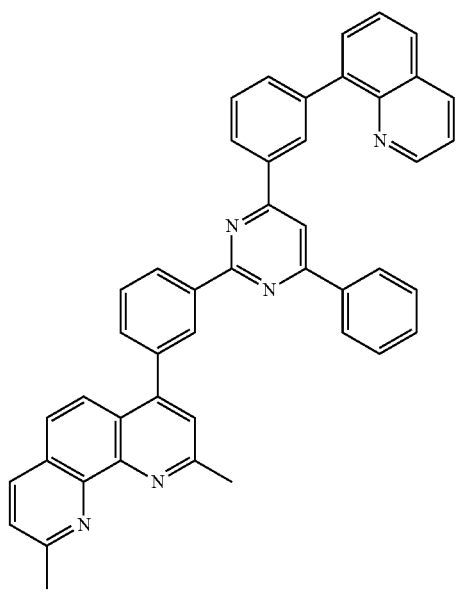
90
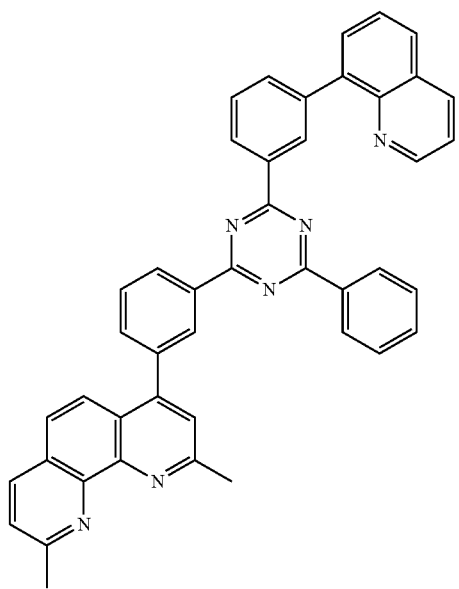

91 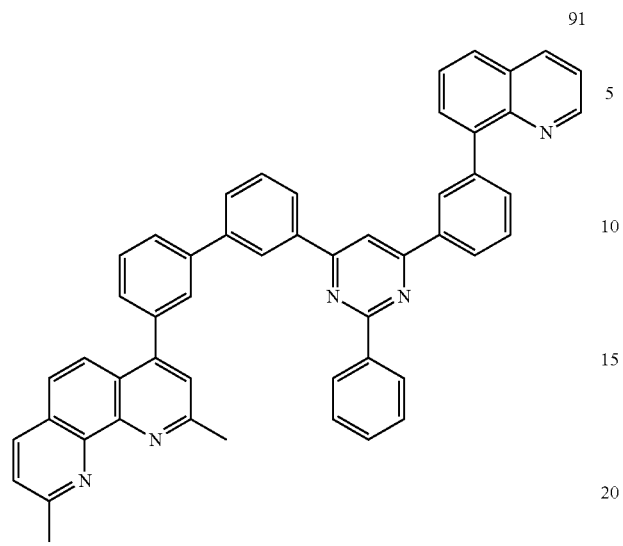
94 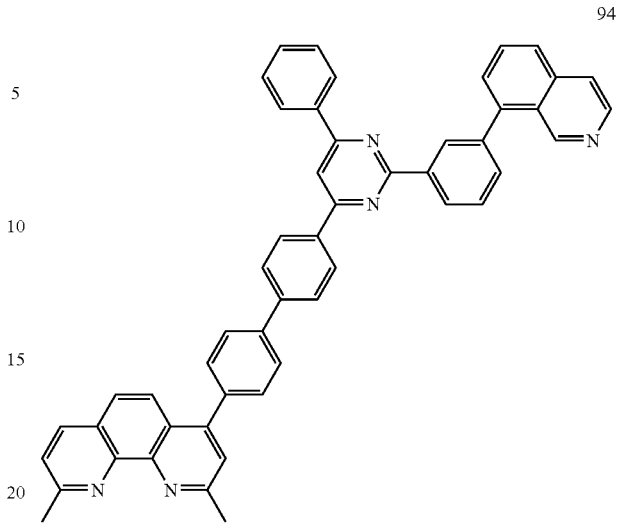
92 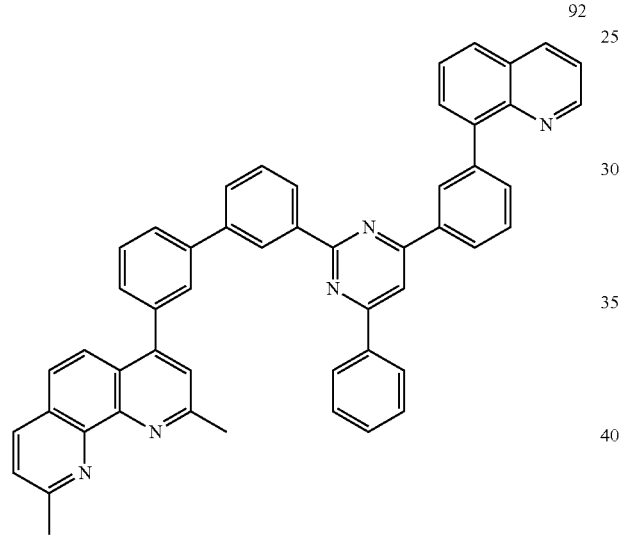
93 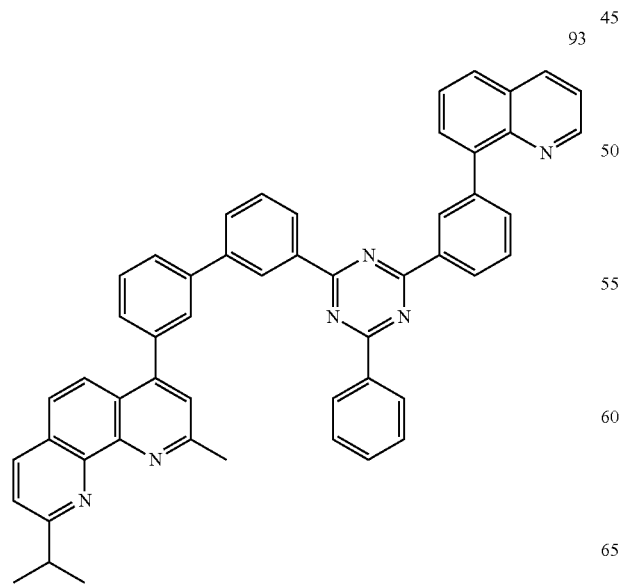
95 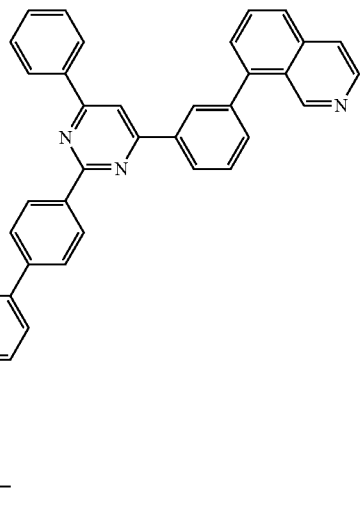

96
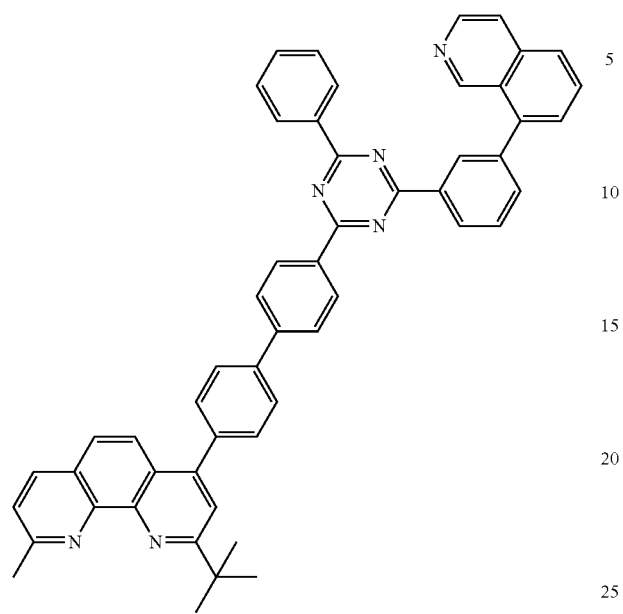
765
98
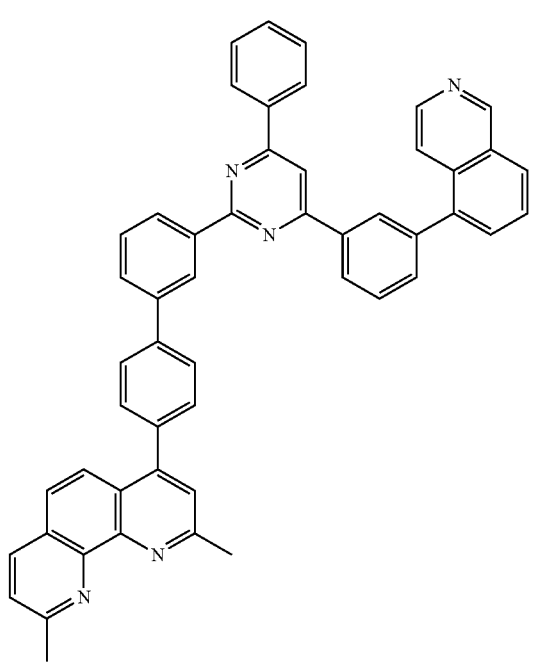
766
97
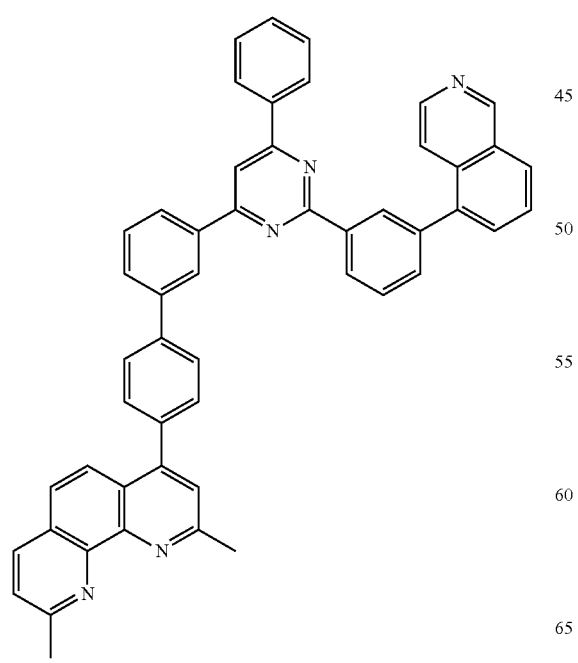
99
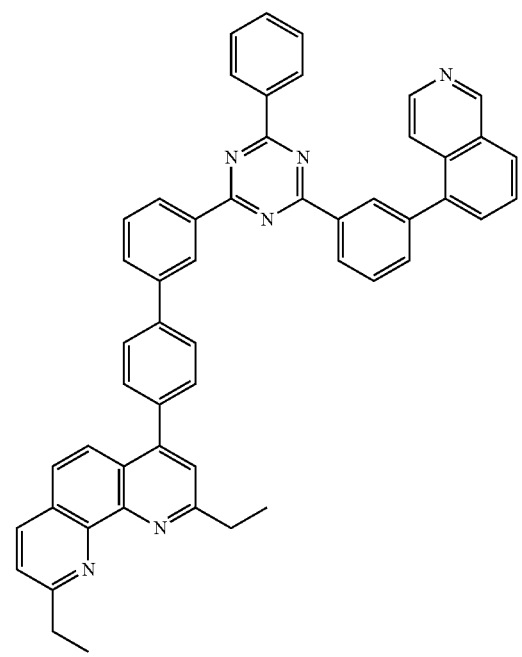

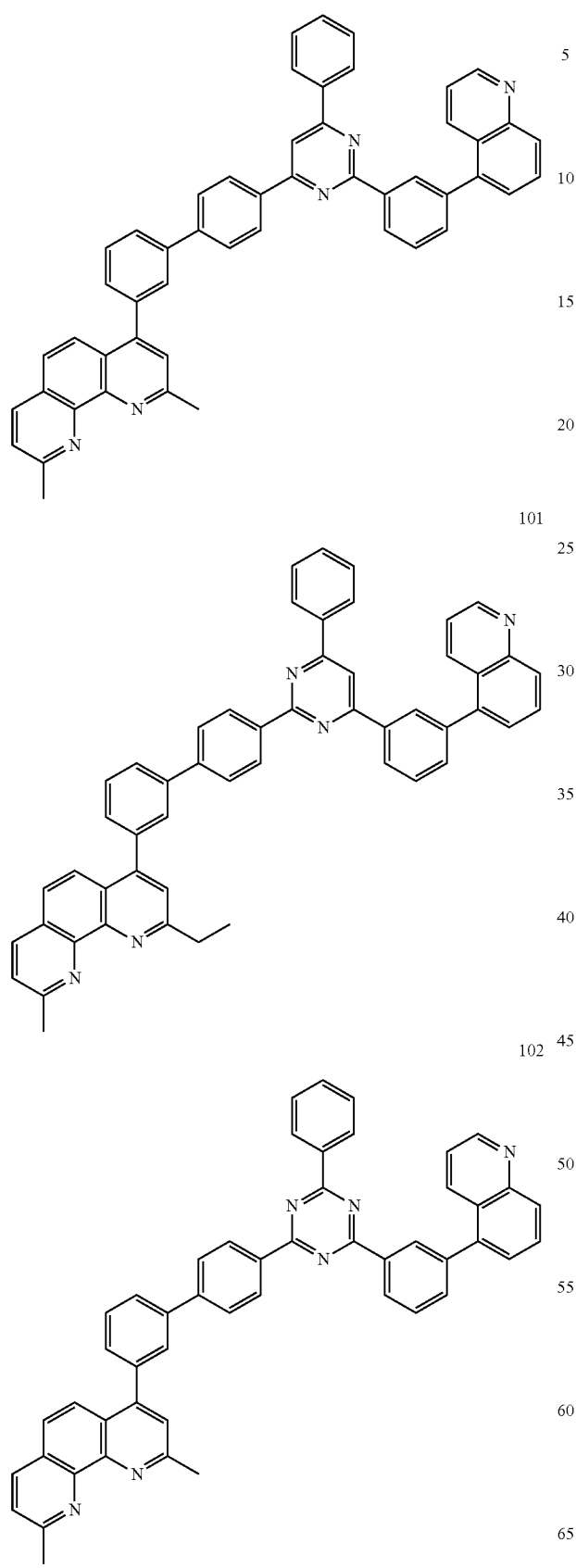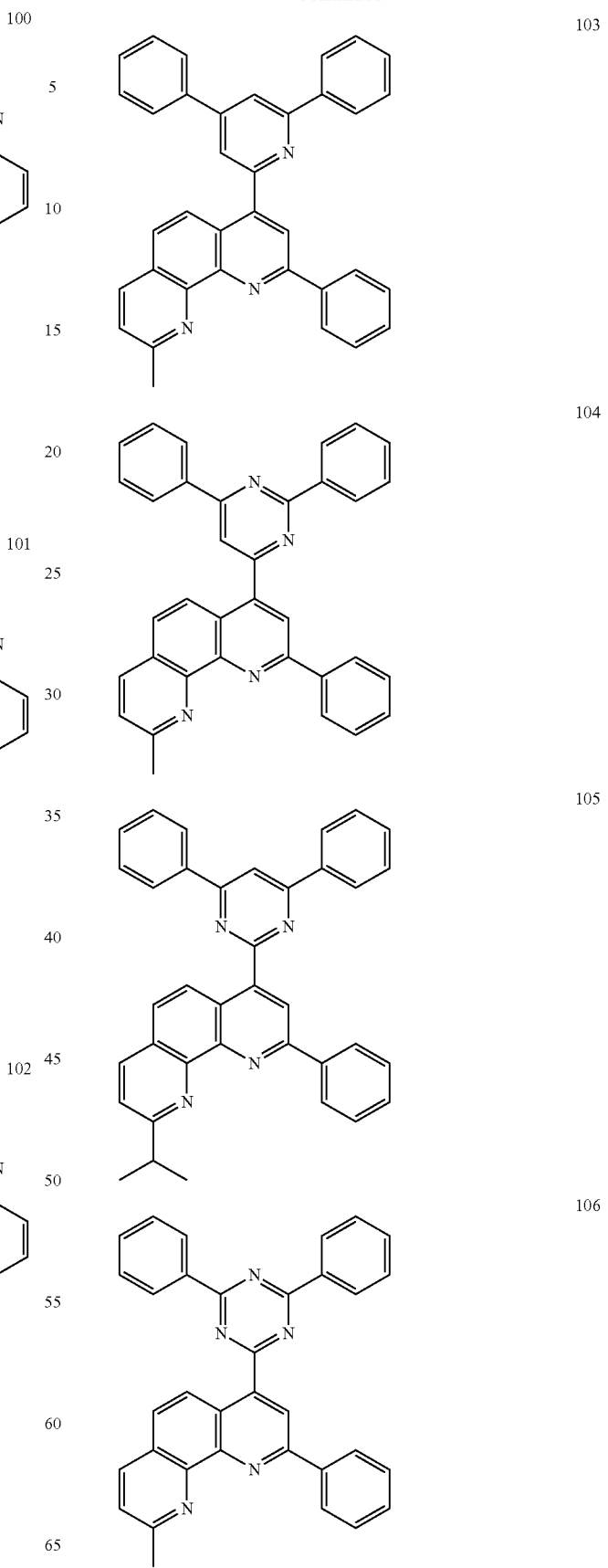

769
-continued
107
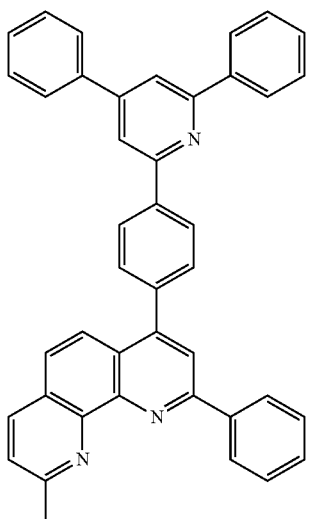
108
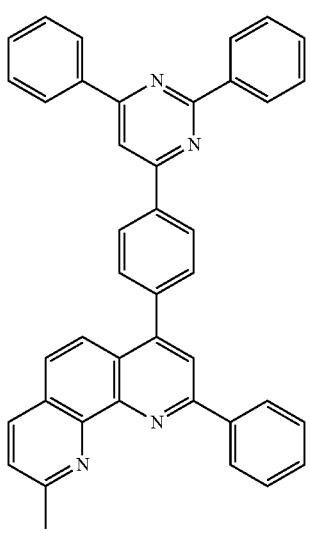
109
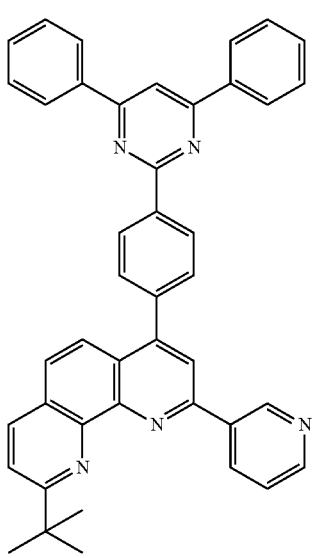
770
-continued
110
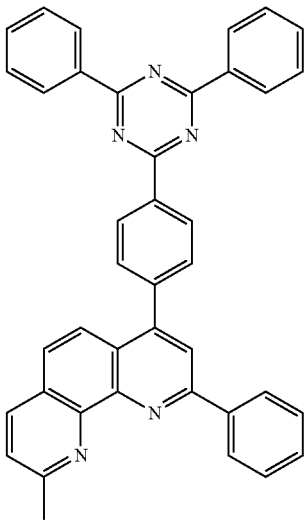
111
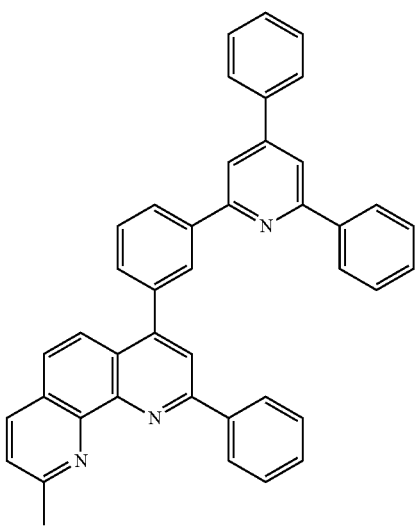
112
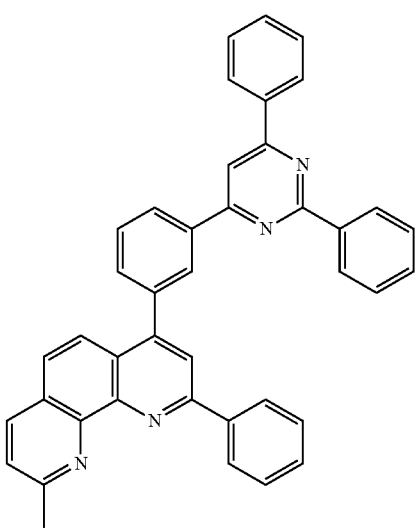

113 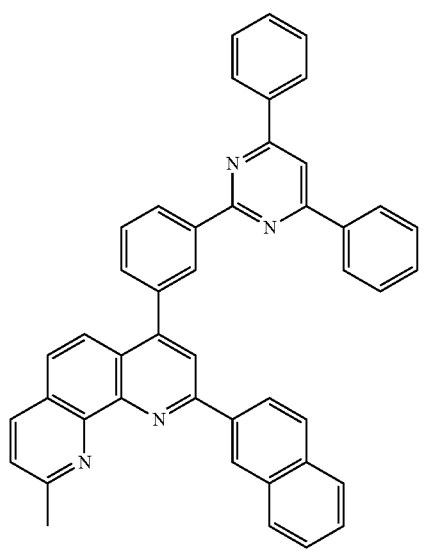
114 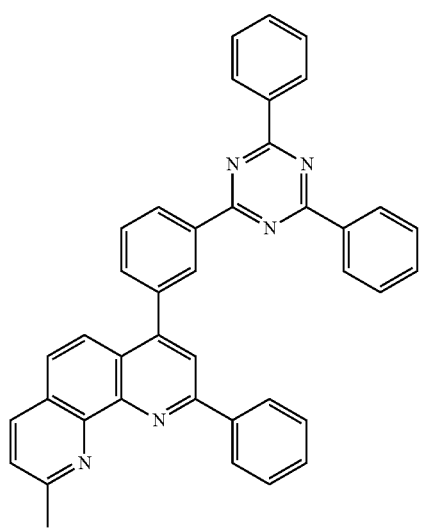
115 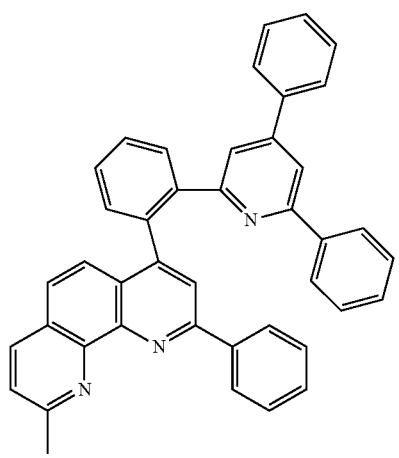
116 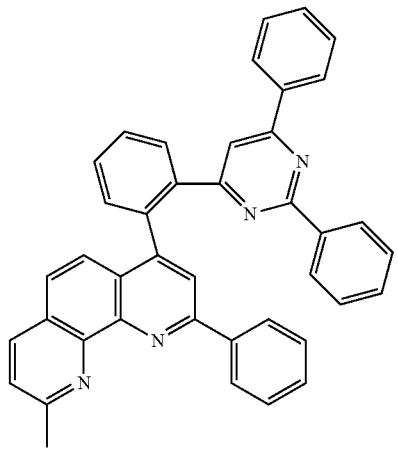
117 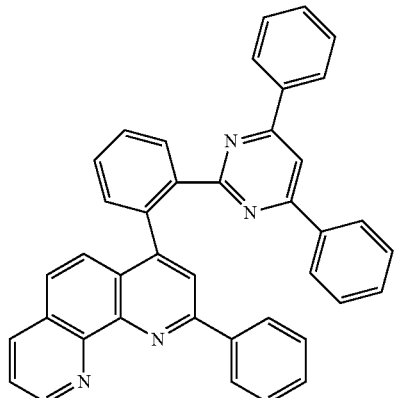
118 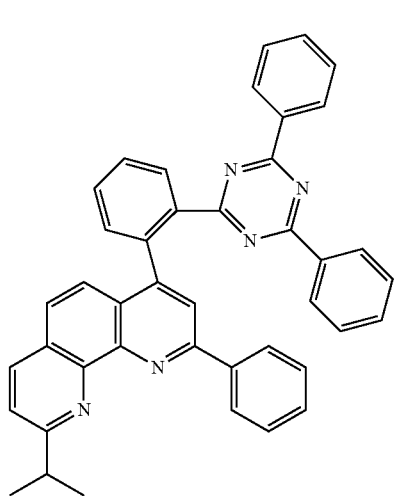

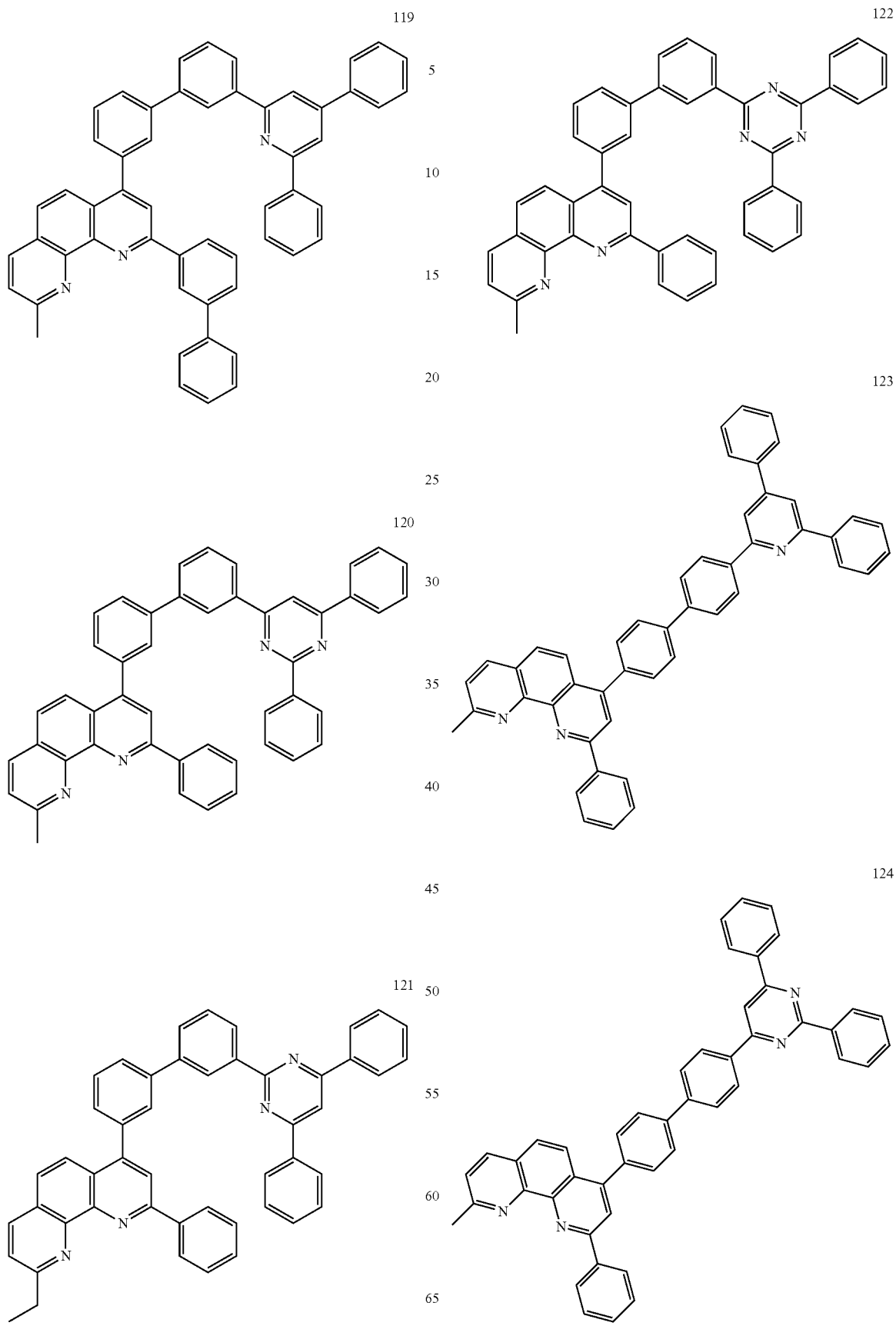

125
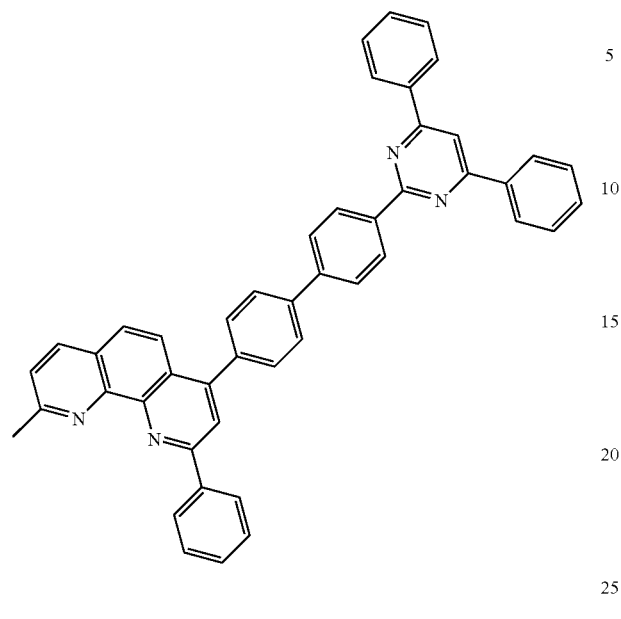
127
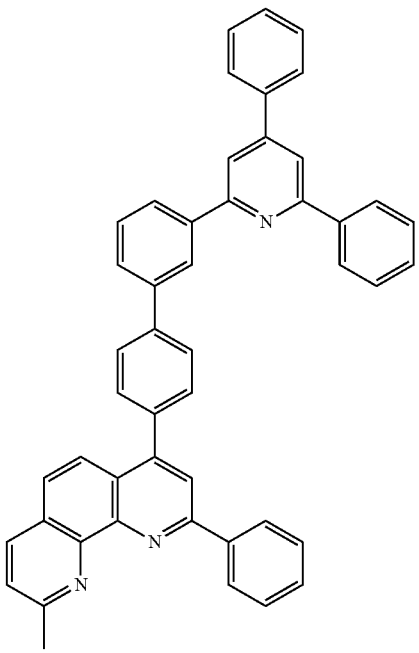
126
128
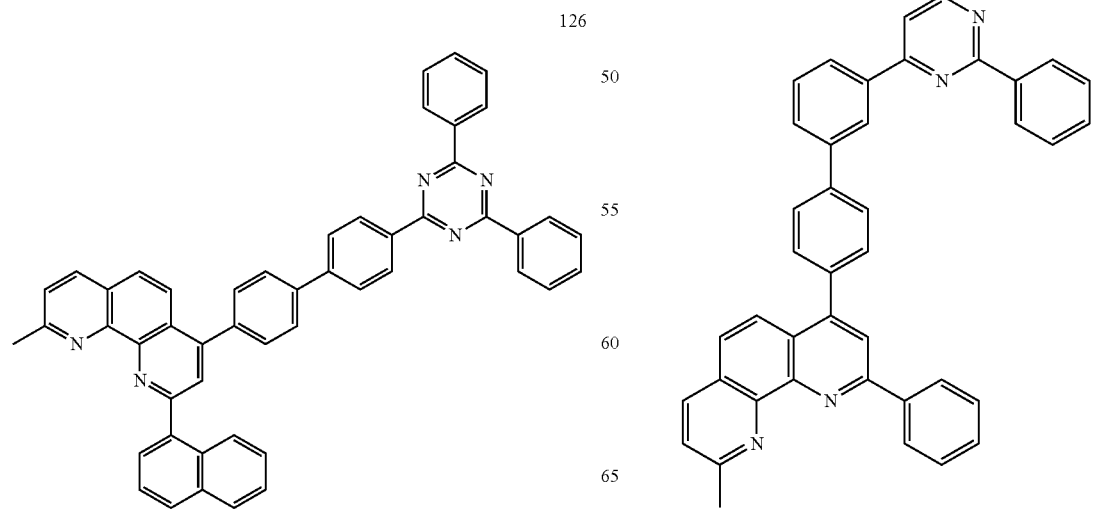

777
-continued
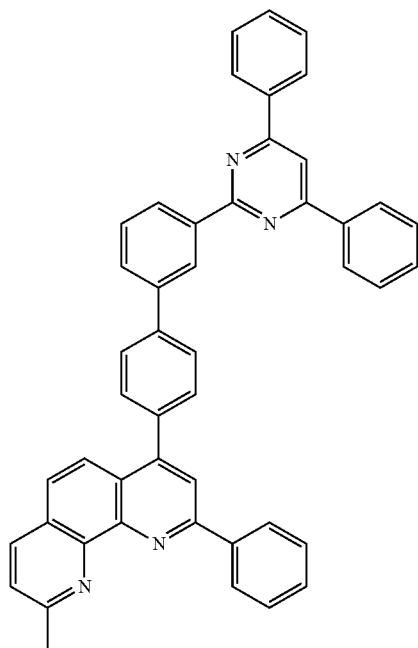
129
778
-continued
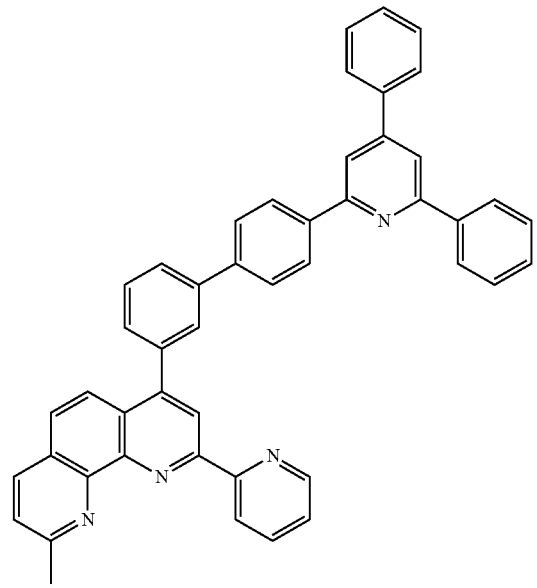
131
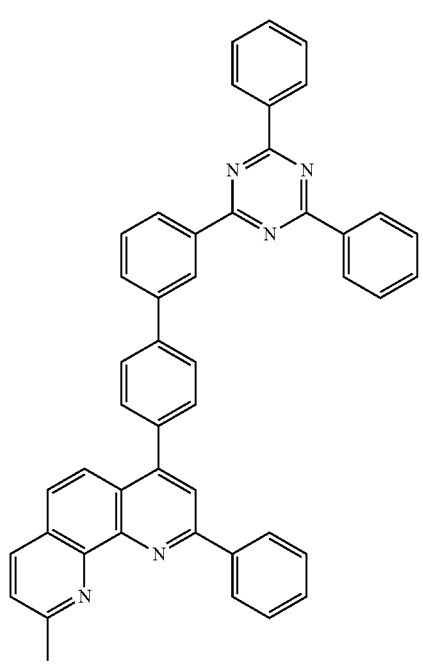
130
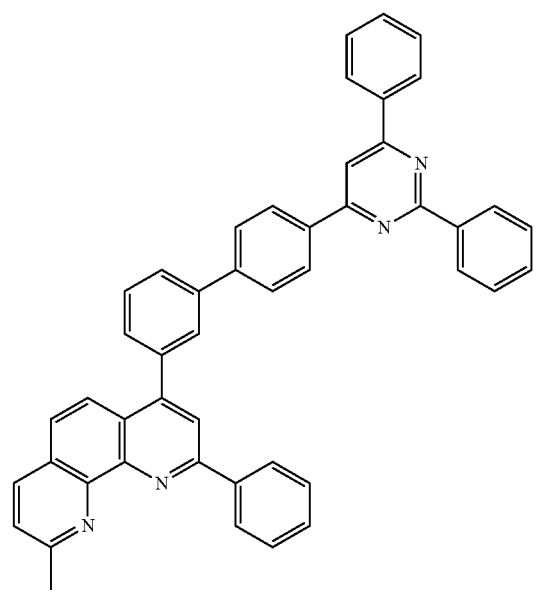
132

133
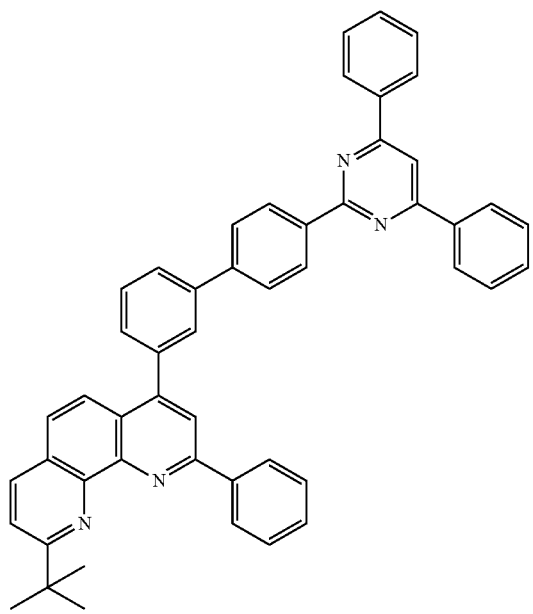
134
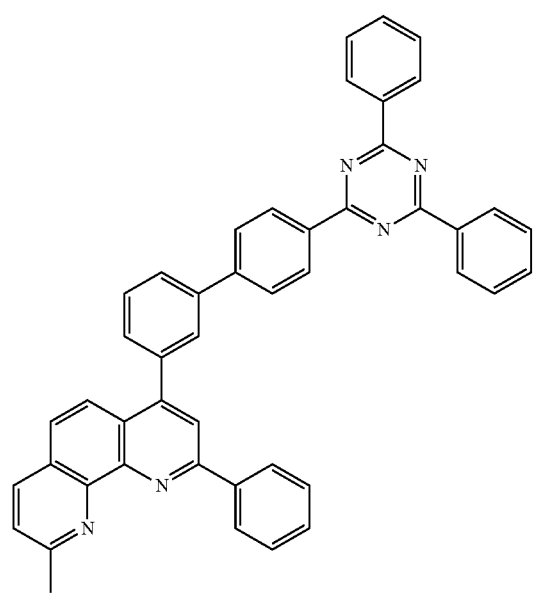
135
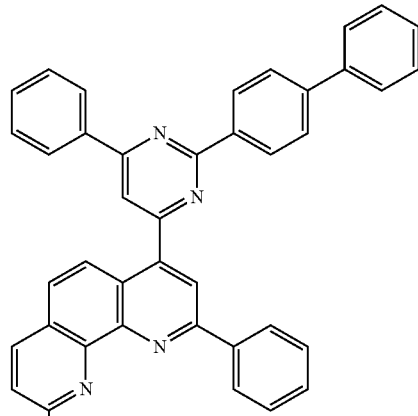
136
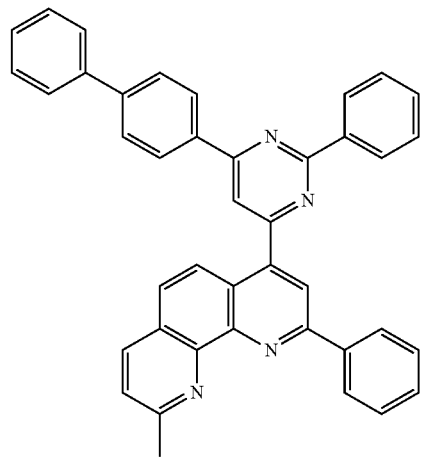
137
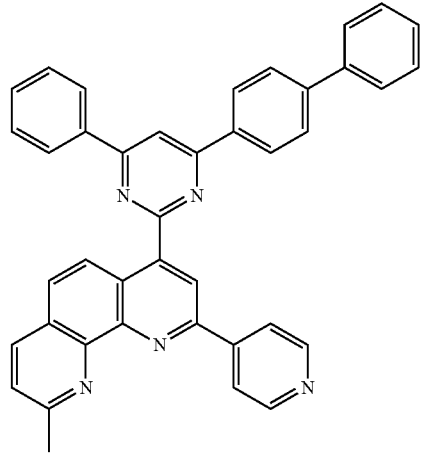

781
-continued
782
-continued
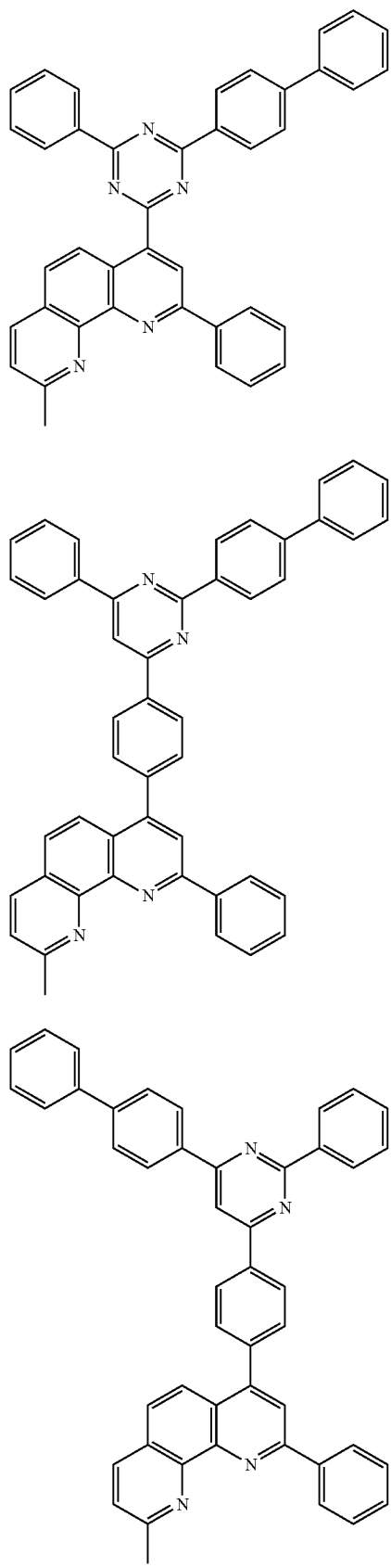
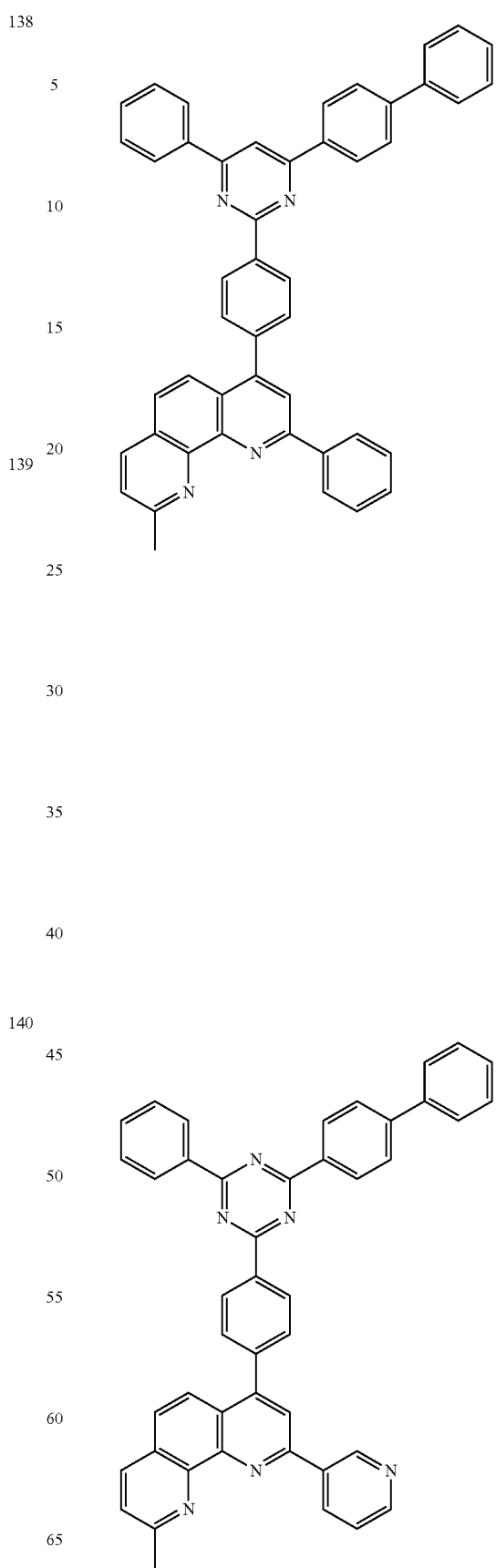

143
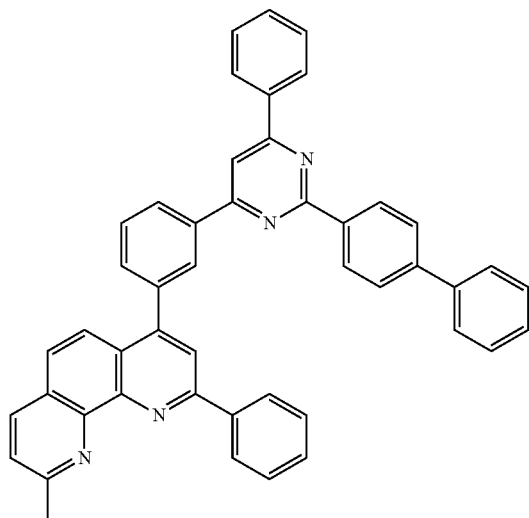
144
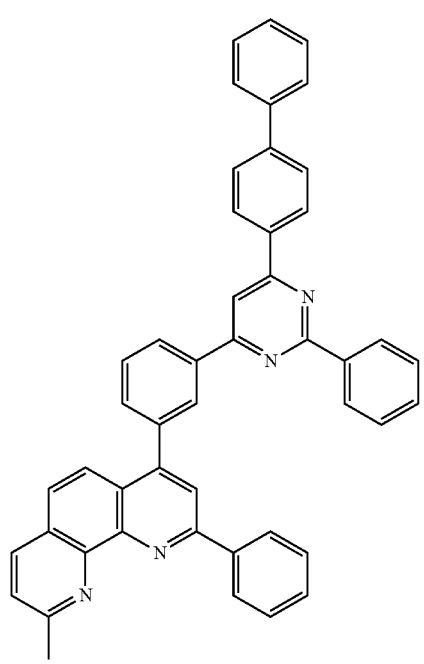
145
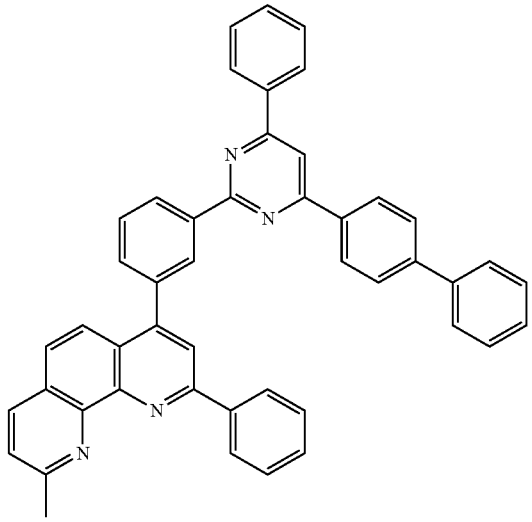
146
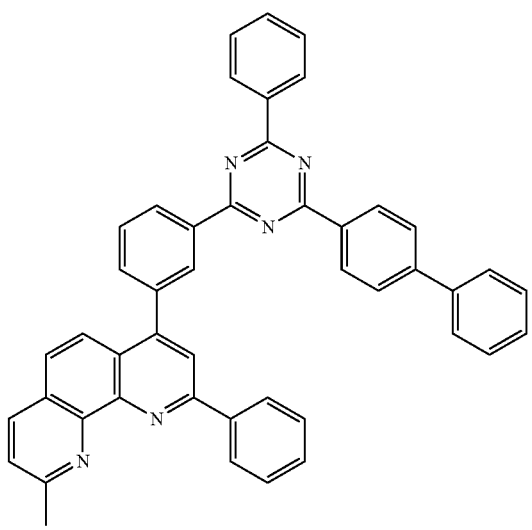
147
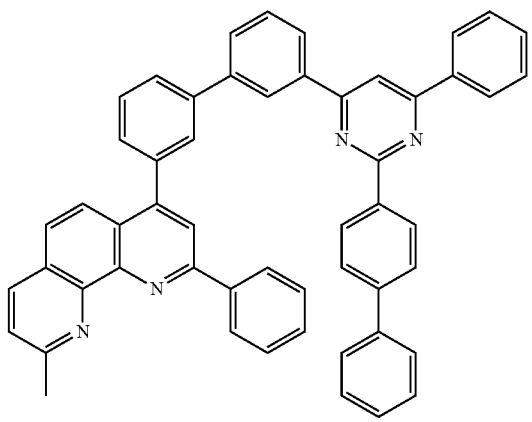

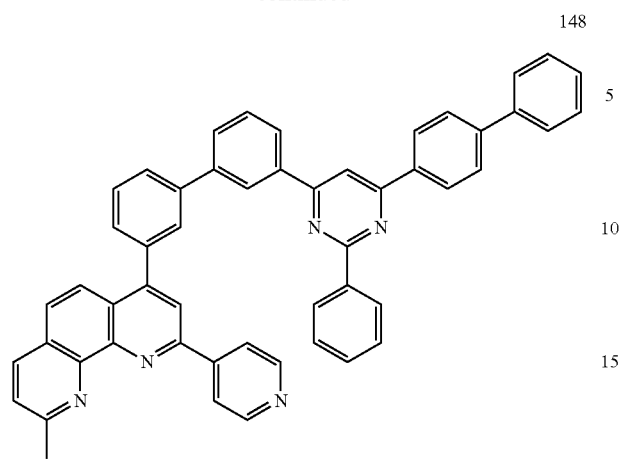
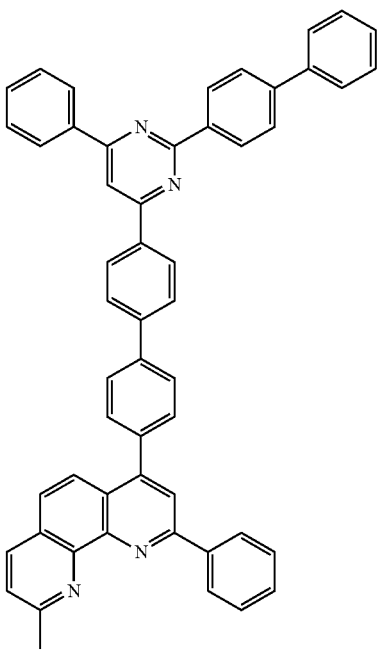
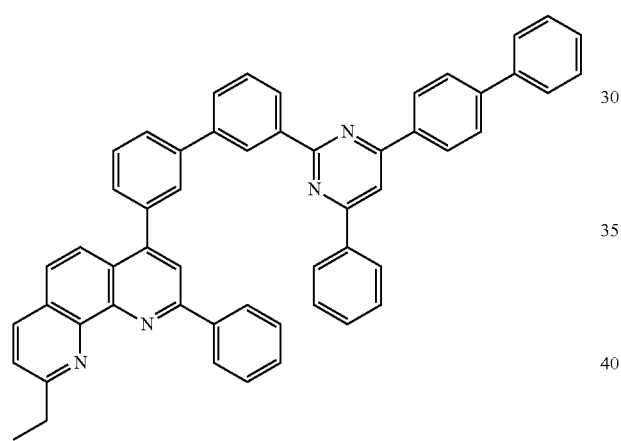
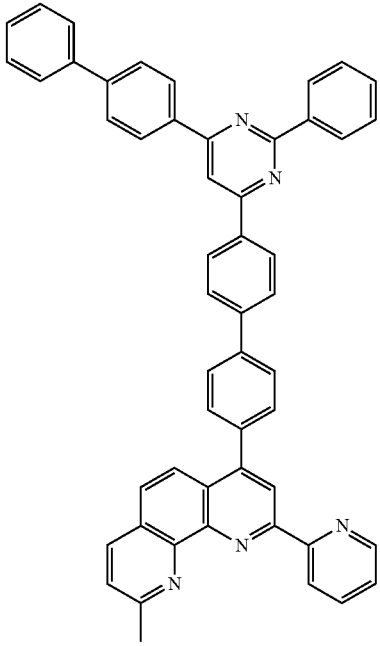

153
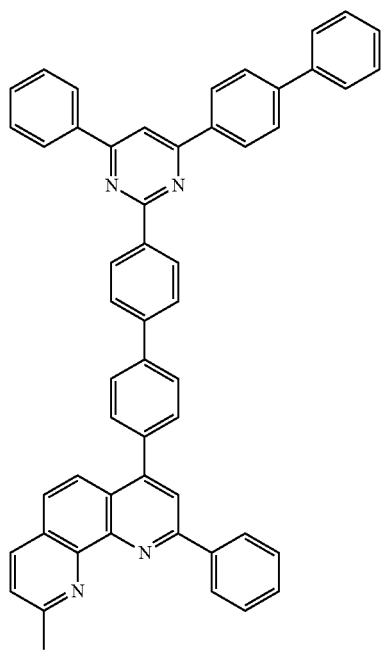
154
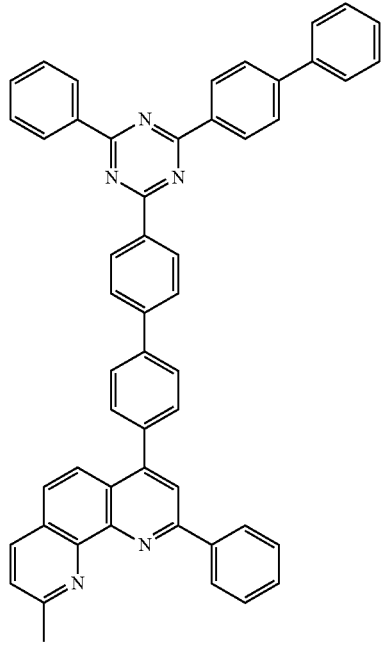
155
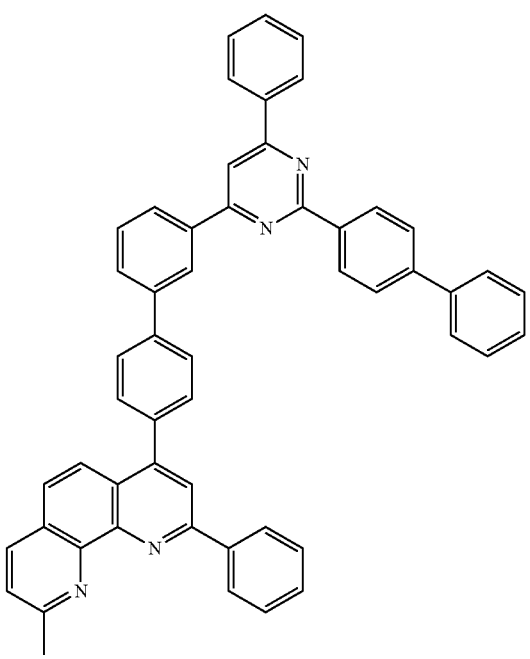
156
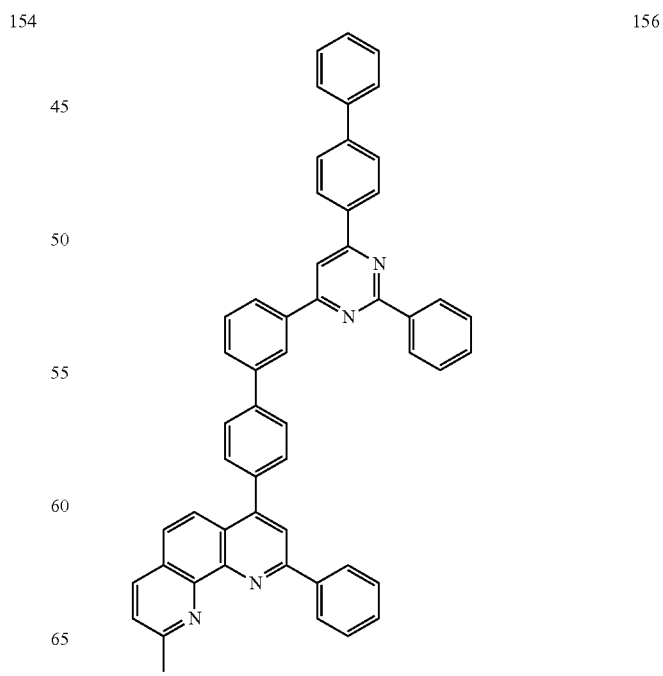

157
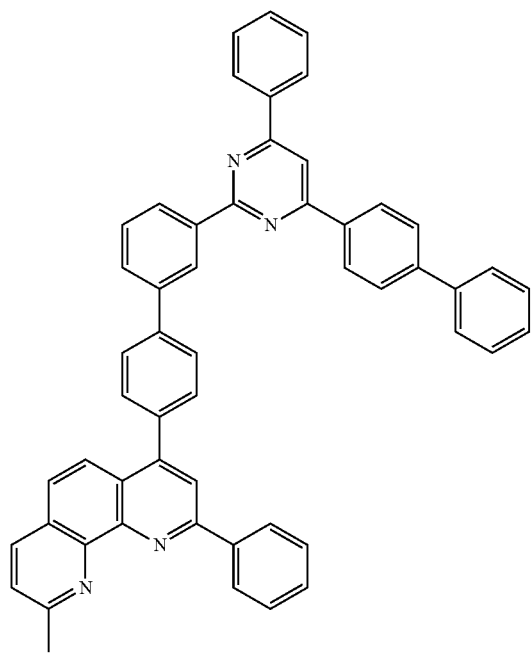
158
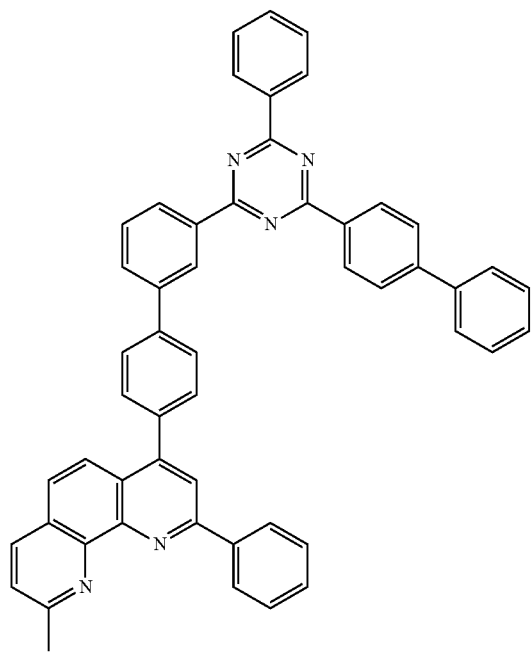
159
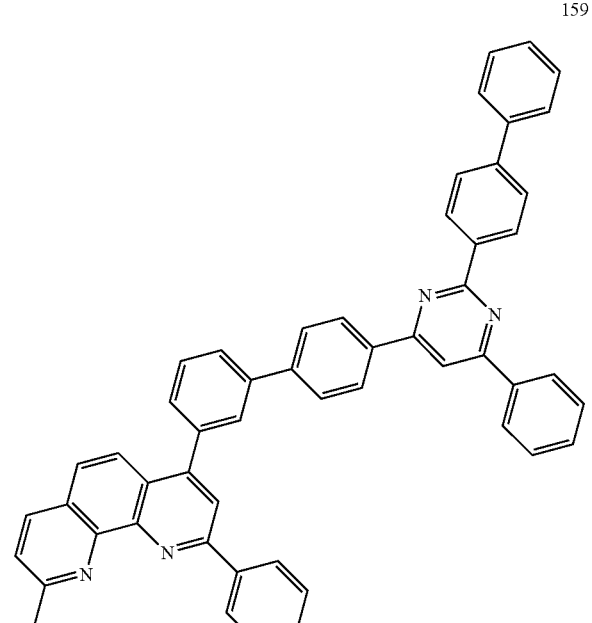
160
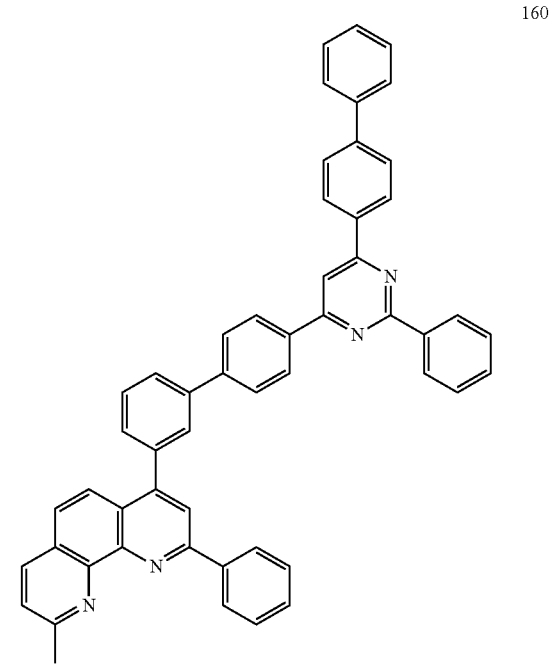

791
-continued
792
-continued
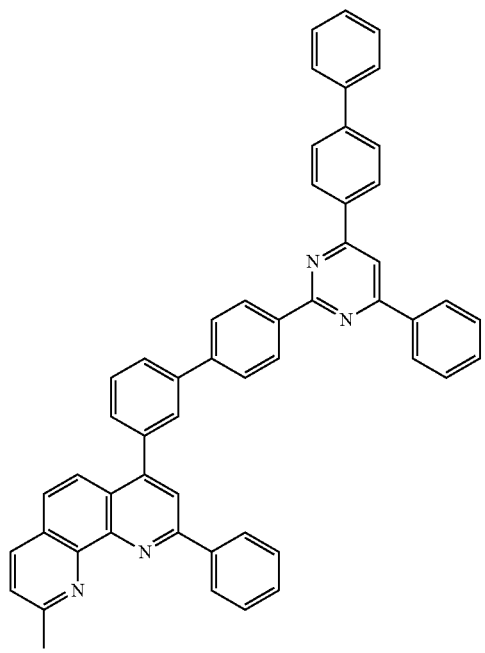
161
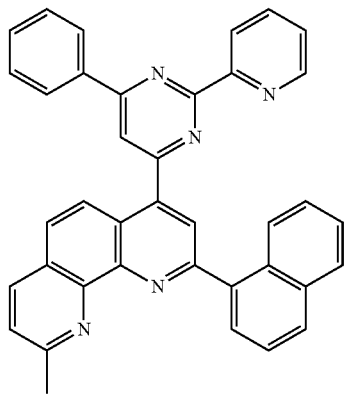
163
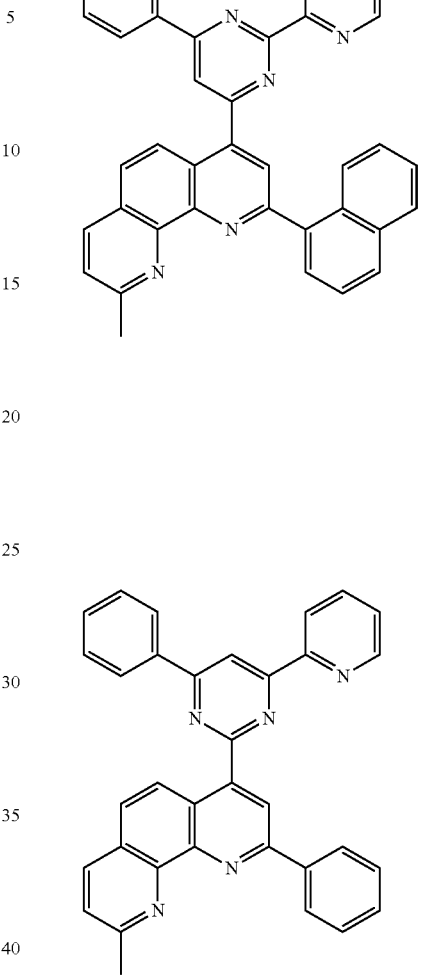
164
165
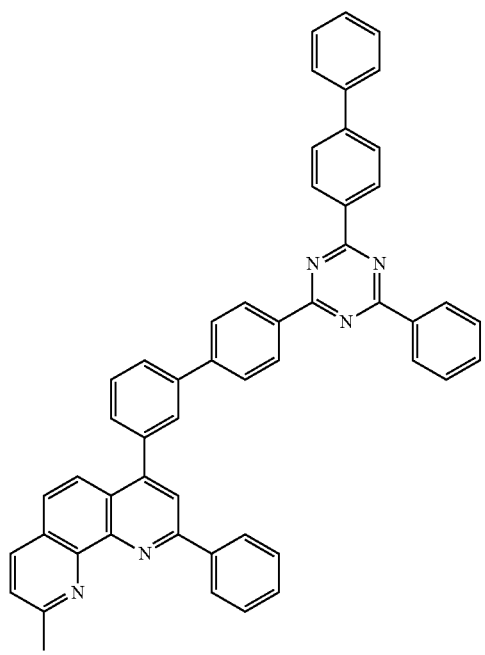
162

166
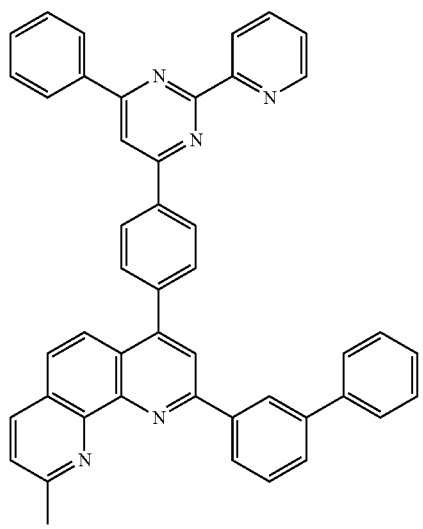
167
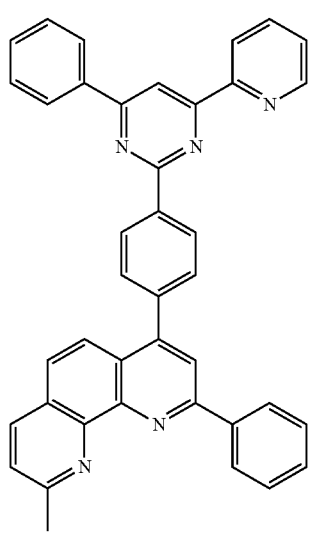
168
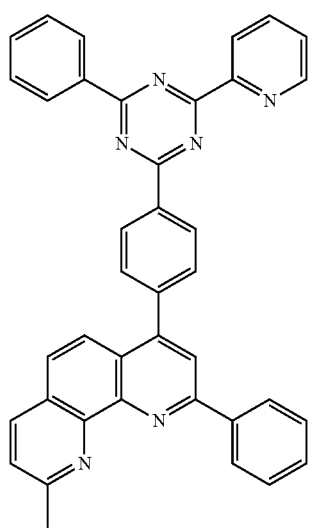
169
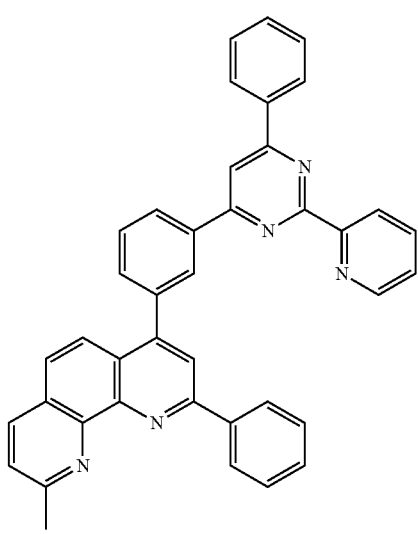
170
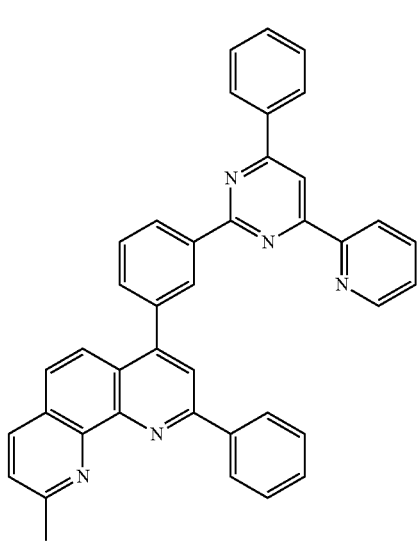
171
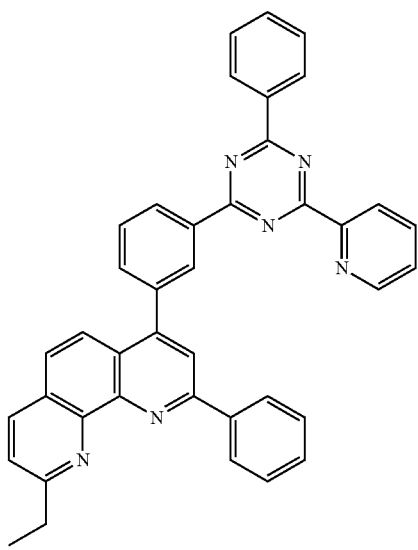

172
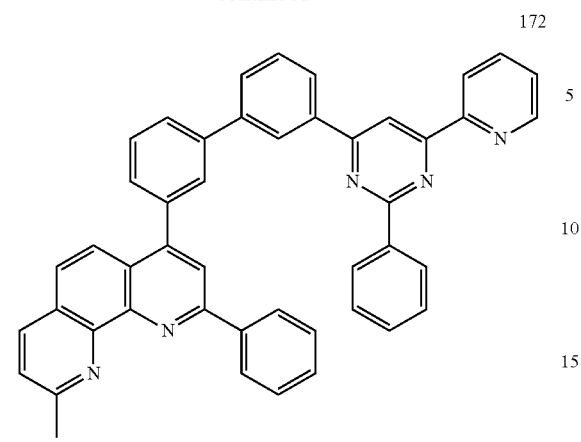
173
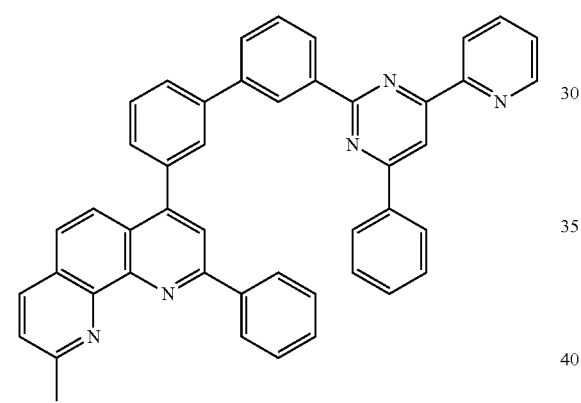
174
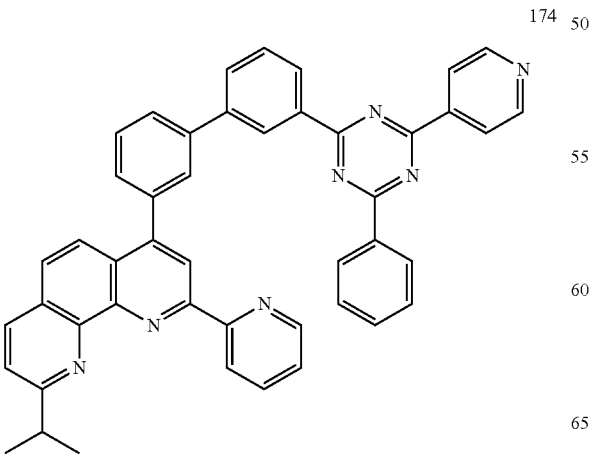
175
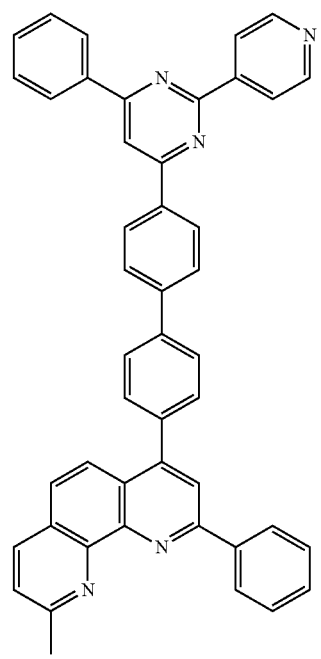
176
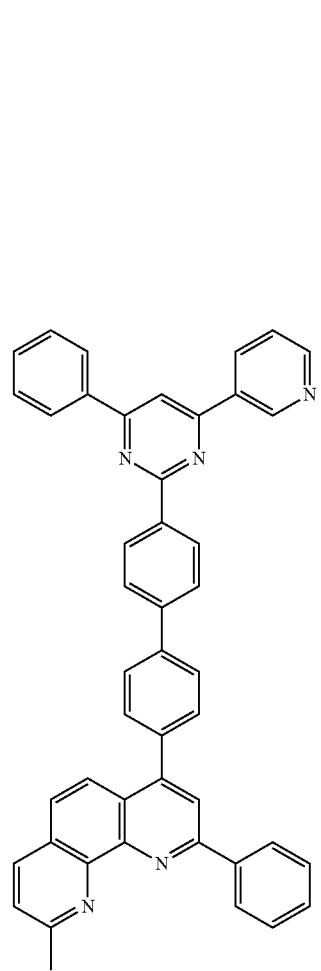

797
-continued
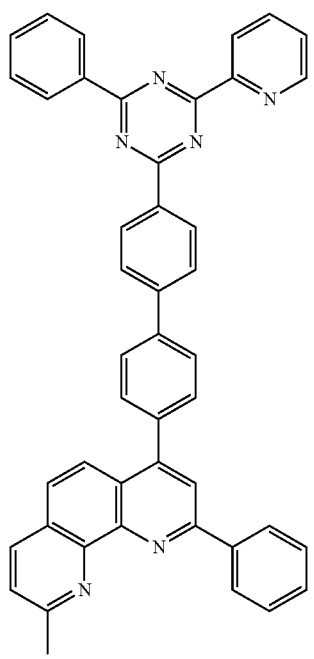
798
-continued
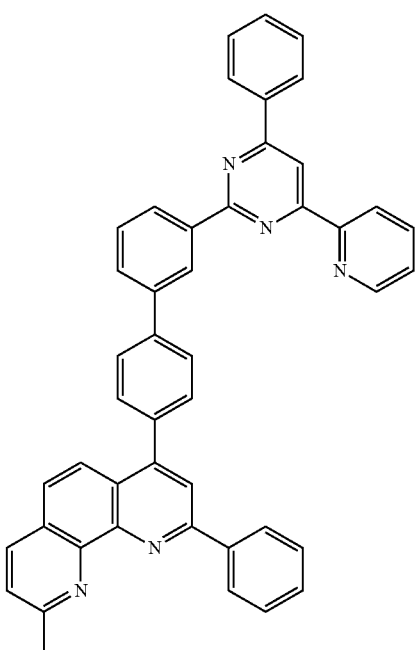
178
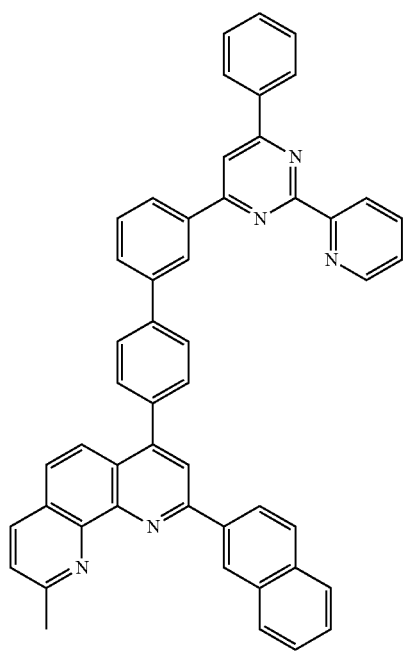
180
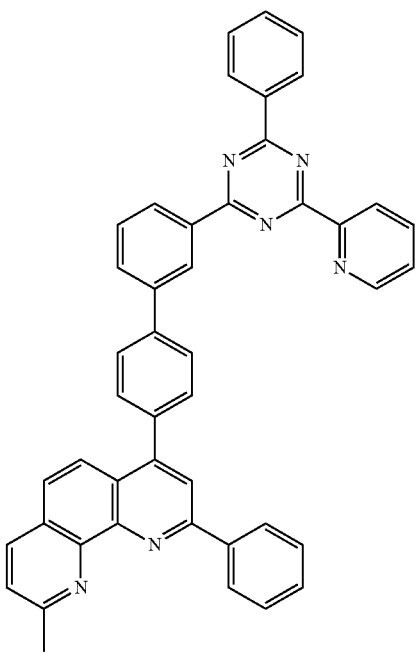

799
-continued
181
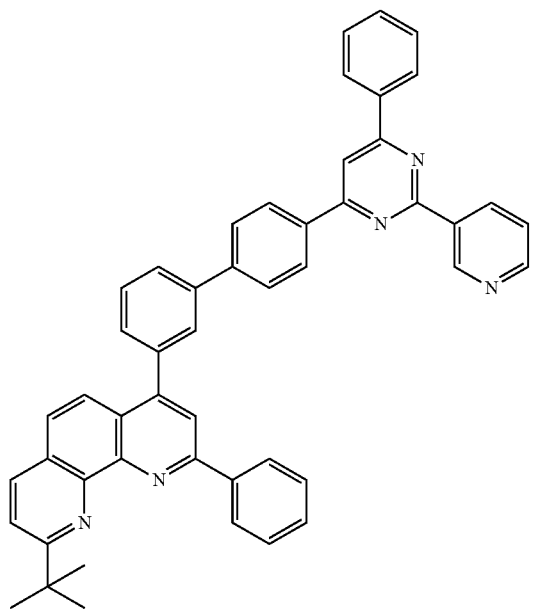
182
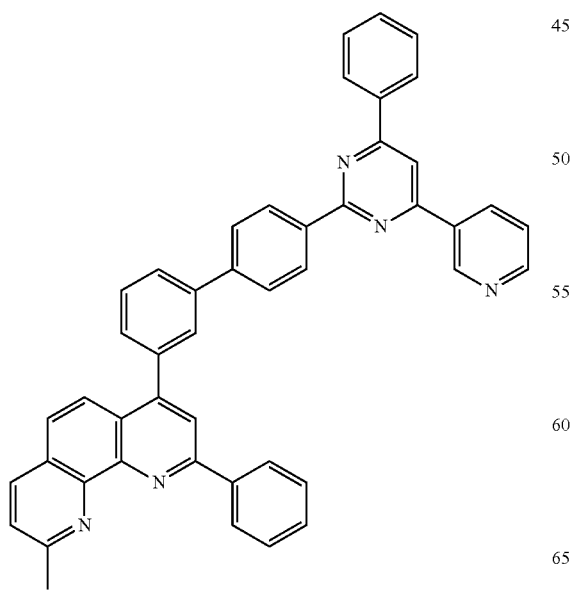
800
-continued
183
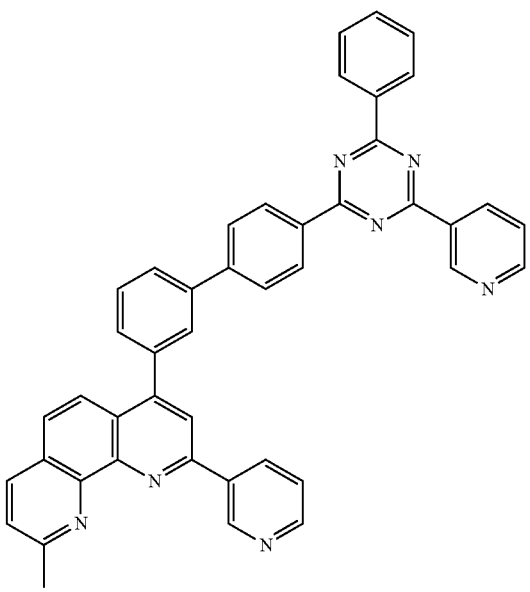
184
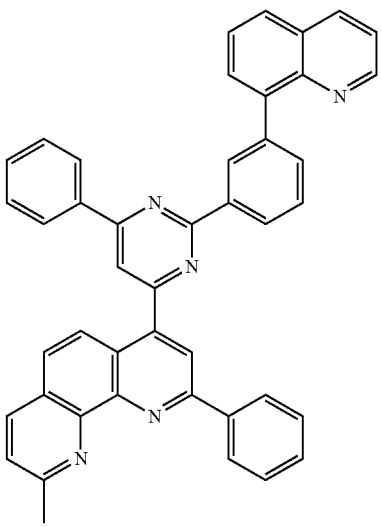

185
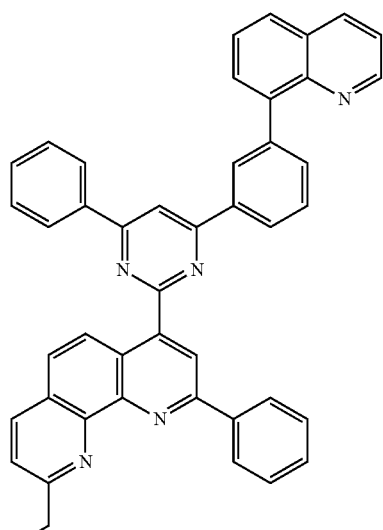
187
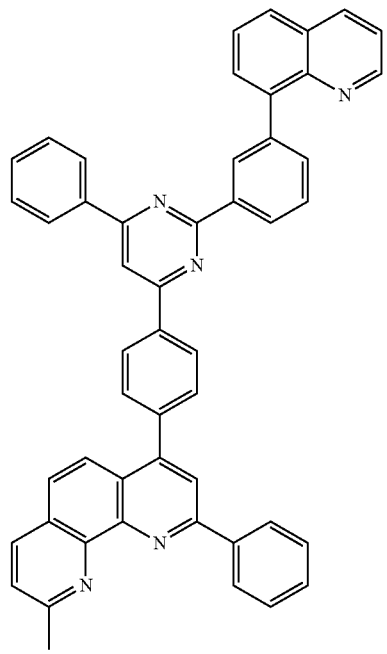
186
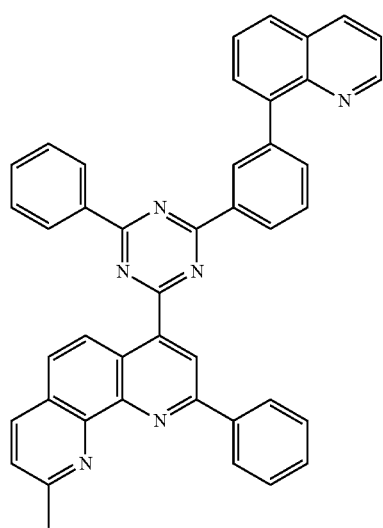
188
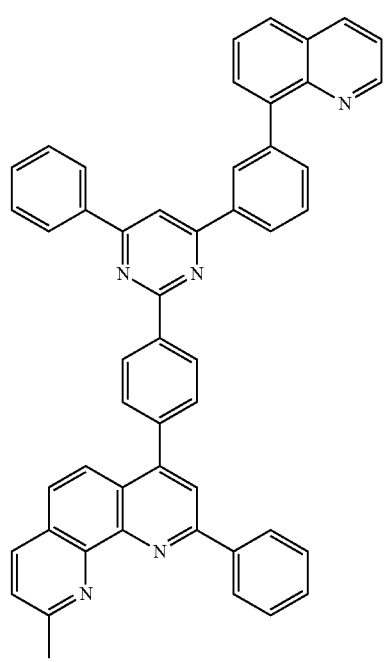

803
-continued
189
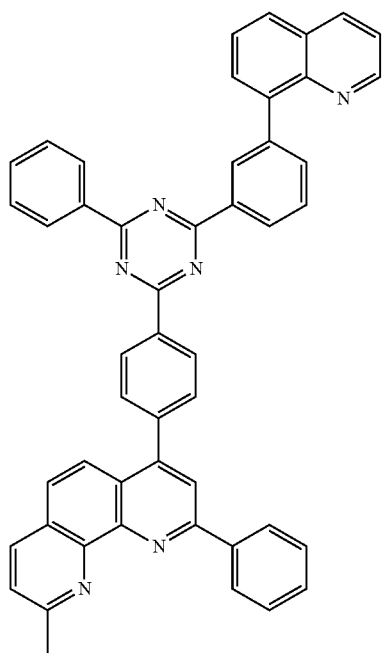
190
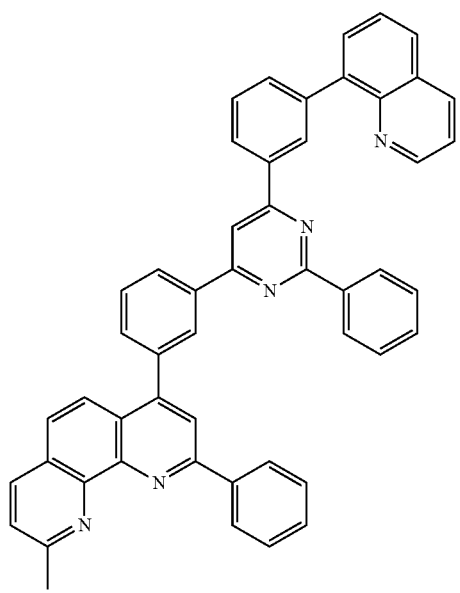
804
-continued
191
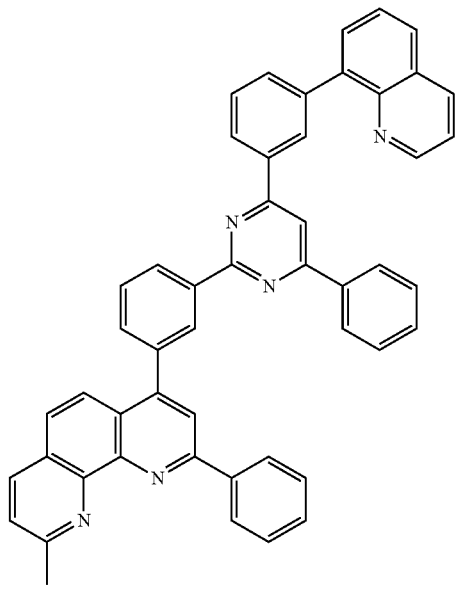
192
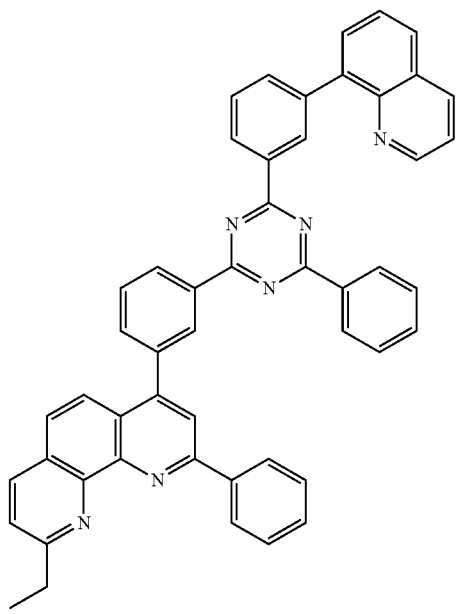

193
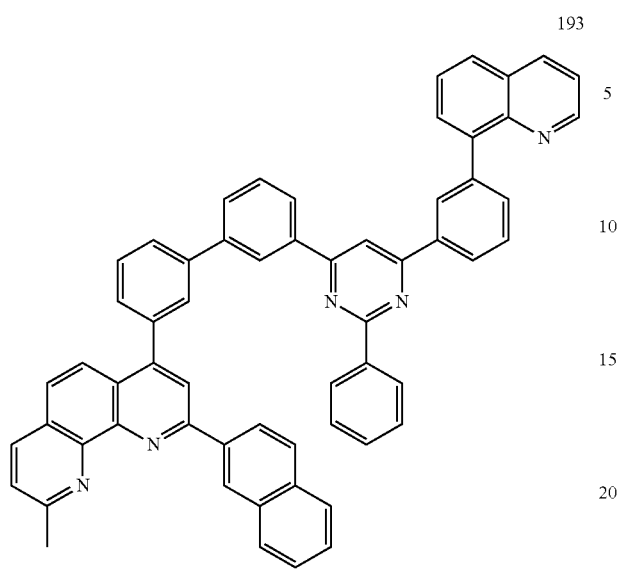
194
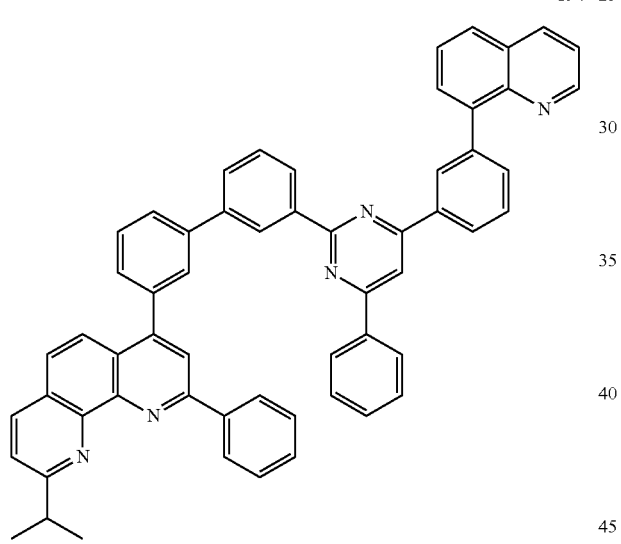
195
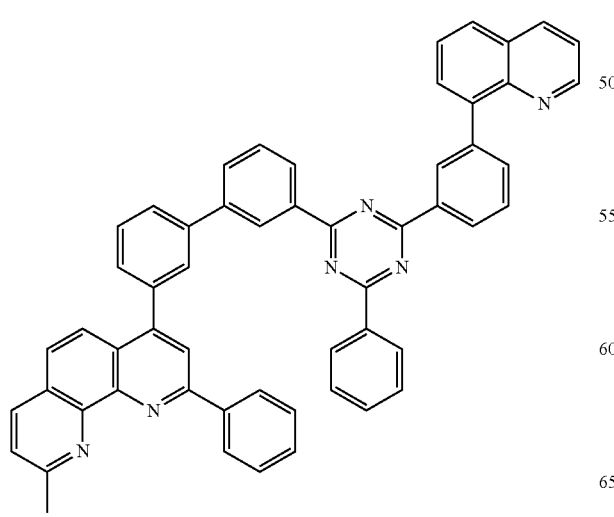
196
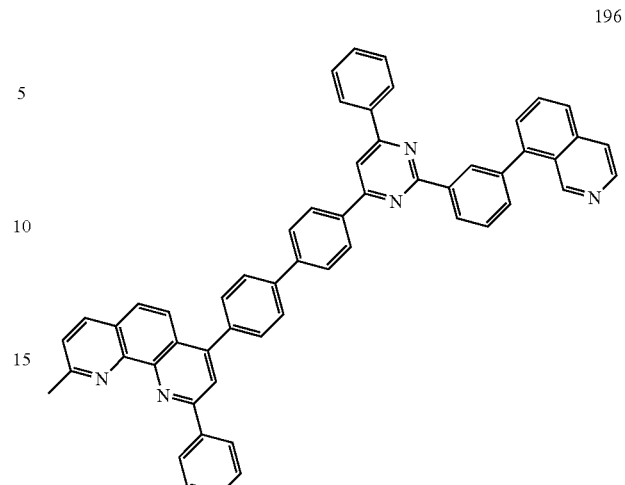
197
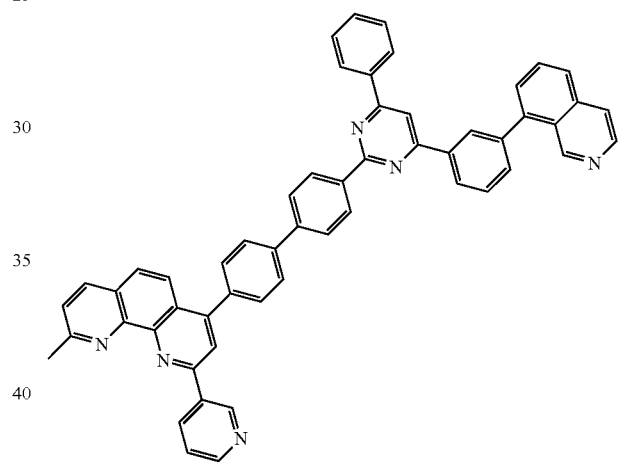
198
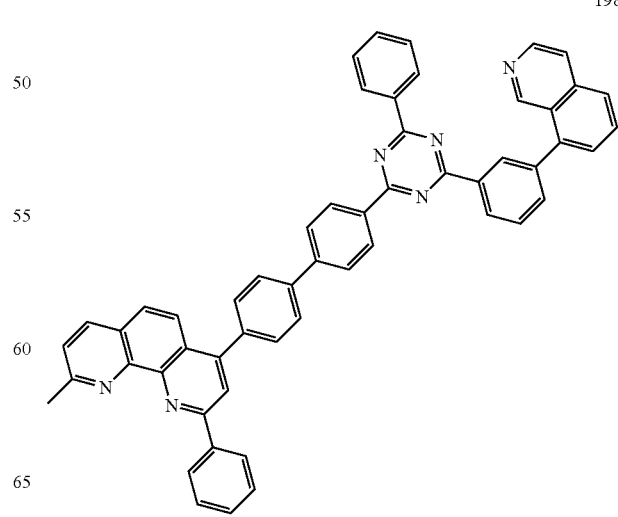

199
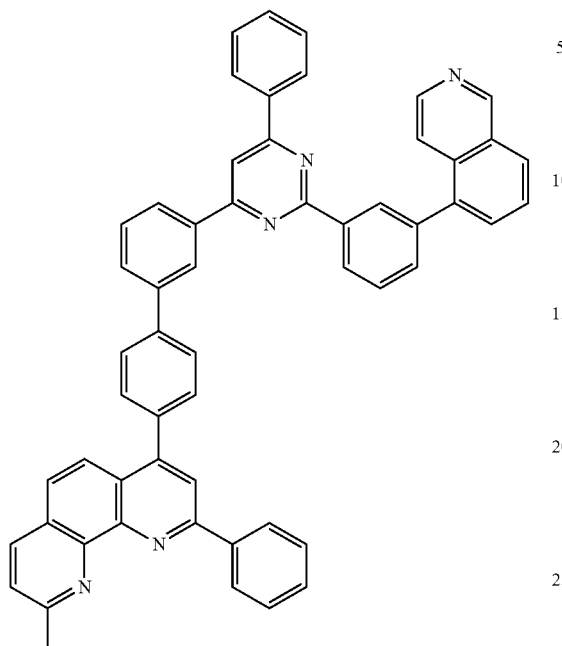
201
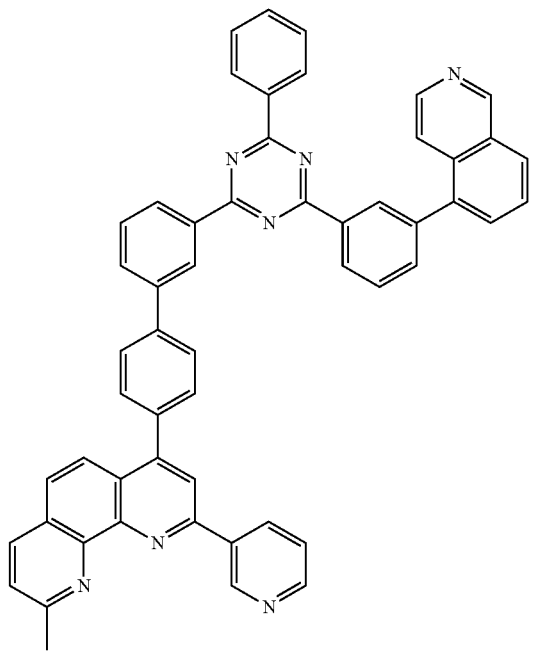
200
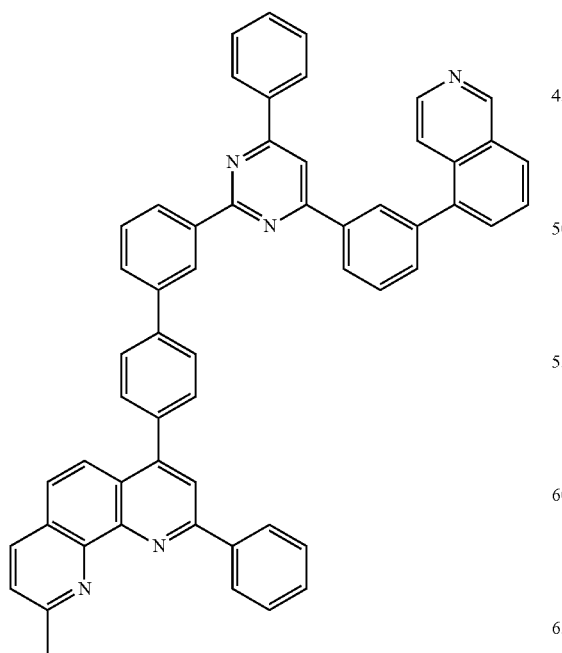
202
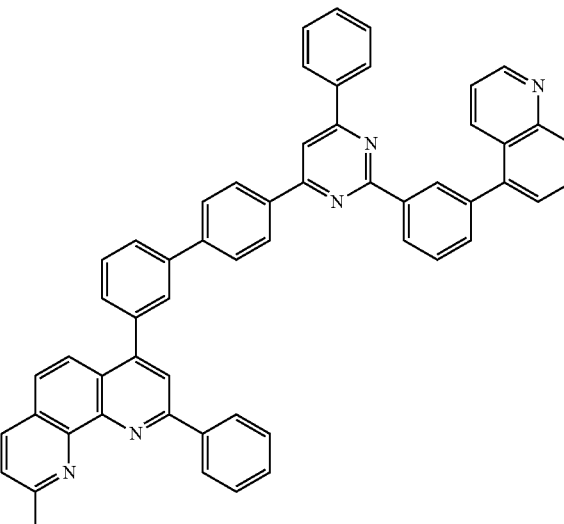

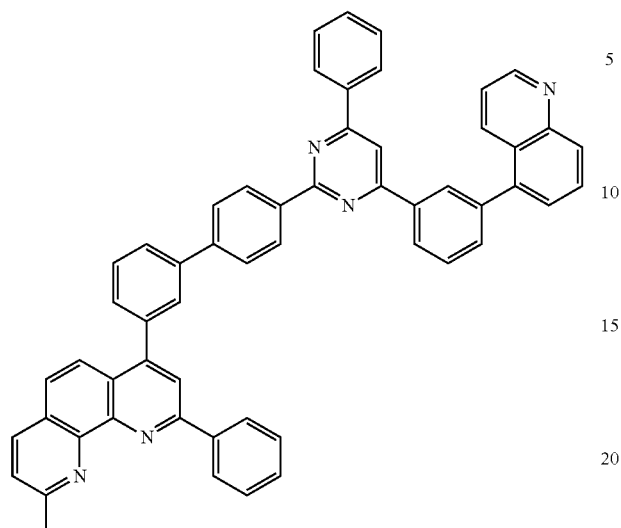
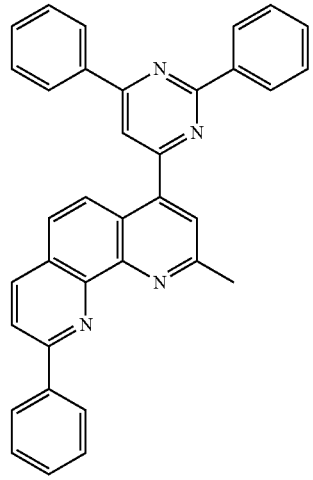
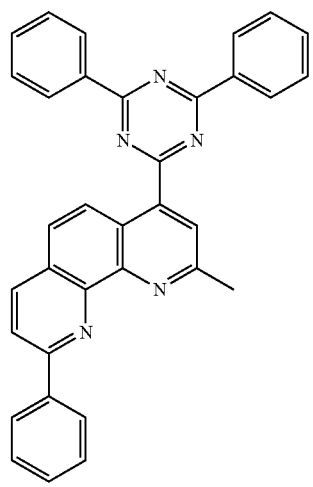

811
-continued
209
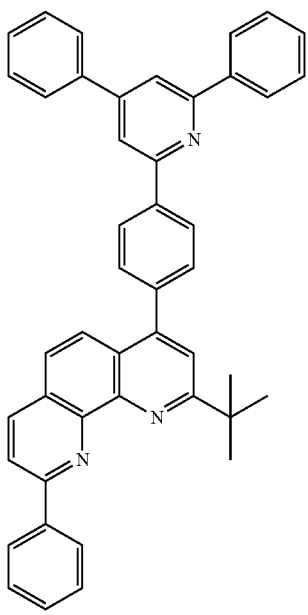
210
812
-continued
211
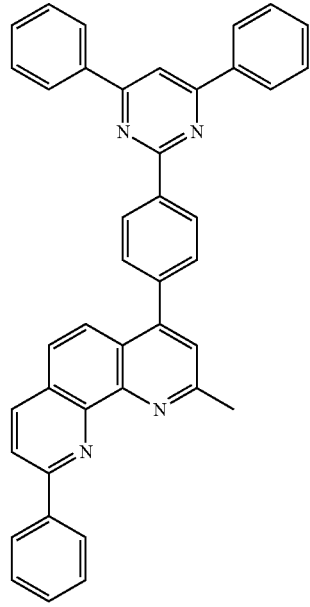
212

213
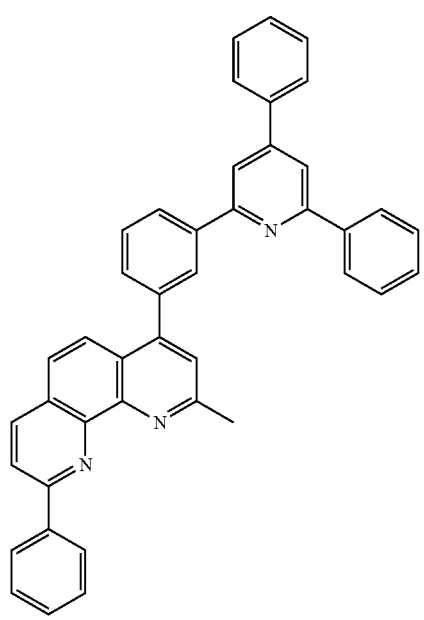
214
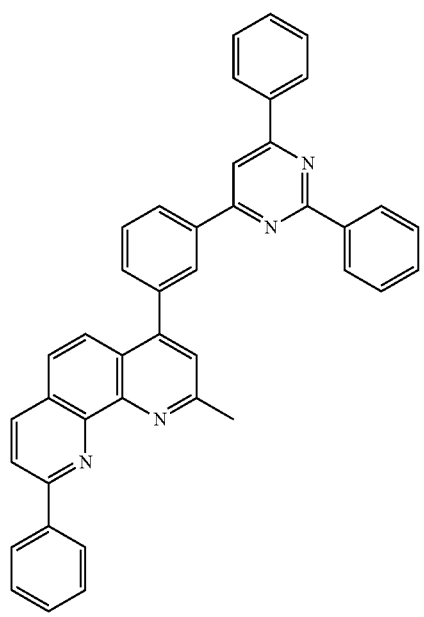
215
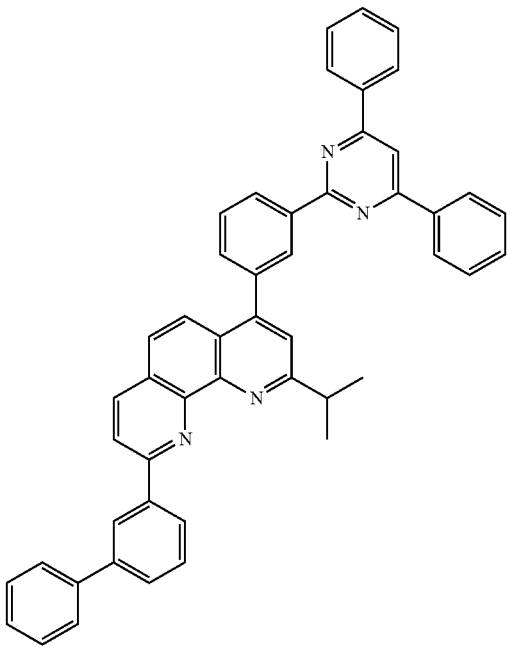
216
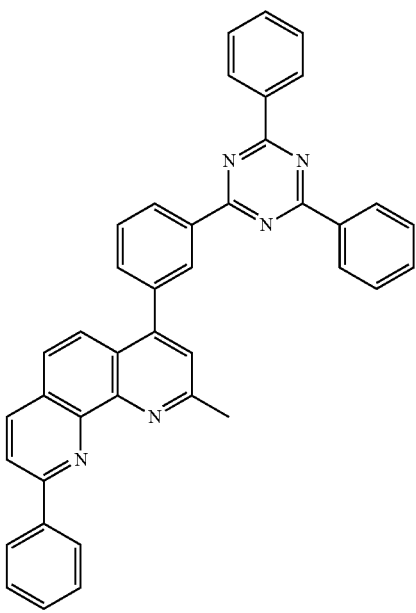

| 217 | 220 |
|---|---|
| 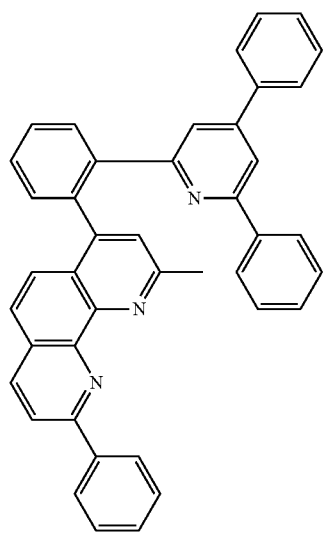 | 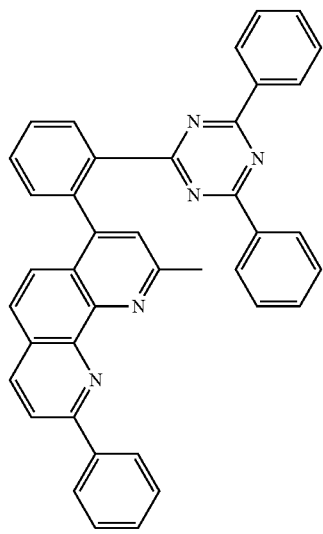 |
| 218 | 221 |
| 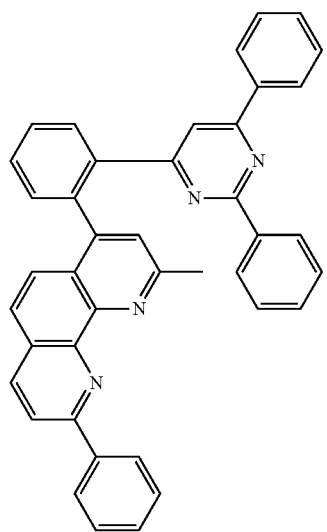 | 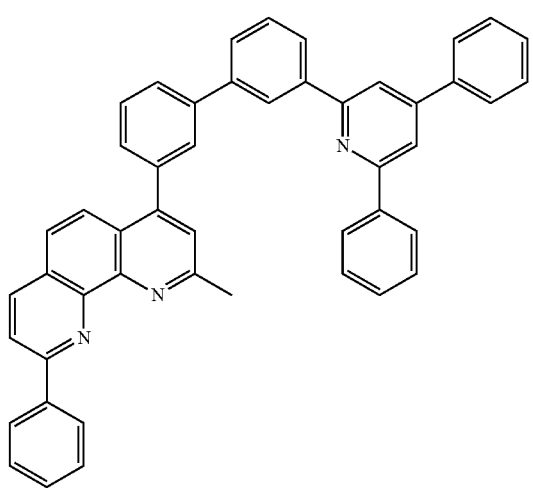 |
| 219 | 222 |
| 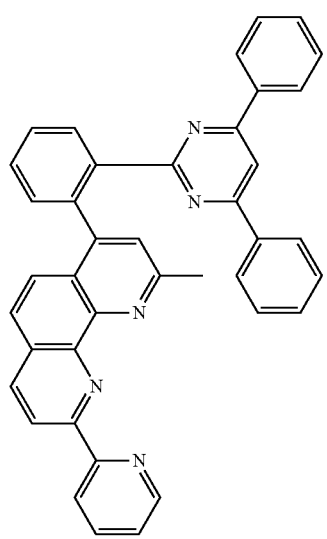 | 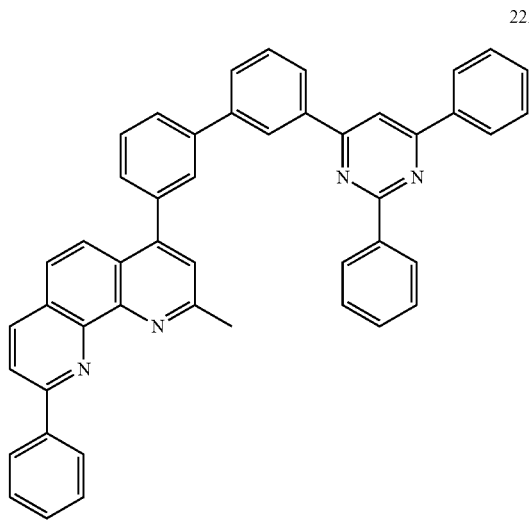 |

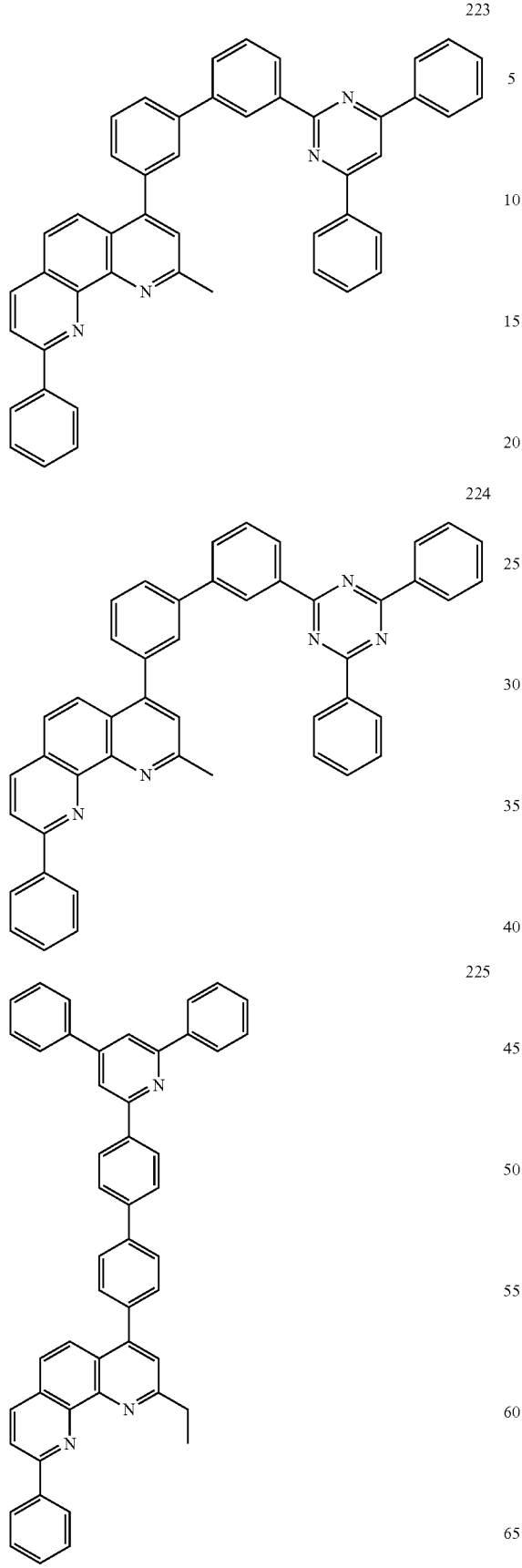

819
-continued
228
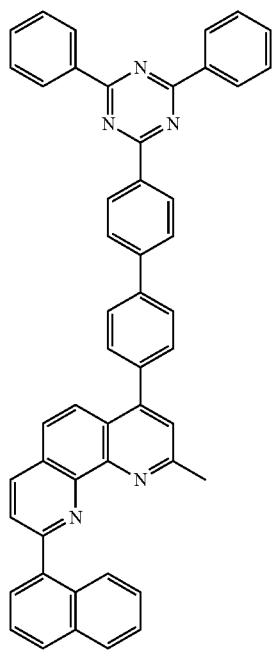
229
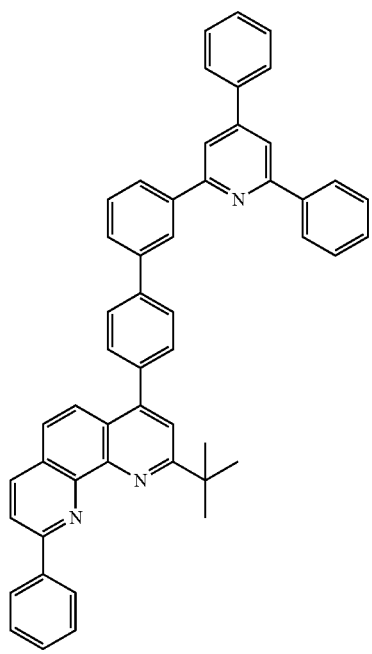
820
-continued
230
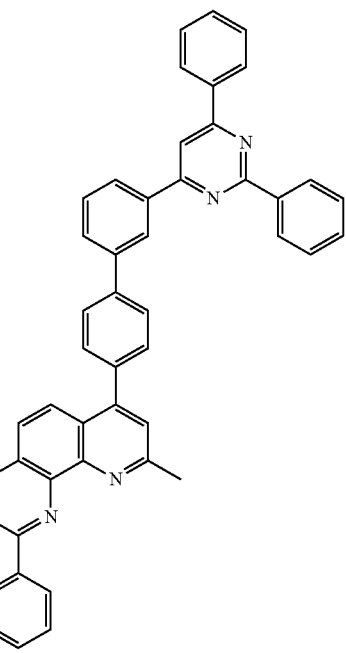
231
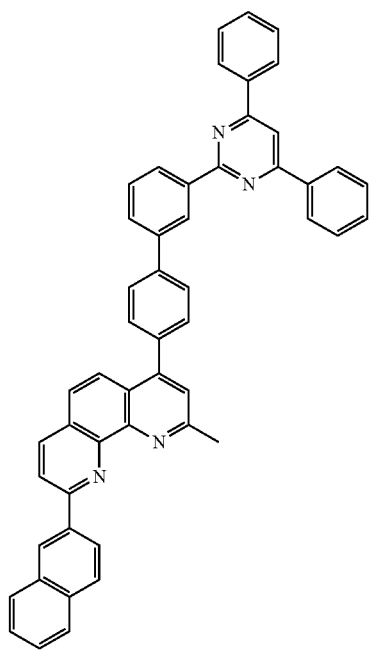

821
-continued
232
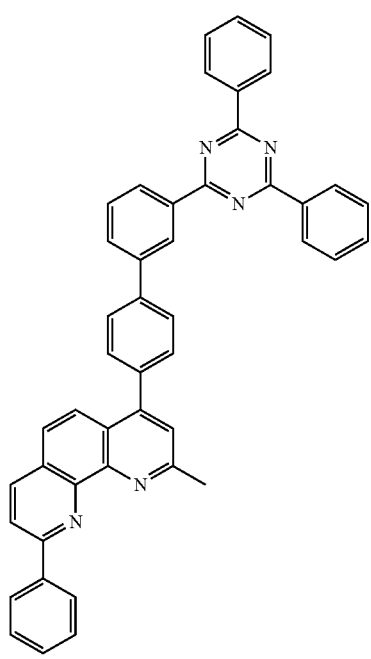
233
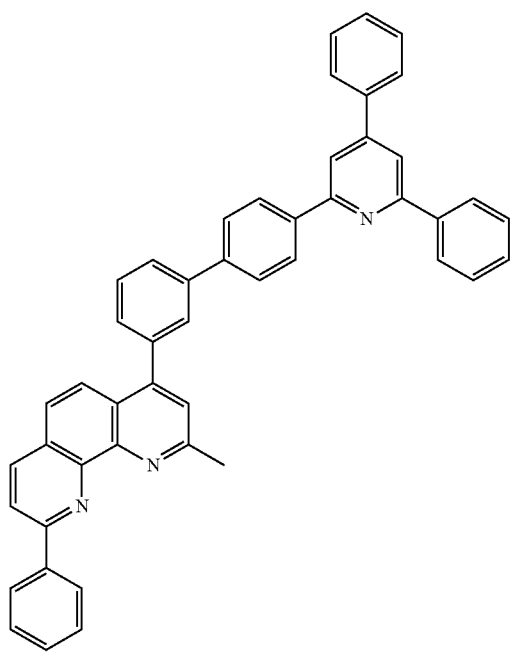
822
-continued
234
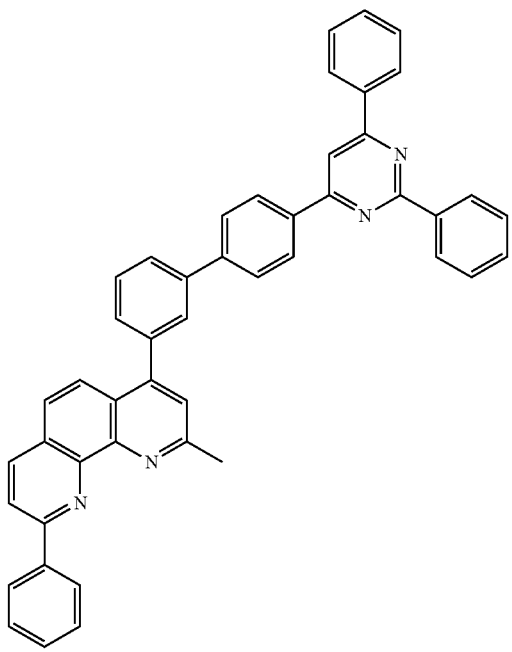
235
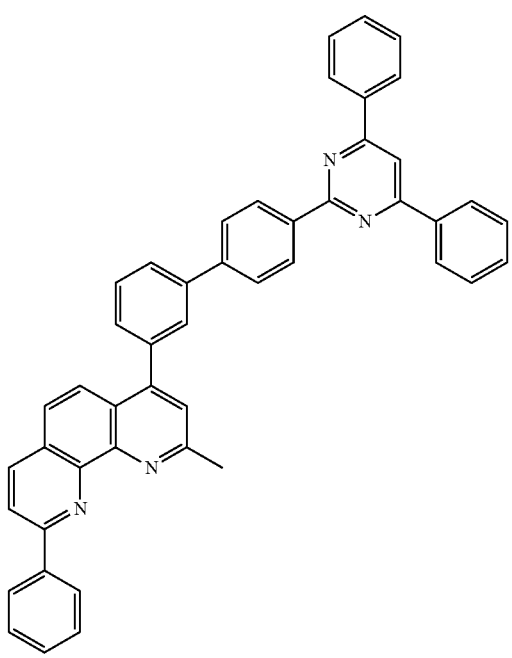

236
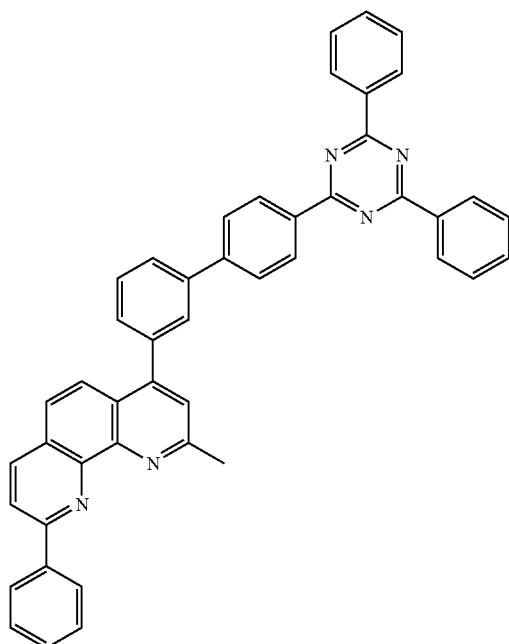
237
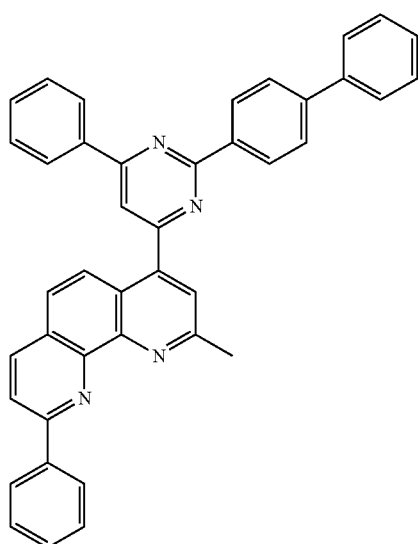
238
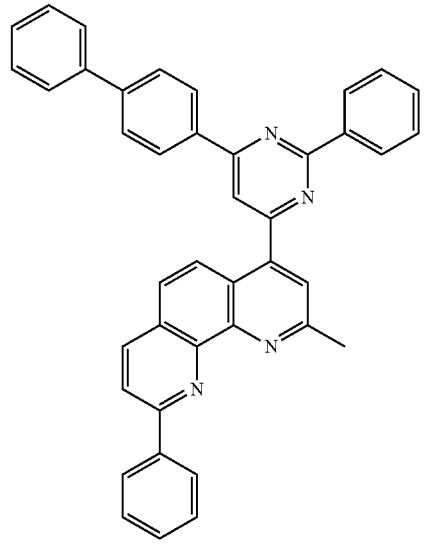
239
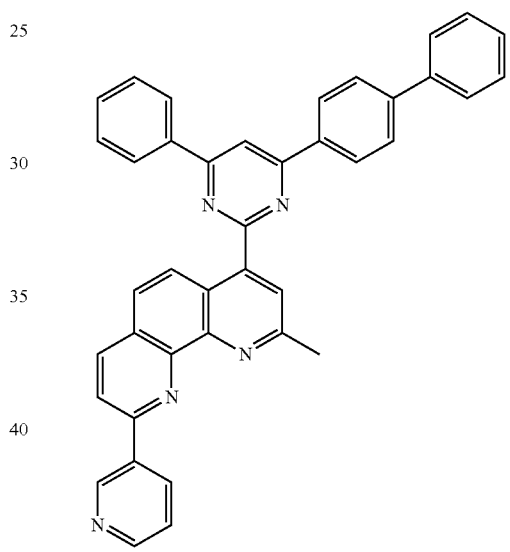
240
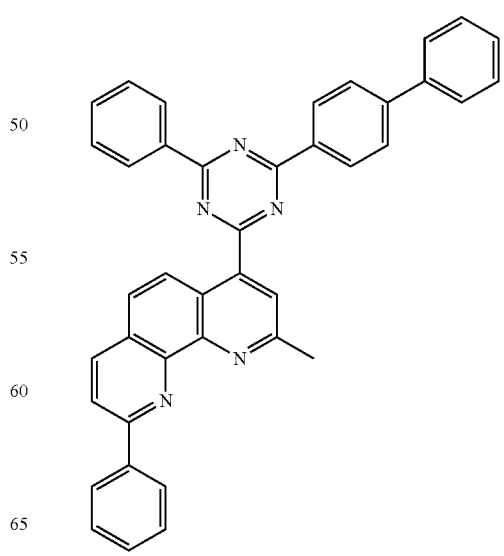

825
-continued
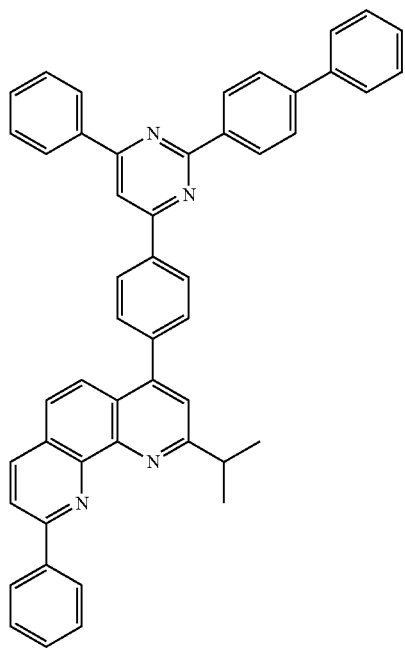
241
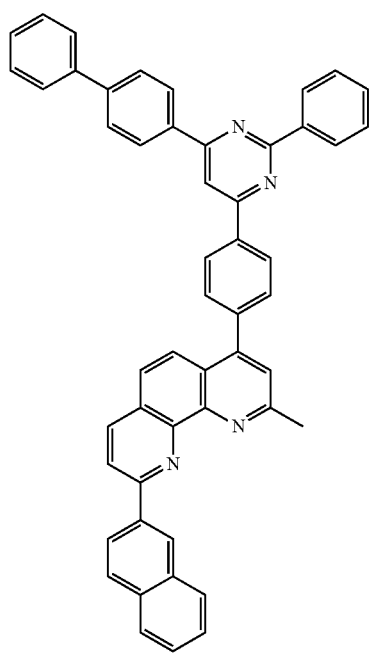
242
826
-continued
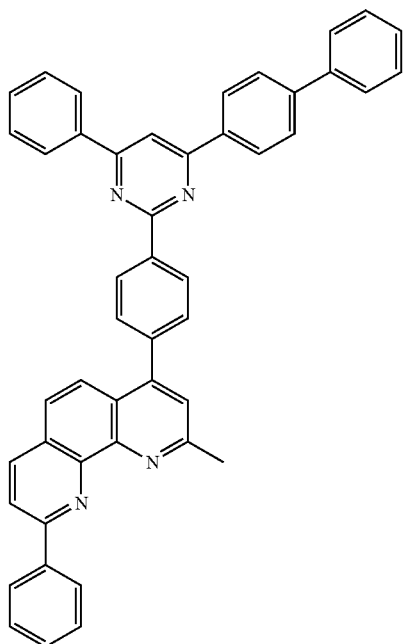
243
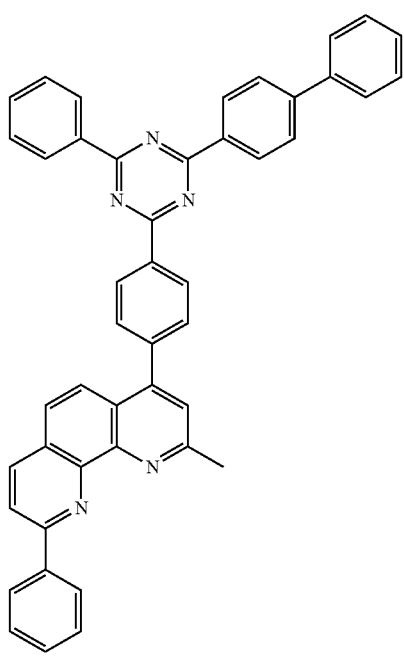
244

245
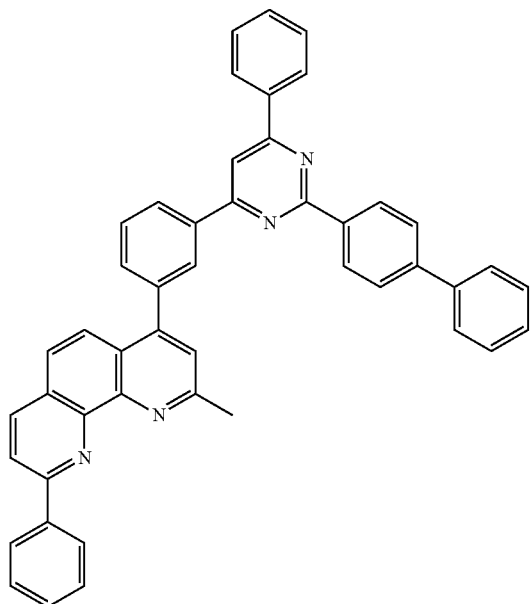
246
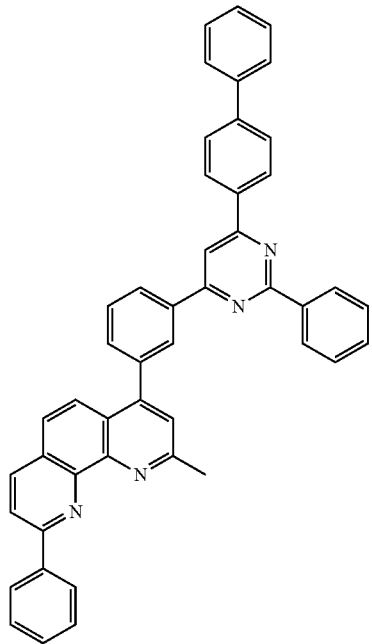
247
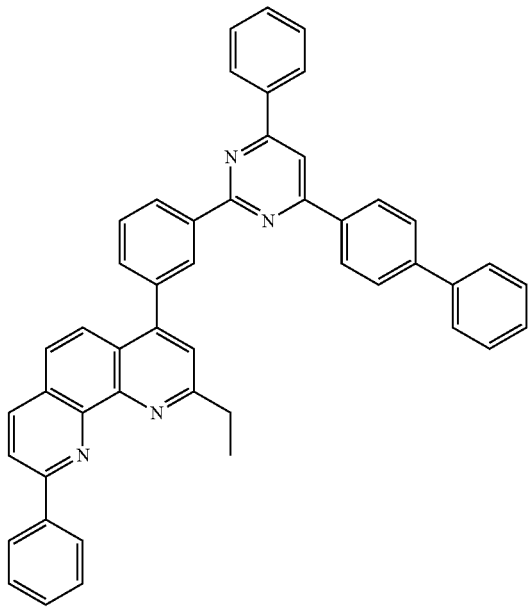
248
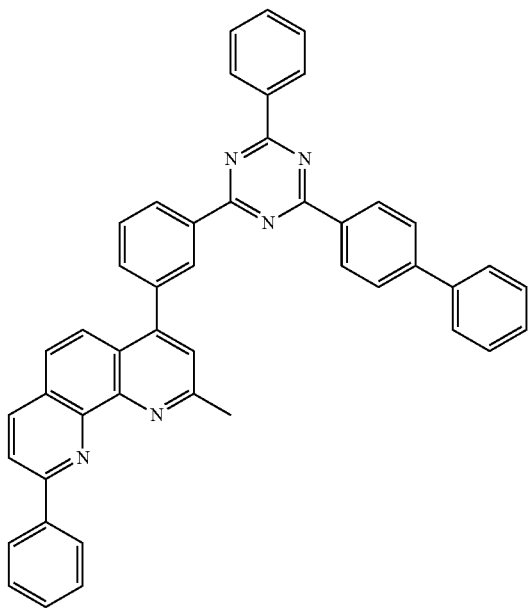

829
-continued
249
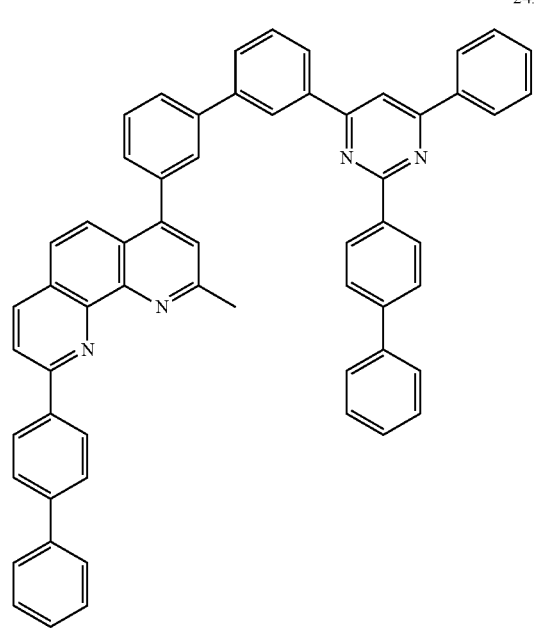
250
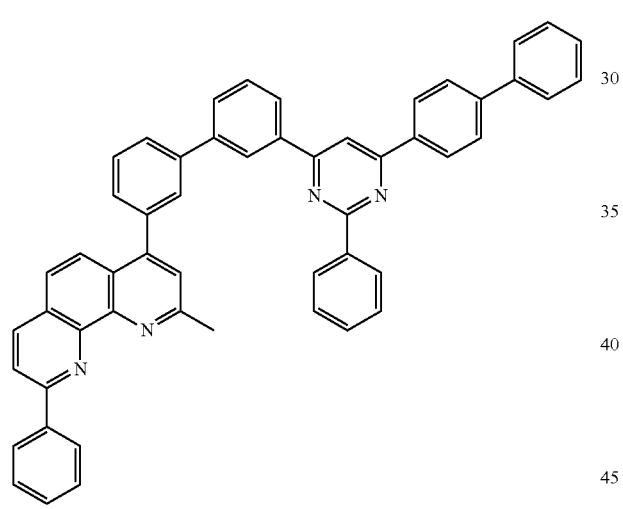
251
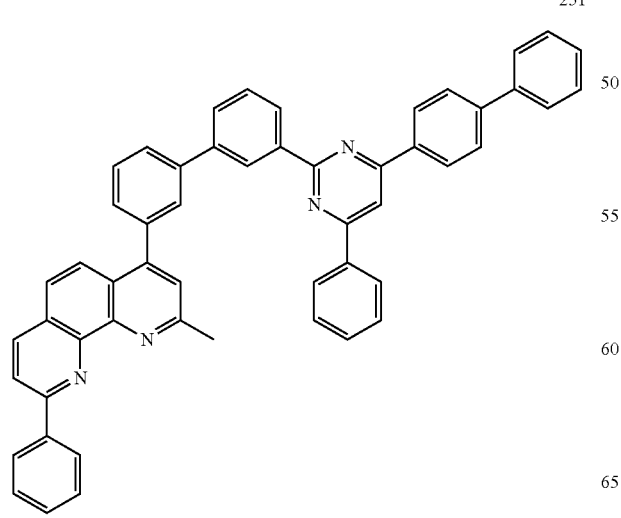
830
-continued
252
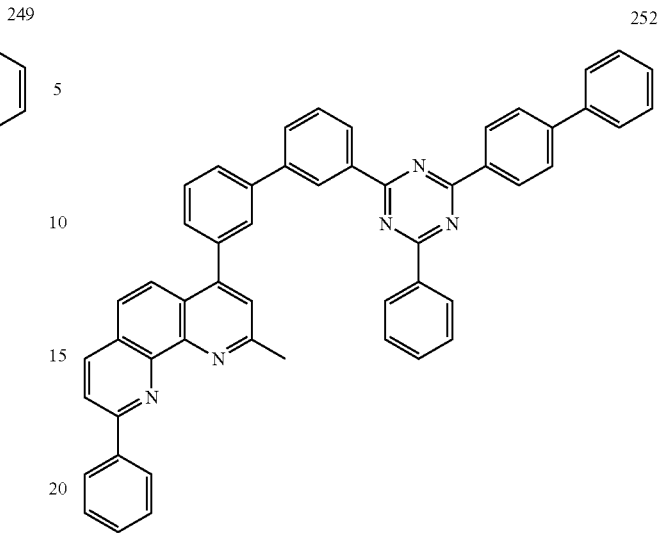
253
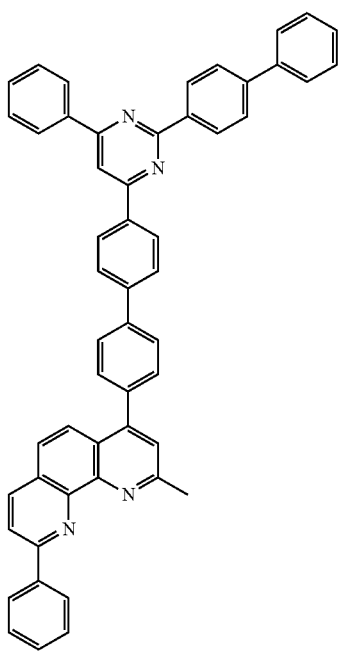

254
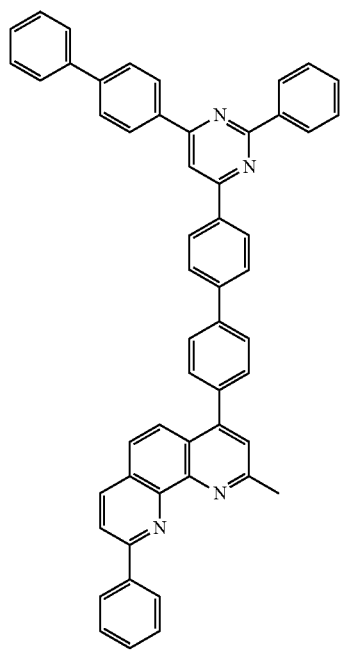
256
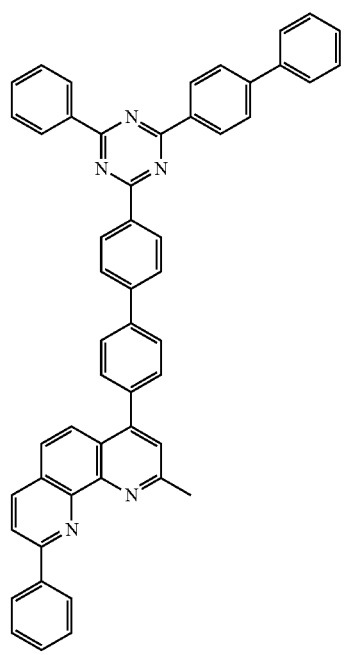
255
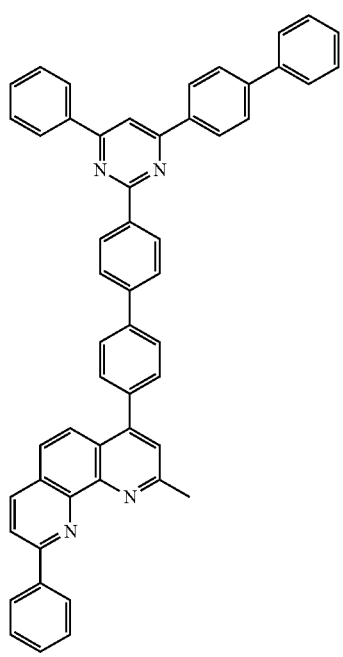
257
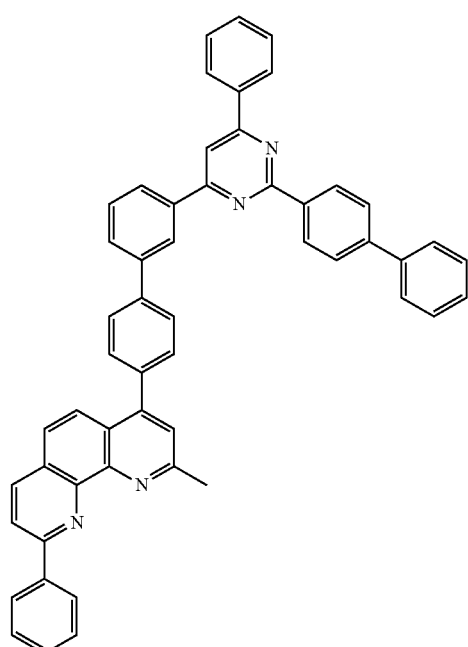

833
-continued
258
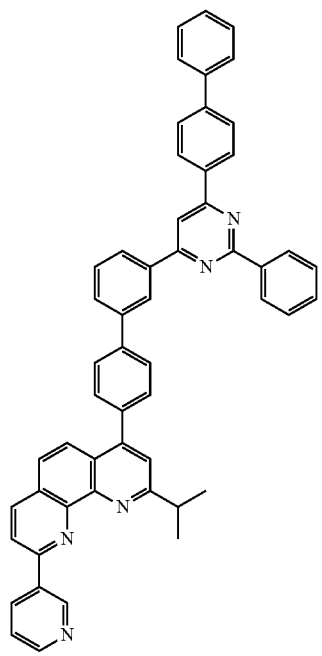
259
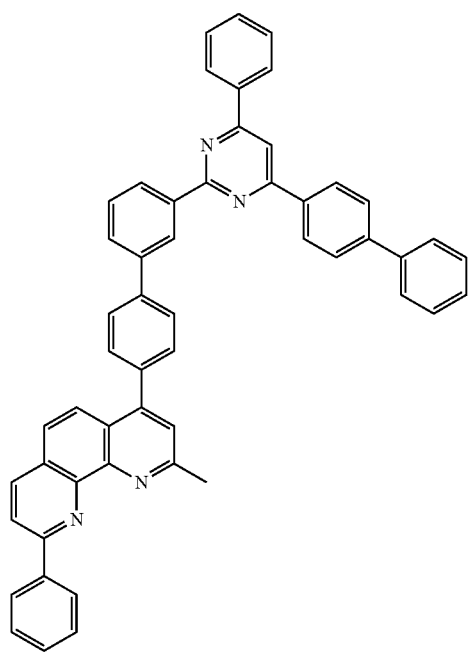
834
-continued
260
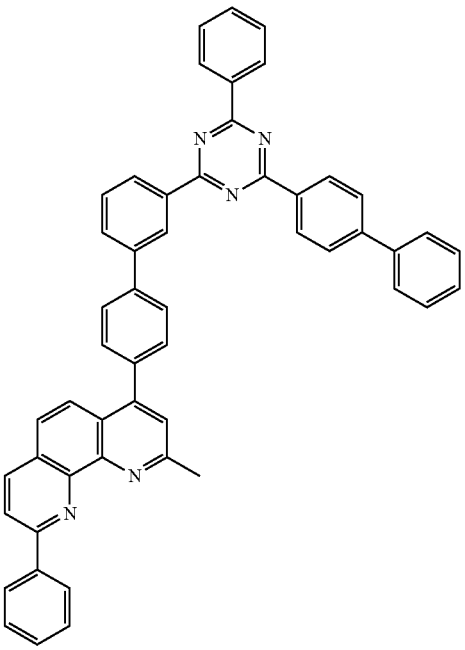
261
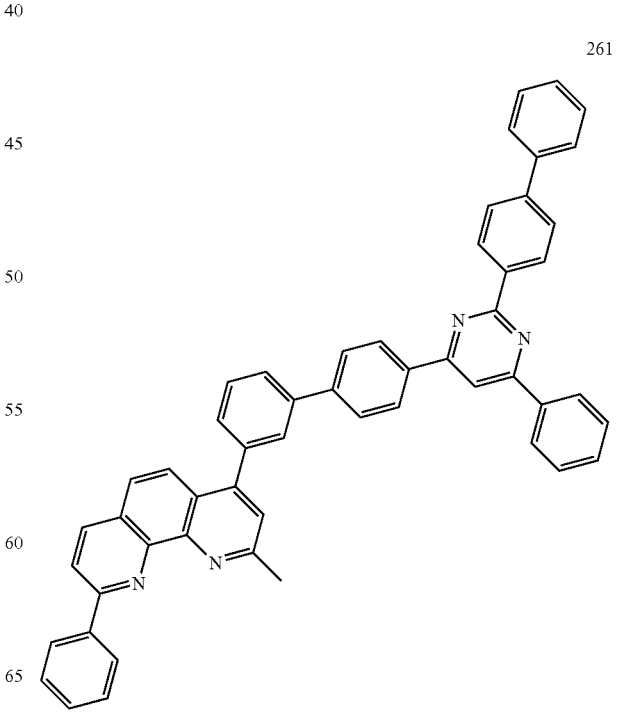

835
-continued
262
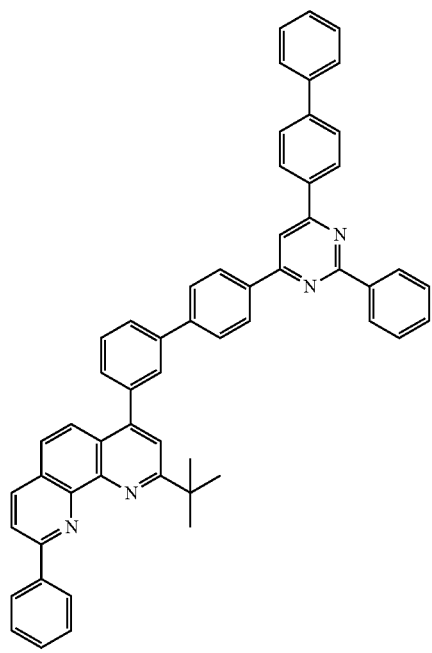
263
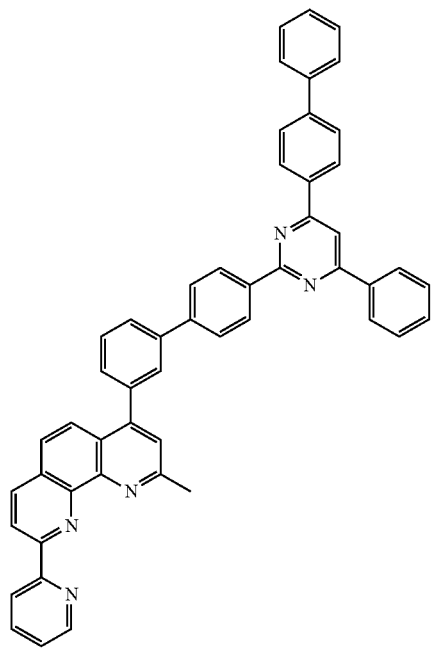
836
-continued
264
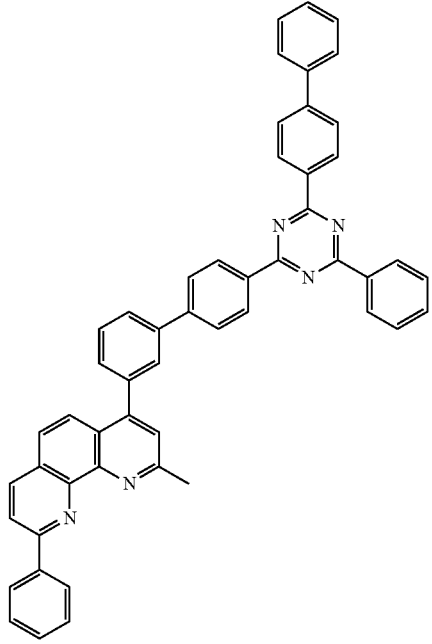
265
266
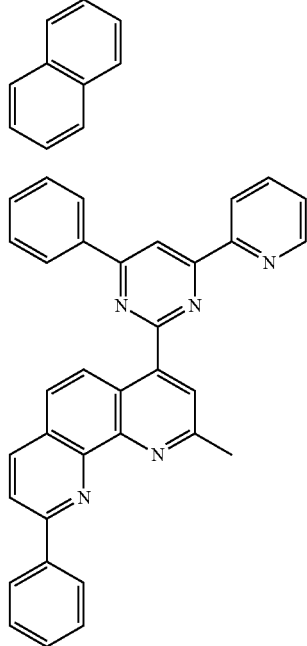

267
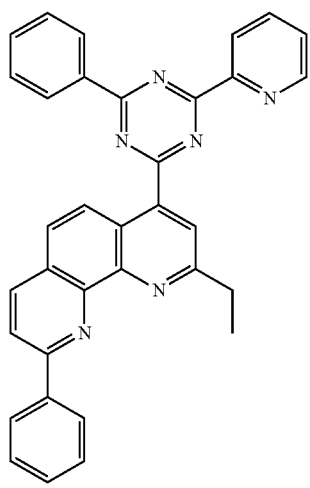
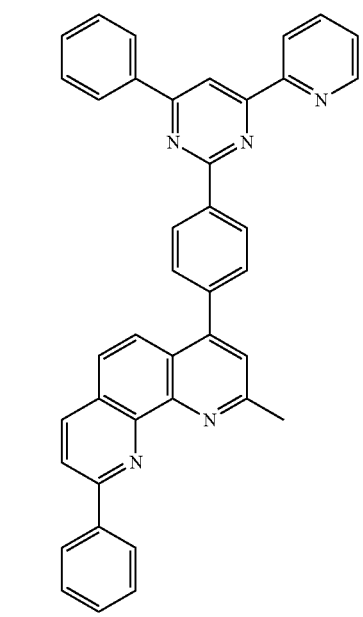
268
269
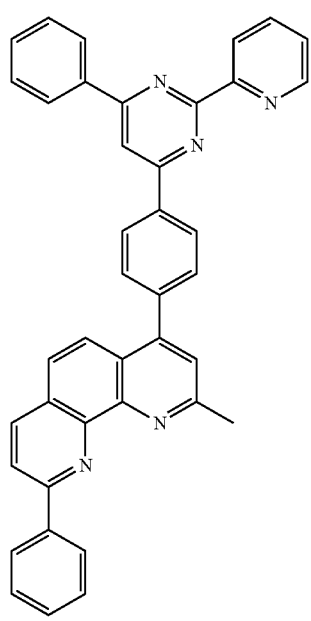
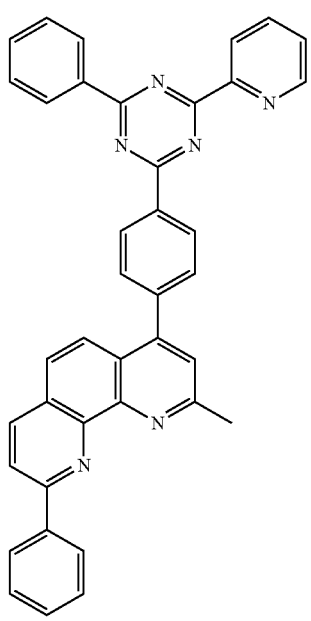
270

271 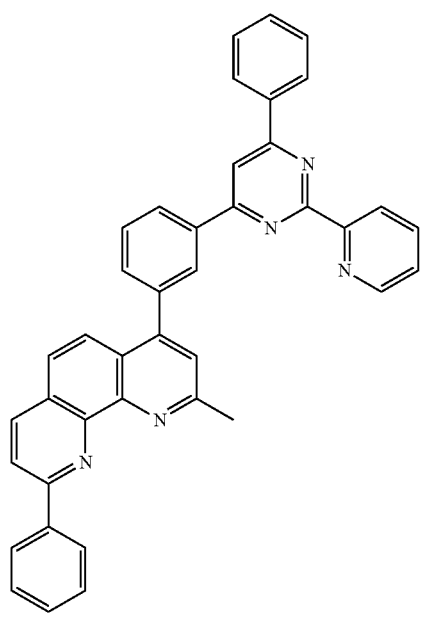
272 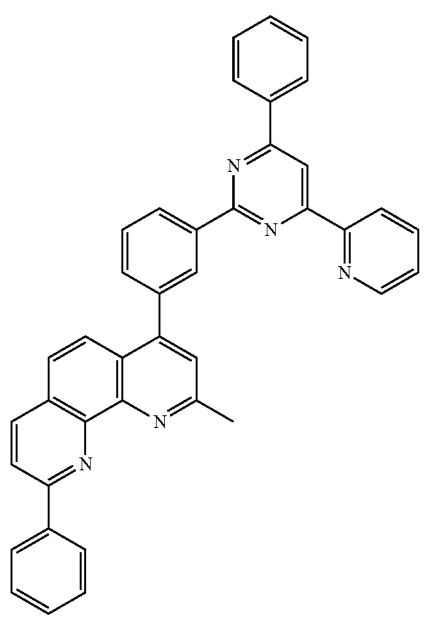
273 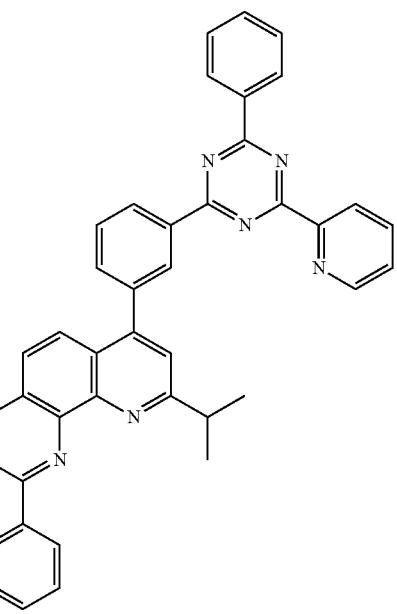
274 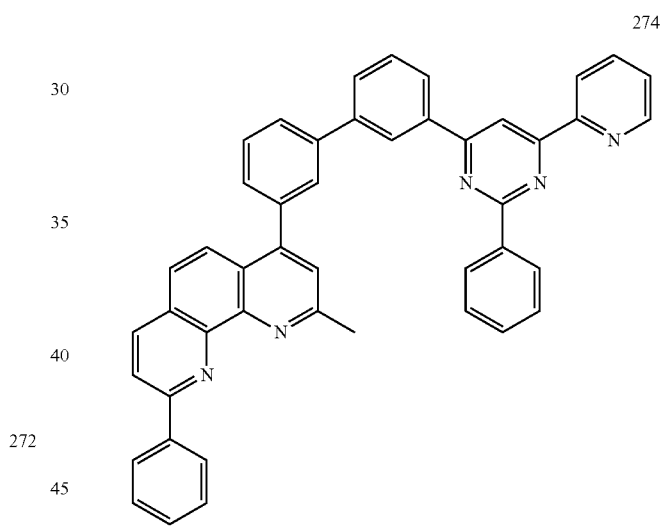
275 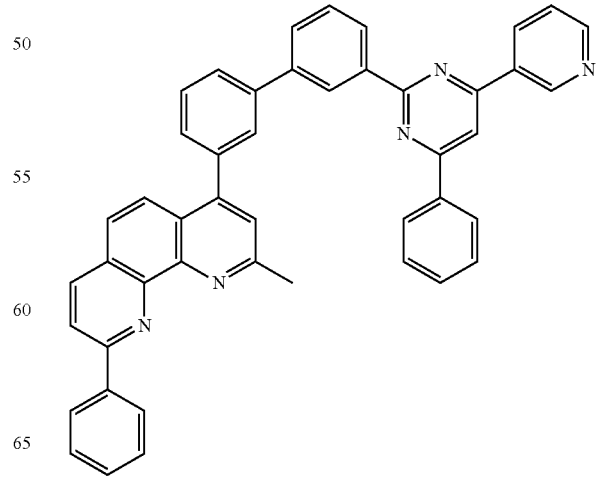

841
-continued
842
-continued
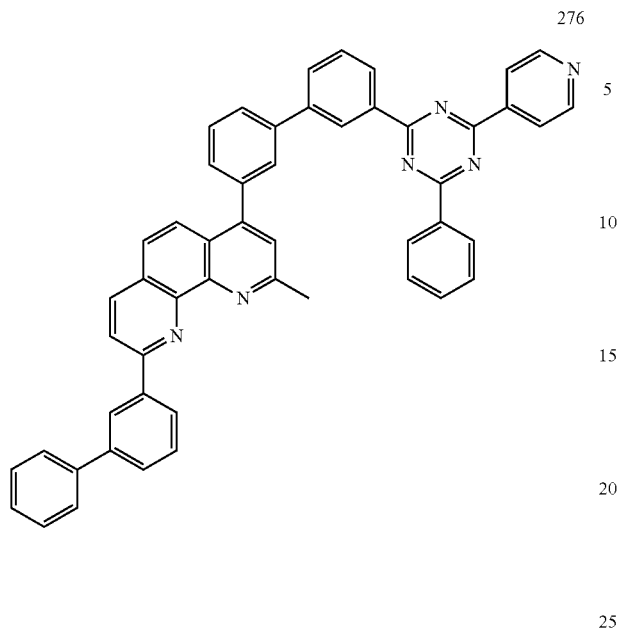
276
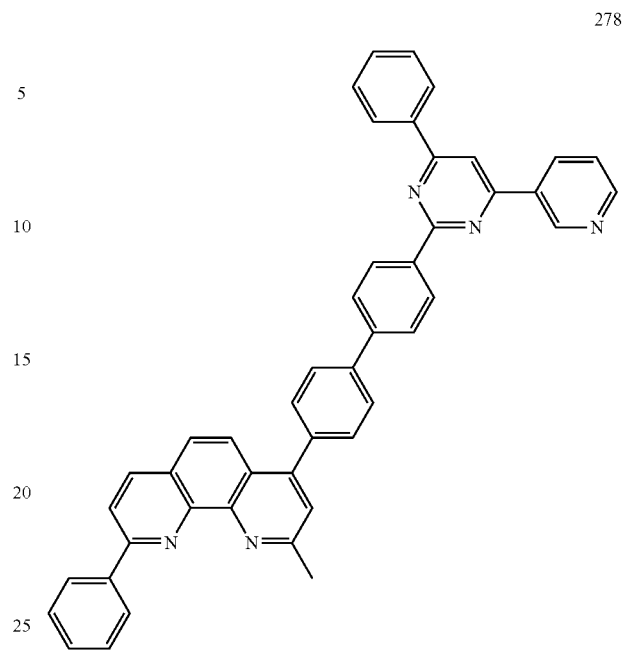
278
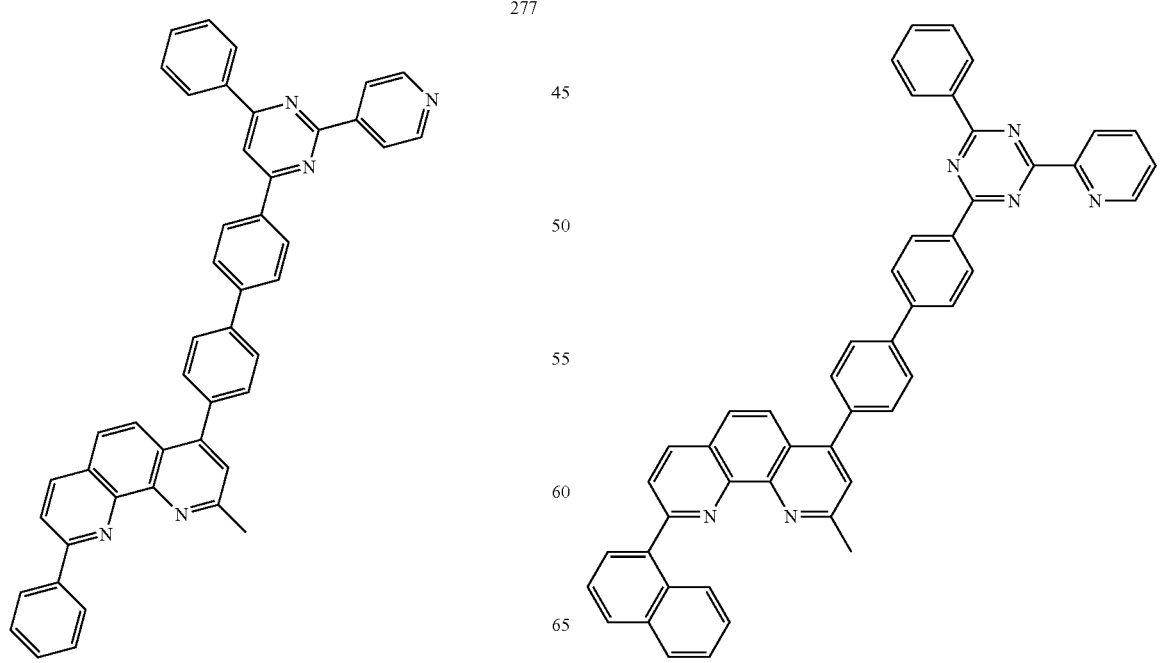

843
-continued
280
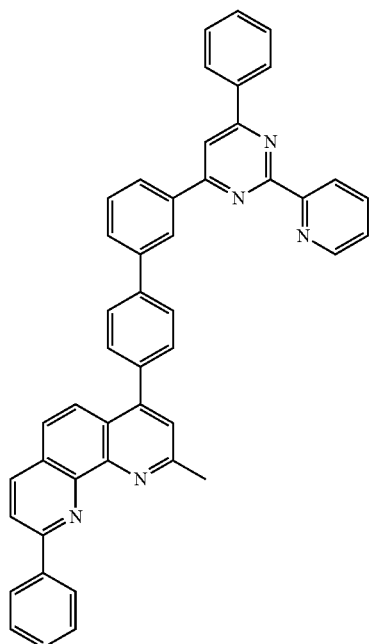
281
844
-continued
282
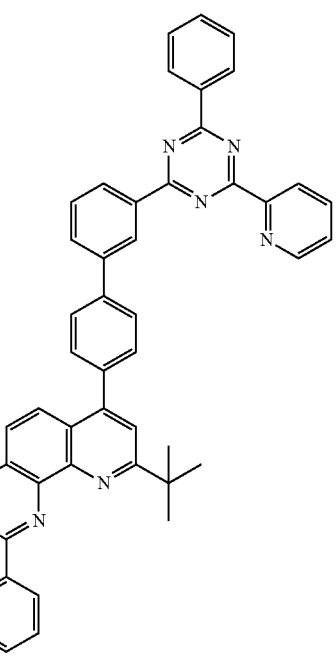
283

845
-continued
284
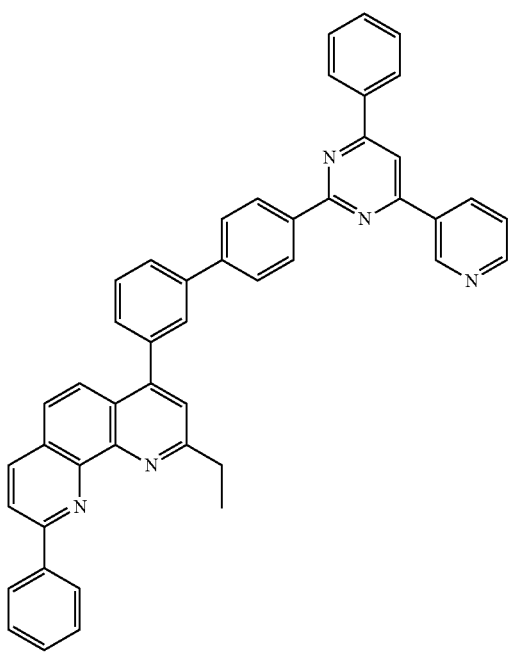
285
846
-continued
286
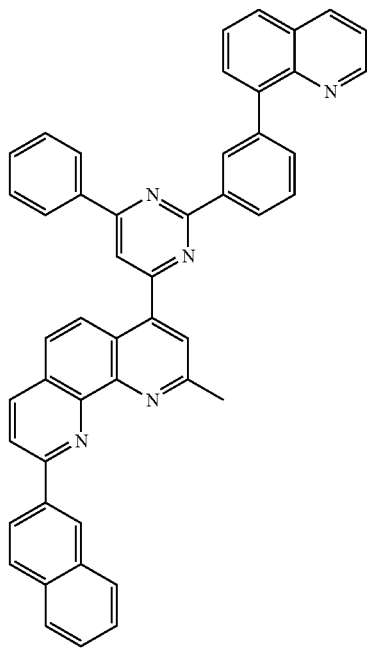
287
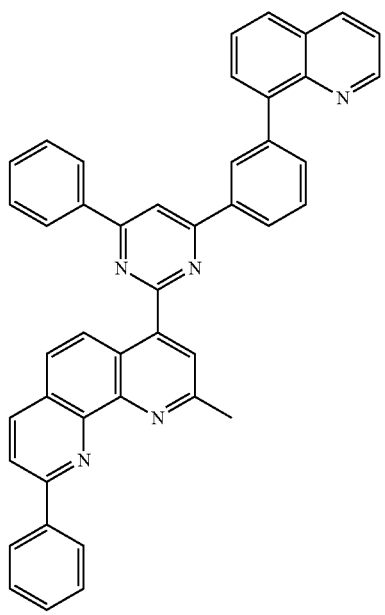

288
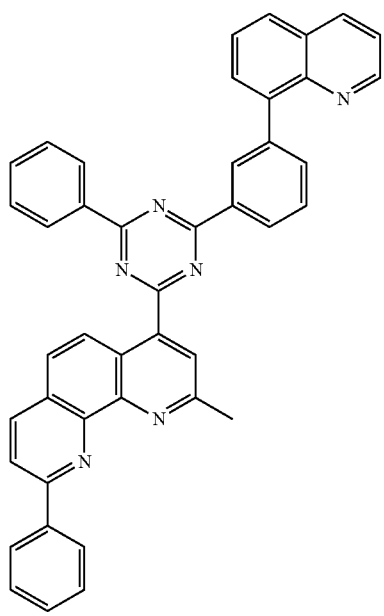
289
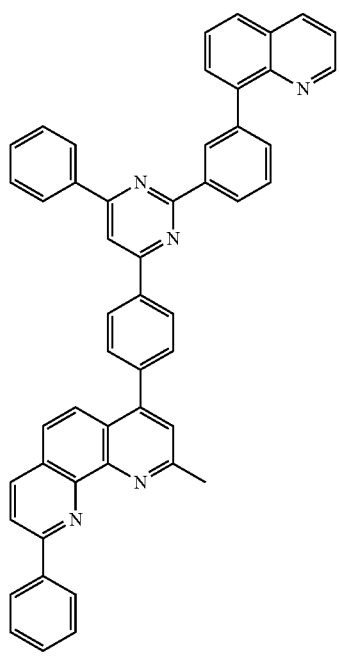
290
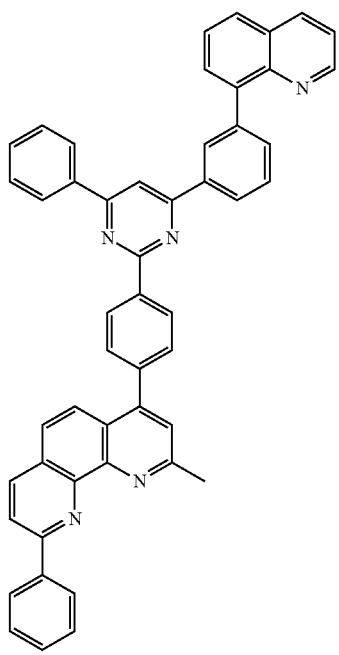
291
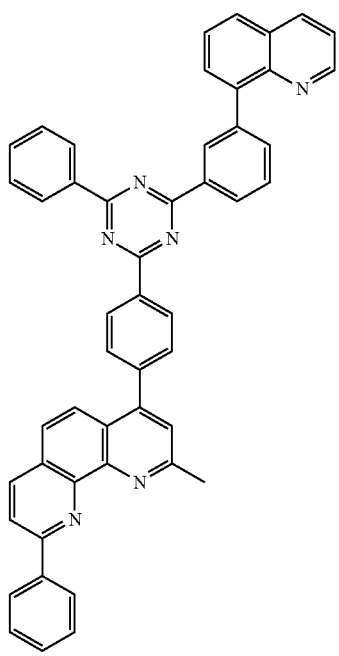

849
-continued
292
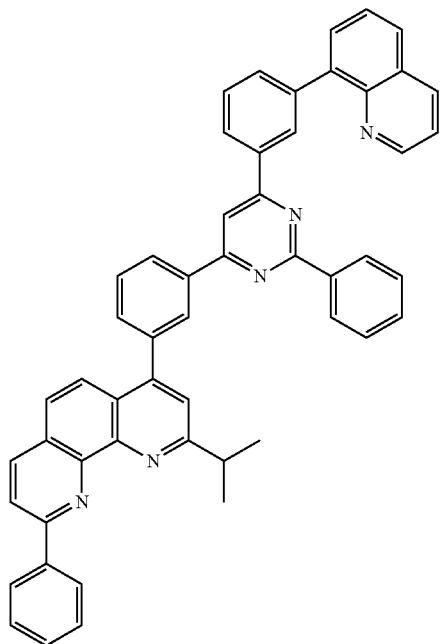
293
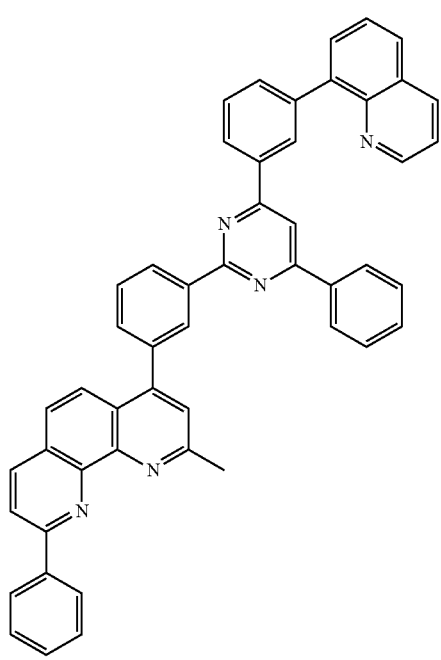
850
-continued
294
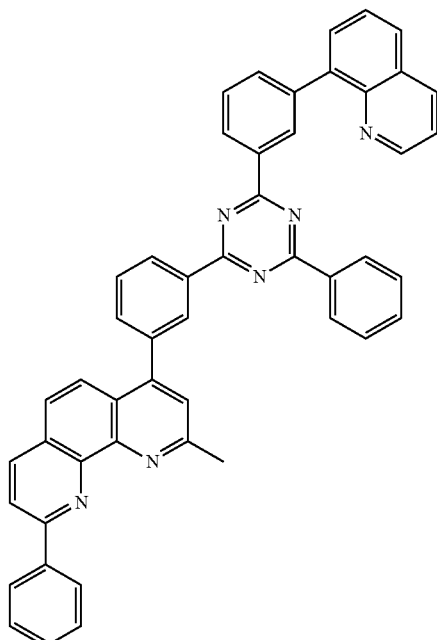
295
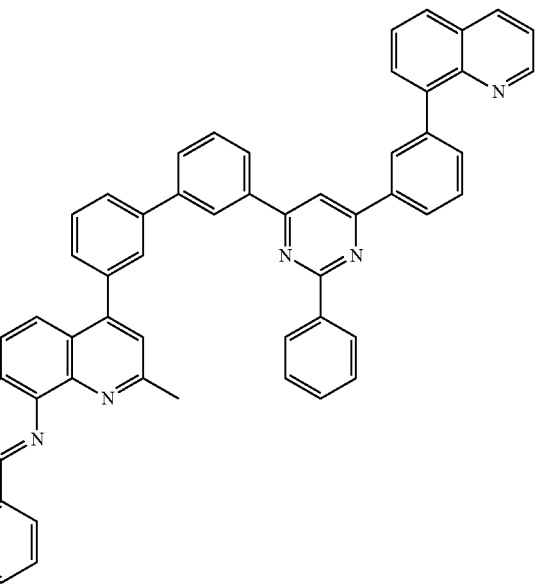

851
-continued
852
-continued
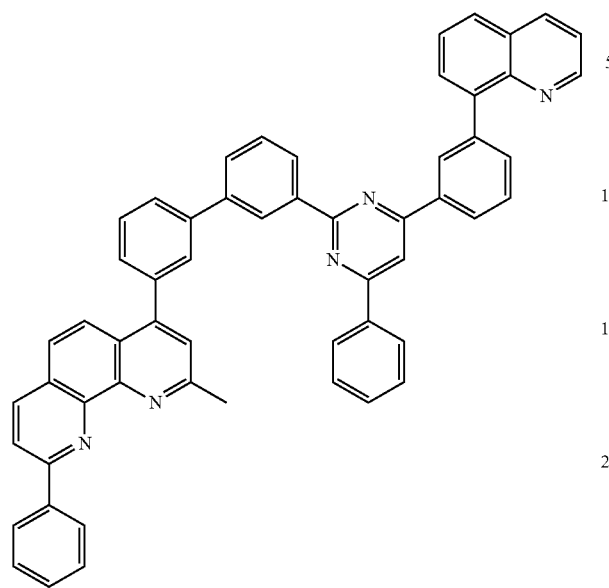
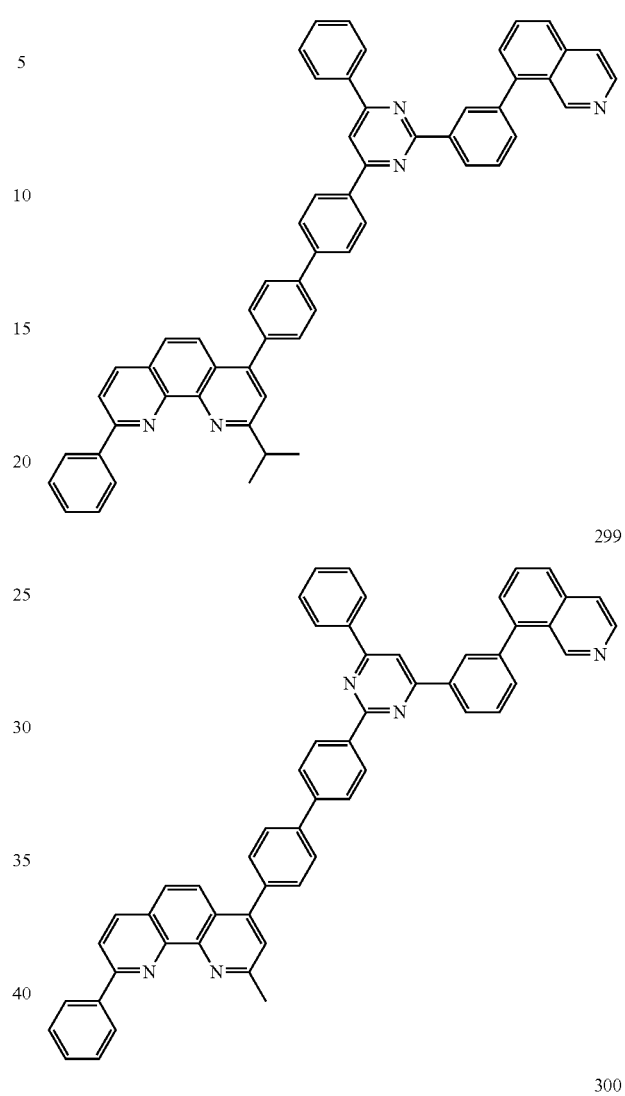

853
-continued
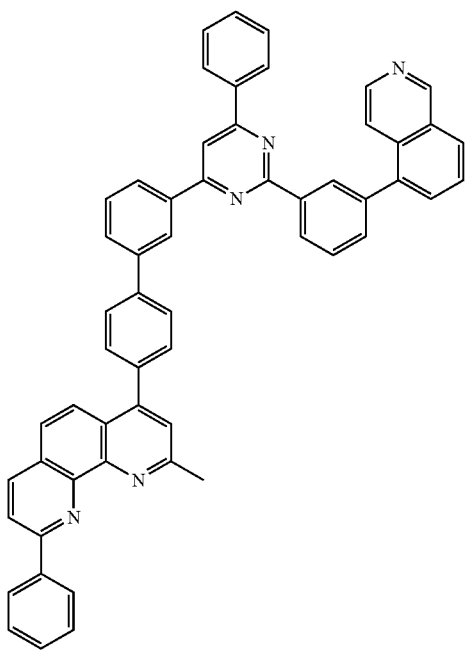
301
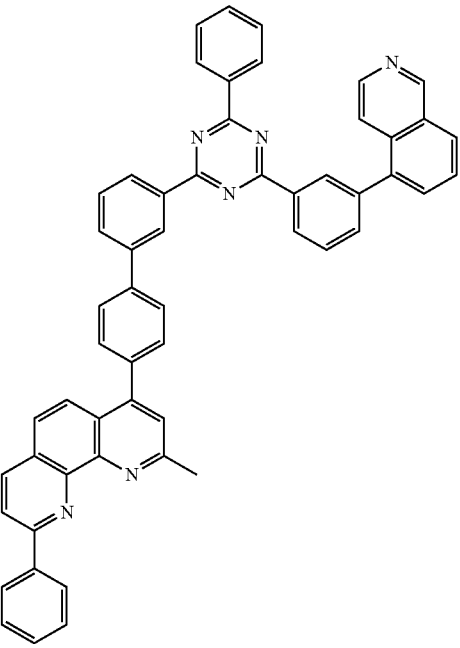
854
-continued
303
302
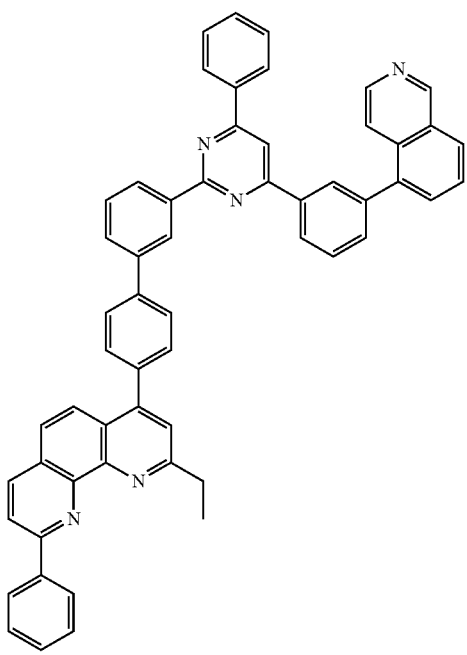
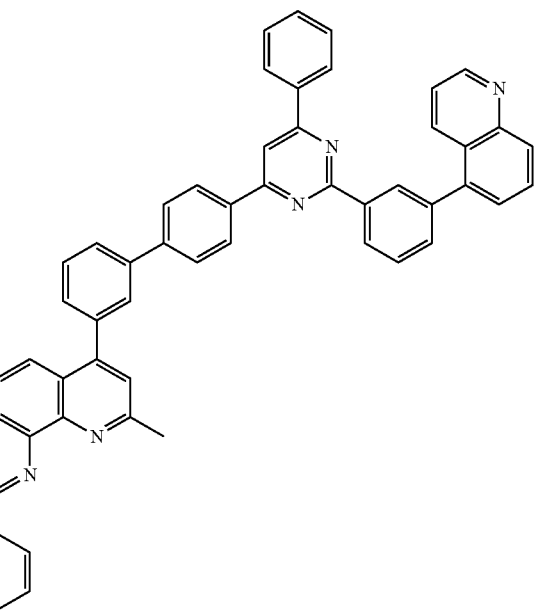
304

855-continued
305
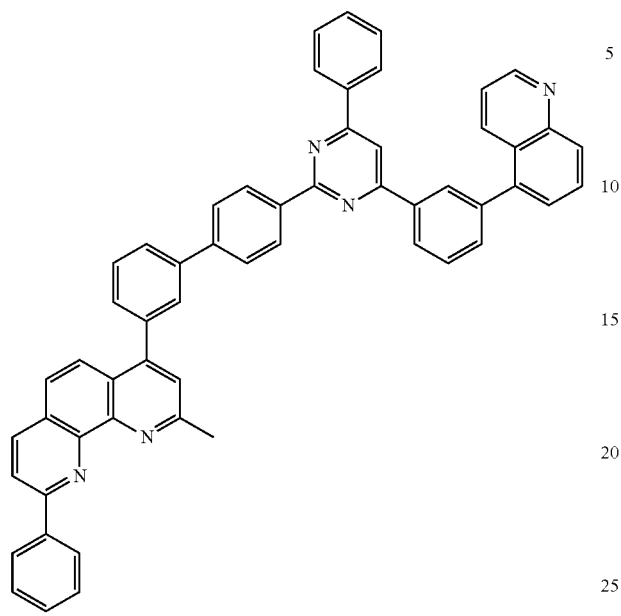
306
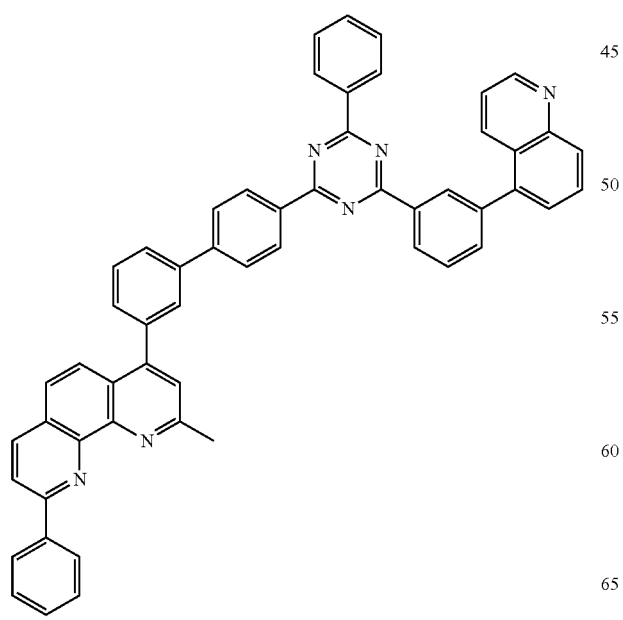
856-continued
307
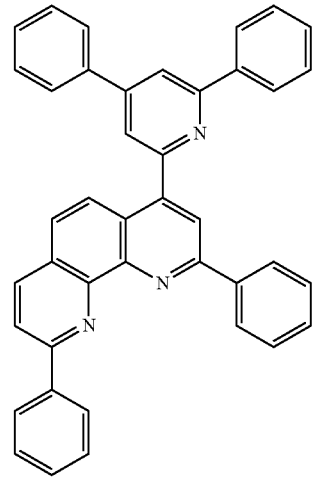
308
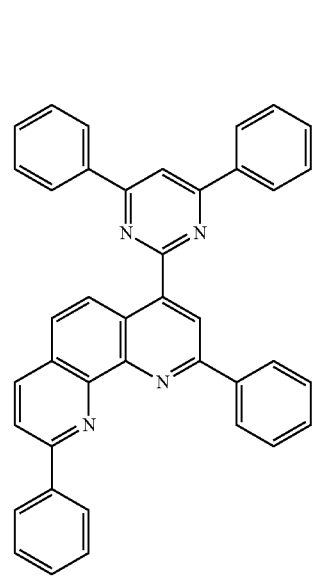
309

857
-continued
310
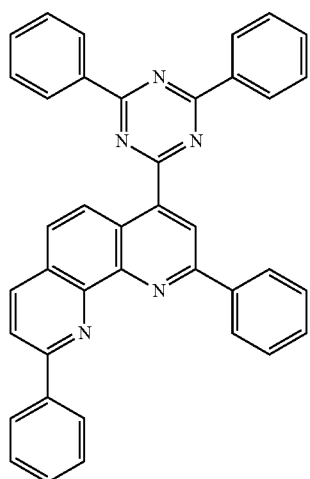
311
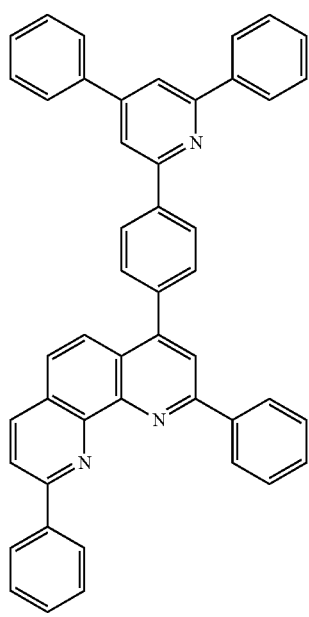
858
-continued
312
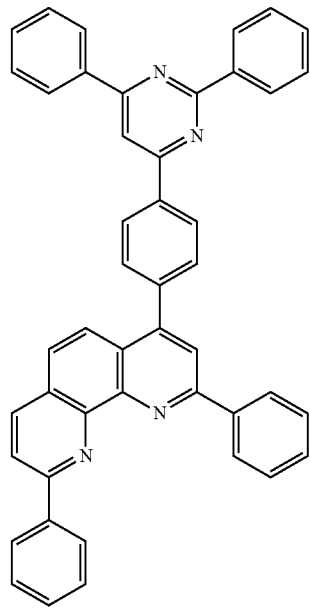
313
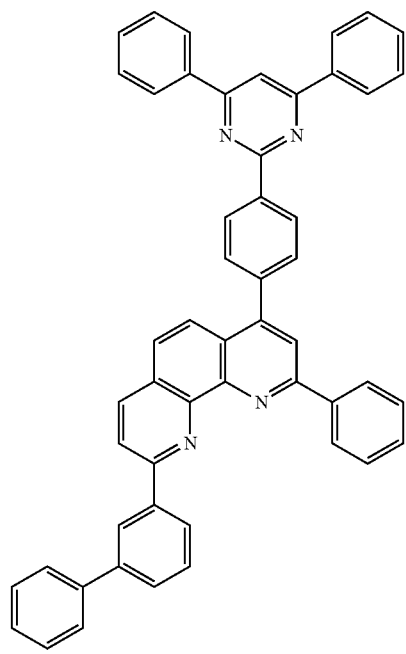

859 -continued
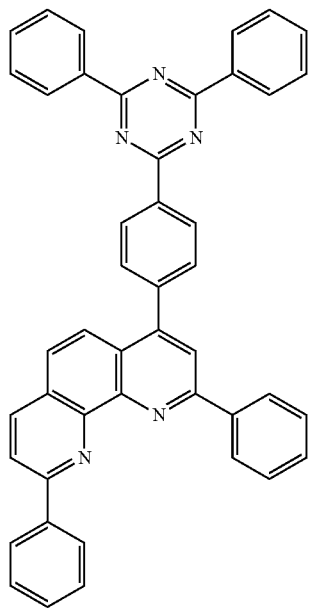
314
860 -continued
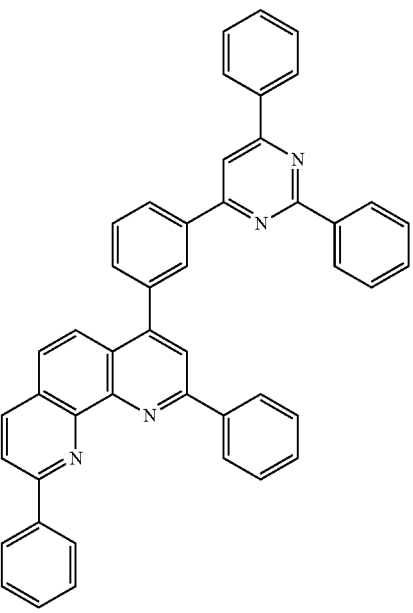
316
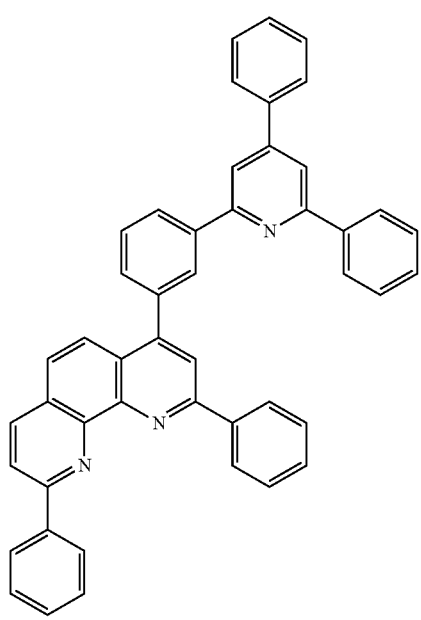
315
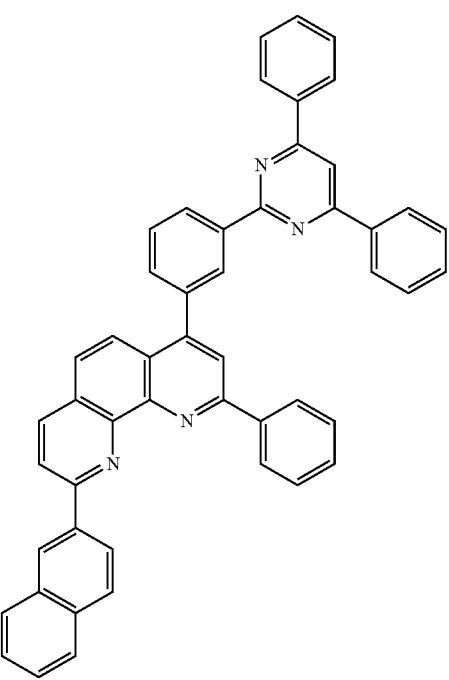
317

318
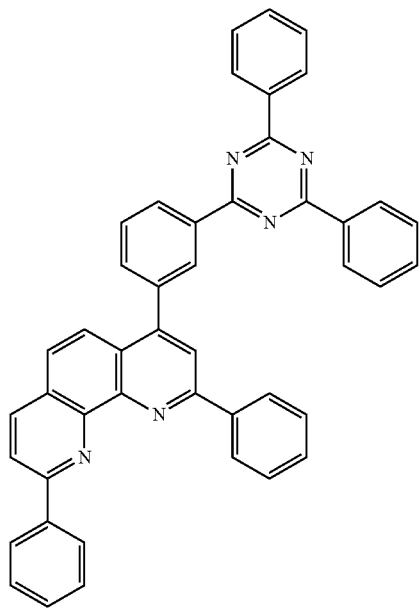
319
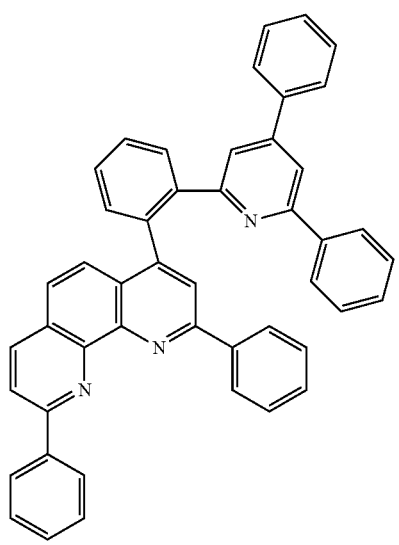
320
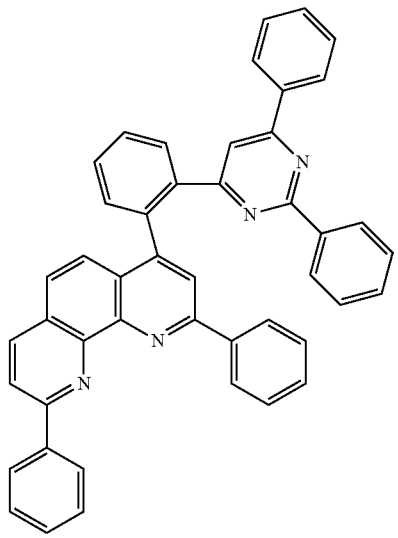
321
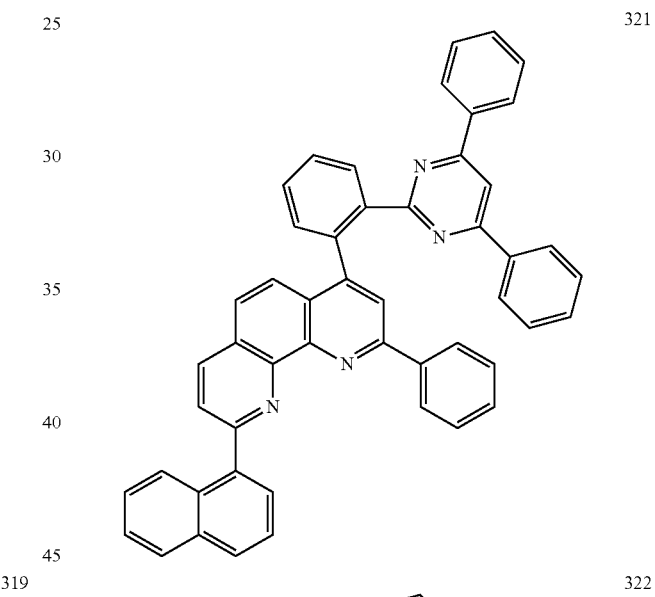
322
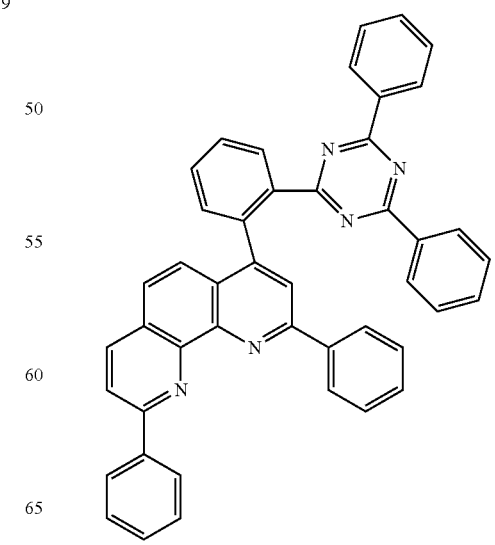

863
-continued
323
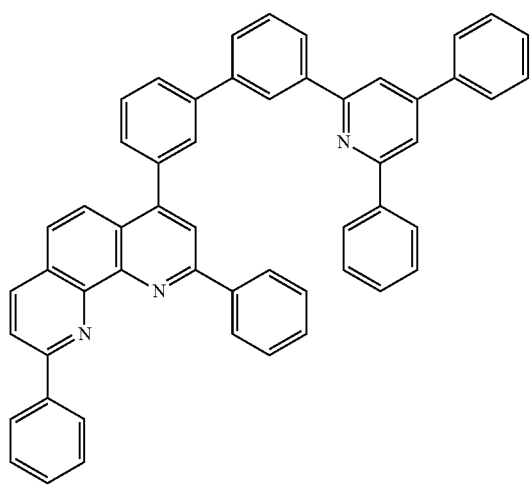
324
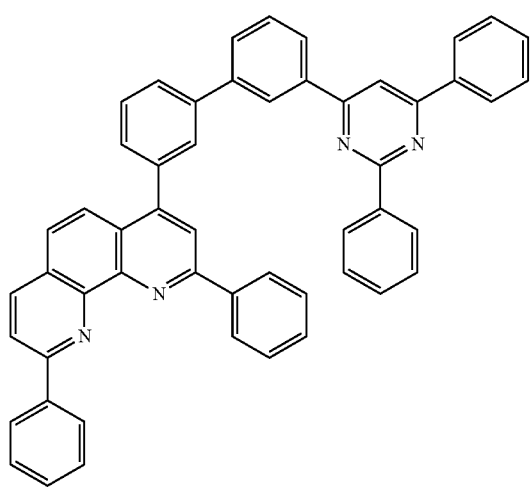
325
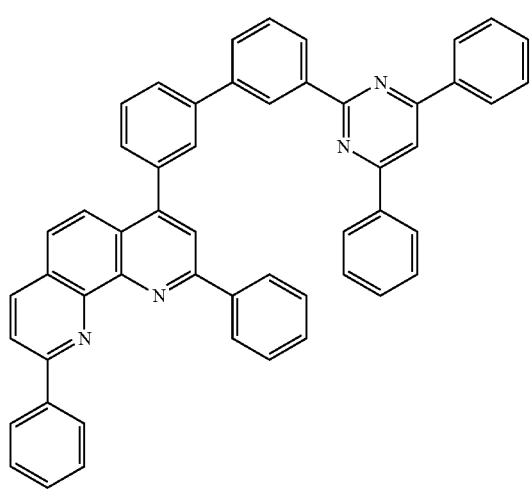
864
-continued
326
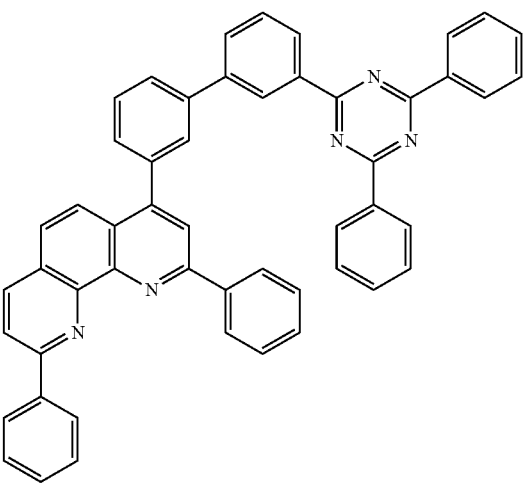
327
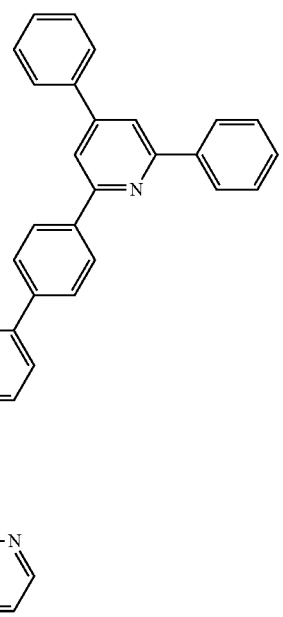

865
-continued
328
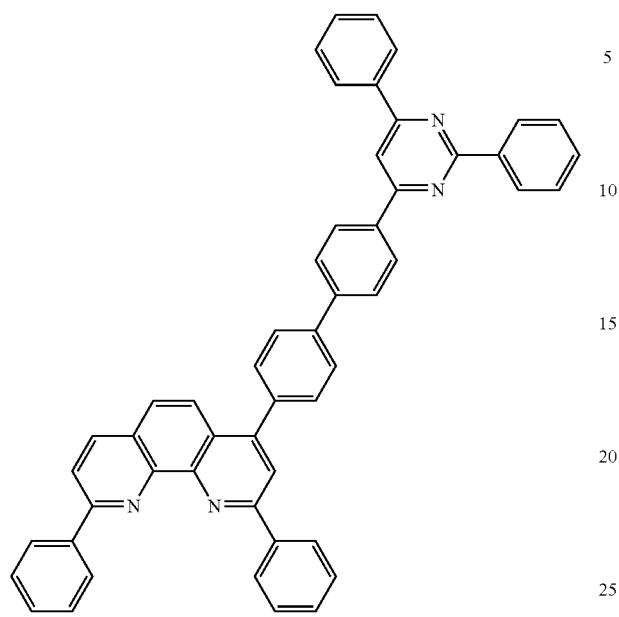
329
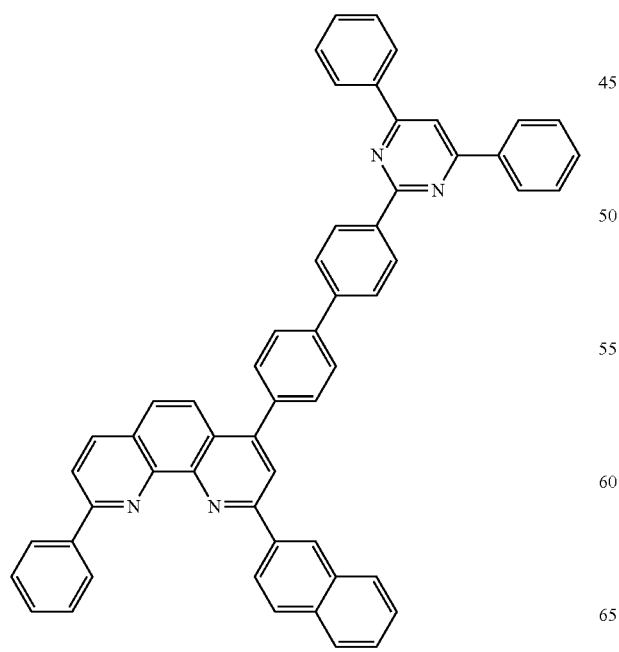
866
-continued
330
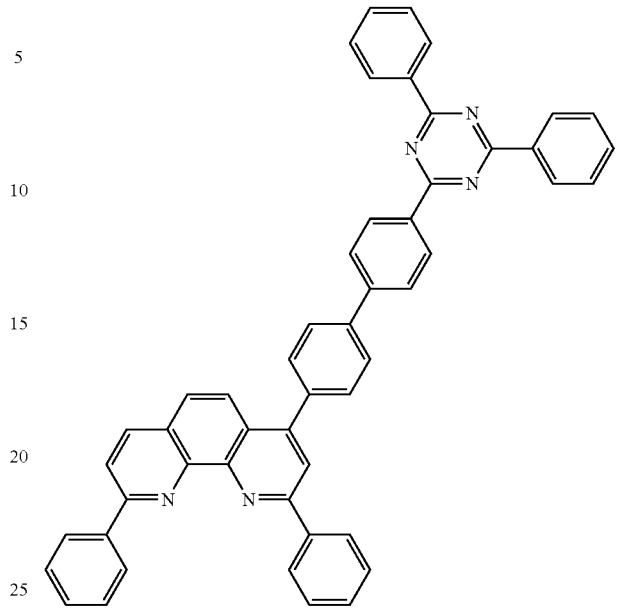
331
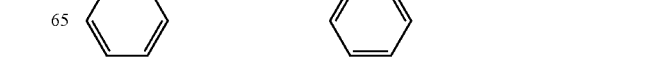

867
-continued
332
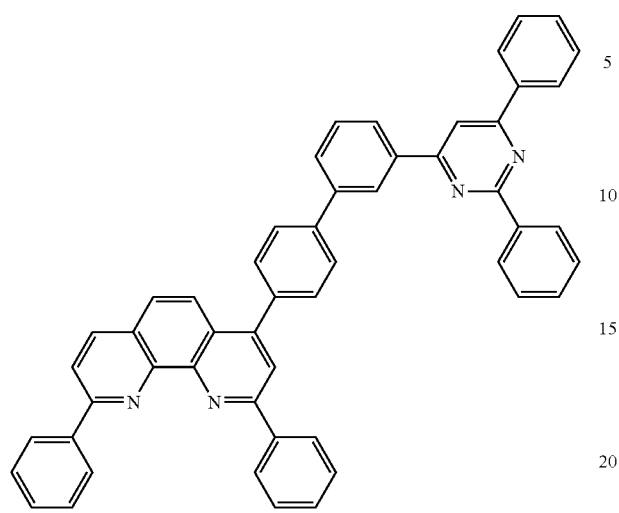
333
334
868
-continued
335
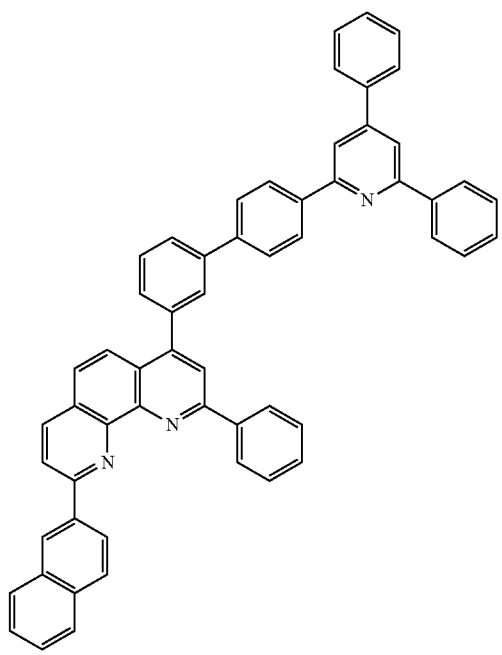
336
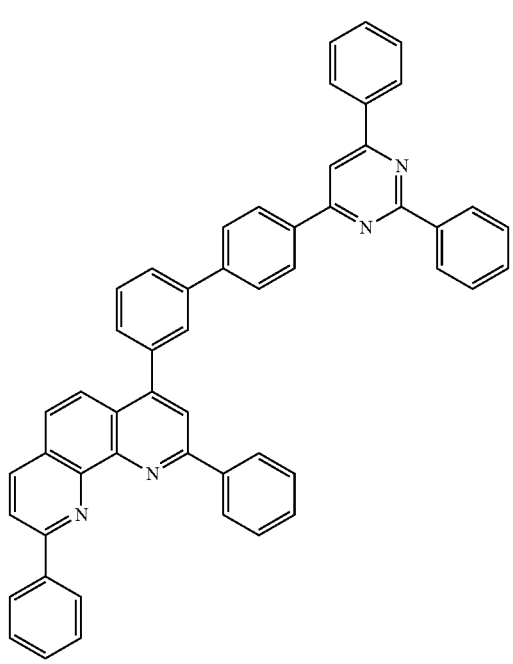

869
-continued
337
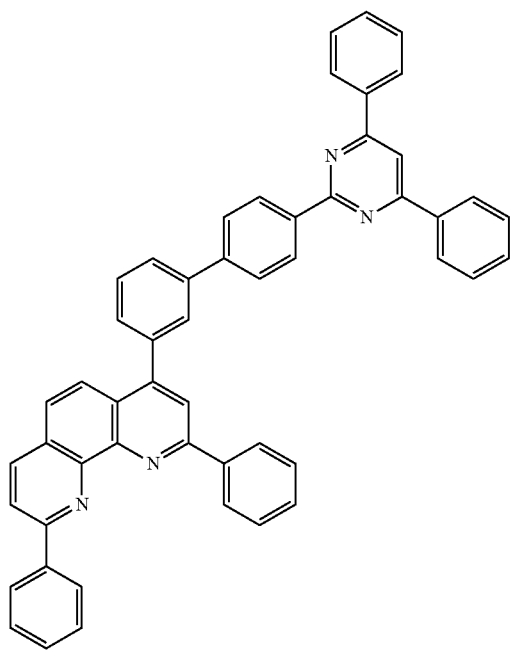
338
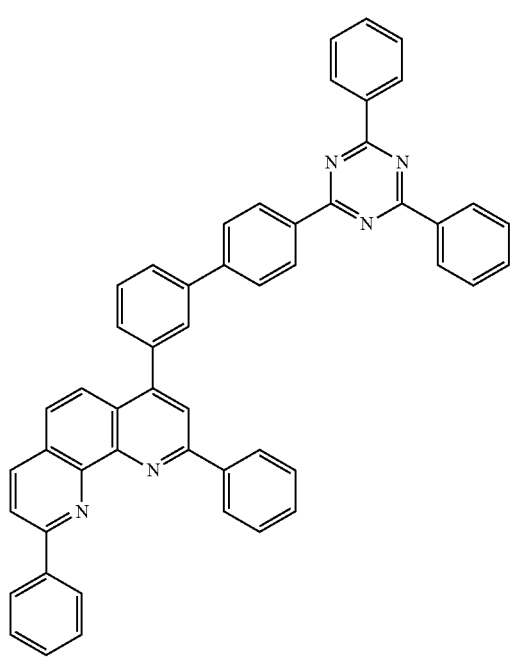
870
-continued
339
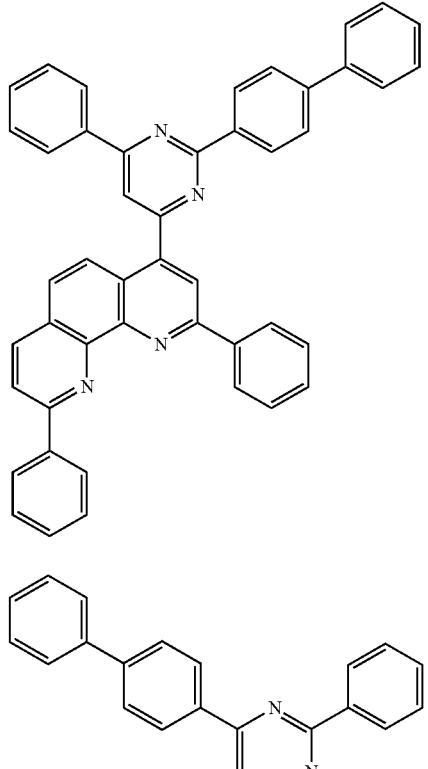
340
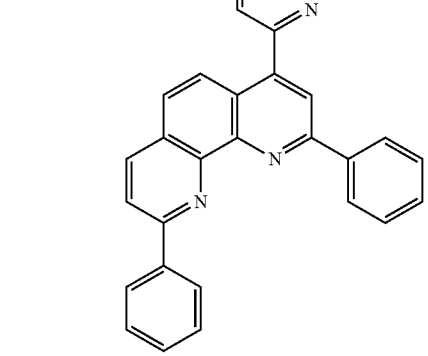
341
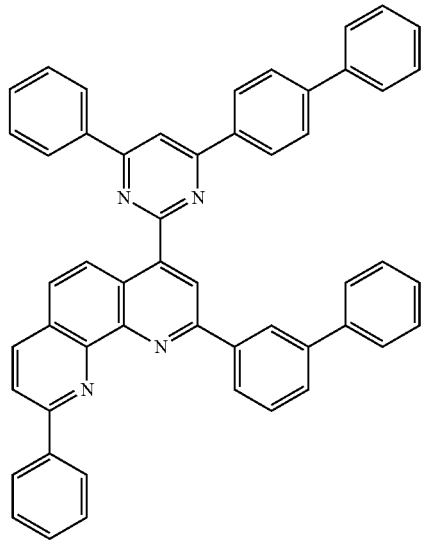

342
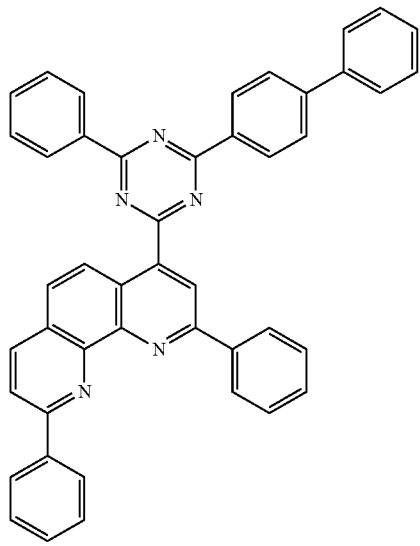
343
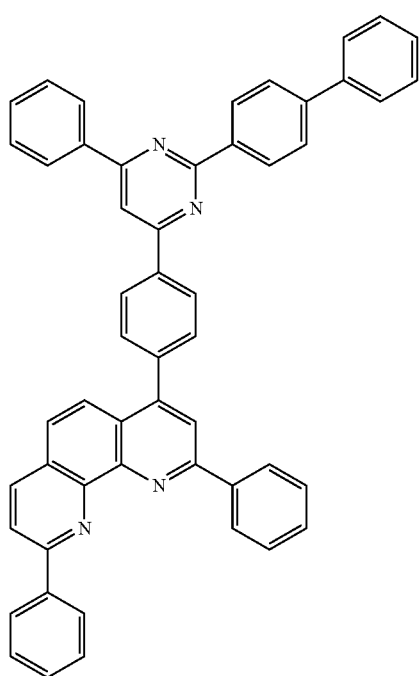
344
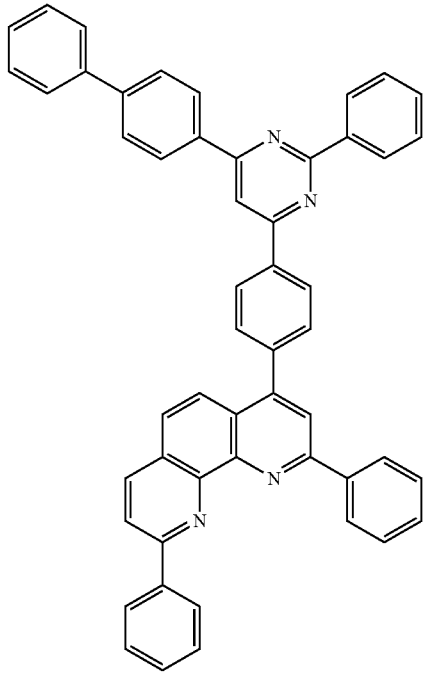
345
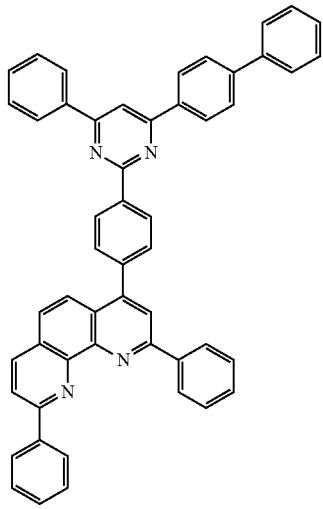

873
-continued
346
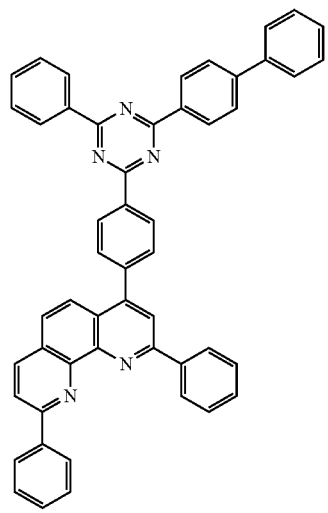
874
-continued
348
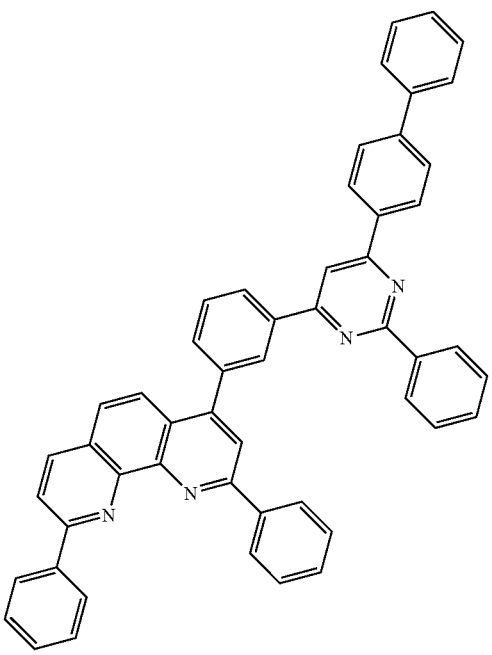
347
349
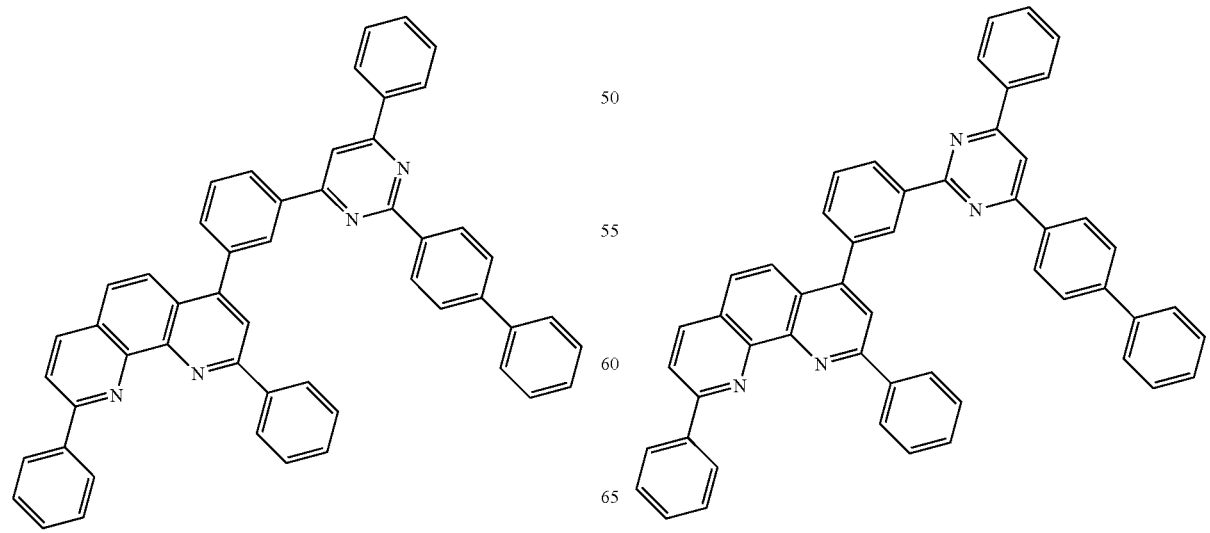

875
350
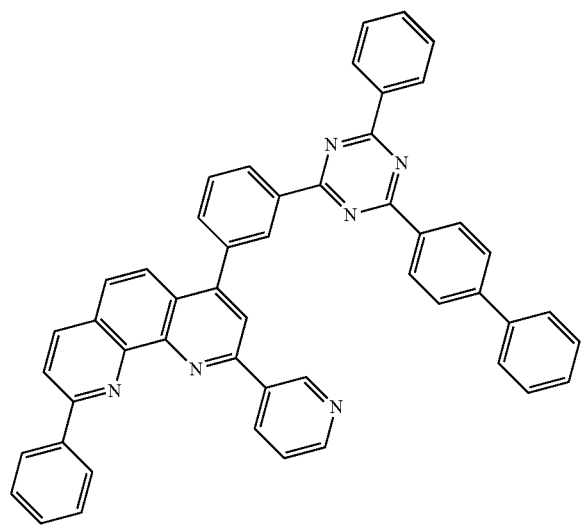
351
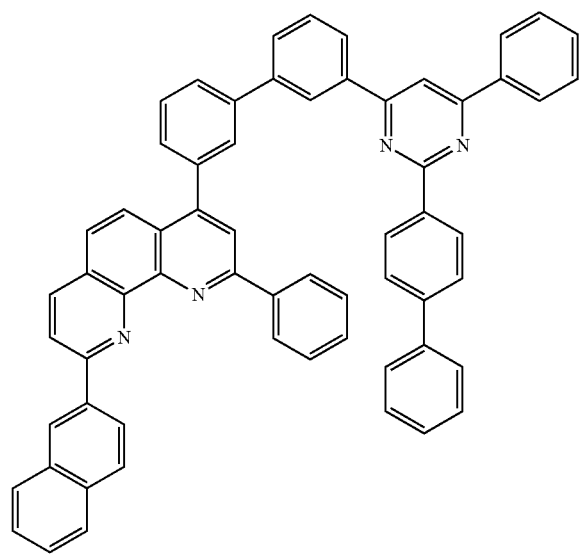
352
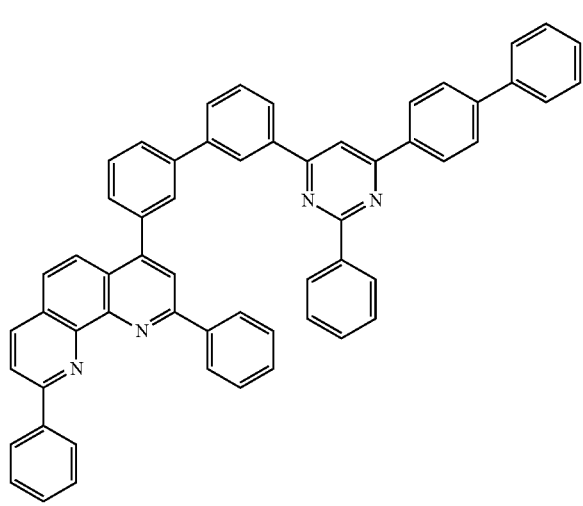
876
353
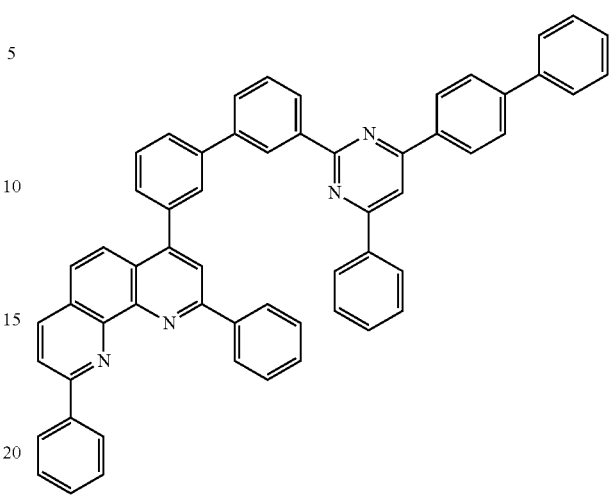
354

877
-continued
355
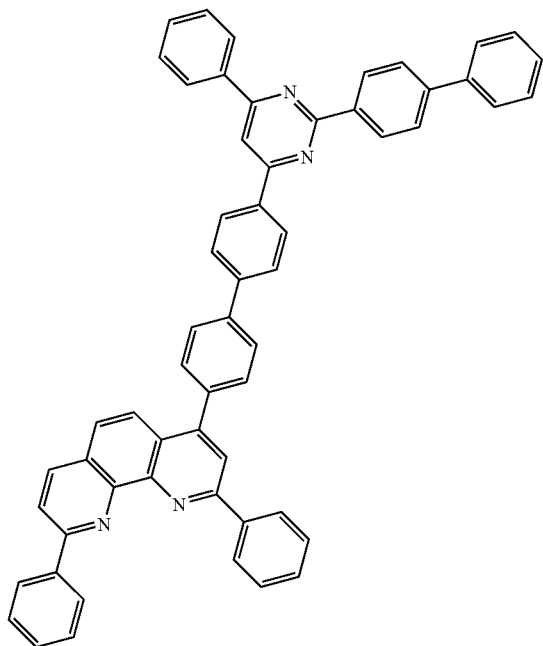
356
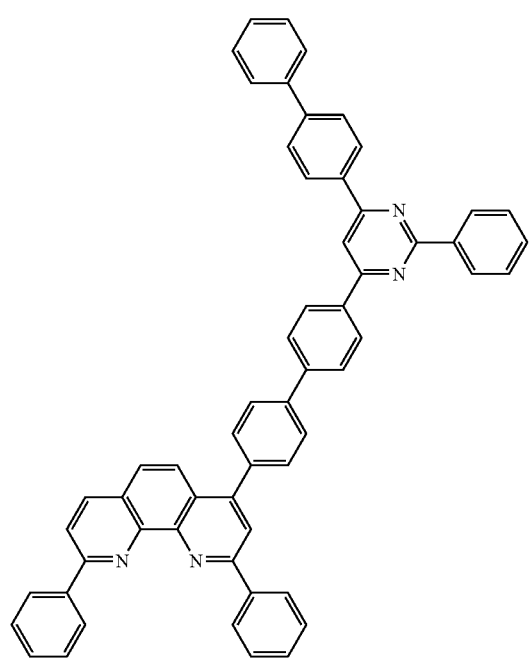
878
-continued
357
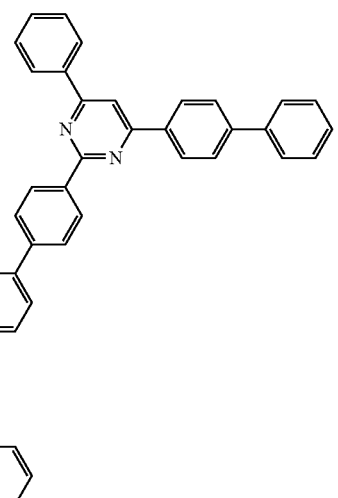
358
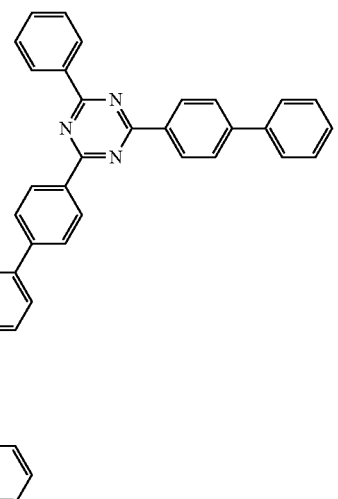
359
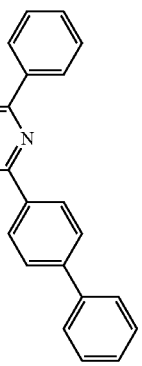

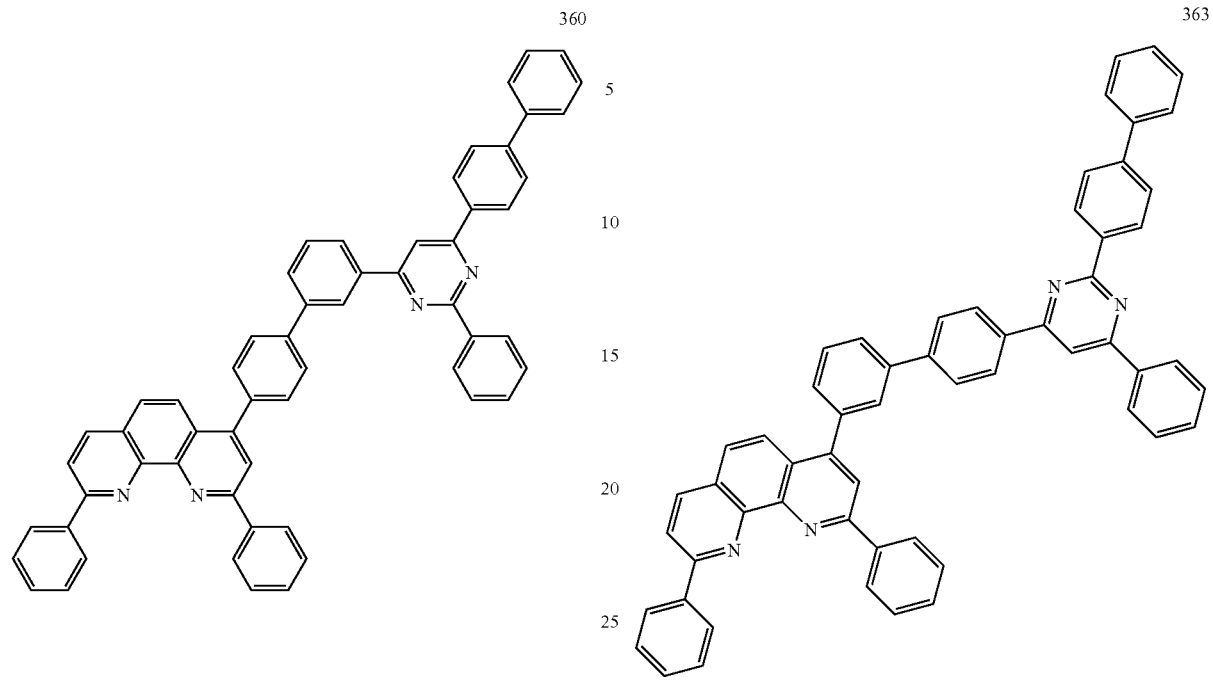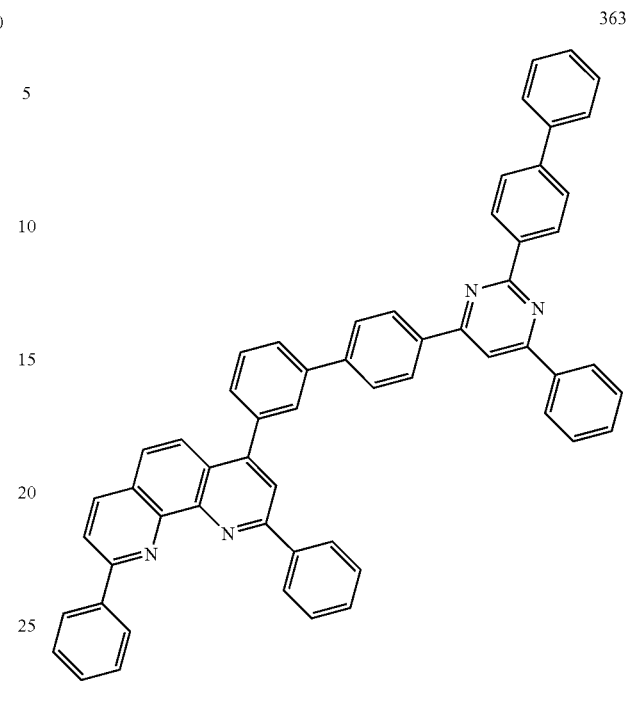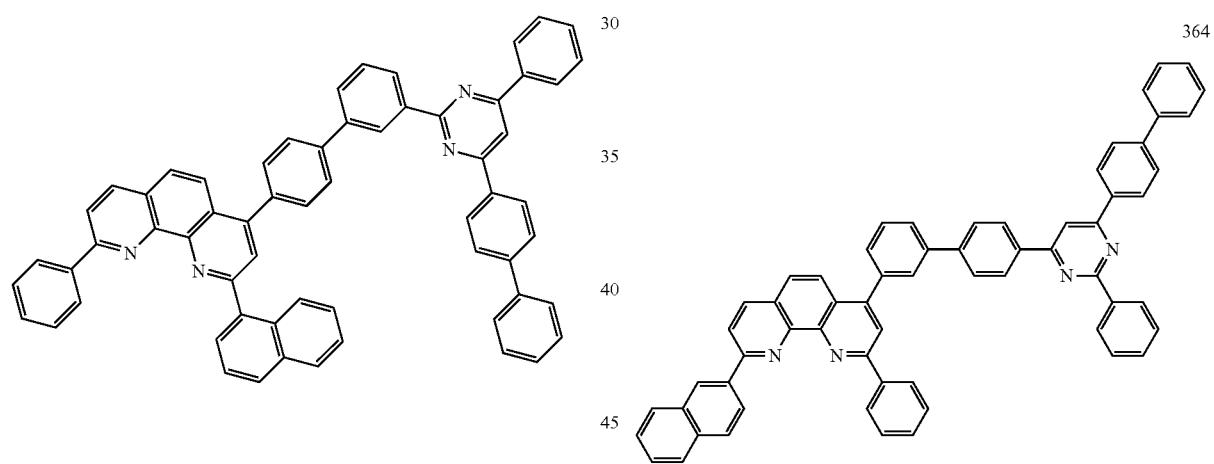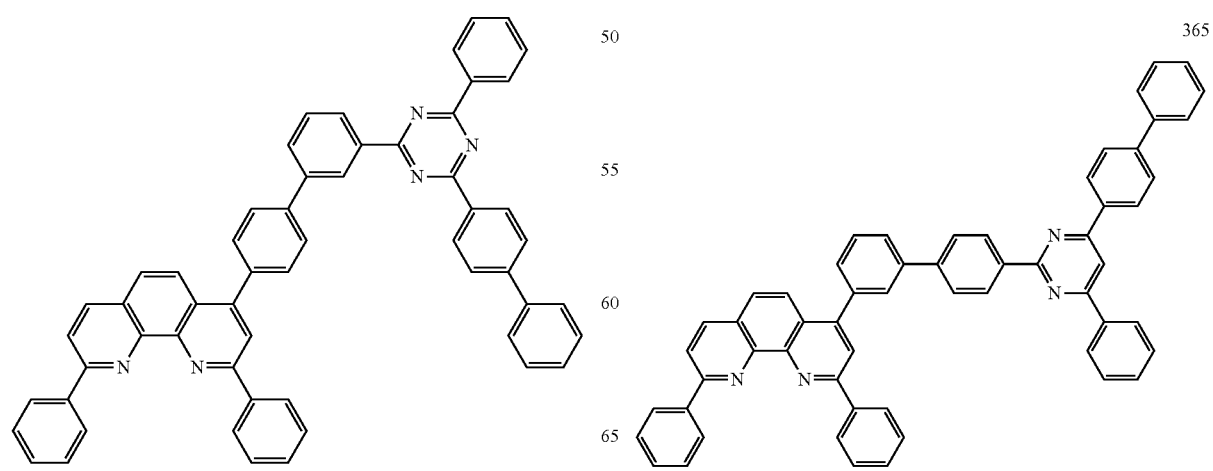

881
-continued
366
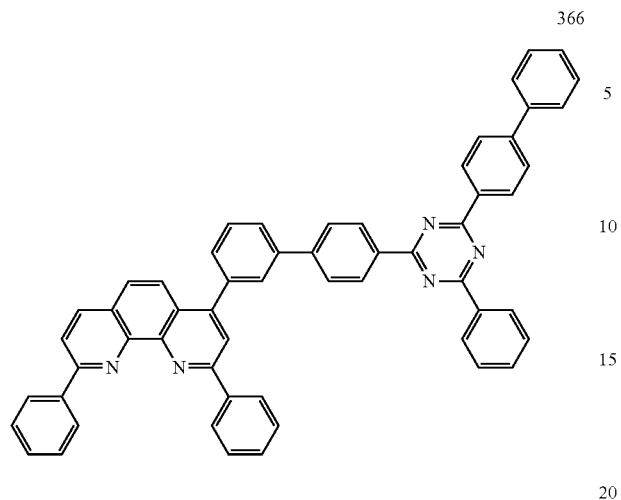
367
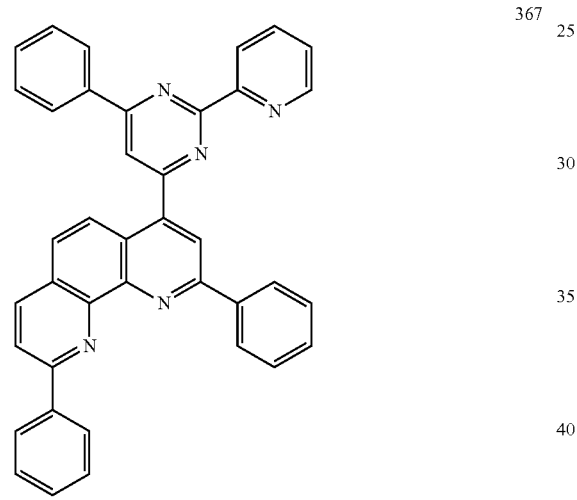
368
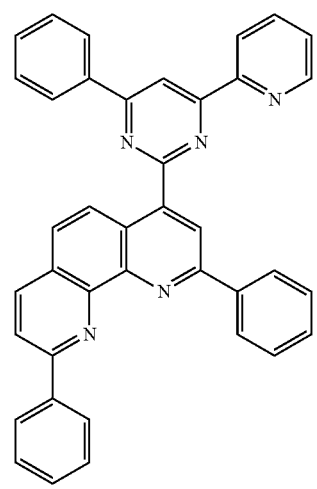
882
-continued
369
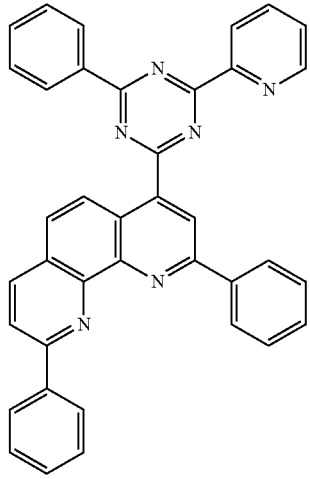
370
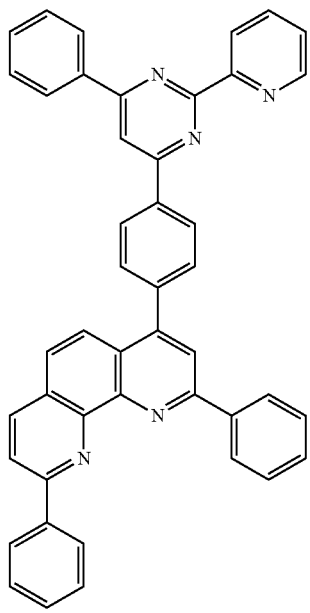

883
-continued
371
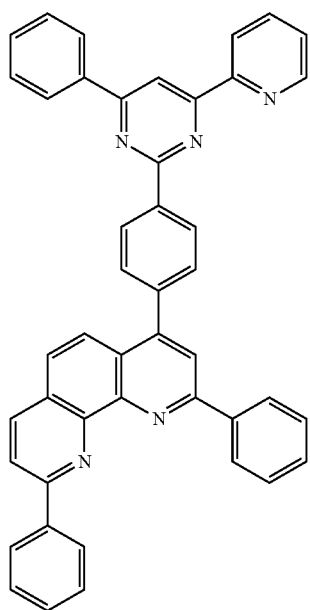
372
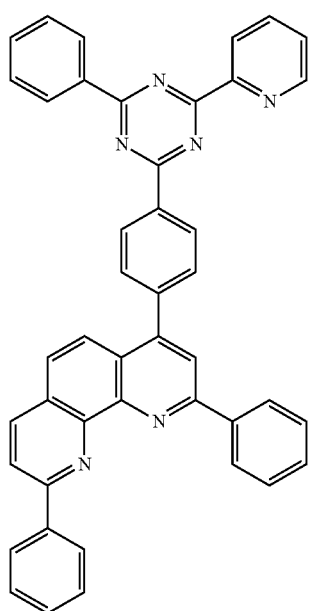
884
-continued
373
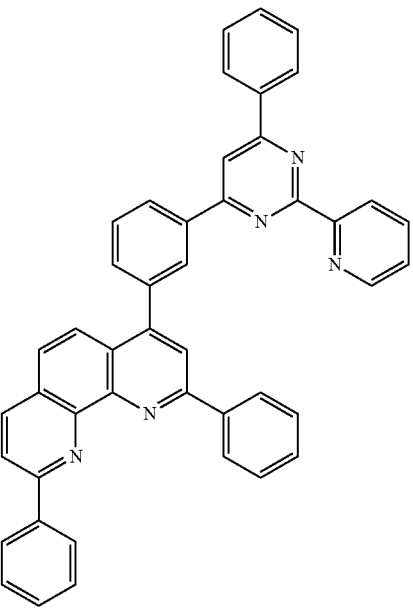
374
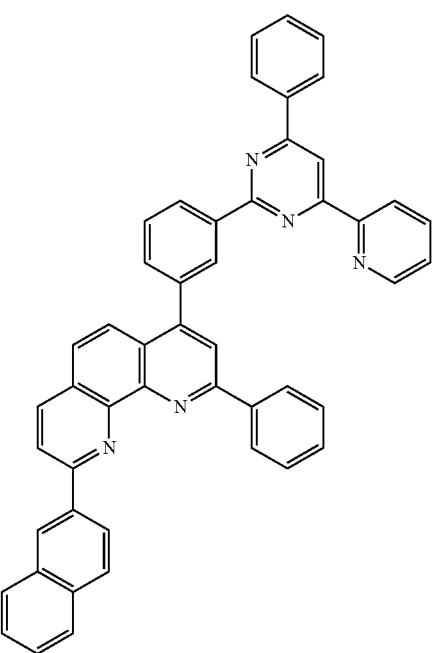

885
-continued
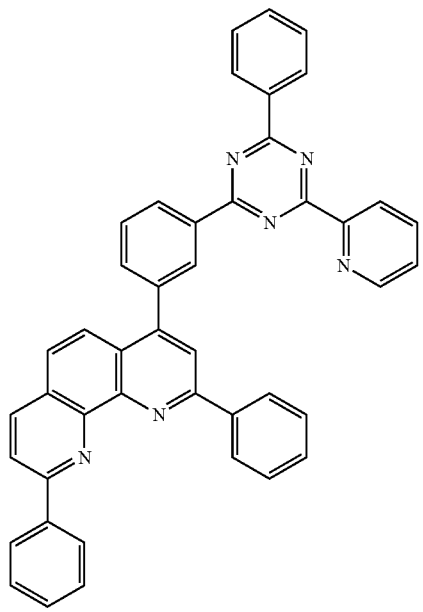
375
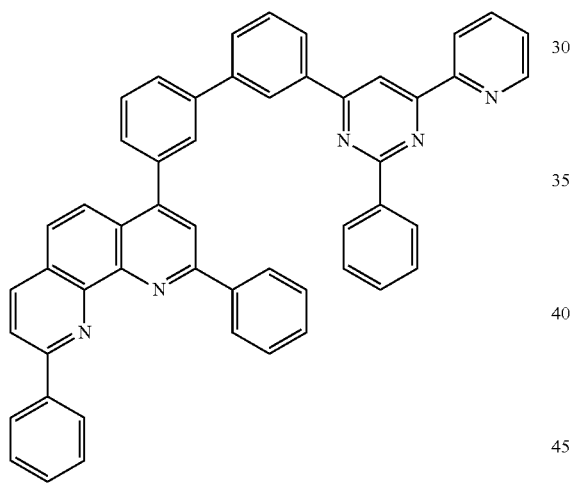
376
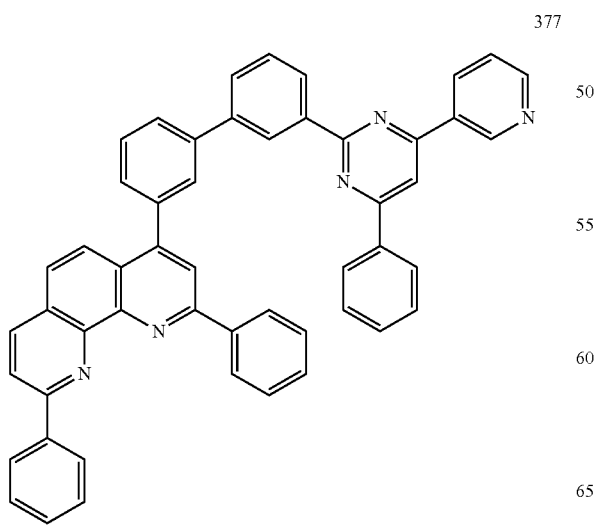
377
886
-continued
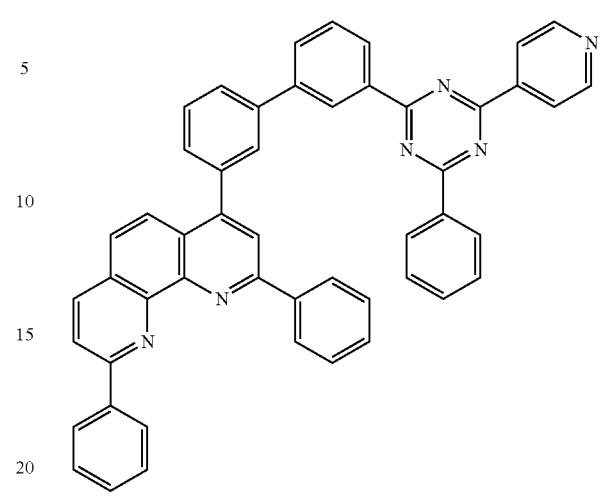
378
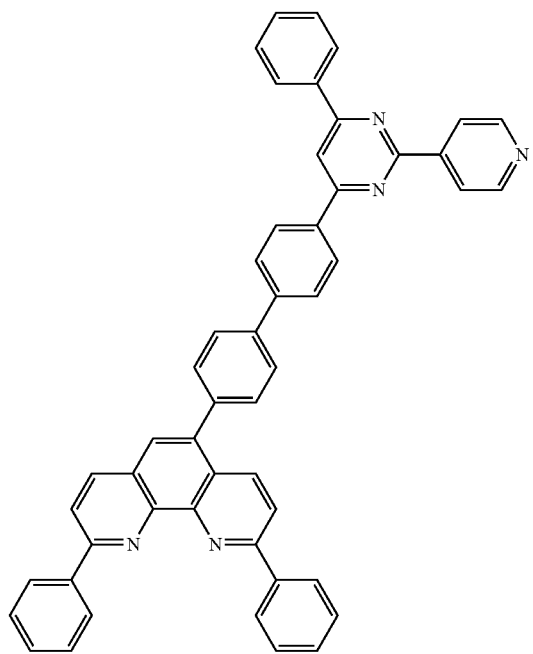
379

887
-continued
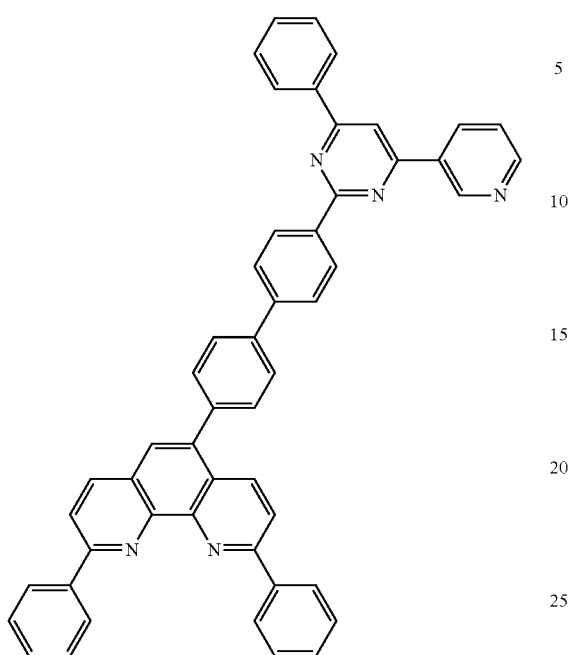
380
888
-continued
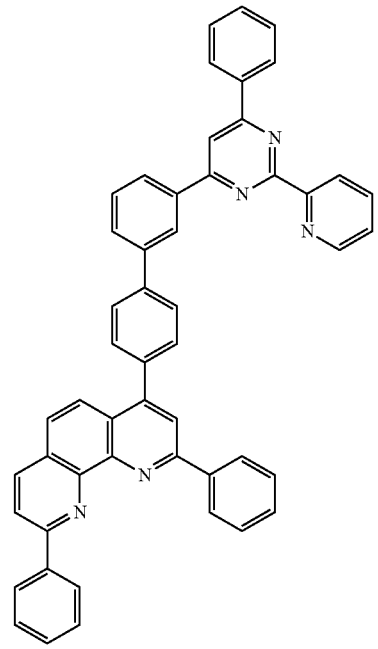
382
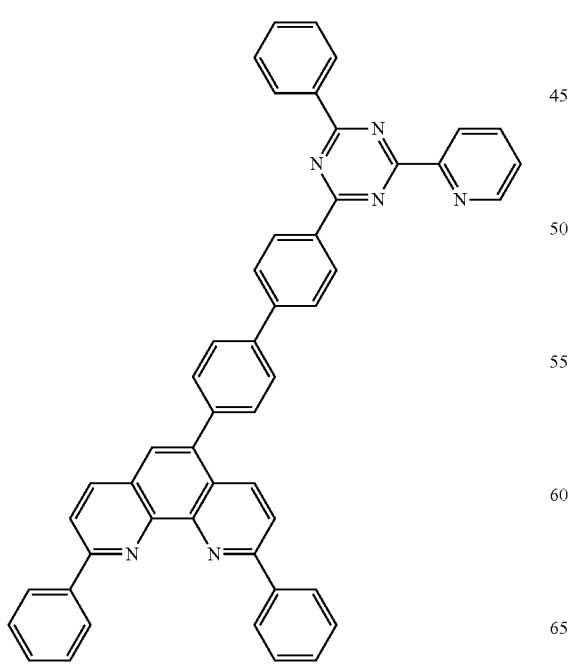
381
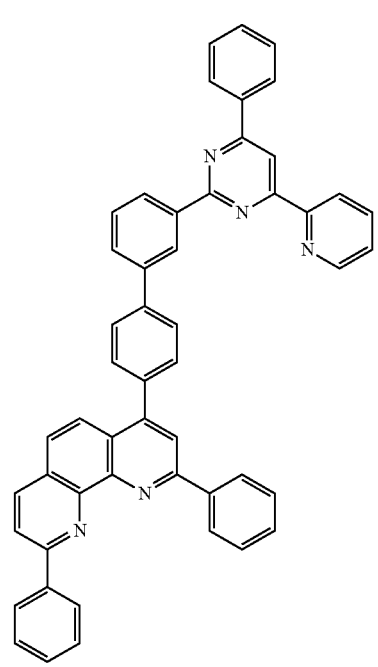
383

889
384
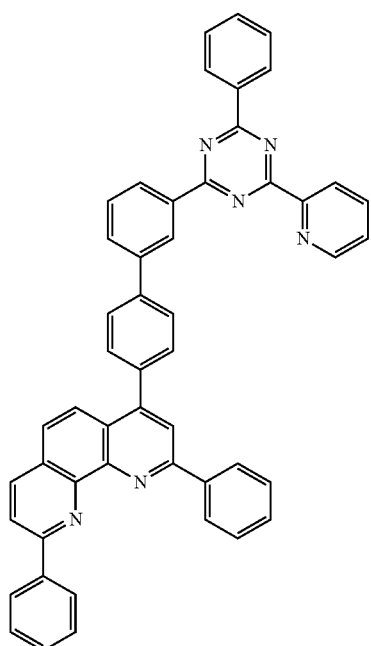
385
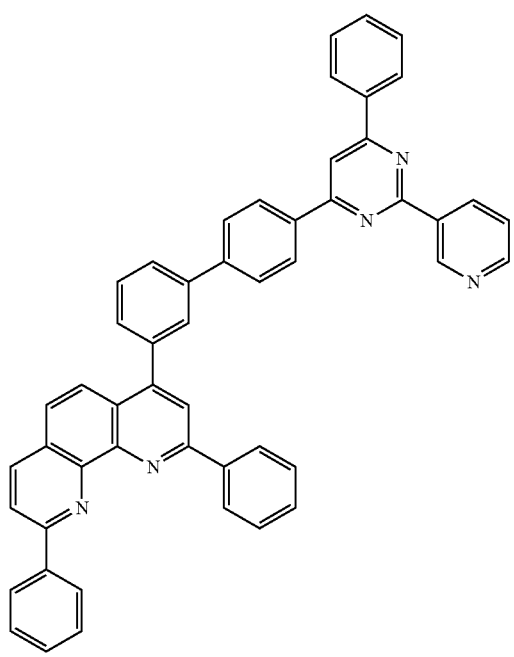
890
386
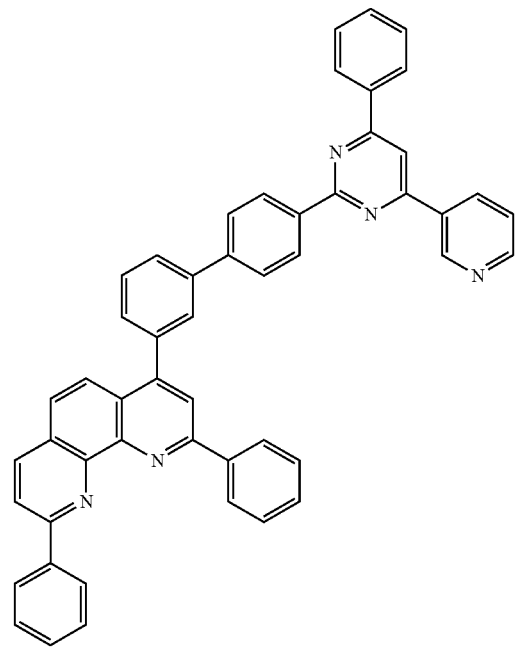
387
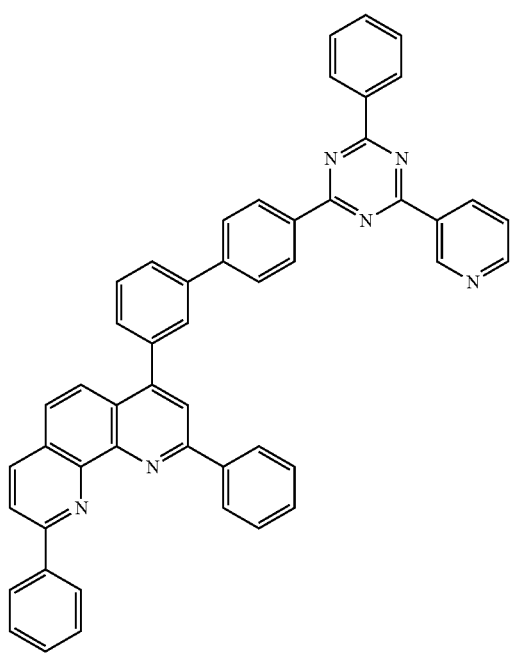

891
-continued
388
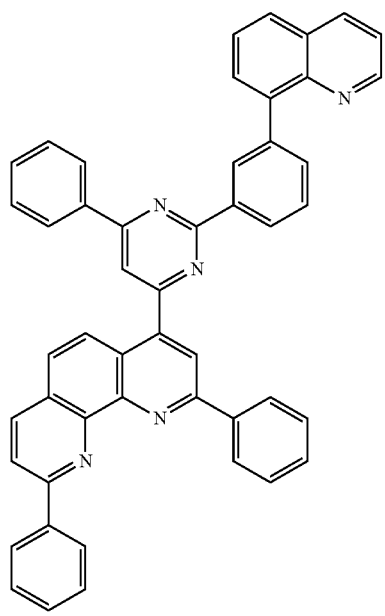
892
-continued
390
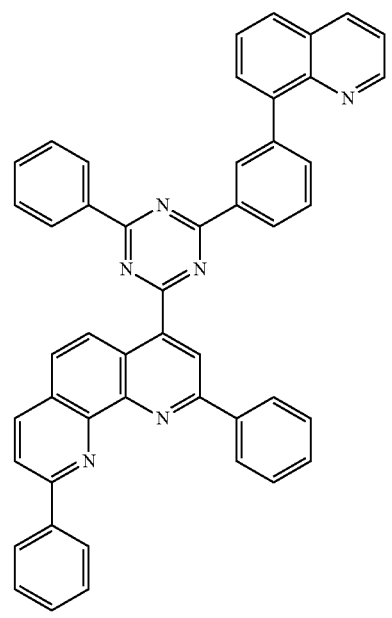
389
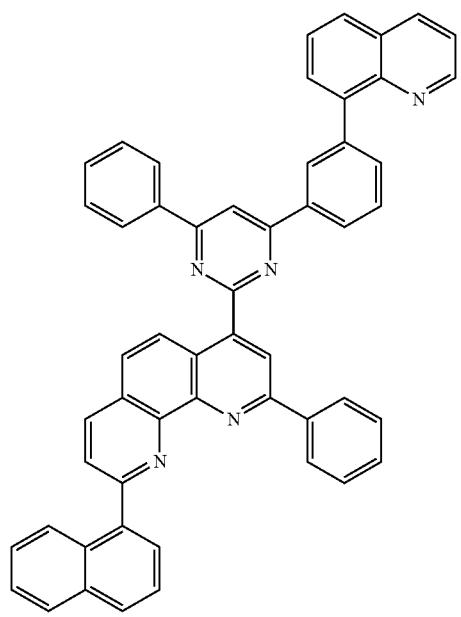
391
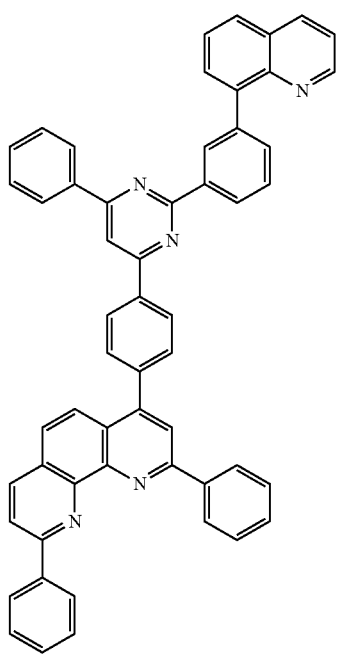

392
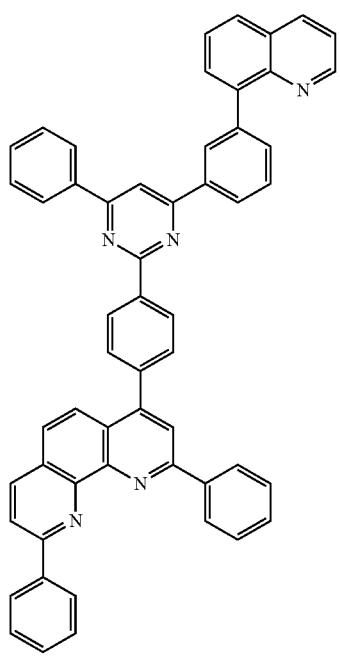
393
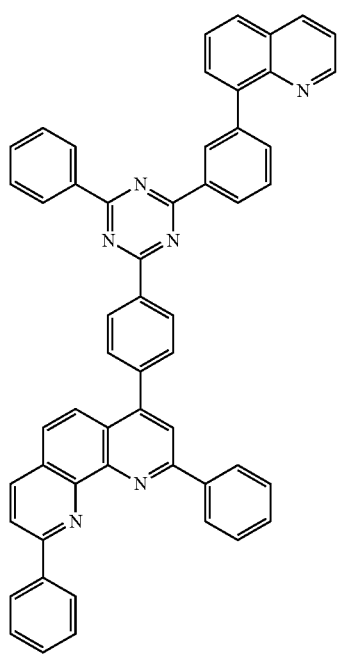
394
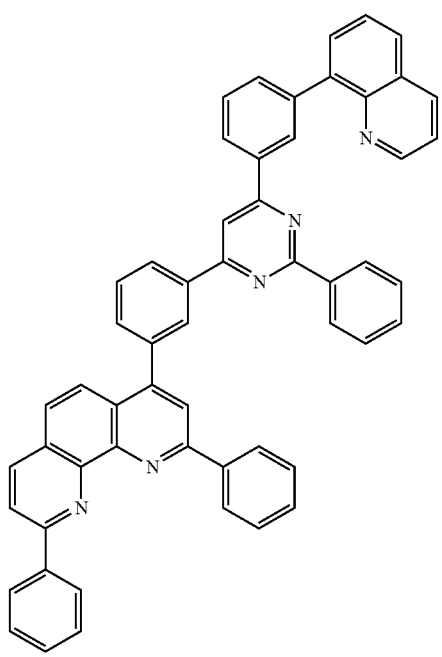
395
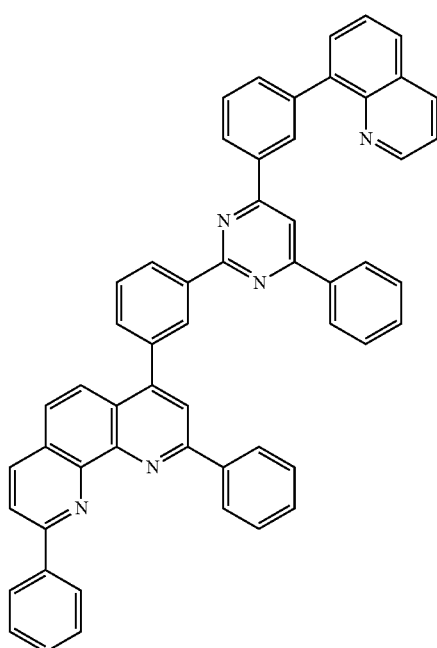

895
-continued
396
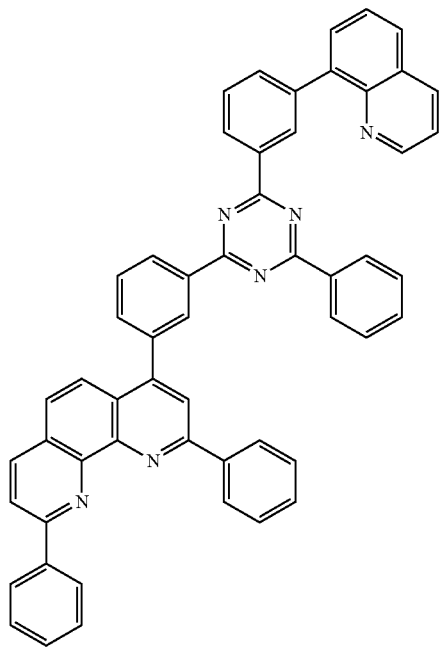
397
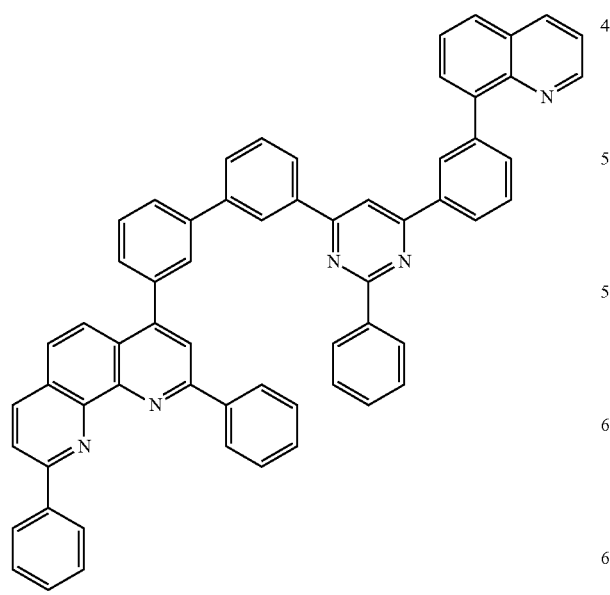
896
-continued
398
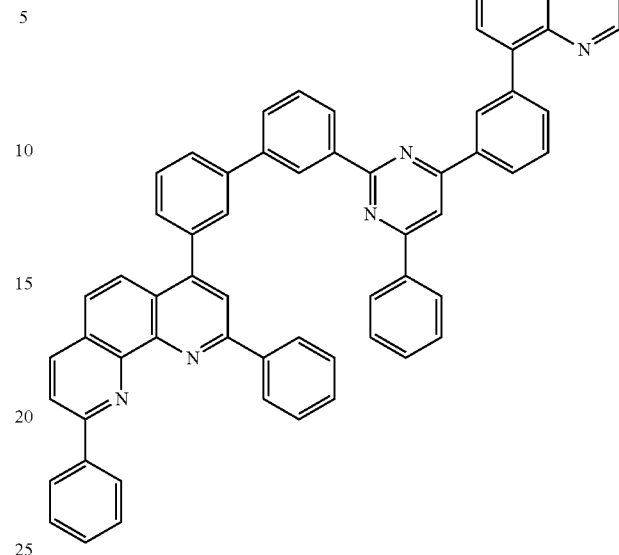
399
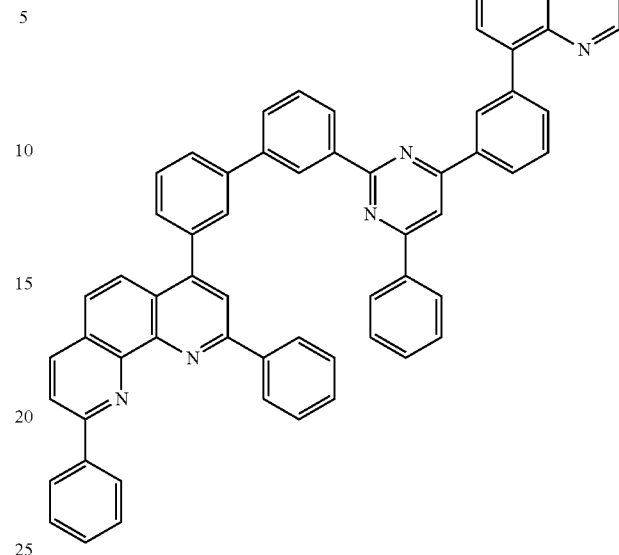

897
-continued
898
-continued
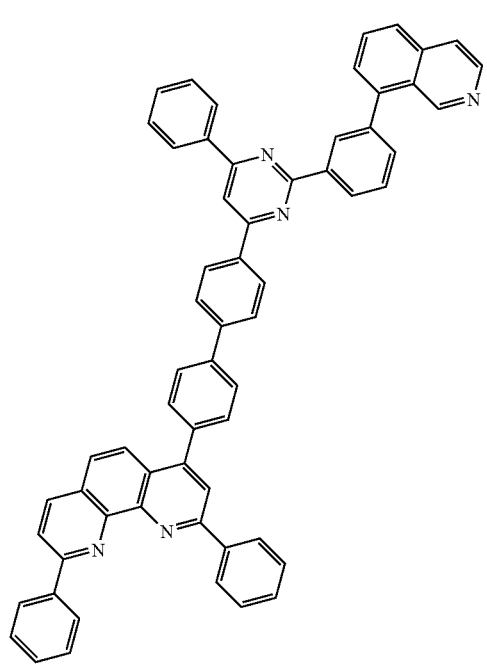
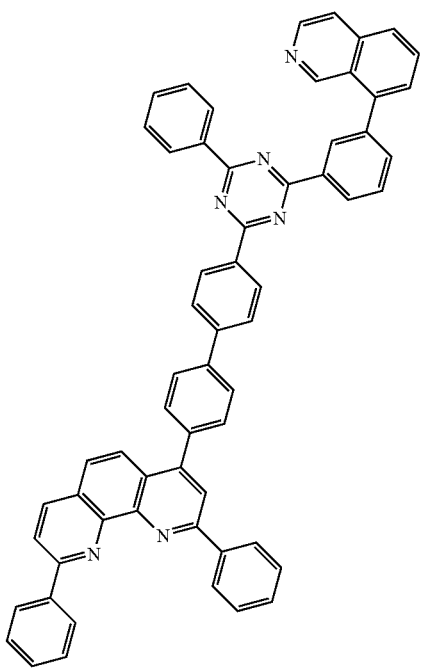

899
-continued
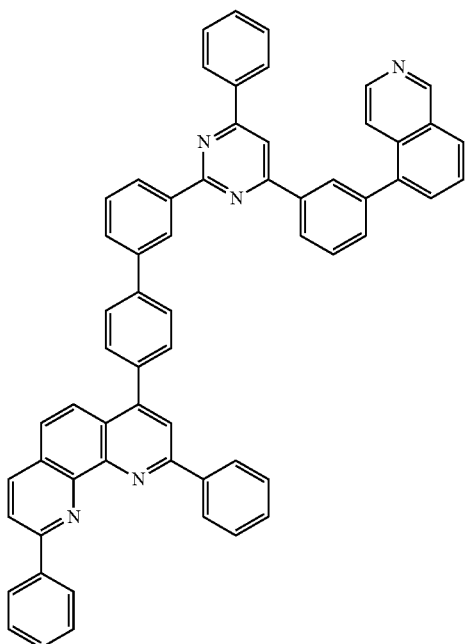
404
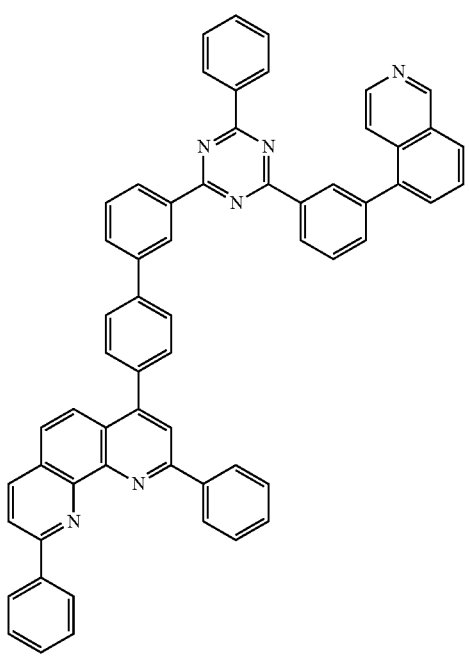
405
900
-continued
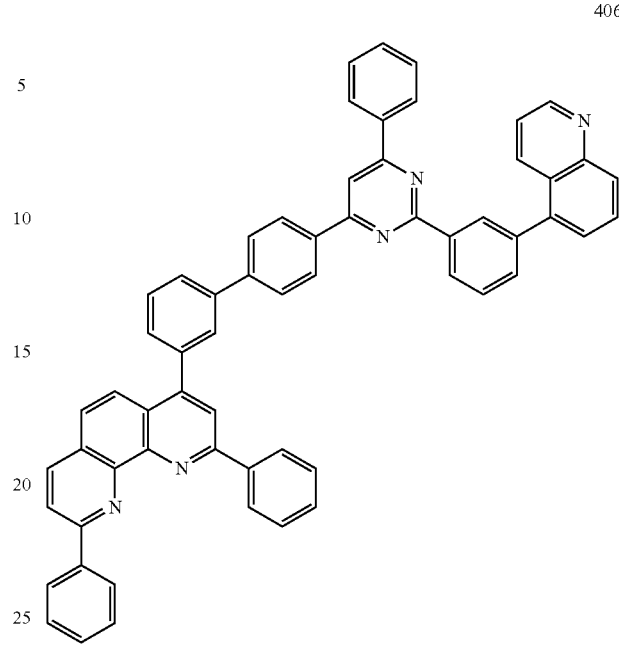
406
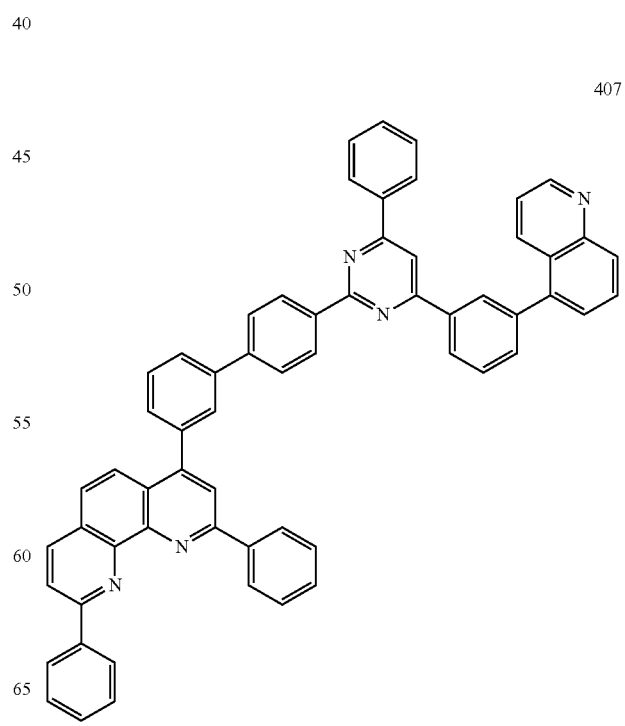
407

408
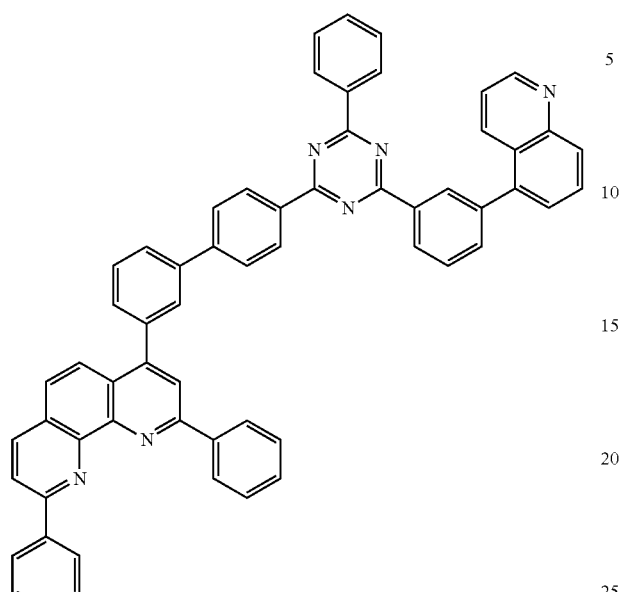
411
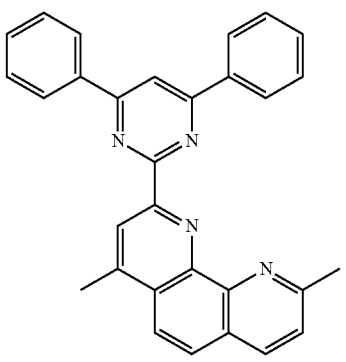
412
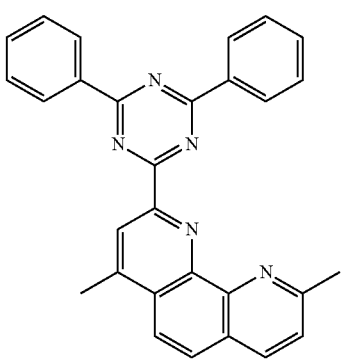
409
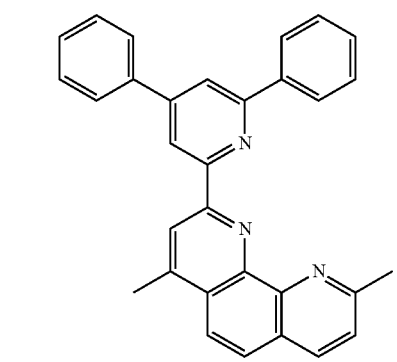
413
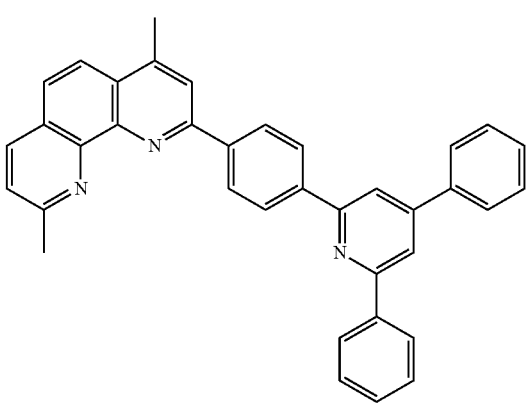
410
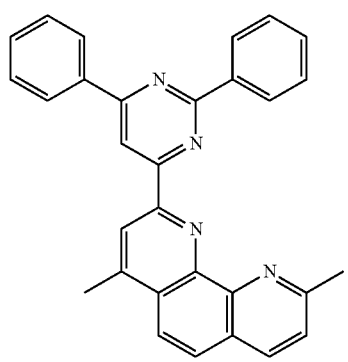
414
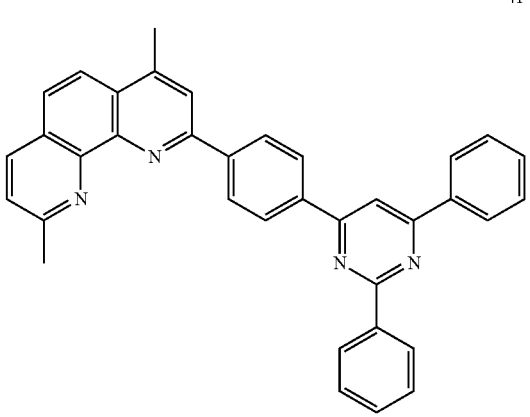

903
-continued
415
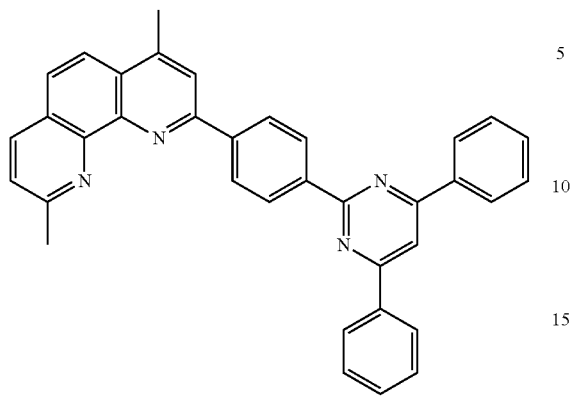
416
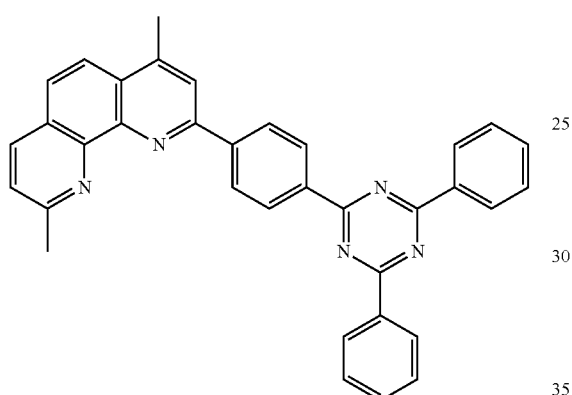
417
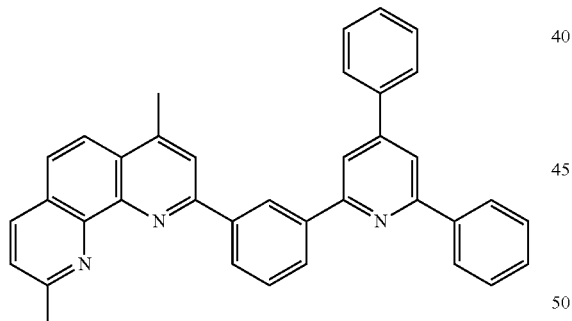
418
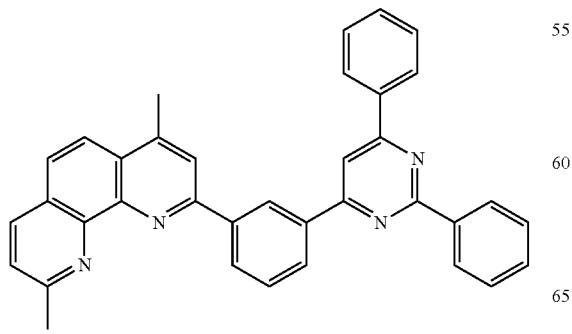
904
-continued
419
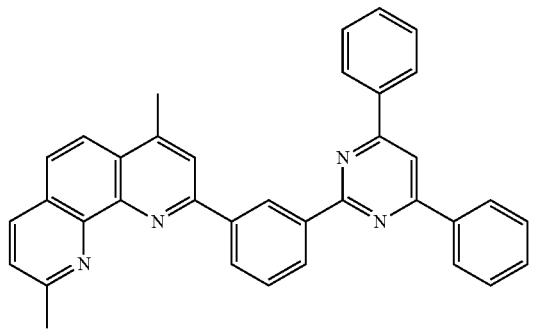
420
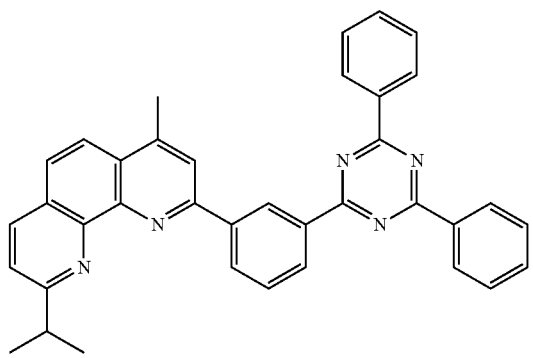
421
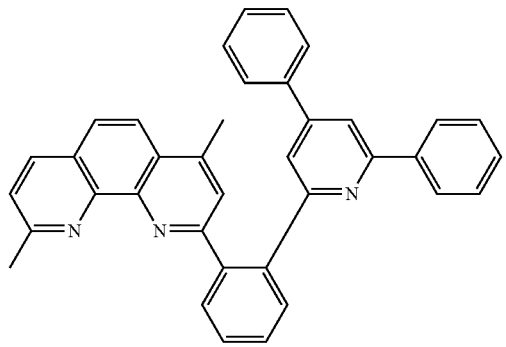
422
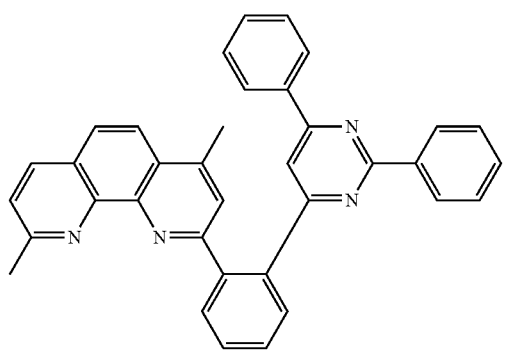

905
-continued
423
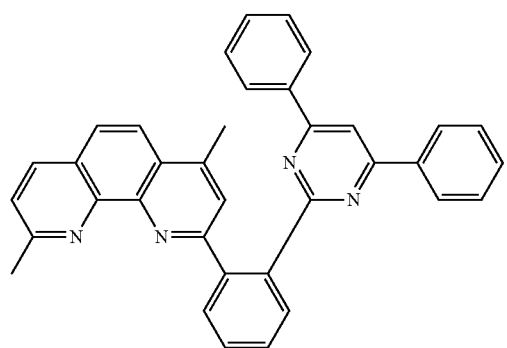
424
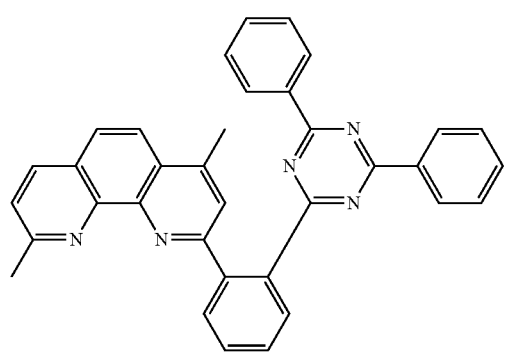
425
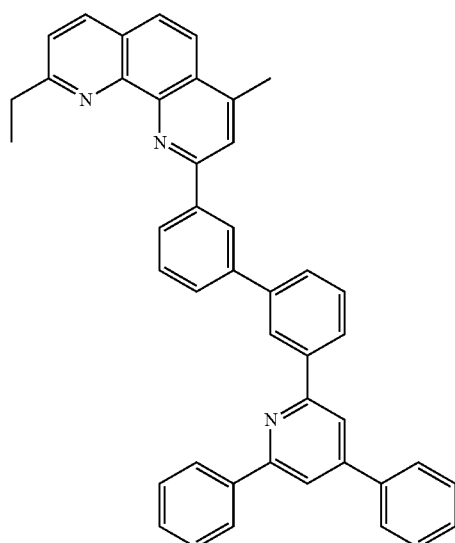
906
-continued
426
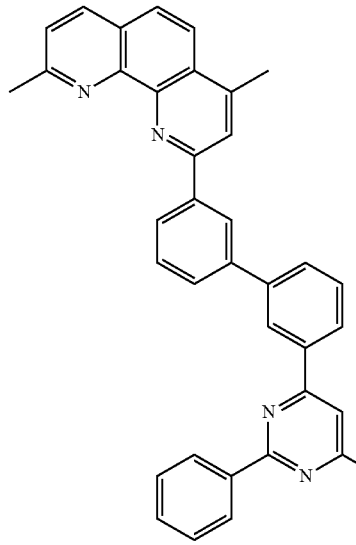
427
428
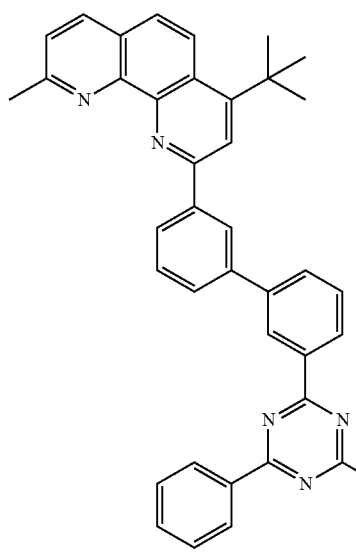

907
-continued
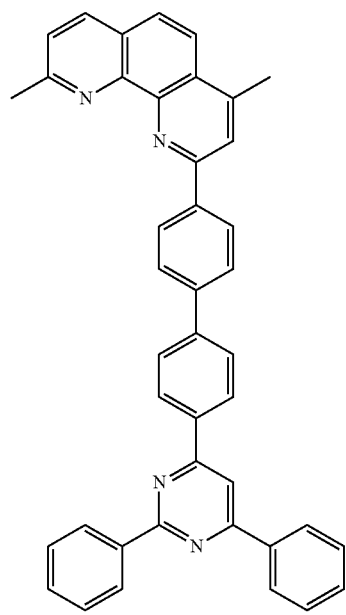
908
-continued
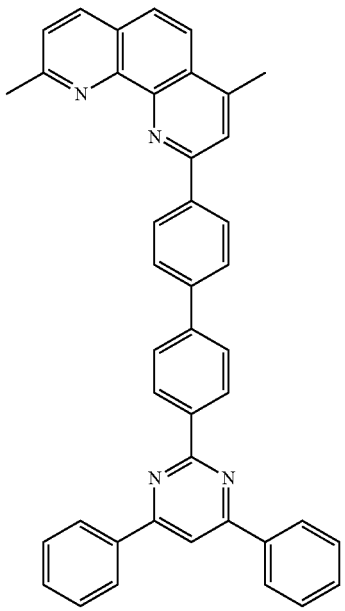
429
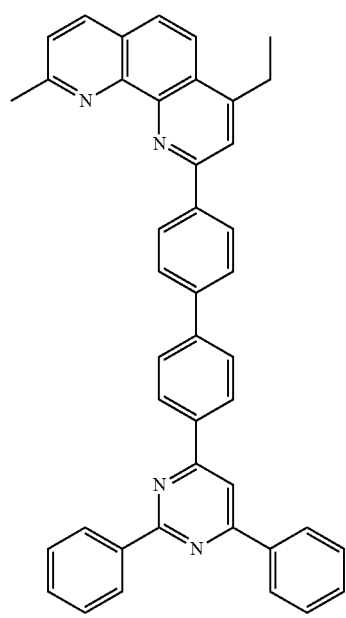
430
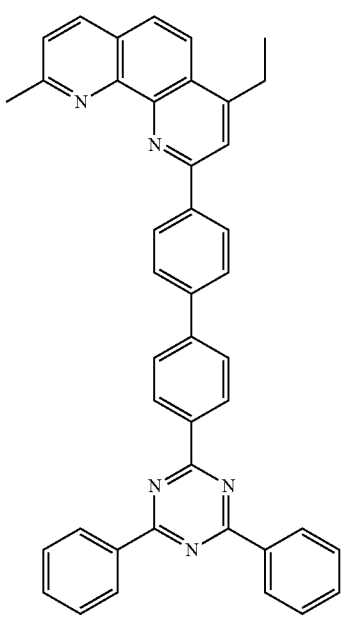
431
432

909
-continued
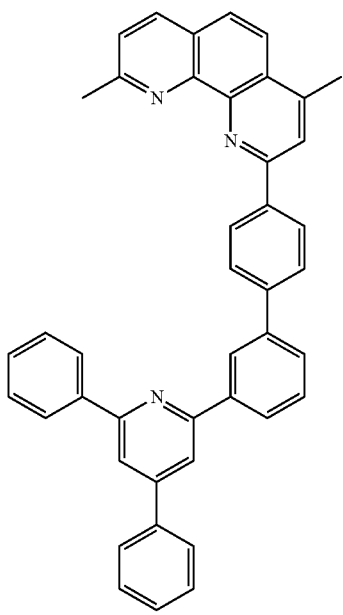
433
910
-continued
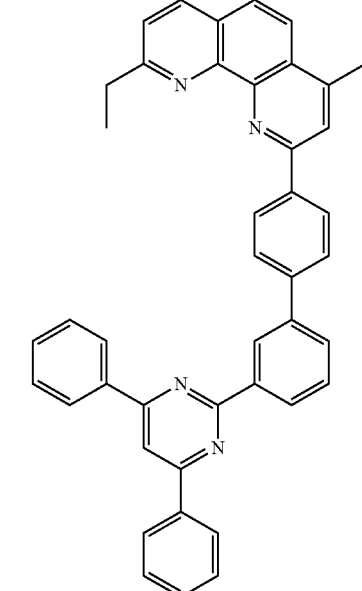
435
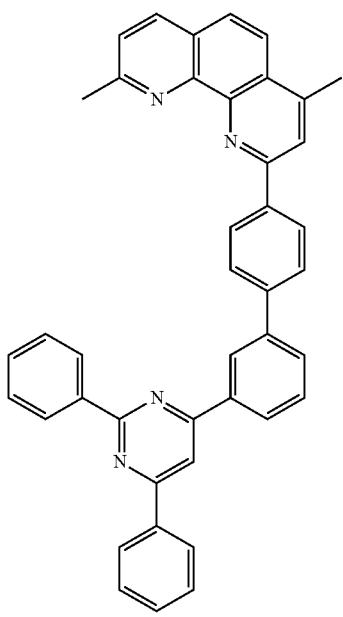
434
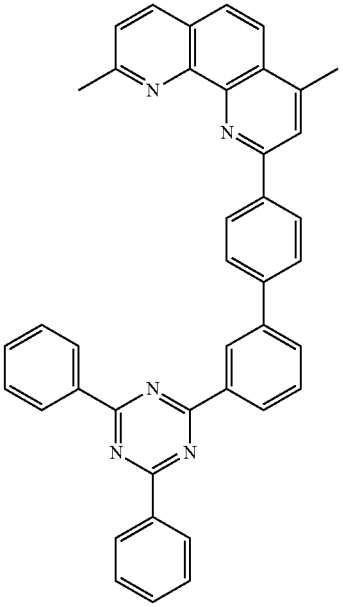
436

911
-continued
437
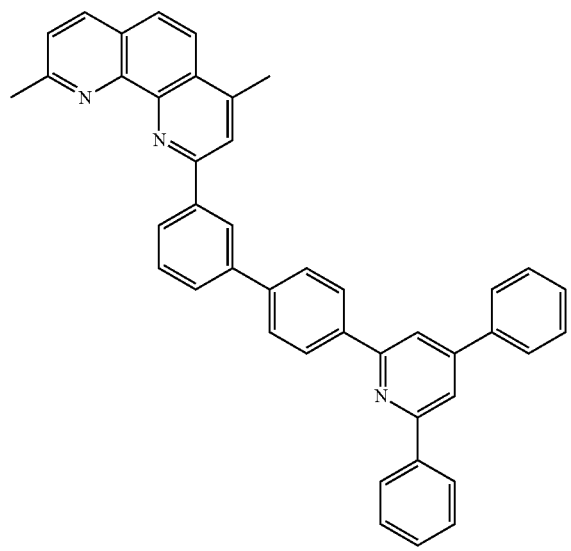
438
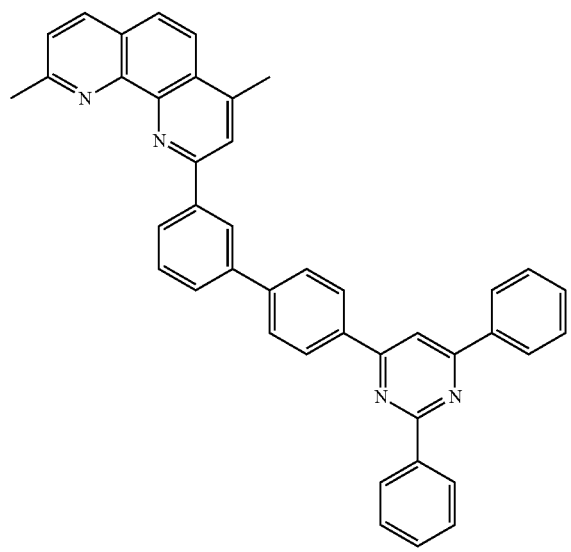
912
-continued
439
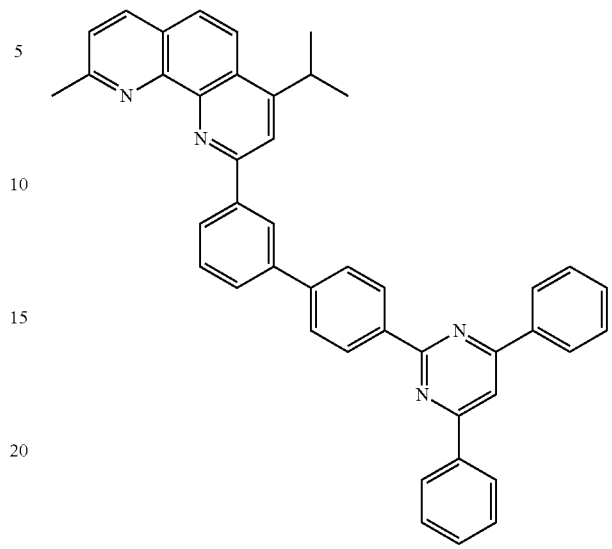
440
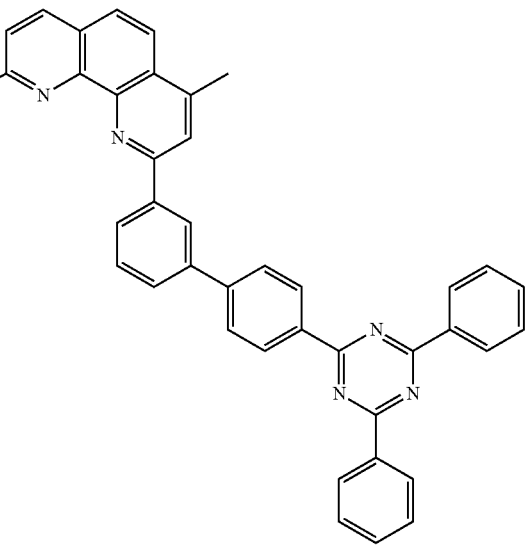
441
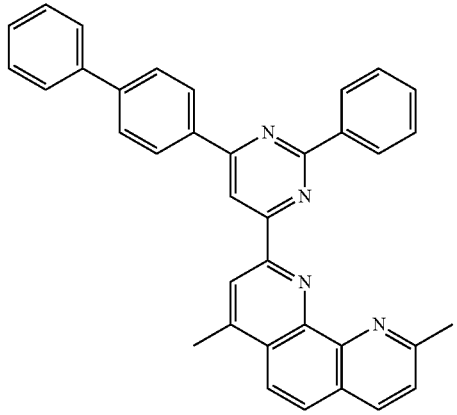

913
-continued
442
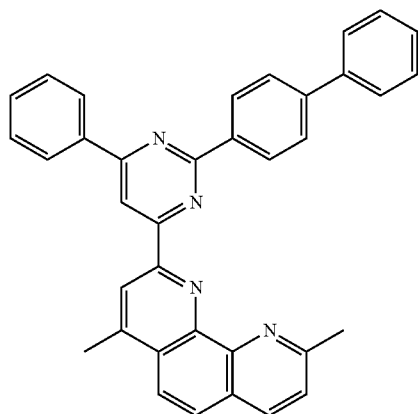
443
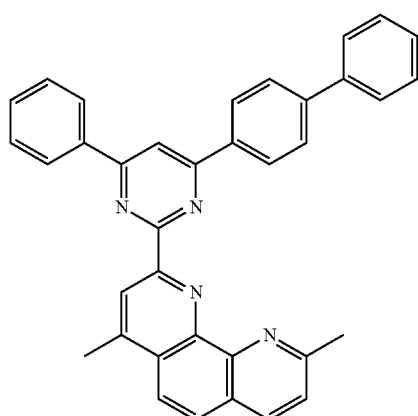
444
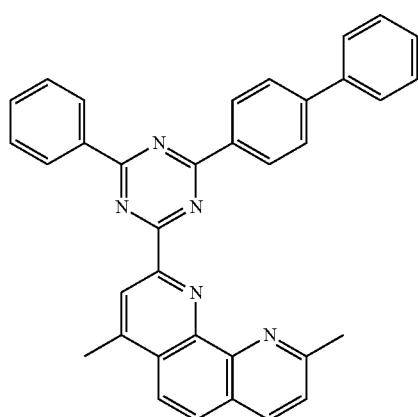
914
-continued
445
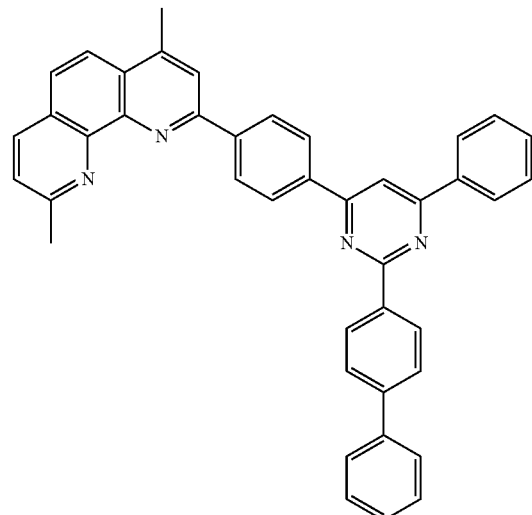
446
447
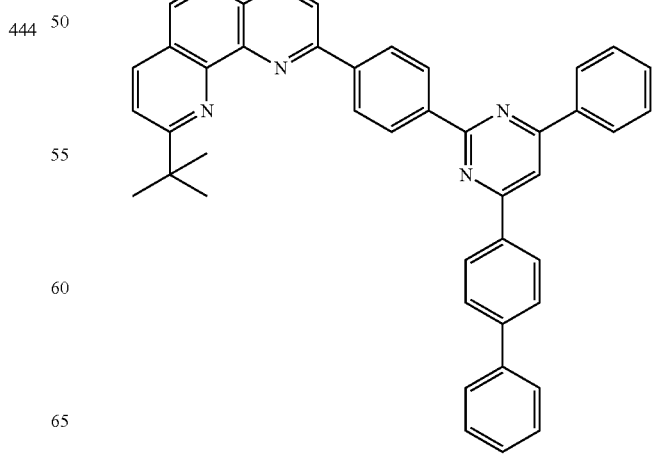

915
-continued
448
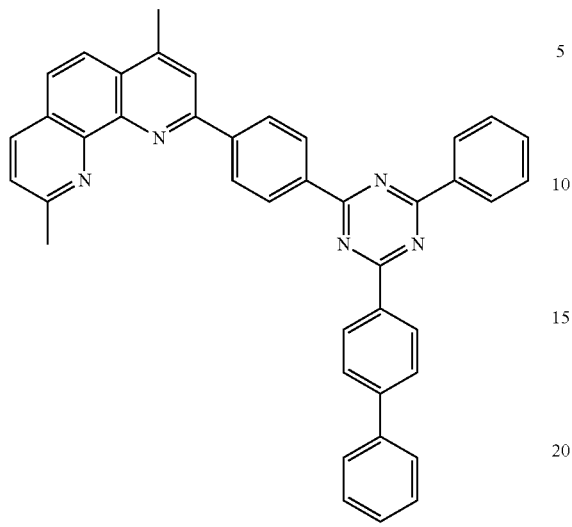
449
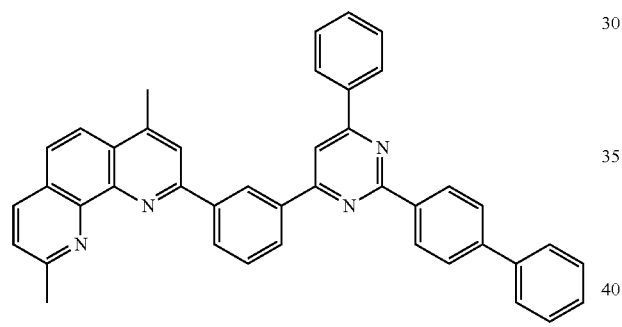
450
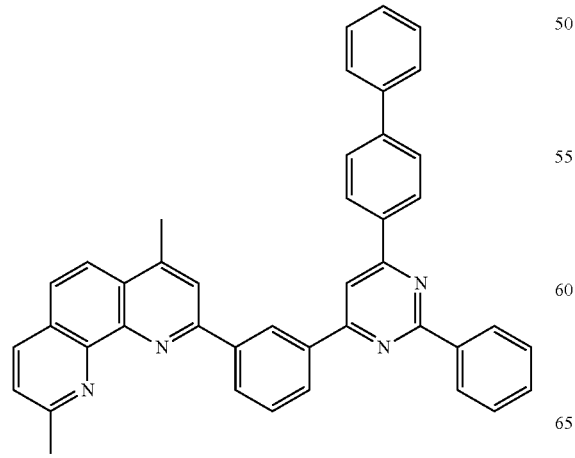
916
-continued
451
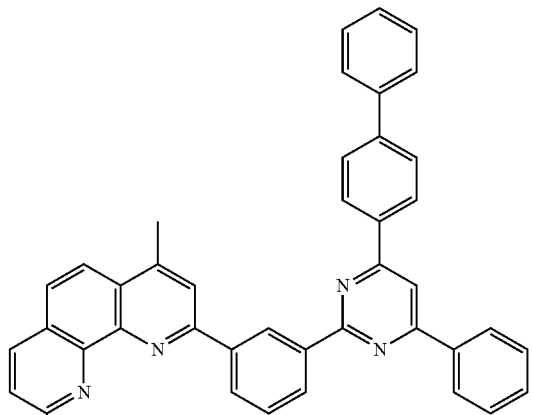
452
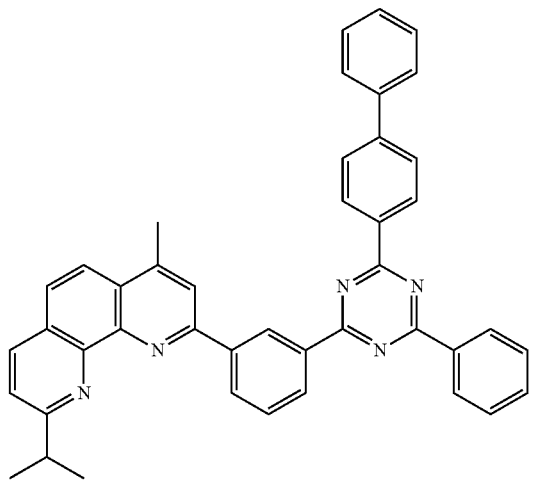
453
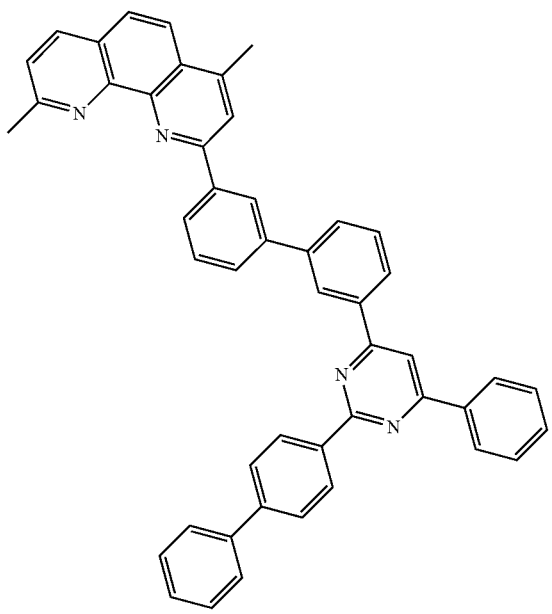

917
-continued
454
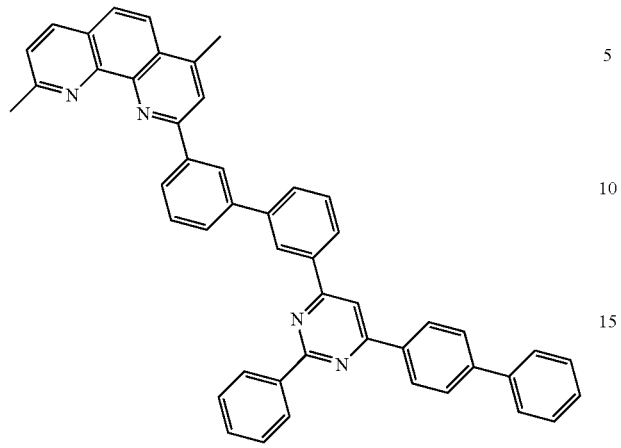
455
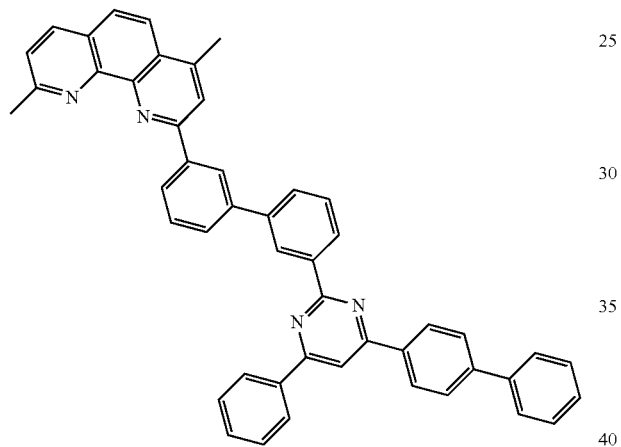
456
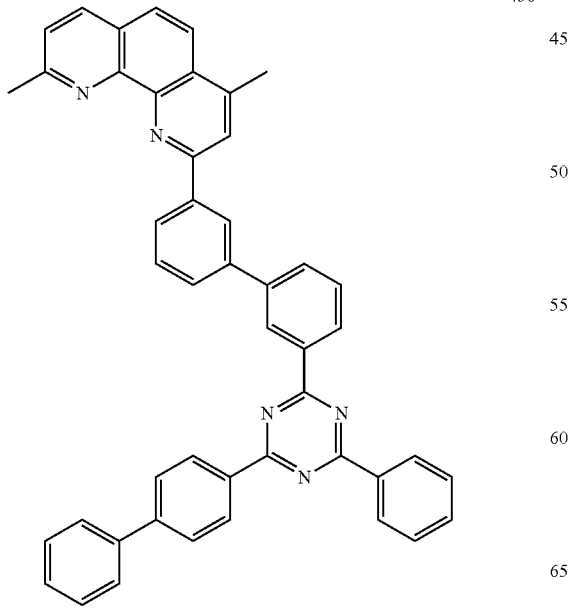
918
-continued
457
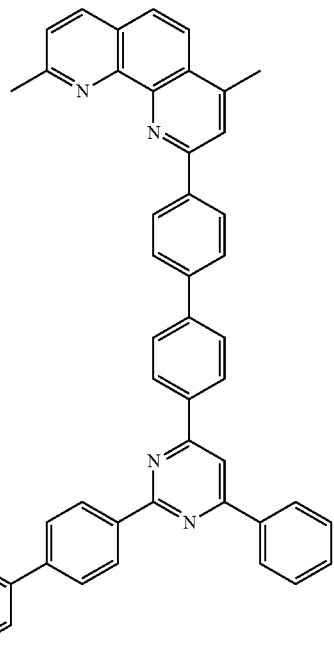
458
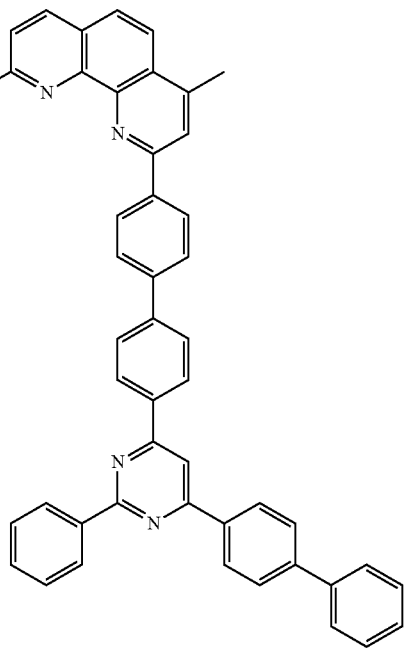

919
-continued
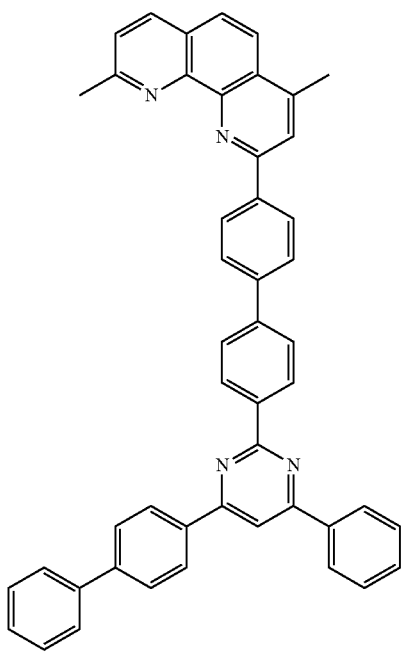
920
-continued
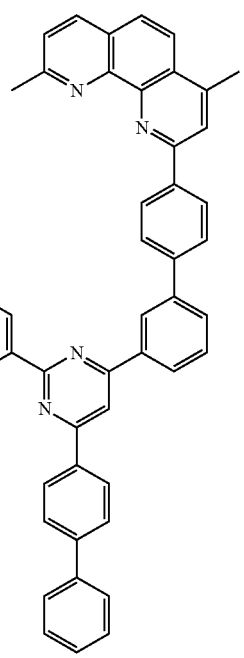
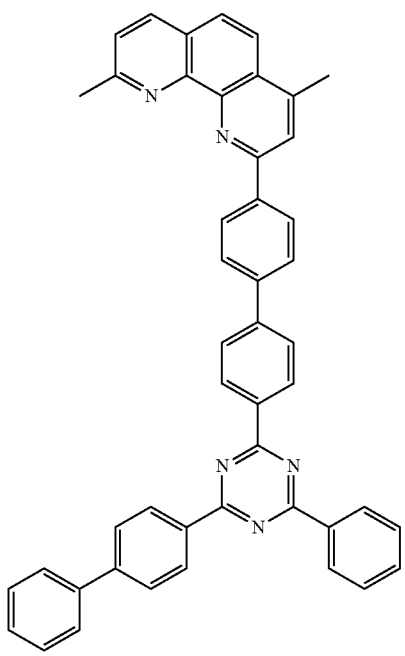
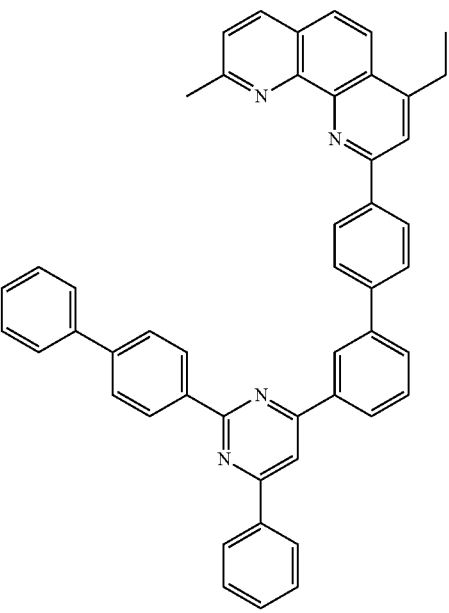

921
-continued
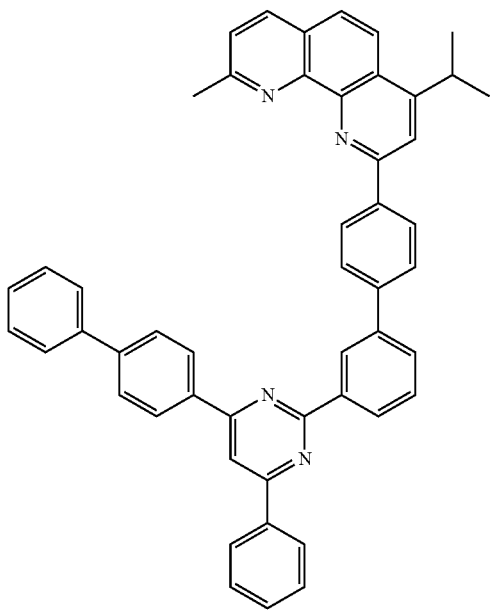
463
922
-continued
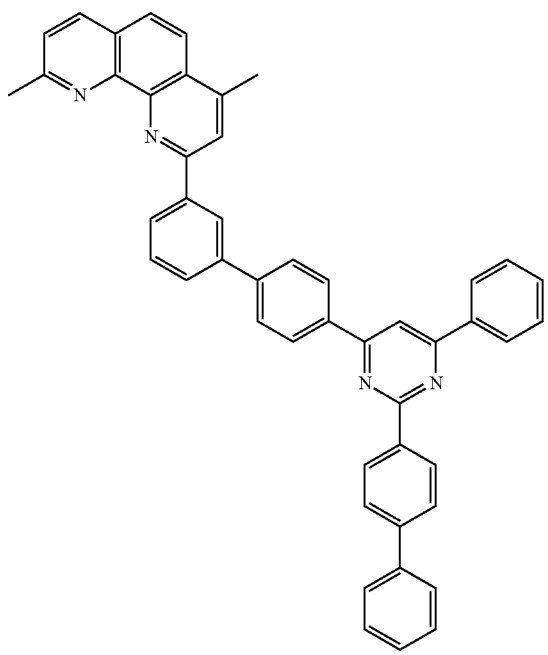
465
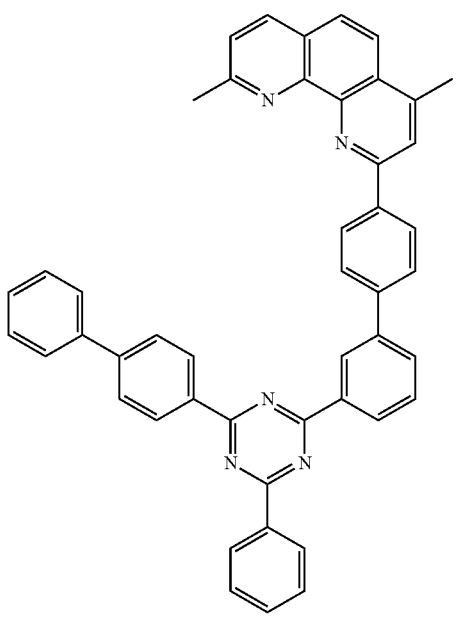
464
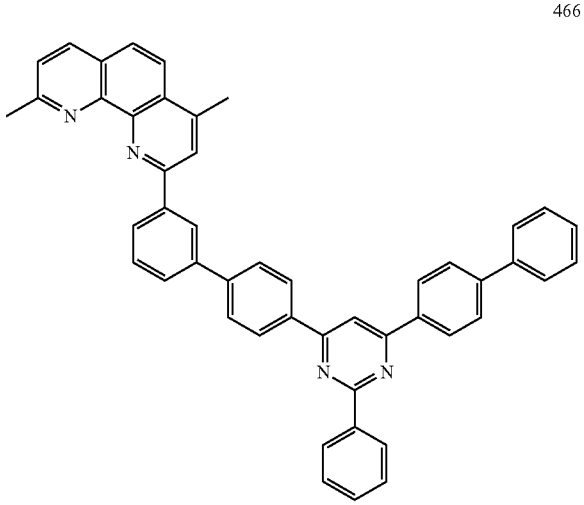
466

923
-continued
467
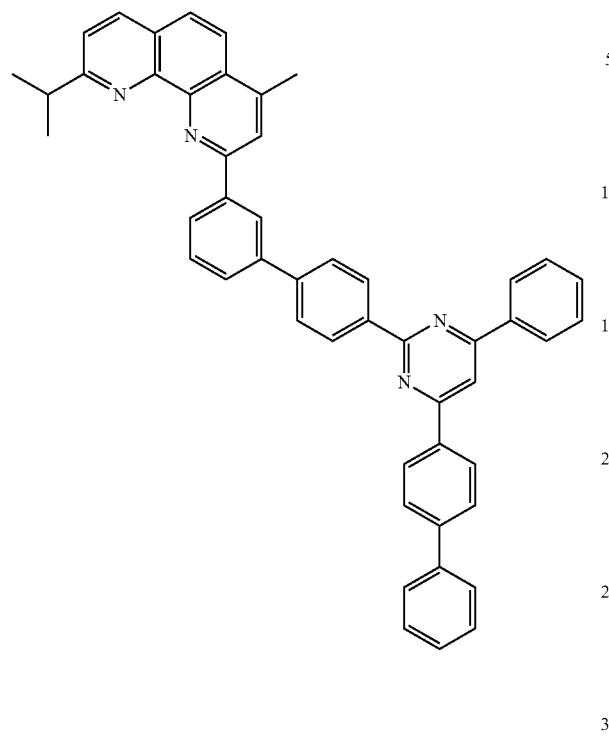
468
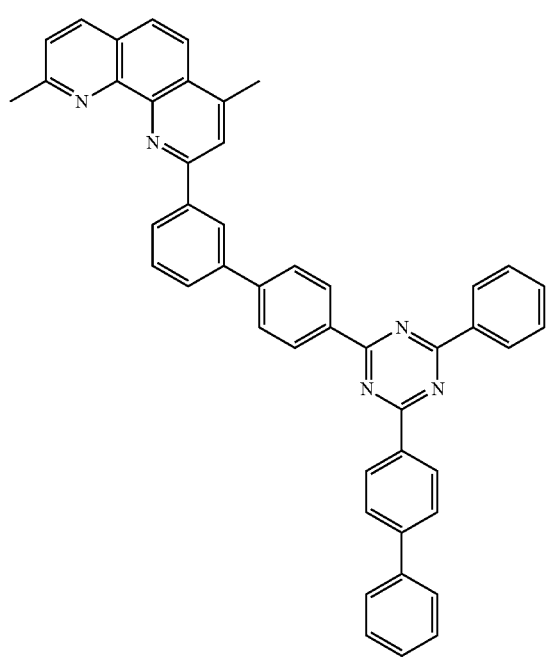
924
-continued
469
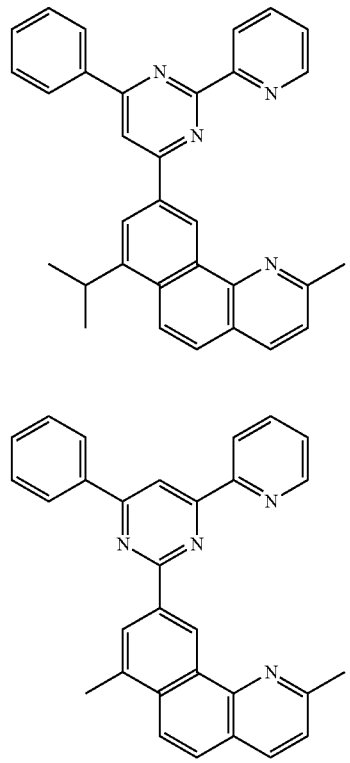
470
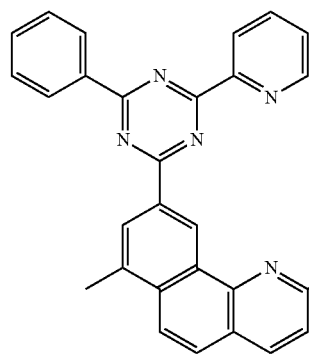
471
472
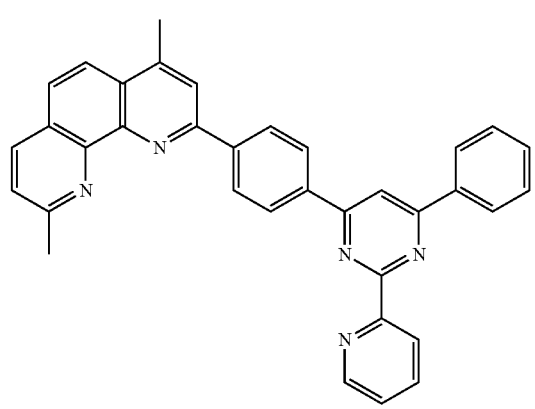

925                                 926
-continued                         -continued
473
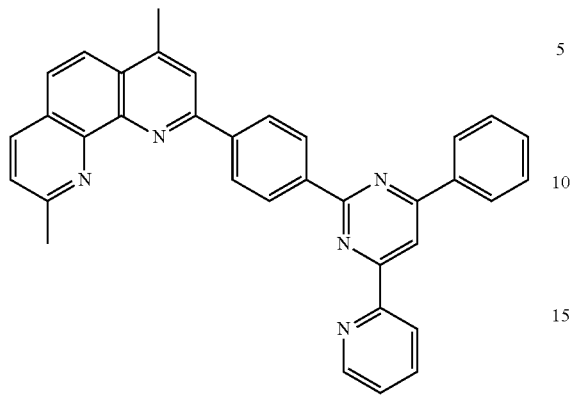
477
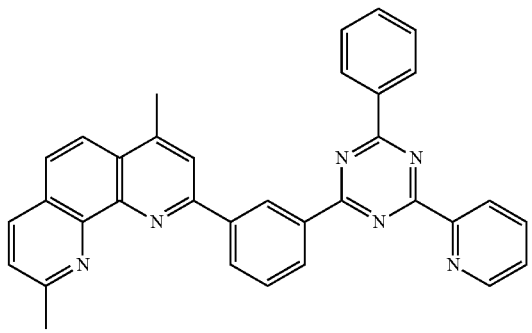
474
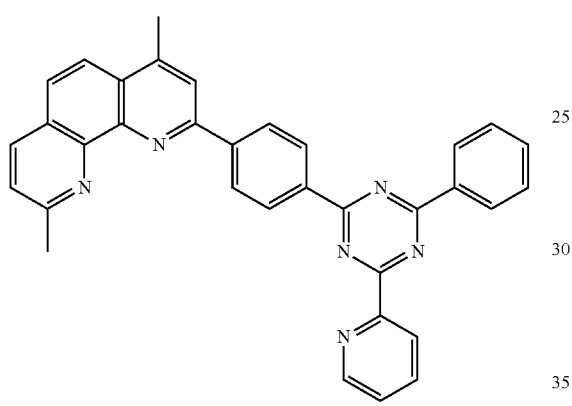
478
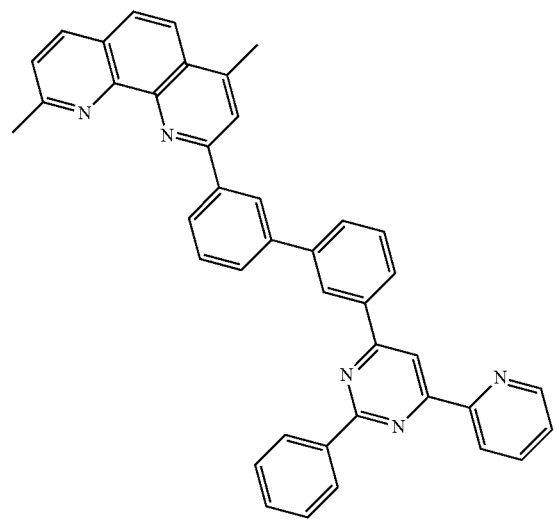
475
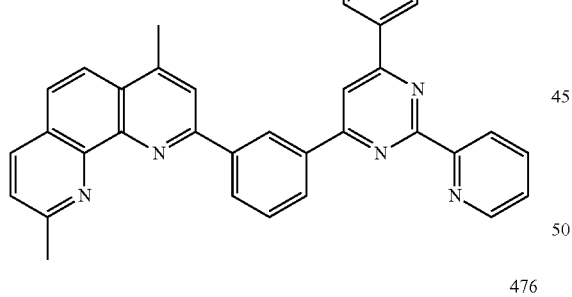
479
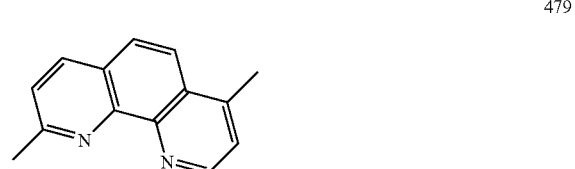
476
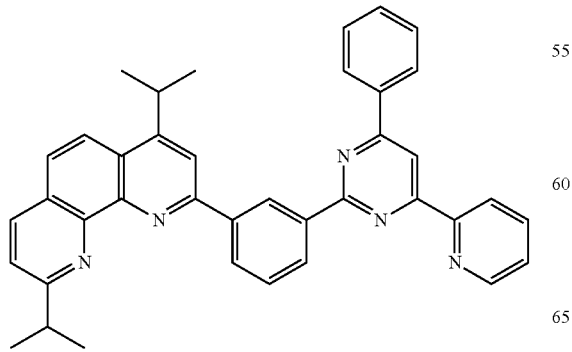
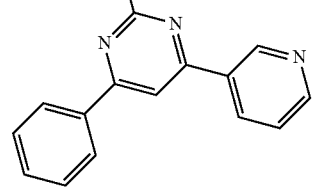

927
-continued
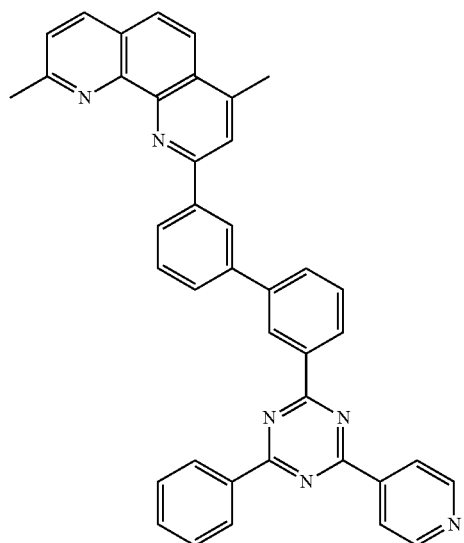
480
928
-continued
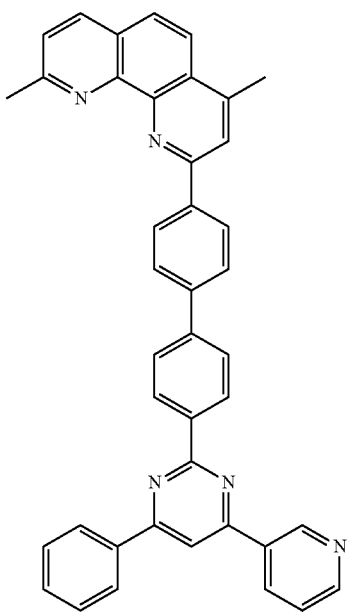
482
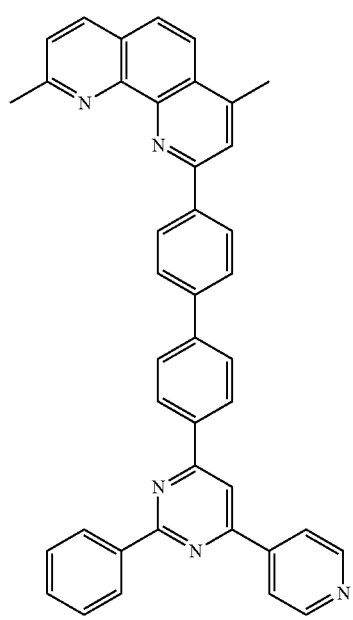
481
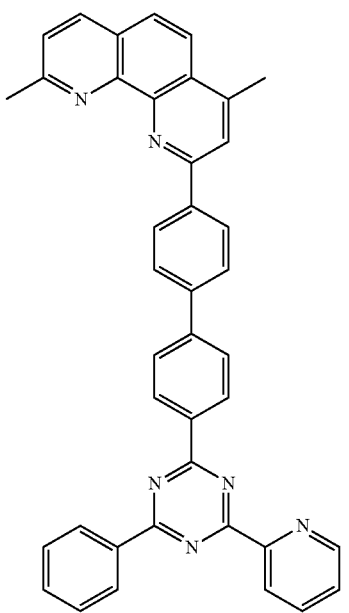
483

929
-continued
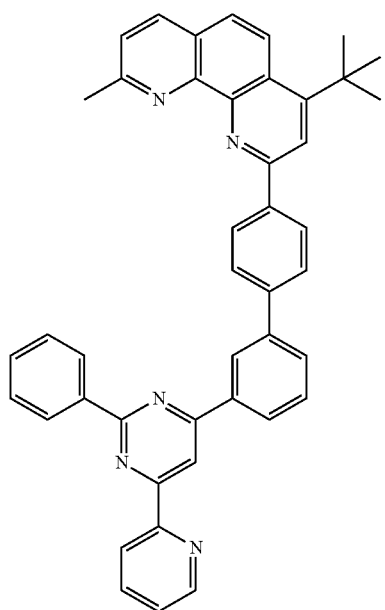
484
930
-continued
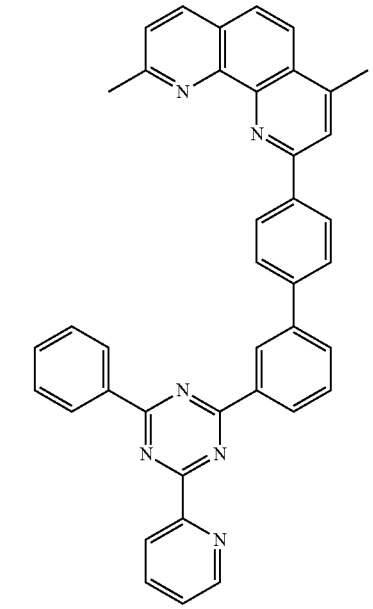
486
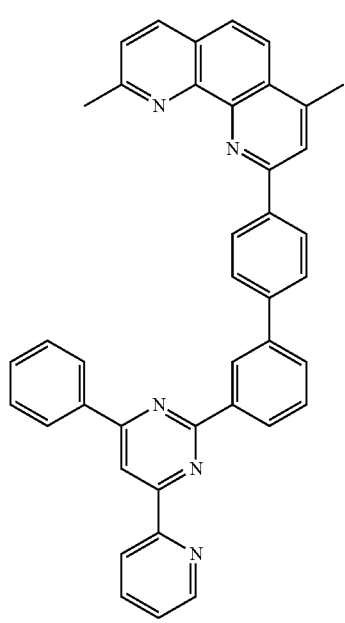
485
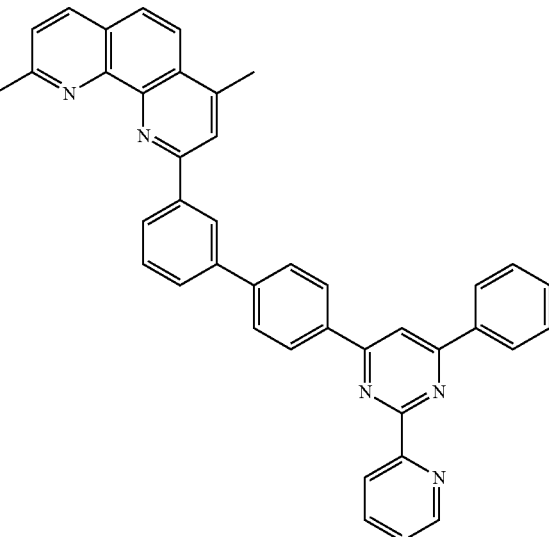
487

931
-continued
488
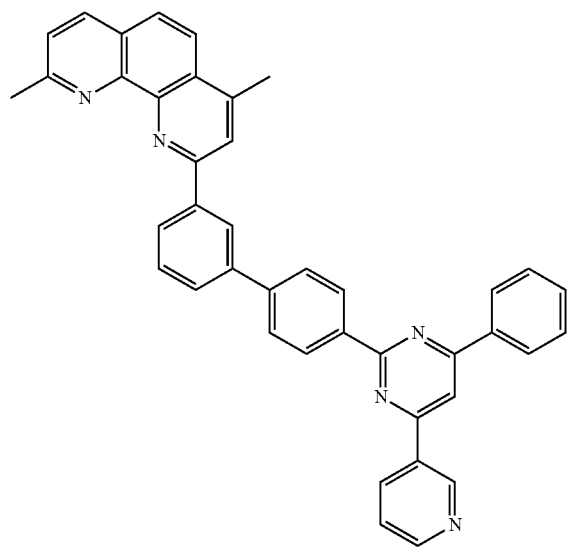
489
932
-continued
491
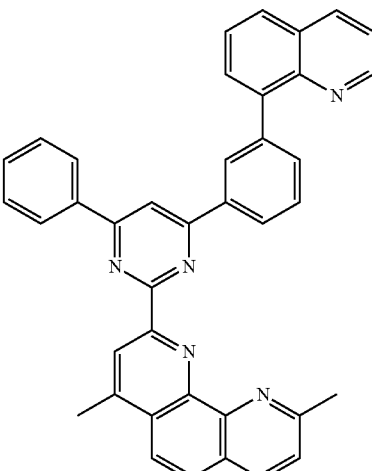
492
490
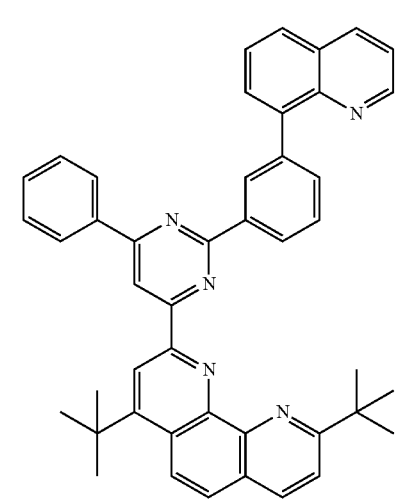
493
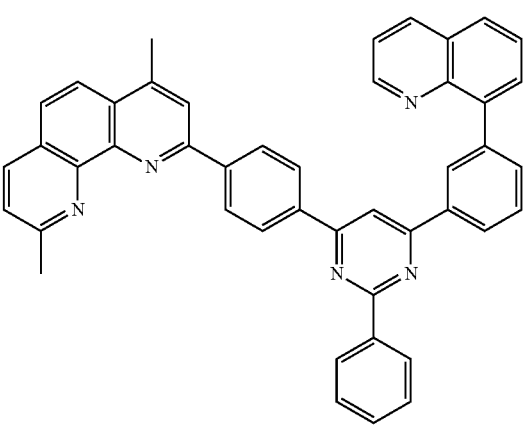

933
-continued
494
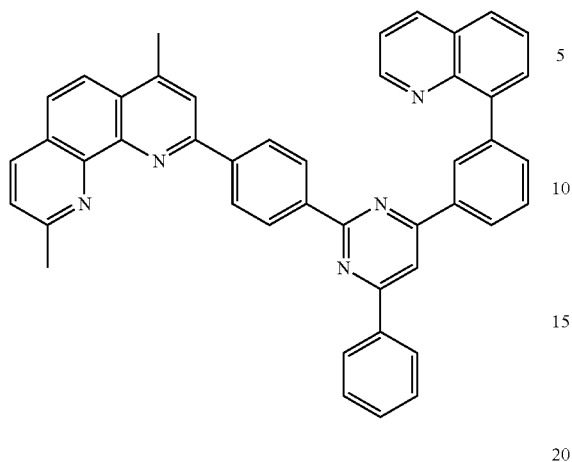
495
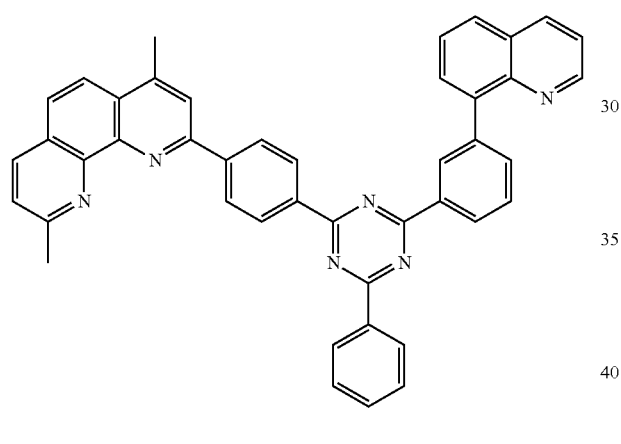
496
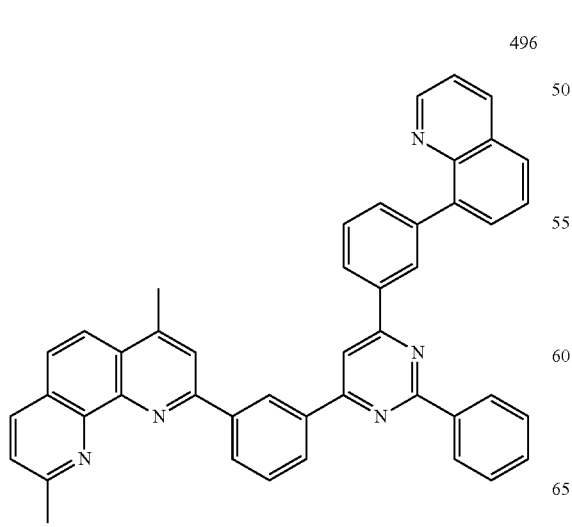
934
-continued
497
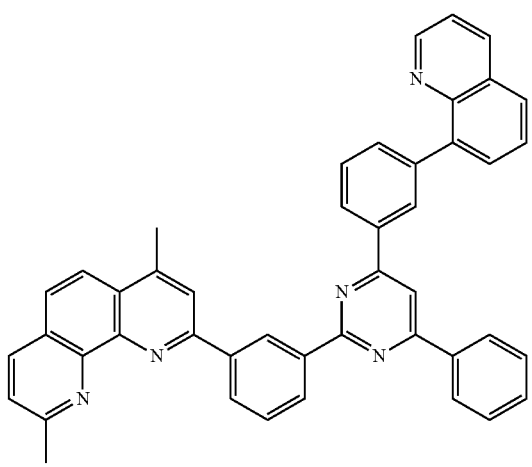
498
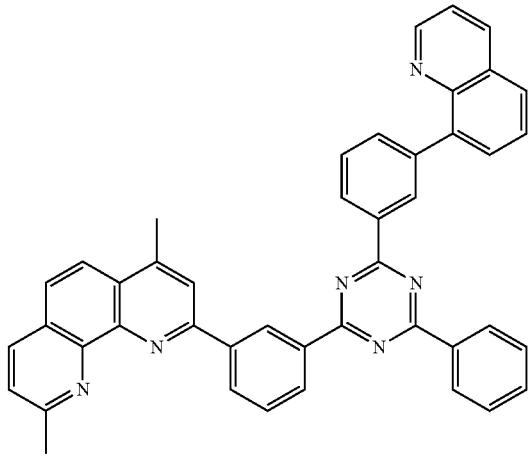
499
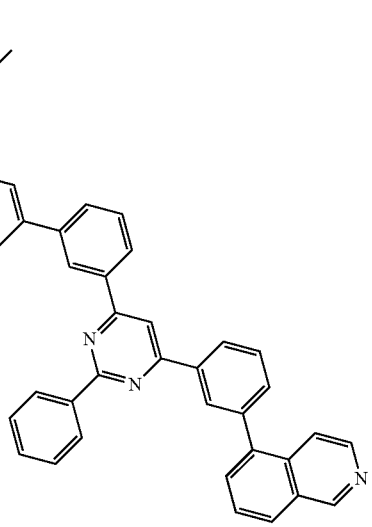

935
-continued
500
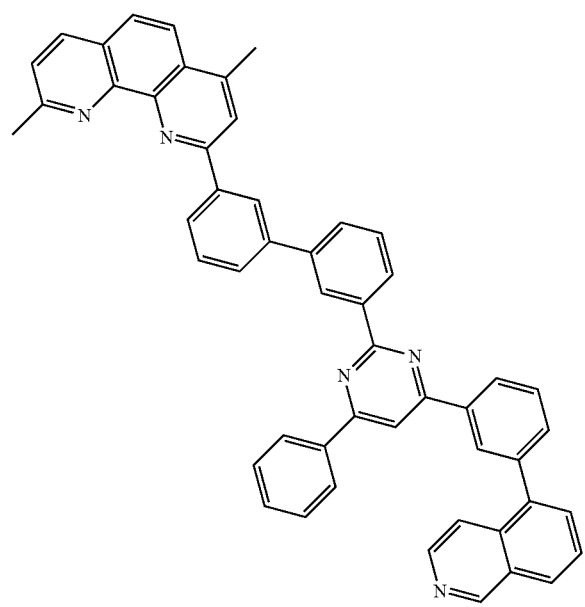
501
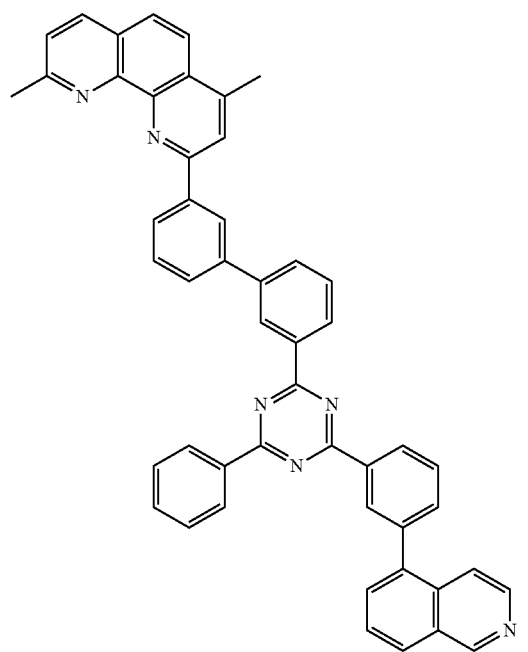
936
-continued
502
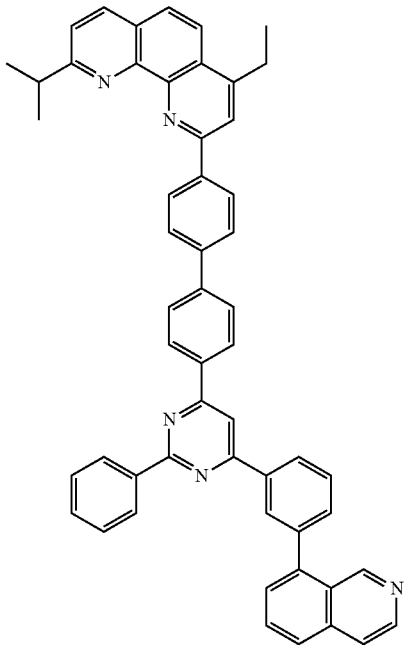
503
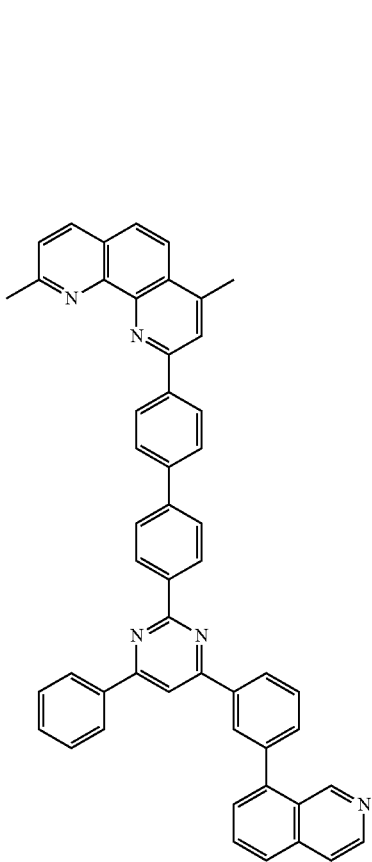

937
-continued
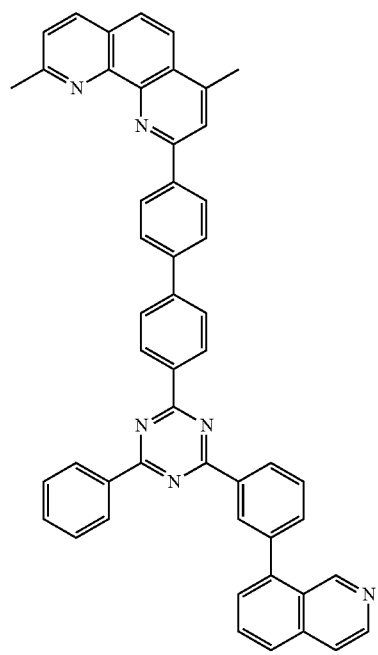
938
-continued
504
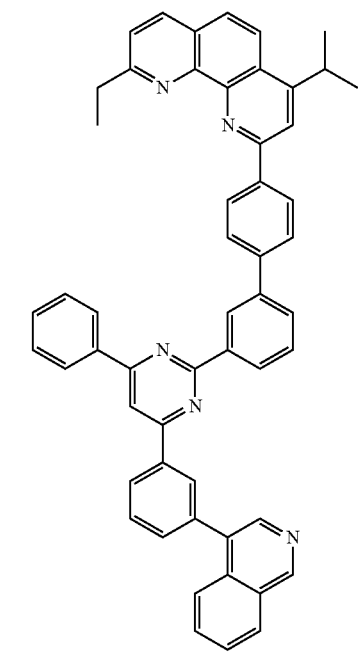
506
505
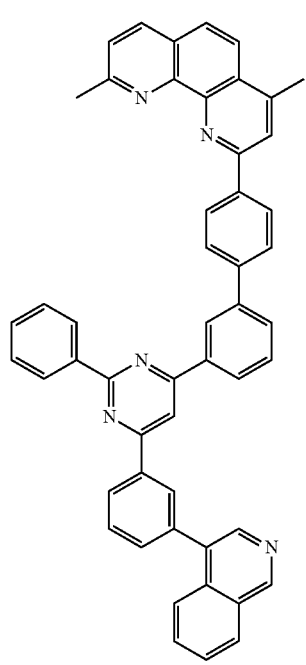
507
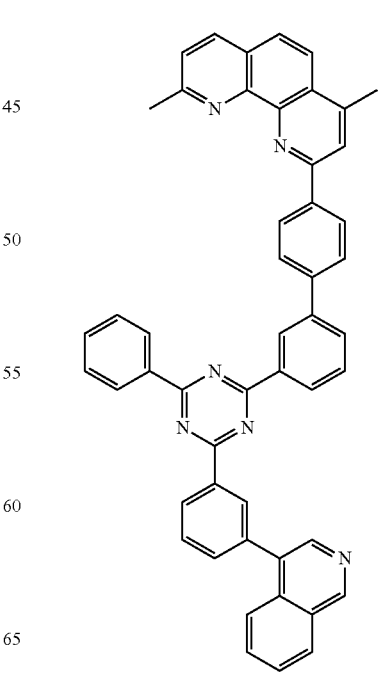

939
-continued
508
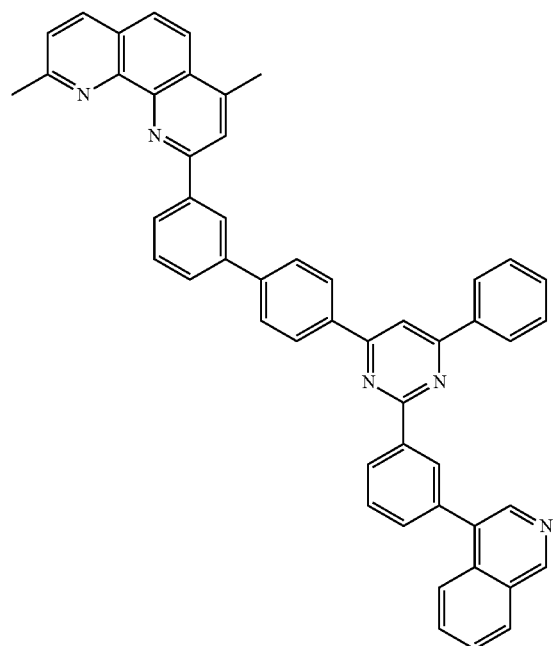
509
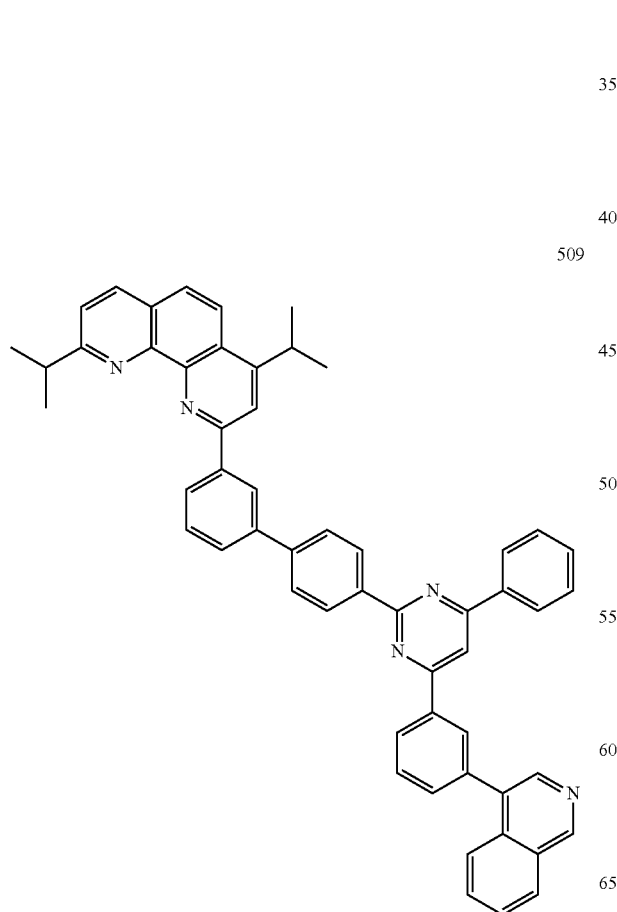
940
-continued
510
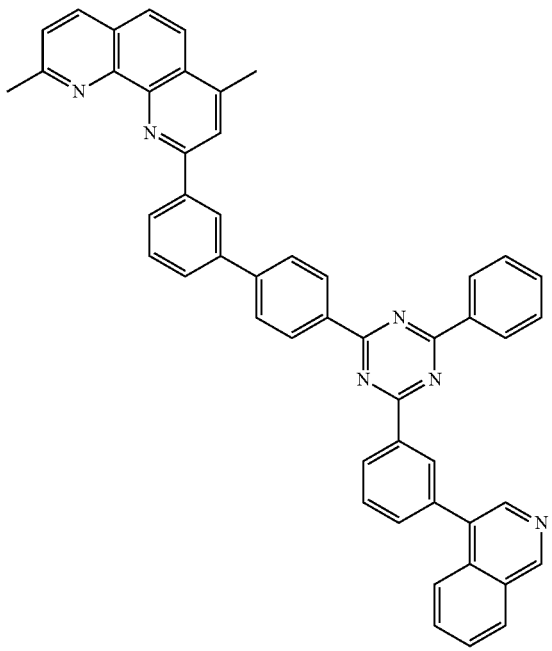
511
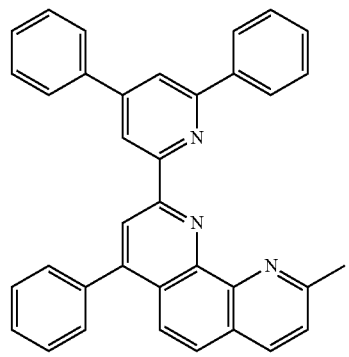
512
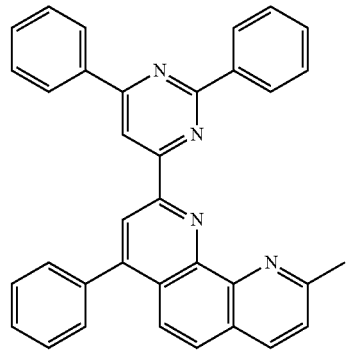

513
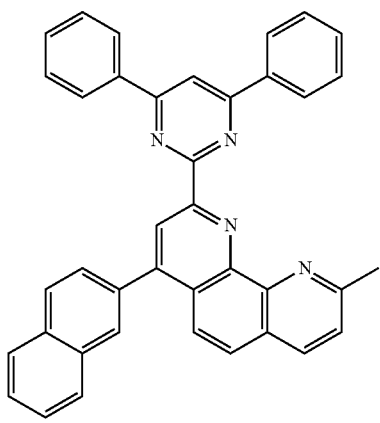
514
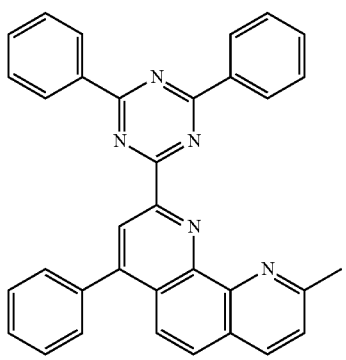
515
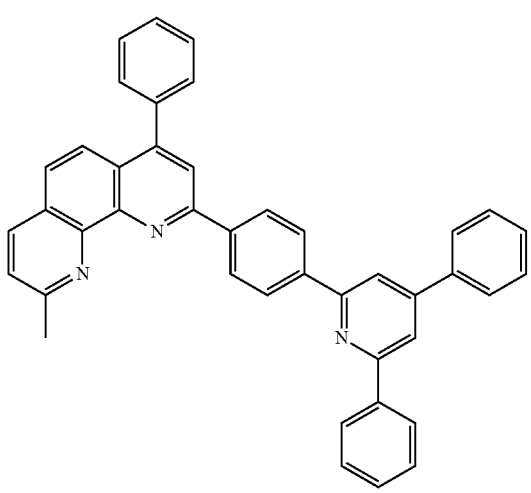
516
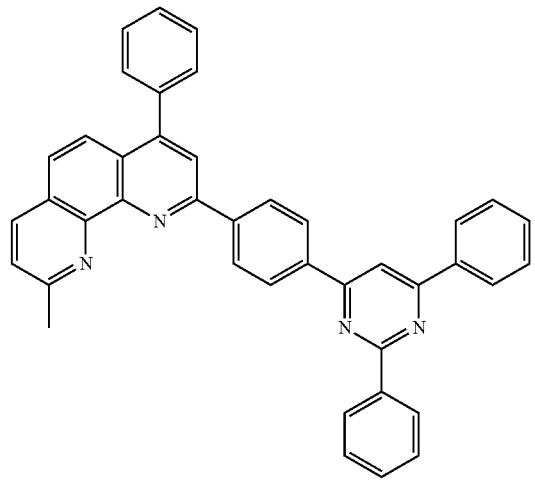
517
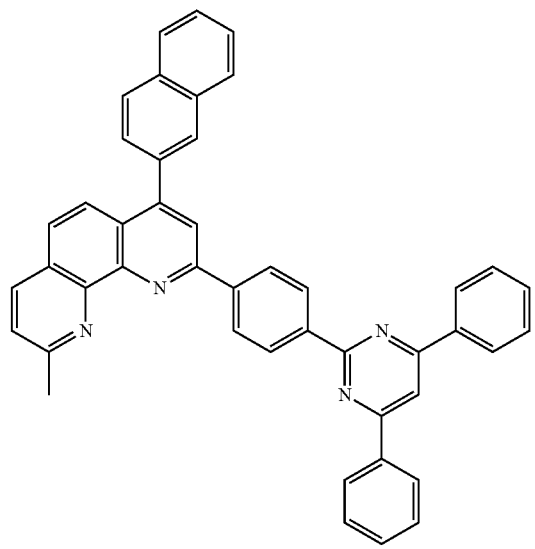
518
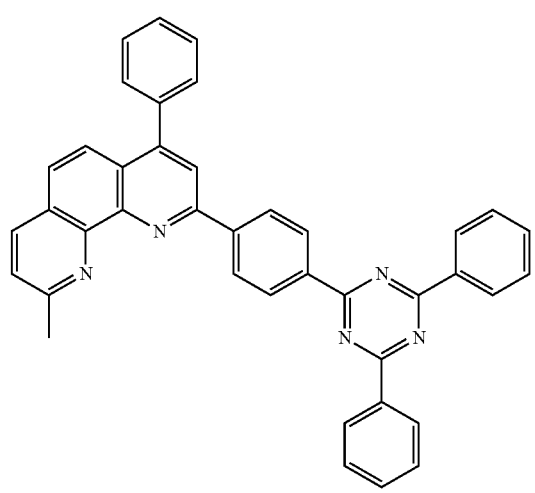

943
-continued
519
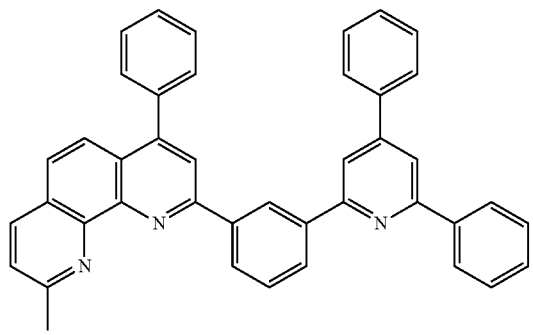
520
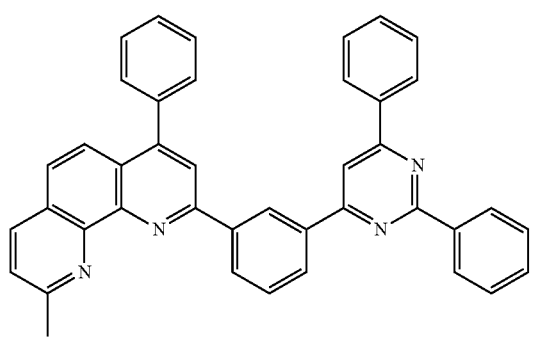
521
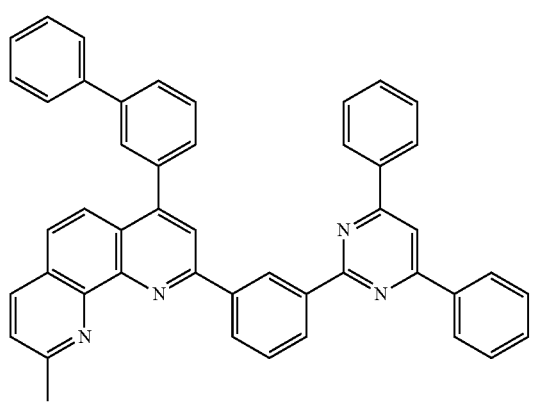
522
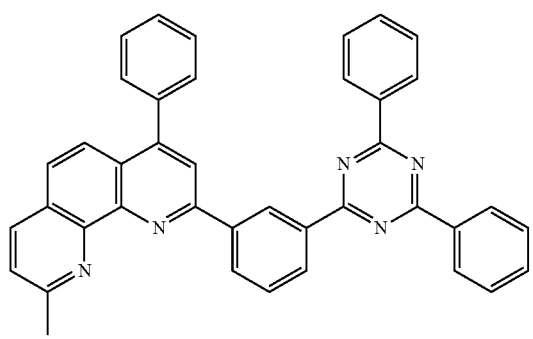
944
-continued
523
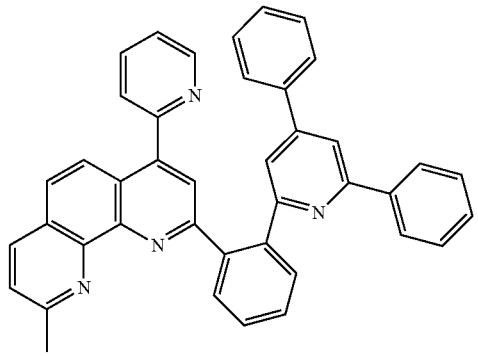
524
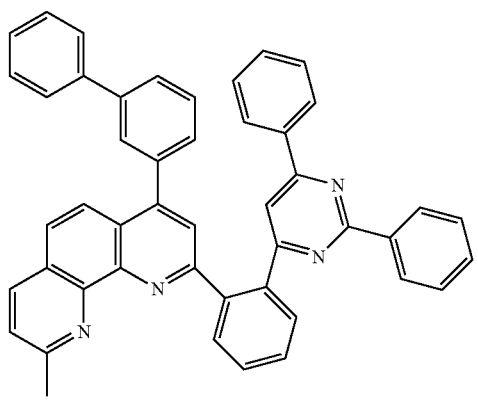
525
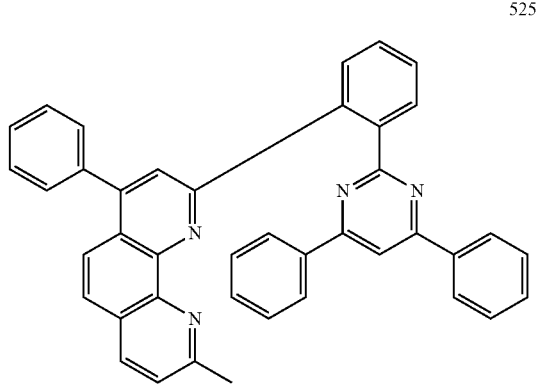
526
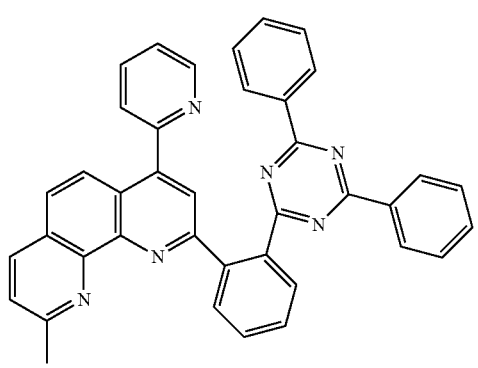

945
-continued
527
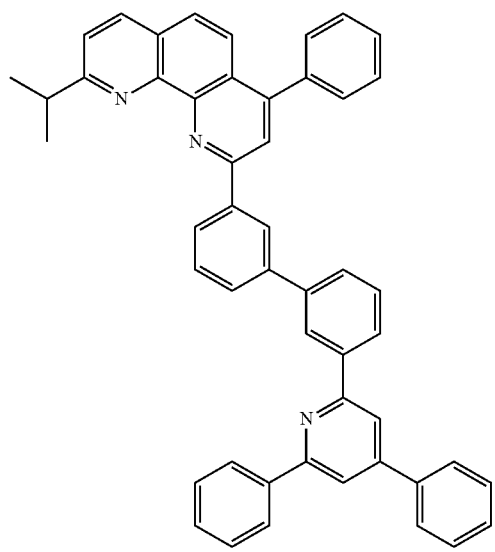
528
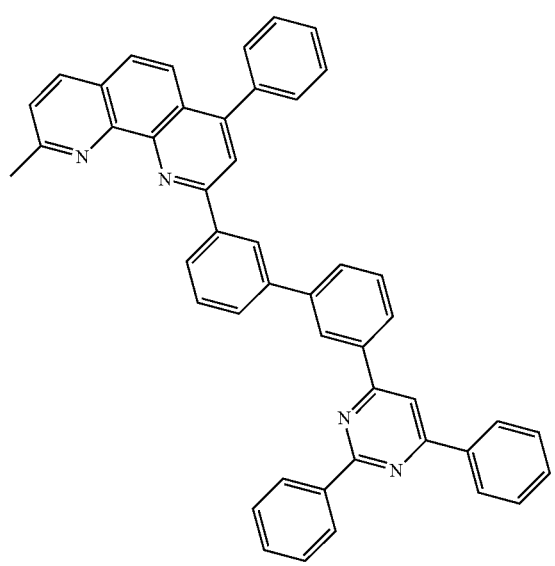
946
-continued
529
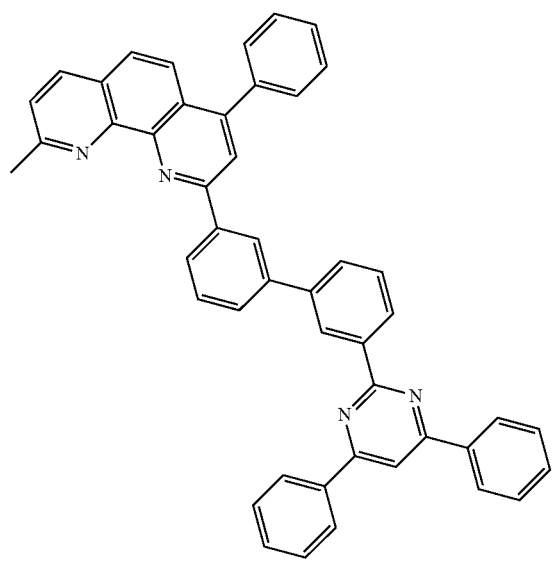
530
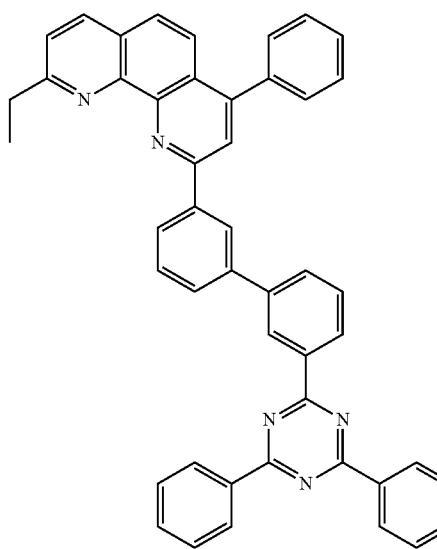

531
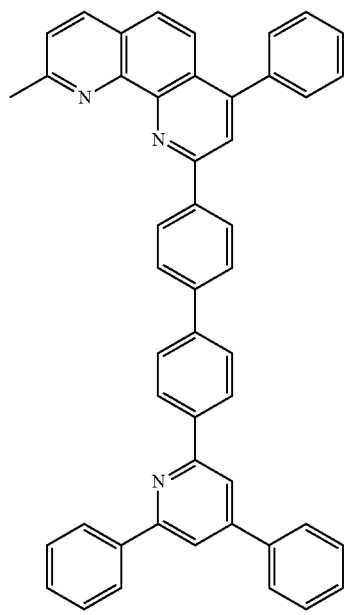
532
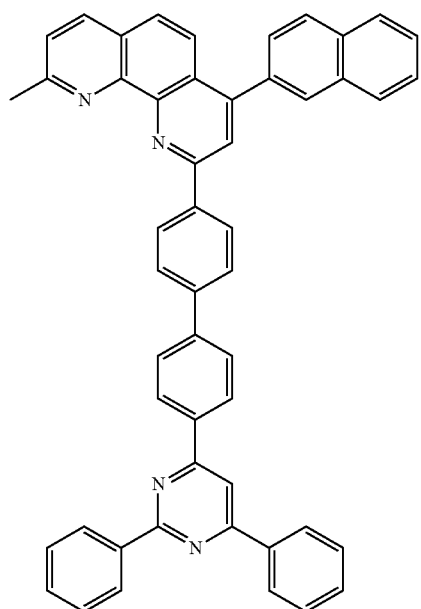
533
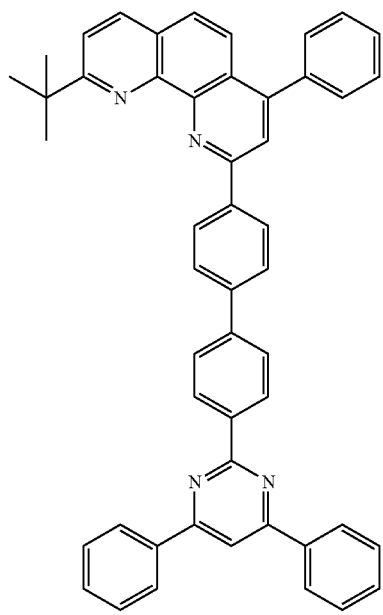
534
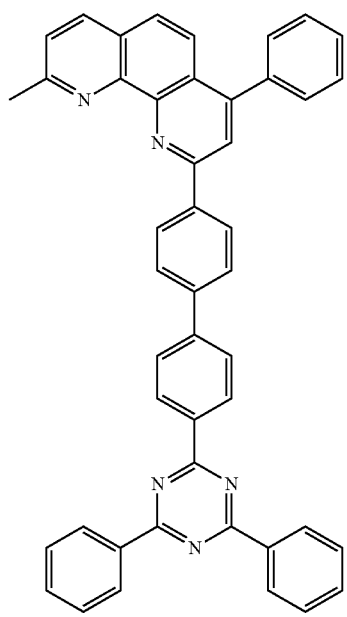

949
-continued
950
-continued
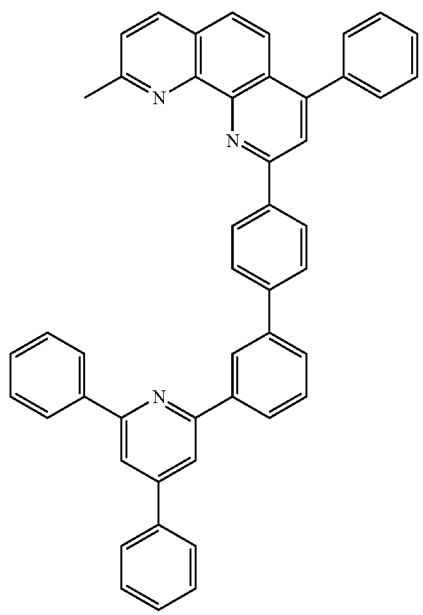
535
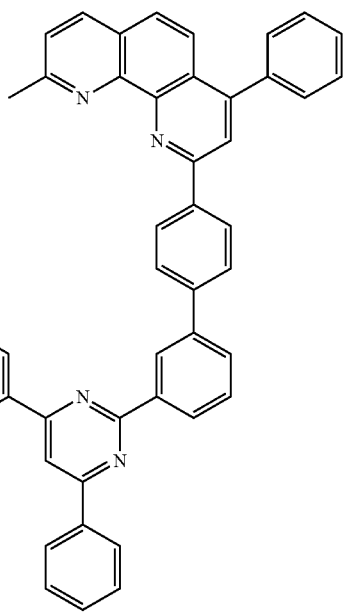
537
536
538

951
-continued
539
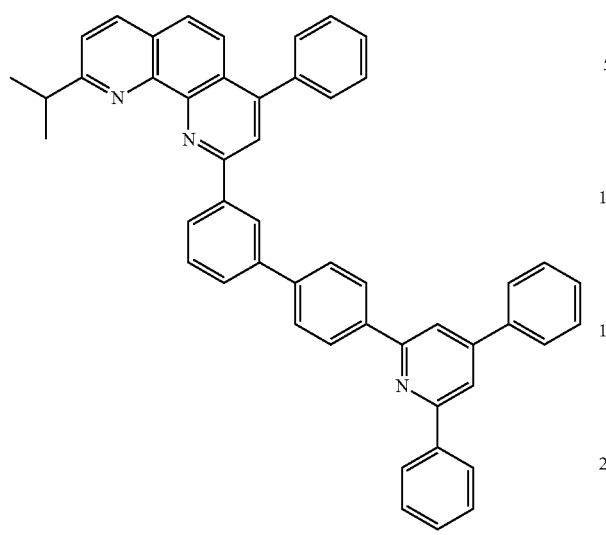
540
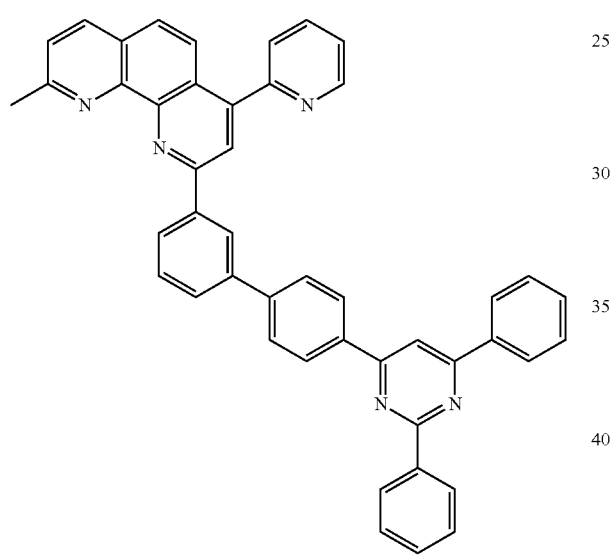
541
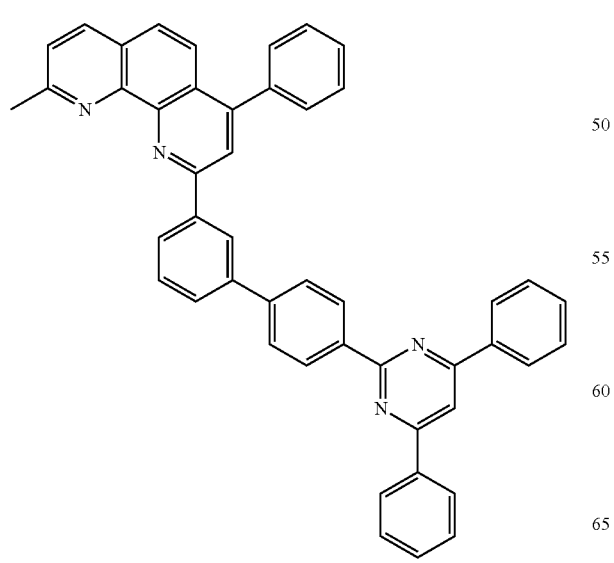
952
-continued
542
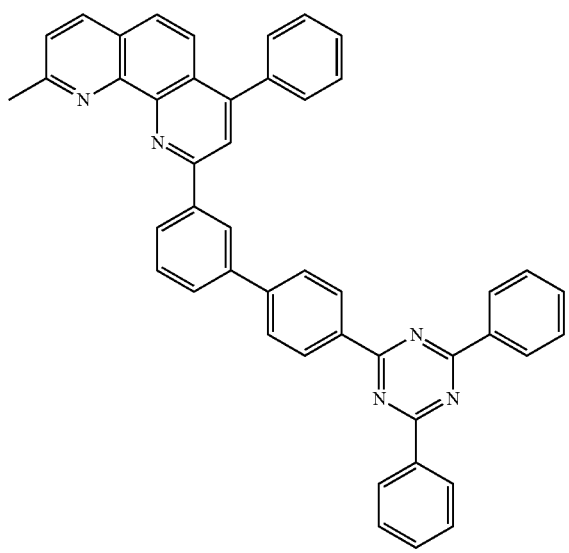
543
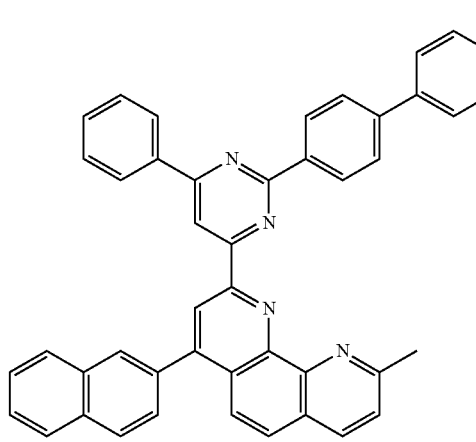
544

| 953 | 954 |
|---|---|
| 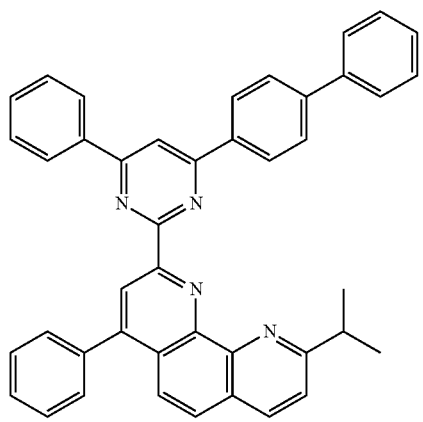 545 | 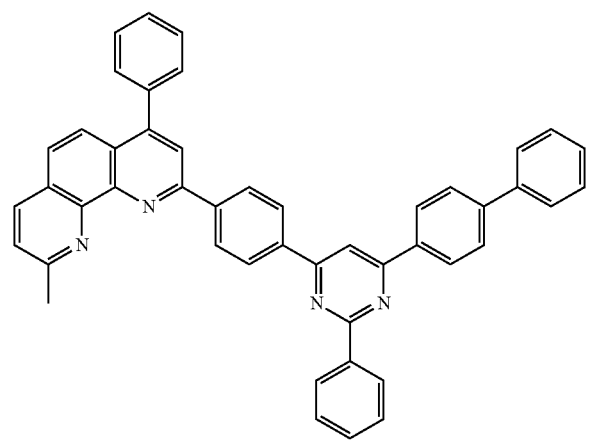 548 |
| 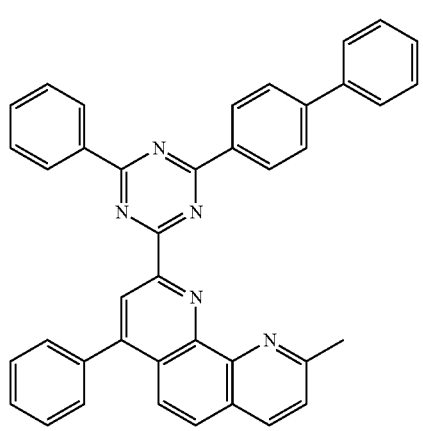 546 | |
| 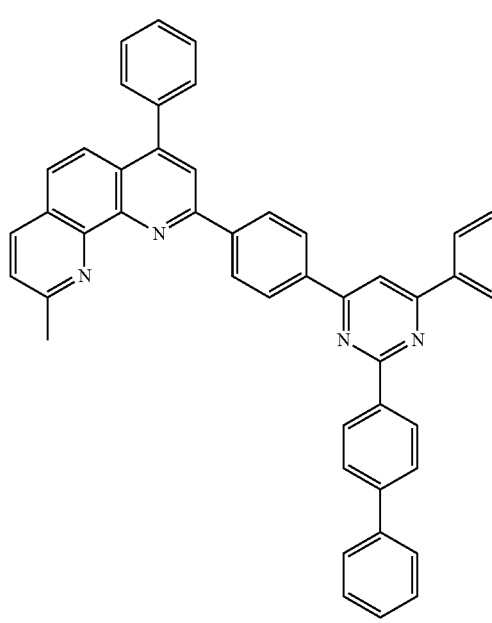 547 | 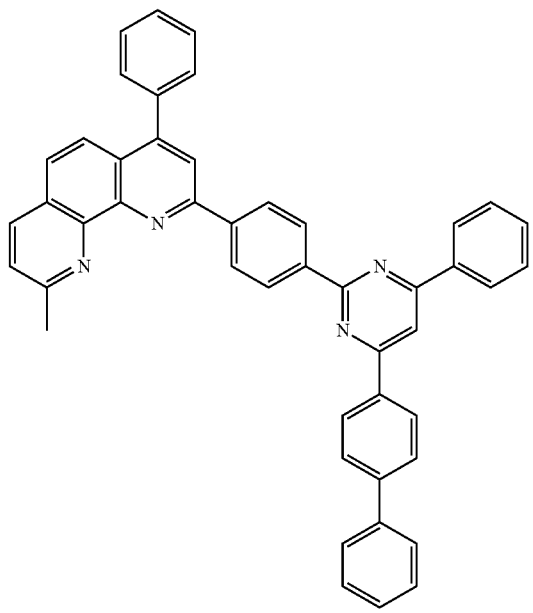 549 |

955
-continued
550
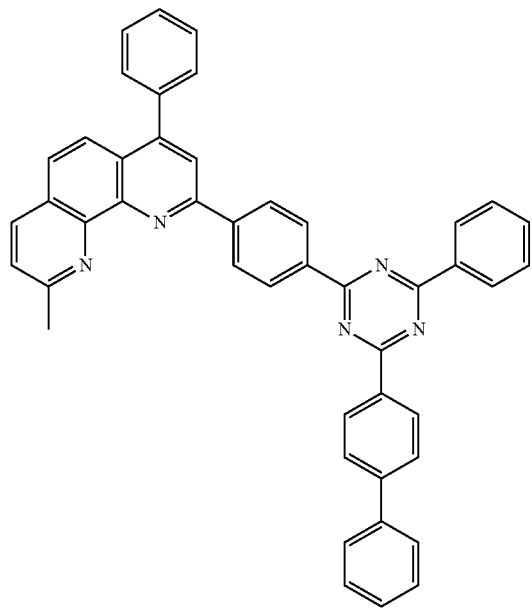
551
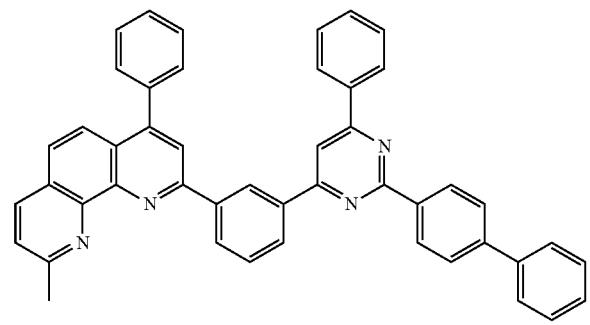
552
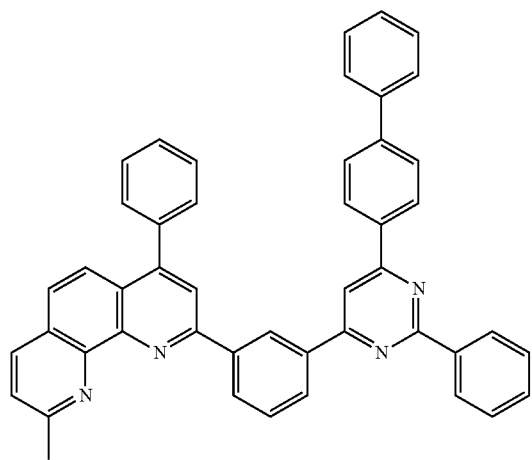
956
-continued
553
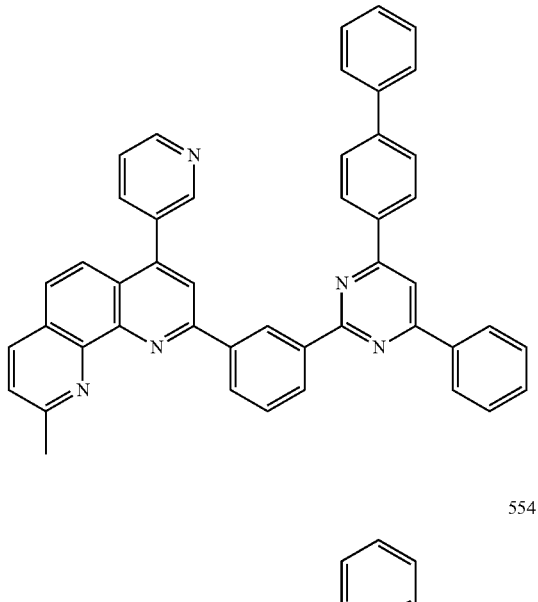
554
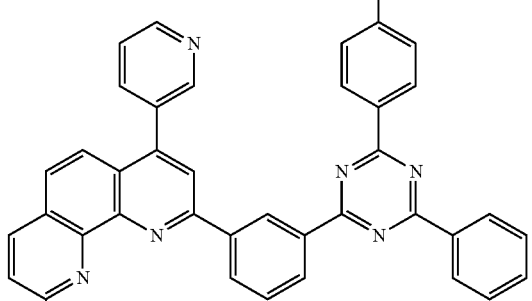
555
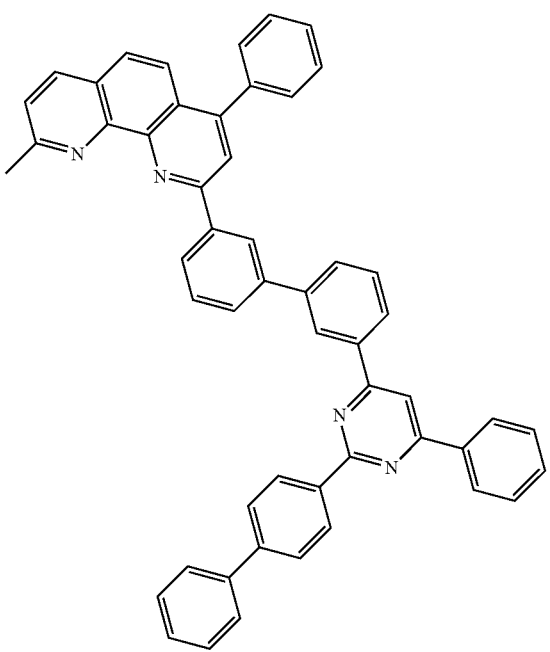

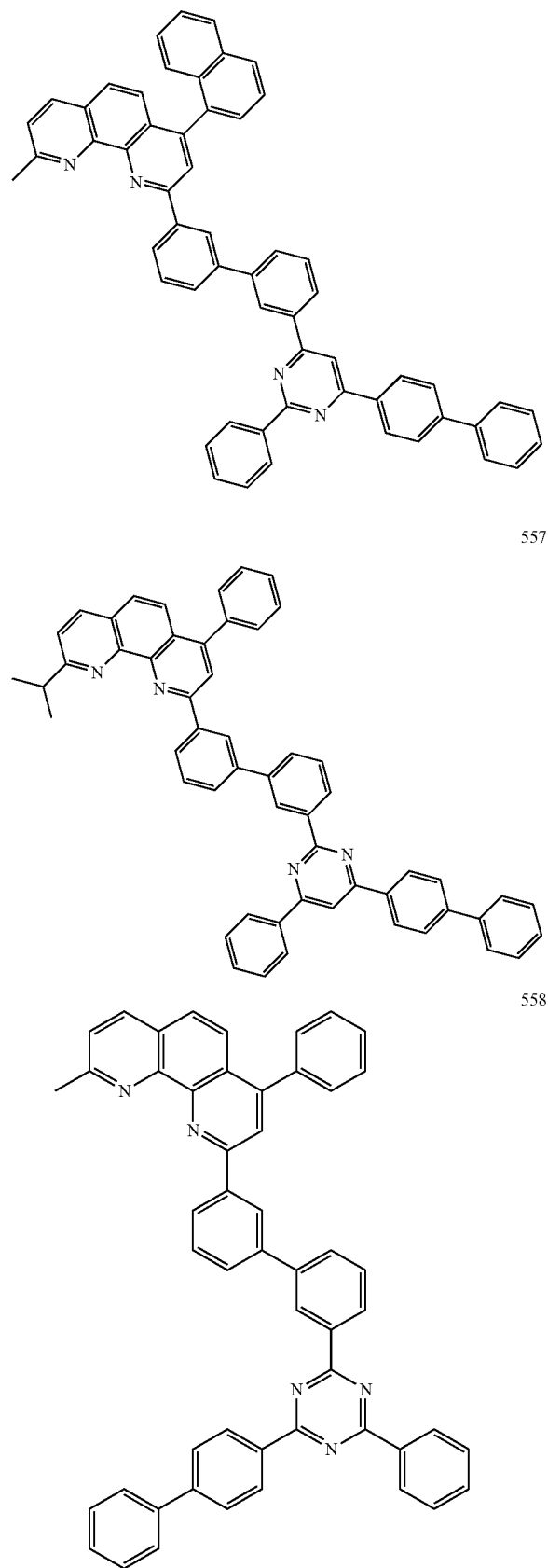

959
-continued
960
-continued
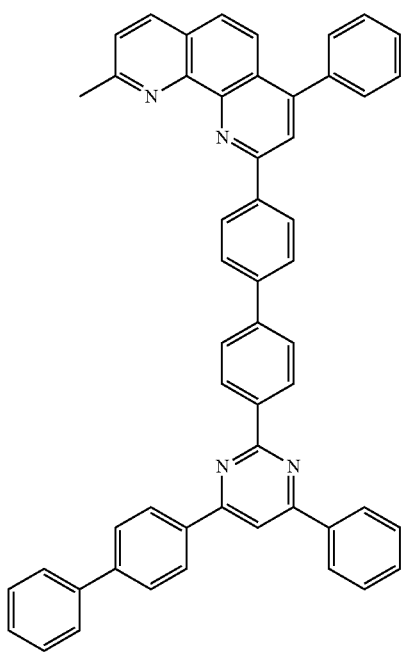
561
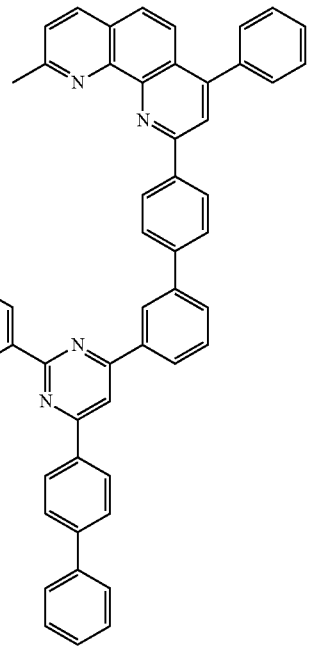
563
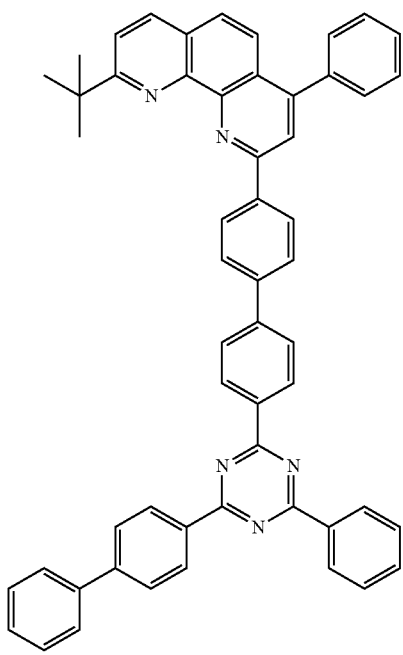
562
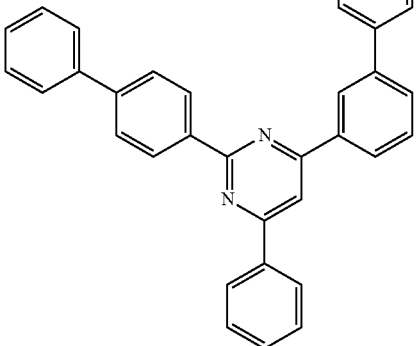
564

961
-continued
962
-continued
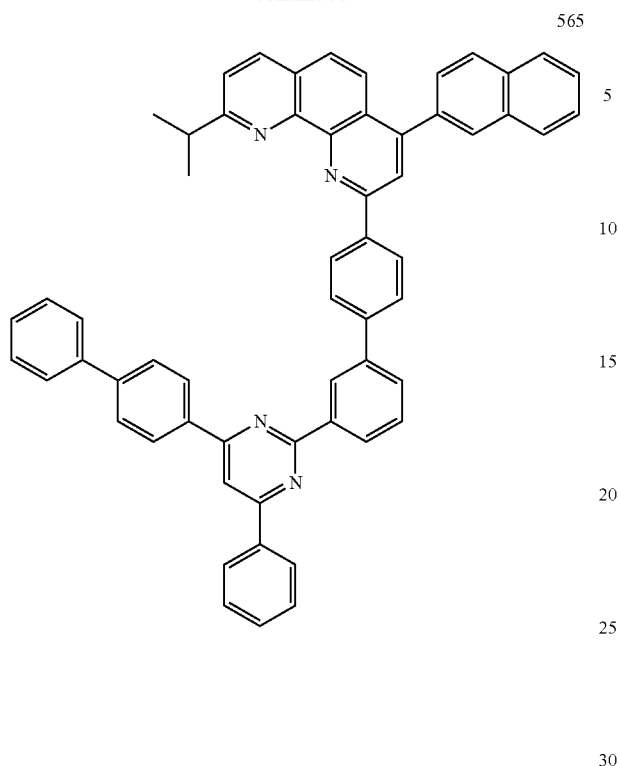
565
566
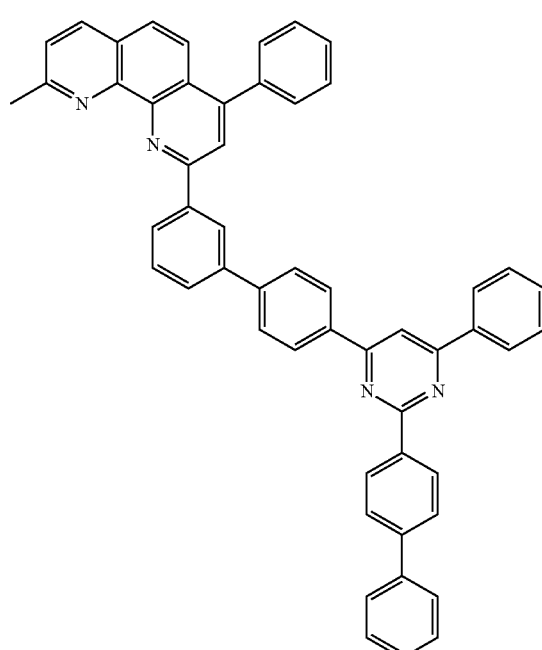
567
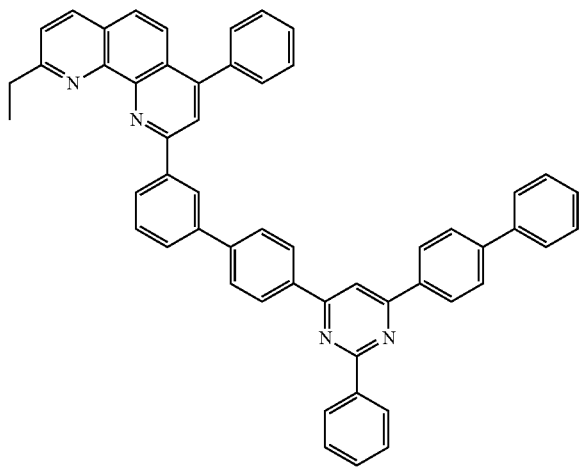
568

569
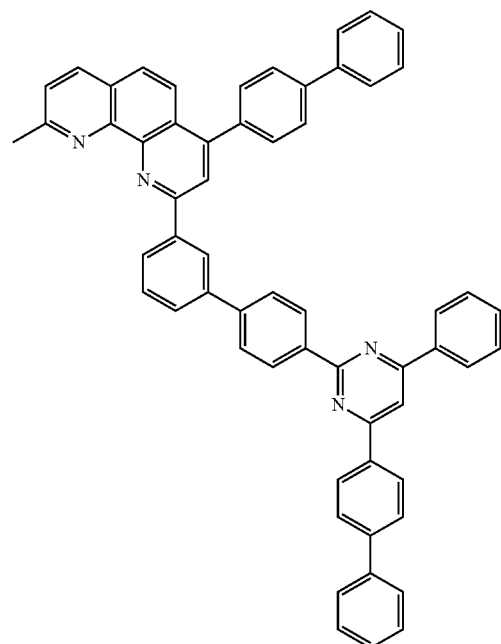
570
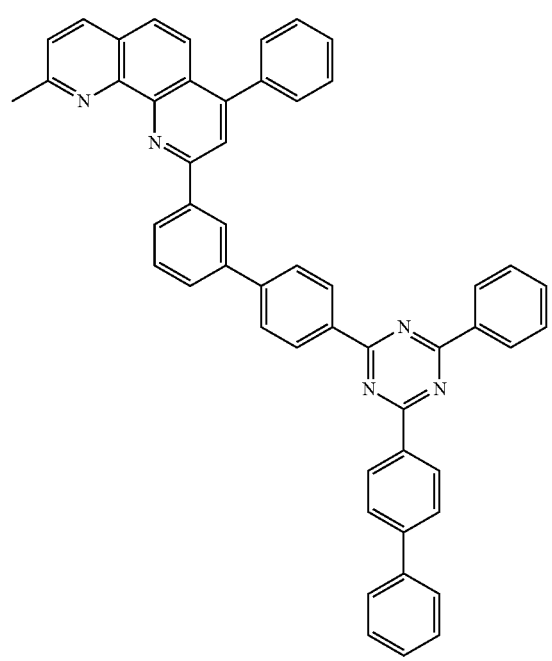
571
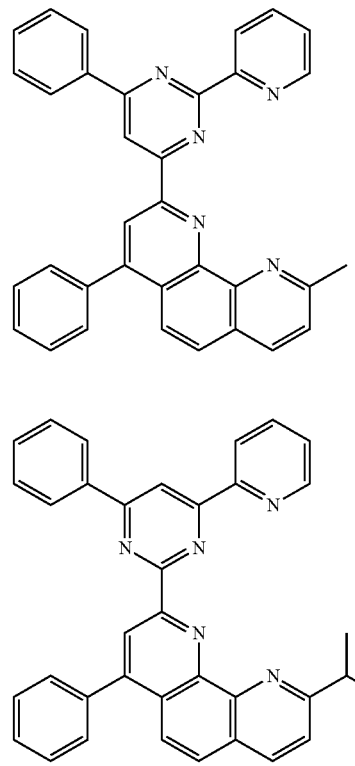
572
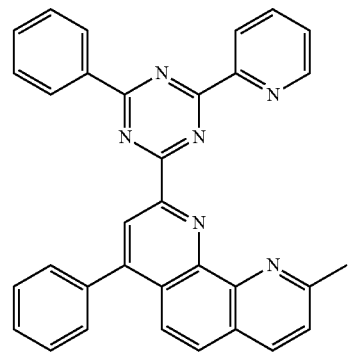
573
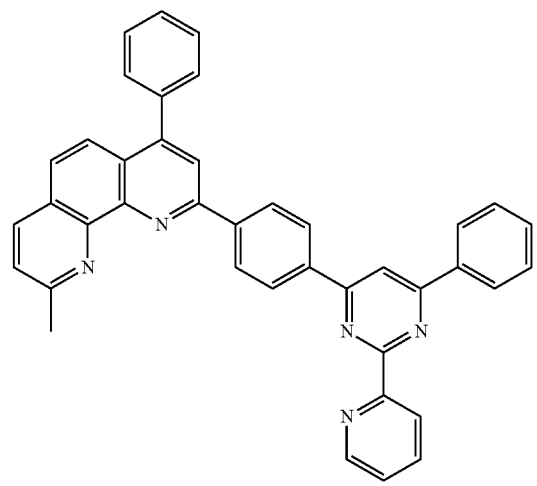
574

965
-continued
966
-continued
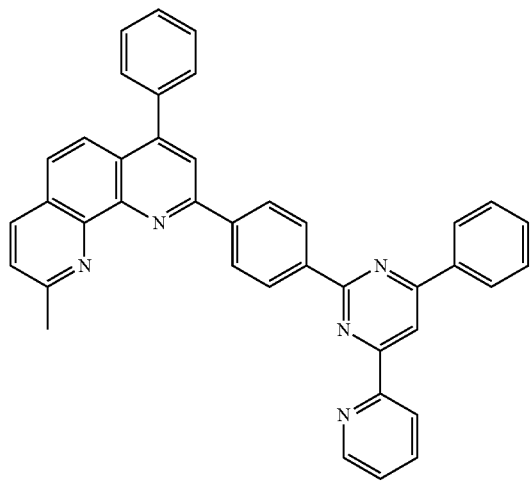
575
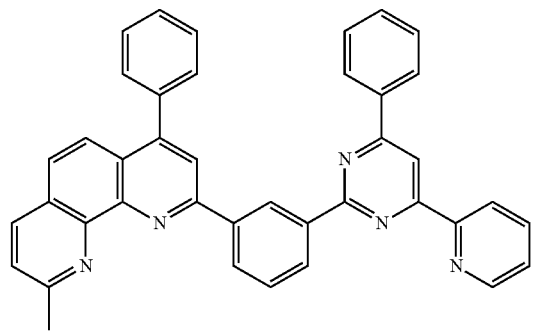
578
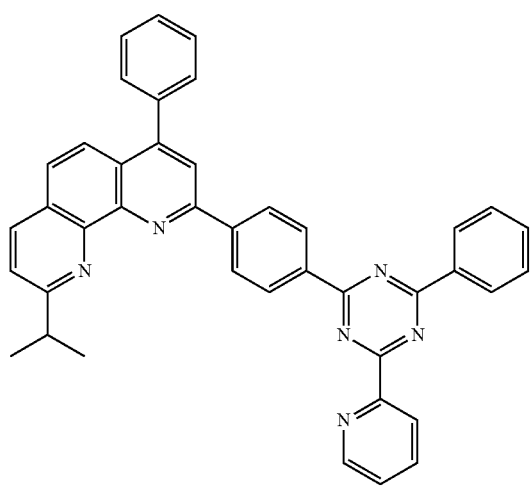
576
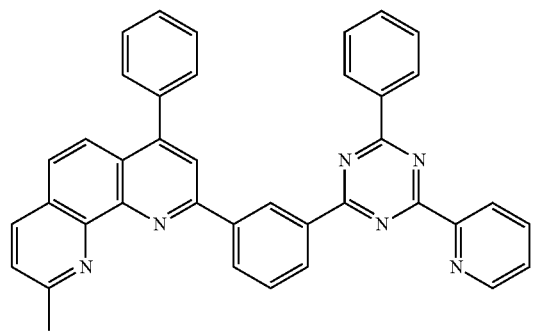
579
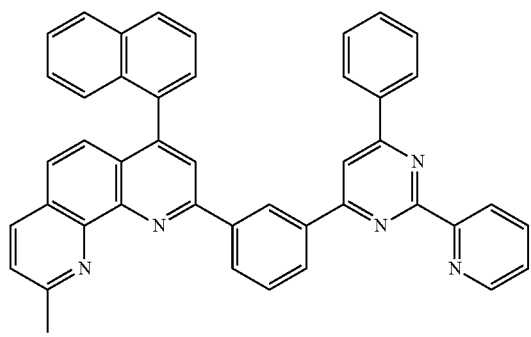
577
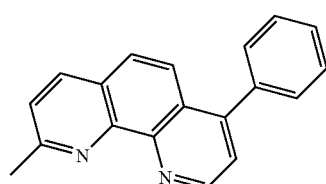
580
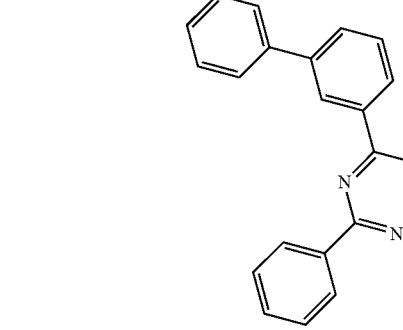

967
581
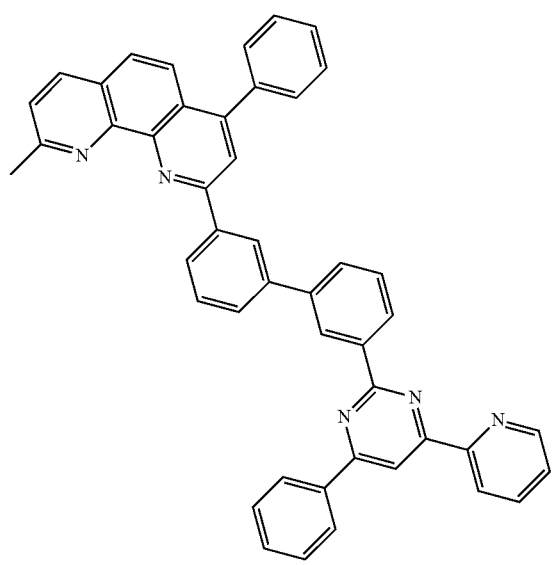
582
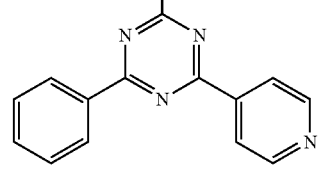
968
583
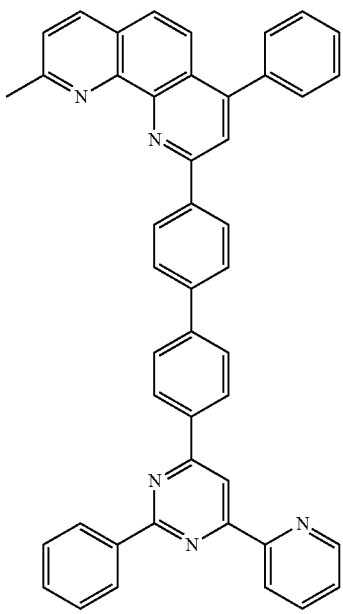
584
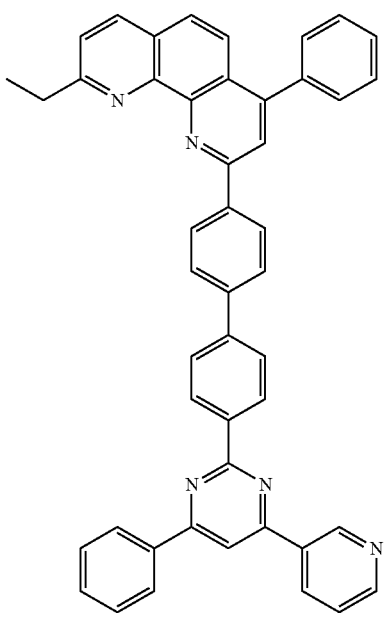

969
-continued
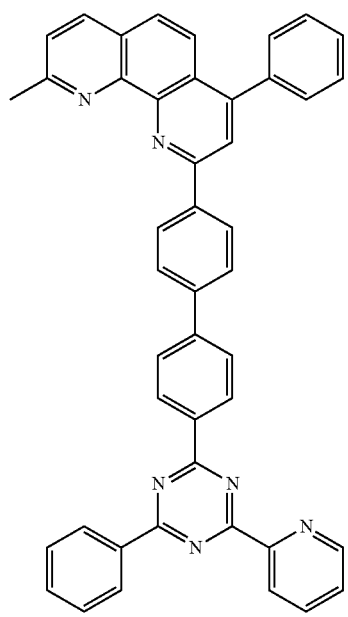
585
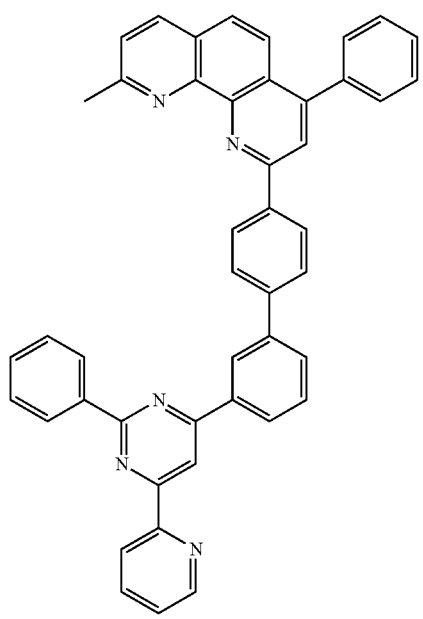
586
970
-continued
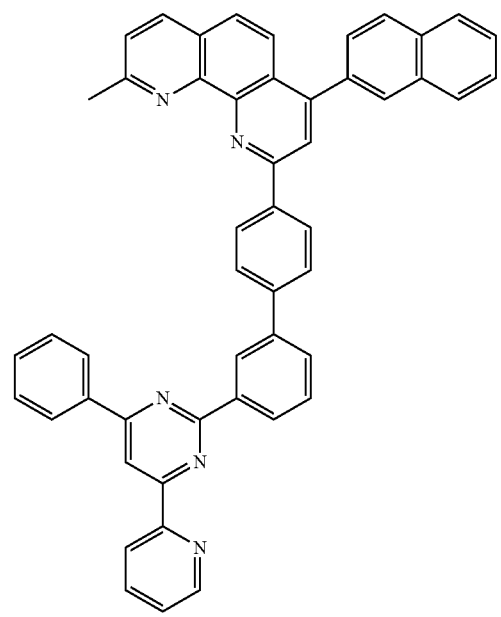
587
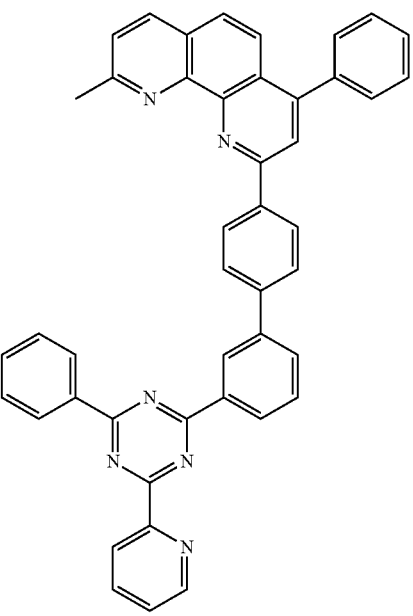
588

971
589
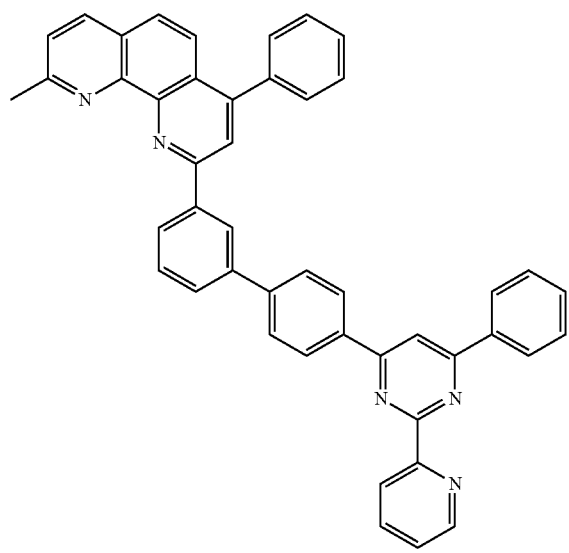
590
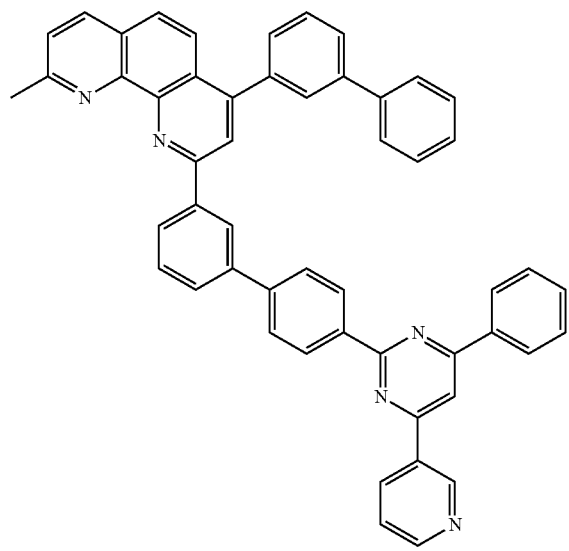
972
-continued
591
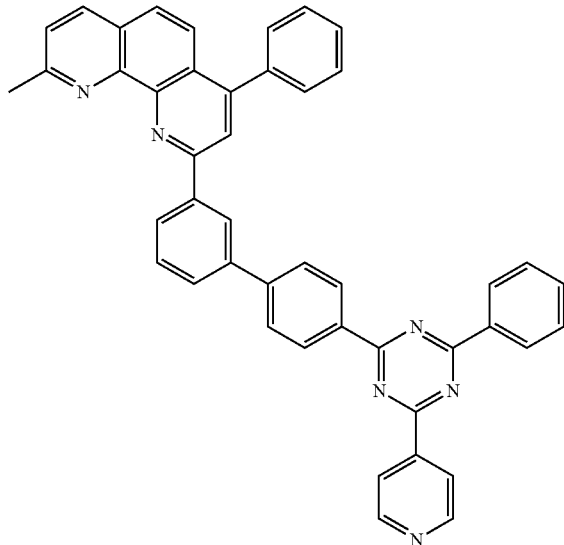
592
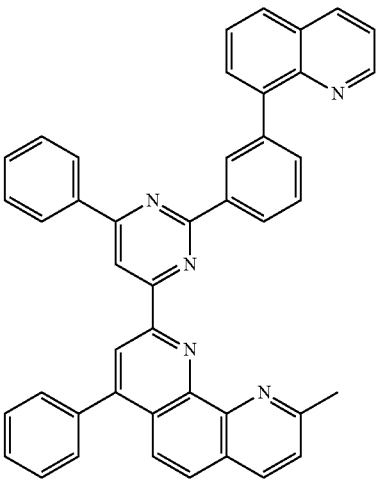
593
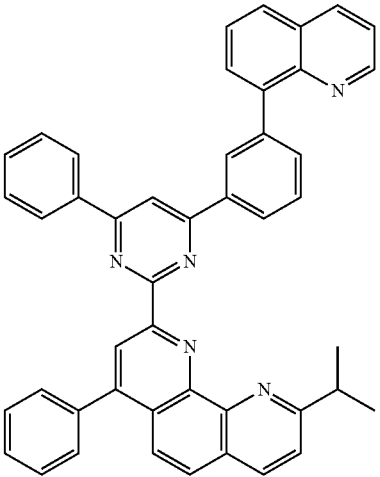

594
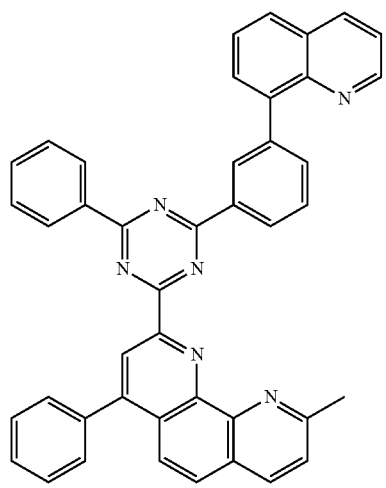
597
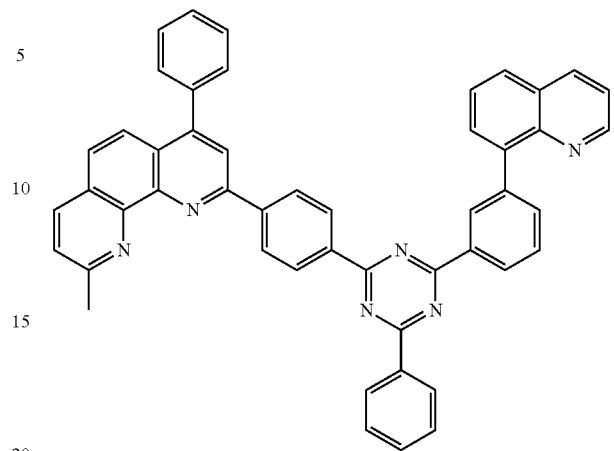
595
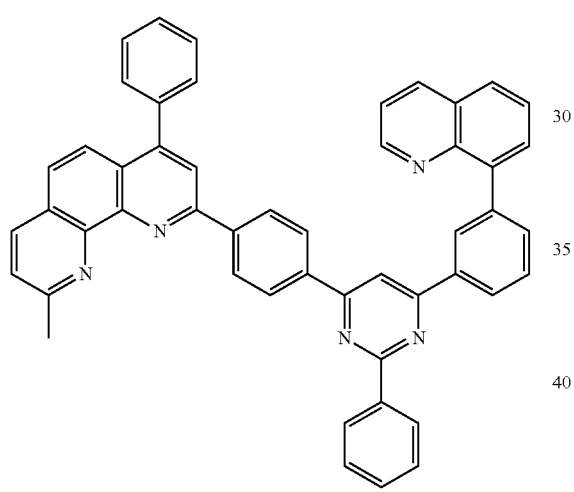
598
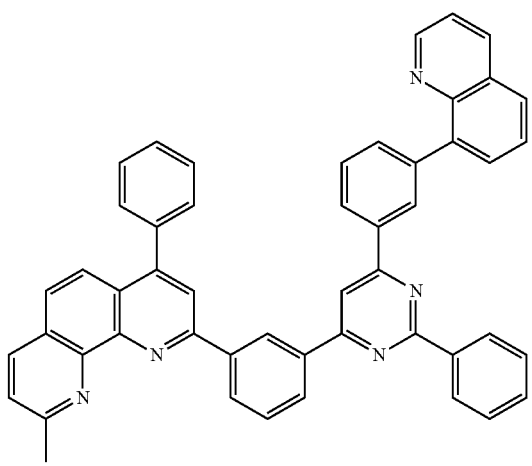
596
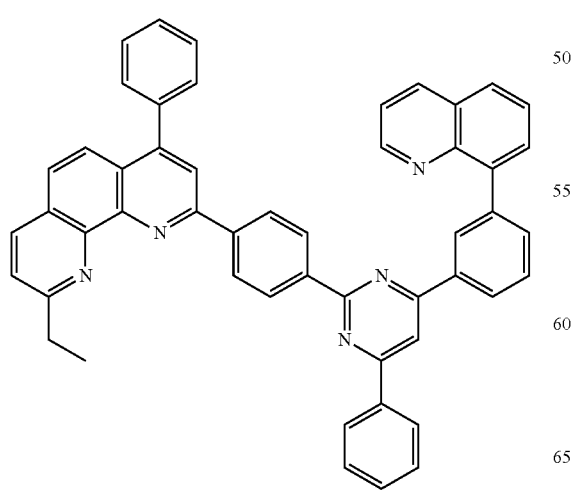
599
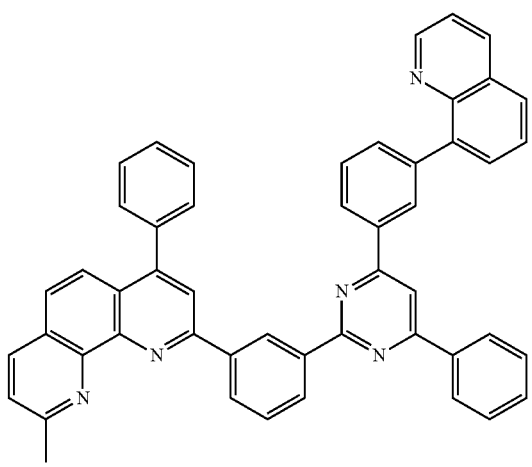

975
-continued
600
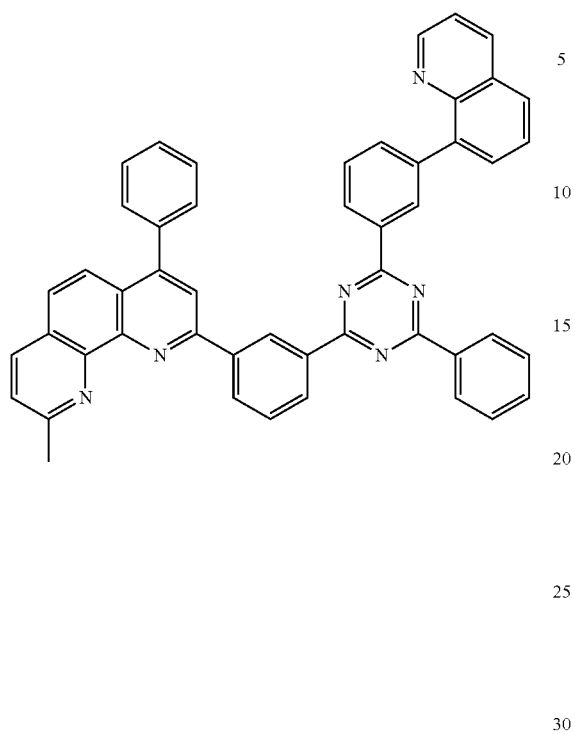
601
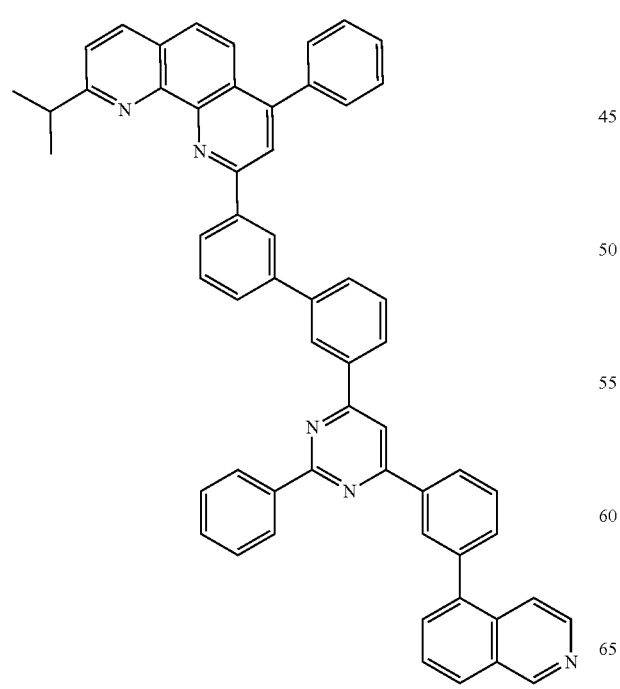
976
-continued
602
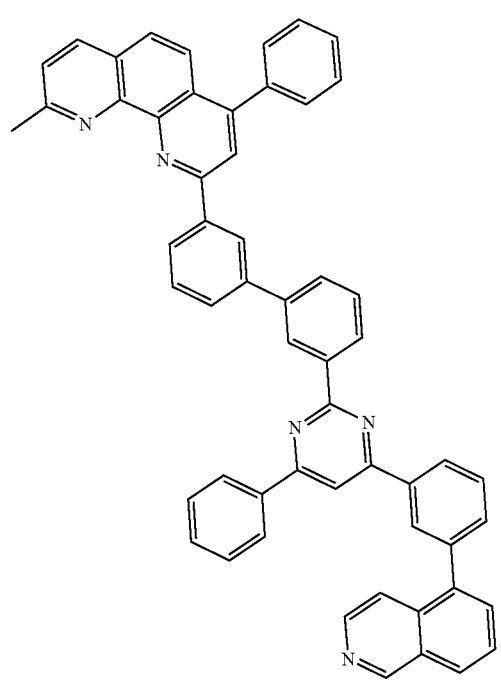
603
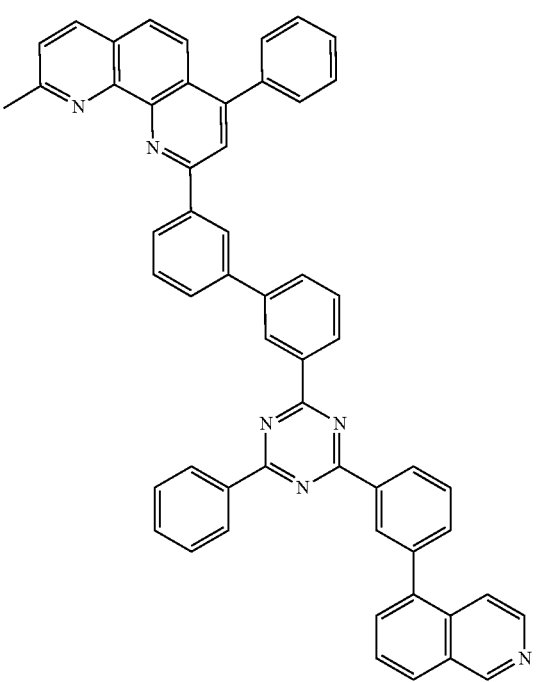

977
-continued
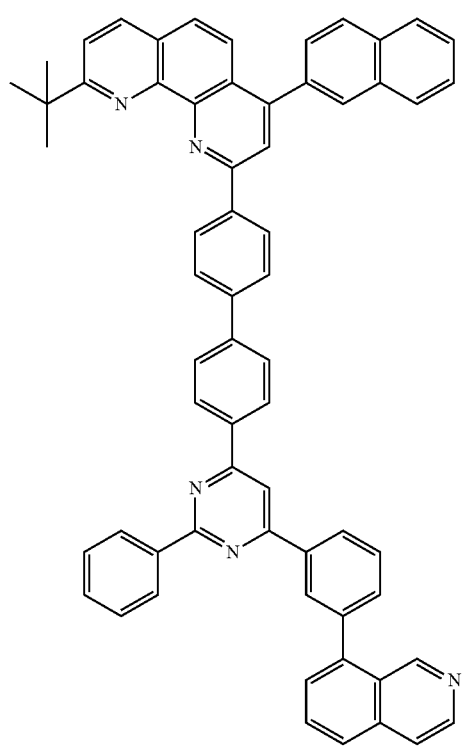
604
978
-continued
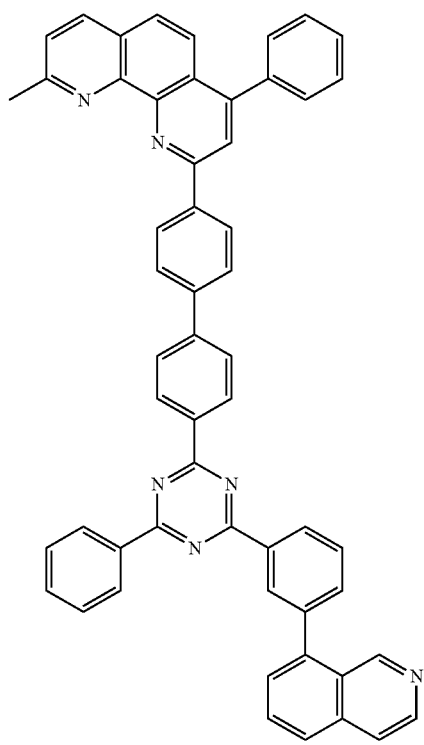
606
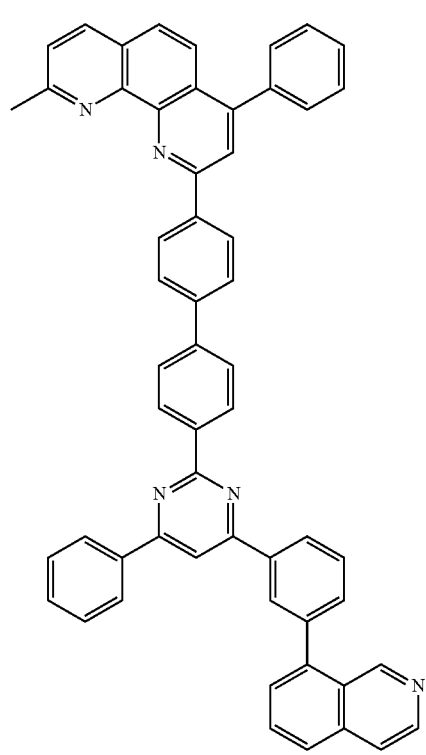
605
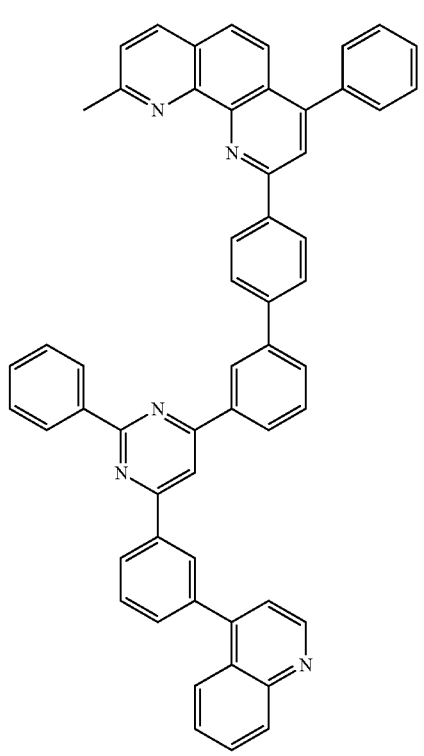
607

979
-continued
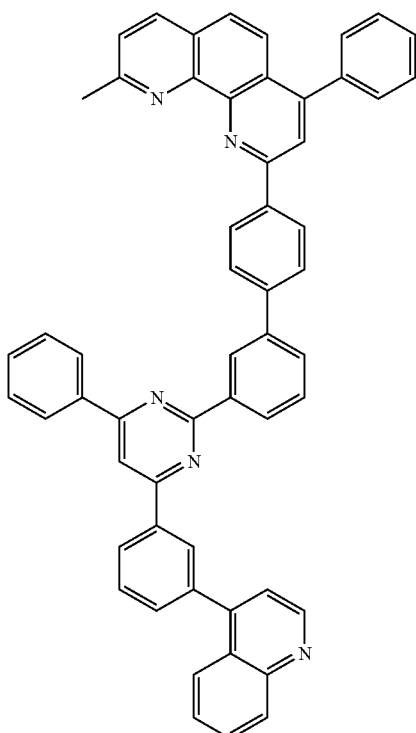
608
980
-continued
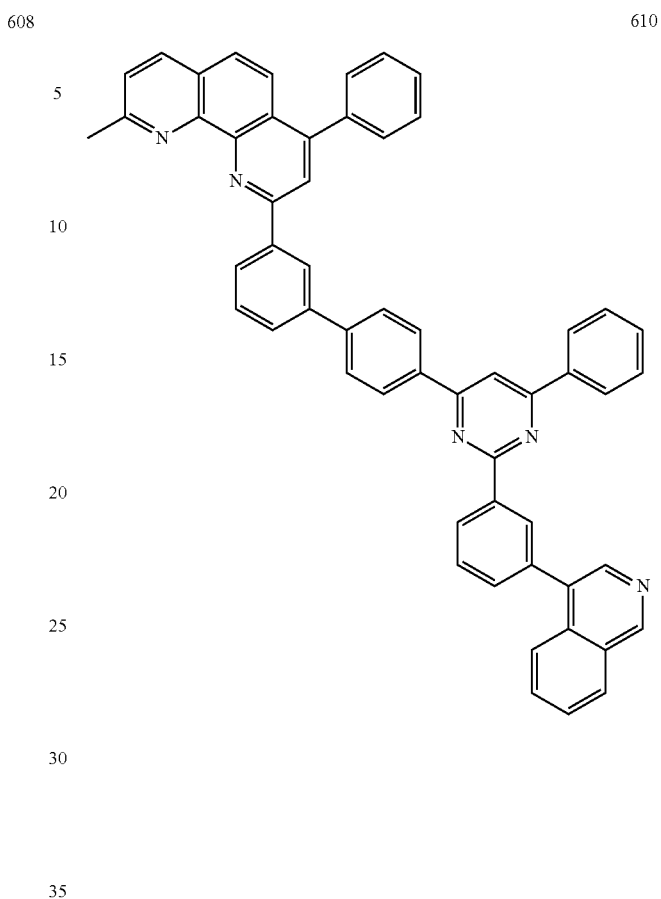
610
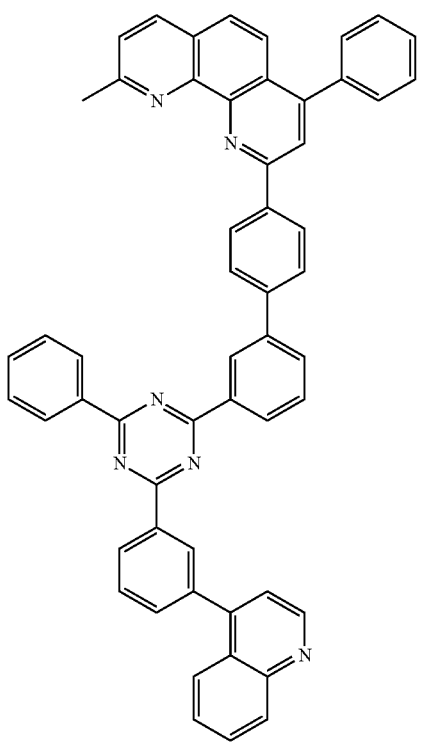
609
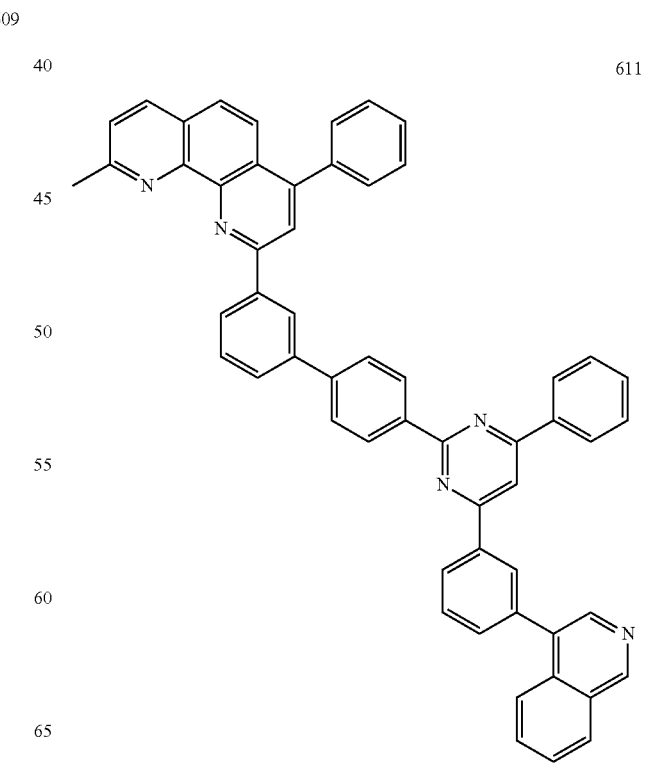
611

| 981 -continued | 982 -continued |
|---|---|
| 612 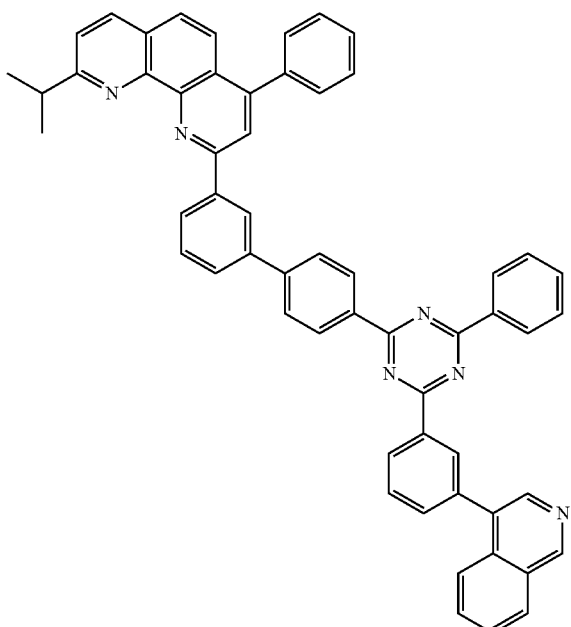 | 615 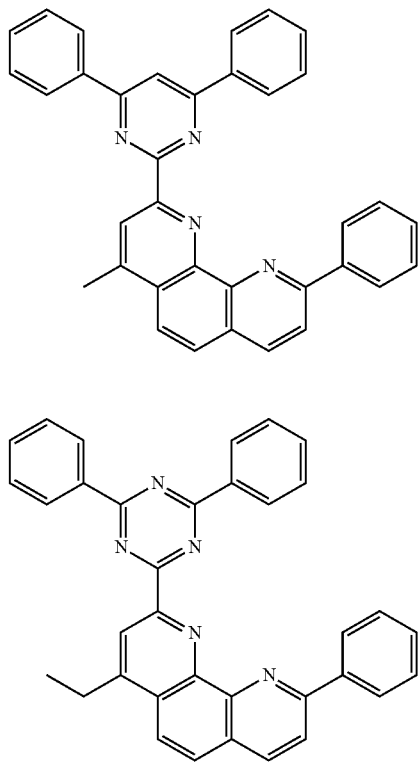 |
| 613 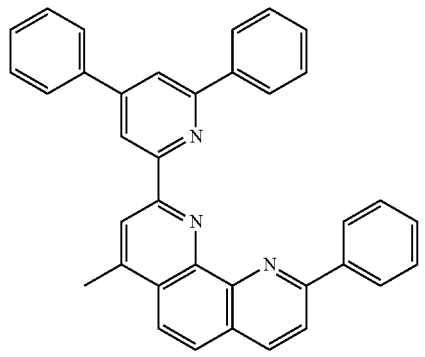 | 616 |
| 614 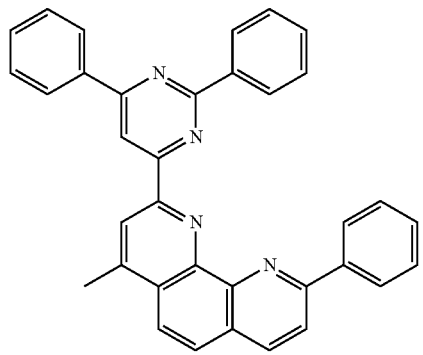 | 617 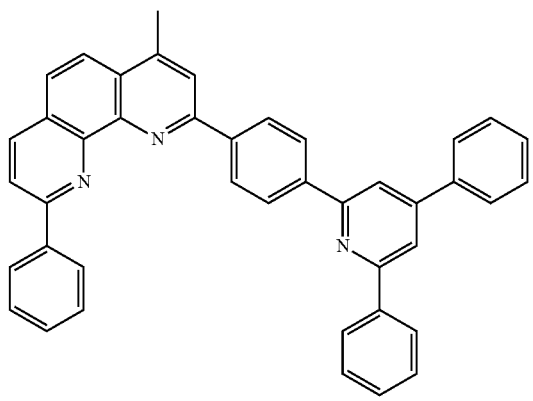 |
| | 618 |

983
-continued
619
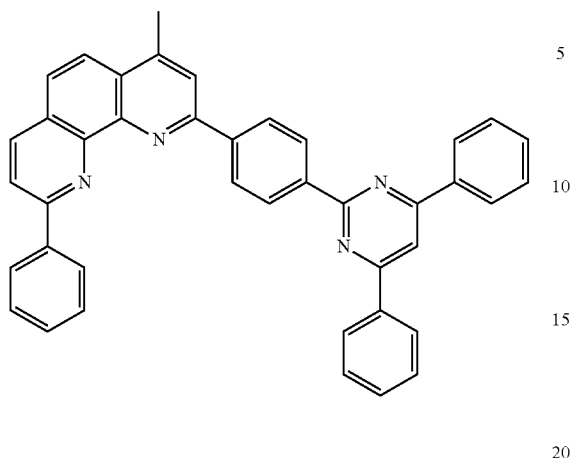
620
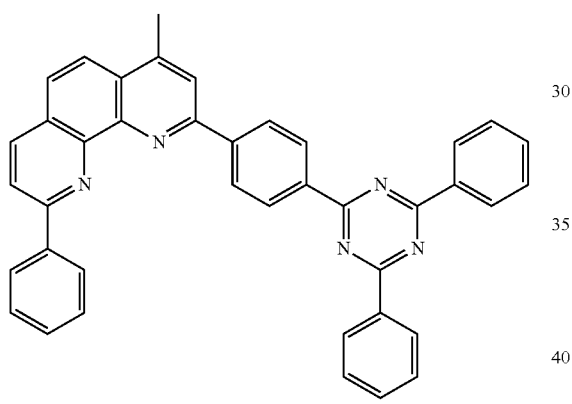
621
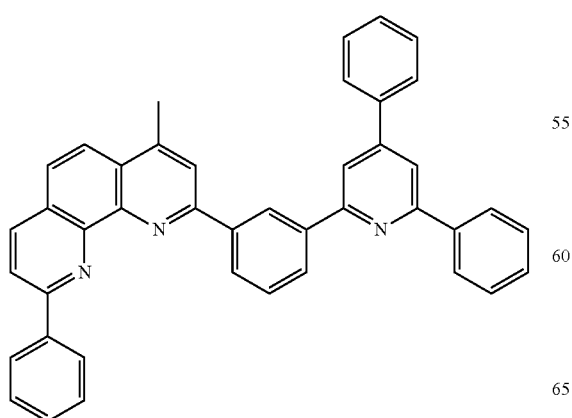
984
-continued
622
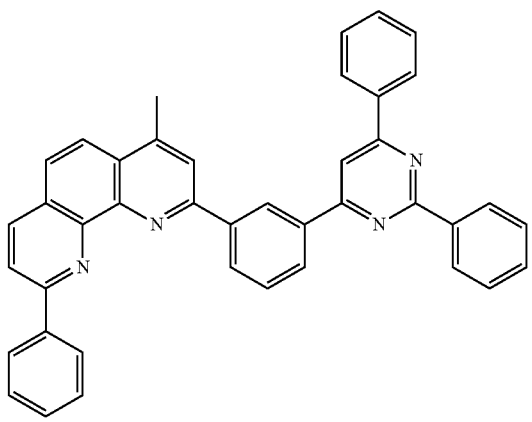
623
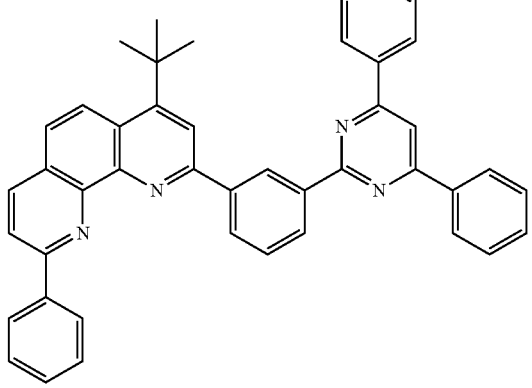
624
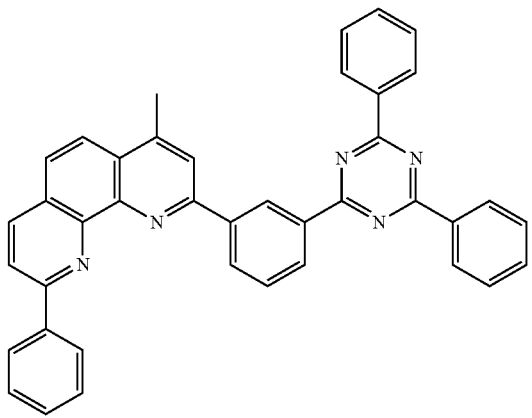

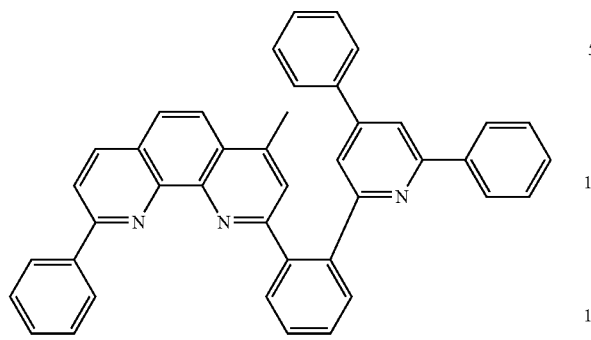
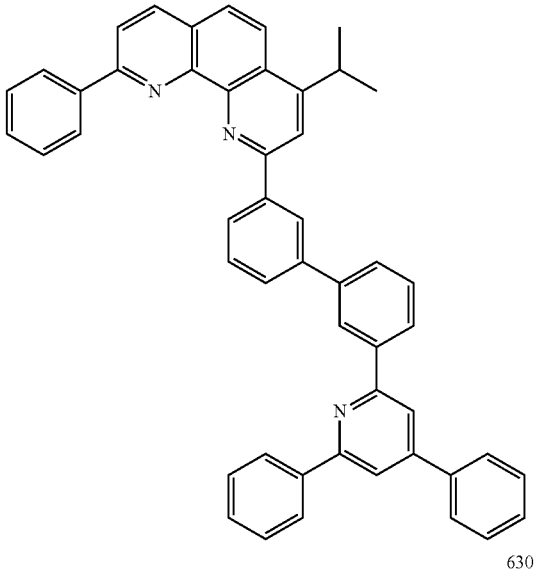
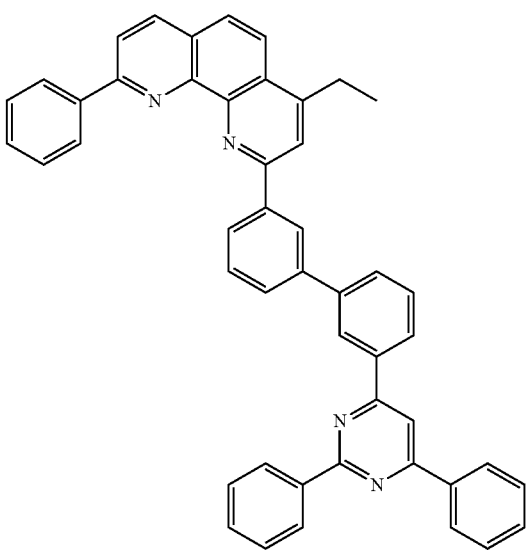
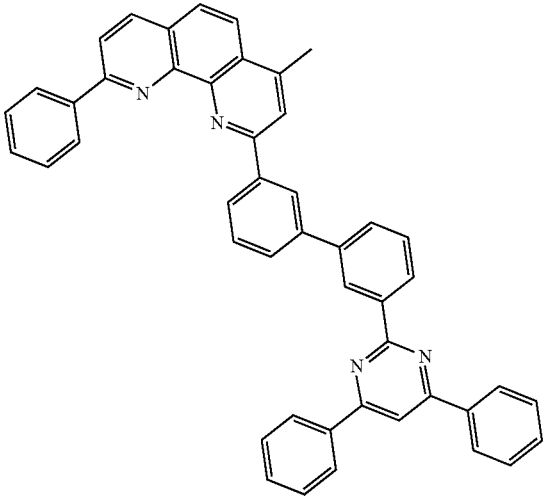

987
-continued
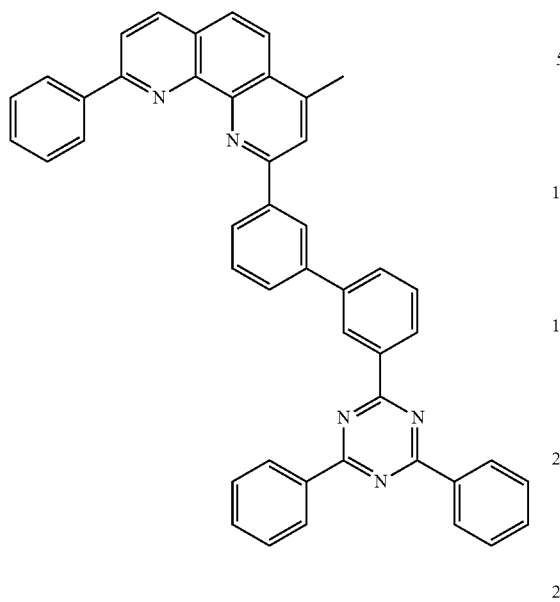
632
988
-continued
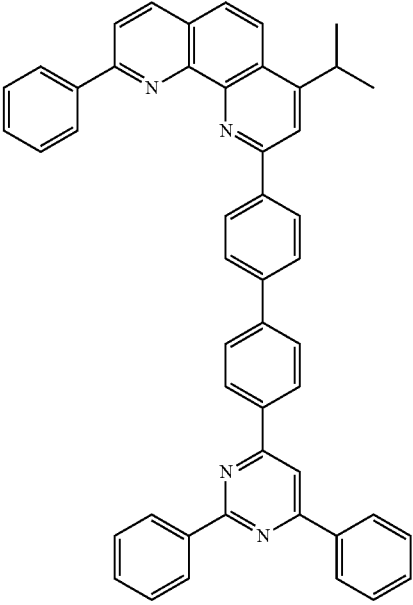
634
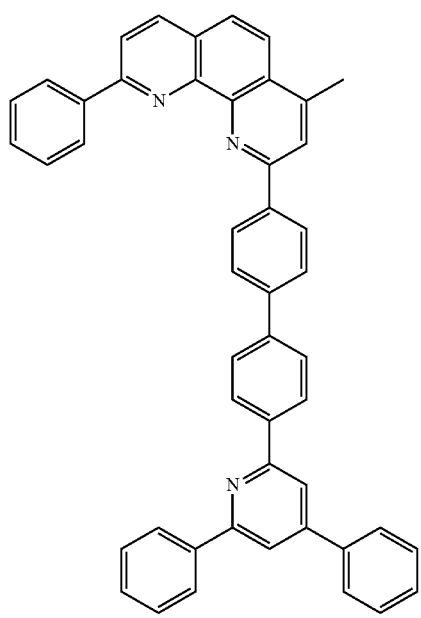
633
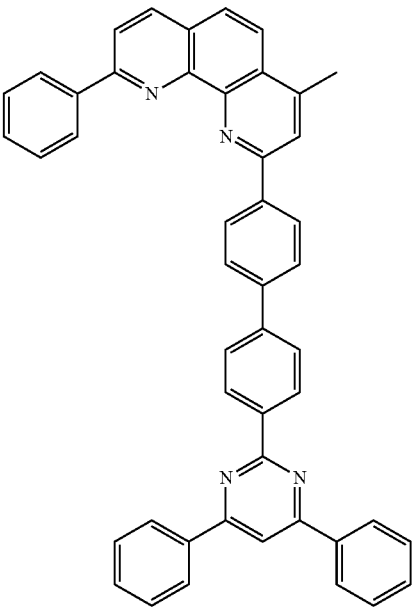
635

989
-continued
990
-continued
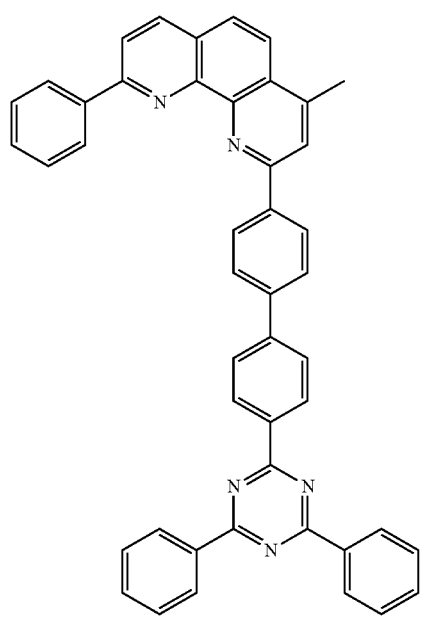
636
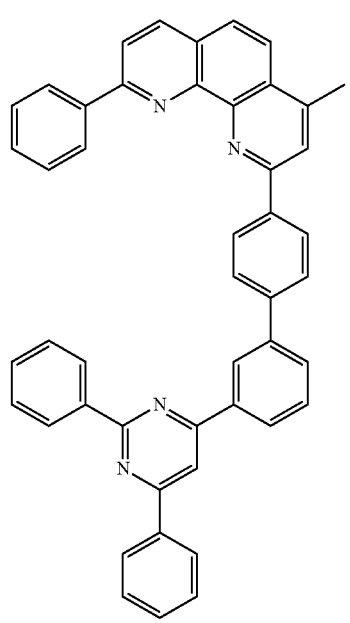
638
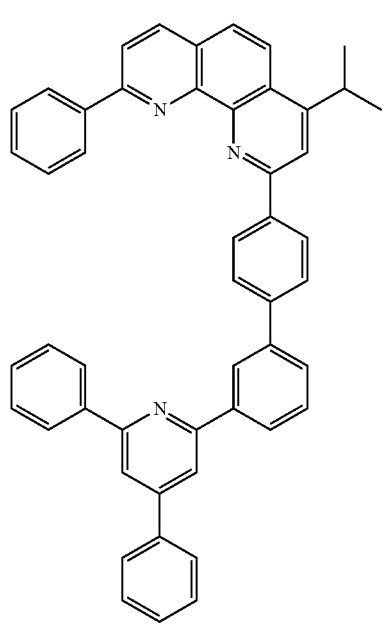
637
639

991
-continued
992
-continued
640
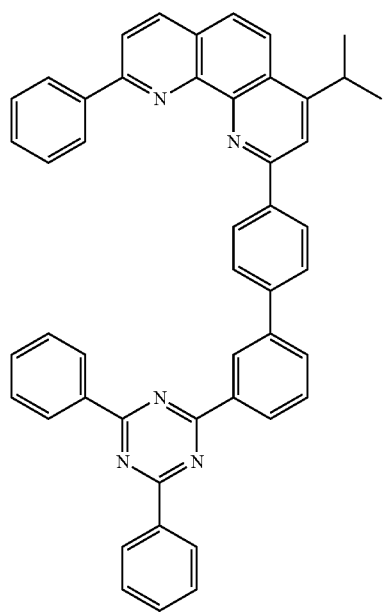
643
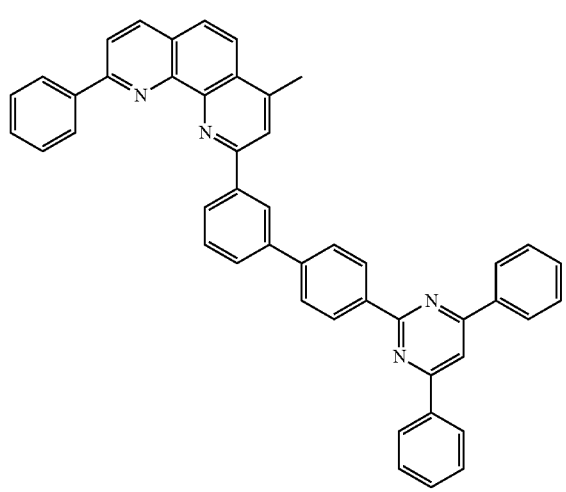
641
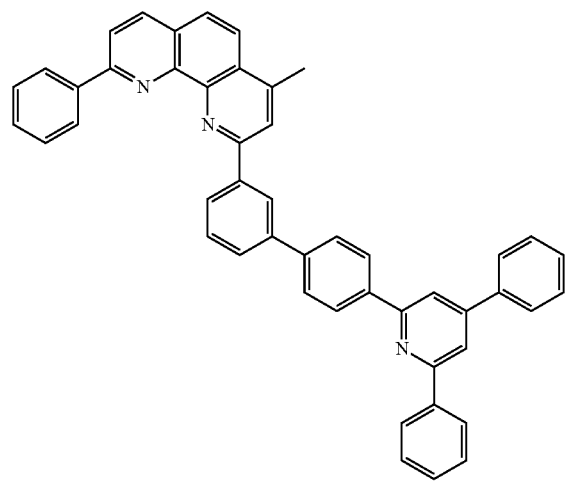
644
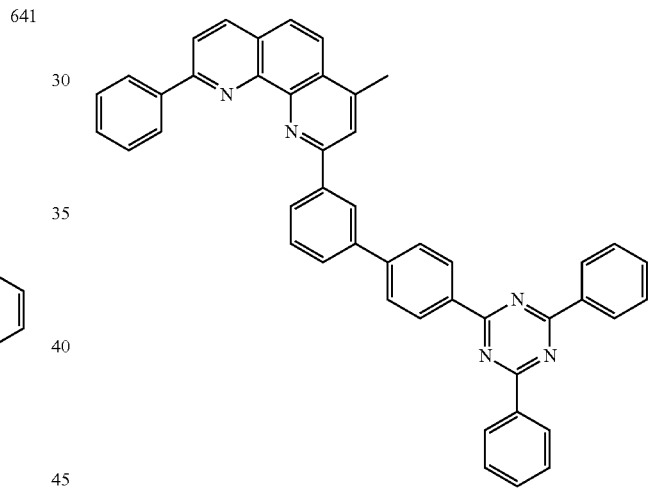
642
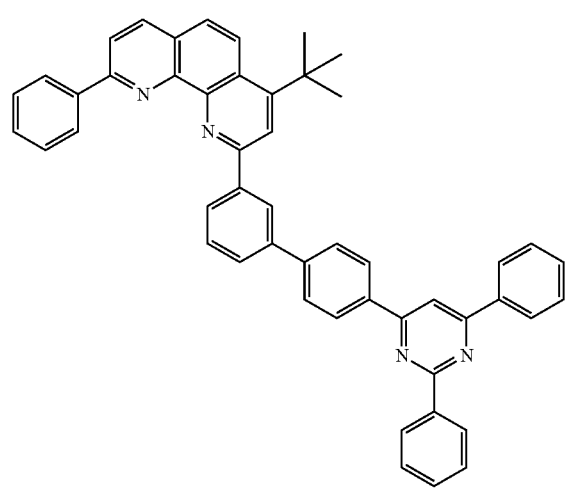
645
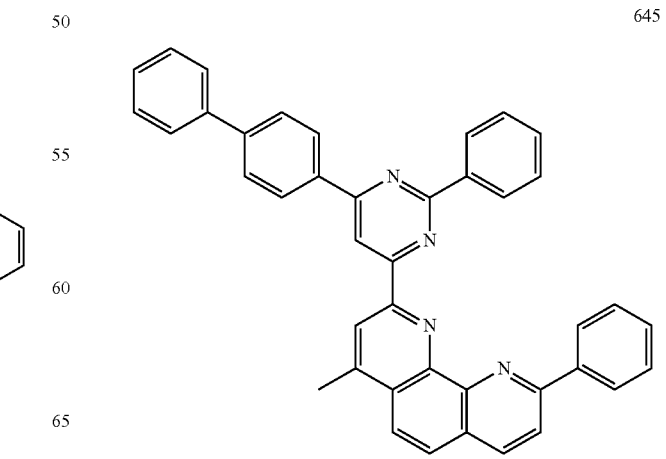

993
-continued
646
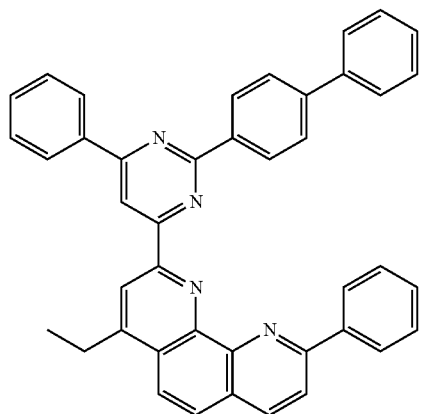
647
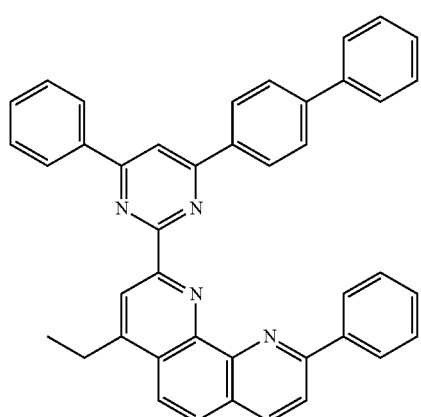
648
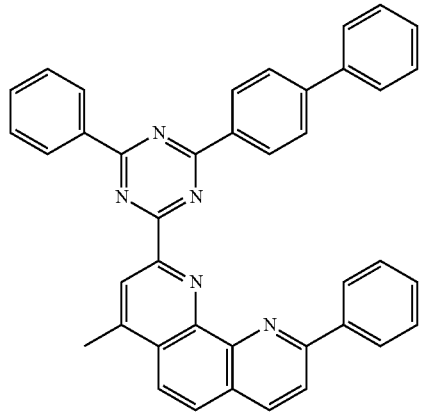
994
-continued
649
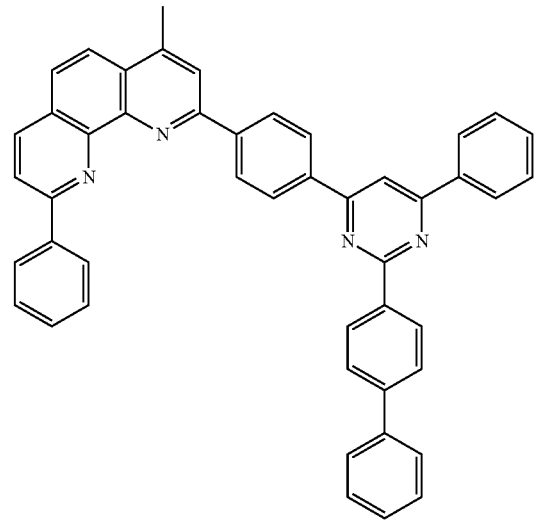
650
651
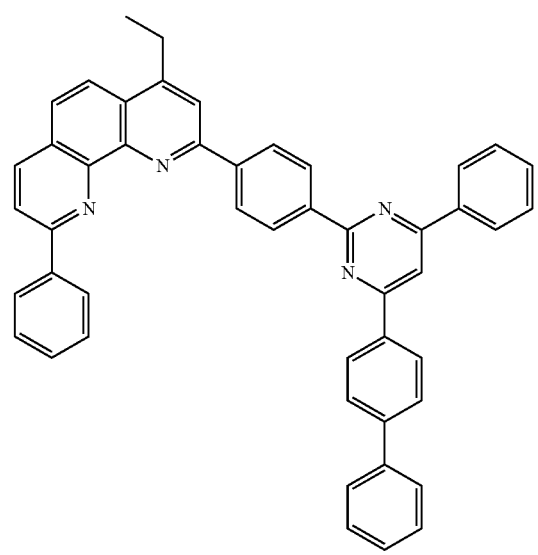

995
-continued
652
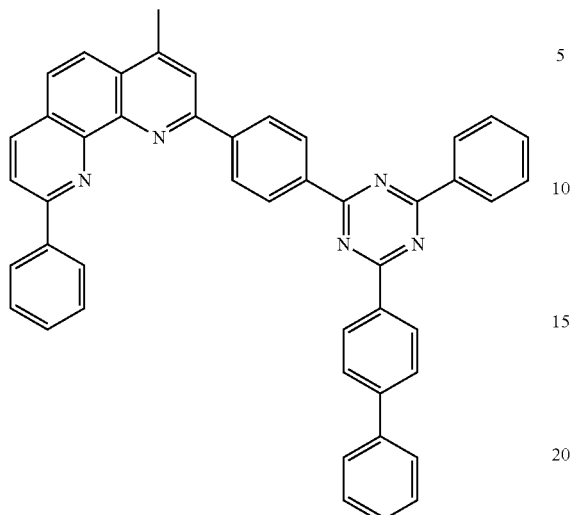
653
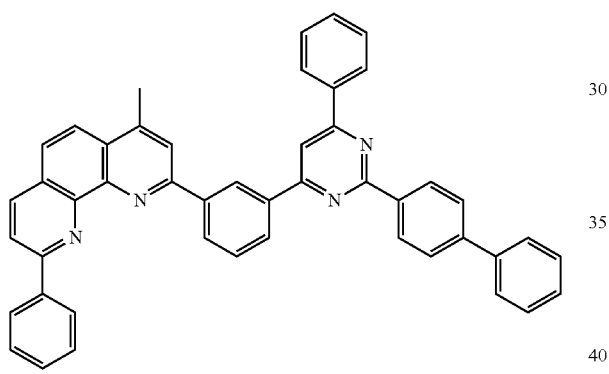
654
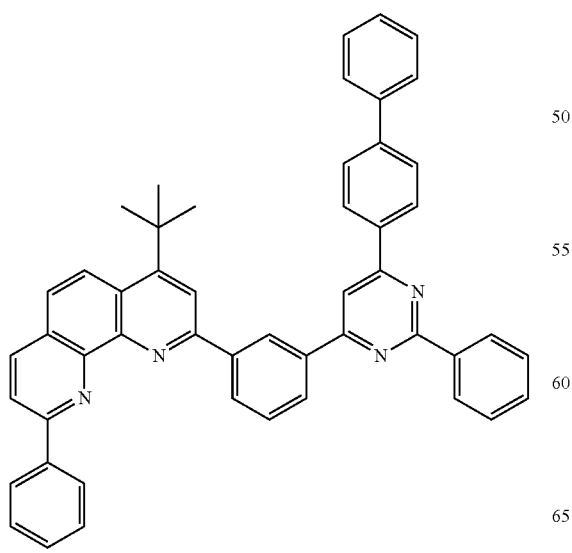
996
-continued
655
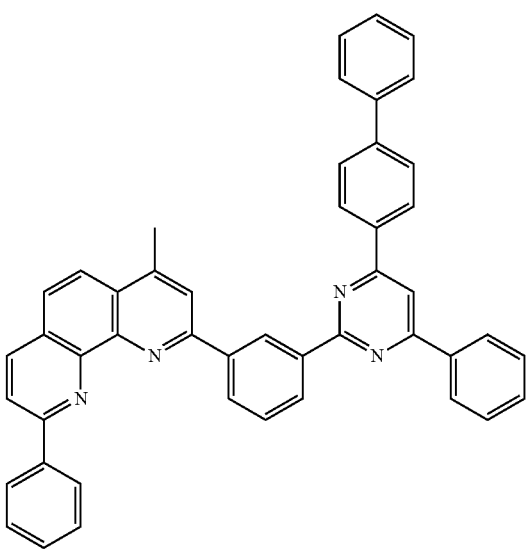
656
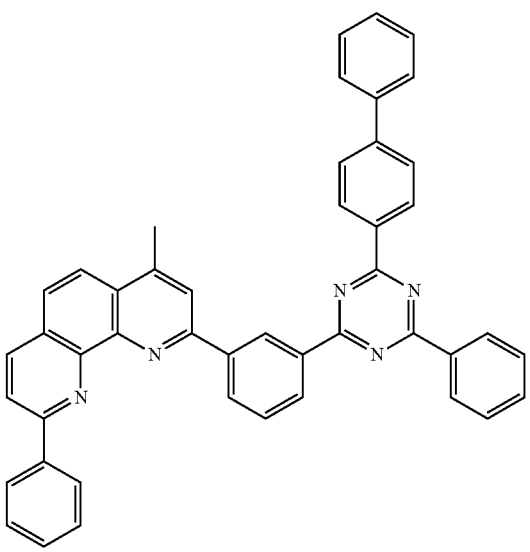

657
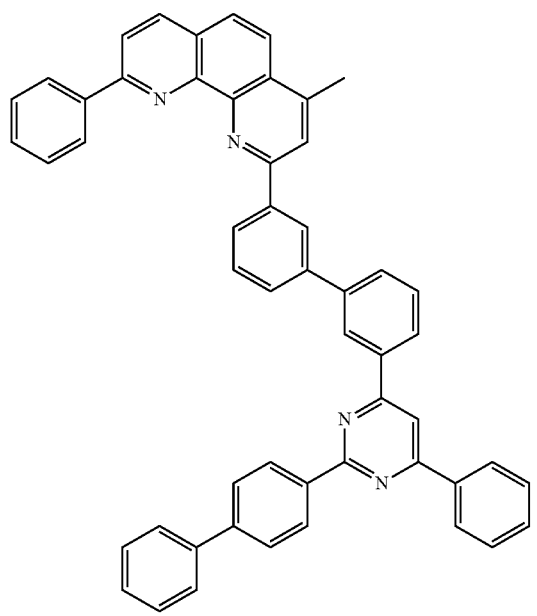
658
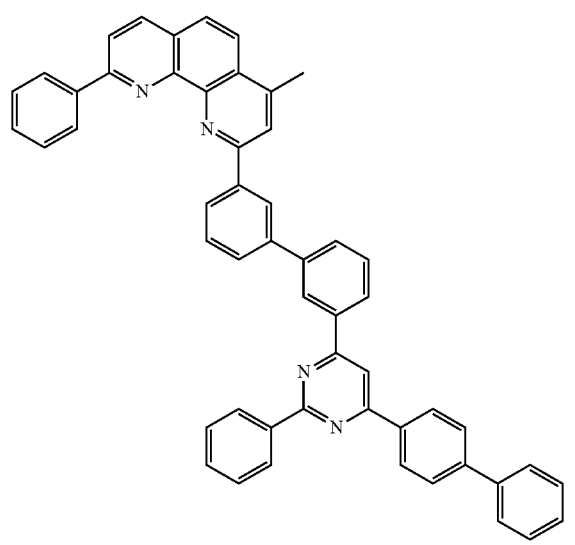
659
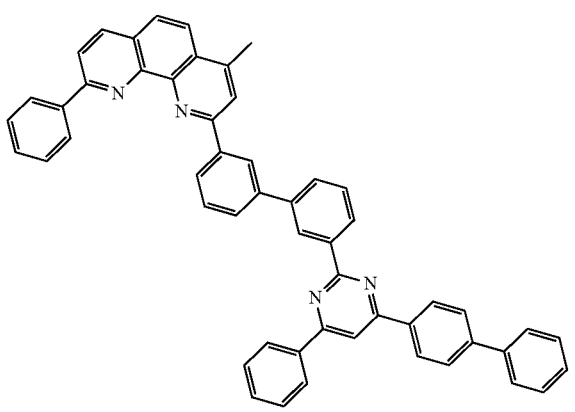
660
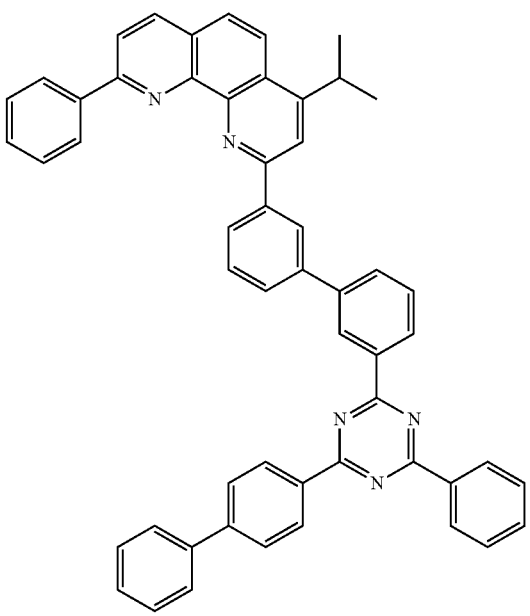
661
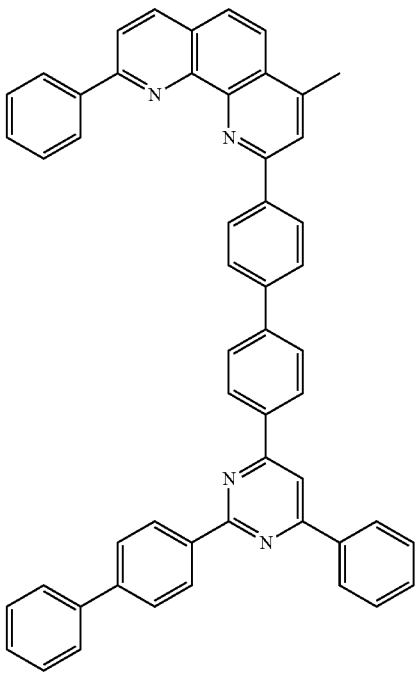

662
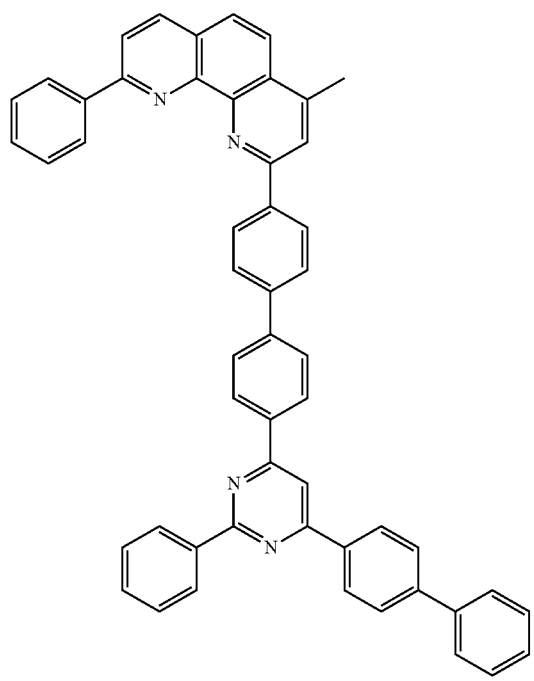
663
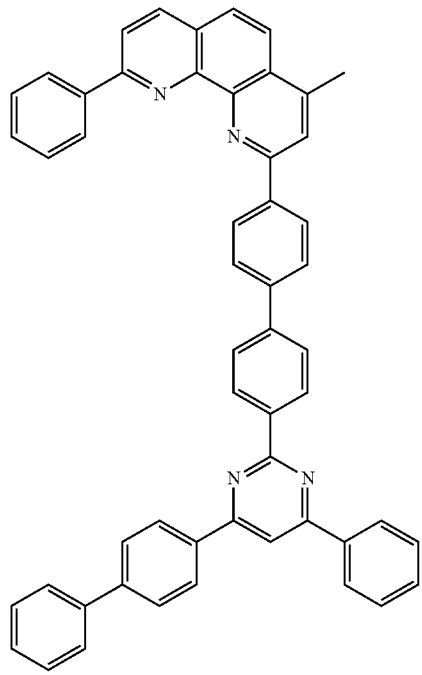
664
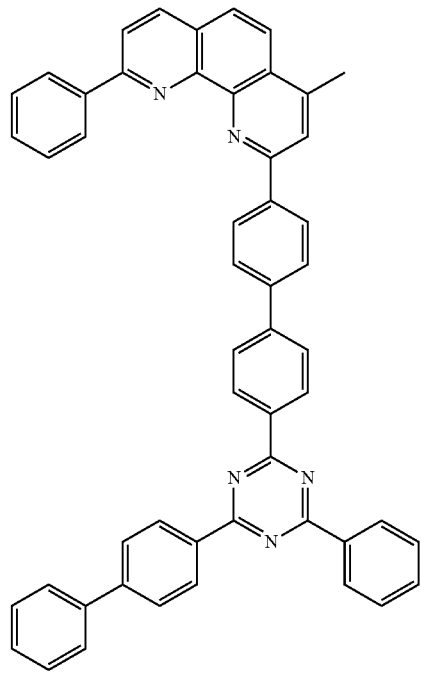
665
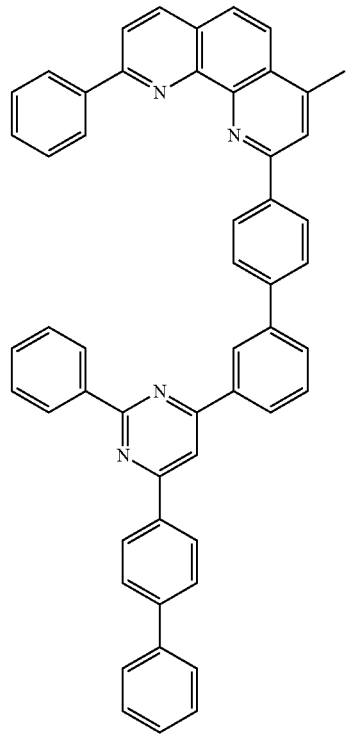

-continued
666
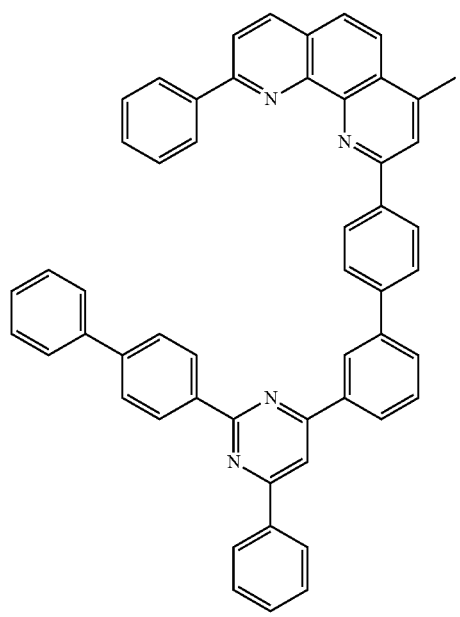
667
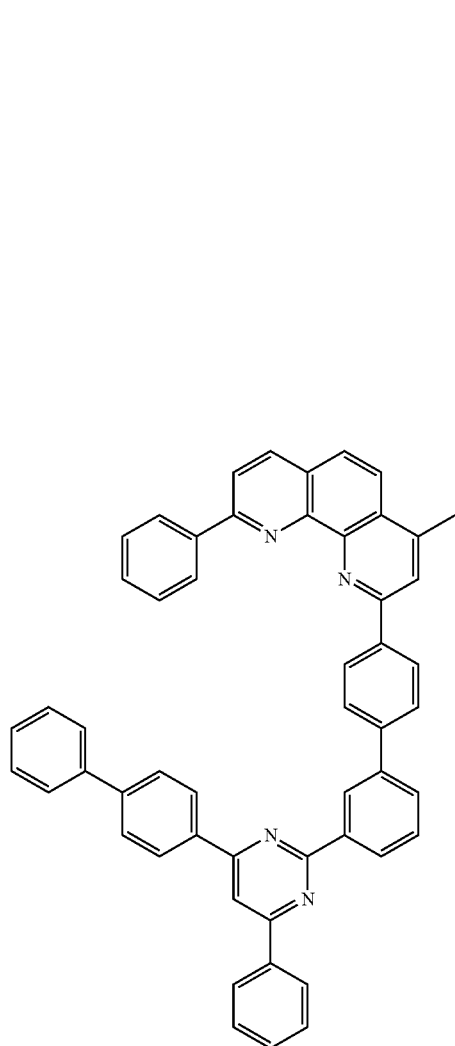
668
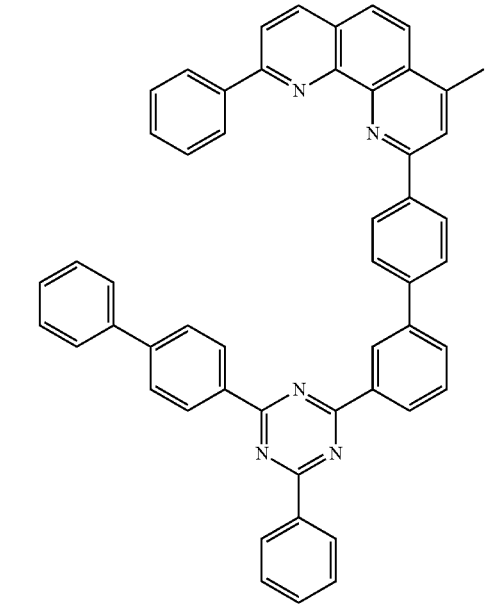
669
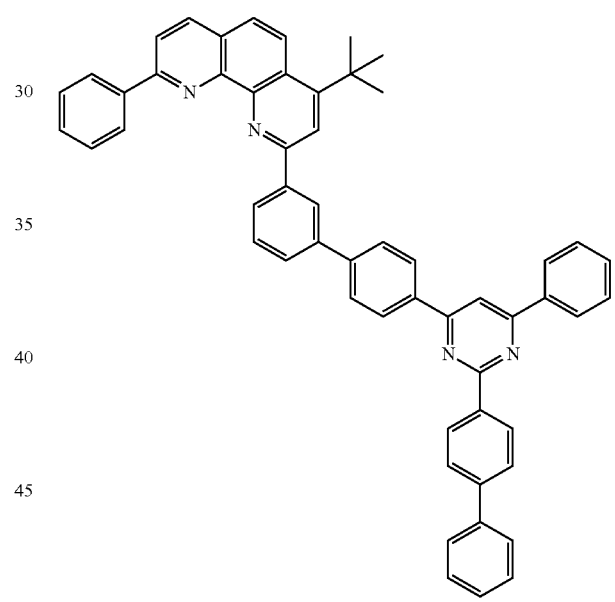
670
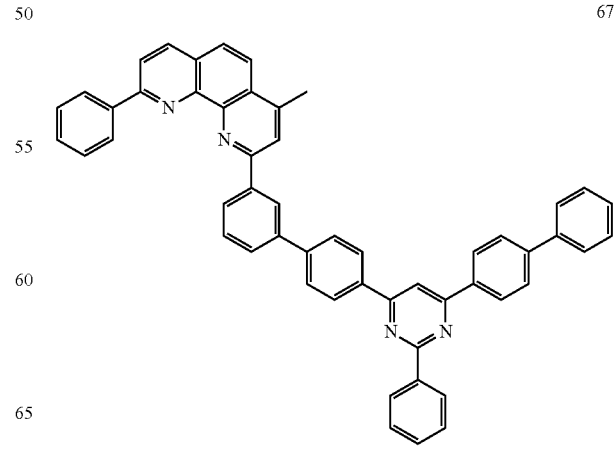

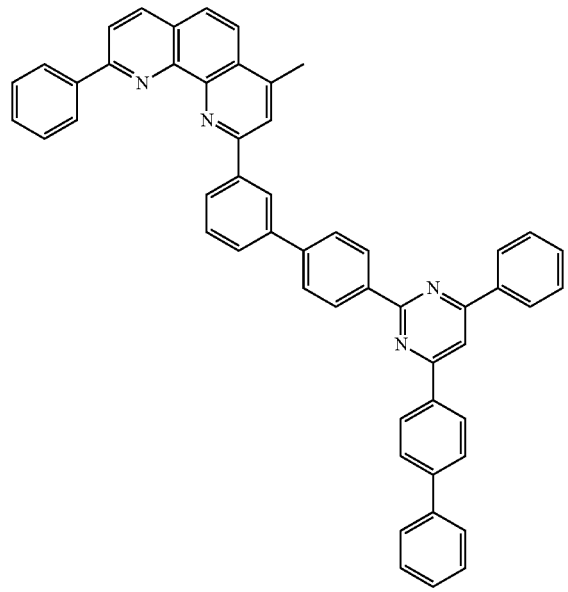
671
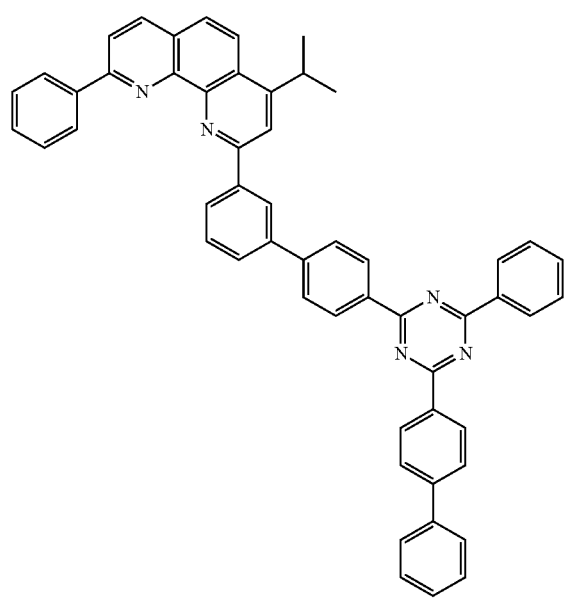
672
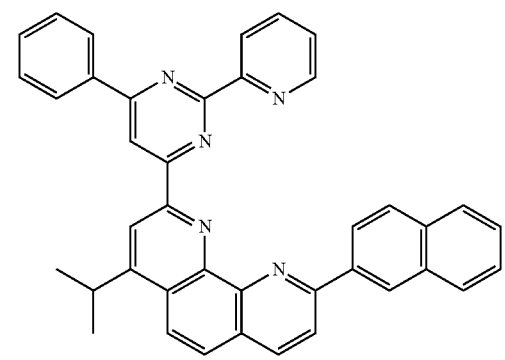
673
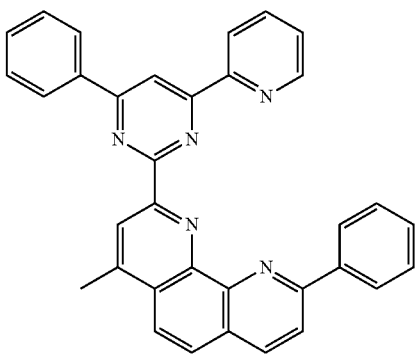
674
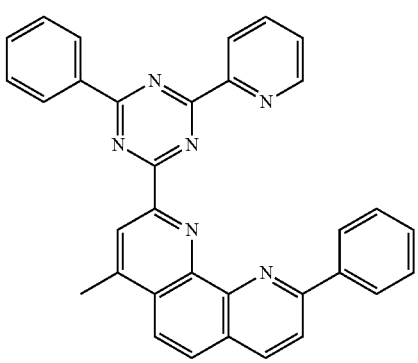
675
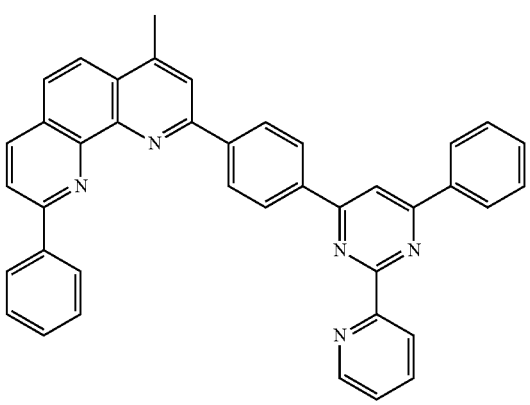
676
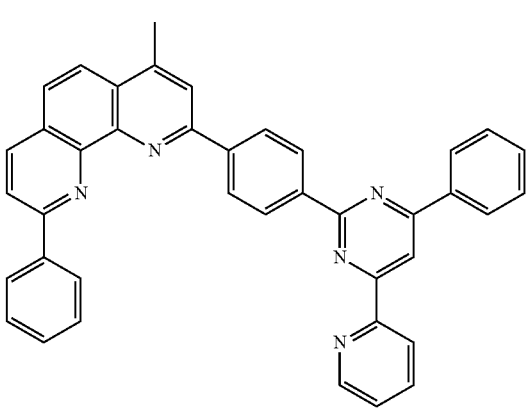
677

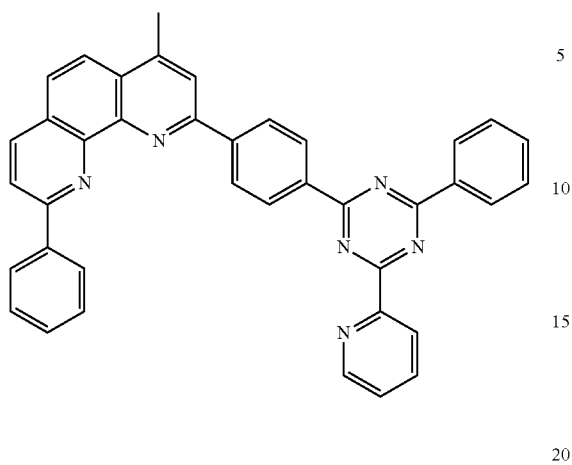
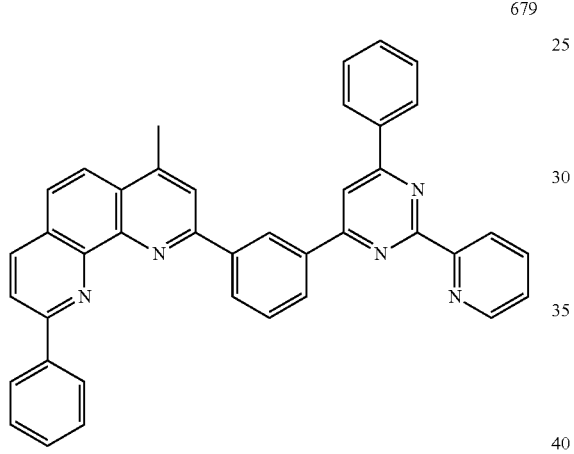
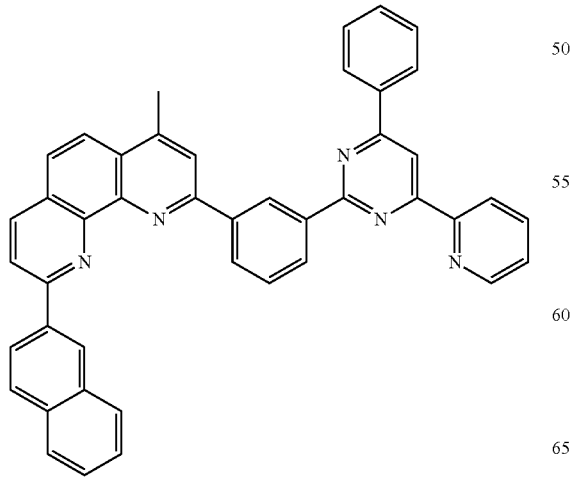
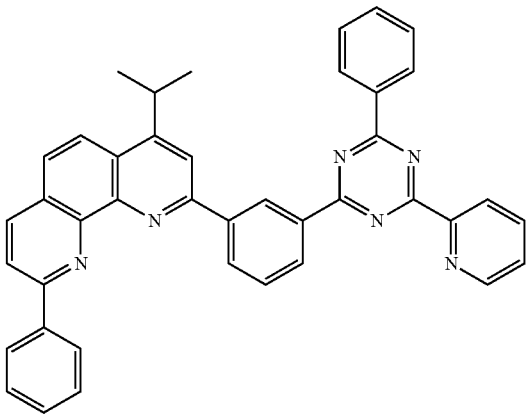
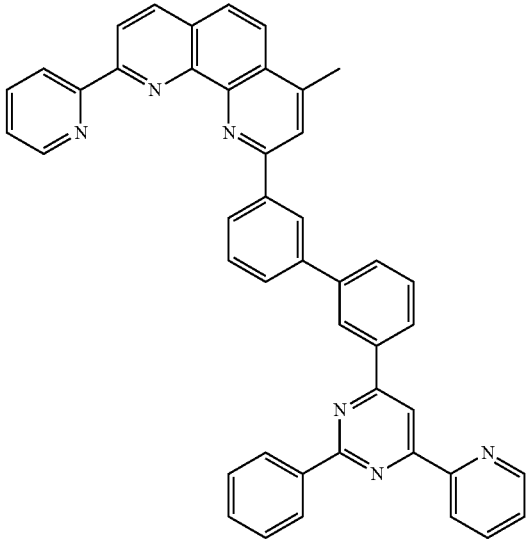
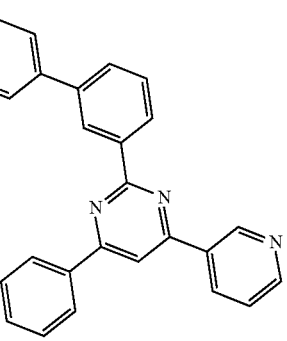

1007
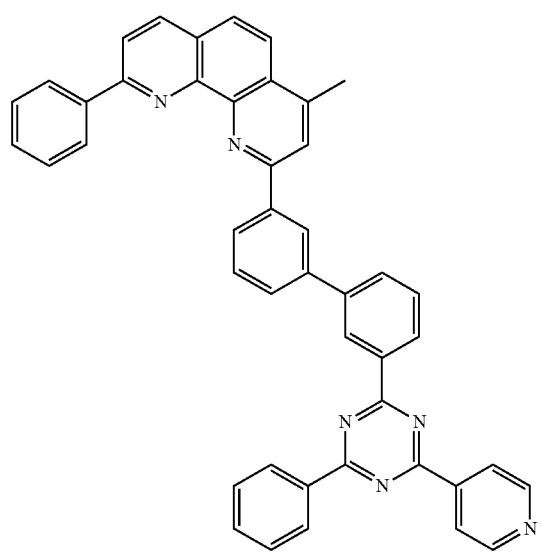
684
1008
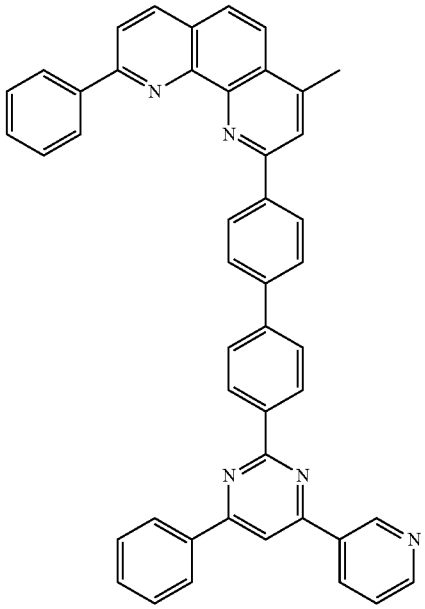
686
685
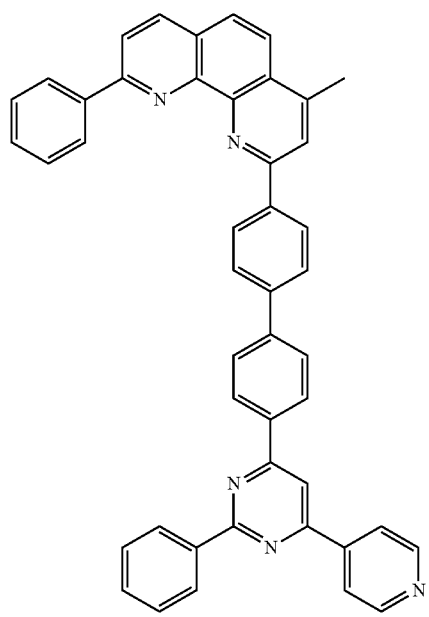
687
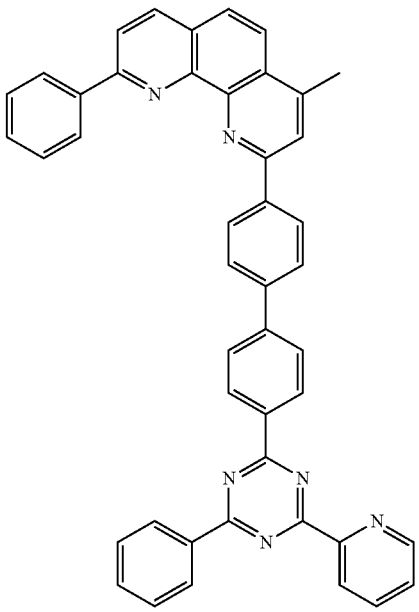

1009
-continued
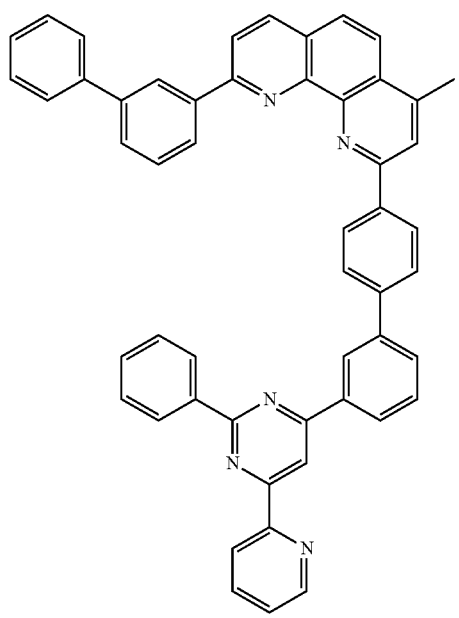
688
1010
-continued
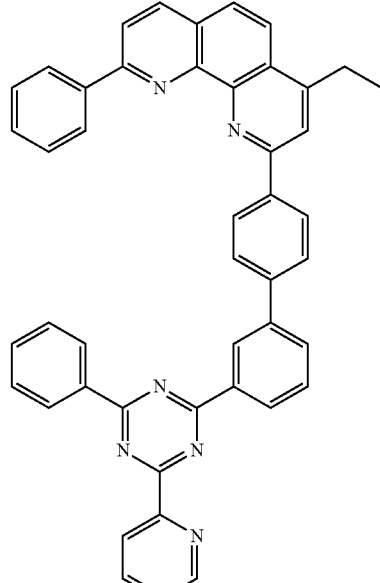
690
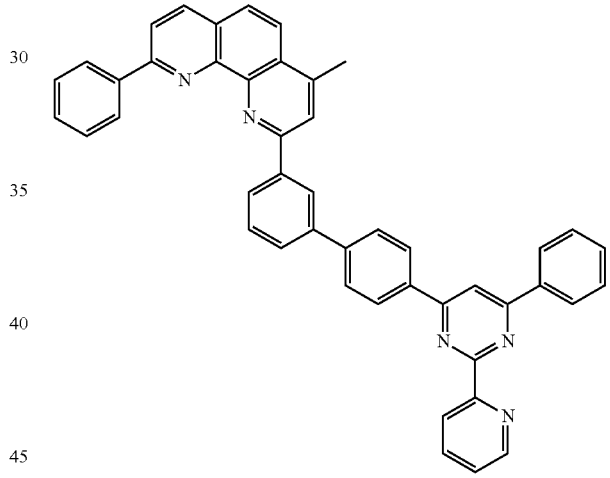
691
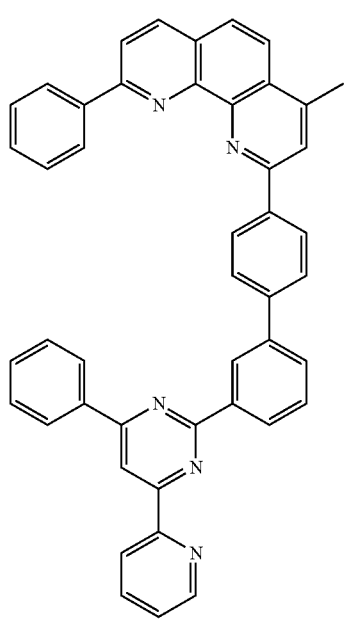
689
692

1011
-continued
693
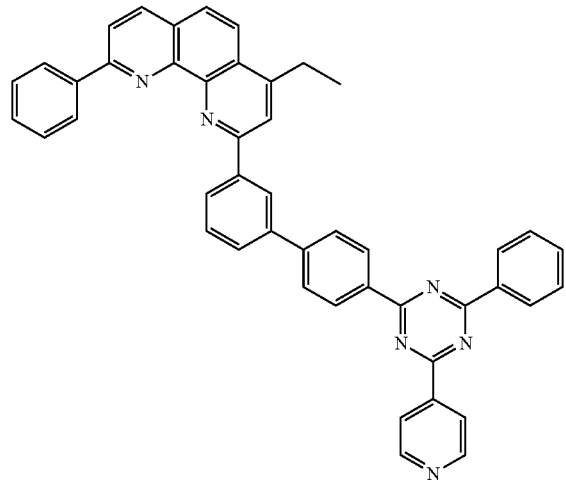
694
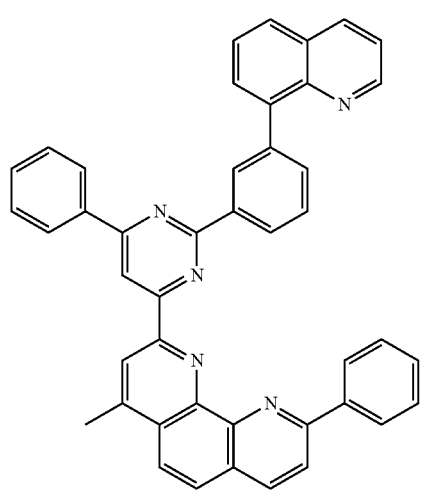
695
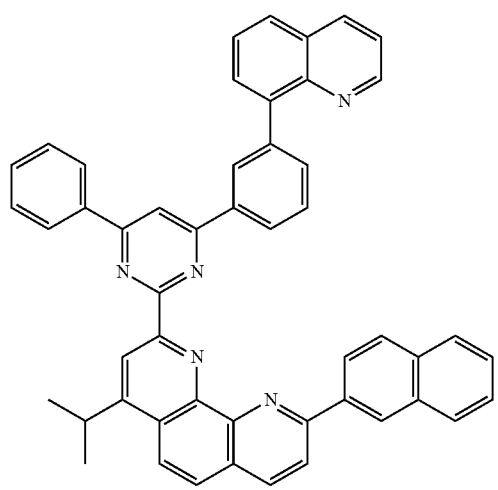
1012
-continued
696
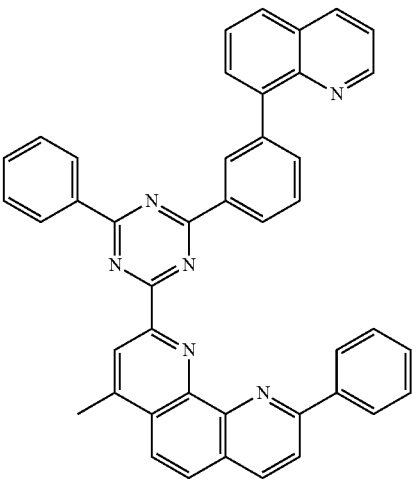
697
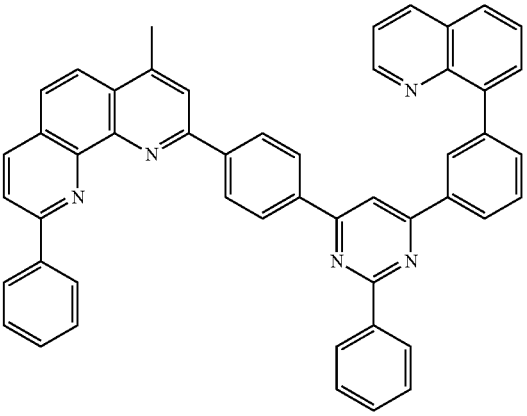
698
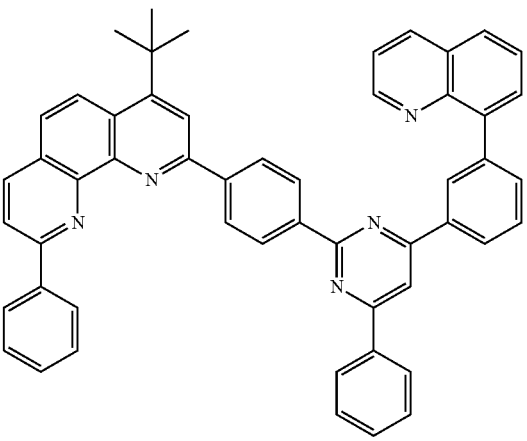

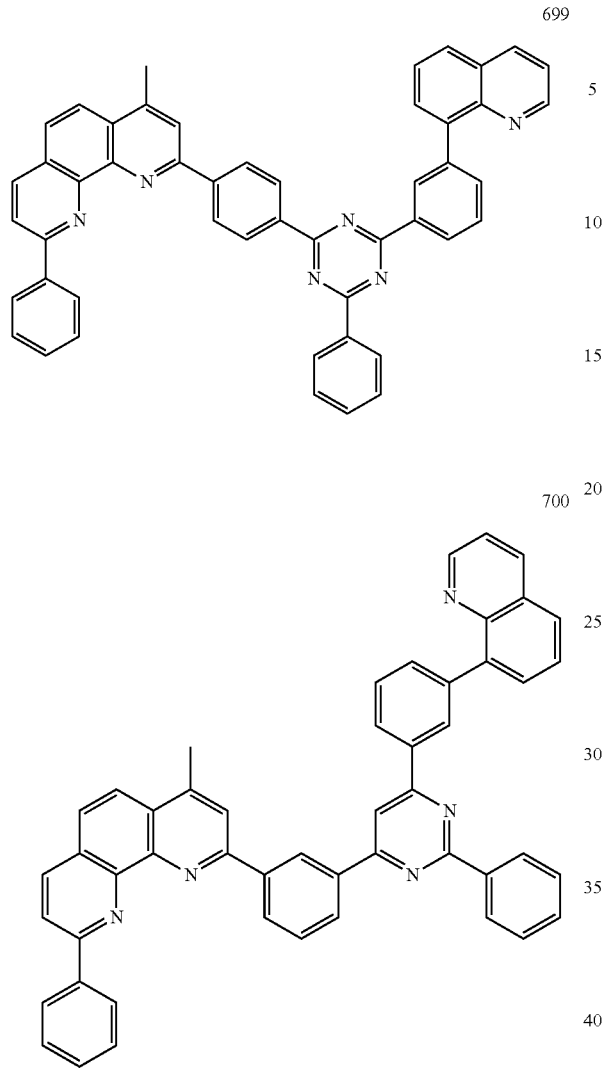
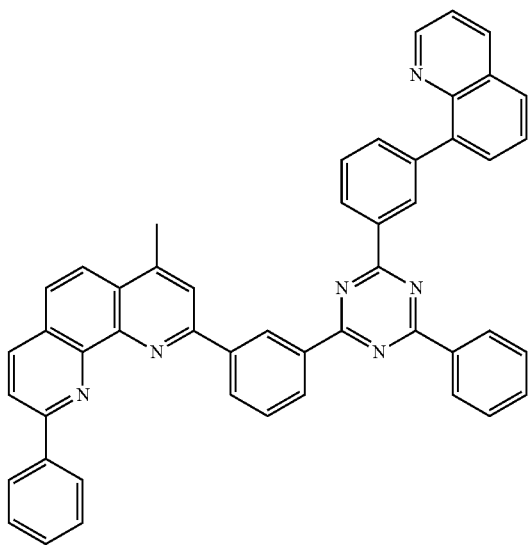
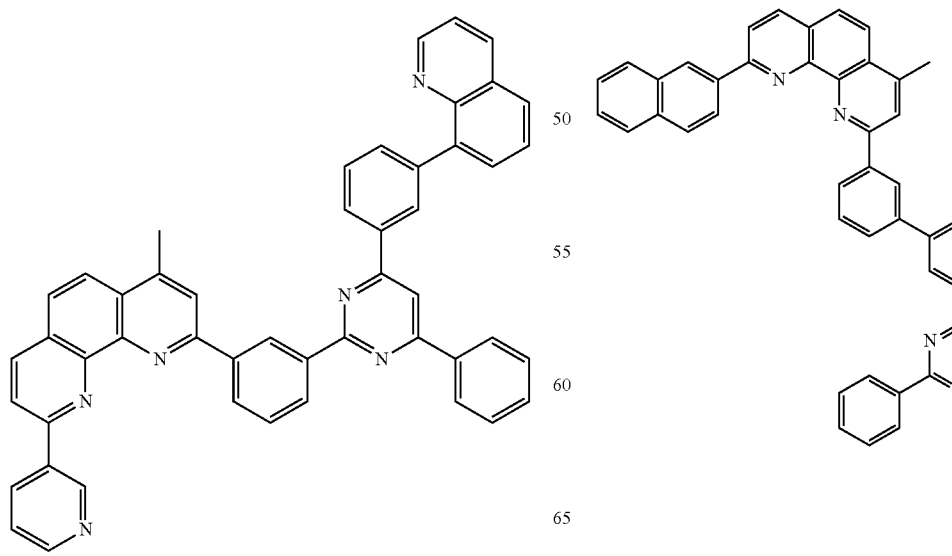

-continued
704
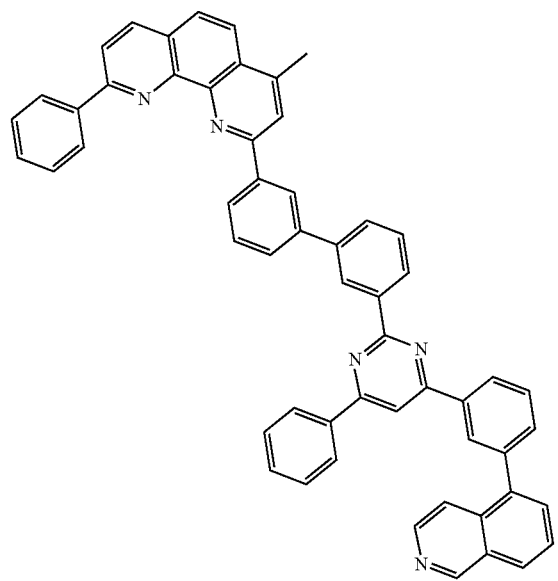
706
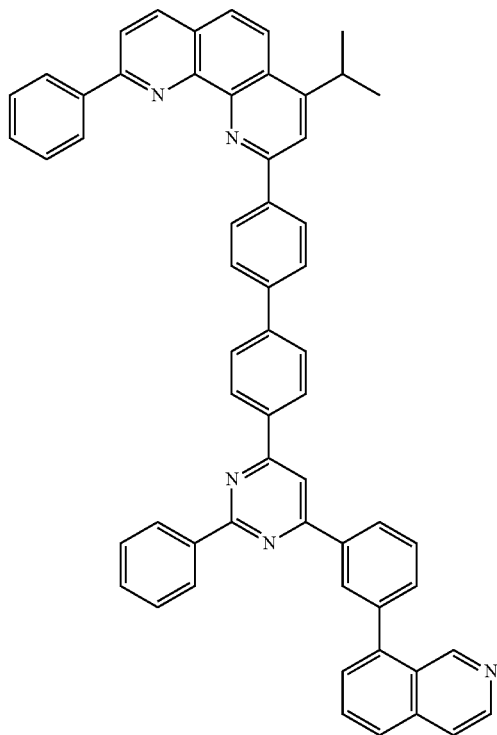
705
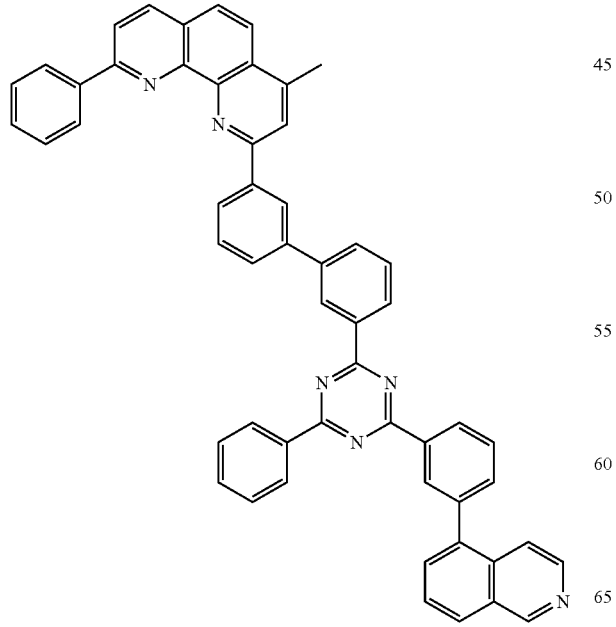
707
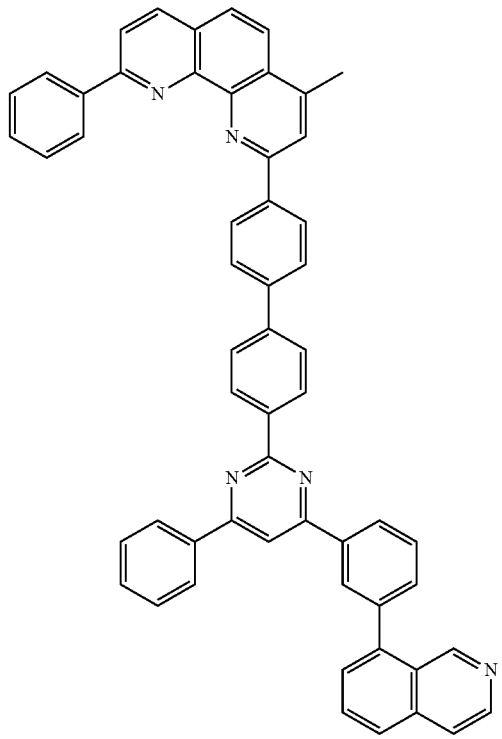

1017-continued
708
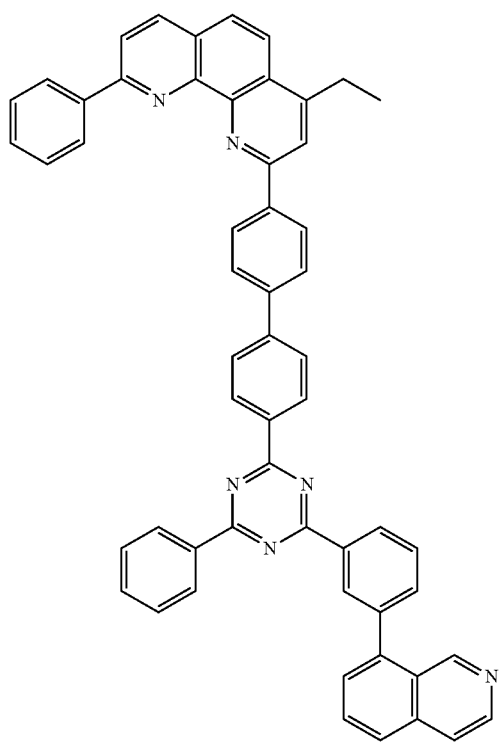
709
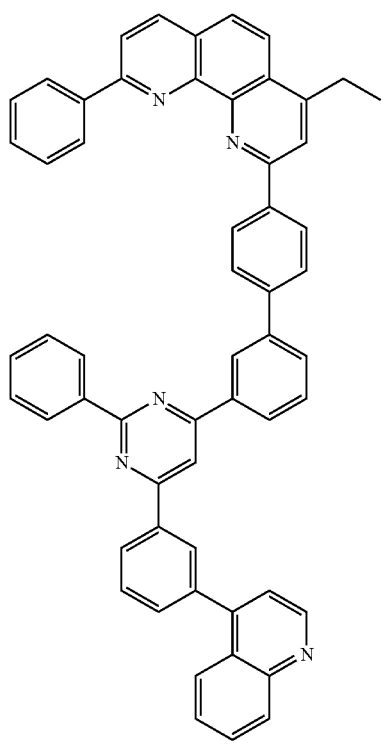
1018-continued
710
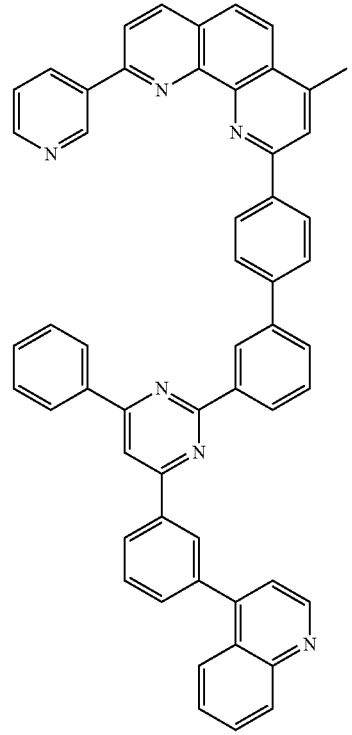
711
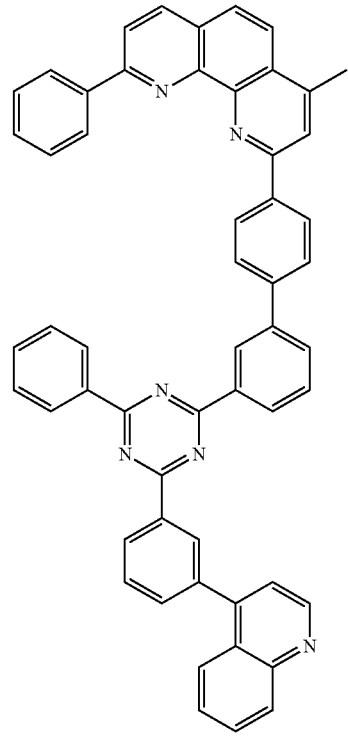

1019
-continued
712
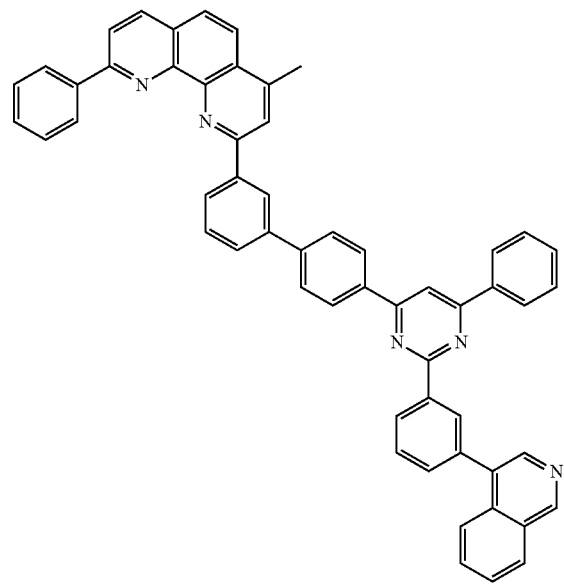
713
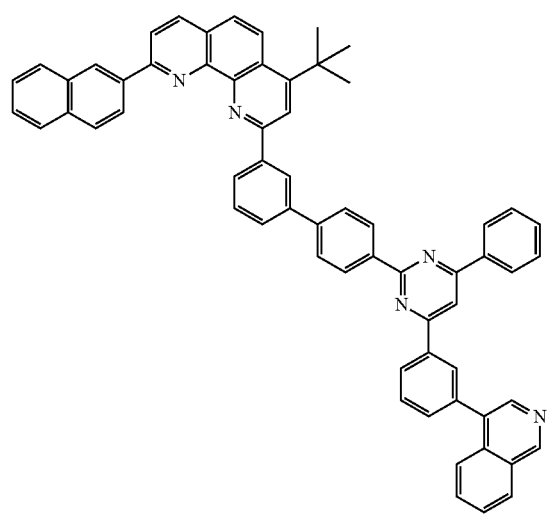
1020
-continued
714
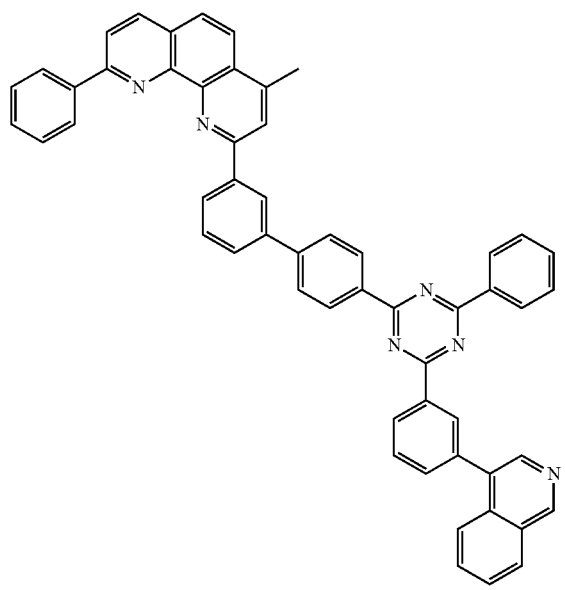
715
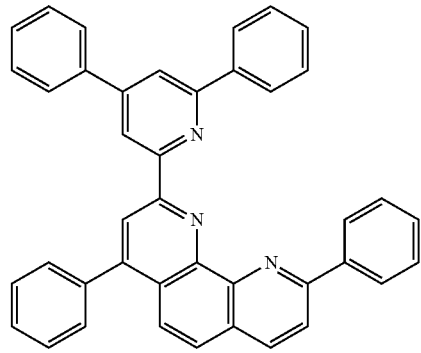
716
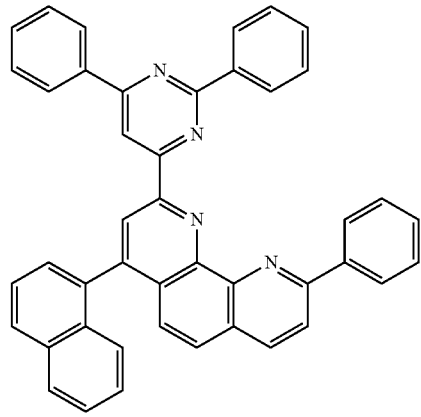

1021
-continued
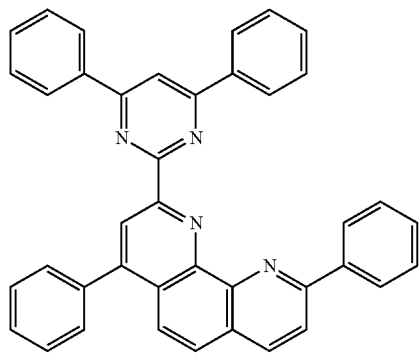
717
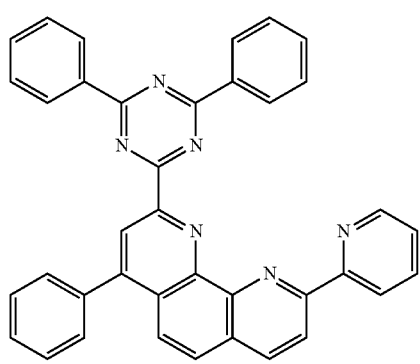
718
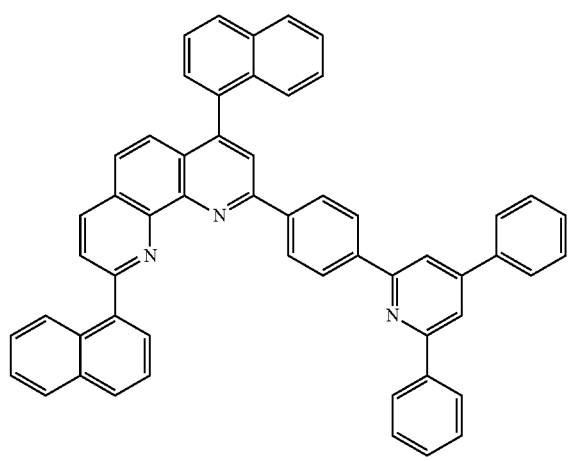
719
1022
-continued
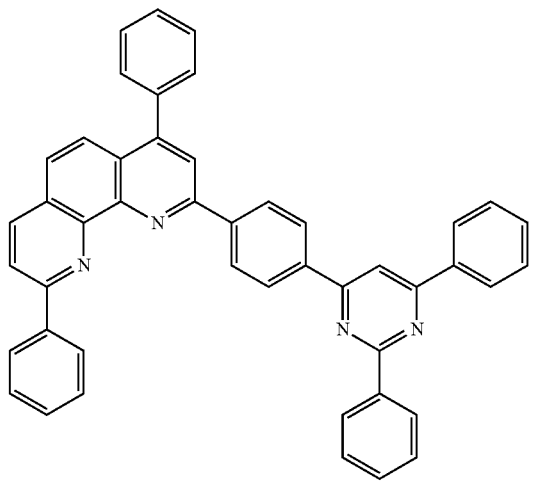
720
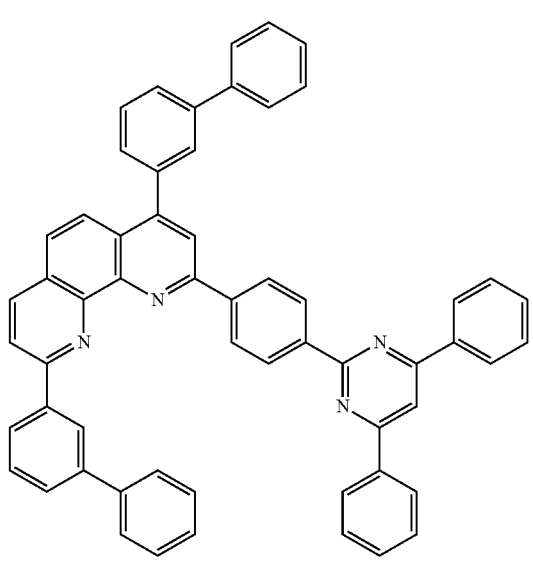
721
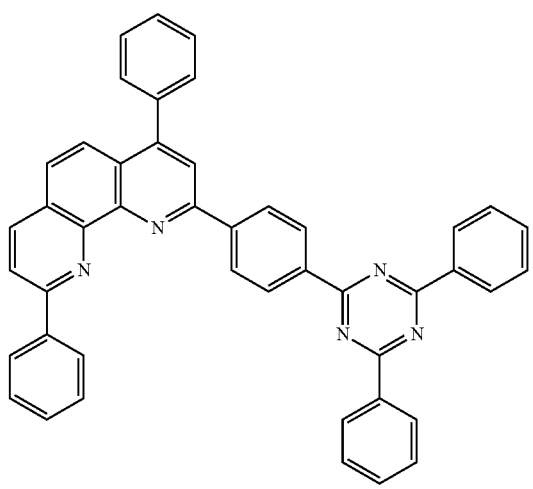
722

1023
-continued
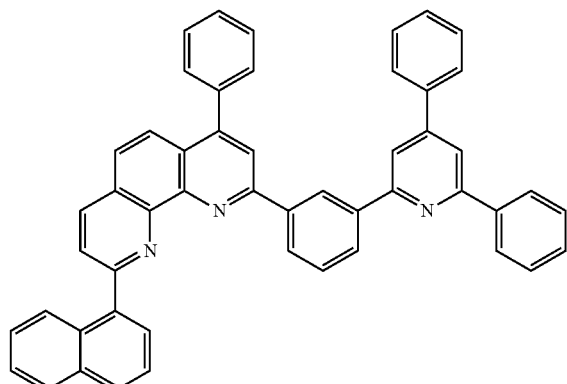
723
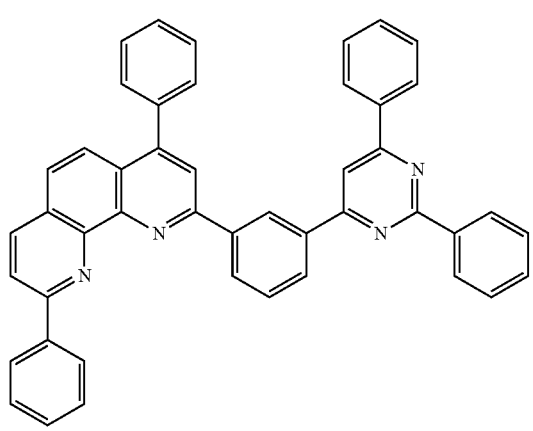
724
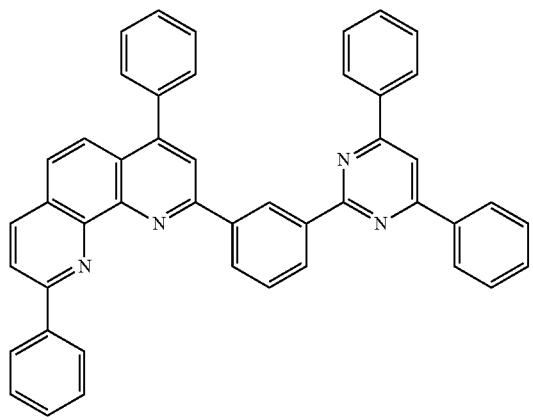
725
1024
-continued
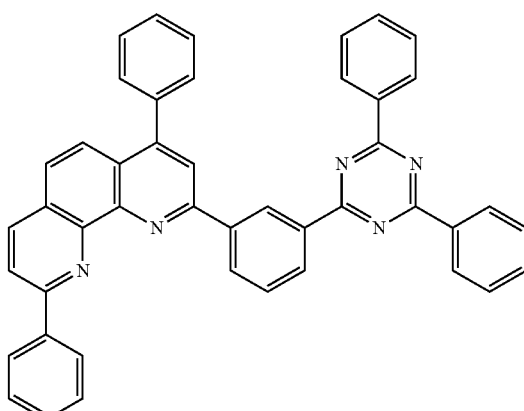
726
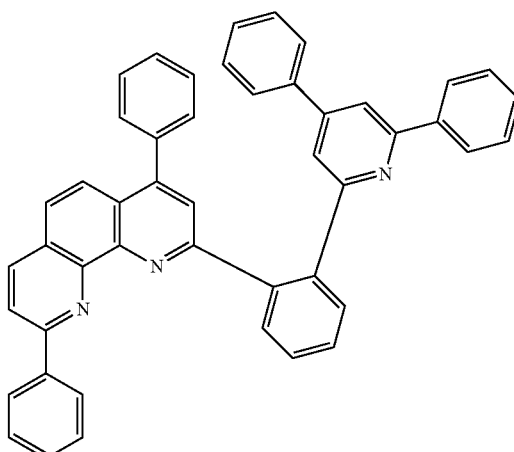
727
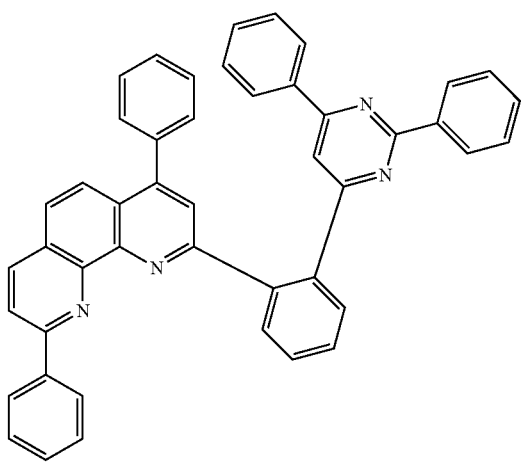
728

1025
-continued
729
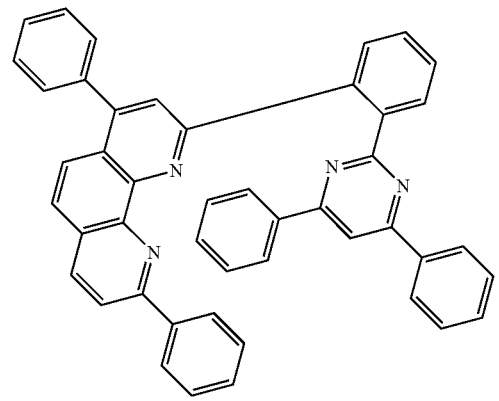
730
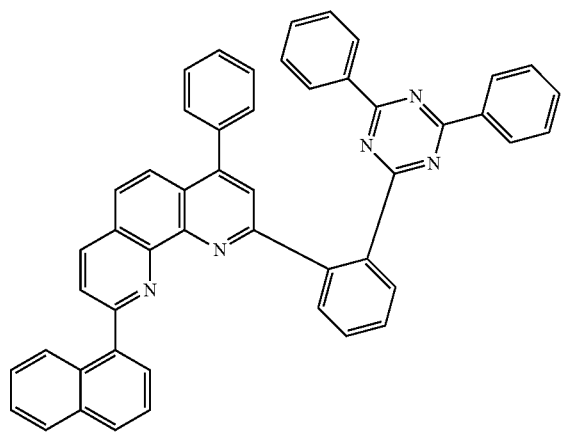
731
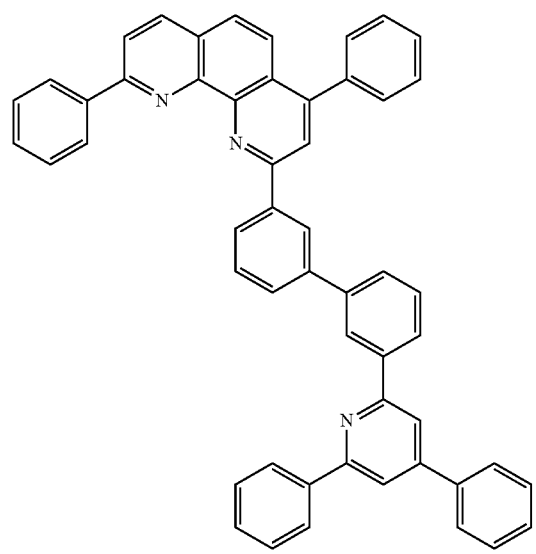
1026
-continued
732
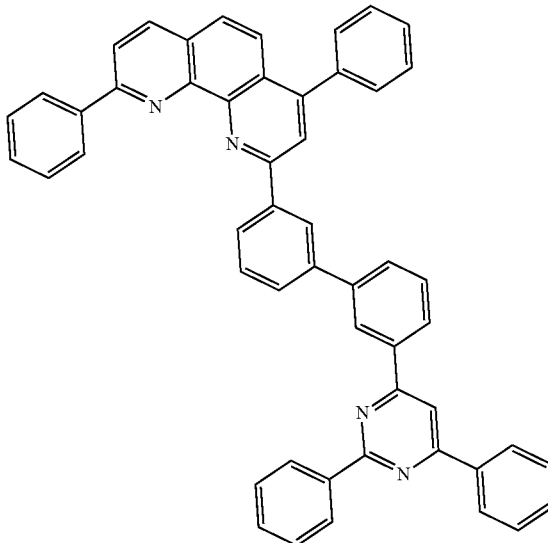
733
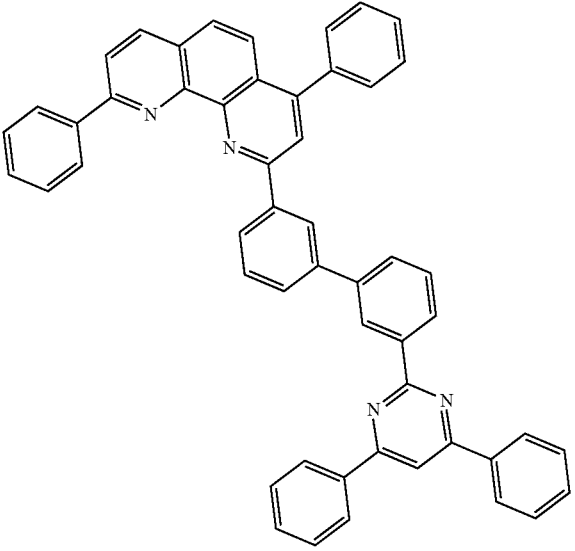

1027
-continued
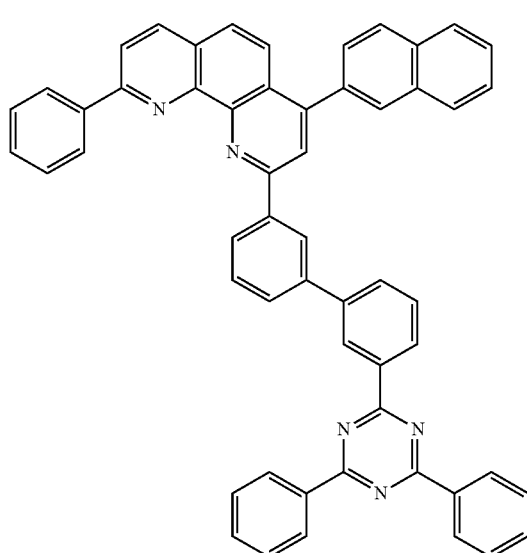
734
1028
-continued
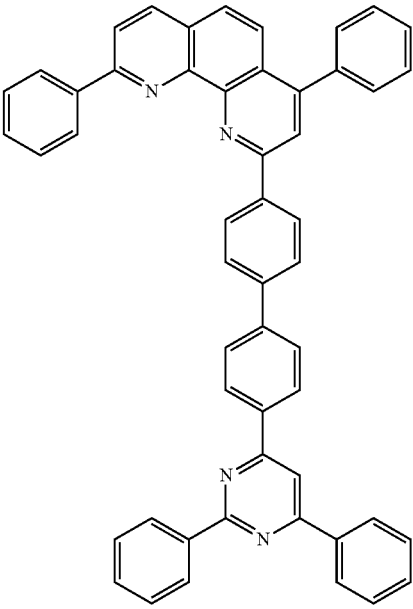
736
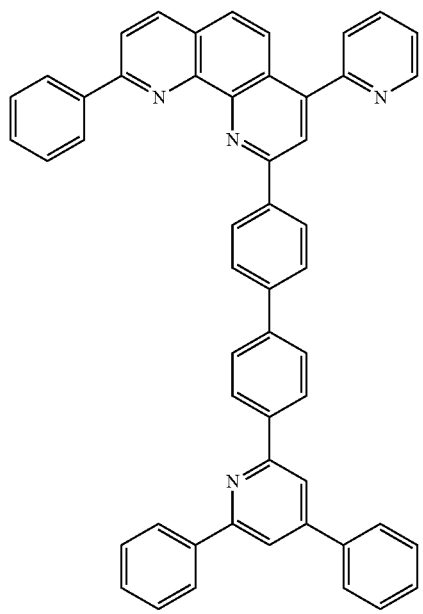
735
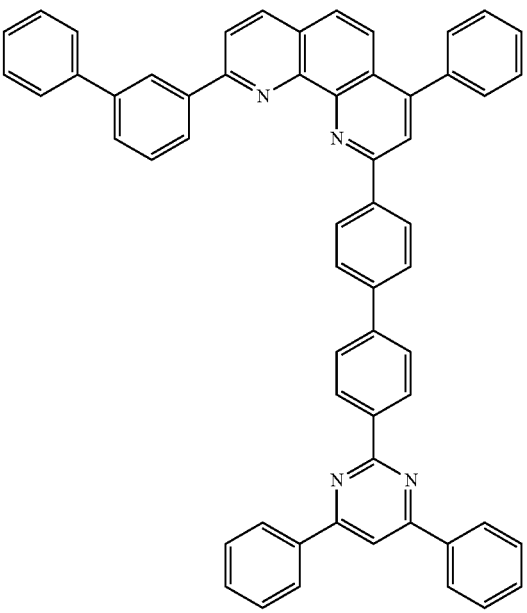
737

1029
-continued
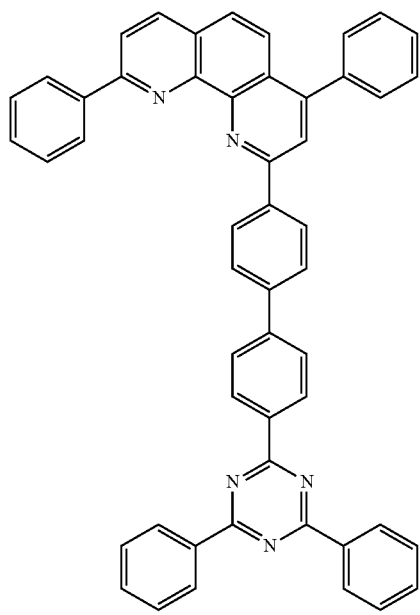
738
1030
-continued
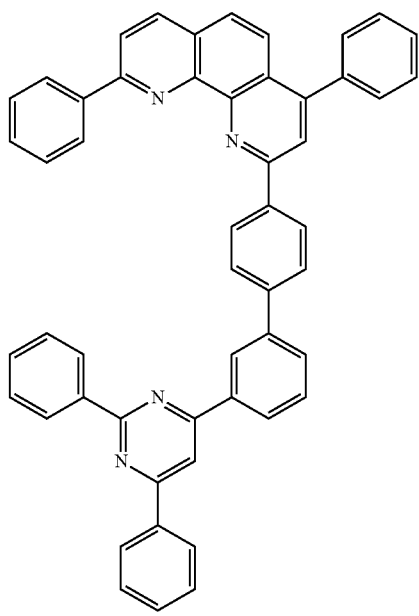
740
739
741

1031
-continued
742
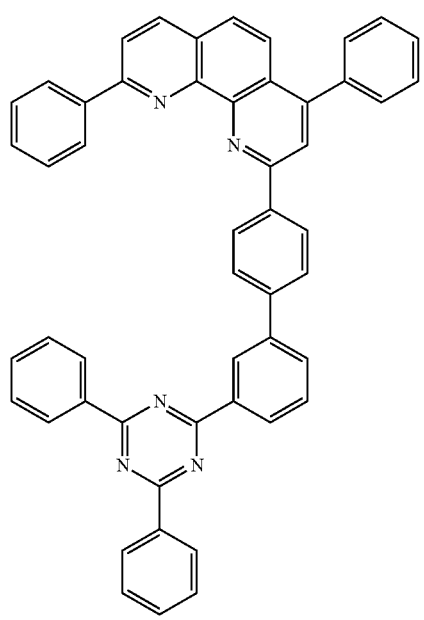
743
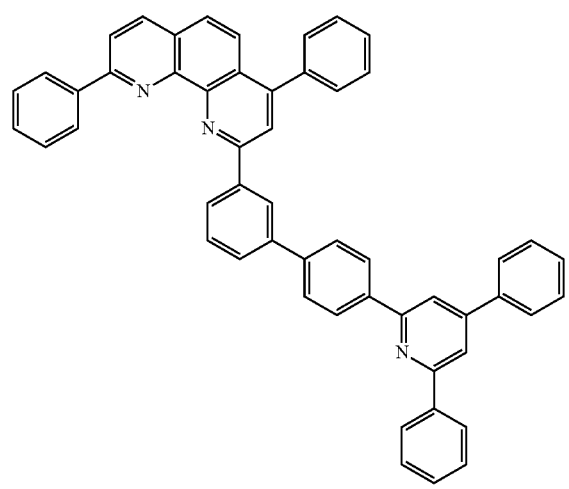
744
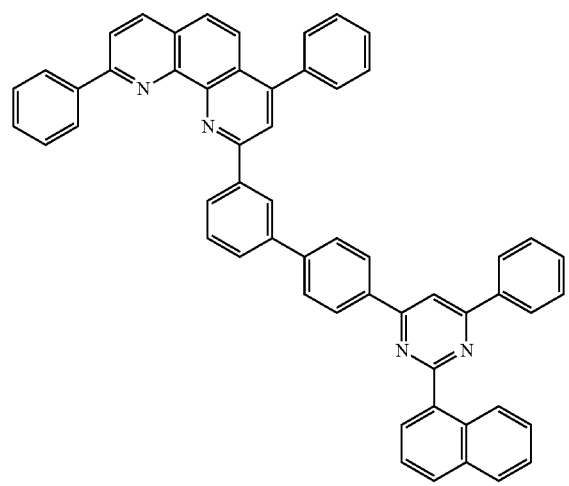
1032
-continued
745
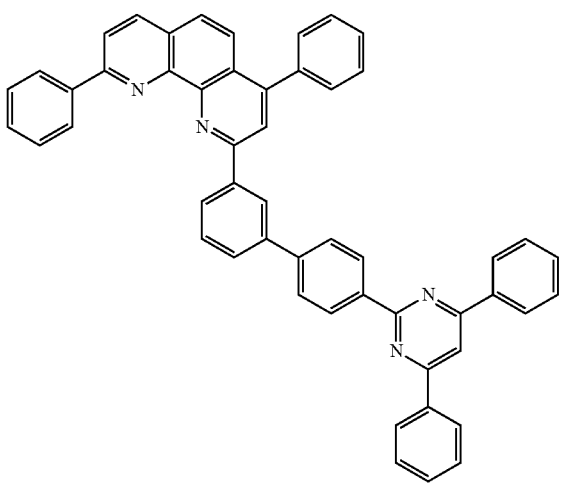
746
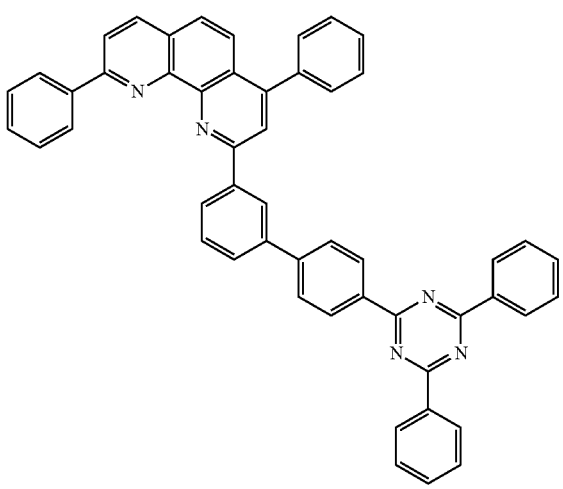
747
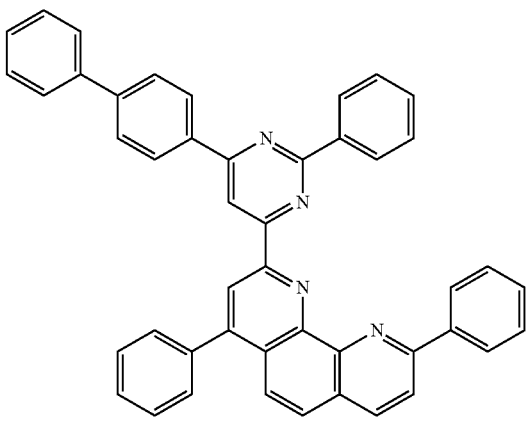

1033 -continued
748
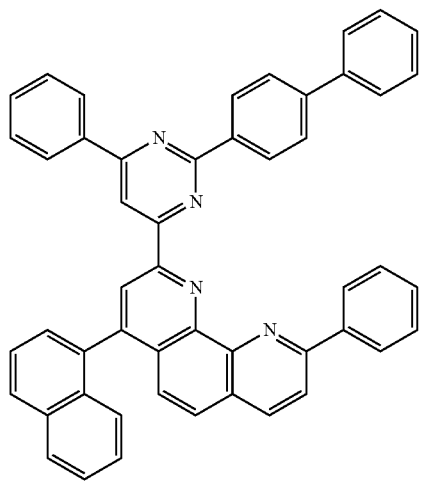
749
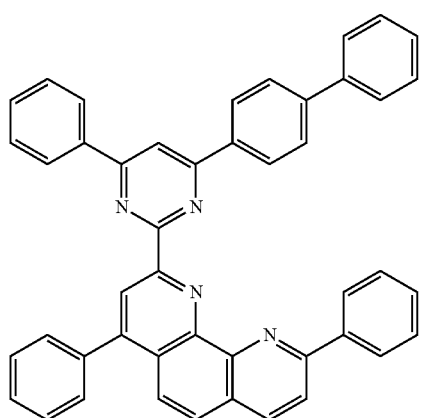
750
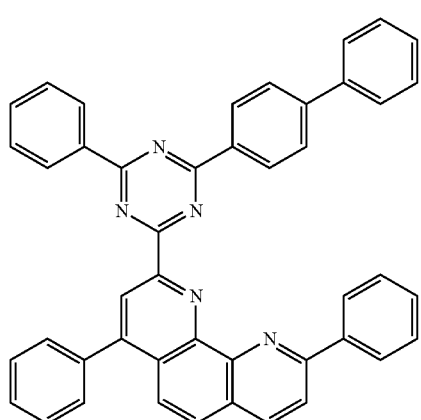
1034 -continued
751
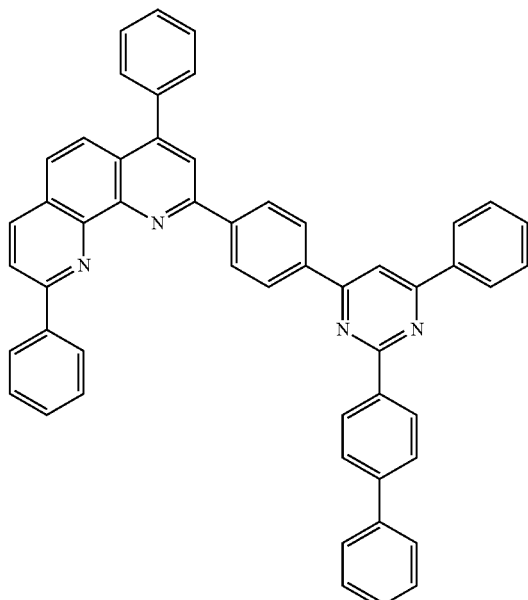
752
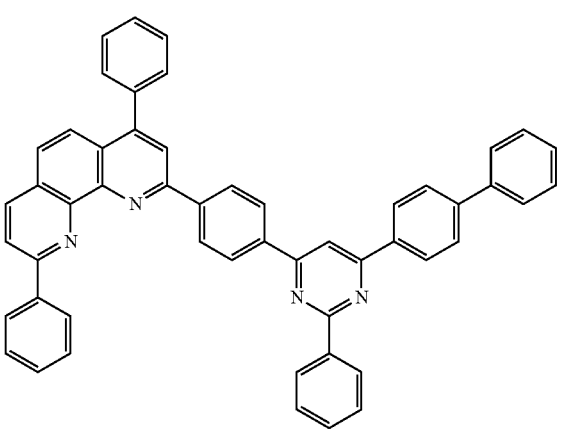

1035
-continued
1036
-continued
753
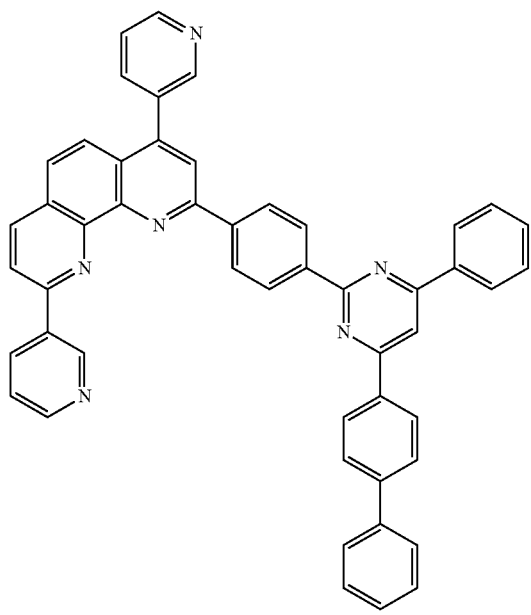
755
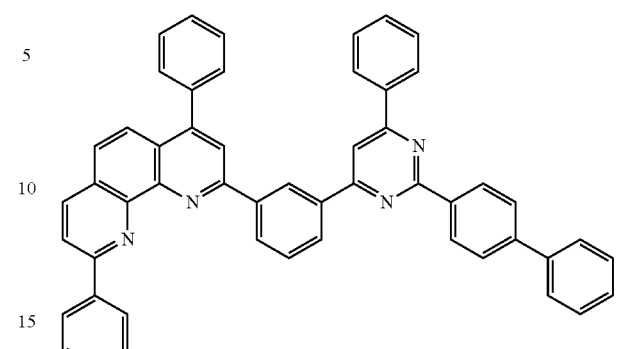
756
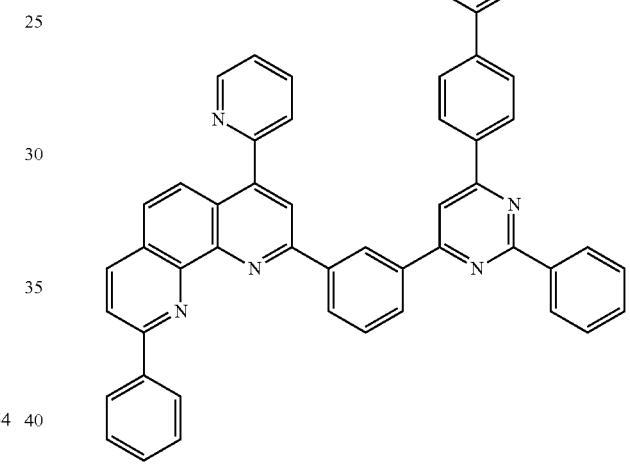
754
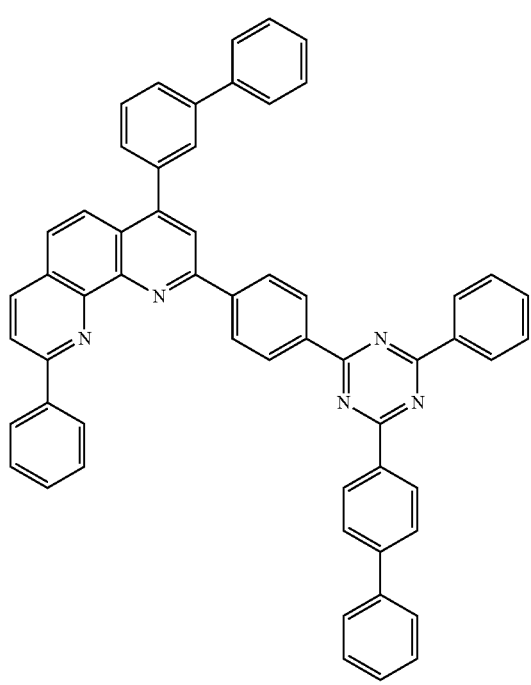
757
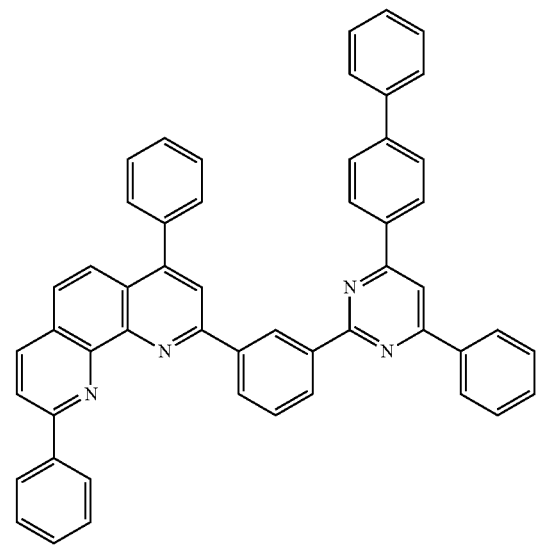

1037
-continued
758
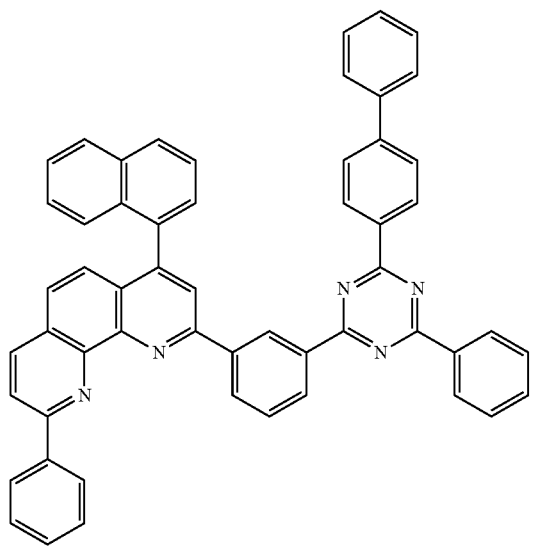
759
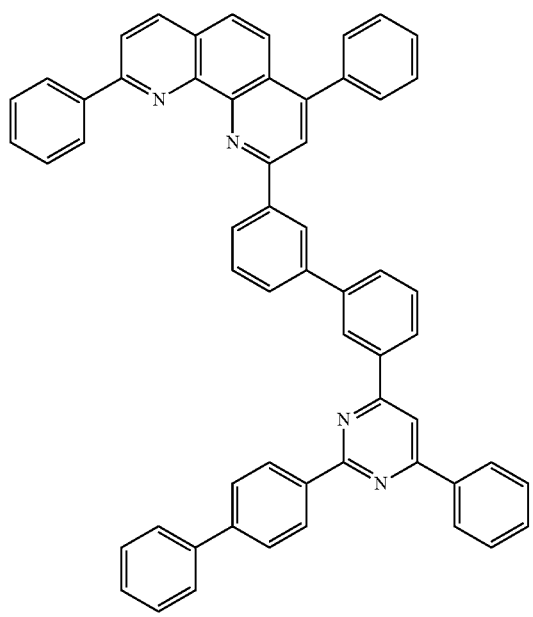
1038
-continued
760
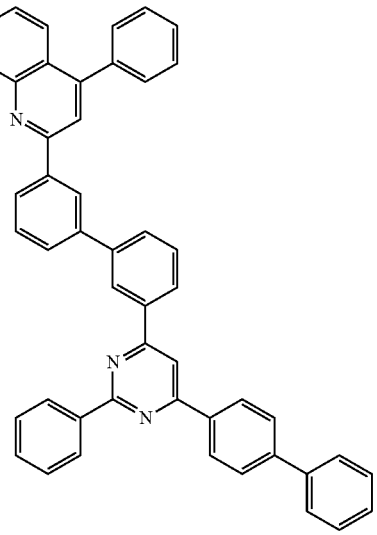
761
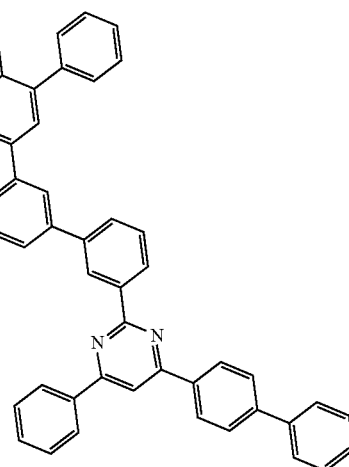

1039
-continued
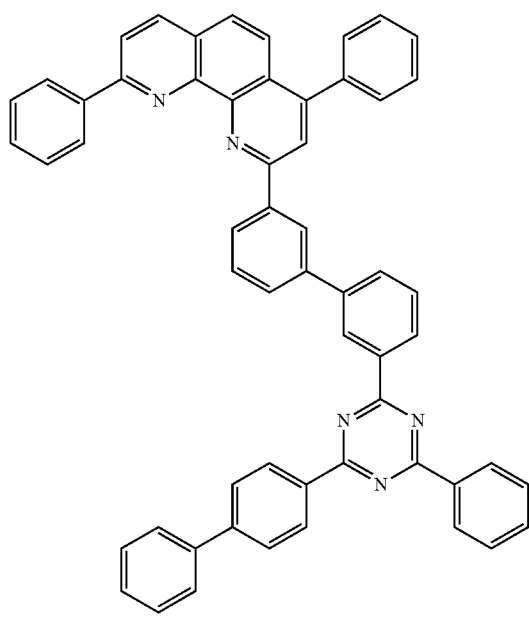
762
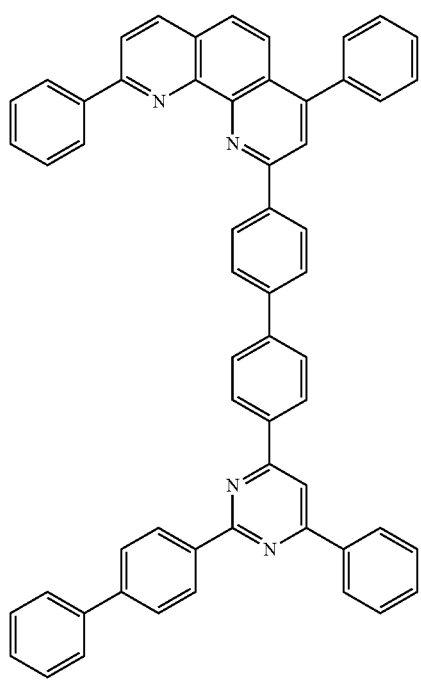
763
1040
-continued
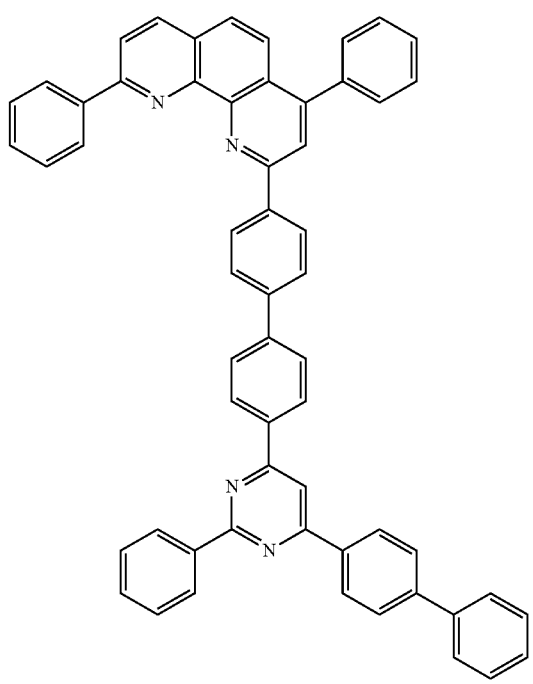
764
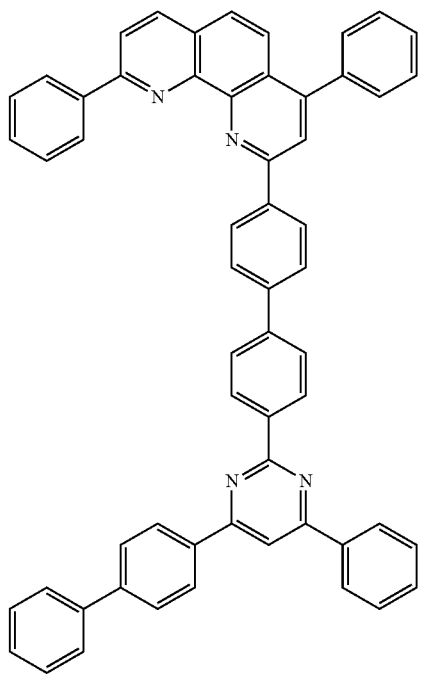
765

1041
-continued
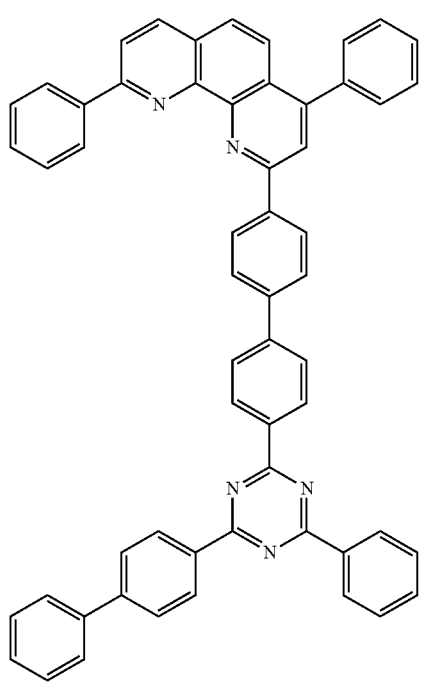
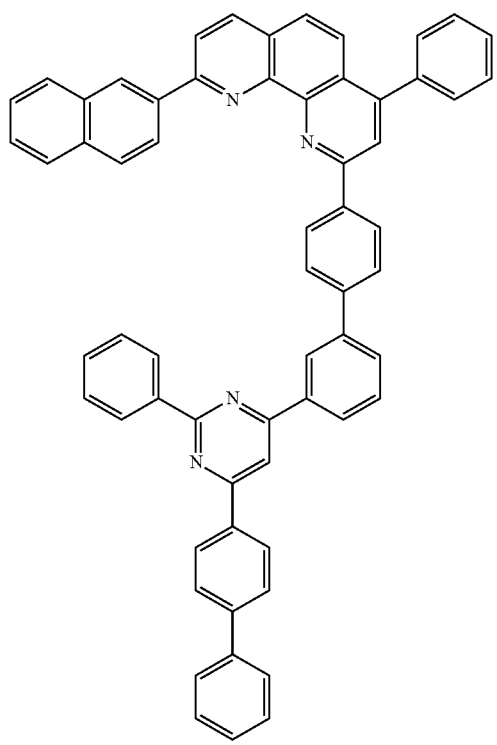
1042
-continued
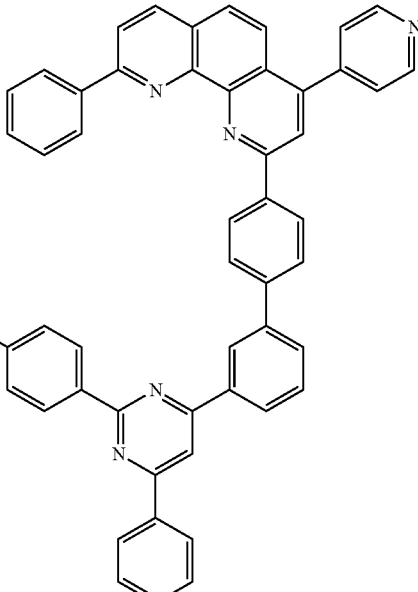
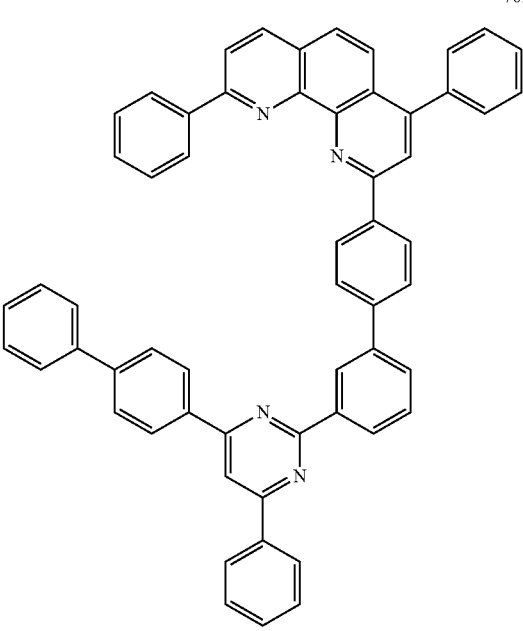

1043
-continued
770
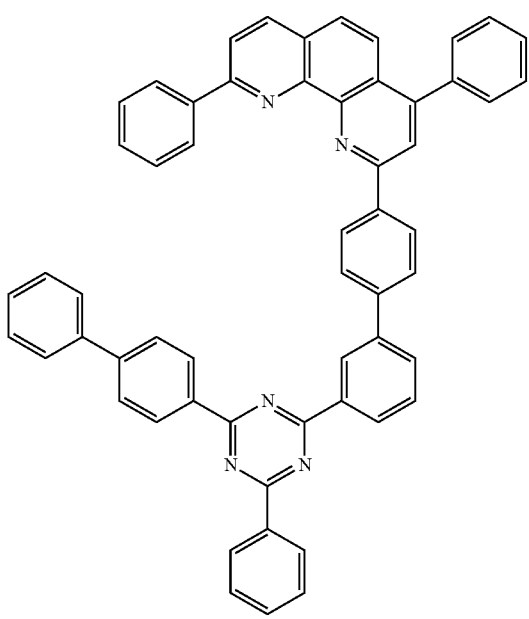
771
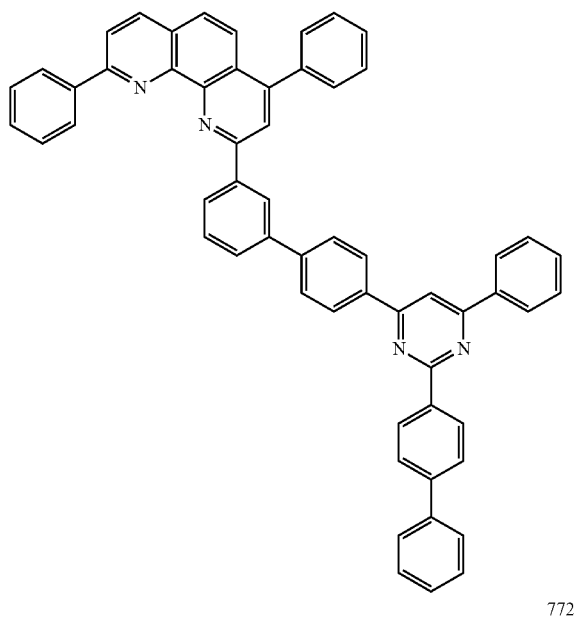
772
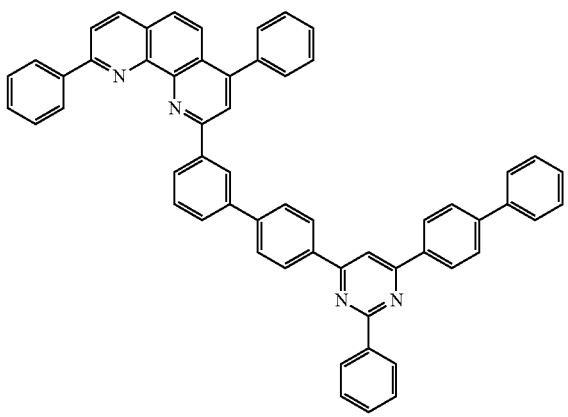
1044
-continued
773
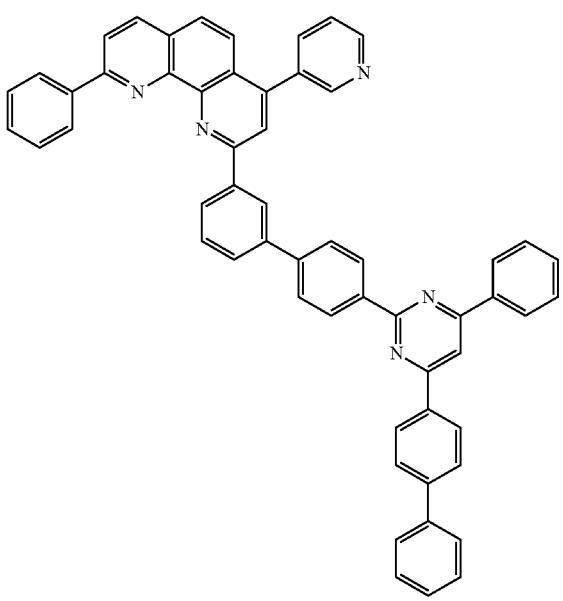
774
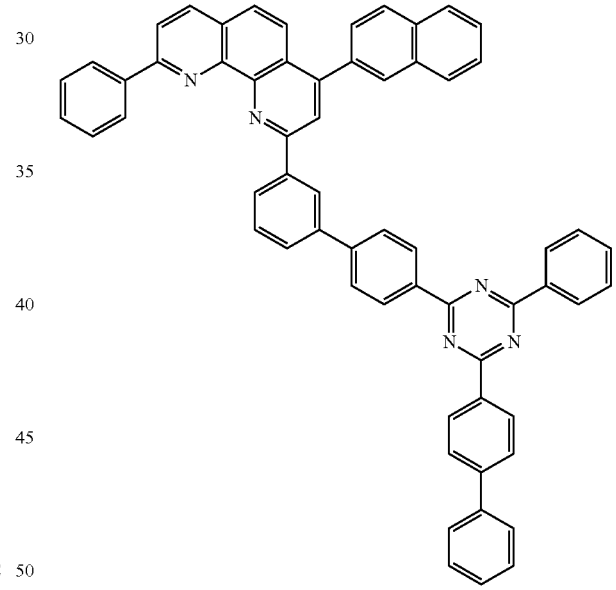
775
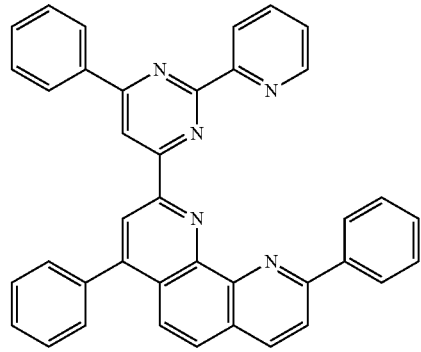

1045
-continued
776
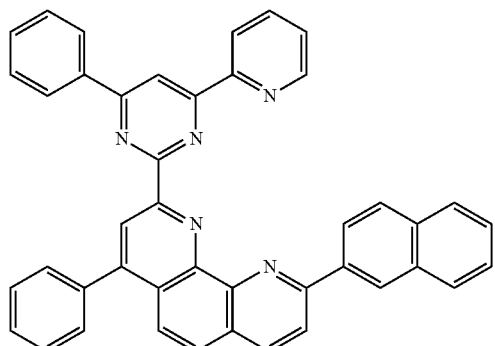
777
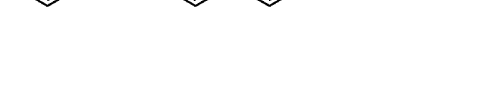
778
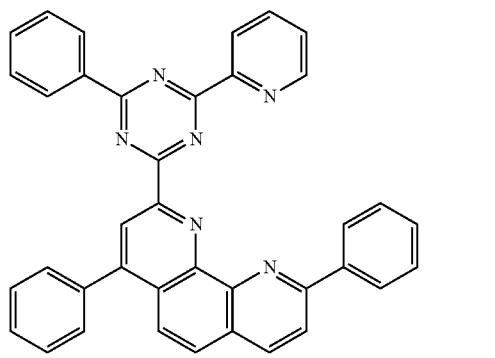
1046
-continued
779
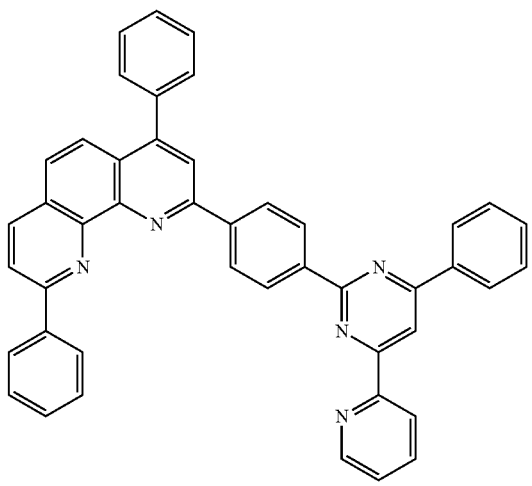
780
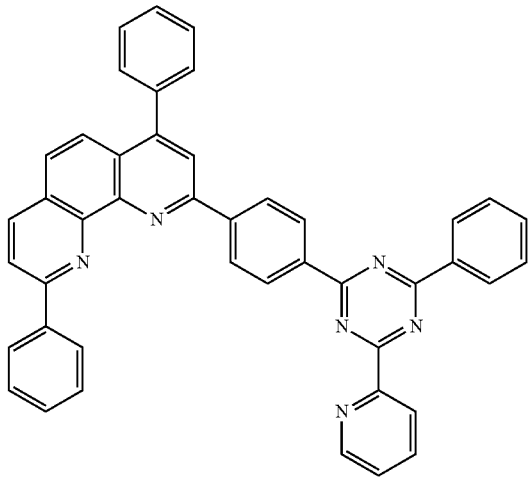
781
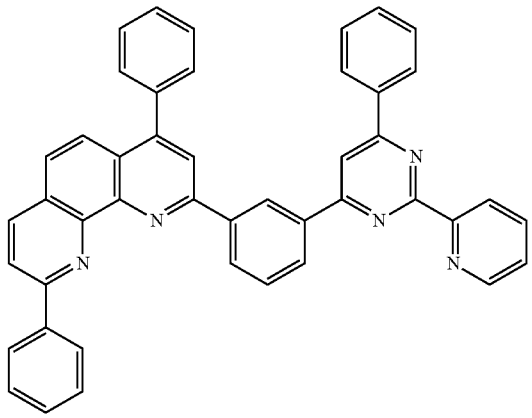

1047
-continued
782
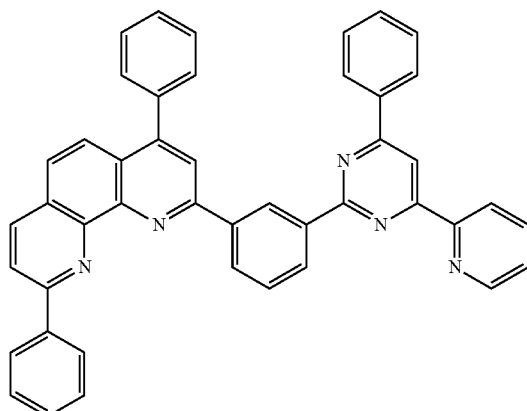
783
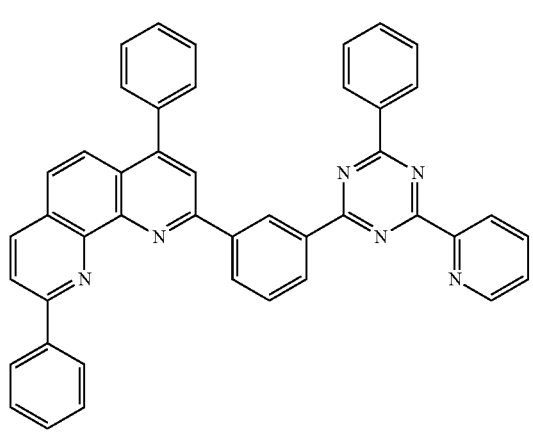
1048
-continued
785
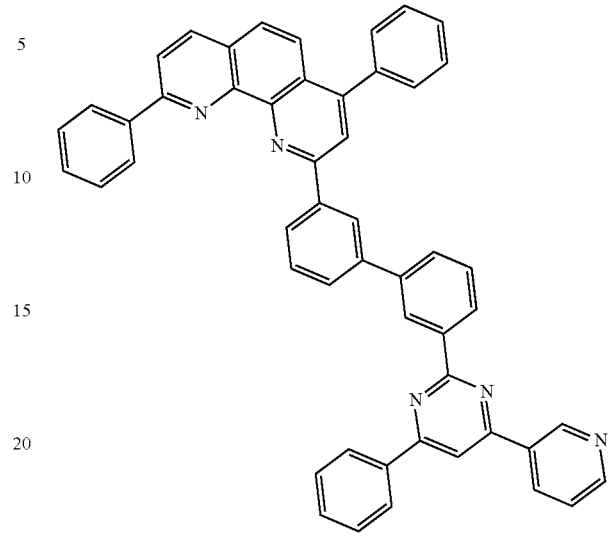
784
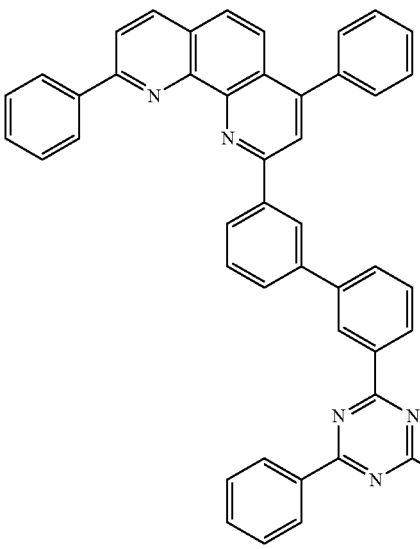
786

1049
-continued
1050
-continued
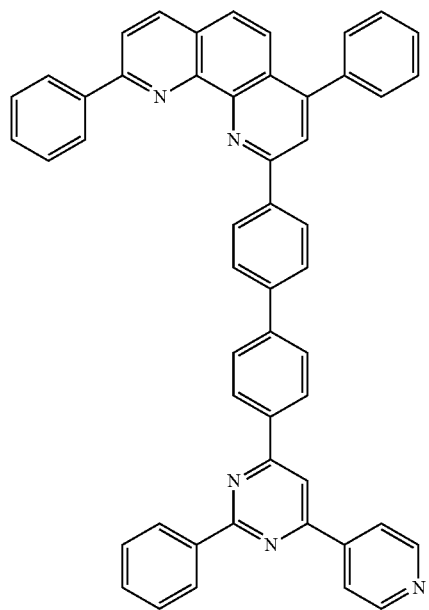
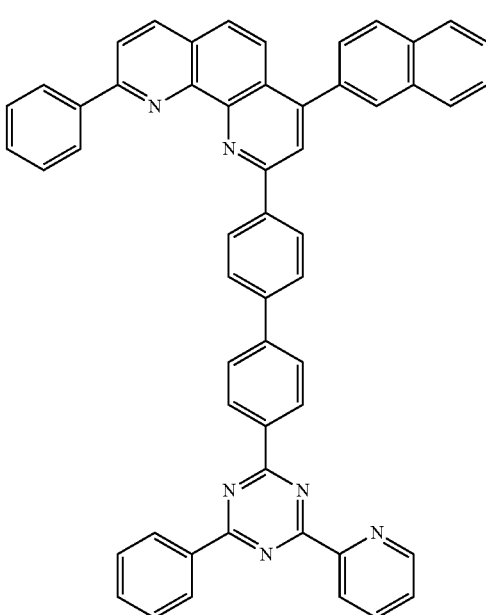

1051
-continued
791
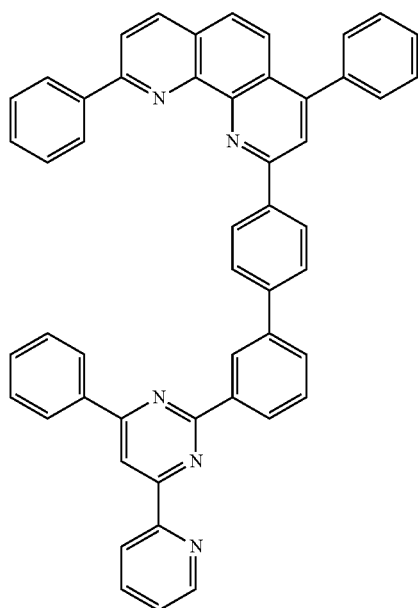
792
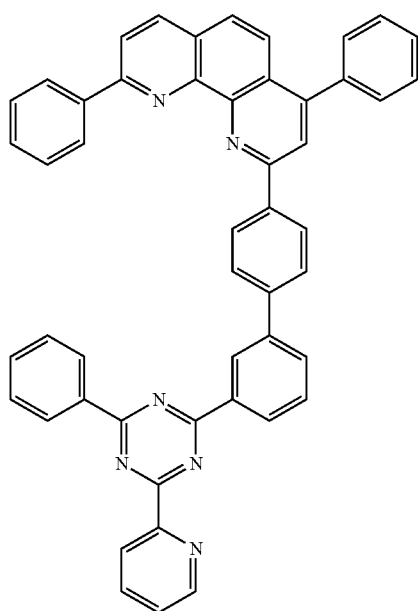
1052
-continued
793
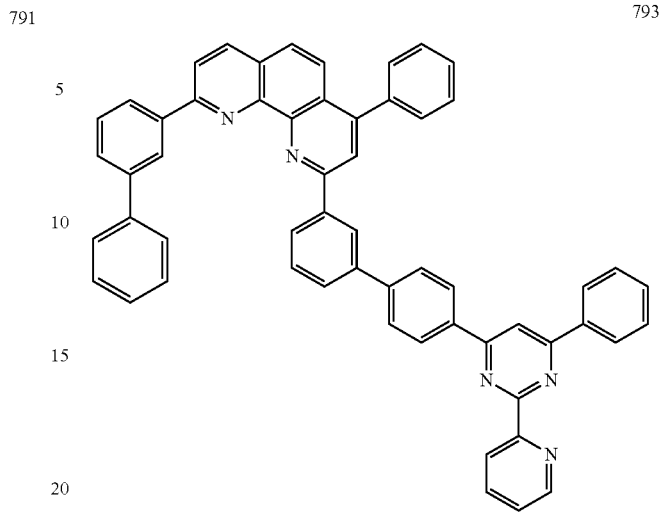
794
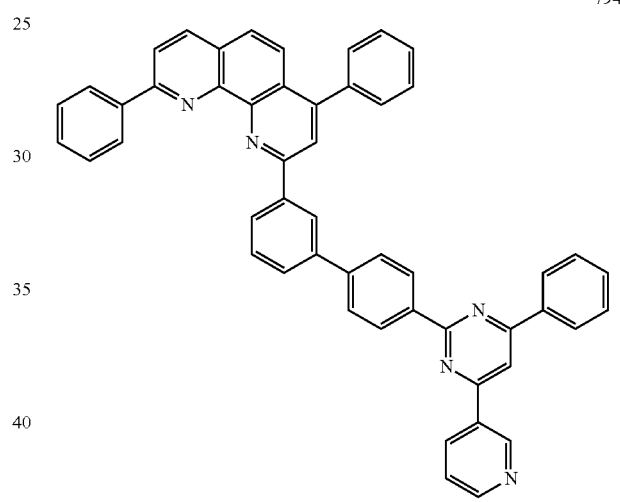
795
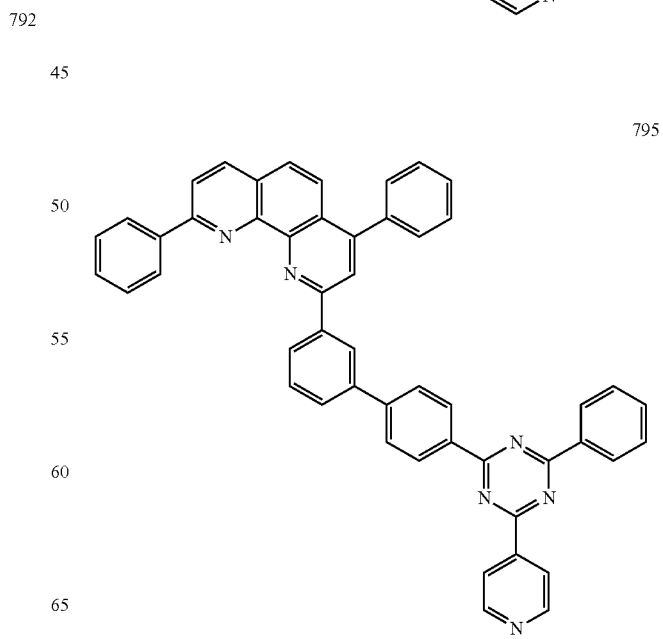

796
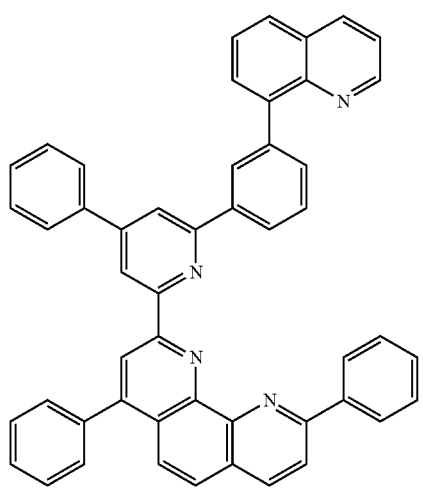
797
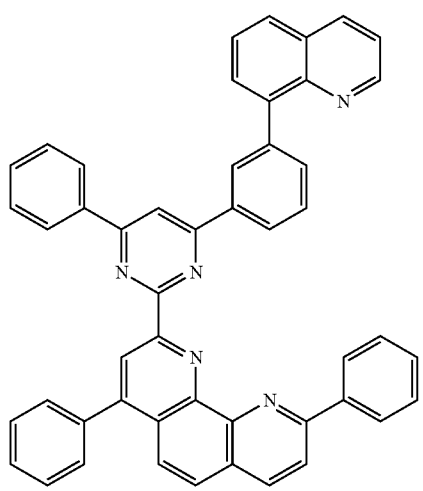
798
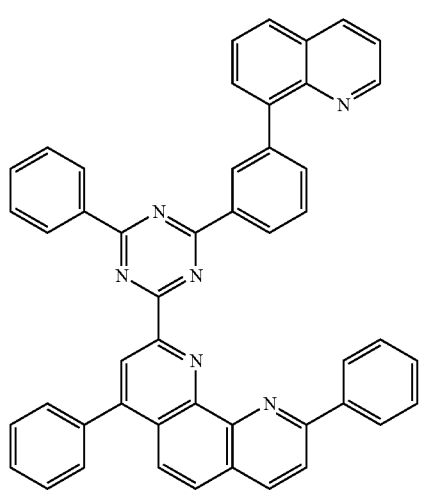
799
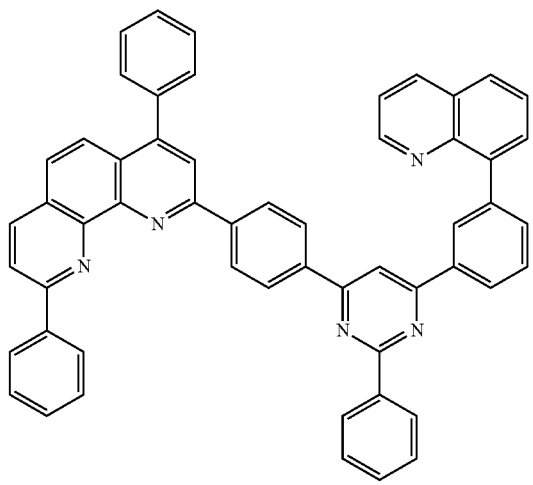
800
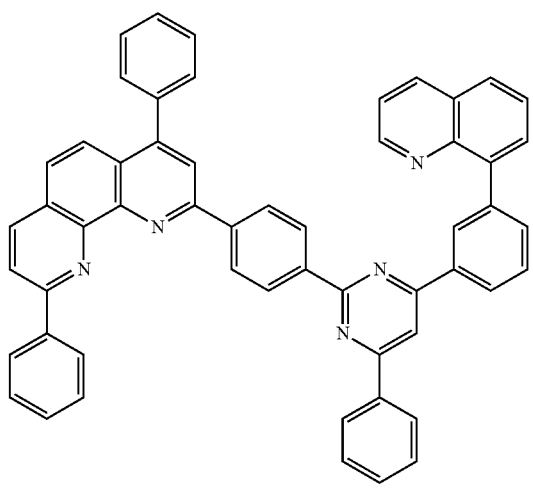
801
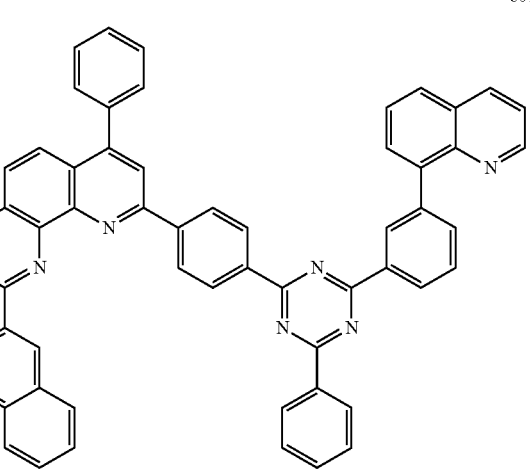

802
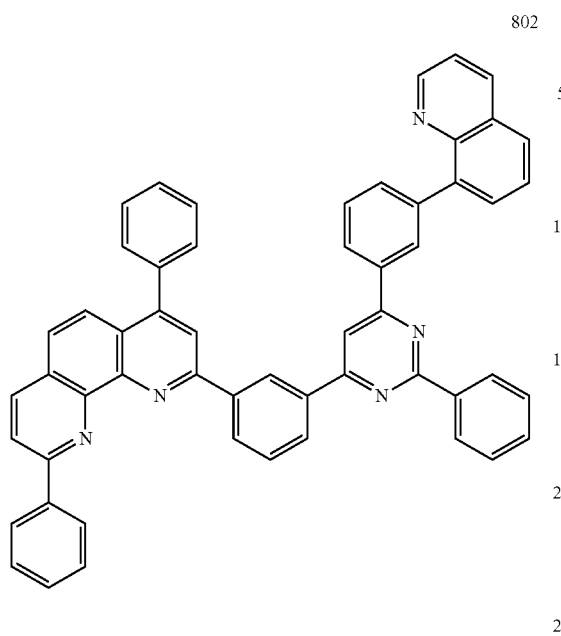
804
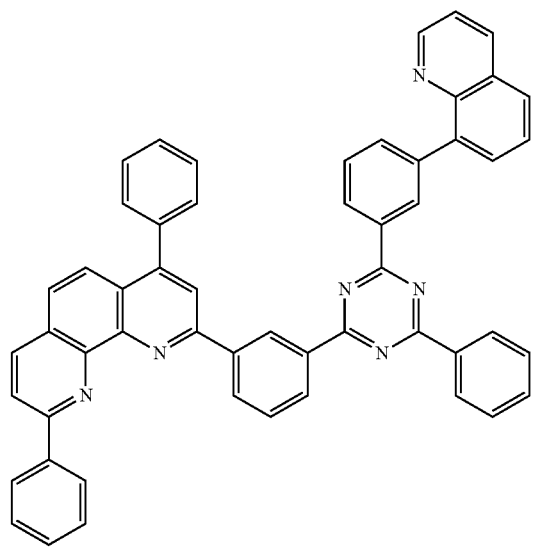
803
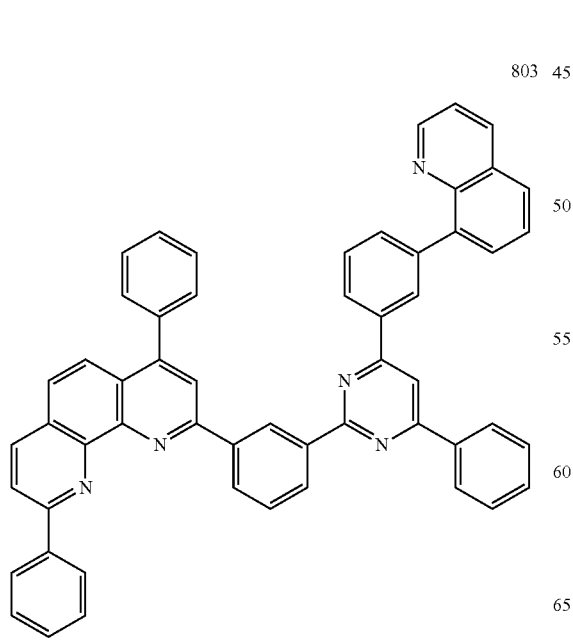
805
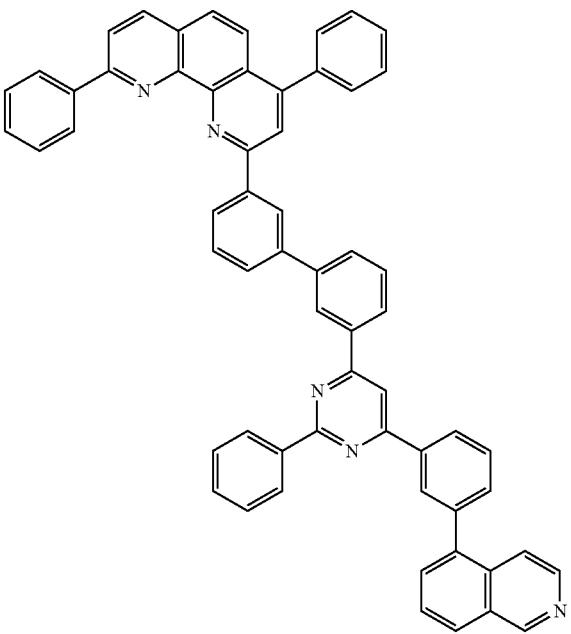

1057
-continued
806
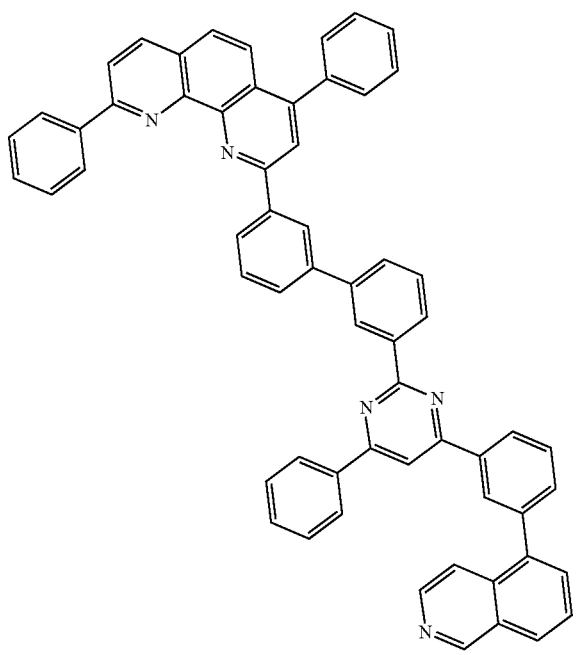
807
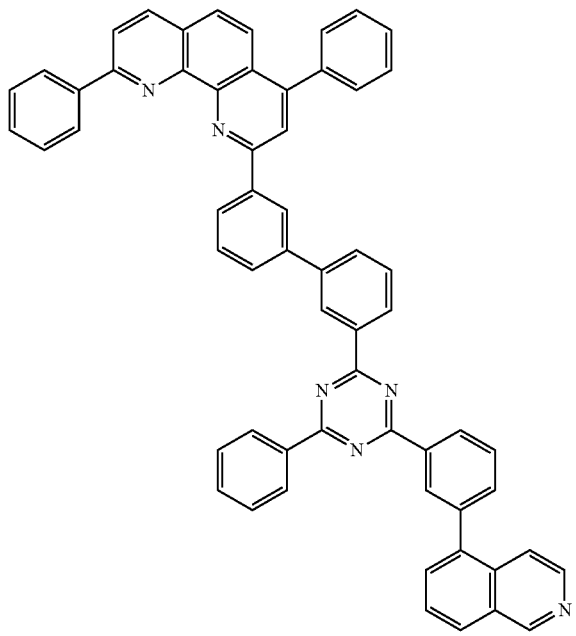
1058
-continued
808
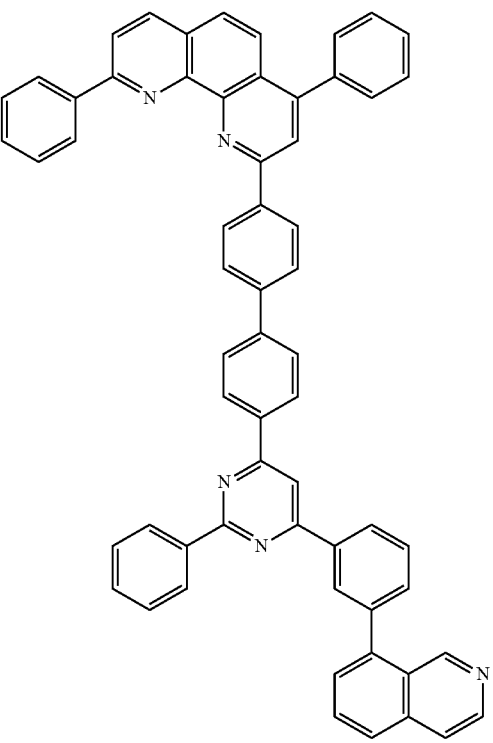
809

1059
-continued
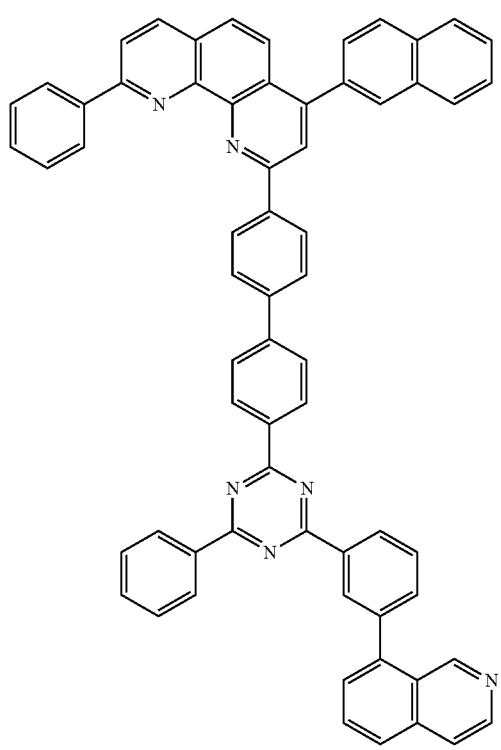
810
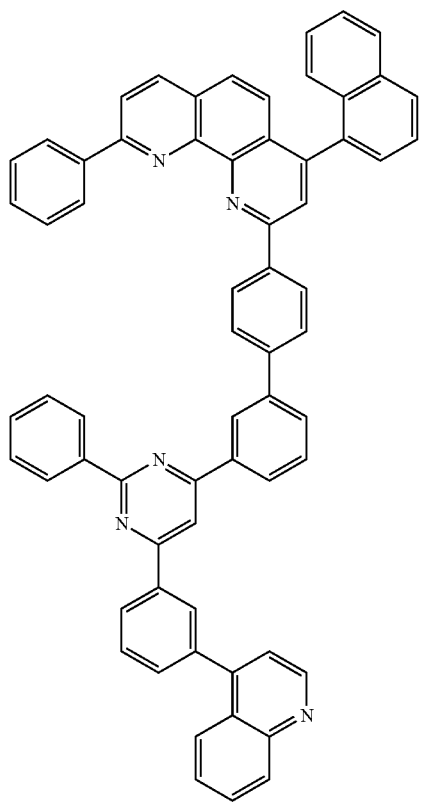
811
1060
-continued
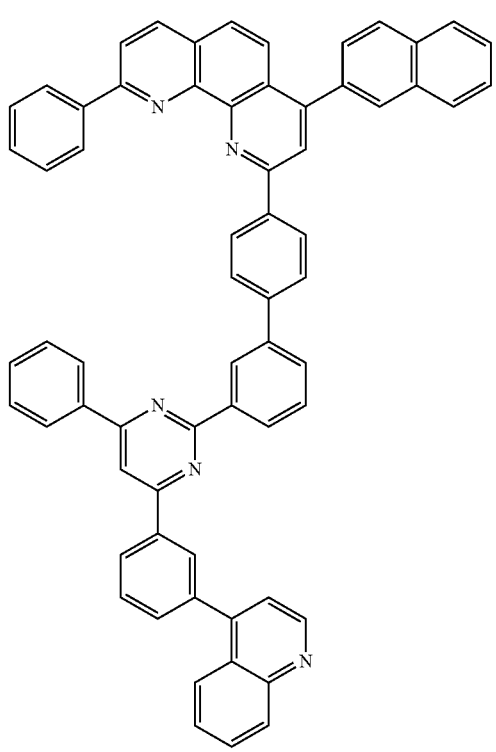
812
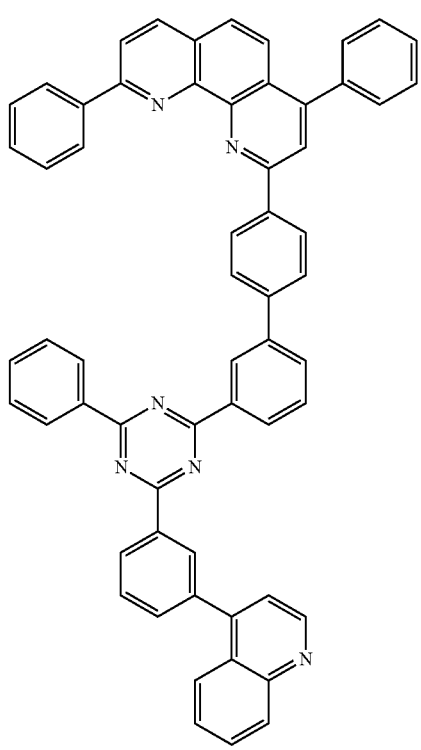
813

1061
-continued
814
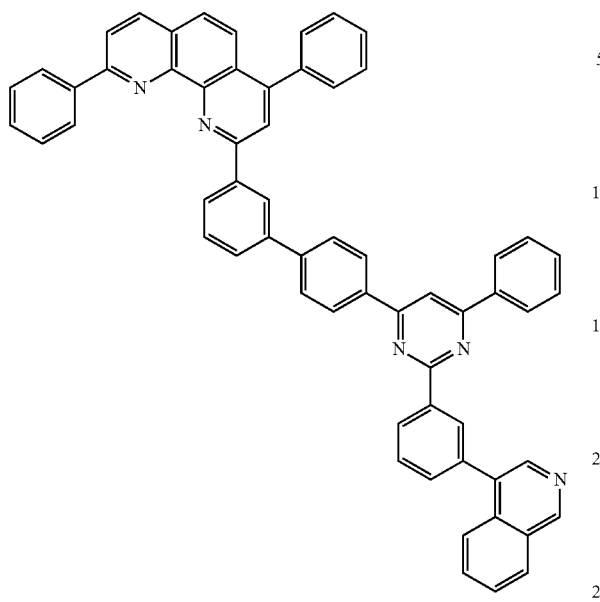
815
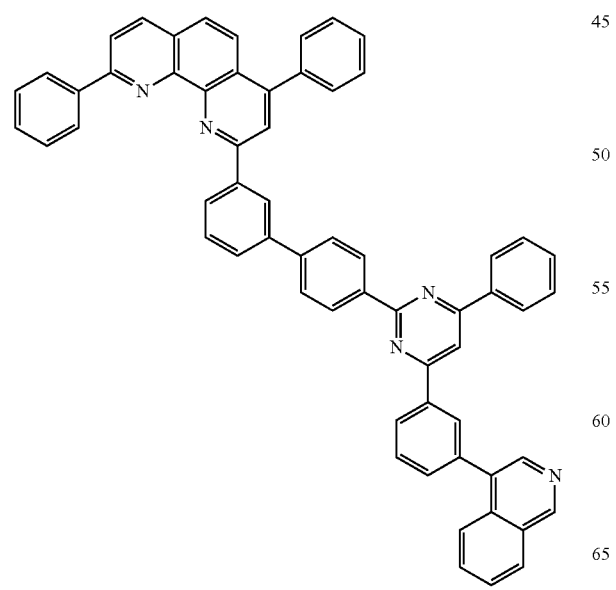
1062
-continued
816
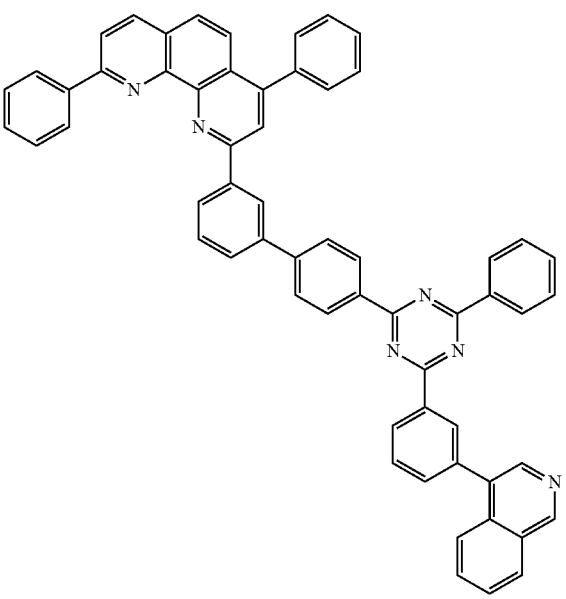
817
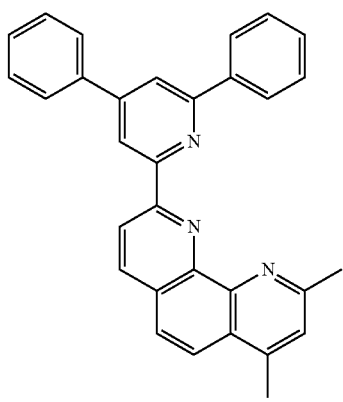
818
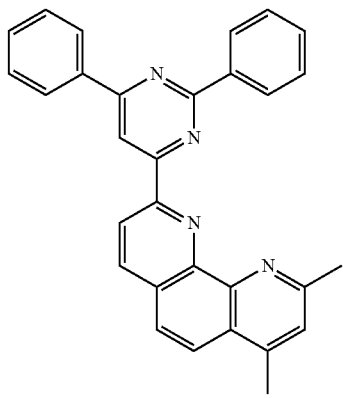

| 1063 -continued | 1064 -continued |
|---|---|
| 819 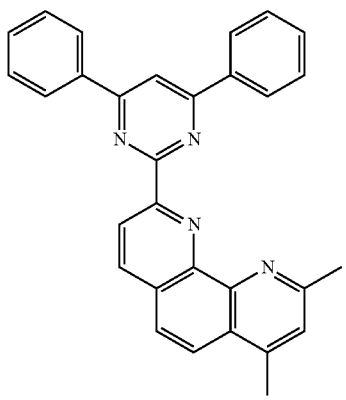 | 823 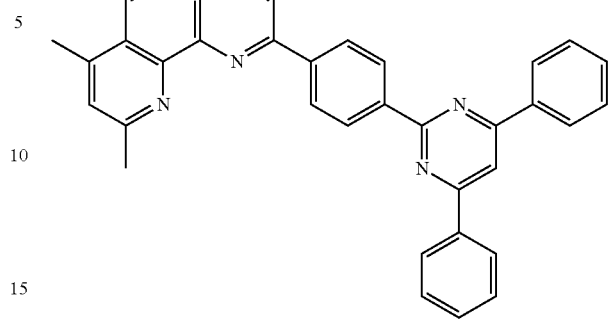 |
| 820 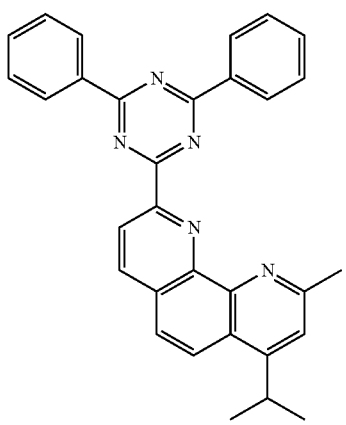 | 824 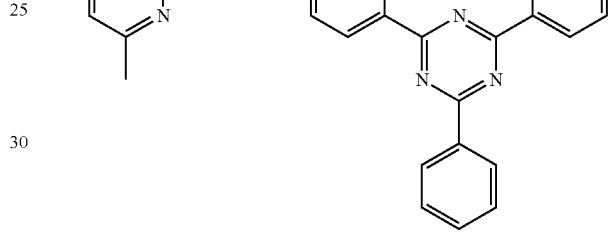 |
| 821 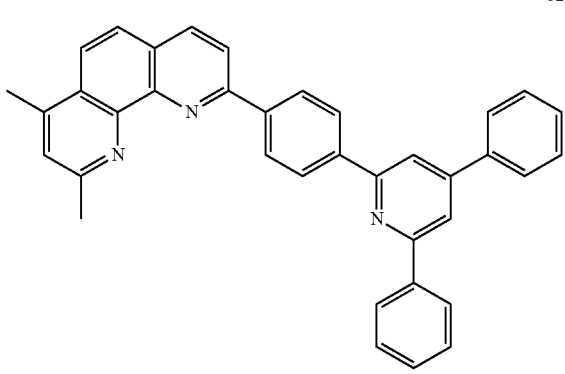 | 825 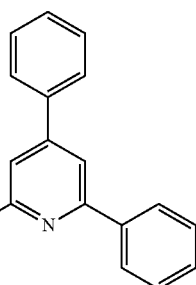 |
| 822 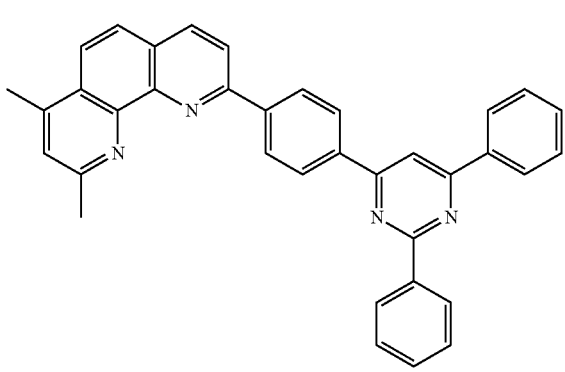 | 826 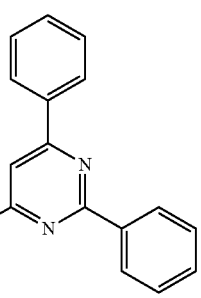 |

1065
-continued
827
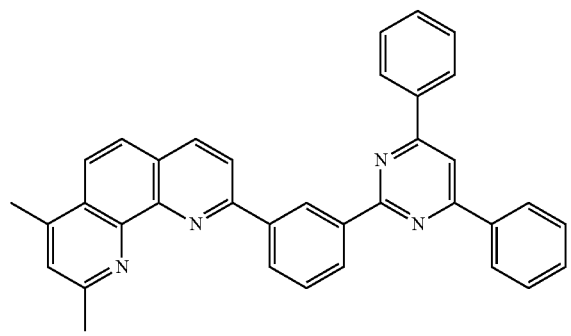
828
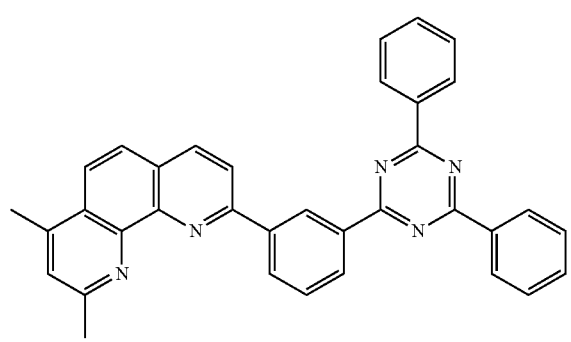
829
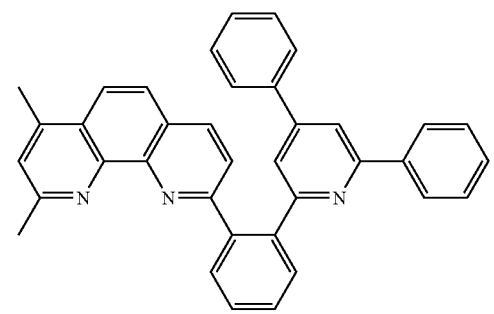
830
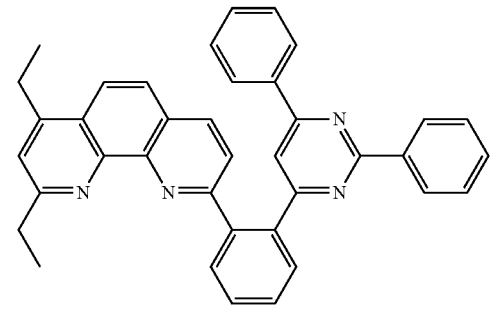
831
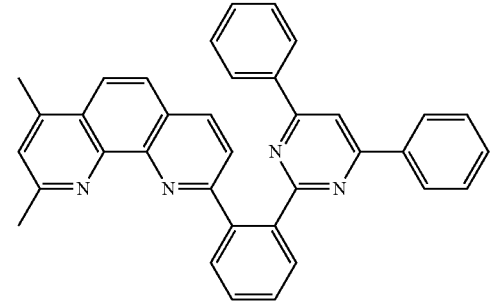
1066
-continued
832
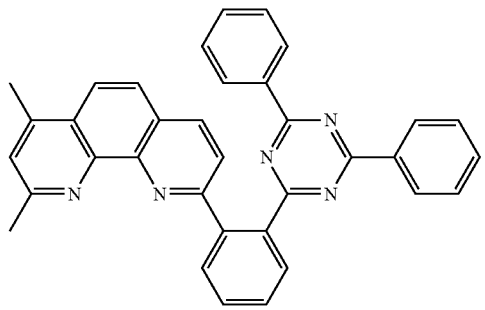
833
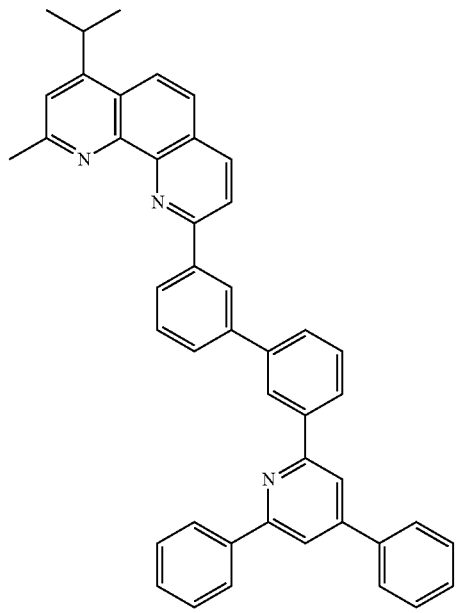
834
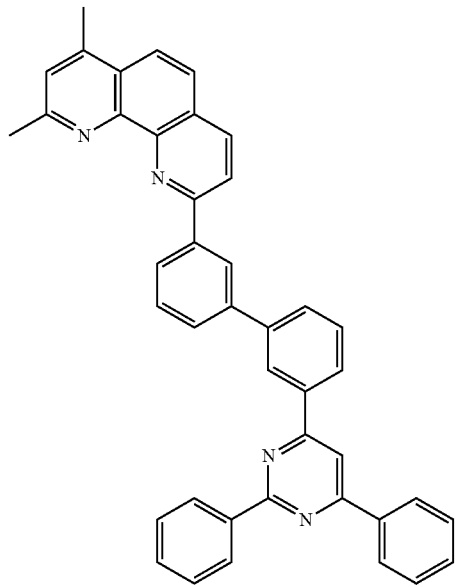

1067
-continued
835
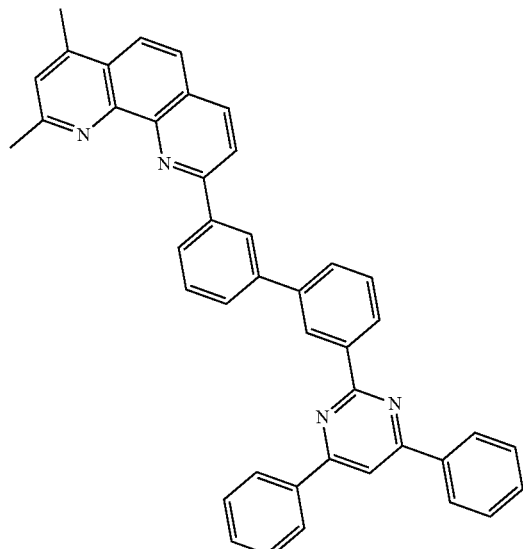
1068
-continued
837
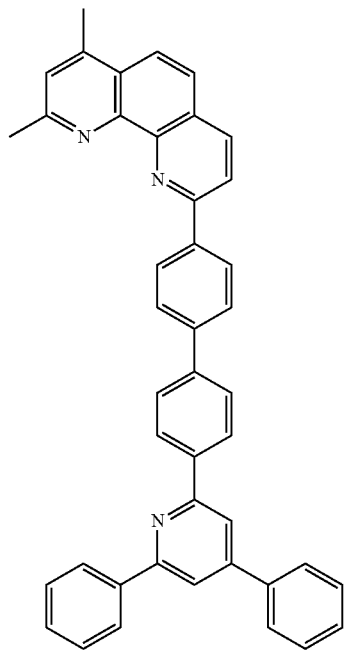
836
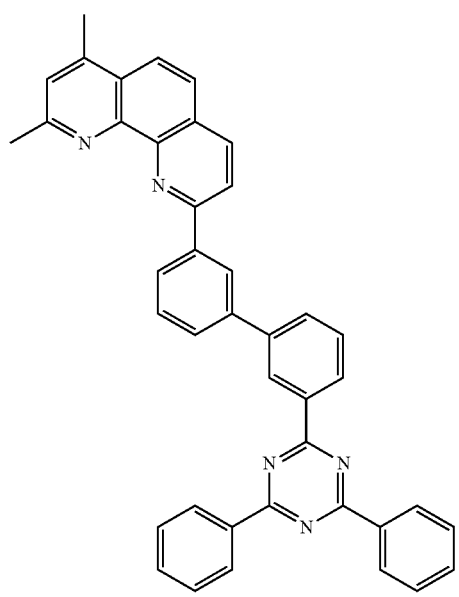
838
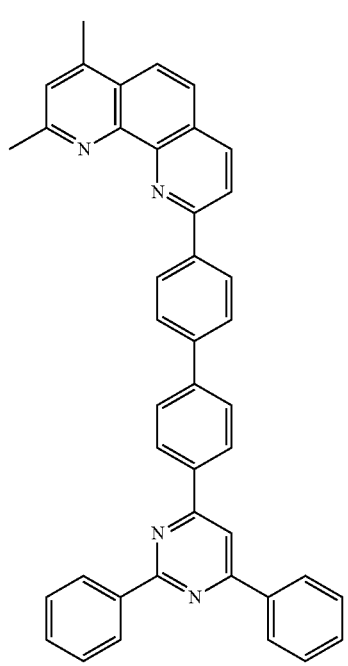

1069
-continued
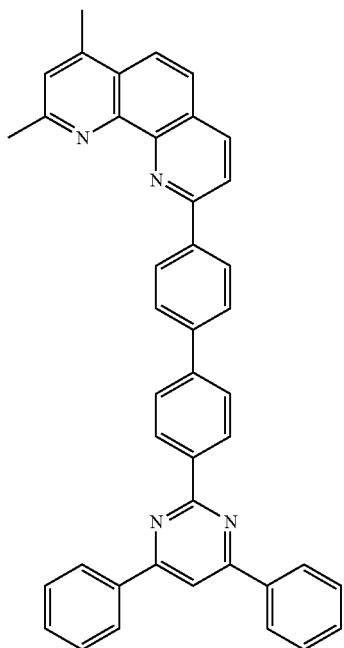
1070
-continued
839
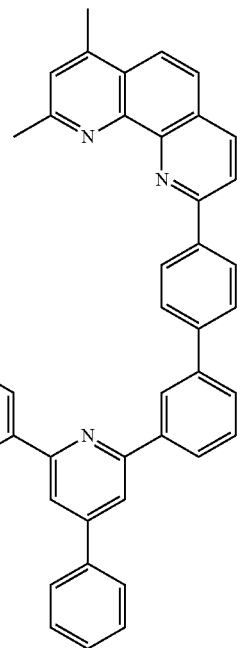
841
840
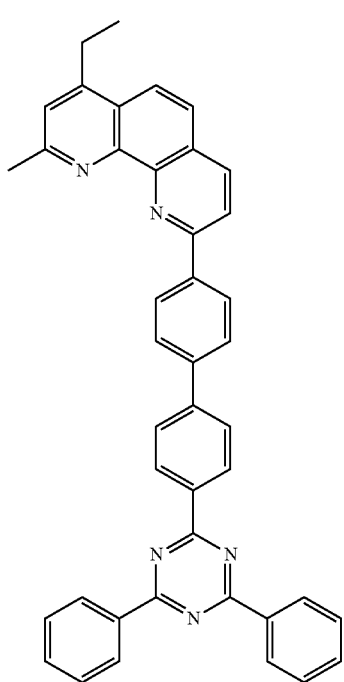
842
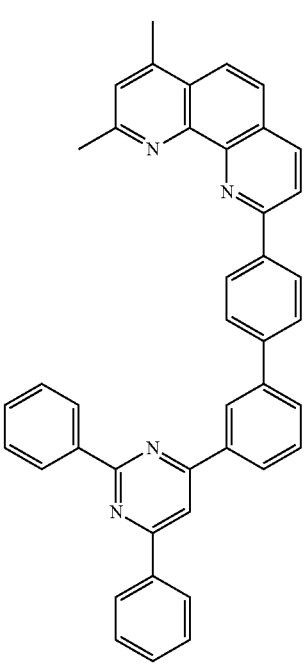

-continued
843
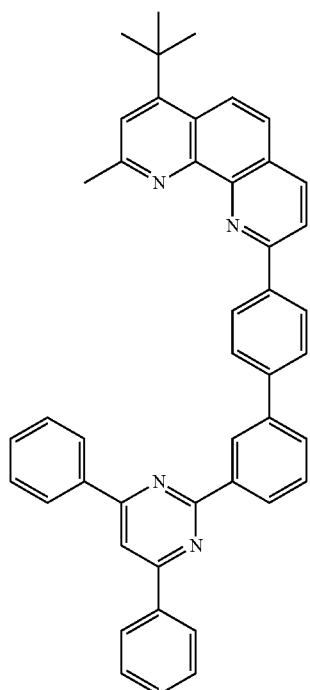
844
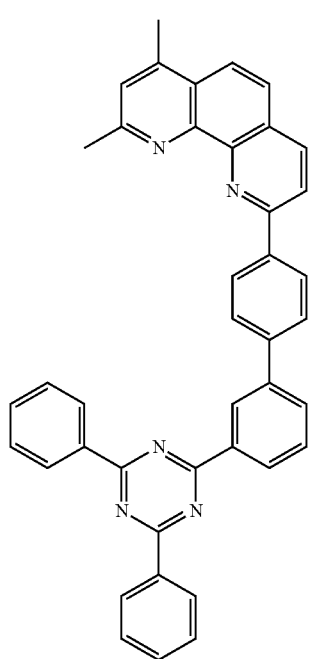
-continued
845
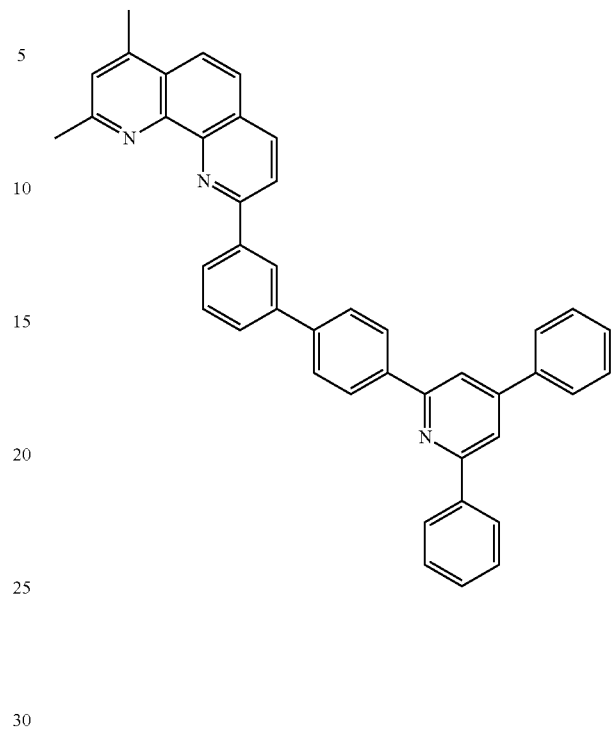
846
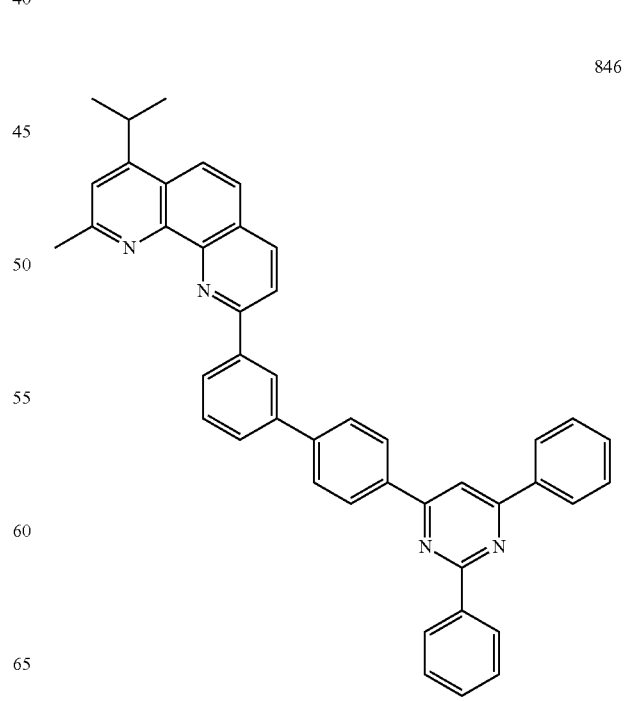

1073
-continued
847
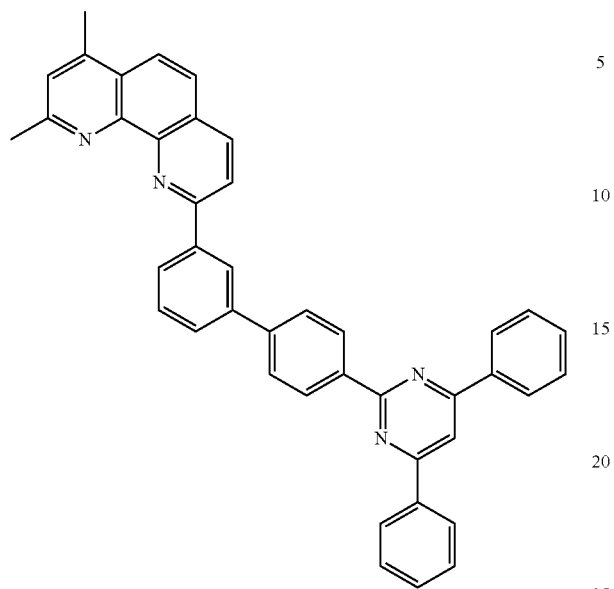
848
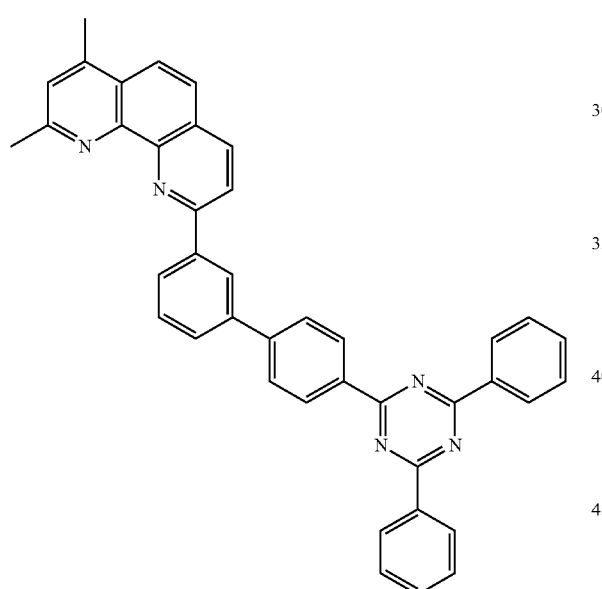
849
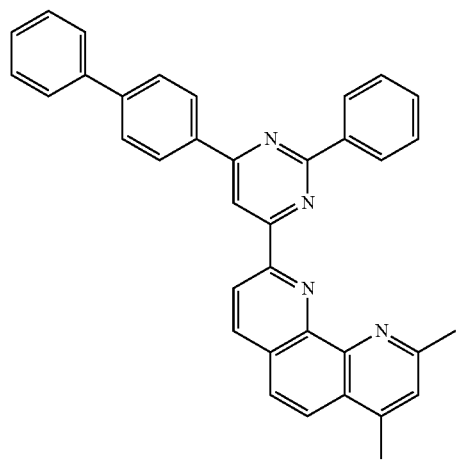
1074
-continued
850
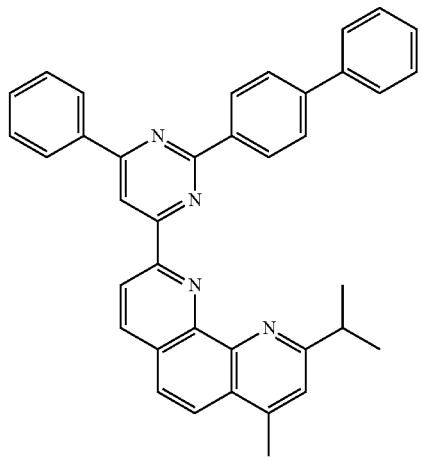
851
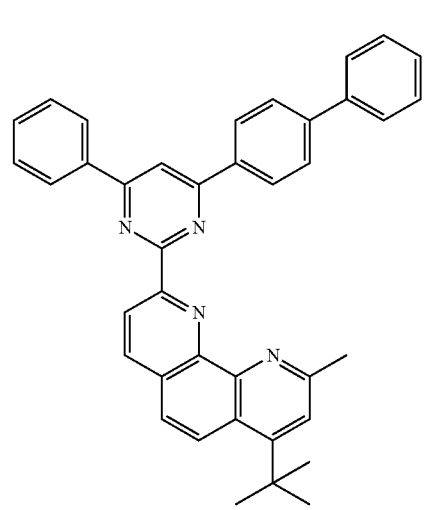
852
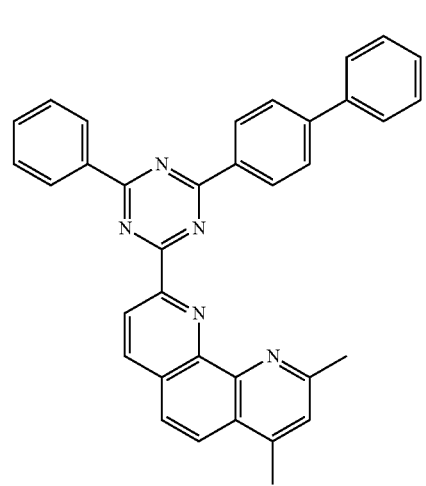

1075 -continued
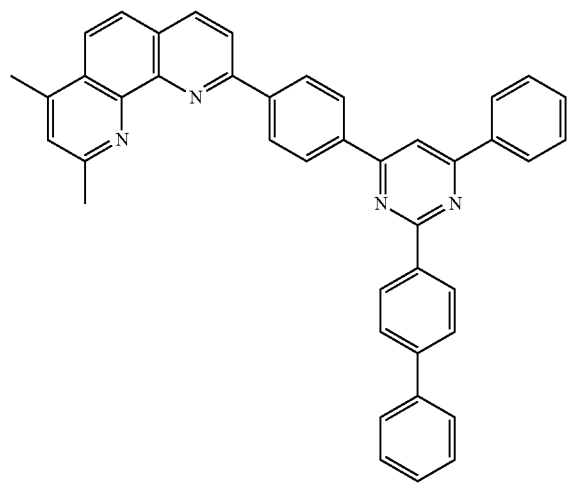
853
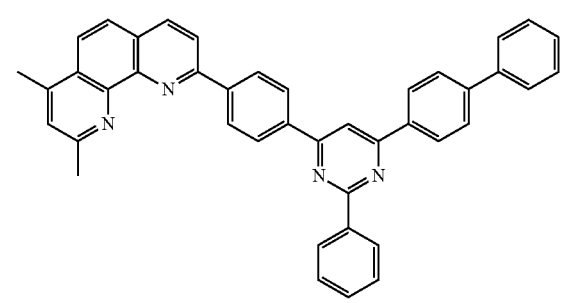
854
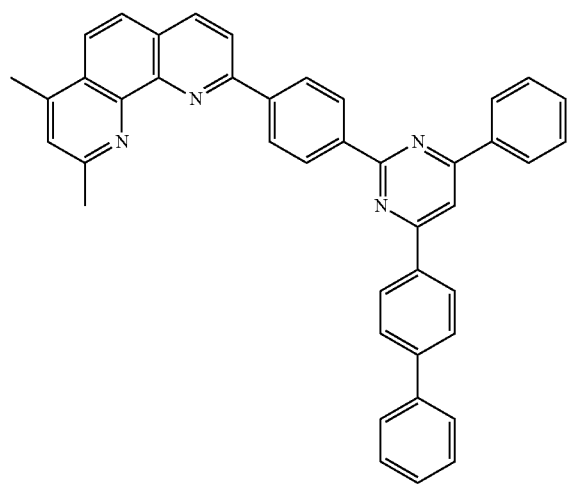
855
1076 -continued
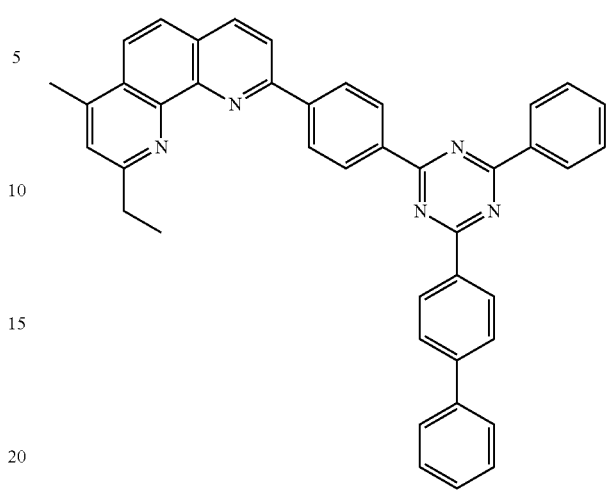
856
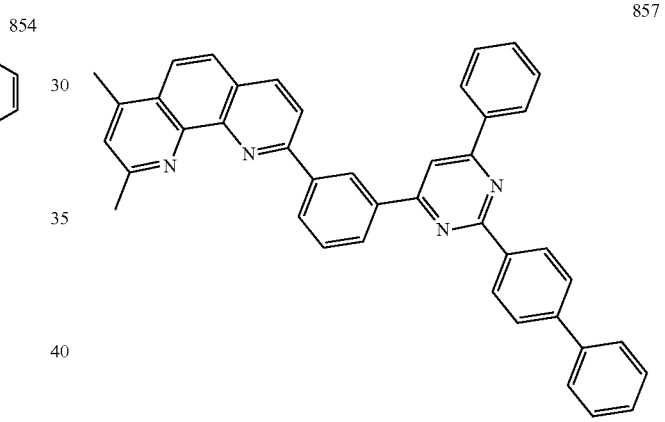
857
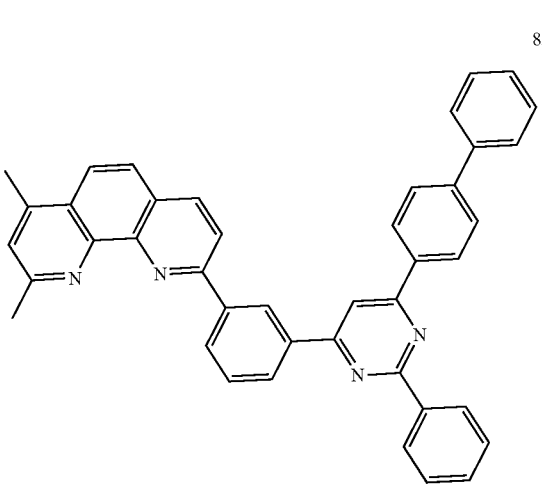
858

1077
-continued
859
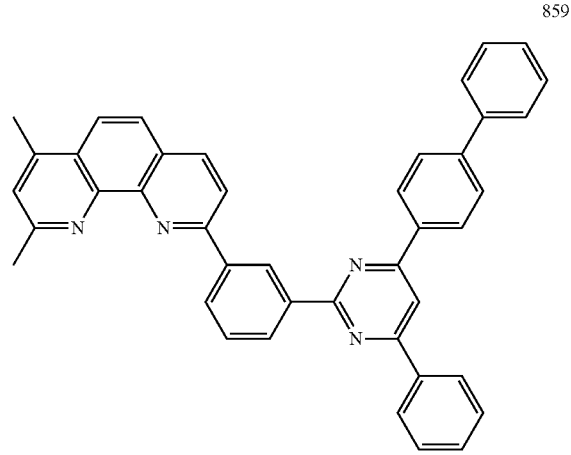
860
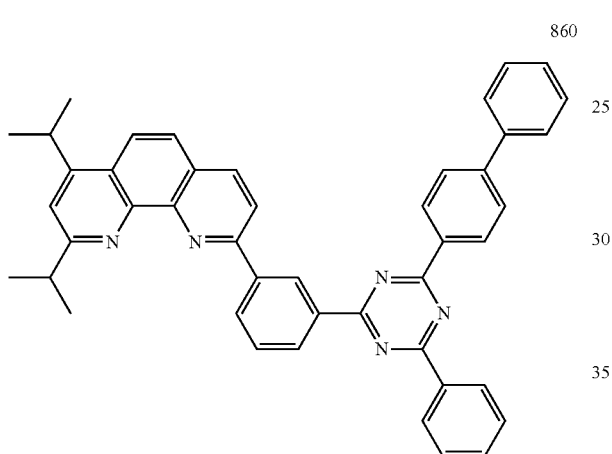
861
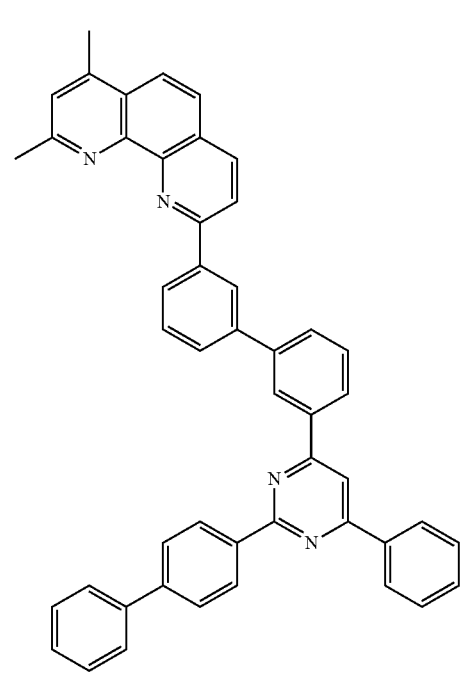
1078
-continued
862
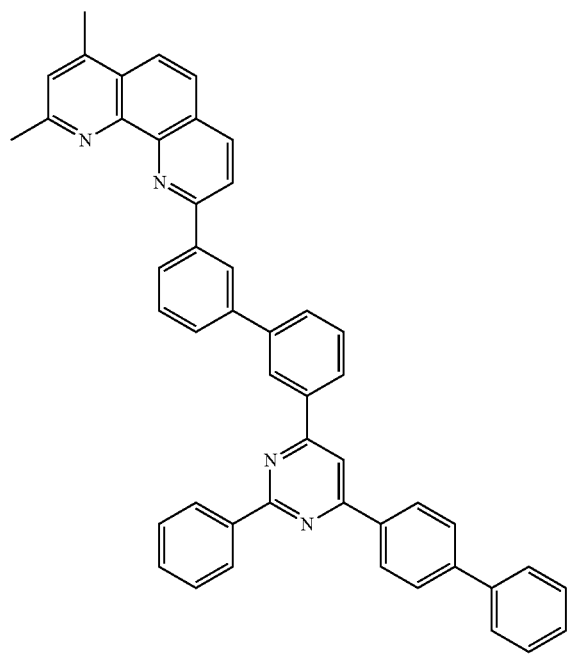
863
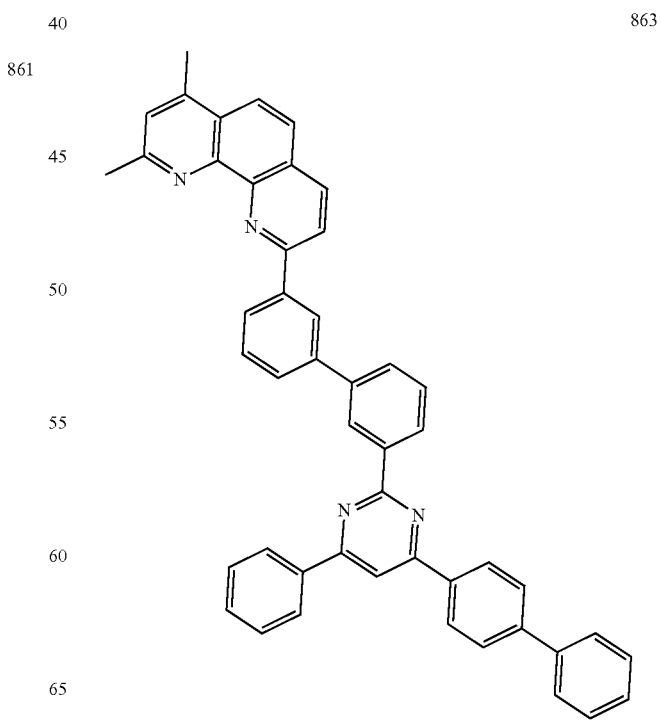

1079
-continued
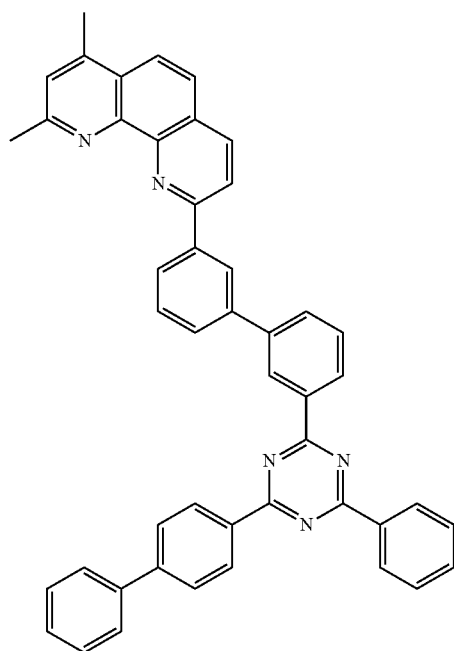
864
1080
-continued
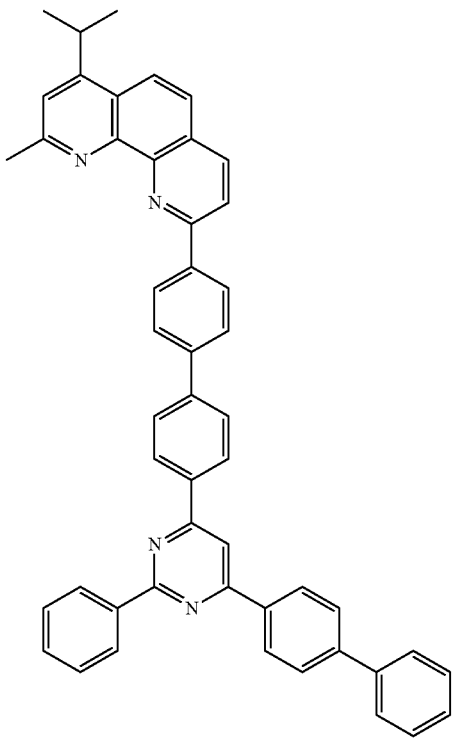
866
865
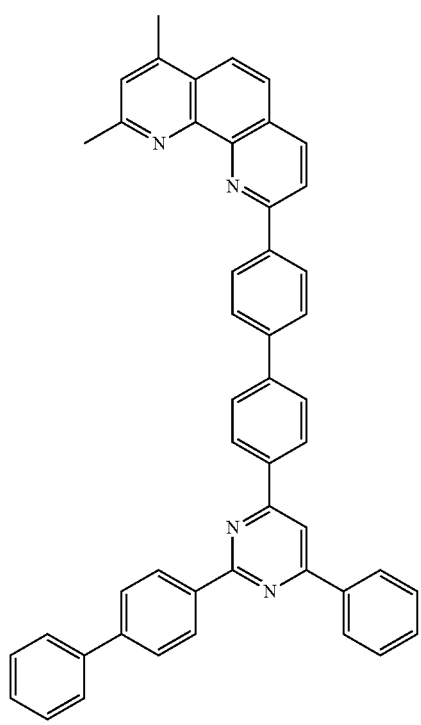
867
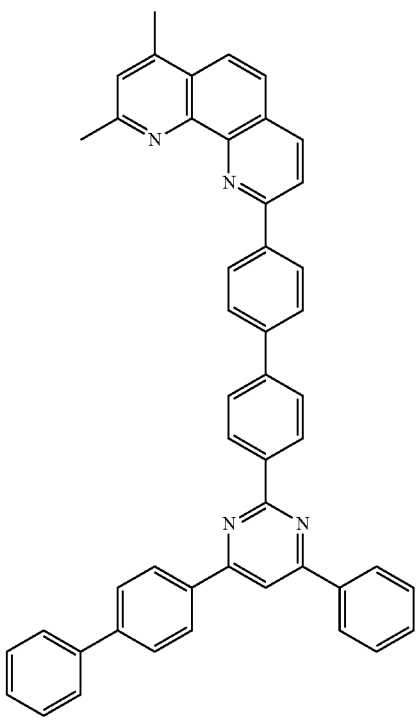

1081
-continued
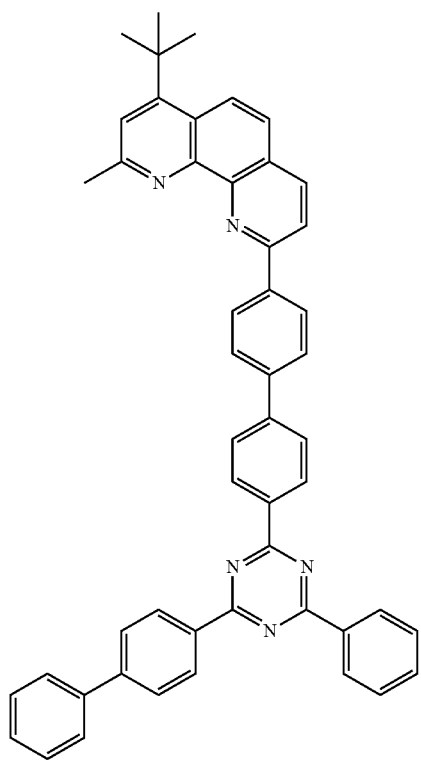
868
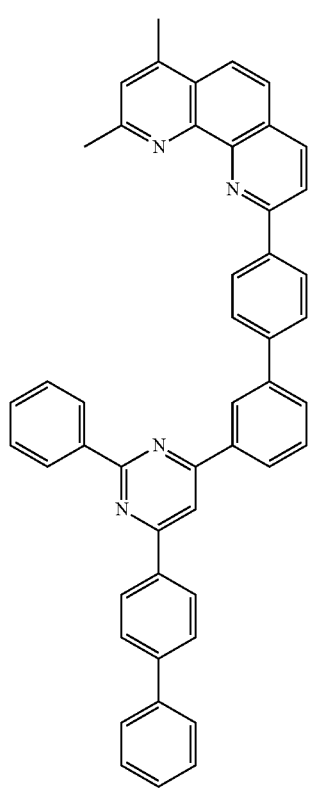
869
1082
-continued
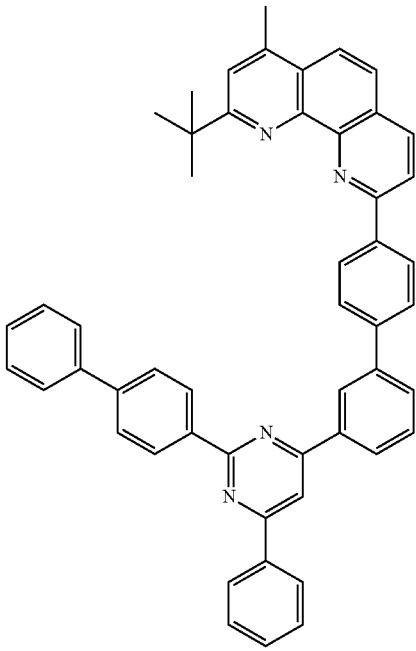
870
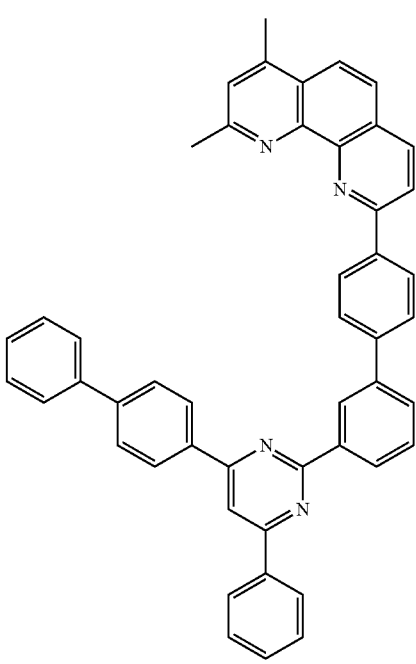
871

1083
-continued
872
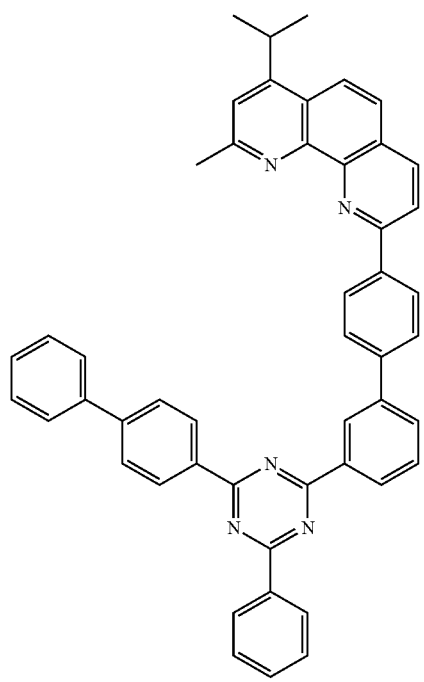
873
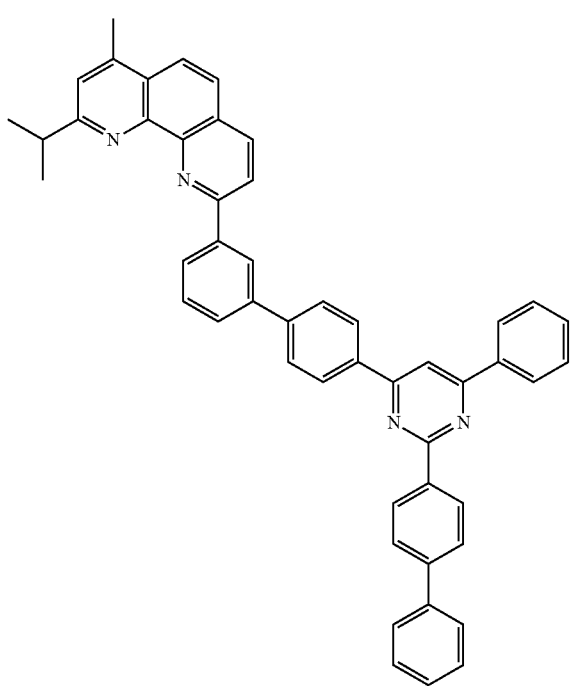
1084
-continued
874
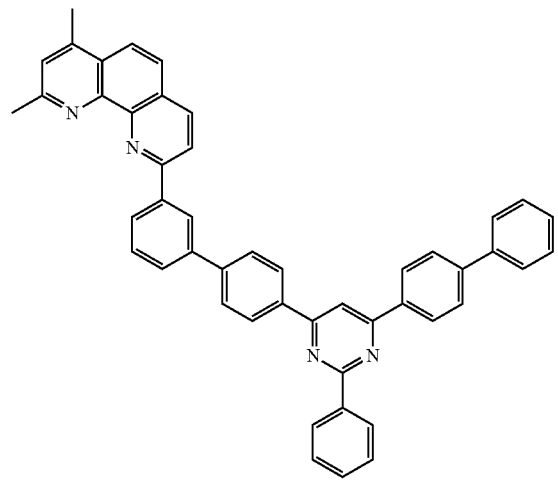
875
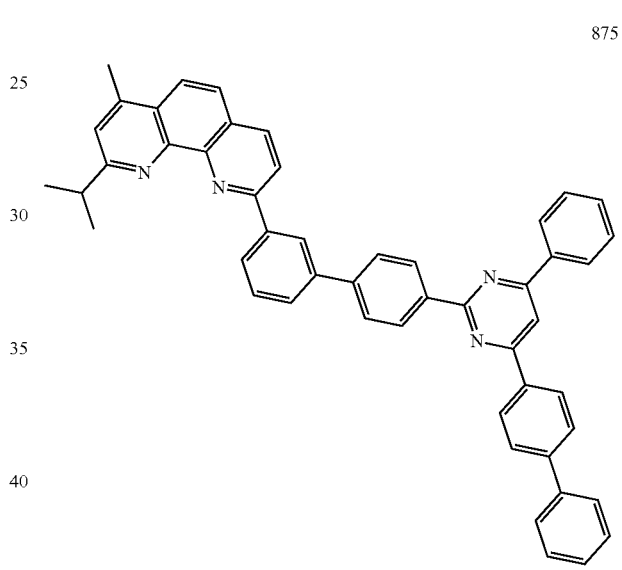
876
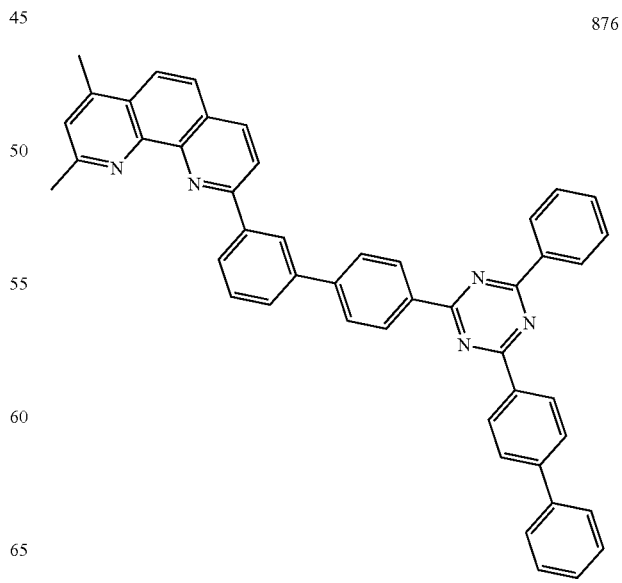

1085
-continued
877 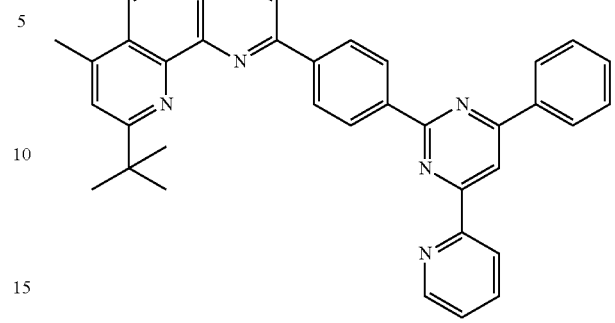
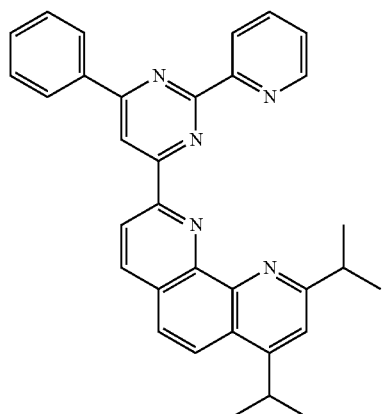
878 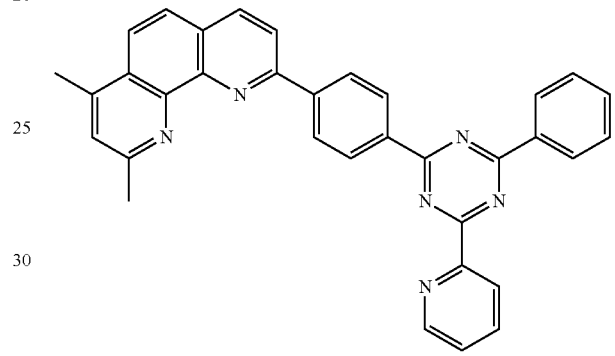
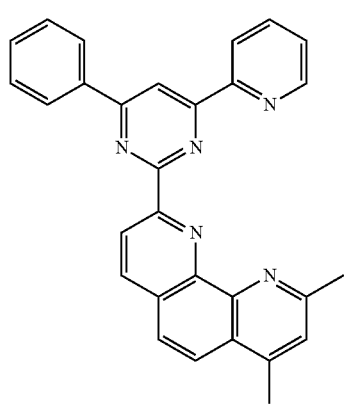
879 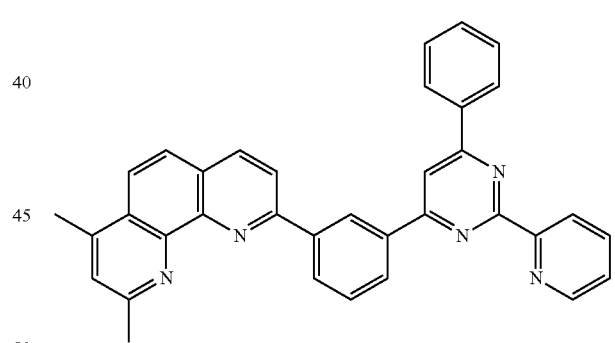
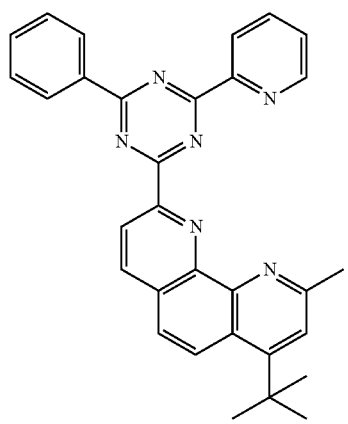
880 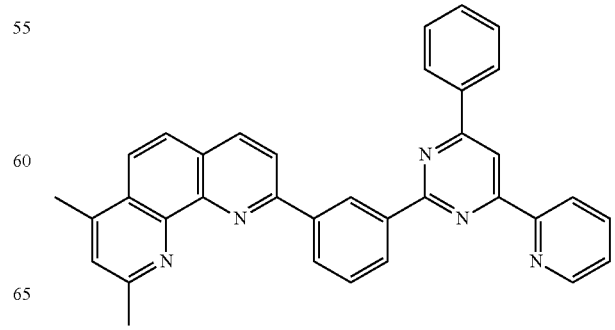
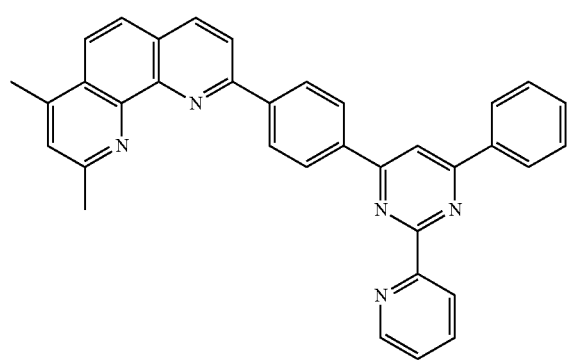
1086
-continued
881
882
883
884

885
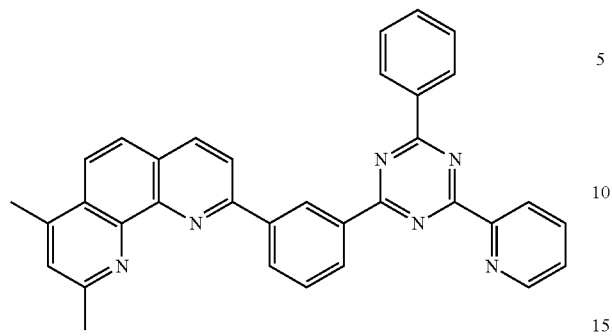
886 887
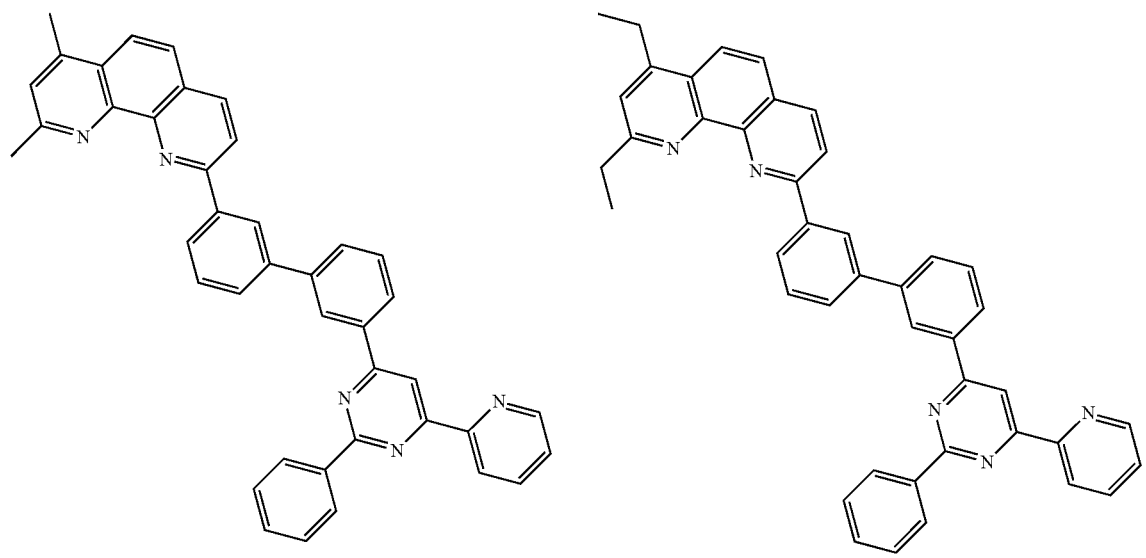
888 889
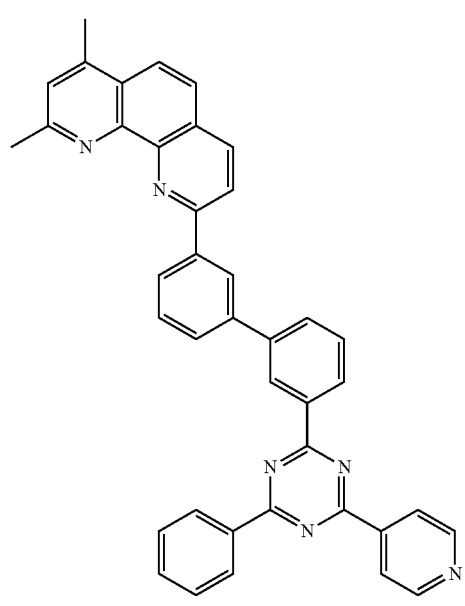
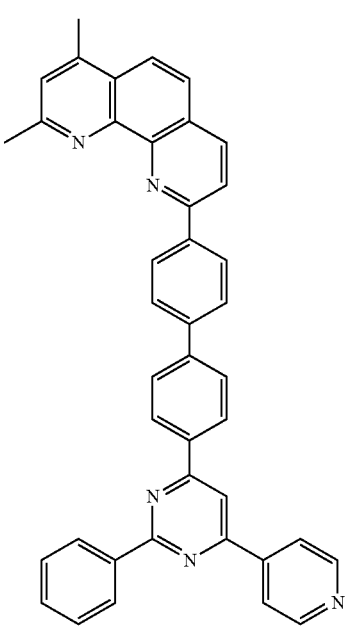

-continued
1089
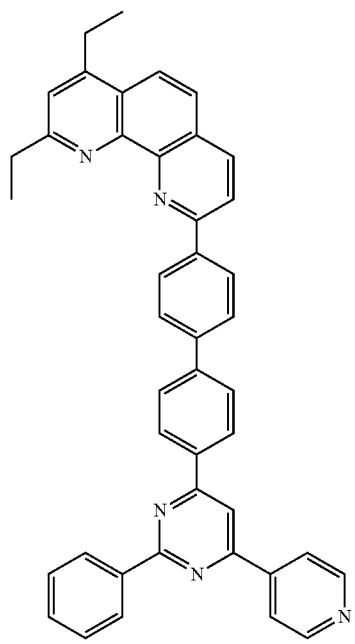
890
1090
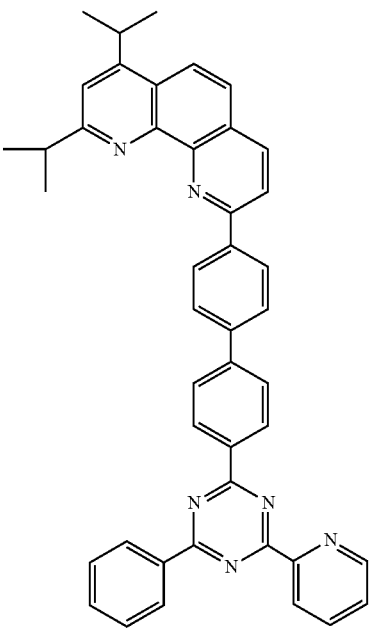
891
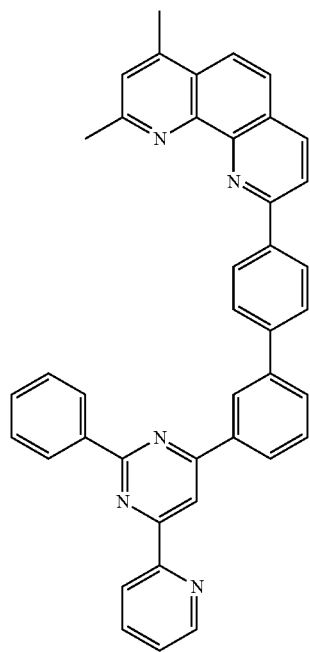
892
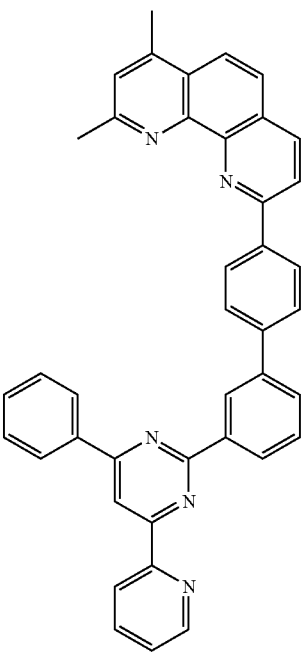
893

-continued
1091
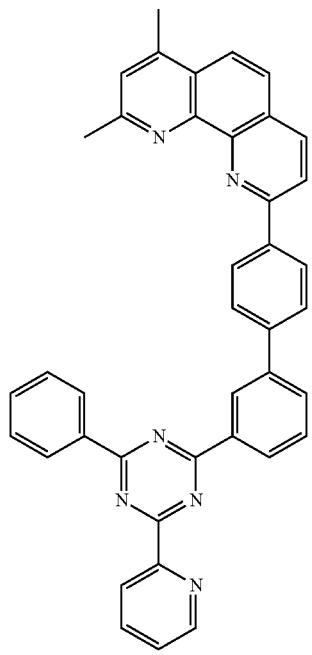
894
1092
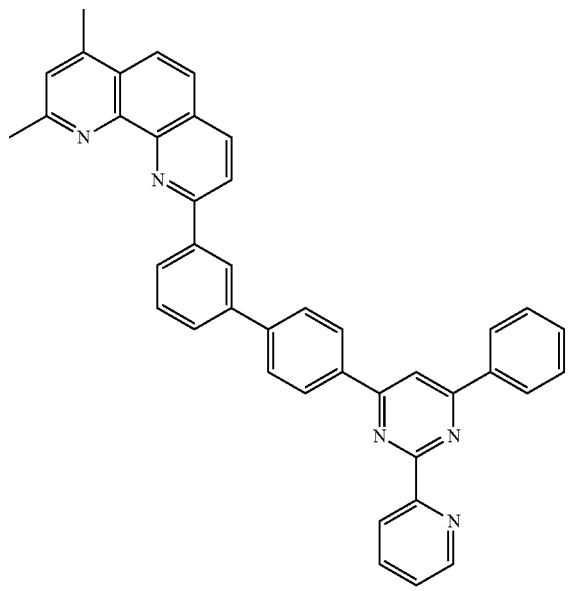
895
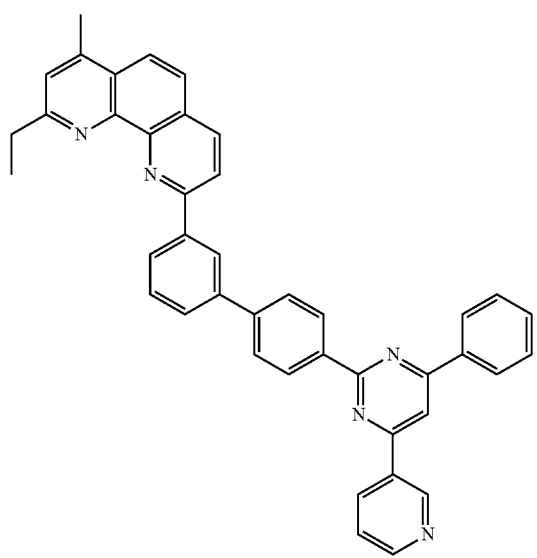
896
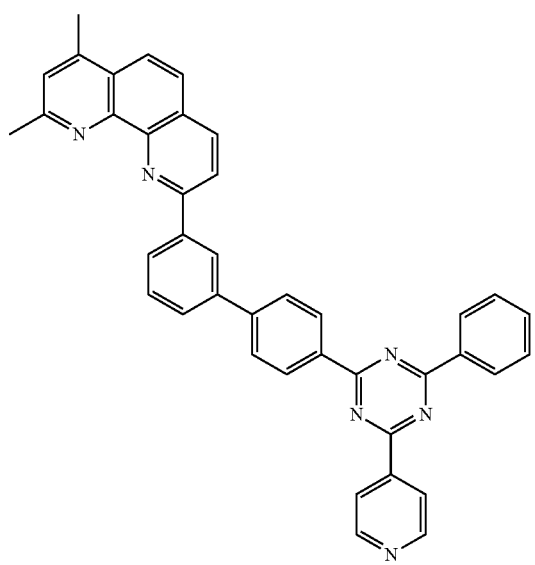
897

1093                                       1094
-continued
898 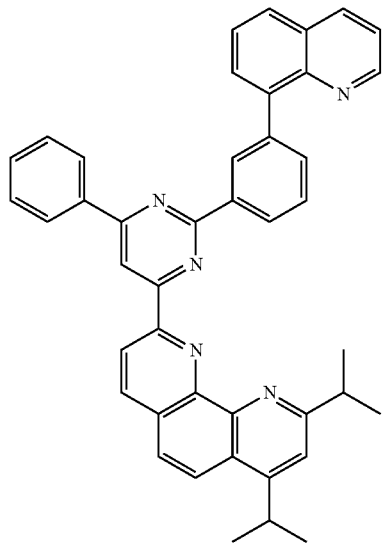
900 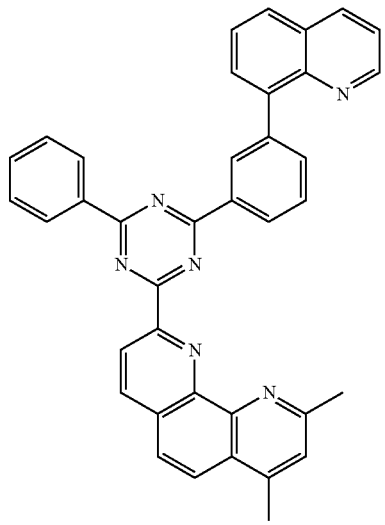
901 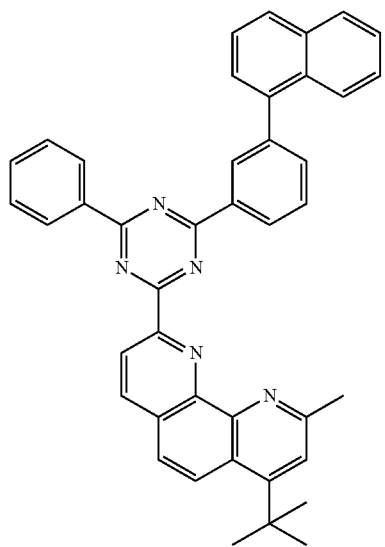
902 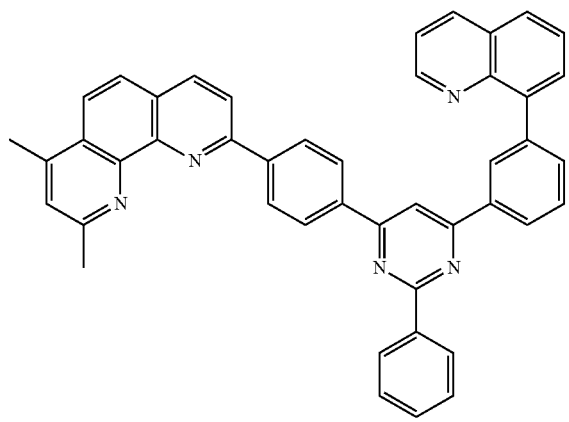
902 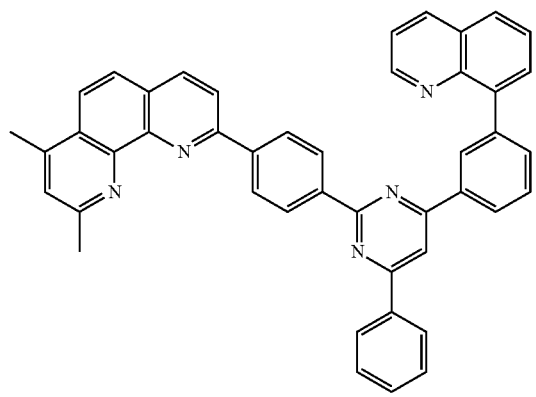
903 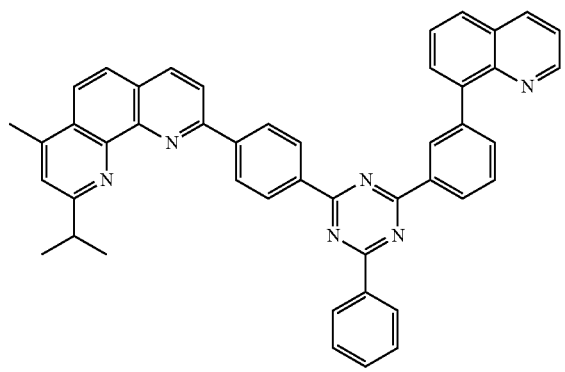

904
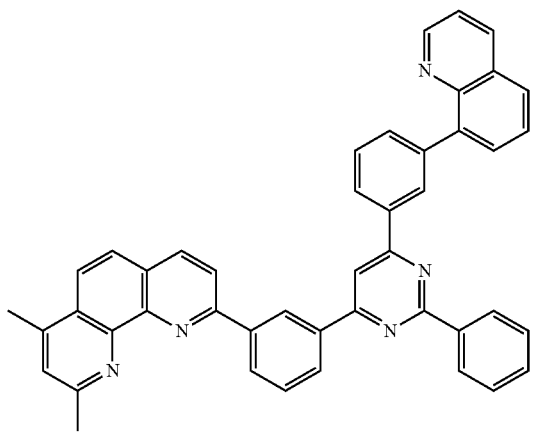
905
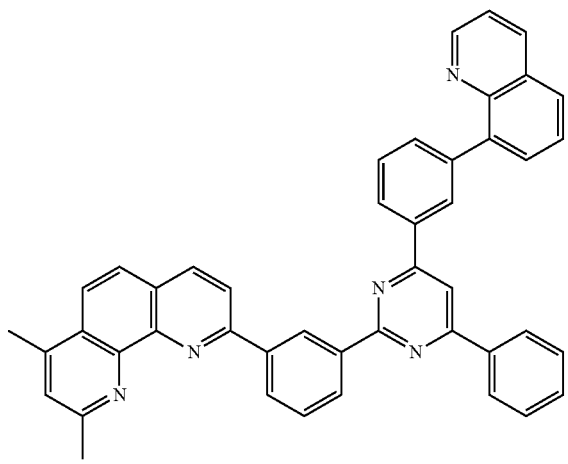
906
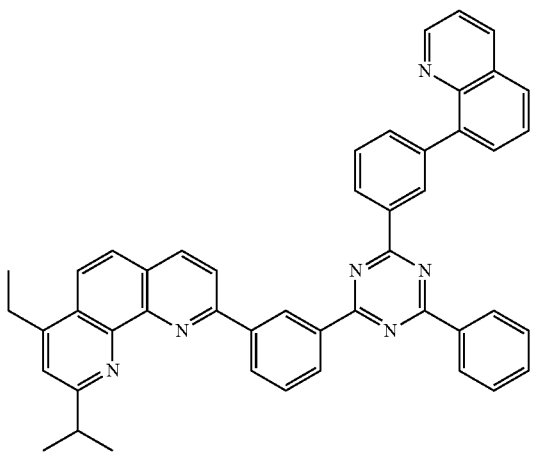
907
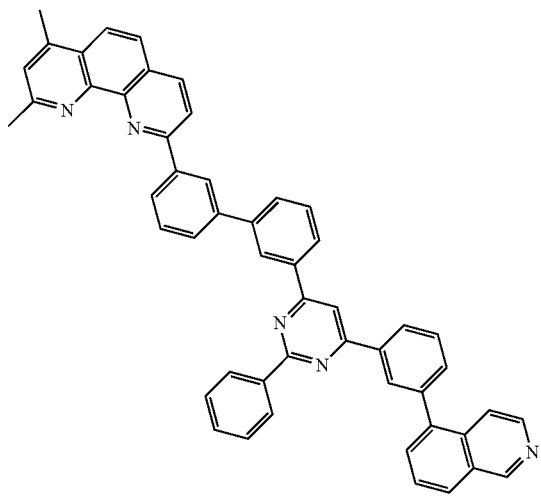
908
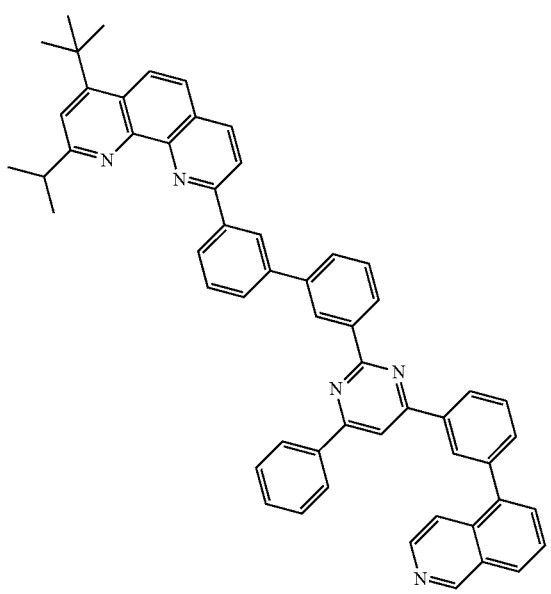
909
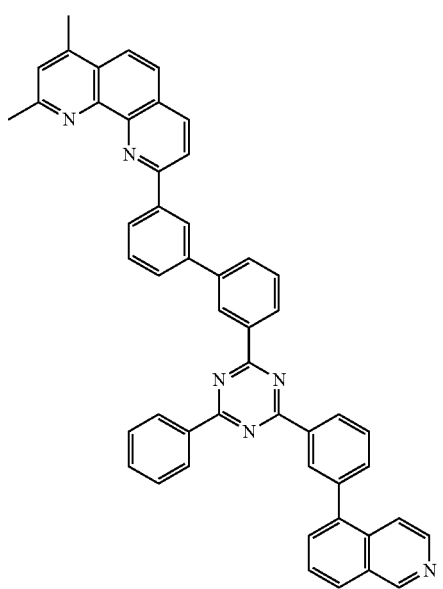

-continued
1097
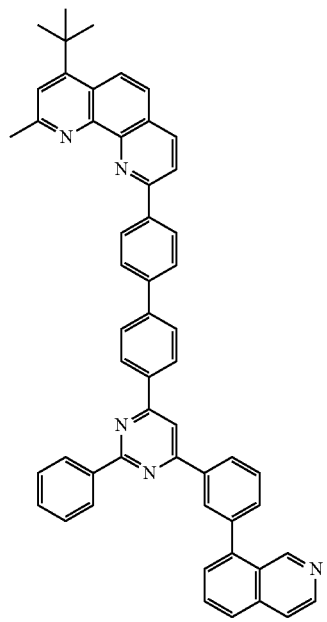
1098
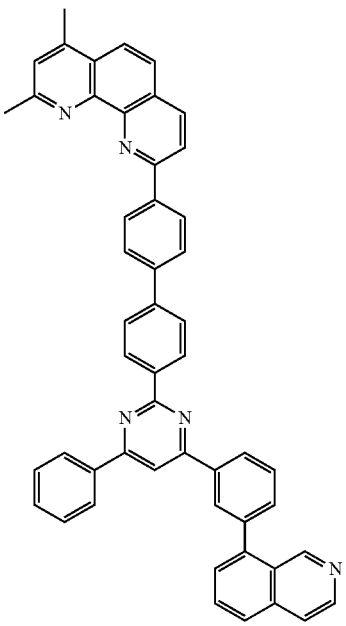
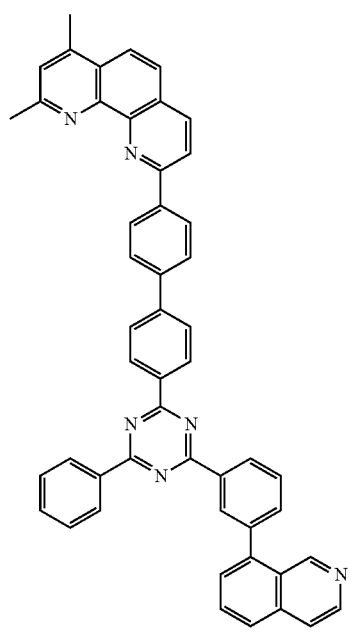

-continued
1099
914
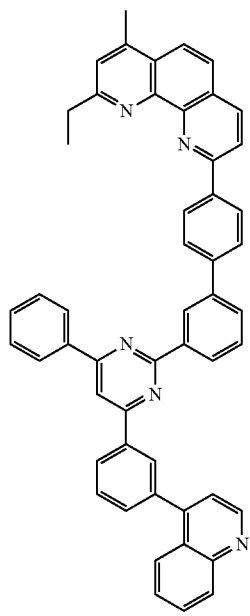
1100
915
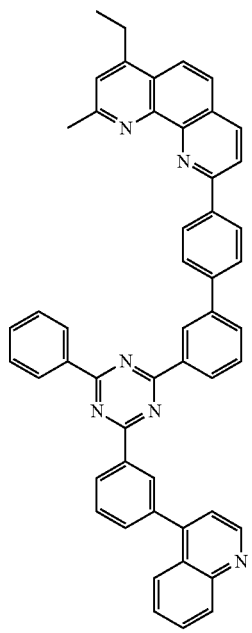
916
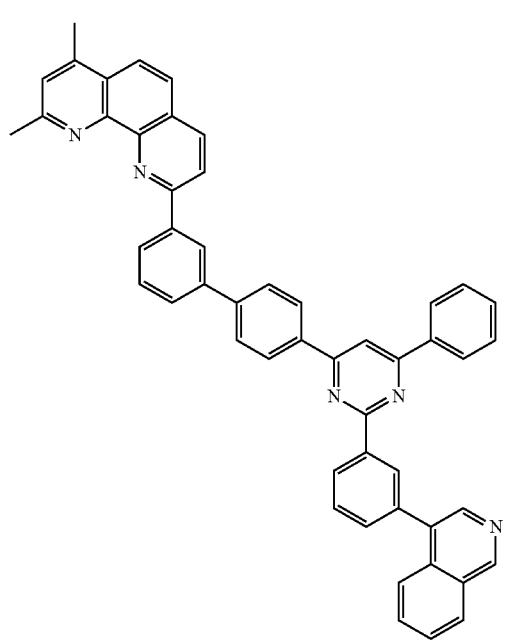
917
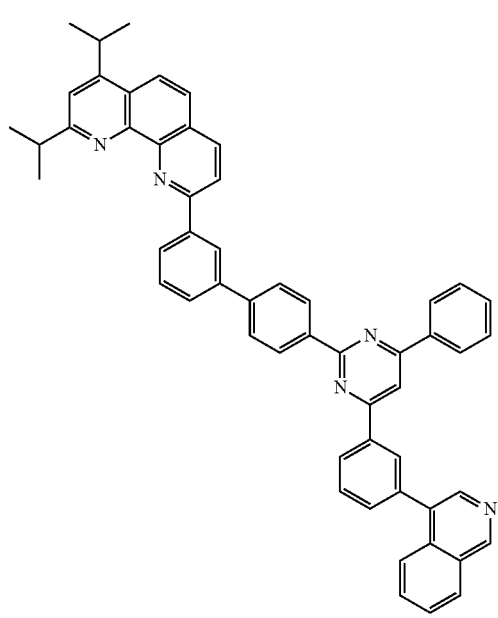

1101    -continued    1102
918
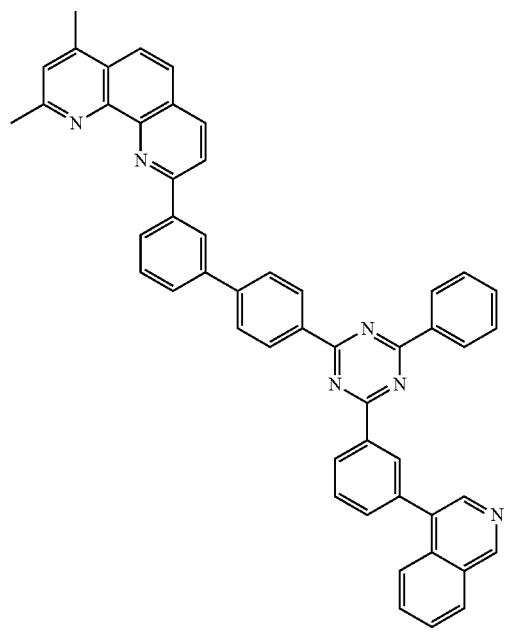
919
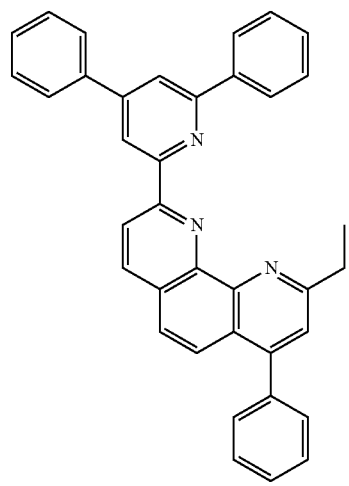
920
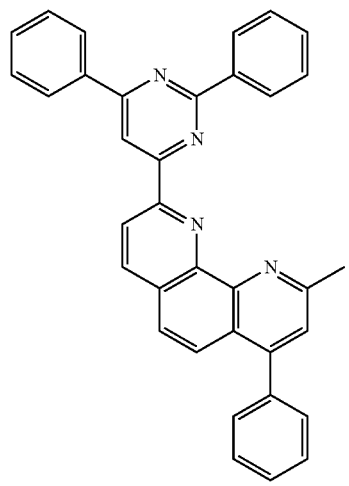
921
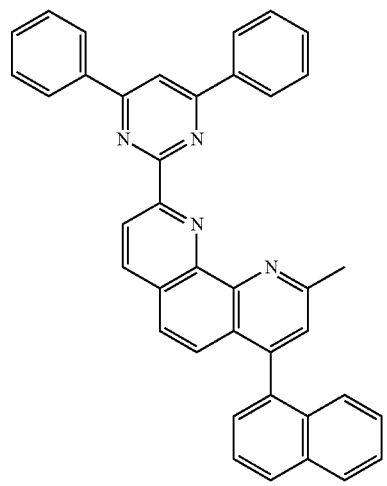
922
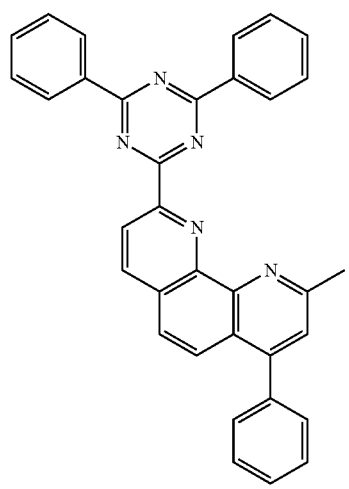
923
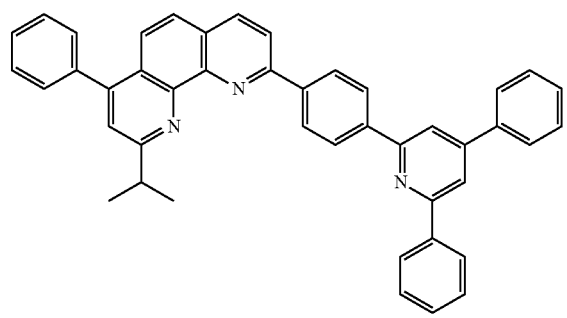

-continued
924
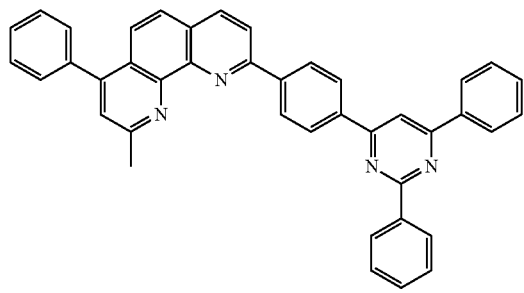
925
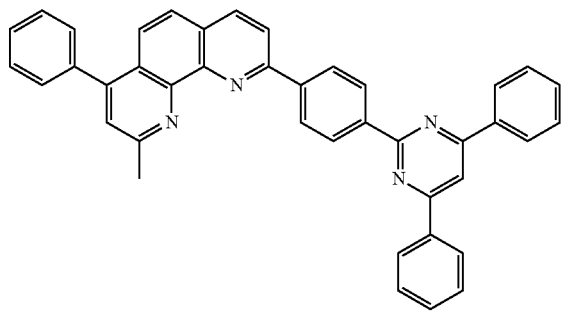
926
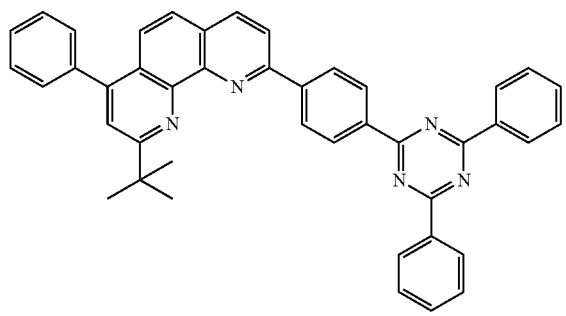
927
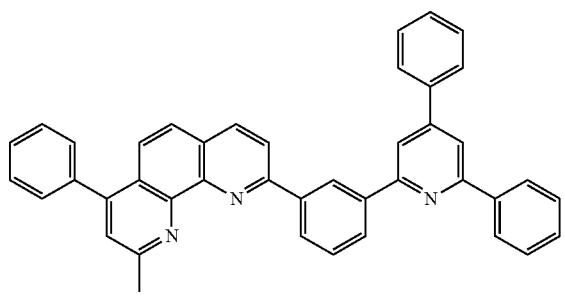
928
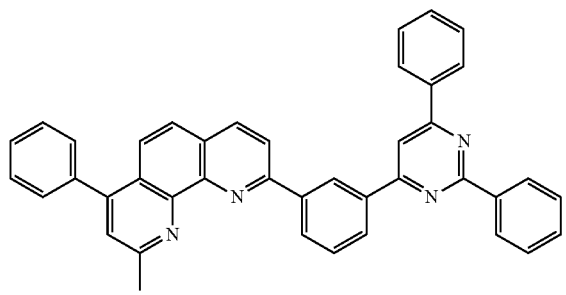
929
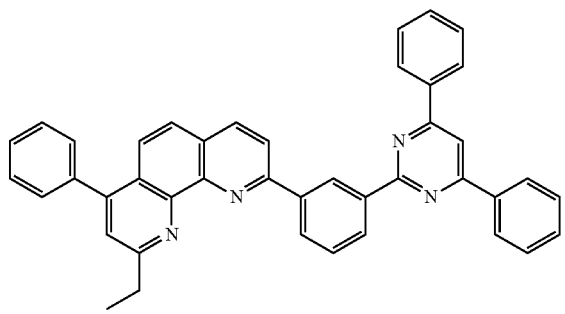
930
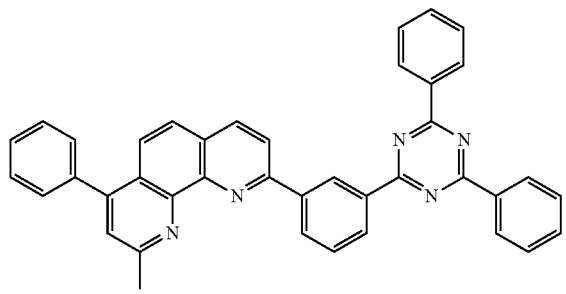
931
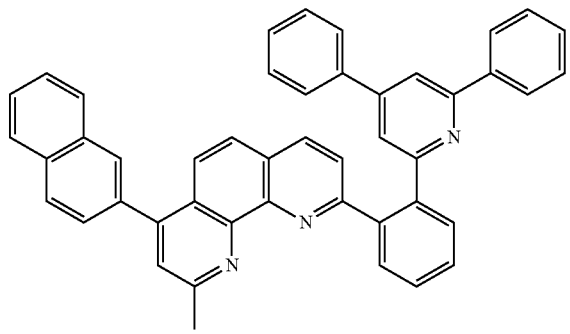

-continued
| 932 | 933 |
|---|---|
| 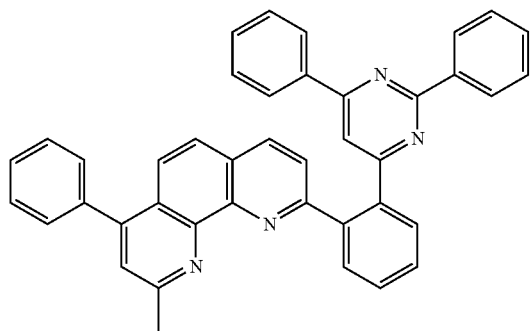 | 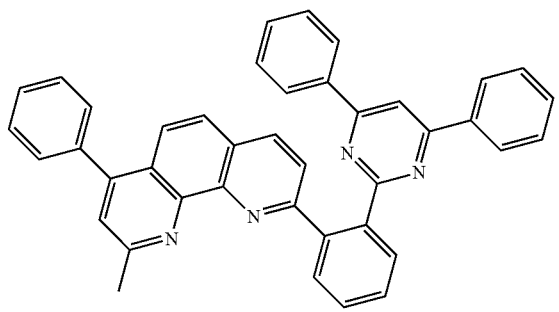 |
| 934 | 935 |
| 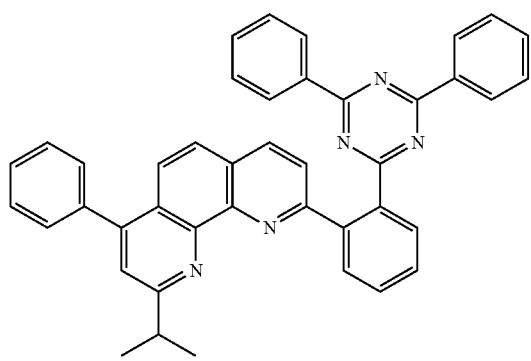 | 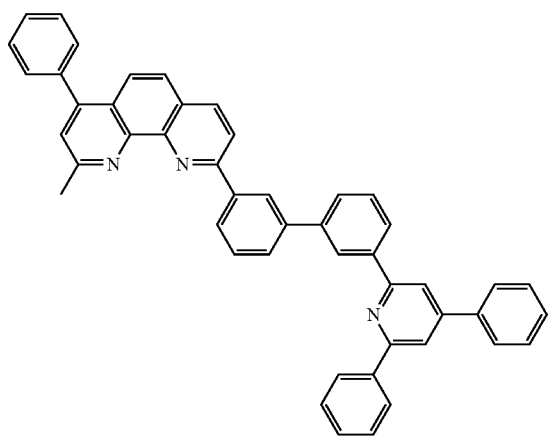 |
| 936 | 937 |
| 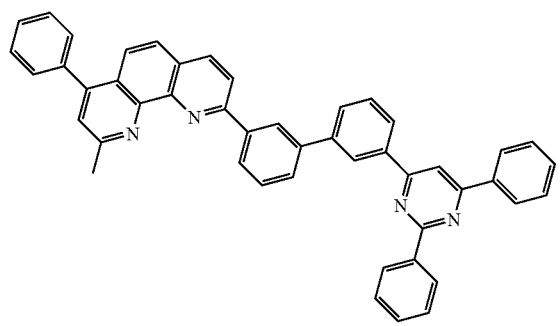 | 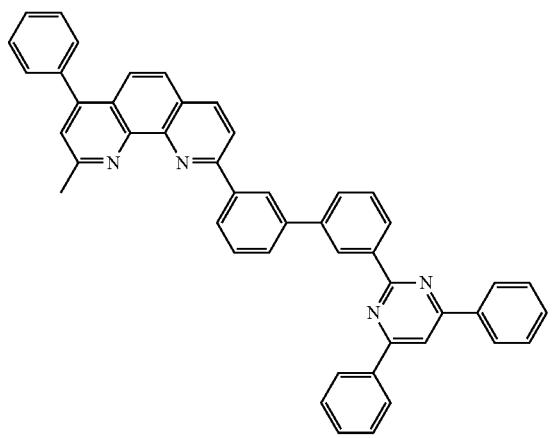 |

-continued
938
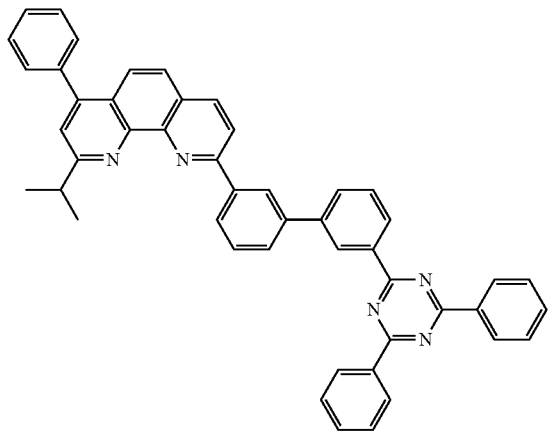
939
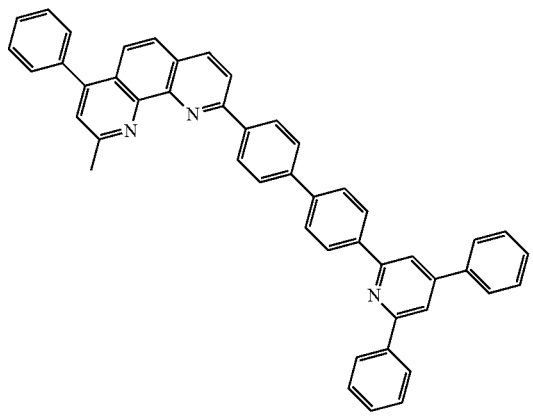
940
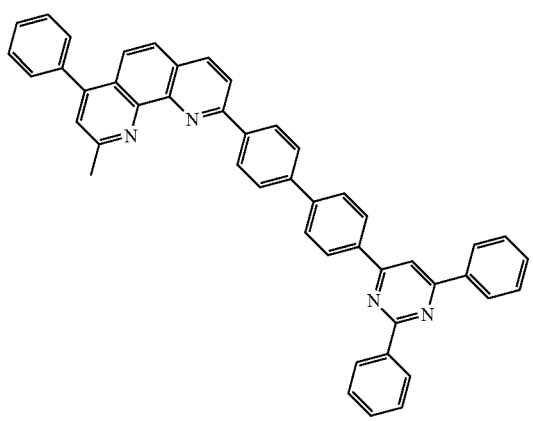
941
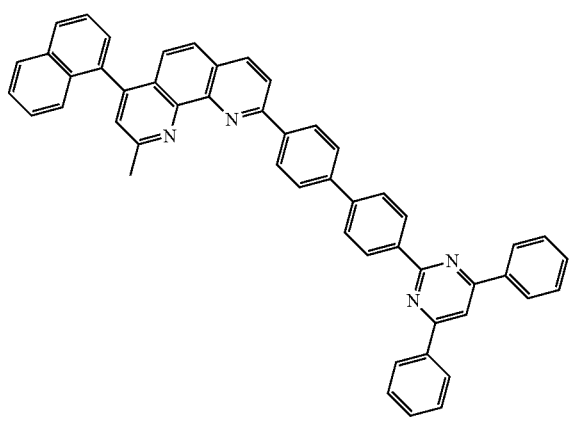
942
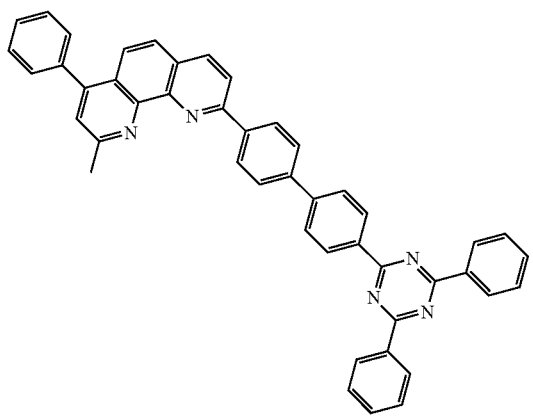
943
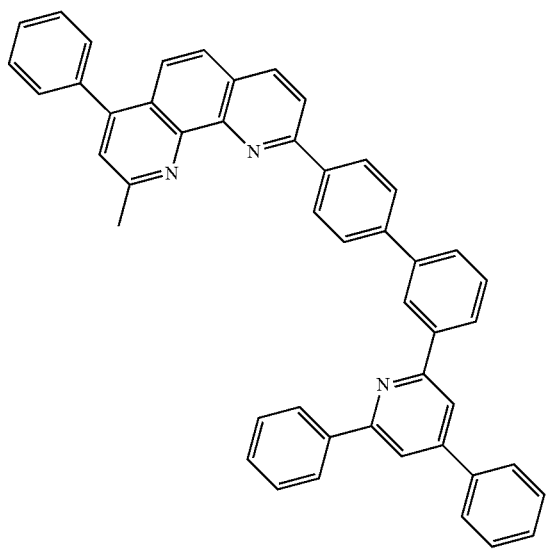

-continued
1109
944
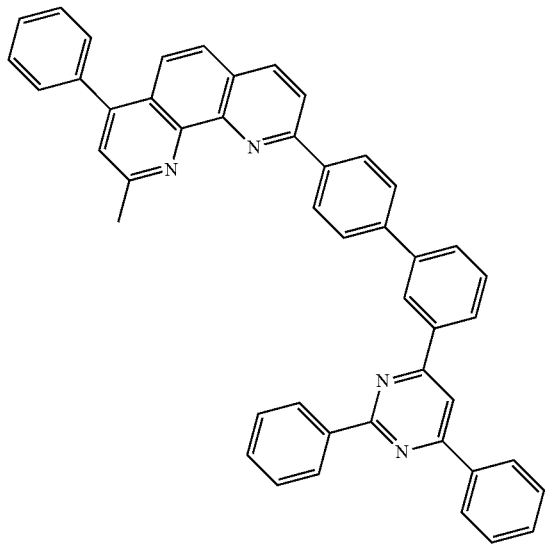
1110
945
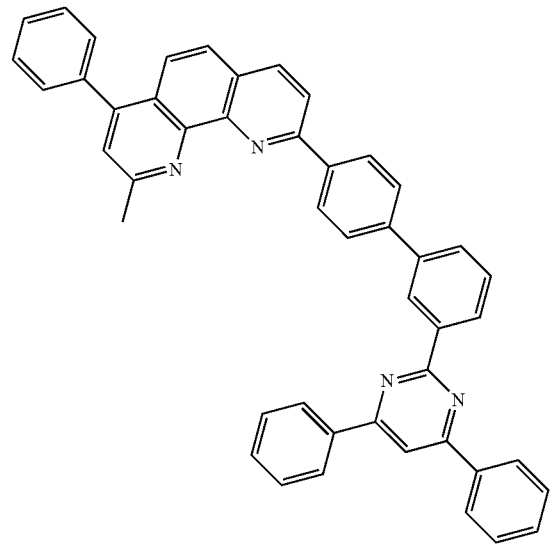
946
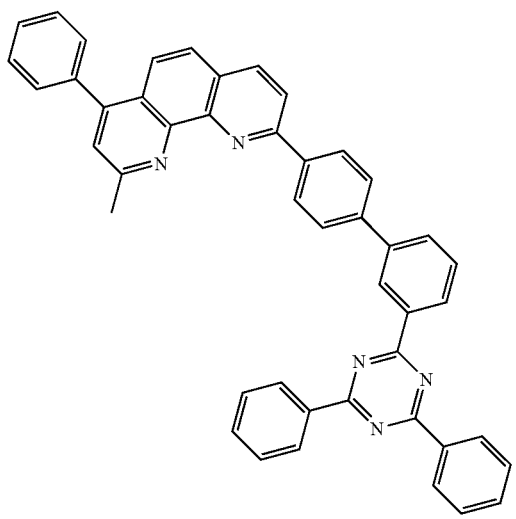
947
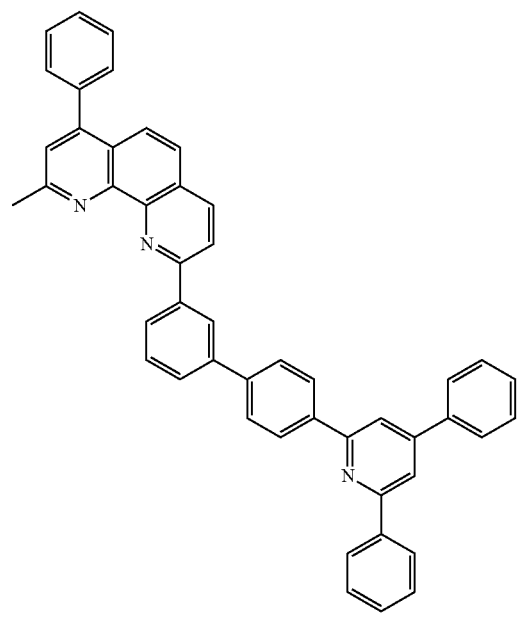

1111 948
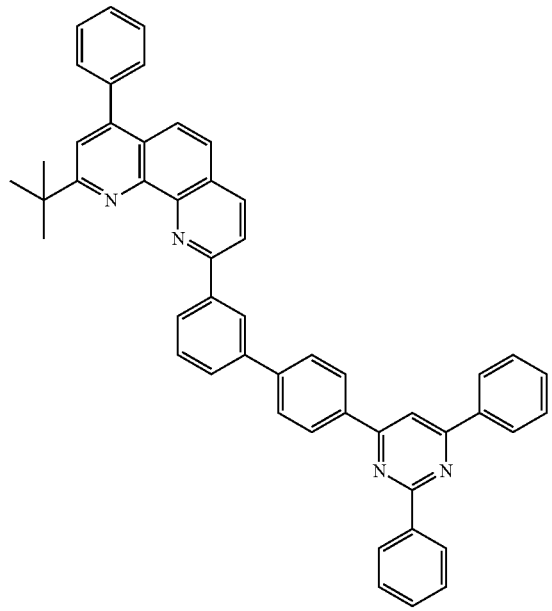
1112 949
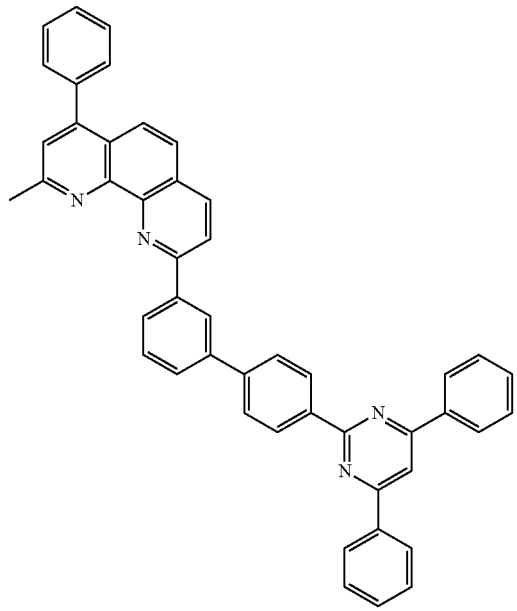
950
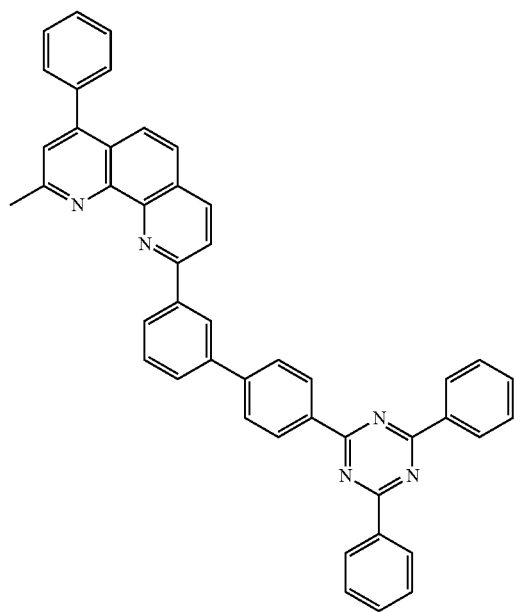
951
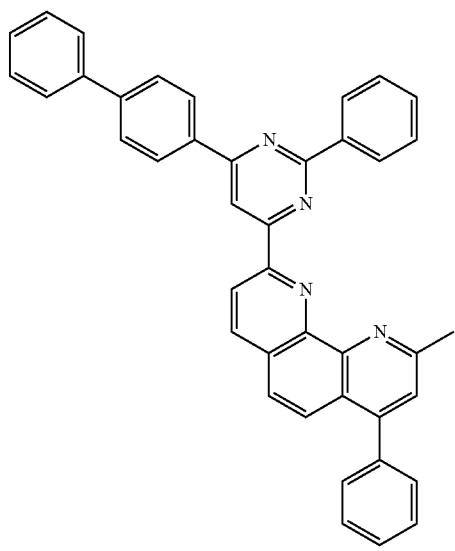

1113 1114
-continued
952 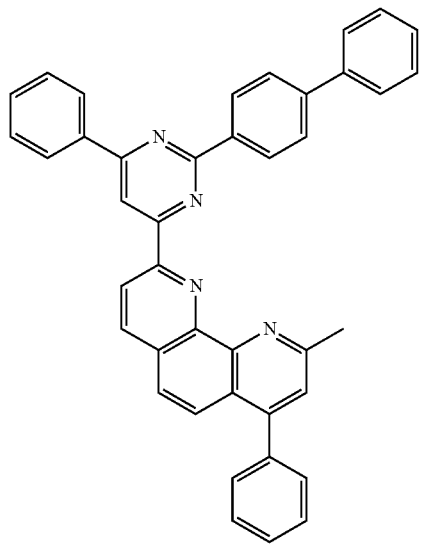
953 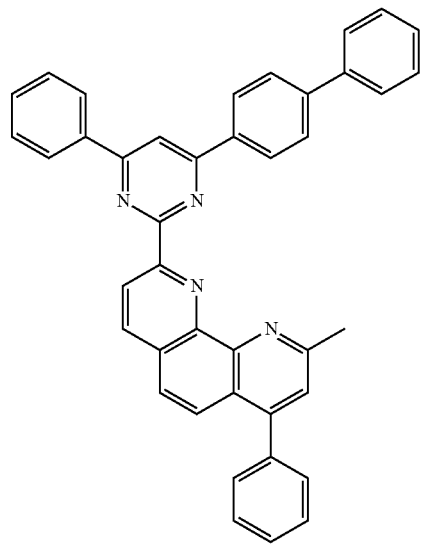
954 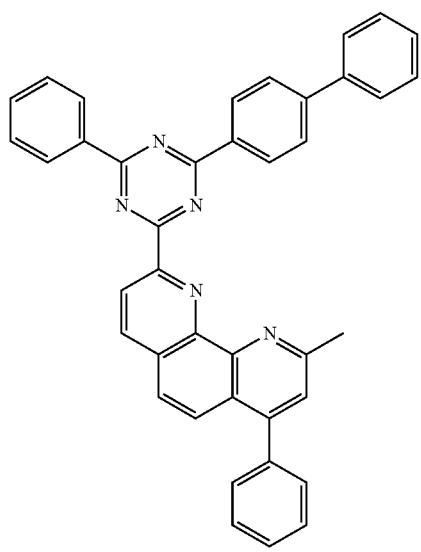
955 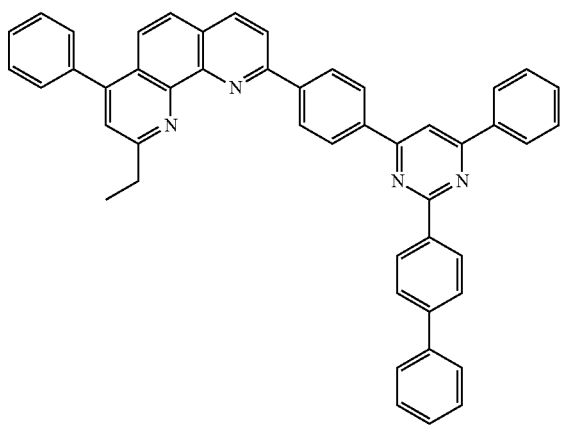
956 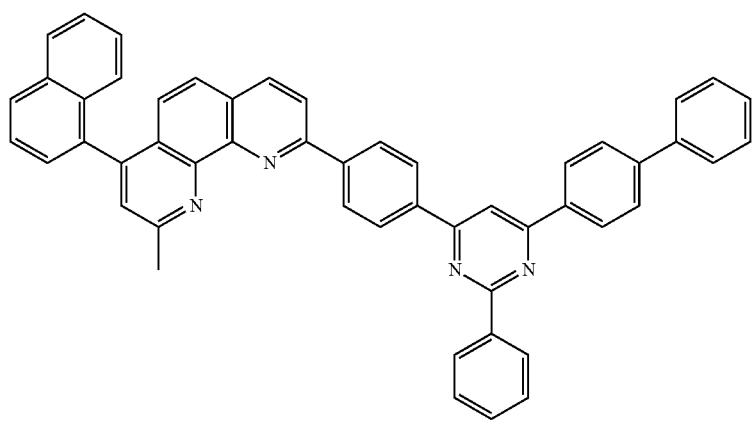

-continued
1115
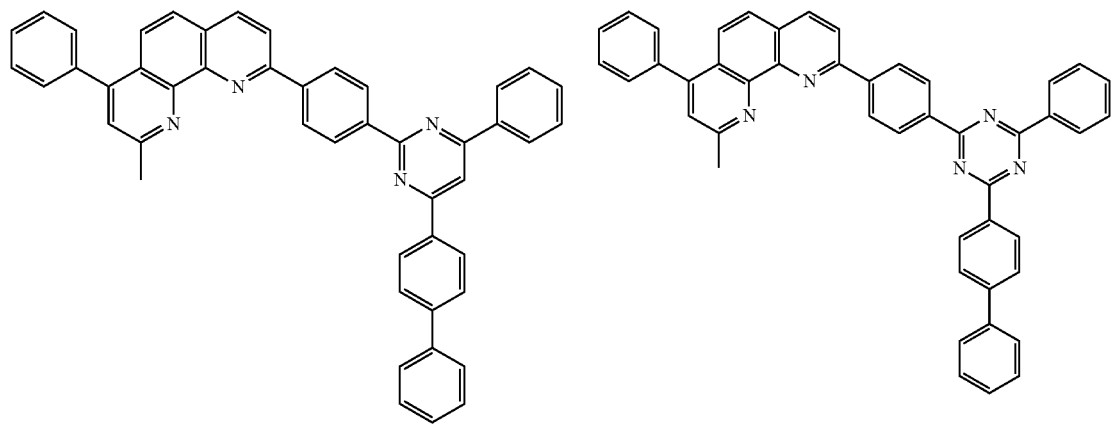
1116
957 958
959
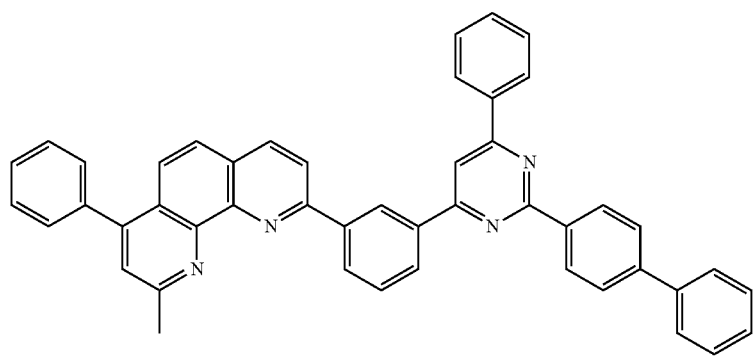
960
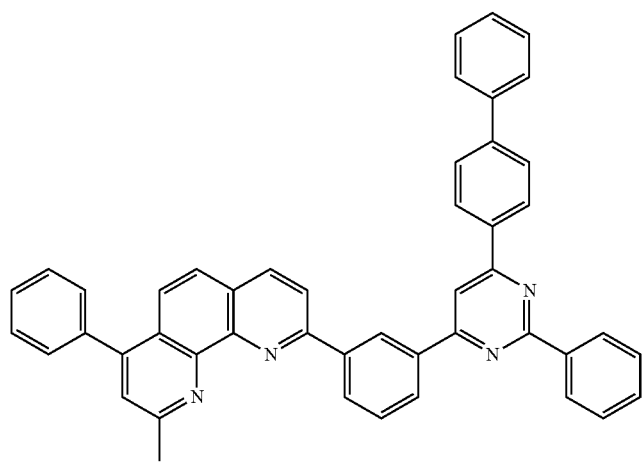

961
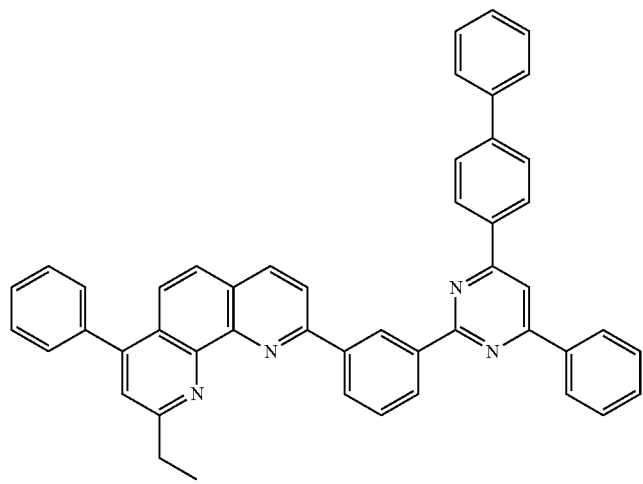
962
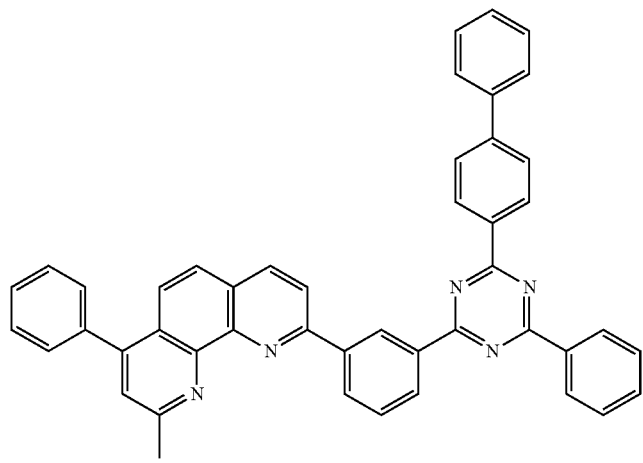
963
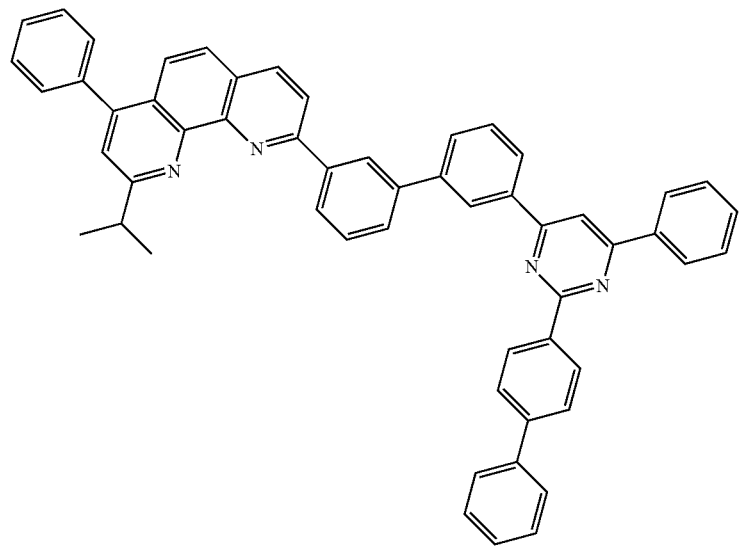

-continued
964
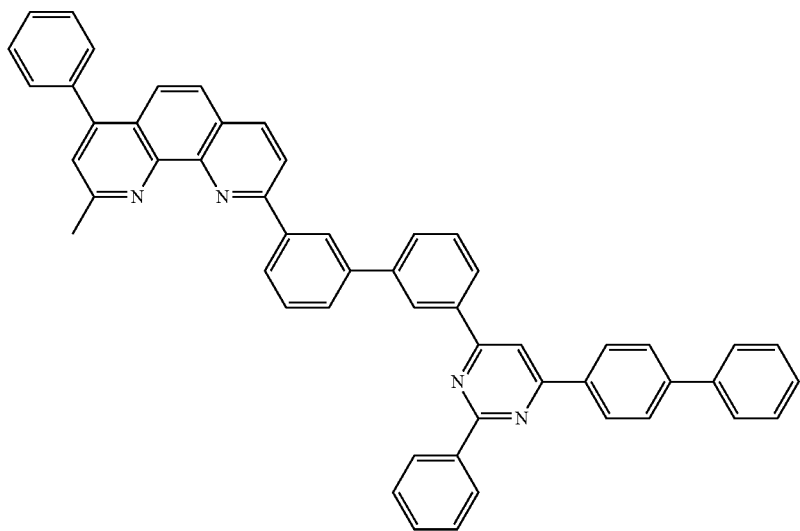
965
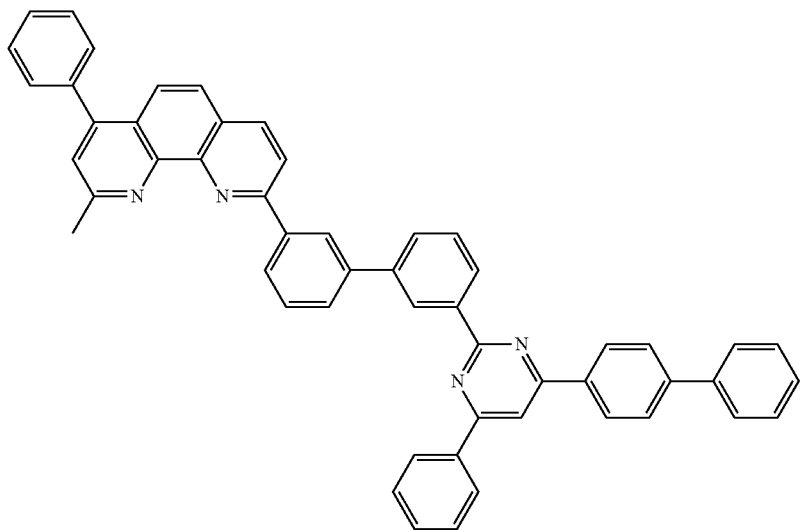
966
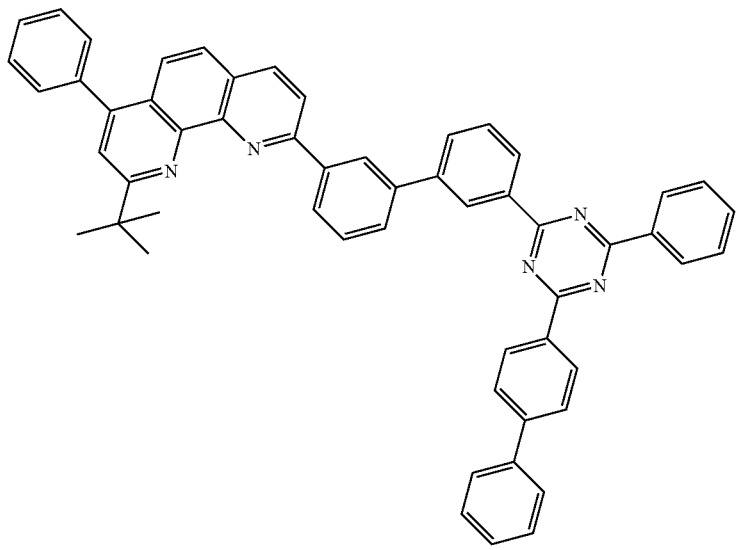

-continued
967
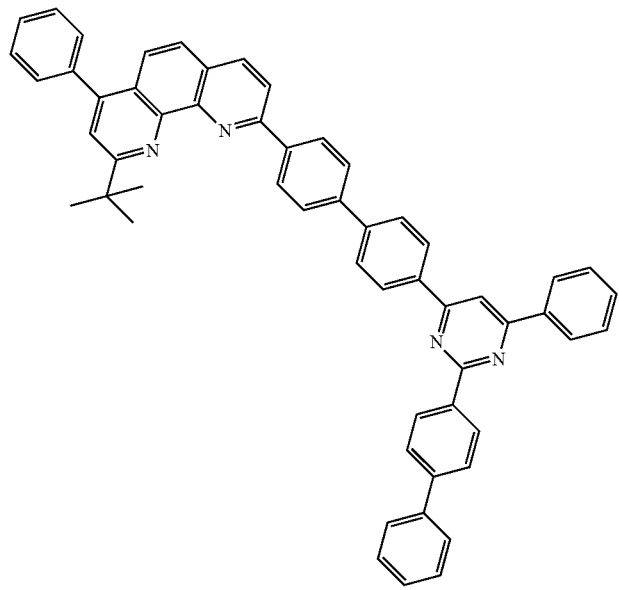
968
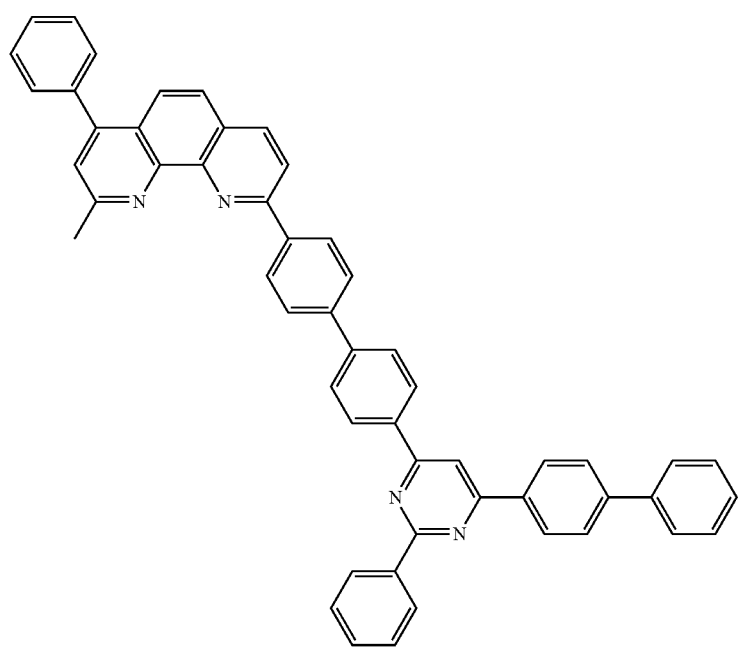

-continued
969
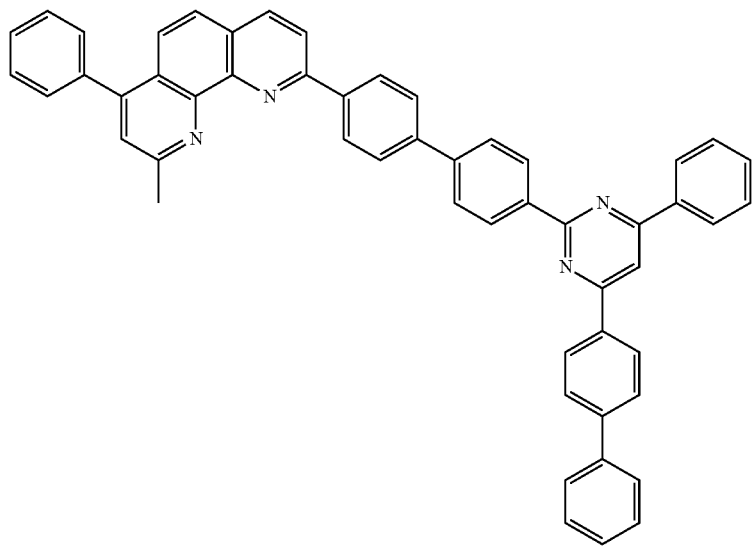
970
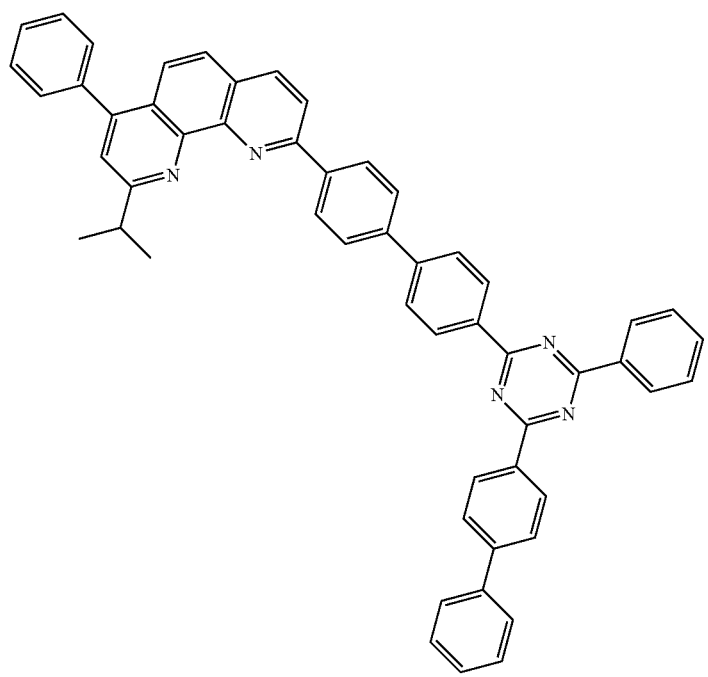
971
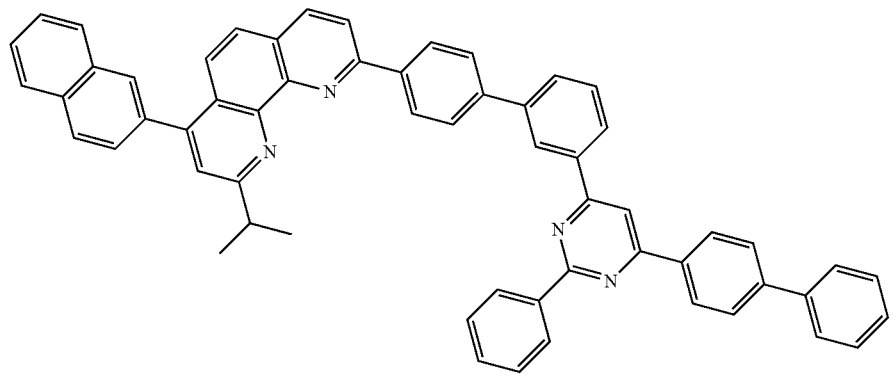

1125 1126
-continued
972
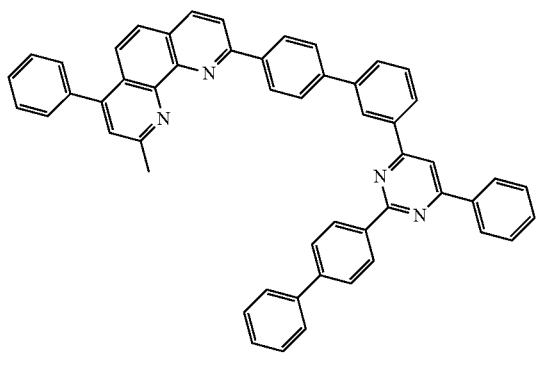
973
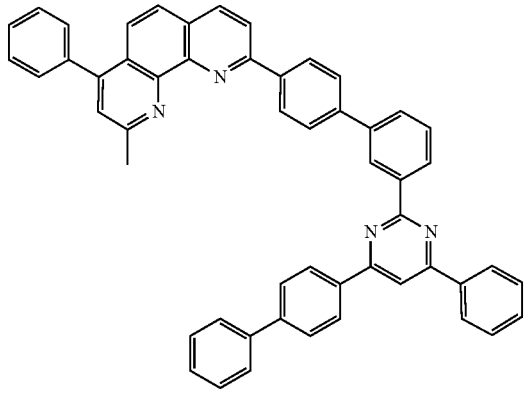
974
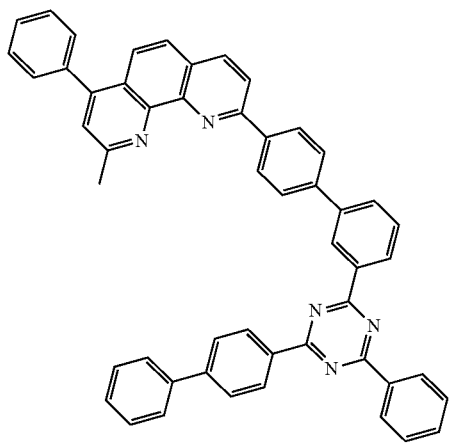
975
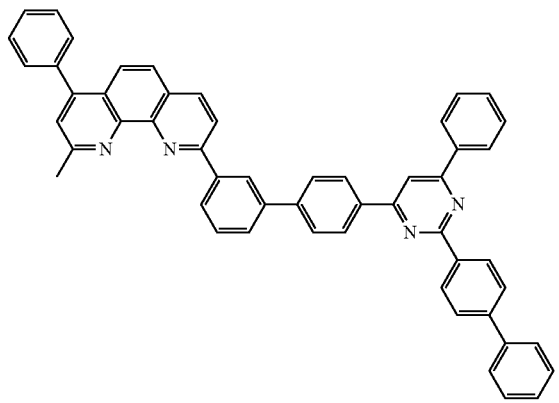
976
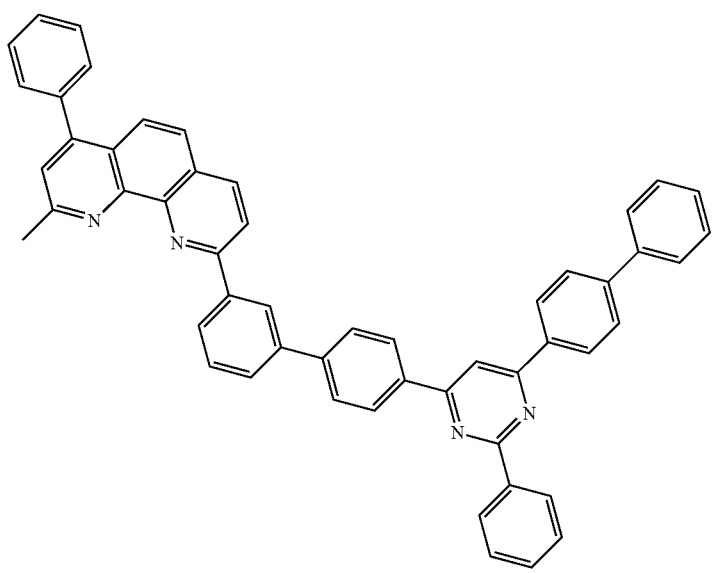

1127 -continued 1128
977
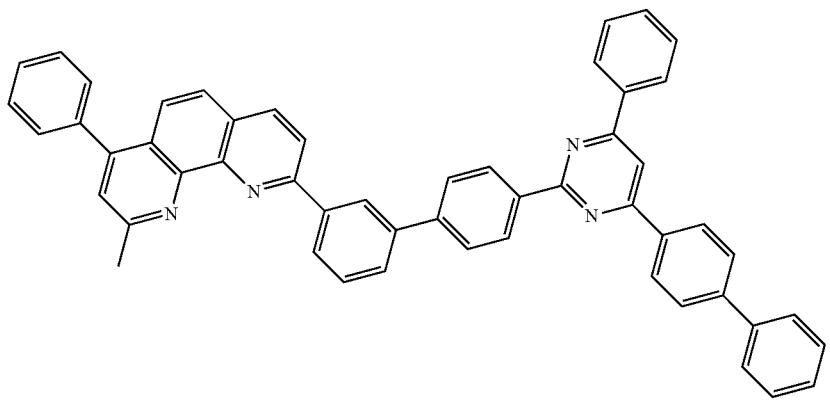
978
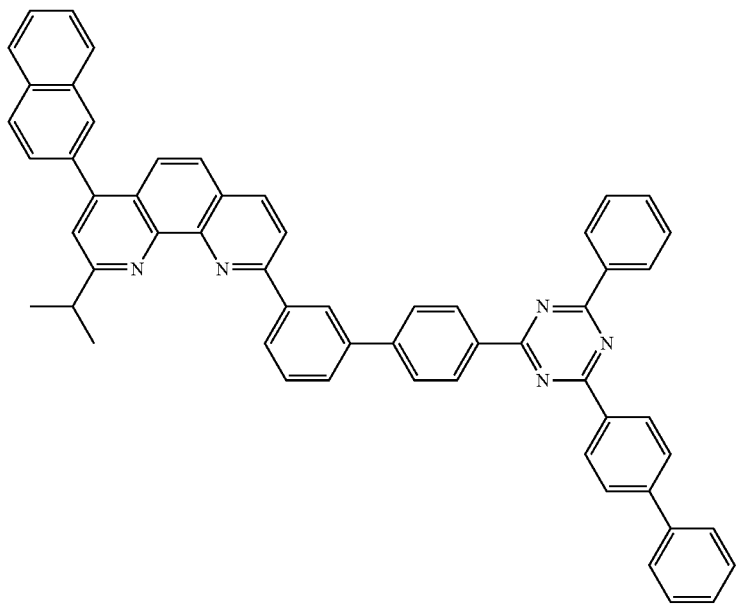
979
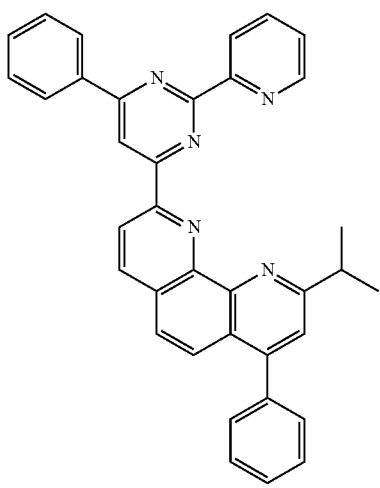
980
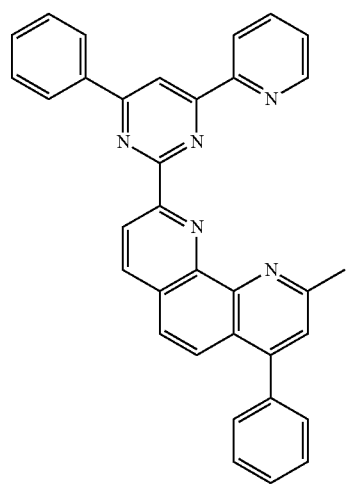

| 1129 | 1130 |
|---|---|
| 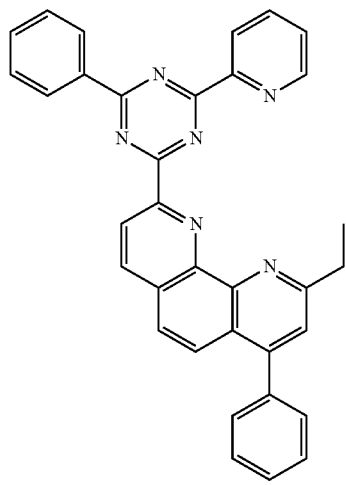 | 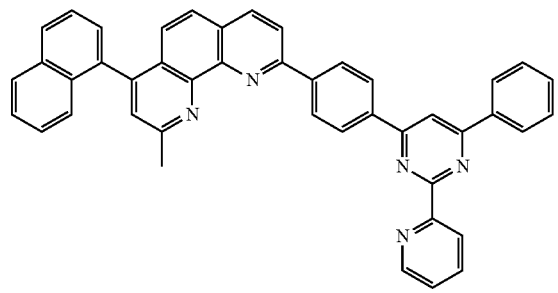 |
| 981 | 982 |
| 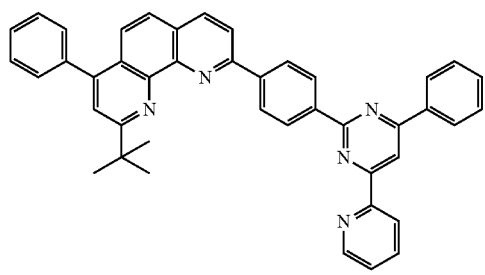 | 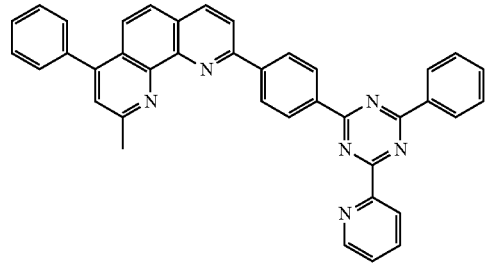 |
| 983 | 984 |
| 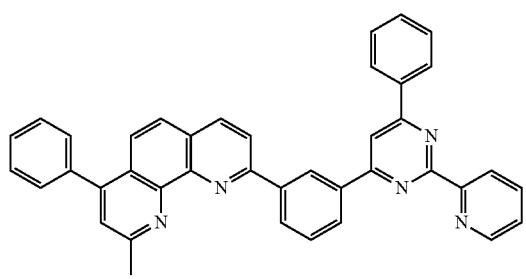 | 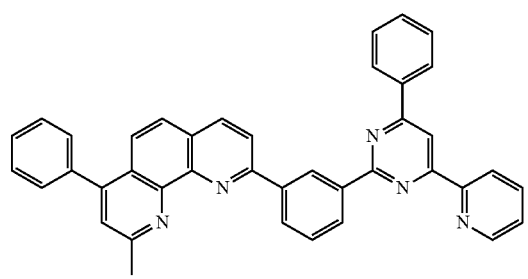 |
| 985 | 986 |

1131 1132
987 988
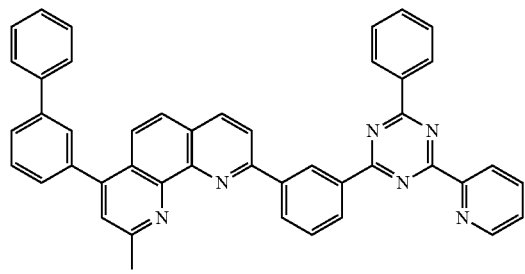
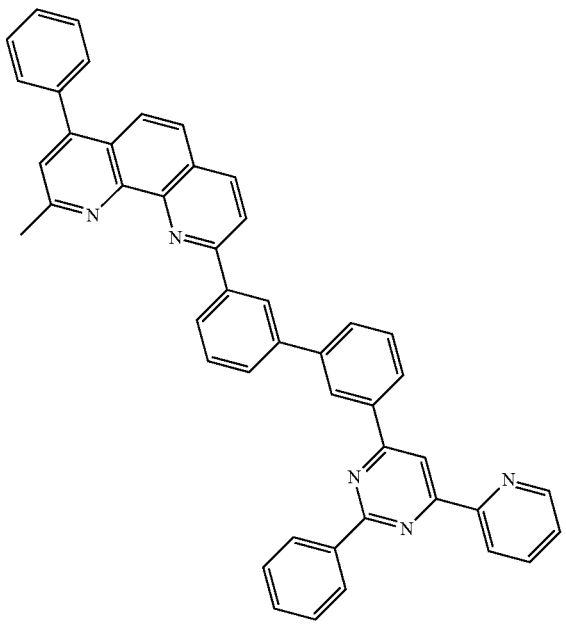
989 990
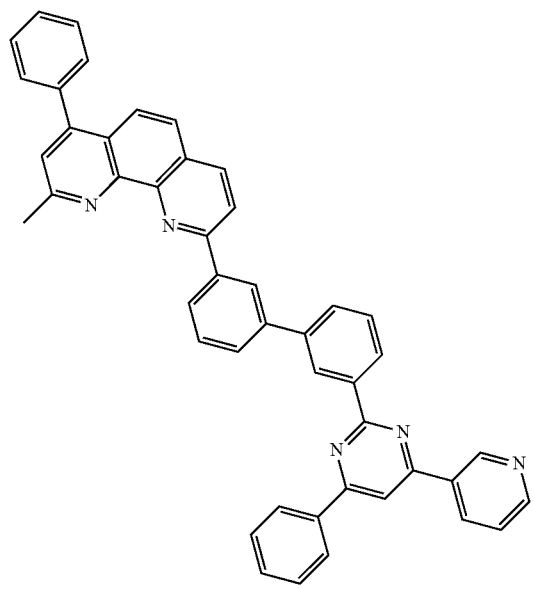
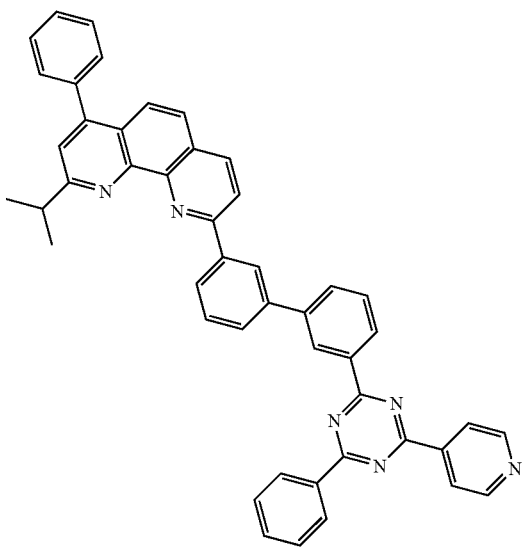

-continued
991
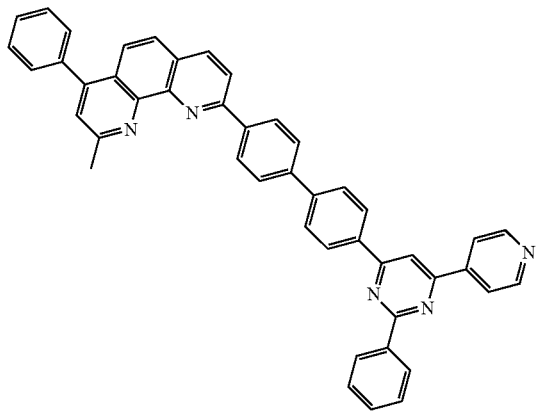
992
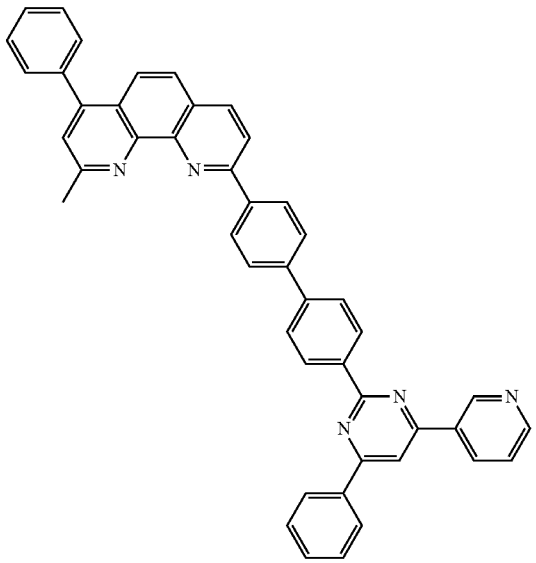
993
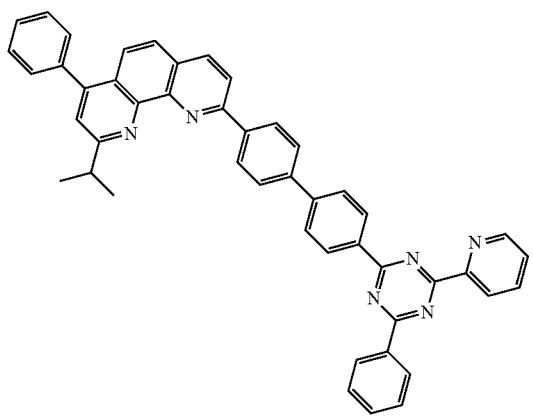
994
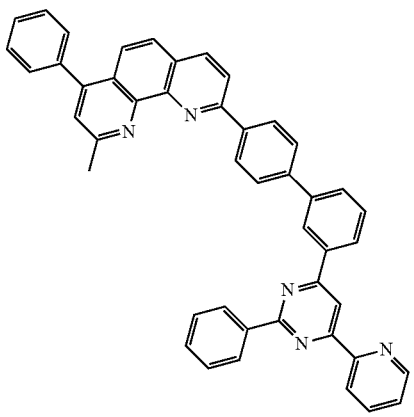
995
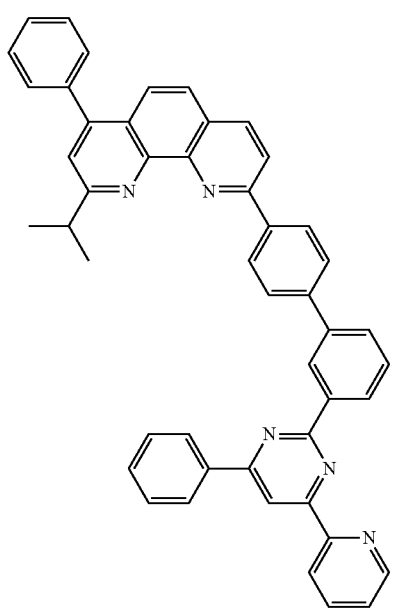
996
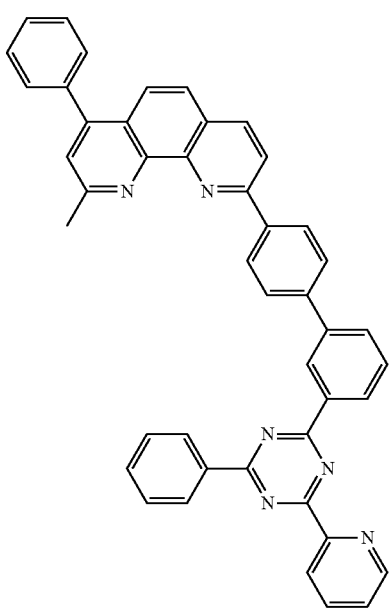

1135
997
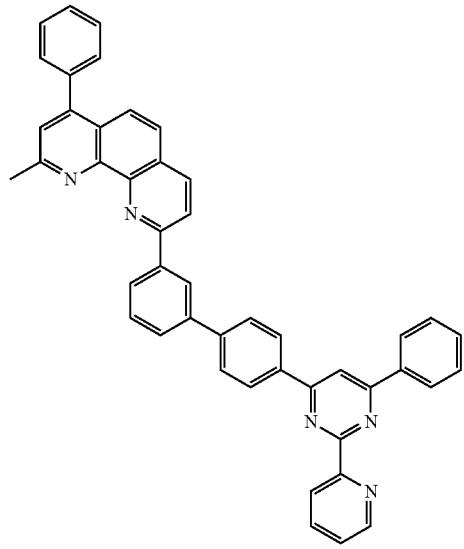
1136
998
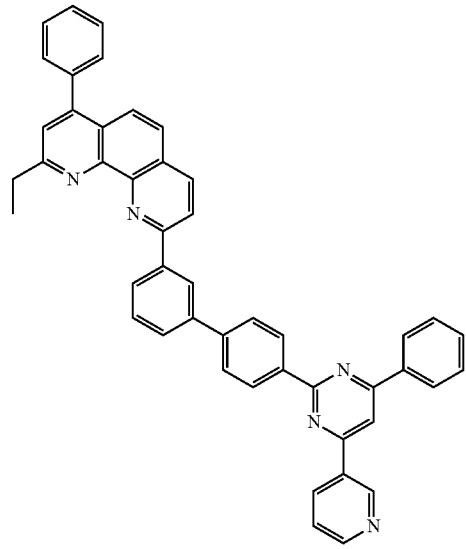
999
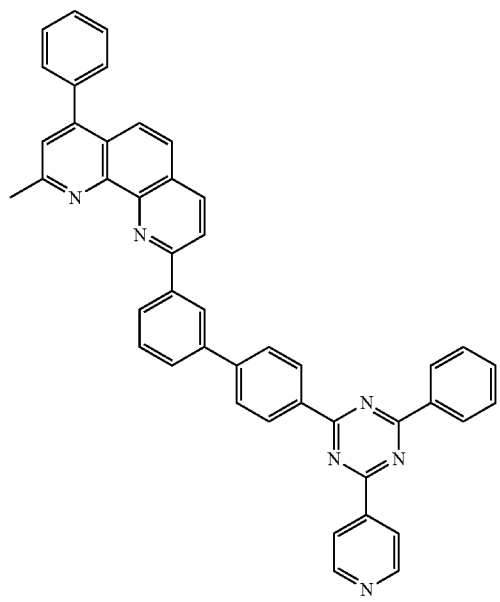
1000
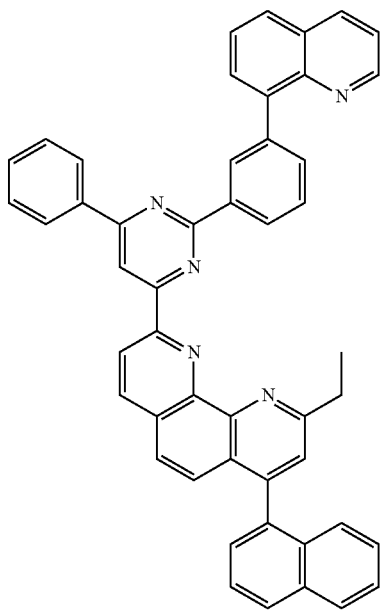

1137 1138
-continued
1001 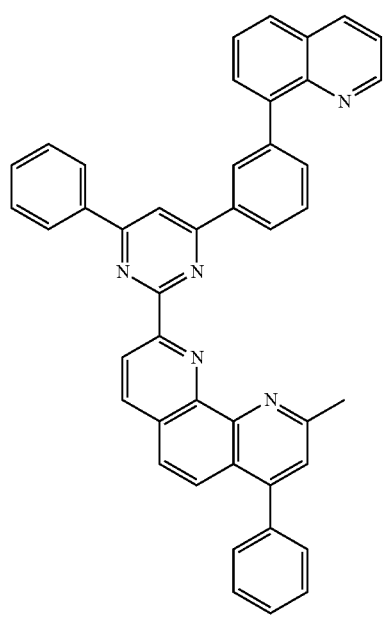 1002 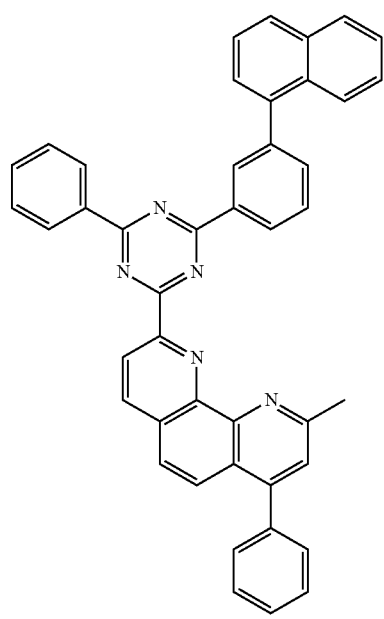
1003 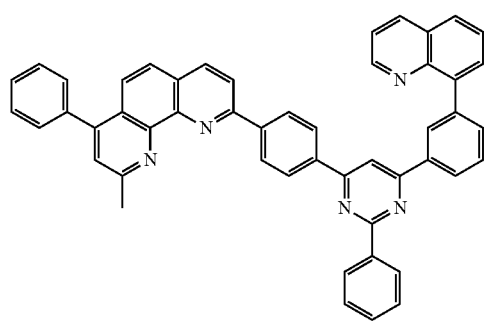 1004 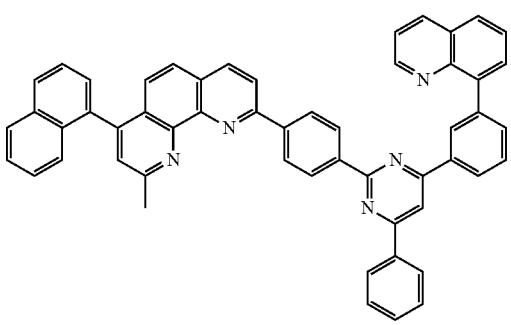
1005 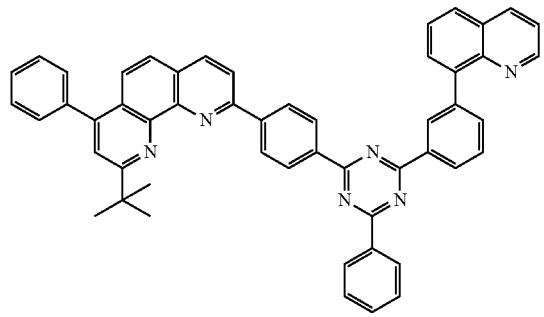 1006 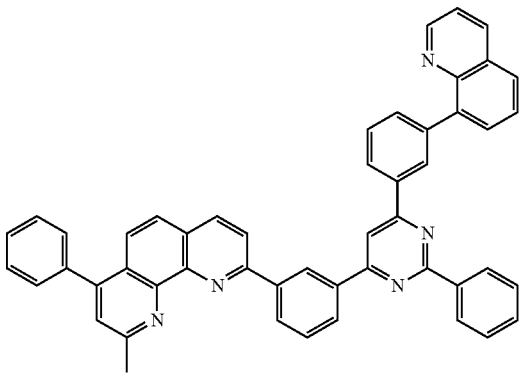

-continued
1007
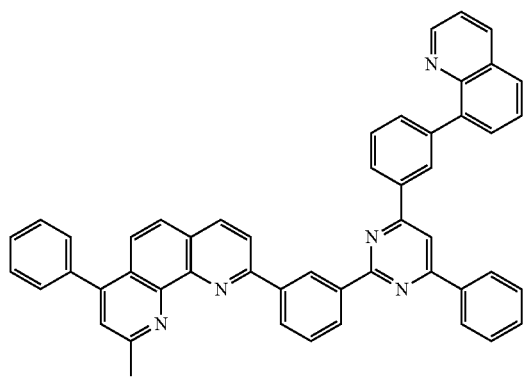
1008
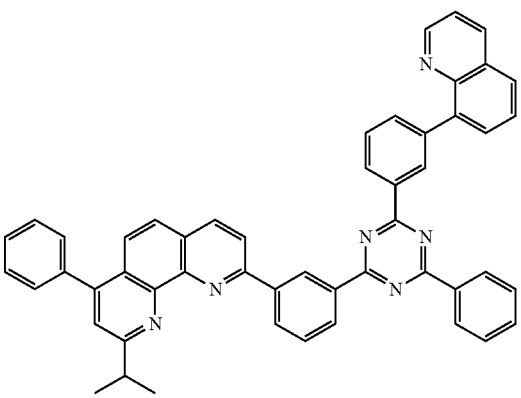
1009
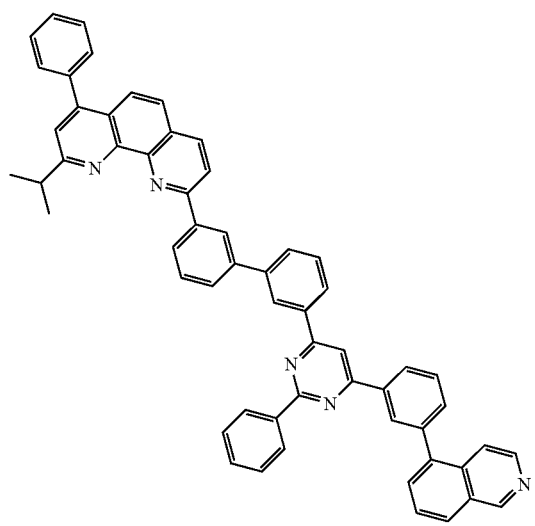
1010
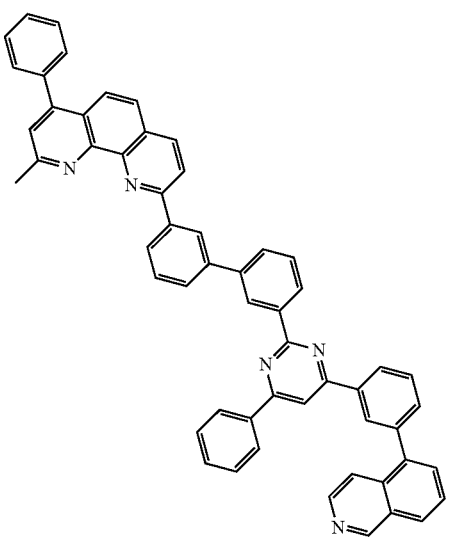
1011
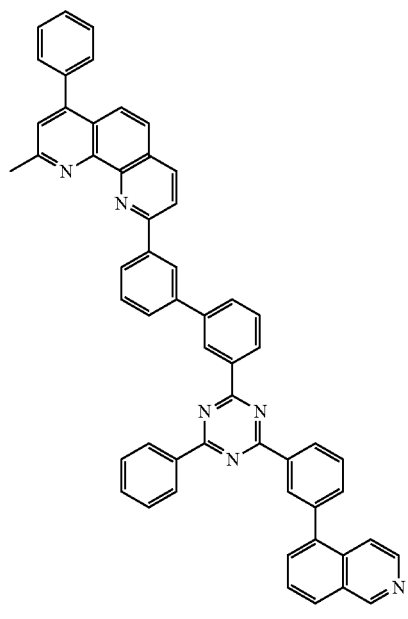
1012
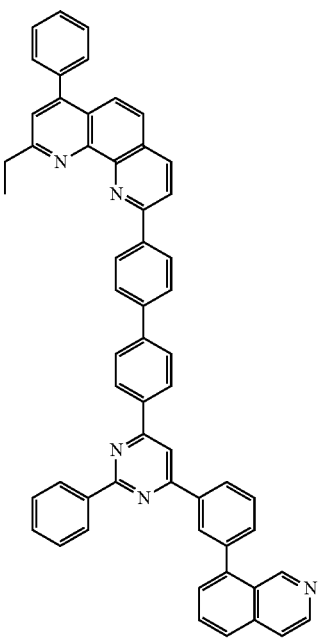

-continued
1013
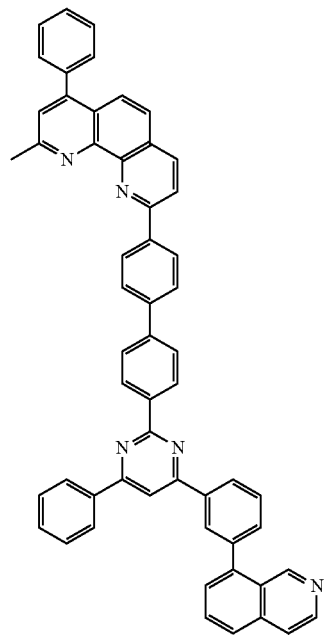
1014
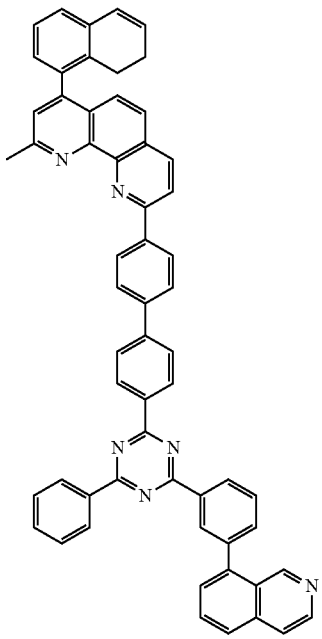
1015
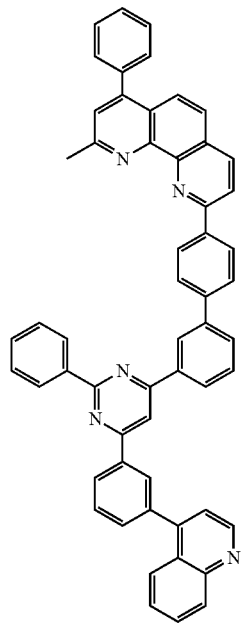
1016
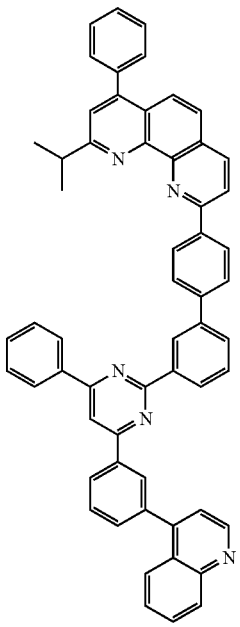

-continued
1143
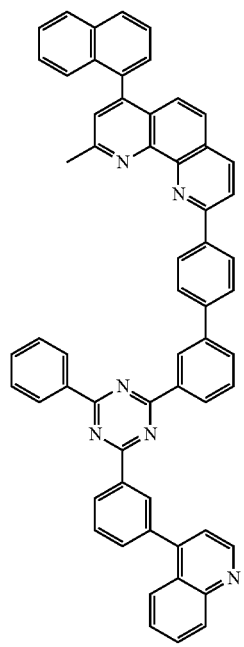
1017
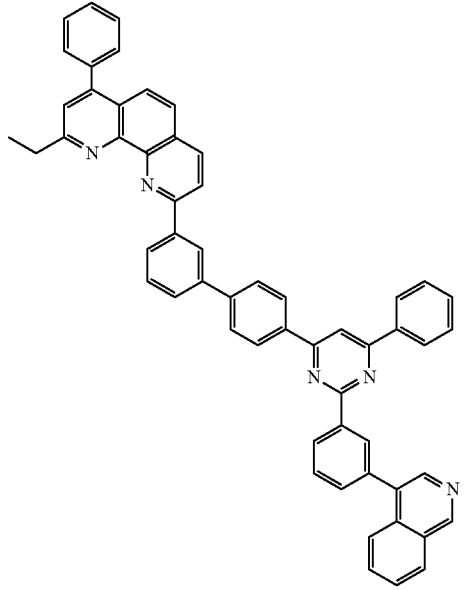
1018
1019
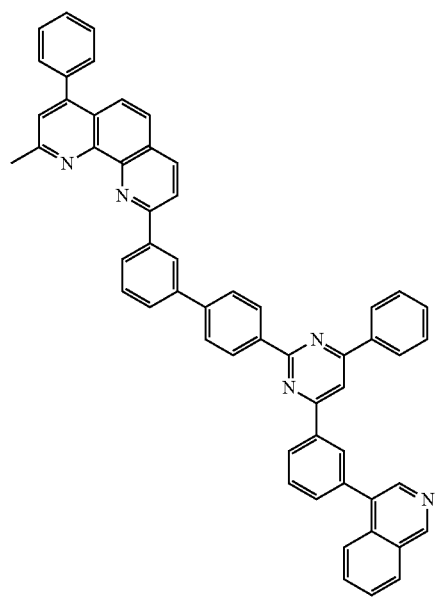
1144
1020
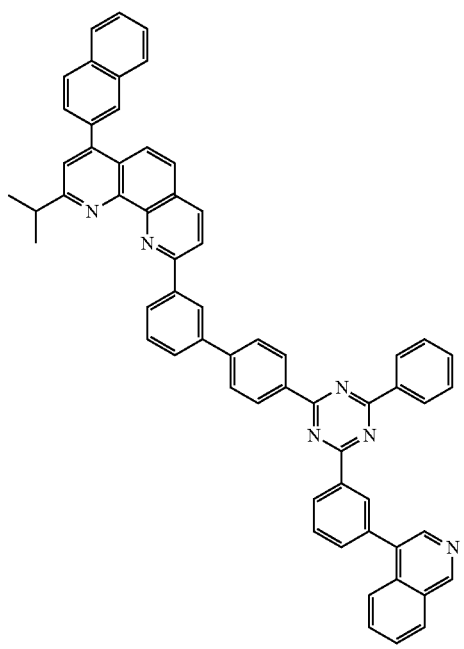

-continued
1145
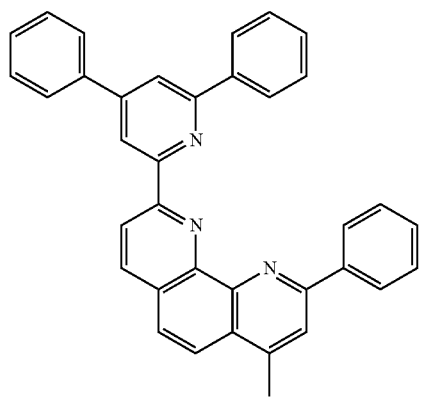
1021
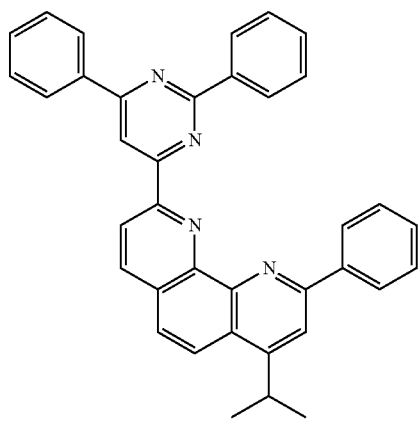
1022
1146
1023
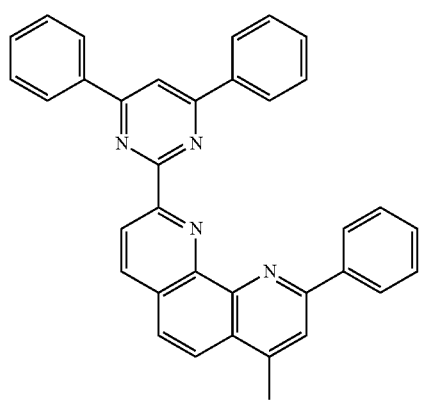
1024
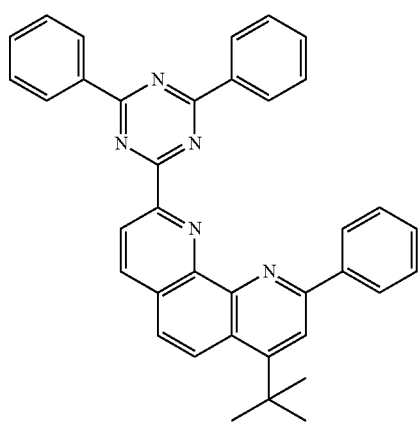
1025
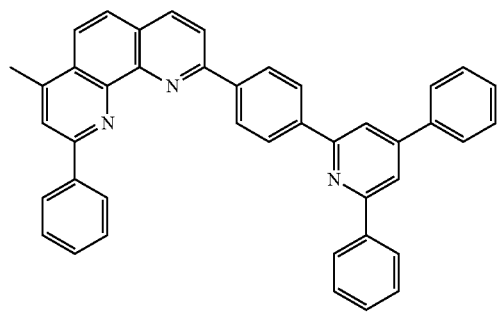
1026
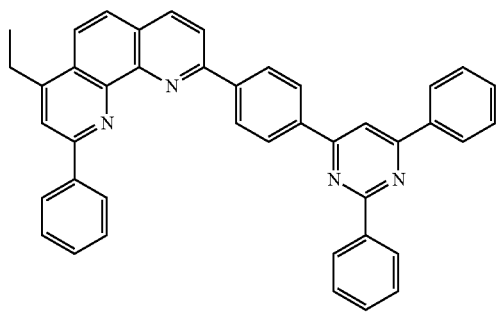
1027
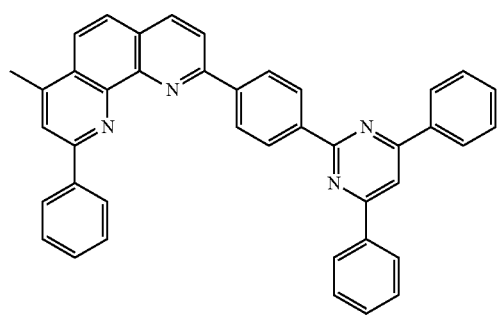
1028
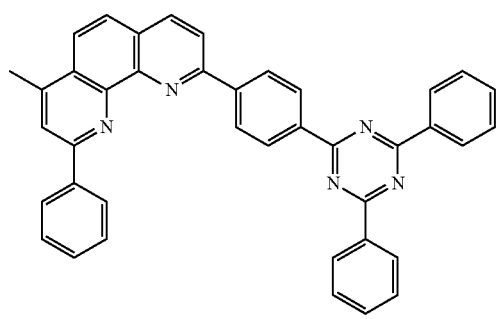

-continued
| 1029 | 1030 |
|---|---|
| 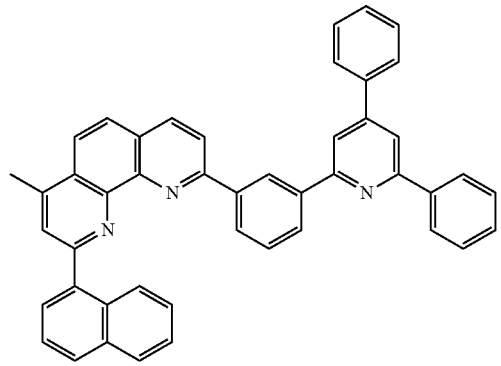 | 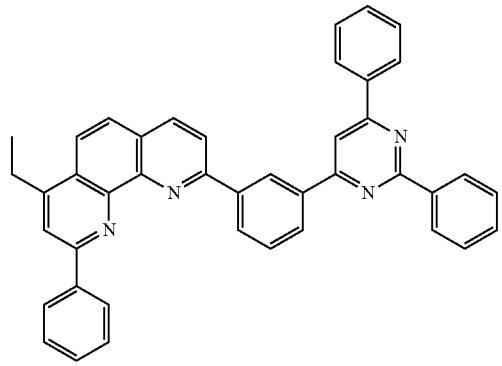 |
| 1031 | 1032 |
| 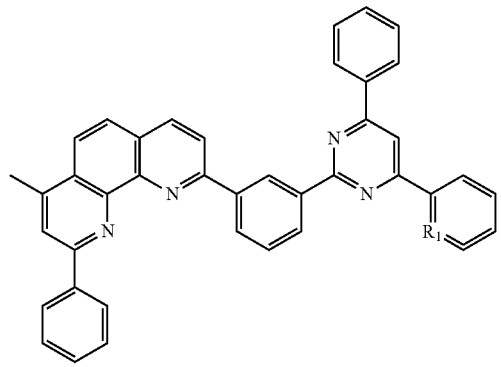 | 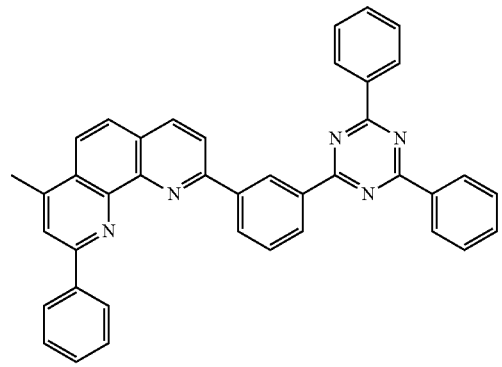 |
| 1033 | 1034 |
| 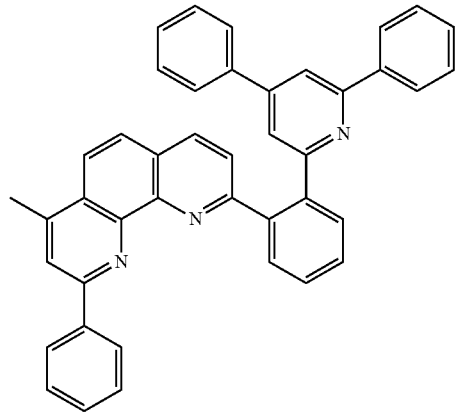 | 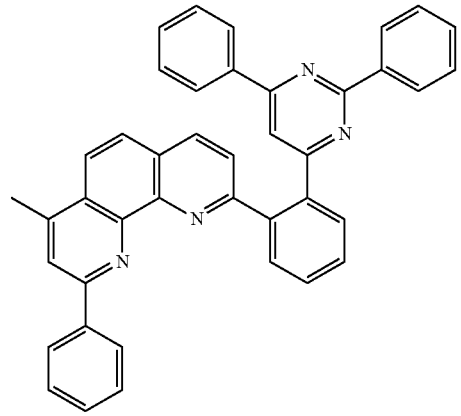 |
| 1035 | 1036 |
| 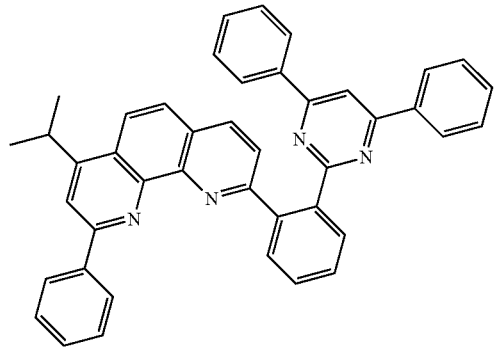 | 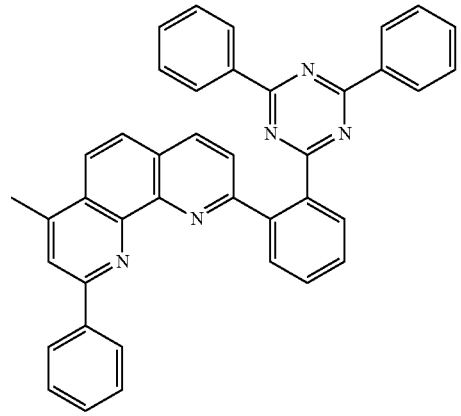 |

-continued
1037
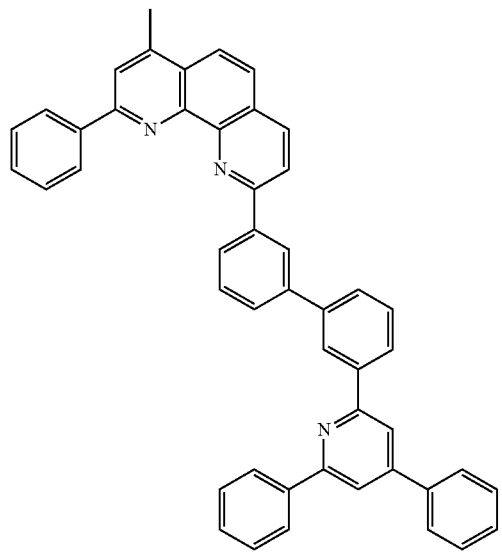
1038
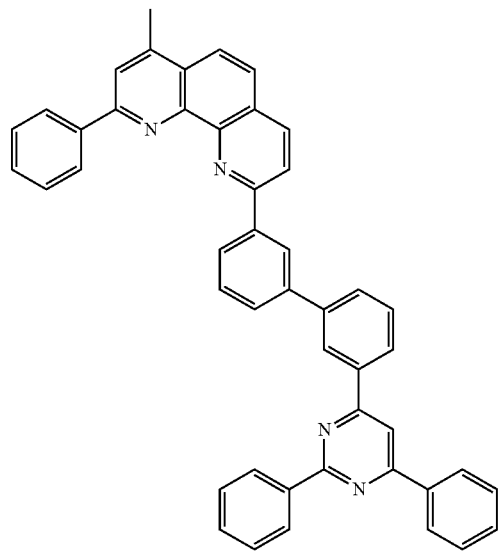
1039
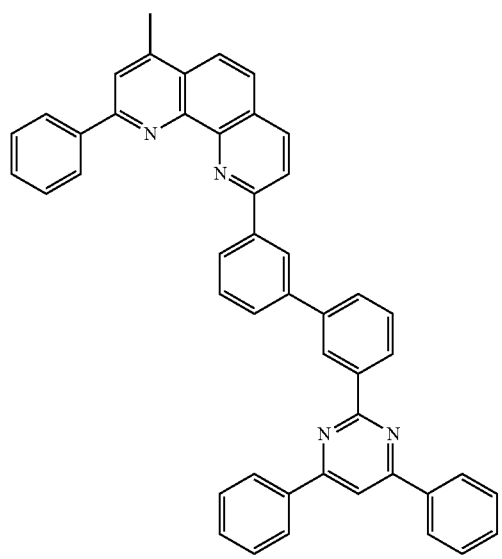
1040
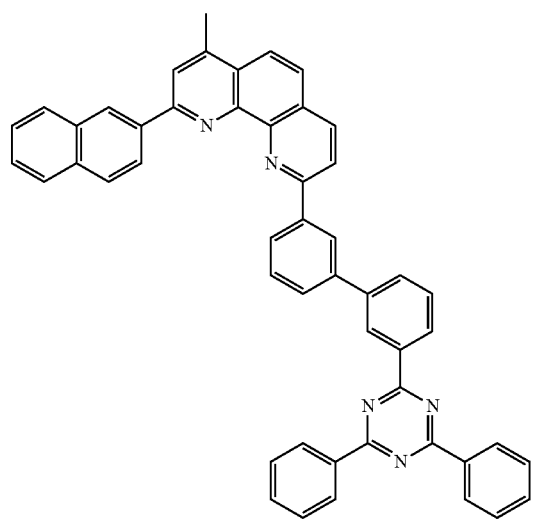

1151 1152
-continued
1041 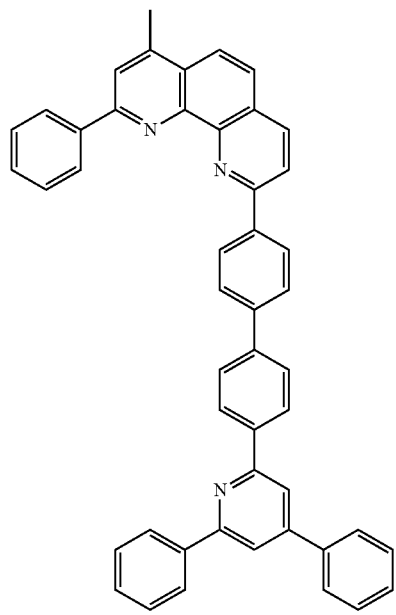 1042 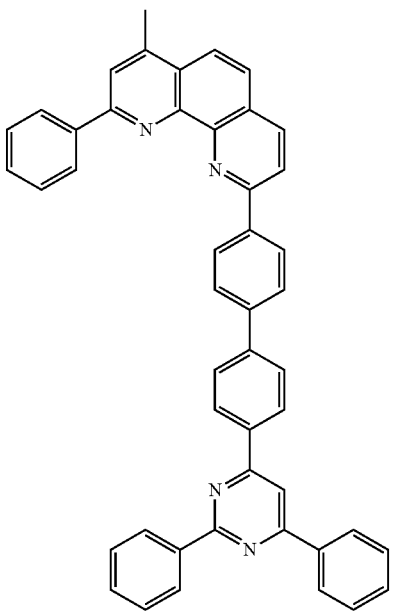
1043 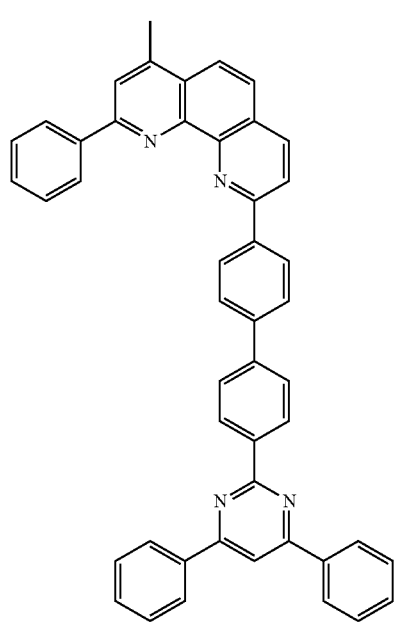 1044 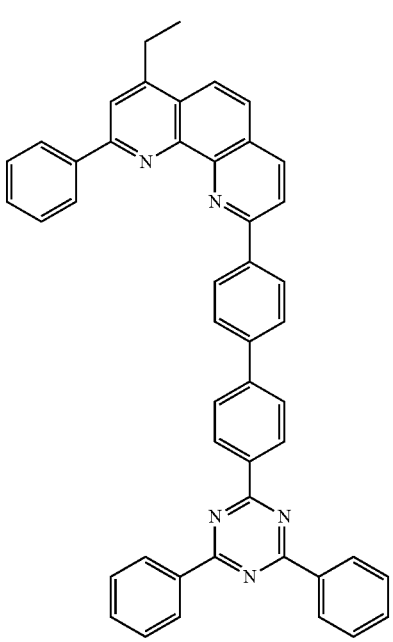

-continued
1045
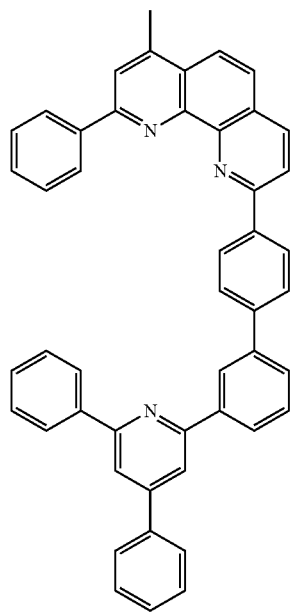
1046
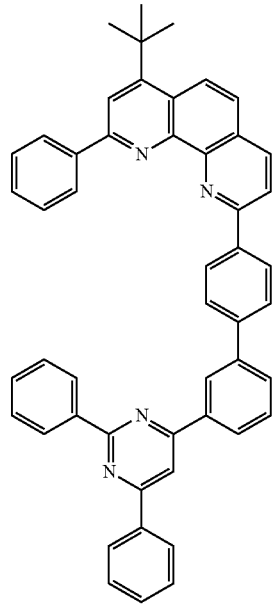
1047
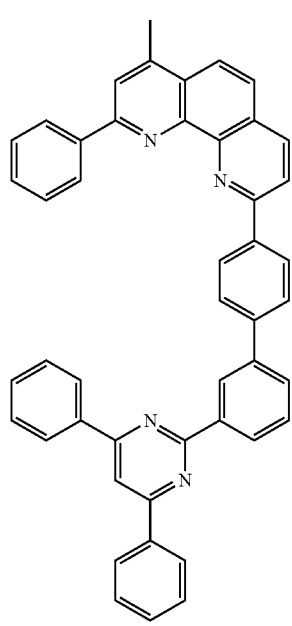
1048
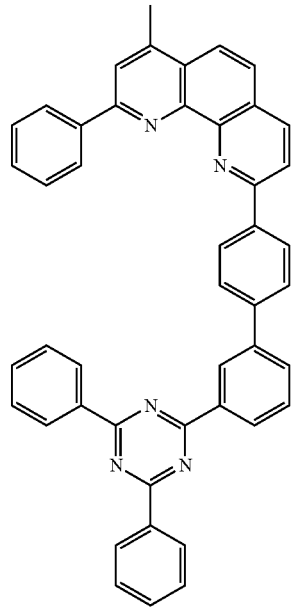

1155 1156
-continued
1049
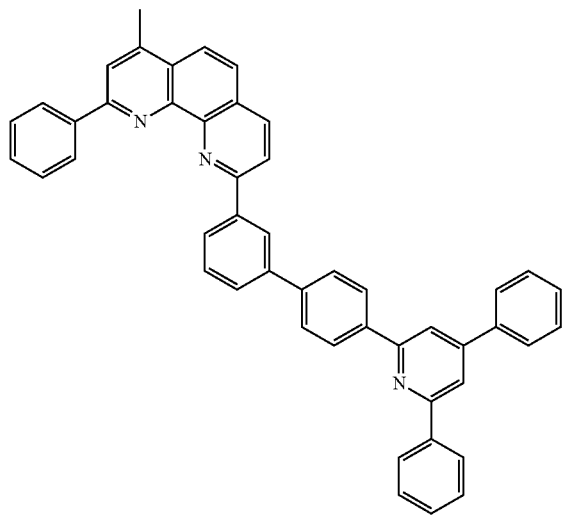
1050
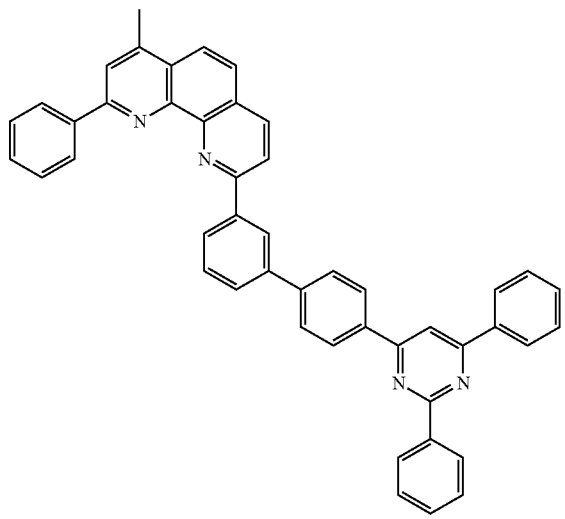
1051
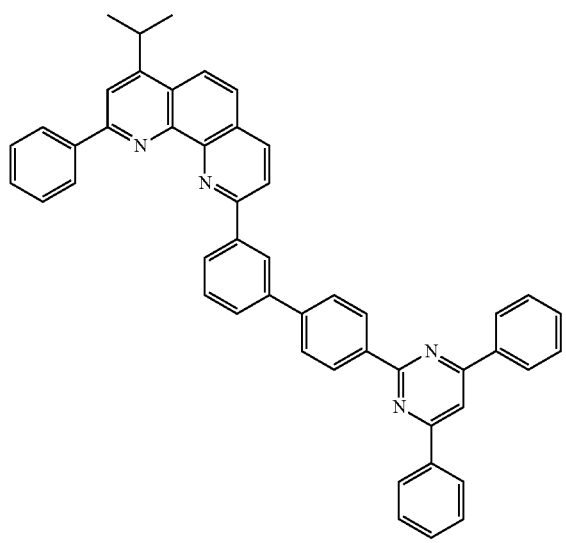
1052
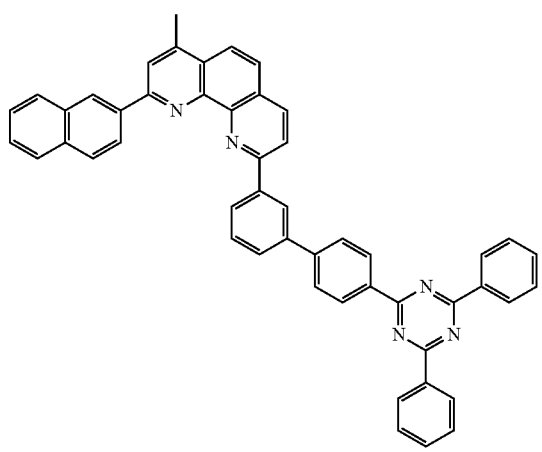
1053
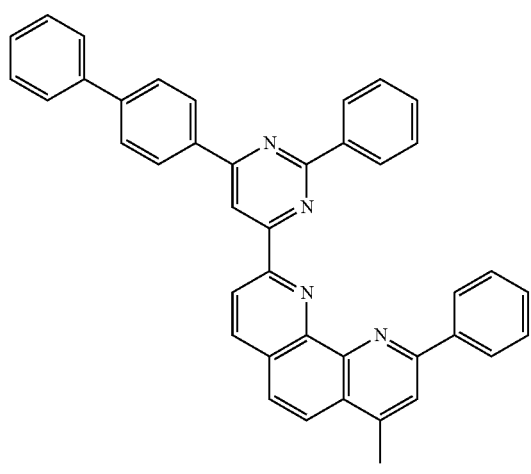
1054
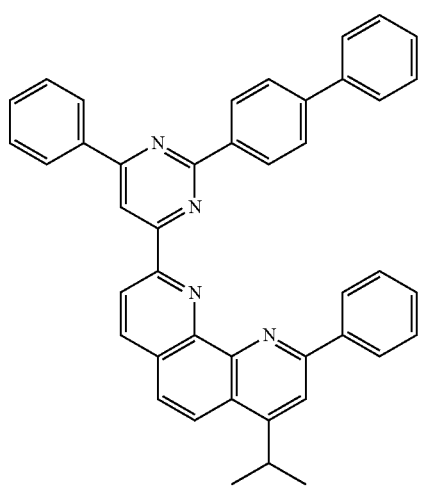

-continued
1055
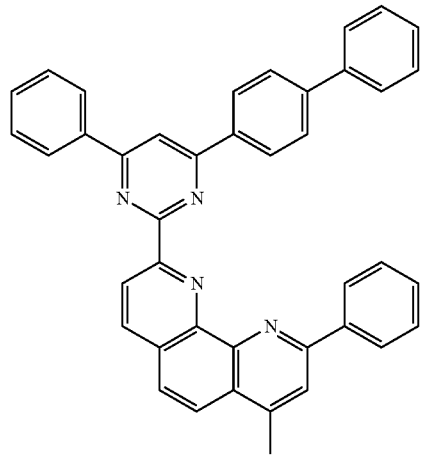
1056
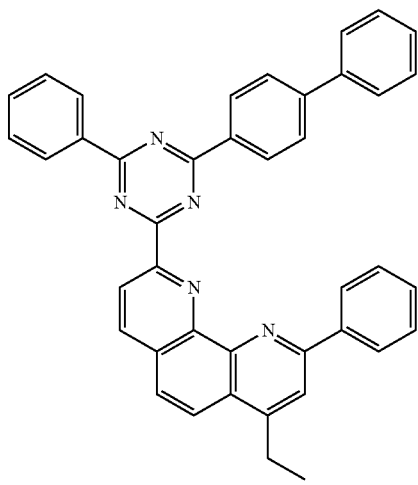
1057
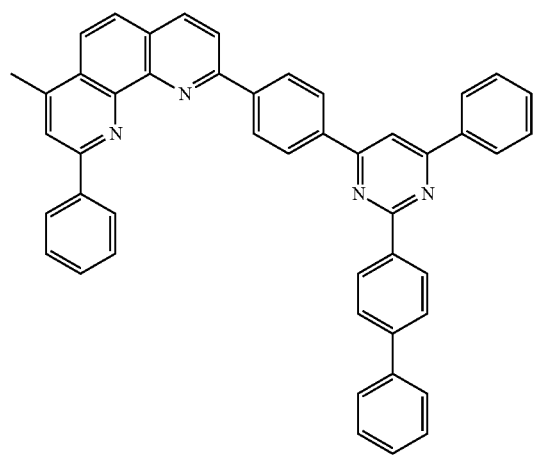
1058
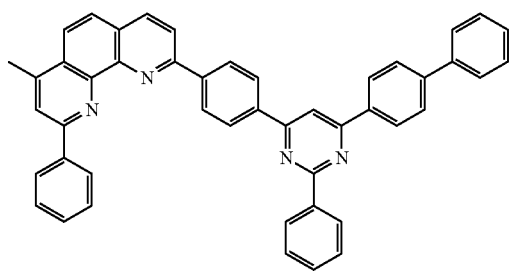
1059
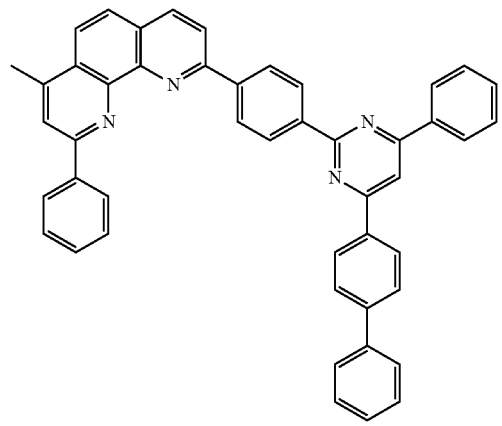
1060
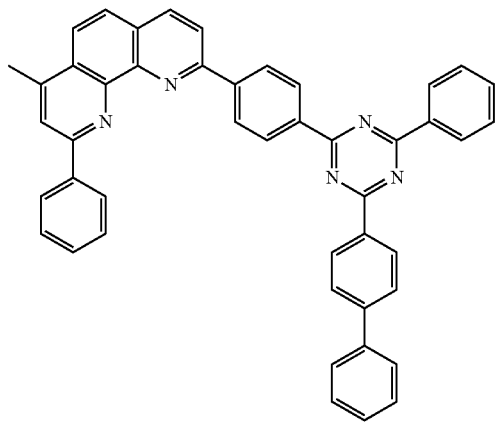

-continued
| 1061 | 1062 |
|---|---|
| 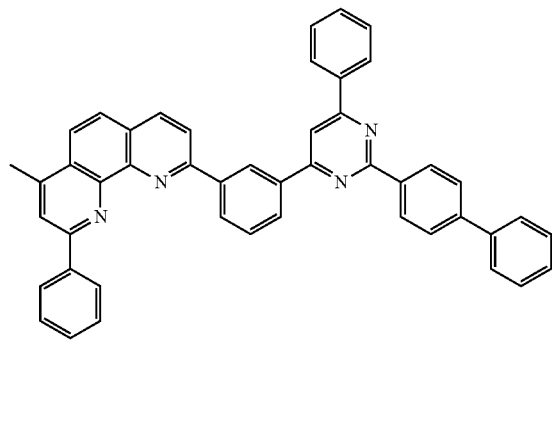 | 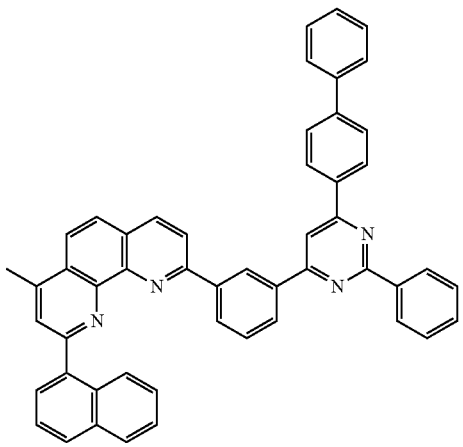 |
| 1063 | 1064 |
| 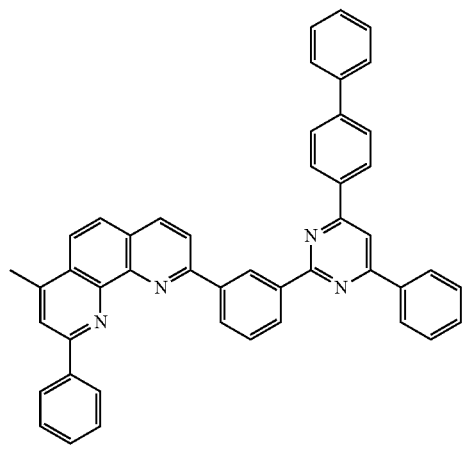 | 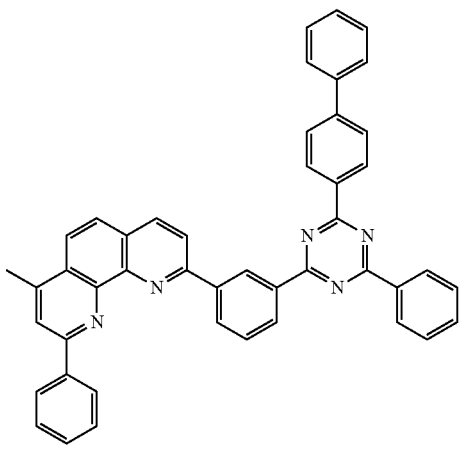 |
| 1065 | 1066 |
| 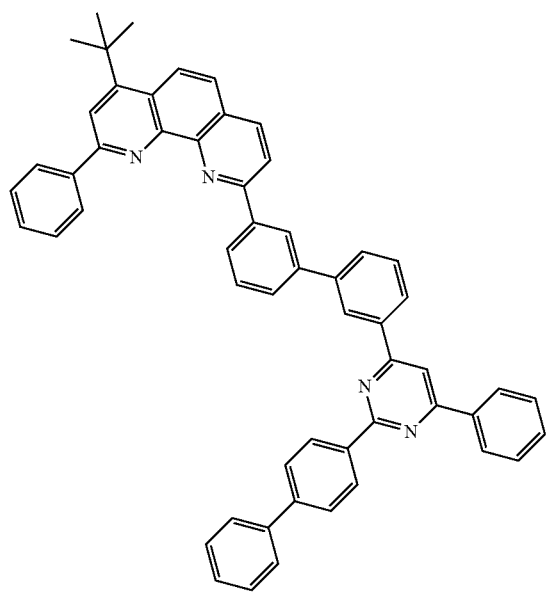 | 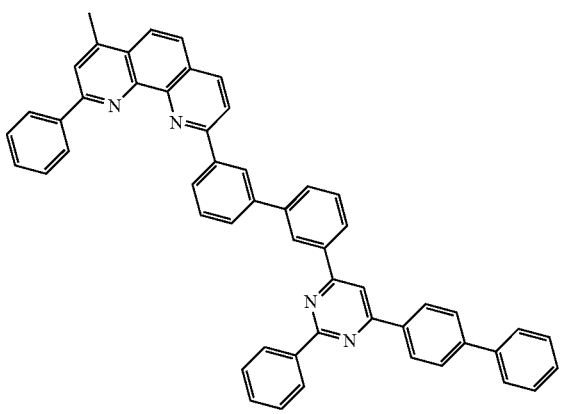 |

1067 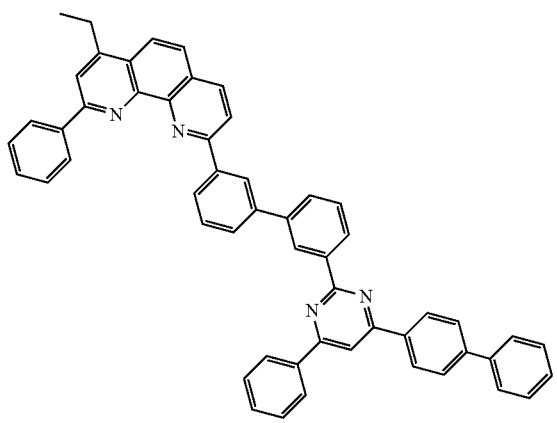
1068 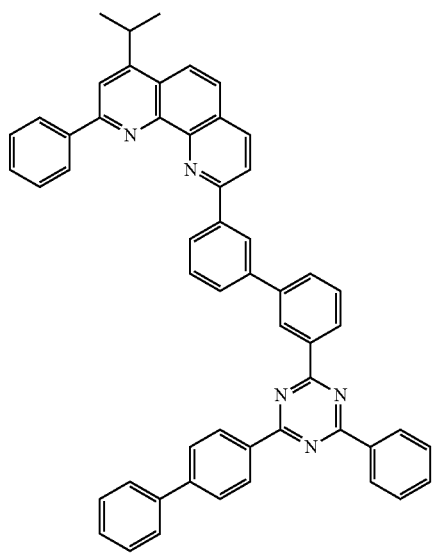
1069 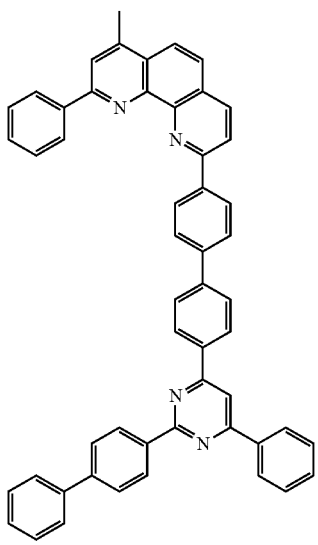
1070 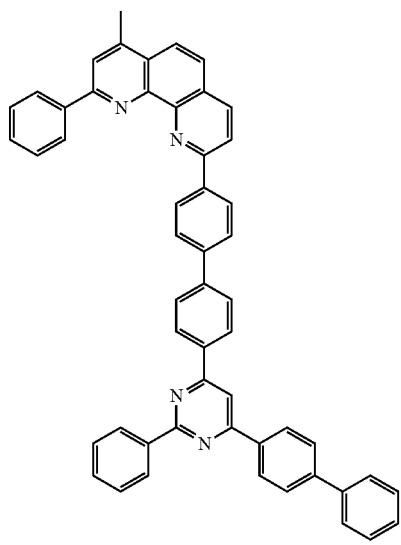
1071 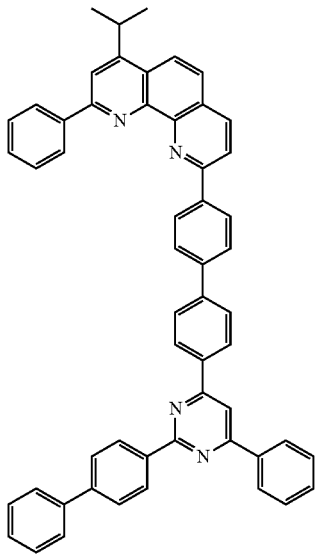
1072 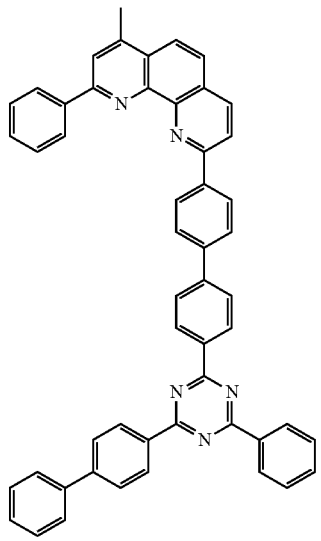

-continued
1073
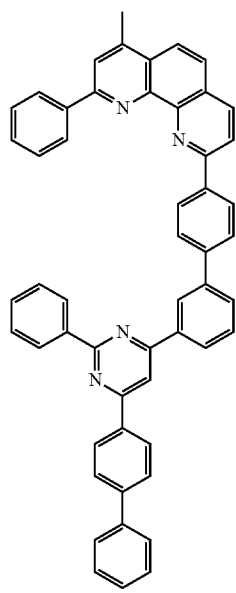
1074
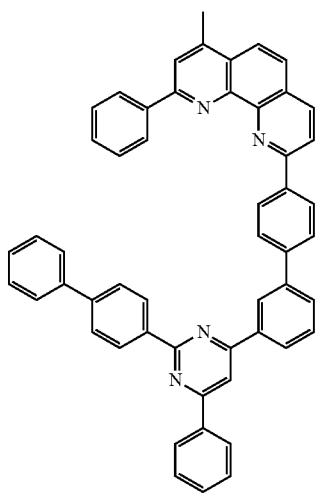
1075
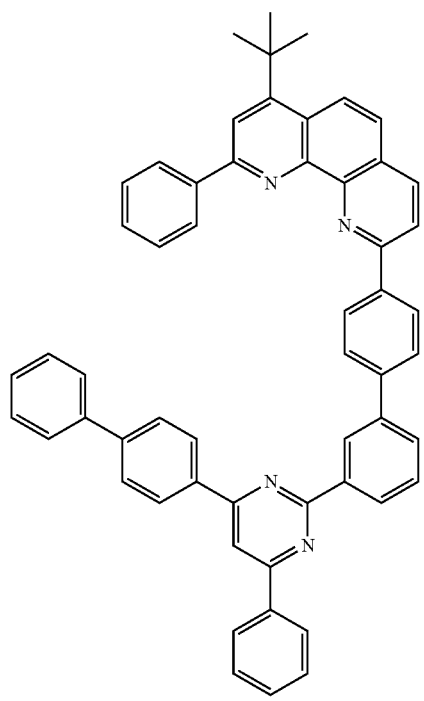
1076
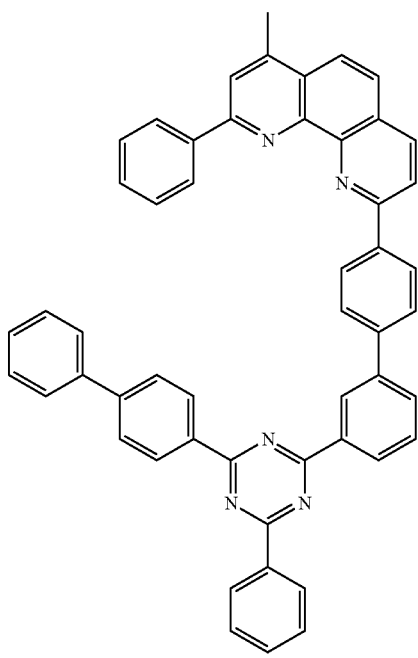

-continued
1077
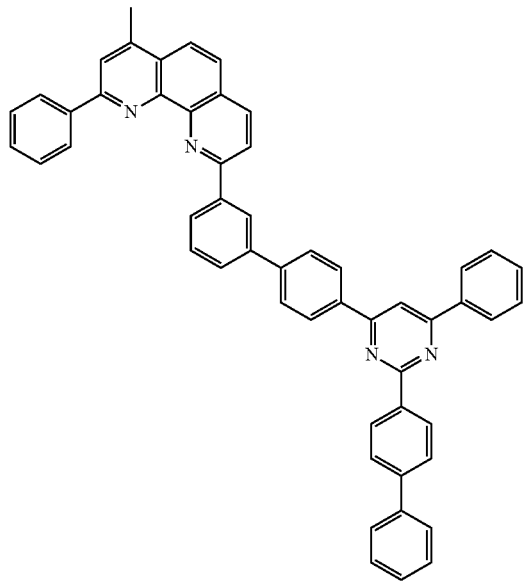
1078
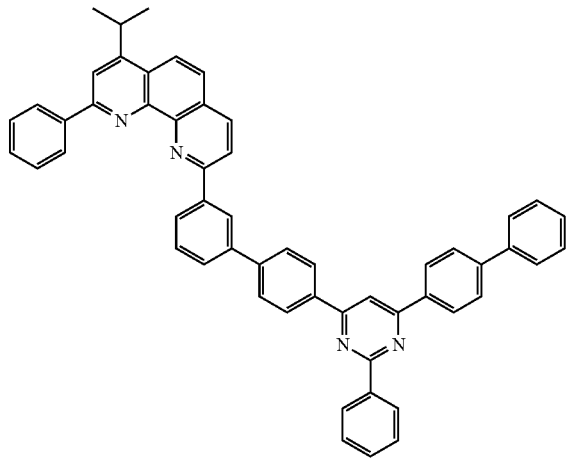
1079
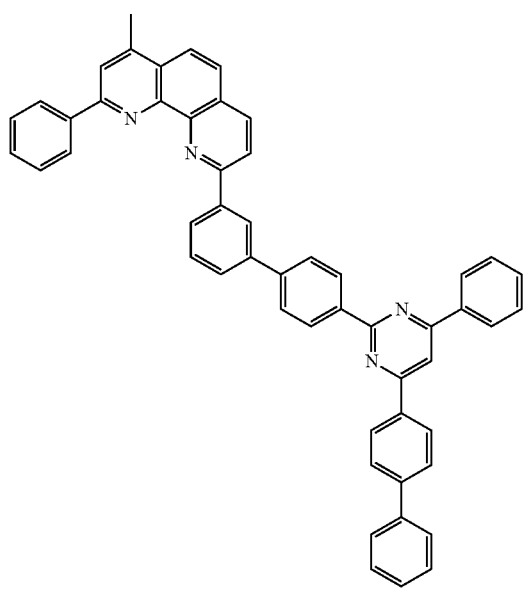
1080
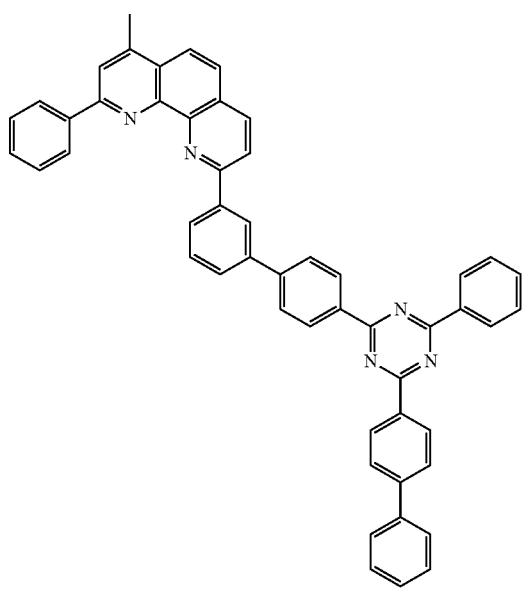
1081
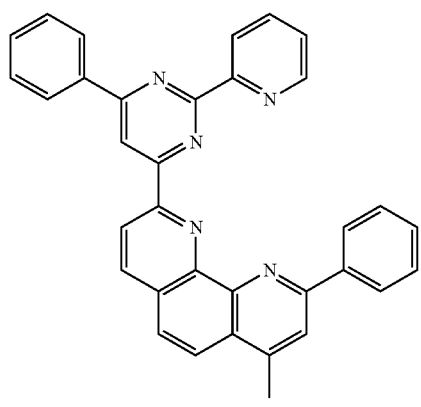
1082
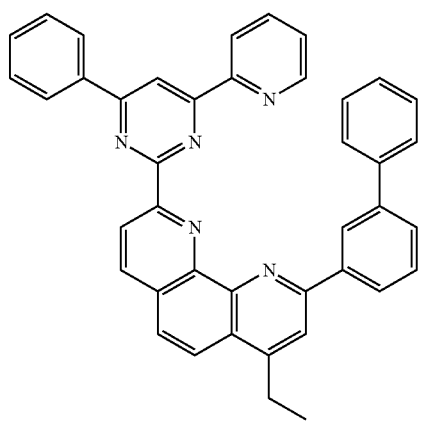

-continued
1167      1168
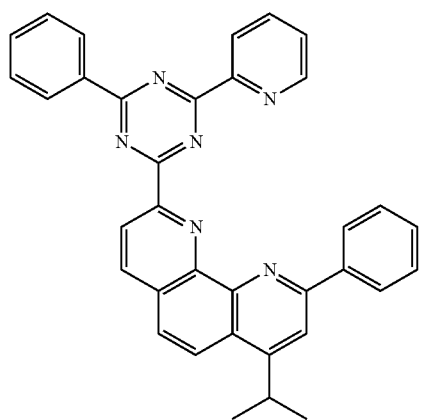
1083
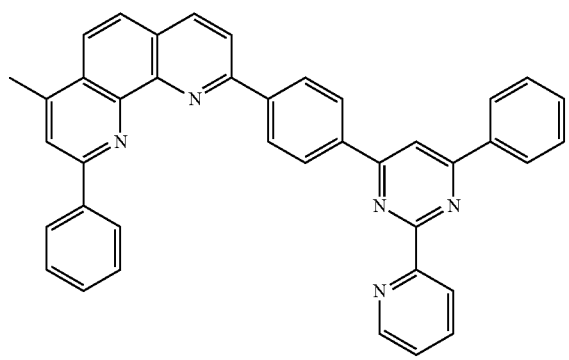
1084
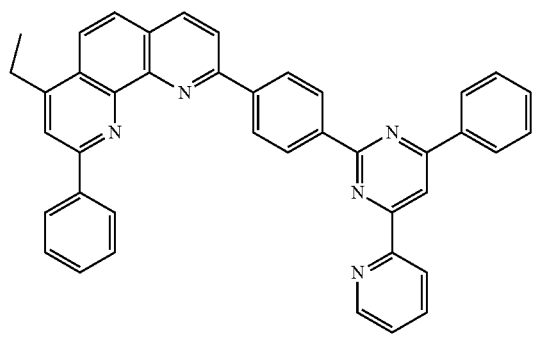
1085
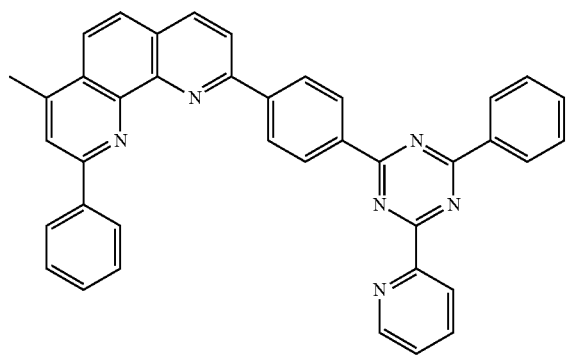
1086
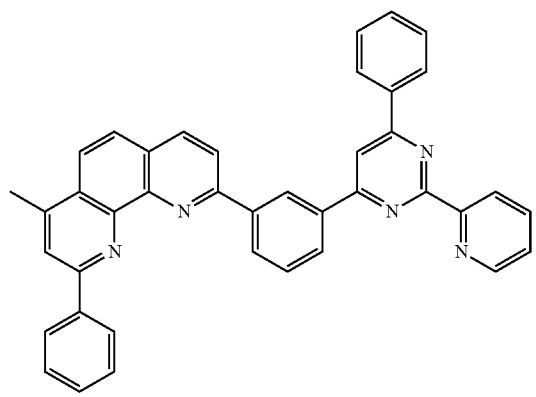
1087
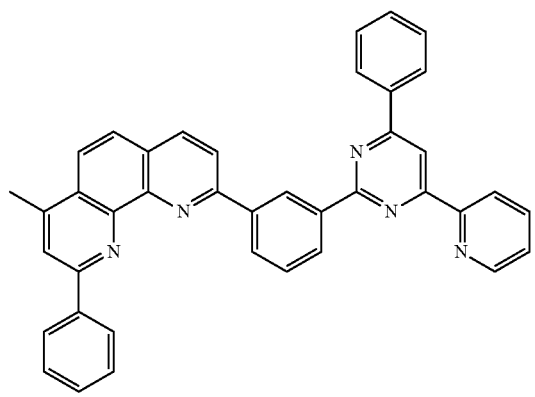
1088

-continued
1089
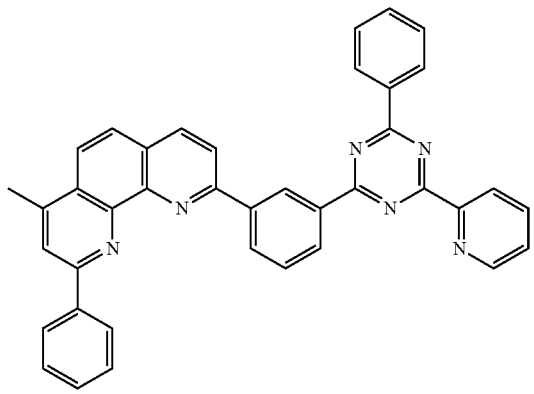
1090
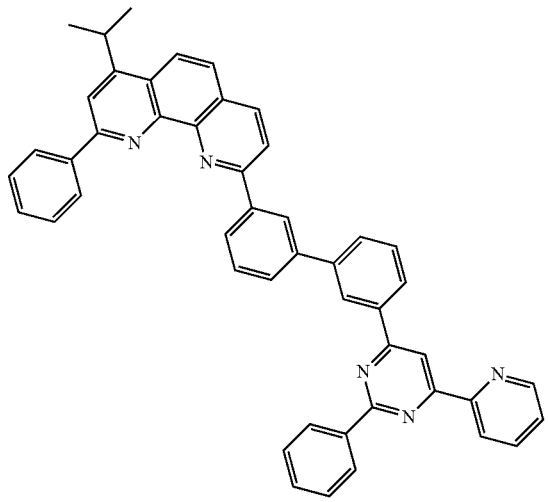
1091
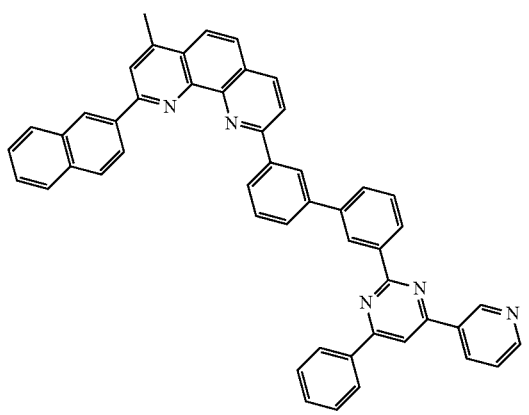
1092
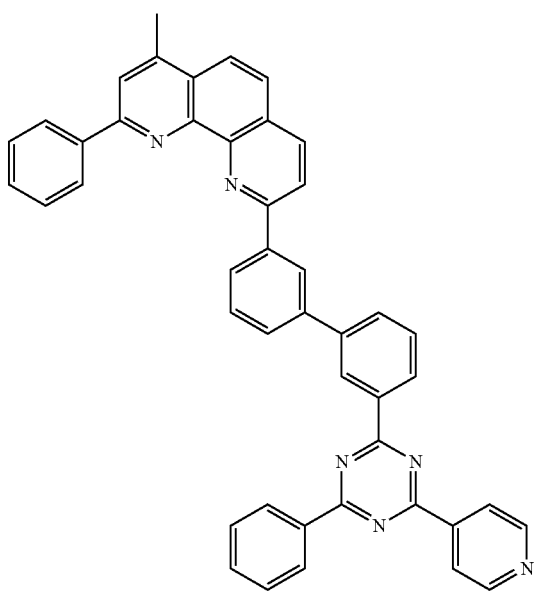

-continued
1093      1094
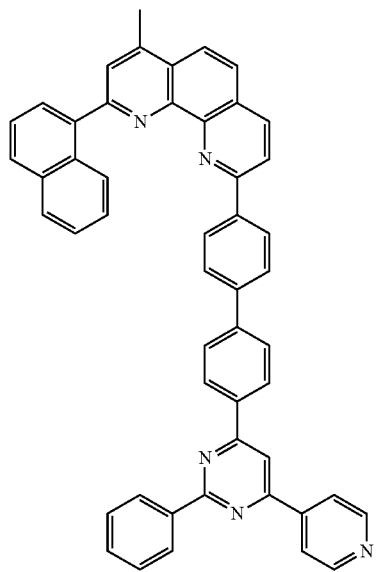
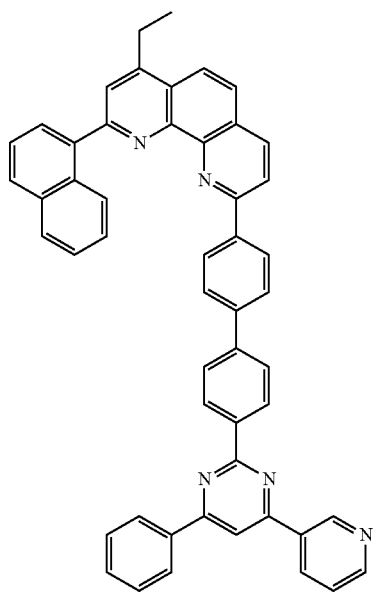
1095      1096
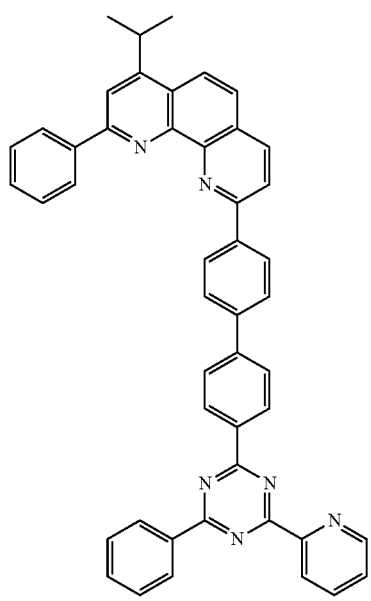
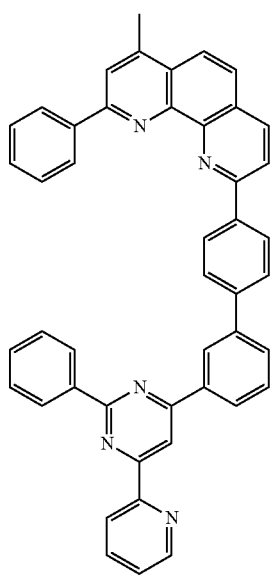

-continued
1097
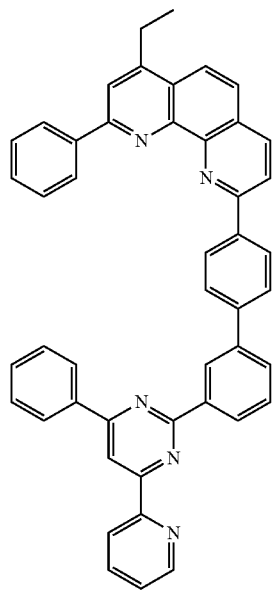
1173
1098
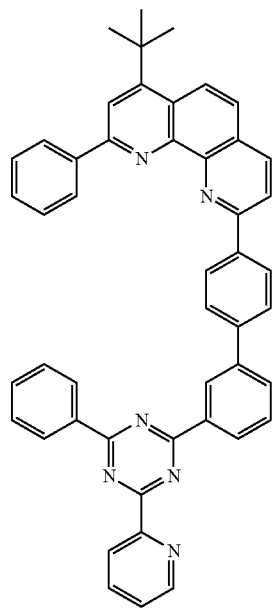
1174
1099
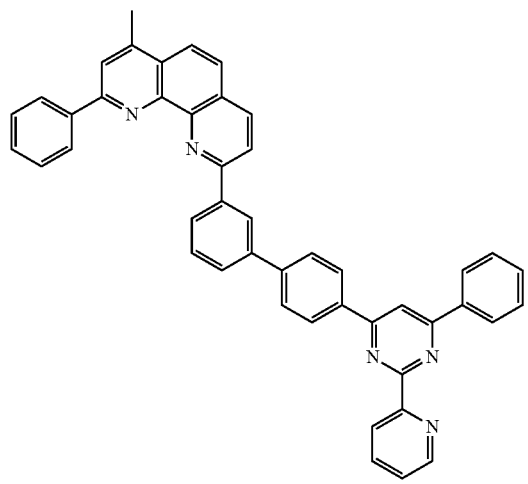
1100
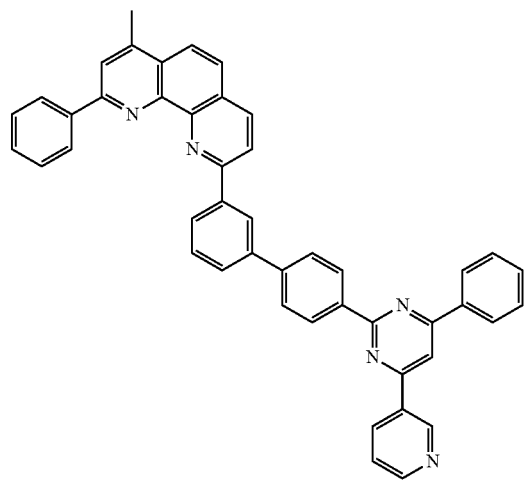
1101
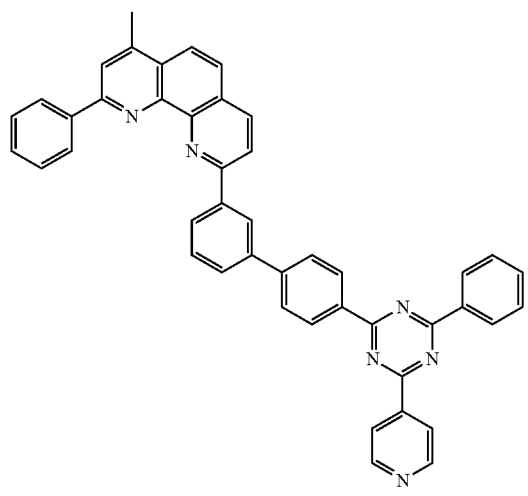
1102
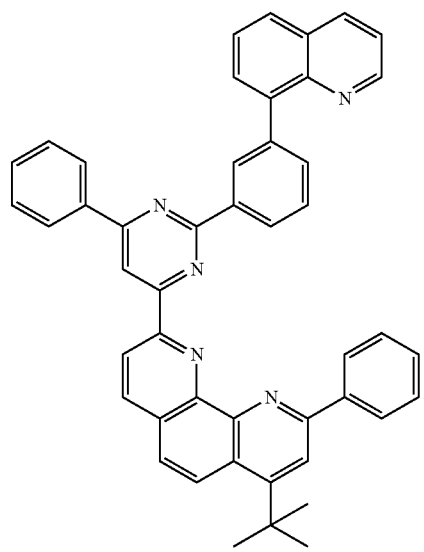

-continued
1175
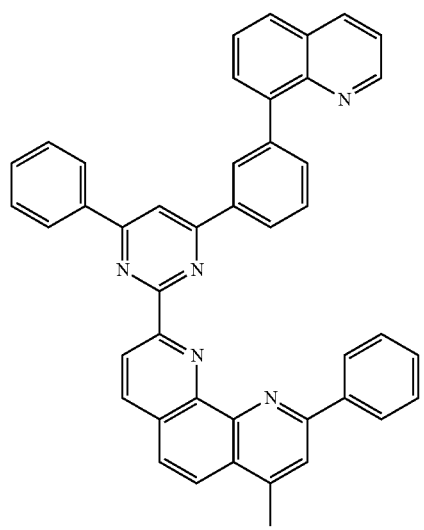
1103
1176
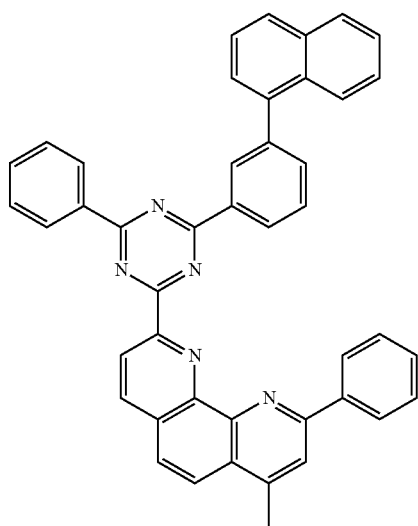
1104
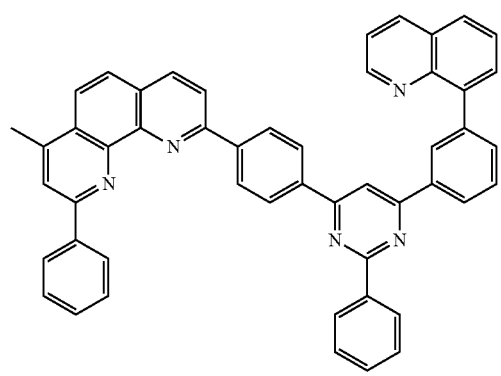
1105
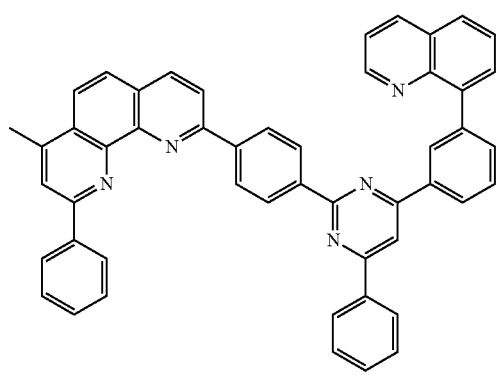
1106
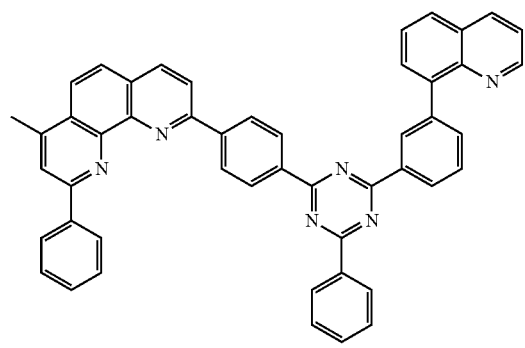
1107
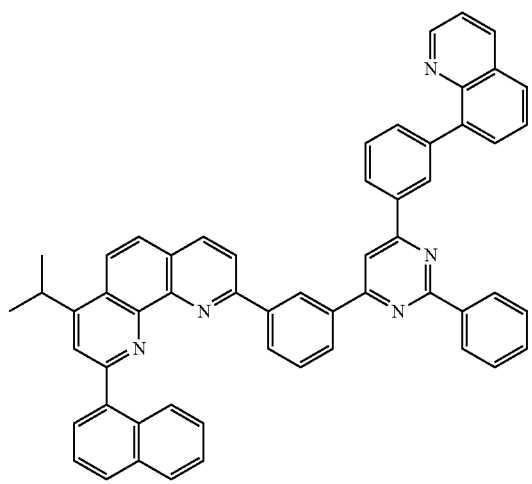
1108

-continued
1109
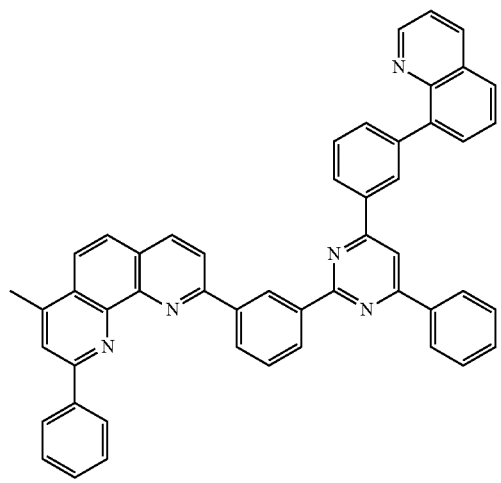
1110
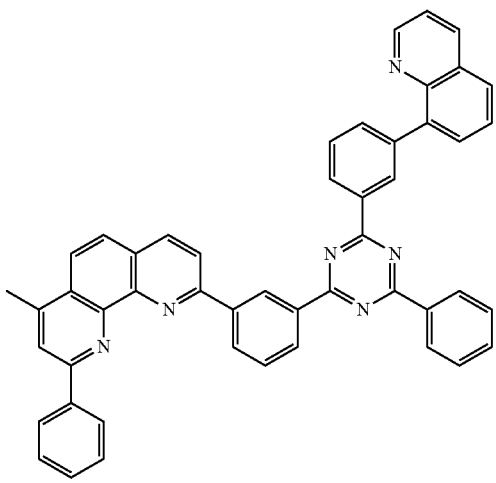
1111
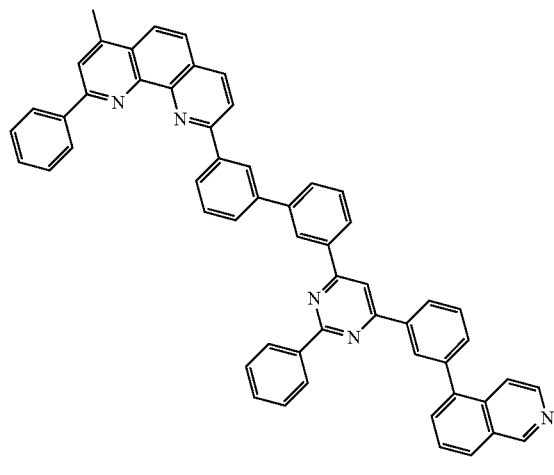
1112
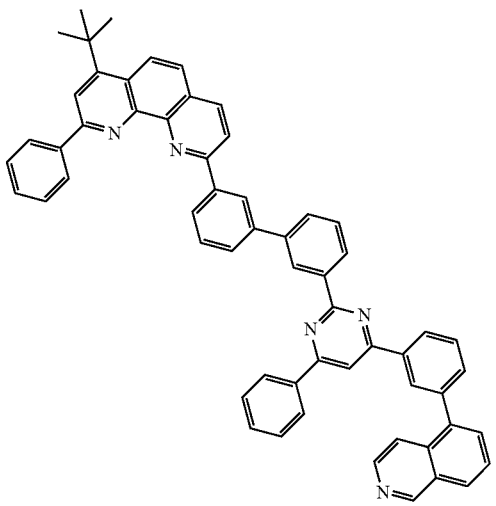
1113
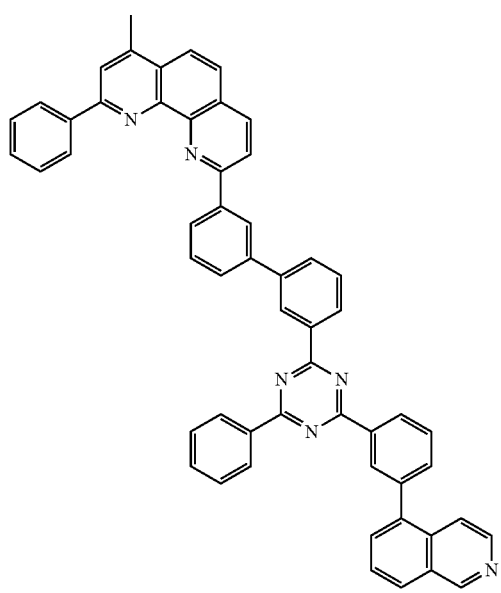
1114
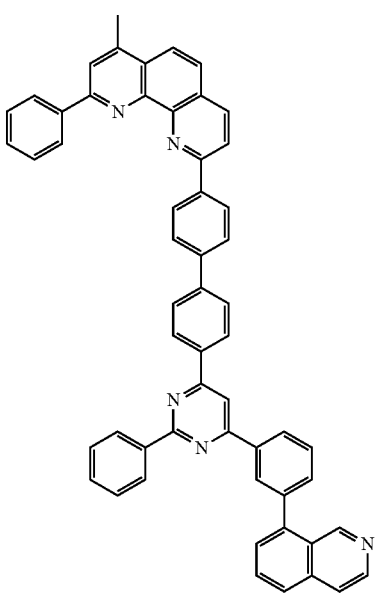

-continued
1115
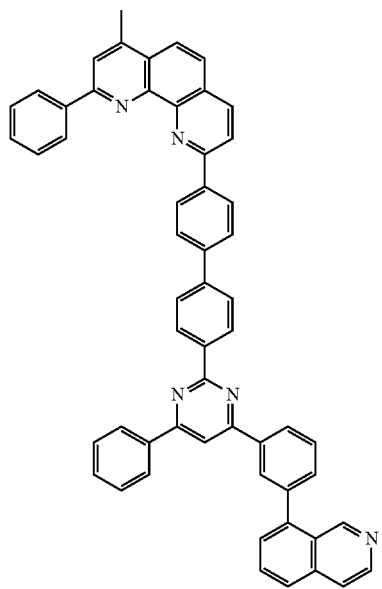
1116
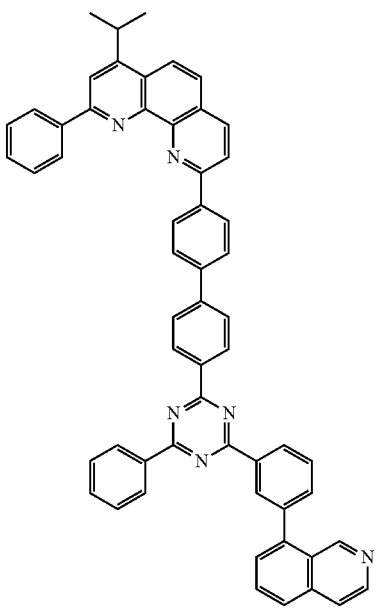
1117
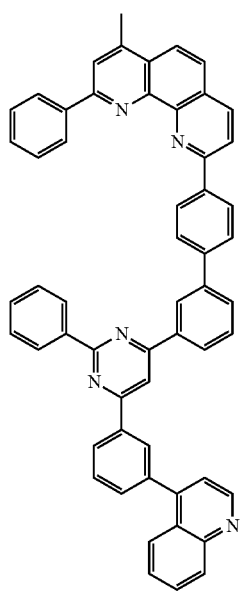
1118

-continued
1119
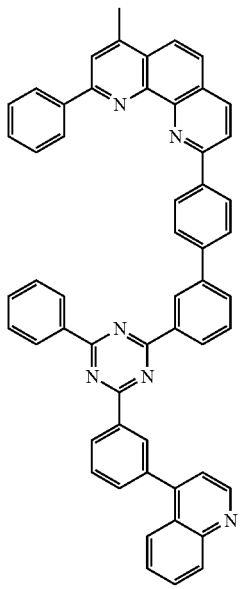
1120
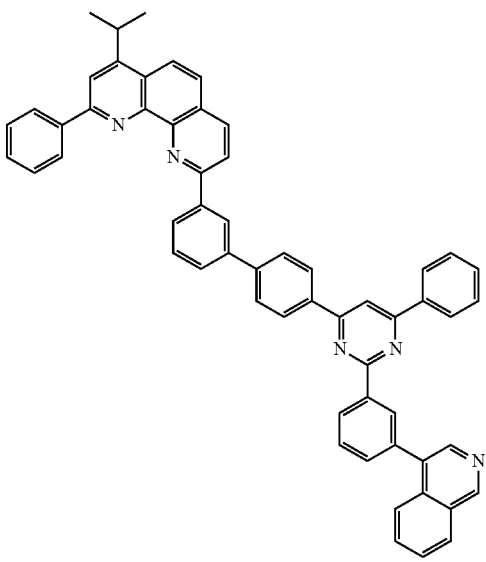
1121
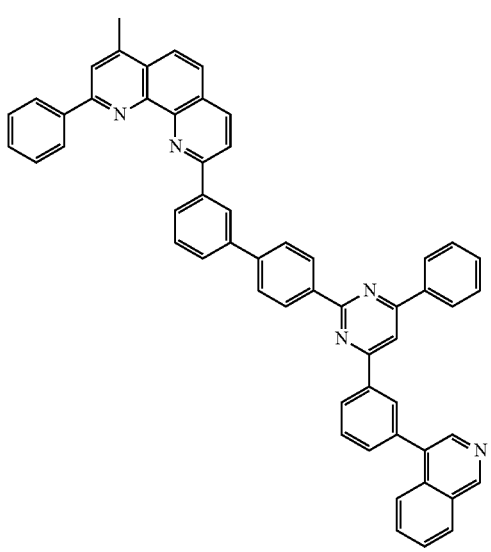
1122
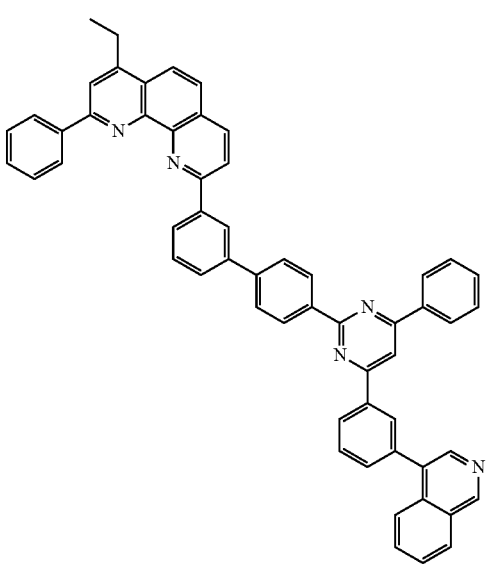
1123
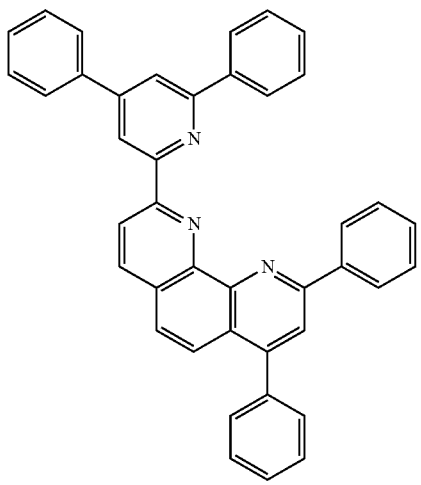

-continued
1125
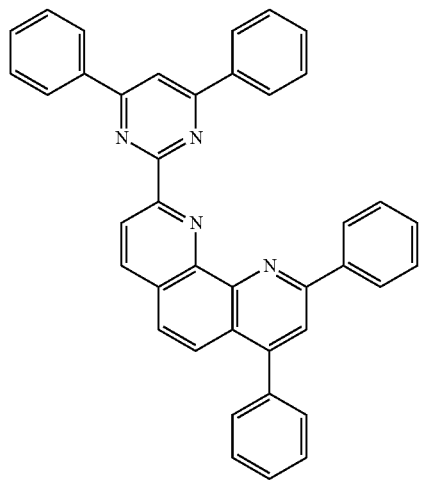
1126
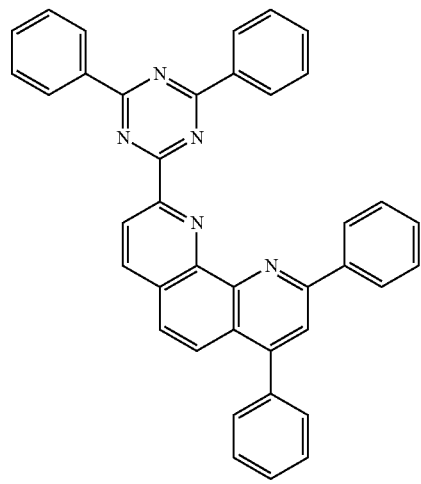
1127
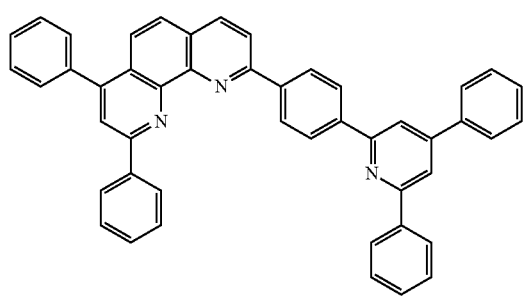
1128
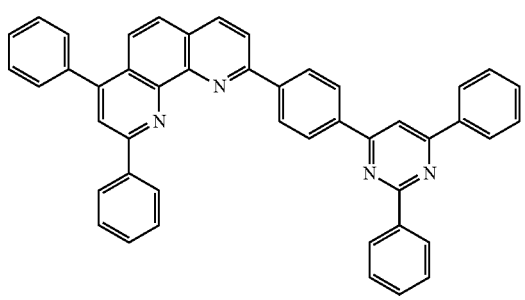
1129
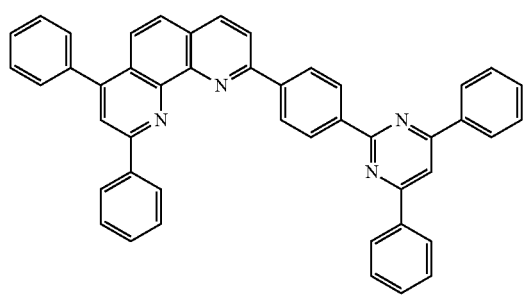
1130
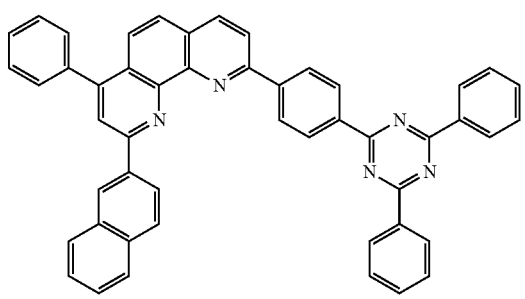
1131
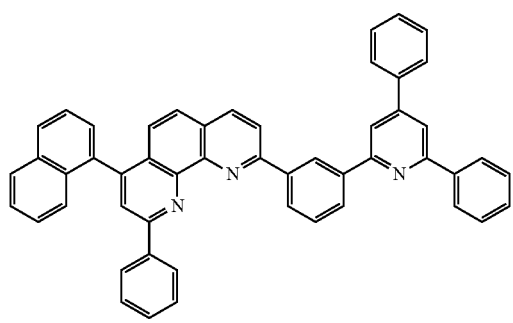
1132
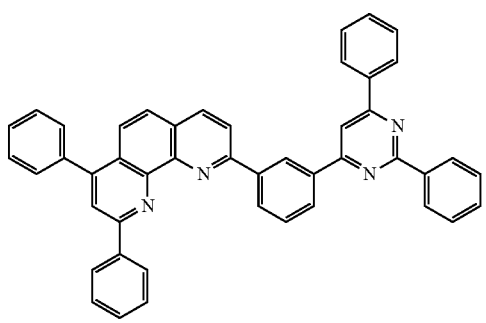

-continued
1133
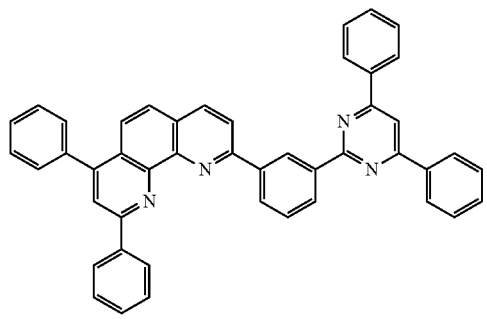
1134
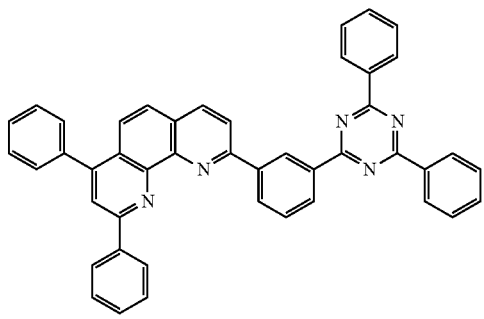
1135
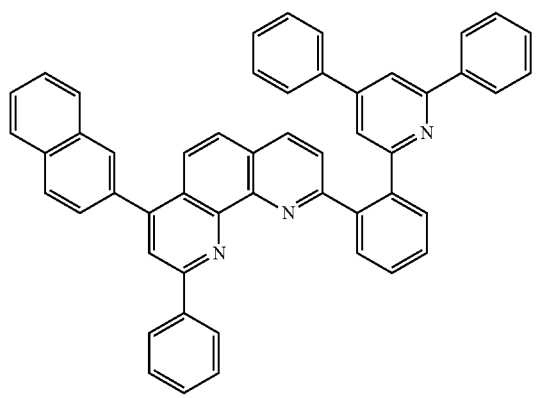
1136
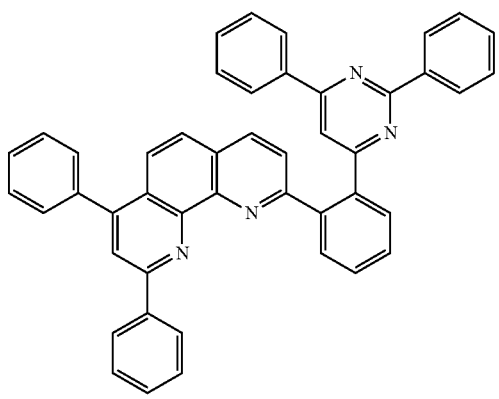
1137
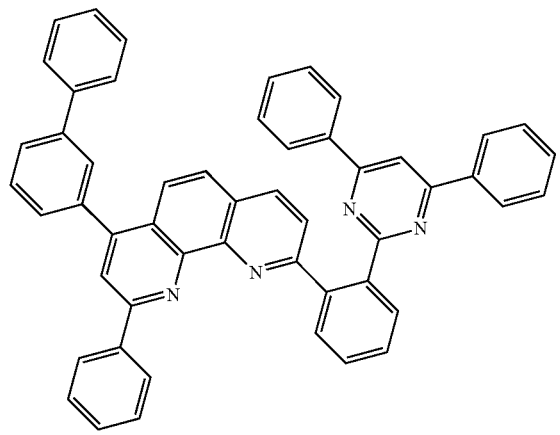
1138
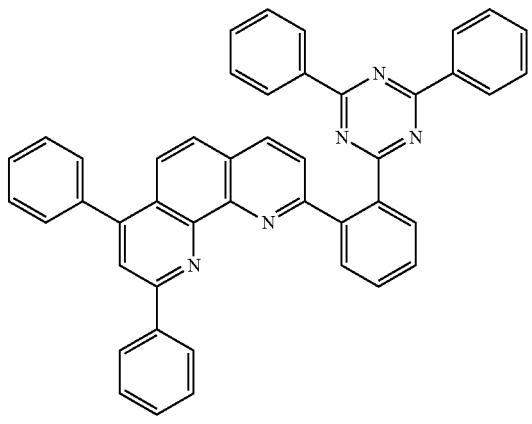
1139
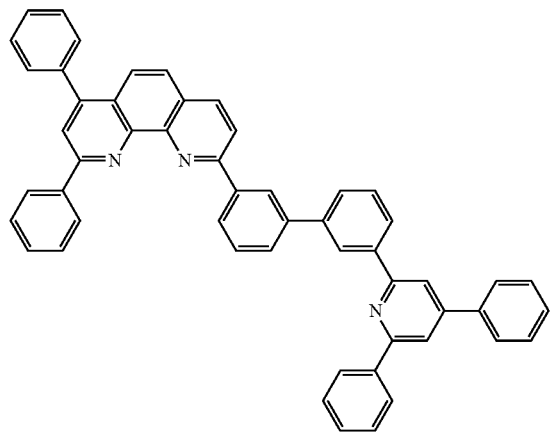
1140
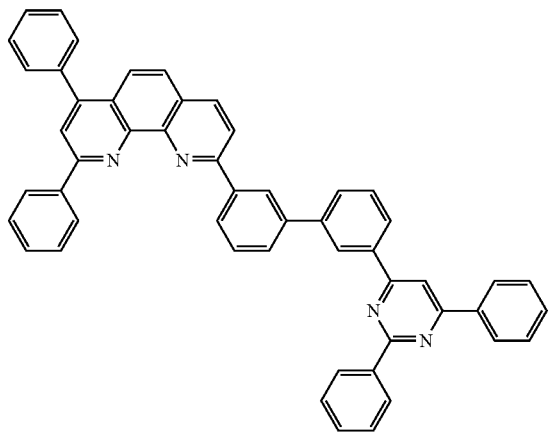

-continued
1141
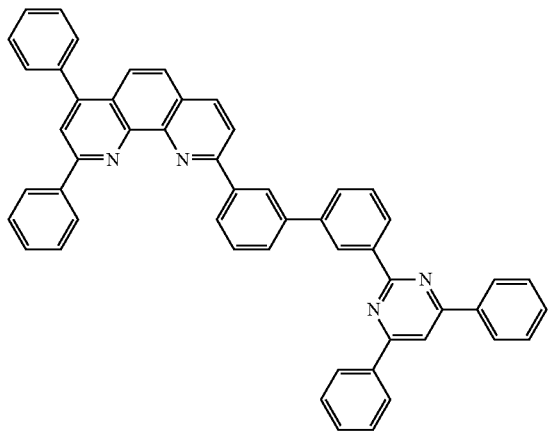
1142
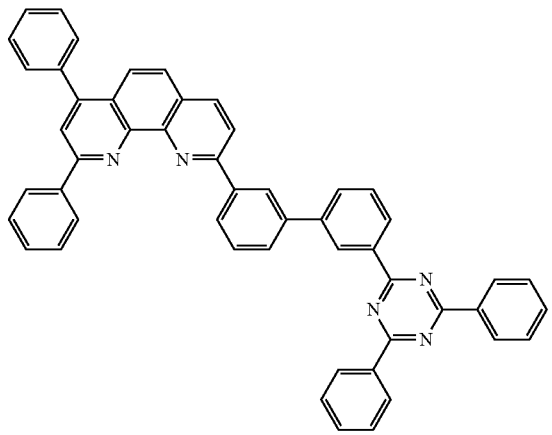
1143
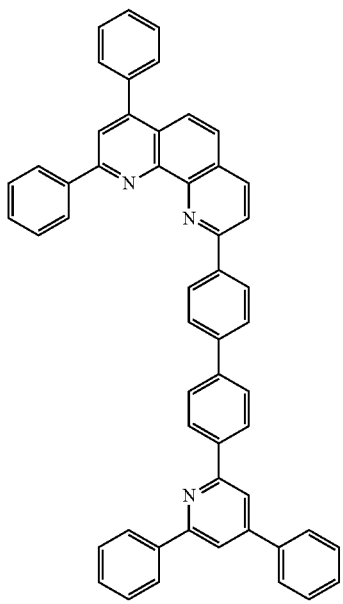
1144
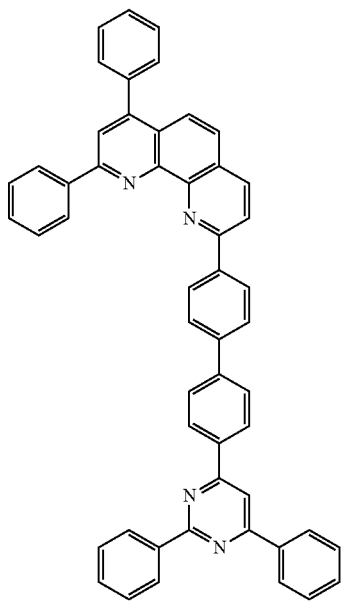
1145
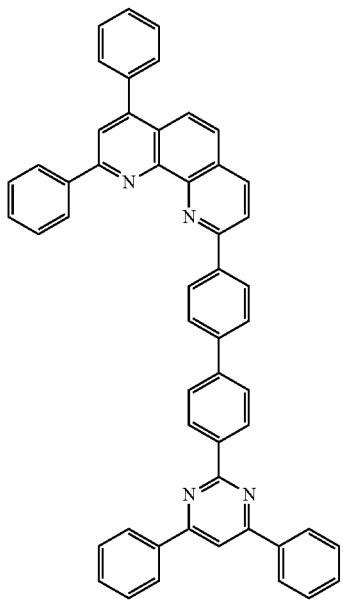
1146
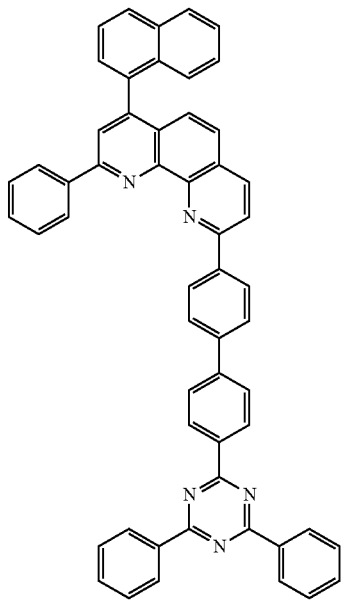

-continued
1147
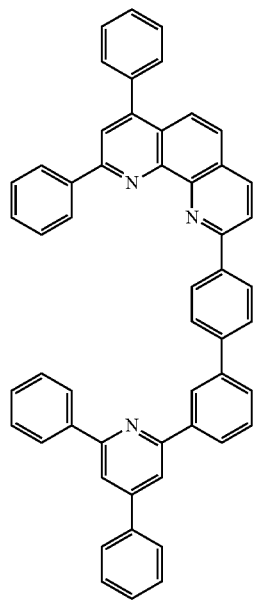
1148
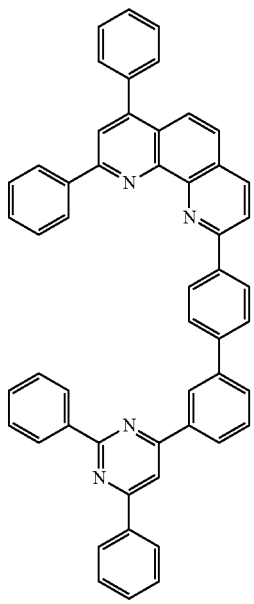
1149
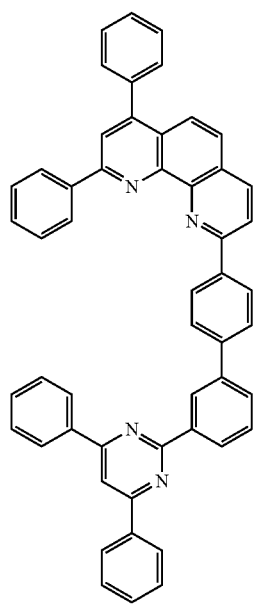
1150
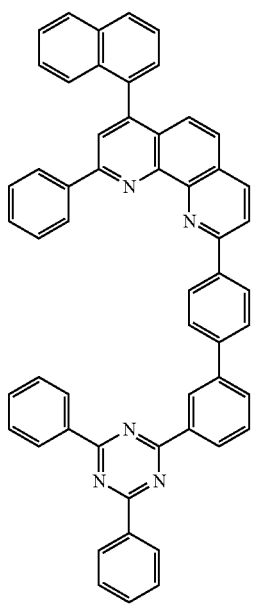

1191
1192
-continued
1151
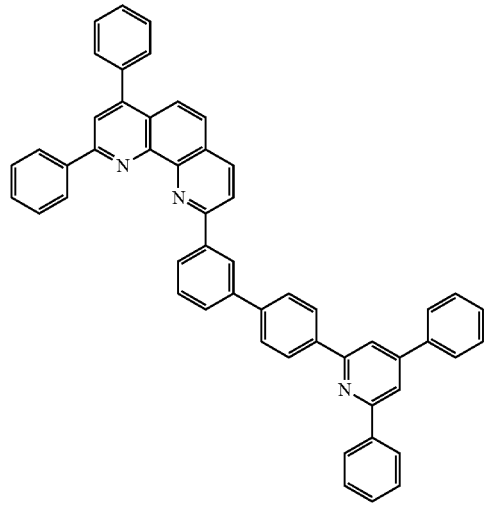
1152
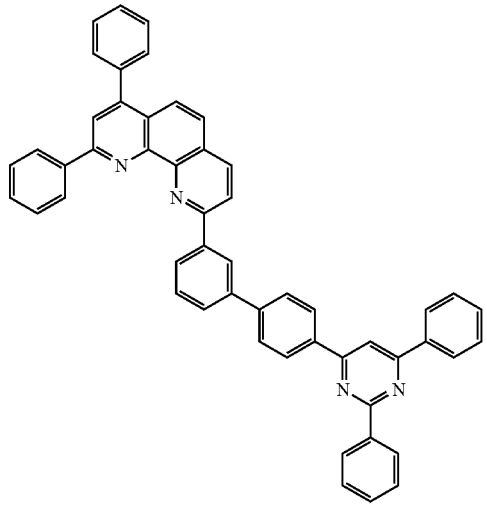
1153
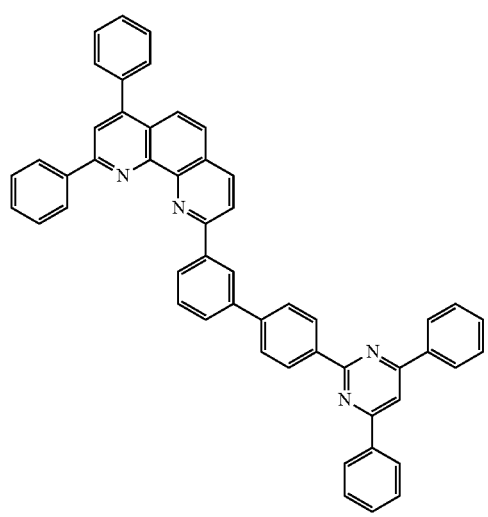
1154
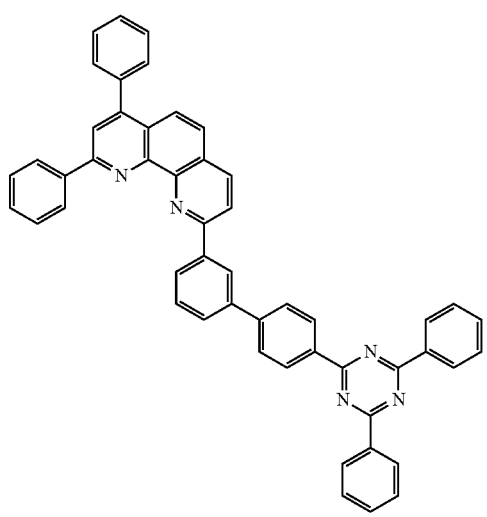
1155
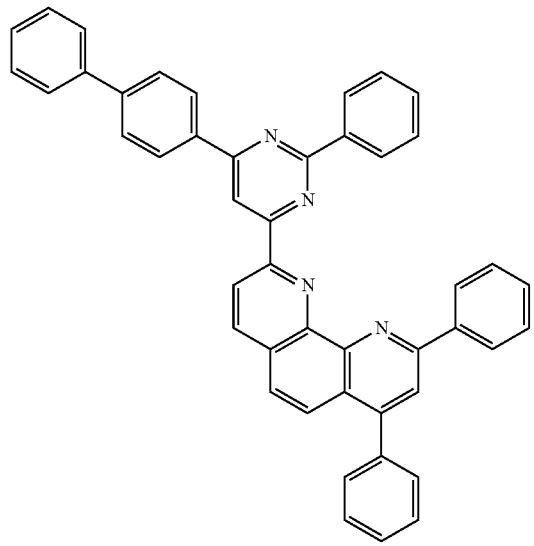
1156
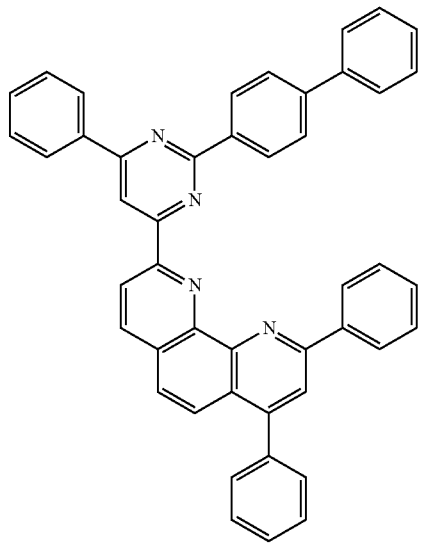

1193
1194
-continued
1157
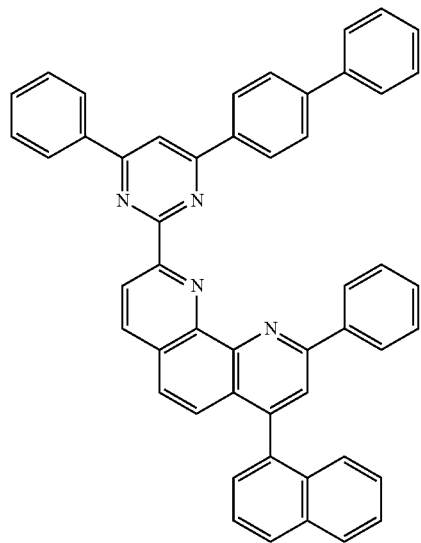
1158
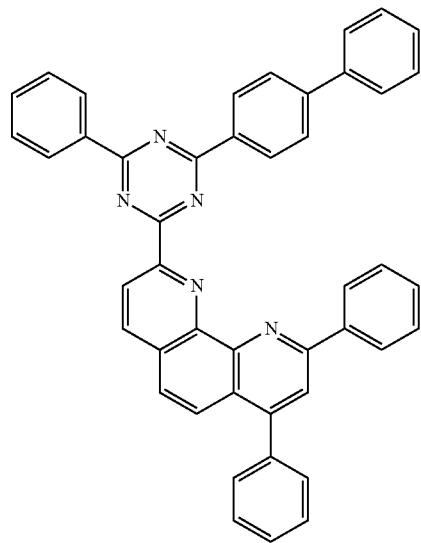
1159
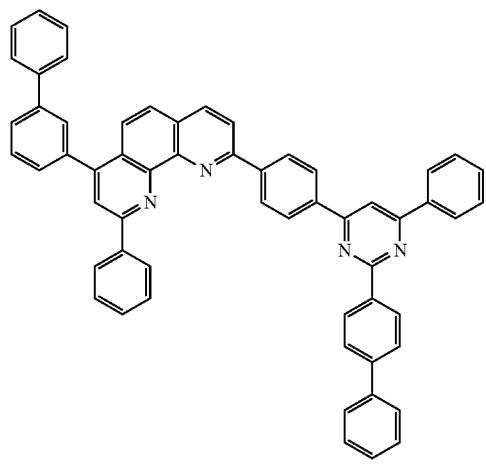
1160
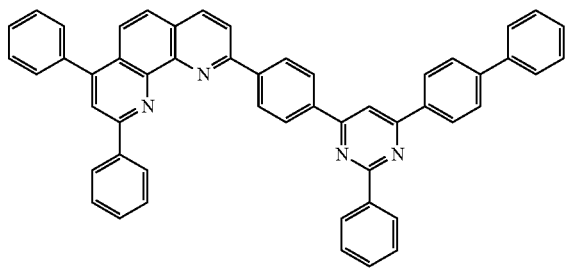
1161
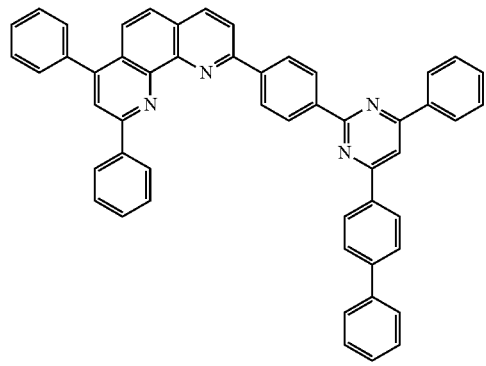
1162
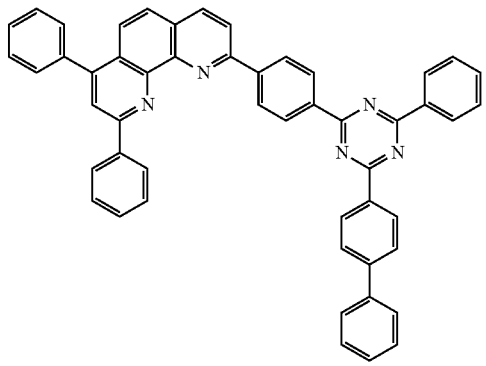

-continued
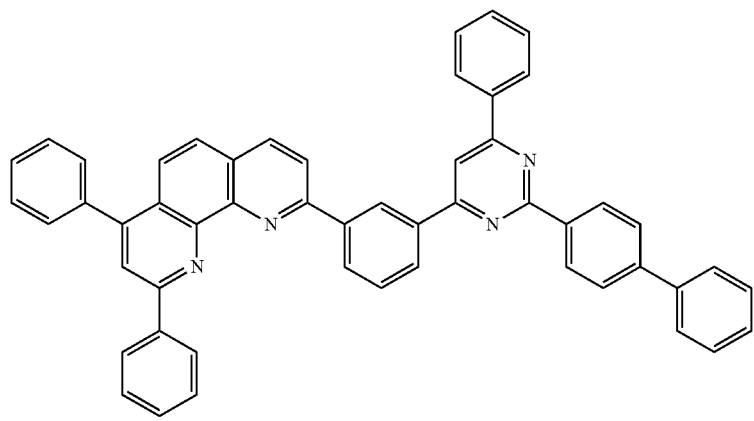
1163
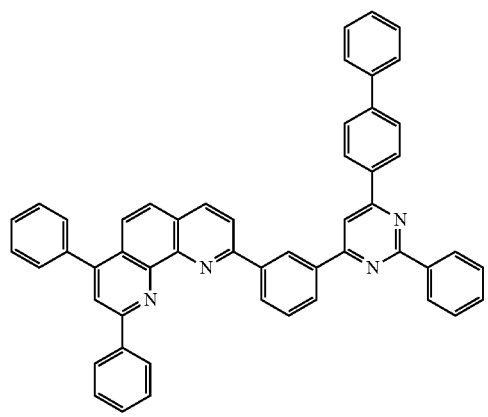
1164
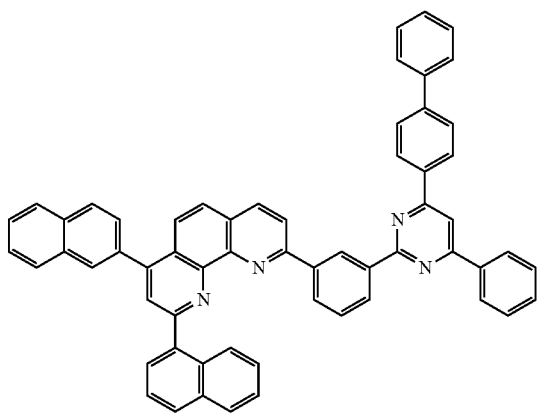
1165
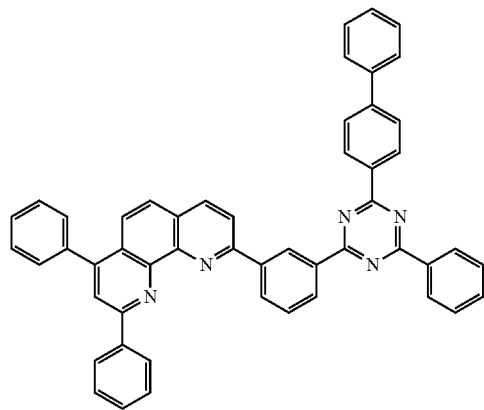
1166
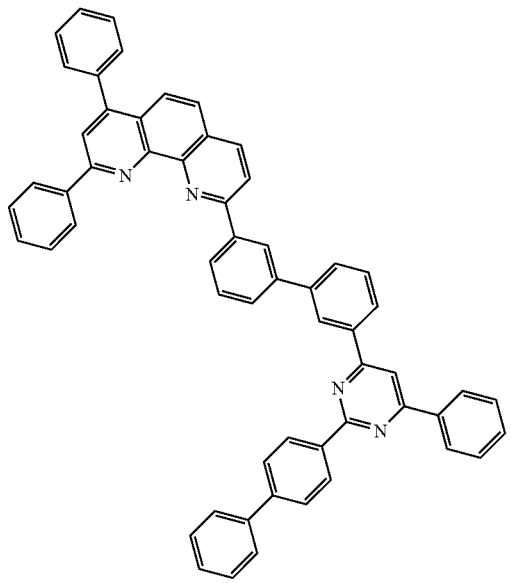
1167

-continued
1168
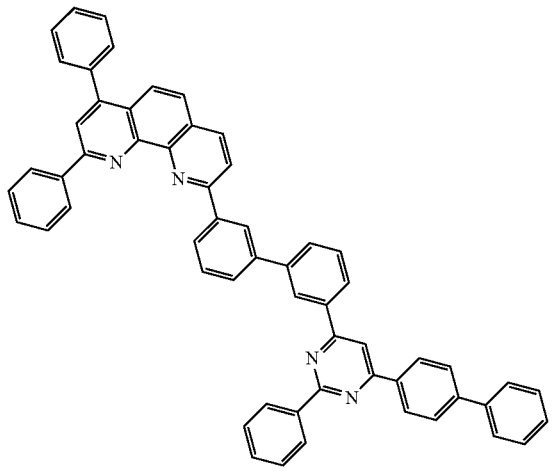
1169
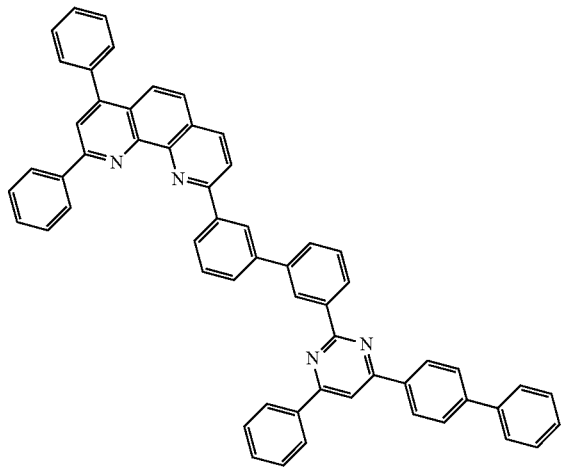
1170
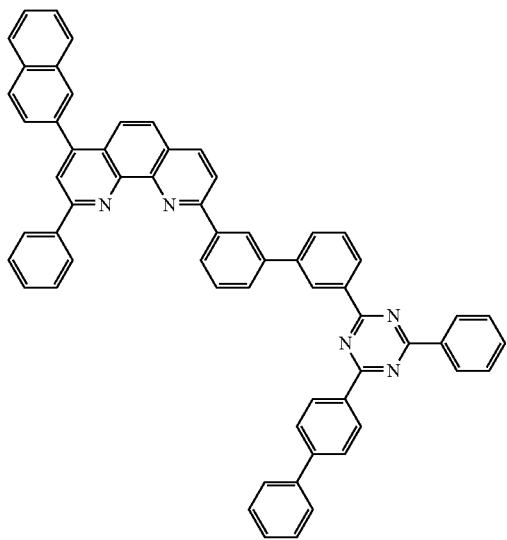
1171
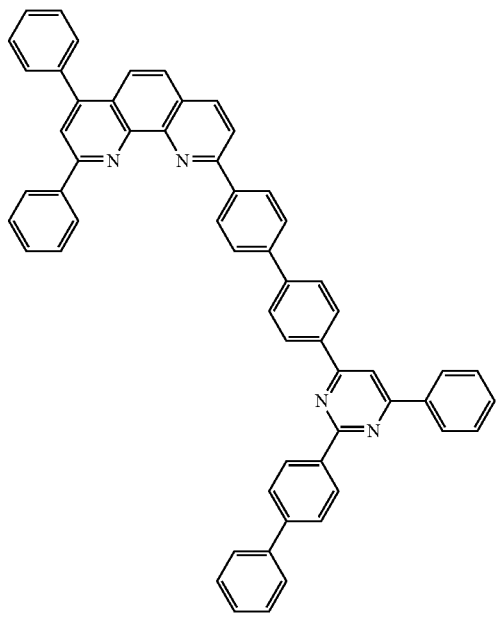

-continued
1199
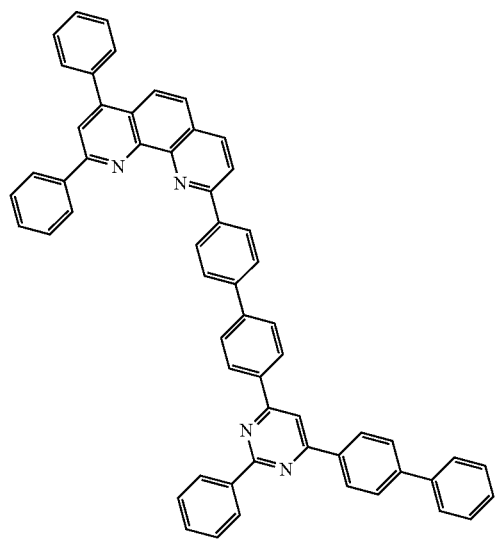
1172
1200
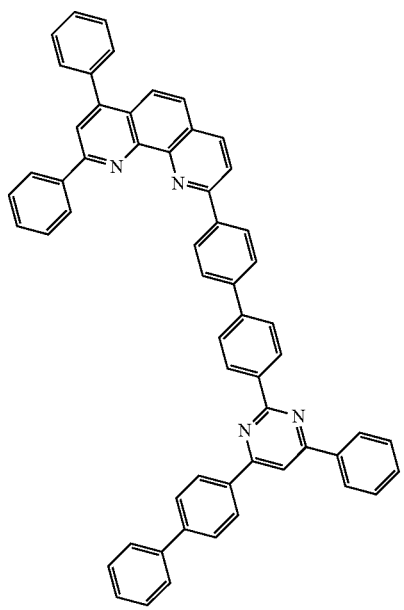
1173
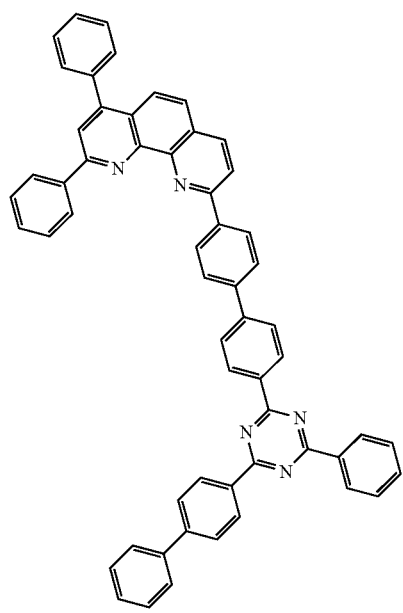
174
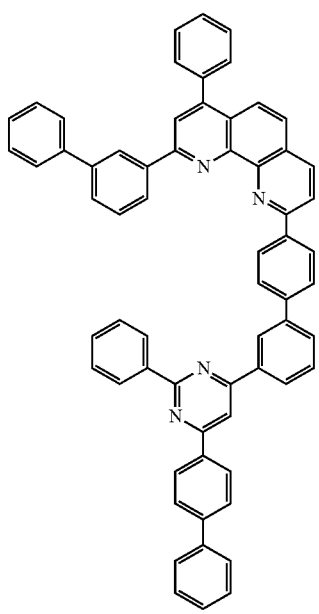
1175

1201
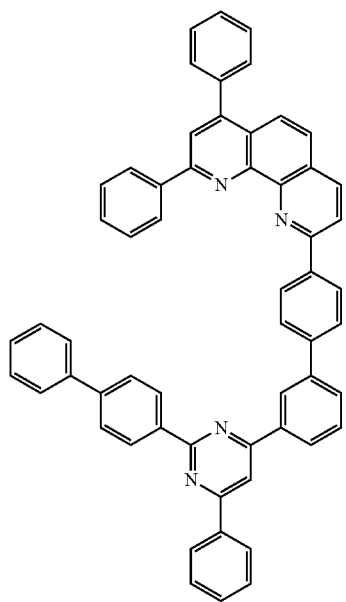
1202
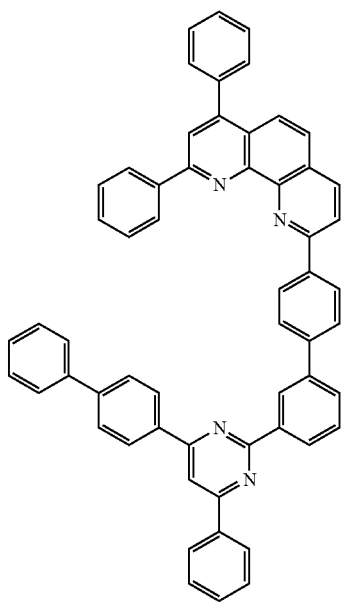
-continued
1176
1177
1178
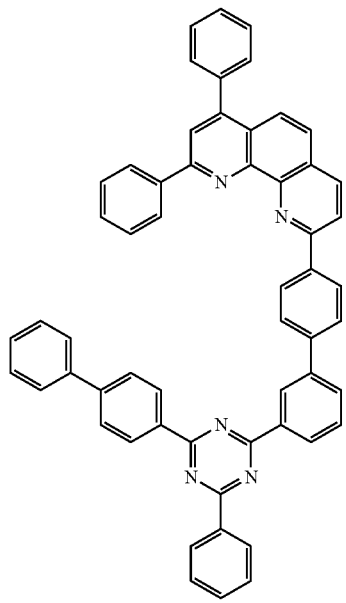
1179
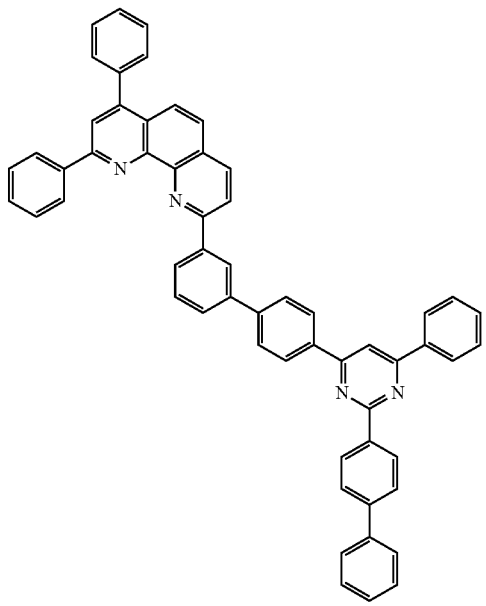

-continued
1203
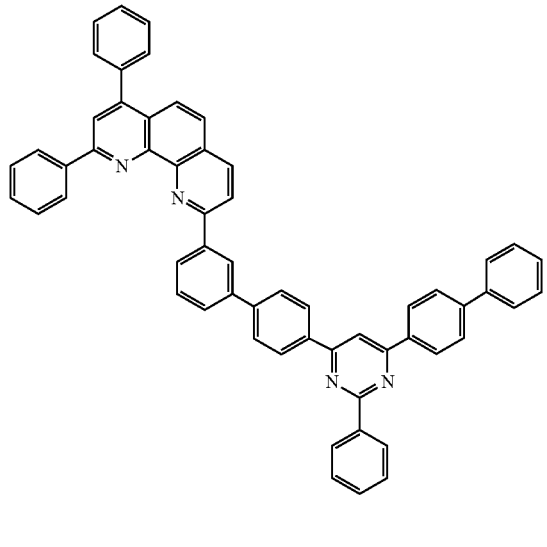
1180
1204
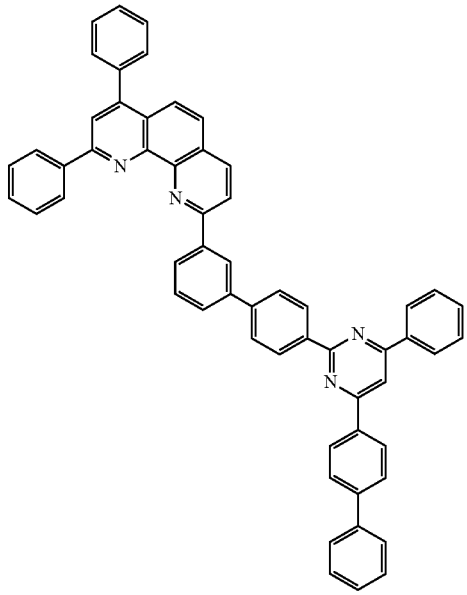
1181
1182
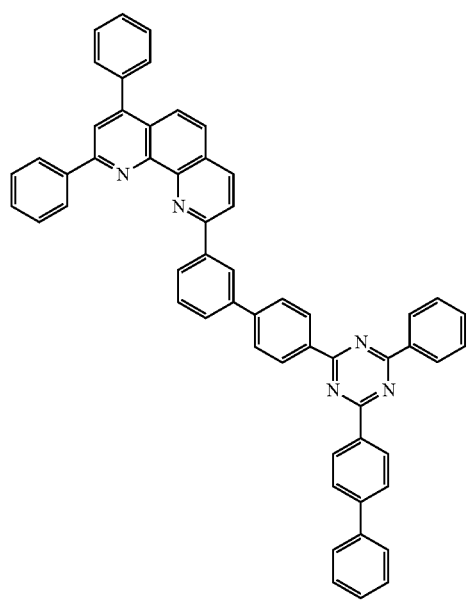

1205 1206
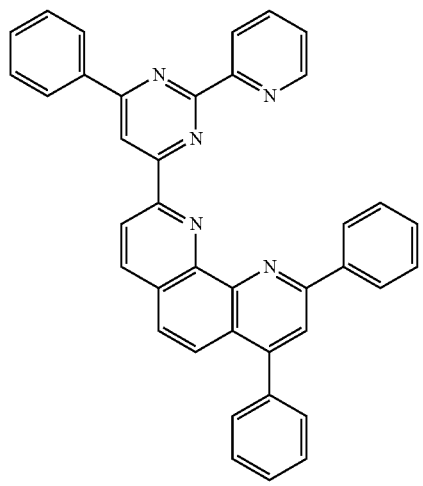
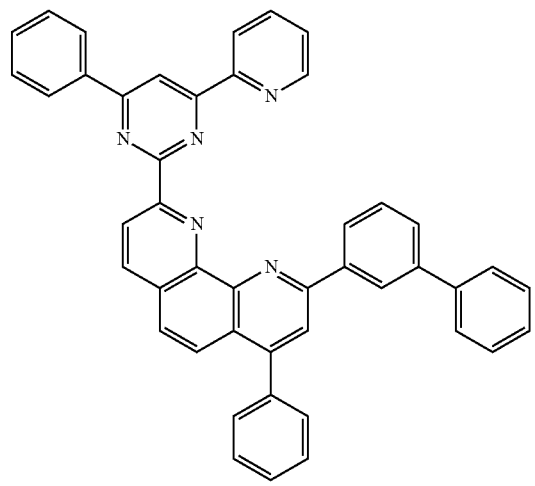
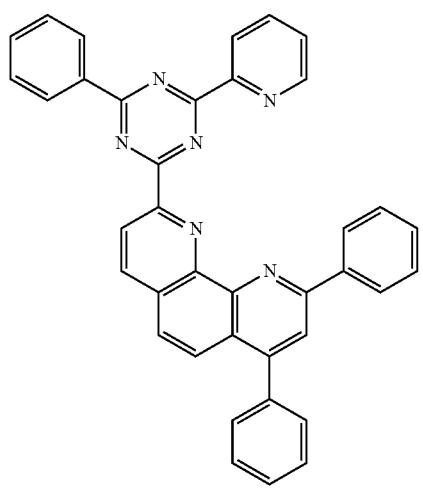
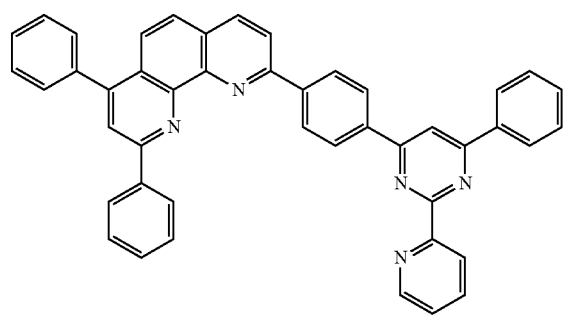
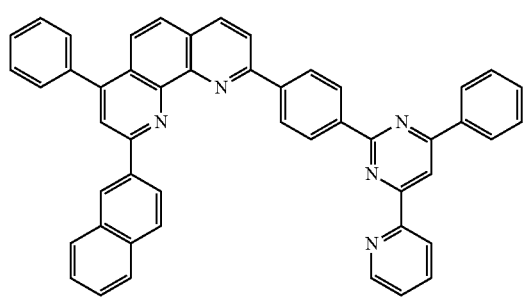
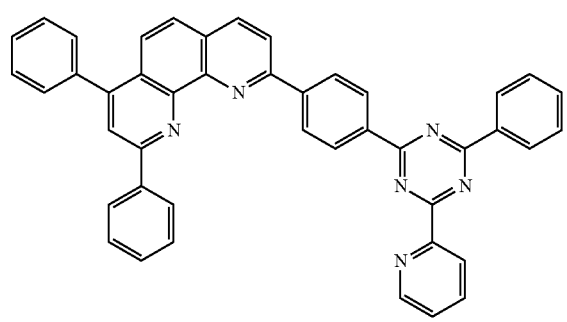

1207 1208
-continued
1189 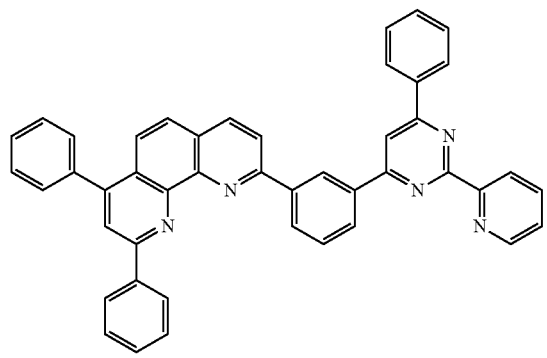
1190 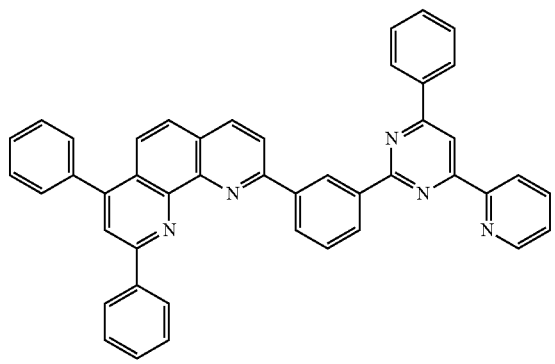
1191 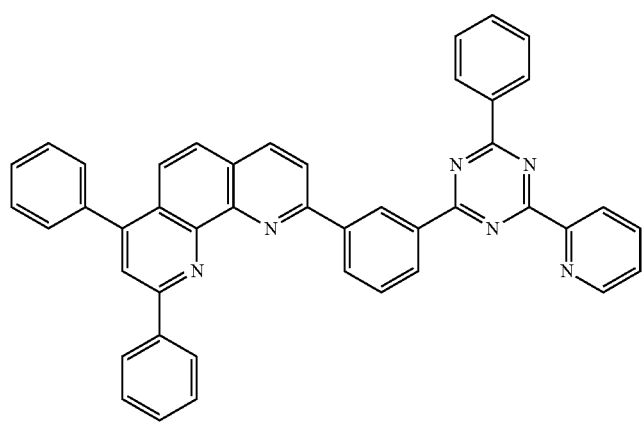
1192 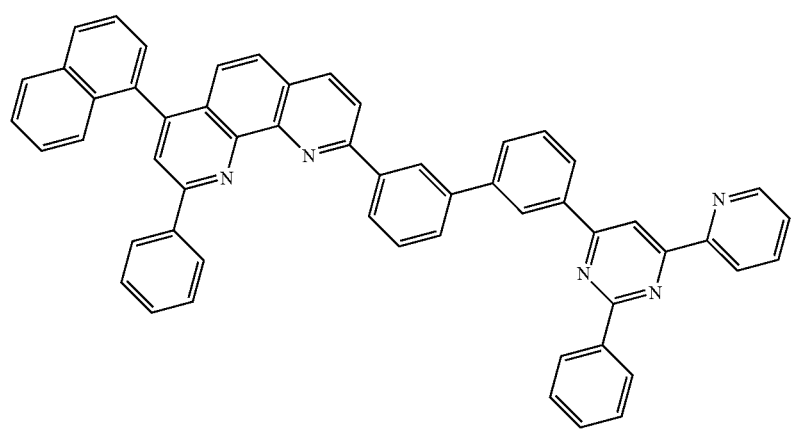

-continued
1193
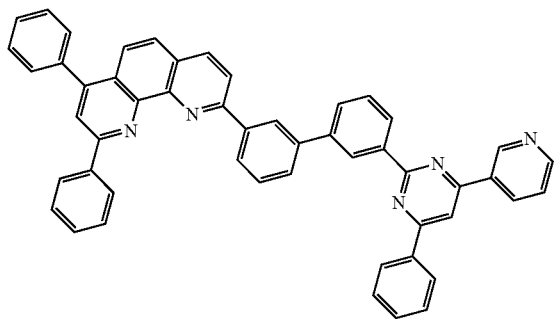
1194
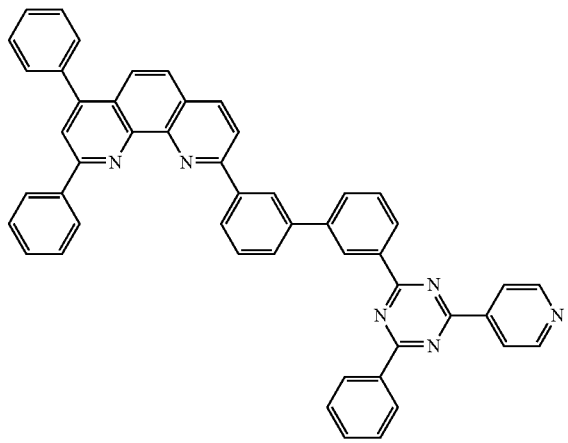
1195
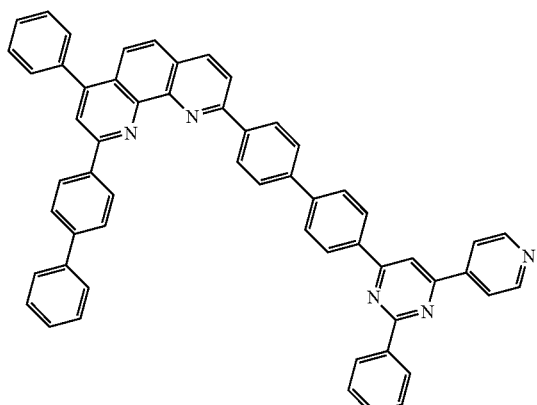
1196
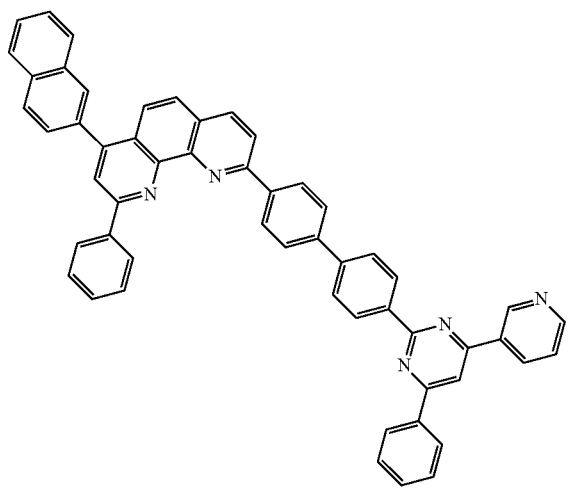
1197
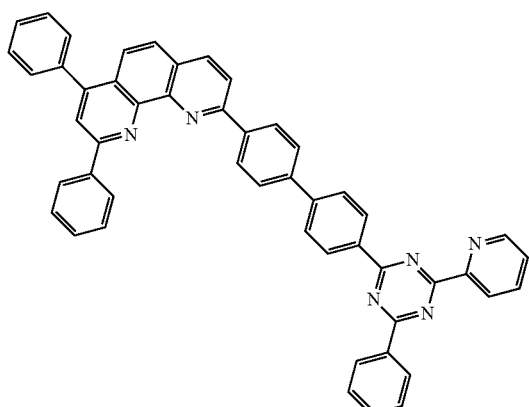
1198
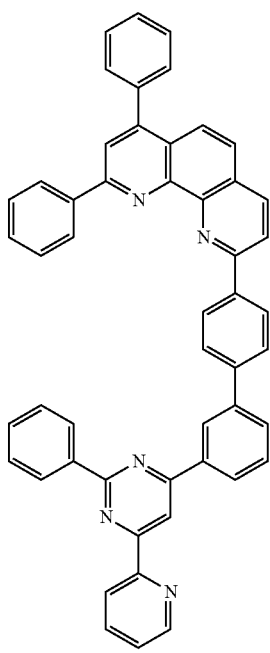

-continued
1211
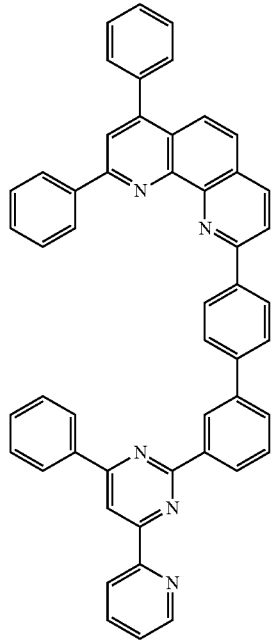
1199
1212
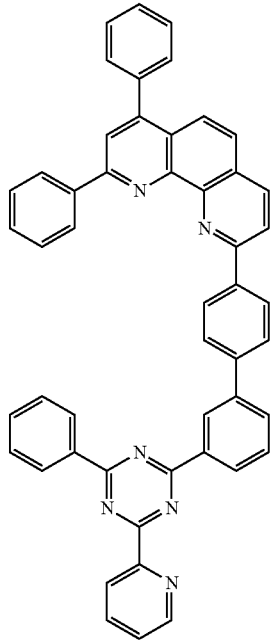
1200
1201
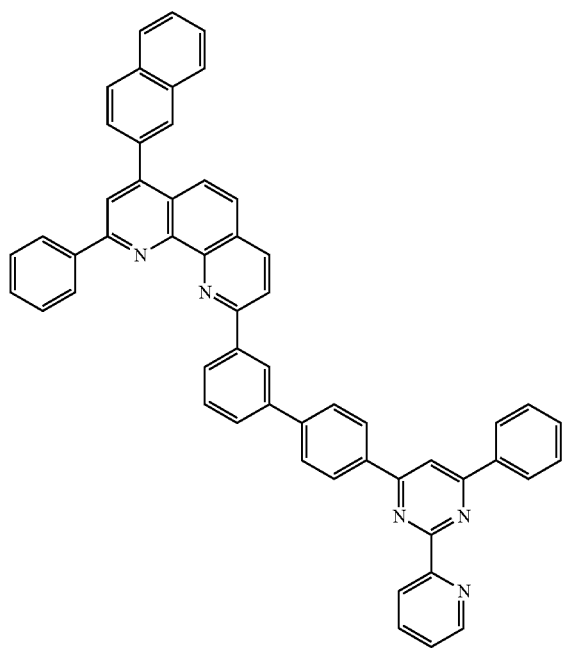
1202
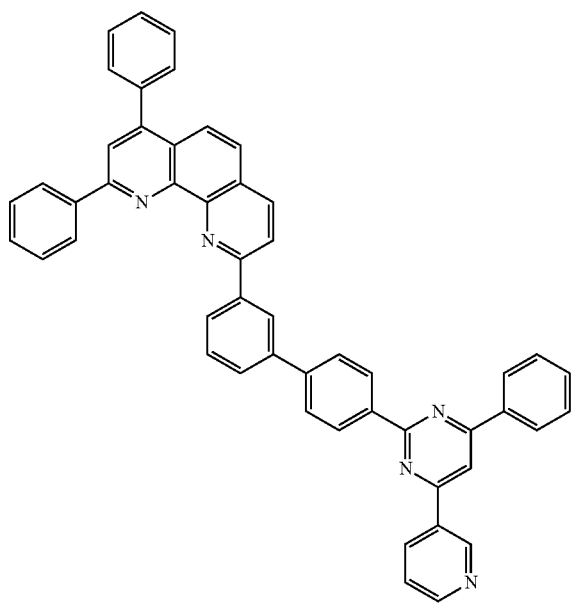

-continued
1203
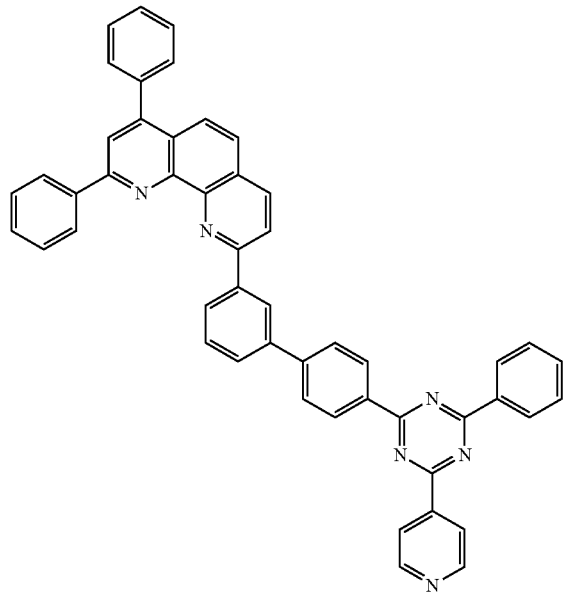
1204
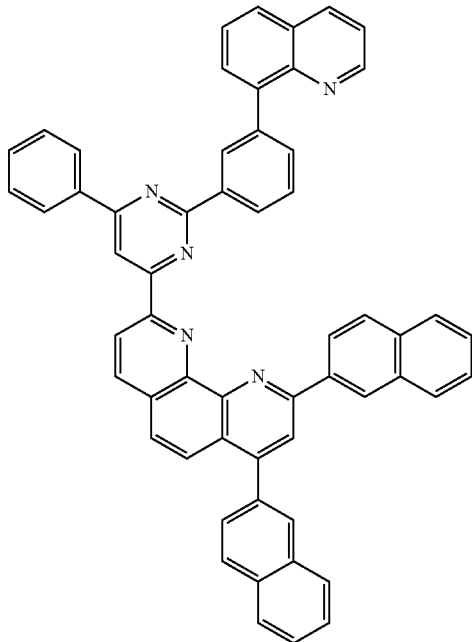
1205
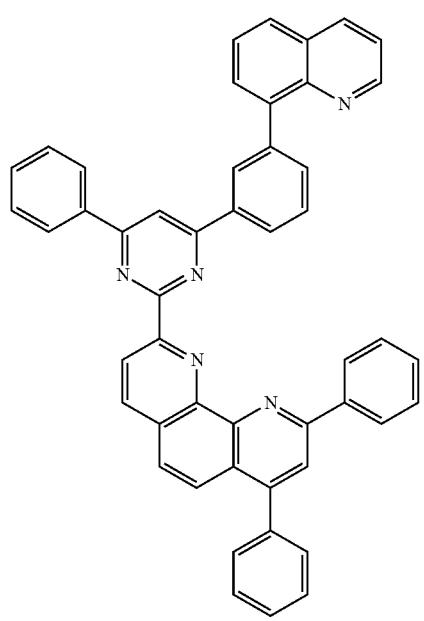
1206
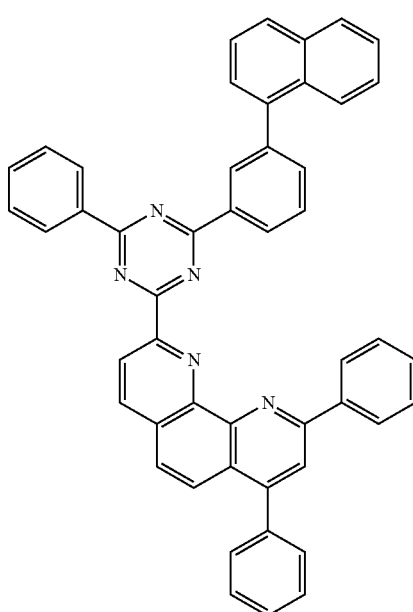
1207
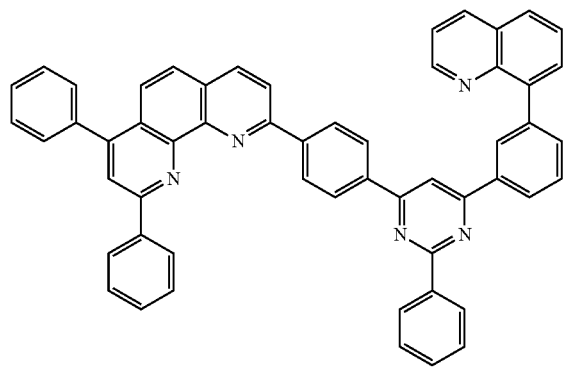
1208
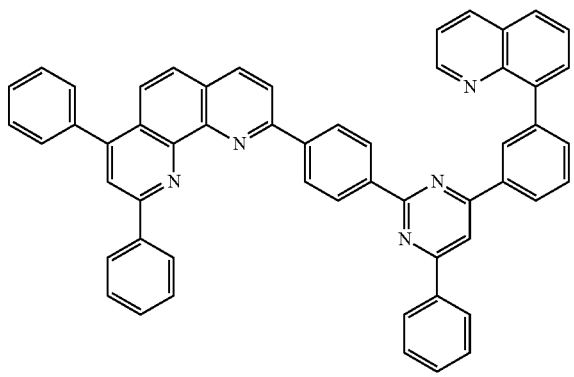

-continued
1209
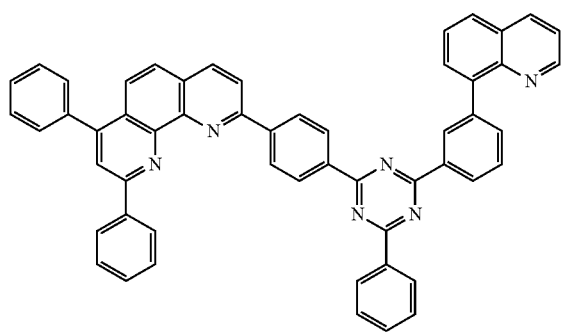
1210
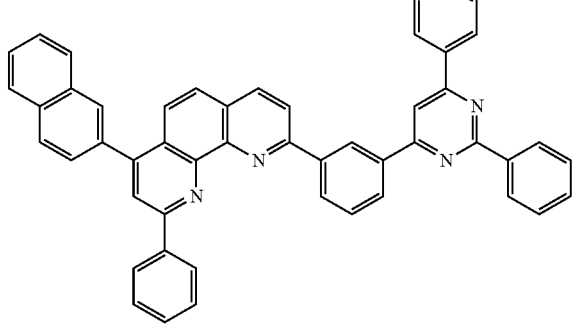
1211
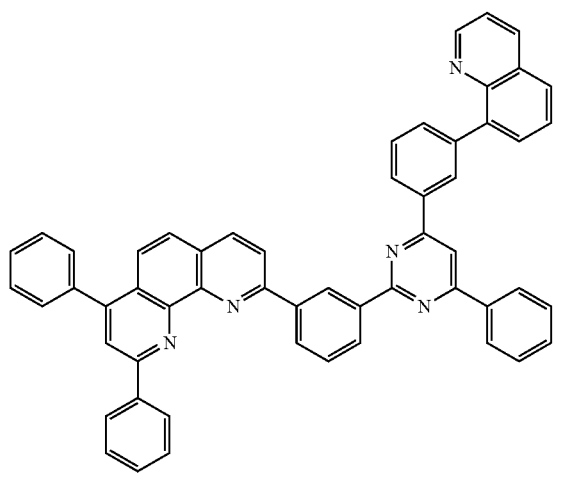
1212
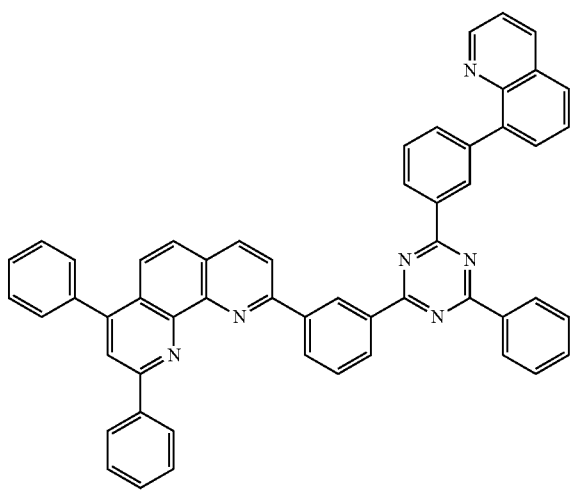
1213
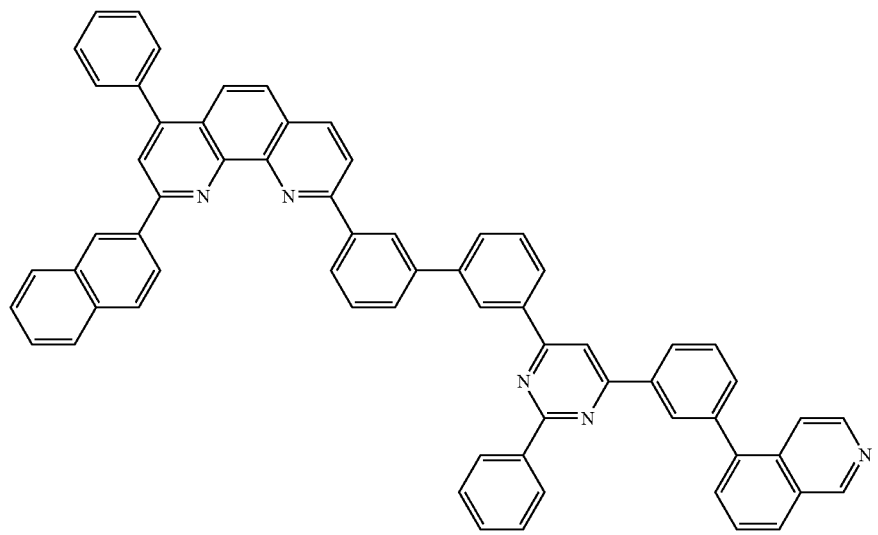

1214
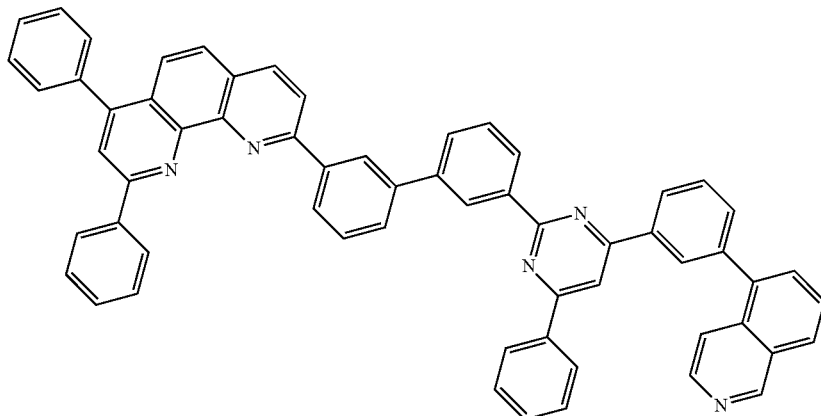
1215
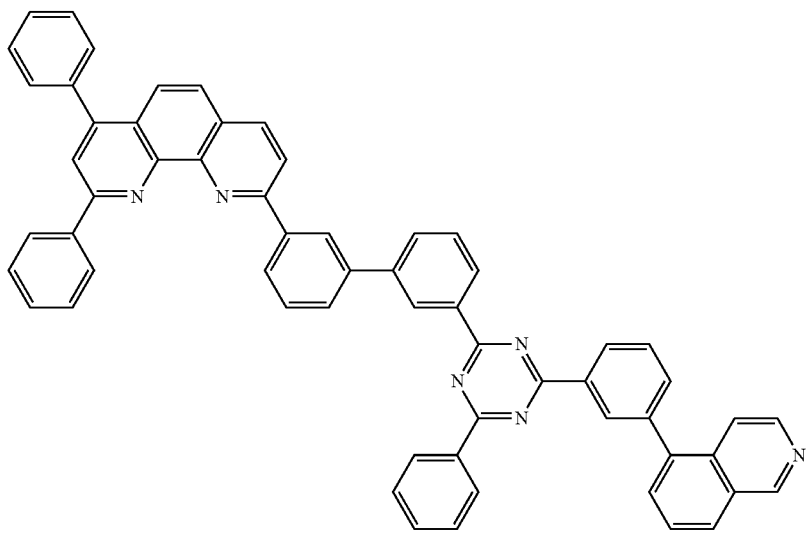
1216
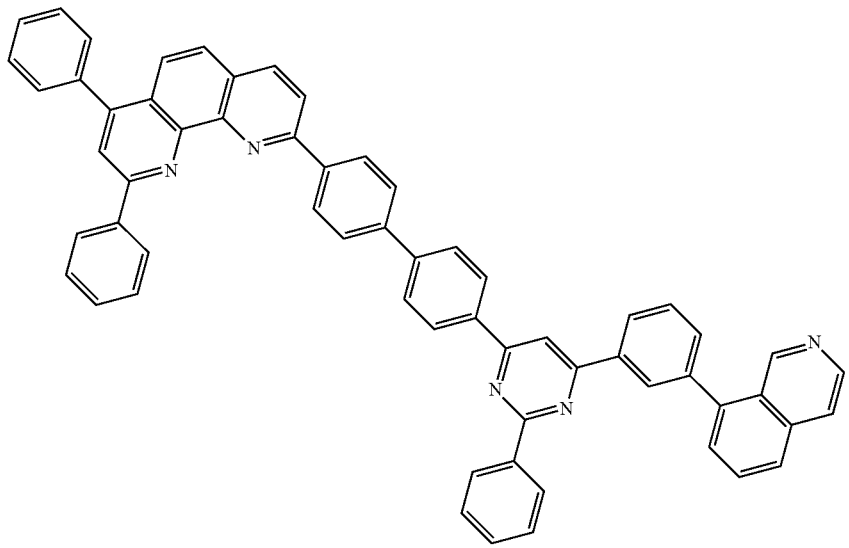

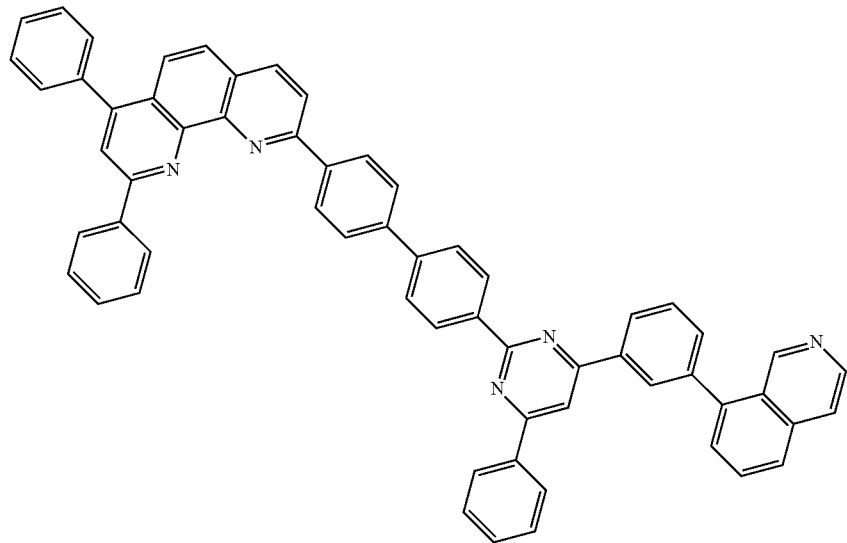
1217
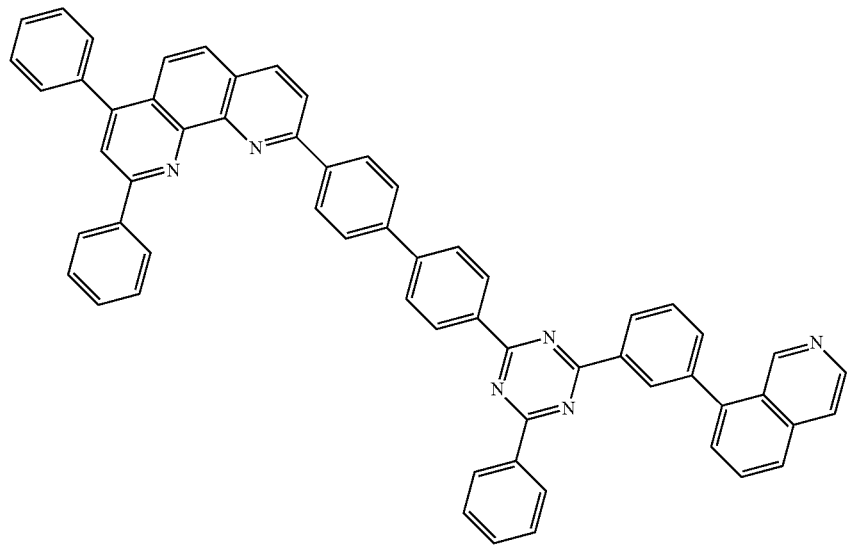
1218
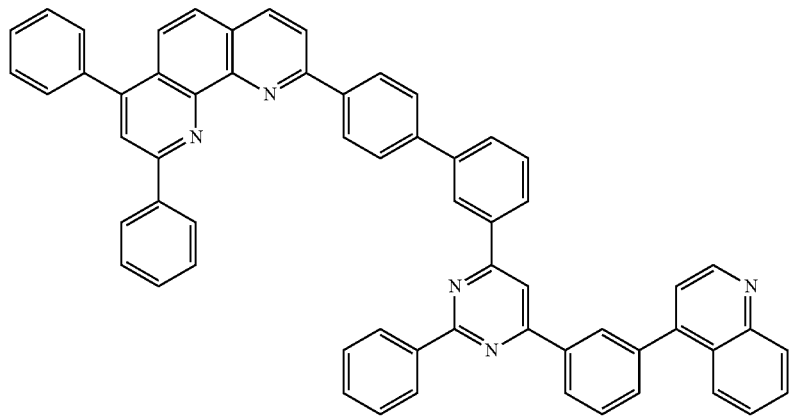
1219

-continued
1220
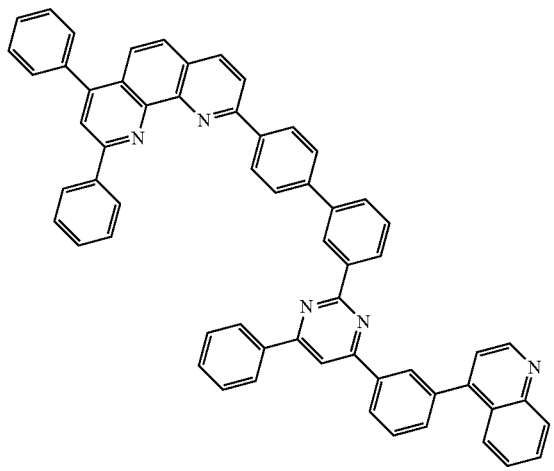
1221
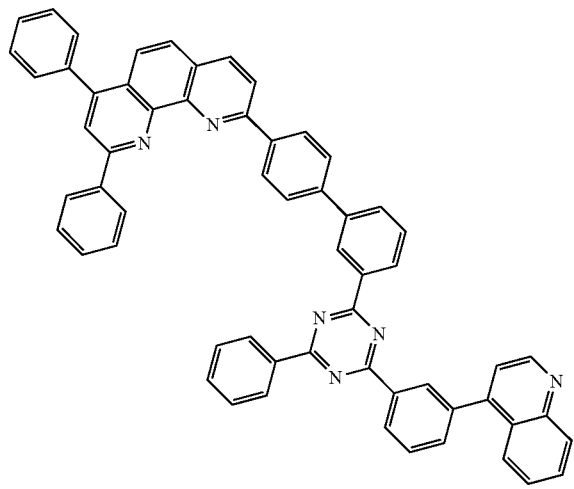
1222
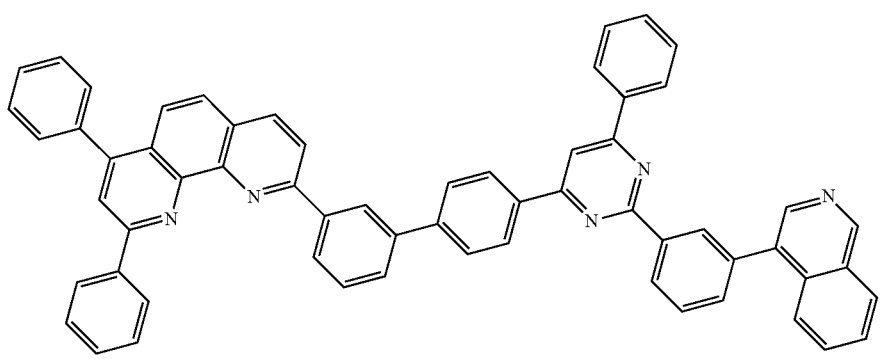
1223
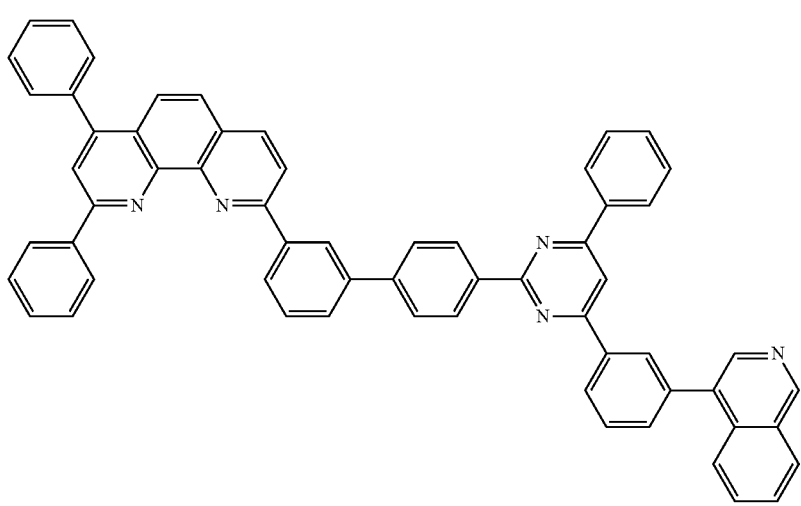

1223 1224
-continued
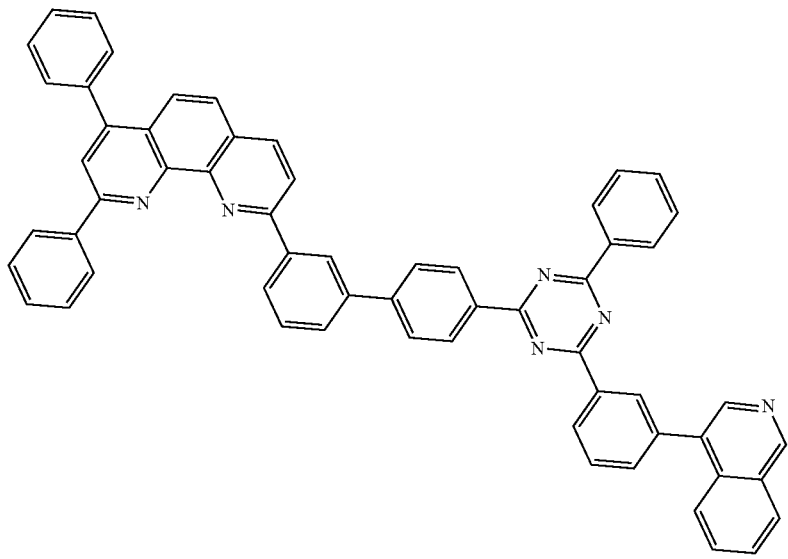
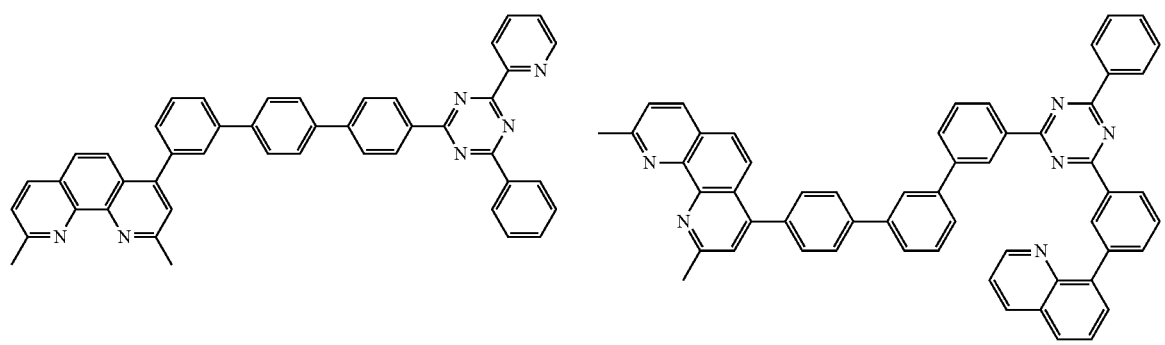
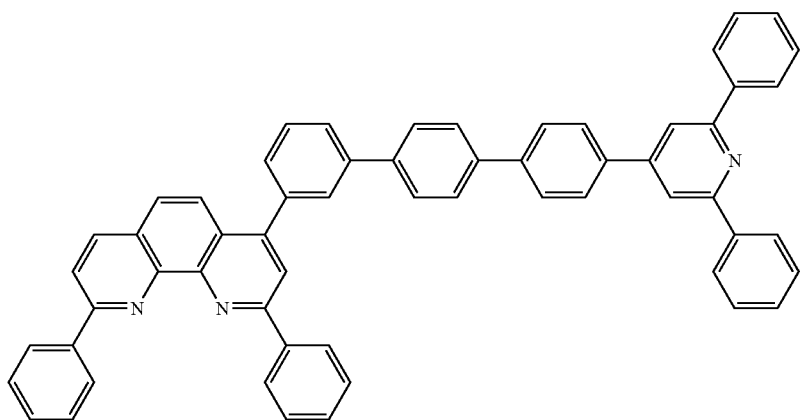

1225 1226
-continued
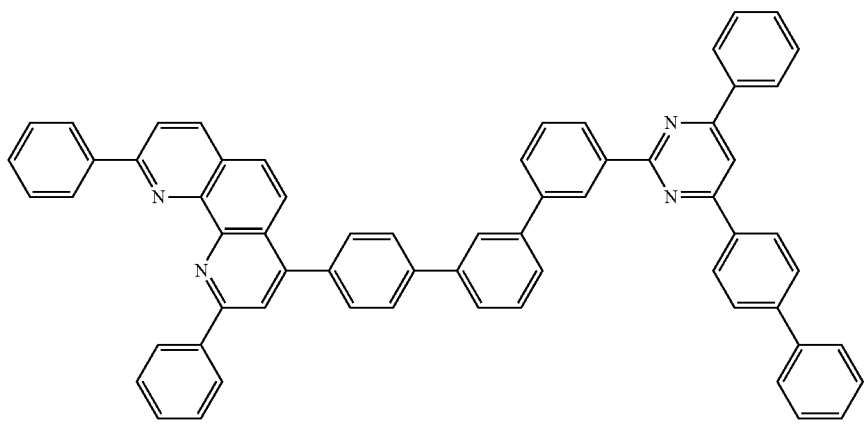
1228
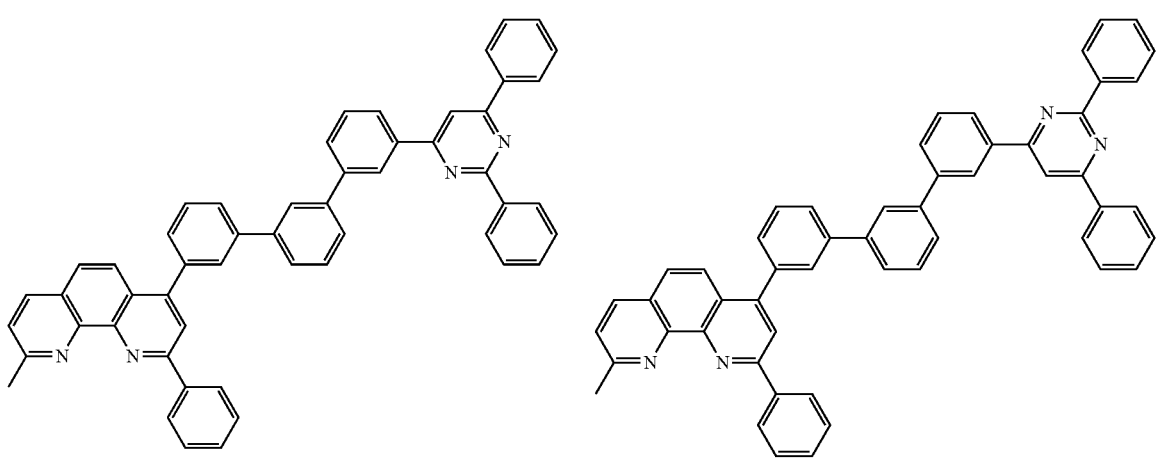
1229 1230
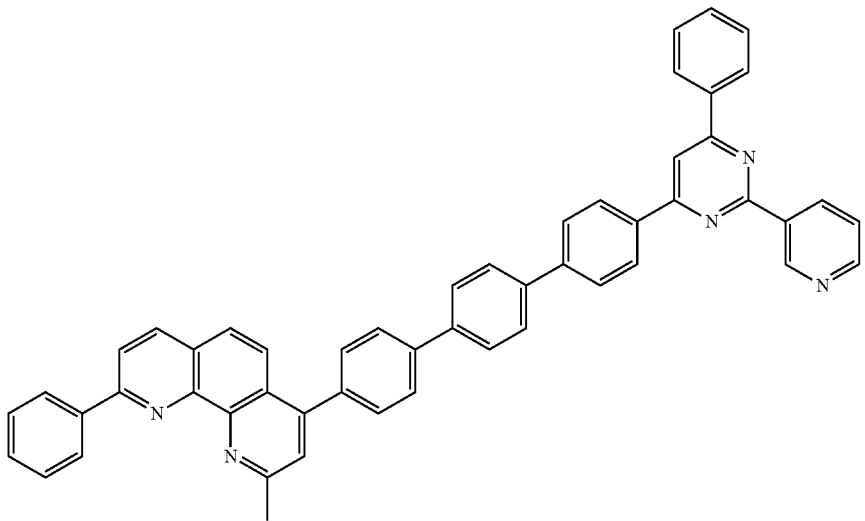
1231

1232
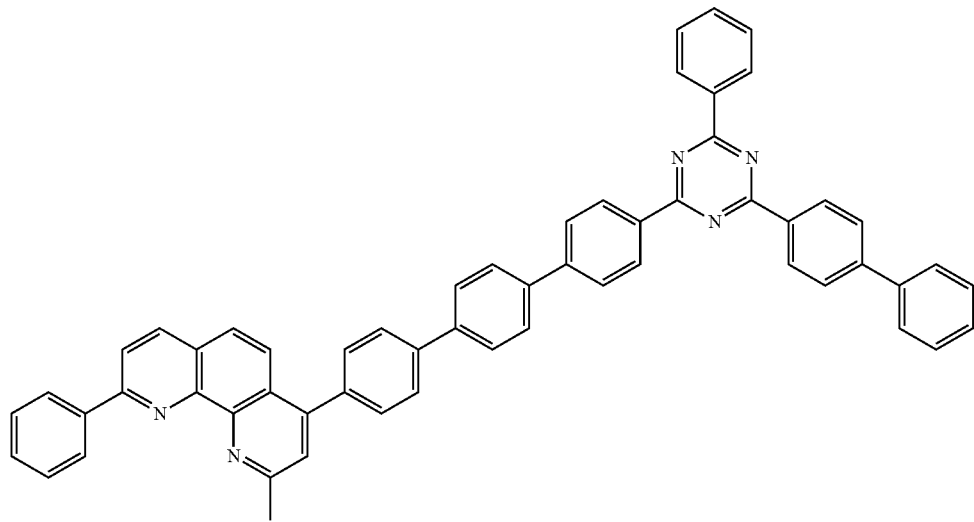
1233 1234
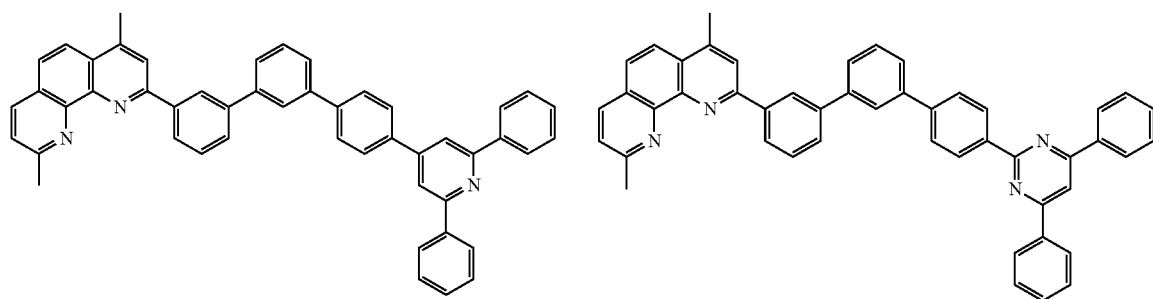
1235
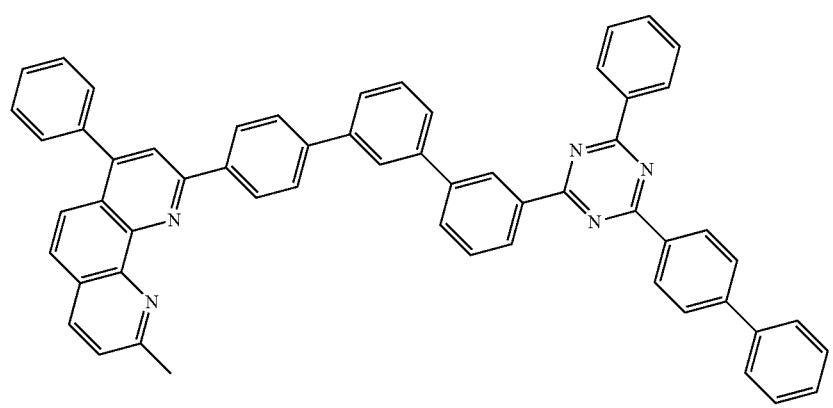

-continued
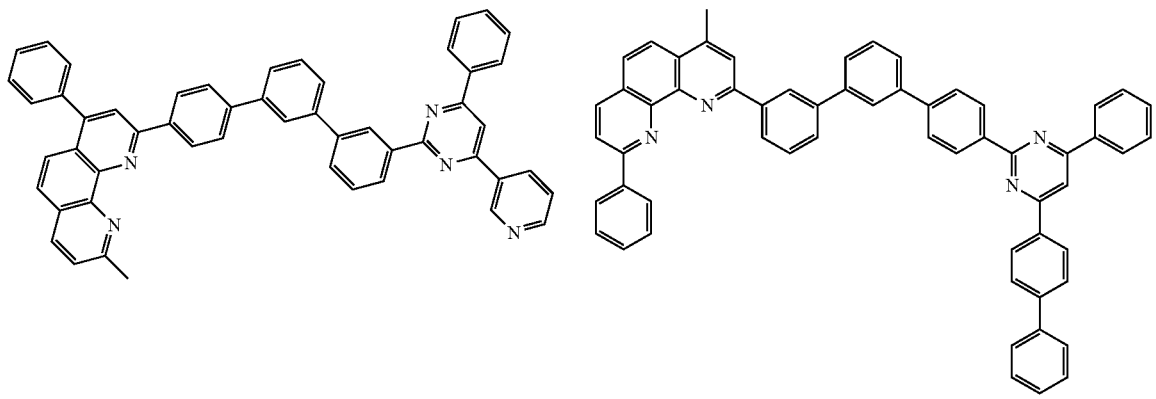
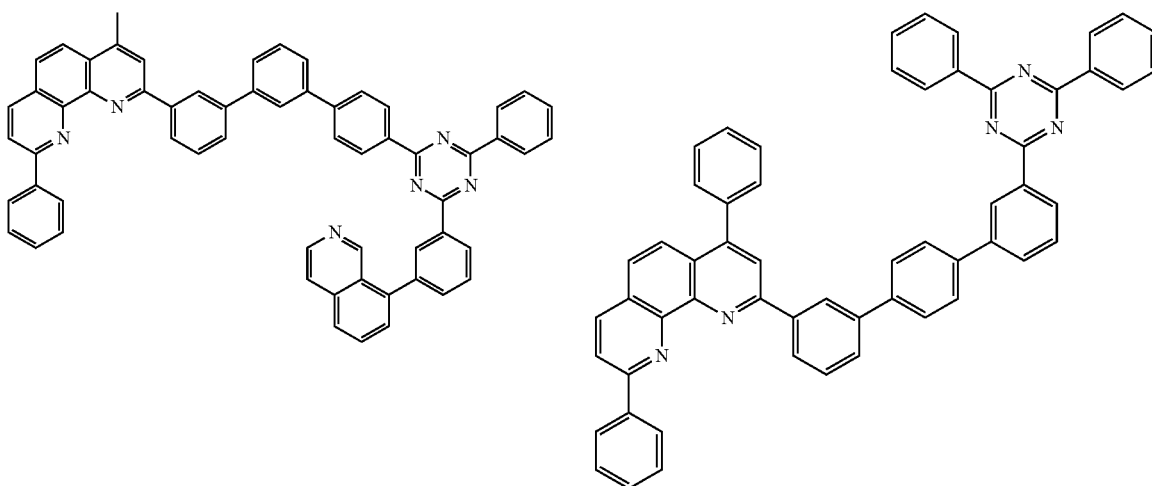
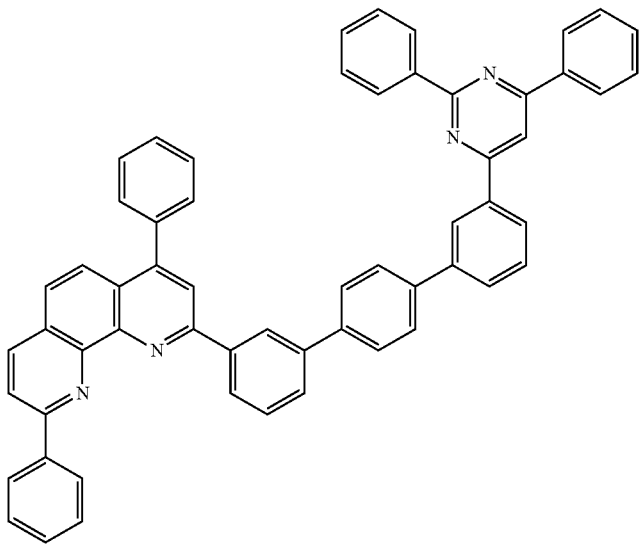

1241
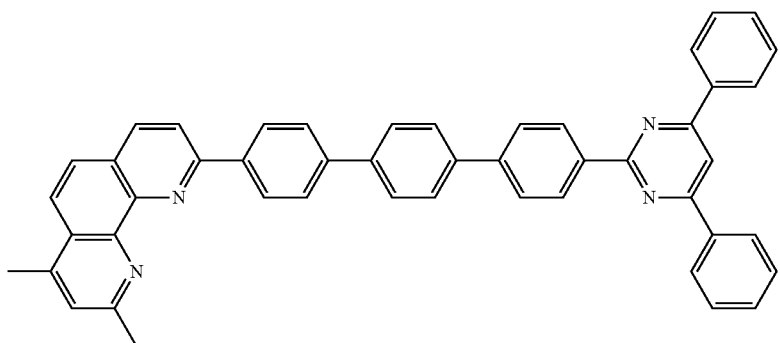
1242
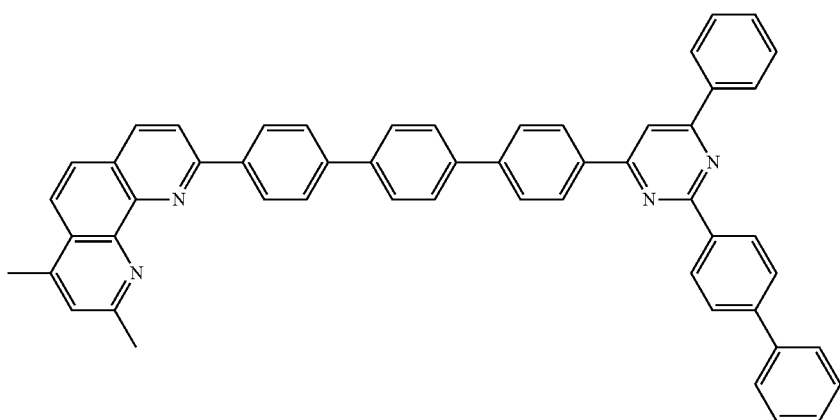
1243
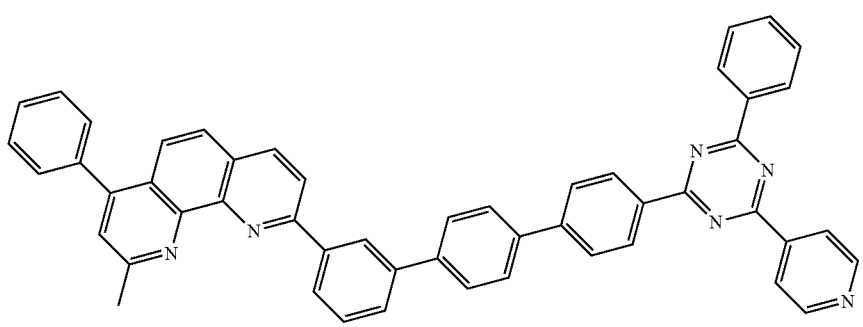
1244
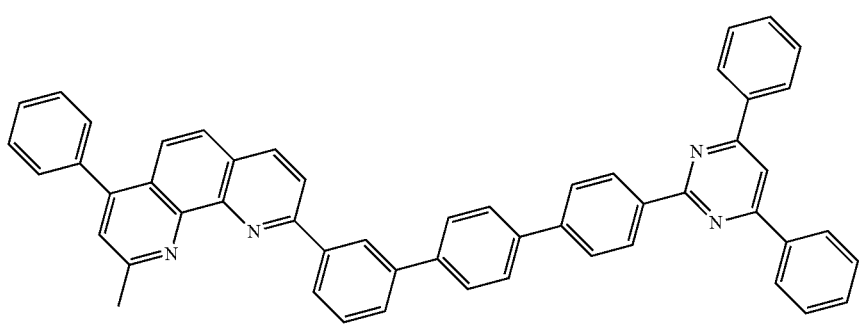

1245
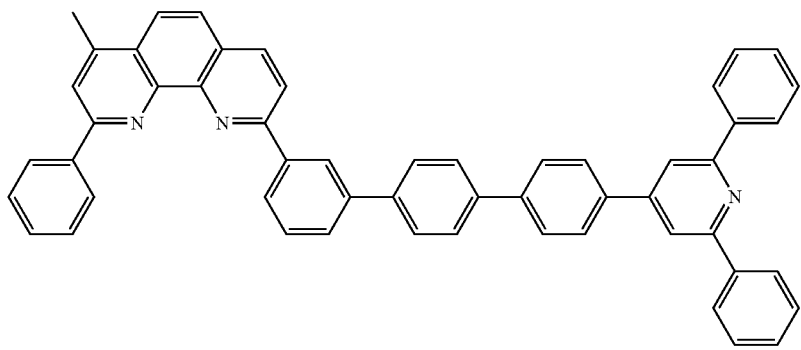
1246
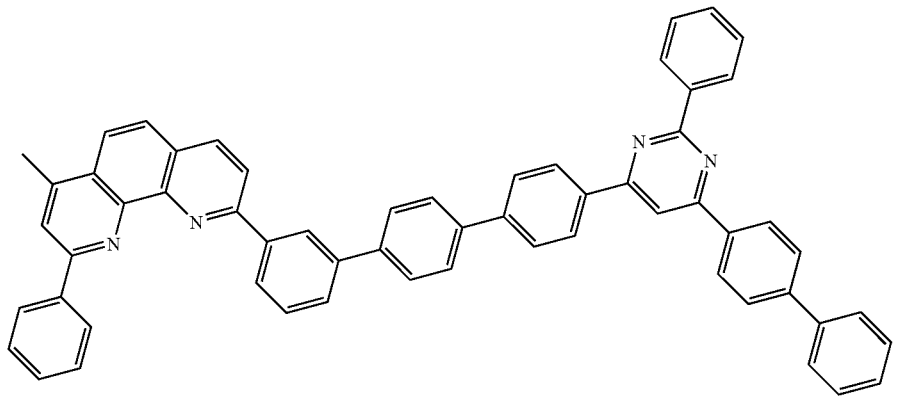
1247
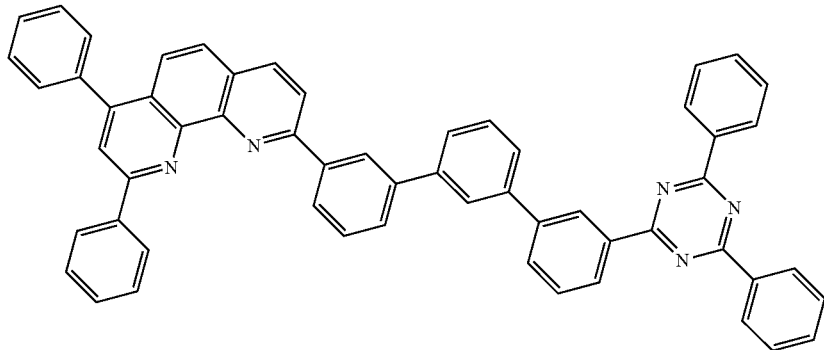
1248 1249
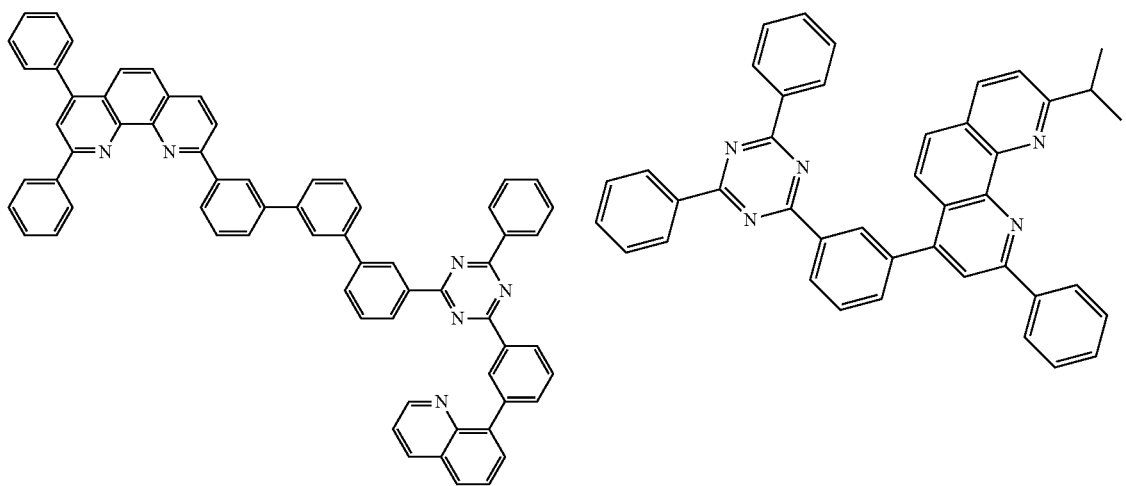

-continued
1250 1251
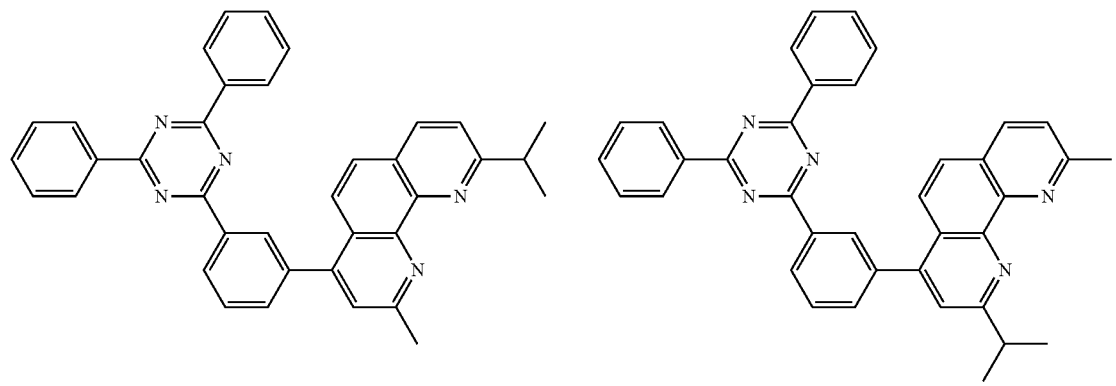
1252 1253
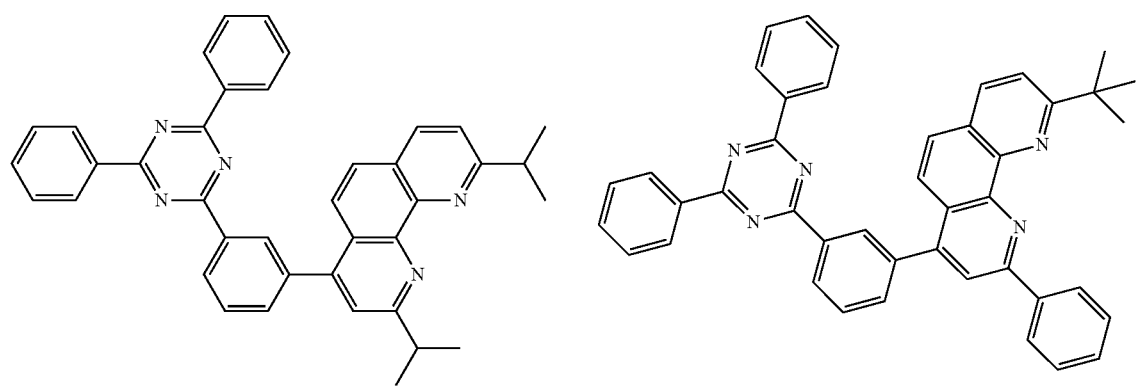
1254 1255
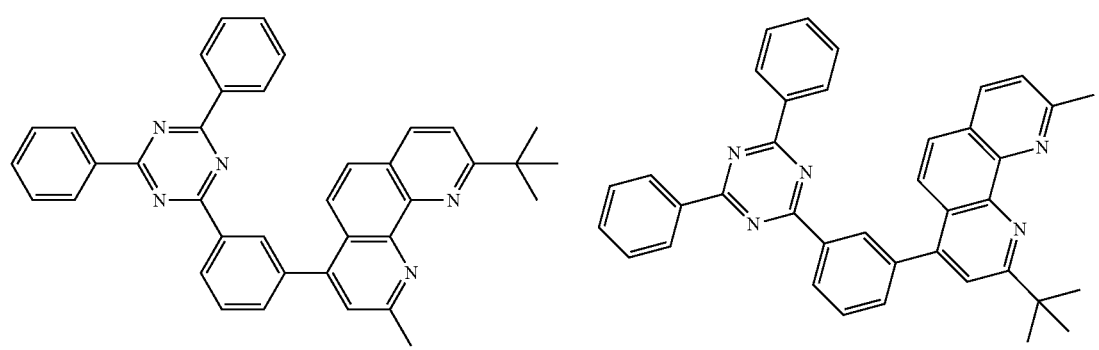
1256 1257
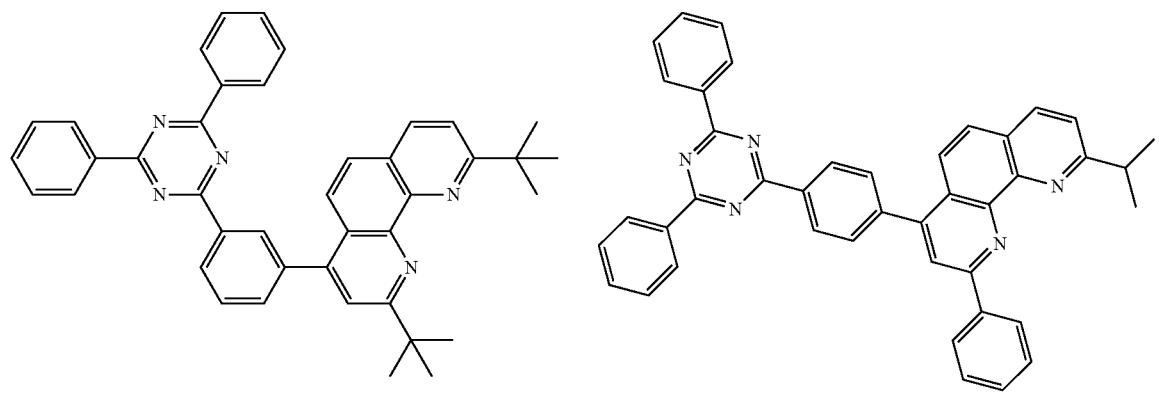

-continued
1258
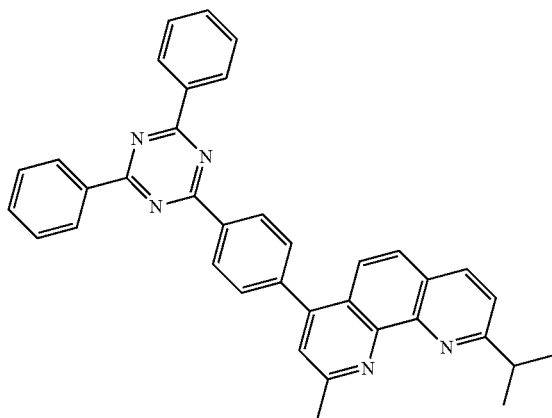
1259
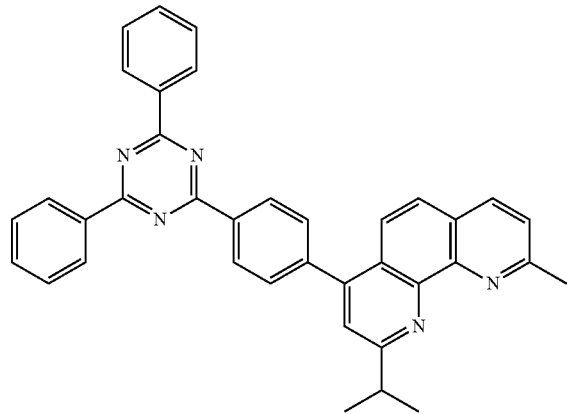
1260
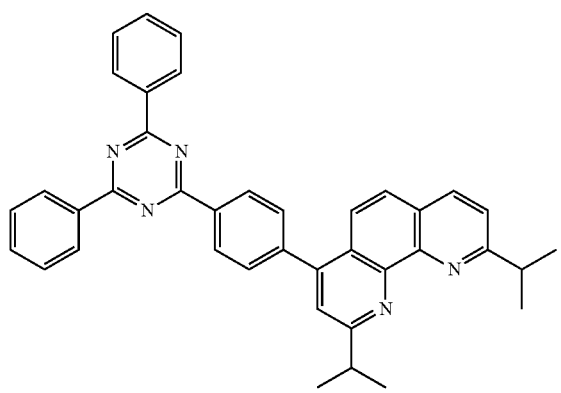
1261
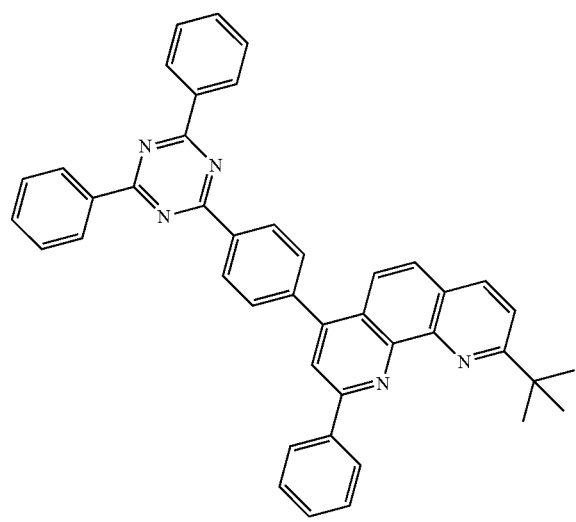
1262
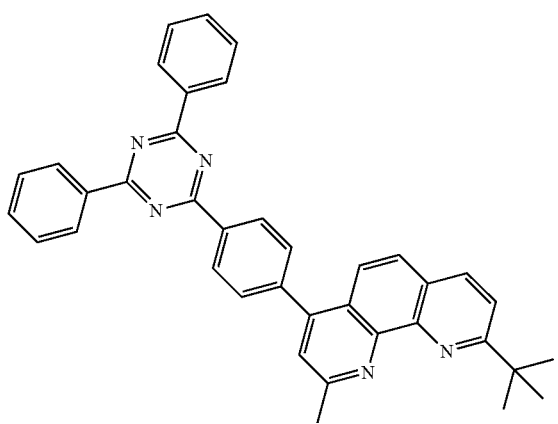
1263
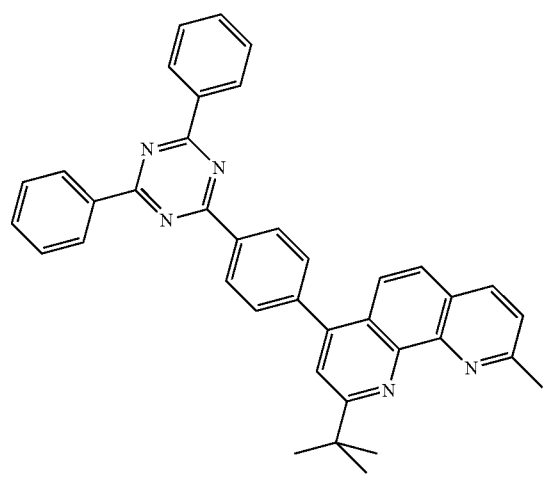

-continued
1264
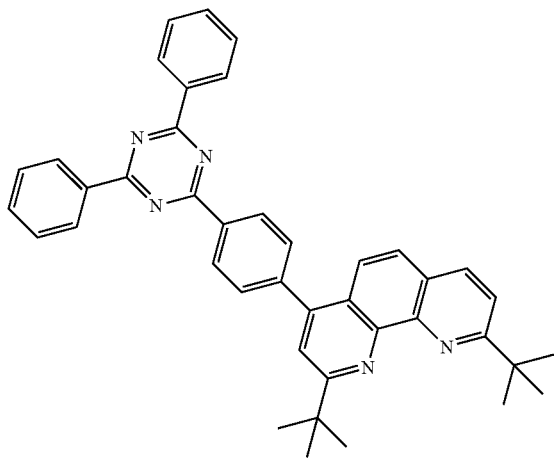
1265
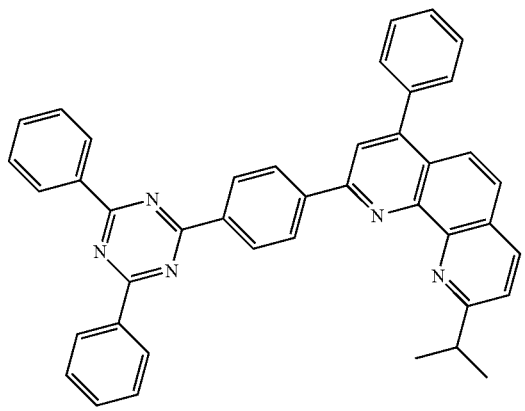
1266
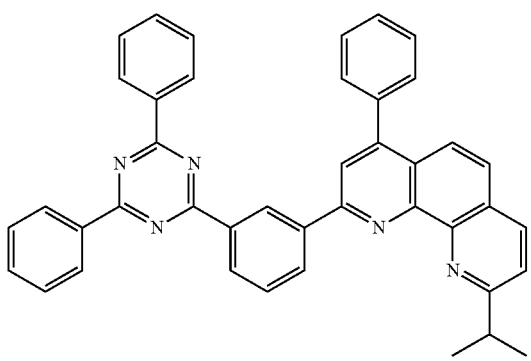
1267
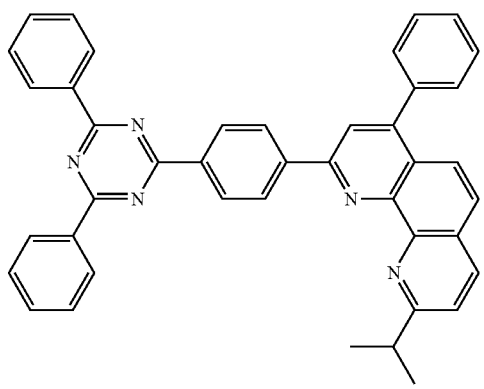
1268
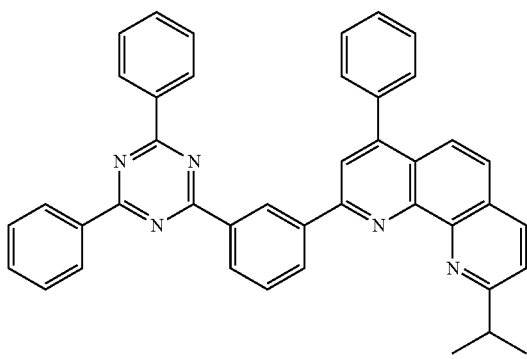
1269
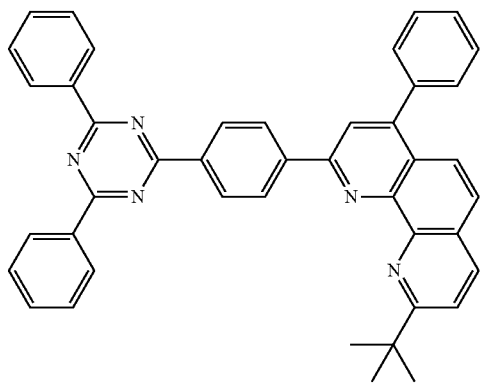

1241 1242
-continued
1270 1271
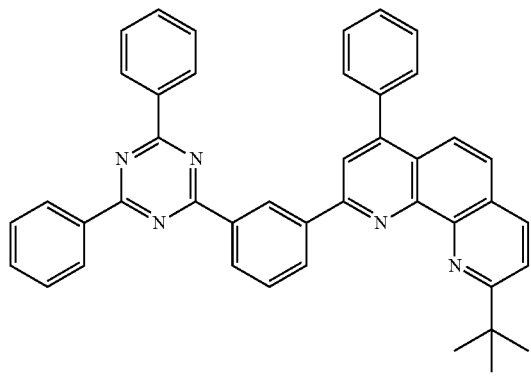
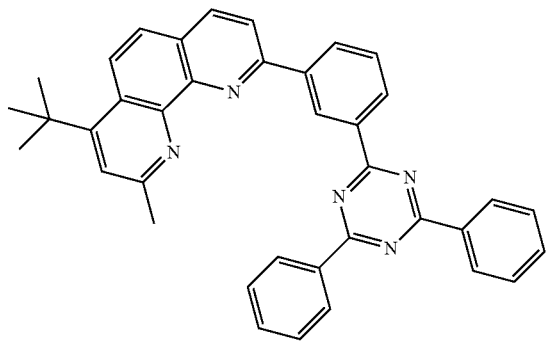
1272
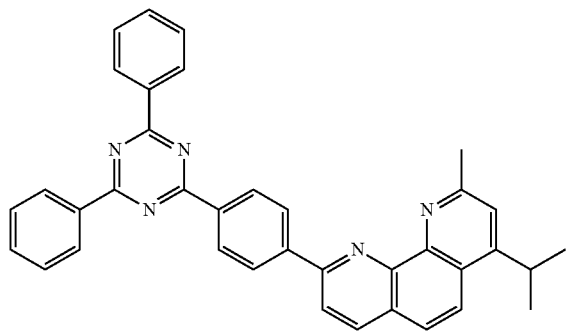
* * * * *